US011352356B2

(12) United States Patent
Papaioannou et al.

(10) Patent No.: US 11,352,356 B2
(45) Date of Patent: Jun. 7, 2022

(54) INHIBITORS OF PLASMA KALLIKREIN AND USES THEREOF

(71) Applicant: Takeda Pharmaceutical Company Limited, Osaka (JP)

(72) Inventors: Nikolaos Papaioannou, Newton, MA (US); Sarah Jocelyn Fink, Arlington, MA (US); Thomas Allen Miller, Wakefield, MA (US); Gerald Wayne Shipps, Jr., Stoneham, MA (US); Jeremy Mark Travins, Southborough, MA (US); David Edward Ehmann, Lexington, MA (US); Alastair Rae, Saffron Walden (GB); John Mark Ellard, Buntingford (GB)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 16/908,497

(22) Filed: Jun. 22, 2020

(65) Prior Publication Data
US 2020/0317667 A1    Oct. 8, 2020

Related U.S. Application Data

(62) Division of application No. 16/299,996, filed on Mar. 12, 2019, now Pat. No. 10,730,874.

(60) Provisional application No. 62/757,728, filed on Nov. 8, 2018, provisional application No. 62/642,376, filed on Mar. 13, 2018.

(51) Int. Cl.
| C07D 471/04 | (2006.01) |
| C07D 519/00 | (2006.01) |
| A61P 9/00 | (2006.01) |
| A61P 29/00 | (2006.01) |

(52) U.S. Cl.
CPC .............. *C07D 471/04* (2013.01); *A61P 9/00* (2018.01); *A61P 29/00* (2018.01); *C07D 519/00* (2013.01)

(58) Field of Classification Search
CPC ....... C07D 471/04; C07D 519/00; A61P 9/00; A61P 29/00
See application file for complete search history.

(56) References Cited

U.S. PATENT DOCUMENTS

| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 7,166,596 B2 | 1/2007 | Yu et al. |
| 8,153,658 B2 | 4/2012 | Hachiya et al. |
| 10,259,803 B2 * | 4/2019 | McDonald ........... C07D 487/04 |
| 10,301,284 B2 | 5/2019 | McDonald et al. |
| 10,730,874 B2 * | 8/2020 | Papaioannou .......... A61P 29/00 |
| 2010/0039029 A1 | 2/2010 | Yang et al. |
| 2014/0213611 A1 | 7/2014 | Evans et al. |
| 2016/0106102 A1 | 4/2016 | Kuebbeler et al. |
| 2016/0168123 A1 | 6/2016 | Edwards et al. |
| 2016/0200704 A1 | 7/2016 | McDonald et al. |
| 2017/0029406 A1 | 2/2017 | McDonald et al. |
| 2017/0305863 A1 | 10/2017 | Evans et al. |
| 2018/0155348 A1 | 6/2018 | Li et al. |
| 2018/0319782 A1 | 11/2018 | Davie et al. |
| 2019/0127366 A1 | 5/2019 | McDonald et al. |
| 2019/0169162 A1 | 6/2019 | Beaton et al. |
| 2019/0284182 A1 | 9/2019 | Papaioannou et al. |
| 2020/0239463 A1 | 7/2020 | Travins et al. |
| 2021/0078999 A1 | 3/2021 | Papaioannou et al. |
| 2021/0079022 A1 | 3/2021 | Papaioannou et al. |

FOREIGN PATENT DOCUMENTS

| CN | 105777632 A | 7/2016 |
| EP | 1908471 A1 | 4/2008 |
| EP | 1908762 A2 | 4/2008 |
| JP | S62181284 A | 8/1987 |
| JP | 2000256286 A | 9/2000 |
| JP | 2012111731 A | 6/2012 |
| WO | WO-92/20350 A1 | 11/1992 |
| WO | WO-96/05309 A2 | 2/1996 |
| WO | WO-97/36876 A1 | 10/1997 |
| WO | WO-02/00651 A2 | 1/2002 |
| WO | WO-02/051831 A1 | 7/2002 |
| WO | WO-2005/005443 A1 | 1/2005 |
| WO | WO-2005/115382 A1 | 12/2005 |
| WO | WO-2006/091898 A2 | 8/2006 |
| WO | WO-2007/009236 A1 | 1/2007 |
| WO | WO-2007/128460 A1 | 11/2007 |
| WO | WO-2008/059854 A1 | 5/2008 |

(Continued)

OTHER PUBLICATIONS

Hampton, S. L. et al, KVD900 as a Single Dose, Rapid, Oral, Plasma Kallikrein Inhibitor for the On-Demand Treatment of Hereditary Angioedema Attacks: Pharmacokinetic and Pharmcodynamic results from a Phase 1 Single Ascending Dose Study, presented at AAAAI 2019, San Francisco, CA, Feb. 22-25, Poster (2019).
International Search Report for PCT/US2019/021897 (Substituted Imidazopyridines as Inhibitors of Plasma Kallikrein and Uses Thereof, filed Mar. 12, 2019), issued by ISA/EPO, 6 pages, (May 9, 2019).
Li, Z. et al., Diversity-oriented synthesis of β-lactams and γ-lactams by post-Ugi nucleophilic cyclization: Lewis acids as regioselective switch, European Journal of Organic Chemistry, 18: 3957-3962, (2015).

(Continued)

*Primary Examiner* — Tracy Vivlemore
*Assistant Examiner* — Ebenezer O Sackey
(74) *Attorney, Agent, or Firm* — Choate, Hall & Stewart LLP; John P. Rearick; Nicholas J. Pace

(57) ABSTRACT

The present invention provides compounds and compositions thereof which are useful as inhibitors of plasma kallikrein and which exhibit desirable characteristics for the same.

29 Claims, No Drawings

(56) References Cited

FOREIGN PATENT DOCUMENTS

| | | |
|---|---|---|
| WO | WO-2008/116665 A1 | 10/2008 |
| WO | WO-2008/154642 A2 | 12/2008 |
| WO | WO-2009/023179 A2 | 2/2009 |
| WO | WO-2010/065760 A1 | 6/2010 |
| WO | WO-2010/091409 A1 | 8/2010 |
| WO | WO-2010/124082 A1 | 10/2010 |
| WO | WO-2010/124086 A1 | 10/2010 |
| WO | WO-2010/124102 A1 | 10/2010 |
| WO | WO-2010/124108 A1 | 10/2010 |
| WO | WO-2010/124112 A1 | 10/2010 |
| WO | WO-2010/124114 A1 | 10/2010 |
| WO | WO-2010/124116 A1 | 10/2010 |
| WO | WO-2010/137738 A1 | 12/2010 |
| WO | WO-2011/135303 A2 | 11/2011 |
| WO | WO-2012/016133 A2 | 2/2012 |
| WO | WO-2012/051361 A1 | 4/2012 |
| WO | WO-2012/058645 A1 | 5/2012 |
| WO | WO-2012/082689 A1 | 6/2012 |
| WO | WO-2012/092471 A2 | 7/2012 |
| WO | WO-2012/116257 A1 | 8/2012 |
| WO | WO-2012/129562 A2 | 9/2012 |
| WO | WO-2012/139425 A1 | 10/2012 |
| WO | WO-2013/081094 A1 | 6/2013 |
| WO | WO-2013/101974 A1 | 7/2013 |
| WO | WO-2013/127269 A1 | 9/2013 |
| WO | WO-2014/187928 A1 | 11/2014 |
| WO | WO-2015/063093 A1 | 5/2015 |
| WO | WO-2015/095449 A1 | 6/2015 |
| WO | WO-2015/099196 A1 | 7/2015 |
| WO | WO-2015/103317 A1 | 7/2015 |
| WO | WO-2015/188051 A1 | 12/2015 |
| WO | WO-2016/011209 A1 | 1/2016 |
| WO | WO-2016/029146 A1 | 2/2016 |
| WO | WO-2016/083816 A1 | 6/2016 |
| WO | WO-2017/001924 A1 | 1/2017 |
| WO | WO-2017/001926 A2 | 1/2017 |
| WO | WO-2017/001936 A2 | 1/2017 |
| WO | WO-2017/161028 A1 | 9/2017 |
| WO | WO-2017/207983 A1 | 12/2017 |
| WO | WO-2017/207985 A1 | 12/2017 |
| WO | WO-2017/208005 A1 | 12/2017 |
| WO | WO-2018/011628 A1 | 1/2018 |
| WO | WO-2018/015818 A2 | 1/2018 |
| WO | WO-2018/141002 A2 | 8/2018 |
| WO | WO-2018/161033 A1 | 9/2018 |
| WO | WO-2018/229543 A2 | 12/2018 |
| WO | WO-2018/234808 A1 | 12/2018 |
| WO | WO-2019/028362 A1 | 2/2019 |
| WO | WO-2019/106375 A1 | 6/2019 |
| WO | WO-2019/106377 A1 | 6/2019 |
| WO | WO-2019/178129 A1 | 9/2019 |
| WO | WO-2021/055589 A1 | 3/2021 |
| WO | WO-2021/055621 A1 | 3/2021 |

OTHER PUBLICATIONS

Longhurst, H. et al, Oral Plasma Inhibitor BCX7353 is Safe and Effective as an On-Demand Treatment of Angioedema Attacks in Hereitary Angioedema (HAE) Patients: Results of the ZENITH-1 Trial, Presented at AAAAI 2019, San Francisco, CA, Feb. 22-25, Poster, (2019).

Nirogi, R. et al., Synthesis and SAR of Imidazo[1,5-a]pyridine derivatives as 5-HT4 receptor partial agonists for the treatment of cognitive disorders associated with Alzheimer's disease, European Journal of Medicinal Chemistry, 103: 289-301, (2015).

International Search Report for PCT/US2020/051249 filed Sep. 17, 2020, 5 pages, (dated Nov. 23, 2020).

International Search Report for PCT/US2020/051293, filed Sep. 17, 2020, 5 pages, (dated Nov. 10, 2020).

* cited by examiner

US 11,352,356 B2

INHIBITORS OF PLASMA KALLIKREIN AND USES THEREOF

I. BACKGROUND OF THE INVENTION

Plasma Kallikrein (pKal) is a serine protease zymogen in blood that is converted to its catalytically active form by coagulation factor XIIa, and contributes to the innate inflammatory response and intrinsic cascade of blood coagulation. The mechanisms that lead to the activation of this pathway in vivo include interactions with polyphosphates released from activated platelets and deficiency of C1 inhibitor (C1-INH), the primary physiological inhibitor of pKal. pKal-mediated cleavage of high-molecular weight kininogen generates the potent vasodilator and pro-inflammatory nonapeptide bradykinin (BK), which activates the bradykinin 2 receptor. Subsequent cleavage of BK by carboxypeptidases generates des-Arg9-BK, which activates the B1 receptor. Both B1 and B2 receptors are expressed by vascular, glial, and neuronal cell types, with the highest levels of retinal expression detected in the ganglion cell layer and inner and outer nuclear layers. Activation of B1 and B2 receptors causes vasodilation and increases vascular permeability.

pKal is also associated with a number of disorders, such as hereditary angioedema (HAE), an autosomal dominant disease characterized by painful, unpredictable, recurrent attacks of inflammation affecting the hands, feet, face, abdomen, urogenital tract, and the larynx. Prevalence for HAE is uncertain but is estimated to be approximately 1 case per 50,000 persons without known differences among ethnic groups. HAE is caused by deficient (Type I) or dysfunctional (Type II) levels of C1-INH, which inhibits pKal, bradykinin, and other serine proteases in the blood. Individuals with hereditary angioedema (HAE) are deficient in C1-INH and consequently undergo excessive bradykinin generation, which in turn cause painful, debilitating, and potentially fatal swelling attacks. If left untreated, HAE can result in a mortality rate as high as 40% primarily due to upper airway obstruction.

II. SUMMARY OF THE INVENTION

The present disclosure is based on, at least in part, the development of a number of compounds which bind to plasma kallikrein and effectively inhibit its activity. Accordingly, provided herein are compounds and uses thereof for targeting pKal and/or treating pKal-mediated diseases and disorders.

In some embodiments, the present invention provides a compound of Formula (I):

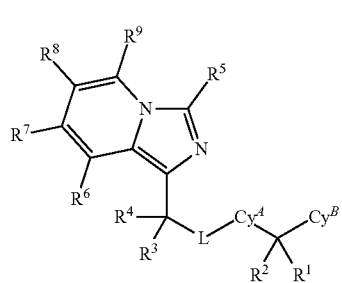

or a pharmaceutically acceptable salt thereof, wherein each of $Cy^A$, $Cy^B$, L, $R^2$, $R^3$, $R^4$, $R^5$, $R^6$, $R^7$, $R^8$, and $R^9$ is defined and described in classes and subclasses herein. In certain embodiments, the present invention provides compounds of Formulae (I)-(V), as defined and described in classes and subclasses herein.

In some embodiments, the present invention also provides methods of using compounds of Formulae (I)-(V).

III. DETAILED DESCRIPTION OF CERTAIN EMBODIMENTS

A. Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The abbreviations used herein have their conventional meaning within the chemical and biological arts. The chemical structures and formulae set forth herein are constructed according to the standard rules of chemical valency known in the chemical arts.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocyclyl," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocyclyl" or "cycloalkyl") refers to a monocyclic $C_3$-$C_7$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "halogen" means F, Cl, Br, or I.

The term "aryl" refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In some embodiments, an 8-10 membered bicyclic aryl group is an optionally substituted naphthyl ring. In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar–" refer to groups having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar–", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted.

As used herein, the terms "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in this context in reference to a ring atom, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein and unless otherwise specified, the suffix "-ene" is used to describe a bivalent group. Thus, any of the terms above can be modified with the suffix "-ene" to describe a bivalent version of that moiety. For example, a bivalent carbocycle is "carbocycylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", and so forth.

As described herein, compounds of the invention may, when specified, contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —$O(CH_2)_{0-4}R^\circ$, —$O(CH_2)_{0-4}C(O)OR^\circ$; —$O(CH_2)_{0-4}OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —$CH=CHPh$, which may be substituted with $R^\circ$; —$(CH_2)_{0-4}O(CH_2)_{0-1}$-pyridyl which may be substituted with $R^\circ$; —$NO_2$; —$CN$; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR^\circ$, —$SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$;

—(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6 membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12 membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^•$, -(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR$^•$, —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•_2$, —NO$_2$, —SiR$^•_3$, —OSiR$^•_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6 membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6 membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12 membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

In certain embodiments, the neutral forms of the compounds are regenerated by contacting the salt with a base or acid and isolating the parent compound in the conventional manner. In some embodiments, the parent form of the compound differs from the various salt forms in certain physical properties, such as solubility in polar solvents.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The term "oxo," as used herein, means an oxygen that is double bonded to a carbon atom, thereby forming a carbonyl.

The symbol "⤳", except when used as a bond to depict unknown or mixed stereochemistry, denotes the point of attachment of a chemical moiety to the remainder of a molecule or chemical formula.

The articles "a" and "an" are used herein to refer to one or to more than one (i.e., to at least one) of the grammatical object of the article. By way of example, "an element" means one element or more than one element.

A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses.

As will be understood from context, a "reference" sample or subject is one that is sufficiently similar to a particular sample or subject of interest to permit a relevant comparison. In some embodiments, information about a reference sample is obtained simultaneously with information about a particular sample. In some embodiments, information about a reference sample is historical. In some embodiments, information about a reference sample is stored, for example in a computer-readable medium. In some embodiments, comparison of a particular sample of interest with a reference sample establishes identity with, similarity to, or difference of the particular sample of interest relative to the reference.

As used herein, the term "sample" refers to a biological sample obtained or derived from a source of interest, as described herein. In some embodiments, a source of interest comprises an organism, such as an animal or human. In some embodiments, a biological sample comprises biological tissue or fluid. In some embodiments, a biological sample may be or comprise bone marrow; blood, e.g., whole blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from a subject. In some embodiments, obtained cells are or include cells from a subject from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood (e.g., whole blood), lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

As used herein, the phrase "therapeutic agent" refers to any agent that has a therapeutic effect and/or elicits a desired biological and/or pharmacological effect, when administered to a subject.

As used herein, the term "therapeutically effective amount" refers to an amount of a therapeutic agent that confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic agent effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular subject may depend upon a variety of factors including the disorder being treated and the severity of the disorder; the activity of the specific therapeutic agent employed; the specific composition employed; the age, body weight, general health, sex and diet of the subject; the time of administration, route of administration, and/or rate of excretion or metabolism of the specific therapeutic agent employed; the duration of the treatment; and like factors as is well known in the medical arts.

As used herein, the term "treatment" (also "treat" or "treating") refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

B. Compounds

In some embodiments, a provided compound is of Formula (I):

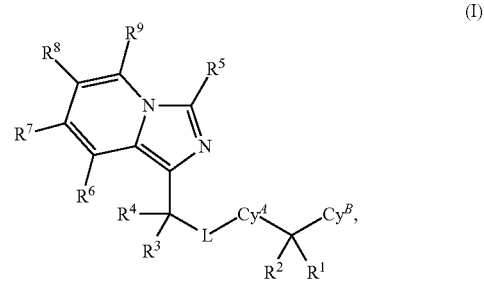

or a pharmaceutically acceptable salt thereof,
wherein:
$Cy^A$ is selected from 3- to 7-membered saturated or partially unsaturated monocyclic heterocyclylene having 1-2 heteroatoms selected from oxygen, nitrogen, or sulfur, 5- to 6-membered heteroarylene having 1-4 heteroatoms selected from oxygen, nitrogen, or sulfur, 7- to 10-membered saturated or partially unsaturated bicyclic heterocyclylene having 1-4 heteroatoms selected from oxygen, nitrogen, or sulfur, and 7- to 10-membered bicyclic heteroarylene having 1-4 heteroatoms selected from oxygen, nitrogen, or sulfur, wherein $Cy^A$ is substituted with 0-4 $R^A$ groups;
each $R^A$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
$Cy^B$ is selected from 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic heterocyclyl having 1-5 heteroatoms selected from oxygen, nitrogen, or sulfur, and 7- to 10-membered bicyclic heteroaryl having 1-5 heteroatoms selected from oxygen, nitrogen, or sulfur, wherein $Cy^B$ is substituted with 0-5 $R^B$ groups;
each $R^B$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
L is selected from -QC(R)$_2$—, —C(R)$_2$Q-, -QC(Q)-, —C(Q)Q-, —C(R)$_2$QC(O)—, and —C(O)QC(R)$_2$—, wherein each Q is independently a monovalent or divalent group as valency allows, selected from the group consisting of O, N(R), or (S);
$R^1$, $R^2$, $R^3$, and $R^4$ are independently selected from hydrogen and $C_{1-6}$ aliphatic;
$R^5$, $R^6$, $R^7$, $R^8$, and $R^9$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur; and each R is independently hydrogen, —CN, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur;
with the proviso that the compound is other than N-((7-chloroimidazo[1,5-a]pyridin-1-yl)methyl)-2-((3-chloroquinolin-6-yl)methyl)isonicotinamide.

In some embodiments, a provided compound, or a pharmaceutically acceptable salt thereof, has a structure of Formula (I), with the proviso that $Cy^A$ is a group other than pyridinediyl and the compound is other than N-((7-chloroimidazo[1,5-a]pyridin-1-yl)methyl)-2-((3-chloroquinolin-6-yl)methyl)isonicotinamide.

In some embodiments, $Cy^A$ is selected from 3- to 7-membered saturated or partially unsaturated monocyclic heterocyclylene having 1-2 heteroatoms selected from oxygen, nitrogen, or sulfur, 5- to 6-membered heteroarylene having 1-4 heteroatoms selected from oxygen, nitrogen, or sulfur, 7- to 10-membered saturated or partially unsaturated bicyclic heterocyclylene having 1-4 heteroatoms selected from oxygen, nitrogen, or sulfur, and 7- to 10-membered bicyclic heteroarylene having 1-4 heteroatoms selected from oxygen, nitrogen, or sulfur, wherein $Cy^A$ is substituted with 0-4 $R^A$ groups.

In some embodiments, $Cy^A$ is selected from 5- to 6-membered heteroarylene having 1-4 heteroatoms selected from oxygen, nitrogen, or sulfur, and 7- to 10-membered bicyclic heteroarylene having 1-4 heteroatoms selected from oxygen, nitrogen, or sulfur wherein $Cy^A$ is substituted with 0-4 $R^A$ groups.

In some embodiments, $Cy^A$ is a 5- to 6-membered heteroarylene having 1-4 heteroatoms selected from oxygen, nitrogen, or sulfur.

In some embodiments, $Cy^A$ is a 6-membered heteroarylene having 1-4 heteroatoms selected from oxygen, nitrogen, or sulfur, wherein $Cy^A$ is substituted with 0-3 $R^A$ groups. In some embodiments, $Cy^A$ is a 6-membered heteroarylene having 1 nitrogen, wherein $Cy^A$ is substituted with 0-3 $R^A$ groups. In some embodiments, $Cy^A$ is pyridinediyl. In some embodiments, $Cy^A$ is selected from either:

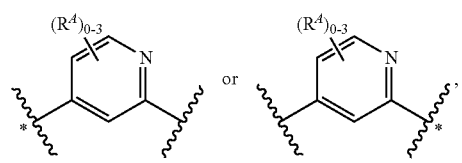

wherein * represents to point of attachment to L.
In some embodiments, $Cy^A$ is a 5-membered heteroarylene having 1-4 heteroatoms selected from oxygen, nitrogen, or sulfur, wherein $Cy^A$ is substituted with 0-2 $R^A$ groups. In some embodiments, $Cy^A$ is a pyrrolediyl substituted with 0-3 $R^A$ groups. In some embodiments, $Cy^A$ is a pyrazolediyl substituted with 0-2 $R^A$ groups. In some embodiments, $Cy^A$ is a triazolediyl substituted with 0-1 $R^A$ groups. In some embodiments, $Cy^A$ is a thiazolediyl substituted with 0-1 $R^A$ groups. In some embodiments, $Cy^A$ is an unsubstituted tetrazolediyl. In some embodiments, $Cy^A$ is an unsubstituted oxadiazolediyl. In some embodiments, $Cy^A$ is an unsubstituted thiadiazolediyl. In some embodiments, $Cy^A$ is an imidazolediyl substituted with 0-2 $R^A$ groups. In some embodiments, $Cy^A$ is a oxazolediyl substituted with 0-1 $R^A$ groups. In some embodiments, $Cy^A$ is a isoxazolediyl substituted with 0-1 $R^A$ groups.

In some embodiments, $Cy^A$ is a 7- to 10-membered bicyclic heteroarylene having 1-4 heteroatoms selected from oxygen, nitrogen, or sulfur wherein $Cy^A$ is substituted with 0-4 $R^A$ groups. In some embodiments, $Cy^A$ is a 9-membered bicyclic heteroarylene having 1-4 heteroatoms selected from oxygen, nitrogen, or sulfur wherein $Cy^A$ is substituted with 0-4 $R^A$ groups. In some embodiments, $Cy^A$ is a 9-membered bicyclic heteroarylene having 2 nitrogens wherein $Cy^A$ is substituted with 0-4 $R^A$ groups. In some embodiments, $Cy^A$ is a pyrrolopyridinediyl substituted with 0-4 $R^A$ groups.

In some embodiments, $Cy^A$ is selected from the group consisting of:

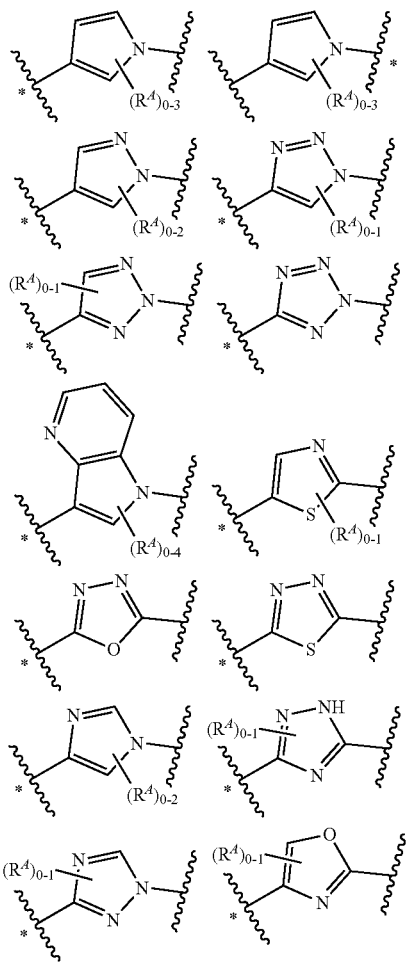

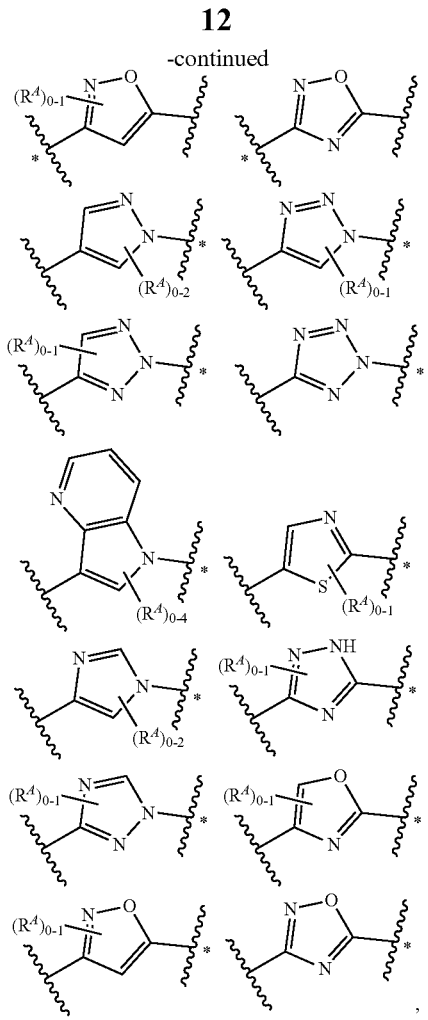

wherein * represents to point of attachment to L.

In some embodiments, each $R^A$ is independently selected from an optionally substituted group selected from $C_{1-6}$ aliphatic, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur.

In some embodiments, substituents on an optionally substituted $R^A$ group are independently halogen, $(CH_2)_{0-4}R^\circ$, $-(CH_2)_{0-4}OR^\circ$; and $-(CH_2)_{0-4}C(O)OR^\circ$, wherein each $R^\circ$ is independently hydrogen, $C_{1-6}$ aliphatic, or a 5-6 membered saturated, partially unsaturated, or aryl ring having 0-4 heteroatoms independently selected from nitrogen, oxygen, or sulfur.

In some embodiments, a single instance of $R^A$ is $C_{1-6}$ aliphatic substituted with halogen.

In some embodiments, a single instance of $R^A$ is $C_{1-6}$ aliphatic substituted with $-(CH_2)_{0-4}OR^\circ$, wherein $R^\circ$ is hydrogen or $C_{1-6}$ aliphatic.

In some embodiments, a single instance of $R^A$ is $C_{1-6}$ aliphatic substituted with $-(CH_2)_{0-4}C(O)OR^\circ$, wherein $R^\circ$ is hydrogen or $C_{1-6}$ aliphatic.

In some embodiments, a single instance of $R^A$ is $C_{1-6}$ aliphatic is substituted with 5-6 membered saturated, partially unsaturated, or aryl ring having 0-4 heteroatoms independently selected from nitrogen, oxygen, or sulfur.

In some embodiments, a single instance of $R^A$ is optionally substituted 3- to 7-membered saturated or partially unsaturated monocyclic carbocyclyl. In some embodiments, a single instance of $R^A$ is optionally substituted cyclopropyl. In some embodiments, a single instance of $R^A$ is cyclopropyl substituted with —$(CH_2)_{0-4}C(O)OR°$ and $R°$ is hydrogen or $C_{1-6}$ aliphatic.

In some embodiments, $Cy^B$ is selected from phenyl, 7- to 10-membered saturated or partially unsaturated bicyclic heterocyclyl having 1-5 heteroatoms selected from oxygen, nitrogen, or sulfur, and 7- to 10-membered bicyclic heteroaryl having 1-5 heteroatoms selected from oxygen, nitrogen, or sulfur, wherein $Cy^B$ is substituted with 0-5 $R^B$ groups. In some embodiments, $Cy^B$ is selected from phenyl and 7- to 10-membered bicyclic heteroaryl having 1-5 heteroatoms selected from oxygen, nitrogen, or sulfur, wherein $Cy^B$ is substituted with 0-5 $R^B$ groups.

In some embodiments, $Cy^B$ is a 7- to 10-membered bicyclic heteroaryl having 1-5 heteroatoms selected from oxygen, nitrogen, or sulfur, wherein $Cy^B$ is substituted with 0-5 $R^B$ groups.

In some embodiments, $Cy^B$ is a 9-membered bicyclic heteroaryl having 1-5 heteroatoms selected from oxygen, nitrogen, or sulfur, wherein $Cy^B$ is substituted with 0-5 $R^B$ groups. In some embodiments, $Cy^B$ is a 9-membered bicyclic heteroaryl having 2-3 nitrogens, wherein $Cy^B$ is substituted with 0-5 $R^B$ groups. In some embodiments, $Cy^B$ is an imidazopyridinyl group substituted with 0-5 $R^B$ groups. In some embodiments, $Cy^B$ is a pyrazolopyridinyl group substituted with 0-5 $R^B$ groups. In some embodiments, $Cy^B$ is a pyrrolopyridinyl group substituted with 0-4 $R^B$ groups. In some embodiments, $Cy^B$ triazolopyridinyl group substituted with 0-4 $R^B$ groups. In some embodiments, $Cy^B$ is a imidazopyrimidinyl group substituted with 0-4 $R^B$ groups. In some embodiments, $Cy^B$ is a imidazopyridazinyl group substituted with 0-4 $R^B$ groups. In some embodiments, $Cy^B$ is a indolizinyl group substituted with 0-5 $R^B$ groups. In some embodiments, $Cy^B$ is pyrazolopyrimidinyl group substituted with 0-4 $R^B$ groups.

In some embodiments, $Cy^B$ is a indolyl group substituted with 0-5 $R^B$ groups. In some embodiments, $Cy^B$ is a benzofuranyl group substituted with 0-5 $R^B$ groups. In some embodiments, $Cy^B$ is a pyrazolopyrimidinyl group substituted with 0-4 $R^B$ groups. In some embodiments, $Cy^B$ is a benzimidazolyl group substituted with 0-4 $R^B$ groups. In some embodiments, $Cy^B$ is a thienopyridinyl group substituted with 0-4 $R^B$ groups.

In some embodiments, $Cy^B$ is selected from the group consisting of:

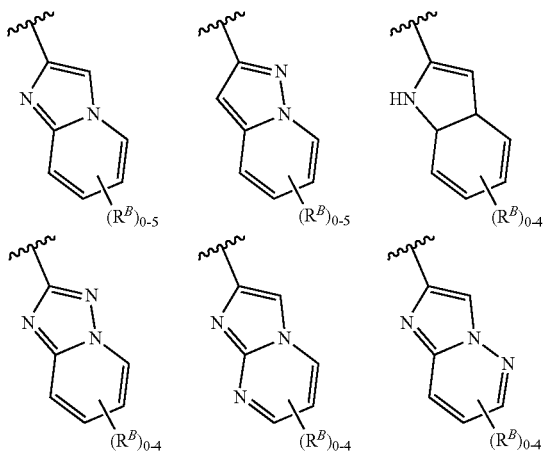

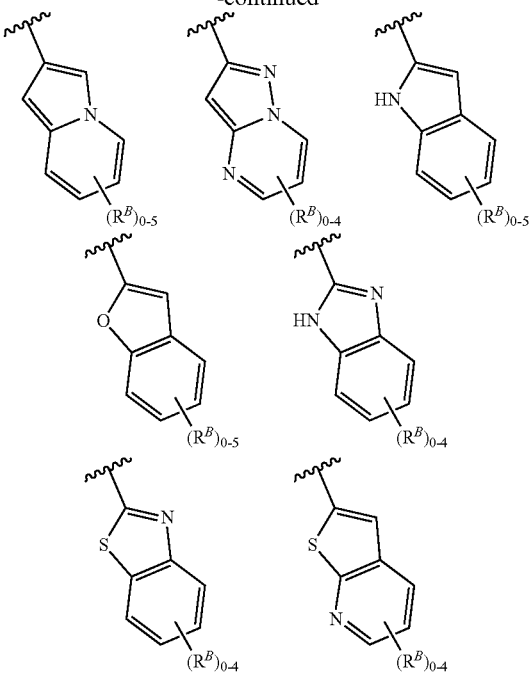

In some embodiments, $Cy^B$ is a 10-membered bicyclic heteroaryl having 1-5 heteroatoms selected from oxygen, nitrogen, or sulfur, wherein $Cy^B$ is substituted with 0-5 $R^B$ groups. In some embodiments, $Cy^B$ is a 10-membered bicyclic heteroaryl having 1 nitrogen, wherein $Cy^B$ is substituted with 0-5 $R^B$ groups. In some embodiments, $Cy^B$ is a quinolonyl group substituted with 0-5 $R^B$ groups. In some embodiments, $Cy^B$ is a quinoxalinyl group substituted with 0-5 $R^B$ groups. In some embodiments, $Cy^B$ is selected from the group consisting of:

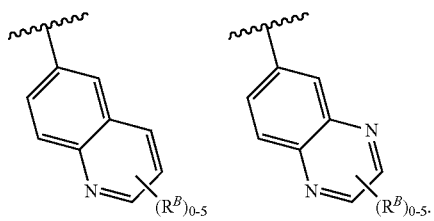

In some embodiments, each $R^B$ is independently selected from halogen, —CN, —C(O)R, —C(O)$_2$R, —N(R)$_2$, —OR, or an optionally substituted group selected from $C_{1-6}$ aliphatic, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur, wherein each R is independently hydrogen or $C_{1-6}$ aliphatic.

In some embodiments, substituents on an optionally substituted $R^B$ group are independently selected from halogen, —$(CH_2)_{0-4}OR°$, —$O(CH_2)_{0-4}OR°$, —$(CH_2)_{0-4}C(O)OR°$, and —$(CH_2)_{0-4}N(R°)_2$ wherein each $R°$ is independently hydrogen, $C_1$, aliphatic, or two independent occurrences of $R°$, taken together with their intervening atom(s), form an optionally substituted 3-12 membered saturated, partially unsaturated, or aryl mono- or bicyclic ring having 0-4 heteroatoms independently selected from nitrogen, oxygen, or sulfur, which may be further substituted.

In some embodiments, a single instance of $R^B$ is halogen. In some embodiments, a single instance of $R^B$ is —CN. In some embodiments, a single instance of $R^B$ is —C(O)R, wherein R hydrogen or $C_{1-6}$ aliphatic. In some embodiments, a single instance of $R^B$ is —C(O)$_2$R, wherein R hydrogen or $C_{1-6}$ aliphatic. In some embodiments, a single instance of $R^B$ is —N(R)$_2$, wherein R hydrogen or $C_{1-6}$ aliphatic. In some embodiments, a single instance of $R^B$ is —OR, wherein R hydrogen or $C_{1-6}$ aliphatic.

In some embodiments, a single instance of $R^B$ is $C_{1-6}$ aliphatic substituted with —(CH$_2$)$_{0-4}$OR°, wherein R° is hydrogen or $C_{1-6}$ aliphatic.

In some embodiments, a single instance of $R^B$ is $C_{1-6}$ aliphatic substituted with —O(CH$_2$)$_{0-4}$OR°, wherein R° is hydrogen or $C_{1-6}$ aliphatic.

In some embodiments, a single instance of $R^B$ is $C_{1-6}$ aliphatic substituted with —(CH$_2$)$_{0-4}$C(O)OR°, wherein R° is hydrogen or $C_{1-6}$ aliphatic.

In some embodiments, a single instance of $R^B$ is optionally substituted 3- to 7-membered saturated or partially unsaturated monocyclic carbocyclyl. In some embodiments, a single instance of $R^B$ is optionally substituted cyclopropyl. In some embodiments, a single instance of $R^B$ is cyclopropyl is substituted with —(CH$_2$)$_{0-4}$OR° and R° is hydrogen or $C_{1-6}$ aliphatic. In some embodiments, a single instance of $R^B$ is cyclopropyl is substituted with —(CH$_2$)$_{0-4}$C(O)OR° and R° is hydrogen or $C_{1-6}$ aliphatic.

In some embodiments, a single instance of $R^B$ is optionally substituted 3- to 7-membered saturated or partially unsaturated monocyclic heterocyclyl having 1-2 heteroatoms selected from oxygen, nitrogen, or sulfur. In some embodiments, a single instance of $R^B$ is optionally substituted 4-membered saturated monocyclic heterocyclyl having 1 oxygen. In some embodiments, a single instance of $R^B$ is 4-membered saturated monocyclic heterocyclyl having 1 oxygen, and substituted with —(CH$_2$)$_{0-4}$OR°, wherein R° is hydrogen or $C_{1-6}$ aliphatic.

In some embodiments, a single instance of $R^B$ is $C_{1-6}$ aliphatic is substituted with —(CH$_2$)$_{0-4}$N(R°)$_2$, wherein two independent occurrences of R°, taken together with their intervening atom(s), form an optionally substituted 3-12 membered saturated, partially unsaturated, or aryl mono- or bicyclic ring having 0-4 heteroatoms independently selected from nitrogen, oxygen, or sulfur, which may be further substituted. In some embodiments, a single instance of $R^B$ is $C_{1-6}$ aliphatic substituted with —(CH$_2$)$_{0-4}$N(R°)$_2$, wherein two independent occurrences of R°, taken together with their intervening atom(s), form an optionally substituted 5-membered saturated monocyclic ring further substituted with =O.

In some embodiments, L is selected from -QC(R)$_2$—, —C(R)$_2$Q-, —C(Q)Q-, or —C(R)$_2$QC(O)—, wherein Q is independently a monovalent or divalent group as valency allows, selected from O, N(R), or (S). In some embodiments, L is selected from -QC(R)$_2$—, —C(R)$_2$Q-, —C(Q)Q-, or —C(R)$_2$QC(O)—, wherein Q is independently a monovalent or divalent group as valency allows, selected from O or N(R). In some embodiments, L is selected from the group consisting of:

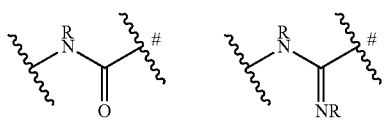

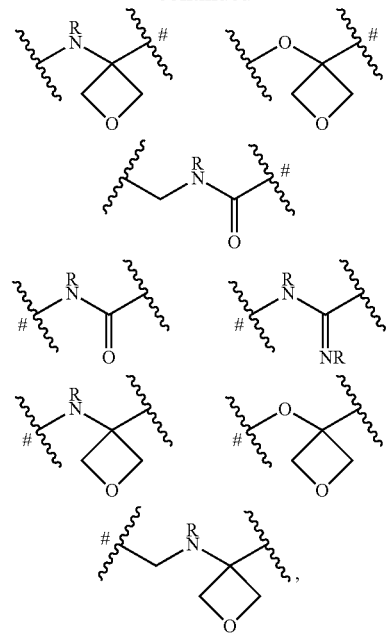

wherein # represents to point of attachment to $Cy^A$.

In some embodiments, L is —N(H)C(O)—. In some embodiments, L is —C(O)N(H)—.

In some embodiments, $R^5$, $R^6$, $R^7$, $R^8$, and $R^9$ are independently selected from hydrogen, halogen, —CN, —N(R)$_2$, —OR, or an optionally substituted group selected from $C_{1-6}$ aliphatic, 3- to 7-membered saturated or partially unsaturated monocyclic carbocyclyl, wherein each R is independently hydrogen or $C_{1-6}$ aliphatic. In some embodiments, $R^5$, $R^8$, and $R^9$ are hydrogen.

In some embodiments, $R^6$ is selected from hydrogen or halogen. In some embodiments, $R^6$ is hydrogen. In some embodiments $R^6$ is halogen. In some embodiments $R^6$ is F. In some embodiments $R^6$ is Cl. In some embodiments $R^6$ is Br. In some embodiments $R^6$ is I.

In some embodiments, $R^7$ is selected from halogen or an optionally substituted $C_{1-6}$ aliphatic. In some embodiments $R^7$ is halogen. In some embodiments $R^7$ is F. In some embodiments $R^7$ is Cl. In some embodiments $R^7$ is Br. In some embodiments $R^7$ is I. In some embodiments, $R^7$ is optionally substituted $C_{1-6}$ aliphatic. In some embodiments, $R^7$ is optionally substituted $C_{1-5}$ aliphatic. In some embodiments, $R^7$ is optionally substituted $C_{1-4}$ aliphatic. In some embodiments, $R^7$ is optionally substituted $C_{1-3}$ aliphatic. In some embodiments, $R^7$ is optionally substituted $C_{1-2}$ aliphatic. In some embodiments, $R^7$ is alkynyl.

In some embodiments, a provided compound is of Formula (II):

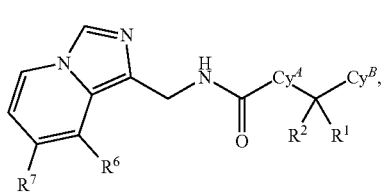

or a pharmaceutically acceptable salt thereof, wherein each of $Cy^A$, $Cy^B$, $R^1$, $R^2$, $R^6$, and $R^7$ is defined and described in classes and subclasses herein;

with the proviso that the compound is other than N-((7-chloroimidazo[1,5-a]pyridin-1-yl)methyl)-2-((3-chloroquinolin-6-yl)methyl)isonicotinamide.

It will be understood that, unless otherwise specified or prohibited by the foregoing definition of Formula (II), embodiments of variables $Cy^A$, $Cy^B$, $R^1$, $R^2$, $R^6$, and $R^7$ as defined above and described in classes and subclasses herein, also apply to compounds of Formula (II), both singly and in combination.

In some embodiments, a provided compound, or a pharmaceutically acceptable salt thereof, has a structure of Formula (II), with the proviso that $Cy^A$ is a group other than pyridinediyl and the compound is other than N-((7-chloro-imidazo[1,5-a]pyridin-1-yl)methyl)-2-((3-chloroquinolin-6 yl)methyl)isonicotinamide.

In some embodiments, a provided compound, or a pharmaceutically acceptable salt thereof, has a structure of Formula (III-a), Formula (III-b), Formula (III-c), Formula (III-d),

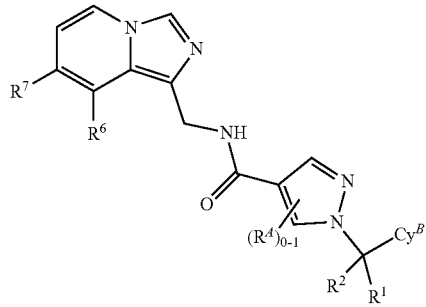

(III-a)

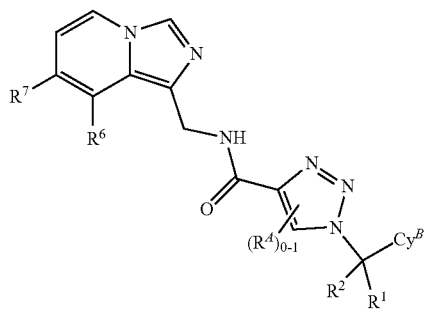

(III-b)

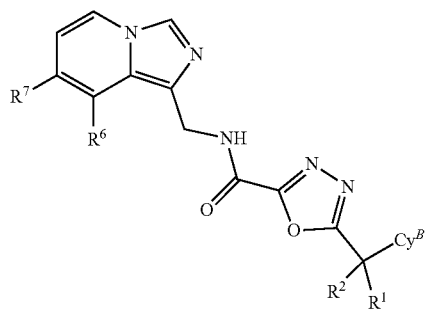

(III-c)

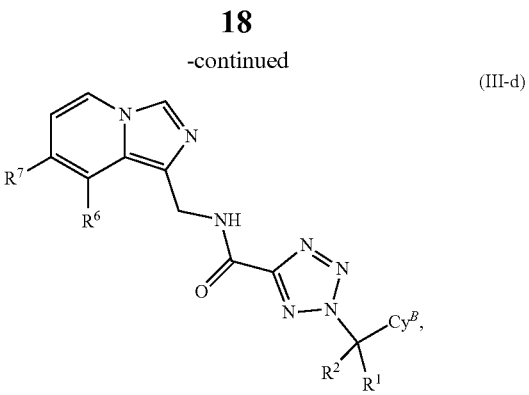

(III-d)

wherein each of $R^A$, $Cy^B$, $R^1$, $R^2$, $R^6$, and $R^7$ is defined and described in classes and subclasses herein.

It will be understood that, unless otherwise specified or prohibited by the foregoing definition of Formula (III), embodiments of variables $R^A$, $Cy^B$, $R^1$, $R^2$, $R^6$, and $R^7$ as defined above and described in classes and subclasses herein, also apply to compounds of Formula (III-a), Formula (III-b), Formula (III-c), and Formula (III-d) both singly and in combination.

In some embodiments of Formulae (I), (II), (III-a), (III-b), (III-c), and (III-d), $Cy^B$ is

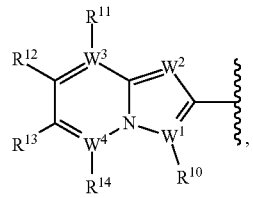

wherein:
$W^1$, $W^2$, $W^3$, and $W^4$ are independently selected from carbon and nitrogen;
$R^{10}$, $R^{11}$, $R^{12}$, $R^{13}$, and $R^{14}$ are each optionally present when attached to a carbon atom, and if present correspond to an occurrence of $R^B$ independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur; and
each R is independently hydrogen, —CN, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur.

In some embodiments, $W^1$ is nitrogen and $W^2$, $W^3$ and $W^4$ are carbon. In some embodiments, $W^2$ is nitrogen and $W^1$, $W^3$ and $W^4$ are carbon. In some embodiments, $W^2$ and $W^3$ are nitrogen and $W^1$ and $W^4$ are carbon. In some embodiments, $W^2$ and $W^4$ are nitrogen and $W^1$ and $W^3$ are carbon.

In some embodiments of Formulae (I), (II), (III-a), (III-b), (III-c), and (III-d), $Cy^B$ is

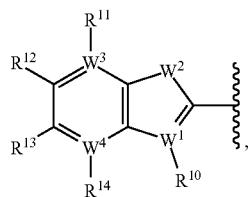

wherein:

$W^2$ is selected from carbon, nitrogen, oxygen, and sulfur;

$W^1$, $W^3$, and $W^4$ are independently selected from carbon and nitrogen;

$R^{10}$, $R^{11}$, $R^{12}$, $R^{13}$, and $R^{14}$ are each optionally present when attached to a carbon atom, and if present correspond to an occurrence of $R^B$ independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur; and each R is independently hydrogen, —CN, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur.

In some embodiments, a provided compound is of Formula (IV):

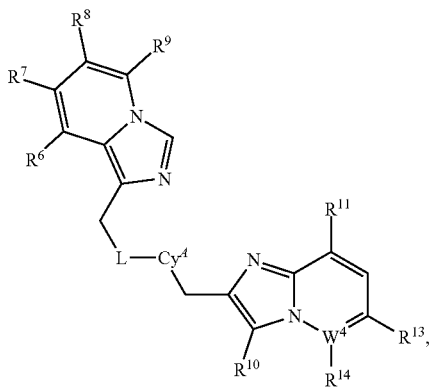

or a pharmaceutically acceptable salt thereof, wherein:

$Cy^A$ is a 5-membered heteroarylene having 1-4 heteroatoms selected from oxygen or nitrogen, wherein $Cy^A$ is substituted with 0-3 $R^A$ groups;

each $R^A$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

L is selected from —NC(O)— and —C(O)N—;

$R^6$, R, and $R^9$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

$R^7$ is —F, —Cl, or —Br;

$W^4$ is carbon or nitrogen;

$R^{10}$ and $R^{11}$ are each optionally present, and if present are independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

$R^{13}$ is selected from halogen, —CN, —C(R)=N(R), —C(O)R, —C(O)$_2$R, —C(O)N(R)$_2$, —NO$_2$, —N(R)—N (R)₂, —N(R)₂, —N(R)C(O)R, —N(R)C(O)₂R, —N(R)C(O)N(R)₂, —N(R)S(O)₂R, —OR, —OC(O)R, —OC(O)N(R)₂, —SR, —S(O)R, —S(O)₂R, —S(O)N(R)₂, —S(O)₂N(R)₂, or an optionally substituted group selected from $C_{2-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

$R^{14}$ is optionally present, and if present and is selected from halogen, —CN, —C(R)═N(R), —C(O)R, —C(O)₂R, —C(O)N(R)₂, —NO₂, —N(R)—N(R)₂, —N(R)C(O)R, —N(R)C(O)₂R, —N(R)C(O)N(R)₂, —N(R)S(O)₂R, —OC(O)R, —OC(O)N(R)₂, —SR, —S(O)R, —S(O)₂R, —S(O)N(R)₂, —S(O)₂N(R)₂, or an optionally substituted group selected from $C_{3-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur; and each R is independently hydrogen, —CN, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur.

In some embodiments, $Cy^4$ is a 5-membered heteroarylene having 1-4 heteroatoms selected from oxygen or nitrogen. In some embodiments, $Cy^4$ is a 5-membered heteroarylene having 1-4 nitrogens. In some embodiments, $Cy^4$ is a 5-membered heteroarylene having 1-4 nitrogens, wherein when $Cy^4$ comprises 3 nitrogens, it is not a a 1,2,4-triazolediyl. In some embodiments, $Cy^4$ is a 5-membered heteroarylene having 1-3 nitrogens. In some embodiments, $Cy^4$ is a 5-membered heteroarylene having 1-2 nitrogens. In some embodiments, $Cy^4$ is a 5-membered heteroarylene having 1 nitrogen. In some embodiments, $Cy^4$ is a 5-membered heteroarylene having 2 nitrogens. In some embodiments, $Cy^4$ is a 5-membered heteroarylene having 3 nitrogens. In some embodiments, $Cy^4$ is a 5-membered heteroarylene having 4 nitrogens.

In some embodiments, $Cy^4$ is selected from the group consisting of:

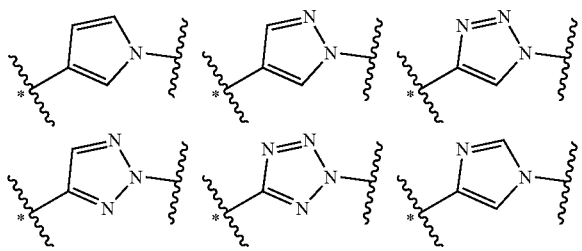

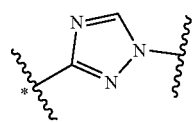

wherein * represents to point of attachment to L.

In some embodiments, $W^4$ is carbon. In some embodiments $W^4$ is nitrogen.

In some embodiments, $R^{11}$ is optionally present, and if present is independently selected from halogen, —CN, —C(R)═N(R), —C(O)R, —C(O)N(R)₂, —NO₂, —N(R)—N(R)₂, —N(R)₂, —N(R)C(O)R, —N(R)C(O)₂R, —N(R)C(O)N(R)₂, —N(R)S(O)₂R, —OR, —OC(O)R, —OC(O)N(R)₂, —SR, —S(O)R, —S(O)₂R, —S(O)N(R)₂, —S(O)₂N(R)₂, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur.

In some embodiments, $R^{13}$ is selected from —CN, —C(R)═N(R), —C(O)R, —C(O)₂R, —C(O)N(R)₂, —NO₂, —N(R)—N(R)₂, —N(R)₂, —N(R)C(O)R, —N(R)C(O)₂R, —N(R)C(O)N(R)₂, —N(R)S(O)₂R, —OR, —OC(O)R, —OC(O)N(R)₂, —SR, —S(O)R, —S(O)₂R, —S(O)N(R)₂, —S(O)₂N(R)₂, or an optionally substituted group selected from phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur.

In some embodiments, $R^{11}$ is selected from halogen, optionally substituted $C_{1-6}$ aliphatic, and optionally substituted 3- to 7-membered saturated or partially unsaturated monocyclic carbocyclyl.

In some embodiments, $R^{11}$ is halogen. In some embodiments, $R^{11}$ is —F. In some embodiments, $R^{11}$ is —Cl. In some embodiments, $R^{11}$ is —Br. In some embodiments, $R^{11}$ is —I.

In some embodiments, $R^{11}$ is optionally substituted $C_{1-6}$ aliphatic. In some embodiments, $R^{11}$ is optionally substituted $C_{1-5}$ aliphatic. In some embodiments, $R^{11}$ is optionally substituted $C_{1-4}$ aliphatic. In some embodiments, $R^{11}$ is optionally substituted $C_{1-3}$ aliphatic. In some embodiments, $R^{11}$ is optionally substituted $C_{1-2}$ aliphatic.

In some embodiments, $R^{11}$ is an optionally substituted 3- to 7-membered saturated or partially unsaturated monocyclic carbocyclyl. In some embodiments, $R^{11}$ is an optionally substituted 3- or 5-7-membered saturated or partially unsaturated monocyclic carbocyclyl. In some embodiments, $R^{11}$ is an optionally substituted 7-membered saturated or partially unsaturated monocyclic carbocyclyl. In some embodiments, $R^{11}$ is an optionally substituted 6-membered saturated or partially unsaturated monocyclic carbocyclyl. In some embodiments, $R^{13}$ is an optionally substituted 5-membered saturated or partially unsaturated monocyclic carbocyclyl. In some embodiments, $R^{11}$ is an optionally substituted 4-membered saturated or partially unsaturated monocyclic carbocyclyl. In some embodiments, $R^{11}$ is an optionally substituted 3-membered saturated or partially unsaturated monocyclic carbocyclyl. In some embodiments, $R^{11}$ is an optionally substituted cyclopropyl.

In some embodiments, a provided compound is of Formula (V):

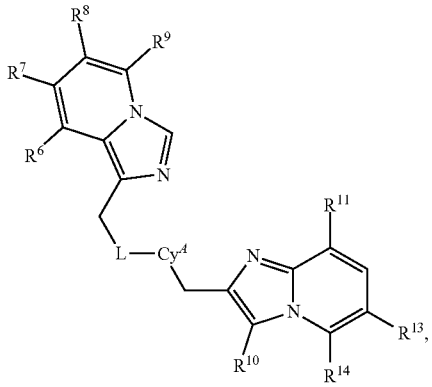

or a pharmaceutically acceptable salt thereof,
wherein:
$Cy^4$ is a 5-membered heteroarylene having 1-4 nitrogens, wherein when $Cy^4$ comprises 3 nitrogens, it is not

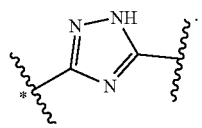 [SMILES: *c1n[nH]c(*)n1]

L is selected from —NC(O)— and —C(O)N—;
$R^6$, R, and $R^9$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
$R^7$ is —F, —Cl, or —Br;
$R^{10}$ is optionally present, and if present is selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
$R^{11}$ is optionally present, and if present is selected from halogen, —CN, —C(R)=N(R), —C(O)R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
$R^{13}$ is selected from —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from phenyl, 5- to 6-membered heteroaryl having 1-4 heteroatoms selected from oxygen, nitrogen, or sulfur, 3- or 5-7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
$R^{14}$ is optionally present, and if present and is selected from halogen, —CN, —C(R)=N(R), —C(O)R, —C(O)$_2$R, —C(O)N(R)$_2$, —NO$_2$, —N(R)—N(R)$_2$, —N(R)C(O)R, —N(R)C(O)$_2$R, —N(R)C(O)N(R)$_2$, —N(R)S(O)$_2$R, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{3-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur; and
each R is independently hydrogen, —CN, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur.

In some embodiments, a provided compound is selected from the group consisting of N-((7-chloroimidazo[1,5-a]pyridin-1-yl)methyl)-1-((3-chloroquinolin-6-yl)methyl)-1H-pyrazole-4-carboxamide, N-((7-chloroimidazo[1,5-a]pyridin-1-yl)methyl)-1-((6-cyclopropylimidazo[1,2-a]pyridin-2-yl)methyl)-1H-pyrazole-4-carboxamide, N-((7-chloroimidazo[1,5-a]pyridin-1-yl)methyl)-2-((3-chloroquinolin-6-yl)methyl)isonicotinamide, 1-((6-cyclopropylimidazo[1,2-a]pyridin-2-yl)methyl)-N-((7-methylimidazo[1,5-a]pyridin-1-yl)methyl)-1H-pyrazole-4-carboxamide, N-((7-bromoimidazo[1,5-a]pyridin-1-yl)methyl)-1-((6-cyclopropylimidazo[1,2-a]pyridin-2-yl)methyl)-1H-pyrazole-4-carboxamide, N-((7-chloroimidazo[1,5-a]pyridin-1-yl)methyl)-1-((6-cyclopropyl-[1,2,4]triazolo[1,5-a]pyridin-2-yl)methyl)-1H-pyrazole-4-carboxamide, 1-((6-chloro-5-methylimidazo[1,2-a]pyridin-2-yl)methyl)-N-((7-chloroimidazo[1,5-a]pyridin-1-yl)methyl)-1H-pyrazole-4-carboxamide, N-((7-chloroimidazo[1,5-a]pyridin-1-yl)methyl)-1-((6-isopropylimidazo[1,2-a]pyridin-2-yl)methyl)-1H-pyrazole-4-carboxamide, N-((7- chloroimidazo[1,5-a]pyridin-1-yl)methyl)-1-((5-methylimidazo[1,2-a]pyridin-2-yl)methyl)-1H-pyrazole-4-carboxamide, N-((7-chloroimidazo[1,5-a]pyridin-1-yl)methyl)-1-((6-(1-methylcyclopropyl)imidazo[1,2-a]pyridin-2-yl)methyl)-1H-pyrazole-4-carboxamide, N-((7-chloroimidazo[1,5-a]pyridin-1-yl)methyl)-1-((6-cyclopropylimidazo[1,2-b]pyridazin-2-yl)methyl)-1H-pyrazole-4-carboxamide, 1-((7-cyclopropylimidazo[1,2-a]pyridin-2-yl)methyl)-N-((6-methoxyimidazo[1,2-a]pyridin-2-yl)methyl)-1H-pyrazole-4-carboxamide, N-((7-chloroimidazo[1,5-a]pyridin-1-yl)methyl)-1-((6-cyclopropyl-5-methylimidazo[1,2-a]pyridin-2-yl)methyl)-1H-pyrazole-4-carboxamide, N-((7-bromoimidazo[1,5-a]pyridin-1-yl)methyl)-1-((6-cyclopropyl-5-methylimidazo[1,2-a]pyridin-2-yl)methyl)-1H-pyrazole-4-carboxamide, N-((7-chloroimidazo[1,5-a]pyridin-1-yl)methyl)-1-((6-cyclopropylimidazo[1,2-b]pyridazin-2-yl)methyl)-1H-pyrazole-4-carboxamide, N-((7-chloroimidazo[1,5-a]pyridin-1-yl)methyl)-1-((6-cyclopropyl-7-methylimidazo[1,2-a]pyridin-2-yl)methyl)-1H-pyrazole-4-carboxamide, N-((7-bromoimidazo[1,5-a]pyridin-1-yl)methyl)-1-((6-cyclopropyl-7-methylimidazo[1,2-a]pyridin-2-yl)methyl)-1H-pyrazole-4-carboxamide, N-((7-chloroimidazo[1,5-a]pyridin-1-yl)methyl)-1-((6-(trifluoromethyl)imidazo[1,2-a]pyridin-2-yl)methyl)-1H-pyrazole-4-carboxamide, N-((7-bromoimidazo[1,5-a]pyridin-1-yl)methyl)-1-((6-(trifluoromethyl)imidazo[1,2-a]pyridin-2-yl)methyl)-1H-pyrazole-4-carboxamide, N-((7-bromoimidazo[1,5-a]pyridin-1-yl)methyl)-1-((6-cyclopropyl-7-fluoroimidazo[1,2-a]pyridin-2-yl)methyl)-1H-pyrazole-4-carboxamide, N-((7-chloroimidazo[1,5-a]pyridin-1-yl)methyl)-1-((6-cyclopropyl-7-fluoroimidazo[1,2-a]pyridin-2-yl)methyl)-1H-pyrazole-4-carboxamide, N-((7-chloroimidazo[1,5-a]pyridin-1-yl)methyl)-1-((5-cyclopropylimidazo[1,2-a]pyridin-2-yl)methyl)-1H-pyrazole-4-carboxamide, 1-((5-chloro-6-cyclopropylimidazo[1,2-a]pyridin-2-yl)methyl)-N-((7-chloroimidazo[1,5-a]pyridin-1-yl)methyl)-1H-pyrazole-4-carboxamide, 1-((7-chloro-6-cyclopropylimidazo[1,2-a]pyridin-2-yl)methyl)-N-((7-chloroimidazo[1,5-a]pyridin-1-yl)methyl)-1H-pyrazole-4-carboxamide, N-((7-bromoimidazo[1,5-a]pyridin-1-yl)methyl)-1-((7-chloro-6-cyclopropylimidazo[1,2-a]pyridin-2-yl)methyl)-1H-pyrazole-4-carboxamide, N-((7-bromoimidazo[1,5-a]pyridin-1-yl)methyl)-1-((5,6-dimethylimidazo[1,2-a]pyridin-2-yl)methyl)-1H-pyrazole-4-carboxamide, 1-((5-bromoimidazo[1,2-a]pyridin-2-yl)methyl)-N-((7-chloroimidazo[1,5-a]pyridin-1-yl)methyl)-1H-pyrazole-4-carboxamide, 1-((6-bromo-7-methylimidazo[1,2-a]pyridin-2-yl)methyl)-N-((7-chloroimidazo[1,5-a]pyridin-1-yl)methyl)-1H-pyrazole-4-carboxamide, N-((7-chloroimidazo[1,5-a]pyridin-1-yl)methyl)-1-((6-cyclopropylimidazo[1,2-a]pyridin-2-yl)methyl)-1H-pyrrolo[3,2-b]pyridine-3-carboxamide, N-((7-bromoimidazo[1,5-a]pyridin-1-yl)methyl)-1-((6-cyclopropylimidazo[1,2-a]pyridin-2-yl)methyl)-1H-pyrrolo[3,2-b]pyridine-3-carboxamide, N-((7-chloroimidazo[1,5-a]pyridin-1-yl)methyl)-1-((6-cyclopropylimidazo[1,2-a]pyridin-2-yl)methyl)-3-(methoxymethyl)-1H-pyrazole-4-carboxamide, N-((7-chloroimidazo[1,5-a]pyridin-1-yl)methyl)-1-((6-cyclopropylimidazo[1,2-a]pyridin-2-yl)methyl)-5-(methoxymethyl)-1H-pyrazole-4-carboxamide, N-((7,8-dichloroimidazo[1,5-a]pyridin-1-yl)methyl)-1-((6-methylimidazo[1,2-a]pyridin-2-yl)methyl)-1H-pyrazole-4-carboxamide, 1-((6-chloro-5-ethylimidazo[1,2-a]pyridin-2-yl)methyl)-N-((7-chloroimidazo[1,5-a]pyridin-1-yl)methyl)-1H-pyrazole-4-carboxamide, N-((7-chloro-8-methylimidazo[1,5-a]pyridin-1-yl)methyl)-1-((6-methylimidazo[1,2-a]pyridin-2-yl)methyl)-1H-pyrazole-4-carboxamide, 1-((6-bromo-7-chloroimidazo[1,2-a]pyridin-2-yl)methyl)-N-((7-chloroimidazo[1,5-a]pyridin-1-yl)methyl)-1H-pyrazole-4-carboxamide, 1-((6-bromo-7-chloroimidazo[1,2-a]pyridin-2-yl)methyl)-N-((7-bromoimidazo[1,5-a]pyridin-1-yl)methyl)-1H-pyrazole-4-carboxamide, N-((7-chloroimidazo[1,5-a]pyridin-1-yl)methyl)-2-((6-cyclopropylimidazo[1,2-a]pyridin-2-yl)methyl)thiazole-5-carboxamide, 1-((6-bromo-5-chloroimidazo[1,2-a]pyridin-2-yl)methyl)-N-((7-chloroimidazo[1,5-a]pyridin-1-yl)methyl)-1H-pyrazole-4-carboxamide, 1-((6-bromo-5-chloroimidazo[1,2-a]pyridin-2-yl)methyl)-N-((7-bromoimidazo[1,5-a]pyridin-1-yl)methyl)-1H-pyrazole-4-carboxamide, N-((7-chloroimidazo[1,5-a]pyridin-1-yl)methyl)-1-((7-(2,2-dimethylcyclopropyl)imidazo[1,2-a]pyridin-2-yl)methyl)-1H-pyrazole-4-carboxamide, N-((7-chloroimidazo[1,5-a]pyridin-1-yl)methyl)-1-((7-(2-methylprop-1-en-1-yl)imidazo[1,2-a]pyridin-2-yl)methyl)-1H-pyrazole-4-carboxamide, N-((7-chloroimidazo[1,5-a]pyridin-1-yl)methyl)-1-((6-(2-methylcyclopropyl)imidazo[1,2-a]pyridin-2-yl)methyl)-1H-pyrazole-4-carboxamide, N-((7-bromoimidazo[1,5-a]pyridin-1-yl)methyl)-1-((6-(2-methylcyclopropyl)imidazo[1,2-a]pyridin-2-yl)methyl)-1H-pyrazole-4-carboxamide, 1-((6-cyclopropylimidazo[1,2-a]pyridin-2-yl)methyl)-N-((7-iodoimidazo[1,5-a]pyridin-1-yl)methyl)-1H-pyrazole-4-carboxamide, N-((7-chloroimidazo[1,5-a]pyridin-1-yl)methyl)-1-((5-ethylimidazo[1,2-a]pyridin-2-yl)methyl)-1H-pyrazole-4-carboxamide, (Z)—N-((7-chloroimidazo[1,5-a]pyridin-1-yl)methyl)-1-((6-(prop-1-en-1-yl)imidazo[1,2-a]pyridin-2-yl)methyl)-1H-pyrazole-4-carboxamide, 1-((6-cyclopropylimidazo[1,2-a]pyridin-2-yl)methyl)-N-((7-cyclopropylimidazo[1,5-a]pyridin-1-yl)methyl)-1H-pyrazole-4-carboxamide, N-((7-bromoimidazo[1,5-a]pyridin-1-yl)methyl)-1-((7-(2,2-dimethylcyclopropyl)imidazo[1,2-a]pyridin-2-yl)methyl)-1H-pyrazole-4-carboxamide, N-((7-chloroimidazo[1,5-a]pyridin-1-yl)methyl)-1-((5-cyclopropylpyrazolo[1,5-a]pyridin-2-yl)methyl)-1H-pyrazole-4-carboxamide, N-((7-chloroimidazo[1,5-a]pyridin-1-yl)methyl)-5-((6-cyclopropylimidazo[1,2-a]pyridin-2-yl)methyl)-1,3,4-oxadiazole-2-carboxamide, N-((7-bromoimidazo[1,5-a]pyridin-1-yl)methyl)-5-((6-cyclopropylimidazo[1,2-a]pyridin-2-yl)methyl)-1,3,4-oxadiazole-2-carboxamide, N-((6-aminoimidazo[1,5-a]pyridin-1-yl)methyl)-1-((6-cyclopropylimidazo[1,2-a]pyridin-2-yl)methyl)-1H-pyrazole-4-carboxamide, N-((7-chloroimidazo[1,5-a]pyridin-1-yl)methyl)-1-((5-cyanoimidazo[1,2-a]pyridin-2-yl)methyl)-1H-pyrazole-4-carboxamide, N-((7-bromoimidazo[1,5-a]pyridin-1-yl)methyl)-1-((5-cyanoimidazo[1,2-a]pyridin-2-yl)methyl)-1H-pyrazole-4-carboxamide, N-((7-bromoimidazo[1,5-a]pyridin-1-yl)methyl)-1-((5-cyclopropylpyrazolo[1,5-a]pyridin-2-yl)methyl)-1H-pyrazole-4-carboxamide, N-((7-bromoimidazo[1,5-a]pyridin-1-yl)methyl)-1-((5-chloro-6-cyclopropylimidazo[1,2-a]pyridin-2-yl)methyl)-1H-pyrazole-4-carboxamide, N-((5-amino-7-chloroimidazo[1,5-a]pyridin-1-yl)methyl)-1-((6-methylimidazo[1,2-a]pyridin-2-yl)methyl)-1H-pyrazole-4-carboxamide, N-((7-chloroimidazo[1,5-a]pyridin-1-yl)methyl)-1-((6-cyclopropyl-5-fluoroimidazo[1,2-a]pyridin-2-yl)methyl)-1H-pyrazole-4-carboxamide, N-((7-bromoimidazo[1,5-a]pyridin-1-yl)methyl)-1-((6-cyclopropyl-5-fluoroimidazo[1,2-a]pyridin-2-yl)methyl)-1H-pyrazole-4-carboxamide, N-((7-chloroimidazo[1,5-a]pyridin-1-yl)methyl)-1-((6-cyclobutylimidazo[1,2-a]pyridin-2-yl)methyl)-1H-pyrazole-4-carboxamide, N-((7-chloroimidazo[1,5-a]pyridin-1-yl)

methyl)-1-((5-(hydroxymethyl)imidazo[1,2-a]pyridin-2-yl)methyl)-1H-pyrazole-4-carboxamide, N-((7-chloroimidazo[1,5-a]pyridin-1-yl)methyl)-1-((5-methoxyimidazo[1,2-a]pyridin-2-yl)methyl)-1H-pyrazole-4-carboxamide, N-((7-chloroimidazo[1,5-a]pyridin-1-yl)methyl)-1-((6-methylimidazo[1,2-a]pyridin-2-yl)methyl)-1H-pyrazole-4-carboxamide, methyl 3-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)propanoate, 1-((6-cyclopropylimidazo[1,2-a]pyridin-2-yl)methyl)-N-((7-ethynylimidazo[1,5-a]pyridin-1-yl)methyl)-1H-pyrazole-4-carboxamide, 1-((6-cyclopropylimidazo[1,2-a]pyridin-2-yl)methyl)-N-((7-ethylimidazo[1,5-a]pyridin-1-yl)methyl)-1H-pyrazole-4-carboxamide, N-((7-bromoimidazo[1,5-a]pyridin-1-yl)methyl)-1-((6-cyclopropylimidazo[1,2-b]pyridazin-2-yl)methyl)-1H-pyrazole-4-carboxamide, N-((7-chloroimidazo[1,5-a]pyridin-1-yl)methyl)-1-(imidazo[1,2-a]pyridin-2-ylmethyl)-1H-pyrazole-4-carboxamide, N-((7-chloroimidazo[1,5-a]pyridin-1-yl)methyl)-5-((6-cyclopropylimidazo[1,2-a]pyridin-2-yl)methyl)-1,3,4-thiadiazole-2-carboxamide, ethyl 2-((4-(((7-chloroimidazo[1,5-a]pyridin-1-yl)methyl)carbamoyl)-1H-pyrazol-1-yl)methyl)-6-cyclopropylimidazo[1,2-a]pyridine-8-carboxylate, 2-((4-(((7-chloroimidazo[1,5-a]pyridin-1-yl)methyl)carbamoyl)-1H-pyrazol-1-yl)methyl)-6-cyclopropylimidazo[1,2-a]pyridine-8-carboxylic acid, 3-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)propanoic acid, N-(1-(7-bromoimidazo[1,5-a]pyridin-1-yl)ethyl)-1-((6-cyclopropylimidazo[1,2-a]pyridin-2-yl)methyl)-1H-pyrazole-4-carboxamide, N-((7-chloroimidazo[1,5-a]pyridin-1-yl)methyl)-1-((6-cyclopropyl-8-(hydroxymethyl)imidazo[1,2-a]pyridin-2-yl)methyl)-1H-pyrazole-4-carboxamide, N-((7-bromoimidazo[1,5-a]pyridin-1-yl)methyl)-1-((6-cyclopropylimidazo[1,2-a]pyrimidin-2-yl)methyl)-1H-pyrazole-4-carboxamide, N-((7-chloroimidazo[1,5-a]pyridin-1-yl)methyl)-1-((5-(methylamino)imidazo[1,2-a]pyridin-2-yl)methyl)-1H-pyrazole-4-carboxamide, N-((7-chloroimidazo[1,5-a]pyridin-1-yl)methyl)-3-cyclopropyl-1-((6-cyclopropylimidazo[1,2-a]pyridin-2-yl)methyl)-1H-pyrazole-4-carboxamide, N-((7-chloroimidazo[1,5-a]pyridin-1-yl)methyl)-1-((6-cyclopropyl-5-ethynylimidazo[1,2-a]pyridin-2-yl)methyl)-1H-pyrazole-4-carboxamide, N-((7-chloroimidazo[1,5-a]pyridin-1-yl)methyl)-1-((6-cyclopropylimidazo[1,2-a]pyridin-2-yl)methyl)-1H-1,2,3-triazole-4-carboxamide, methyl 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)acetate, methyl 3-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-5-yl)propanoate, N-((7-bromo-3-(difluoromethyl)imidazo[1,5-a]pyridin-1-yl)methyl)-1-((6-cyclopropylimidazo[1,2-a]pyridin-2-yl)methyl)-1H-pyrazole-4-carboxamide, N-((7-chloroimidazo[1,5-a]pyridin-1-yl)methyl)-1-((6-cyclopropyl-1H-pyrrolo[3,2-b]pyridin-2-yl)methyl)-1H-pyrazole-4-carboxamide, N-((7-bromoimidazo[1,5-a]pyridin-1-yl)methyl)-3-cyclopropyl-1-((6-cyclopropylimidazo[1,2-a]pyridin-2-yl)methyl)-1H-pyrazole-4-carboxamide, 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)acetic acid, N-((7-chloroimidazo[1,5-a]pyridin-1-yl)methyl)-1-((6-cyclopropyl-8-(hydroxyethyl)imidazo[1,2-a]pyridin-2-yl)methyl)-1H-pyrazole-4-carboxamide, 1-((5-amino-6-cyclopropylimidazo[1,2-a]pyridin-2-yl)methyl)-N-((7-chloroimidazo[1,5-a]pyridin-1-yl)methyl)-1H-pyrazole-4-carboxamide, 1-((5-amino-8-cyclopropylimidazo[1,2-a]pyridin-2-yl)methyl)-N-((7-chloroimidazo[1,5-a]pyridin-1-yl)methyl)-1H-pyrazole-4-carboxamide, N-((7-chloroimidazo[1,5-a]pyridin-1-yl)methyl-d2)-1-((6-cyclopropylimidazo[1,2-a]pyridin-2-yl)methyl)-1H-pyrazole-4-carboxamide, methyl 2-((4-(((7-chloroimidazo[1,5-a]pyridin-1-yl)methyl)carbamoyl)-1H-pyrazol-1-yl)methyl)imidazo[1,2-a]pyridine-6-carboxylate, N-((7-chloroimidazo[1,5-a]pyridin-1-yl)methyl)-1-((8-cyano-6-cyclopropylimidazo[1,2-a]pyridin-2-yl)methyl)-1H-pyrazole-4-carboxamide, ethyl 3-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)propanoate, N-(2-(7-chloroimidazo[1,5-a]pyridin-1-yl)ethyl)-1-((6-cyclopropylimidazo[1,2-a]pyridin-2-yl)methyl)-1H-pyrazole-4-carboxamide, N-((7-bromoimidazo[1,5-a]pyridin-1-yl)methyl)-1-((6-cyclopropylimidazo[1,2-a]pyridin-2-yl)methyl)-3-(difluoromethyl)-1H-pyrazole-4-carboxamide, 2-((4-(((7-chloroimidazo[1,5-a]pyridin-1-yl)methyl)carbamoyl)-1H-pyrazol-1-yl)methyl)imidazo[1,2-a]pyridine-6-carboxylic acid, N-((7-bromo-8-fluoroimidazo[1,5-a]pyridin-1-yl)methyl)-1-((6-cyclopropylimidazo[1,2-a]pyridin-2-yl)methyl)-1H-pyrazole-4-carboxamide, 1-((6-cyclopropylimidazo[1,2-b]pyridazin-2-yl)methyl)-N-((7-ethynylimidazo[1,5-a]pyridin-1-yl)methyl)-1H-pyrazole-4-carboxamide, N-((7-chloroimidazo[1,5-a]pyridin-1-yl)methyl)-1-((6-cyclopropylimidazo[1,2-a]pyridin-2-yl)methyl)-3-(difluoromethyl)-1H-pyrazole-4-carboxamide, ethyl 3-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)acrylate, ethyl 3-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)propanoate, 3-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)propanoic acid, N-((7-chloroimidazo[1,5-a]pyridin-1-yl)methyl)-1-((6-cyclopropyl-8-(morpholinomethyl)imidazo[1,2-a]pyridin-2-yl)methyl)-1H-pyrazole-4-carboxamide, N-((7-chloroimidazo[1,5-a]pyridin-1-yl)methyl)-1-((6-cyclopropylimidazo[1,2-a]pyridin-2-yl)methyl)-3-(oxetan-3-yl)-1H-pyrazole-4-carboxamide, N-((7-chloroimidazo[1,5-a]pyridin-1-yl)methyl)-1-((6-cyclopropyl-8-(2-methoxyethoxy)imidazo[1,2-a]pyridin-2-yl)methyl)-1H-pyrazole-4-carboxamide, 1-((8-acetyl-6-cyclopropylimidazo[1,2-a]pyridin-2-yl)methyl)-N-((7-chloroimidazo[1,5-a]pyridin-1-yl)methyl)-1H-pyrazole-4-carboxamide, N-((7-chloroimidazo[1,5-a]pyridin-1-yl)methyl)-1-((6-cyclopropyl-8-(2-hydroxypropan-2-yl)imidazo[1,2-a]pyridin-2-yl)methyl)-1H-pyrazole-4-carboxamide, ethyl 2-(2-((4-(((7-bromo-8-fluoroimidazo[1,5-a]pyridin-1-yl)methyl)carbamoyl)-1H-pyrazol-1-yl)methyl)-6-cyclopropylimidazo[1,2-a]pyridin-8-yl)acetate, 2-(2-((4-(((7-bromo-8-fluoroimidazo[1,5-a]pyridin-1-yl)methyl)carbamoyl)-1H-pyrazol-1-yl)methyl)-6-cyclopropylimidazo[1,2-a]pyridin-8-yl)acetic acid, N-((7-chloroimidazo[1,5-a]pyridin-1-yl)methyl)-1-((6-cyclopropyl-8-(3-hydroxypropyl)imidazo[1,2-a]pyridin-2-yl)methyl)-1H-pyrazole-4-carboxamide, N-((7-bromo-8-fluoroimidazo[1,5-a]pyridin-1-yl)methyl)-1-((6-cyclopropylimidazo[1,2-b]pyridazin-2-yl)methyl)-1H-pyrazole-4-carboxamide, N-((7-chloroimidazo[1,5-a]pyridin-1-yl)methyl)-1-((6-cyclopropyl-8-(2-hydroxy-2-methylpropyl)imidazo[1,2-a]pyridin-2-yl)methyl)-1H-pyrazole-4-carboxamide, N-((7-chloroimidazo[1,5-a]pyridin-1-yl)methyl)-2-((6-cyclopropylimidazo[1,2-a]pyridin-2-yl)methyl)-2H-tetrazole-5-carboxamide, N-((7- chloroimidazo[1,5-a]pyridin-1-yl)methyl)-1-((6-cyclopropylimidazo[1,2-b]pyridazin-2-yl)methyl)-1H-1,2,3-triazole-4-carboxamide, N-((7-chloroimidazo[1,5-a]pyridin-1-yl)methyl)-1-((8-cyano-6-cyclopropylimidazo[1,2-a]pyridin-2-yl)methyl)-1H-1,2,3-triazole-4-carboxamide, ethyl 2-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)cyclopropane-1-carboxylate, N-((7-chloroimidazo[1,5-a]pyridin-1-yl)methyl)-1-((6-cyclopropyl-8-(2-oxopyrrolidin-1-yl)imidazo[1,2-a]pyridin-2-yl)methyl)-1H-pyrazole-4-carboxamide, ethyl 1-(2-((4-(((7-chloroimidazo[1,5-a]pyridin-1-yl)methyl)carbamoyl)-1H-pyrazol-1-yl)methyl)imidazo[1,2-a]pyridin-8-yl)cyclopropane-1-carboxylate, 1-(2-((4-(((7-chloroimidazo[1,5-a]pyridin-1-yl)methyl)carbamoyl)-1H-pyrazol-1-yl)methyl)imidazo[1,2-a]pyridin-8-yl)cyclopropane-1-carboxylic acid, N-((7-chloroimidazo[1,5-a]pyridin-1-yl)methyl)-1-((8-(1-(hydroxymethyl)cyclopropyl)imidazo[1,2-a]pyridin-2-yl)methyl)-1H-pyrazole-4-carboxamide, 1-((6-cyclopropylimidazo[1,2-a]pyridin-2-yl)methyl)-N-((7-vinylimidazo[1,5-a]pyridin-1-yl)methyl)-1H-pyrazole-4-carboxamide, N-((7-chloroimidazo[1,5-a]pyridin-1-yl)methyl)-1-((6-cyclopropyl-8-(3-hydroxy-3-methylbutyl)imidazo[1,2-a]pyridin-2-yl)methyl)-1H-pyrazole-4-carboxamide, 2-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)cyclopropane-1-carboxylic acid, N-((7-chloroimidazo[1,5-a]pyridin-1-yl)methyl)-2-((6-cyclopropylimidazo[1,2-a]pyridin-2-yl)methyl)-2H-1,2,3-triazole-4-carboxamide, N-((7-chloroimidazo[1,5-a]pyridin-1-yl)methyl)-1-((6-cyclopropyl-8-(3-hydroxyoxetan-3-yl)imidazo[1,2-a]pyridin-2-yl)methyl)-1H-pyrazole-4-carboxamide, N'-((7-chloroimidazo[1,5-a]pyridin-1-yl)methyl)-N-cyano-1-((6-cyclopropylimidazo[1,2-a]pyridin-2-yl)methyl)-1H-pyrazole-4-carboximidamide, N-((7-chloroimidazo[1,5-a]pyridin-1-yl)methyl)-1-(1-(6-cyclopropylimidazo[1,2-a]pyridin-2-yl)ethyl)-1H-1,2,3-triazole-4-carboxamide, N-((7-chloroimidazo[1,5-a]pyridin-1-yl)methyl)-1-((6-cyclopropyl-8-(2-methoxyethyl)imidazo[1,2-a]pyridin-2-yl)methyl)-1H-pyrazole-4-carboxamide, 3-((2H-tetrazol-5-yl)methyl)-N-((7-chloroimidazo[1,5-a]pyridin-1-yl)methyl)-1-((6-cyclopropylimidazo[1,2-a]pyridin-2-yl)methyl)-1H-pyrazole-4-carboxamide, ethyl 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)cyclopropane-1-carboxylate, N-((7-chloroimidazo[1,5-a]pyridin-1-yl)methyl)-5-((8-cyano-6-cyclopropylimidazo[1,2-a]pyridin-2-yl)methyl)-1,3,4-oxadiazole-2-carboxamide, and N-((7-chloroimidazo[1,2-a]pyridin-2-yl)methyl)-1-((5,6-dimethylimidazo[1,2-a]pyridin-2-yl)methyl)-1H-pyrazole-4-carboxamide, N-((7-bromo-8-fluoroimidazo[1,5-a]pyridin-1-yl)methyl)-1-((8-cyano-6-cyclopropylimidazo[1,2-a]pyridin-2-yl)methyl)-1H-1,2,3-triazole-4-carboxamide, N-((7-chloroimidazo[1,5-a]pyridin-1-yl)methyl)-1-((6-cyclopropyl-8-(oxetan-3-yl)imidazo[1,2-a]pyridin-2-yl)methyl)-1H-pyrazole-4-carboxamide, 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)cyclopropane-1-carboxylic acid, N-((7-bromo-8-fluoroimidazo[1,5-a]pyridin-1-yl)methyl)-1-((6-cyclopropylimidazo[1,2-a]pyridin-2-yl)methyl)-1H-1,2,3-triazole-4-carboxamide, N-((7-bromo-8-fluoroimidazo[1,5-a]pyridin-1-yl)methyl)-2-((6-cyclopropylimidazo[1,2-a]pyridin-2-yl)methyl)-2H-tetrazole-5-carboxamide, N-((7-bromo-8-fluoroimidazo[1,5-a]pyridin-1-yl)methyl)-5-((6-cyclopropylimidazo[1,2-a]pyridin-2-yl)methyl)-1,3,4-oxadiazole-2-carboxamide, N-((7-bromo-8-fluoroimidazo[1,5-a]pyridin-1-yl)methyl)-5-((6-cyclopropylimidazo[1,2-a]pyridin-2-yl)methyl)-1,3,4-oxadiazole-2-carboxamide, N-((7-chloroimidazo[1,5-a]pyridin-1-yl)methyl)-5-((6-cyclopropylimidazo[1,2-b]pyridazin-2-yl)methyl)-1,3,4-oxadiazole-2-carboxamide, N-((7-bromo-8-fluoroimidazo[1,5-a]pyridin-1-yl)methyl)-1-((6-cyclopropylimidazo[1,2-b]pyridazin-2-yl)methyl)-1H-1,2,3-triazole-4-carboxamide, N-((7-bromo-8-fluoroimidazo[1,5-a]pyridin-1-yl)methyl)-5-((6-cyclopropylimidazo[1,2-b]pyridazin-2-yl)methyl)-1,3,4-oxadiazole-2-carboxamide, N-((7-chloroimidazo[1,5-a]pyridin-1-yl)methyl)-1-((6-cyclopropyl-8-(hydroxy(oxetan-3-yl)methyl)imidazo[1,2-a]pyridin-2-yl)methyl)-1H-pyrazole-4-carboxamide, N-((7-chloroimidazo[1,5-a]pyridin-1-yl)methyl)-1-((6-cyclopropyl-5-methoxyimidazo[1,2-a]pyridin-2-yl)methyl)-1H-pyrazole-4-carboxamide, N-((7-chloroimidazo[1,5-a]pyridin-1-yl)methyl)-1-((6-cyclopropyl-8-(trifluoromethyl)imidazo[1,2-a]pyridin-2-yl)methyl)-1H-pyrazole-4-carboxamide, N-((7-chloroimidazo[1,5-a]pyridin-1-yl)methyl)-1-((6-cyclopropyl-5-fluoroimidazo[1,2-a]pyridin-2-yl)methyl)-1H-1,2,3-triazole-4-carboxamide, N-((7-bromo-8-fluoroimidazo[1,5-a]pyridin-1-yl)methyl)-1-((6-cyclopropyl-5-fluoroimidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropylimidazo[1,2-b]pyridazin-2-yl)methyl)-1H-pyrazole-4-carboxamide, N-((7-chloro-8-fluoroimidazo[1,5-a]pyridin-1-yl)methyl)-1-((6-cyclopropylimidazo[1,2-a]pyridin-2-yl)methyl)-1H-pyrazole-4-carboxamide, N-((7-chloro-8-fluoroimidazo[1,5-a]pyridin-1-yl)methyl)-1-((6-cyclopropylimidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((8-cyano-6-cyclopropylimidazo[1,2-a]pyridin-2-yl)methyl)-1H-1,2,3-triazole-4-carboxamide, N-((7-bromo-8-fluoroimidazo[1,5-a]pyridin-1-yl)methyl)-1-((6-cyclopropylimidazo[1,2-b]pyridazin-2-yl)methyl)-1H-1,2,3-triazole-4-carboxamide, N-((7-bromo-6-fluoroimidazo[1,5-a]pyridin-1-yl)methyl)-1-((6-cyclopropylimidazo[1,2-a]pyridin-2-yl)methyl)-1H-pyrazole-4-carboxamide, N-((7-chloroimidazo[1,5-a]pyridin-1-yl)methyl)-1-((6-cyclopropylimidazo[1,2-a]pyridin-2-yl)methyl)-1H-1,2,4-triazole-3-carboxamide, N-((7-chloroimidazo[1,5-a]pyridin-1-yl)methyl)-1-((6-cyclopropyl-8-(3-hydroxyoxetan-3-yl)imidazo[1,2-a]pyridin-2-yl)methyl)-1H-1,2,3-triazole-4-carboxamide, N-((7-bromo-8-fluoroimidazo[1,5-a]pyridin-1-yl)methyl)-5-((8-cyano-6-cyclopropylimidazo[1,2-a]pyridin-2-yl)methyl)-1,3,4-oxadiazole-2-carboxamide, 1-((8-((1,3,4-oxadiazol-2-yl)methyl)-6-cyclopropylimidazo[1,2-a]pyridin-2-yl)methyl)-N-((7-chloroimidazo[1,5-a]pyridin-1-yl)methyl)-1H-pyrazole-4-carboxamide, N-((7-chloro-8-fluoroimidazo[1,5-a]pyridin-1-yl)methyl)-5-((6-cyclopropylimidazo[1,2-b]pyridazin-2-yl)methyl)-1,3,4-oxadiazole-2-carboxamide, ethyl 2-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)acetate, 2-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)acetic acid, N-((7-chloro-8-fluoroimidazo[1,5-a]pyridin-1-yl)methyl)-5-((8-cyano-6-cyclopropylimidazo[1,2-a]pyridin-2-yl)methyl)-1,3,4-oxadiazole-2-carboxamide, N-((7-chloroimidazo[1,5-a]pyridin-1-yl)methyl)-1-((6-cyclopropyl-8-(methylsulfonyl)imidazo[1,2-a]pyridin-2-yl)methyl)-1H-pyrazole-4-carboxamide, N-((7-chloroimidazo[1,5-a]pyridin-1-yl)methyl)-5-((6-cyclopropylimidazo[1,2-a]pyridin-2-yl)

methyl)-1-methyl-1H-1,2,4-triazole-3-carboxamide, N-((7-chloroimidazo[1,5-a]pyridin-1-yl)methyl)-5-((6-cyclopropylimidazo[1,2-a]pyridin-2-yl)methyl)-4H-1,2,4-triazole-3-carboxamide, ethyl 3-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)-2,2-dimethylpropanoate, ethyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)propanoate, 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)propanoic acid, N-((7-bromo-8-fluoroimidazo[1,5-a]pyridin-1-yl)methyl)-1-((6-cyclopropyl-5-fluoroimidazo[1,2-a]pyridin-2-yl)methyl)-1H-pyrazole-4-carboxamide, N-((7-chloro-8-fluoroimidazo[1,5-a]pyridin-1-yl)methyl)-1-((6-cyclopropylimidazo[1,2-a]pyrimidin-2-yl)methyl)-1H-1,2,3-triazole-4-carboxamide, ethyl 2-(4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridine-8-carboxylate, 2-(4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridine-8-carboxylic acid, N-((7-chloro-8-fluoroimidazo[1,5-a]pyridin-1-yl)methyl)-1-((6-cyclopropyl-8-(3-fluorooxetan-3-yl)imidazo[1,2-a]pyridin-2-yl)methyl)-1H-1,2,3-triazole-4-carboxamide, ethyl 3-(2-((4-(((7-chloroimidazo[1,5-a]pyridin-1-yl)methyl)carbamoyl)-1H-1,2,3-triazol-1-yl)methyl)-6-cyclopropylimidazo[1,2-a]pyridin-8-yl)-2,2-dimethylpropanoate, N-((7-chloro-8-fluoroimidazo[1,5-a]pyridin-1-yl)methyl)-1-((6-cyclopropyl-8-(oxetan-3-yl)imidazo[1,2-a]pyridin-2-yl)methyl)-1H-1,2,3-triazole-4-carboxamide, 3-(2-((4-(((7-chloroimidazo[1,5-a]pyridin-1-yl)methyl)carbamoyl)-1H-1,2,3-triazol-1-yl)methyl)-6-cyclopropylimidazo[1,2-a]pyridin-8-yl)-2,2-dimethylpropanoic acid, N-((7-chloro-8-fluoroimidazo[1,5-a]pyridin-1-yl)methyl)-1-((6-cyclopropyl-8-fluoroimidazo[1,2-a]pyridin-2-yl)methyl)-1H-1,2,3-triazole-4-carboxamide, 1-((6-chloro-5-methylimidazo[1,2-a]pyridin-2-yl)methyl)-N-((7-chloro-8-fluoroimidazo[1,5-a]pyridin-1-yl)methyl)-1H-1,2,3-triazole-4-carboxamide, N-((7-chloro-8-fluoroimidazo[1,5-a]pyridin-1-yl)methyl)-1-((6-cyclopropyl-8-morpholinoimidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(2H-tetrazol-5-yl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((5-cyclopropylpyrazolo[1,5-a]pyridin-2-yl)methyl)-1H-1,2,3-triazole-4-carboxamide, N-((7-chloroimidazo[1,5-a]pyridin-1-yl)methyl)-5-((6-cyclopropylimidazo[1,2-a]pyridin-2-yl)methyl)isoxazole-3-carboxamide, N-((7-chloroimidazo[1,5-a]pyridin-1-yl)methyl)-5-((6-cyclopropylimidazo[1,2-a]pyridin-2-yl)methyl)-1,2,4-oxadiazole-3-carboxamide, N-((7-chloro-8-fluoroimidazo[1,5-a]pyridin-1-yl)methyl)-1-((7-cyclopropyl-[1,2,4]triazolo[1,5-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(1H-tetrazol-1-yl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(4H-1,2,4-triazol-4-yl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(hydroxymethyl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-formylimidazo[1,2-a]pyridin-2-yl)methyl)-1H-1,2,3-triazole-4-carboxamide, 1-((8-(3-amino-3-oxopropyl)-6-cyclopropylimidazo[1,2-a]pyridin-2-yl)methyl)-N-((7-chloroimidazo[1,5-a]pyridin-1-yl)methyl)-1H-1,2,3-triazole-4-carboxamide, N-((7-chloroimidazo[1,5-a]pyridin-1-yl)methyl)-1-((8-(2-cyanoethyl)-6-cyclopropylimidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(trifluoromethyl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(oxetan-3-ylmethyl)imidazo[1,2-a]pyridin-2-yl)methyl)-1H-1,2,3-triazole-4-carboxamide, 1-((6-chloro-8-(oxetan-3-yl)imidazo[1,2-a]pyridin-2-yl)methyl)-N-((7-chloro-8-fluoroimidazo[1,5-a]pyridin-1-yl)methyl)-1H-1,2,3-triazole-4-carboxamide, N-((7-chloro-8-fluoroimidazo[1,5-a]pyridin-1-yl)methyl)-1-((6,7-dichloroimidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((5-cyclopropylthieno[2,3-b]pyridin-2-yl)methyl)-1H-1,2,3-triazole-4-carboxamide, N-((7-chloroimidazo[1,5-a]pyridin-1-yl)methyl)-3-((6-cyclopropylimidazo[1,2-a]pyridin-2-yl)methyl)-1,2,4-oxadiazole-5-carboxamide, N-((7-chloroimidazo[1,5-a]pyridin-1-yl)methyl)-1-((5-cyclopropylbenzofuran-2-yl)methyl)-1H-1,2,3-triazole-4-carboxamide, N-((7-chloro-8-fluoroimidazo[1,5-a]pyridin-1-yl)methyl)-1-((6-cyclopropyl-8-(difluoromethyl)imidazo[1,2-a]pyridin-2-yl)methyl)-1H-1,2,3-triazole-4-carboxamide, 1-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)-1H-pyrazole-4-carboxylic acid, 1-((8-(2-(1H-tetrazol-5-yl)ethyl)-6-cyclopropylimidazo[1,2-a]pyridin-2-yl)methyl)-N-((7-chloroimidazo[1,5-a]pyridin-1-yl)methyl)-1H-1,2,3-triazole-4-carboxamide, N-((7-chloro-8-fluoroimidazo[1,5-a]pyridin-1-yl)methyl)-2-((6-cyclopropylimidazo[1,2-a]pyridin-2-yl)methyl)oxazole-4-carboxamide, N-((7-chloro-8-fluoroimidazo[1,5-a]pyridin-1-yl)methyl)-1-((6-chlorobenzofuran-2-yl)methyl)-1H-1,2,3-triazole-4-carboxamide, N-((7-chloro-8-fluoroimidazo[1,5-a]pyridin-1-yl)methyl)-1-(1-(6-cyclopropylimidazo[1,2-a]pyridin-2-yl)ethyl)-1H-1,2,3-triazole-4-carboxamide, N-((7-chloro-8-fluoroimidazo[1,5-a]pyridin-1-yl)methyl)-1-((6-cyclopropyl-8-(2-oxotetrahydrofuran-3-yl)imidazo[1,2-a]pyridin-2-yl)methyl)-1H-1,2,3-triazole-4-carboxamide, N-((7-bromo-8-fluoroimidazo[1,5-a]pyridin-1-yl)methyl)-1-((6-cyclopropyl-8-fluoroimidazo[1,2-a]pyridin-2-yl)methyl)-1H-1,2,3-triazole-4-carboxamide, 1-((8-((1H-pyrazol-1-yl)methyl)-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide, 1-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)-1H-pyrazole-3-carboxylic acid, N-((7-chloro-8-fluoroimidazo[1,5-a]pyridin-1-yl)methyl)-1-((6-cyclopropyl-8-(2-oxopyrrolidin-1-yl)imidazo[1,2-a]pyridin-2-yl)methyl)-1H-1,2,3-triazole-4-carboxamide, 1-((8-bromo-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide, ethyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2,2-dimethylpropanoate, 3-(2-((4-(((7-chloro-8-fluoroimidazo[1,5-a]pyridin-1-yl)methyl)carbamoyl)-1H-

1,2,3-triazol-1-yl)methyl)-6-cyclopropylimidazo[1,2-a]pyridin-8-yl)-2,2-dimethylpropanoic acid, ethyl 2-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)oxy)acetate, 2-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)oxy)acetic acid, N-((7-chloro-8-fluoroimidazo[1,5-a]pyridin-1-yl)methyl)-1-((6-cyclopropylpyrazolo[1,5-a]pyrimidin-2-yl)methyl)-1H-1,2,3-triazole-4-carboxamide, ethyl 5-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)-1,3,4-oxadiazole-2-carboxylate, 1-((8-((1,3,4-oxadiazol-2-yl)methyl)-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide, N-((7-chloro-8-fluoroimidazo[1,5-a]pyridin-1-yl)methyl)-1-((5-cyclopropyl-3-(trifluoromethyl)-1H-indol-2-yl)methyl)-1H-1,2,3-triazole-4-carboxamide, 2-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)oxy)-2-methylpropanoic acid, N-((7-chloro-8-fluoroimidazo[1,5-a]pyridin-1-yl)methyl)-1-((6-cyclopropyl-8-(1-fluoroethyl)imidazo[1,2-a]pyridin-2-yl)methyl)-1H-1,2,3-triazole-4-carboxamide, 1-((8-((1,3,4-oxadiazol-2-yl)methyl)-6-cyclopropylimidazo[1,2-a]pyridin-2-yl)methyl)-N-((7-chloro-8-fluoroimidazo[1,5-a]pyridin-1-yl)methyl)-1H-pyrazole-4-carboxamide, N-((7-chloro-8-fluoroimidazo[1,5-a]pyridin-1-yl)methyl)-1-((6-cyclopropyl-8-(oxetan-3-yl)imidazo[1,2-a]pyridin-2-yl)methyl)-1H-pyrazole-4-carboxamide, N-((7-chloro-8-fluoroimidazo[1,5-a]pyridin-1-yl)methyl)-1-((6-cyclopropyl-8-(2-oxooxazolidin-3-yl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((7-cyclopropylimidazo[1,2-b]pyridazin-2-yl)methyl)-1H-1,2,3-triazole-4-carboxamide, N-((7-chloro-8-fluoro-imidazo[1,5-a]pyridin-1-yl)methyl)-1-((5-cyclopropylbenzo[b]thiophen-2-yl)methyl)-1H-1,2,3-triazole-4-carboxamide, N-((7-chloro-8-fluoroimidazo[1,5-a]pyridin-1-yl)methyl)-1-((6-cyclopropylbenzofuran-2-yl)methyl)-1H-1,2,3-triazole-4-carboxamide, N-((7-chloro-8-fluoroimidazo[1,5-a]pyridin-1-yl)methyl)-1-((6-cyclopropyl-8-(1H-pyrazol-1-yl)imidazo[1,2-a]pyridin-2-yl)methyl)-1H-1,2,3-triazole-4-carboxamide, methyl 1-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)cyclopentane-1-carboxylate, 1-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)cyclopentane-1-carboxylic acid, 1-((2-((4-(((7-chloro-8-ethoxyimidazo[1,5-a]pyridin-1-yl)methyl)carbamoyl)-1H-1,2,3-triazol-1-yl)methyl)-6-cyclopropylimidazo[1,2-a]pyridin-8-yl)methyl)cyclopentane-1-carboxylic acid, 1-((6-chloro-1H-indol-2-yl)methyl)-N-((7-chloro-8-fluoroimidazo[1,5-a]pyridin-1-yl)methyl)-1H-1,2,3-triazole-4-carboxamide, ethyl 2-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)oxy)-2-methylpropanoate, methyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2-fluoropropanoate, 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2-fluoropropanoic acid, N-((7-chloro-8-fluoroimidazo[1,5-a]pyridin-1-yl)methyl)-1-((6-cyclopropyl-8-(isoxazol-4-yl)imidazo[1,2-a]pyridin-2-yl)methyl)-1H-1,2,3-triazole-4-carboxamide, 1-(2-((4-((7-chloro-8-fluoroimidazo[1,5-a]pyridin-1-yl)methylcarbamoyl)-1H-1,2,3-triazol-1-yl)methyl)-6-cyclopropylimidazo[1,2-a]pyridin-8-yl)-1H-imidazole-4-carboxylic acid, ethyl 3-(4-(((7-chloro-8-fluoroimidazo[1,5-a]pyridin-1-yl)methyl)carbamoyl)-1H-1,2,3-triazol-1-yl)-3-(6-cyclopropylimidazo[1,2-a]pyridin-2-yl)propanoate, 3-(4-(((7-chloro-8-fluoroimidazo[1,5-a]pyridin-1-yl)methyl)carbamoyl)-1H-1,2,3-triazol-1-yl)-3-(6-cyclopropylimidazo[1,2-a]pyridin-2-yl)propanoic acid, 3-(4-(((7-chloro-8-fluoroimidazo[1,5-a]pyridin-1-yl)methyl)carbamoyl)-1H-1,2,3-triazol-1-yl)-3-(6-cyclopropylimidazo[1,2-a]pyridin-2-yl)propanoic acid, N-((7-chloro-8-fluoroimidazo[1,5-a]pyridin-1-yl)methyl)-1-((6-cyclopropylbenzo[b]thiophen-2-yl)methyl)-1H-1,2,3-triazole-4-carboxamide, 1-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-1H-pyrazole-4-carboxylic acid, N-((7-chloro-8-fluoroimidazo[1,5-a]pyridin-1-yl)methyl)-1-((5-cyclopropyl-7-(trifluoromethyl)pyrazolo[1,5-a]pyridin-2-yl)methyl)-1H-1,2,3-triazole-4-carboxamide, N-((7-chloro-8-fluoroimidazo[1,5-a]pyridin-1-yl)methyl)-1-((5-cyclopropyl-1H-indol-2-yl)methyl)-1H-1,2,3-triazole-4-carboxamide, N-((7-chloro-8-fluoroimidazo[1,5-a]pyridin-1-yl)methyl)-1-((5-cyclopropyl-1-methyl-1H-indol-2-yl)methyl)-1H-1,2,3-triazole-4-carboxamide, N-((7-chloro-8-fluoroimidazo[1,5-a]pyridin-1-yl)methyl)-1-((6-chlorobenzo[b]thiophen-2-yl)methyl)-1H-1,2,3-triazole-4-carboxamide, N-((7-chloro-8-fluoroimidazo[1,5-a]pyridin-1-yl)methyl)-1-((6-cyclopropyl-1H-indol-2-yl)methyl)-1H-1,2,3-triazole-4-carboxamide, N-((7-chloro-8-fluoroimidazo[1,5-a]pyridin-1-yl)methyl)-1-((5-cyclopropyl-1H-benzo[d]imidazol-2-yl)methyl)-1H-1,2,3-triazole-4-carboxamide, N-((7-chloro-8-fluoroimidazo[1,5-a]pyridin-1-yl)methyl)-1-((8-(2-cyano-2-methylpropyl)-6-cyclopropylimidazo[1,2-a]pyridin-2-yl)methyl)-1H-pyrazole-4-carboxamide, N-((7-chloro-8-fluoroimidazo[1,5-a]pyridin-1-yl)methyl)-1-((6-cyclopropyl-8-(2-methyl-2-(2H-tetrazol-5-yl)propyl)imidazo[1,2-a]pyridin-2-yl)methyl)-1H-pyrazole-4-carboxamide, N-((7-chloro-8-fluoroimidazo[1,5-a]pyridin-1-yl)methyl)-1-((6-cyclopropyl-7-fluoroimidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-3-fluoroimidazo[1,2-a]pyridin-2-yl)methyl)-1H-1,2,3-triazole-4-carboxamide, ethyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-3-hydroxy-2,2-dimethylpropanoate, 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-3-hydroxy-2,2-dimethylpropanoic acid, N-((7-chloro-8-fluoroimidazo[1,5-a]pyridin-1-yl)methyl)-1-((6-cyclopropyl-8-(1-ethyl-5,6-dioxo-5,6-dihydro-1,2,4-triazin-4(1H)-yl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-5-((6-cyclopropylimidazo[1,2-a]pyridin-2-yl)difluoromethyl)-1,3,4-oxadiazole-2-carboxamide, 2-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)acetic acid, ethyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2-methylpropanoate, 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2-methylpropanoic acid, methyl 2-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)acetate, N-((7-chloro-8-fluoroimidazo[1,5-a]pyridin-1-yl)methyl)-1-((6-cyclopropyl-8-(5,6-dioxo-5,6-dihydro-1,2,4-triazin-4(1H)-yl)imidazo[1,2-a]pyridin-2-yl)methyl)-1H-1,2,3-triazole-4-carboxamide, ethyl 4-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-4H-1,2,4-triazole-3-carboxylate, N-((7-chloro-8-fluoroimidazo[1,5-a]pyridin-1-yl)methyl)-1-((6-cyclopropyl-8-(3-methyl-4H-1,2,4-triazol-4-yl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(2-oxa-6-azaspiro[3.3]heptan-6-yl)imidazo[1,2-a]pyridin-2-yl)methyl)-1H-1,2,3-triazole-4-carboxamide, ethyl 3-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)propanoate, 3-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)propanoic acid, N-((7-chloro-8-fluoroimidazo[1,5-a]pyridin-1-yl)methyl)-1-((6-cyclopropylbenzo[d]thiazol-2-yl)methyl)-1H-1,2,3-triazole-4-carboxamide, N-((7-chloro-8-fluoroimidazo[1,5-a]pyridin-1-yl)methyl)-1-((6-cyclopropyl-8-(3,5-dimethyl-4H-1,2,4-triazol-4-yl)imidazo[1,2-a]pyridin-2-yl)methyl)-1H-1,2,3-triazole-4-carboxamide, methyl 4-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)benzoate, 1-((5-chloro-7-cyclopropyl-[1,2,4]triazolo[1,5-a]pyridin-2-yl)methyl)-N-((7-chloro-8-fluoroimidazo[1,5-a]pyridin-1-yl)methyl)-1H-1,2,3-triazole-4-carboxamide, N-((7-chloro-8-fluoroimidazo[1,5-a]pyridin-1-yl)methyl)-1-((6-cyclopropylindolizin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(2-methylthiazol-5-yl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(3-methyl-1H-1,2,4-triazol-1-yl)imidazo[1,2-a]pyridin-2-yl)methyl)-1H-1,2,3-triazole-4-carboxamide, 4-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)benzoic acid, ethyl 4-(((7-chloro-8-fluoroimidazo[1,5-a]pyridin-1-yl)methyl)carbamoyl)-1-((6-cyclopropylimidazo[1,2-a]pyridin-2-yl)methyl)-1H-imidazole-2-carboxylate, 4-(((7-chloro-8-fluoroimidazo[1,5-a]pyridin-1-yl)methyl)carbamoyl)-1-((6-cyclopropylimidazo[1,2-a]pyridin-2-yl)methyl)-1H-imidazole-2-carboxylic acid, N-((7-chloro-8-fluoroimidazo[1,5-a]pyridin-1-yl)methyl)-1-((5-cyclopropyl-7-(2-oxopyrrolidin-1-yl)pyrazolo[1,5-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(thiazol-5-yl)imidazo[1,2-a]pyridin-2-yl)methyl)-1H-1,2,3-triazole-4-carboxamide, 4-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)morpholine-2-carboxylic acid, methyl 1-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-b]pyridazin-8-yl)azetidine-3-carboxylate, 1-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-b]pyridazin-8-yl)azetidine-3-carboxylic acid, methyl 1-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-b]pyridazin-8-yl)pyrrolidine-3-carboxylate, 1-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-b]pyridazin-8-yl)pyrrolidine-3-carboxylic acid, ethyl 2-((4-(((7-chloro-8-fluoroimidazo[1,5-a]pyridin-1-yl)methyl)carbamoyl)-1H-1,2,3-triazol-1-yl)methyl)-6-cyclopropylindolizine-3-carboxylate, N-((7-chloro-8-fluoroimidazo[1,5-a]pyridin-1-yl)methyl)-1-((1,2,3-trimethyl-1H-indol-5-yl)methyl)-1H-1,2,3-triazole-4-carboxamide, methyl 4-(((7-chloro-8-fluoroimidazo[1,5-a]pyridin-1-yl)methyl)carbamoyl)-1-((6-cyclopropylimidazo[1,2-a]pyridin-2-yl)methyl)-1H-pyrrole-2-carboxylate, 4-(((7-chloro-8-fluoroimidazo[1,5-a]pyridin-1-yl)methyl)carbamoyl)-1-((6-cyclopropylimidazo[1,2-a]pyridin-2-yl)methyl)-1H-pyrrole-2-carboxylic acid, N-((7-chloro-8-fluoroimidazo[1,5-a]pyridin-1-yl)methyl)-1-((6-cyclopropylimidazo[1,2-a]pyridin-2-yl)methyl)-1H-imidazole-4-carboxamide, methyl 2-((4-(((7-chloro-8-fluoroimidazo[1,5-a]pyridin-1-yl)methyl)carbamoyl)-1H-1,2,3-triazol-1-yl)methyl)-6-cyclopropyl-1H-indole-3-carboxylate, N-((7-chloro-8-fluoroimidazo[1,5-a]pyridin-1-yl)methyl)-1-((6-cyclopropyl-8-(hydroxy(3-(hydroxymethyl)oxetan-3-yl)methyl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((8-cyano-3-cyclopropylquinolin-6-yl)methyl)-1H-1,2,3-triazole-4-carboxamide, 2-((4-(((7-chloro-8-fluoroimidazo[1,5-a]pyridin-1-yl)methyl)carbamoyl)-1H-1,2,3-triazol-1-yl)methyl)-6-cyclopropyl-1H-indole-3-carboxylic acid, 6-((4-(((7-chloro-8-fluoroimidazo[1,5-a]pyridin-1-yl)methyl)carbamoyl)-1H-1,2,3-triazol-1-yl)methyl)-3-cyclopropylquinoline-8-carboxamide, N-((7-chloro-8-fluoroimidazo[1,5-a]pyridin-1-yl)methyl)-1-((6-cyclopropylimidazo[1,2-a]pyridin-2-yl)methyl)-1H-pyrrole-3-carboxamide, N-((7-chloro-6-fluoroimidazo[1,5-a]pyridin-1-yl)methyl)-1-((6-cyclopropylimidazo[1,2-a]pyridin-2-yl)methyl)-1H-1,2,3-triazole-4-carboxamide, N-(1-(7-chloro-8-fluoroimidazo[1,5-a]pyridin-1-yl)ethyl)-1-(1-(6-cyclopropylimidazo[1,2-a]pyridin-2-yl)ethyl)-1H-1,2,3-triazole-4-carboxamide, N-((7-chloro-8-fluoroimidazo[1,5-a]pyridin-1-yl)methyl)-1-((6-cyclopropyl-8-(hydroxy(oxetan-3-yl)methyl)imidazo[1,2-a]pyridin-2-yl)methyl)-1H-1,2,3-triazole-4-carboxamide, N-(1-(7-chloro-8-fluoroimidazo[1,5-a]pyridin-1-yl)ethyl)-1-((6-cyclopropyl-8-(hydroxy(oxetan-3-yl)methyl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-((N-(2,2,2-trifluoroethyl)sulfamoyl)methyl)imidazo[1,2-a]pyridin-2-yl)methyl)-1H-1,2,3-triazole-4-carboxamide, 1-([1,2,4]triazolo[1,5-a]pyridin-2-ylmethyl)-N-((7-chloro-8-fluoroimidazo[1,5-a]pyridin-1-yl)methyl)-1H-pyrazole-4-carboxamide, N-((7-chloro-8-fluoroimidazo[1,5-a]pyridin-1-yl)methyl)-2-((6-cyclopropylimidazo[1,2-a]pyridin-2-yl)methyl)-2H-tetrazole-5-carboxamide, N-((7-chloro-8-fluoroimidazo[1,5-a]pyridin-1-yl)methyl)-1-(imidazo[1,2-a]pyridin-2-ylmethyl)-1H-pyrazole-4-carboxamide, N-((7-chloro-8-fluoroimidazo[1,5-a]pyridin-1-yl)methyl)-1-(imidazo[1,2-b]pyridazin-2-ylmethyl)-1H-pyrazole-4-carboxamide, N-((7-chloro-8-fluoroimidazo[1,5-a]pyridin-1-yl)methyl)-

1-(imidazo[1,2-a]pyridin-2-ylmethyl)-1H-1,2,3-triazole-4-carboxamide, 1-([1,2,4]triazolo[1,5-a]pyridin-2-ylmethyl)-N-((7-chloro-8-fluoroimidazo[1,5-a]pyridin-1-yl)methyl)-1H-1,2,3-triazole-4-carboxamide, N-((7-chloro-8-fluoroimidazo[1,5-a]pyridin-1-yl)methyl)-1-((6-cyclopropylimidazo[1,2-b]pyridazin-2-yl)methyl)-1H-imidazole-4-carboxamide, N-((7-chloro-8-fluoroimidazo[1,5-a]pyridin-1-yl)methyl)-2-((6-cyclopropylimidazo[1,2-b]pyridazin-2-yl)methyl)-2H-tetrazole-5-carboxamide, N-((7-chloro-8-fluoroimidazo[1,5-a]pyridin-1-yl)methyl)-1-(imidazo[1,2-b]pyridazin-2-ylmethyl)-1H-1,2,3-triazole-4-carboxamide, N-((7-chloro-8-fluoroimidazo[1,5-a]pyridin-1-yl)methyl)-1-(imidazo[1,2-b]pyridazin-2-ylmethyl)-1H-imidazole-4-carboxamide, N-((7-chloro-8-fluoroimidazo[1,5-a]pyridin-1-yl)methyl)-1-(quinoxalin-6-ylmethyl)-1H-1,2,3-triazole-4-carboxamide, N-((7-chloro-8-fluoroimidazo[1,5-a]pyridin-1-yl)methyl)-1-(quinoxalin-6-ylmethyl)-1H-pyrazole-4-carboxamide, 1-((8-(4H-1,2,4-triazol-4-yl)imidazo[1,2-b]pyridazin-2-yl)methyl)-N-((7-chloro-8-fluoroimidazo[1,5-a]pyridin-1-yl)methyl)-1H-1,2,3-triazole-4-carboxamide, N-((7-chloro-8-fluoroimidazo[1,5-a]pyridin-1-yl)methyl)-1-((6-cyclopropyl-8-(pyrrolidin-1-ylmethyl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((8-(oxetan-3-ylmethyl)imidazo[1,2-b]pyridazin-2-yl)methyl)-1H-1,2,3-triazole-4-carboxamide, N-((7-chloro-8-fluoroimidazo[1,5-a]pyridin-1-yl)methyl)-1-(imidazo[1,2-a]pyridin-2-ylmethyl)-1H-imidazole-4-carboxamide, 1-((8-(aminomethyl)-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide, N-((7-chloro-8-fluoroimidazo[1,5-a]pyridin-1-yl)methyl)-1-((6-cyclopropyl-8-((2-(dimethylamino)ethoxy)methyl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(((3,3,3-trifluoro-2-hydroxypropyl)amino)methyl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-((2-hydroxyethoxy)methyl)imidazo[1,2-a]pyridin-2-yl)methyl)-1H-1,2,3-triazole-4-carboxamide, 1-((8-((2-aminoethoxy)methyl)-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide, N-((7-bromoimidazo[1,5-a]pyridin-1-yl)methyl)-1-((6-cyclopropylimidazo[1,2-a]pyridin-2-yl)methyl)-1H-1,2,3-triazole-4-carboxamide, or a pharmaceutically acceptable salt thereof.

C. Pharmaceutical Compositions

In another aspect, the present invention provides pharmaceutical compositions comprising a compound of Formulae (I)-(V) or a compound of Formulae (I)-(V) in combination with a pharmaceutically acceptable excipient (e.g., carrier).

The pharmaceutical compositions include optical isomers, diastereomers, or pharmaceutically acceptable salts of the inhibitors disclosed herein. A compound of Formulae (I)-(III-d) included in the pharmaceutical composition may be covalently attached to a carrier moiety, as described above. Alternatively, a compound of Formulae (I)-(V) included in the pharmaceutical composition is not covalently linked to a carrier moiety.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be coadministered to the subject. Coadministration is meant to include simultaneous or sequential administration of the compounds individually or in combination (more than one compound). The preparations can also be combined, when desired, with other active substances (e.g. to reduce metabolic degradation).

In some embodiments, a test agent as described herein can be incorporated into a pharmaceutical composition for administration by methods known to those skilled in the art and described herein for provided compounds.

D. Formulations

Compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

E. Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat HAE, such compositions will contain an amount of active ingredient effective to achieve the desired result (e.g. inhibiting pKal and/or decreasing the amount of bradykinin in a subject).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to pKal inhibition); presence of other diseases or other health-related problems; kind of concurrent treatment; and complications from any disease or treatment regimen. Other therapeutic regimens or agents can be used in conjunction with the methods and compounds of the invention.

For any provided compound or test agent, the therapeutically effective amount can be initially determined from cell culture assays. Target concentrations will be those concentrations of active compound(s) that are capable of decreasing pKal enzymatic activity as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring pKal inhibition and adjusting the dosage upwards or downwards, as described above.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments, the dosage range is 0.001% to 10% (w/v). In some embodiments, the dosage range is 0.1% to 5% (w/v).

Dosage amounts and intervals can be adjusted individually to provide levels of the administered compound effective for the particular clinical indication being treated. This will provide a therapeutic regimen that is commensurate with the severity of the individual's disease state.

F. Methods of Treatment

The present disclosure provides compounds for use in medicine. The present disclosure further provides the use of any compounds described herein for inhibiting the activity of pKal, which would be beneficial to treatment of pKal-mediated diseases and conditions. Exemplary pKal-mediated disorders include edema, which refers to swelling in the whole body of a subject or a part thereof due to inflammation or injury when small blood vessels become leaky and releases fluid into nearby tissues. In some examples, the edema is HAE. In other examples, the edema occurs in eyes, e.g., diabetic macular edema (DME). The present disclosure provides methods of inhibiting the activity of pKal. In certain embodiments, the application provides a method of inhibiting the activity of pKal in vitro via contacting any of the compounds described herein with pKal molecules in a sample, such as a biological sample. In certain embodiments, the application provides a method of inhibiting the activity of pKal in vivo via delivering an effective amount of any of the compounds described herein to a subject in need of the treatment through a suitable route.

In certain embodiments, the methods comprise administering to a subject in need thereof (e.g., a subject such as a human patient with edema) any of the compounds described herein or a pharmaceutically acceptable salt thereof. In certain embodiments, the methods comprise administering a compound of Formulae (I)-(V), or a pharmaceutically acceptable salt or composition thereof, to a subject in need thereof. In some embodiments, the method comprises administering a pharmaceutical composition comprising a compound of Formulae (I)-(V), or a pharmaceutically acceptable salt to a subject in need thereof.

In certain embodiments, the subject to be treated by any of the methods described herein is a human patient having, suspected of having, or at risk for edema, for example, HAE or diabetic macular edema (DME). A subject having an edema can be identified by routine medical examination, e.g., laboratory tests. A subject suspected of having an edema might show one or more symptoms of the disease/disorder. A subject at risk for edema can be a subject having one or more of the risk factors associated with the disease, for example, deficiency in C1-INH as for HAE.

In certain embodiments, provided herein are methods of alleviating one or more symptoms of HAE in a human patient who is suffering from an HAE attack. Such a patient can be identified by routine medical procedures. An effective amount of one or more of the provided compounds can be given to the human patient via a suitable route, for example, those described herein. The compounds described herein may be used alone, or may be used in combination with other anti-HAE agents, for example, a C1 esterase inhibitor (e.g., Cinryze® or Berinert®), a pKal inhibitor (e.g., ecallantide or lanadelumab) or a bradykinin B2 receptor antagonist (e.g., Firazyr®).

In other embodiments, provided herein are methods or reducing the risk of HAE attack in a human HAE patient who is in quiescent stage. Such a patient can be identified based on various factors, including history of HAE attack. An effective amount of one or more of the compounds can be given to the human patient via a suitable route, for example, those described herein. The compounds described herein may be used alone, or may be used in combination with other anti-HAE agents, for example, a C1 esterase inhibitor (e.g., Cinryze® or Berinert®), a pKal inhibitor (e.g., ecallantide or lanadelumab) or a bradykinin B2 receptor antagonist (e.g., Firazyr®).

In yet other embodiments, provided herein are prophylactic treatment of HAE in human patients having risk to HAE attacks with one or more of the compounds described herein. Patients suitable for such prophylactic treatment may be human subjects having history of HAE attacks (e.g., human subjects experiencing more than 2 attacks per month). Alternatively, patients suitable for the prophylactic treatment may be human subjects having no HAE attack history but bearing one or more risk factors for HAE (e.g., family history, genetic defects in C1-INH gene, etc.) Such prophylactic treatment may involve the compounds described herein as the sole active agent, or involve additional anti-HAE agents, such as those described herein.

In certain embodiments, provided herein are methods for preventing or reducing edema in an eye of a subject (e.g., a human patient). In some examples, the human patient is a diabetic having, suspected of having, or at risk for diabetic macular edema (DME). DME is the proliferative form of diabetic retinopathy characterized by swelling of the retinal layers, neovascularization, vascular leak, and retinal thickening in diabetes mellitus due to leaking of fluid from blood vessels within the macula. To practice this method, an effective amount of one or more of the compounds described herein, or pharmaceutically acceptable salts thereof, may be delivered into the eye of the subject where treatment is needed. For example, the compound may be delivered by intraocular injection, or intravitreal injection. A subject may be treated with the compound as described herein, either as the sole active agent, or in combination with another treatment for DME. Non-limiting examples of treatment for DME include laser photocoagulation, steroids, VEGF pathway targeting agents (e.g., Lucentis® (ranibizumab) or Eylea® (aflibercept)), and/or anti-PDGF agents.

In certain embodiments, the methods disclosed herein comprise administering to the subject an effective amount of a compound of Formulae (I)-(V), or a pharmaceutically acceptable salt or composition thereof. In some embodiments, the effective amount is a therapeutically effective amount. In some embodiments, the effective amount is a prophylactically effective amount.

In certain embodiments, the subject being treated is an animal. The animal may be of either sex and may be at any stage of development. In certain embodiments, the subject is a mammal. In certain embodiments, the subject being treated is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Certain methods described herein may comprise administering one or more additional pharmaceutical agent(s) in combination with the compounds described herein. The additional pharmaceutical agent(s) may be administered at the same time as the compound of Formulae (I)-(V), or at different times than the compound of Formulae (I)-(V). For example, the compound of Formulae (I)-(V) and any additional pharmaceutical agent(s) may be on the same dosing schedule or different dosing schedules. All or some doses of the compound of Formulae (I)-(V) may be administered before all or some doses of an additional pharmaceutical agent, after all or some does an additional pharmaceutical agent, within a dosing schedule of an additional pharmaceutical agent, or a combination thereof. The timing of administration of the compound of Formulae (I)-(V) and additional pharmaceutical agents may be different for different additional pharmaceutical agents.

In certain embodiments, the additional pharmaceutical agent comprises an agent useful in the treatment of an edema, such as HAE or DME. Examples of such agents are provided herein.

The following numbered embodiments, while non-limiting, are exemplary of certain aspects of the present disclosure:

1. A compound of Formula (I):

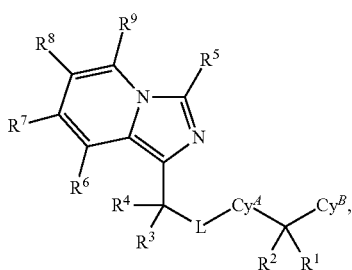

(I)

or a pharmaceutically acceptable salt thereof, wherein:

$Cy^A$ is selected from 3- to 7-membered saturated or partially unsaturated monocyclic heterocyclyenel having 1-2 heteroatoms selected from oxygen, nitrogen, or sulfur, 5- to 6-membered heteroarylene having 1-4 heteroatoms selected from oxygen, nitrogen, or sulfur, 7- to 10-membered saturated or partially unsaturated bicyclic heterocyclylene having 1-4 heteroatoms selected from oxygen, nitrogen, or sulfur, and 7- to 10-membered bicyclic heteroarylene having 1-4 heteroatoms selected from oxygen, nitrogen, or sulfur, wherein $Cy^A$ is substituted with 0-4 $R^A$ groups;

each $R^A$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

$Cy^B$ is selected from 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic heterocyclyl having 1-5 heteroatoms selected from oxygen, nitrogen, or sulfur, and 7- to 10-membered bicyclic heteroaryl having 1-5 heteroatoms selected from oxygen, nitrogen, or sulfur, wherein $Cy^B$ is substituted with 0-5 $R^B$ groups;

each $R^B$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

L is selected from -QC(R)$_2$—, —C(R)$_2$Q-, -QC(Q)-, —C(Q)Q-, —C(R)$_2$QC(O)—, and —C(O)QC(R)$_2$—, wherein each Q is independently a monovalent or divalent group as valency allows, selected from the group consisting of O, N(R), or (S);

$R^1$, $R^2$, $R^3$, and $R^4$ are independently selected from hydrogen and $C_{1-6}$ aliphatic;

$R^5$, $R^6$, $R^7$, $R^8$, and $R^9$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur; and each R is independently hydrogen, —CN, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur;

with the proviso that the compound is other than N-((7-chloroimidazo[1,5-a]pyridin-1-yl)methyl)-2-((3-chloroquinolin-6-yl)methyl)isonicotinamide.

2. The compound of embodiment 1, wherein the compound is of Formula (IV):

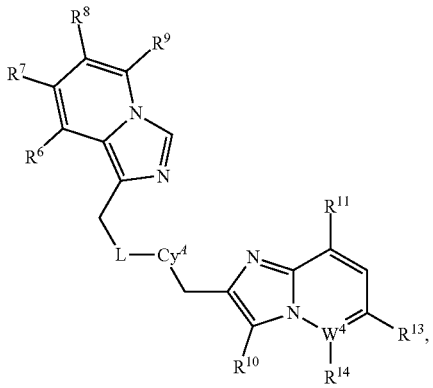

IV or a pharmaceutically acceptable salt thereof,
wherein:
Cy$^4$ is a 5-membered heteroarylene having 1-4 heteroatoms selected from oxygen or nitrogen, wherein Cy$^4$ is substituted with 0-3 R$^4$ groups;
L is selected from —NC(O)— and —C(O)N—;
R$^6$, R$^8$, and R$^9$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
R$^7$ is —F, —Cl, or —Br;
W$^4$ is carbon or nitrogen;
R$^{10}$ and R$^{11}$ are each optionally present, and if present are independently selected from halogen, —CN, —C(R)=N (R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$ R, —N(R)C(O)N(R)$_2$, —N(R)S(O)$_2$R, —OR, —OC(O) R, —OC(O)N(R)$_2$, —SR, —S(O)R, —S(O)$_2$R, —S(O)N (R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
R$^{13}$ is selected from halogen, —CN, —C(R)=N(R), —C(O)R, —C(O)$_2$R, —C(O)N(R)$_2$, —NO$_2$, —N(R)—N (R)$_2$, —N(R)$_2$, —N(R)C(O)R, —N(R)C(O)$_2$R, —N(R)C (O)N(R)$_2$, —N(R)S(O)$_2$R, —OR, —OC(O)R, —OC(O) N(R)$_2$, —SR, —S(O)R, —S(O)$_2$R, —S(O)N(R)$_2$, —S(O)$_2$ N(R)$_2$, or an optionally substituted group selected from C$_{2-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

R$^{14}$ is optionally present, and if present and is selected from halogen, —CN, —C(R)=N(R), —C(O)R, —C(O)$_2$R, —C(O)N(R)$_2$, —NO$_2$, —N(R)—N(R)$_2$, —N(R)C(O)R, —N(R)C(O)$_2$R, —N(R)C(O)N(R)$_2$, —N(R)S(O)$_2$R, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{3-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur; and each R is independently hydrogen, —CN, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur.

3. The compound of any one of the preceding embodiments, wherein the compound is of Formula (V):

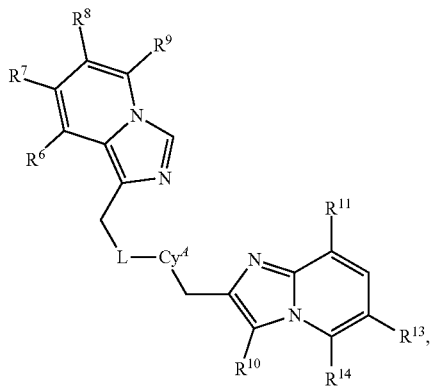

V or a pharmaceutically acceptable salt thereof,
wherein:
Cy$^4$ is a 5-membered heteroarylene having 1-4 nitrogens, wherein when Cy$^4$ comprises 3 nitrogens, Cy$^4$ is not

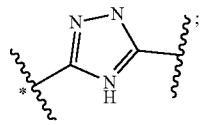 [SMILES: *c1n[nH]c(*)n1]

L is selected from —NC(O)— and —C(O)N—;
R$^6$, R, and R$^9$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

$R^7$ is —F, —Cl, or —Br;

$R^{10}$ is optionally present, and if present is selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

$R^{11}$ is optionally present, and if present is selected from halogen, —CN, —C(R)=N(R), —C(O)R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_1$, aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

$R^{13}$ is selected from —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from phenyl, 5- to 6-membered heteroaryl having 1-4 heteroatoms selected from oxygen, nitrogen, or sulfur, 3- or 5-7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

$R^{14}$ is optionally present, and if present and is selected from halogen, —CN, —C(R)=N(R), —C(O)R, —C(O)$_2$R, —C(O)N(R)$_2$, —NO$_2$, —N(R)—N(R)$_2$, —N(R)C(O)R, —N(R)C(O)$_2$R, —N(R)C(O)N(R)$_2$, —N(R)S(O)$_2$R, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{3-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur; and each R is independently hydrogen, —CN, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur.

4. The compound of any one of the preceding embodiments, wherein L is selected from -QC(R)$_2$—, —C(R)$_2$Q-, —C(Q)Q-, or —C(R)$_2$QC(O)—, wherein Q is independently a monovalent or divalent group as valency allows, selected from O or N(R).

5. The compound of any one of of the preceding embodiments, wherein L is —N(H)C(O)—.

6. The compound of any one of of the preceding embodiments, L is —C(O)N(H)—. The compound of any one of the preceding embodiments, wherein L is selected from the group consisting of:

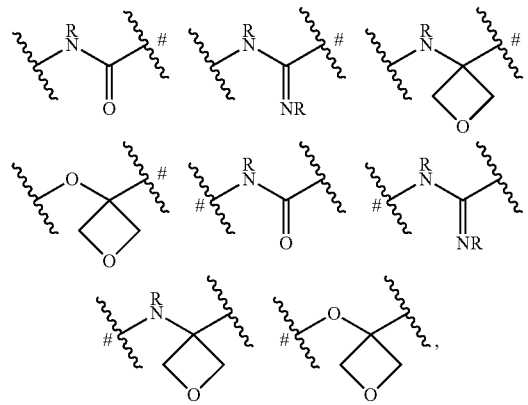

wherein # represents to point of attachment to $Cy^A$.

7. The compound of any one of the preceding embodiments, wherein L is selected from the group consisting of:

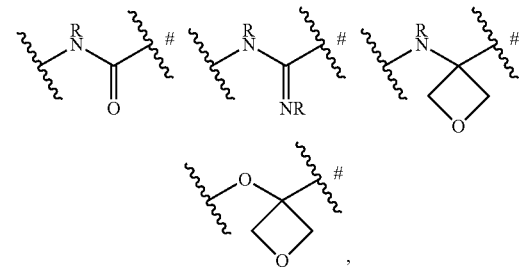

wherein # represents to point of attachment to $Cy^A$.

8. The compound of any one of the preceding embodiments, wherein L is:

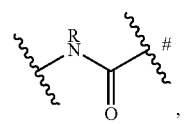

wherein # represents to point of attachment to $Cy^A$.

9. The compound of any one of the preceding embodiments, wherein $R^3$ and $R^4$ are hydrogen.

10. The compound of any one of the preceding embodiments, wherein the compound is of Formula (II):

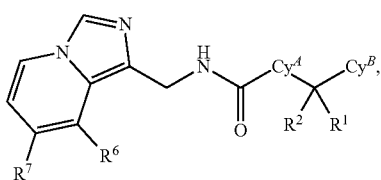

(II)

or a pharmaceutically acceptable salt thereof,
wherein:

$Cy^A$ is selected from 3- to 7-membered saturated or partially unsaturated monocyclic heterocyclyenel having 1-2 heteroatoms selected from oxygen, nitrogen, or sulfur, 5- to 6-membered heteroarylene having 1-4 heteroatoms selected from oxygen, nitrogen, or sulfur, 7- to 10-membered saturated or partially unsaturated bicyclic heterocyclylene having 1-4 heteroatoms selected from oxygen, nitrogen, or sulfur, and 7- to 10-membered bicyclic heteroarylene having 1-4 heteroatoms selected from oxygen, nitrogen, or sulfur, wherein $Cy^A$ is substituted with 0-4 $R^A$ groups;

each $R^A$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

$Cy^B$ is selected from 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic heterocyclyl having 1-5 heteroatoms selected from oxygen, nitrogen, or sulfur, and 7- to 10-membered bicyclic heteroaryl having 1-5 heteroatoms selected from oxygen, nitrogen, or sulfur, wherein $Cy^B$ is substituted with 0-5 $R^B$ groups;

each $R^B$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

$R^1$ and $R^2$ are independently selected from hydrogen and $C_{1-6}$ aliphatic;

$R^6$ and $R^7$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur; and each R is independently hydrogen, —CN, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur;

with the proviso that the compound is other than N-((7-chloroimidazo[1,5-a]pyridin-1-yl)methyl)-2-((3-chloroquinolin-6-yl)methyl)isonicotinamide.

11. The compound of any one of the preceding embodiments, with the proviso that $Cy^A$ is a group other than pyridinediyl and the compound is other than N-((7-chloroimidazo[1,5-a]pyridin-1-yl)methyl)-2-((3-chloroquinolin-6-yl)methyl)isonicotinamide.

12. The compound of any one of the preceding embodiments, wherein $Cy^A$ is selected from 5- to 6-membered heteroaryl having 1-4 heteroatoms selected from oxygen, nitrogen, or sulfur, and 7- to 10-membered bicyclic heteroaryl having 1-4 heteroatoms selected from oxygen, nitrogen, or sulfur wherein $Cy^A$ is substituted with 0-4 $R^A$ groups.

13. The compound of any one of the preceding embodiments, wherein $Cy^A$ is a 6-membered heteroarylene having 1-4 heteroatoms selected from oxygen, nitrogen, or sulfur, wherein $Cy^A$ is substituted with 0-3 $R^A$ groups.

14. The compound of any one of the preceding embodiments, wherein $Cy^A$ is a 6-membered heteroarylene having 1 nitrogen, wherein $Cy^A$ is substituted with 0-3 $R^A$ groups.

15. The compound of any one of the preceding embodiments, wherein $Cy^A$ is selected from either:

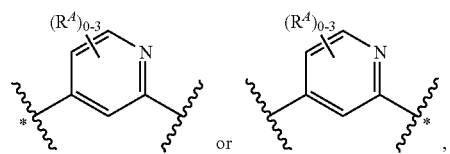

wherein * represents to point of attachment to L.

16. The compound of any one of the preceding embodiments, wherein $Cy^A$ is a 7- to 10-membered bicyclic heteroarylene having 1-4 heteroatoms selected from oxygen, nitrogen, or sulfur wherein $Cy^A$ is substituted with 0-4 $R^A$ groups.

17. The compound of any one of the preceding embodiments, wherein Cy$^A$ is a 9-membered bicyclic heteroarylene having 2 nitrogens wherein Cy$^A$ is substituted with 0-4 R$^A$ groups.

18. The compound of any one of the preceding embodiments, wherein Cy$^A$ is a pyrrolopyridinediyl substituted with 0-4 R$^A$ groups.

19. The compound of any one of the preceding embodiments, wherein Cy$^A$ is a 5-membered heteroarylene having 1-4 heteroatoms selected from oxygen, nitrogen, or sulfur, wherein Cy$^A$ is substituted with 0-2 R$^A$ groups.

20. The compound of any one of the preceding embodiments, wherein Cy$^A$ is selected from the group consisting of: pyrrolediyl substituted with 0-3 R$^A$ groups, pyrazolediyl substituted with 0-2 R$^A$ groups, triazolediyl substituted with 0-1 R$^A$ groups, thiazolediyl substituted with 0-1 R$^A$ groups, imidazolediyl substituted with 0-2 R$^A$ groups, oxazolediyl substituted with 0-1 R$^A$ groups, isoxazolediyl substituted with 0-1 R$^A$ groups, unsubstituted tetrazolediyl, unsubstituted oxadiazolediyl, and unsubstituted thiadiazolediyl.

21. The compound of any one of the preceding embodiments, wherein Cy$^A$ is selected from the group consisting of:

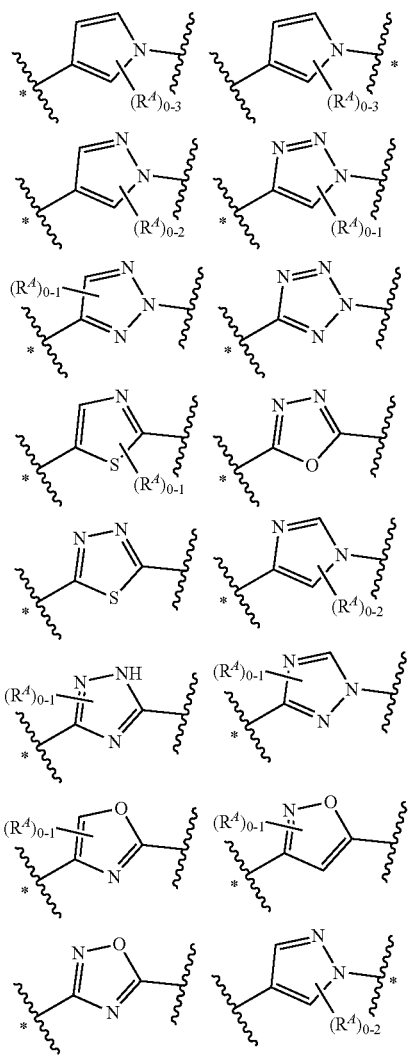

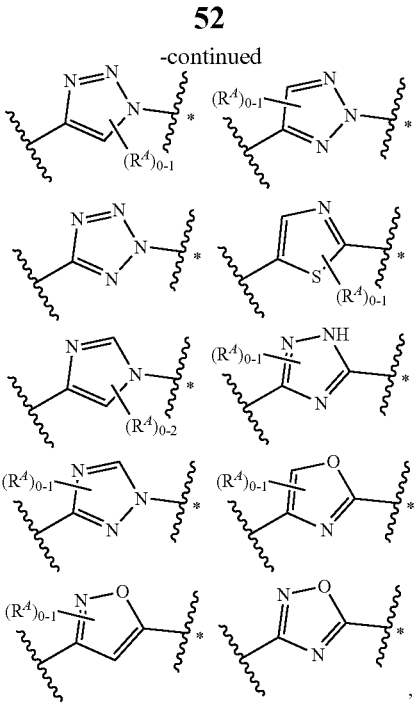

wherein * represents to point of attachment to L.

22. The compound of any one of the preceding embodiments, wherein Cy$^A$ is a 5-membered heteroarylene having 1-4 heteroatoms selected from oxygen or nitrogen.

23. The compound of any one of the preceding embodiments, wherein Cy$^A$ is a 5-membered heteroarylene having 1-4 nitrogens.

24. The compound of any one of the preceding embodiments, wherein Cy$^A$ is a 5-membered heteroarylene having 1-4 nitrogen, wherein when Cy$^A$ comprises 3 nitrogen, it is not a a 1,2,4, triazolediyl.

25. The compound of any one of the preceding embodiments, wherein Cy$^A$ is selected from the group consisting of:

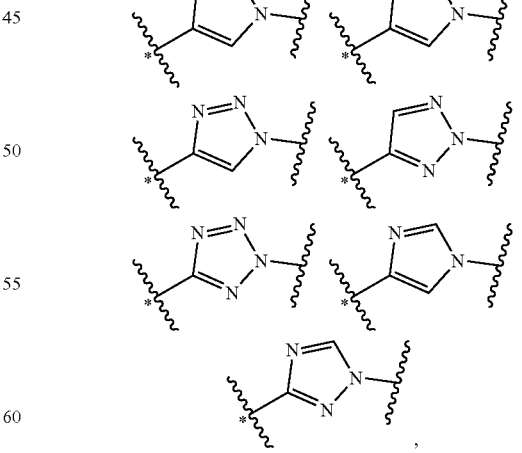

wherein * represents to point of attachment to L.

26. The compound of any one of the preceding embodiments, wherein the compound is of Formula (III-a) through (III-d):

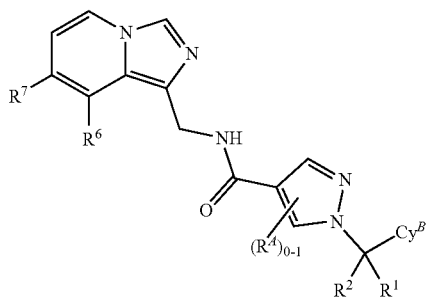

(III-a)

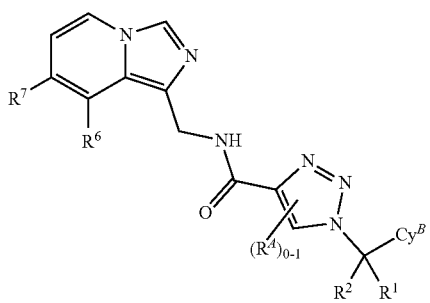

(III-b)

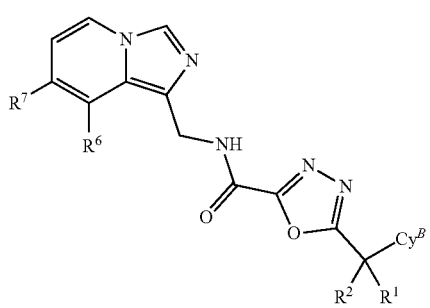

(III-c)

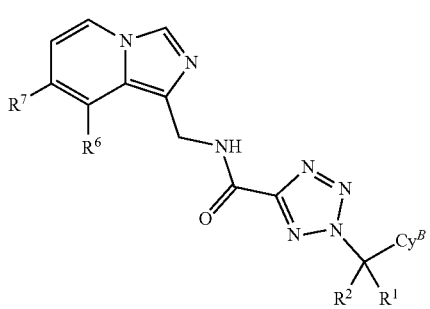

(III-d)

or a pharmaceutically acceptable salt thereof,
wherein:
each $R^A$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

Cy$^B$ is selected from 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic heterocyclyl having 1-5 heteroatoms selected from oxygen, nitrogen, or sulfur, and 7- to 10-membered bicyclic heteroaryl having 1-5 heteroatoms selected from oxygen, nitrogen, or sulfur, wherein Cy$^B$ is substituted with 0-5 R$^B$ groups;

each R$^B$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

R$^1$ and R$^2$ are independently selected from hydrogen and C$_{1-6}$ aliphatic;

R$^6$ and R$^7$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur; and each R is independently hydrogen, —CN, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur.

27. The compound of any one of the preceding embodiments, wherein Cy$^B$ is selected from phenyl, 7- to 10-membered saturated or partially unsaturated bicyclic heterocyclyl having 1-5 heteroatoms selected from oxygen, nitrogen, or sulfur, and 7- to 10-membered bicyclic heteroaryl having 1-5 heteroatoms selected from oxygen, nitrogen, or sulfur, wherein Cy$^B$ is substituted with 0-5 R$^B$ groups.

28. The compound of any one of the preceding embodiments, wherein Cy$^B$ is a 7- to 10-membered bicyclic heteroaryl having 1-5 heteroatoms selected from oxygen, nitrogen, or sulfur, wherein Cy$^B$ is substituted with 0-5 R$^B$ groups.

29. The compound of any one of the preceding embodiments, wherein Cy$^B$ is a 10-membered bicyclic heteroaryl having 1-5 heteroatoms selected from oxygen, nitrogen, or sulfur, wherein $Cy^B$ is substituted with 0-5 $R^B$ groups.

30. The compound of any one of the preceding embodiments, wherein $Cy^B$ is a 10-membered bicyclic heteroaryl having 1 nitrogen, wherein $Cy^B$ is substituted with 0-5 $R^B$ groups.

31. The compound of any one of the preceding embodiments, wherein $Cy^B$ is selected from the group consisting of: quinolonyl group substituted with 0-5 $R^B$ groups and quinoxalinyl group substituted with 0-5 $R^B$ groups.

32. The compound of any one of the preceding embodiments, wherein $Cy^B$ is selected from the group consisting of:

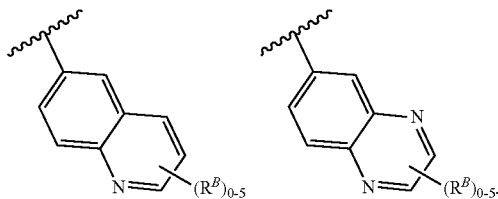

33. The compound of any one of the preceding embodiments, wherein $Cy^B$ is a 9-membered bicyclic heteroaryl having 1-5 heteroatoms selected from oxygen, nitrogen, or sulfur, wherein $Cy^B$ is substituted with 0-5 $R^B$ groups.

34. The compound of any one of the preceding embodiments, wherein $Cy^B$ is

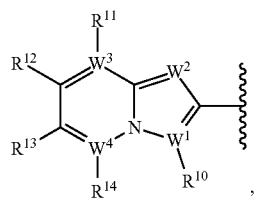

wherein:
$W^1$, $W^2$, $W^3$, and $W^4$ are independently selected from carbon and nitrogen;
$R^{10}$, $R^{11}$, $R^{12}$, $R^{13}$, and $R^{14}$ are each optionally present when attached to a carbon atom, and if present correspond to an occurrence of $R^B$ independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur; and
each R is independently hydrogen, —CN, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur.

35. The compound of any one of the preceding embodiments, $W^4$ is carbon.

36. The compound of any one of the preceding embodiments, $W^4$ is nitrogen.

37. The compound of any one of the preceding embodiments, $W^1$ is nitrogen and $W^2$, $W^3$ and $W^4$ are carbon.

38. The compound of any one of the preceding embodiments, $W^2$ is nitrogen and $W^1$, $W^3$ and $W^4$ are carbon.

39. The compound of any one of the preceding embodiments, nitrogen and $W^1$ and $W^4$ are carbon.

40. The compound of any one of the preceding embodiments, $W^2$ and $W^4$ are nitrogen and $W^1$ and $W^3$ are carbon.

41. The compound of any one of the preceding embodiments, wherein $Cy^B$ is selected from the group consisting of imidazopyridinyl substituted with 0-5 $R^B$ groups, pyrazolopyridinyl substituted with 0-5 $R^B$ groups, pyrrolopyridinyl substituted with 0-4 $R^B$ groups, triazolopyridinyl substituted with 0-4 $R^B$ groups, imidazopyrimidinyl substituted with 0-4 $R^B$ groups, imidazopyridazinyl substituted with 0-4 $R^B$ groups, indolizinyl substituted with 0-5 $R^B$ groups, and pyrazolopyrimidinyl substituted with 0-4 $R^B$ groups.

42. The compound of any one of the preceding embodiments, wherein $Cy^B$ is selected from the group consisting of:

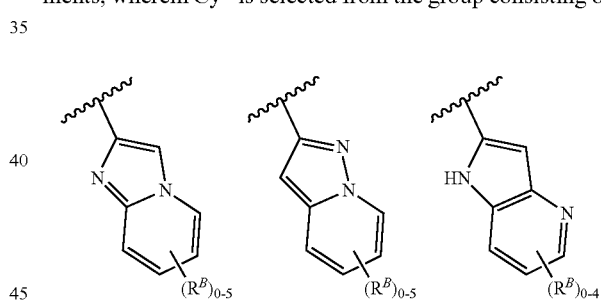

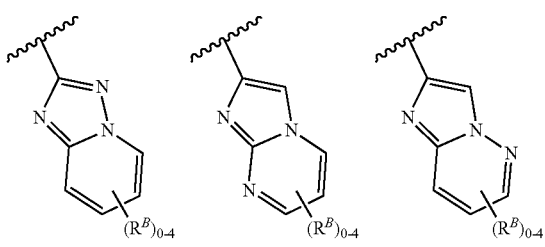

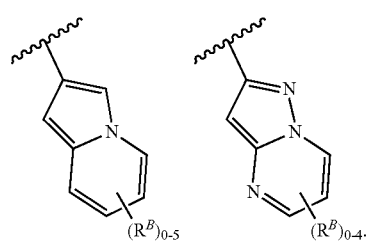

43. The compound of any one of the preceding embodiments, wherein $Cy^B$ is

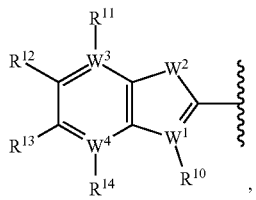

wherein:
$W^2$ is selected from carbon, nitrogen, oxygen, and sulfur; $W^1$, $W^3$, and $W^4$ are independently selected from carbon and nitrogen;
$R^{10}$, $R^{11}$, $R^{12}$, $R^{13}$, and $R^{14}$ are each optionally present when attached to a carbon atom, and if present correspond to an occurrence of $R^B$ independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur; and
each R is independently hydrogen, —CN, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur.

44. The compound of any one of the preceding embodiments, wherein $Cy^B$ is selected from the group consisting of a indolyl substituted with 0-5 $R^B$ groups, a benzofuranyl substituted with 0-5 $R^B$ groups, a benzimidazolyl substituted with 0-4 $R^B$ groups, and a thienopyridinyl substituted with 0-4 $R^B$ groups.

45. The compound of any one of the preceding embodiments, wherein $Cy^B$ is selected from the group consisting of:

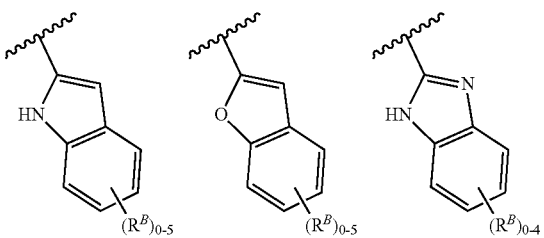

-continued

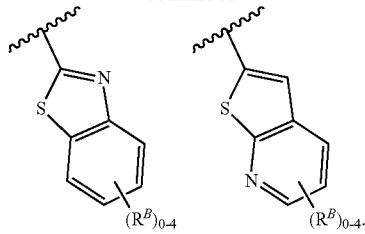

46. The compound of any one of the preceding embodiments, wherein each $R^A$ is independently selected from an optionally substituted group selected from $C_{1-6}$ aliphatic, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur.

47. The compound of any one of the preceding embodiments, wherein substituents on an optionally substituted $R^A$ group are independently halogen, $(CH_2)_{0-4}R°$, —$(CH_2)_{0-4}OR°$; and —$(CH_2)_{0-4}C(O)OR°$, wherein each $R°$ is independently hydrogen, $C_{1-6}$ aliphatic, or a 5-6 membered saturated, partially unsaturated, or aryl ring having 0-4 heteroatoms independently selected from nitrogen, oxygen, or sulfur.

48. The compound of any one of the preceding embodiments, wherein a single instance of $R^A$ is $C_{1-6}$ aliphatic substituted with halogen.

49. The compound of any one of the preceding embodiments, wherein a single instance of $R^A$ is $C_{1-6}$ aliphatic substituted with —$(CH_2)_{0-4}OR°$, wherein $R°$ is hydrogen or $C_{1-6}$ aliphatic.

50. The compound of any one of the preceding embodiments, wherein a single instance of $R^A$ is $C_{1-6}$ aliphatic substituted with —$(CH_2)_{0-4}C(O)OR°$, wherein $R°$ is hydrogen or $C_{1-6}$ aliphatic.

51. The compound of any one of the preceding embodiments, wherein a single instance of $R^A$ is $C_{1-6}$ aliphatic is substituted with 5-6 membered saturated, partially unsaturated, or aryl ring having 0-4 heteroatoms independently selected from nitrogen, oxygen, or sulfur.

52. The compound of any one of the preceding embodiments, wherein a single instance of $R^A$ is optionally substituted 3- to 7-membered saturated or partially unsaturated monocyclic carbocyclyl. In some embodiments, a single instance of $R^A$ is optionally substituted cyclopropyl. In some embodiments, a single instance of $R^A$ is cyclopropyl substituted with —$(CH_2)_{0-4}C(O)OR°$ and $R°$ is hydrogen or $C_{1-6}$ aliphatic.

53. The compound of any one of the preceding embodiments, wherein $R^5$, $R^6$, $R^7$, $R^8$, and $R^9$ are independently selected from hydrogen, halogen, —CN, —N(R)$_2$, —OR, or an optionally substituted group selected from $C_{1-4}$ aliphatic, 3- to 7-membered saturated or partially unsaturated monocyclic carbocyclyl, wherein each R is independently hydrogen or $C_{1-6}$ aliphatic.

54. The compound of any one of the preceding embodiments, wherein $R^5$, $R^6$, and $R^9$ are hydrogen.

55. The compound of any one of the preceding embodiments, wherein $R^6$ is selected from hydrogen or halogen.

56. The compound of any one of the preceding embodiments, wherein R is hydrogen.

57. The compound of any one of the preceding embodiments, wherein R is halogen.

58. The compound of any one of the preceding embodiments, wherein $R^6$ is —F.

59. The compound of any one of the preceding embodiments, wherein $R^6$ is —Cl.

60. The compound of any one of the preceding embodiments, wherein R is —Br.

61. The compound of any one of the preceding embodiments, wherein $R^7$ is selected from halogen or an optionally substituted $C_{1-6}$ aliphatic.

62. The compound of any one of the preceding embodiments, wherein $R^7$ is halogen.

63. The compound of any one of the preceding embodiments, wherein $R^7$ is —F.

64. The compound of any one of the preceding embodiments, wherein $R^7$ is —Cl.

65. The compound of any one of the preceding embodiments, wherein $R^7$ is —Br.

66. The compound of any one of the preceding embodiments, wherein $R^7$ is optionally substituted $C_{1-6}$ aliphatic.

67. The compound of any one of the preceding embodiments, wherein $R^{11}$ is optionally present, and if present is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur.

68. The compound of any one of the preceding embodiments, wherein $R^{11}$ is selected from —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur.

69. The compound of any one of the preceding embodiments, wherein $R^{11}$ is selected from halogen, optionally substituted $C_{1-6}$ aliphatic, and optionally substituted 3- to 7-membered saturated or partially unsaturated monocyclic carbocyclyl.

70. The compound of any one of the preceding embodiments, wherein $R^{11}$ is halogen.

71. The compound of any one of the preceding embodiments, wherein $R^{11}$ is optionally substituted $C_{1-4}$ aliphatic.

72. The compound of any one of the preceding embodiments, wherein $R^{11}$ is an optionally substituted 3- to 7-membered saturated or partially unsaturated monocyclic carbocyclyl.

73. The compound of any one of the preceding embodiments, wherein $R^{11}$ is an optionally substituted 3- or 5-7-membered saturated or partially unsaturated monocyclic carbocyclyl.

74. The compound of any one of the preceding embodiments, wherein $R^{11}$ is an optionally substituted cyclopropyl.

75. The compound of any one of the preceding embodiments, wherein the compound is any one of compounds I-1 through I-303, or a pharmaceutically acceptable salt thereof.

76. A pharmaceutical composition comprising any one of the preceding compounds.

77. The pharmaceutical composition comprising any one of the preceding compounds further comprising a pharmaceutically acceptable excipient.

78. The pharmaceutical composition of any one of embodiments 76-77, wherein the composition is suitable for oral administration.

79. The pharmaceutical composition of any one of embodiments 76-77, wherein the composition is suitable for administration by injection.

80. A method of treating a plasma kallikrein-mediated disease or disorder using a compound or composition of any one of the preceding embodiments.

81. The method of embodiment 80, wherein the disease or disorder is hereditary angioedema or diabetic macular edema.

82. A method of treating hereditary angioedema or diabetic macular edema comprising administering to a patient in need thereof a compound of any one of the preceding embodiments.

The following numbered embodiments, while non-limiting, are also exemplary of certain aspects of the present disclosure:

83. A compound of Formula (I):

(I)

or a pharmaceutically acceptable salt thereof, wherein:

$Cy^A$ is selected from 3- to 7-membered saturated or partially unsaturated monocyclic heterocyclyenel having 1-2 heteroatoms selected from oxygen, nitrogen, or sulfur, 5- to 6-membered heteroarylene having 1-4 heteroatoms selected from oxygen, nitrogen, or sulfur, 7- to 10-membered saturated or partially unsaturated bicyclic heterocyclylene having 1-4 heteroatoms selected from oxygen, nitrogen, or sulfur, and 7- to 10-membered bicyclic heteroarylene having 1-4 heteroatoms selected from oxygen, nitrogen, or sulfur, wherein $Cy^A$ is substituted with 0-4 $R^A$ groups;

each $R^A$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

Cy$^B$ is selected from 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic heterocyclyl having 1-5 heteroatoms selected from oxygen, nitrogen, or sulfur, and 7- to 10-membered bicyclic heteroaryl having 1-5 heteroatoms selected from oxygen, nitrogen, or sulfur, wherein Cy$^B$ is substituted with 0-5 R$^B$ groups;

each R$^B$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

L is selected from -QC(R)$_2$—, —C(R)$_2$Q-, -QC(Q)-, —C(Q)Q-, —C(R)$_2$QC(O)—, and —C(O)QC(R)$_2$—, wherein each Q is independently a monovalent or divalent group as valency allows, selected from the group consisting of O, N(R), or (S);

R$^1$, R$^2$, R$^3$, and R$^4$ are independently selected from hydrogen and C$_{1-6}$ aliphatic;

R$^5$, R$^6$, R$^7$, R$^8$, and R$^9$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur; and each R is independently hydrogen, —CN, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur;

with the proviso that the compound is other than N-((7-chloroimidazo[1,5-a]pyridin-1-yl)methyl)-2-((3-chloroquinolin-6-yl)methyl)isonicotinamide.

84. The compound of embodiment 83, wherein the compound is of Formula (II):

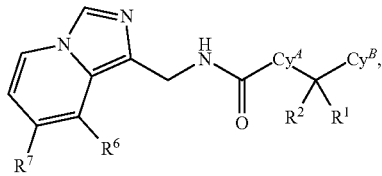

or a pharmaceutically acceptable salt thereof.

85. The compound of any one of the preceding embodiments, with the proviso that Cy$^A$ is a group other than pyridinediyl and the compound is other than N-((7-chloroimidazo[1,5-a]pyridin-1-yl)methyl)-2-((3-chloroquinolin-6-yl)methyl)isonicotinamide.

86. The compound of any one of the preceding embodiments, wherein Cy$^A$ is selected from 5- to 6-membered heteroaryl having 1-4 heteroatoms selected from oxygen, nitrogen, or sulfur, and 7- to 10-membered bicyclic heteroaryl having 1-4 heteroatoms selected from oxygen, nitrogen, or sulfur wherein Cy$^A$ is substituted with 0-4 R$^A$ groups.

87. The compound of any one of the preceding embodiments, wherein Cy$^A$ is selected from the group consisting of pyrrolopyridinediyl substituted with 0-4 R$^A$, pyrazolediyl substituted with 0-2 R$^A$ groups, triazolediyl substituted with 0-1 R$^A$ groups, thiazolediyl substituted with 0-1 R$^A$(R$^A$ (groups, imidazolediyl substituted with 0-2 R$^A$ groups, oxazolediyl substituted with 0-1 R$^A$ groups, isoxazolediyl substituted with 0-1 R$^A$ groups, unsubstituted tetrazolediyl, unsubstituted oxadiazolediyl, and unsubstituted thiadiazolediyl.

88. The compound of any one of the preceding embodiments, wherein Cy$^A$ is selected from the group consisting of:

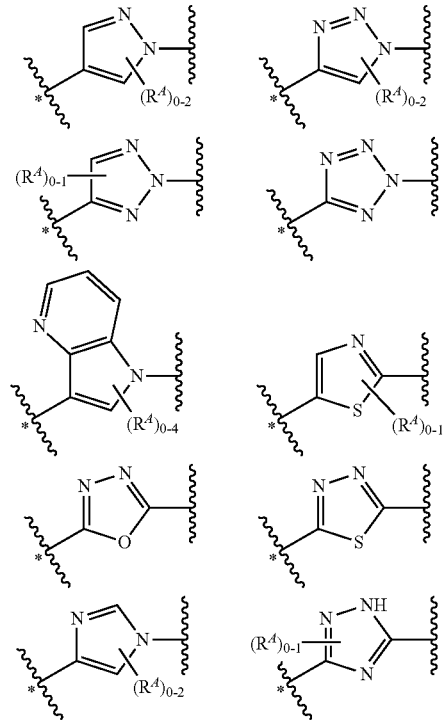

-continued

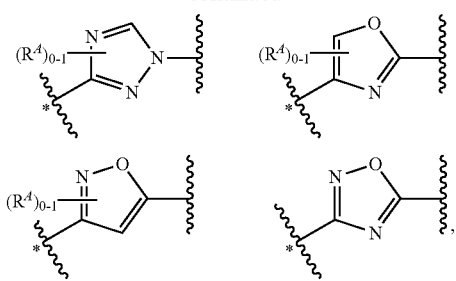

wherein * represents to point of attachment to L.

89. The compound of any one of the preceding embodiments, wherein the compound has a structure selected from the group consisting of:

(III-a)

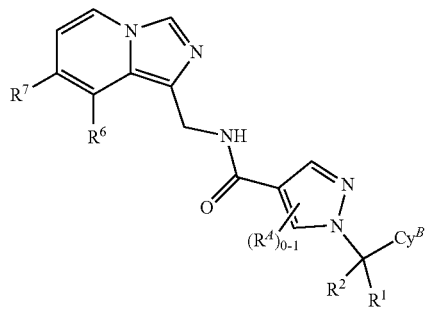

(III-b)

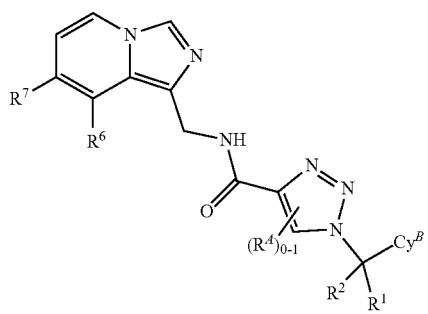

(III-c)

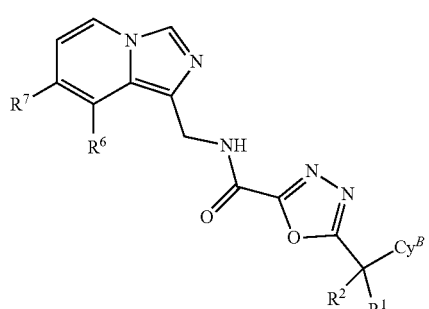

-continued (III-d)

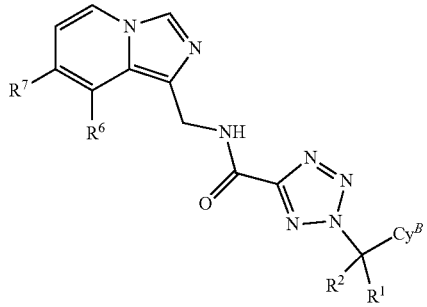

or a pharmaceutically acceptable salt thereof.

90. The compound of any one of the preceding embodiments, wherein $Cy^B$ is a 7- to 10-membered bicyclic heteroaryl having 1-5 heteroatoms selected from oxygen, nitrogen, or sulfur, wherein $Cy^B$ is substituted with 0-5 $R^B$ groups.

91. The compound of any one of the preceding embodiments, wherein $Cy^B$ is wherein:

$W^1$, $W^2$, $W^3$, and $W^4$ are independently selected from carbon and nitrogen;

$R^{10}$, $R^{11}$, $R^{12}$, $R^{13}$, and $R^{14}$ are each optionally present when attached to a carbon atom, and if present correspond to an occurrence of $R^B$ independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur; and each R is independently hydrogen, —CN, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur.

92. The compound of any one of the preceding embodiments, wherein $Cy^B$ is selected from the group consisting of imidazopyridinyl substituted with 0-5 $R^B$ groups, pyrazolopyridinyl substituted with 0-5 $R^B$ groups, pyrrolopyridinyl substituted with 0-4 $R^B$ groups, triazolopyridinyl substituted with 0-4 $R^B$ groups, imidazopyrimidinyl substituted with 0-4 $R^B$ groups, imidazopyridazinyl substituted with 0-4 $R^B$ groups, indolizinyl substituted with 0-5 $R^B$ groups, and pyrazolopyrimidinyl substituted with 0-4 $R^B$ groups.

93. The compound of any one of the preceding embodiments, wherein $Cy^B$ is selected from the group consisting of:

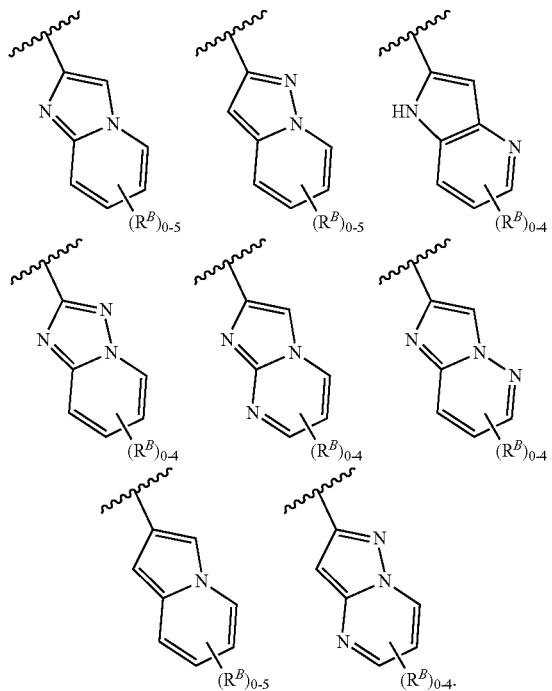

94. The compound of any one of embodiments 83-90, wherein $Cy^B$ is

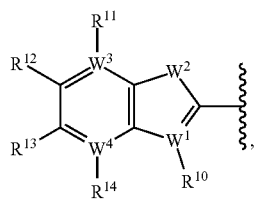

wherein:
W² is selected from carbon, nitrogen, oxygen, and sulfur;
W¹, W³, and W⁴ are independently selected from carbon and nitrogen;
$R^{10}$, $R^{11}$, $R^{12}$, $R^{13}$, and $R^{14}$ are each optionally present when attached to a carbon atom, and if present correspond to an occurrence of $R^B$ independently selected from halogen, —CN, —C(R)=N(R), —C(O)R, —C(O)₂R, —C(O)N(R)₂, —NO₂, —N(R)—N(R)₂, —N(R)₂, —N(R)C(O)R, —N(R)C(O)₂R, —N(R)C(O)N(R)₂, —N(R)S(O)₂R, —OR, —OC(O)R, —OC(O)N(R)₂, —SR, —S(O)R, —S(O)₂R, —S(O)N(R)₂, —S(O)₂N(R)₂, or an optionally substituted group selected from C₁₋₆ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur; and each R is independently hydrogen, —CN, or an optionally substituted group selected from C₁₋₆ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur.

95. The compound of any one of embodiments 83-90 and 94, wherein $Cy^B$ is selected from the group consisting of a indolyl substituted with 0-5 $R^B$ groups, a benzofuranyl substituted with 0-5 $R^B$ groups, a pyrazolopyrimidinyl substituted with 0-4 $R^B$ groups, a benzimidazolyl substituted with 0-4 $R^B$ groups, and a thienopyridinyl substituted with 0-4 $R^B$ groups.

96. The compound of any one of embodiments 83-90 and 94-95, wherein $Cy^B$ is selected from the group consisting of:

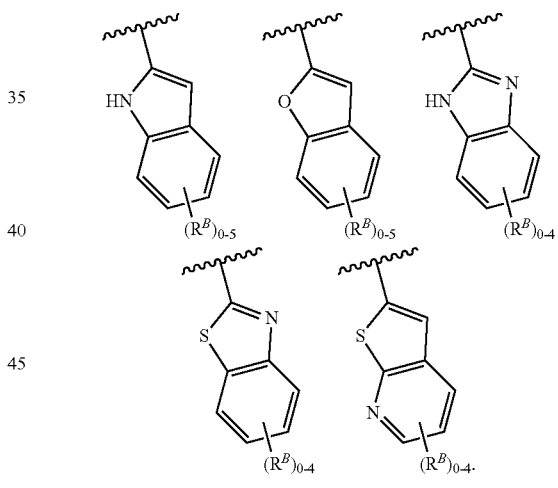

97. The compound of any one of embodiments 83-90, wherein $Cy^B$ is a quinolondiyl group substituted with 0-5 $R^B$ groups.

98. The compound of embodiment any one of embodiments 83-90 and 97, wherein $Cy^B$ is

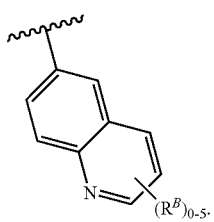

99. The compound of any one of the preceding embodiments, wherein L is —N(H)C(O)— or embodiments, L is —C(O)N(H)—.
100. The compound of any one of the preceding embodiments, wherein $R^6$ is halogen.
101. The compound of embodiment 91 or 94, wherein $R^{11}$ is selected from halogen, optionally substituted $C_{1-6}$ aliphatic, and optionally substituted 3- to 7-membered saturated or partially unsaturated monocyclic carbocyclyl.
102. The compound of embodiment 91 or 94, wherein $R^{11}$ is an optionally substituted cyclopropyl.
103. A pharmaceutical composition comprising any one of the preceding compounds.
104. The pharmaceutical composition of embodiment 103 further comprising a pharmaceutically acceptable excipient.
105. The pharmaceutical composition of any one of embodiments 103-104, wherein the composition is suitable for oral administration.
106. The pharmaceutical composition of any one of embodiments 103-104, wherein the composition is suitable for administration by injection.
107. A method of treating a plasma kallikrein-mediated disease or disorder using a compound any one of embodiments 83-102 or composition according to of any one of embodiments 103-106.
108. The method of embodiment 27, wherein the disease or disorder is hereditary angioedema or diabetic macular edema.
109. A method of treating hereditary angioedema or diabetic macular edema comprising administering to a patient in need thereof a compound of any one of embodiments 83-102 or composition according to of any one of embodiments 103-106.

IV. EXAMPLES

Example 1

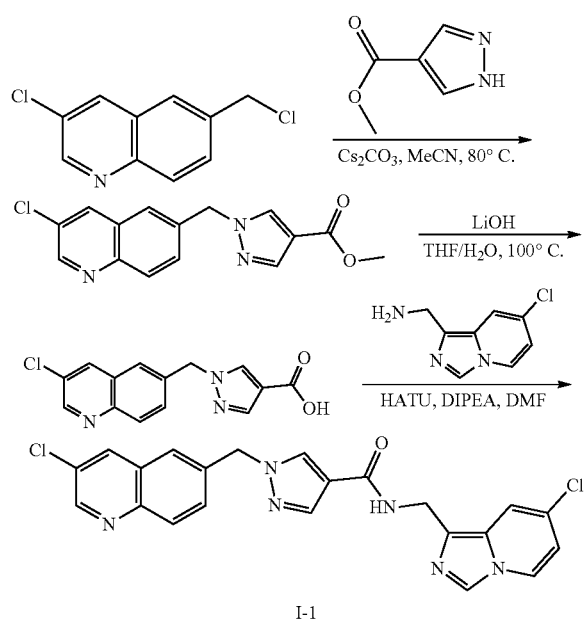

I-1

Synthesis of Methyl 1-((3-chloroquinolin-6-yl)methyl)-1H-pyrazole-4-carboxylate

A mixture of 3-chloro-6-(chloromethyl)quinoline (200 mg, 0.95 mmol), methyl 1H-pyrazole-4-carboxylate (1.2 g, 0.95 mmol) and $Cs_2CO_3$ (930 mg, 2.85 mmol) in McCN (5 mL) was stirred at 70° C. for 1 h. Water was added and extracted with EtOAc, the combined organic layers were concentrated and purified by silcial gel column (EA/PE=1/10) to give methyl 1-((3-chloroquinolin-6-yl)methyl)-1H-pyrazole-4-carboxylate (200 mg, yield: 78%) as a white solid. ESI-MS $[M+H]^+$: 302.1.

Synthesis of 1-((3-chloroquinolin-6-yl)methyl)-1H-pyrazole-4-carboxylic Acid

A mixture of methyl 1-((3-chloroquinolin-6-yl)methyl)-1H-pyrazole-4-carboxylate (200 mg, 0.66 mmol) and LiOH (158 mg, 6.6 mmol) in THF (10 mL) and $H_2O$ (5 mL) was stirred at 100° C. for overnight. Water was added and the pH value of the mixture was adjusted to 4-5 by added 1 M HCl solution. The mixture was then extracted with EtOAc (20 mL×3), the combined organic layers were concentrated to give 1-((3-chloroquinolin-6-yl)methyl)-1H-pyrazole-4-carboxylic acid (150 mg, yield: 72%) as a white solid, which was used into next step without further purification. ESI-MS $[M+H]^+$: 288.0.

Synthesis of N-((7-chloroimidazo[1,5-a]pyridin-1-yl)methyl)-1-((3-chloroquinolin-6-yl)methyl)-1H-pyrazole-4-carboxamide (I-1)

A mixture of 1-((3-chloroquinolin-6-yl)methyl)-1H-pyrazole-4-carboxylic acid (50 mg, 0.17 mmol), (7-chloroimidazo[1,5-a]pyridin-1-yl)methanamine (37 mg, 0.17 mmol), and HATU (98 mg, 0.06 mmol) and DIPEA (66 mg, 0.51 mmol) in DMF (2 mL) was stirred at RT overnight. Water (10 mL) was added and extracted with EtOAc (20 mL×3), the combined organic layers were concentrated and purified by prep-HPLC to give N-((7-chloroimidazo[1,5-a]pyridin-1-yl)methyl)-1-((3-chloroquinolin-6-yl)methyl)-1H-pyrazole-4-carboxamide (17.3 mg, yield: 20%) as a white solid. ESI-MS $[M+H]^+$: 451.1. Purity: 99.49%. $^1$H NMR (400 MHz, DMSO): δ 8.88 (d, J=2.2 Hz, 1H), 8.64-8.58 (m, 2H), 8.36-8.31 (m, 3H), 8.03 (d, J=8.7 Hz, 1H), 7.94 (s, 1H), 7.80 (d, J=8.7 Hz, 2H), 7.65 (d, J=8.7 Hz, 1H), 6.67 (dd, J=7.4, 1.8 Hz, 1H), 5.56 (s, 2H), 4.57 (d, J=5.4 Hz, 2H).

Example 2

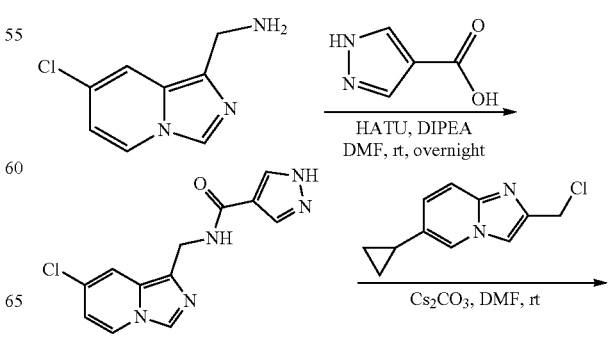

69

-continued

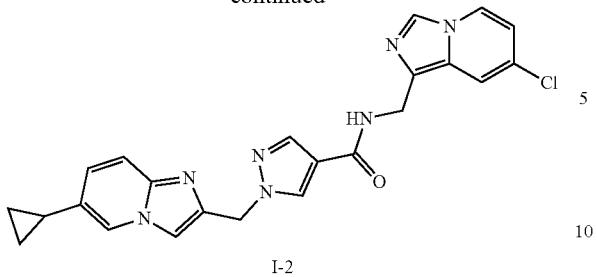

I-2

Synthesis of N-((7-chloroimidazo[1,5-a]pyridin-1-yl)methyl)-1H-pyrazole-4-carboxamide To a mixture of (7-chloroimidazo[1,5-a]pyridin-1-yl)methanamine hydrochloride (2.5 g, 11.52 mmol), 1H-pyrazole-4-carboxylic acid (920 mg, 8.23 mmol), HATU (3.9 g, 10.29 mmol) in DMF (300 mL) was added DIPEA (7.3 mL, 41.14 mmol). The resulting reaction mixture was stirred at RT for 14 h. The reaction was then concentrated to remove most of the DMF, and the residue was poured into H$_2$O (150 mL) and brown solid was precipitated out. The precipitate was filtered and the filtrated cake was triturated with DCM and dried to give the N-((7-chloroimidazo[1,5-a]pyridin-1-yl)methyl)-1H-pyrazole-4-carboxamide, which was used into next step without further purification (2 g, yield: 88%). ESI-MS [M+H]$^+$: 276.2.

Synthesis of N-((7-chloroimidazo[1,5-a]pyridin-1-yl)methyl)-1-((6-cyclopropylimidazo[1,2-a]pyridin-2-yl)methyl)-1H-pyrazole-4-carboxamide (I-2)

A mixture of N-((7-chloroimidazo[1,5-a]pyridin-1-yl)methyl)-1H-pyrazole-4-carboxamide (2 g, 7.27 mmol), 2-(chloromethyl)-6-cyclopropylimidazo[1,2-a]pyridine (1.96 g, 9.45 mmol) and Cs$_2$CO$_3$ (7.1 g, 21.81 mmol) in DMF (50 mL) was stirred at 50° C. for 14 h. H$_2$O (200 mL) was added, extracted with EtOAc (300 mL×3). The combined organic layers were washed with brine, dried over Na$_2$SO$_4$, concentrated in vacuo to give the crude, which was purified with silica gel chromatography (DCM/MeOH=10/1) to give the N-((7-chloroimidazo[1,5-a]pyridin-1-yl)methyl)-1-((6-cyclopropylimidazo[1,2-a]pyridin-2-yl)methyl)-1H-pyrazole-4-carboxamide as a white solid (1.5 g, yield: 46%). LCMS m/z: 446.1 [M+H]*, t$_R$=1.040 min, purity: 98.6% (214 nm), 97.4% (254 nm). $^1$H NMR (400 MHz, DMSO): δ 8.58 (t, J=5.7 Hz, 1H), 8.32-8.29 (m, 3H), 8.20 (s, 1H), 7.85 (s, 1H), 7.78 (s, 1H), 7.71 (s, 1H), 7.39 (d, J=9.3 Hz, 1H), 7.00-6.98 (m, 1H), 6.64 (dd, J=7.5, 2.0 Hz, 1H), 5.38 (s, 2H), 4.55 (d, J=5.7 Hz, 2H), 1.91 (ddd, J=13.5, 8.4, 5.1 Hz, 1H), 0.99-0.87 (m, 2H), 0.77-0.61 (m, 2H).

Example 3

Scheme 3

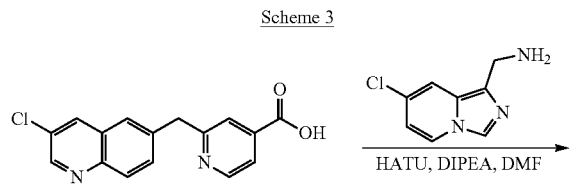

70

-continued

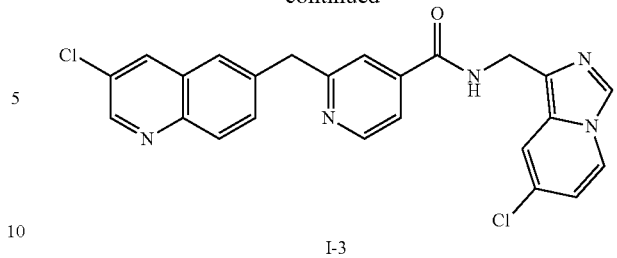

I-3

Synthesis of N-((7-chloroimidazo[1,5-a]pyridin-1-yl)methyl)-2-((3-chloroquinolin-6-yl)methyl)isonicotinamide (I-3)

To a solution of 2-((3-chloroquinolin-6-yl)methyl)isonicotinic acid (60 mg, 0.20 mmol), (7-chloroimidazo[1,5-a]pyridin-1-yl)methanamine (44 mg, 0.24 mmol) and HATU (115 mg, 0.30 mmol) in DMF (8 mL) was added DIPEA (77 mg, 0.60 mmol). The resulting reaction was stirred at RT for 12 h. H$_2$O (20 mL) was added, extracted with EtOAc (20 mL×3). The combined organic layers were washed with brine, dried over Na$_2$SO$_4$, concentrated in vacuo to give the crude, which was purified with prep-TLC (DCM/MeOH=10/1) to give the N-((7-chloroimidazo[1,5-a]pyridin-1-yl)methyl)-2-((3-chloroquinolin-6-yl)methyl)isonicotinamide (20 mg, yield: 22%) as a white solid. ESI-MS [M+H]$^+$: 462.0. Purity: 98.3%. $^1$H NMR (400 MHz, DMSO): δ 9.27-9.24 (m, 1H), 8.84-8.81 (m, 1H), 8.62 (d, J=5.0 Hz, 1H), 8.51 (s, 1H), 8.38-8.26 (m, 2H), 7.97 (d, J=8.6 Hz, 1H), 7.90-7.69 (m, 4H), 7.62 (d, J=4.7 Hz, 1H), 6.66 (d, J=7.4 Hz, 1H), 4.64 (d, J=5.5 Hz, 2H), 4.35 (s, 2H).

Example 4

Scheme 4

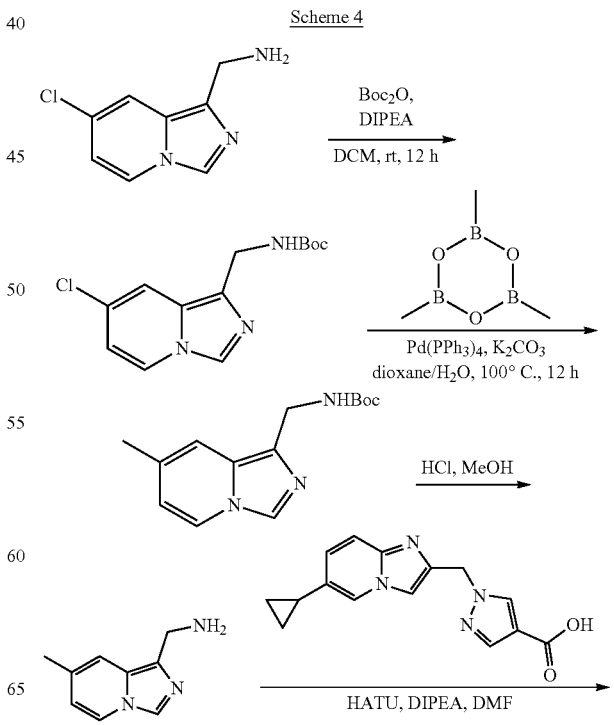

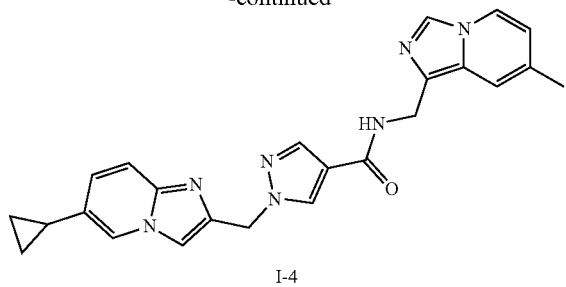

I-4

Synthesis of tert-butyl ((7-chloroimidazo[1,5-a]pyridin-1-yl)methyl)carbamate A mixture of (7-chloroimidazo[1,5-a]pyridin-1-yl)methanamine (300 mg, 1.65 mmol), Boc$_2$O (537 mg, 2.4 mmol) and DIPEA (1.06 g, 8.25 mmol) in DCM (40 mL) was stirred at RT for 12 h. The reaction was quenched with H$_2$O (50 mL), extracted with DCM (50 mL×2). The combined organic layers were washed with brine, dried over Na$_2$SO$_4$, concentrated in vacuo to give the crude, which was purified with silica gel chromatography (PE/EA=1/1) to give the tert-butyl ((7-chloroimidazo[1,5-a]pyridin-1-yl)methyl)carbamate (210 mg, yield: 45%) as a yellow solid. ESI-MS [M+H]$^+$: 282.2.

Synthesis of tert-butyl ((7-methylimidazo[1,5-a]pyridin-1-yl)methyl)carbamate A mixture of tert-butyl ((7-chloroimidazo[1,5-a]pyridin-1-yl)methyl)carbamate (210 mg, 0.75 mmol), 2,4,6-trimethyl-1,3,5,2,4,6-trioxatriborinane (188 mg, 1.5 mmol), Pd(PPh$_3$)$_4$ (87 mg, 0.075 mmol) and K$_2$CO$_3$ (310 mg, 2.25 mmol) in dioxane/H$_2$O (10 mL/1 mL) in a sealed tube was stirred at 100° C. for 12 h. H$_2$O (30 mL) was added to the reaction, extracted with EtOAc (30 mL×3). The combined organic layers were washed with brine, dried over Na$_2$SO$_4$, concentrated in vacuo to give the crude, which was purified with silica gel chromatography (EA/PE=1/1) to give the tert-butyl ((7-methylimidazo[1,5-a]pyridin-1-yl)methyl)carbamate (150 mg, yield: 77%) as a light yellow solid. ESI-MS [M+H]$^+$: 262.3.

Synthesis of (7-methylimidazo[1,5-a]pyridin-1-yl)methanamine Hydrochloride

To a solution of tert-butyl ((7-methylimidazo[1,5-a]pyridin-1-yl)methyl)carbamate (150 mg, 0.57 mmol) in MeOH (3 mL) was added HCl (4 M solution in MeOH, 3 mL). The resulting reaction was stirred at RT for 2 h. The reaction was concentrated in vacuo to give the (7-methylimidazo[1,5-a]pyridin-1-yl)methanamine hydrochloride (95 mg, yield: 85%). ESI-MS [M+H]$^+$: 162.2.

Synthesis of 1-((6-cyclopropylimidazo[1,2-a]pyridin-2-yl)methyl)-N-((7-methylimidazo[1,5-a]pyridin-1-yl)methyl)-1H-pyrazole-4-carboxamide (I-4)

To a solution of 1-((6-cyclopropylimidazo[1,2-a]pyridin-2-yl)methyl)-1H-pyrazole-4-carboxylic acid (136 mg, 0.48 mmol), (7-methylimidazo[1,5-a]pyridin-1-yl)methanamine hydrochloride (95 mg, 0.48 mmol) and HATU (238 mg, 0.63 mmol) in DMF (15 mL) was added DIPEA (310 mg, 2.4 mmol). The resulting reaction was stirred at RT for 12 h. H$_2$O (25 mL) was added to the reaction, extracted with EtOAc (30 mL×3). The combined organic layers were washed with brine, dried over Na$_2$SO$_4$, concentrated in vacuo to give the crude, which was purified with prep-TLC (DCM/MeOH=10/1) to give the 1-((6-cyclopropylimidazo[1,2-a]pyridin-2-yl)methyl)-N-((7-methylimidazo[1,5-a]pyridin-1-yl)methyl)-1H-pyrazole-4-carboxamide (21 mg, yield: 10%) as a white solid. ESI-MS [M+H]$^+$: 426.2. Purity: 96.4%. $^1$H NMR (400 MHz, DMSO): δ 8.47 (s, 1H), 8.39-8.04 (m, 5H), 7.86 (s, 1H), 7.71 (s, 1H), 7.40-7.35 (m, 2H), 6.99 (d, J=9.1 Hz, 1H), 6.45 (d, J=7.0 Hz, 1H), 5.38 (s, 2H), 4.54 (d, J=4.5 Hz, 2H), 2.20 (s, 3H), 1.95-1.88 (m, 1H), 0.93-0.90 (m, 2H), 0.68-0.63 (m, 2H).

Example 5

Scheme 5

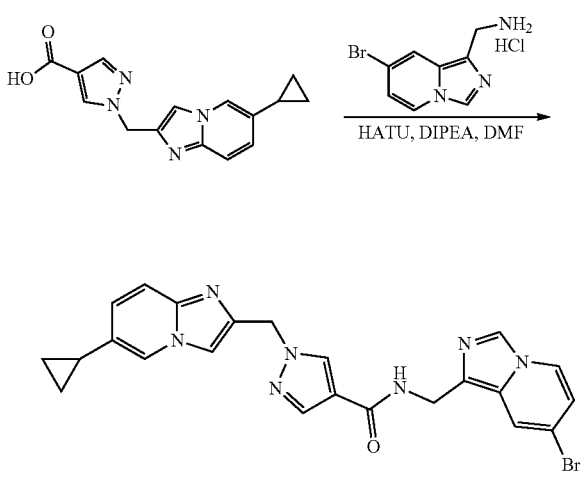

I-5

Synthesis of N-((7-bromoimidazo[1,5-a]pyridin-1-yl)methyl)-1-((6-cyclopropylimidazo[1,2-a]pyridin-2-yl)methyl)-1H-pyrazole-4-carboxamide. (I-5)

To a solution of 1-((6-cyclopropylimidazo[1,2-a]pyridin-2-yl)methyl)-1H-pyrazole-4-carboxylic acid (154 mg, 0.54 mmol), (7-bromoimidazo[1,5-a]pyridin-1-yl)methanamine (120 mg, 0.54 mmol) and HATU (310 mg, 0.82 mmol) in DMF (4 mL) was added DIPEA (210 mg, 1.63 mmol). The resulting reaction was stirred at RT for 12 h. H$_2$O (20 mL) was added, extracted with EtOAc (25 mL×3). The combined organic layers were washed with brine, dried over Na$_2$SO$_4$, concentered in vacuo to give the crude, which was purified with prep-TLC (DCM/MeOH=10/1) to give the N-((7-bromoimidazo[1,5-a]pyridin-1-yl)methyl)-1-((6-cyclopropylimidazo[1,2-a]pyridin-2-yl)methyl)-1H-pyrazole-4-carboxamide (24 mg, yield: 9%) as a white solid. ESI-MS [M+H]$^+$: 490.1. Purity: 98.24%. $^1$H NMR (400 MHz, DMSO): δ 8.57 (t, J=8.0 Hz, 1H), 8.32 (d, J=4.2 Hz, 2H), 8.24 (d, J=7.5 Hz, 1H), 8.20 (s, 1H), 7.95 (s, 1H), 7.85 (s, 1H), 7.71 (s, 1H), 7.39 (d, J=9.4 Hz, 1H), 6.99 (d, J=9.3 Hz, 1H), 6.72 (dd, J=7.4, 1.8 Hz, 1H), 5.38 (s, 2H), 4.54 (d, J=5.7 Hz, 2H), 1.98-1.87 (m, 1H), 1.01-0.76 (m, 2H), 0.76-0.55 (m, 2H).

Example 6

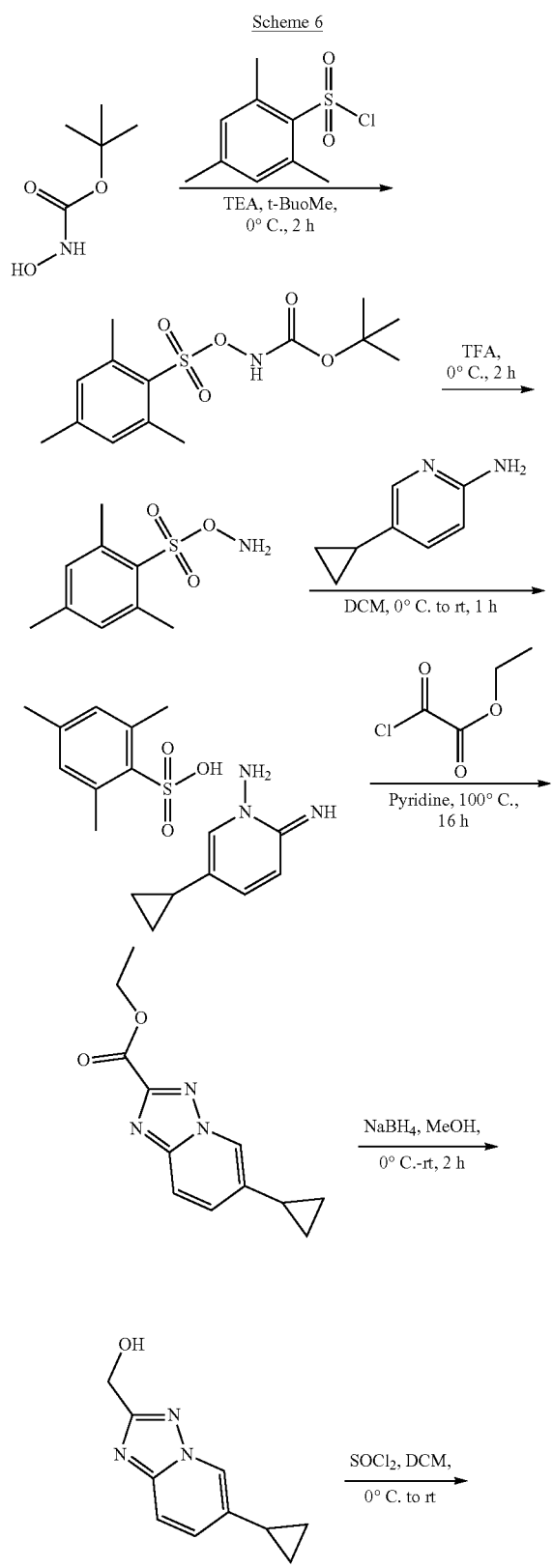

Synthesis of tert-butyl ((mesitylsulfonyl)oxy)carbamate

To a mixture of tert-butyl hydroxycarbamate (3 g, 22.5 mmol) and 2,4,6-trimethylbenzenesulfonyl chloride (4.9 g, 22.5 mmol) in MTBE (100 mL) was added $Et_3N$ (2.43 g, 24.0 mmol) at 0° C. The mixture was stirred at 0° C. for 2 h. The reaction mixture was filtered and washed with MTBE. The filtrate was concentrated to give tert-butyl ((mesitylsulfonyl)oxy)carbamate (7.1 g, yield: 100%) as a light yellow solid. ESI-MS [M+Na]$^+$: 338.1.

Synthesis of O-(mesitylsulfonyl)hydroxylamine

The mixture of tert-butyl ((mesitylsulfonyl)oxy)carbamate (5.9 g, 18.71 mmol) in TFA (20 mL) was stirred for at 0° C. for 2 h. The reaction mixture was poured into $H_2O$ (150 mL) and stirred for 30 min. The precipitate was collected and dried to give O-(mesitylsulfonyl)hydroxylamine (2.2 g, yield: 55%) as a white solid which was used into next step without further purification. ESI-MS [M+H]$^+$: 216.2.

Synthesis of 5-cyclopropylpyridin-2-amine

The mixture of 5-bromopyridin-2-amine (4 g, 23.12 mmol), cyclopropylboronic acid (2.98 g, 34.68 mmol), $Pd(OAc)_2$ (130 mg, 0.578 mmol), tricyclohexyl phosphine (324 mg, 1.16 mmol) and $K_3PO_4$ (17.18 g, 80.92 mmol) in toluene (100 mL) and $H_2O$ (10 mL) was stirred at 90° C. for 16 h. The reaction mixture was filtered and rinsed with EtOAc. The combined filtrate was washed with $H_2O$ (150 mL×1) and brine (150 mL×1), dried over $Na_2SO_4$, concentrated and purified by silica gel chromatography (EA/PE=1/

1) to give 5-cyclopropylpyridin-2-amine (2.76 g, yield: 89%) as a yellow solid. ESI-MS [M+H]$^+$: 135.2.

Synthesis of
5-cyclopropyl-2-iminopyridin-1(2H)-amine
2,4,6-trimethylbenzenesulfonate To a stirred solution of O-(mesitylsulfonyl)hydroxylamine (2.2 g, 10.22 mmol) in DCM (40 mL) was added 5-cyclopropylpyridin-2-amine (1.37 g, 10.22 mmol) in four portions at 0° C. The mixture was stirred at 0° C. for 10 min and warmed to RT and stirred for 1 h. The reaction mixture was concentrated and dried in vacuo to give 5-cyclopropyl-2-iminopyridin-1(2H)-amine 2,4,6-trimethylbenzenesulfonate (3.57 g, yield: 100%) as a light brown syrup. ESI-MS [M+H]$^+$: 150.2.

Synthesis of Ethyl 6-cyclopropyl-[1,2,4]triazolo[1,5-a]pyridine-2-carboxylate

To a stirred solution of 5-cyclopropyl-2-iminopyridin-1(2H)-amine 2,4,6-trimethylbenzenesulfonate (3.57 g, 10.22 mmol) in pyridine (30 mL) was added ethyl 2-chloro-2-oxoacetate (2.79 g, 20.44 mmol) at RT. The mixture was stirred at 100° C. for 16 h. The reaction mixture was concentrated. The residue was dissolved in EtOAc (100 mL) and washed with H$_2$O (100 mL×1) brine (100 mL×1), dried over Na$_2$SO$_4$, concentrated and purified by silica gel chromatography (EA/PE=1/1) to give ethyl 6-cyclopropyl-[1,2,4]triazolo[1,5-a]pyridine-2-carboxylate (1.1 g, yield: 47%) as a yellow solid. ESI-MS [M+H]$^+$: 232.1.

Synthesis of (6-cyclopropyl-[1,2,4]triazolo[1,5-a]pyridin-2-yl)methanol

To a stirred solution of ethyl 6-cyclopropyl-[1,2,4]triazolo[1,5-a]pyridine-2-carboxylate (300 mg, 1.30 mmol) in MeOH (10 mL) was added NaBH$_4$ (246 mg, 6.5 mmol) in portions at 0° C. The mixture was stirred at RT for 2 h. The reaction mixture was then quenched with NH$_4$C aqueous. MeOH was removed and the reaction was diluted with H$_2$O (50 mL) and extracted with EtOAc (30 mL×3). The combined organics was washed with brine (80 mL×1), dried over Na$_2$SO$_4$, concentrated and purified by silica gel chromatography (EA/MeOH=10/1) to give (6-cyclopropyl-[1,2,4]triazolo[1,5-a]pyridin-2-yl)methanol (210 mg, yield: 85%) as a yellow solid. ESI-MS [M+H]$^+$: 190.2.

Synthesis of 2-(chloromethyl)-6-cyclopropyl-[1,2,4]triazolo[1,5-a]pyridine

To a stirred solution of (6-cyclopropyl-[1,2,4]triazolo[1,5-a]pyridin-2-yl)methanol (110 mg, 0.58 mmol) in DCM (5 mL) was added SOCl$_2$ (690 mg, 5.8 mmol) at 0° C. The mixture was stirred at RT for 1 h. The reaction mixture was then concentrated, the residue was dissolved in EtOAc (60 mL) and washed with NaHCO$_3$ (50 mL×1), brine (50 mL×1), dried over Na$_2$SO$_4$, concentrated to give 2-(chloromethyl)-6-cyclopropyl-[1,2,4]triazolo[1,5-a]pyridine (115 mg, yield: 96%) as a yellow solid, which was used into next step without further purification. ESI-MS [M+H]$^+$: 208.1.

Synthesis of N-((7-chloroimidazo[1,5-a]pyridin-1-yl)methyl)-1-((6-cyclopropyl-[1,2,4]triazolo[1,5-a]pyridin-2-yl)methyl)-1H-pyrazole-4-carboxamide
(I-6)

The mixture of 2-(chloromethyl)-6-cyclopropyl-[1,2,4]triazolo[1,5-a]pyridine (15.8 mg, 0.0762 mmol), N-((7-chloroimidazo[1,5-a]pyridin-1-yl)methyl)-1H-pyrazole-4-carboxamide (20 mg, 0.0725 mmol) and Cs$_2$CO$_3$ (35 mg, 0.109 mmol) in DMF (3 mL) was stirred at RT for 2 h. The reaction mixture was poured into H$_2$O (30 mL) and extracted with EtOAc (50 mL×3). The combined organic layers were washed with brine (60 mL×3), dried over Na$_2$SO$_4$, concentrated and purified by prep-TLC (DCM/MeOH=5/1) to give N-((7-chloroimidazo[1,5-a]pyridin-1-yl)methyl)-1-((6-cyclopropyl-[1,2,4]triazolo[1,5-a]pyridin-2-yl)methyl)-1H-pyrazole-4-carboxamide (15 mg, yield: 47%) as a yellow solid. ESI-MS [M+H]$^+$: 447.1. Purity: 99%. $^1$H NMR (400 MHz, DMSO): δ 8.73 (s, 1H), 8.62 (t, J=5.7 Hz, 1H), 8.31 (d, J=7.9 Hz, 3H), 7.86 (s, 1H), 7.80 (d, J=0.9 Hz, 1H), 7.66 (d, J=9.2 Hz, 1H), 7.42 (dd, J=9.2, 1.7 Hz, 1H), 6.65 (dd, J=7.5, 2.1 Hz, 1H), 5.56 (s, 2H), 4.57 (d, J=5.7 Hz, 2H), 2.03 (m, 1H), 0.97 (m, 2H), 0.78 (m, 2H).

Example 7

Scheme 7

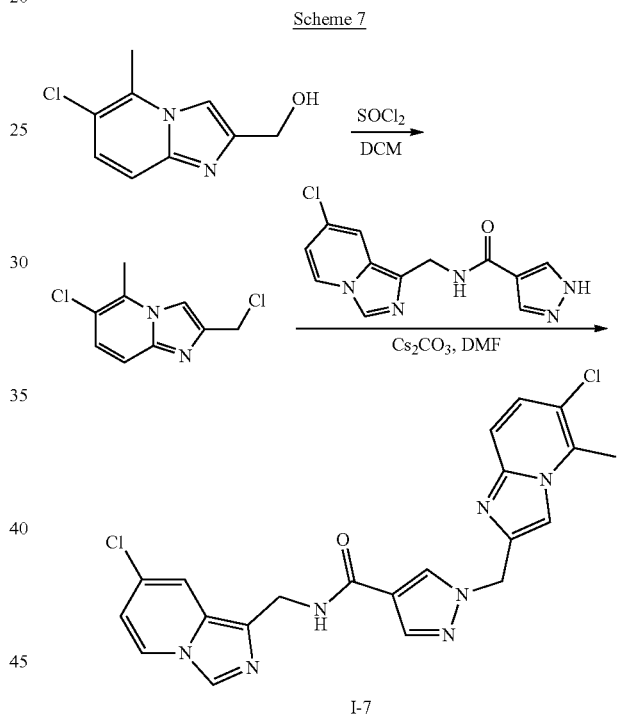

I-7

Synthesis of 6-chloro-2-(chloromethyl)-5-methylimidazo[1,2-a]pyridine

To a solution (6-chloro-5-methylimidazo[1,2-a]pyridin-2-yl)methanol (60 mg, 0.31 mmol) in DCM (10 mL) was added SOCl$_2$ (1 mL) at RT. The resulting reaction was stirred at 45° C. for 2 h. The solution was evaporated to give the 6-chloro-2-(chloromethyl)-5-methylimidazo[1,2-a]pyridine (50 mg, crude) as a light yellow solid, which was used in the next step without further purification. ESI-MS [M+H]$^+$: 215.2.

Synthesis of 1-((6-chloro-5-methylimidazo[1,2-a]pyridin-2-yl)methyl)-N-((7-chloroimidazo[1,5-a]pyridin-1-yl)methyl)-1H-pyrazole-4-carboxamide
(I-7)

To a solution 6-chloro-2-(chloromethyl)-5-methylimidazo [1,2-a]pyridine (50 mg, 0.23 mmol) in DMF (10 mL)

was added N-((7-chloroimidazo[1,5-a]pyridin-1-yl)methyl)-1H-pyrazole-4-carboxamide (41 mg, 0.15 mmol) and Cs$_2$CO$_3$ (146 mg, 0.45 mmol) at RT. The resulting reaction was stirred at RT for 12 h. H$_2$O (30 mL) was added to the reaction and then extracted with EtOAc (20 mL×3). The combined organic layers were washed with brine, dried over Na$_2$SO$_4$, concentrated in vacuo to give the crude, which was purified with prep-TLC (DCM/MeOH=10/1) to give 1-((6-chloro-5-methylimidazo[1,2-a]pyridin-2-yl)methyl)-N-((7-chloroimidazo[1,5-a]pyridin-1-yl)methyl)-1H-pyrazole-4-carboxamide (40 mg, yield: 58%) as a white solid. ESI-MS [M+H]$^+$: 454.1. Purity: 100%. $^1$H NMR (400 MHz, DMSO): δ 8.59 (t, J=5.5 Hz, 1H), 8.31-8.29 (m, 2H), 8.23 (s, 1H), 7.92 (s, 1H), 7.86 (s, 1H), 7.78 (s, 1H), 7.47 (d, J=9.5 Hz, 1H), 7.34 (d, J=9.5 Hz, 1H), 6.65 (d, J=7.4 Hz, 1H), 5.44 (s, 2H), 4.55 (d, J=5.6 Hz, 2H), 2.66 (s, 3H).

Example 8

Scheme 8

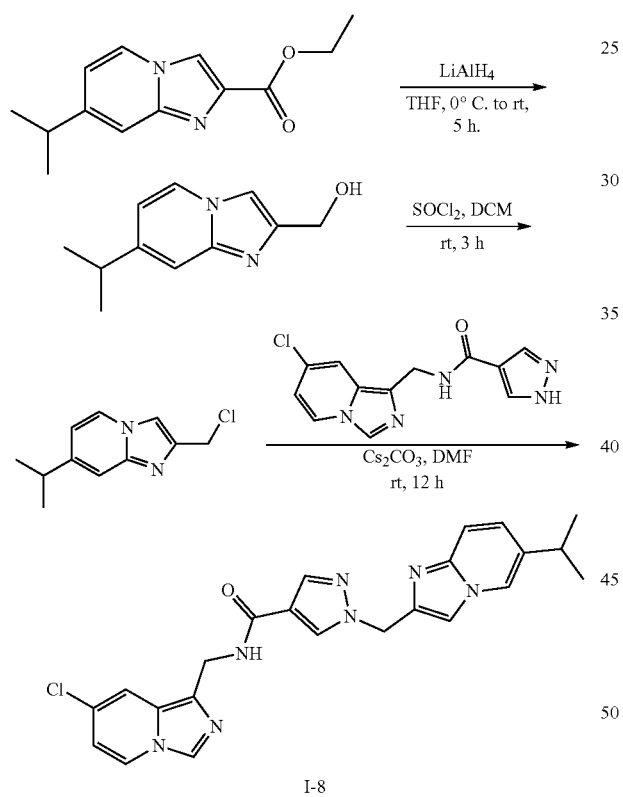

I-8

Synthesis of (7-isopropylimidazo[1,2-a]pyridin-2-yl)methanol

To a solution of ethyl 7-isopropylimidazo[1,2-a]pyridine-2-carboxylate (200 mg, 0.86 mmol) in THF (4 mL) was added LiAlH4 (65.5 mg, 1.72 mmol). The resulting reaction was stirred at RT for 4 h. The reaction was quenched with saturated Na$_2$SO$_4$ (aq.), filtered and concentrated and purified by silica gel column (DCM/MeOH=10/1) to give the (7-isopropylimidazo[1,2-a]pyridin-2-yl)methanol (130 mg, 80%) as a brown liquid. ESI-MS [M+H]$^+$: 191.2.

Synthesis of 2-(chloromethyl)-7-isopropylimidazo[1,2-a]pyridine

To a solution of (7-isopropylimidazo[1,2-a]pyridin-2-yl)methanol (190 mg, 1 mmol) in DCM (10 mL) was added SOCl$_2$ (2 mL). The resulting reaction was stirred at 50° C. for 2 h. The reaction was concentrate in vacuo to give 2-(chloromethyl)-7-isopropylimidazo[1,2-a]pyridine (220 mg crude), which was used into next step without further purification. ESI-MS [M+H]$^+$: 209.2.

Synthesis of N-((7-chloroimidazo[1,5-a]pyridin-1-yl)methyl)-1-((6-isopropylimidazo[1,2-a]pyridin-2-yl)methyl)-1H-pyrazole-4-carboxamide (I-8)

A mixture of 2-(chloromethyl)-7-isopropylimidazo[1,2-a] pyridine (46 mg, 0.22 mmol), N-((7-chloroimidazo[1,5-a] pyridin-1-yl)methyl)-1H-pyrazole-4-carboxamide (38 mg, 0.14 mmol) and Cs$_2$CO$_3$ (142 mg, 0.44 mmol) in DMF (8 mL) was stirred at 80° C. for 12 h. H$_2$O (15 mL) was added to the reaction, extracted with EtOAc (20 mL×3). The combined organic layers were washed with brine, dried over Na$_2$SO$_4$, concentrated in vacuo to give the crude, which was purified with prep-TLC (DCM/MeOH=10/1) to give the N-((7-chloroimidazo[1,5-a]pyridin-1-yl)methyl)-1-((6-isopropylimidazo[1,2-a]pyridin-2-yl)methyl)-1H-pyrazole-4-carboxamide (15 mg, 24%) as a white solid. ESI-MS [M+H]$^+$: 448.2. Purity: 100%. $^1$H NMR (400 MHz, DMSO): δ 8.58 (t, J=5.6 Hz, 1H), 8.32 (m, 3H), 8.20 (s, 1H), 7.85 (s, 1H), 7.77 (m, 2H), 7.43 (d, J=9.3 Hz, 1H), 7.21 (d, J=9.3 Hz, 1H), 6.64 (dd, J=7.4, 1.9 Hz, 1H), 5.39 (s, 2H), 4.55 (d, J=5.7 Hz, 2H), 2.96-2.80 (m, 1H), 1.22 (d, J=6.9 Hz, 6H).

Example 9

Scheme 9

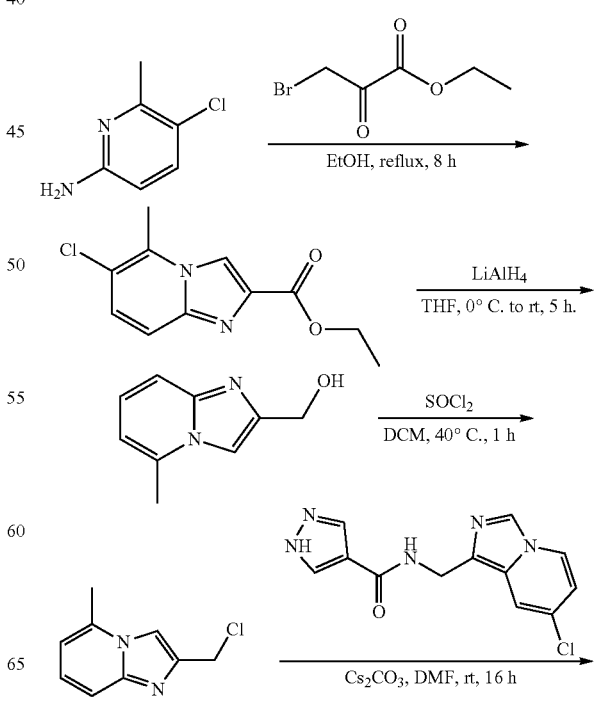

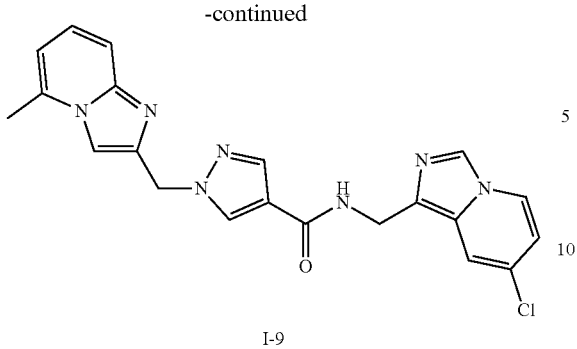

I-9

Synthesis of (5-methylimidazo[1,2-a]pyridin-2-yl)methanol

A solution of 5-chloro-6-methylpyridin-2-amine (568 mg, 4.0 mmol), ethyl 3-bromo-2-oxopropanoate (1.2 g, 6.0 mmol) in dry EtOH (10 mL) was stirred at 80° C. for 8 h. The mixture was concentrated and purified by silica gel chromatography (DCM/MeOH=20/1) to give ethyl 6-chloro-5-methylimidazo[1,2-a]pyridine-2-carboxylate (800 mg, yield: 84.0%) as a yellow solid. ESI-MS [M+H]$^+$: 239.1.

Synthesis of (5-methylimidazo[1,2-a]pyridin-2-yl)methanol

To a solution of ethyl 6-chloro-5-methylimidazo[1,2-a]pyridine-2-carboxylate (240 mg, 1.0 mmol) in dry THF (10 mL) was added LiAlH$_4$ (115 mg, 3.0 mmol) slowly at 0° C. The reaction mixture was stirred at RT for 5 h, then quenched with Na$_2$SO$_4$·10H$_2$O. The mixture was filtered and the filtrate was washed with EtOAc (20 mL). The filtrate was concentrated to give (5-methylimidazo[1,2-a]pyridin-2-yl)methanol (150 mg, yield: 92%) as a yellow oil which was used in the next step without further purification. ESI-MS [M+H]$^+$: 163.1.

Synthesis of 2-(chloromethyl)-5-methylimidazo[1,2-a]pyridine

To a solution of (5-methylimidazo[1,2-a]pyridin-2-yl)methanol (150 mg, 0.925 mmol) in dry DCM (5 mL) was added SOCl$_2$ (0.5 mL) at RT. The mixture was stirred at 40° C. for 1 h. The mixture was concentrated to give crude 2-(chloromethyl)-5-methylimidazo[1,2-a]pyridine (140 mg, yield: 94.6%) as a yellow solid. ESI-MS [M+H]$^+$: 181.2.

Synthesis of N-((7-chloroimidazo[1,5-a]pyridin-1-yl)methyl)-1-((5-methylimidazo[1,2-a]pyridin-2-yl)methyl)-1H-pyrazole-4-carboxamide (I-9)

A mixture of 2-(chloromethyl)-5-methylimidazo[1,2-a]pyridine (30 mg, 0.16 mmol), N-((7-chloroimidazo[1,5-a]pyridin-1-yl)methyl)-1H-pyrazole-4-carboxamide (30 mg, 0.11 mmol) and Cs$_2$CO$_3$ (110 mg, 0.33 mmol) in DMF (3 mL) was stirred at RT for 16 h. Water (30 mL) was added and the reaction was extracted with EtOAc (30 mL×3). The combined organic layers were concentrated and purified by prep-TLC (DCM/MeOH=10/1) to give N-((7-chloroimidazo[1,5-a]pyridin-1-yl)methyl)-1-((5-methylimidazo[1,2-a]pyridin-2-yl)methyl)-1H-pyrazole-4-carboxamide (11.5 mg, yield: 25%) as a light yellow solid. ESI-MS [M+H]$^+$: 420.1.

Purity: 97.4%. $^1$H NMR (400 MHz, DMSO): δ 8.58 (t, J=5.4 Hz, 1H), 8.31-8.29 (m, 2H), 8.23 (s, 1H), 7.86 (s, 1H), 7.78 (s, 2H), 7.41 (d, J=9.1 Hz, 1H), 7.24-7.20 (m, 1H), 6.78 (d, J=6.8 Hz, 1H), 6.64 (dd, J=7.5, 1.9 Hz, 1H), 5.43 (s, 2H), 4.55 (d, J=5.7 Hz, 2H), 2.56 (s, 3H).

Example 10

Scheme 10

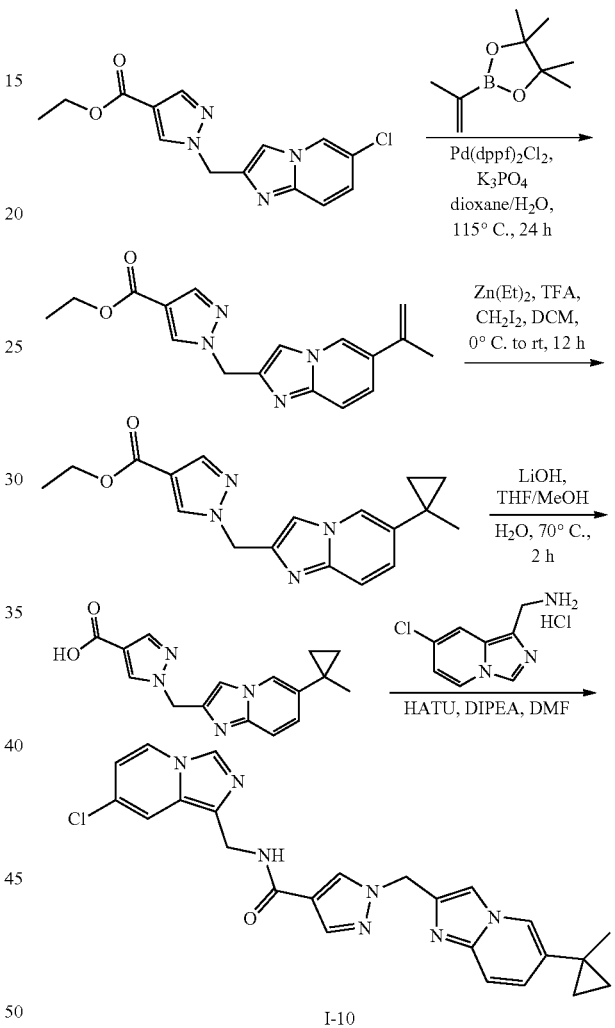

I-10

Synthesis of Ethyl 1-((6-(prop-1-en-2-yl)imidazo[1,2-a]pyridin-2-yl)methyl)-1H-pyrazole-4-carboxylate A mixture of ethyl 1-((6-chloroimidazo[1,2-a]pyridin-2-yl)methyl)-1H-pyrazole-4-carboxylate (600 mg, 1.97 mmol), 4,4,5,5-tetramethyl-2-(prop-1-en-2-yl)-1,3,2-dioxaborolane (662 mg, 3.94 mmol), Pd(dppf)$_2$Cl$_2$ (160 mg, 0.2 mmol) and K$_3$PO$_4$ (1.25 g, 5.91 mmol) in dioxane/H$_2$O (20 mL/2 mL) was stirred at 115° C. for 24 h. H$_2$O (50 mL) was added to the reaction, extracted with EtOAc (50 mL×3). The combined organic layers were washed with brine, dried over Na$_2$SO$_4$, and concentrated in vacuo to give the crude, which was purified by prep-HPLC (chromatographic columns: Gemini-C18 150×21.2 mm, 5 um, mobile phase: acetonitrile-H$_2$O (0.1% FA), gradient: 10-20) to give ethyl 1-((6-(prop-1-en-2-yl)imidazo[1,2-a]pyridin-2-yl)methyl)-1H-pyrazole-4-carboxylate (450 mg, yield: 73%) as a white solid. ESI-MS [M+H]$^+$: 311.2.

Synthesis of Ethyl 1-((6-(1-methylcyclopropyl)imidazo[1,2-a]pyridin-2-yl)methyl)-1H-pyrazole-4-carboxylate To a solution of Zn(Et)$_2$ (1.9 mL, 1 M solution in hexane, 1.9 mmol) in DCM (4 mL) was added TFA (220 mg, 1.9 mmol, in 1 mL DCM) dropwisely at 0° C. The resulting reaction was stirred at 0° C. for 20 min. Then a solution of CH$_2$I$_2$ (509 mg, 1.9 mmol, in 2 mL DCM) was added at 0° C. After stirring for another 20 min, a solution of ethyl 1-((6-(prop-1-en-2-yl)imidazo[1,2-a]pyridin-2-yl)methyl)-1H-pyrazole-4-carboxylate (50 mg, 0.16 mmol) in DCM (1 mL) was added. The resulting reaction was warmed to RT and stirred for 16 h. The reaction was quenched with H$_2$O (20 mL) and extracted with DCM (25 mL×3). The combined organic layers were washed with brine, dried over Na$_2$SO$_4$, and concentrated in vacuo to give the crude, which was purified with prep-TLC (DCM/MeOH=15/1) to give ethyl 1-((6-(1-methylcyclopropyl)imidazo[1,2-a]pyridin-2-yl)methyl)-1H-pyrazole-4-carboxylate (17 mg, yield: 33%) as a yellow solid. ESI-MS [M+H]$^+$: 325.1.

Synthesis of 1-((6-(1-methylcyclopropyl)imidazo[1,2-a]pyridin-2-yl)methyl)-1H-pyrazole-4-carboxylic Acid A mixture of ethyl 1-((6-(1-methylcyclopropyl)imidazo[1,2-a]pyridin-2-yl)methyl)-1H-pyrazole-4-carboxylate (17 mg, 0.052 mmol) and LiOH (4 mg, 0.16 mmol) in THF/MeOH/H$_2$O (2 mL/2 mL/1 mL) was stirred at 70° C. for 2 h. The pH of the reaction was adjusted to 4 and H$_2$O (5 mL) was added and the mixture was extracted with EtOAc (20 mL×3). The combined organic layers were then concentrated in vacuo to give the 1-((6-(1-methylcyclopropyl)imidazo[1,2-a]pyridin-2-yl)methyl)-1H-pyrazole-4-carboxylic acid (15 mg, yield: 98%) as a yellow oil which was used in the next step without further purification. ESI-MS [M+H]$^+$: 297.1.

Synthesis of N-((7-chloroimidazo[1,5-a]pyridin-1-yl)methyl)-1-((6-(1-methylcyclopropyl)imidazo[1,2-a]pyridin-2-yl)methyl)-1H-pyrazole-4-carboxamide (I-10)

To a solution of 1-((6-(1-methylcyclopropyl)imidazo[1,2-a]pyridin-2-yl)methyl)-1H-pyrazole-4-carboxylic acid (15 mg, 0.05 mmol), (7-chloroimidazo[1,5-a]pyridin-1-yl)methanamine hydrochloride (13 g, 0.06 mmol) and HATU (28 mg, 0.075 mmol) in DMF (3 mL) was added DIPEA (32 mg, 0.25 mmol). The resulting reaction was stirred at RT for 12 h. H$_2$O (15 mL) was added to the reaction and then extracted with EtOAc (25 mL×3). The combined organic layers were washed with brine, dried over Na$_2$SO$_4$, concentered in vacuo to give the crude, which was purified with prep-TLC (DCM/MeOH=10/1) to give N-((7-chloroimidazo[1,5-a]pyridin-1-yl)methyl)-1-((6-(1-methylcyclopropyl)imidazo[1,2-a]pyridin-2-yl)methyl)-1H-pyrazole-4-carboxamide (7.5 mg, yield: 33%) as a white solid. ESI-MS [M+H]$^+$: 460.2. Purity: 93.5%. $^1$H NMR (400 MHz, MeOD): δ 8.27-8.25 (m, 2H), 8.16 (d, J=7.5 Hz, 1H), 8.12 (s, 1H), 7.91 (s, 1H), 7.73-7.72 (m, 2H), 7.40 (d, J=9.4 Hz, 1H), 7.26 (d, J=9.4 Hz, 1H), 6.62 (d, J=7.3 Hz, 1H), 5.44 (s, 2H), 4.68 (s, 2H), 1.41 (s, 3H), 0.90-0.87 (m, 2H), 0.78-0.76 (m, 2H).

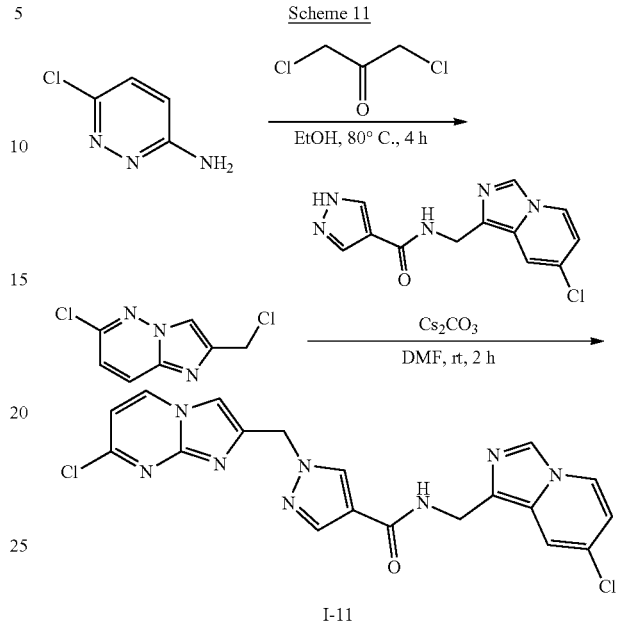

Scheme 11

I-11

Synthesis of 6-chloro-2-(chloromethyl)imidazo[1,2-b]pyridazine

A solution of 6-chloropyridazin-3-amine (5 g, 39 mmol) and 1, 3-dichloropropan-2-one (20 g, 156 mmol) in EtOH (50 mL) was stirred at 90° C. for 4 h. Then the reaction mixture was diluted with H$_2$O (100 mL) and extracted with EtOAc (100 mL×3). The combined organic layers were dried over Na$_2$SO$_4$, concentrated and purified by column chromatography (PE/EA=5/1) to give the desired product 6-chloro-2-(chloromethyl)imidazo[1,2-b]pyridazine (2.6 g, yield: 33%) as a yellow solid. ESI-MS [M+H]$^+$: 202.2.

Synthesis of N-((7-chloroimidazo[1,5-a]pyridin-1-yl)methyl)-1-((6-cyclopropylimidazo[1,2-b]pyridazin-2-yl)methyl)-1H-pyrazole-4-carboxamide (I-11)

A solution of 6-chloro-2-(chloromethyl)imidazo[1,2-b]pyridazine (50 mg, 0.25 mmol), N-((7-chloroimidazo[1,5-a]pyridin-1-yl)methyl)-1H-pyrazole-4-carboxamide (66 mg, 0.24 mmol), Cs$_2$CO$_3$ (160 mg, 0.5 mmol) in DMF (3 mL) was stirred at RT for 2 h. Then the reaction mixture was diluted with H$_2$O (30 mL) and extracted with EtOAc (30 mL×3). The combined organic layers were dried over Na$_2$SO$_4$, concentrated and purified by column chromatography (CH$_2$Cl$_2$/MeOH=10/1) to give the desired compound N-((7-chloroimidazo[1,5-a]pyridin-1-yl)methyl)-1-((6-cyclopropylimidazo[1,2-b]pyridazin-2-yl)methyl)-1H-pyrazole-4-carboxamide (29.5 mg, yield: 27%) as a white solid. ESI-MS [M+H]$^+$: 441.1. Purity: 98%. $^1$H NMR (400 MHz, DMSO): δ 8.58 (s, 1H), 8.31 (s, 3H), 8.25 (s, 1H), 8.17 (d, J=9.3 Hz, 1H), 7.86 (s, 1H), 7.78 (s, 1H), 7.38 (d, J=9.5 Hz, 1H), 6.65 (d, J=7.1 Hz, 1H), 5.47 (s, 2H), 4.56 (d, J=5.0 Hz, 2H).

Example 12

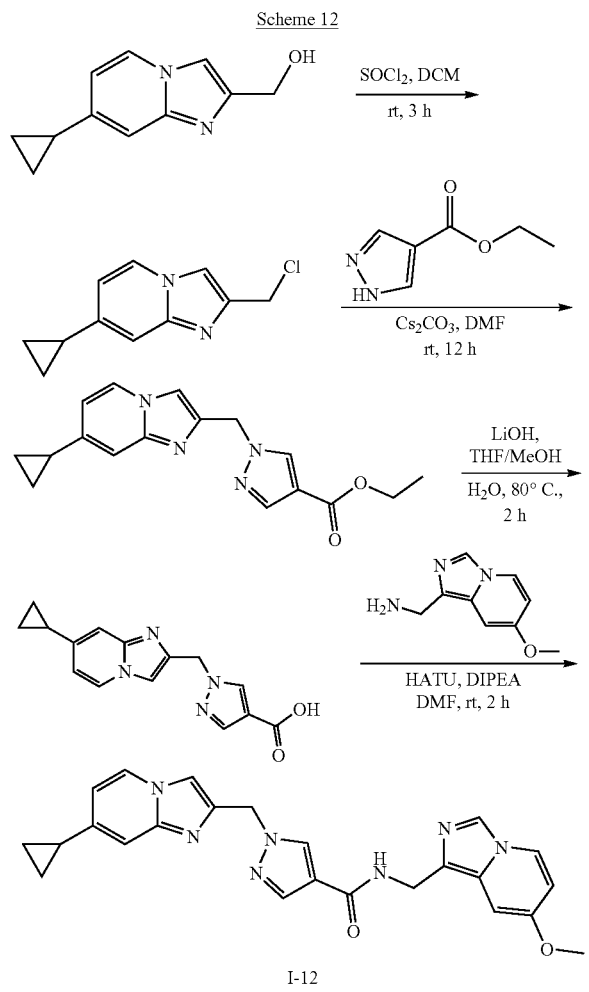

Synthesis of 2-(chloromethyl)-7-cyclopropylimidazo[1,2-a]pyridine

To a solution of (7-cyclopropylimidazo[1,2-a]pyridin-2-yl)methanol (126 mg, 0.67 mmol) in DCM (10 mL) was added SOCl$_2$ (2 mL). The resulting reaction was stirred at 45° C. for 4 h. The reaction was concentrated in vacuo to give the 2-(chloromethyl)-7-cyclopropylimidazo[1,2-a]pyridine (150 mg crude), which was used in the next step without further purification. ESI-MS [M+H]$^+$: 207.2.

Synthesis of Ethyl 1-((7-cyclopropylimidazo[1,2-a]pyridin-2-yl)methyl)-1H-pyrazole-4-carboxylate A mixture of 2-(chloromethyl)-7-cyclopropylimidazo[1,2-a]pyridine (0.15 g crude from previous step), ethyl 1H-pyrazole-4-carboxylate (126 mg, 0.9 mmol) and Cs$_2$CO$_3$ (1.17 g, 3.6 mmol) in DMF (8 mL) was stirred at 80° C. for 12 h. H$_2$O (15 mL) was added to the reaction and then extracted with EtOAc (20 mL×3). The combined organic layers were washed with brine, dried over Na$_2$SO$_4$, concentrated in vacuo to give the crude, which was purified with prep-TLC (DCM/MeOH=10/1) to give ethyl 1-((7-cyclopropylimidazo[1,2-a]pyridin-2-yl)methyl)-1H-pyrazole-4-carboxylate (100 mg, 36%) as a yellow solid. ESI-MS [M+H]$^+$: 311.2.

Synthesis of 1-((7-cyclopropylimidazo[1,2-a]pyridin-2-yl)methyl)-1H-pyrazole-4-carboxylic Acid A mixture of ethyl 1-((7-cyclopropylimidazo[1,2-a]pyridin-2-yl)methyl)-1H-pyrazole-4-carboxylate (600 mg, 1.94 mmol) and LiOH (270 mg, 11.6 mmol) in THF/EtOH/H$_2$O (6 mL/6 mL/4 mL) was stirred at 80° C. for 2 h. The pH of reaction was adjusted to around 5 and a yellow solid was precipitated out. The mixture was filtered and the solid was dried to give 1-((7-cyclopropylimidazo[1,2-a]pyridin-2-yl)methyl)-1H-pyrazole-4-carboxylic acid (550 mg, yield: 100%) as a brown solid. ESI-MS [M+H]$^+$: 283.1.

Synthesis of 1-((7-cyclopropylimidazo[1,2-a]pyridin-2-yl)methyl)-N-((6-methoxyimidazo[1,2-a]pyridin-2-yl)methyl)-1H-pyrazole-4-carboxamide (I-12)

To a solution of 1-((7-cyclopropylimidazo[1,2-a]pyridin-2-yl)methyl)-1H-pyrazole-4-carboxylic acid (23 mg, 0.08 mmol), (7-methoxyimidazo[1,5-a]pyridin-1-yl)methanamine (14 mg, 0.08 mmol) and HATU (45.6 mg, 0.12 mmol) in DMF (3 mL) was added DIPEA (30 mg, 0.24 mmol). The resulting reaction stirred at RT for overnight. H$_2$O (20 mL) was added to the reaction and then extracted with EtOAc (30 mL×3). The combined organic layers were washed with brine, dried over Na$_2$SO$_4$, and concentrated in vacuo to give the crude, which was purified with prep-TLC (DCM/MeOH=10/1) to give 1-((7-cyclopropylimidazo[1,2-a]pyridin-2-yl)methyl)-N-((6-methoxyimidazo[1,2-a]pyridin-2-yl)methyl)-1H-pyrazole-4-carboxamide (30 mg, yield: 85%). ESI-MS [M+H]$^+$: 442.1. Purity: 98.3%. $^1$H NMR (400 MHz, MeOD): δ 8.22 (s, 1H), 8.15 (s, 1H), 8.12 (s, 1H), 8.06 (d, J=7.6 Hz, 1H), 7.94 (s, 1H), 7.73 (s, 1H), 7.41 (d, J=9.4 Hz, 1H), 7.14 (d, J=9.4 Hz, 1H), 6.90 (s, 1H), 6.41 (dd, J=7.6, 2.2 Hz, 1H), 5.46 (s, 2H), 4.69 (s, 2H), 3.81 (s, 3H), 2.05-1.83 (m, 1H), 1.07-0.92 (m, 2H), 0.86-0.63 (m, 2H).

Example 13

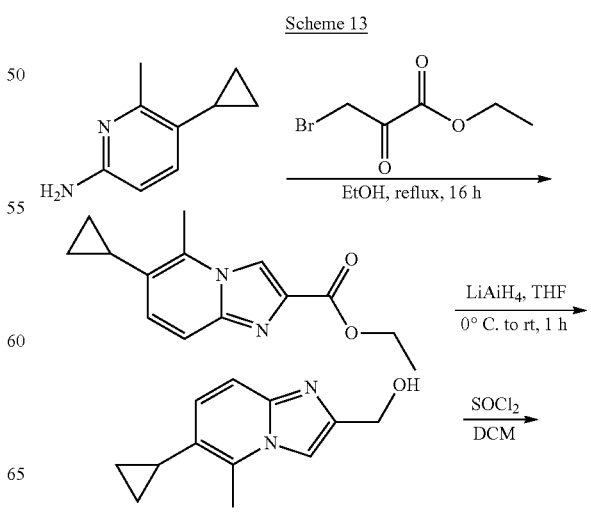

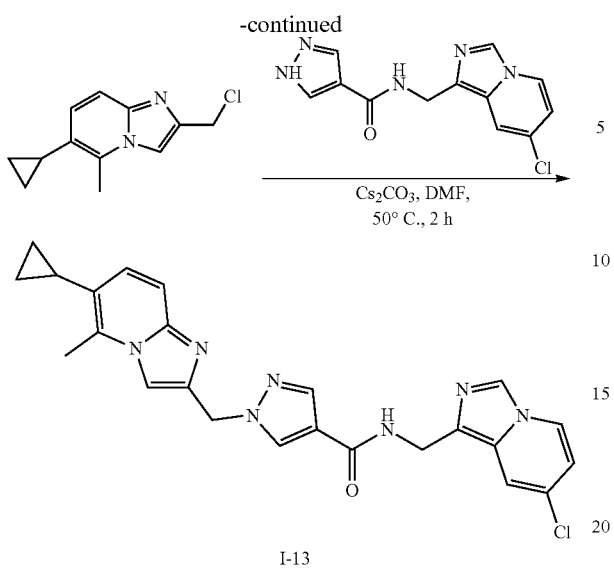

I-13

Synthesis of Ethyl 6-cyclopropyl-5-methylimidazo[1,2-a]pyridine-2-carboxylate A mixture of 5-cyclopropyl-6-methylpyridin-2-amine (1.3 g, 8.78 mmol), ethyl 3-bromo-2-oxopropanoate (3.5 g, 17.57 mmol) in EtOH (30 mL) was stirred at 90° C. for 16 h. The mixture was concentrated and purified by silica gel chromatography (DCM/MeOH=20/1) to give ethyl 6-cyclopropyl-5-methylimidazo[1,2-a]pyridine-2-carboxylate (150 mg, yield: 7%) as a yellow solid. ESI-MS [M+H]$^+$: 245.1.

Synthesis of (6-cyclopropyl-5-methylimidazo[1,2-a]pyridin-2-yl)methanol

To a solution of ethyl 6-cyclopropyl-5-methylimidazo[1,2-a]pyridine-2-carboxylate (110 mg, 0.45 mmol) in dry THF (5 mL) was added LiAlH$_4$ (50 mg, 1.12 mmol) slowly at 0° C. After the mixture was stirred at RT for 1 h, it was quenched with Na$_2$SO$_4$.10H$_2$O. The mixture was filtered and the filtrate was washed with EtOAc (20 mL). The filtrate was concentrated and purified by prep-TLC (DCM/MeOH=15/1) to give (6-cyclopropyl-5-methylimidazo[1,2-a]pyridin-2-yl) methanol (50 mg, yield: 55%) as a yellow solid. ESI-MS [M+H]$^+$: 203.1.

Synthesis of 2-(chloromethyl)-6-cyclopropyl-5-methylimidazo[1,2-a]pyridine

To a solution of (6-cyclopropyl-5-methylimidazo[1,2-a]pyridin-2-yl)methanol (50 mg, 0.25 mmol) in dry DCM (2.5 mL) was added SOCl$_2$ (0.5 mL) at RT. The mixture was stirred at 40° C. for 1 h. The mixture was concentrated to give 2-(chloromethyl)-6-cyclopropyl-5-methylimidazo [1,2-a]pyridine (50 mg, yield: 90.9%) as a yellow oil. which was used in the next step without further purification. ESI-MS [M+H]$^+$: 221.2.

Synthesis of N-((7-chloroimidazo[1,5-a]pyridin-1-yl)methyl)-1-((6-cyclopropyl-5-methylimidazo[1,2-a]pyridin-2-yl)methyl)-1H-pyrazole-4-carboxamide (I-13)

A mixture of 2-(chloromethyl)-6-cyclopropyl-5-methylimidazo[1,2-a]pyridine (25 mg, 0.11 mmol), N-((7-chloroimidazo[1,5-a]pyridin-1-yl)methyl)-1H-pyrazole-4-carboxamide (30 mg, 0.11 mmol) and Cs$_2$CO$_3$ (110 mg, 0.33 mmol) in DMF (3 mL) was stirred at 50° C. for 2 h. Water (20 mL) was added and extracted with EtOAc (20 mL×3). The combined organic layers were concentrated and purified by prep-TLC (DCM/MeOH=10/1) to give N-((7-chloroimidazo[1,5-a]pyridin-1-yl)methyl)-1-((6-cyclopropyl-5-methylimidazo[1,2-a]pyridin-2-yl)methyl)-1H-pyrazole-4-carboxamide (17 mg, yield: 33.7%) as a light yellow solid. ESI-MS [M+H]$^+$: 460.2. Purity: 99.5%. $^1$H NMR (400 MHz, DMSO): δ 8.57 (s, 1H), 8.30 (d, J=7.1 Hz, 2H), 8.20 (s, 1H), 7.85 (s, 1H), 7.77 (s, 2H), 7.33 (d, J=9.6 Hz, 1H), 6.97 (d, J=8.6 Hz, 1H), 6.64 (d, J=7.3 Hz, 1H), 5.40 (s, 2H), 4.54 (d, J=5.1 Hz, 2H), 2.64 (s, 3H), 2.02 (s, 1H), 0.94 (d, J=8.2 Hz, 2H), 0.64 (s, 2H).

Example 14

Scheme 14

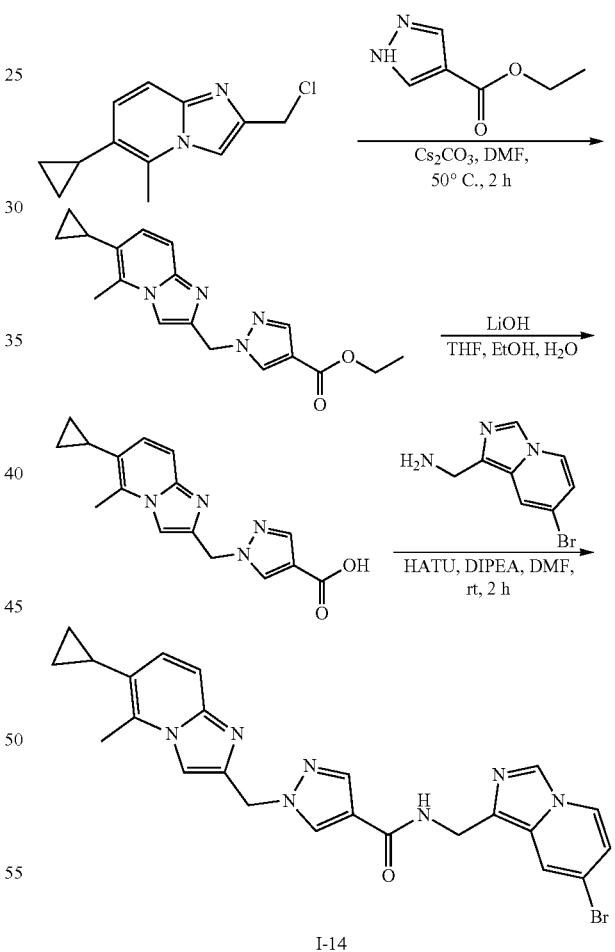

I-14

Synthesis of Ethyl 1-((6-cyclopropyl-5-methylimidazo[1,2-a]pyridin-2-yl)methyl)-1H-pyrazole-4-carboxylate A mixture of 2-(chloromethyl)-6-cyclopropyl-5-methylimidazo[1,2-a]pyridine (65 mg, 0.30 mmol), ethyl 1H-pyrazole-4-carboxylate (45 mg, 0.32 mmol) and Cs$_2$CO$_3$ (245 mg, 0.75 mmol) in DMF (5 mL) was stirred at 50° C. for 2 h. Water (20 mL) was added and extracted with EtOAc (20 mL×3). The combined organic layers were concentrated to give ethyl 1-((6-cyclopropyl-5-methylimidazo[1,2-a]pyridin-2-yl)methyl)-1H-pyrazole-4-carboxylate (65 mg, yield: 67%) as a yellow solid. ESI-MS [M+H]⁺: 325.1.

Synthesis of 1-((6-cyclopropyl-5-methylimidazo[1,2-a]pyridin-2-yl)methyl)-1H-pyrazole-4-carboxylic Acid A solution of ethyl 1-((6-cyclopropyl-5-methylimidazo[1,2-a]pyridin-2-yl)methyl)-1H-pyrazole-4-carboxylate (65 mg, 0.2 mmol) and LiOH.H₂O (25 mg, 0.6 mmol) in THF/MeOH/H₂O (1 mL/1 mL/0.5 mL) was stirred at 80° C. for 1 h. The pH of the mixture was adjusted to 4 by adding 1 M HCl solution. Water (10 mL) was added and the reaction was extracted with EtOAc (20 mL×3). The combined organic layers were concentrated to give 1-((6-cyclopropyl-5-methylimidazo[1,2-a]pyridin-2-yl)methyl)-1H-pyrazole-4-carboxylic acid (59 mg, yield: 99.7%) as a yellow oil. which was used directly in the next step without further purification. ESI-MS [M+H]⁺: 297.1.

Synthesis of N-((7-bromoimidazo[1,5-a]pyridin-1-yl)methyl)-1-((6-cyclopropyl-5-methylimidazo[1,2-a]pyridin-2-yl)methyl)-1H-pyrazole-4-carboxamide (I-14)

A mixture of 1-((6-cyclopropyl-5-methylimidazo[1,2-a]pyridin-2-yl)methyl)-1H-pyrazole-4-carboxylic acid (59 mg, 0.2 mmol), (7-bromoimidazo[1,5-a]pyridin-1-yl)methanamine (70 mg, 0.25 mmol), HATU (120 mg, 0.3 mmol) and DIPEA (0.1 mL, 0.6 mmol) in DMF (4 mL) was stirred at RT for 2 h. Water (20 mL) was added and the reaction was extracted with EtOAc (30 mL×3). The organic layers were concentrated and purified by prep-TLC (DCM/MeOH=10/1) to give N-((7-bromoimidazo[1,5-a]pyridin-1-yl)methyl)-1-((6-cyclopropyl-5-methylimidazo[1,2-a]pyridin-2-yl)methyl)-1H-pyrazole-4-carboxamide (42.2 mg, yield: 41.9%) as a white solid. ESI-MS [M+H]⁺: 504.1. Purity: 93.5%. ¹H NMR (400 MHz, DMSO): δ 8.57 (t, J=5.7 Hz, 1H), 8.31 (s, 1H), 8.27-8.17 (m, 2H), 7.94 (s, 1H), 7.85 (s, 1H), 7.77 (s, 1H), 7.33 (d, J=9.3 Hz, 1H), 6.97 (d, J=9.3 Hz, 1H), 6.71 (dd, J=7.4, 1.9 Hz, 1H), 5.41 (s, 2H), 4.54 (d, J=5.7 Hz, 2H), 2.64 (s, 3H), 2.01-1.98 (m, 1H), 0.94 (dd, J=8.4, 1.7 Hz, 2H), 0.74-0.58 (m, 2H).

Example 15

Scheme 15

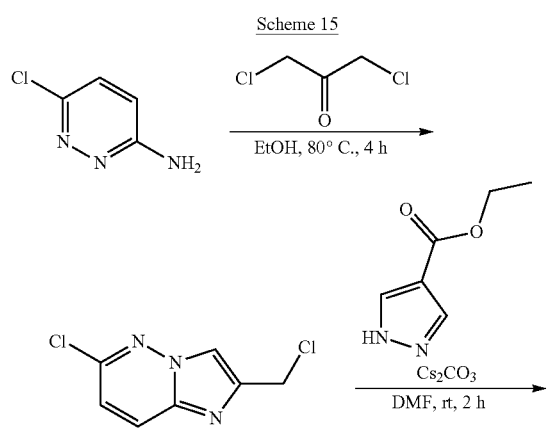

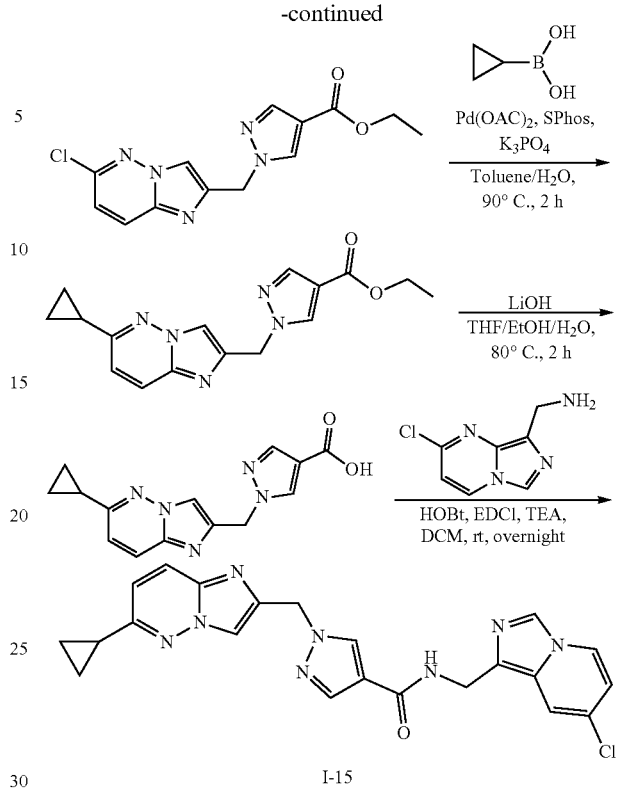

Synthesis of 6-chloro-2-(chloromethyl)imidazo[1,2-b]pyridazine

A solution of 6-chloropyridazin-3-amine (20.0 g, 155.0 mmol) and 1,3-dichloropropan-2-one (49.2 g, 387.5 mmol) in EtOH (200 mL) was stirred at 80° C. for 4 h. Then the reaction mixture was concentrated and diluted with H₂O (300 mL×3) and extracted with EtOAc (500 mL×3). The combined organic layer were dried over Na₂SO₄, concentrated and purified by column chromatography (DCM:MeOH=10:1) to give the desired product 6-chloro-2-(chloromethyl)imidazo[1,2-b]pyridazine (17.0 g, yield: 54%) as a yellow solid. ESI-MS [M+H]⁺: 202.1.

Synthesis of Ethyl 1-((6-chloroimidazo[1,2-b]pyridazin-2-yl)methyl)-1H-pyrazole-4-carboxylate A solution of 6-chloro-2-(chloromethyl)imidazo[1,2-b]pyridazine (10.0 g, 49.5 mmol), ethyl 1H-pyrazole-4-carboxylate (6.2 g, 44.5 mmol), Cs₂CO₃ (48.4 g, 148.5 mmol) in DMF (200 mL) was stirred at RT for 2 h. Most of the DMF was concentrated, the residue was diluted with H₂O (300 mL) and extracted with EtOAc (500 mL×3). The combined organic layer were dried over Na₂SO₄, concentrated and purified by column chromatography (EtOAc:PE=2:1) to give the desired compound ethyl 1-((6-chloroimidazo[1,2-b]pyridazin-2-yl)methyl)-1H-pyrazole-4-carboxylate (10.0 g, yield: 65%) as a yellow solid, ESI-MS [M+H]⁺: 306.1.

Synthesis of Methyl 1-((6-cyclopropylimidazo[1,2-b]pyridazin-2-yl)methyl)-1H-pyrazole-4-carboxylate A solution of ethyl 1-((6-chloroimidazo[1,2-b]pyridazin-2-yl)methyl)-1H-pyrazole-4-carboxylate (10.0 g, 32 mmol), cyclopropylboronic acid (4.2 g, 49 mmol), Pd(OAc)$_2$ (718.4 mg, 3.2 mmol), SPhos (1.3 g, 3.2 mmol) and K$_3$PO$_4$ (21.0 g, 96 mmol) in Tol/H$_2$O (100 mL/10 mL) was stirred at RT for 2 h. Then the reaction mixture was diluted with H$_2$O (100 mL) and extracted with EtOAc (300 mL×3). The combined organic layer were dried over Na$_2$SO$_4$, concentrated and purified by column chromatography (EtOAc:PE=2:1) to give the desired compound ethyl 1-((6-cyclopropylimidazo[1,2-b]pyridazin-2-yl)methyl)-1H-pyrazole-4-carboxylate (9.8 g, yield: 100%) as a white solid. ESI-MS [M+H]$^+$: 312.2.

Synthesis of 1-((6-cyclopropylimidazo[1,2-b]pyridazin-2-yl)methyl)-1H-pyrazole-4-carboxylic Acid A solution of ethyl 1-((6-cyclopropylimidazo[1,2-b]pyridazin-2-yl)methyl)-1H-pyrazole-4-carboxylate (9.8 g, 32.0 mmol) and LiOH (1.5 g, 64.0 mmol) in THF/EtOH/H$_2$O (80 mL/80 mL/80 mL) was stirred at 80° C. for 2 h. Then the reaction mixture was concentrated and diluted with H$_2$O (50 mL). The pH of the solution was adjusted to 5 by adding 1 M HCl solution. Solid precipitated and was filtered to give the desired compound 1-((6-cyclopropylimidazo[1,2-b]pyridazin-2-yl)methyl)-1H-pyrazole-4-carboxylic acid (9.5 g, yield: 104.6%) as a white solid. ESI-MS [M+H]$^+$: 284.1.

Synthesis of N-((7-chloroimidazo[1,5-a]pyridin-1-yl)methyl)-1-((6-cyclopropylimidazo[1,2-b]pyridazin-2-yl)methyl)-1H-pyrazole-4-carboxamide (I-15)

A solution of 1-((6-cyclopropylimidazo[1,2-b]pyridazin-2-yl)methyl)-1H-pyrazole-4-carboxylic acid (9.5 g, 33.5 mmol), (7-chloroimidazo[1,5-a]pyridin-1-yl)methanamine (9.5 g, 43.5 mmol), EDCI (7.7 g, 40.2 mmol), HOBT (5.4 g, 40.2 mmol) and TEA (10.1 g, 13.9 mL, 100.5 mmol) in dry DCM (800 mL) was stirred at RT overnight. Then the reaction mixture was diluted with H$_2$O (500 mL×3) and extracted with DCM (1 L×3). The combined organic layer were dried over Na$_2$SO$_4$, concentrated and purified by column chromatography (DCM:MeOH=10:1) to give the desired compound N-((7-chloroimidazo[1,5-a]pyridin-1-yl)methyl)-1-((6-cyclopropylimidazo[1,2-b]pyridazin-2-yl)methyl)-1H-pyrazole-4-carboxamide (6.1 g, yield: 40.9%) as a white solid. ESI-MS [M+H]$^+$: 447.1. Purity: 99.05%. $^1$H NMR (400 MHz, DMSO): δ 8.58-8.55 (t, J=5.7 Hz, 1H), 8.30-8.28 (m, J=7.5, 0.6 Hz, 2H), 8.21 (s, 1H), 8.07 (s, 1H), 7.91 (d, J=9.5 Hz, 1H), 7.84 (s, 1H), 7.77-7.76 (m, 1H), 7.08 (d, J=9.5 Hz, 1H), 6.63 (dd, J=7.5, 2.1 Hz, 1H), 5.40 (s, 2H), 4.54 (d, J=5.7 Hz, 2H), 2.50-2.14 (m, J=9.0, 4.1 Hz, 1H), 1.07-1.03 (m, J=6.0, 4.1 Hz, 2H), 0.97-0.93 (m, 2H).

Example 16

Scheme 16

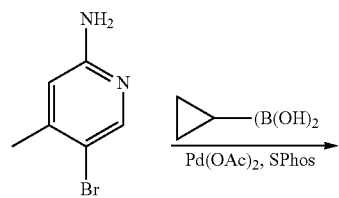

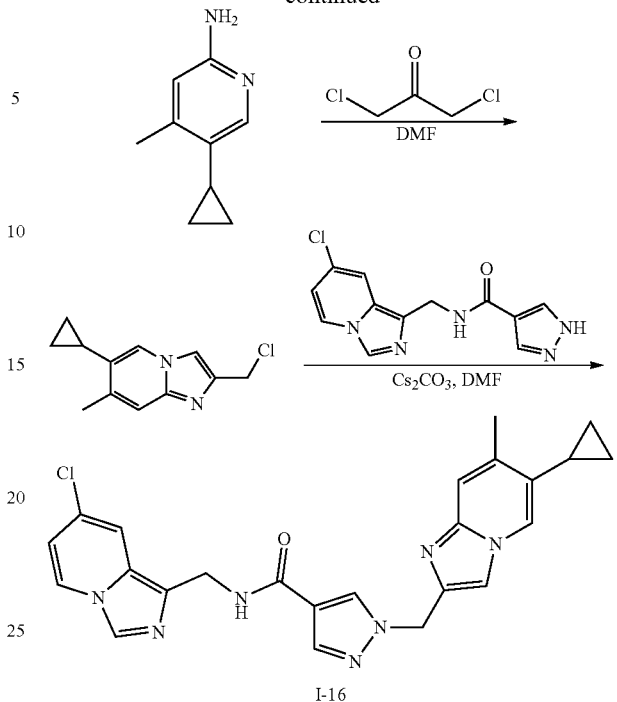

I-16

Synthesis of 5-cyclopropyl-4-methylpyridin-2-amine

To a solution of 5-bromo-4-methylpyridin-2-amine (2 g, 10.7 mmol) in toluene/H$_2$O (50 mL/5 mL) was added cyclopropylboronic acid (1.36 g, 16.0 mmol), Pd(OAc)$_2$ (240 mg, 1.07 mmol), SPhos (439 mg, 1.07 mmol) and K$_3$PO$_4$ (6.8 g, 32.1 mmol). The reaction mixture was stirred at 95° C. for 12 h under nitrogen, then diluted with DCM (200 mL), washed with H$_2$O and brine, and concentrated to give the crude residue which was purified by silica gel chromatography (PE/EtOAc=1/1) to afford 5-cyclopropyl-4-methylpyridin-2-amine as a yellow solid (4 g, yield: 90%). ESI-MS [M+H]$^+$: 149.2.

Synthesis of 2-(chloromethyl)-6-cyclopropyl-7-methylimidazo[1,2-a]pyridine

To a solution 5-cyclopropyl-4-methylpyridin-2-amine (200 mg, 1.35 mmol) in DMF (10 mL) was added 1,3-dichloropropan-2-one (514 mg, 4.05 mmol) at RT. The resulting reaction was stirred at 85° C. for 2 h. The solution was quenched with H$_2$O (30 mL), adjusted to pH 8 by adding saturated NaHCO$_3$ solution, and then extracted with EtOAc (30 mL×3). The combined organic layers were washed with brine, dried over Na$_2$SO$_4$, and concentrated in vacuo to give the crude, which was purified by prep-TLC (PE/EtOAc=1/1) to give the 2-(chloromethyl)-6-cyclopropyl-7-methylimidazo[1,2-a]pyridine (150 mg, yield: 51%) as a light yellow oil. ESI-MS [M+H]$^+$: 221.2.

Synthesis of N-((7-chloroimidazo[1,5-a]pyridin-1-yl)methyl)-1-((6-cyclopropyl-7-methylimidazo[1,2-a]pyridin-2-yl)methyl)-1H-pyrazole-4-carboxamide (I-17)

To a solution 2-(chloromethyl)-6-cyclopropyl-7-methylimidazo[1,2-a]pyridine (55 mg, 0.25 mmol) in DMF (4 mL)

was added N-((7-chloroimidazo[1,5-a]pyridin-1-yl)methyl)-1H-pyrazole-4-carboxamide (45 mg, 0.16 mmol) and Cs$_2$CO$_3$ (156 mg, 0.48 mmol) at RT. The resulting reaction was stirred at RT for 12 h. H$_2$O (20 mL) was added to the reaction and extracted with EtOAc (30 mL×3). The combined organic layers were washed with brine, dried over Na$_2$SO$_4$, concentrated in vacuo to give the crude, which was purified by prep-TLC (DCM/MeOH=10/1) to give the N-((7-chloroimidazo[1,5-a]pyridin-1-yl)methyl)-1-((6-cyclopropyl-7-methylimidazo[1,2-a]pyridine-2-yl)methyl)-1H-pyrazole-4-carboxamide (20 mg, yield: 27%) as a white solid. ESI-MS [M+H]$^+$: 460.1. $^1$H NMR (400 MHz, DMSO): δ 8.58 (t, J=5.7 Hz, 1H), 8.35-8.27 (m, 2H), 8.23 (s, 1H), 8.19 (s, 1H), 7.86 (s, 1H), 7.79-7.74 (m, 1H), 7.66 (s, 1H), 7.30 (s, 1H), 6.66-6.63 (m, 1H), 5.38 (s, 2H), 4.55 (d, J=5.7 Hz, 2H), 2.42 (s, 3H), 1.88-1.82 (m, 1H), 0.94-0.84 (m, 2H), 0.62-0.54 (m, 2H).

Example 17

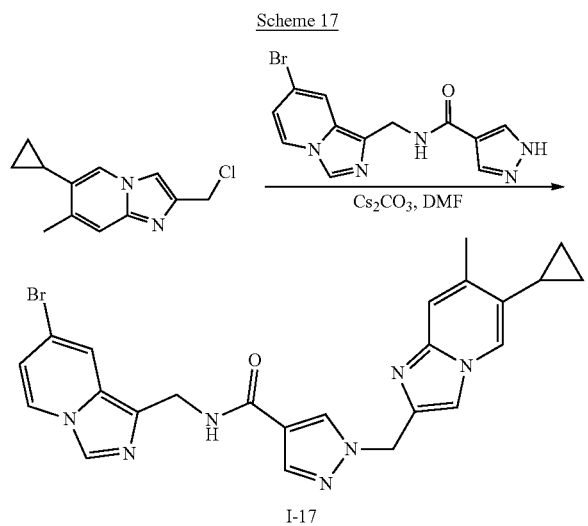

Scheme 17

I-17

Synthesis of N-((7-bromoimidazo[1,5-a]pyridin-1-yl)methyl)-1-((6-cyclopropyl-7-methylimidazo[1,2-a]pyridin-2-yl)methyl)-1H-pyrazole-4-carboxamide (I-17)

To a solution of 2-(chloromethyl)-6-cyclopropyl-7-methylimidazo[1,2-a]pyridine (50 mg, 0.23 mmol) in DMF (4 mL) was added N-((7-bromoimidazo[1,5-a]pyridin-1-yl)methyl)-1H-pyrazole-4-carboxamide (48 mg, 0.15 mmol) and Cs$_2$CO$_3$ (147 mg, 0.45 mmol) at RT. The resulting reaction was stirred at RT for 12 h. the reaction was quenched with H$_2$O (20 mL) and extracted with EtOAc (30 mL×3). The combined organic layers were washed with brine, dried over Na$_2$SO$_4$, concentrated in vacuo to give the crude, which was purified by prep-TLC (DCM/MeOH=10/1) to give the N-((7-bromoimidazo[1,5-a]pyridin-1-yl)methyl)-1-((6-cyclopropyl-7-methylimidazo[1,2-a]pyridin-2-yl)methyl)-1H-pyrazole-4-carboxamide (22 mg, yield: 29%) as a white solid. ESI-MS [M+H]$^+$: 506.1. Purity: 91.6%. $^1$H NMR (400 MHz, DMSO): δ 8.58-8.55 (m, 1H), 8.31 (s, 1H), 8.24 (d, J=7.4 Hz, 1H), 8.19-8.17 (m, 2H), 7.95 (s, 1H), 7.84 (s, 1H), 7.62 (s, 1H), 7.26 (s, 1H), 6.73-6.70 (m, 1H), 5.35 (s, 2H), 4.54 (d, J=5.7 Hz, 2H), 2.40 (s, 3H), 1.85-1.81 (m, 1H), 0.89-0.87 (m, 2H), 0.58-0.56 (m, 2H).

Example 18

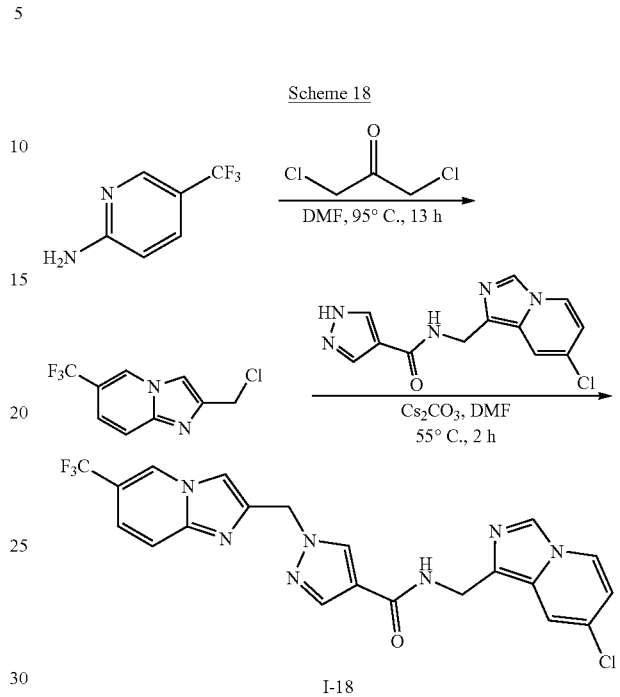

Scheme 18

I-18

Synthesis of 2-(chloromethyl)-6-(trifluoromethyl) imidazo[1,2-a]pyridine

A solution of 5-(trifluoromethyl)pyridin-2-amine (500 mg, 3.1 mmol) and 1,3-dichloropropan-2-one (1.2 g, 9.3 mmol) in DMF (15 mL) was stirred at 95° C. for 13 h. The reaction was quenched with aqueous NaHCO$_3$ solution (20 mL) and extracted with EtOAc (30 mL×3). The combined organic layers were washed with brine, dried over Na$_2$SO$_4$, concentrated in vacuo to give the crude, which was purified with silica gel chromatography (PE/EA=1/2) to give the 2-(chloromethyl)-6-(trifluoromethyl)imidazo[1,2-a]pyridine (350 mg, yield: 48%) as a yellow solid. ESI-MS [M+H]$^+$: 235.2.

Synthesis of N-((7-chloroimidazo[1,5-a]pyridin-1-yl)methyl)-1-((6-(trifluoromethyl)imidazo[1,2-a] pyridin-2-yl)methyl)-1H-pyrazole-4-carboxamide (I-18)

A mixture of 2-(chloromethyl)-6-(trifluoromethyl)imidazo[1,2-a]pyridine (200 mg, 0.85 mmol), N-((7-chloroimidazo[1,5-a]pyridin-1-yl)methyl)-1H-pyrazole-4-carboxamide (234 mg, 0.85 mmol) and Cs$_2$CO$_3$ (831 mg, 2.55 mmol) in DMF (10 mL) was stirred at 55° C. for 2 h. H$_2$O (30 mL) was added to the reaction and extracted with EtOAc (30 mL×3). The combined organic layers were washed with brine, dried over Na$_2$SO$_4$ and concentrated in vacuo to give the crude, which was purified by prep-TLC (DCM/MeOH=10/1) to give the N-((7-chloroimidazo[1,5-a]pyridin-1-yl)methyl)-1-((6-(trifluoromethyl)imidazo[1,2-a]pyridin-2-yl)methyl)-1H-pyrazole-4-carboxamide (25 mg, yield: 6.2%) as a white solid. ESI-MS [M+H]$^+$: 474.2. Purity: 99.7%. $^1$H NMR (400 MHz, MeOD): δ 8.99 (s, 1H), 8.27 (s, 1H), 8.19-8.17 (m, 2H), 7.93 (s, 2H), 7.75 (s, 1H), 7.66 (d, J=9.5 Hz, 1H), 7.50 (dd, J=9.5, 1.5 Hz, 1H), 6.63 (dd, J=7.5, 1.9 Hz, 1H), 5.52 (s, 2H), 4.70 (s, 2H).

Example 19

Scheme 19

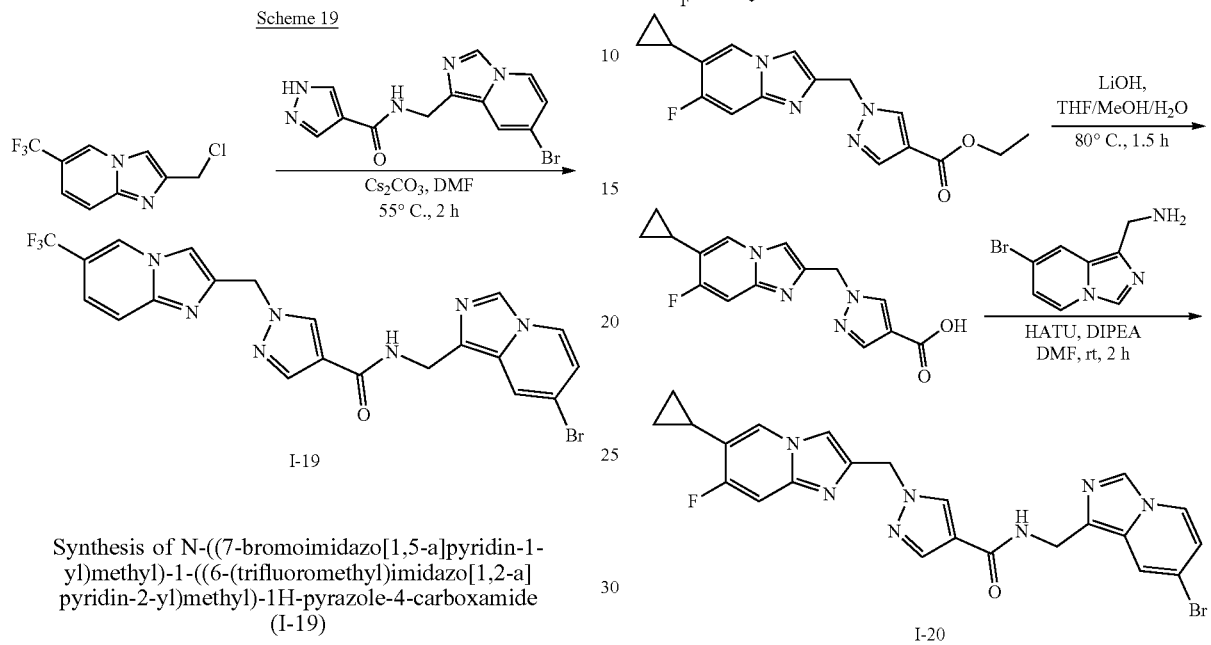

I-19

Synthesis of N-((7-bromoimidazo[1,5-a]pyridin-1-yl)methyl)-1-((6-(trifluoromethyl)imidazo[1,2-a]pyridin-2-yl)methyl)-1H-pyrazole-4-carboxamide (I-19)

A mixture of 2-(chloromethyl)-6-(trifluoromethyl)imidazo[1,2-a]pyridine (200 mg, 0.85 mmol), N-((7-bromoimidazo[1,5-a]pyridin-1-yl)methyl)-1H-pyrazole-4-carboxamide (271 mg, 0.85 mmol) and $Cs_2CO_3$ (831 mg, 2.55 mmol) in DMF (10 mL) was stirred at 55° C. for 2 h. $H_2O$ (30 mL) was added to the reaction and extracted with EtOAc (30 mL×3). The combined organic layers were washed with brine, dried over $Na_2SO_4$ and concentrated in vacuo to give the crude, which was purified by prep-TLC (DCM/MeOH=10/1) to give the N-((7-bromoimidazo[1,5-a]pyridin-1-yl)methyl)-1-((6-(trifluoromethyl)imidazo[1,2-a]pyridin-2-yl)methyl)-1H-pyrazole-4-carboxamide (40 mg, yield: 9%) as a white solid. ESI-MS [M+H]$^+$: 518.0. Purity: 94.14%. $^1$H NMR (400 MHz, MeOD): δ 8.99 (s, 1H), 8.27 (s, 1H), 8.19 (s, 1H), 8.11 (d, J=7.4 Hz, 1H), 7.94 (s, 3H), 7.66 (d, J=9.5 Hz, 1H), 7.50 (d, J=9.5 Hz, 1H), 6.75-6.67 (m, 1H), 5.52 (s, 2H), 4.70 (s, 2H).

Example 20

Scheme 20

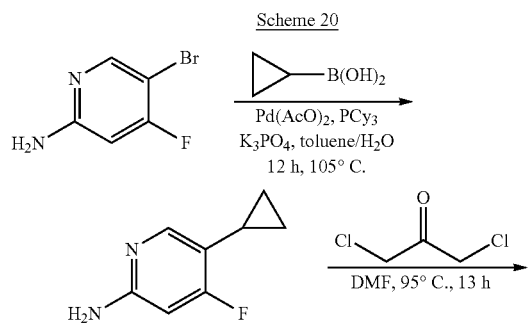

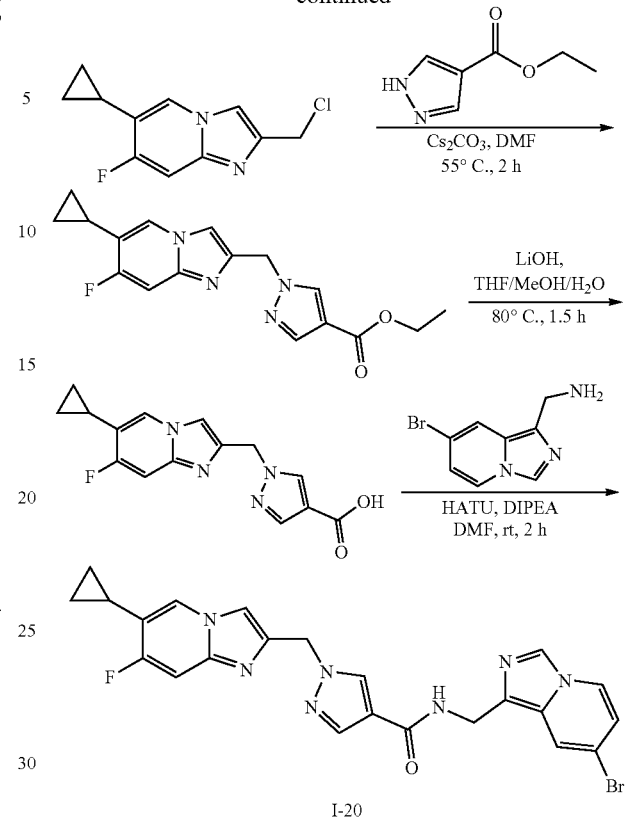

I-20

Synthesis of 5-cyclopropyl-4-fluoropyridin-2-amine

A mixture of 5-bromo-4-fluoropyridin-2-amine (1 g, 5.2 mmol), cyclopropylboronic acid (675 mg, 7.9 mmol), Pd(AcO)$_2$ (116 mg, 0.52 mmol), PCy$_3$ (280 mg, 1 mmol) and $K_3PO_4$ (3.3 g, 15.6 mmol) in toluene/$H_2O$ (50 mL/5 mL) was stirred in a sealed tube at 105° C. under $N_2$ for 12 h. The reaction was concentrated to give the crude, which was purified by silica gel chromatography (PE/EA=1/1) to give the 5-cyclopropyl-4-fluoropyridin-2-amine (500 mg, yield: 64%) as a white solid. ESI-MS [M+H]$^+$: 153.2.

Synthesis of 2-(chloromethyl)-6-cyclopropyl-7-fluoroimidazo[1,2-a]pyridine

A mixture of 5-cyclopropyl-4-fluoropyridin-2-amine (500 mg, 3.3 mmol) and 1,3-dichloropropan-2-one (1.25 g, 9.9 mmol) in DMF (30 mL) was stirred at 95° C. for 13 h. The pH of the reaction was adjusted to 9 by addition of aqueous NaHCO$_3$ and then extracted with EtOAc (50 mL×3). The combined organic layers were washed with brine, dried over Na$_2$SO$_4$, and concentrated in vacuo to give the crude, which was purified with silica gel chromatography (PE/EA=3/1) to give the 2-(chloromethyl)-6-cyclopropyl-7-fluoroimidazo[1,2-a]pyridine (150 mg, yield: 20%) as a yellow solid. ESI-MS [M+H]$^+$: 225.1.

Synthesis of Ethyl 1-((6-cyclopropyl-7-fluoroimidazo[1,2-a]pyridin-2-yl)methyl)-1H-pyrazole-4-carboxylate A mixture of 2-(chloromethyl)-6-cyclopropyl-7-fluoroimidazo[1,2-a]pyridine (150 mg, 0.67 mmol), ethyl 1H-pyrazole-4-carboxylate (103 mg, 0.74 mmol) and Cs$_2$CO$_3$ (655 mg, 2.01 mmol) in DMF (10 mL) was stirred at 55° C. for 2 h. H$_2$O (30 mL) was added to the reaction and extracted with EtOAc (30 mL×3). The combined organic layers were washed with brine, dried over Na$_2$SO$_4$, and concentrated in vacuo to give the crude, which was purified with silica gel chromatography (DCM/MeOH=20/1) to give the ethyl 1-((6-cyclopropyl-7-fluoroimidazo[1,2-a]pyridin-2-yl)methyl)-1H-pyrazole-4-carboxylate (100 mg, yield: 45%) as yellow solid. ESI-MS [M+H]$^+$: 329.2.

Synthesis of 1-((6-cyclopropyl-7-fluoroimidazo[1,2-a]pyridin-2-yl)methyl)-1H-pyrazole-4-carboxylic Acid To a solution of ethyl 1-((6-cyclopropyl-7-fluoroimidazo[1,2-a]pyridin-2-yl)methyl)-1H-pyrazole-4-carboxylate (100 mg, 0.31 mmol) in THF/EtOH/H$_2$O (4 mL/4 mL/2 mL) was added LiOH (22 mg, 0.91 mmol). The resulting reaction was stirred at 80° C. for 1.5 h. Most of the solvent was removed. The pH of the residue was adjusted to around 5 and a yellow solid was precipitate out. The mixture was filtered and the solid was dried to give the 1-((6-cyclopropyl-7-fluoroimidazo[1,2-a]pyridin-2-yl)methyl)-1H-pyrazole-4-carboxylic acid (75 mg, yield: 81%) as a yellow solid. ESI-MS [M+H]$^+$: 301.1.

Synthesis of N-((7-bromoimidazo[1,5-a]pyridin-1-yl)methyl)-1-((6-cyclopropyl-7-fluoroimidazo[1,2-a]pyridin-2-yl)methyl)-1H-pyrazole-4-carboxamide (I-20)

To a solution of 1-((6-cyclopropyl-7-fluoroimidazo[1,2-a]pyridin-2-yl)methyl)-1H-pyrazole-4-carboxylic acid (35 mg, 0.12 mmol), (7-bromoimidazo[1,5-a]pyridin-1-yl)methanamine (35 mg, 0.15 mmol) and HATU (68 mg, 0.18 mmol) in DMF (5 mL) was added DIPEA (77 mg, 0.6 mmol). The resulting reaction was stirred at RT for 2 h. Water (30 mL) was added and extracted with EtOAc (50 mL×2). The combined organic layers were washed with brine, dried over Na$_2$SO$_4$, concentrated in vacuo to give the crude, which was purified with prep-TLC (DCM/MeOH=10/1) to give N-((7-bromoimidazo[1,5-a]pyridin-1-yl)methyl)-1-((6-cyclopropyl-7-fluoroimidazo[1,2-a]pyridin-2-yl)methyl)-1H-pyrazole-4-carboxamide (19 mg, yield: 32%). ESI-MS [M+H]$^+$: 508.1. Purity: 90.5%. $^1$H NMR (400 MHz, MeOD): δ 8.26 (s, 1H), 8.18 (d, J=7.1 Hz, 1H), 8.13 (s, 1H), 8.10 (d, J=7.4 Hz, 1H), 7.92 (s, 1H), 7.91 (s, 1H), 7.67 (s, 1H), 7.12 (d, J=10.3 Hz, 1H), 6.72 (d, J=7.4 Hz, 1H), 5.41 (s, 2H), 4.68 (s, 2H), 2.04-1.87 (m, 1H), 1.02-0.97 (m, 2H), 0.76-0.72 (m, 2H).

Example 21

Scheme 21

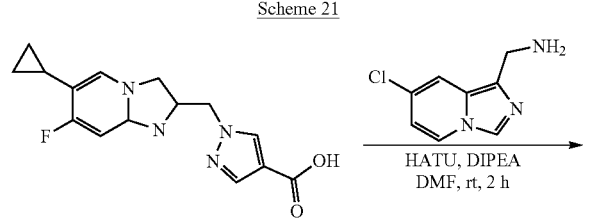

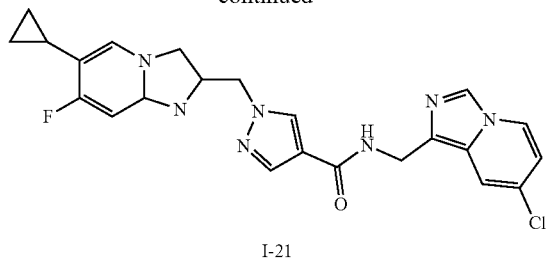

I-21

Synthesis of N-((7-chloroimidazo[1,5-a]pyridin-1-yl)methyl)-1-((6-cyclopropyl-7-fluoroimidazo[1,2-a]pyridin-2-yl)methyl)-1H-pyrazole-4-carboxamide (I-21)

To a solution of 1-((6-cyclopropyl-7-fluoroimidazo[1,2-a]pyridin-2-yl)methyl)-1H-pyrazole-4-carboxylic acid (35 mg, 0.12 mmol), (7-chloroimidazo[1,5-a]pyridin-1-yl)methanamine (28 mg, 0.15 mmol) and HATU (68 mg, 0.18 mmol) in DMF (5 mL) was added DIPEA (77 mg, 0.6 mmol). The resulting reaction was stirred at RT for 2 h. Water (30 mL) was added and extracted with EtOAc (50 mL×2). The combined organic layers were washed with brine, dried over Na$_2$SO$_4$, concentrated in vacuo to give the crude, which was purified with prep-TLC (DCM/MeOH=10/1) to give N-((7-chloroimidazo[1,5-a]pyridin-1-yl)methyl)-1-((6-cyclopropyl-7-fluoroimidazo[1,2-a]pyridin-2-yl)methyl)-1H-pyrazole-4-carboxamide (20 mg, yield: 32%). ESI-MS [M+H]$^+$: 464.1. Purity: 94.8%. $^1$H NMR (400 MHz, MeOD): δ 8.25 (s, 1H), 8.19-8.12 (m, 3H), 7.90 (s, 1H), 7.73 (s, 1H), 7.68 (s, 1H), 7.13 (d, J=10.3 Hz, 2H), 6.62 (dd, J=7.5, 1.9 Hz, 1H), 5.41 (s, 2H), 4.68 (s, 2H), 1.37 (dd, J=6.7, 3.3 Hz, 1H), 1.02-0.97 (m, 2H), 0.75-0.71 (m, 2H).

Example 22

Scheme 22

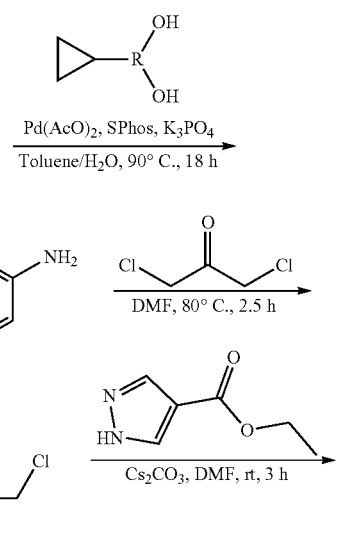

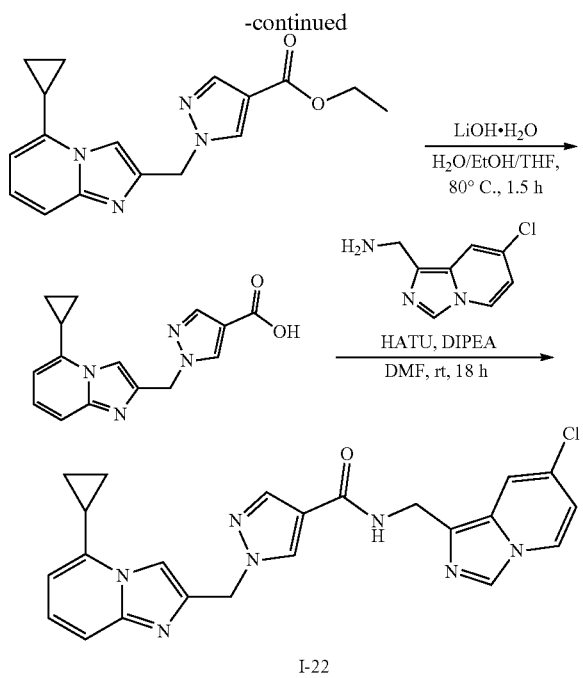

dried over anhydrous sodium sulfate and concentrated. The residue was purified by flash column chromatography to give ethyl 1-((5-cyclopropylimidazo[1,2-a]pyridin-2-yl)methyl)-1H-pyrazole-4-carboxylate (220 mg, yield: 80%). ESI-MS [M+H]$^+$: 311.2.

Synthesis of 1-((5-cyclopropylimidazo[1,2-a]pyridin-2-yl)methyl)-1H-pyrazole-4-carboxylic Acid To a solution of ethyl 1-((5-cyclopropylimidazo[1,2-a]pyridin-2-yl)methyl)-1H-pyrazole-4-carboxylate (210 mg, 0.68 mmol) in a mixture solvent of THF/EtOH/H$_2$O (3 mL/3 mL/1.5 mL) was added lithium hydroxide (82 mg, 3.39 mmol). The resulting mixture was stirred at 80° C. for 1.5 h. Water (50 mL) was added and the pH of the mixture was adjusted to 4-5 by adding HCl solution. The mixture was then extracted with DCM (3×30 mL), The organic layers were washed with brine, dried over anhydrous sodium sulfate, and concentrated to give 1-((5-cyclopropylimidazo[1,2-a]pyridin-2-yl)methyl)-1H-pyrazole-4-carboxylic acid (140 mg, Yield: 60%) which was used in the next step without further purification. ESI-MS [M+H]$^+$: 283.1.

Synthesis of N-((7-chloroimidazo[1,5-a]pyridin-1-yl)methyl)-1-((5-cyclopropylimidazo[1,2-a]pyridin-2-yl)methyl)-1H-pyrazole-4-carboxamide (I-22)

To the solution of 1-((5-cyclopropylimidazo[1,2-a]pyridin-2-yl)methyl)-1H-pyrazole-4-carboxylic acid (67 mg, 0.21 mmol) in dry DMF (3 mL) was added HATU (116 mg, 0.305 mmol), DIPEA (16 mg, 0.125 mmol) and (7-chloroimidazo[1,5-a]pyridin-1-yl)methanamine (44 mg, 0.24 mmol) at RT. The reaction was stirred at RT for 2 h. Water (30 mL) was added and the mixture was extracted with ethyl acetate (20 mL×3). The combined organic layer was washed with brine, dried over anhydrous sodium sulfate and concentrated. The residue was purified by prep-HPLC to give N-((7-chloroimidazo[1,5-a]pyridin-1-yl)methyl)-1-((5-cyclopropylimidazo[1,2-a]pyridin-2-yl)methyl)-1H-pyrazole-4-carboxamide (36 mg, yield: 30%) as a white solid. ESI-MS [M+H]$^+$: 446.2. Purity: 98.74. $^1$H NMR (400 MHz, DMSO): δ 8.59 (t, J=5.6 Hz, 1H), 8.34-8.26 (m, 2H), 8.25 (s, 1H), 8.02 (s, 1H), 7.86 (s, 1H), 7.78 (s, 1H), 7.41 (d, J=9.0 Hz, 1H), 7.24-7.14 (m, 1H), 6.72-6.61 (m, 2H), 5.45 (s, 2H), 4.55 (d, J=5.8 Hz, 2H), 2.18 (s, 1H), 1.13-1.1.02 (m, 2H), 0.83-0.74 (m, 2H).

Synthesis of 6-cyclopropylpyridin-2-amine

To a solution of 2-amino-6-bromopyridine (1.0 g, 5.75 mmol) in toluene/H$_2$O (15 mL/3 mL) was added cyclopropylboronic acid (1.98 g, 23 mmol), Palladium diacetate (134 mg, 0.63 mmol), 2-dicyclohexylphosphino-2', 6-dimethoxybihenyl (240 mg, 0.6 mmol) and potassium phosphate (4.24 g, 20.12 mmol). The resulting mixture was stirred at 90° C. for 16 h. The reaction was diluted with H$_2$O (20 mL), extracted with ethyl acetate (3×50 mL), The combined organic layers were washed with brine, dried over anhydrous sodium sulfate and concentrated. The residue was purified by flash column chromatography to give 6-cyclopropylpyridin-2-amine (621 mg, yield: 81%). ESI-MS [M+H]$^+$: 135.2.

Synthesis of 2-(chloromethyl)-5-cyclopropylimidazo[1,2-a]pyridine

To a solution of 5-cyclopropylpyrimidin-2-amine (600 mg, 4.5 mmol) in N,N-dimethylformamine (2 mL) was added 1,3-dichloropropan-2-one (2.2 g, 18.0 mmol). The resulting mixture was stirred at 80° C. for 2.5 h. The reaction mixture was quenched with H$_2$O (50 mL) and extracted with ethyl acetate (3×30 mL), The organic layer was washed with brine, dried over anhydrous sodium sulfate and concentrated. The residue was purified by flash column chromatography to give 2-(chloromethyl)-5-cyclopropylimidazo[1, 2-a]pyridine (300 mg, yield: 33%). ESI-MS [M+H]$^+$: 207.1.

Synthesis of Ethyl 1-((5-cyclopropylimidazo[1,2-a]pyridin-2-yl)methyl)-1H-pyrazole-4-carboxylate To a solution of 2-(chloromethyl)-5-cyclopropylimidazo[1,2-a]pyridine (150 mg, 0.73 mmol) in N,N-dimethylformamine (2 mL) was added cesium carbonate (949 mg, 2.92 mmol) and ethyl 1H-pyrazole-4-carboxylate (102 mg, 0.73 mmol). The resulting mixture was stirred at RT for 3 h. Water (50 mL) was added and extracted with ethyl acetate (3×30 mL). The organic layers were washed with brine, Example 23

Scheme 23

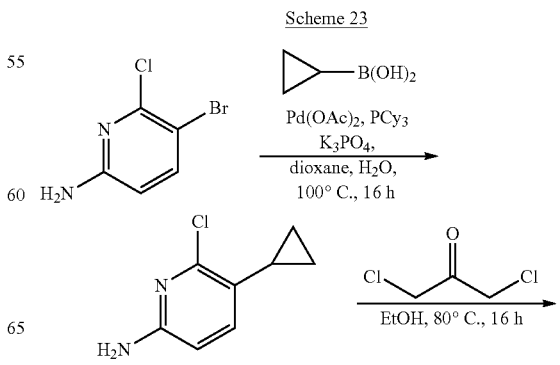

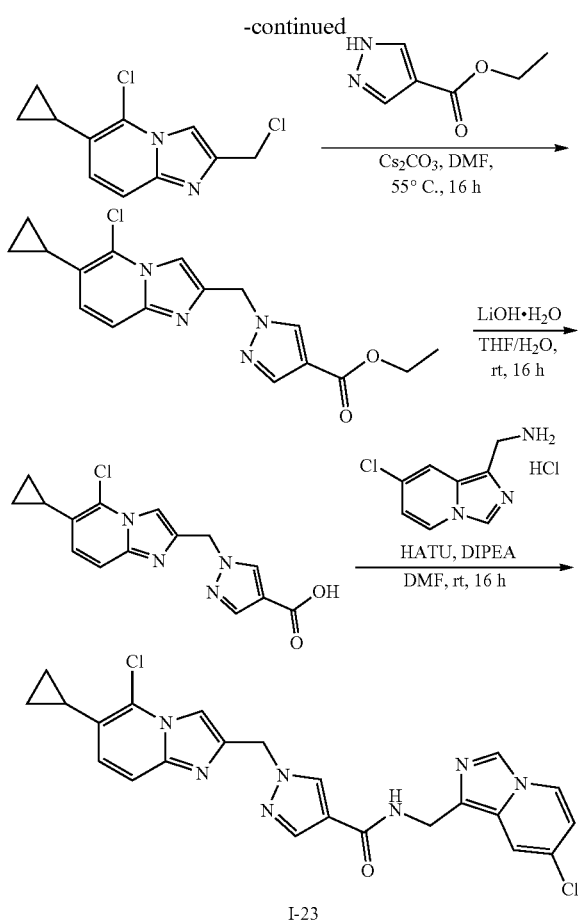

I-23

Synthesis of 6-chloro-5-cyclopropylpyridin-2-amine

A mixture of 5-bromo-6-chloropyridin-2-amine (3 g, 14 mmol) and cyclopropyl boronic acid (2.4 g, 28 mmol), Pd(OAc)$_2$ (313.6 mg, 1.4 mmol), tricyclohexylphosphene (784 mg, 2.8 mmol) and K$_3$PO$_4$ (5.9 g, 28 mmol) in dioxane/H$_2$O (20 mL/20 mL) was stirred in a sealed tube at 100° C. under N$_2$ for 16 h. The reaction was concentrated to give the crude, which was purified by silica gel chromatography (PE/EA=5/1) to give the 6-chloro-5-cyclopropylpyridin-2-amine (2.4 g, yield: 98%) as a white solid. ESI-MS [M+H]+: 169.2.

Synthesis of 5-chloro-2-(chloromethyl)-6-cyclopropylimidazo[1,2-a]pyridine

A mixture of 6-chloro-5-cyclopropylpyridin-2-amine (2.4 g, 14.2 mmol) and 1,3-dichloropropan-2-one (7.16 g, 56.8 mmol) in ethanol (30 mL) was stirred at 78° C. for 16 h. The mixture was quenched with saturated NaHCO$_3$ (50 mL) and extracted with DCM (100 mL×3). The combined organic layers were concentrated and purified by flash column silica gel chromatography (DCM/MeOH=15/1) to give the 5-chloro-2-(chloromethyl)-6-cyclopropylimidazo[1,2-a]pyridine (1.8 g, yield: 53%) as a yellow solid. ESI-MS [M+H]+: 241.1.

Synthesis of Ethyl 1-((5-chloro-6-cyclopropylimidazo[1,2-a]pyridin-2-yl)methyl)-1H-pyrazole-4-carboxylate To a solution of 5-chloro-2-(chloromethyl)-6-cyclopropylimidazo[1,2-a]pyridine (800 mg, 3.33 mmol) in dry DMF (10 mL) was added ethyl 1H-pyrazole-4-carboxylate (512.4 mg, 3.66 mmol) and Cs$_2$CO$_3$ (3.25 g, 10 mmol). Then the reaction mixture was stirred at 55° C. for 16 h under N$_2$ atmosphere. The mixture was cooled to RT, diluted with H$_2$O (20 mL) and extracted with ethyl acetate (30 mL×3). The combined organic layers were washed with brine (20 mL×2), dried over anhydrous sodium sulfate and concentrated in vacuo. The residue was purified by flash chromatography on silica gel (DCM/MeOH=10/1) to give the ethyl 1-((5-chloro-6-cyclopropylimidazo[1,2-a]pyridin-2-yl)methyl)-1H-pyrazole-4-carboxylate (870 mg, yield: 76%) as a white solid. ESI-MS [M+H]+: 345.2.

Synthesis of 1-((5-chloro-6-cyclopropylimidazo[1,2-a]pyridin-2-yl)methyl)-1H-pyrazole-4-carboxylic Acid To a solution of ethyl 1-((5-chloro-6-cyclopropylimidazo[1,2-a]pyridin-2-yl)methyl)-1H-pyrazole-4-carboxylate (300 mg, 0.87 mmol) in THF (5 mL) and H$_2$O (5 mL) was added LiOH.H$_2$O (110 mg, 2.62 mmol), then the reaction mixture was stirred at 50° C. for 16 h. The solvent was removed. and the pH of the residue was adjusted to around 5 by adding 1 M HCl solution allowing a yellow solid was precipitate out. The mixture was filtered and the solid was dried to give the 1-((5-chloro-6-cyclopropylimidazo[1,2-a]pyridin-2-yl)methyl)-1H-pyrazole-4-carboxylic acid (175 mg, yield: 64%) as a white solid. ESI-MS [M+H]+: 317.1.

Synthesis of 1-((5-chloro-6-cyclopropylimidazo[1,2-a]pyridin-2-yl)methyl)-N-((7-chloroimidazo[1,5-a]pyridin-1-yl)methyl)-1H-pyrazole-4-carboxamide (I-23)

To a solution of 1-((5-chloro-6-cyclopropylimidazo[1,2-a]pyridin-2-yl)methyl)-1H-pyrazole-4-carboxylic acid (100 mg, 0.32 mmol) in dry DMF (3 mL) was added (7-chloroimidazo[1,5-a]pyridin-1-yl)methanamine hydrochloride (69.4 mg, 0.32 mmol), HATU (182 mg, 0.48 mmol) and DIPEA (124 mg, 0.96 mmol), the reaction mixture was stirred at RT for 16 h. The reaction mixture diluted with H$_2$O (20 mL), extracted with ethyl acetate (30 mL×3). The combined organic layers were washed with brine (20 mL×2), dried over anhydrous sodium sulfate and concentrated in vacuo. The residue was purified by prep-TLC (DCM/MeOH=10/1) to afford 1-((5-chloro-6-cyclopropylimidazo[1,2-a]pyridin-2-yl)methyl)-N-((7-chloroimidazo[1,5-a]pyridin-1-yl)methyl)-1H-pyrazole-4-carboxamide (15 mg, yield: 9.8%) as a white solid. ESI-MS [M+H]+: 480.1. Purity: 90.37%. $^1$H NMR (400 MHz, DMSO-d6): δ 8.58 (t, J=5.5 Hz, 1H), 8.30 (d, J=6.8 Hz, 2H), 8.24 (s, 1H), 7.92 (s, 1H), 7.86 (s, 1H), 7.78 (s, 1H), 7.50 (d, J=9.3 Hz, 1H), 6.98 (d, J=9.3 Hz, 1H), 6.64 (d, J=7.5, 1.9 Hz, 1H), 5.46 (d, J=9.6 Hz, 2H), 4.55 (d, J=5.6 Hz, 2H), 2.19-2.06 (m, 1H), 1.03 (m, 2H), 0.78 (m, 2H).

Example 24

Scheme 24

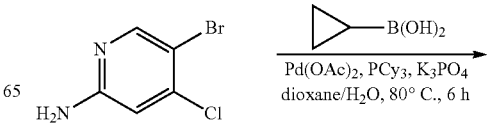

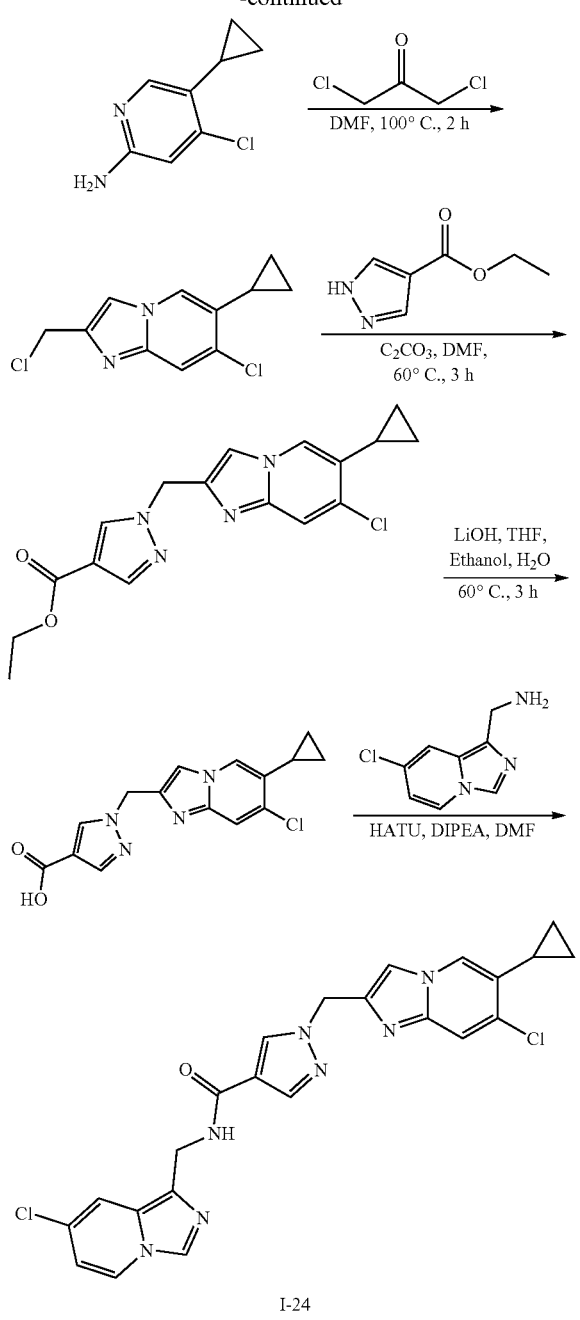

Synthesis of 4-chloro-5-cyclopropylpyridin-2-amine

A mixture of 5-bromo-4-chloropyridin-2-amine (3.24 g, 15.6 mmol), cyclopropylboronic acid (2.01 g, 23.4 mmol), Pd(OAc)$_2$ (350 mg, 1.56 mmol), K$_3$PO$_4$ (6.62 g, 31.2 mmol) and PCy$_3$ (875 mg, 3.12 mmol) in toluene (40 mL) and H$_2$O (5 mL) was stirred at 80° C. overnight. Water (100 mL) was added and the mixture was extracted with EtOAc (100 mL×3). The combined organics were concentrated and purified by silica gel chromatography (EA/PE=2:3 to 10:1) to give 4-chloro-5-cyclopropylpyridin-2-amine (1.89 g, yield: 18.7%) as a yellow solid. ESI-MS [M+H]$^+$: 169.1.

Synthesis of 7-chloro-2-(chloromethyl)-6-cyclopropylimidazo[1,2-a]pyridine

To a solution of 4-chloro-5-cyclopropylpyridin-2-amine (1.2 g, 7.1 mmol) in DMF (20 mL) was added 1,3-dichloropropan-2-one (1.8 g, 14.2 mmol) at RT. After the mixture was stirred at 100° C. for 2 h, H$_2$O (50 mL) was added and extracted with EtOAc (100 mL×3). The combined organic layers were concentrated and purified by silica gel chromatography (EA/PE=1:10 to 3:7) to give 7-chloro-2-(chloromethyl)-6-cyclopropylimidazo[1,2-a]pyridine (674 mg, yield: 38%) as a yellow solid. ESI-MS [M+H]$^+$: 241.1.

Synthesis of Ethyl 1-((7-chloro-6-cyclopropylimidazo[1,2-a]pyridin-2-yl)methyl)-1H-pyrazole-4-carboxylate A mixture of 7-chloro-2-(chloromethyl)-6-cyclopropylimidazo[1,2-a]pyridine (480 mg, 2.0 mmol), ethyl 1H-pyrazole-4-carboxylate (689 mg, 4.92 mmol) and Cs$_2$CO$_3$ (2.4 g, 7.38 mmol) in DMF (10 mL) was stirred at 60° C. for 3 h. Water (50 mL) was added and the mixture was extracted with EtOAc (50 mL×3). The combined organic layers were washed with brine, dried over Na$_2$SO$_4$, filtered and concentrated to give the crude, which was purified by silica gel chromatography (EA/PE=7:3 to 10:1) to ethyl 1-((7-chloro-6-cyclopropylimidazo[1,2-a]pyridin-2-yl)methyl)-1H-pyrazole-4-carboxylate (390 mg, yield: 57%) as a white solid. ESI-MS [M+H]$^+$: 345.1.

Synthesis of 1-((7-chloro-6-cyclopropylimidazo[1,2-a]pyridin-2-yl)methyl)-1H-pyrazole-4-carboxylic Acid To a solution of ethyl 1-((7-chloro-6-cyclopropylimidazo[1,2-a]pyridin-2-yl)methyl)-1H-pyrazole-4-carboxylate (200 mg, 0.58 mmol) in ethanol/THF/H$_2$O (3 mL/3 mL/1.5 mL) was added LiOH.H$_2$O (97 mg, 2.32 mmol). The reaction mixture was stirred at 65° C. for 3 h. The mixture was then concentrated and then diluted with H$_2$O (20 mL). The pH of the aqueous layer was adjust to 4 by adding 1 M HCl solution and extracted with EtOAc (50 mL×3). The combined organic layers were concentrated to give crude 1-((7-chloro-6-cyclopropylimidazo[1,2-a]pyridin-2-yl)methyl)-1H-pyrazole-4-carboxylic acid (230 mg) as a white solid, which was used in the next step without further purification. ESI-MS [M+H]$^+$: 317.1.

Synthesis of 1-((7-chloro-6-cyclopropylimidazo[1,2-a]pyridin-2-yl)methyl)-N-((7-chloroimidazo[1,5-a]pyridin-1-yl)methyl)-1H-pyrazole-4-carboxamide (I-24)

A mixture of crude 1-((7-chloro-6-cyclopropylimidazo[1,2-a]pyridin-2-yl)methyl)-1H-pyrazole-4-carboxylic acid (230 mg, 0.73 mmol), (7-chloroimidazo[1,5-a]pyridin-1-yl)methanamine (65.1 mg, 0.3 mmol), HATU (278 mg, 0.73 mmol) and DIPEA (375 mg, 2.9 mmol) in DMF (5 mL) was stirred at RT for 3 h. Water (30 mL) was added and the mixture was extracted with EtOAc (50 mL×3). The combined organic layers were concentrated and purified by prep-TLC (DCM:MeOH=8:1) to give 1-((7-chloro-6-cyclopropylimidazo[1,2-a]pyridin-2-yl)methyl)-N-((7-chloroimidazo[1,5-a]pyridin-1-yl)methyl)-1H-pyrazole-4-carboxamide (11.1 mg, yield: 7.7%) as a white solid. ESI-MS [M+H]$^+$: 480.0. Purity: 98.15%. $^1$H NMR (400 MHz, DMSO): δ 8.58 (t, J=5.3 Hz, 1H), 8.40 (s, 1H), 8.31-8.30 (m, 2H), 8.20 (s, 1H), 7.86 (s, 1H), 7.78 (s, 1H), 7.72 (s, 1H), 7.68 (s, 1H), 6.65 (dd, J=7.4, 1.8 Hz, 1H), 5.40 (s, 2H), 4.55 (d, J=5.6 Hz, 2H), 1.98-1.94 (m, 1H), 0.95-0.94 (m, 2H), 0.66-0.65 (m, 2H).

Example 25

Scheme 25

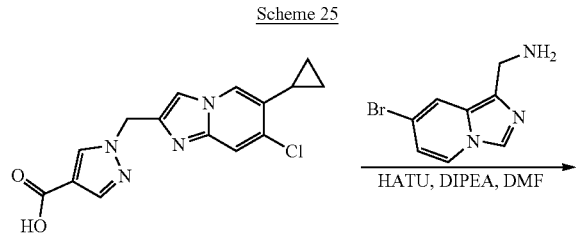

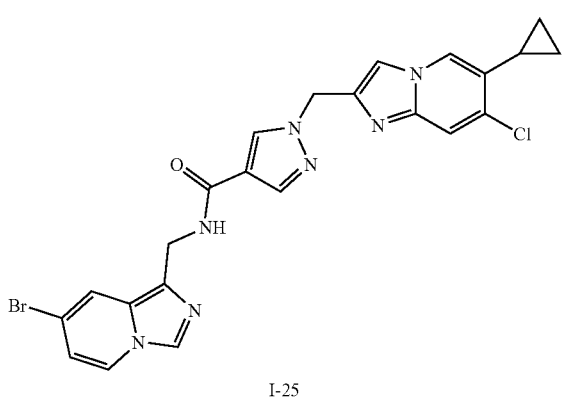

I-25

Synthesis of N-((7-bromoimidazo[1,5-a]pyridin-1-yl)methyl)-1-((7-chloro-6-cyclopropylimidazo[1,2-a]pyridin-2-yl)methyl)-1H-pyrazole-4-carboxamide (I-25)

A mixture of crude 1-((7-chloro-6-cyclopropylimidazo[1,2-a]pyridin-2-yl)methyl)-1H-pyrazole-4-carboxylic acid (230 mg, 0.73 mmol), (7-bromoimidazo[1,5-a]pyridin-1-yl)methanamine (67.8 mg, 0.3 mmol), HATU (278 mg, 0.73 mmol) and DIPEA (375 mg, 2.9 mmol) in DMF (5 mL) was stirred at RT for 3 h. Water (30 mL) was added and the mixture was extracted with EtOAc (50 mL×3). The combined organic layers were concentrated and purified by prep-TLC (DCM:MeOH=8:1) to give N-((7-bromoimidazo[1,5-a]pyridin-1-yl)methyl)-1-((7-chloro-6-cyclopropylimidazo[1,2-a]pyridin-2-yl)methyl)-1H-pyrazole-4-carboxamide (31.5 mg, yield: 20%) as a white solid. ESI-MS [M+H]⁺: 524.0. Purity: 97%. ¹H NMR (400 MHz, DMSO): δ 8.58-8.57 (m, 1H), 8.39 (s, 1H), 8.31 (s, 1H), 8.23-8.20 (m, 2H), 7.94 (s, 1H), 7.85 (s, 1H), 7.69 (d, J=13.8 Hz, 2H), 6.72-6.71 (m, 1H), 5.39 (s, 2H), 4.54 (s, 2H), 1.95-1.93 (m, 1H), 0.94-0.93 (m, 2H), 0.65-0.64 (m, 2H).

Example 26

Scheme 26

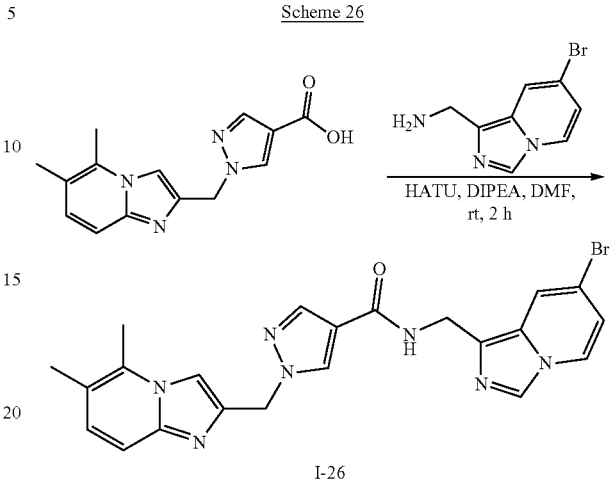

I-26

Synthesis of N-((7-bromoimidazo[1,5-a]pyridin-1-yl)methyl)-1-((5,6-dimethylimidazo[1,2-a]pyridin-2-yl)methyl)-1H-pyrazole-4-carboxamide (I-26)

To the solution of 1-((5,6-dimethylimidazo[1,2-a]pyridin-2-yl)methyl)-1H-pyrazole-4-carboxylic acid (54 mg, 0.2 mmol) in dry DMF (3 mL) was added HATU (114 mg, 0.3 mmol), DIPEA (129 mg, 1.0 mmol) and (7-bromoimidazo[1,5-a]pyridin-1-yl)methanamine hydrochloride (52.4 mg, 0.2 mmol) at RT. The reaction was stirred at RT for 2 h. Water (30 mL) was added and the mixture was extracted with ethyl acetate (30 mL×3). The combined organic layers were washed with brine, dried over anhydrous sodium sulfate and concentrated. The residue was purified by prep-HPLC to give N-((7-bromoimidazo[1,5-a]pyridin-1-yl)methyl)-1-((5,6-dimethylimidazo[1,2-a]pyridin-2-yl)methyl)-1H-pyrazole-4-carboxamide (9.7 mg, yield: 10.2%). ESI-MS [M+H]⁺: 478.1. Purity: 90.33%. ¹H NMR (400 MHz, DMSO): δ 8.58 (t, J=5.6 Hz, 1H), 8.31 (s, 1H), 8.28-8.18 (m, 2H), 7.95 (s, 1H), 7.85 (s, 1H), 7.76 (s, 1H), 7.33 (d, J=9.1 Hz, 1H), 7.14 (d, J=9.2 Hz, 1H), 6.76-6.67 (m, 1H), 5.40 (s, 2H), 4.54 (d, J=5.7 Hz, 2H), 2.49 (s, 3H), 2.29 (s, 3H).

Example 27

Scheme 27

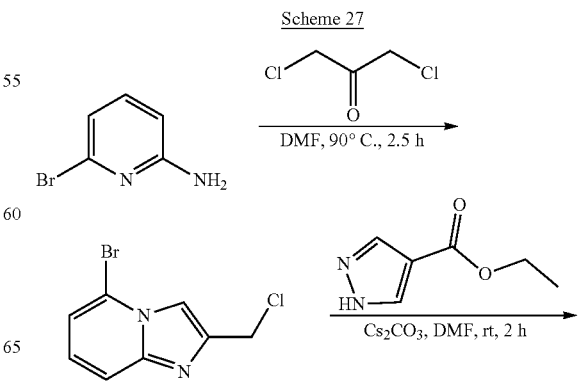

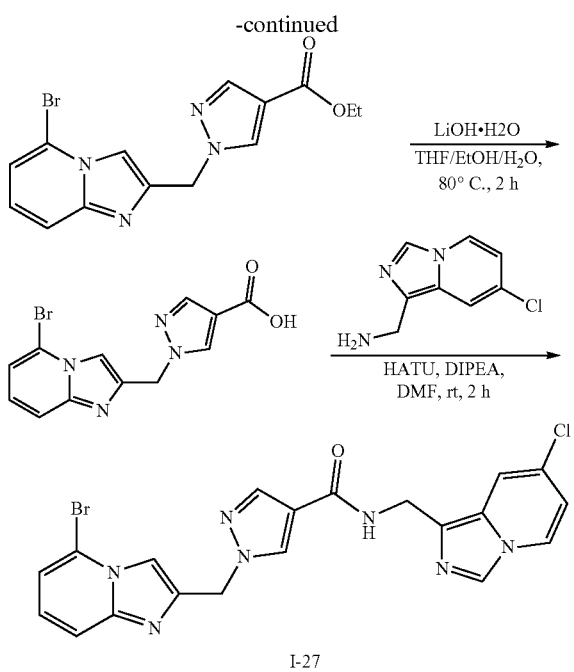

Synthesis of 5-bromo-2-(chloromethyl)imidazo[1,2-a]pyridine

To a solution of 6-bromopyridin-2-amine (800 mg, 4.6 mmol) in N,N-dimethylformamine (5 mL) was added 1,3-dichloropropan-2-one (3.05 g, 24.0 mmol). The resulting mixture was stirred at 90° C. for 2.5 h. The reaction mixture was diluted with H$_2$O (50 mL) and extracted with ethyl acetate (3×30 mL). The organic layers were washed with brine, dried over anhydrous sodium sulfate and concentrated. The residue was purified by flash column chromatography to give 5-bromo-2-(chloromethyl)imidazo[1,2-a]pyridine (600 mg, yield: 53%). ESI-MS [M+H]$^+$: 245.0.

Synthesis of Ethyl 1-((5-bromoimidazo[1,2-a]pyridin-2-yl)methyl)-1H-pyrazole-4-carboxylate To a solution of 5-bromo-2-(chloromethyl)imidazo[1,2-a]pyridine (200 mg, 0.82 mmol) in N,N-dimethylformamine (3 mL) was added cesium carbonate (1.1 g, 3.28 mmol) and ethyl 1H-pyrazole-4-carboxylate (115 mg, 0.82 mmol). The resulting mixture was stirred at RT for 2 h then diluted with H$_2$O (50 mL) and extracted with ethyl acetate (3×30 mL). The organic layers were washed with brine, dried over anhydrous sodium sulfate and concentrated. The residue was purified by flash column chromatography to give ethyl 1-((5-cyclopropylimidazo[1,2-a]pyridin-2-yl)methyl)-1H-pyrazole-4-carboxylate (236 mg, yield: 83%). ESI-MS [M+H]$^+$: 349.0.

Synthesis of 1-((5-bromoimidazo[1,2-a]pyridin-2-yl)methyl)-1H-pyrazole-4-carboxylic Acid To a solution of ethyl 1-((5-cyclopropylimidazo[1,2-a]pyridin-2-yl)methyl)-1H-pyrazole-4-carboxylate (236 mg, 0.68 mmol) in the mixture of THF/H$_2$O (3 mL/3 mL) was added lithium hydroxide (82 mg, 3.4 mmol). The resulting mixture was stirred at 80° C. for 2 h. THF was evaporated and the pH of the H$_2$O phase was adjusted to 5 by adding 1 M HCl solution. The resulting solid precipitate was filtered to give 1-((5-bromoimidazo[1,2-a]pyridin-2-yl)methyl)-1H-pyrazole-4-carboxylic acid (131 mg, Yield: 60%), which was used in the next step without further purification. ESI-MS [M+H]$^+$: 321.0.

Synthesis of 1-((5-bromoimidazo[1,2-a]pyridin-2-yl)methyl)-N-((7-chloroimidazo[1,5-a]pyridin-1-yl)methyl)-1H-pyrazole-4-carboxamide (I-27)

To the solution of 1-((5-bromoimidazo[1,2-a]pyridin-2-yl)methyl)-1H-pyrazole-4-carboxylic acid (65 mg, 0.20 mmol) in dry DMF (3 mL) was added HATU (116 mg, 0.305 mmol), DIPEA (131 mg, 1.02 mmol) and (7-chloroimidazo[1,5-a]pyridin-1-yl)methanamine hydrochloride (44 mg, 0.20 mmol) at RT. The reaction was stirred at RT for 2 h. Water (30 mL) was added and the mixture was extracted with ethyl acetate (20 mL×3). The combined organic layers were washed with brine, dried over anhydrous sodium sulfate and concentrated. The residue was purified by prep-HPLC to give 1-((5-bromoimidazo[1,2-a]pyridin-2-yl)methyl)-N-((7-chloroimidazo[1,5-a]pyridin-1-yl)methyl)-1H-pyrazole-4-carboxamide (41 mg, yield: 37%). ESI-MS [M+H]$^+$: 484.0. Purity: 100%. $^1$H NMR (400 MHz, DMSO): δ 8.60 (t, J=5.6 Hz, 1H), 8.39 (s, 1H), 8.32 (d, J=7.5 Hz, 1H), 8.26 (s, 1H), 7.97 (s, 1H), 7.88 (s, 1H), 7.81 (s, 1H), 7.61 (d, J=8.8 Hz, 1H), 7.33 (d, J=7.2 Hz, 1H), 7.31-7.21 (m, J=8.7, 7.4 Hz, 1H), 6.72-6.63 (m, 1H), 5.48 (s, 2H), 4.57 (d, J=5.7 Hz, 2H).

Example 28

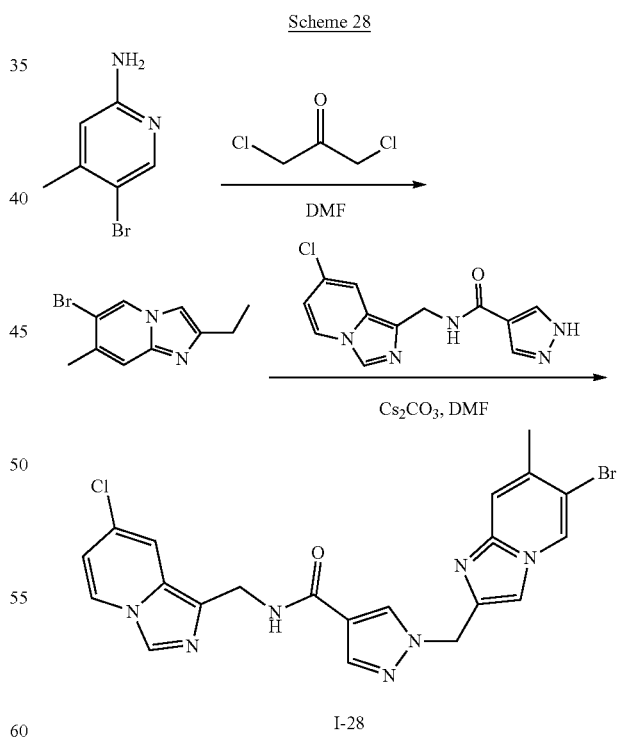

Synthesis of 6-bromo-2-(chloromethyl)-7-methyl-imidazo[1,2-a]pyridine

To a solution of 5-bromo-4-methylpyridin-2-amine (1000 mg, 5.37 mmol) in DMF (15 mL) was added 1,3-dichloropropan-2-one (2.04 g, 16.1 mmol) at RT. The resulting reaction was stirred at 85° C. for 2 h. The solution was quenched with H₂O (40 mL) and the pH of the mixture was adjusted to 8 by adding saturated a NaHCO₃ solution. The resulting mixture was then extracted with EtOAc (50 mL×3). The combined organic layers were washed with brine, dried over Na₂SO₄ and concentrated in vacuo to give the crude, which was purified with a silica gel column (PE/EtOAc=1/1) to give the 6-bromo-2-(chloromethyl)-7-methylimidazo[1,2-a]pyridine (500 mg, yield: 36%) as a light yellow oil. ESI-MS [M+H]⁺: 259.2.

Synthesis of 1-((6-bromo-7-methylimidazo[1,2-a]pyridin-2-yl)methyl)-N-((7-chloroimidazo[1,5-a]pyridin-1-yl)methyl)-1H-pyrazole-4-carboxamide (I-28)

To a solution 6-bromo-2-(chloromethyl)-7-methylimidazo[1,2-a]pyridine (56 mg, 0.22 mmol) in DMF (3 mL) was added N-((7-chloroimidazo[1,5-a]pyridin-1-yl)methyl)-1H-pyrazole-4-carboxamide (40 mg, 0.14 mmol) and Cs₂CO₃ (140 mg, 0.43 mmol) at RT. The resulting reaction was stirred at RT for 12 h. H₂O (30 mL) was added to the reaction and extracted with EtOAc (30 mL×3). The combined organic layers were washed with brine, dried over Na₂SO₄ and concentrated in vacuo to give the crude, which was purified with prep-TLC (DCM/MeOH=10/1) to give the 1-((6-bromo-7-methylimidazo [1,2-a]pyridin-2-yl)methyl)-N-((7-chloroimidazo[1,5-a]pyridin-1-yl)methyl)-1H-pyrazole-4-carboxamide (22 mg, yield: 32%) as a white solid. ESI-MS [M+H]⁺: 498.0. Purity: 98.7%. ¹H NMR (400 MHz, DMSO): δ 8.89 (s, 1H), 8.60-8.57 (m, 1H), 8.31-8.29 (m, 2H), 8.22 (s, 1H), 7.87 (s, 1H), 7.78 (s, 1H), 7.72 (s, 1H), 7.51 (s, 1H), 6.65 (d, J=7.4 Hz, 1H), 5.40 (s, 2H), 4.55 (d, J=5.6 Hz, 2H), 2.36 (s, 3H).

Example 29

Scheme 29

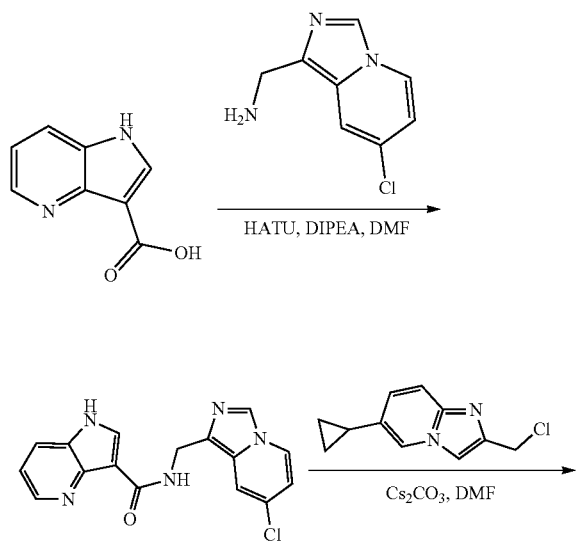

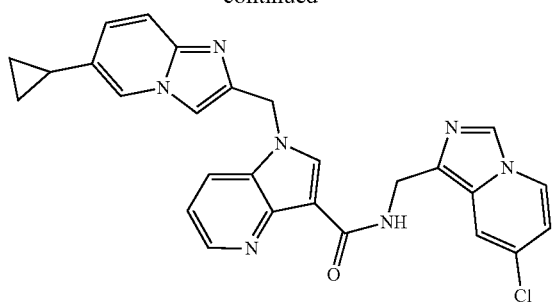

I-29

Synthesis of N-((7-chloroimidazo[1,5-a]pyridin-1-yl)methyl)-1H-pyrrolo[3,2-b]pyridine-3-carboxamide A mixture of 1H-pyrrolo[3,2-b]pyridine-3-carboxylic acid (100 mg, 0.62 mmol), 7-chloroimidazo[1,5-a]pyridin-1-yl)methanamine hydrochloride (160 mg, 0.74 mmol), HATU (290 mg, 0.78 mmol) and DIPEA (0.32 mL, 1.86 mmol) in DMF (5 mL) was stirred at RT for 16 h. Water (30 mL) was added and extracted with EtOAc (30 mL×3). The combined organic layers were concentrated and purified by prep-TLC (DCM/MeOH=10/1) to give N-((7-bromoimidazo[1,5-a]pyridin-1-yl)methyl)-1-((6-cyclopropyl-5-methylimidazo[1,2-a]pyridin-2-yl)methyl)-1H-pyrazole-4-carboxamide (60 mg, yield: 30%) as a yellow solid. ESI-MS [M+H]⁺: 326.1.

Synthesis of N-((7-chloroimidazo[1,5-a]pyridin-1-yl)methyl)-1-((6-cyclopropylimidazo[1,2-a]pyridin-2-yl)methyl)-1H-pyrrolo[3,2-b]pyridine-3-carboxamide (I-29)

A mixture of N-((7-chloroimidazo[1,5-a]pyridin-1-yl)methyl)-1H-pyrrolo[3,2-b]pyridine-3-carboxamide (50 mg, 0.15 mmol), 2-(chloromethyl)-6-cyclopropylimidazo[1,2-a]pyridine (40 mg, 0.19 mmol) and Cs₂CO₃ (125 mg, 0.39 mmol) in DMF (5 mL) was stirred at RT for 4 h. Water (30 mL) was added and extracted with EtOAc (30 mL×3). The combined organic layers were concentrated and purified by prep-HPLC to give N-((7-chloroimidazo[1,5-a]pyridin-1-yl)methyl)-1-((6-cyclopropylimidazo[1,2-a]pyridin-2-yl)methyl)-1H-pyrrolo[3,2-b]pyridine-3-carboxamide (9.1 mg, yield: 12%) as a yellow solid. ESI-MS [M+H]⁺: 496.1. Purity: 86.0%. ¹H NMR (400 MHz, DMSO): δ 9.06 (t, J=5.8 Hz, 1H), 8.43 (d, J=4.7 Hz, 1H), 8.40-8.25 (m, 4H), 8.14 (d, J=8.3 Hz, 1H), 7.87 (s, 1H), 7.73 (s, 1H), 7.37 (d, J=9.4 Hz, 1H), 7.26 (dd, J=8.3, 4.7 Hz, 1H), 6.97 (d, J=9.4 Hz, 1H), 6.66 (dd, J=7.4, 2.0 Hz, 1H), 5.59 (s, 2H), 4.77 (d, J=5.7 Hz, 2H), 1.96-1.81 (m, 1H), 0.96-0.83 (m, 2H), 0.73-0.56 (m, 2H).

Example 30

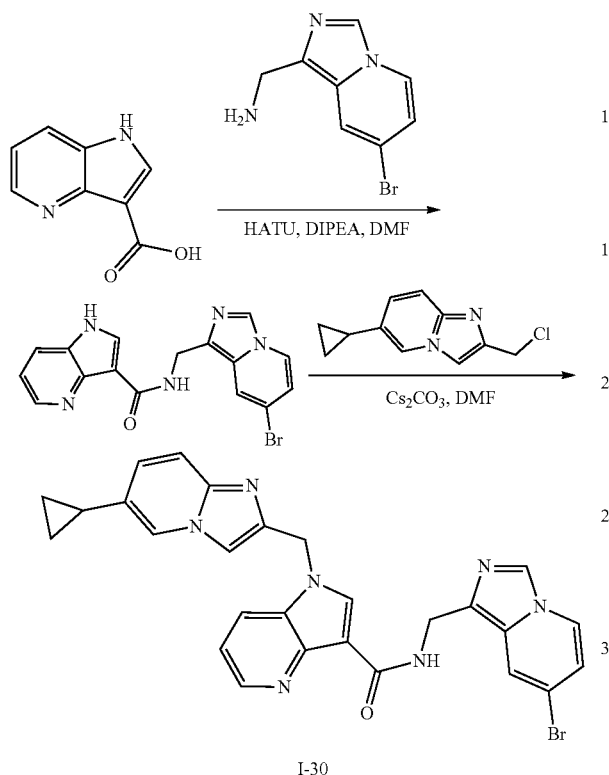

Synthesis of N-((7-bromoimidazo[1,5-a]pyridin-1-yl)methyl)-1H-pyrrolo[3,2-b]pyridine-3-carboxamide A mixture of 1H-pyrrolo[3,2-b]pyridine-3-carboxylic acid (100 mg, 0.62 mmol), 7-bromoimidazo[1,5-a]pyridin-1-yl)methanamine hydrochloride (190 mg, 0.74 mmol), HATU (350 mg, 0.93 mmol) and DIPEA (0.32 mL, 1.86 mmol) in DMF (5 mL) was stirred at RT for 16 h. Water (30 mL) was added and the mixture was extracted with EtOAc (30 mL×3). The combined organic layers were concentrated and purified by prep-TLC (DCM/MeOH=10/1) to give N-((7-bromoimidazo[1,5-a]pyridin-1-yl)methyl)-1H-pyrrolo[3,2-b]pyridine-3-carboxamide (60 mg, yield: 20%) as a yellow solid. ESI-MS [M+H]+: 370.1.

Synthesis of N-((7-bromoimidazo[1,5-a]pyridin-1-yl)methyl)-1-((6-cyclopropylimidazo[1,2-a]pyridin-2-yl)methyl)-1H-pyrrolo[3,2-b]pyridine-3-carboxamide (I-30)

A mixture of N-((7-bromoimidazo[1,5-a]pyridin-1-yl)methyl)-1H-pyrrolo[3,2-b]pyridine-3-carboxamide (60 mg, 0.16 mmol), 2-(chloromethyl)-6-cyclopropylimidazo[1,2-a]pyridine (40 mg, 0.19 mmol) and Cs2CO3 (125 mg, 0.39 mmol) in DMF (5 mL) was stirred at RT for 4 h. Water (30 mL) was added and the mixture was extracted with EtOAc (30 mL×3). The combined organic layers were concentrated and purified by prep-HPLC to give N-((7-bromoimidazo[1,5-a]pyridin-1-yl)methyl)-1-((6-cyclopropylimidazo[1,2-a]pyridin-2-yl)methyl)-1H-pyrrolo[3,2-b]pyridine-3-carboxamide (13.0 mg, yield: 15%) as a yellow solid. ESI-MS [M+H]+: 540.1. Purity: 89.1%. 1H NMR (400 MHz, DMSO): δ 9.06 (t, J=6.0 Hz, 1H), 8.43 (d, J=3.7 Hz, 1H), 8.36 (d, J=5.4 Hz, 2H), 8.31-8.22 (m, 2H), 8.14 (d, J=8.0 Hz, 1H), 8.04 (s, 1H), 7.73 (s, 1H), 7.37 (d, J=9.2 Hz, 1H), 7.26 (dd, J=8.3, 4.7 Hz, 1H), 6.97 (d, J=9.5 Hz, 1H), 6.81-6.67 (m, 1H), 5.59 (s, 2H), 4.77 (d, J=5.8 Hz, 2H), 1.89 (d, J=5.1 Hz, 1H), 0.96-0.84 (m, 2H), 0.64 (d, J=5.1 Hz, 2H).

Example 31

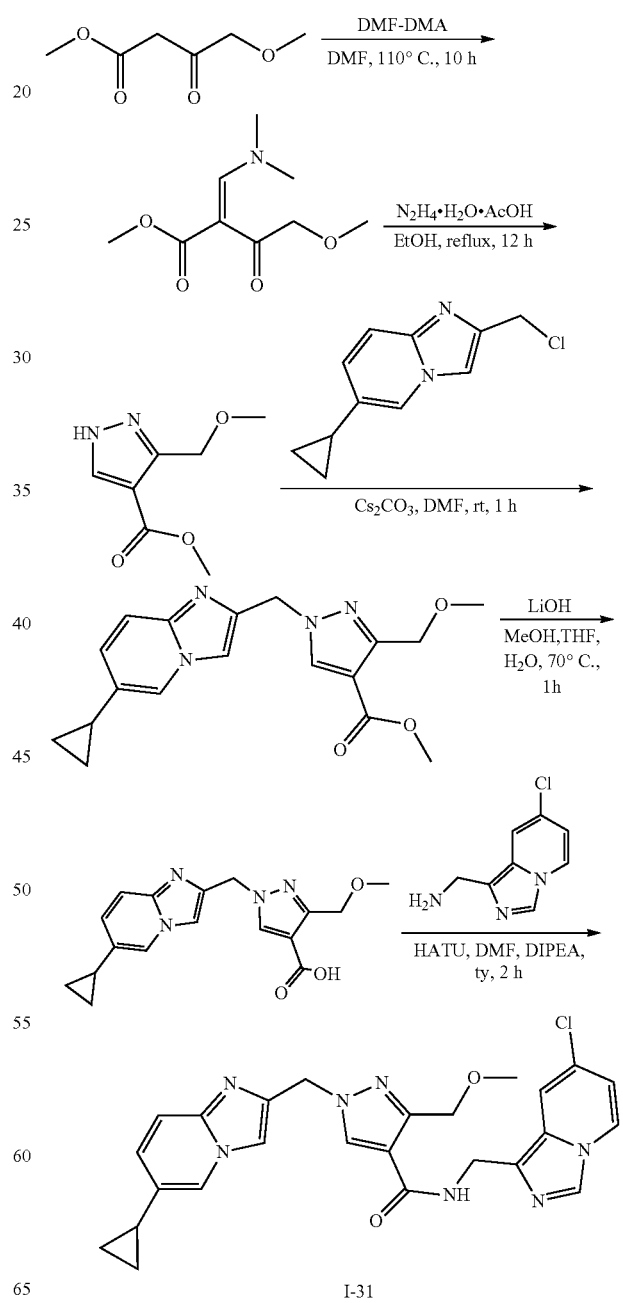

Synthesis of Methyl 2-((dimethylamino)methylene)-4-methoxy-3-oxobutanoate

A mixture of methyl 4-methoxy-3-oxobutanoate (500 mg, 3.42 mmol) and DMF-DMA (410 mg, 3.42 mmol) in dry DMF (5 mL) was stirred at 110° C. for 10 h. The mixture was concentrated to give methyl 2-((dimethylamino)methylene)-4-methoxy-3-oxobutanoate (600 mg, yield: 87%) as a yellow oil. ESI-MS [M+H]+: 202.1.

Synthesis of Methyl 3-(methoxymethyl)-1H-pyrazole-4-carboxylate

A solution of methyl 2-((dimethylamino)methylene)-4-methoxy-3-oxobutanoate (600 mg, 3.0 mmol), $N_2H_4 \cdot H_2O$ (0.15 mL, 3.0 mmol) and AcOH (0.21 mL, 3.6 mmol) in dry EtOH (10 mL) was stirred at reflux for 12 h. The mixture was concentrated and purified by prep-TLC (DCM/MeOH=30/1) to give methyl 3-(methoxymethyl)-1H-pyrazole-4-carboxylate (400 mg, yield: 78%) as a brown solid. ESI-MS [M+H]+: 171.1.

Synthesis of Methyl 1-((6-cyclopropylimidazo[1,2-a]pyridin-2-yl)methyl)-3-(methoxymethyl)-1H-pyrazole-4-carboxylate and methyl 1-((6-cyclopropylimidazo[1,2-a]pyridin-2-yl)methyl)-5-(methoxymethyl)-1H-pyrazole-4-carboxylate A mixture of methyl 3-(methoxymethyl)-1H-pyrazole-4-carboxylate (100 mg, 0.59 mmol), 2-(chloromethyl)-6-cyclopropylimidazo[1,2-a]pyridine (150 mg, 0.70 mmol) and $Cs_2CO_3$ (480 mg, 1.48 mmol) in DMF (5 mL) was stirred at RT for 16 h. Water (50 mL) was added and the mixture was extracted with EtOAc (50 mL×3). The combined organic layers were concentrated and purified by prep-TLC (DCM/MeOH=15/1) to give methyl 1-((6-cyclopropylimidazo[1,2-a]pyridin-2-yl)methyl)-3-(methoxymethyl)-1H-pyrazole-4-carboxylate (100 mg, yield: 50.0%) as a light yellow solid. ESI-MS [M+H]+: 341.1 and methyl 1-((6-cyclopropylimidazo[1,2-a]pyridin-2-yl)methyl)-5-(methoxymethyl)-1H-pyrazole-4-carboxylate (50 mg, yield: 25.0%) as a light yellow solid. ESI-MS [M+H]+: 341.1.

Synthesis of 1-((6-cyclopropylimidazo[1,2-a]pyridin-2-yl)methyl)-3-(methoxymethyl)-1H-pyrazole-4-carboxylic Acid A solution of methyl 1-((6-cyclopropylimidazo[1,2-a]pyridin-2-yl)methyl)-3-(methoxymethyl)-1H-pyrazole-4-carboxylate (100 mg, 0.29 mmol) and LiOH $H_2O$ (40 mg, 0.88 mmol) in THF/MeOH/$H_2O$ (2 mL/2 mL/1 mL) was stirred at 70° C. for 1 h. Solvent was evaporated and the pH value of the residue was adjusted to 5 by adding 1 M HCl solution. The resulting solid precipitate was filtered to give 1-((6-cyclopropylimidazo[1,2-a]pyridin-2-yl)methyl)-3-(methoxymethyl)-1H-pyrazole-4-carboxylic acid (90 mg, yield: 94.7%) as a yellow oil which was used in the next step without purification. ESI-MS [M+H]+: 327.1.

Synthesis of N-((7-chloroimidazo[1,5-a]pyridin-1-yl)methyl)-1-((6-cyclopropylimidazo[1,2-a]pyridin-2-yl)methyl)-3-(methoxymethyl)-1H-pyrazole-4-carboxamide (I-31)

A mixture of 1-((6-cyclopropylimidazo[1,2-a]pyridin-2-yl)methyl)-3-(methoxymethyl)-1H-pyrazole-4-carboxylic acid (45 mg, 0.14 mmol), (7-chloroimidazo[1,5-a]pyridin-1-yl)methanamine (36 mg, 0.17 mmol), HATU (105 mg, 0.28 mmol) and DIPEA (0.1 mL, 0.41 mmol) in DMF (3 mL) was stirred at RT for 2 h. Water (30 mL) was added and the mixture was extracted with EtOAc (30 mL×3). The combined organic layers were concentrated and purified by prep-TLC (DCM/MeOH=10/1) to give N-((7-chloroimidazo[1,5-a]pyridin-1-yl)methyl)-1-((6-cyclopropylimidazo[1,2-a]pyridin-2-yl)methyl)-3-(methoxymethyl)-1H-pyrazole-4-carboxamide (19.6 mg, yield: 29%) as a white solid. ESI-MS [M+H]+: 490.1. Purity: 97.6%. $^1$H NMR (400 MHz, DMSO): δ 8.49 (s, 1H), 8.41-8.28 (m, 3H), 8.23 (s, 1H), 7.90 (s, 1H), 7.79 (s, 1H), 7.55 (d, J=9.0 Hz, 1H), 7.29 (s, 1H), 6.66 (d, J=6.3 Hz, 1H), 5.46 (s, 2H), 4.57 (d, J=5.2 Hz, 2H), 4.53 (s, 2H), 3.20 (s, 3H), 1.99 (s, 1H), 0.97 (d, J=7.5 Hz, 2H), 0.71 (d, J=5.4 Hz, 2H).

Example 32

Scheme 32

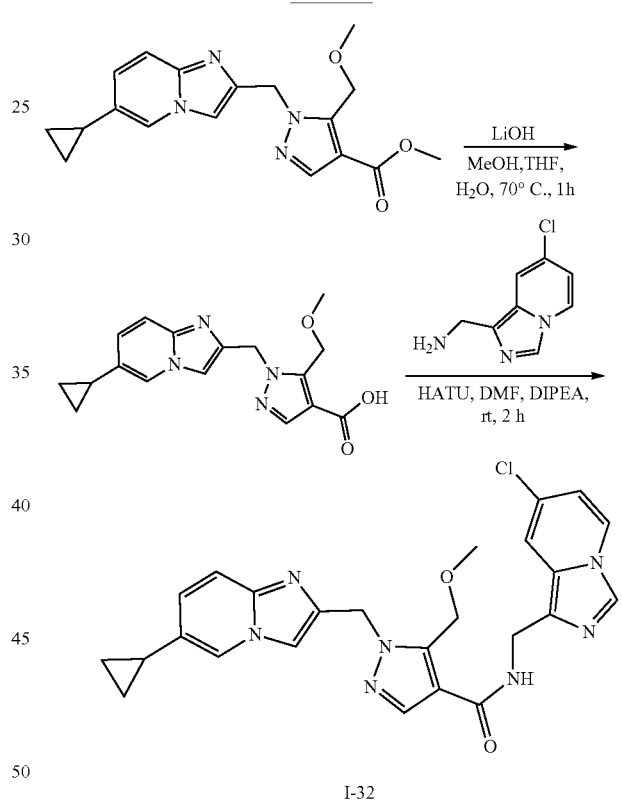

I-32

Synthesis of 1-((6-cyclopropylimidazo[1,2-a]pyridin-2-yl)methyl)-5-(methoxymethyl)-1H-pyrazole-4-carboxylic Acid A solution of methyl 1-((6-cyclopropylimidazo[1,2-a]pyridin-2-yl)methyl)-5-(methoxymethyl)-1H-pyrazole-4-carboxylate (50 mg, 0.15 mmol) and LiOH $H_2O$ (20 mg, 0.44 mmol) in THF/MeOH/$H_2O$ (2 mL/2 mL/1 mL) was stirred at 70° C. for 1 h. Solvent was evaporated and the pH of the residue was adjusted to 5 by adding 1 M HCl solution. Solid precipitated and was filtered to give 1-((6-cyclopropylimidazo[1,2-a]pyridin-2-yl)methyl)-5-(methoxymethyl)-1H-pyrazole-4-carboxylic acid (45 mg, yield: 94.7%) as a yellow oil. ESI-MS [M+H]+: 327.1.

Synthesis of N-((7-chloroimidazo[1,5-a]pyridin-1-yl)methyl)-1-((6-cyclopropylimidazo[1,2-a]pyridin-2-yl)methyl)-5-(methoxymethyl)-1H-pyrazole-4-carboxamide (I-32)

A mixture of 1-((6-cyclopropylimidazo[1,2-a]pyridin-2-yl)methyl)-3-(methoxymethyl)-1H-pyrazole-4-carboxylic acid (45 mg, 0.14 mmol), (7-chloroimidazo[1,5-a]pyridin-1-yl)methanamine (36 mg, 0.17 mmol), HATU (105 mg, 0.28 mmol) and DIPEA (0.1 mL, 0.41 mmol) in DMF (5 mL) was stirred at RT for 2 h. Water (30 mL) was added and the mixture was extracted with EtOAc (30 mL×3). The combined organic layers were concentrated and purified by prep-TLC (DCM/MeOH=10/1) to give N-((7-chloroimidazo[1,5-a]pyridin-1-yl)methyl)-1-((6-cyclopropylimidazo[1,2-a]pyridin-2-yl)methyl)-5-(methoxymethyl)-1H-pyrazole-4-carboxamide (40.0 mg, yield: 59%) as a white solid. ESI-MS [M+H]$^+$: 490.1. Purity: 99.2%. $^1$H NMR (400 MHz, DMSO): δ 8.67 (s, 1H), 8.58 (s, 1H), 8.44-8.27 (m, 2H), 8.02 (s, 1H), 7.94 (s, 1H), 7.81 (s, 1H), 7.67 (s, 1H), 7.52 (s, 1H), 6.67 (d, J=7.2 Hz, 1H), 5.58 (s, 2H), 4.95 (s, 2H), 4.60 (d, J=5.5 Hz, 2H), 3.25 (s, 3H), 2.05 (d, J=16.1 Hz, 1H), 1.04 (t, J=18.0 Hz, 2H), 0.74 (s, 2H).

Example 33

Scheme 33

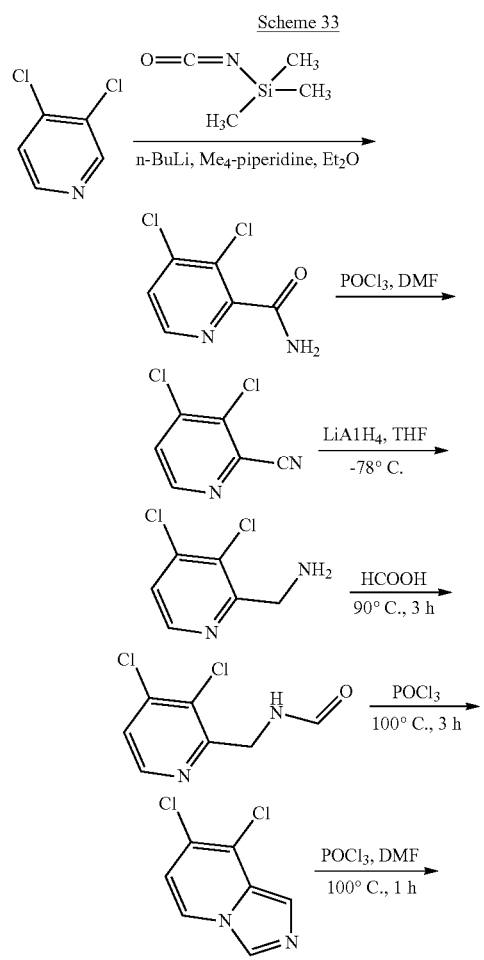

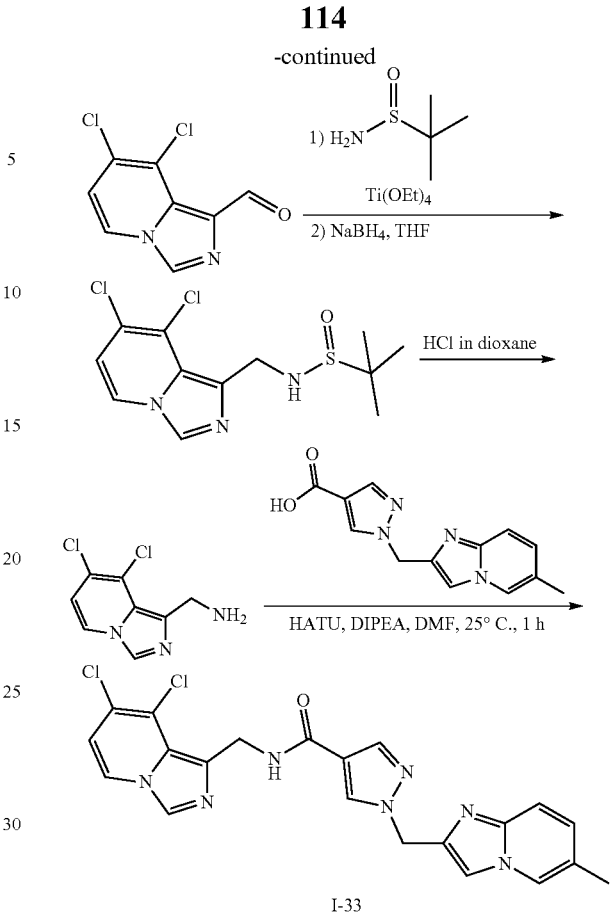

Synthesis of 3,4-dichloropicolinamide

To a solution of 2,2,6,6-tetramethylpiperidine (5.2 g, 37.2 mmol) in diethyl ether (80 mL) at 0° C. was added n-BuLi (2.4 M, 15.5 mL, 37.2 mmol) dropwise. The resulting solution was stirred at 0° C. for 0.5 h and at −78° C. for 0.5 h. To this mixture was then slowly added a solution of 3,4-dichloropyridine (5 g, 33.8 mmol) in diethyl ether (10 mL) dropwise. The resulting mixture was stirred at −78° C. for 2 h before the addition of isocyanotrimethylsilane (5.83 g, 50.7 mmol). After the addition, the cooling bath was removed and the reaction mixture was allowed to warm to RT over 1 h. The reaction mixture was stirred at 25° C. for 16 h, H$_2$O (100 mL) was added, extracted with ethyl acetate (100 mL×3), washed with brine (30 mL), dried over MgSO$_4$ and concentrated in vacuo. The residue was suspended in 20 mL of diethyl ether and sonicated. The solid was collected through filtration and washed with minimum amount of diethyl ether to give 3,4-dichloropicolinamide (2.3 g, yield: 35%) as a yellow solid. ESI-MS [M+H]$^+$: 191.1.

Synthesis of 3,4-dichloropicolinonitrile

To a solution of 3,4-dichloropicolinamide (500 mg, 2.63 mmol) in DMF (20 mL) was added POCl$_3$ (2.4 g, 15.79 mmol) dropwise at 0° C. The mixture was stirred at 25° C. for 16 h, then saturated NaHCO$_3$ (aq., 120 mL) was added and the reaction mixture was extracted with EtOAc (100 mL×3). The combined organic layers were washed with brine (100 mL), dried over Na$_2$SO$_4$, concentrated to give 3,4-dichloropicolinonitrile (420 mg, yield: 93%) as a brown solid. ESI-MS [M+H]+: 173.0.

Synthesis of (3,4-dichloropyridin-2-yl)methanamine

To a mixture of LiAlH₄ (110 mg, 2.9 mmol) in dry THF (3 mL) was added 3,4-dichloropicolinonitrile (200 mg, 1.16 mmol) in THF at −78° C. The mixture was stirred at −78° C. for 30 min, then stirred at −40° C. for 30 min. The mixture was quenched with H₂O (10 mL), extracted with EtOAc (50 mL×3). The combined organic layers were washed with brine, dried over Na₂SO₄, concentrated to give (3,4-dichloropyridin-2-yl)methanamine (100 mg, yield: 49%) as a yellow oil. ESI-MS [M+H]+: 177.0.

Synthesis of N-((3,4-dichloropyridin-2-yl)methyl)formamide

The mixture of (3,4-dichloropyridin-2-yl)methanamine (100 mg, 0.57 mmol) in HCOOH (2 mL) was stirred at 90° C. for 3 h and then concentrated to give the crude. The crude was purified by prep-TLC (DCM/MeOH=10/1) to give N-((3,4-dichloropyridin-2-yl)methyl)formamide (70 mg, yield: 60%) as a yellow oil. ESI-MS [M+H]+: 205.1.

Synthesis of 7,8-dichloroimidazo[1,5-a]pyridine

The mixture of N-((3,4-dichloropyridin-2-yl)methyl)formamide (70 mg, 0.34 mmol) in POCl₃ (2 mL) was stirred at 100° C. for 3 h. Then POCl₃ was concentrated, H₂O (10 mL) was added, followed by saturated Na₂CO₃ (20 mL). The mixture was extracted with EtOAc (50 mL*3) and the combined organic layers were washed with brine, dried over Na₂SO₄, and concentrated to give the crude, which was purified by prep-TLC (PE/EA=1/2) to give 7,8-dichloroimidazo[1,5-a]pyridine (40 mg, yield: 63%) as a yellow solid. ESI-MS [M+H]+: 187.0.

Synthesis of 7,8-dichloroimidazo[1,5-a]pyridine-1-carbaldehyde

To a solution of 7,8-dichloroimidazo[1,5-a]pyridine (100 mg, 0.54 mmol) in dry DMF (0.2 mL) was added POCl₃ (123 mg, 0.81 mmol) at 0° C. The mixture was stirred at 100° C. for 1 h then cooled and poured into ice H₂O. The mixture was basified with NH₄OH, extracted with DCM (50 mL×3) and concentrated to give the crude, which was purified by prep-TLC (DCM/MeOH=20/1) to give 7,8-dichloroimidazo[1,5-a]pyridine-1-carbaldehyde (25 mg, yield: 22%) as a yellow solid. ESI-MS [M+H]+: 215.0.

Synthesis of N-((7,8-dichloroimidazo[1,5-a]pyridin-1-yl)methyl)-2-methylpropane-2-sulfinamide To a mixture of 7,8-dichloroimidazo[1,5-a]pyridine-1-carbaldehyde (25 mg, 0.12 mmol) and 2-methylpropane-2-sulfinamide (17 mg, 0.14 mmol) in dry THF (2 mL) was added tetraethoxytitanium (80 mg, 0.35 mmol). The mixture was stirred at 75° C. for 16 h and then cooled to 25° C. NaBH₄ (18 mg, 0.47 mmol) was added and stirred at 25° C. for 3 h. The reaction was quenched with H₂O (10 mL) and extracted with EtOAc (30 mL×3). The combined organic layers were washed with brine, dried over Na₂SO₄, concentrated to give N-((7,8-dichloroimidazo[1,5-a]pyridin-1-yl)methyl)-2-methylpropane-2-sulfinamide (37 mg, yield: 100%) as a yellow solid. ESI-MS [M+H]+: 320.0.

Synthesis of (7,8-dichloroimidazo[1,5-a]pyridin-1-yl)methanamine

The mixture of N-((7,8-dichloroimidazo[1,5-a]pyridin-1-yl)methyl)-2-methylpropane-2-sulfinamide (37 mg, 0.12 mmol) and HCl in dioxane (1 mL, 4 M) was stirred at 25° C. for 3 h. The resulting mixture was concentrated to give (7,8-dichloroimidazo[1,5-a]pyridin-1-yl)methanamine hydrochloride (25 mg, yield: 84%) as a yellow solid which was used in the next step without purification. ESI-MS [M−16]: 199.0.

Synthesis of N-((7,8-dichloroimidazo[1,5-a]pyridin-1-yl)methyl)-1-((6-methylimidazo[1,2-a]pyridin-2-yl)methyl)-1H-pyrazole-4-carboxamide (I-33)

To a mixture of (7,8-dichloroimidazo[1,5-a]pyridin-1-yl) methanamine hydrochloride (25 mg, 0.1 mmol) and 1-((6-methylimidazo[1,2-a]pyridin-2-yl)methyl)-1H-pyrazole-4-carboxylic acid (25 mg, 0.1 mmol) in dry DMF (2 mL) was added DIPEA (64 mg, 0.5 mmol) and HATU (76 mg, 0.2 mmol). The mixture was stirred at 25° C. for 1 h. Water (20 mL) was added and extracted with EtOAc (30 mL×3). The combined organic phase was washed with brine, dried over Na₂SO₄, and concentrated to give the crude, which was purified by prep-TLC (DCM/MeOH=10/1) to give N-((7,8-dichloroimidazo[1,5-a]pyridin-1-yl)methyl)-1-((6-methylimidazo[1,2-a]pyridin-2-yl)methyl)-1H-pyrazole-4-carboxamide (13.3 mg, yield: 30%) as a yellow solid. ESI-MS [M+H]+: 454.1. Purity: 96.7%. ¹H NMR (400 MHz, DMSO): δ 8.44 (s, 1H), 8.35 (d, J=7.4 Hz, 1H), 8.32-8.27 (m, 2H), 8.22 (s, 1H), 7.85 (s, 1H), 7.76 (s, 1H), 7.41 (d, J=9.2 Hz, 1H), 7.11 (d, J=9.2 Hz, 1H), 6.83 (d, J=7.4 Hz, 1H), 5.39 (s, 2H), 4.80 (d, J=4.9 Hz, 2H), 2.25 (s, 3H).

Example 34

Scheme 34

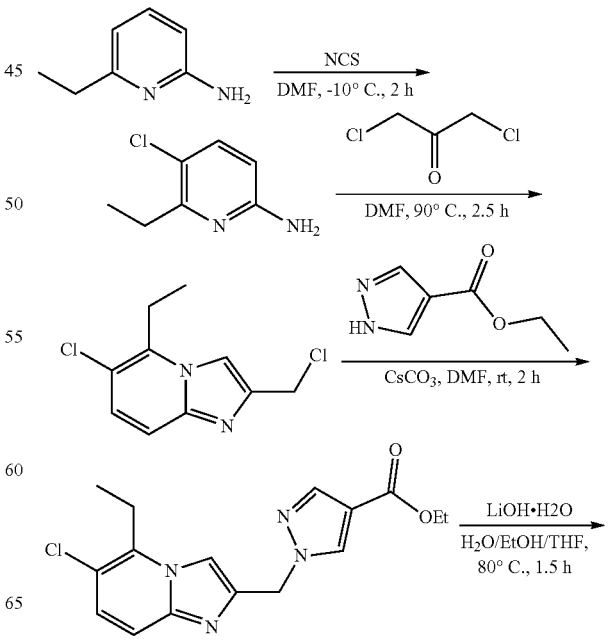

117

-continued

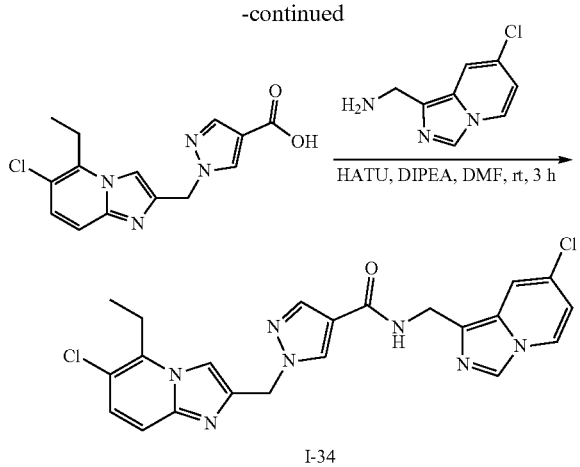

I-34

Synthesis of 5-chloro-6-ethylpyridin-2-amine

To a solution of 6-ethylpyridin-2-amine (1.0 g, 8.20 mmol) in dry DMF (16 mL) was added NCS (1.09 g, 8.2 mmol) at −10° C. and stirred at −10° C. for 2 h. The reaction mixture was diluted with $H_2O$ (50 mL) and extracted with ethyl acetate (3×50 mL). The organic layers were washed with brine, dried over anhydrous sodium sulfate and concentrated. The residue was purified by flash column chromatography to give 5-chloro-6-ethylpyridin-2-amine (500 mg, yield: 39%). ESI-MS [M+H]$^+$: 157.1.

Synthesis of 6-chloro-2-(chloromethyl)-5-ethylimidazo[1,2-a]pyridine

To a solution of 5-chloro-6-ethylpyridin-2-amine (500 mg, 3.2 mmol) in N,N-dimethylformamine (3 mL) was added 1,3-dichloropropan-2-one (1.62 g, 12.8 mmol). The resulting mixture was stirred at 90° C. for 2.5 h. The reaction mixture was diluted with $H_2O$ (50 mL), adjust to approximately pH 9 by adding saturated $NaHCO_3$ solution, and then extracted with ethyl acetate (3×30 mL). The organic layers were washed with brine, dried over anhydrous sodium sulfate and concentrated. The residue was purified by flash column chromatography to give 6-chloro-2-(chloromethyl)-5-ethylimidazo[1,2-a]pyridine (390 mg, yield: 37%). ESI-MS [M+H]$^+$: 229.1.

Synthesis of Ethyl 1-((6-chloro-5-ethylimidazo[1,2-a]pyridin-2-yl)methyl)-1H-pyrazole-4-carboxylate To a solution of 6-chloro-2-(chloromethyl)-5-ethylimidazo[1,2-a]pyridine (250 mg, 1.11 mmol) in N,N-dimethylformamine (3 mL) was added cesium carbonate (1.80 g, 3.33 mmol) and ethyl 1H-pyrazole-4-carboxylate (155 mg, 1.11 mmol). The resulting mixture was diluted with $H_2O$ (30 mL) and extracted with ethyl acetate (3×30 mL). The organic layers were washed with brine, dried over anhydrous sodium sulfate and concentrated. The residue was purified by flash column chromatography to give ethyl 1-((6-chloro-5-ethyl-imidazo[1,2-a]pyridin-2-yl)methyl)-1H-pyrazole-4-carboxylate (360 mg, yield: 87%). ESI-MS [M+H]$^+$: 333.1.

Synthesis of 1-((6-chloro-5-ethylimidazo[1,2-a]pyridin-2-yl)methyl)-1H-pyrazole-4-carboxylic Acid To a solution of give ethyl 1-((6-chloro-5-ethylimidazo[1,2-a]pyridin-2-yl)methyl)-1H-pyrazole-4-carboxylate

118

(436 mg, 1.3 mmol) in a mixed solvent of THF/EtOH/$H_2O$ (3 mL/3 mL/1 mL) was added lithium hydroxide (126 mg, 5.3 mmol). The resulting mixture was stirred at 85° C. for 1.5 h and diluted with $H_2O$ (15 mL). The pH of the mixture was then adjusted to 5 by adding 1 M HCl and then extracted with DCM/MeOH (5/1, 3×50 mL). The combined organic layers were concentrated to give 1-((6-chloro-5-ethylimidazo[1,2-a]pyridin-2-yl)methyl)-1H-pyrazole-4-carboxylic acid (200 mg, yield: 50%), which was used in the next step without further purification. ESI-MS [M+H]$^+$: 305.1.

Synthesis of 1-((6-chloro-5-ethylimidazo[1,2-a]pyridin-2-yl)methyl)-N-((7-chloroimidazo[1,5-a]pyridin-1-yl)methyl)-1H-pyrazole-4-carboxamide (I-34)

To the solution of 1-((6-chloro-5-ethylimidazo[1,2-a]pyridin-2-yl)methyl)-1H-pyrazole-4-carboxylic acid (65 mg, 0.21 mmol) in dry DMF (3 mL) was added HATU (120 mg, 0.32 mmol), DIPEA (135 mg, 1.05 mmol) and (7-chloroimidazo[1,5-a]pyridin-1-yl)methanamine hydrochloride (46 mg, 0.21 mmol) at RT. The reaction was stirred at RT for 2 h. Water (30 mL) was added and the mixture was extracted with ethyl acetate (30 mL×3). The combined organic layers were washed with brine, dried over anhydrous sodium sulfate and concentrated. The residue was purified by prep-HPLC to give N-((7-chloroimidazo[1,5-a]pyridin-1-yl)methyl)-1-((5-cyclopropylimidazo[1,2-a]pyridin-2-yl)methyl)-1H-pyrazole-4-carboxamide (41 mg, yield: 38%) as a white solid. ESI-MS [M+H]$^+$: 468.0. Purity: 100%. 1H NMR (400 MHz, DMSO): δ 8.59 (t, J=5.7 Hz, 1H), 8.34-8.26 (m, 2H), 8.24 (s, 1H), 8.10 (s, 1H), 7.86 (s, 1H), 7.78 (s, 1H), 7.46 (d, J=9.5 Hz, 1H), 7.34 (d, J=9.5 Hz, 1H), 6.69-6.60 (m, 1H), 5.43 (s, 2H), 4.55 (d, J=5.7 Hz, 2H), 3.20-3.10 (m, 2H), 1.20 (t, J=7.5 Hz, 3H).

Example 35

Scheme 35

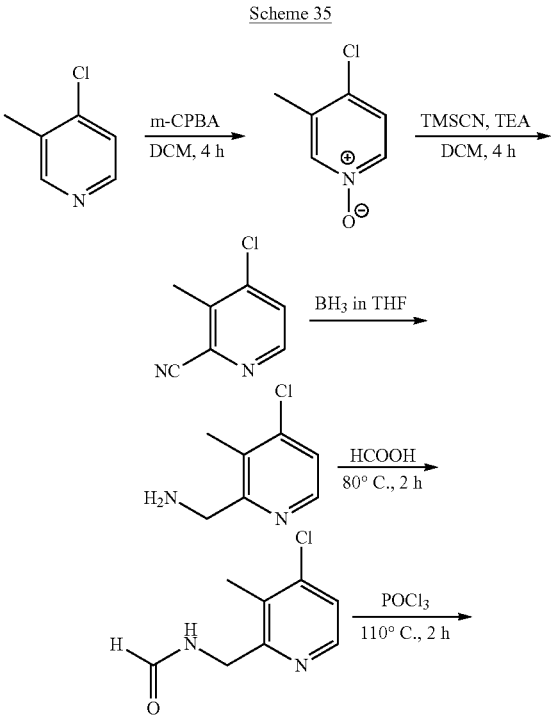

119

-continued

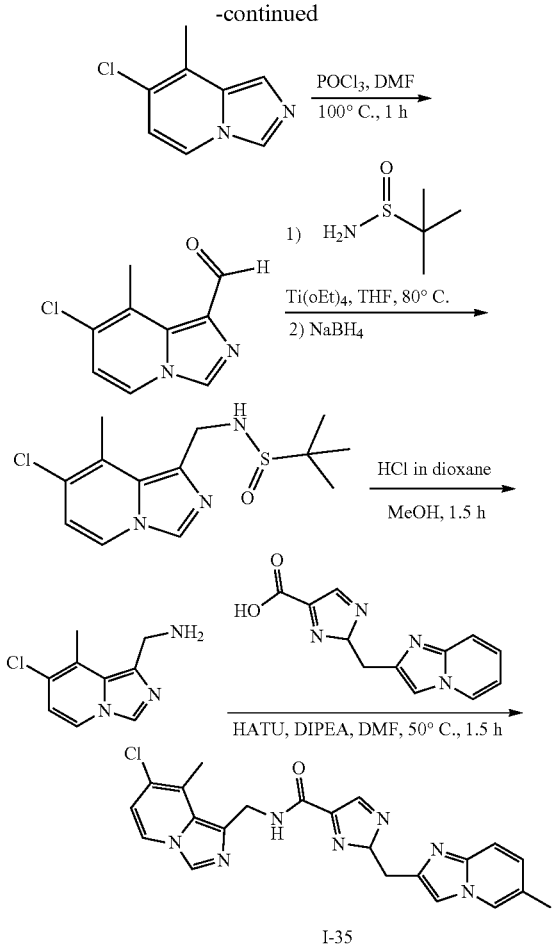

I-35

Synthesis of 4-chloro-3-methylpyridine 1-oxide

To a solution of 4-chloro-3-methylpyridine (5 g, 30.6 mmol) in dry DMF (100 mL) was added m-CPBA (10.8 g, 58.9 mmol). The reaction was stirred at RT for 3 h. The mixture was diluted with DCM (300 mL) and followed by saturated NaHCO₃ (300 mL). Then the mixture was extracted with DCM (300 mL×3). The combined organic layers were concentrated and purified by silica gel chromatography (DCM/MeOH=15/1) to give 4-chloro-3-methylpyridine 1-oxide (2.43 g, yield: 55.4%) as a white solid. ESI-MS [M+H]⁺: 144.2.

Synthesis of 4-chloro-3-methylpicolinonitrile

To a solution of 4-chloro-3-methylpyridine 1-oxide (2.43 g, 17.0 mmol), dimethylcarbamic chloride (1.92 g, 17.9 mmol) and TMSCN (2.02 g, 20.4 mmol) in dry DMF (45 mL) was added Et₃N (4.7 mL, 34 mmol), the mixture was stirred at 100° C. for 3 h. The reaction mixture was then quenched with saturated NaHCO₃ (200 mL) solution at 0° C. and extracted with EtOAc (100 mL×3). The combined organic layers were concentrated and purified by silica gel chromatography (EA/PE=1/10) to give 4-chloro-3-methylpicolinonitrile (1.87 g, yield: 72%) as a yellow oil. ESI-MS [M+H]⁺: 153.1.

120

Synthesis of (4-chloro-3-methylpyridin-2-yl)methanamine

To a solution of 4-chloro-3-methylpicolinonitrile (1.7 g, 11 mmol) in dry THF (6 mL) was added BH₃-THF (1 M, 27.5 mL) at 0° C. The mixture was stirred at 0° C. for 1 h and then stirred at RT overnight. The mixture was quenched with MeOH and stirred at RT for 1 h, then concentrated to give (4-chloro-3-methylpyridin-2-yl)methanamine (2.1 g, crude) as a yellow solid which was used in the next step without purification. ESI-MS [M+H]⁺: 185.1.

Synthesis of N-((4-chloro-3-methylpyridin-2-yl)methyl)formamide

To a solution of 4-chloro-3-methylpicolinonitrile (2.1 g, 13.5 mmol) and formic acid (20 mL) was stirred at 80° C. for 3 h. The mixture was concentrated and purified by silica gel chromatography to give N-((4-chloro-3-methylpyridin-2-yl)methyl)formamide (1.3 g, yield: 54%) as a brown oil. ESI-MS [M+H]⁺: 185.1.

Synthesis of 7-chloro-8-methylimidazo[1,5-a]pyridine

To a solution of N-((4-chloro-3-methylpyridin-2-yl)methyl)formamide (1.3 g, 7 mmol) and POCl₃ (22 mL) was stirred at 110° C. for 2 h. POCl₃ was removed in vacuo. Water was added and followed by saturated Na₂CO₃ (aq.). The mixture was extracted with EtOAc (100 mL×3). The combined organic layers were washed with brine, dried over Na₂SO₄, filtered and concentrated to give the crude, which was purified by silica gel chromatography (EA/PE=1/1) to give 7-chloro-8-methylimidazo[1,5-a]pyridine (700 mg, yield: 60%) as a brown solid. ESI-MS [M+H]⁺: 167.1.

Synthesis of 7-chloro-8-methylimidazo[1,5-a]pyridine-1-carbaldehyde

A mixture of 7-chloro-8-methylimidazo[1,5-a]pyridine (660 mg, 3.96 mmol), DMF (289.4 mg, 3.96 mmol) in POCl₃ (5 mL) was stirred at 100° C. for 1 h. Then the reaction mixture was poured to ice H₂O. NH₄OH solution was added to adjust pH to about 8 and then the mixture was extracted with EtOAc (50 mL×3). The combined organic layers were concentrated and purified by silica gel chromatography to give 7-chloro-8-methylimidazo[1,5-a]pyridine-1-carbaldehyde (165 mg, yield: 21%) as a white solid. ESI-MS [M+H]⁺: 195.1.

Synthesis of N-((7-chloro-8-methylimidazo[1,5-a]pyridin-1-yl)methyl)-2-methylpropane-2-sulfinamide A mixture of 7-chloro-8-methylimidazo[1,5-a]pyridine-1-carbaldehyde (154 mg, 0.8 mmol), 2-methylpropane-2-sulfinamide (116.35 mg, 0.96 mmol) and Ti(OEt)₄ (0.58 mL, 2.8 mmol) in THF (10 mL) was stirred at 80° C. overnight. After cooled to RT, NaBH₄ (151.32 mg, 4 mmol) was added. The reaction mixture was stirred at RT for 3 h. The reaction was quenched with H₂O (20 mL) and extracted with EtOAc (50 mL×3). The combined organic layers were concentrated and purified by silica gel chromatography (DCM/CH₃OH=10:1) to give N-((7-chloro-8-methylimidazo[1,5-a]pyridin-1-yl)methyl)-2-methylpropane-2-sulfinamide (87 mg, yield: 36%) as a yellow solid. ESI-MS [M+H]⁺: 300, and (131 mg, yield: 36%) as a yellow solid. ESI-MS [M+13]⁺: 312.

Synthesis of (7-chloro-8-methylimidazo[1,5-a]pyridin-1-yl)methanamine

To a solution of N-((7-chloro-8-methylimidazo[1,5-a]pyridin-1-yl)methyl)-2-methylpropane-2-sulfinamide (187 mg, 0.62 mmol) in CH₃OH (8 mL) was added HCl (4 M in dioxane, 8 mL). The mixture was stirred at RT for 1.5 h. Then concentrated to give (7-chloro-8-methylimidazo[1,5-a]pyridin-1-yl)methanamine hydrochloride (168 mg, crude) as a white solid which was used in the next step without purification. ESI-MS [M−16]⁺: 179.1.

Synthesis of N-((7-chloro-8-methylimidazo[1,5-a]pyridin-1-yl)methyl)-1-((6-methylimidazo[1,2-a]pyridin-2-yl)methyl)-1H-pyrazole-4-carboxamide (I-35)

A mixture (7-chloro-8-methylimidazo[1,5-a]pyridin-1-yl)methanamine (44 mg, 0.22 mmol), 1-((6-methylimidazo[1,2-a]pyridin-2-yl)methyl)-1H-pyrazole-4-carboxylic acid (57 mg, 0.22 mmol), HATU (167.2 mg, 0.44 mmol) and DIPEA (113.5 mg, 0.88 mmol) in DMF (5 mL) was stirred at RT for 1.5 h. Water (30 mL) was added, extracted with EtOAc (30 mL×3), the combined organic phase were washed with brine, dried over Na₂SO₄ and concentrated to give the crude, which was purified by silica gel chromatography (DCM/MeOH=10:1) to give N-((7-chloro-8-methylimidazo[1,5-a]pyridin-1-yl)methyl)-1-((6-methylimidazo[1,2-a]pyridin-2-yl)methyl)-1H-pyrazole-4-carboxamide (27 mg, yield: 28%) as a white solid. ESI-MS [M+H]⁺: 434.1. Purity: 99.42%. ¹H NMR (400 MHz, DMSO): δ 8.33 (t, J=4.7 Hz, 1H), 8.26 (s, 2H), 8.17 (s, 1H), 8.13 (d, J=7.3 Hz, 1H), 7.81 (s, 1H), 7.72 (s, 1H), 7.36 (d, J=9.2 Hz, 1H), 7.08 (d, J=9.2 Hz, 1H), 6.59 (d, J=7.4 Hz, 1H), 5.33 (s, 2H), 4.62 (d, J=4.9 Hz, 2H), 2.51 (s, 3H), 2.19 (s, 3H).

Example 36

Scheme 36

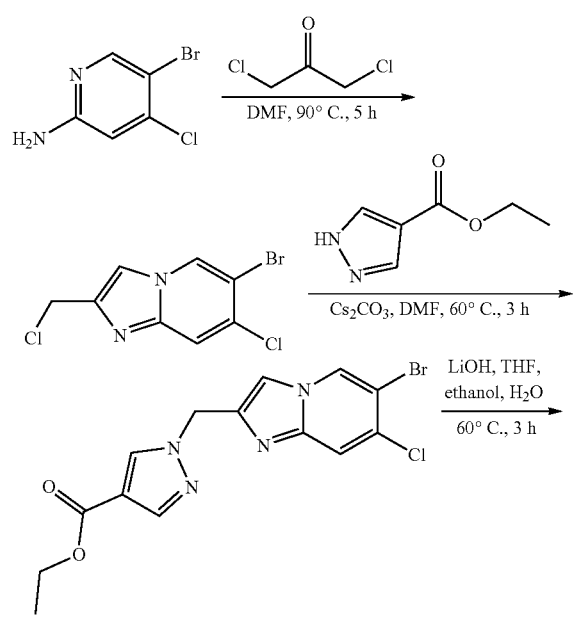

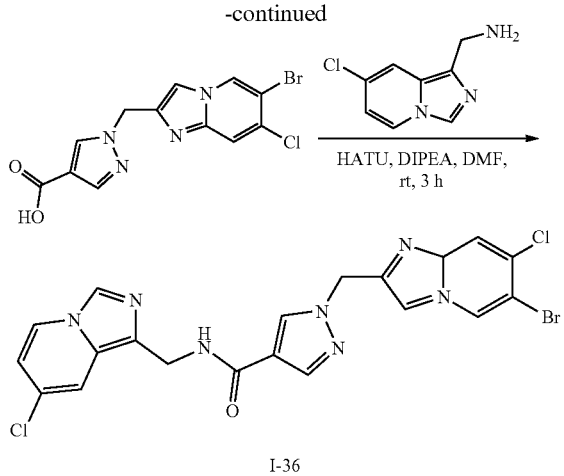

I-36

Synthesis of 6-bromo-7-chloro-2-(chloromethyl)imidazo[1,2-a]pyridine

A mixture of 5-bromo-4-chloropyridin-2-amine (1.67 g, 9.9 mmol), 1,3-dichloropropan-2-one (2.5 g, 19.8 mmol) in DMF (15 mL) was stirred at 90° C. for 5 h. The reaction mixture was diluted with H₂O (50 mL), adjusted to approximately pH 9 by adding saturated a NaHCO₃ solution, and extracted with ethyl acetate (3×30 mL). The combined organic layers were concentrated and purified by silica gel chromatography (EA/PE=7:1) to give 6-bromo-7-chloro-2-(chloromethyl)imidazo[1,2-a]pyridine (900 mg, yield: 32%) as a yellow solid. ESI-MS [M+H]⁺: 278.9.

Synthesis of Ethyl 1-((6-bromo-7-chloroimidazo[1,2-a]pyridin-2-yl)methyl)-1H-pyrazole-4-carboxylate A mixture of 6-bromo-7-chloro-2-(chloromethyl)imidazo[1,2-a]pyridine (560 mg, 2.0 mmol), ethyl 1H-pyrazole-4-carboxylate (560 mg, 4.0 mmol) and Cs₂CO₃ (1.95 g, 6.0 mmol) in DMF (10 mL) was stirred at 60° C. for 3 h. The resulting mixture was diluted with H₂O (30 mL) and extracted with ethyl acetate (3×30 mL), The combined organic layers were concentrated and purified by silica gel chromatography (EA/PE=10:1 to 7:13) to give ethyl 1-((6-bromo-7-chloroimidazo[1,2-a]pyridin-2-yl)methyl)-1H-pyrazole-4-carboxylate (400 mg, yield: 52%) as a white solid. ESI-MS [M+H]⁺: 383.0.

Synthesis of 1-((6-bromo-7-chloroimidazo[1,2-a]pyridin-2-yl)methyl)-1H-pyrazole-4-carboxylic Acid To a solution of ethyl 1-((6-bromo-7-chloroimidazo[1,2-a]pyridin-2-yl)methyl)-1H-pyrazole-4-carboxylate (216 mg, 0.56 mmol) in ethanol (3 mL), THF (3 mL) and H₂O (1.5 mL) was added LiOH.H₂O (95 mg, 2.25 mmol). The mixture was stirred at 65° C. for 3 h. Most of the solvent was concentrated and the residue was adjusted to pH to 4 by adding 1 M HCl solution. The resulting precipitate was filtered to give 1-((6-bromo-7-chloroimidazo[1,2-a]pyridin-2-yl)methyl)-1H-pyrazole-4-carboxylic acid (190 mg, yield: 95%) as a white solid. ESI-MS [M+H]⁺: 355.0.

Synthesis of 1-((6-bromo-7-chloroimidazo[1,2-a]pyridin-2-yl)methyl)-N-((7-chloroimidazo[1,5-a]pyridin-1-yl)methyl)-1H-pyrazole-4-carboxamide (I-36)

A mixture of 1-((6-bromo-7-chloroimidazo[1,2-a]pyridin-2-yl)methyl)-1H-pyrazole-4-carboxylic acid (95 mg, 0.27 mmol), (7-chloroimidazo[1,5-a]pyridin-1-yl)methanamine (55 mg, 0.25 mmol), HATU (190 mg, 0.5 mmol) and DIPEA (97 mg, 0.75 mmol) in DMF (4 mL) was stirred at RT for 3 h. Water (30 mL) was added and extracted with ethyl acetate (3×30 mL). The combined organic layers were concentrated and purified by prep-TLC (DCM:MeOH=8:1) to give 1-((6-bromo-7-chloroimidazo[1,2-a]pyridin-2-yl)methyl)-N-((7-chloroimidazo[1,5-a]pyridin-1-yl)methyl)-1H-pyrazole-4-carboxamide (49.2 mg, yield: 38%) as a white solid. ESI-MS [M+H]$^+$: 517.9. Purity: 96.34%. $^1$H NMR (400 MHz, DMSO): δ 9.06 (s, 1H), 8.58 (t, 8.30-8.22 (m, 3H), 7.92-7.77 (m, 4H), 6.64 (s, 1H), 5.42 (s, 2H), 4.54 (s, 2H).

Example 37

Scheme 37

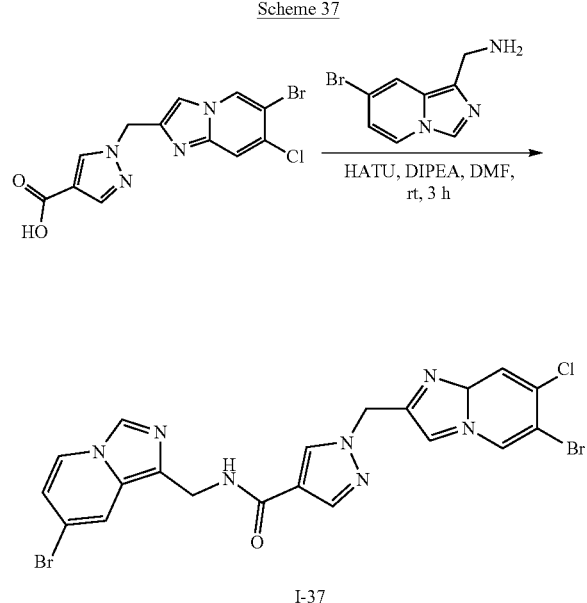

I-37

Synthesis of 1-((6-bromo-7-chloroimidazo[1,2-a]pyridin-2-yl)methyl)-N-((7-bromoimidazo[1,5-a]pyridin-1-yl)methyl)-1H-pyrazole-4-carboxamide (I-37)

A mixture of 1-((6-bromo-7-chloroimidazo[1,2-a]pyridin-2-yl)methyl)-1H-pyrazole-4-carboxylic acid (95 mg, 0.27 mmol), (7-bromoimidazo[1,5-a]pyridin-1-yl)methanamine (56 mg, 0.25 mmol), HATU (190 mg, 0.5 mmol) and DIPEA (97 mg, 0.75 mmol) in DMF (4 mL) was stirred at RT for 3 h. Water (30 mL) was added and the mixture was extracted with ethyl acetate (3×30 mL). The combined organic layers were concentrated and purified by prep-TLC (DCM:MeOH=8:1) to give 1-((6-bromo-7-chloroimidazo[1,2-a]pyridin-2-yl)methyl)-N-((7-bromoimidazo[1,5-a]pyridin-1-yl)methyl)-1H-pyrazole-4-carboxamide (43.3 mg, yield: 31%) as a white solid. ESI-MS [M+H]$^+$: 561.9. Purity: 90%. 1H NMR (400 MHz, DMSO): δ 9.06 (s, 1H), 8.58 (t, J=4.9 Hz, 1H), 8.31 (s, 1H), 8.23-8.22 (m, 2H), 7.94-7.93 (m, 2H), 7.86 (s, 1H), 7.80 (s, 1H), 6.71 (d, J=7.3 Hz, 1H), 5.43 (s, 2H), 4.54 (d, J=5.3 Hz, 2H).

Example 38

Scheme 38

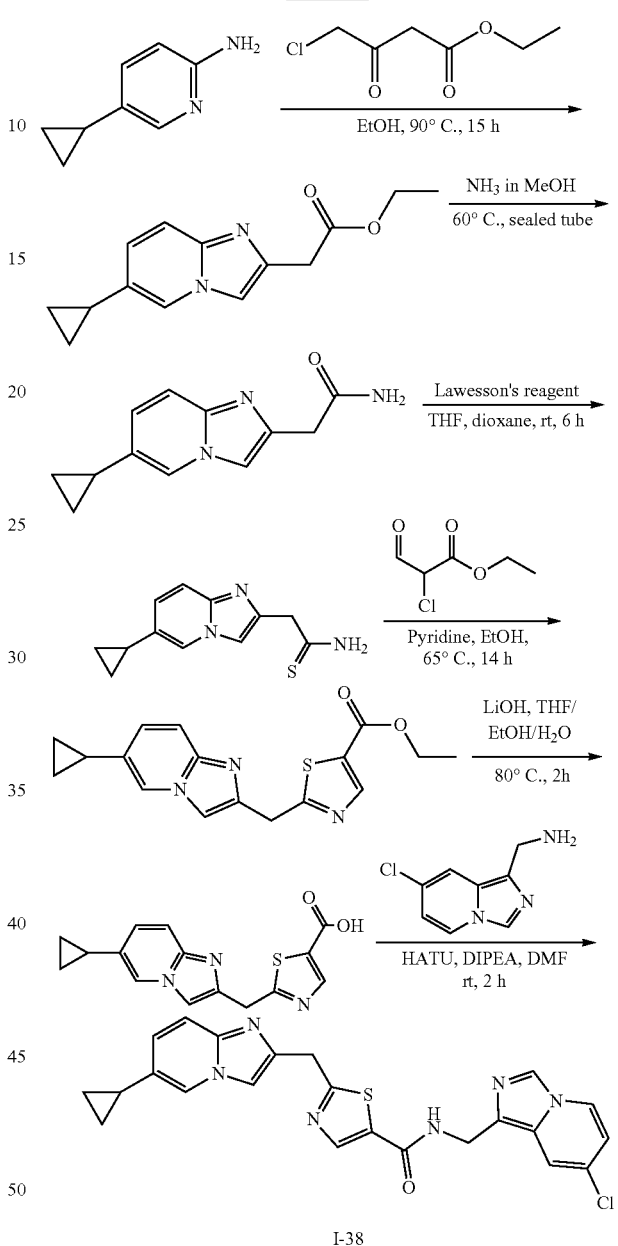

I-38

Synthesis of Ethyl 2-(6-cyclopropylimidazo[1,2-a]pyridin-2-yl)acetate

A mixture of 5-cyclopropylpyridin-2-amine (3 g, 22.4 mmol) and ethyl 4-chloro-3-oxobutanoate (11 g, 67.2 mmol) in EtOH (150 mL) was stirred at 90° C. for 15 h. The pH of the reaction was adjusted to 8-9 with NaHCO$_3$ (4 M, 50 mL) and extracted with EtOAc (70 mL×3). The combined organic layers were washed with brine, dried over Na$_2$SO$_4$ and concentrated to give the crude, which was purified by silica gel chromatography (EA/PE=1/1) to give ethyl 2-(6-cyclopropylimidazo[1,2-a]pyridin-2-yl)acetate (3.6 g, yield: 72%) as a black solid. ESI-MS [M+H]$^+$: 225.2.

Synthesis of 2-(6-cyclopropylimidazo[1,2-a]pyridin-2-yl)acetamide

A solution of ethyl 2-(6-cyclopropylimidazo[1,2-a]pyridin-2-yl)acetate (3.6 g, 16 mmol) in NH$_3$ (7 M solution in MeOH, 50 mL) in sealed tube was stirred at 60° C. for 12 h. The reaction was concentrated to give the 2-(6-cyclopropylimidazo[1,2-a]pyridin-2-yl)acetamide, which was used in the next step without further purification (3.4 g, yield: 99%) as a yellow oil. ESI-MS [M+H]$^+$: 216.2.

Synthesis of 2-(6-cyclopropylimidazo[1,2-a]pyridin-2-yl)ethanethioamide

To a solution of 2-(6-cyclopropylimidazo[1,2-a]pyridin-2-yl)acetamide (3.4 g, 15.8 mmol) in dioxane (50 mL) was added Lawesson's reagent (6.3 g, 15.8 mmol) at 0° C. The resulting mixture was stirred at RT for 6 h. The reaction was quenched with H$_2$O (70 mL) and extracted with EtOAc (50 mL×3). The combined organic layers were washed with brine, dried over Na$_2$SO$_4$, filtered and concentrated to give the 2-(6-cyclopropylimidazo[1,2-a]pyridin-2-yl)ethanethioamide which was used in the next step without further purification. (3 g, yield: 82%) as a yellow oil. ESI-MS [M+H]$^+$: 232.2.

Synthesis of Ethyl 2-((6-cyclopropylimidazo[1,2-a]pyridin-2-yl)methyl)thiazole-5-carboxylate A mixture of 2-(6-cyclopropylimidazo[1,2-a]pyridin-2-yl)ethanethioamide (700 mg, 3.1 mmol), pyridine (480 mg, 6.2 mmol) and ethyl 2-chloro-3-oxopropanoate (678 mg, 4.65 mmol) in EtOH (25 mL) was stirred at 65° C. for 14 h. The reaction was concentrated to give the crude, which was purified with silica gel chromatography (EA/PE=1/1) to give the ethyl 2-((6-cyclopropylimidazo[1,2-a]pyridin-2-yl)methyl)thiazole-5-carboxylate (105 mg, yield: 10.7%) as a yellow solid. ESI-MS [M+H]$^+$: 327.1.

Synthesis of 2-((6-cyclopropylimidazo[1,2-a]pyridin-2-yl)methyl)thiazole-5-carboxylic Acid A mixture of ethyl 2-((6-cyclopropylimidazo[1,2-a]pyridin-2-yl)methyl)thiazole-5-carboxylate (105 mg, 0.32 mmol) and LiOH (23 mg, 0.96 mmol) in THF/EtOH/H$_2$O (2 mL/2 mL/1 mL) was stirred at 80° C. for 2 h. The pH value of the reaction was adjusted to 4 by adding 1 M HCl solution, and then concentrated to give the crude, which was used in the next step without further purification (105 mg, crude yield: 100%). ESI-MS [M+H]$^+$: 300.2.

Synthesis of N-((7-chloroimidazo[1,5-a]pyridin-1-yl)methyl)-2-((6-cyclopropylimidazo[1,2-a]pyridin-2-yl)methyl)thiazole-5-carboxamide (I-38)

To a solution of 2-((6-cyclopropylimidazo[1,2-a]pyridin-2-yl)methyl)thiazole-5-carboxylic acid (105 mg, crude from last step) in DMF (5 mL) was added HATU (160 mg, 0.42 mmol) and DIPEA (226 mg, 1.75 mmol). The mixture reaction was stirred for 30 min, then (7-chloroimidazo[1,5-a]pyridin-1-yl)methanamine hydrochloride (99 mg, 0.45 mmol) was added. The resulting mixture was stirred at RT for 12 h. Water (25 mL) was added and the mixture was extracted with EtOAc (30 mL×3). The combined organic layers were washed with brine, dried over Na$_2$SO$_4$, concentrated to give the crude, which was purified with prep-TLC (DCM/MeOH=10/1) to give the N-((7-chloroimidazo[1,5-a]pyridin-1-yl)methyl)-2-((6-cyclopropylimidazo[1,2-a]pyridin-2-yl)methyl)thiazole-5-carboxamide as a white solid (15 mg, yield: 9.3%). ESI-MS [M+H]$^+$: 463.1. Purity: 98.5%. $^1$H NMR (400 MHz, MeOD): δ 8.30-8.27 (m, 2H), 8.19-8.16 (m, 2H), 7.81 (s, 1H), 7.73 (s, 1H), 7.49 (d, J=9.4 Hz, 1H), 7.30 (dd, J=9.4, 1.5 Hz, 1H), 6.63 (dd, J=7.5, 2.0 Hz, 1H), 4.70 (s, 2H), 4.53 (s, 2H), 1.99-1.97 (m, 1H), 1.11-1.00 (m, 2H), 0.77-0.74 (m, 2H).

Example 39

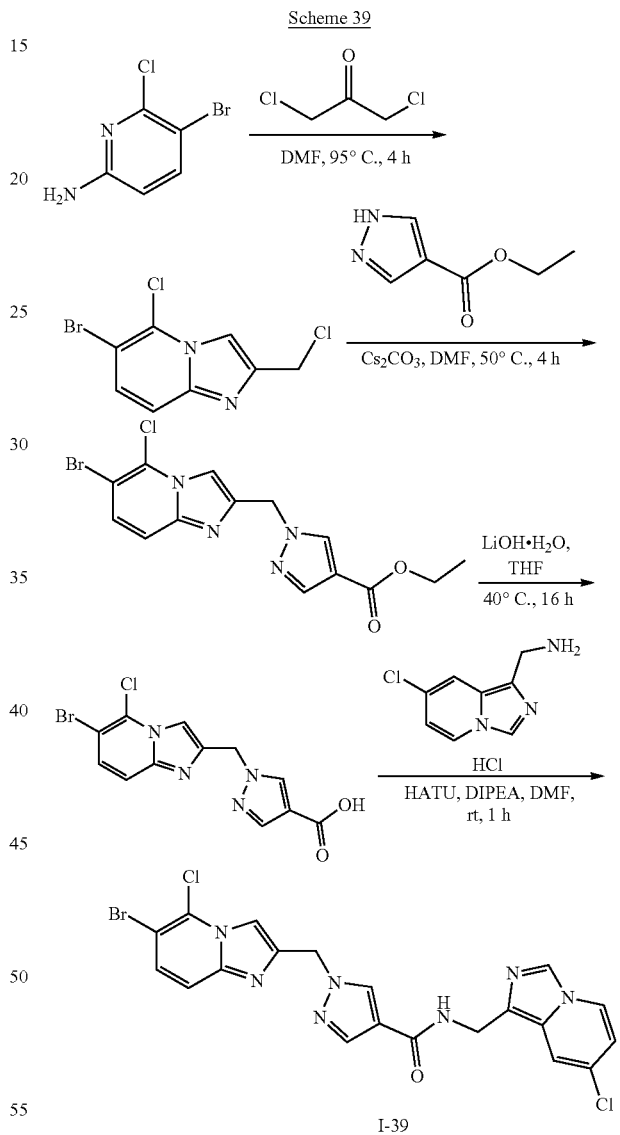

Synthesis of 6-bromo-5-chloro-2-(chloromethyl)imidazo[1,2-a]pyridine

The mixture of 5-bromo-6-chloropyridin-2-amine (1.38 g, 6.65 mmol) and 1,3-dichloropropan-2-one (3.35 g, 26.61 mmol) in DMF (20 mL) was stirred at 95° C. for 4 h. The reaction mixture was quenched with H$_2$O (150 mL) followed by adding saturated NaHCO$_3$ (20 mL) solution, the mixture was then extracted with EtOAc (100 mL×2). The combined organic layers were washed with brine (150 mL×2), dried over Na$_2$SO$_4$, concentrated and purified by trituration with EtOAc to give 6-bromo-5-chloro-2-(chloromethyl)imidazo[1,2-a]pyridine (480 mg, 26%) as a light brown solid. ESI-MS [M+H]$^+$: 279.0.

Synthesis of Ethyl 1-((6-bromo-5-chloroimidazo[1,2-a]pyridin-2-yl)methyl)-1H-pyrazole-4-carboxylate The mixture of 6-bromo-5-chloro-2-(chloromethyl)imidazo[1,2-a]pyridine (380 mg, 1.36 mmol), ethyl 1H-pyrazole-4-carboxylate (190 mg, 1.36 mmol) and CsCO$_3$ (663 mg, 2.04 mmol) in DMF (10 mL) was stirred for at 50° C. for 4 h. The reaction mixture was diluted with H$_2$O (80 mL) and extracted with EtOAc (100 mL×3). The combined organic layers were washed with brine, dried over Na$_2$SO$_4$, concentrated and purified by silica gel chromatography (EA/PE=1/4) to give ethyl 1-((6-bromo-5-chloroimidazo[1,2-a]pyridin-2-yl)methyl)-1H-pyrazole-4-carboxylate (400 mg, yield: 77%) as a yellow solid. ESI-MS [M+H]$^+$: 383.0.

Synthesis of 1-((6-bromo-5-chloroimidazo[1,2-a]pyridin-2-yl)methyl)-1H-pyrazole-4-carboxylic Acid A mixture of ethyl 1-((6-bromo-5-chloroimidazo[1,2-a]pyridin-2-yl)methyl)-1H-pyrazole-4-carboxylate (350 mg, 0.912 mmol) and LiOH.H$_2$O (307 mg, 7.30 mmol) in THF (10 mL) and H$_2$O (2 mL) was stirred at 40° C. for 16 h. Most of the solvent was removed and the residue was diluted with H$_2$O (10 mL). The pH value of mixture was adjusted to 4-5 by adding HCl (1 M). The precipitate was collected and dried to give 1-((6-bromo-5-chloroimidazo[1,2-a]pyridin-2-yl)methyl)-1H-pyrazole-4-carboxylic acid (285 mg, yield: 88%) as a white solid. ESI-MS [M+H]$^+$: 354.9.

Synthesis of 1-((6-bromo-5-chloroimidazo[1,2-a]pyridin-2-yl)methyl)-N-((7-chloroimidazo[1,5-a]pyridin-1-yl)methyl)-1H-pyrazole-4-carboxamide (I-39)

The mixture of 1-((6-bromo-5-chloroimidazo[1,2-a]pyridin-2-yl)methyl)-1H-pyrazole-4-carboxylic acid (80 mg, 0.22 mmol), HATU (92 mg, 0.242 mmol) and DIPEA (85 mg, 0.66 mmol) in DMF (3 mL) was stirred at RT for 10 min. (7-chloroimidazo[1,5-a]pyridin-1-yl)methanamine hydrochloride (48 mg, 0.22 mmol) was added and stirred at RT for 1 h. The reaction mixture was quenched with H$_2$O (50 mL) and extracted with EtOAc/THF (40 mL×3, 5/1 (v/v)). The combined organic layers was washed with brine (100 mL×3), dried over Na$_2$SO$_4$, concentrated and purified by prep-TLC (DCM/MeOH=7/1) to give 1-((6-bromo-5-chloroimidazo[1,2-a]pyridin-2-yl)methyl)-N-((7-chloroimidazo[1,5-a]pyridin-1-yl)methyl)-1H-pyrazole-4-carboxamide (50 mg, yield: 43%) as a yellow solid. ESI-MS [M+H]$^+$: 518.0. Purity: 99.23%. $^1$H NMR (400 MHz, DMSO): δ 8.59 (t, J=5.7 Hz, 1H), 8.33-8.28 (m, 2H), 8.25 (s, 1H), 8.02 (s, 1H), 7.87 (s, 1H), 7.78-7.77 (m, 1H), 7.62-7.55 (m, 2H), 6.66-6.63 (m, 1H), 5.47 (s, 2H), 4.55 (d, J=5.7 Hz, 2H).

Example 40

Scheme 40

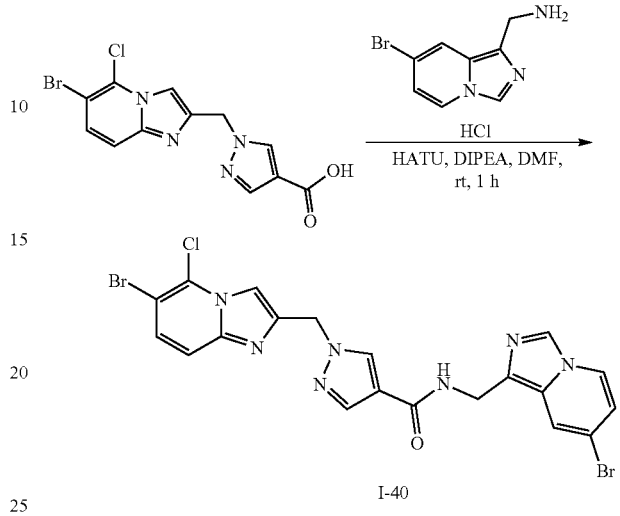

I-40

Synthesis of 1-((6-bromo-5-chloroimidazo[1,2-a]pyridin-2-yl)methyl)-N-((7-bromoimidazo[1,5-a]pyridin-1-yl)methyl)-1H-pyrazole-4-carboxamide (I-40)

The mixture of 1-((6-bromo-5-chloroimidazo[1,2-a]pyridin-2-yl)methyl)-1H-pyrazole-4-carboxylic acid (70 mg, 0.20 mmol), HATU (82 mg, 0.217 mmol) and DIPEA (76 mg, 0.591 mmol) in DMF (3 mL) was stirred at RT for 10 min. (7-bromoimidazo[1,5-a]pyridin-1-yl)methanamine hydrochloride (52 mg, 0.20 mmol) was added and stirred at RT for 1 h. The reaction mixture was diluted with H$_2$O (50 mL) and extracted with EtOAc/THF (40 mL×3, 5/1 (v/v)). The combined organic layers were washed with brine (100 mL×3), dried over Na$_2$SO$_4$, concentrated and purified by prep-TLC (DCM/MeOH=7/1) to give 1-((6-bromo-5-chloroimidazo[1,2-a]pyridin-2-yl)methyl)-N-((7-bromoimidazo[1,5-a]pyridin-1-yl)methyl)-1H-pyrazole-4-carboxamide (40 mg, yield: 36%) as a yellow solid. ESI-MS [M+H]$^+$: 561.9. Purity: 92.54%. $^1$H NMR (400 MHz, DMSO): δ 8.58 (t, J=5.5 Hz, 1H), 8.32 (s, 1H), 8.26-8.22 (m, 2H), 8.02 (s, 1H), 7.95 (s, 1H), 7.87 (s, 1H), 7.61-7.55 (m, 2H), 6.72 (d, J=8.9 Hz, 1H), 5.47 (s, 2H), 4.55 (d, J=5.6 Hz, 2H).

Example 41

Scheme 41

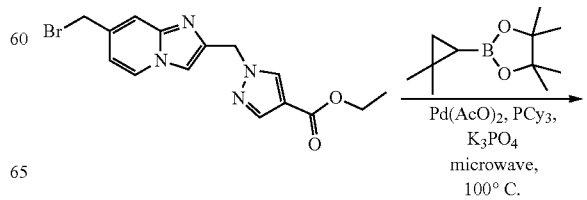

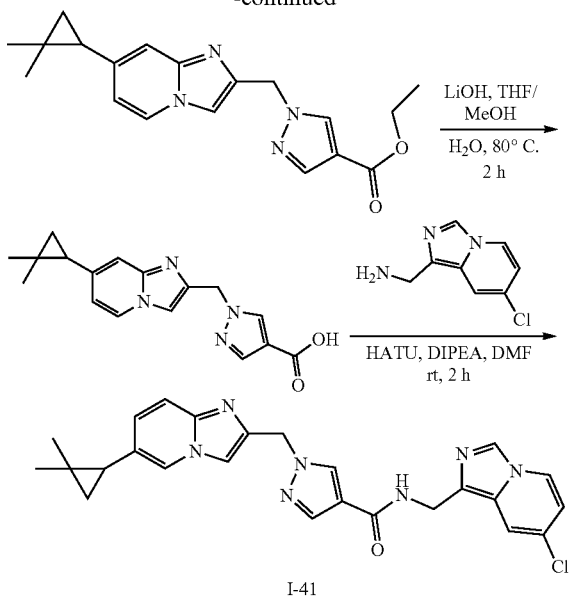

I-41

Synthesis of Ethyl 1-((7-(2,2-dimethylcyclopropyl)imidazo[1,2-a]pyridin-2-yl)methyl)-1H-pyrazole-4-carboxylate A mixture of ethyl 1-((7-bromoimidazo[1,2-a]pyridin-2-yl)methyl)-1H-pyrazole-4-carboxylate (120 mg, 0.34 mmol), 2-(2,2-dimethylcyclopropyl)-4,4,5,5-tetramethyl-1,3,2-dioxaborolane (0.33 g, 1.7 mmol), Pd(OAc)$_2$ (8 mg, 0.034), PCy$_3$ (10 mg, 0.034 mmol), and K$_3$PO$_4$ (220 mg, 1.3 mmol) in 1,4-dioxane (3 mL) and H$_2$O (1 mL) was stirred at 100° C. under microwave for 7 h. The reaction was filtered through celite and washed with DCM/MeOH (10/1, 30 mL). The filtrate was concentrated and purified by silica gel (DCM/MeOH=10/1) to give the 1-((7-(2,2-dimethylcyclopropyl)imidazo[1,2-a]pyridin-2-yl)methyl)-1H-pyrazole-4-carboxylate (60 mg, 70%) as a yellow solid. ESI-MS [M+H]$^+$: 339.1.

Synthesis of Ethyl 1-((7-(2,2-dimethylcyclopropyl)imidazo[1,2-a]pyridin-2-yl)methyl)-1H-pyrazole-4-carboxylate A mixture of 1-((7-(2,2-dimethylcyclopropyl)imidazo[1,2-a]pyridin-2-yl)methyl)-1H-pyrazole-4-carboxylate (61 mg, 0.18 mmol) and LiOH (27.6 mg, 1.2 mmol) in THF/EtOH/H$_2$O (3 mL/3 mL/2 mL) was stirred at 80° C. for 2 h. The pH value of the reaction was adjusted to around 5 and a yellow solid precipitated out. The solid was filtered and the filter cake was dried to give 1-((7-(2,2-dimethylcyclopropyl)imidazo[1,2-a]pyridin-2-yl)methyl)-1H-pyrazole-4-carboxylate (50 mg, yield: 89%) as a yellow solid. ESI-MS [M+H]$^+$: 311.1.

Synthesis of N-((7-chloroimidazo[1,5-a]pyridin-1-yl)methyl)-1-((7-(2,2-dimethylcyclopropyl)imidazo[1,2-a]pyridin-2-yl)methyl)-1H-pyrazole-4-carboxamide (I-41)

To a solution of 1-((7-(2,2-dimethylcyclopropyl)imidazo[1,2-a]pyridin-2-yl)methyl)-1H-pyrazole-4-carboxylate (55 mg, 0.18 mmol), (7-chloroimidazo[1,5-a]pyridin-1-yl)methanamine (38 mg, 0.21 mmol) and HATU (101 mg, 0.27 mmol) in DMF (15 mL) was added DIPEA (187 mg, 1.55 mmol). The resulting reaction was stirred at RT for 2 h. H$_2$O (30 mL) was added to the reaction and extracted with EtOAc (30 mL×3). The combined organic layers were washed with brine, dried over Na$_2$SO$_4$, concentrated in vacuo to give the crude, which was purified with prep-TLC (DCM/MeOH=10/1) to give the N-((7-chloroimidazo[1,5-a]pyridin-1-yl)methyl)-1-((7-(2,2-dimethylcyclopropyl)imidazo[1,2-a]pyridin-2-yl)methyl)-1H-pyrazole-4-carboxamide (12.3 mg, yield: 10%) as a white solid. ESI-MS [M+H]$^+$: 474.1. Purity: 94.0%. $^1$H NMR (400 MHz, MeOD): δ 8.27 (d, J=2.7 Hz, 2H), 8.20-8.15 (m, 2H), 7.93 (s, 1H), 7.85 (s, 1H), 7.74 (m, 1H), 7.52-7.47 (m, 2H), 6.68-6.60 (m, 1H), 5.52 (s, 2H), 4.69 (s, 2H), 1.95-1.88 (m, 1H), 1.26 (s, 3H), 0.89 (s, 1H), 0.88 (d, J=2.5 Hz, 1H), 0.83 (s, 3H).

Synthesis of 2-(2,2-dimethylcyclopropyl)-4,4,5,5-tetramethyl-1,3,2-dioxaborolane To a solution of 4,4,5,5-tetramethyl-2-(2-methylprop-1-en-1-yl)-1,3,2-dioxaborolane (100 mg, 0.55 mmol) in toluene (5 mL) was added CH$_2$I$_2$ (0.42 g, 1.54 mmol) dropwise at 0° C. The resulting reaction was stirred at 55° C. overnight. The reaction was filtered and washed with DCM (10 mL). The crude product was extracted with H$_2$O (10 mL), dried over Na$_2$SO$_4$, concentrated to give the 2-(2,2-dimethylcyclopropyl)-4,4,5,5-tetramethyl-1,3,2-dioxaborolane (200 mg crude) which was used in the next step without further purification. ESI-MS [M+H]$^+$: 197.1.

Example 42

Scheme 42

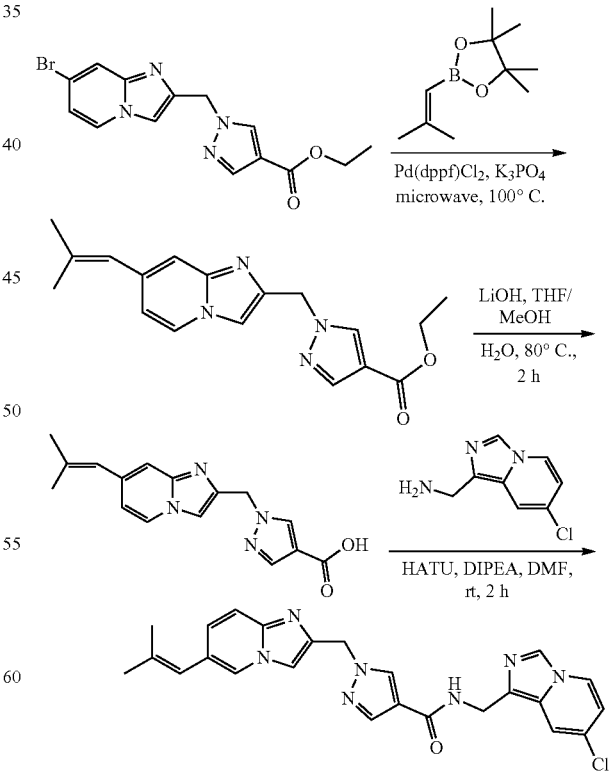

I-42

131

Synthesis of Ethyl 1-((7-(2-methylprop-1-en-1-yl) imidazo[1,2-a]pyridin-2-yl)methyl)-1H-pyrazole-4-carboxylate A solution of ethyl 1-((7-bromoimidazo[1,2-a]pyridin-2-yl)methyl)-1H-pyrazole-4-carboxylate (200 mg, 0.57 mmol), 4,4,5,5-tetramethyl-2-(2-methylprop-1-en-1-yl)-1,3,2-dioxaborolane (207 mg, 1.14 mmol), Pd(dppf)Cl$_2$ (42, 0.057 mg), and K$_3$PO$_4$ (364 mg, 1.72 mmol) in 1,4-dioxane (10 mL) and H$_2$O (1 mL) in a sealed tube was stirred at 100° C. under microwave for 3 h. The reaction was filtered through celite and washed with EtOAc. The filtrate was concentrated and purified by silica gel (PE/EA=1:2) to give the 1-((7-(2-methylprop-1-en-1-yl)imidazo[1,2-a]pyridin-2-yl)methyl)-1H-pyrazole-4-carboxylate (200 mg, 90%) as a brown solid. ESI-MS [M+H]$^+$: 325.1.

Synthesis of 1-((7-(2-methylprop-1-en-1-yl)imidazo[1,2-a]pyridin-2-yl)methyl)-1H-pyrazole-4-carboxylic Acid A mixture of 1-((7-(2-methylprop-1-en-1-yl)imidazo[1,2-a]pyridin-2-yl)methyl)-1H-pyrazole-4-carboxylate (60 mg, 0.18 mmol) and LiOH (27 mg, 1.2 mmol) in THF/EtOH/H$_2$O (3 mL/3 mL/2 mL) was stirred at 80° C. for 2 h. The pH value of reaction was adjusted to around 5 by adding 1 M HCl solution and a solid was precipitated. The solid was filtered and the filter cake was dried to give 1-((7-(2-methylprop-1-en-1-yl)imidazo[1,2-a]pyridin-2-yl)methyl)-1H-pyrazole-4-carboxylic acid (50 mg, yield: 89%) as a brown solid. ESI-MS [M+H]$^+$: 297.1.

Synthesis of N-((7-chloroimidazo[1,5-a]pyridin-1-yl)methyl)-1-((7-(2-methylprop-1-en-1-yl)imidazo[1,2-a]pyridin-2-yl)methyl)-1H-pyrazole-4-carboxamide (I-42)

To a solution of 1-((7-(2-methylprop-1-en-1-yl)imidazo[1,2-a]pyridin-2-yl)methyl)-1H-pyrazole-4-carboxylic acid (53 mg, 0.18 mmol), (7-chloroimidazo[1,5-a]pyridin-1-yl)methanamine (38 mg, 0.21 mmol) and HATU (101 mg, 0.27 mmol) in DMF (15 mL) was added DIPEA (200 mg, 1.55 mmol). The resulting reaction stirred at RT for 2 h. H$_2$O (30 mL) was added and the reaction mixture was extracted with EtOAc (30 mL×3). The combined organic layers were washed with brine, dried over Na$_2$SO$_4$, concentrated in vacuo to give the crude, which was purified by prep-TLC (DCM/MeOH=10/1) to give the N-((7-chloroimidazo[1,5-a]pyridin-1-yl)methyl)-1-((7-(2-methylprop-1-en-1-yl)imidazo[1,2-a]pyridin-2-yl)methyl)-1H-pyrazole-4-carboxamide (30 mg, yield: 36%) as a white solid. ESI-MS [M+H]$^+$: 460.1. Purity: 95.2%. $^1$H NMR (400 MHz, MeOD): δ 8.35 (s, 1H), 8.28 (s, 1H), 8.18-8.46 (m, 2H), 7.94 (s, 1H), 7.90 (s, 1H), 7.74 (s, 1H), 7.54 (d, J=9.3 Hz, 1H), 7.49-7.38 (m, 1H), 6.63 (dd, J=7.5, 1.9 Hz, 1H), 6.22 (s, 1H), 5.54 (s, 2H), 4.69 (s, 2H), 1.95 (s, 3H), 1.88 (s, 3H).

132

Example 43

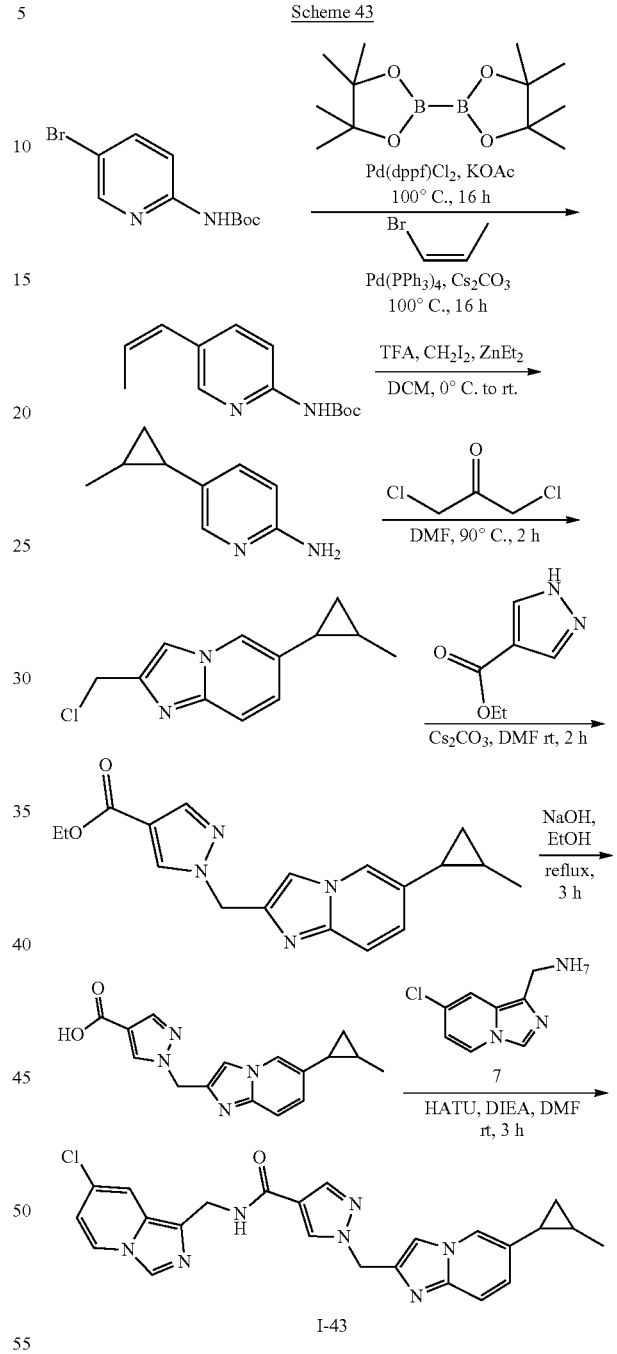

Scheme 43

Synthesis of tert-butyl (Z)-(5-(prop-1-en-1-yl)pyridin-2-yl)carbamate

To a mixture of tert-butyl (5-bromopyridin-2-yl)carbamate (2.73 g, 10 mmol), 4,4,4',4',5,5,5',5'-octamethyl-2,2'-bi(1,3,2-dioxaborolane) (3.81 g, 15 mmol) and KOAc (3.0 g, 30 mmol) in dioxane (30 mL) was added Pd(dppf)Cl$_2$ (881 mg, 1 mmol). The mixture was stirred at 100° C. for 16 h. After cooling, (Z)-1-bromoprop-1-ene (3.6 g, 30 mmol), Cs$_2$CO$_3$ (6.4 g, 20 mmol) and Pd(PPh$_3$)$_4$ (500 mg, 0.5 mmol)

were added. The mixture was stirred 100° C. for another 16 h. Water (100 mL) was added and the mixture was extracted with EtOAc (100 mL×3). The combined organic layers were concentrated and purified by silica gel chromatography (EA/PE=1/2) to give tert-butyl (Z)-(5-(prop-1-en-1-yl)pyridin-2-yl)carbamate (230 mg, yield: 10%) as a white solid. ESI-MS [M+H]$^+$: 235.1.

Synthesis of 5-(2-methylcyclopropyl)pyridin-2-amine

To a solution of ZnEt$_2$ (1 M, 10 mmL) in DCM (20 mL) was added TFA (1.14 g, 10 mmol), followed by CH$_2$I$_2$ (2.68 g, 10 mmol). After the resulting mixture was stirred at 0° C. for 10 min, tert-butyl (Z)-(5-(prop-1-en-1-yl)pyridin-2-yl)carbamate (230 mg, 1.0 mmol) was added. The mixture was stirred at RT for 3 h. Water (50 mL) was added and extracted with EtOAc (100 mL×3). The combined organic layers were concentrated and purified by prep-HPLC to give 5-(2-methylcyclopropyl)pyridin-2-amine (60 mg, yield: 12%) as a yellow oil. ESI-MS [M+H]$^+$: 149.1.

Synthesis of 2-(chloromethyl)-6-(2-methylcyclopropyl)imidazo[1,2-a]pyridine

To a solution of 5-(2-methylcyclopropyl)pyridin-2-amine (600 mg, 0.4 mmol) in DMF (5 mL) was added 1,3-dichloropropan-2-one (206 mg, 1.6 mmol). The mixture was stirred at 90° C. for 2 h. Water (50 mL) was added and extracted with EtOAc (50 mL×3). The combined organic layers were washed with brine, dried over Na$_2$SO$_4$, filtered and concentrated to give the crude, which was purified by silica gel chromatography (EA/PE=1/1) to give 2-(chloromethyl)-6-(2-methylcyclopropyl)imidazo[1,2-a]pyridine (40 mg, yield: 79%) as a yellow oil. ESI-MS [M+H]$^+$: 221.1.

Synthesis of Ethyl 1-((6-(2-methylcyclopropyl)imidazo[1,2-a]pyridin-2-yl)methyl)-1H-pyrazole-4-carboxylate To a solution of 2-(chloromethyl)-6-(2-methylcyclopropyl)imidazo[1,2-a]pyridine (40 mg, 0.18 mmol) and ethyl 1H-pyrazole-4-carboxylate (30 mg, 0.22 mmol) in DMF (3 mL) was added CsCO$_3$ (118 mg, 0.36 mmol) at RT. The mixture was stirred at RT for 2 h. The reaction was diluted with H$_2$O (30 mL) and extracted with ethyl acetate (3×50 mL). The combined organic layers were washed with brine, dried over sodium sulfate, concentrated and purified by prep-TLC (MeOH/DCM=1/10) to give ethyl 1-((6-(2-methylcyclopropyl)imidazo[1,2-a]pyridin-2-yl)methyl)-1H-pyrazole-4-carboxylate (30 mg, yield: 50%) as a yellow oil. ESI-MS [M+H]$^+$: 325.1.

Synthesis of 1-((6-(2-methylcyclopropyl)imidazo[1,2-a]pyridin-2-yl)methyl)-1H-pyrazole-4-carboxylic Acid To a solution of ethyl 1-((6-((1S,2R)-2-methylcyclopropyl)imidazo[1,2-a]pyridin-2-yl)methyl)-1H-pyrazole-4-carboxylate (30 mg, 0.1 mmol) in a mixed solvent of THF/EtOH/H$_2$O (2 mL/2 mL/1 mL) was added NaOH (4 M, 0.1 mL, 0.4 mmol). The mixture was stirred at refluxed for 3 h. Most of the solvent was removed and the residue was diluted with H$_2$O (3 mL) and the pH value of mixture was adjusted to 4-5 by adding HCl aqueous (1 M). The mixture was freeze-dried to give 1-((6-(2-methylcyclopropyl)imidazo[1,2-a]pyridin-2-yl)methyl)-1H-pyrazole-4-carboxylic acid (crude, 40 mg) as a yellow solid which was used in the next step without purification. ESI-MS [M+H]$^+$: 297.1.

Synthesis of N-((7-chloroimidazo[1,5-a]pyridin-1-yl)methyl)-1-((6-(2-methylcyclopropyl)imidazo[1,2-a]pyridin-2-yl)methyl)-1H-pyrazole-4-carboxamide (I-43)

To a solution of 1-((6-(2-methylcyclopropyl)imidazo[1,2-a]pyridin-2-yl)methyl)-1H-pyrazole-4-carboxylic acid (40 mg, crude from last step) and (7-chloroimidazo[1,5-a]pyridin-1-yl)methanamine hydrochloride (44 mg, 0.2 mmol) in dry DMF (1 mL) was added HATU (106 mg, 0.28 mmol) and DIPEA (90 mg, 0.7 mmol) at RT. The reaction was stirred at RT for 3 h. Water (20 mL) was added and the mixture was extracted with EtOAc (30 mL×3). The combined organic layers were washed with brine (5 mL), dried over sodium sulfate, concentrated and purified by prep-TLC (DCM/MeOH=10/1) to give N-((7-chloroimidazo[1,5-a]pyridin-1-yl)methyl)-1-((6-(2-methylcyclopropyl)imidazo[1,2-a]pyridin-2-yl)methyl)-1H-pyrazole-3-carboxamide (25 mg, yield: 54% for two steps) as a yellow solid. ESI-MS [M+H]$^+$: 460.1. Purity: 91%. $^1$H NMR (400 MHz, DMSO): δ 8.58 (t, J=5.3 Hz, 1H), 8.31-8.29 (m, 3H), 8.23 (s, 1H), 7.86 (s, 1H), 7.78 (s, 1H), 7.73 (s, 1H), 7.40 (d, J=9.0 Hz, 1H), 7.14 (d, J=8.9 Hz, 1H), 6.64 (dd, J=7.5, 1.9 Hz, 1H), 5.39 (s, 2H), 4.55 (d, J=5.7 Hz, 2H), 2.02 (dd, J=14.3, 8.6 Hz, 1H), 1.18-1.07 (m, 1H), 1.04-0.88 (m, 1H), 0.75 (d, J=6.2 Hz, 3H), 0.60 (dd, J=10.5, 5.2 Hz, 1H).

Example 44

Scheme 44

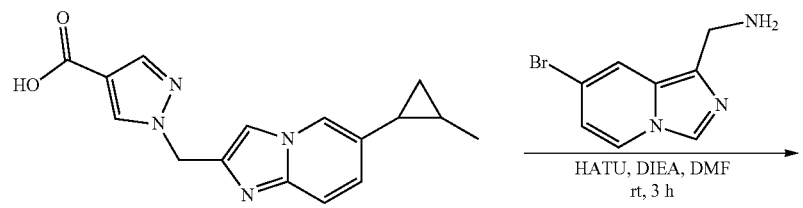

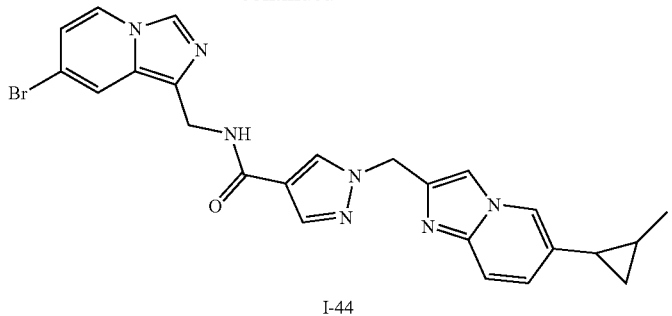

I-44

Synthesis of N-((7-bromoimidazo[1,5-a]pyridin-1-yl)methyl)-1-((6-(2-methylcyclopropyl)imidazo[1,2-a]pyridin-2-yl)methyl)-1H-pyrazole-4-carboxamide (I-44)

To a solution of 1-((6-(2-methylcyclopropyl)imidazo[1,2-a]pyridin-2-yl)methyl)-1H-pyrazole-4-carboxylic acid (40 mg, 0.1 mmol) and (7-bromoimidazo[1,5-a]pyridin-1-yl)methanamine hydrochloride (52 mg, 0.2 mmol) in dry DMF (3 mL) was added HATU (106 mg, 0.28 mmol) and DIPEA (90 mg, 0.7 mmol) at RT. The reaction was stirred at RT for 3 h. Water (20 mL) was added and the mixture was extracted with EtOAc (30 mL×3). The combined organic layers were washed with brine (50 mL), dried over sodium sulfate, concentrated and purified by prep-TLC (DCM/MeOH=10/1) to give N-((7-bromoimidazo[1,5-a]pyridin-1-yl)methyl)-1-((6-(2-methylcyclopropyl)imidazo[1,2-a]pyridin-2-yl)methyl)-1H-pyrazole-4-carboxamide (25.5 mg, yield: 37%) as a yellow solid. ESI-MS [M+H]$^+$: 504.1. Purity: 91.53%. $^1$H NMR (400 MHz, DMSO): δ 8.59 (t, J=5.7 Hz, 1H), 8.31 (s, 2H), 8.26-8.19 (m, 2H), 8.00-7.92 (m, 1H), 7.86 (s, 1H), 7.73 (s, 1H), 7.40 (d, J=9.3 Hz, 1H), 7.15 (dd, J=9.3, 1.6 Hz, 1H), 6.72 (dd, J=7.4, 1.9 Hz, 1H), 5.39 (s, 2H), 4.55 (d, J=5.7 Hz, 2H), 2.02 (dd, J=14.4, 8.4 Hz, 1H), 1.18-1.11 (m, 1H), 0.99-0.93 (m, 1H), 0.75 (d, J=6.2 Hz, 3H), 0.60 (dd, J=10.7, 5.5 Hz, 1H).

Example 45

Synthesis of 1-((6-cyclopropylimidazo[1,2-a]pyridin-2-yl)methyl)-N-((7-iodoimidazo[1,5-a]pyridin-1-yl)methyl)-1H-pyrazole-4-carboxamide (I-45)

To a solution of 1-((6-cyclopropylimidazo[1,2-a]pyridin-2-yl)methyl)-1H-pyrazole-4-carboxylic acid (60 mg, 0.21 mmol), (7-iodoimidazo[1,5-a]pyridin-1-yl)methanamine hydrochloride (99 mg, 0.32 mmol) and HATU (120 mg, 0.31 mmol) in DMF (5 mL) was added DIPEA (81 mg, 0.63 mmol). The resulting reaction was stirred at RT for 12 h. H$_2$O (25 mL) was added to the reaction, extracted with EtOAc (50 mL×3). The combined organic layers were washed with brine, dried over Na$_2$SO$_4$ and concentrated in vacuo to give the crude, which was purified with prep-TLC (DCM/MeOH=10/1) to give the 1-((6-cyclopropyl[1,2-a]pyridin-2-yl)methyl)-N-((7-iodoimidazo[1,5-a]pyridin-1-yl)methyl)-1H-pyrazole-4-carboxamide (20 mg, yield: 18%) as a white solid. ESI-MS [M+H]$^+$: 538.0. Purity: 97.4%. $^1$H NMR (400 MHz, DMSO): δ 8.56 (t, J=5.7 Hz, 1H), 8.32 (s, 1H), 8.29 (s, 1H), 8.20 (s, 1H), 8.13 (s, 1H), 8.12-8.08 (m, 1H), 7.85 (s, 1H), 7.71 (s, 1H), 7.39 (d, J=9.3 Hz, 1H), 6.99 (dd, J=9.3, 1.7 Hz, 1H), 6.78 (dd, J=7.3, 1.6 Hz, 1H), 5.39 (s, 2H), 4.54 (d, J=5.7 Hz, 2H), 1.94-1.88 (m, 1H), 0.96-0.85 (m, 2H), 0.71-0.58 (m, 2H).

Scheme 45

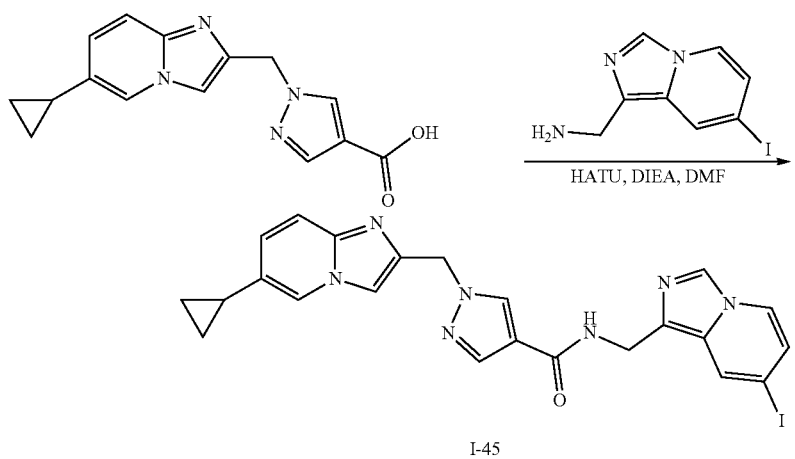

I-45

Example 46

Scheme 46

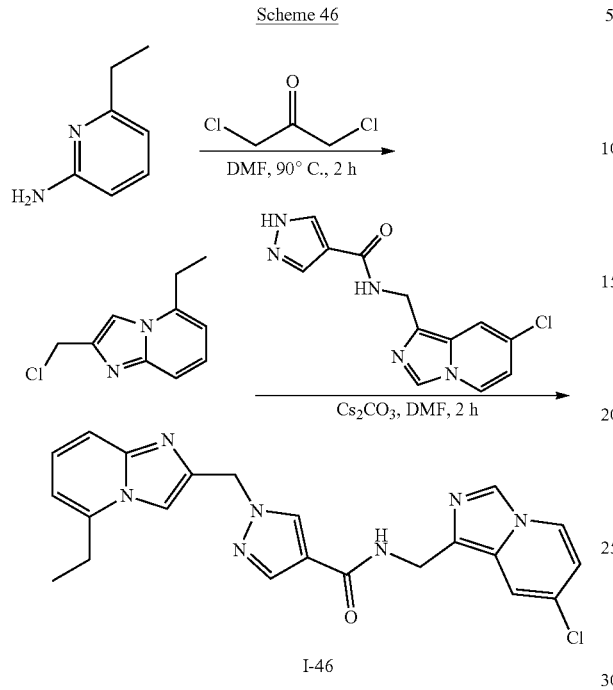

I-46

Synthesis of 2-(chloromethyl)-5-ethylimidazo[1,2-a]pyridine

A solution of 6-ethylpyridin-2-amine (1 g, 8.2 mmol) and 1, 3-dichloropropan-2-one (4.7 g, 36.9 mmol) in DMF (10 mL) was stirred at 90° C. for 3 h. Then the reaction mixture was diluted with $H_2O$ (100 mL) and extracted with EtOAc (100 mL×3). The combined organic layers were dried over $Na_2SO_4$, concentrated and purified by column chromatography ($CH_2Cl_2$:MeOH=20:1) to give the desired product 2-(chloromethyl)-5-ethylimidazo[1,2-a]pyridine (450 mg, yield: 28%) as a white solid. ESI-MS [M+H]$^+$: 195.1.

Synthesis of N-((7-chloroimidazo[1,5-a]pyridin-1-yl)methyl)-1-((5-ethylimidazo[1,2-a]pyridin-2-yl)methyl)-1H-pyrazole-4-carboxamide (I-46)

A solution of 2-(chloromethyl)-5-ethylimidazo[1,2-a]pyridine (60 mg, 0.31 mmol), N-((7-chloroimidazo[1,5-a]pyridin-1-yl)methyl)-1H-pyrazole-4-carboxamide and $Cs_2CO_3$ (303 mg, 0.93 mmol) in DMF (3 mL) was stirred at RT for 2 h. Then the reaction mixture was diluted with $H_2O$ (50 mL) and extracted with EtOAc (50 mL×3). The combined organic layers were dried over $Na_2SO_4$, concentrated and purified by column chromatography ($CH_2Cl_2$/MeOH=20/1) to give the desired compound N-((7-chloroimidazo[1,5-a]pyridin-1-yl)methyl)-1-((5-ethylimidazo[1,2-a]pyridin-2-yl)methyl)-1H-pyrazole-4-carboxamide (16 mg, yield: 12%) as a white solid. ESI-MS [M+H]$^+$: 434.1. Purity: 98.90%. $^1$H NMR (400 MHz, DMSO): δ 8.58 (t, J=5.8 Hz, 2H), 8.33-8.27 (m, 2H), 8.23 (s, 1H), 7.86 (d, J=6.8 Hz, 2H), 7.80-7.75 (m, 1H), 7.42 (d, J=9.0 Hz, 1H), 7.29-7.21 (m, 1H), 6.78-6.73 (m, 1H), 6.67-6.61 (m, 1H), 5.42 (s, 2H), 4.55 (d, J=5.8 Hz, 2H), 2.95-2.86 (m, 2H), 1.36-1.27 (m, 3H).

Example 47

Scheme 47

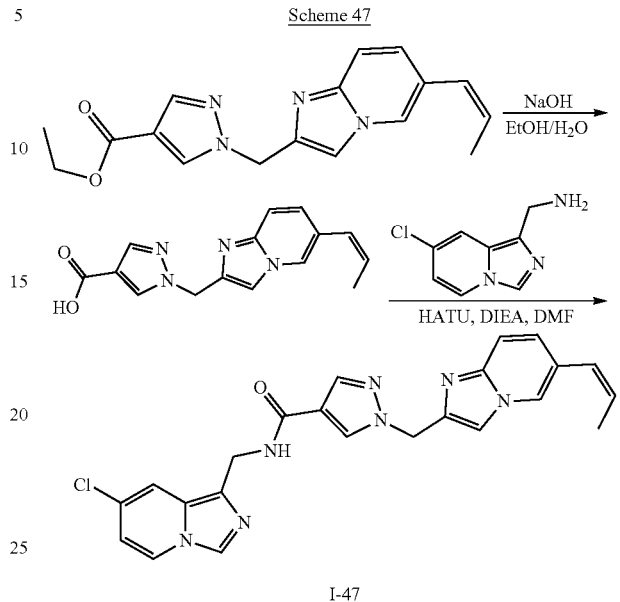

I-47

Synthesis of (Z)-1-((6-(prop-1-en-1-yl)imidazo[1,2-a]pyridin-2-yl)methyl)-1H-pyrazole-4-carboxylic Acid A mixture of ethyl (Z)-1-((6-(prop-1-en-1-yl)imidazo[1,2-a]pyridin-2-yl)methyl)-1H-pyrazole-4-carboxylate (150 mg, 0.48 mmol) and NaOH (40 mg, 1.6 mmol) in EtOH/H2O (2 mL/1 mL) was stirred at 50° C. for 3 h. The reaction was monitored by LCMS until the starting material consumed. The pH value of mixture was adjusted to 2-3 by adding 1 M aqueous HCl solution and extracted with EtOAc (50 mL×3). The combined organic layers were concentrated to give (Z)-1-((6-(prop-1-en-1-yl)imidazo[1,2-a]pyridin-2-yl)methyl)-1H-pyrazole-4-carboxylic acid (65 mg, 48% yield) as a white solid. ESI-MS [M+H]$^+$: 283.0.

Synthesis of (Z)—N-((7-chloroimidazo[1,5-a]pyridin-1-yl)methyl)-1-((6-(prop-1-en-1-yl)imidazo[1,2-a]pyridin-2-yl)methyl)-1H-pyrazole-4-carboxamide (I-47)

A mixture of 1-((6-methylimidazo[1,2-a]pyridin-2-yl)methyl)-1H-pyrazole-4-carboxylic acid (65 mg, 0.23 mmol) in DMF (3 mL) was added (5-chloro-2H-indazol-3-yl)methanamine hydrochloride (100 mg, 0.46 mmol), DIPEA (150 mg, 1.15 mmol) and HATU (133 mg, 0.35 mmol). The resulting mixture was stirred at RT for 3 h. The reaction was quenched with $H_2O$ (30 mL) and extracted with EtOAc (30 mL×3). The combined organic layers were washed with brine, dried over $Na_2SO_4$, concentrated in vacuo to give the crude, which was purified with prep-TLC (EA/PE=1/5) to give the (Z)—N-((7-chloroimidazo[1,5-a]pyridin-1-yl)methyl)-1-((6-(prop-1-en-1-yl)imidazo[1,2-a]pyridin-2-yl)methyl)-1H-pyrazole-4-carboxamide (9.3 mg, yield: 6.2%) as a white solid. ESI-MS [M+H]$^+$: 446.1. Purity: 95.3%. $^1$H NMR (400 MHz, DMSO): δ 8.60 (t, J=5.6 Hz, 1H), 8.50 (s, 1H), 8.38-8.26 (m, 2H), 8.24 (s, 1H), 7.87 (s, 1H), 7.80 (d, J=14.2 Hz, 2H), 7.48 (d, J=9.3 Hz, 1H), 7.22 (d, J=9.3 Hz, 1H), 6.65 (dd, J=7.4, 2.0 Hz, 1H), 6.35 (d, J=11.5 Hz, 1H), 5.84 (td, J=14.4, 7.1 Hz, 1H), 5.42 (s, 2H), 4.56 (d, J=5.7 Hz, 2H), 1.87 (dd, J=7.2, 1.6 Hz, 3H).

Example 48

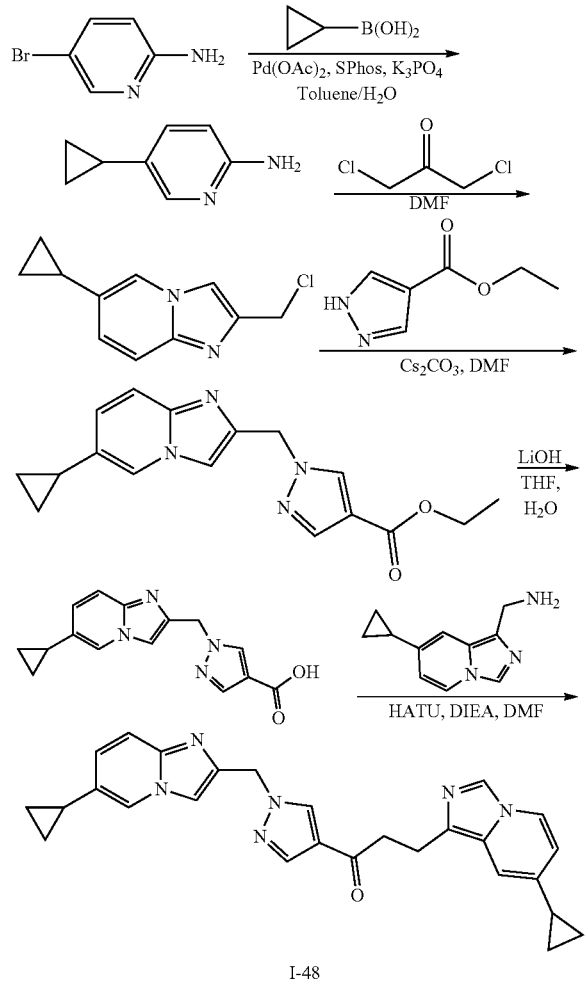

I-48

Synthesis of 5-cyclopropylpyridin-2-amine

A solution of 5-bromopyridin-2-amine (5 g, 29.1 mmol), cyclopropylboronic acid (3.75 g, 43.6 mmol), Pd(OAc)$_2$ (651 mg, 2.91 mmol), SPhos (1.19 g, 2.91 mmol) and K$_3$PO$_4$ (18.5 g, 87.3 mmol) in toluene/H$_2$O (100 mL/10 mL) was stirred at 95° C. for 12 h under nitrogen. Then the reaction mixture was quenched with H$_2$O (50 mL) and extracted with DCM (200 mL). The combined organic layers were dried over Na$_2$SO$_4$ and concentrated in vacuo to give the crude residue which was purified by silica gel chromatography (PE/EtOAc=1/1) to give the 5-cyclopropylpyridin-2-amine as yellow solid (3.8 g, 97.4% yield). ESI-MS [M+H]$^+$: 135.2.

Synthesis of 2-(chloromethyl)-6-cyclopropylimidazo [1,2-a]pyridine

To a solution 5-cyclopropyl-4-methylpyridin-2-amine (500 mg, 3.70 mmol) in DMF (10 mL) was added 1,3-dichloropropan-2-one (1409 mg, 11.1 mmol) at RT. The resulting reaction was stirred at 85° C. for 2 h. The solution was quenched with H$_2$O (60 mL), adjusted to pH 8 by adding saturated NaHCO$_3$ solution, and extracted with EtOAc (50 mL×3). The combined organic layers were washed with brine, dried over Na$_2$SO$_4$, and concentrated in vacuo to give the crude, which was purified with prep-TLC (PE/EtOAc=1/1) to give the 2-(chloromethyl)-6-cyclopropyl-7-methylimidazo[1,2-a]pyridine (300 mg, yield: 39%) as a light yellow oil. ESI-MS [M+H]$^+$: 207.2.

Synthesis of Ethyl 1-((6-cyclopropylimidazo[1,2-a] pyridin-2-yl)methyl)-1H-pyrazole-4-carboxylate To a solution 2-(chloromethyl)-6-cyclopropylimidazo[1, 2-a]pyridine (2 g, 9.70 mmol) in DMF (20 mL) was added ethyl 1H-pyrazole-4-carboxylate (906 mg, 6.46 mmol) and Cs$_2$CO$_3$ (6.32 g, 19.38 mmol) at RT. The resulting reaction was stirred at RT for 12 h. H$_2$O (150 mL) was added to the reaction and then the mixture was extracted with EtOAc (100 mL×3). The combined organic layers were washed with brine, dried over Na$_2$SO$_4$, concentrated in vacuo to give the crude, which was purified with silica gel chromatography (DCM/MeOH=20/1) to give the ethyl 1-((6-cyclopropylimidazo[1,2-a]pyridin-2-yl)methyl)-1H-pyrazole-4-carboxylate (1.5 g, yield: 75%) as a white solid. ESI-MS [M+H]$^+$: 311.2.

Synthesis of 1-((6-cyclopropylimidazo[1,2-a]pyridin-2-yl)methyl)-1H-pyrazole-4-carboxylic Acid To a solution of ethyl 1-((6-cyclopropylimidazo[1,2-a] pyridin-2-yl) methyl)-1H-pyrazole-4-carboxylate (1.2 g, 3.87 mmol) in THF (20 mL) and H$_2$O (10 mL) was added LiOH (464 mg, 19.35 mmol). The mixture was stirred at RT for 16 h. Most of the THF was removed and the pH was adjusted to 4-5 by adding HCl (1 M). The resulting precipitate was collected and dried to give the 1-((6-cyclopropylimidazo [1,2-a]pyridin-2-yl)methyl)-1H-pyrazole-4-carboxylic acid as a white solid (1.0 g, yield: 91%). ESI-MS [M+H]$^+$: 283.2.

Synthesis of 1-((6-cyclopropylimidazo[1,2-a]pyridin-2-yl)methyl)-N-((7-cyclopropylimidazo[1,5-a] pyridin-1-yl)methyl)-1H-pyrazole-4-carboxamide (I-48)

To a solution of 1-((6-cyclopropylimidazo[1,2-a]pyridin-2-yl)methyl)-1H-pyrazole-4-carboxylic acid (60 mg, 0.21 mmol), (7-cyclopropylimidazo[1,5-a]pyridin-1-yl)methanamine (59 mg, 0.32 mmol) and HATU (120 mg, 0.31 mmol) in DMF (5 mL) was added DIPEA (81 mg, 0.63 mmol). The resulting reaction was stirred at RT for 12 h. H$_2$O (30 mL) was added to the reaction, extracted with EtOAc (50 mL×3). The combined organic layers were washed with brine, dried over Na$_2$SO$_4$ and concentrated in vacuo to give the crude, which was purified with prep-TLC (DCM/MeOH=10/1) to give the 1-((6-cyclopropylimidazo [1,2-a]pyridin-2-yl)methyl)-N-((7-cyclopropylimidazo[1,5-a]pyridin-1-yl)methyl)-1H-pyrazole-4-carboxamide (20 mg, yield: 21%) as a white solid. ESI-MS [M+H]$^+$: 452.2. Purity: 99.8%. $^1$H NMR (400 MHz, DMSO): δ 8.47 (t, J=5.6 Hz, 1H), 8.32 (s, 1H), 8.21 (s, 1H), 8.16-8.14 (m, 2H), 7.86 (s, 1H), 7.71 (s, 1H), 7.40-7.38 (m, 1H), 7.32 (s, 1H), 7.00-6.97 (m, 1H), 6.32-6.30 (m, 1H), 5.38 (s, 2H), 4.55 (d, J=5.6 Hz, 2H), 1.95-1.78 (m, 2H), 0.95-0.83 (m, 4H), 0.70-0.60 (m, 4H).

Example 49

Scheme 49

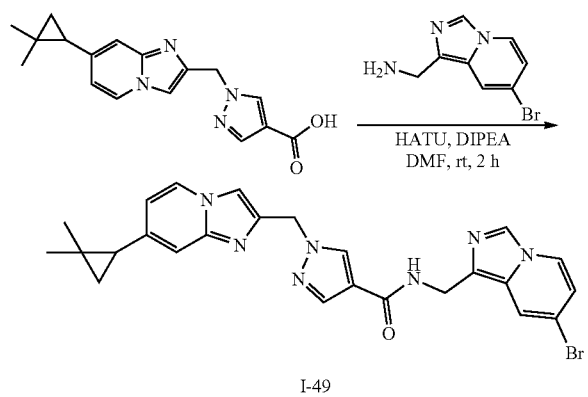

Synthesis of N-((7-bromoimidazo[1,5-a]pyridin-1-yl)methyl)-1-((7-(2,2-dimethylcyclopropyl)imidazo[1,2-a]pyridin-2-yl)methyl)-1H-pyrazole-4-carboxamide (I-49)

To a solution of 1-((7-(2,2-dimethylcyclopropyl)imidazo[1,2-a]pyridin-2-yl)methyl)-1H-pyrazole-4-carboxylate (56 mg, 0.18 mmol), (7-bromoimidazo[1,5-a]pyridin-1-yl)methanamine hydrochloride (55 mg, 0.21 mmol) and HATU (102 mg, 0.27 mmol) in DMF (10 mL) was added DIPEA (199 mg, 1.55 mmol). The resulting reaction stirred at RT for 2 h. H$_2$O (30 mL) was added to the reaction and extracted with EtOAc (30 mL×3). The combined organic layers were washed with brine, dried over Na$_2$SO$_4$ and concentrated in vacuo to give the crude, which was purified with prep-TLC (DCM/MeOH=10/1) to give the N-((7-bromoimidazo[1,5-a]pyridin-1-yl)methyl)-1-((7-(2,2-dimethylcyclopropyl)imidazo[1,2-a]pyridin-2-yl)methyl)-1H-pyrazole-4-carboxamide (17.5 mg, yield: 18.8%) as a white solid. ESI-MS [M+H]$^+$: 518.1. Purity: 91.25%. H NMR (400 MHz, MeOD): δ 8.85 (s, 1H), 8.53 (s, 1H), 8.30 (s, 1H), 8.24 (d, J=7.5 Hz, 1H), 8.11 (s, 2H), 7.98 (s, 1H), 7.87 (dd, J=9.3, 1.4 Hz, 1H), 7.75 (d, J=9.3 Hz, 1H), 6.98 (dd, J=7.5, 1.4 Hz, 1H), 5.68 (s, 2H), 4.77 (s, 2H), 2.03-1.98 (m, 1H), 1.29 (s, 3H), 1.00-0.93 (m, 2H), 0.85 (s, 3H).

Example 50

Scheme 50

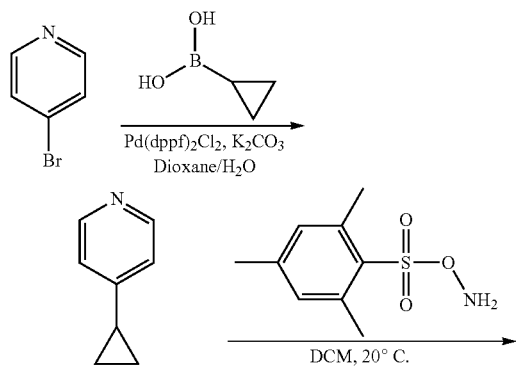

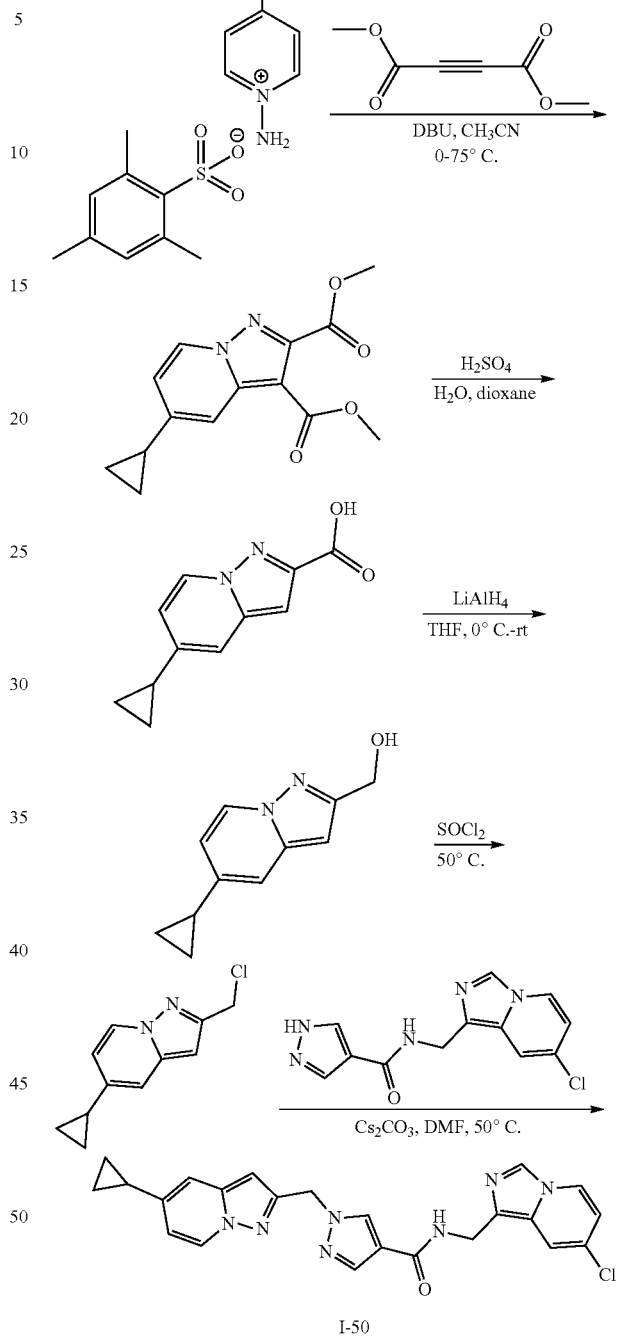

Synthesis of 4-cyclopropylpyridine

A mixture of 4-bromopyridine (5 g, 25.71 mmol), cyclopropylboronic acid (2.5 g, 28.28 mmol), K$_2$CO$_3$ (10.6 g, 77.13 mmol) and Pd(dppf)$_2$Cl$_2$ (2.1 g, 2.57 mmol) in dioxane (80 mL) and H$_2$O (16 mL) was refluxed under N$_2$ for 16 h. The reaction mixture was filtered through celite and washed with EtOAc (20 mL). The solvent was evaporated, the residue was diluted with H$_2$O (30 mL) and extracted with EtOAc (50 mL×3). The combined organic layers were dried over Na₂SO₄, filtered and concentrated to give a yellow oil, which was purified by silica gel chromatography to give 4-cyclopropylpyridine (2.774 g, yield: 91.5%) as a yellow oil. ESI-MS [M+H]⁺: 120.1.

Synthesis of 1-amino-4-cyclopropylpyridin-1-ium 2,4,6-trimethylbenzenesulfonate

To a solution of 4-cyclopropylpyridine (1.5 g, 12.61 mmol) in DCM (5 mL) was added O-(mesitylsulfonyl) hydroxylamine (2.7 g, 12.61 mmol) at 0° C., then the reaction mixture was stirred at RT for 2 h. The reaction mixture was concentrated to give the 1-amino-4-cyclopropylpyridin-1-ium 2,4,6-trimethylbenzenesulfonate (4.2 g, yield: 100%) as a yellow oil, which was used in the next step without further purification. ESI-MS [M+H]⁺: 135.1.

Synthesis of dimethyl 5-cyclopropylpyrazolo[1,5-a]pyridine-2,3-dicarboxylate

To a solution of 1-amino-4-cyclopropylpyridin-1-ium 2,6-dimethylbenzenesulfonate (4.2 g, 12.6 mmol) and dimethyl but-2-ynedioate (3.6 g, 25.22 mmol) in CH₃CN (60 mL) was added DBU (3.8 g, 25.22 mmol) at 0° C. for 30 min. Then the resulting mixture was stirred at RT for 16 h. The reaction mixture was concentrated to give the crude, which was purified with silica gel chromatography (PE/EA=2/1) to give dimethyl 5-cyclopropylpyrazolo[1,5-a]pyridine-2, 3-dicarboxylate (2.5 g, yield: 72.4%) as a yellow oil. ESI-MS [M+H]⁺: 275.1.

Synthesis of 5-cyclopropylpyrazolo[1,5-a]pyridine-2-carboxylic Acid

A mixture of dimethyl 5-cyclopropylpyrazolo [1, 5-a]pyridine-2, 3-dicarboxylate (1.5 g, 5.47 mmol) and 50% H₂SO₄ in dioxane (8 mL) was heated at 85° C. for 5 h. Water (20 mL) was added and the mixture was extracted with EtOAc (50 mL×3). The combined organic layers were washed with brine, dried over Na₂SO₄ and concentrated in vacuo to give the crude, which was purified by silica gel chromatography (PE/EA=1/1) to give 5-cyclopropylpyrazolo [1,5-a]pyridine-2-carboxylic acid (600 mg, yield: 54.0%) as a white solid. ESI-MS [M+H]⁺: 203.1.

Synthesis of (5-cyclopropylpyrazolo[1,5-a]pyridin-2-yl)methanol

To a solution of 5-cyclopropylpyrazolo[1,5-a]pyridine-2-carboxylic acid (202 mg, 1.0 mmol) in THF (10 mL) was added LiAH₄ (1.5 mL, 1 M) at 0° C., the reaction mixture was stirred at 0° C. for 30 min. then warmed to RT and stirred for 4 h. The reaction was quenched by H₂O (10 mL) resulting in a precipitate. The filtrate was concentrated to give (5-cyclopropylpyrazolo[1,5-a]pyridin-2-yl)methanol (140 mg, yield: 74.5%) as a yellow oil which was used in the next step without further purification. ESI-MS [M+H]⁺: 189.1.

Synthesis of 2-(chloromethyl)-5-cyclopropylpyrazolo[1,5-a]pyridine

A mixture of (5-cyclopropylpyrazolo [1,5-a]pyridin-2-yl)methanol (140 mg, 0.74 mmol) and SOCl₂ (3 mL) was stirred at 50° C. for 1 h. The reaction mixture was concentrated to give the crude product 2-(chloromethyl)-5-cyclo-propylpyrazolo[1,5-a]pyridine (200 mg, crude) as a black oil which was used in the next step without purification. ESI-MS [M+H]⁺: 207.1.

Synthesis of N-((7-chloroimidazo[1,5-a]pyridin-1-yl)methyl)-1-((5-cyclopropylpyrazolo[1,5-a]pyridin-2-yl)methyl)-1H-pyrazole-4-carboxamide (I-50)

A mixture of 2-(chloromethyl)-5-cyclopropylpyrazolo[1,5-a]pyridine (30 mg, 0.15 mmol), N-((7-chloroimidazo [1,5-a] pyridin-1-yl) methyl)-1H-pyrazole-4-carboxamide (42 mg, 0.15 mmol), Cs₂CO₃ (200 mg, 0.61 mmol) in DMF (3 mL) was stirred at 50° C. for 16 h. Water (30 mL) was added and extracted with EtOAc (30 mL×3). The combined organic layers were washed with brine, dried over Na₂SO₄, filtered, concentrated and purified by prep-HPLC to obtained product as a white solid (2.2 mg, yield: 3.3%). ESI-MS [M+H]⁺: 446.7. Purity: 100%. ¹H NMR (400 MHz, DMSO): δ 8.62-8.50 (m, 2H), 8.47 (d, J=8.0 Hz, 1H), 8.32 (s, 2H), 8.30 (s, 1H), 8.23 (s, 1H), 7.87 (s, 1H), 7.78 (s, 1H), 7.32 (s, 1H), 6.65 (d, J=8.0 Hz, 1H), 6.57 (dd, J=8.0, 2.0 Hz, 1H), 6.27 (s, 1H), 5.45 (s, 2H), 4.55 (d, J=4.0 Hz, 2H), 1.99-1.93 (m, 1H), 1.02-0.95 (m, 2H), 0.78-0.70 (m, 2H).

Scheme 51

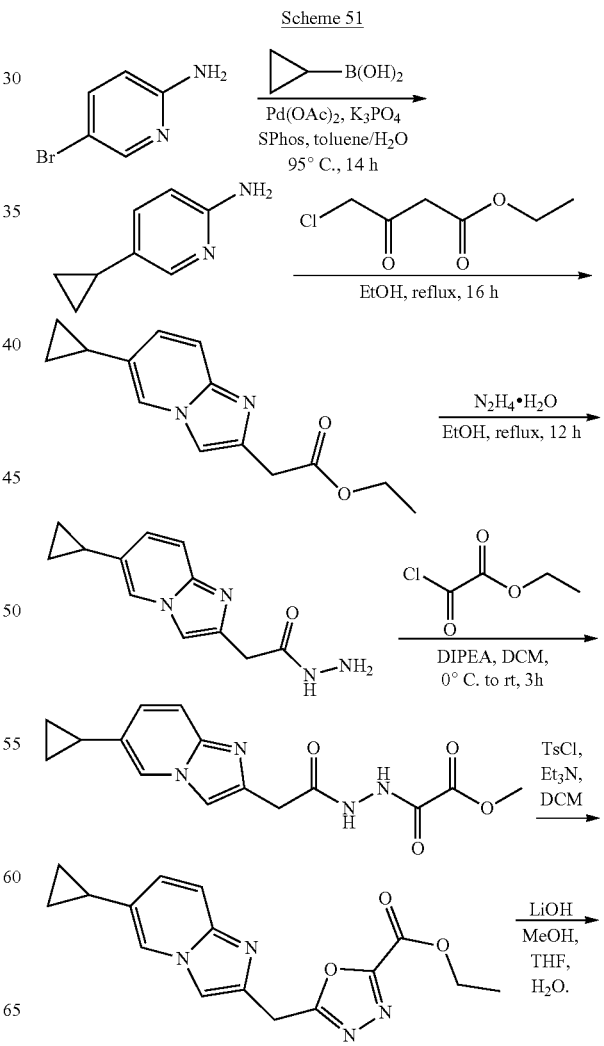

-continued

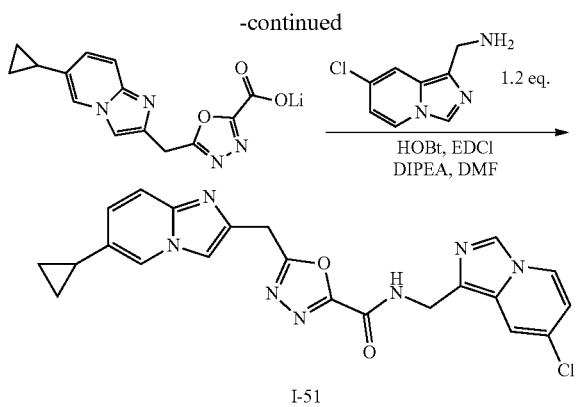

I-51

Synthesis of 5-cyclopropylpyridin-2-amine

To a solution of 5-bromopyridin-2-amine (50 g, 290 mmol) in toluene/H$_2$O (700 mL/70 mL) was added cyclopropylboronic acid (37.4 g, 435 mmol), Pd(OAc)$_2$ (6.49 g, 29.0 mmol), SPhos (12.8 g, 29.0 mmol) and K$_3$PO$_4$ (184.4 g, 870 mmol). The reaction mixture was stirred at 95° C. for 14 h under nitrogen. Then the mixture was concentrated in vacuo. Water (400 mL) was added and the mixture was extracted with DCM (500 mL×2). The combined organic layers were concentrated to give the crude product, which was purified by silica gel chromatography (PE/EtOAc=1/1) to give the 5-cyclopropylpyridin-2-amine as a yellow solid (38 g, yield: 97%). ESI-MS [M+H]$^+$: 135.2.

Synthesis of Ethyl 2-(6-cyclopropylimidazo[1,2-a]pyridin-2-yl)acetate

To a solution 5-cyclopropyl-4-methylpyridin-2-amine (30 g, 223.9 mmol) in EtOH (400 mL) was added ethyl 4-chloro-3-oxobutanoate (110 g, 671.7 mmol) at RT. The resulting mixture was stirred at 90° C. for 16 h and then concentrated in vacuo. H$_2$O (500 mL) was added, the pH value of the mixture was adjusted to 8 by adding saturated NaHCO$_3$ solution, and then the mixture was extracted with EtOAc (400 mL×3). The combined organic layers were washed with brine, dried over Na$_2$SO$_4$, and concentrated to give the crude product, which was purified by silica gel chromatography (DCM/MeOH=10/1) to give ethyl 2-(6-cyclopropylimidazo[1,2-a]pyridin-2-yl)acetate (40 g, impure) as a black solid. ESI-MS [M+H]$^+$: 245.2.

Synthesis of 2-(6-cyclopropylimidazo[1,2-a]pyridin-2-yl)acetohydrazide

A mixture of ethyl 2-(6-cyclopropylimidazo[1,2-a]pyridin-2-yl)acetate (40 g, impure) and N$_2$H$_4$—H$_2$O (50 mL) in EtOH (300 mL) was stirred at 85° C. for 12 h. The mixture was then concentrated and purified by silica gel chromatography (DCM/MeOH=10/1) to give 2-(6-cyclopropylimidazo[1,2-a]pyridin-2-yl)acetohydrazide (17.1 g, yield: 31.5% in 2 steps) as a yellow solid. ESI-MS [M+H]$^+$: 231.1.

Synthesis of Ethyl 2-(2-(2-(6-cyclopropylimidazo[1,2-a]pyridin-2-yl)acetyl)hydrazinyl)-2-oxoacetate To a solution of 2-(6-cyclopropylimidazo[1,2-a]pyridin-2-yl)acetohydrazide (17 g, 73.9 mmol) and DIPEA (38 mL, 222 mmol) in DCM (300 mL) was added ethyl 2-chloro-2-oxoacetate (15 g, 111 mmol) slowly at 0° C. The reaction mixture was stirred at RT for 2 h. Water (200 mL) was added and the mixture was extracted with DCM (200 mL×2). The combined organic layers were concentrated to give the crude product, which was purified by silica gel chromatography (DCM/MeOH=10/1) to give (ethyl 2-(2-(2-(6-cyclopropylimidazo[1,2-a] pyridin-2-yl)acetyl)hydrazinyl)-2-oxoacetate (17 g, yield: 70%) as a yellow solid. ESI-MS [M+H]$^+$: 331.1.

Synthesis of Ethyl 5-((6-cyclopropylimidazo[1,2-a]pyridin-2-yl)methyl)-1,3,4-oxadiazole-2-carboxylate To a solution of ethyl 2-(2-(2-(6-cyclopropylimidazo[1,2-a]pyridin-2-yl)acetyl) hydrazinyl)-2-oxoacetate (17 g, 51.5 mmol) and Et$_3$N (14 mL, 2 mmol) in DCM (300 mL) was added a solution of TsCl (11.8 g, 61.8 mmol) in DCM (50 mL) at RT. The reaction mixture was stirred at this temperature for 16 h. Water (200 mL) was added and the mixture was extracted with DCM (200 mL×2). The combined organic layers were concentrated and purified by silica gel chromatography (DCM/MeOH=10/1) to give 2-(chloromethyl)-5-methylimidazo[1,2-a]pyridine (8.2 g, yield: 51%) as a yellow oil. ESI-MS [M+H]$^+$: 313.2.

Synthesis of lithium 5-((6-cyclopropylimidazo[1,2-a]pyridin-2-yl)methyl)-1,3,4-oxadiazole-2-carboxylate A solution of ethyl 5-((6-cyclopropylimidazo[1,2-a]pyridin-2-yl)methyl)-1,3,4-oxadiazole-2-carboxylate (8.0 g, 25.6 mmol) and LiOH H$_2$O (2.1 g, 51.2 mmol) in a mixed solvent of THF/MeOH/H$_2$O (50 mL/50 mL/50 mL) was stirred at RT for 2 h. THF and methanol were removed in vacuo at 20° C. and the remaining H$_2$O phase was lyophilized to give lithium 5-((6-cyclopropylimidazo[1,2-a]pyridin-2-yl)methyl)-1,3,4-oxadiazole-2-carboxylate (7.4 g, yield: 100%) as a yellow solid. This material was used directly in the next step without further purification. ESI-MS [M+H]$^+$: 285.1.

Synthesis of N-((7-chloroimidazo[1,5-a]pyridin-1-yl)methyl)-5-((6-cyclopropylimidazo[1,2-a]pyridin-2-yl)methyl)-1,3,4-oxadiazole-2-carboxamide (I-51)

A mixture of lithium 5-((6-cyclopropylimidazo[1,2-a]pyridin-2-yl)methyl)-1,3,4-oxadiazole-2-carboxylate (7 g, 24 mmol), (7-chloroimidazo[1,5-a]pyridin-1-yl)methanamine (6.28 g, 28.8 mmol), EDCI (9.2 g, 48 mmol), HOBT (6.48 g, 48 mmol) and DIPEA (12 mL, 72 mmol) in DMF (100 mL) was stirred at 20° C. for 48 h. The mixture was concentrated to remove DMF, diluted with DCM/MeOH (300 mL, 10/1 (v/v)) and washed with H$_2$O (100 mL×2). The organic layer was separated, dried over Na$_2$SO$_4$, and concentrated in vacuo to give the crude product, which was purified by silica gel chromatography (DCM/MeOH=10/1) and then triturated with methanol to give N-((7-chloroimidazo[1,5-a]pyridin-1-yl)methyl)-5-((6-cyclopropylimidazo[1,2-a] pyridin-2-yl)methyl)-1,3,4-oxadiazole-2-carboxamide (3.1 g, yield: 28.7%) as a light yellow solid. ESI-MS [M+H]$^+$: 448.2. Purity: 99%. $^1$H NMR (400 MHz, DMSO): δ 9.73 (t, J=5.8 Hz, 1H), 8.32-8.29 (m, 3H), 7.83 (d, J=1.0 Hz, 1H), 7.79 (s, 1H), 7.37 (d, J=9.3 Hz, 1H), 6.98 (dd, J=9.4, 1.7 Hz, 1H), 6.67 (dd, J=7.4, 2.1 Hz, 1H), 4.62 (d, J=5.9 Hz, 2H), 4.42 (s, 2H), 1.98-1.85 (m, 1H), 0.97-0.85 (m, 2H), 0.75-0.59 (m, 2H).

Example 52

Scheme 52

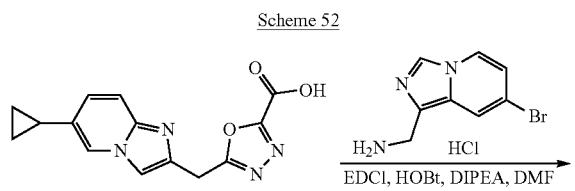

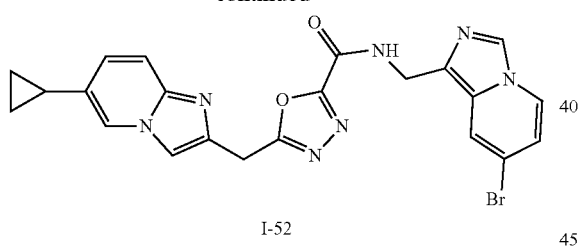

I-52

Synthesis of N-((7-bromoimidazo[1,5-a]pyridin-1-yl)methyl)-5-((6-cyclopropylimidazo[1,2-a]pyridin-2-yl)methyl)-1,3,4-oxadiazole-2-carboxamide (I-52)

A mixture of 5-((6-cyclopropylimidazo[1,2-a]pyridin-2-yl)methyl)-1,3,4-oxadiazole-2-carboxylic acid (50 mg, 0.18 mmol), (7-bromoimidazo[1,5-a]pyridin-1-yl)methanamine hydrochloride (55 mg, 0.21 mmol), EDCI (70 mg, 0.35 mmol), HOBT (50 mg, 0.35 mmol) and DIPEA (0.1 mL, 0.53 mmol) in DMF (3 mL) was stirred at 50° C. for 16 h. Water (30 mL) was added and extracted with EtOAc (30 mL×3). The combined organic layers concentrated and purified by prep-HPLC to give N-((7-bromoimidazo[1,5-a] pyridin-1-yl)methyl)-5-((6-cyclopropylimidazo[1,2-a]pyridin-2-yl)methyl)-1,3,4-oxadiazole-2-carboxamide (3.0 mg, yield: 3.5%) as a light yellow solid. ESI-MS [M+H]$^+$: 492.1. Purity: 96.8%. $^1$H NMR (400 MHz, DMSO): δ 9.73 (t, J=5.9 Hz, 1H), 8.32 (s, 2H), 8.25 (d, J=7.4 Hz, 1H), 8.00 (s, 1H), 7.79 (s, 1H), 7.37 (d, J=9.4 Hz, 1H), 6.98 (dd, J=9.3, 1.7 Hz, 1H), 6.74 (dd, J=7.4, 1.9 Hz, 1H), 4.62 (d, J=5.9 Hz, 2H), 4.42 (s, 2H), 1.95-1.89 (m, 1H), 0.99-0.82 (m, 2H), 0.68-0.66 (m, 2H).

Example 53

Scheme 53

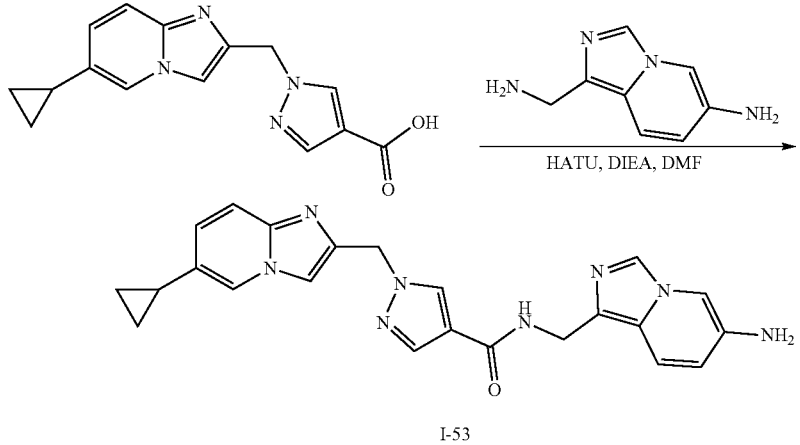

I-53

Synthesis of N-((6-aminoimidazo[1,5-a]pyridin-1-yl)methyl)-1-((6-cyclopropylimidazo[1,2-a]pyridin-2-yl)methyl)-1H-pyrazole-4-carboxamide (I-53)

To a solution of 1-((6-cyclopropylimidazo[1,2-a]pyridin-2-yl)methyl)-1H-pyrazole-4-carboxylic acid (60 mg, 0.21 mmol), 1-(aminomethyl)imidazo[1,5-a]pyridin-6-amine (51 mg, 0.32 mmol) and HATU (120 mg, 0.31 mmol) in DMF (5 mL) was added DIPEA (81 mg, 0.63 mmol). The resulting reaction was stirred at RT for 12 h. H$_2$O (25 mL) was added and the reaction was extracted with EtOAc (50 mL×3). The combined organic layers were washed with brine, dried over Na$_2$SO$_4$, concentrated in vacuo to give the crude, which was purified with prep-TLC (DCM/MeOH=10/1) to give the N-((6-aminoimidazo[1,5-a]pyridin-1-yl)methyl)-1-((6-cyclopropylimidazo[1,2-a]pyridin-2-yl)methyl)-1H-pyrazole-4-carboxamide (10 mg, yield: 11%) as a white solid. ESI-MS [M+H]$^+$: 427.2. Purity: 92.3%. $^1$H NMR (400 MHz, DMSO): δ 8.47 (t, J=5.6 Hz, 1H), 8.32 (s, 1H), 8.21 (s, 1H), 8.16-8.14 (m, 2H), 7.86 (s, 1H), 7.71 (s, 1H), 7.40-7.38 (m, 1H), 7.32 (s, 1H), 7.00-6.97 (m, 1H), 6.32-6.30 (m, 1H), 5.38 (s, 2H), 4.55 (d, J=5.6 Hz, 2H), 1.95-1.78 (m, 2H), 0.95-0.83 (m, 4H), 0.70-0.60 (m, 4H).

Example 54

Scheme 54

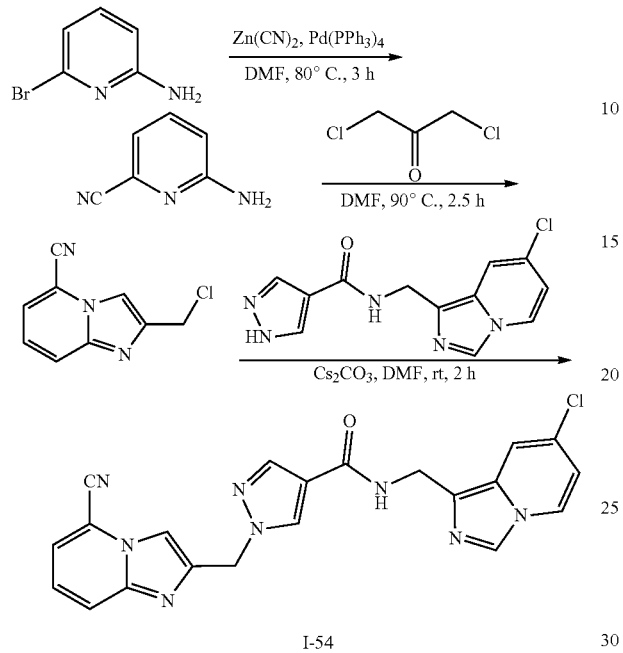

I-54

Synthesis of 6-aminopicolinonitrile

To a solution of 6-bromopyridin-2-amine (500 mg, 2.9 mmol) in DMF (10 mL) was added $Zn(CN)_2$ (480 mg, 4.1 mmol) and tetrakis(triphenylphosphine)palladium(O) (335 mg, 0.29 mmol). The resulting mixture was stirred at 80° C. under nitrogen for 3 h. The reaction mixture was filtered through celite and the filtrate was diluted with $H_2O$ (100 mL) and extracted with ethyl acetate (3×50 mL). The combined organic layers were washed with brine, dried over anhydrous sodium sulfate and concentrated. The residue was purified by flash column chromatography to give 6-aminopicolinonitrile (250 mg, yield: 72%). ESI-MS $[M+H]^+$: 120.1.

Synthesis of 2-(chloromethyl)imidazo[1,2-a]pyridine-5-carbonitrile

To a solution of 6-aminopicolinonitrile (200 mg, 1.67 mmol) in DMF (3 mL) was added 1,3-dichloropropan-2-one (1.0 g, 8.33 mmol). The resulting mixture was stirred at 90° C. for 2.5 h. The reaction mixture was diluted with $H_2O$ (50 mL), extracted with ethyl acetate (3×50 mL), The combined organic layers were washed with brine, dried over anhydrous sodium sulfate and concentrated. The residue was purified by flash column chromatography to give 2-(chloromethyl)imidazo[1,2-a]pyridine-5-carbonitrile (150 mg, yield: 47%). ESI-MS $[M+H]^+$: 192.0.

Synthesis of N-((7-chloroimidazo[1,5-a]pyridin-1-yl)methyl)-1-((5-cyanoimidazo[1,2-a]pyridin-2-yl)methyl)-1H-pyrazole-4-carboxamide (I-54)

To a solution of 2-(chloromethyl)imidazo[1,2-a]pyridine-5-carbonitrile (44 mg, 0.23 mmol) in DMF (3 mL) was added cesium carbonate (224 mg, 0.69 mmol) and N-((7-chloroimidazo[1,5-a]pyridin-1-yl)methyl)-1H-pyrazole-4-carboxamide (63 mg, 0.23 mmol). The resulting mixture was diluted with $H_2O$ (30 mL), extracted with ethyl acetate (3×50 mL), The combined organic layers were washed with brine, dried over anhydrous sodium sulfate and concentrated. The residue was purified by prep-HPLC to give N-((7-chloroimidazo[1,5-a]pyridin-1-yl)methyl)-1-((5-cyanoimidazo[1,2-a]pyridin-2-yl)methyl)-1H-pyrazole-4-carboxamide (12.7 mg, yield: 12.8%). ESI-MS $[M+H]^+$: 431.1. Purity: 99.08%. $^1H$ NMR (400 MHz, DMSO): δ 8.59 (t, J=5.8 Hz, 1H), 8.34-8.26 (m, 2H), 8.26 (s, 1H), 8.14 (s, 1H), 7.94 (d, J=9.1 Hz, 1H), 7.87 (s, 1H), 7.84-7.79 (m, 1H), 7.79-7.77 (m, 1H), 7.41-7.35 (m, 1H), 6.67-6.62 (m, 1H), 5.50 (s, 2H), 4.56 (d, J=5.7 Hz, 2H).

Example 55

Scheme 55

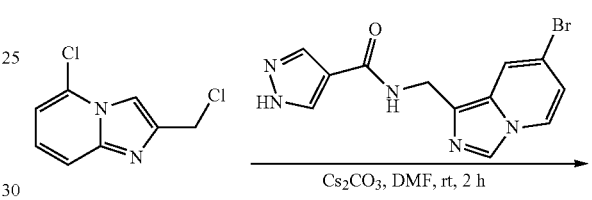

I-55

Synthesis of N-((7-bromoimidazo[1,5-a]pyridin-1-yl)methyl)-1-((5-cyanoimidazo[1,2-a]pyridin-2-yl)methyl)-1H-pyrazole-4-carboxamide (I-75)

To a solution of 2-(chloromethyl)imidazo[1,2-a]pyridine-5-carbonitrile (49 mg, 0.26 mmol) in DMF (3 mL) was added cesium carbonate (250 mg, 0.77 mmol) and N-((7-bromoimidazo[1,5-a]pyridin-1-yl)methyl)-1H-pyrazole-4-carboxamide (83 mg, 0.26 mmol). The resulting mixture was diluted with $H_2O$ (30 mL) and extracted with ethyl acetate (3×30 mL). The combined organic layer were washed with brine, dried over anhydrous sodium sulfate and concentrated. The residue was purified by prep-HPLC to give N-((7-chloroimidazo[1,5-a]pyridin-1-yl)methyl)-1-((5-cyanoimidazo[1,2-a]pyridin-2-yl)methyl)-1H-pyrazole-4-carboxamide (21 mg, yield: 17%). ESI-MS $[M+H]^+$: 475.1. Purity: 97.73%. $^1H$ NMR (400 MHz, DMSO): δ 8.59 (t, J=5.6 Hz, 1H), 8.32 (s, 1H), 8.26 (s, 1H), 8.26-8.22 (m, 1H), 8.14 (s, 1H), 7.97-7.92 (m, 2H), 7.87 (s, 1H), 7.83-7.79 (m, 1H), 7.41-7.35 (m, 1H), 6.74-6.70 (m, 1H), 5.50 (s, 2H), 4.55 (d, J=5.7 Hz, 2H).

Example 56

Scheme 56

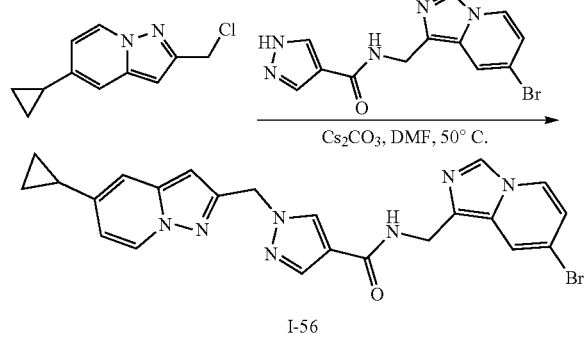

Synthesis of N-((7-bromoimidazo[1,5-a]pyridin-1-yl)methyl)-1-((5-cyclopropylpyrazolo[1,5-a]pyridin-2-yl)methyl)-1H-pyrazole-4-carboxamide (I-56)

A mixture of 2-(chloromethyl)-5-cyclopropylpyrazolo[1,5-a]pyridine (30 mg, 0.15 mmol), N-((7-bromoimidazo[1,5-a]pyridin-1-yl) methyl)-1H-pyrazole-4-carboxamide (48 mg, 0.15 mmol) and Cs$_2$CO$_3$ (200 mg, 0.61 mmol) in DMF (3 mL) was stirred at 50° C. for 16 h. Water (30 mL) was added and extracted with EtOAc (30 mL×3). The combined organic layers were washed with brine, dried over Na$_2$SO$_4$, filtered, concentrated and purified by prep-HPLC to give N-((7-bromoimidazo[1,5-a]pyridin-1-yl)methyl)-1-((5-cyclopropylpyrazolo[1,5-a]pyridin-2-yl)methyl)-1H-pyrazole-4-carboxamide (10 mg, yield: 13%) as a white solid. ESI-MS [M+H]$^+$: 490.0. Purity: 86.77%. $^1$H NMR (400 MHz, DMSO): δ 8.62-8.55 (m, 1H), 8.47 (d, J=8.0 Hz, 1H), 8.32 (s, 1H), 8.25 (d, J=0.8 Hz, 1H), 8.23 (s, 1H), 7.95 (d, J=1.2 Hz, 1H), 7.87 (s, 1H), 7.32 (s, 1H), 6.72 (dd, J=8.0, 2.0 Hz, 1H), 6.57 (dd, J=8.0, 2.0 Hz, 1H), 6.27 (s, 1H), 5.45 (s, 2H), 4.55 (d, J=4.0 Hz, 2H), 2.00-1.90 (m, 1H), 1.03-0.92 (m, 2H), 0.78-0.70 (m, 2H).

Example 57

Scheme 57

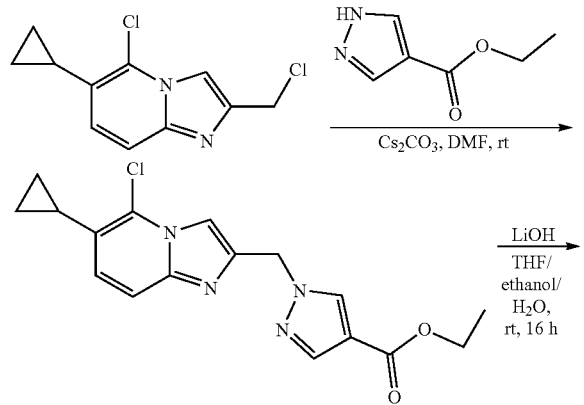

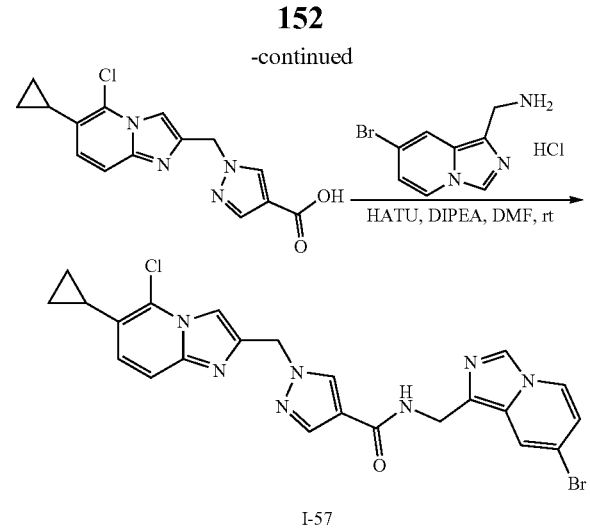

Synthesis of Ethyl 1-((5-chloro-6-cyclopropylimidazo[1,2-a]pyridin-2-yl)methyl)-1H-pyrazole-4-carboxylate A mixture of 5-chloro-2-(chloromethyl)-6-cyclopropylimidazo[1,2-a]pyridine (190 mg, 0.79 mmol), ethyl 1H-pyrazole-4-carboxylate (221 mg, 1.58 mmol) and Cs$_2$CO$_3$ (769 mg, 2.36 mmol) in DMF (6 mL) was stirred at 60° C. for 3 h. Water (50 mL) was added and the mixture was extracted with EtOAc (100 mL×3). The combined organic layers were concentrated and purified by silica gel chromatography (EA/PE=2:3 to 10:1) to give ethyl 1-((5-chloro-6-cyclopropylimidazo[1,2-a]pyridin-2-yl)methyl)-1H-pyrazole-4-carboxylate (220 mg, yield: 64%) as a white solid. ESI-MS [M+H]$^+$: 345.2.

Synthesis of 1-((5-chloro-6-cyclopropylimidazo[1,2-a]pyridin-2-yl)methyl)-1H-pyrazole-4-carboxylic Acid To a solution of 1-((5-chloro-6-cyclopropylimidazo[1,2-a]pyridin-2-yl)methyl)-1H-pyrazole-4-carboxylate (220 mg, 0.64 mmol) in a mixed solvent of ethanol/THF/H$_2$O (3 mL/3 mL/1.5 mL) was added LiOH H$_2$O (107 mg, 2.55 mmol). The mixture was stirred at 60° C. for 3 h. Most of the solvent was removed and the residue was diluted with H$_2$O (10 mL), the pH value of mixture was adjusted to 4-5 by adding aqueous HCl (1 M). The solution was extracted with EtOAc (50 mL×4). The combined organic layers were concentrated to give 1-((5-chloro-6-cyclopropylimidazo[1,2-a]pyridin-2-yl)methyl)-1H-pyrazole-4-carboxylic acid (160 mg, yield: 80%) as a white solid. ESI-MS [M+H]$^+$: 317.2.

Synthesis of N-((7-bromoimidazo[1,5-a]pyridin-1-yl)methyl)-1-((5-chloro-6-cyclopropylimidazo[1,2-a]pyridin-2-yl)methyl)-1H-pyrazole-4-carboxamide (I-57)

A mixture of 1-((5-chloro-6-cyclopropylimidazo[1,2-a]pyridin-2-yl)methyl)-1H-pyrazole-4-carboxylic acid (63.2 mg, 0.2 mmol), (7-bromoimidazo[1,5-a]pyridin-1-yl)methanamine hydrochloride (52.4 mg, 0.2 mmol), HATU (190 mg, 0.5 mmol) and DIPEA (77.5 mg, 0.6 mmol) in DMF (3 mL) was stirred at RT for 3 h. Water (30 mL) was added and the mixture was extracted with EtOAc (50 mL×3). The combined organic layers were concentrated and purified by prep-TLC (DCM:MeOH=8:1) to give N-((7-bromoimidazo[1,5-a]pyridin-1-yl)methyl)-1-((5-chloro-6-cyclopropylimidazo[1,2-a]pyridin-2-yl)methyl)-1H-pyrazole-4-carboxamide (19.9 mg, yield: 19%) as a white solid. ESI-MS [M+H]$^+$: 524.1. Purity: 92.44%. $^1$H NMR (400 MHz, DMSO): δ 8.58 (t, J=5.6 Hz, 1H), 8.31 (s, 1H), 8.24-8.22 (m, 2H), 7.94-7.86 (m, 3H), 7.49 (d, J=9.3 Hz, 1H), 6.97 (d, J=9.3 Hz, 1H), 6.71 (dd, J=7.4, 1.8 Hz, 1H), 5.45 (s, 2H), 4.54 (d, J=5.7 Hz, 2H), 2.14-2.09 (m 1H), 1.03-1.0 (m, 2H), 0.78-0.74 (m, 2H).

Example 58

Scheme 58

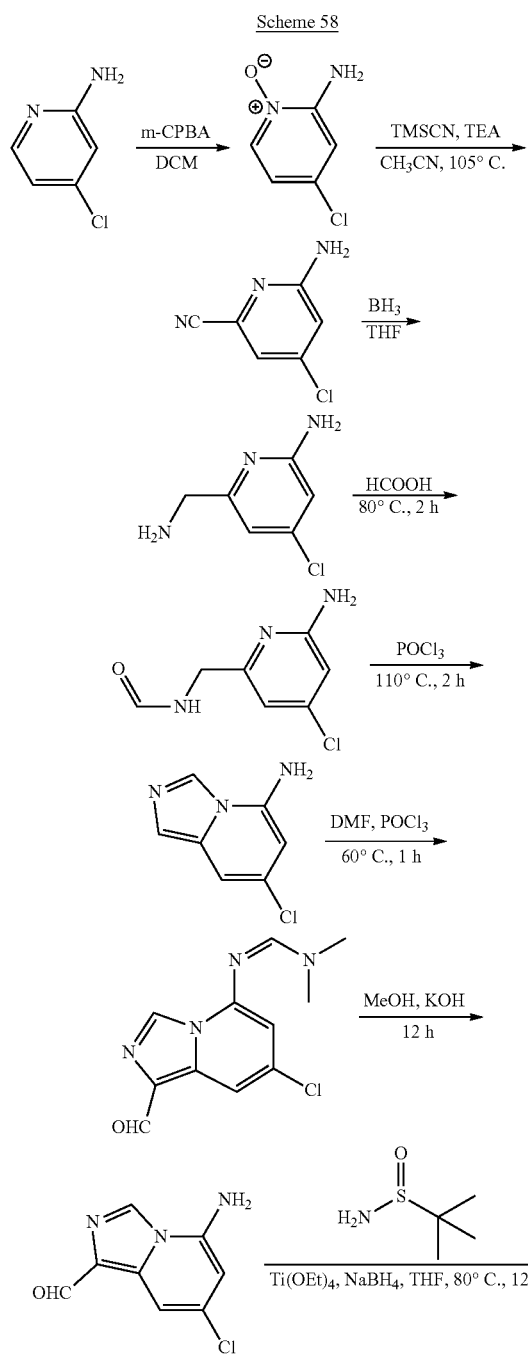

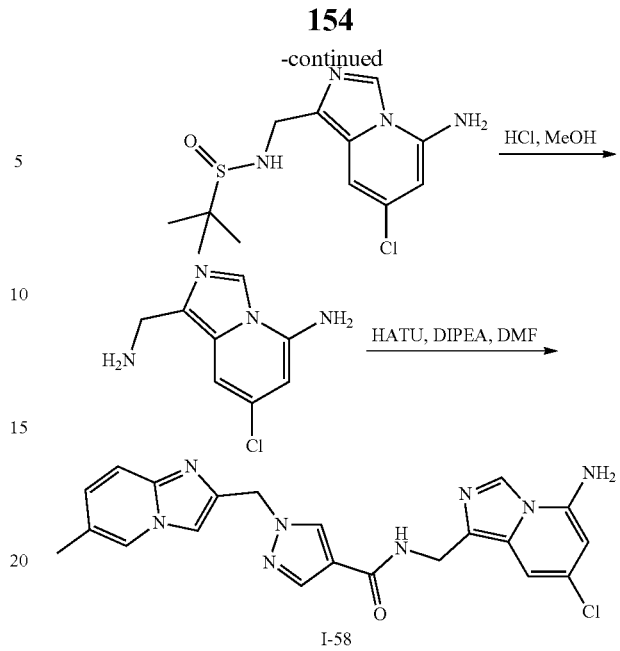

I-58

Synthesis of 2-amino-4-chloropyridine 1-oxide

To a solution of 4-chloropyridin-2-amine (5.14 g, 40 mmol) in DCM (200 mL) at 0° C. was added m-CPBA slowly. The reaction mixture was stirred at RT for 4 h. Water (100 mL) was added and the pH of the mixture was adjusted to 8 by adding saturated NaHCO$_3$ solution. Then the H$_2$O layer was extracted with DCM/CH$_3$OH (10:1, 100 mL×5). The combined organic layers were concentrated to give 2-amino-4-chloropyridine 1-oxide (3.4 g, yield: 61%) as a yellow solid, which was used in the next step without further purification. ESI-MS [M+H]$^+$: 145.1.

Synthesis of 6-amino-4-chloropicolinonitrile

A mixture of 2-amino-4-chloropyridine 1-oxide (1.74 g, 12 mmol), TMSCN (24 mL, 192 mmol) and TEA (26 mL, 192 mmol) in CH$_3$CN (20 mL) was stirred at 105° C. overnight in a sealed tube. Saturated aqueous NaHCO$_3$ was added to adjust the pH to 8, and then extracted with DCM (100 mL×2). The combined organic layers were concentrated and purified by silica gel chromatography (EA/PE=1/4) to give 6-amino-4-chloropicolinonitrile (1.16 g, yield: 63%) as a yellow solid. ESI-MS [M+H]$^+$: 154.1.

Synthesis of 6-(aminomethyl)-4-chloropyridin-2-amine

To a solution of 6-amino-4-chloropicolinonitrile (1.16 g, 7.6 mmol) in dry THF (10 mL) was added BH$_3$ (1 M in THF, 19 mL) dropwise. The mixture was stirred at RT overnight. Then the mixture was quenched with CH$_3$OH and stirred at RT for 1 h. the resulting mixture was then concentrated to give 6-(aminomethyl)-4-chloropyridin-2-amine (1.18 g, yield: 99%) as a yellow solid, which was used in the next step without further purification. ESI-MS [M+H]$^+$: 158.1.

Synthesis of N-((6-amino-4-chloropyridin-2-yl)methyl)formamide

A solution of 6-(aminomethyl)-4-chloropyridin-2-amine (1.18 g, 7.5 mmol), HCOOH (20 mL) and EtOH (20 mL)

was stirred at 80° C. for 2 h. Solvent was concentrated, H₂O (20 mL) was added, and the pH of the mixture was adjusted to 8 by adding saturated aqueous NaHCO₃ solution. The mixture was then extracted with EtOAc (50 mL×5). The combined organic layers were concentrated to give N-((6-amino-4-chloropyridin-2-yl)methyl)formamide (1.05 g, yield: 75%) as a white solid. ESI-MS [M+H]⁺: 186.1.

Synthesis of 7-chloroimidazo[1,5-a]pyridin-5-amine

A solution of N-((6-amino-4-chloropyridin-2-yl)methyl) formamide (1.6 g, 8.6 mmol) in POCl₃ (15 mL) was stirred at 120° C. for 2 h. Solvent was concentrated and the residue was diluted with H₂O (20 mL). The pH of the mixture was adjusted to 8 by adding saturated NaHCO₃ solution and then extracted with EtOAc (100 mL×3). The combined organics were concentrated and purified by silica gel chromatography (CH₂Cl₂/CH₃OH=10/1) to give 7-chloroimidazo[1,5-a]pyridin-5-amine (3.4 g, yield: 61%) as a gray solid. ESI-MS [M+H]⁺: 168.1

Synthesis of N'-(7-chloro-1-formylimidazo[1,5-a]pyridin-5-yl)-N,N-dimethylformimidamide A mixture of 7-chloroimidazo[1,5-a]pyridin-5-amine (155 mg, 0.92 mmol), DMF (203 mg, 2.76 mmol) and POCl₃ (3 mL) was stirred at 60° C. for 1 h. Then the reaction mixture was poured in to ice H₂O and NH₄OH was added to adjust pH to about 8. The resulting mixture was extracted with EtOAc (30 mL×5). The combined organic layers were concentrated to give N'-(7-chloro-1-formylimidazo[1,5-a]pyridin-5-yl)-N,N-dimethylformimidamide (220 mg, yield: 96%) as a yellow solid. ESI-MS [M+H]⁺: 251.1.

Synthesis of 5-amino-7-chloroimidazo[1,5-a]pyridine-1-carbaldehyde

A mixture of N'-(7-chloro-1-formylimidazo[1,5-a]pyridin-5-yl)-N,N-dimethylformimidamide (220 mg, 0.88 mmol), CH₃OH (5 mL) and aqueous KOH (5 M, 1 mL) was stirred at RT overnight. Water (20 mL) was added and the mixture was extracted with EtOAc (50 mL×3). The combined organic layers were concentrated and purified by silica gel chromatography (CH₂Cl₂/CH₃H=9/1) to give 5-amino-7-chloroimidazo[1,5-a]pyridine-1-carbaldehyde (50 mg, yield: 29%) as an orange solid. ESI-MS [M+H]⁺: 196.1.

Synthesis of N-((5-amino-7-chloroimidazo[1,5-a]pyridin-1-yl)methyl)-2-methylpropane-2-sulfinamide A mixture of 5-amino-7-chloroimidazo[1,5-a]pyridine-1-carbaldehyde (22 mg, 0.11 mmol), 2-methylpropane-2-sulfinamide (15.7 mg, 0.13 mmol) and Ti(OEt)₄ (0.12 mL, 0.55 mmol) in THF (0.2 mL) was stirred at 80° C. overnight. After cooled to RT, NaBH₄ (20.8 mg, 0.55 mmol) was added. The reaction mixture was stirred at RT for 3 h. Water (10 mL) and EtOAc (10 mL) was added and the mixture was filtered. The filtration was extracted with EtOAc (30 mL×3). The combined organic layers were concentrated and purified by silica gel chromatography (CH₂Cl₂/CH₃OH=10/1) to give N-((5-amino-7-chloroimidazo[1,5-a]pyridin-1-yl)methyl)-2-methylpropane-2-sulfinamide (10 mg, yield: 30%) as a yellow solid. ESI-MS [M+H]⁺: 313.1.

Synthesis of 1-(aminomethyl)-7-chloroimidazo[1,5-a]pyridin-5-amine

To a solution of N-((5-amino-7-chloroimidazo[1,5-a]pyridin-1-yl)methyl)-2-methylpropane-2-sulfinamide (48 mg, 0.16 mmol) in CH₃OH (2 mL) was added HCl (4 M in dioxane, 0.25 mL). The mixture was stirred at RT for 1 h, then concentrated to give 1-(aminomethyl)-7-chloroimidazo[1,5-a]pyridin-5-amine (31 mg, yield: 99%) as a yellow solid which was used in the next step without purification. ESI-MS [M−16]⁺: 180.1.

Synthesis of N-((5-amino-7-chloroimidazo[1,5-a]pyridin-1-yl)methyl)-1-((6-methylimidazo[1,2-a]pyridin-2-yl)methyl)-1H-pyrazole-4-carboxamide (I-58)

A mixture of 1-(aminomethyl)-7-chloroimidazo[1,5-a]pyridin-5-amine (22 mg, 0.11 mmol), 1-((6-methylimidazo[1,2-a]pyridin-2-yl)methyl)-1H-pyrazole-4-carboxylic acid (28 mg, 0.11 mmol), HATU (84 mg, 0.22 mmol), and DIPEA (43 mg, 0.33 mmol) in DMF (2 mL) was stirred at RT for 2 h. Water (10 mL) was added and extracted with DCM/MeOH (30 mL×3, 10/1, (v/v)). The combined organic layers were concentrated and purified by silica gel chromatography (DCM/CH₃OH=6/1) to give N-((5-amino-7-chloroimidazo[1,5-a]pyridin-1-yl)methyl)-1-((6-methylimidazo[1,2-a]pyridin-2-yl)methyl)-1H-pyrazole-4-carboxamide (9 mg, yield: 9%) as a white solid. ESI-MS [M+H]⁺: 435.2. Purity: 100%. ¹H NMR (400 MHz, DMSO): δ 8.50 (t, J=5.6 Hz, 1H), 8.31 (s, 1H), 8.27 (s, 1H), 8.21 (s, 1H), 7.86 (s, 1H), 7.75 (s, 1H), 7.41 (d, J=9.2 Hz, 1H), 7.10 (dd, J=9.2, 1.3 Hz, 1H), 7.03 (d, J=1.3 Hz, 1H), 6.84 (s, 2H), 5.64 (d, J=1.8 Hz, 1H), 5.39 (s, 2H), 4.53 (d, J=5.7 Hz, 2H), 2.24 (s, 3H).

Example 59

Scheme 59

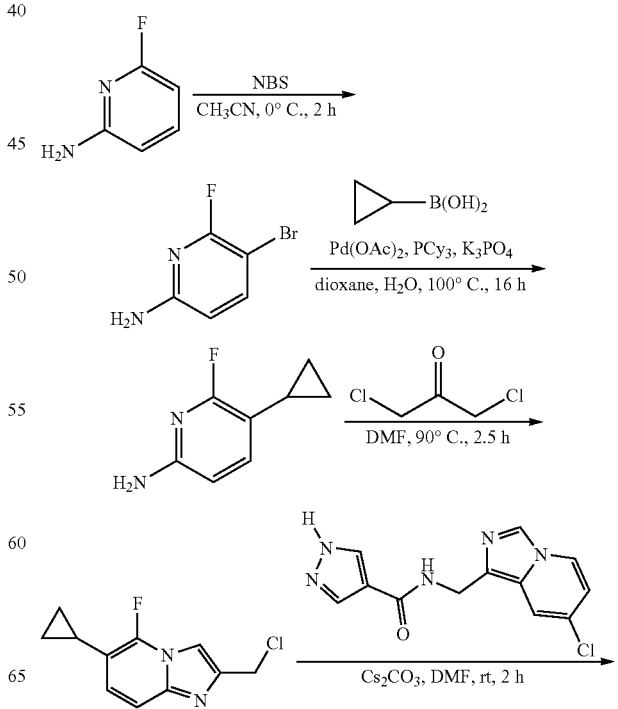

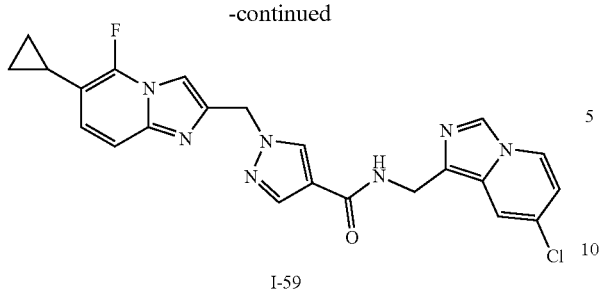

I-59

Synthesis of 6-fluoropyridin-2-amine

A mixture of 6-fluoropyridin-2-amine (3 g, 26.8 mmol) and N-bromosuccinimide (5.25 g, 29.5 mmol) in dry CH₃CN (20 mL) was stirred at 0° C. for 2 h. Water (100 mL) was added and the mixture was extracted with EtOAc (100 mL×3). The combined organic layers were concentrated and purified by silica gel chromatography (EA/PE=1/5) to give 5-bromo-6-fluoropyridin-2-amine (4.31 g, yield: 84.2%) as a white solid. ESI-MS [M+H]$^+$: 191.0.

Synthesis of 5-cyclopropyl-6-fluoropyridin-2-amine

A solution of 5-bromo-6-fluoropyridin-2-amine (3.0 g, 15.8 mmol), cyclopropylboronic acid (2.04 mg, 23.7 mmol), Pd(OAc)$_2$ (354 mg, 1.58 mmol), PCy$_3$ (886.2 mg, 3.16 mmol) and K$_3$PO$_4$ (6.7 g, 31.6 mmol) in dioxane/H$_2$O (30 mL/3 mL) was stirred at 100° C. for 16 h. Then the reaction mixture was diluted with H$_2$O (50 mL) and extracted with EtOAc (100 mL×3). The combined organic layers were dried over Na$_2$SO$_4$ and concentrated to give the desired compound 5-cyclopropyl-6-fluoropyridin-2-amine (yellow oil, 2.2 g). ESI-MS [M+H]$^+$: 153.2.

Synthesis of 2-(chloromethyl)-6-cyclopropyl-5-fluoroimidazo[1,2-a]pyridine

A solution of 5-cyclopropyl-6-fluoropyridin-2-amine (1.5 g, 10 mmol) and 1,3-dichloropropan-2-one (3.8 g, 30 mmol) in dry DMF (15 mL) was stirred at 90° C. for 2.5 h. Then the reaction mixture was diluted with H$_2$O (100 mL) and extracted with EtOAc (100 mL×3). The combined organic layers were dried over Na$_2$SO$_4$, concentrated and purified by column chromatography (PE:EA=5:1) to give the desired product 2-(chloromethyl)-6-cyclopropyl-5-fluoroimidazo[1,2-a]pyridine (325 mg, yield: 15%) as a yellow solid. ESI-MS [M+H]$^+$: 225.1.

Synthesis of N-((7-chloroimidazo[1,5-a]pyridin-1-yl)methyl)-1-((6-cyclopropyl-5-fluoroimidazo[1,2-a]pyridin-2-yl)methyl)-1H-pyrazole-4-carboxamide (I-59)

A solution of 2-(chloromethyl)-6-cyclopropyl-5-fluoroimidazo[1,2-a]pyridine (22 mg, 0.1 mmol), N-((7-chloroimidazo[1,5-a]pyridin-1-yl)methyl)-1H-pyrazole-4-carboxamide (28 mg, 0.1 mmol), and Cs$_2$CO$_3$ (98 mg, 0.3 mmol) in dry DMF (2 mL) was stirred at RT for 2 h. Then the reaction mixture was diluted with H$_2$O (20 mL) and extracted with EtOAc (30 mL×3). The combined organic layers were dried over Na$_2$SO$_4$, concentrated and purified by column chromatography (DCM/MeOH=15/1) to give the desired compound N-((7-chloroimidazo[1,5-a]pyridin-1-yl)methyl)-1-((6-cyclopropyl-5-fluoroimidazo[1,2-a]pyridin-2-yl)methyl)-1H-pyrazole-4-carboxamide (17 mg, yield: 33%) as a yellow solid, ESI-MS [M+H]$^+$: 446.2; [M/2+H]$^+$: 232.7. Purity: 97.80%. $^1$H NMR (400 MHz, DMSO): δ 8.57 (t, J=5.7 Hz, 1H), 8.30-8.28 (m, 2H), 8.21 (s, 1H), 7.85 (d, J=3.3 Hz, 2H), 7.76-7.76 (m, 1H), 7.33 (d, J=9.3 Hz, 1H), 7.04-7.00 (m, 1H), 6.63 (dd, J=7.5, 2.1 Hz, 1H), 5.41 (s, 2H), 4.54 (d, J=5.8 Hz, 2H), 2.04-2.00 (m, 1H), 0.97-0.94 (m, 2H), 0.76-0.72 (m, 2H).

Example 60

Scheme 60

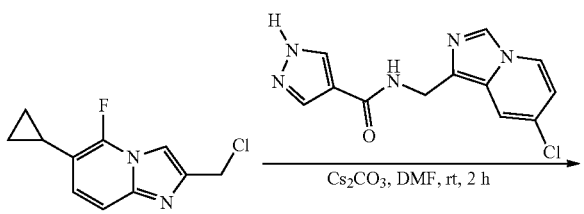

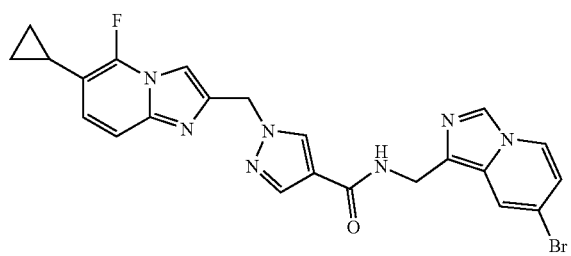

I-60

Synthesis of N-((7-bromoimidazo[1,5-a]pyridin-1-yl)methyl)-1-((6-cyclopropyl-5-fluoroimidazo[1,2-a]pyridin-2-yl)methyl)-1H-pyrazole-4-carboxamide (I-60)

A solution of 2-(chloromethyl)-6-cyclopropyl-5-fluoroimidazo[1,2-a]pyridine (22 mg, 0.1 mmol), N-((7-bromoimidazo[1,5-a]pyridin-1-yl)methyl)-1H-pyrazole-4-carboxamide (32 mg, 0.1 mmol), and Cs$_2$CO$_3$ (98 mg, 0.3 mmol) in dry DMF (2 mL) was stirred at RT for 2 h. Then the reaction mixture was diluted with H$_2$O (10 mL) and extracted with EtOAc (30 mL×3). The combined organic layers were dried over Na$_2$SO$_4$, concentrated and purified by column chromatography (DCM/MeOH=15/1) to give the desired compound N-((7-bromoimidazo[1,5-a]pyridin-1-yl)methyl)-1-((6-cyclopropyl-5-fluoroimidazo[1,2-a]pyridin-2-yl)methyl)-1H-pyrazole-4-carboxamide (11 mg, yield: 22%) as a yellow solid. ESI-MS [M+H]$^+$: 508.1; [M/2+H]$^+$: 254.7. Purity: 91.63%. $^1$H NMR (400 MHz, DMSO): δ 8.58 (t, J=5.7 Hz, 1H), 8.31 (s, 1H), 8.25-8.22 (m, 2H), 7.95 (s, 1H), 7.86 (d, J=3.8 Hz, 2H), 7.34 (d, J=9.3 Hz, 1H), 7.03 (t, J=8.8 Hz, 1H), 6.72 (dd, J=7.4, 1.9 Hz, 1H), 5.43 (s, 2H), 4.55 (d, J=5.7 Hz, 2H), 2.05-2.01 (m, 1H), 0.98-0.95 (m, 2H), 0.82-0.65 (m, 2H).

Example 61

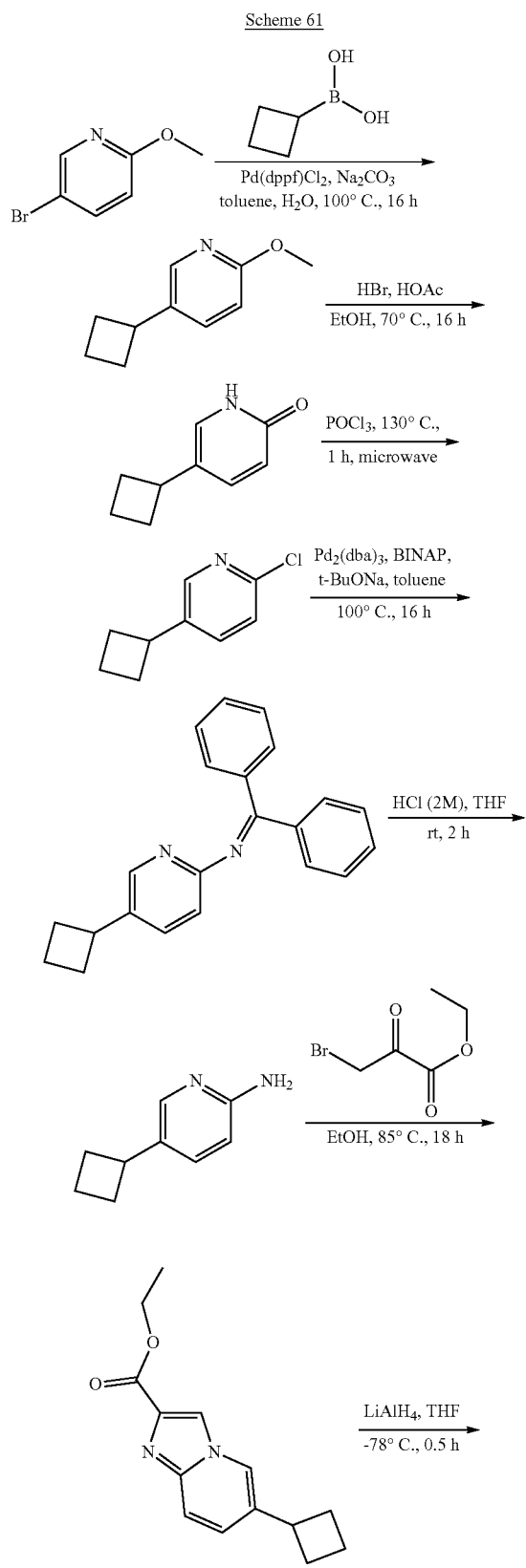

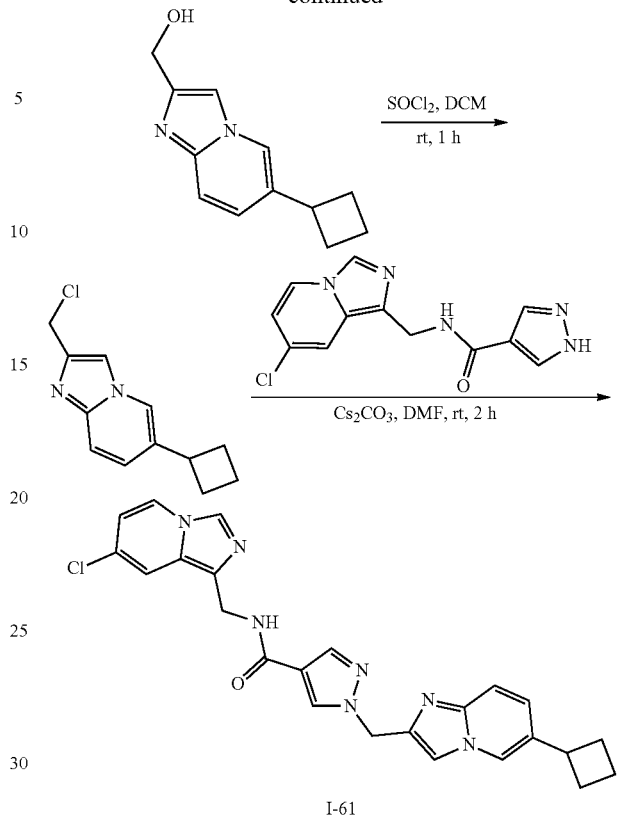

I-61

Synthesis of 5-cyclobutyl-2-methoxypyridine

A mixture of 5-bromo-2-methoxypyridine (4.0 g, 21.27 mmol), cyclobutylboronic acid (2.34 g, 23.40 mmol), Pd(dppf)Cl$_2$ (1.55 g, 2.13 mmol) and Na$_2$CO$_3$ (2.93 g, 27.65 mmol) in toluene (100 mL) and H$_2$O (20 mL) was stirred at 100° C. for 16 h. The reaction mixture was concentrated, diluted with EtOAc (100 mL) and filtered. The filtrate was washed with H$_2$O (100 mL×1) and brine (100 mL×1), dried over Na$_2$SO$_4$, concentrated and purified by silica gel chromatography (EA/PE=1/60) to give 5-cyclobutyl-2-methoxypyridine (1.5 g, yield: 43%) as yellow oil. ESI-MS [M+H]$^+$: 164.2.

Synthesis of 5-cyclobutylpyridin-2(1H)-one

A mixture of 5-cyclobutyl-2-methoxypyridine (1.5 g, 9.19 mmol) and HBr (15 mL, 40% (v/v) in H$_2$O) in EtOH (6 mL) was stirred for at 80° C. for 48 h. The reaction mixture was cooled to RT, concentrated, neutralized with NaHCO$_3$ aqueous to adjust the pH to 7 and extracted with DCM/MeOH (60 mL×3, 10/1 (v/v)). The combined organics was washed with brine (150 mL×1), dried over Na$_2$SO$_4$, concentrated and purified by silica gel chromatography (EA) to give 5-cyclobutylpyridin-2(1H)-one (260 mg, yield: 19%) as a yellow syrup. ESI-MS [M+H]$^+$: 150.2.

Synthesis of 2-chloro-5-cyclobutylpyridine

A solution of 5-cyclobutylpyridin-2(1H)-one (260 mg, 1.74 mmol) in POCl$_3$ (3 mL) was stirred at 130° C. for 1 h under microwave. The reaction mixture was concentrated and the residue was dissolved in EtOAc (100 mL), washed with NaHCO$_3$ aqueous (50 mL×1) and brine (50 mL×1), dried over Na$_2$SO$_4$, concentrated and then purified by silica gel chromatography (EA/PE=1/50) to give 2-chloro-5-cyclobutylpyridine (250 mg, yield: 86%) as yellow oil. ESI-MS [M+H]$^+$: 168.1.

Synthesis of N-(5-cyclobutylpyridin-2-yl)-1,1-diphenylmethanimine

A mixture of 2-chloro-5-cyclobutylpyridine (220 mg, 1.31 mmol), diphenylmethanimine (357 mg, 1.97 mmol), Pd$_2$(dba)$_3$ (120 mg, 0.131 mmol), BINAP (163 mg, 0.262 mmol) and t-BuONa (315 mg, 3.28 mmol) in toluene (8 mL) was stirred at 100° C. for 16 h. The reaction mixture was then diluted in EtOAc (100 mL) and filtered. The filtrate was washed with H$_2$O (50 mL×1), dried over Na$_2$SO$_4$, concentrated and purified by silica gel chromatography (EA/PE=1/8) to give N-(5-cyclobutylpyridin-2-yl)-1,1-diphenylmethanimine (130 mg, yield: 32%) as a yellow solid. ESI-MS [M+H]$^+$: 313.2.

Synthesis of 5-cyclobutylpyridin-2-amine

A mixture of N-(5-cyclobutylpyridin-2-yl)-1, 1-diphenylmethanimine (130 mg, 0.41 mmol) and HCl (2 mL, 2 M) in THF (4 mL) was stirred at RT for 2 h. The reaction mixture was concentrated. Water (20 mL) was added and the pH of the mixture was adjusted to 9 by adding saturated aqueous NaHCO$_3$ solution. This resulting mixture was extracted with DCM/MeOH (50 mL×3, 10/1 (v/v)). The combined organics was washed with brine (100 mL×1), dried over Na$_2$SO$_4$, concentrated and purified by prep-TLC (EA) to give 5-cyclobutylpyridin-2-amine (35 mg, yield: 57%) as a yellow syrup. ESI-MS [M+H]$^+$: 149.2.

Synthesis of Ethyl 6-cyclobutylimidazo[1,2-a]pyridine-2-carboxylate

The mixture of 5-cyclobutylpyridin-2-amine (28 mg, 0.19 mmol) and ethyl 3-bromo-2-oxopropanoate (41 mg, 0.20 mmol) in EtOH (5 mL) was heated to reflux and stirred for 18 h. The reaction mixture was concentrated and the residue was dissolved in EtOAc (20 mL), washed with NaHCO$_3$ aqueous (20 mL×1) and brine (20 mL×1), dried over Na$_2$SO$_4$, concentrated and purified by silica gel chromatography (EA) to give ethyl 6-cyclobutylimidazo[1,2-a]pyridine-2-carboxylate (15 mg, yield: 33%) as a yellow solid. ESI-MS [M+H]$^+$: 245.2.

Synthesis of (6-cyclobutylimidazo[1,2-a]pyridin-2-yl)methanol

To a stirred solution of LiAlH$_4$ (19 mg, 0.49 mmol) in THF (2 mL) was added dropwise the solution of 6-cyclobutylimidazo[1,2-a]pyridine-2-carboxylate (15 mg, 0.061 mmol) in THF (1 mL) at −78° C. The mixture was stirred at −78° C. for 30 min. The reaction mixture was then quenched with Na$_2$SO$_4$.10H$_2$O and filtered. The filtrate was washed with THF (10 mL) and concentrated to give (6-cyclobutylimidazo[1,2-a]pyridin-2-yl)methanol (8 mg, yield: 64%) as a yellow solid which was used in the next step without purification. ESI-MS [M+H]$^+$: 203.2.

Synthesis of 2-(chloromethyl)-6-cyclobutylimidazo[1,2-a]pyridine

To a stirred solution of (6-cyclobutylimidazo[1,2-a]pyridin-2-yl)methanol (8 mg, 0.039 mmol) in DCM (1 mL) was added SOCl$_2$ (47 mg, 0.39 mmol) in DCM (0.5 mL). The mixture was stirred at RT for 1 h. The reaction mixture was concentrated to give 2-(chloromethyl)-6-cyclobutylimidazo[1,2-a]pyridine (10 mg, yield: 100%) as a yellow solid. ESI-MS [M+H]$^+$: 221.1.

Synthesis of N-((7-chloroimidazo[1,5-a]pyridin-1-yl)methyl)-1-((6-cyclobutylimidazo[1,2-a]pyridin-2-yl)methyl)-1H-pyrazole-4-carboxamide (I-61)

The mixture of 2-(chloromethyl)-6-cyclobutylimidazo[1,2-a]pyridine (10 mg, 0.045 mmol), N-((7-chloroimidazo[1,5-a]pyridin-1-yl)methyl)-1H-pyrazole-4-carboxamide (12 mg, 0.045 mmol) and Cs$_2$CO$_3$ (30 mg, 0.09 mmol) in DMF (2 mL) was stirred at RT for 2 h. Water (10 mL) was added and the mixture was extracted with EtOAc/THF (15 mL×3, 5/1 (v/v)). The combined organic layers were washed with brine (40 mL×3), dried over Na$_2$SO$_4$, concentrated and purified by prep-TLC (DCM/MeOH=10/1) to give N-((7-chloroimidazo[1,5-a]pyridin-1-yl)methyl)-1-((6-cyclobutylimidazo[1,2-a]pyridin-2-yl)methyl)-1H-pyrazole-4-carboxamide (8 mg, yield: 38%) as a white solid. ESI-MS [M+H]$^+$: 460.2. Purity: 95.58%. $^1$H NMR (400 MHz, DMSO): δ 8.57 (t, J=5.7 Hz, 1H), 8.34 (s, 1H), 8.30 (m, 2H), 8.20 (s, 1H), 7.86 (s, 1H), 7.77 (m, 2H), 7.44 (d, J=9.3 Hz, 1H), 7.18 (dd, J=9.3, 1.7 Hz, 1H), 6.64 (dd, J=7.4, 2.1 Hz, 1H), 5.39 (s, 2H), 4.55 (d, J=5.8 Hz, 2H), 3.50 (m, 1H), 2.28 (m, 2H), 2.04 (m, 3H), 1.83 (m, 1H).

Example 62

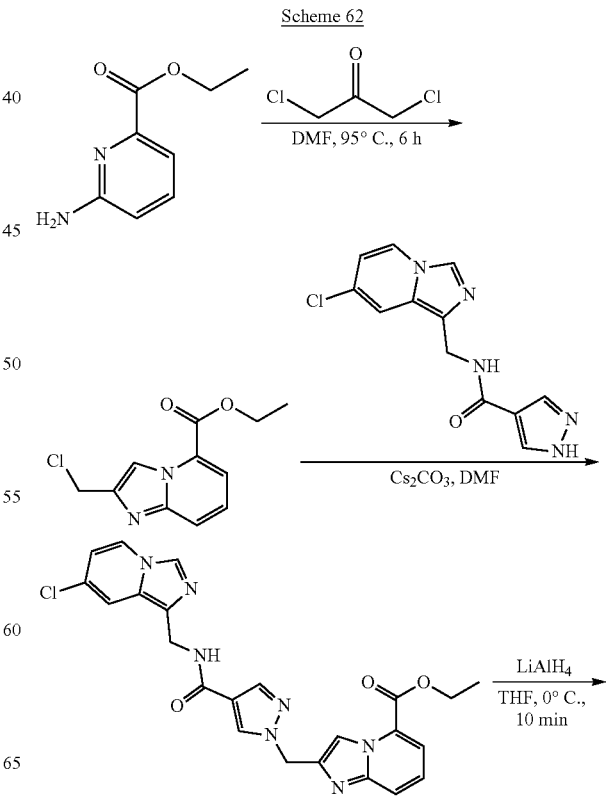

Scheme 62

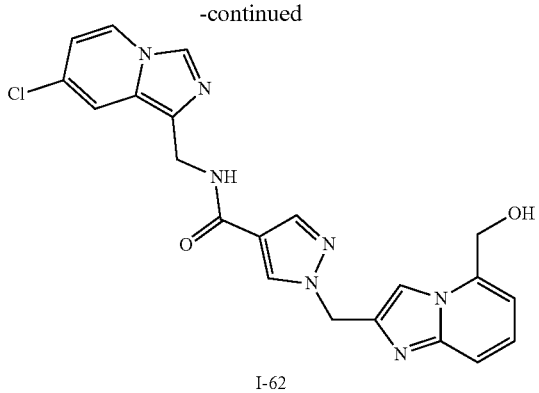

I-62

Synthesis of Ethyl 2-(chloromethyl)imidazo[1,2-a]pyridine-5-carboxylate

A mixture of ethyl 6-aminopicolinate (166 mg, 1.0 mmol) and 1, 3-dichloropropan-2-one (630 mg, 5.0 mmol) in dry DMF (10 mL) was stirred at 95° C. for 6 h. Water (100 mL) was added and the mixture was extracted with EtOAc (50 mL×3). The combined organic layers were concentrated and purified by silica gel chromatography (EA/PE=1/1) to give ethyl 2-(chloromethyl)imidazo[1,2-a]pyridine-5-carboxylate (70 mg, yield: 29%) as a yellow oil. ESI-MS [M+H]$^+$: 239.1.

Synthesis of Ethyl 2-((4-((7-chloroimidazo[1,5-a]pyridin-1-yl)methylcarbamoyl)-1H-pyrazol-1-yl)methyl)imidazo[1,2-a]pyridine-5-carboxylate A mixture of ethyl 2-(chloromethyl)imidazo[1,2-a]pyridine-5-carboxylate (70 mg, 0.29 mmol), N-((7-chloroimidazo[1,5-a]pyridin-1-yl)methyl)-1H-pyrazole-4-carboxamide (80 mg, 0.29 mmol) and Cs$_2$CO$_3$ (270 mg, 0.87 mmol) in DMF (5 mL) was stirred at RT for 4 h. Water (30 mL) was added and extracted with EtOAc (50 mL×3). The combined organic layers were concentrated and purified by prep-TLC (DCM/MeOH=10/1) to give ethyl 2-((4-((7-chloroimidazo[1,5-a]pyridin-1-yl)methylcarbamoyl)-1H-pyrazol-1-yl)methyl)imidazo[1,2-a]pyridine-5-carboxylate (90 mg, yield: 65%) as a yellow solid. ESI-MS [M+H]$^+$: 478.1.

Synthesis of N-((7-chloroimidazo[1,5-a]pyridin-1-yl)methyl)-1-((5-(hydroxymethyl)imidazo[1,2-a]pyridin-2-yl)methyl)-1H-pyrazole-4-carboxamide (I-62)

To a solution of ethyl 2-((4-((7-chloroimidazo[1,5-a]pyridin-1-yl)methylcarbamoyl)-1H-pyrazol-1-yl)methyl)imidazo[1,2-a]pyridine-5-carboxylate (30 mg, 0.06 mmol) in dry THF (5 mL) was added LiAlH$_4$ (7 mg, 0.18 mmol) at 0° C. and the mixture was stirred at 0° C. for 10 min. Water (10 mL) was added to quench the reaction and extracted with EtOAc (30 mL×3). The combined organic layers were concentrated and purified by prep-TLC (DCM/MeOH=10/1) to give N-((7-chloroimidazo[1,5-a]pyridin-1-yl)methyl)-1-((5-(hydroxymethyl)imidazo[1,2-a]pyridin-2-yl)methyl)-1H-pyrazole-4-carboxamide (16.5 mg, yield: 63.5%) as a light yellow solid. ESI-MS [M+H]$^+$: 436.1. Purity: 95.3%.
$^1$H NMR (400 MHz, DMSO): δ 8.59 (s, 1H), 8.30 (d, J=6.7 Hz, 2H), 8.23 (s, 1H), 7.84 (d, J=9.7 Hz, 2H), 7.78 (s, 1H), 7.47 (d, J=9.1 Hz, 1H), 7.33-7.20 (m, 1H), 6.91 (d, J=6.6 Hz, 1H), 6.64 (dd, J=7.5, 2.1 Hz, 1H), 5.67 (t, J=5.7 Hz, 1H), 5.44 (s, 2H), 4.71 (d, J=5.5 Hz, 2H), 4.55 (d, J=5.8 Hz, 2H).

Example 63

Scheme 63

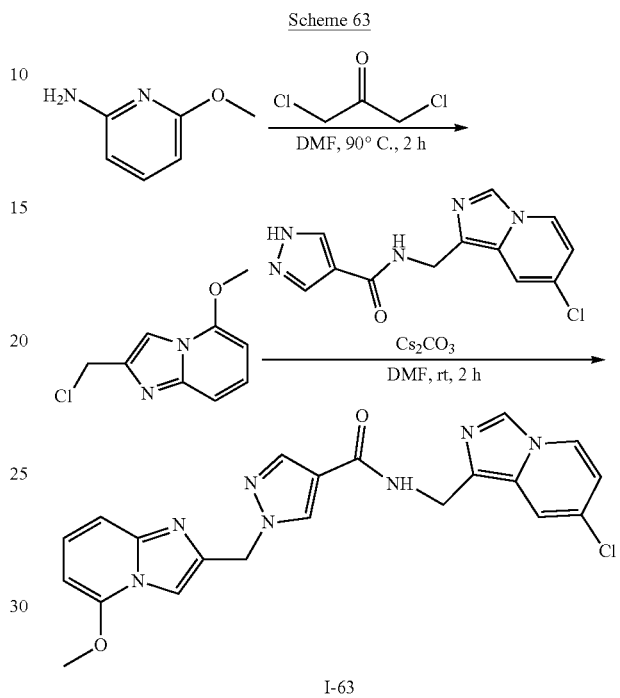

I-63

Synthesis of 2-(chloromethyl)-5-methoxyimidazo[1,2-a]pyridine

A solution of 6-methoxypyridin-2-amine (500 mg, 4.1 mmol) and 1,3-dichloropropan-2-one (2.58 g, 20.5 mmol) in DMF (10 mL) was stirred at 90° C. for 2 h. Then the reaction mixture was diluted with H$_2$O (100 mL) and extracted with EtOAc (100 mL×3). The combined organic layers were dried over Na$_2$SO$_4$, concentrated and purified by column chromatography (CH$_2$Cl$_2$/MeOH=3/1) to give the desired product 2-(chloromethyl)-5-methoxyimidazo[1,2-a]pyridine (200 mg, yield: 25%) as brown oil. ESI-MS [M+H]$^+$: 197.1.

Synthesis of N-((7-chloroimidazo[1,5-a]pyridin-1-yl)methyl)-1-((5-methoxyimidazo[1,2-a]pyridin-2-yl)methyl)-1H-pyrazole-4-carboxamide (I-63)

A solution of 2-(chloromethyl)-5-methoxyimidazo[1,2-a]pyridine (36 mg, 0.18 mmol), N-((7-chloroimidazo[1,5-a]pyridin-1-yl)methyl)-1H-pyrazole-4-carboxamide (50 mg, 0.18 mmol) and Cs$_2$CO$_3$ (235 mg, 0.72 mmol) in DMF (3 mL) was stirred at RT for 2 h. Water (30 mL) was added and extracted with EtOAc (50 mL×3). The combined organic layers were dried over Na$_2$SO$_4$, concentrated and purified by column chromatography (CH$_2$Cl$_2$/MeOH=10/1) to give the desired compound N-((7-chloroimidazo[1,5-a]pyridin-1-yl)methyl)-1-((5-methoxyimidazo[1,2-a]pyridin-2-yl)methyl)-1H-pyrazole-4-carboxamide (20 mg, yield: 28%) as a white solid. ESI-MS [M+H]$^+$: 436.1. Purify: 96.0%. $^1$H NMR (400 MHz, DMSO): δ 8.58 (t, J=5.7 Hz, 1H), 8.32-8.27 (m, 2H), 8.22 (s, 1H), 7.85 (s, 1H), 7.78 (s, 1H), 7.66 (s, 1H), 7.33-7.27 (m, 1H), 7.14 (d, J=9.0 Hz, 1H), 6.66-6.62 (m, 1H), 6.35 (d, J=7.4 Hz, 1H), 5.41 (s, 2H), 4.55 (d, J=5.7 Hz, 2H), 4.07 (s, 3H).

Example 64

Scheme 64

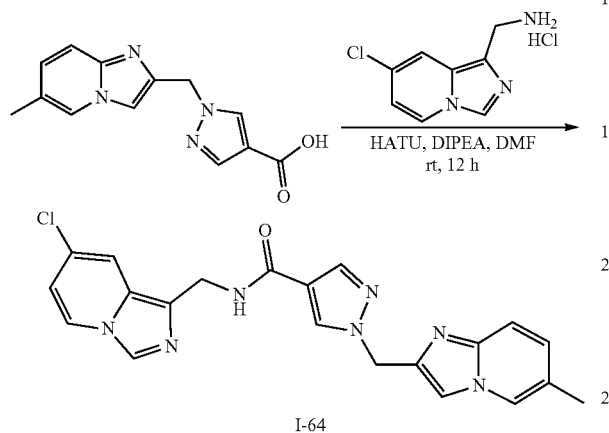

I-64

Synthesis of N-((7-chloroimidazo[1,5-a]pyridin-1-yl)methyl)-1-((6-methylimidazo[1,2-a]pyridin-2-yl)methyl)-1H-pyrazole-4-carboxamide (I-64)

To a solution of 1-((6-methylimidazo[1,2-a]pyridin-2-yl)methyl)-1H-pyrazole-4-carboxylic acid (128 mg, 0.5 mmol), (7-chloroimidazo[1,5-a]pyridin-1-yl)methanamine hydrochloride (141 mg, 0.65 mmol) and HATU (285 mg, 0.75 mmol) in DMF (10 mL) was added DIPEA (323 mg, 2.5 mmol). The resulting reaction was stirred at RT for 12 h. H$_2$O (25 mL) was added to the reaction and extracted with EtOAc (25 mL×4). The combined organic layers were washed with brine, dried over Na$_2$SO$_4$ and concentrated in vacuo to give the crude, which was purified with prep-TLC (DCM/MeOH=10/1) to give the N-((7-chloroimidazo[1,5-a]pyridin-1-yl)methyl)-1-((6-methylimidazo[1,2-a]pyridin-2-yl)methyl)-1H-pyrazole-4-carboxamide (55 mg, yield: 26%) as a white solid. ESI-MS [M+H]$^+$: 420.1. Purity: 96.6%. $^1$H NMR (400 MHz, DMSO): δ 8.59 (s, 1H), 8.35-8.30 (m, 4H), 8.22 (s, 1H), 7.89 (s, 1H), 7.78-7.76 (m, 2H), 7.41 (d, J=9.0 Hz, 1H), 7.11 (d, J=9.0 Hz, 1H), 6.65 (d, J=6.8 Hz, 1H), 5.39 (s, 2H), 4.55 (d, J=5.2 Hz, 2H), 2.25 (s, 3H).

Example 65

Scheme 65

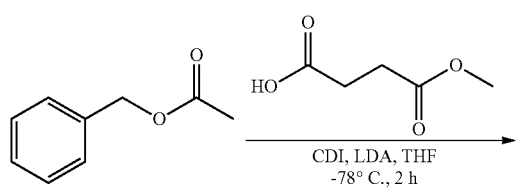

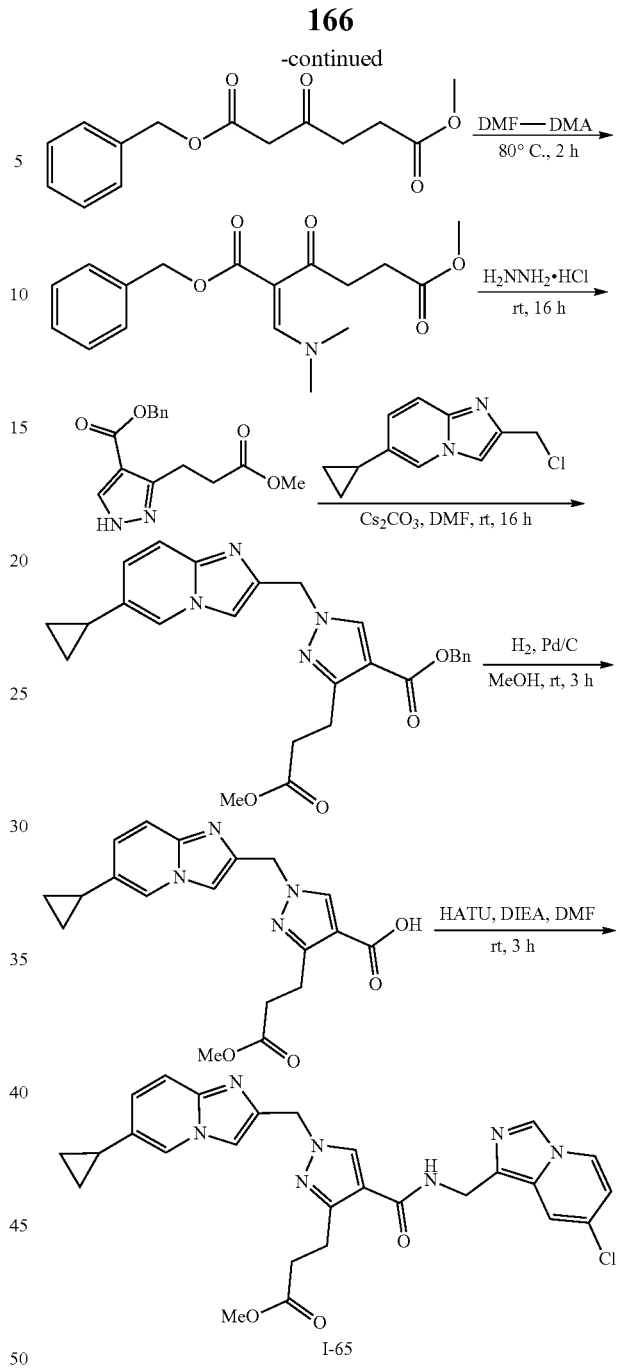

I-65

Synthesis of 1-benzyl 6-methyl 3-oxohexanedioate

To a solution of benzyl acetate (1.5 g, 10 mmol) in THF (10 mL) was added LDA (1 M, 15 mmol) at −78° C. and stirred for 1 h (solution A). To a solution of 4-methoxy-4-oxobutanoic acid (1.58 g, 12 mmol) in THF (10 mL) was added CDI (1.94 g, 12 mmol) and stirred at RT for 30 min (solution B). Solution B was added to solution A at −78° C. and stirred for another 2 h. Saturated NH$_4$Cl (100 mL) was added to quenched the reaction and the reaction mixture was extracted with EtOAc (100 mL×3). The combined organics were concentrated and purified by silica gel chromatography (EA/PE=1/10) to give 1-benzyl 6-methyl 3-oxohexanedioate (500 mg, yield: 19%) as a colorless oil. ESI-MS [M+H]$^+$: 265.1.

Synthesis of 1-benzyl 6-methyl (E)-2-((dimethylamino)methylene)-3-oxohexanedioate A solution of 1-benzyl 6-methyl 3-oxohexanedioate (490 mg, 1.86 mmol) in DMFDMA (443 mg, 3.72 mmol) was heated to 80° C. for 2 h. The resulting mixture was concentrated to give 1-benzyl 6-methyl (E)-2-((dimethylamino)methylene)-3-oxohexanedioate (600 mg, crude) as a yellow oil which was used in the next step without purification. ESI-MS [M+H]$^+$: 320.1.

Synthesis of benzyl 3-(3-methoxy-3-oxopropyl)-1H-pyrazole-4-carboxylate

To a solution of 1-benzyl 6-methyl (E)-2-((dimethylamino)methylene)-3-oxohexanedioate (600 mg, 1.86 mmol) in MeOH (6 mL) was added hydrazine hydrochloride (255 mg, 3.72 mmol). The mixture was stirred at RT for 16 h. The reaction was concentrated to give the crude, which was purified by silica gel chromatography (EA/PE=1/1) to give benzyl 3-(3-methoxy-3-oxopropyl)-1H-pyrazole-4-carboxylate (384 mg, yield: 64% for two steps) as a yellow oil. ESI-MS [M+H]$^+$: 289.1.

Synthesis of benzyl 1-((6-cyclopropylimidazo[1,2-a]pyridin-2-yl)methyl)-3-(3-methoxy-3-oxopropyl)-1H-pyrazole-4-carboxylate To a solution of benzyl 3-(3-methoxy-3-oxopropyl)-1H-pyrazole-4-carboxylate (90 mg, 0.31 mmol) and 2-(chloromethyl)-6-cyclopropylimidazo[1,2-a]pyridine (78 mg, 0.38 mmol) in DMF (5 mL) was added CsCO$_3$ (302 mg, 0.93 mmol) at RT. The mixture was stirred at RT for 16 h. The reaction was diluted with H$_2$O (30 mL) and extracted with ethyl acetate (3×50 mL). The combined organic layers were washed with brine, dried over sodium sulfate and concentrated. The residue was purified by prep-TLC (MeOH/DCM=1/15) to give benzyl 1-((6-cyclopropylimidazo[1,2-a]pyridin-2-yl)methyl)-3-(3-methoxy-3-oxopropyl)-1H-pyrazole-4-carboxylate (70 mg, yield: 50%) as a yellow oil. ESI-MS [M+H]$^+$: 459.1.

Synthesis of 1-((6-cyclopropylimidazo[1,2-a]pyridin-2-yl)methyl)-3-(3-methoxy-3-oxopropyl)-1H-pyrazole-4-carboxylic Acid To a solution of benzyl 1-((6-cyclopropylimidazo[1,2-a]pyridin-2-yl)methyl)-3-(3-methoxy-3-oxopropyl)-1H-pyrazole-4-carboxylate (100 mg, 0.22 mmol) in MeOH (10 mL) was added Pd/C (10%, 30 mg). The mixture was stirred at RT for 3 h under H$_2$. The mixture was filtered and concentrated to give 1-((6-cyclopropylimidazo[1,2-a]pyridin-2-yl)methyl)-3-(3-methoxy-3-oxopropyl)-1H-pyrazole-4-carboxylic acid (67 mg, 83%) as a white solid. ESI-MS [M+H]$^+$: 369.1.

Synthesis of Methyl 3-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)propanoate (I-65)

To a solution of 1-((6-cyclopropylimidazo[1,2-a]pyridin-2-yl)methyl)-3-(3-methoxy-3-oxopropyl)-1H-pyrazole-4-carboxylic acid (80 mg, 0.22 mmol) and (7-chloroimidazo[1,5-a]pyridin-1-yl)methanamine hydrochloride (56 mg, 0.26 mmol) in dry DMF (4 mL) was added HATU (125 mg, 0.33 mmol) and DIPEA (114 mg, 0.88 mmol) at RT. The reaction was stirred at RT for 3 h. Water (20 mL) was added and the mixture was extracted with EtOAc (30 mL×3). The organic layers were washed with brine (50 mL), dried over sodium sulfate, and concentrated. The crude residue was purified by prep-TLC (DCM/MeOH=10/1) to give methyl 3-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)propanoate (70 mg, yield: 61%) as a yellow solid. ESI-MS [M+H]$^+$: 532.2. Purity: 95.2%. $^1$H NMR (400 MHz, DMSO): δ 8.53 (t, J=5.7 Hz, 0.3H), 8.43-8.38 (m, 0.7H), 8.36-8.27 (m, 3H), 8.15 (s, 0.7H), 7.92 (s, 0.3H), 7.84-7.67 (m, 1.75H), 7.58 (s, 0.3H), 7.40-7.35 (m, 1H), 7.03-6.93 (m, 1H), 6.66-6.63 (m, 1H), 5.42 (s, 0.6H), 5.28 (s, 1.4H), 4.64-4.47 (m, 2H), 3.57-3.56 (m, 3H), 3.29-3.19 (m, 0.6H), 3.17-2.99 (m, 1.4H), 2.74-2.55 (m, 2H), 1.97-1.84 (m, 1H), 0.94-0.89 (m, 2H), 0.68-0.64 (m, 2H).

Example 66

Scheme 66

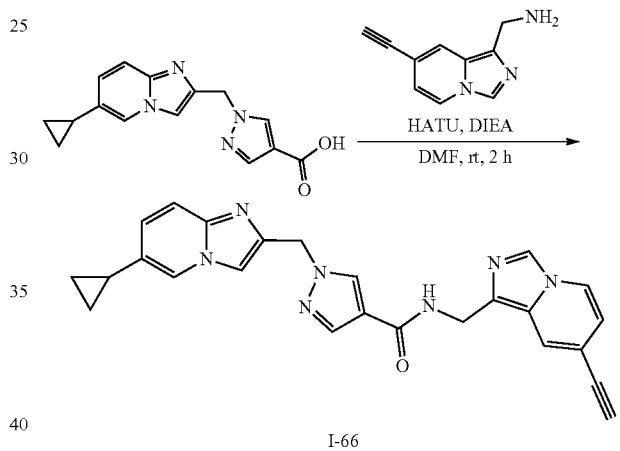

I-66

Synthesis of 1-((6-cyclopropylimidazo[1,2-a]pyridin-2-yl)methyl)-N-((7-ethynylimidazo[1,5-a]pyridin-1-yl)methyl)-1H-pyrazole-4-carboxamide (I-66)

A solution of 1-((6-cyclopropylimidazo[1,2-a]pyridin-2-yl)methyl)-1H-pyrazole-4-carboxylic acid (68 mg, 0.24 mmol), (7-ethynylimidazo[1,5-a]pyridin-1-yl)methanamine (50 mg, 0.24 mmol), HATU (183 mg, 0.48 mmol) and DIPEA (93 mg, 0.72 mmol) in DMF (3 mL) was stirred at RT for 2 h. Then the reaction mixture was diluted with H$_2$O (50 mL) and extracted with EtOAc (50 mL×3). The combined organic layers were dried over Na$_2$SO$_4$, concentrated and purified by column chromatography (CH$_2$Cl$_2$/MeOH=10/1) to give the desired compound 1-((6-cyclopropylimidazo[1,2-a]pyridin-2-yl)methyl)-N-((7-ethynylimidazo[1,5-a]pyridin-1-yl)methyl)-1H-pyrazole-4-carboxamide (40 mg, yield: 38%) as a white solid. ESI-MS [M+H]$^+$: 436.2. Purity: 100%. $^1$H NMR (400 MHz, DMSO): δ 8.59 (t, J=5.7 Hz, 1H), 8.34-8.31 (m, 2H), 8.26-8.22 (m 1H), 8.20 (s, 1H), 7.88 (s, 1H), 7.86 (s, 1H), 7.71 (s, 1H), 7.39 (d, J=9.4 Hz, 1H), 7.01-6.97 (m, 1H), 6.59-6.55 (m, 1H), 5.38 (s, 2H), 4.58 (d, J=5.8 Hz, 2H), 4.26 (s, 1H), 1.95-1.88 (m, 1H), 0.93-0.88 (m, 2H), 0.68-0.64 (m, 2H).

Example 67

Scheme 67

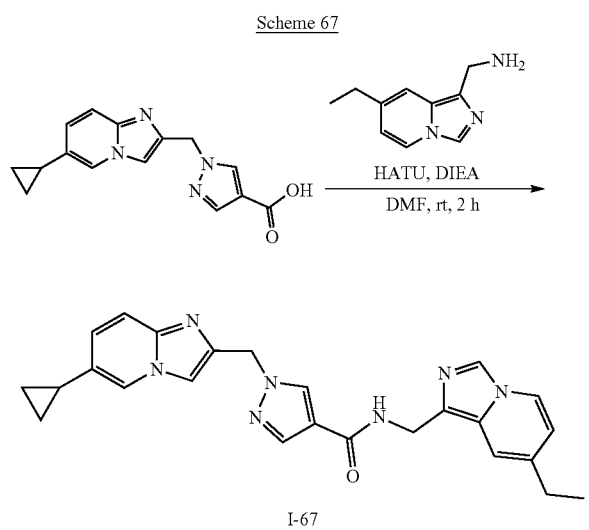

I-67

Synthesis of 1-((6-cyclopropylimidazo[1,2-a]pyridin-2-yl)methyl)-N-((7-ethylimidazo[1,5-a]pyridin-1-yl)methyl)-1H-pyrazole-4-carboxamide (I-67)

A solution of 1-((6-cyclopropylimidazo[1,2-a]pyridin-2-yl)methyl)-1H-pyrazole-4-carboxylic acid (64 mg, 0.23 mmol), (7-ethylimidazo[1,5-a]pyridin-1-yl)methanamine hydrochloride (49 mg, 0.23 mmol), HATU (175 mg, 0.46 mmol) and DIPEA (90 mg, 0.69 mmol) in DMF (3 mL) was stirred at RT for 2 h. Then the reaction mixture was diluted with H$_2$O (30 mL) and extracted with EtOAc (30 mL×3). The combined organic layers were dried over Na$_2$SO$_4$, concentrated and purified by column chromatography (CH$_2$Cl$_2$/MeOH=10/1) to give the desired compound 1-((6-cyclopropylimidazo[1,2-a]pyridin-2-yl)methyl)-N-((7-ethylimidazo[1,5-a]pyridin-1-yl)methyl)-1H-pyrazole-4-carboxamide (50 mg, yield: 49%) as a white solid. ESI-MS [M+H]$^+$: 440.2. Purity: 97%. $^1$H NMR (400 MHz, DMSO): δ 8.47 (t, J=5.5 Hz, 1H), 8.32 (s, 1H), 8.22-8.16 (m, 3H), 7.86 (s, 1H), 7.71 (s, 1H), 7.42-7.32 (m, 2H), 7.01-6.96 (m, 1H), 6.52-6.48 (m, 1H), 5.38 (s, 2H), 4.56 (d, J=5.6 Hz, 2H), 3.33-3.29 (m, 2H), 1.94-1.88 (m, 1H), 1.14 (t, J=7.5 Hz, 3H), 0.93-0.88 (m, 2H), 0.69-0.63 (m, 2H).

Example 68

Scheme 68

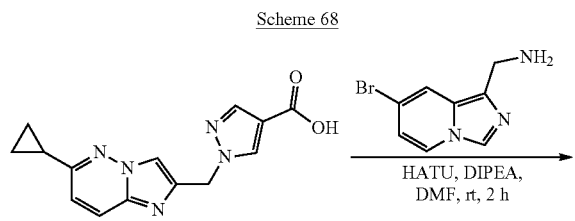

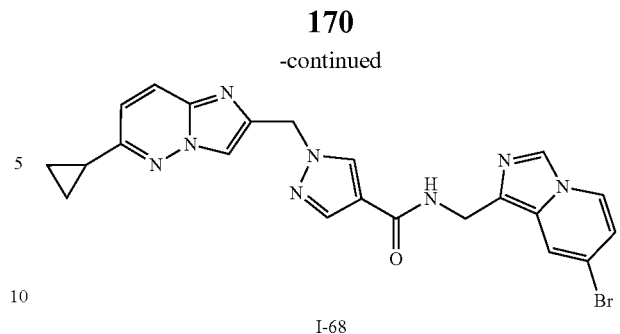

I-68

Synthesis of N-((7-bromoimidazo[1,5-a]pyridin-1-yl)methyl)-1-((6-cyclopropylimidazo[1,2-b]pyridazin-2-yl)methyl)-1H-pyrazole-4-carboxamide (I-68)

A solution of 1-((6-cyclopropylimidazo[1,2-b]pyridazin-2-yl)methyl)-1H-pyrazole-4-carboxylic acid (48 mg, 0.17 mmol), (7-bromoimidazo[1,5-a]pyridin-1-yl)methanamine hydrochloride (45 mg, 0.17 mmol), HATU (134 mg, 0.35 mmol) and DIPEA (65 mg, 0.53 mmol) in DMF (3 mL) was stirred at RT for 2 h. Then the reaction mixture was diluted with H$_2$O (30 mL) and extracted with EtOAc (50 mL×3). The combined organic layers were dried over Na$_2$SO$_4$, concentrated and purified by column chromatography (CH$_2$Cl$_2$/MeOH=8/1) to give the desired compound N-((7-bromoimidazo[1,5-a]pyridin-1-yl)methyl)-1-((6-cyclopropylimidazo[1,2-b]pyridazin-2-yl)methyl)-1H-pyrazole-4-carboxamide (20 mg, yield: 24%) as a white solid. ESI-MS [M+H]$^+$: 491.1. Purity: 93%. $^1$H NMR (400 MHz, DMSO): δ 8.56 (t, J=5.7 Hz, 1H), 8.31 (s, 1H), 8.26-8.19 (m, 2H), 8.08 (s, 1H), 7.96-7.90 (m, 2H), 7.85 (s, 1H), 7.09 (d, J=9.5 Hz, 1H), 6.74-6.69 (m, 1H), 5.41 (s, 2H), 4.54 (d, J=5.7 Hz, 2H), 2.20-2.14 (m, 1H), 1.09-1.03 (m, 2H), 0.99-0.93 (m, 2H).

Example 69

Scheme 69

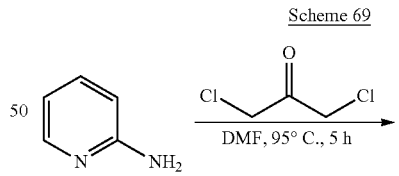

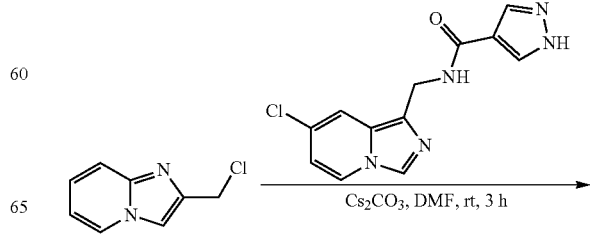

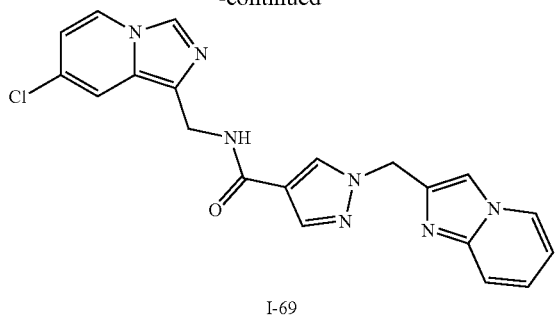

I-69

Synthesis of 2-(chloromethyl)imidazo[1,2-a]pyridine

A mixture of pyridin-2-amine (600 mg, 6.4 mmol) and 1,3-dichloropropan-2-one (4.0 g, 32.0 mmol) in dry DMF (10 mL) was stirred at 95° C. for 6 h. Water (100 mL) was added and the mixture was extracted with EtOAc (80 mL×3). The combined organic layers were concentrated and purified by silica gel chromatography (EA/PE=1/1) to give 2-(chloromethyl)imidazo[1,2-a]pyridine (80 mg, yield: 7.5%) as a yellow oil. ESI-MS [M+H]$^+$: 167.1.

Synthesis of N-((7-chloroimidazo[1,5-a]pyridin-1-yl)methyl)-1-(imidazo[1,2-a]pyridin-2-ylmethyl)-1H-pyrazole-4-carboxamide (I-69)

A mixture of 2-(chloromethyl)imidazo[1,2-a]pyridine (80 mg, 0.48 mmol), N-((7-chloroimidazo[1,5-a]pyridin-1-yl)methyl)-1H-pyrazole-4-carboxamide (130 mg, 0.48 mmol) and Cs$_2$CO$_3$ (469 mg, 1.44 mmol) in DMF (5 mL) was stirred at RT for 3 h. Water (50 mL) was added and extracted with EtOAc (50 mL×3). The combined organic layer were concentrated and purified by prep-TLC (DCM/MeOH=10/1) to give N-((7-chloroimidazo[1,5-a]pyridin-1-yl)methyl)-1-(imidazo[1,2-a]pyridin-2-ylmethyl)-1H-pyrazole-4-carboxamide (27 mg, yield: 14%) as a white solid. ESI-MS [M+H]$^+$: 406.2. Purity: 99.6%. $^1$H NMR (400 MHz, DMSO): δ 8.59 (t, J=5.7 Hz, 1H), 8.51 (d, J=6.8 Hz, 1H), 8.30 (d, J=7.1 Hz, 2H), 8.23 (s, 1H), 7.85 (d, J=14.5 Hz, 2H), 7.78 (s, 1H), 7.49 (d, J=9.1 Hz, 1H), 7.27-7.18 (m, 1H), 6.87 (t, J=6.7 Hz, 1H), 6.65 (dd, J=7.4, 2.0 Hz, 1H), 5.42 (s, 2H), 4.55 (d, J=5.7 Hz, 2H).

Example 70

Scheme 70

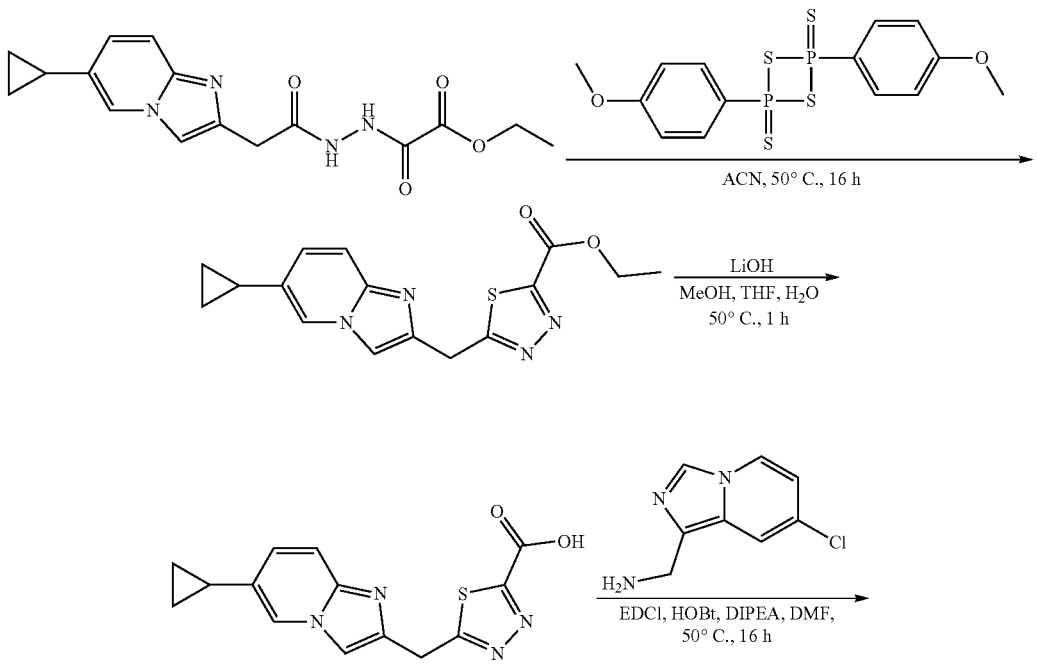

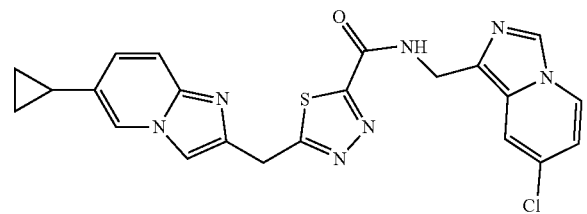

I-70

Synthesis of Ethyl 5-((6-cyclopropylimidazo[1,2-a]pyridin-2-yl)methyl)-1,3,4-thiadiazole-2-carboxylate A mixture of ethyl 2-(2-(2-(6-cyclopropylimidazo[1,2-a]pyridin-2-yl)acetyl)hydrazinyl)-2-oxoacetate (330 mg, 1.0 mmol) and Lawesson's Regent (600 mg, 1.5 mmol) in CH$_3$CN (20 mL) was stirred at 50° C. for 16 h under N$_2$. The mixture was concentrated and purified by silica gel chromatography (DCM/MeOH=10/1) to give ethyl 5-((6-cyclopropylimidazo[1,2-a]pyridin-2-yl)methyl)-1,3,4-thiadiazole-2-carboxylate (280 mg, yield: 85.4%) as a yellow oil. ESI-MS [M+H]$^+$: 329.1

Synthesis of lithium 5-((6-cyclopropylimidazo[1,2-a]pyridin-2-yl)methyl)-1,3,4-thiadiazole-2-carboxylate A solution of ethyl 5-((6-cyclopropylimidazo[1,2-a]pyridin-2-yl)methyl)-1,3,4-thiadiazole-2-carboxylate (280 mg, 0.85 mmol) and LiOH.H$_2$O (70 mg, 1.70 mmol) in THF/MeOH/H$_2$O (2 mL/2 mL/2 mL) was stirred at 50° C. for 2 h. The mixture was concentrated to give lithium 5-((6-cyclopropylimidazo[1,2-a]pyridin-2-yl)methyl)-1,3,4-thiadiazole-2-carboxylate (320 mg, crude) as a yellow solid. ESI-MS [M+H]$^+$: 301.1.

Synthesis of N-((7-chloroimidazo[1,5-a]pyridin-1-yl)methyl)-5-((6-cyclopropylimidazo[1,2-a]pyridin-2-yl)methyl)-1,3,4-thiadiazole-2-carboxamide (I-70)

A mixture of 5-((6-cyclopropylimidazo[1,2-a]pyridin-2-yl)methyl)-1,3,4-thiadiazole-2-carboxylic acid (100 mg, crude), (7-chloroimidazo[1,5-a]pyridin-1-yl)methanamine hydrochloride (72 mg, 0.33 mmol), EDCI (130 mg, 0.66 mmol), HOBT (90 mg, 0.66 mmol) and DIPEA (0.2 mL, 0.99 mmol) in DMF (4 mL) was stirred at 50° C. for 16 h. Water (30 mL) was added and extracted with EtOAc (50 mL×3). The combined organic layers were concentrated and purified by prep-HPLC to give N-((7-chloroimidazo[1,5-a]pyridin-1-yl)methyl)-5-((6-cyclopropylimidazo[1,2-a]pyridin-2-yl)methyl)-1,3,4-thiadiazole-2-carboxamide (12.1 mg, yield: 7.9%) as a light yellow solid. ESI-MS [M+H]$^+$: 464.1. Purity: 95.4%. $^1$H NMR (400 MHz, DMSO): δ 9.62 (t, J=5.9 Hz, 1H), 8.40 (s, 1H), 8.35-8.26 (m, 2H), 7.91-7.80 (m, 2H), 7.49 (d, J=9.3 Hz, 1H), 7.13 (d, J=9.4 Hz, 1H), 6.67 (dd, J=7.5, 2.1 Hz, 1H), 4.74-4.48 (m, 4H), 1.99-1.93 (m, 1H), 1.00-0.88 (m, 2H), 0.71-0.69 (m, 2H).

Example 71

Scheme 71

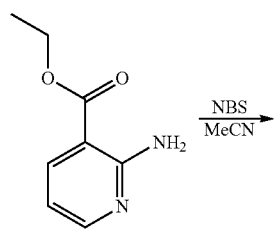

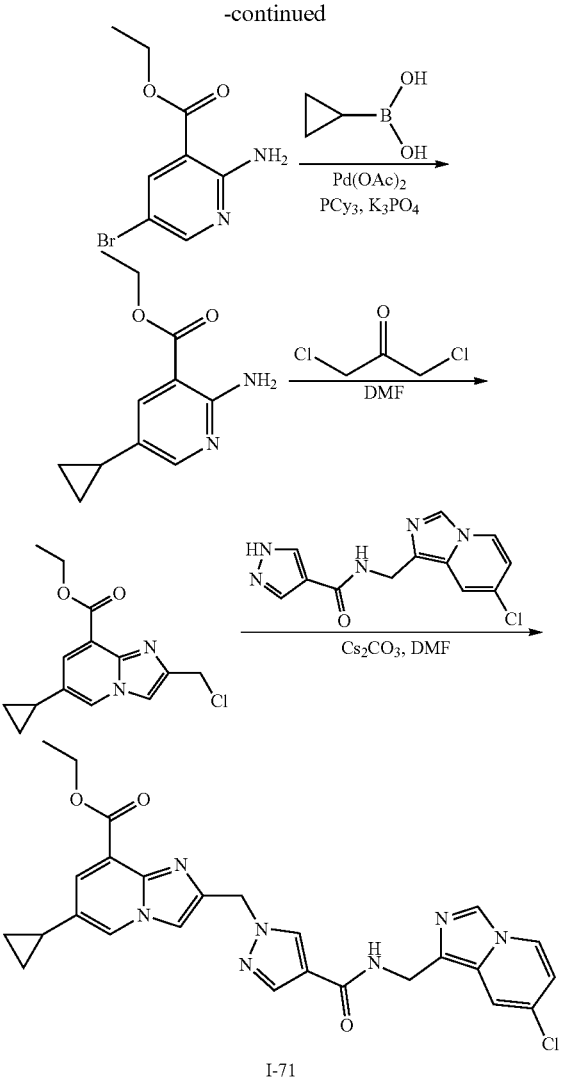

I-71

Synthesis of Ethyl 2-amino-5-bromonicotinate

To a solution of ethyl 2-aminonicotinate (500 mg, 3.00 mmol) in dry MeCN (20 mL) was added NBS (643 mg, 3.6 mmol) slowly at RT. The resulting mixture was stirred at RT for 1 h. The reaction was then quenched with H$_2$O (30 mL) and extracted with EtOAc (30 mL×3). The combined organic layers were washed with brine, dried over Na$_2$SO$_4$, and concentrated in vacuo to give the crude product of ethyl 2-amino-5-bromonicotinate (700 mg, yield: 95.2%) as a white solid, which was used in the next step without purification. ESI-MS [M+H]$^+$: 245.0.

Synthesis of Ethyl 2-amino-5-cyclopropylnicotinate

A mixture ethyl 2-amino-5-bromonicotinate (700 mg, 2.85 mmol), cyclopropylboronic acid (728 mg, 8.5 mmol), Pd(OAc)$_2$ (140 mg, 0.05 mmol), K$_3$PO$_4$ (3 g, 14.2 mmol) and PCy$_3$ (0.3 g, 1.14 mmol) in dioxane/H$_2$O (50 mL/5 mL) was stirred at 95° C. for 12 h in N$_2$. The resulting mixture was quenched with H$_2$O (40 mL), extracted with EtOAc (50 mL×3). The combined organic layers were washed with brine, dried with Na$_2$SO$_4$ and concentrated in vacuo to give the crude, which was purified with silica gel chromatography with PE/EA (1/1) to give ethyl 2-amino-5-cyclopropylnicotinate (500 mg, 86% yield) as a white solid. ESI-MS [M+H]⁺: 207.1. Purity: 95%.

Synthesis of Ethyl 2-(chloromethyl)-6-cyclopropylimidazo[1,2-a]pyridine-8-carboxylate To a solution of ethyl 2-amino-5-cyclopropylnicotinate (500 mg, 1.94 mmol) in DMF (10 mL) was added 1,3-dichloropropan-2-one (986 mg, 77.7 mmol) at 95° C. for 3 h. Water (50 mL) was added and the pH of the reaction was adjusted to 8 with NaHCO₃ and then extracted with EtOAc (30 mL×3). The combined organic layers were washed with brine, dried over Na₂SO₄ and concentrated in vacuo to give the crude, which was purified with silica gel chromatography (EtOAc/PE=1/2) to give ethyl 2-(chloromethyl)-6-cyclopropylimidazo[1,2-a]pyridine-8-carboxylate (550 mg, yield: 65.3%) as a white solid. ESI-MS [M+H]⁺: 278.7. Purity: 90%.

Synthesis of Ethyl 2-((4-(((7-chloroimidazo[1,5-a]pyridin-1-yl)methyl)carbamoyl)-1H-pyrazol-1-yl)methyl)-6-cyclopropylimidazo[1,2-a]pyridine-8-carboxylate (I-71)

A mixture of ethyl 2-(chloromethyl)-6-cyclopropylimidazo[1,2-a]pyridine-8-carboxylate (173 mg, 0.6 mmol) in DMF (3 mL) was added N-((7-chloroimidazo[1,5-a]pyridin-1-yl)methyl)-1H-pyrazole-4-carboxamide (138 mg, 0.5 mmol) and Cs₂CO₃ (406 mg, 1.25 mmol). The resulting mixture was stirred at RT for 3 h. The reaction was quenched with H₂O (30 mL) and extracted with EtOAc (30 mL×3). The combined organic layers were washed with brine, dried over Na₂SO₄ and concentrated in vacuo to give the crude, which was purified with prep-TLC (DCM/MeOH=10/1) to give the ethyl 2-((4-(((7-chloroimidazo[1,5-a]pyridin-1-yl)methyl)carbamoyl)-1H-pyrazol-1-yl)methyl)-6-cyclopropylimidazo[1,2-a]pyridine-8-carboxylate (10 mg, yield: 3.2%) as a white solid. ESI-MS [M+H]⁺: 518.2. Purity: 91.3%. ¹H NMR (400 MHz, DMSO): δ 8.63-8.49 (m, 2H), 8.31-8.29 (m, 2H), 8.21 (s, 1H), 7.89 (s, 1H), 7.78 (d, J=1.9 Hz, 1H), 7.75 (s, 1H), 7.60 (d, J=1.7 Hz, 1H), 6.64 (dd, J=7.5, 2.1 Hz, 1H), 5.45 (s, 2H), 4.55 (d, J=5.7 Hz, 2H), 4.33 (q, J=7.1 Hz, 2H), 2.03-1.96 (m, 1H), 1.31 (t, J=7.1 Hz, 3H), 1.00-0.86 (m, 2H), 0.75-0.59 (m, 2H).

Example 72

Scheme 72

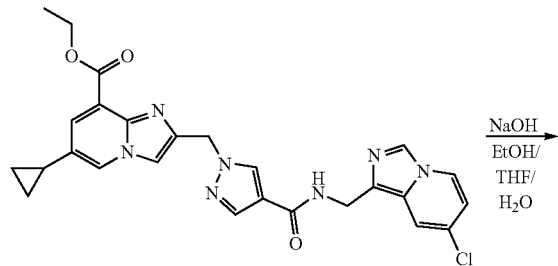

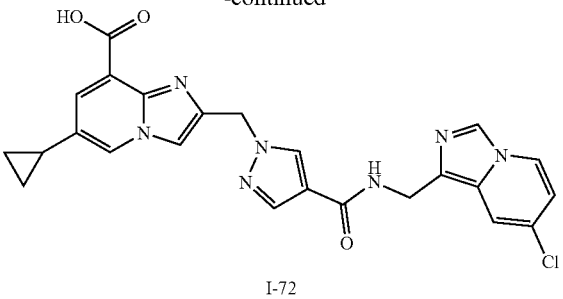

I-72

Synthesis of 2-((4-(((7-chloroimidazo[1,5-a]pyridin-1-yl)methyl)carbamoyl)-1H-pyrazol-1-yl)methyl)-6-cyclopropylimidazo[1,2-a]pyridine-8-carboxylic acid (I-72)

To a solution of ethyl 2-((4-(((7-chloroimidazo[1,5-a]pyridin-1-yl)methyl)carbamoyl)-1H-pyrazol-1-yl)methyl)-6-cyclopropylimidazo[1,2-a]pyridine-8-carboxylate (40 mg, 0.077 mmol) in EtOH/THF/H₂O (2 mL/2 mL/1 mL) was added NaOH (0.5 mL, 1 M), then the reaction was stirred at RT for 1 h. Most of the solvent was removed and the residue was diluted with H₂O (3 mL). The pH of mixture was adjusted to 4-5 by adding HCl aqueous (1 M). The resulting mixture was concentrated to give the crude, which was purified by prep-HPLC to give 2-((4-(((7-chloroimidazo[1,5-a]pyridin-1-yl)methyl)carbamoyl)-1H-pyrazol-1-yl)methyl)-6-cyclopropylimidazo[1,2-a]pyridine-8-carboxylate (9.7 mg, 26% yield) as a white solid. ESI-MS [M+H]⁺: 490.1. Purity: 97.9%. ¹H NMR (400 MHz, DMSO): δ 8.66-8.54 (m, 2H), 8.34-8.27 (m, 2H), 8.25 (s, 1H), 7.90 (s, 1H), 7.84 (s, 1H), 7.79-7.74 (m, 1H), 7.70 (d, J=1.7 Hz, 1H), 6.64 (dd, J=7.5, 2.1 Hz, 1H), 5.49 (s, 2H), 4.56 (d, J=5.7 Hz, 2H), 2.08-2.00 (m, 1H), 0.99-0.94 (m, 2H), 0.74-0.70 (m, 2H).

Example 73

Scheme 73

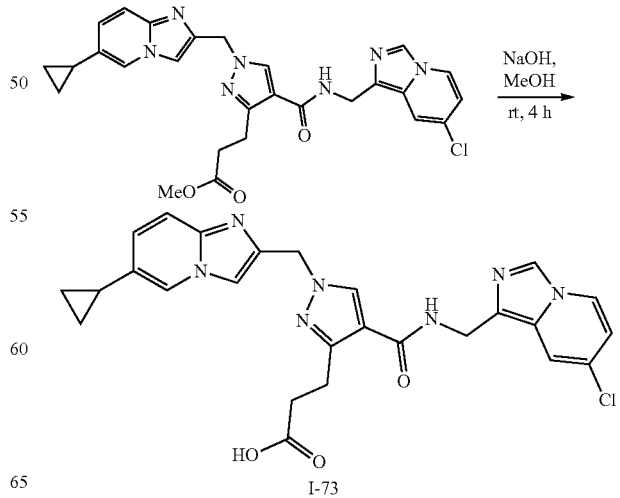

I-73

Synthesis of 3-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)propanoic acid (I-73)

To a solution of methyl 3-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)propanoate (53 mg, 0.1 mmol) in MeOH/H$_2$O (2 mL/0.5 mL) was added aqueous NaOH (4 M, 0.1 mL). The reaction was stirred at RT for 4 h. The pH of mixture was adjusted to 4 by add in HCl (1 M). After concentrating the mixture, the crude product was purified by prep-HPLC to give 3-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)propanoic acid (40 mg, yield: 77%) as a white solid. ESI-MS [M+H]$^+$: 518.1. Purity: 97.7%. $^1$H NMR (400 MHz, DMSO): δ 9.31 (s, 2H), 8.37-8.24 (m, 3H), 8.03 (s, 1H), 7.80 (d, J=1.0 Hz, 1H), 7.71 (s, 1H), 7.39 (d, J=9.3 Hz, 1H), 6.99 (dd, J=9.4, 1.7 Hz, 1H), 6.63 (dd, J=7.5, 2.1 Hz, 1H), 5.28 (s, 2H), 4.53 (d, J=5.7 Hz, 2H), 2.89 (t, J=7.3 Hz, 2H), 2.43 (t, J=7.3 Hz, 2H), 1.95-1.88 (s, 1H), 0.96-0.85 (m, 2H), 0.68-0.64 (m, 2H).

Example 74

Scheme 74

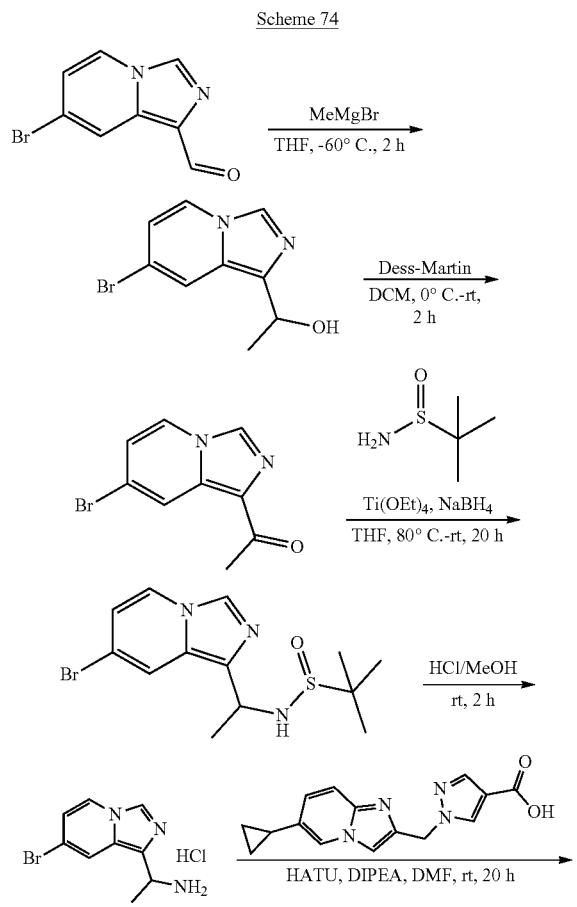

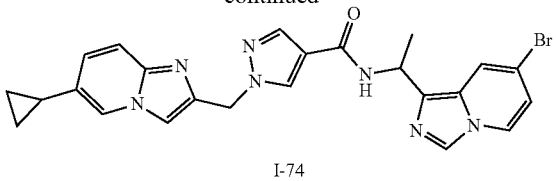

I-74

Synthesis of 1-(7-bromoimidazo[1,5-a]pyridin-1-yl)ethan-1-ol

To a solution of 7-bromoimidazo[1,5-a] pyridine-1-carbaldehyde (550 mg, 2.46 mmol) in THF (10 mL) was added methylmagnesium bromide (4.1 mL, 12.3 mmol) at −60° C. The mixture was stirred at −60° C. for 2 h. LCMS confirmed the starting material consumed completely. Saturated ammonium chloride solution (30 mL) was added and the mixture was extracted with ethyl acetate (20 mL×3). The combined organic layers were washed with saturated salt H$_2$O and concentrated. The residue was purified by flash column chromatography (ethyl acetate/petroleum ether from 0 to 20%) to give 1-(7-bromoimidazo[1,5-a]pyridin-1-yl)ethan-1-ol (300 mg, yield: 51%) as a brown oil. ESI-MS [M+H]$^+$: 241.0.

Synthesis of 1-(7-bromoimidazo[1,5-a]pyridin-1-yl)ethan-1-one

To the solution of 1-(7-bromoimidazo[1,5-a]pyridin-1-yl)ethan-1-ol (290 mg, 1.2 mL) in DCM (10 mL) was added Dess-Martin (1.0 g, 2.4 mmol) at 0° C., Then the reaction mixture was warmed to RT and stirred for 2 h. Saturated sodium bicarbonate solution (40 mL) was added and the mixture was extracted with DCM (30 mL×3). The combined organic layers were washed with saturated salt H$_2$O and concentrated. The residue was purified by flash column chromatography (ethyl acetate/petroleum ether from 0 to 15%) to give 1-(7-bromoimidazo[1,5-a]pyridin-1-yl)ethan-1-one (150 mg, yield: 52%) as a brown solid. ESI-MS [M+H]$^+$: 239.0.

Synthesis of N-(1-(7-bromoimidazo[1,5-a]pyridin-1-yl)ethyl)-2-methylpropane-2-sulfinamide To the mixture of 1-(7-bromoimidazo[1,5-a]pyridin-1-yl)ethan-1-one (150 mg, 0.63 mmol) and 2-methylpropane-2-sulfinamide (92 mg, 0.76 mmol) in THF (5 mL) was added tetraethyl titanate (429 mg, 1.90 mmol). The mixture was stirred at 80° C. for 18 h and cooled to RT. Sodium borohydride (120 mg, 3.15 mmol) was added and the mixture was stirred at RT for 2 h. Saturated ammonium chloride solution (30 mL) was added and the mixture was extracted with ethyl acetate (30 mL×3). The combined organic layers were concentrated and purified by flash column chromatography (ethyl acetate/petroleum ether from 0 to 15%) to give N-(1-(7-bromoimidazo[1,5-a]pyridin-1-yl)ethyl)-2-methylpropane-2-sulfinamide (40 mg, yield: 18.5%) as a brown oil. ESI-MS [M+H]$^+$: 344.0.

Synthesis of 1-(7-bromoimidazo[1,5-a]pyridin-1-yl)ethan-1-amine hydrochloride A mixture of N-(1-(7-bromoimidazo[1,5-a]pyridin-1-yl)ethyl)-2-methylpropane-2-sulfinamide (40 mg, 0.12 mmol) in HCl/MeOH (5 mL, 4 M) was stirred at RT for 2 h and concentrated to give 1-(7-bromoimidazo[1,5-a]pyridin-1-yl)ethan-1-amine hydrochloride (30 mg, yield: 94%) which was used in the next step directly. ESI-MS [M+H]⁺: 240.0

Synthesis of N-(1-(7-bromoimidazo[1,5-a]pyridin-1-yl)ethyl)-1-((6-cyclopropylimidazo[1,2-a]pyridin-2-yl)methyl)-1H-pyrazole-4-carboxamide (I-74)

To the solution of 1-(7-bromoimidazo[1,5-a]pyridin-1-yl)ethan-1-amine hydrochloride (30 mg, crude) and 1-((6-cyclopropylimidazo[1,2-a]pyridin-2-yl)methyl)-1H-pyrazole-4-carboxylic acid (20 mg, 0.042 mmol) in dry DMF (3 mL) was added HATU (24 mg, 0.63 mmol) and DIPEA (16 mg, 0.125 mmol) at RT. The reaction was stirred at RT for 18 h. Water (30 mL) was added and the mixture was extracted with ethyl acetate (30 mL×3). The combined organic layers were washed with brine, dried over anhydrous sodium sulfate and concentrated. The residue was purified by prep-HPLC to give N-(1-(7-bromoimidazo[1,5-a]pyridin-1-yl)ethyl)-1-((6-cyclopropylimidazo[1,2-a]pyridin-2-yl)methyl)-1H-pyrazole-4-carboxamide (4.4 mg, yield: 21%) as a white solid. ESI-MS [M+H]⁺: 504.1. Purity: 98.49%. ¹H NMR (400 MHz, DMSO): δ 8.41 (d, J=8.0 Hz, 1H), 8.33 (s, 1H), 8.31 (s, 1H), 8.27-8.19 (m, 2H), 7.89-7.85 (m, 2H), 7.72 (s, 1H), 7.39 (d, J=9.3 Hz, 1H), 7.02-6.97 (m, 1H), 6.72-6.67 (m, 1H), 5.49-5.40 (m, 1H), 5.38 (s, 2H), 1.96-1.87 m, 1H), 1.54 (d, J=7.0 Hz, 3H), 0.94-0.88 (m, 2H), 0.69-0.63 (m, 2H).

Example 75

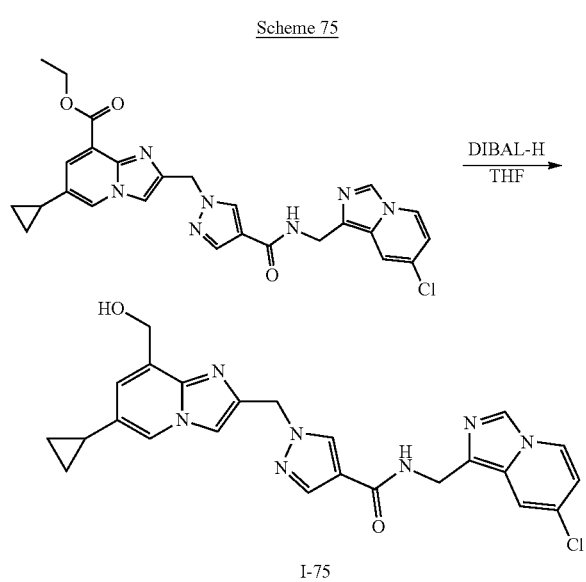

I-75

Synthesis of N-((7-chloroimidazo[1,5-a]pyridin-1-yl)methyl)-1-((6-cyclopropyl-8-(hydroxymethyl)imidazo[1,2-a]pyridin-2-yl)methyl)-1H-pyrazole-4-carboxamide (I-75)

A solution of ethyl 2-((4-(((7-chloroimidazo[1,5-a]pyridin-1-yl)methyl)carbamoyl)-1H-pyrazol-1-yl)methyl)-6-cyclopropylimidazo[1,2-a]pyridine-8-carboxylate (40 mg, 0.074 mmol) in THF (3 mL) was added DIBAL-H (0.5 mL, 1 M) and the mixture was stirred at RT for 1 h. The reaction was quenched with saturated NH₄Cl solution (10 mL) and extracted with EtOAc (30 mL×3). The combined organic layers were concentrated to give the crude, which was purified by prep-HPLC to give N-((7-chloroimidazo[1,5-a]pyridin-1-yl)methyl)-1-((6-cyclopropyl-8-(hydroxymethyl)imidazo[1,2-a]pyridin-2-yl)methyl)-1H-pyrazole-4-carboxamide (26.4 mg, 75% yield) as a white solid. ESI-MS [M+H]⁺: 476.2. Purity: 100%. ¹H NMR (400 MHz, DMSO): δ 8.58 (t, J=5.6 Hz, 1H), 8.31-8.29 (m, 2H), 8.21-8.19 (m, 2H), 7.87 (s, 1H), 7.78 (s, 1H), 7.69 (s, 1H), 7.00 (s, 1H), 6.64 (dd, J=7.4, 2.0 Hz, 1H), 5.38 (s, 2H), 5.32 (t, J=3.8 Hz, 1H), 4.74 (d, J=3.8 Hz, 2H), 4.55 (d, J=5.7 Hz, 2H), 1.97-1.90 (m, 1H), 0.97-0.86 (m, 2H), 0.70-0.60 (m, 2H).

Example 76

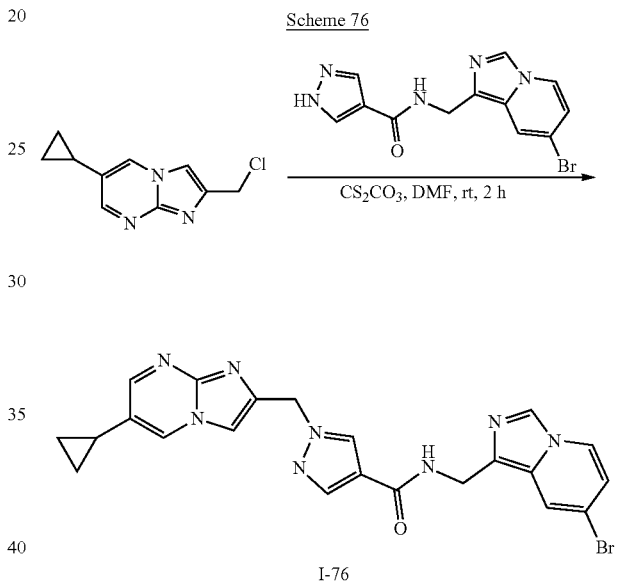

I-76

Synthesis of N-((7-bromoimidazo[1,5-a]pyridin-1-yl)methyl)-1-((6-cyclopropylimidazo[1,2-a]pyrimidin-2-yl)methyl)-1H-pyrazole-4-carboxamide (I-76)

A mixture of 2-(chloromethyl)-6-cyclopropylimidazo[1,2-a]pyrimidine (40 mg, 0.19 mmol), N-((7-bromoimidazo[1,5-a]pyridin-1-yl)methyl)-1H-pyrazole-4-carboxamide (61 mg, 0.19 mmol), Cs₂CO₃ (248 mg, 0.76 mmol) in DMF (2 mL) was stirred at RT for 2 h. Then the reaction mixture was diluted with H₂O (30 mL) and extracted with EtOAc (30 mL×3). The combined organic layers were dried over Na₂SO₄, concentrated and purified by column chromatography (PE/EA=10/1) to give the desired compound N-((7-bromoimidazo[1, 5-a]pyridin-1-yl)methyl)-1-((6-cyclopropylimidazo[1,2-a]pyrimidin-2-yl)methyl)-1H-pyrazole-4-carboxamide (25 mg, yield: 27%) as a white solid. ESI-MS [M+H]⁺: 491.1. Purity: 96.39%. ¹H NMR (400 MHz, DMSO): δ 8.69 (d, J=2.4 Hz, 1H), 8.59 (t, J=5.7 Hz, 1H), 8.41 (d, J=2.5 Hz, 1H), 8.32 (s, 1H), 8.27-8.20 (m 2H), 7.95 (d, J=0.9 Hz, 1H), 7.87 (s, 1H), 7.63 (s, 1H), 6.75-6.69 (m, 1H), 5.43 (s, 2H), 4.55 (d, J=5.7 Hz, 2H), 2.02-1.93 (m, 1H), 1.02-0.92 (m, 2H), 0.79-0.70 (m, 2H).

Example 77

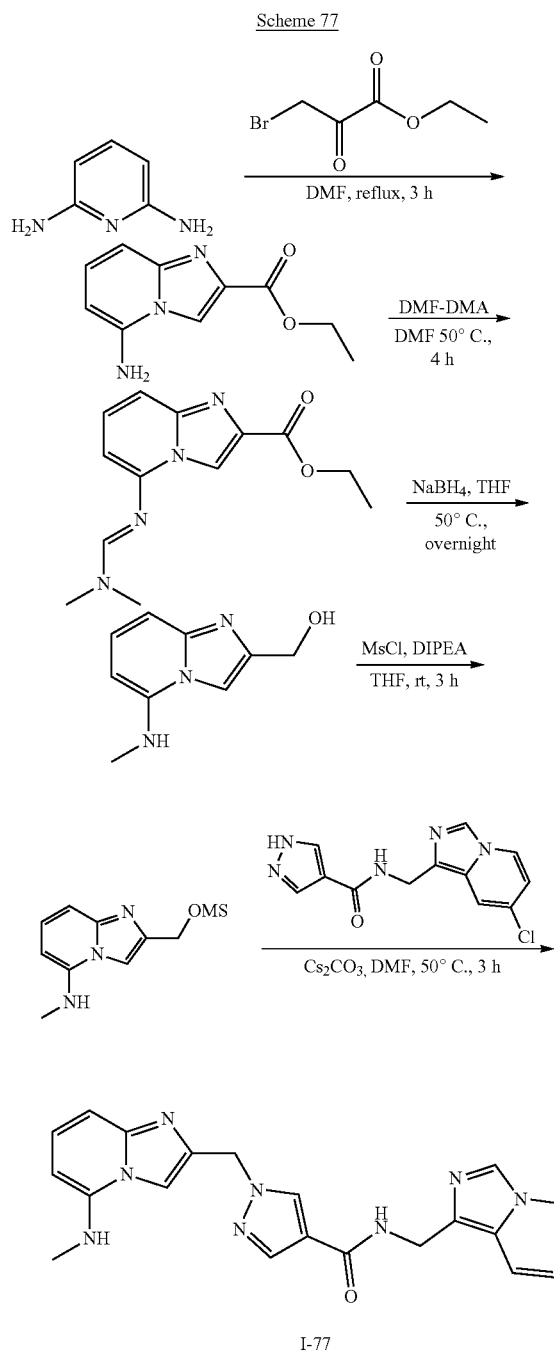

Synthesis of Ethyl 5-aminoimidazo[1,2-a]pyridine-2-carboxylate

A mixture of pyridine-2,6-diamine (1.09 g, 10 mmol), ethyl 3-bromo-2-oxopropanoate (1.62 g, 8.3 mmol) in DMF (10 mL) was stirred at 90° C. for 3 h. The mixture was concentrated to give crude ethyl 5-aminoimidazo[1,2-a]pyridine-2-carboxylate (2.7 g, yield: 100%) as a black solid, which was used in the next step without further purification. ESI-MS [M+H]+: 206.2.

Synthesis of Ethyl (E)-5-(((dimethylamino)methylene)amino)imidazo[1,2-a]pyridine-2-carboxylate A mixture of ethyl 5-aminoimidazo[1,2-a]pyridine-2-carboxylate (1.7 g, crude) and DMF-DMA (5 mL) in DMF (5 mL) was stirred at 50° C. for 3 h. The mixture was diluted with H₂O (50 mL), extracted with EtOAc (50 mL×3). The combined organic layers were washed with brine, dried over Na₂SO₄ and concentrated in vacuo to give the crude, which was purified by silica gel chromatography (MeOH/DCM=1/10) to give ethyl (E)-5-(((dimethylamino)methylene)amino) imidazo[1,2-a]pyridine-2-carboxylate (307 mg, yield: 14%) as a white solid. ESI-MS [M+H]+: 261.2.

Synthesis of (5-(methylamino)imidazo[1,2-a]pyridin-2-yl)methanol

A mixture of ethyl (E)-5-(((dimethylamino)methylene) amino)imidazo[1,2-a]pyridine-2-carboxylate (217 mg, 0.83 mmol) and NaBH₄ (314 mg, 8.3 mmol) in THF (10 mL) was stirred at 60° C. overnight. The mixture was then quenched with 1 M HCl solution and filtered. The filtrate was concentrated to get a crude, which was purified by prep-TLC (MeOH/DCM=1/3) to give (5-(methylamino)imidazo[1,2-a] pyridin-2-yl)methanol (52 mg, yield: 35%) as a white solid. ESI-MS [M+H]+: 178.2.

Synthesis of (5-(methylamino)imidazo[1,2-a]pyridin-2-yl)methyl methanesulfonate To a solution of (5-(methylamino)imidazo[1,2-a]pyridin-2-yl)methanol (32 mg, 0.18 mmol) and DIPEA (70 mg, 0.54 mmol) in THF (10 mL) was added methanesulfonyl chloride (50.4 mg, 2.4 mmol). The mixture was stirred at RT for 3 h. Water (50 mL) was added and extracted with EtOAc (50 mL×3). The combined organic layers were concentrated to give the (5-(methylamino)imidazo[1,2-a]pyridin-2-yl) methyl methanesulfonate, which was used into the next step without further purification. ESI-MS [M+H]+: 256.2.

Synthesis of N-((7-chloroimidazo[1,5-a]pyridin-1-yl)methyl)-1-((5-(methylamino)imidazo[1,2-a]pyridin-2-yl)methyl)-1H-pyrazole-4-carboxamide (I-77)

A mixture of (5-(methylamino)imidazo[1,2-a]pyridin-2-yl)methyl methanesulfonate (45.9 mg, crude), N-((7-chloroimidazo[1,5-a]pyridin-1-yl)methyl)-1H-pyrazole-4-carboxamide (50 mg, 0.18 mmol), and Cs₂CO₃ (596 mg, 1.8 mmol) in DMF (5 mL) was stirred at 50° C. for 3 h. Water (30 mL) was added to the reaction and extracted with EtOAc (50 mL×3). The combined organic layers were washed with brine, dried over Na₂SO₄ and concentrated in vacuo to give the crude, which was purified by prep-HPLC (DCM/MeOH=10/1) to give N-((7-chloroimidazo[1,5-a]pyridin-1-yl)methyl)-1-((5-(methylamino)imidazo[1,2-a]pyridin-2-yl)methyl)-1H-pyrazole-4-carboxamide (5.2 mg, yield: 6.6%) as a white solid. ESI-MS [M+H]+: 435.2. Purity: 96.21%. ¹H NMR (400 MHz, DMSO): δ 8.59 (t, J=5.6 Hz, 1H), 8.31-8.29 (m, 2H), 8.22 (s, 1H), 7.87 (s, 1H), 7.79-7.78 (m, 1H), 7.70 (s, 1H), 7.20-7.16 (m, 1H), 6.80-6.77 (m, 2H), 6.64 (dd, J=7.4, 2.1 Hz, 1H), 5.80 (d, J=7.4 Hz, 1H), 5.40 (s, 2H), 4.55 (d, J=5.7 Hz, 2H), 2.86 (d, J=4.6 Hz, 3H).

Example 78

Scheme 78

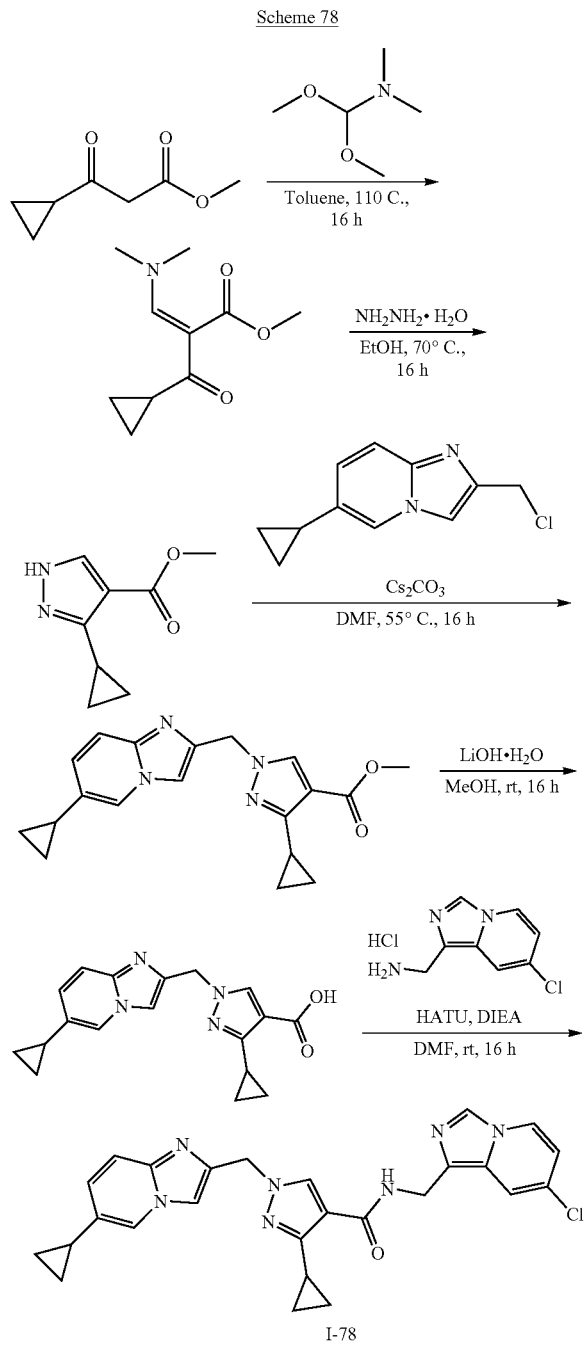

I-78

Synthesis of Methyl (Z)-2-(cyclopropanecarbonyl)-3-(dimethylamino)acrylate

To a mixture of 3-cyclopropyl-3-oxo-propionic acid methyl ester (5 g, 35 mmol) in yoluene (20 mL) was added DMF-DMA (8 mL, 36.75 mmol). The resulting reaction was heated at 110° C. for 16 h. After cooled to RT, the mixture was concentrated to give crude 2-cyclopropanecarbonyl-3-dimethylamino-acrylic acid methyl ester (5.3 g, yield: 77%) as a white solid, which was used in the next step without further purification. ESI-MS [M+H]$^+$: 198.1.

Synthesis of Methyl 3-cyclopropyl-1H-pyrazole-4-carboxylate

To a solution of methyl (Z)-2-(cyclopropanecarbonyl)-3-(dimethylamino)acrylate (5.3 g, 27 mmol) in EtOH (20 mL) was added hydrazine hydrate (4 mL) dropwise. The reaction mixture was stirred at 70° C. for 16 h under N$_2$ atmosphere. The reaction mixture was concentrated to give the residue, which was purified by silica gel column chromatography (petroleum ether/ethyl acetate=5/1) to give methyl 3-cyclopropyl-1H-pyrazole-4-carboxylate (2.9 g, yield 65%) as a white solid. ESI-MS [M+H]$^+$: 167.1.

Synthesis of Methyl 3-cyclopropyl-1-((6-cyclopropylimidazo[1,2-a]pyridin-2-yl)methyl)-1H-pyrazole-4-carboxylate To a solution of methyl 3-cyclopropyl-1H-pyrazole-4-carboxylate (200 mg, 1.20 mmol) in dry DMF (5 mL) was added 2-(chloromethyl)-6-cyclopropylimidazo[1,2-a]pyridine (248 mg, 1.20 mmol) and Cs$_2$CO$_3$ (1.17 g, 3.6 mmol). Then the reaction mixture was stirred at 55° C. for 16 h under N$_2$ atmosphere. After cooling to RT, the reaction was diluted with H$_2$O (50 mL), extracted with ethyl acetate (50 mL×3). The combined organic layers were washed with brine (20 mL), dried over anhydrous Na$_2$SO$_4$ and concentrated in vacuo to give the residue, which was purified by silica gel column chromatography (DCM/methanol=10/1) to give methyl 3-cyclopropyl-1-((6-cyclopropylimidazo[1,2-a]pyridin-2-yl)methyl)-1H-pyrazole-4-carboxylate (390 mg, yield 96%) as a white solid. ESI-MS [M+H]$^+$: 337.4.

Synthesis of 3-cyclopropyl-1-((6-cyclopropylimidazo[1,2-a]pyridin-2-yl)methyl)-1H-pyrazole-4-carboxylic Acid To a solution of methyl 3-cyclopropyl-1-((6-cyclopropylimidazo[1,2-a]pyridin-2-yl)methyl)-1H-pyrazole-4-carboxylate (300 mg, 0.89 mmol) in methanol (5 mL) and H$_2$O (5 mL) was added LiOH H$_2$O (187 mg, 4.45 mmol). The resulting reaction was stirred at 50° C. for 16 h. Most of the solvent was removed and the residue was diluted with H$_2$O (10 mL), the pH value of mixture was adjusted to 4-5 by adding HCl (1 M). The precipitate was collected and dried to give 3-cyclopropyl-1-((6-cyclopropylimidazo[1,2-a]pyridin-2-yl)methyl)-1H-pyrazole-4-carboxylic acid (230 mg yield 80%) as a white solid. ESI-MS [M+H]$^+$: 323.1.

Synthesis of N-((7-chloroimidazo[1,5-a]pyridin-1-yl)methyl)-3-cyclopropyl-1-((6-cyclopropylimidazo[1,2-a]pyridin-2-yl)methyl)-1H-pyrazole-4-carboxamide (I-78)

To a solution of 3-cyclopropyl-1-((6-cyclopropylimidazo[1,2-a]pyridin-2-yl)methyl)-1H-pyrazole-4-carboxylic acid (110 mg, 0.34 mmol) in dry DMF (3 mL) was added (7-chloroimidazo[1,5-a]pyridin-1-yl)methanamine hydrochloride (148 mg, 0.68 mmol), HATU (194 mg, 0.51 mmol) and DIPEA (132 mg, 1.02 mmol). The reaction mixture was stirred at RT for 16 h. The reaction mixture was diluted with H$_2$O (20 mL) and extracted with EtOAc (30 mL×3). The combined organic layers were washed with brine (20 mL×2), dried over anhydrous Na$_2$SO$_4$ and concentrated in vacuo to give a residue, which was purified by prep-TLC (DCM/MeOH=10/1) to afford N-((7-chloroimidazo[1,5-a]pyridin-1-yl)methyl)-3-cyclopropyl-1-((6-cyclopropylimidazo[1,2-a]pyridin-2-yl)methyl)-1H-pyrazole-4-carboxamide (47 mg, yield: 29%) as a white solid. ESI-MS [M+H]+: 486.2. Purity: 100%. 1H NMR (400 MHz, DMSO-d6): δ 8.34-8.29 (m, 4H), 8.07 (s, 1H), 7.83-7.72 (m, 1H), 7.70 (s, 1H), 7.39 (d, J=9.3 Hz, 1H), 6.99 (dd, J=9.4, 1.7 Hz, 1H), 6.64 (dd, J=7.5, 2.1 Hz, 1H), 5.24 (s, 2H), 4.53 (d, J=5.7 Hz, 2H), 2.71-2.60 (m, 1H), 1.97-1.86 (m, 1H), 0.95-0.88 (m, 2H), 0.85-0.79 (m, 2H), 0.76-0.72 (m, 2H), 0.68-0.64 (m, 2H).

Example 79

Scheme 79

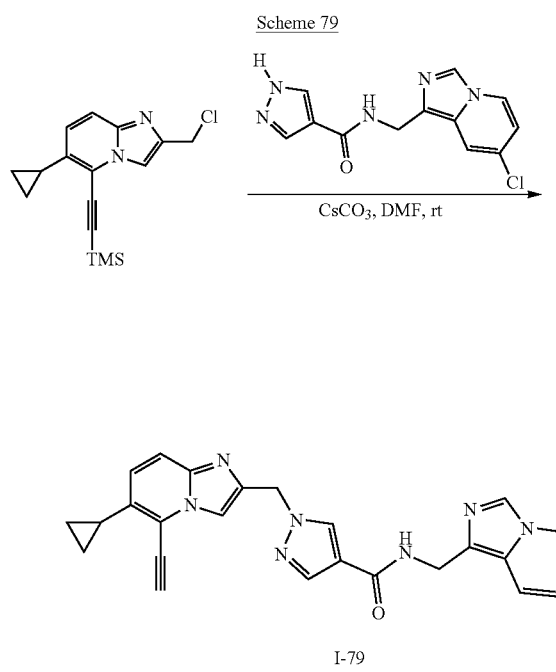

I-79

N-((7-chloroimidazo[1,5-a]pyridin-1-yl)methyl)-1-((6-cyclopropyl-5-ethynylimidazo[1,2-a]pyridin-2-yl)methyl)-1H-pyrazole-4-carboxamide (I-79)

To a solution of 2-(chloromethyl)-6-cyclopropyl-5-((trimethylsilyl)ethynyl)imidazo[1,2-a]pyridine (30 mg, 0.1 mmol) and N-((7-chloroimidazo[1,5-a]pyridin-1-yl)methyl)-1H-pyrazole-4-carboxamide (27.5 mg, 0.1 mmol) in DMF (4 mL) was added Cs2CO3 (174 mg, 0.8 mmol). The reaction was stirred at RT for 4 h. The reaction mixture was concentrated to give the crude which was purified by prep-HPLC to give N-((7-chloroimidazo[1,5-a]pyridin-1-yl)methyl)-1-((6-cyclopropyl-5-ethynylimidazo[1,2-a]pyridin-2-yl)methyl)-1H-pyrazole-4-carboxamide (7.7 mg, yield: 16.7%) as a pale solid. ESI-MS [M+H]+: 470.1. Purity: 100%. 1H NMR (400 MHz, DMSO) 8.58 (t, J=5.7 Hz, 1H), 8.33-8.27 (m, 2H), 8.22 (s, 1H), 7.90 (s, 1H), 7.86 (s, 1H), 7.80-7.74 (m, 1H), 7.54 (d, J=9.4 Hz, 1H), 6.81 (d, J=9.5 Hz, 1H), 6.67-6.62 (m, 1H), 5.46-5.42 (m, 3H), 4.55 (d, J=5.7 Hz, 2H), 2.30-2.22 (m, 1H), 1.12-1.01 (m, 2H), 0.85-0.75 (m, 2H).

Example 80

Scheme 80

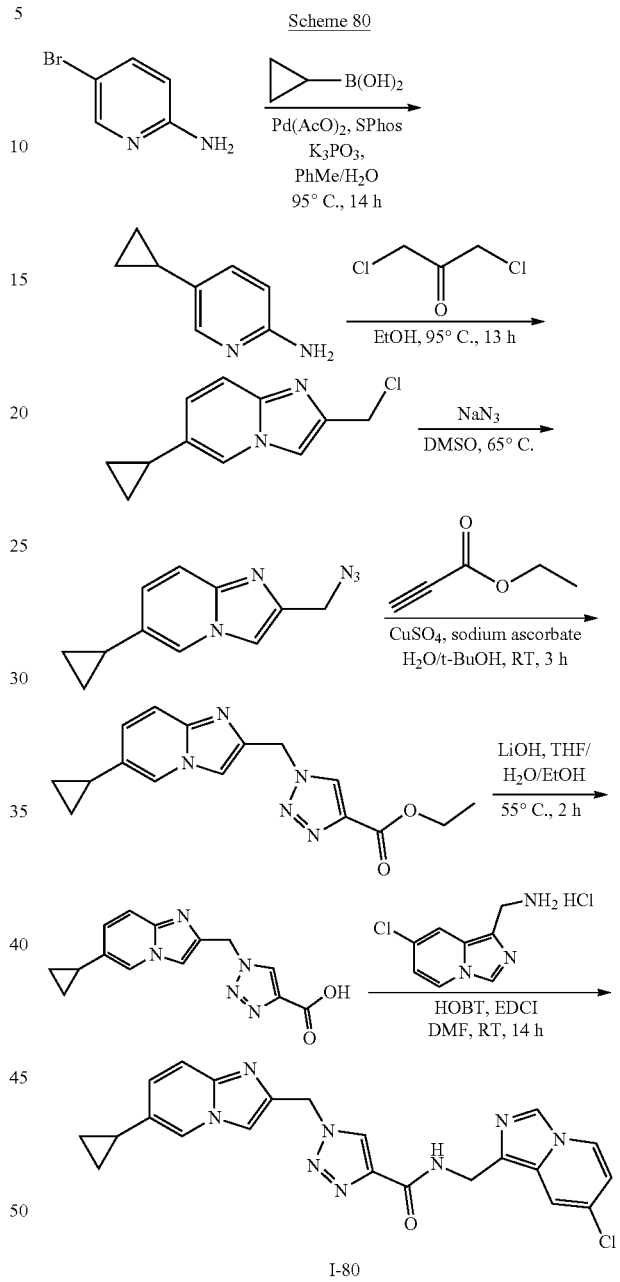

I-80

Synthesis of 5-cyclopropylpyridin-2-amine

A mixture of 5-bromopyridin-2-amine (100 g, 585 mmol), cyclopropylboronic acid (60 g, 701 mmol), Pd(AcO)2 (6.5 g, 29 mmol), SPhos (24 g, 58.5 mmol) and K3PO4 (372 g, 1.755 mol) in toluene/H2O (1.2 L/0.12 L) was stirred at 90° C. for 14 h under N2. The reaction was concentrated in vacuo to give the crude, which was purified with silica gel chromatography (PE/EA=1/2) to give the 5-cyclopropylpyridin-2-amine (61 g, yield: 78%) as a yellow solid. ESI-MS [M+H]+: 135.1.

Synthesis of 2-(chloromethyl)-6-cyclopropylimidazo[1,2-a]pyridine

A mixture of 5-cyclopropylpyridin-2-amine (61 g, 455 mmol) and 1,3-dichloropropan-2-one (172 g, 1365 mmol) in EtOH (1 L) was stirred at 95° C. for 13 h. The reaction was concentrated to remove the EtOH. The pH of the residue was adjusted to 9 by addition of aqueous NaHCO$_3$ and extracted with EtOAc (1 L×3). The combined organic layers were washed with brine, dried over Na$_2$SO$_4$ and concentrated in vacuo to give the crude, which was purified with silica gel chromatography (EA) to give the 2-(chloromethyl)-6-cyclopropylimidazo[1,2-a]pyridine (40 g, yield: 42%) as a yellow solid. ESI-MS [M+H]$^+$: 207.1.

Synthesis of 2-(azidomethyl)-6-cyclopropylimidazo[1,2-a]pyridine

To a solution of 2-(chloromethyl)-6-cyclopropylimidazo[1,2-a]pyridine (40 g, 193 mmol) in DMF (600 mL) was added NaN$_3$ (18.8 g, 290 mmol). The resulting reaction was stirred at RT for 2 h. The reaction was diluted with H$_2$O (500 mL) and extracted with EtOAc (500 mL×3). The combined organic layers were washed with brine, dried over Na$_2$SO$_4$ and concentrated in vacuo to give the crude, which was purified with silica gel chromatography (PE/EA=2/1) to give the 2-(azidomethyl)-6-cyclopropylimidazo[1,2-a]pyridine (35 g, yield: 85%) as a yellow solid. ESI-MS [M+H]$^+$: 214.1.

Synthesis of Ethyl 1-((6-cyclopropylimidazo[1,2-a]pyridin-2-yl)methyl)-1H-1,2,3-triazole-4-carboxylate A mixture of 2-(azidomethyl)-6-cyclopropylimidazo[1,2-a]pyridine (35 g, 163.5 mmol), ethyl propiolate (17.6 g, 180 mmol), CuSO$_4$ (2.6 g, 16.35 mmol) and sodium ascorbate (3.3 g, 16.35 mmol) in H$_2$O/t-BuOH (150 mL/150 mL) was stirred at RT for 3 h. Yellow solid was precipitated after 3 h and the mixture was filtered. The cake was dried to give the ethyl 1-((6-cyclopropylimidazo[1,2-a]pyridin-2-yl)methyl)-1H-1,2,3-triazole-4-carboxylate (29 g, yield: 57%) as a yellow solid, which was used in the next step without further purification. ESI-MS [M+H]$^+$: 312.1.

Synthesis of 1-((6-cyclopropylimidazo[1,2-a]pyridin-2-yl)methyl)-1H-1,2,3-triazole-4-carboxylic Acid A mixture of ethyl 1-((6-cyclopropylimidazo[1,2-a]pyridin-2-yl)methyl)-1H-1,2,3-triazole-4-carboxylate (29 g, 93.2 mmol) and LiOH (6.7 g, 279.6 mmol, solution in 50 mL H$_2$O) in THF/EtOH (150 mL/150 mL) was stirred at 50° C. for 2 h. The reaction was concentrated to remove most of the solvent. The pH of the residue was adjusted to 4 by 2N HCl and a pink solid was precipitated out. The mixture was filtered and the filter cake was dried to give 1-((6-cyclopropylimidazo[1,2-a]pyridin-2-yl)methyl)-1H-1,2,3-triazole-4-carboxylic acid (20 g, 77%) as a pink solid. ESI-MS [M+H]$^+$: 284.1.

Synthesis of N-((7-chloroimidazo[1,5-a]pyridin-1-yl)methyl)-1-((6-cyclopropylimidazo[1,2-a]pyridin-2-yl)methyl)-1H-1,2,3-triazole-4-carboxamide (I-80)

To a solution of 1-((6-cyclopropylimidazo[1,2-a]pyridin-2-yl)methyl)-1H-1,2,3-triazole-4-carboxylic acid (10 g, 35.3 mmol), (7-chloroimidazo[1,5-a]pyridin-1-yl)methanamine hydrochloride (9.2 g, 42.4 mmol), HOBT (6.67 g, 49.42 mmol) and EDCI (9.5 g, 49.42 mmol) in DMF (500 mL) was added DIPEA (31.3 mL, 176.5 mmol). The resulting mixture was stirred at RT for 14 h. The reaction was poured into H$_2$O (1 L) and yellow solid was precipitated out. The mixture was filtered and the cake was dried to give the crude, which was purified with silica gel chromatography (DCM/MeOH=10/1) to give the N-((7-chloroimidazo[1,5-a]pyridin-1-yl)methyl)-1-((6-cyclopropylimidazo[1,2-a]pyridin-2-yl)methyl)-1H-1,2,3-triazole-4-carboxamide (7.2 g, yield: 45.9%) as a white solid. HPLC Purity: 99.09% (214 nm), 99.18% (254 nm). LCMS m/z: 447.1 [M+H]*, t$_R$=1.098 (min). $^1$H NMR (400 MHz, DMSO): δ 8.91 (t, J=5.8 Hz, 1H), 8.56 (s, 1H), 8.34 (s, 1H), 8.31-8.29 (m, 2H), 7.84-7.82 (m, 2H), 7.40 (d, J=9.3 Hz, 1H), 7.01 (dd, J=9.4, 1.7 Hz, 1H), 6.64 (dd, J=7.5, 2.1 Hz, 1H), 5.72 (s, 2H), 4.62 (d, J=5.9 Hz, 2H), 1.95-1.89 (m, 1H), 0.94-0.89 (m, 2H), 0.69-0.65 (m, 2H).

Example 81

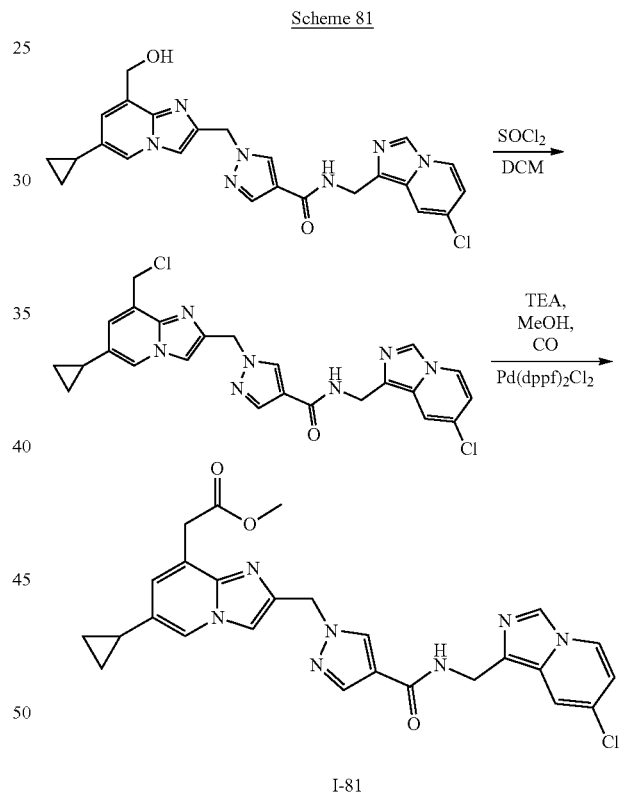

Scheme 81

I-81

Synthesis of N-((7-chloroimidazo[1,5-a]pyridin-1-yl)methyl)-1-((8-(chloromethyl)-6-cyclopropylimidazo[1,2-a]pyridin-2-yl)methyl)-1H-pyrazole-4-carboxamide To a solution of N-((7-chloroimidazo[1,5-a]pyridin-1-yl)methyl)-1-((6-cyclopropyl-8-(hydroxymethyl)imidazo[1,2-a]pyridin-2-yl)methyl)-1H-pyrazole-4-carboxamide (80 mg, 0.17 mmol) in DCM (5 mL) was added SOCl$_2$ (0.5 mL, 1.7 mmol) slowly at 0° C. The resulting mixture was stirred at RT for 2 h. The reaction was concentrated in vacuo to give the crude, which was purified by silica gel chromatography (EtOAc/PE=2/1) to give methyl 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)acetate (20 mg, yield: 24%) as a white solid. ESI-MS [M+H]$^+$: 494.2.

Synthesis of Methyl 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)acetate (I-81)

A mixture methyl 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)acetate (40 mg, 0.08 mmol), Pd(dppf)$_2$Cl$_2$ (20 mg, 0.016 mmol), TEA (0.5 mL, 0.4 mmol) in MeOH (15 mL) was stirred at 55° C. for 3 h under CO atmosphere. The reaction was monitored by LCMS until the starting material consumed. The reaction was concentrated in vacuo to give the crude, which was purified by prep-HPLC to give methyl 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)acetate (22.7 mg, 55% yield) as a white solid. ESI-MS [M+H]$^+$: 518.1. Purity: 95.6%. $^1$H NMR (400 MHz, DMSO): δ 8.58 (t, J=5.7 Hz, 1H), 8.34-8.28 (m, 2H), 8.25 (d, J=1.3 Hz, 1H), 8.18 (s, 1H), 7.87 (s, 1H), 7.80-7.74 (m, 1H), 7.66 (s, 1H), 6.94 (d, J=1.2 Hz, 1H), 6.64 (dd, J=7.4, 2.1 Hz, 1H), 5.38 (s, 2H), 4.55 (d, J=5.7 Hz, 2H), 3.89 (s, 2H), 3.57 (s, 3H), 1.94-1.87 (m, 1H), 0.94-0.89 (m, 2H), 0.69-0.60 (m, 2H).

Example 82

Scheme 82

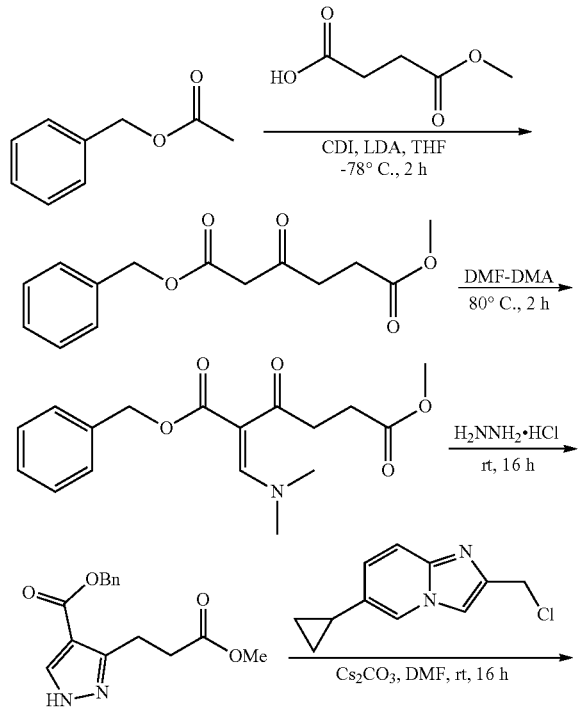

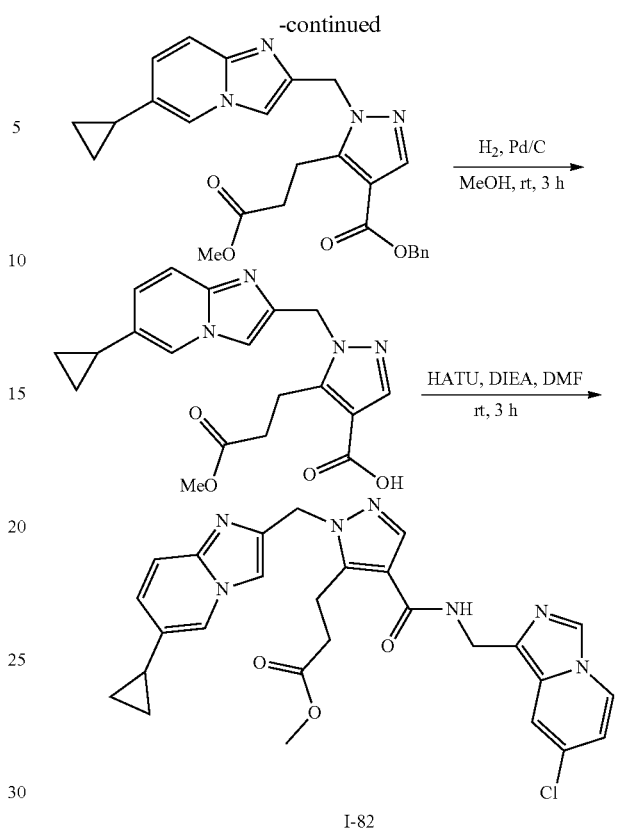

I-82

Synthesis of 1-benzyl 6-methyl 3-oxohexanedioate

To a solution of benzyl acetate (1.5 g, 10 mmol) in THF (10 mL) was added LDA (1 M, 15 mmol) at −78° C. and stirred for 1 h (solution A). To a solution of 4-methoxy-4-oxobutanoic acid (1.58 g, 12 mmol) in THF (10 mL) was added CDI (1.94 g, 12 mmol) and stirred at RT for 30 min (solution B). Solution B was added to solution A at −78° C. and stirred for another 2 h. Saturated NH$_4$Cl (100 mL) was added to quenched the reaction and the reaction mixture was extracted with EtOAc (100 mL×3). The combined organics were concentrated and purified by silica gel chromatography (EA/PE=1/10) to give 1-benzyl 6-methyl 3-oxohexanedioate (500 mg, yield: 19%) as a colorless oil. ESI-MS [M+H]$^+$: 265.1.

Synthesis of 1-benzyl 6-methyl (E)-2-((dimethylamino)methylene)-3-oxohexanedioate A solution of 1-benzyl 6-methyl 3-oxohexanedioate (490 mg, 1.86 mmol) in DMF-DMA (443 mg, 3.72 mmol) was heated to 80° C. for 2 h and then concentrated to give 1-benzyl 6-methyl (E)-2-((dimethylamino)methylene)-3-oxohexanedioate (600 mg, crude) as a yellow oil which was used in the next step without purification. ESI-MS [M+H]$^+$: 320.1.

Synthesis of benzyl 3-(3-methoxy-3-oxopropyl)-1H-pyrazole-4-carboxylate

To a solution of 1-benzyl 6-methyl (E)-2-((dimethylamino)methylene)-3-oxohexanedioate (600 mg, 1.86 mmol) in MeOH (6 mL) was added hydrazine hydrochloride (255 mg, 3.72 mmol). The mixture was stirred at RT for 16 h. The reaction was concentrated to give the crude, which was purified by silica gel chromatography (EA/PE=1/1) to give benzyl 3-(3-methoxy-3-oxopropyl)-1H-pyrazole-4-carboxylate (384 mg, yield: 64% for two steps) as a yellow oil. ESI-MS [M+H]+: 289.1.

Synthesis of benzyl 1-((6-cyclopropylimidazo[1,2-a]pyridin-2-yl)methyl)-5-(3-methoxy-3-oxopropyl)-1H-pyrazole-4-carboxylate To a solution of benzyl 3-(3-methoxy-3-oxopropyl)-1H-pyrazole-4-carboxylate (90 mg, 0.31 mmol) and 2-(chloromethyl)-6-cyclopropylimidazo[1,2-a]pyridine (78 mg, 0.38 mmol) in DMF (5 mL) was added Cs$_2$CO$_3$ (302 mg, 0.93 mmol) at RT. The mixture was stirred at RT for 16 h. The reaction was quenched with H$_2$O (10 mL) and extracted with ethyl acetate (3×50 mL). The organic layers were washed with brine, dried over Na$_2$SO$_4$, and the solvent is evaporated under reduced pressure to give a residue which was purified by prep-TLC (MeOH/DCM=1/15) to give benzyl 1-((6-cyclopropylimidazo[1,2-a]pyridin-2-yl)methyl)-5-(3-methoxy-3-oxopropyl)-1H-pyrazole-4-carboxylate (30 mg, yield: 20%) as yellow oil. ESI-MS [M+H]+: 459.1.

Synthesis of 1-((6-cyclopropylimidazo[1,2-a]pyridin-2-yl)methyl)-5-(3-methoxy-3-oxopropyl)-1H-pyrazole-4-carboxylic Acid To a solution of benzyl 1-((6-cyclopropylimidazo[1,2-a]pyridin-2-yl)methyl)-5-(3-methoxy-3-oxopropyl)-1H-pyrazole-4-carboxylate (100 mg, 0.22 mmol) in MeOH (10 mL) was added Pd/C (10%, 30 mg). The mixture was stirred at RT for 3 h under H$_2$. The reaction was filtrated and concentrated to give 1-((6-cyclopropylimidazo[1,2-a]pyridin-2-yl)methyl)-5-(3-methoxy-3-oxopropyl)-1H-pyrazole-4-carboxylic acid (67 mg, 83%) as a white solid. ESI-MS [M+H]+: 369.1.

Synthesis of Methyl 3-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-5-yl)propanoate (I-82)

To a solution of 1-((6-cyclopropylimidazo[1,2-a]pyridin-2-yl)methyl)-5-(3-methoxy-3-oxopropyl)-1H-pyrazole-4-carboxylic acid (80 mg, 0.22 mmol) and (7-chloroimidazo[1,5-a]pyridin-1-yl)methanamine hydrochloride (48 mg, 0.26 mmol) in dry DMF (4 mL) was added HATU (125 mg, 0.33 mmol) and DIPEA (114 mg, 0.88 mmol) at RT. The reaction was stirred for 3 h. Water (30 mL) was added and the mixture was extracted with EtOAc (50 mL×3). The organic layers were washed with brine (80 mL), dried over Na$_2$SO$_4$ and concentrated in vacuo to give the crude, which was purified by prep-HPLC (DCM/MeOH=10/1) to give methyl 3-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-5-yl)propanoate (15.4 mg, yield: 13%) as a yellow solid. ESI-MS [M+H]+: 532.2. Purity: 98.7%. $^1$H NMR (400 MHz, DMSO): δ 8.70-8.54 (m, 2H), 8.48 (s, 1H), 8.34 (dd, J=7.5, 0.8 Hz, 1H), 8.04-8.01 (m, 2H), 7.87-7.79 (m, 1H), 7.74 (d, J=9.3 Hz, 1H), 7.62 (d, J=9.0 Hz, 1H), 6.72 (dd, J=7.5, 2.1 Hz, 1H), 5.66 (s, 2H), 4.61 (d, J=5.7 Hz, 2H), 3.58 (s, 3H), 3.33-3.24 (m, 2H), 2.69-2.59 (m, 2H), 2.13-1.97 (m, 1H), 1.09-0.97 (m, 2H), 0.81-0.69 (m, 2H).

Example 83

Scheme 83

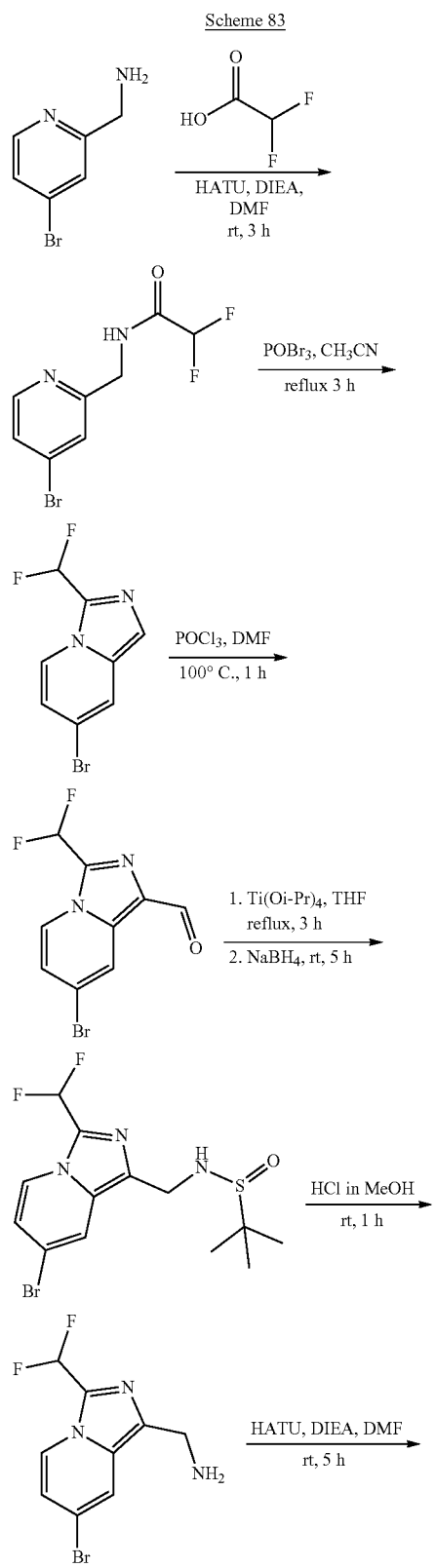

-continued

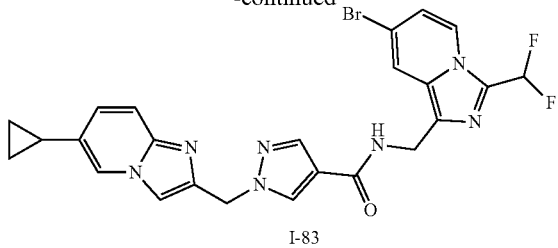

I-83

Synthesis of N-((4-bromopyridin-2-yl)methyl)-2,2-difluoroacetamide

To a mixture of (4-bromopyridin-2-yl)methanamine (500 mg, 2.67 mmol), DIPEA (1.7 g, 13.4 mmol) and 2,2-difluoroacetic acid (256 mg, 2.67 mmol) in DMF (10 mL) was added HATU (2.0 g, 5.34 mmol). The mixture was stirred at RT for 3 h. Water (100 mL) was added and the mixture was extracted with EtOAc (100 mL×3). The combined organics were washed with brine, dried over Na$_2$SO$_4$ and concentrated to give the crude, which was purified by silica gel chromatography (EA/PE=1/2) to give N-((4-bromopyridin-2-yl)methyl)-2,2-difluoroacetamide (400 mg, yield: 56%) as a yellow oil. ESI-MS [M+H]$^+$: 265.0

Synthesis of 7-bromo-3-(difluoromethyl)imidazo[1,5-a]pyridine

To a solution of N-((4-bromopyridin-2-yl)methyl)-2,2-difluoroacetamide (400 mg, 1.5 mmol) in CH$_3$CN (10 mL) was added POBr$_3$ (2.2 g, 7.5 mmol), The mixture was heated to reflux for 3 h. After cooled to RT, H$_2$O (50 mL) was added and extracted with EtOAc (50 mL×4). The organic layers were dried over Na$_2$SO$_4$ and concentrated to give the crude, which was purified by silica gel chromatography (EA/PE=1/2) to give 7-bromo-3-(difluoromethyl)imidazo[1,5-a]pyridine (180 mg, yield: 49%) as a yellow oil. ESI-MS [M+H]2:6247.0.

Synthesis of 7-bromo-3-(difluoromethyl)imidazo[1,5-a]pyridine-1-carbaldehyde To a solution of 7-bromo-3-(difluoromethyl)imidazo[1,5-a]pyridine (180 mg, 0.73 mmol) in DMF (3 mL) was added POCl$_3$ (223 m, 1.46 mmol). The mixture was stirred at 100° C. for 1 h. After cooled to RT, H$_2$O (30 mL) was added and extracted with EtOAc (50 mL×3). The organic phase was dried over Na$_2$SO$_4$, concentrated and purified by silica gel chromatography (EA/PE=1/2) to give 7-bromo-3-(difluoromethyl)imidazo[1,5-a]pyridine-1-carbaldehyde (100 mg, yield: 50%) as a yellow oil. ESI-MS [M+H]$^+$: 275.0.

Synthesis of N-((7-bromo-3-(difluoromethyl)imidazo[1,5-a]pyridin-1-yl)methyl)-2-methylpropane-2-sulfinamide To a solution of 7-bromo-3-(difluoromethyl)imidazo[1,5-a]pyridine-1-carbaldehyde (100 mg, 0.36 mmol) and 2-methylpropane-2-sulfinamide (65 mg, 0.54 mmol) in THF (5 mL) was added Ti(Oi-Pi)$_4$ (305 mg, 1.08 mmol). The mixture was refluxed for 3 h. After cooled to RT, NaBH$_4$ (69 mg, 1.8 mmol) was added. The mixture was stirred at RT for 5 h. The reaction was then quenched with H$_2$O (20 mL) and the mixture was extracted with ethyl acetate (3×50 mL). The combined organic layers were washed with brine, dried over Na$_2$SO$_4$ and concentrated in vacuo to give the residue, which was purified by prep-TLC (MeOH/DCM=1/25) to give N-((7-bromo-3-(difluoromethyl)imidazo[1,5-a]pyridin-1-yl)methyl)-2-methylpropane-2-sulfinamide (100 mg, yield: 73%) as a yellow oil. ESI-MS [M+H]$^+$: 380.0.

Synthesis of (7-bromo-3-(difluoromethyl)imidazo[1,5-a]pyridin-1-yl)methanamine A mixture of N-((7-bromo-3-(difluoromethyl)imidazo[1,5-a]pyridin-1-yl)methyl)-2-methylpropane-2-sulfinamide (100 mg, 0.26 mmol) in HCl (4 M solution in MeOH, 5 mL) was stirred at RT for 1 h. The reaction was concentrated to give (7-bromo-3-(difluoromethyl)imidazo[1,5-a]pyridin-1-yl)methanamine (60 mg, 83%) as a white solid, which was used in the next step without further purification. ESI-MS [M+H]$^+$: 276.0.

Synthesis of N-((7-bromo-3-(difluoromethyl)imidazo[1,5-a]pyridin-1-yl)methyl)-1-((6-cyclopropylimidazo[1,2-a]pyridin-2-yl)methyl)-1H-pyrazole-4-carboxamide (I-83)

To a solution of (7-bromo-3-(difluoromethyl)imidazo[1,5-a]pyridin-1-yl)methanamine (40 mg, 0.15 mmol) and 1-((6-cyclopropylimidazo[1,2-a]pyridin-2-yl)methyl)-1H-pyrazole-4-carboxylic acid (49 mg, 0.17 mmol) in dry DMF (3 mL) was added HATU (83 mg, 0.22 mmol) and DIPEA (75 mg, 0.58 mmol) at RT. The reaction was stirred at RT for 5 h. Water (20 mL) was added and the mixture was extracted with EtOAc (25 mL×3). The organic layers were washed with brine (50 mL), dried over Na$_2$SO$_4$ and concentrated under reduced pressure to give the crude product, which was purified by prep-HPLC (DCM/MeOH=10/1) to give N-((7-bromo-3-(difluoromethyl)imidazo[1,5-a]pyridin-1-yl)methyl)-1-((6-cyclopropylimidazo[1,2-a]pyridin-2-yl)methyl)-1H-pyrazole-4-carboxamide (6 mg, yield: 8%) as a yellow solid. ESI-MS [M+H]$^+$: 540.1. Purity: 71.3%. $^1$H NMR (400 MHz, DMSO): δ 8.68 (t, J=5.5 Hz, 1H), 8.46 (s, 1H), 8.33 (d, J=7.4 Hz, 1H), 8.25 (s, 1H), 8.18 (s, 1H), 7.90-7.87 (m, 2H), 7.61-7.48 (m, 2H), 7.25 (d, J=8.7 Hz, 1H), 7.00 (dd, J=7.5, 1.8 Hz, 1H), 5.49 (s, 2H), 4.59 (d, J=5.6 Hz, 2H), 1.99-1.94 (m, 1H), 1.06-0.86 (m, 2H), 0.72-0.69 (m, 2H).

Example 84

Scheme 84

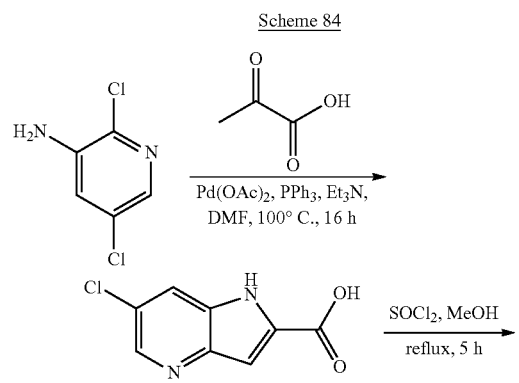

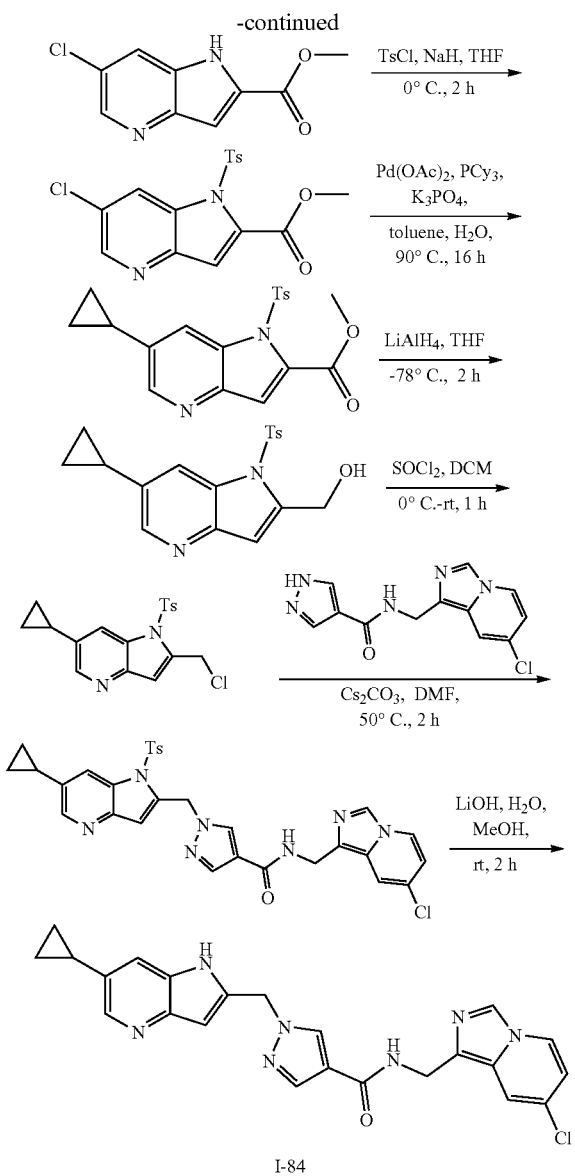

I-84

Synthesis of 6-chloro-1H-pyrrolo[3,2-b]pyridine-2-carboxylic Acid

A mixture of 2,5-dichloropyridin-3-amine (2.0 g, 12.27 mmol), 2-oxopropanoic acid (3.24 g, 36.81 mmol), Pd(OAc)$_2$ (551 mg, 2.45 mmol), PPh$_3$ (2.57 g, 9.82 mmol) and Et$_3$N (4.97 g, 49.08 mmol) in DMF (30 mL) was stirred at 100° C. for 16 h. The reaction mixture was concentrated to give a crude which was purified by silica gel chromatography (DCM/MeOH=5/1) to give 6-chloro-1H-pyrrolo[3,2-b]pyridine-2-carboxylic acid (2.41 g, yield: 100%) as a yellow solid. ESI-MS [M+H]$^+$: 197.0.

Synthesis of Methyl 6-chloro-1H-pyrrolo[3,2-b]pyridine-2-carboxylate

To a stirred solution of 6-chloro-1H-pyrrolo[3,2-b]pyridine-2-carboxylic acid (2.41 g, 12.27 mmol) in MeOH (80 mL) was added SOCl$_2$ (4.38 g, 36.81 mmol) at RT. The mixture was stirred at 80° C. for 5 h. The reaction mixture was concentrated to give the residue, which was dissolved in EtOAc (100 mL) and washed with NaHCO$_3$ (100 mL) and brine (100 mL), dried over Na$_2$SO$_4$, concentrated and purified by silica gel chromatography (EA/PE=1/5) to give methyl 6-chloro-1H-pyrrolo[3,2-b]pyridine-2-carboxylate (1.0 g, yield: 39%) as a yellow solid. ESI-MS [M+H]$^+$: 211.1.

Synthesis of Methyl 6-chloro-1-tosyl-1H-pyrrolo[3,2-b]pyridine-2-carboxylate To a stirred solution of NaH (42 mg, 1.04 mmol) in THF (4 mL) was added the solution of 6-chloro-1H-pyrrolo[3,2-b]pyridine-2-carboxylate (200 mg, 0.95 mmol) in THF (1 mL) at 0° C. After stirring for 20 min, a solution of TsCl (199 mg, 1.04 mmol) in THF (1 mL) was added thereto at 0° C. The resulting mixture was stirred at 0° C. for another 2 h. The reaction mixture was quenched with 1 M HCl, diluted with H$_2$O (20 mL) and extracted with EtOAc (25 mL×3). The combined organics were washed with NaHCO$_3$ (20 mL), brine (80 mL), dried over Na$_2$SO$_4$, concentrated and purified by silica gel chromatography (EA/PE=1/5) to give methyl 6-chloro-1-tosyl-1H-pyrrolo[3,2-b]pyridine-2-carboxylate (240 mg, yield: 69%) as a yellow solid. ESI-MS [M+H]$^+$: 365.1.

Synthesis of Methyl 6-cyclopropyl-1-tosyl-1H-pyrrolo[3,2-b]pyridine-2-carboxylate A mixture of methyl 6-chloro-1-tosyl-1H-pyrrolo[3,2-b]pyridine-2-carboxylate (240 mg, 0.658 mmol), cyclopropylboronic acid (170 mg, 1.97 mmol), Pd(OAc)$_2$ (15 mg, 0.0658 mmol), tricyclohexyl phosphine (37 mg, 0.132 mmol) and K$_3$PO$_4$ (489 mg, 2.30 mmol) in toluene (10 mL) and H$_2$O (2 mL) was stirred at 100° C. for 16 h. The reaction mixture was filtered and washed with EtOAc (50 mL). The combined filtrate was washed with H$_2$O (50 mL×1) and brine (50 mL×1), dried over Na$_2$SO$_4$, concentrated and purified by silica gel chromatography (EA/PE=1/3) to give methyl 6-cyclopropyl-1-tosyl-1H-pyrrolo[3,2-b]pyridine-2-carboxylate (180 mg, yield: 74%) as a yellow solid. ESI-MS [M+H]$^+$: 371.1.

Synthesis of (6-cyclopropyl-1-tosyl-1H-pyrrolo[3,2-b]pyridin-2-yl)methanol

To a stirred solution of LiAlH$_4$ (74 mg, 1.94 mmol) in THF (5 mL) was added the solution of methyl 6-cyclopropyl-1-tosyl-1H-pyrrolo[3,2-b]pyridine-2-carboxylate (180 mg, 0.486 mmol) in THF (1 mL) at −78° C. dropwise. The mixture was stirred at −78° C. for 2 h. The reaction mixture was quenched with Na$_2$SO$_4$.10H$_2$O and filtered. The filtrate was concentrated and dried to give (6-cyclopropyl-1-tosyl-1H-pyrrolo[3,2-b]pyridin-2-yl)methanol (105 mg, yield: 63%) as a yellow solid. ESI-MS [M+H]$^+$: 343.1.

Synthesis of 2-(chloromethyl)-6-cyclopropyl-1-tosyl-1H-pyrrolo[3,2-b]pyridine To a stirred solution of (6-cyclopropyl-1-tosyl-1H-pyrrolo[3,2-b]pyridin-2-yl)methanol (105 mg, 0.307 mmol) in DCM (10 mL) was added the solution of SOCl$_2$ (182 mg, 1.53 mmol) in DCM (1 mL) at 0° C. dropwise. The mixture was stirred at RT for 1 h. The reaction mixture was concentrated to give the residue, which was dissolved in EtOAc (40 mL) and washed with NaHCO$_3$ (40 mL) and brine (40 mL), dried over Na$_2$SO$_4$, concentrated and dried in vacuo to give 2-(chloromethyl)-6-cyclopropyl-1-tosyl-1H-pyrrolo[3,2-b]pyridine (110 mg, yield: 99%) as a yellow syrup. ESI-MS [M+H]⁺: 361.1.

Synthesis of N-((7-chloroimidazo[1,5-a]pyridin-1-yl)methyl)-1-((6-cyclopropyl-1-tosyl-1H-pyrrolo[3,2-b]pyridin-2-yl)methyl)-1H-pyrazole-4-carboxamide A mixture of 2-(chloromethyl)-6-cyclopropyl-1-tosyl-1H-pyrrolo[3,2-b]pyridine (110 mg, 0.305 mmol), N-((7-chloroimidazo[1,5-a]pyridin-1-yl)methyl)-1H-pyrazole-4-carboxamide (70 mg, 0.254 mmol) and Cs₂CO₃ (248 mg, 0.762 mmol) in DMF (5 mL) was stirred at 50° C. for 2 h. The reaction mixture was poured into H₂O (40 mL) and extracted with EtOAc/THF (50 mL×3, 5/1 (v/v)). The combined organic layers were washed with brine, dried over Na₂SO₄, concentrated and purified by prep-TLC (DCM/MeOH=10/1) to give N-((7-chloroimidazo[1,5-a]pyridin-1-yl)methyl)-1-((6-cyclopropyl-1-tosyl-1H-pyrrolo[3,2-b]pyridin-2-yl)methyl)-1H-pyrazole-4-carboxamide (38 mg, yield: 25%) as a yellow solid. ESI-MS [M+H]⁺: 600.1.

Synthesis of N-((7-chloroimidazo[1,5-a]pyridin-1-yl)methyl)-1-((6-cyclopropyl-1H-pyrrolo[3,2-b]pyridin-2-yl)methyl)-1H-pyrazole-4-carboxamide (I-84)

A mixture of N-((7-chloroimidazo[1,5-a]pyridin-1-yl)methyl)-1-((6-cyclopropyl-1-tosyl-1H-pyrrolo[3,2-b]pyridin-2-yl)methyl)-1H-pyrazole-4-carboxamide (35 mg, 0.0583 mmol) and LiOH.H₂O (307 mg, 7.30 mmol) in MeOH/H₂O (2 mL/0.5 mL) was stirred at RT for 2 h. The reaction was concentrated in vacuo to remove the MeOH. And the residue was diluted in H₂O (15 mL) and extracted with EtOAc (30 mL×3). The combined organics were washed with brine (90 mL), dried over Na₂SO₄, concentrated and purified by prep-TLC (DCM/MeOH=7/1) to give N-((7-chloroimidazo[1,5-a]pyridin-1-yl)methyl)-1-((6-cyclopropyl-1H-pyrrolo[3,2-b]pyridin-2-yl)methyl)-1H-pyrazole-4-carboxamide (12 mg, yield: 46%) as a white solid. ESI-MS [M+H]⁺: 446.0. Purity: 97.56%. ¹H NMR (400 MHz, DMSO): δ 11.22 (s, 1H), 8.59 (t, J=5.4 Hz, 1H), 8.30 (m, 2H), 8.18 (d, J=20.8 Hz, 2H), 7.90 (s, 1H), 7.77 (s, 1H), 7.28 (s, 1H), 6.64 (d, J=7.3 Hz, 1H), 6.45 (s, 1H), 5.47 (s, 2H), 4.55 (d, J=5.5 Hz, 2H), 2.01 (m, 1H), 0.96 (m, 2H), 0.68 (m, 2H).

Example 85

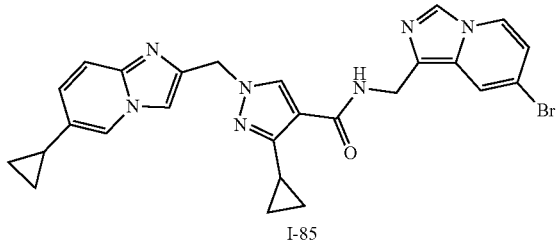

I-85

Synthesis of N-((7-bromoimidazo[1,5-a]pyridin-1-yl)methyl)-3-cyclopropyl-1-((6-cyclopropylimidazo[1,2-a]pyridin-2-yl)methyl)-1H-pyrazole-4-carboxamide (I-85)

To a solution of 3-cyclopropyl-1-((6-cyclopropylimidazo[1,2-a]pyridin-2-yl)methyl)-1H-pyrazole-4-carboxylic acid (50 mg, 0.16 mmol), in dry DMF (5 mL), was added (7-bromoimidazo[1,5-a]pyridin-1-yl)methanamine hydrochloride (54 mg, 0.21 mmol), HATU (91 mg, 0.24 mmol) and DIPEA (62 mg, 0.48 mmol). The reaction mixture was stirred at RT for 16 h. The reaction mixture diluted with H₂O (20 mL) and extracted with ethyl acetate (30 mL×3). The combined organic layers were washed with brine (20 mL×2), dried over anhydrous Na₂SO₄ and concentrated in vacuo. The residue was purified by prep-TLC (DCM/MeOH=10:1) to afford N-((7-bromoimidazo[1,5-a]pyridin-1-yl)methyl)-3-cyclopropyl-1-((6-cyclopropylimidazo[1,2-a]pyridin-2-yl)methyl)-1H-pyrazole-4-carboxamide (30 mg, yield: 36%) as a white solid. ESI-MS [M+H]⁺: 532.2. Purity: 99.12%. ¹H NMR (400 MHz, DMSO-d6): δ 8.33 (m, 3H), 8.24 (d, J=7.4 Hz, 1H), 8.07 (s, 1H), 7.94 (d, J=0.8 Hz, 1H), 7.70 (s, 1H), 7.39 (d, J=9.3 Hz, 1H), 6.99 (dd, J=9.4, 1.6 Hz, 1H), 6.71 (dd, J=7.4, 1.9 Hz, 1H), 5.24 (s, 2H), 4.53 (d, J=5.7 Hz, 2H), 2.67-2.61 (m, 1H), 1.93-1.88 (m, 1H), 0.94-0.89 (m, 2H), 0.85-0.80 (m, 2H), 0.75-0.73 (m, 2H), 0.69-0.64 (m, 2H).

Example 86

Scheme 85

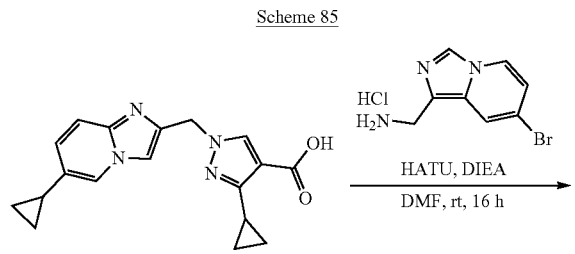

Scheme 86

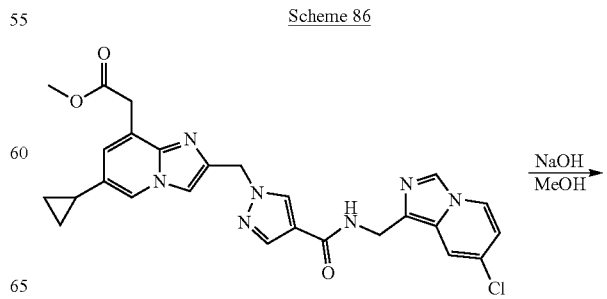

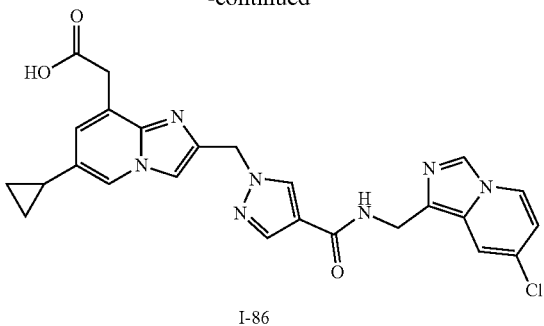

I-86

Synthesis of 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)acetic acid (I-86)

To a solution of methyl 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)acetate (50 mg, 0.096 mmol) in EtOH (3 mL) was added NaOH (3 mL, 1 M solution in H$_2$O). The resulting reaction was stirred at RT for 1 h. HCl (1 M, 3 mL) was added and the reaction was concentrated to give a crude product, which was purified by prep-HPLC to give 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)acetic acid (16.6 mg, 35% yield) as a white solid. ESI-MS [M+H]$^+$: 504.1. Purity: 97.1%. $^1$H NMR (400 MHz, DMSO): δ 8.64 (t, J=5.6 Hz, 1H), 8.30-8.28 (m, 2H), 8.23 (s, 1H), 8.10 (s, 1H), 7.87 (s, 1H), 7.78 (s, 1H), 7.61 (s, 1H), 6.84 (s, 1H), 6.63 (dd, J=7.4, 2.0 Hz, 1H), 5.38 (s, 2H), 4.55 (d, J=5.7 Hz, 2H), 3.51 (s, 2H), 1.87-1.81 (m, 1H), 0.89-0.83 (m, 2H), 0.62-0.56 (m, 2H).

Example 87

Scheme 87

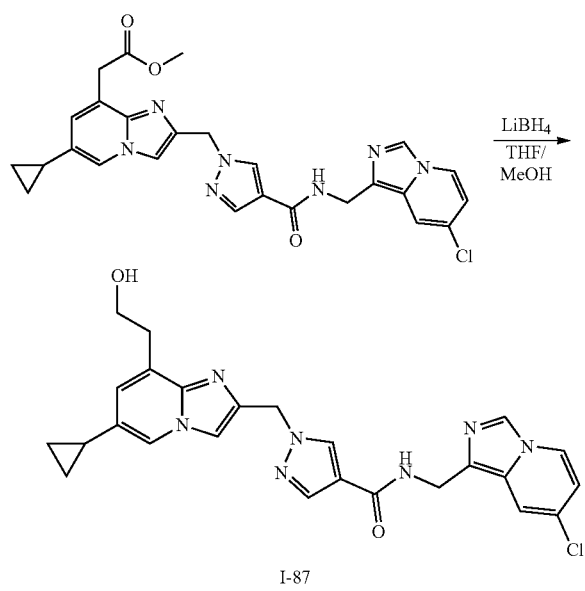

I-87

Synthesis of N-((7-chloroimidazo[1,5-a]pyridin-1-yl)methyl)-1-((6-cyclopropyl-8-(hydroxyethyl)imidazo[1,2-a]pyridin-2-yl)methyl)-1H-pyrazole-4-carboxamide (I-87)

To the solution of methyl 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)acetate (20 mg, 0.039 mmol) in THF/MeOH (3 mL/1 mL) was added LiBH$_4$ (4.25 mg, 0.195 mmol). The resulting reaction was stirred at RT for 1 h. The reaction was quenched with H$_2$O (3 mL) and concentrated in vacuo to give the crude, which was purified with prep-HPLC to give N-((7-chloroimidazo[1,5-a]pyridin-1-yl)methyl)-1-((6-cyclopropyl-8-(hydroxyethyl)imidazo[1,2-a]pyridin-2-yl)methyl)-1H-pyrazole-4-carboxamide (7.1 mg, 37% yield) as a white solid. ESI-MS [M+H]$^+$: 490.2. Purity: 99.6%. $^1$H NMR (400 MHz, DMSO): δ 8.58 (t, J=5.7 Hz, 1H), 8.34-8.28 (m, 2H), 8.20-8.12 (m, 2H), 7.87 (s, 1H), 7.79-7.73 (m, 1H), 7.65 (s, 1H), 6.84 (s, 1H), 6.65 (dd, J=7.5, 2.1 Hz, 1H), 5.39 (s, 2H), 4.78 (t, J=5.8 Hz, 1H), 4.55 (d, J=5.8 Hz, 2H), 3.74-3.70 (m, 2H), 2.96 (t, J=6.7 Hz, 2H), 1.91-1.85 (m, 1H), 0.92-0.79 (m, 2H), 0.67-0.63 (m, 2H).

Example 88

See Example 89 for Synthesis of 1-((5-amino-6-cyclopropylimidazo[1,2-a]pyridin-2-yl)methyl)-N-((7-chloroimidazo[1,5-a]pyridin-1-yl)methyl)-1H-pyrazole-4-carboxamide (I-88)

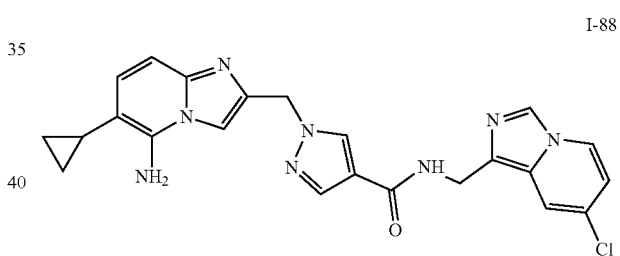

I-88

Example 89

Scheme 88

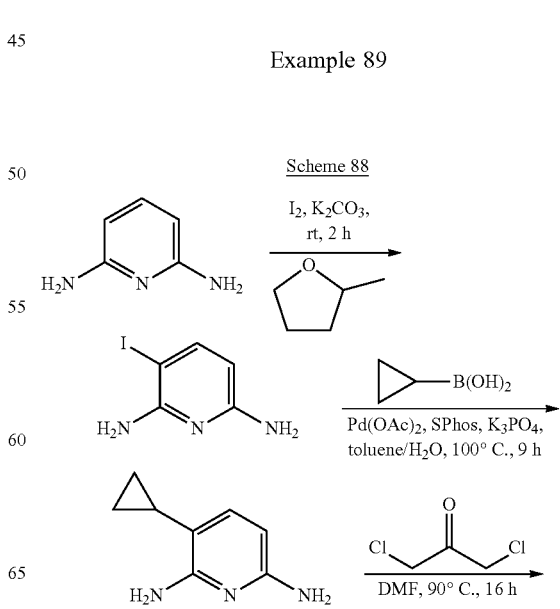

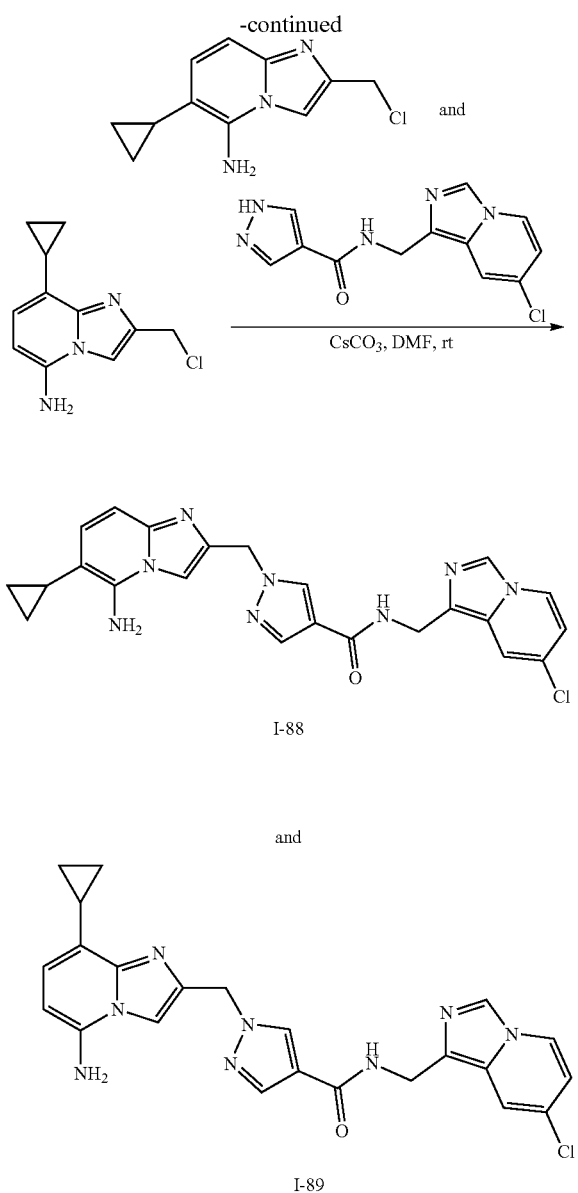

mmol), SPhos (1.0 g, 2.6 mmol) and Pd(OAc)$_2$ (0.3 g, 1.3 mmol). The resulting mixture was stirred at 90° C. for 16 h under N$_2$ atmosphere. Water (100 mL) was added to the reaction and extracted with EtOAc (100 mL×3). The combined organic layers were concentrated and purified by silica gel chromatography (DCM/MeOH=20/1) to give 3-cyclopropylpyridine-2,6-diamine (0.78 g, yield: 61.9%) as a yellow solid. ESI-MS [M+H]$^+$: 150.3.

Synthesis of 2-(chloromethyl)-6-cyclopropylimidazo[1,2-a]pyridin-5-amine and 2-(chloromethyl)-8-cyclopropylimidazo[1,2-a]pyridin-5-amine To a solution of 3-cyclopropylpyridine-2,6-diamine (0.48 g, 3.22 mmol) in DMF (10 mL) was added 1, 3-dichloropropan-2-one (2.04 g, 16.1 mmol). The mixture was stirred at 90° C. for 16 h. Water (50 mL) was added to the reaction and extracted with EtOAc (50 mL×3). The combined organic layers were concentrated and purified by silica gel chromatography (DCM/MeOH=20/1) to give mixture of 2-(chloromethyl)-6-cyclopropylimidazo[1,2-a]pyridin-5-amine and 2-(chloromethyl)-8-cyclopropylimidazo[1,2-a]pyridin-5-amine (0.18 g, yield: 16.4%) as a yellow solid. ESI-MS [M+H]$^+$: 222.3.

Synthesis of 1-((5-amino-6-cyclopropylimidazo[1,2-a]pyridin-2-yl)methyl)-N-((7-chloroimidazo[1,5-a]pyridin-1-yl)methyl)-1H-pyrazole-4-carboxamide (I-88) and 1-((5-amino-8-cyclopropylimidazo[1,2-a]pyridin-2-yl)methyl)-N-((7-chloroimidazo[1,5-a]pyridin-1-yl)methyl)-1H-pyrazole-4-carboxamide (I-89)

To a mixture of 2-(chloromethyl)-6-cyclopropylimidazo[1,2-a]pyridin-5-amine and 2-(chloromethyl)-8-cyclopropylimidazo[1,2-a]pyridin-5-amine (80 mg, 0.36 mmol) and N-((7-chloroimidazo[1,5-a]pyridin-1-yl)methyl)-1H-pyrazole-4-carboxamide (99 mg, 0.36 mmol) in DMF (4 mL) was added Cs$_2$CO$_3$ (234 mg, 0.72 mmol). The mixture was stirred at RT for 8 h. Water (50 mL) was added to the reaction and extracted with EtOAc (50 mL×3). The combined organic layers were concentrated and purified by prep-HPLC to give 1-((5-amino-6-cyclopropylimidazo[1,2-a]pyridin-2-yl)methyl)-N-((7-chloroimidazo[1,5-a]pyridin-1-yl)methyl)-1H-pyrazole-4-carboxamide (16.4 mg, yield: 10.0%) as a white solid. ESI-MS [M+H]$^+$: 461.2. Purity: 99.5% and 1-((5-amino-8-cyclopropylimidazo[1,2-a]pyridin-2-yl)methyl)-N-((7-chloroimidazo[1,5-a]pyridin-1-yl)methyl)-1H-pyrazole-4-carboxamide (4.1 mg, yield: 2.5%) as a white solid. ESI-MS [M+H]$^+$: 461.1. Purity: 95.3%. 1-((5-amino-6-cyclopropylimidazo[1,2-a]pyridin-2-yl)methyl)-N-((7-chloroimidazo[1,5-a]pyridin-1-yl)methyl)-1H-pyrazole-4-carboxamide $^1$H NMR (400 MHz, DMSO): δ 8.58 (t, J=5.6 Hz, 1H), 8.37-8.13 (m, 3H), 7.82 (d, J=31.9 Hz, 3H), 6.92 (d, J=9.0 Hz, 1H), 6.74-6.58 (m, 2H), 6.41 (s, 2H), 5.36 (s, 2H), 4.55 (d, J=5.7 Hz, 2H), 1.76 (m, 1H), 0.88 (m, 2H), 0.51 (t, J=4.7 Hz, 2H). 1-((5-amino-8-cyclopropylimidazo[1,2-a]pyridin-2-yl)methyl)-N-((7-chloroimidazo[1,5-a]pyridin-1-yl)methyl)-1H-pyrazole-4-carboxamide. $^1$H NMR (400 MHz, DMSO): δ 8.60 (t, J=5.7 Hz, 1H), 8.30 (d, J=7.1 Hz, 1H), 8.22 (s, 1H), 7.89 (s, 1H), 7.79 (s, 1H), 7.65 (s, 1H), 6.84-6.59 (m, 2H), 6.28 (s, 2H), 5.85 (d, J=7.6 Hz, 1H), 5.42 (s, 2H), 4.55 (d, J=5.7 Hz, 2H), 2.23 (m, 1H), 0.92-0.79 (m, 2H), 0.72 (m, 1H).

Synthesis of 3-iodopyridine-2,6-diamine

To a solution of 3-iodopyridine-2,6-diamine (5.0 g, 45.9 mmol) in 2-methyltetrahydrofuran (35 mL) was added K$_2$CO$_3$ (6.7 g, 48.2 mmol) followed by addition of a solution of I$_2$ (12.2 g, 48.2 mmol) in 2-methyltetrahydrofuran (20 mL) dropwise over 0.5 h. The resulting reaction was stirred at RT for 5 h. Water (100 mL) was added to the reaction and extracted with EtOAc (150 mL×2). The combined organic layers were concentrated in vacuo to give the crude, which was purified by silica gel chromatography (DCM/MeOH=20/1) to give 3-iodopyridine-2,6-diamine (8.5 g, yield: 78.7%) as a yellow solid. ESI-MS [M+H]$^+$: 236.0.

Synthesis of 3-cyclopropylpyridine-2,6-diamine

To a solution of 3-iodopyridine-2,6-diamine (2.0 g, 8.5 mmol) and cyclopropylboronic acid (2.2 g, 25.5 mmol) in toluene/H$_2$O (30 mL/3 mL) was added K$_3$PO$_4$ (6.3 g, 29.8

Example 90

Scheme 89

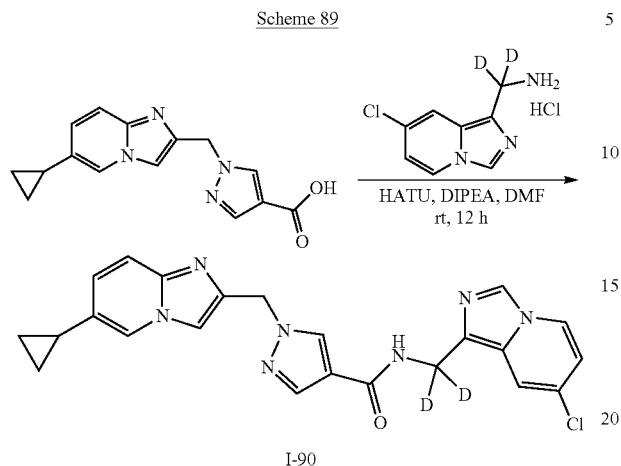

I-90

Synthesis of N-((7-chloroimidazo[1,5-a]pyridin-1-yl)methyl-d2)-1-((6-cyclopropylimidazo[1,2-a]pyridin-2-yl)methyl)-1H-pyrazole-4-carboxamide (I-90)

To a solution of 1-((6-cyclopropylimidazo[1,2-a]pyridin-2-yl)methyl)-1H-pyrazole-4-carboxylic acid (65 mg, 0.23 mmol), (7-chloroimidazo[1,5-a]pyridin-1-yl)methan-d2-amine hydrochloride (50 mg, 0.23 mmol) and HATU (114 mg, 0.3 mmol) in DMF (15 mL) was added DIPEA (148 mg, 1.15 mmol). The resulting reaction was stirred at RT for 12 h. $H_2O$ (25 mL) was added to the reaction and extracted with EtOAc (25 mL×3). The combined organic layers were washed with brine, dried over $Na_2SO_4$, concentrated to give the crude, which was purified with prep-TLC (DCM/MeOH=10/1) to give the N-((7-chloroimidazo[1,5-a]pyridin-1-yl)methyl-d2)-1-((6-cyclopropylimidazo[1,2-a]pyridin-2-yl)methyl)-1H-pyrazole-4-carboxamide (20 mg, yield: 19%). ESI-MS [M+H]$^+$: 448.2. Purity: 95.1%. $^1$H NMR (400 MHz, DMSO): δ 8.56 (s, 1H), 8.32-8.29 (m, 3H), 8.20 (s, 1H), 7.85 (s, 1H), 7.78 (s, 1H), 7.71 (s, 1H), 7.39 (d, J=9.3 Hz, 1H), 6.99 (d, J=9.3 Hz, 1H), 6.71-6.58 (m, 1H), 5.38 (s, 2H), 1.91 (ddd, J=13.3, 8.6, 5.1 Hz, 1H), 0.91 (q, J=5.7 Hz, 2H), 0.66 (q, J=5.0 Hz, 2H).

Example 91

Scheme 90

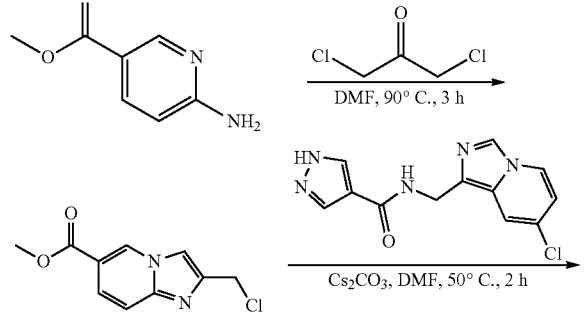

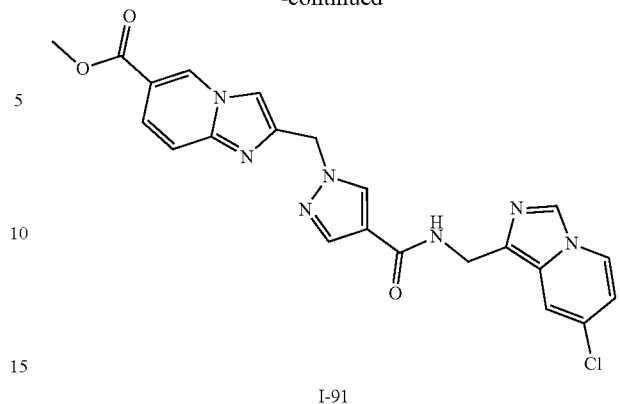

I-91

Synthesis of Methyl 2-(chloromethyl)imidazo[1,2-a]pyridine-6-carboxylate

The mixture of methyl 6-aminonicotinate (1.20 g, 7.88 mmol) and 1,3-dichloropropan-2-one (2.0 g, 15.77 mmol) in DMF (10 mL) was heated to 90° C. and stirred for 3 h. The reaction mixture was poured into $H_2O$ (60 mL), adjusted pH to 9 by addition of aqueous $NaHCO_3$ and extracted with EtOAc (60 mL×3). The combined organics were washed with brine (100 mL), dried over anhydrous $Na_2SO_4$, concentrated and purified by column chromatography (EtOAc/PE=1:1) to afford methyl 2-(chloromethyl)imidazo[1,2-a]pyridine-6-carboxylate (570 mg, 32%) as a yellow solid. ESI-MS [M+H]$^+$: 225.1.

Synthesis of Methyl 2-((4-(((7-chloroimidazo[1,5-a]pyridin-1-yl)methyl)carbamoyl)-1H-pyrazol-1-yl)methyl)imidazo[1,2-a]pyridine-6-carboxylate (I-91)

A mixture of N-((7-chloroimidazo[1,5-a]pyridin-1-yl)methyl)-1H-pyrazole-4-carboxamide (100 mg, 0.36 mmol), methyl 2-(chloromethyl)imidazo[1,2-a]pyridine-6-carboxylate (90 mg, 0.40 mmol) and $Cs_2CO_3$ (235 mg, 0.72 mmol) in DMF (5 mL) was stirred for 2 h at 50° C. The reaction mixture was poured into $H_2O$ (50 mL), solid was precipitated and filtered to give the crude product, which was purified by column chromatography (DCM:MeOH=10:1) to afford methyl 2-((4-(((7-chloroimidazo[1,5-a]pyridin-1-yl)methyl)carbamoyl)-1H-pyrazol-1-yl)methyl)imidazo[1,2-a]pyridine-6-carboxylate (70 mg, 42%) as a yellow solid. ESI-MS [M+H]$^+$: 464.1. Purity: 99.39%. $^1$H NMR (400 MHz, DMSO): δ 9.32 (s, 1H), 8.59 (t, J=5.5 Hz, 1H), 8.29 (m, 3H), 8.01 (s, 1H), 7.88 (s, 1H), 7.79 (s, 1H), 7.60 (dd, J=25.5, 9.5 Hz, 2H), 6.65 (dd, J=7.5, 1.8 Hz, 1H), 5.46 (s, 2H), 4.56 (d, J=5.6 Hz, 2H), 3.87 (s, 3H).

Example 92

Scheme 91

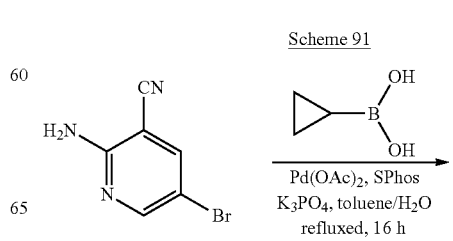

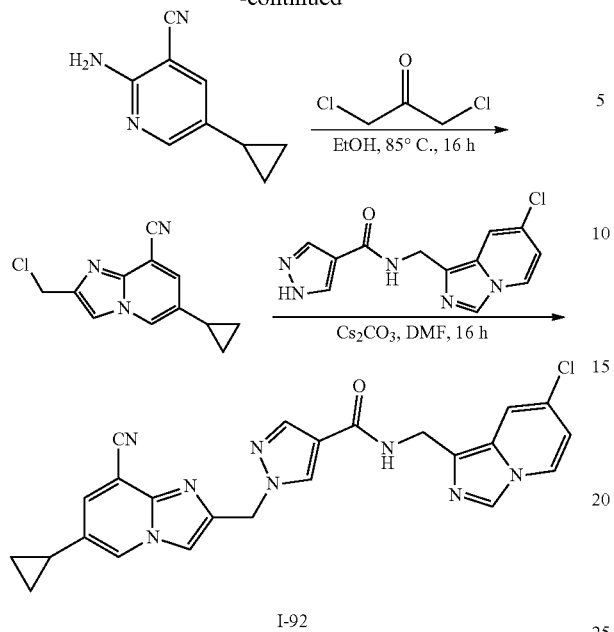

I-92

Synthesis of 2-amino-5-cyclopropylnicotinonitrile

To a mixture of 2-amino-5-bromonicotinonitrile (1 g, 5.1 mmol), cyclopropylboronic acid (647 mg, 7.6 mmol) and $K_3PO_4$ (3.78 g, 17.85 mmol) in toluene/$H_2O$ (20 mL/2 mL) was added Pd(OAc)$_2$ (114 mg, 0.51 mmol) and SPhos (209 mg, 0.51 mmol). The mixture was stirred at 95° C. for 16 h. The reaction was cooled to RT and the reaction residue was filtered. The filtrate was concentrated to give the crude product which was purified by silica gel chromatography (EA/PE=4/1) to give 2-amino-5-cyclopropylnicotinonitrile (570 mg, yield: 71%) as a yellow solid. ESI-MS [M+H]$^+$: 160.1.

Synthesis of 2-(chloromethyl)-6-cyclopropylimidazo[1,2-a]pyridine-8-carbonitrile To a solution of 2-amino-5-cyclopropylnicotinonitrile (570 mg, 3.58 mmol) in EtOH (20 mL) was added 1,3-dichloropropan-2-one (1.37 g, 10.75 mmol). The reaction mixture was stirred at 85° C. for 16 h. The reaction was concentrated and the residue was diluted with NaHCO$_3$ (aq, 20 mL) and extracted with EtOAc (50 mL×3). The combined organic layers were concentrated to give the crude which was purified by silica gel chromatography (EA/PE=2/1) to give 2-(chloromethyl)-6-cyclopropylimidazo[1,2-a]pyridine-8-carbonitrile (500 mg, yield: 58%) as a yellow solid. ESI-MS [M+H]$^+$: 232.1.

Synthesis of N-((7-chloroimidazo[1,5-a]pyridin-1-yl)methyl)-1-((8-cyano-6-cyclopropylimidazo[1,2-a]pyridin-2-yl)methyl)-1H-pyrazole-4-carboxamide (I-92)

To a mixture of 2-(chloromethyl)-6-cyclopropylimidazo[1,2-a]pyridine-8-carbonitrile (80 mg, 0.35 mmol) in dry DMF (5 mL) was added N-((7-chloroimidazo[1,5-a]pyridin-1-yl)methyl)-1H-pyrazole-4-carboxamide (95 mg, 0.35 mmol) and Cs$_2$CO$_3$ (338 mg, 1.04 mmol). The mixture was stirred at RT for 16 h. Then H$_2$O (30 mL) was added to the reaction and extracted with EtOAc (30 mL×3). The combined organic layers were washed with brine, dried over Na$_2$SO$_4$, filtered and concentrated to give the crude, which was purified by prep-TLC (DCM/MeOH=10/1) to give N-((7-chloroimidazo[1,5-a]pyridin-1-yl)methyl)-1-((8-cyano-6-cyclopropylimidazo[1,2-a]pyridin-2-yl)methyl)-1H-pyrazole-4-carboxamide (34.5 mg, yield: 21%) as a white solid. ESI-MS [M+H]$^+$: 471.1. Purity: 98.67%. $^1$H NMR (400 MHz, DMSO): δ 8.67 (d, J=1.5 Hz, 1H), 8.60 (t, J=5.7 Hz, 1H), 8.31-8.29 (m, 2H), 8.24 (s, 1H), 7.87 (d, J=13.6 Hz, 2H), 7.78 (t, J=1.9 Hz, 2H), 6.65 (dd, J=7.4, 2.1 Hz, 1H), 5.47 (s, 2H), 4.56 (d, J=5.7 Hz, 2H), 1.99-1.95 (m, 1H), 0.97-0.93 (m, 2H), 0.77-0.73 (m, 2H).

Example 93

Scheme 92

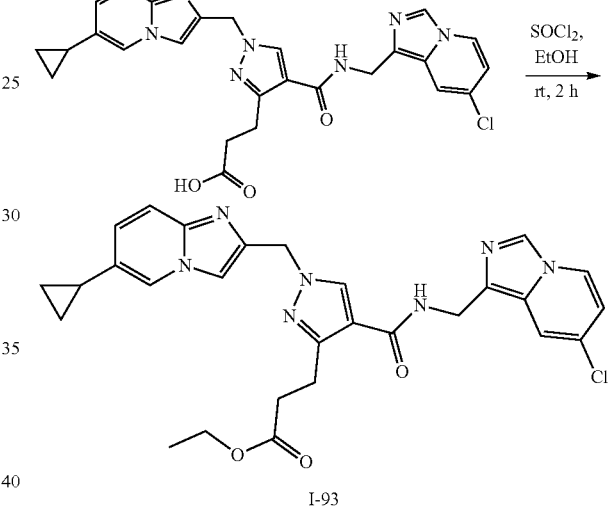

I-93

Synthesis of Ethyl 3-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)propanoate (I-93)

To a solution of 3-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)propanoic acid (20 mg, 0.04 mmol) in EtOH (4 mL) was added SOCl$_2$ (0.5 mL). The reaction was stirred at RT for 2 h. After concentration, the crude product was purification by prep-TLC (DCM/MeOH=10/1) to give ethyl 3-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)propanoate (13 mg, yield: 57%) as a white solid. ESI-MS [M+H]$^+$: 546.2. Purity: 89.6%. $^1$H NMR (400 MHz, MeOD): δ 8.23 (s, 1H), 8.17-8.11 (m, 2H), 8.01 (d, J=3.3 Hz, 1H), 7.71 (d, J=0.8 Hz, 1H), 7.66 (s, 1H), 7.35 (d, J=9.4 Hz, 1H), 7.07 (dd, J=9.4, 1.7 Hz, 1H), 6.60 (dd, J=7.5, 2.0 Hz, 1H), 5.33 (s, 2H), 4.65 (s, 2H), 4.03 (q, J=7.1 Hz, 2H), 3.15 (t, J=7.6 Hz, 2H), 2.69 (t, J=7.6 Hz, 2H), 1.95-1.89 (m, 1H), 1.14 (t, J=7.1 Hz, 3H), 1.01-0.90 (m, 2H), 0.72-0.66 (m, 2H).

Example 94

Scheme 93

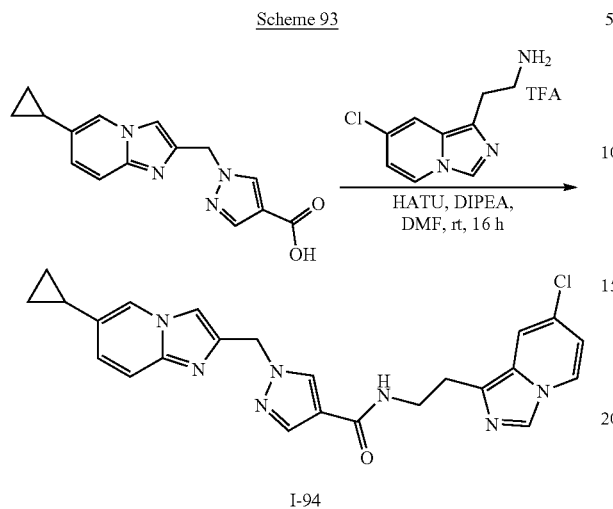

I-94

Synthesis of N-(2-(7-chloroimidazo[1,5-a]pyridin-1-yl)ethyl)-1-((6-cyclopropylimidazo[1,2-a] pyridin-2-yl)methyl)-1H-pyrazole-4-carboxamide (I-94)

A mixture of 1-((6-cyclopropylimidazo[1,2-a]pyridin-2-yl)methyl)-1H-pyrazole-4-carboxylic acid (60 mg, 0.2 mmol), 2-(7-chloroimidazo[1,5-a]pyridin-1-yl)ethanamine (60 mg, 0.2 mmol), HATU (90 mg, 0.24 mmol) and DIPEA (0.1 mL, 0.5 mmol) in DMF (10 mL) was stirred at RT for 16 h. H$_2$O (20 mL) was added to reaction and extracted with EtOAc (50 mL×3). The combined organic layers were washed with brine, dried over Na$_2$SO$_4$ and concentrated in vacuo to give the crude, which was purified by prep-HPLC to give N-(2-(7-chloroimidazo[1,5-a]pyridin-1-yl)ethyl)-1-((6-cyclopropylimidazo[1,2-a]pyridin-2-yl)methyl)-1H-pyrazole-4-carboxamide (31 mg, yield: 33.8%) as a yellow solid. ESI-MS [M+H]$^+$: 460.1. Purity: 100.0%. H NMR (400 MHz, DMSO): δ 8.34 (s, 1H), 8.29 (s, 1H), 8.26 (d, J=7.4 Hz, 1H), 8.14 (s, 2H), 7.76 (d, J=22.4 Hz, 2H), 7.60 (d, J=0.9 Hz, 1H), 7.40 (d, J=9.4 Hz, 1H), 7.00 (dd, J=9.4, 1.7 Hz, 1H), 6.57 (dd, J=7.5, 2.0 Hz, 1H), 5.39 (s, 2H), 3.44 (dd, J=13.2, 6.9 Hz, 3H), 2.95 (t, J=7.2 Hz, 2H), 2.01-1.77 (m, 1H), 1.00-0.76 (m, 2H), 0.75-0.54 (m, 2H).

Example 95

Scheme 94

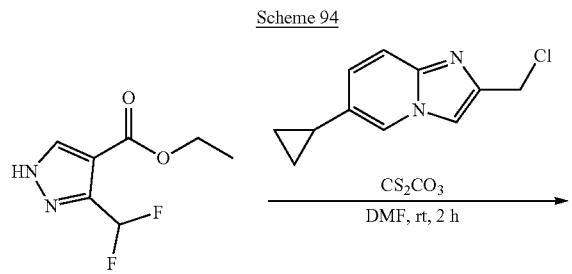

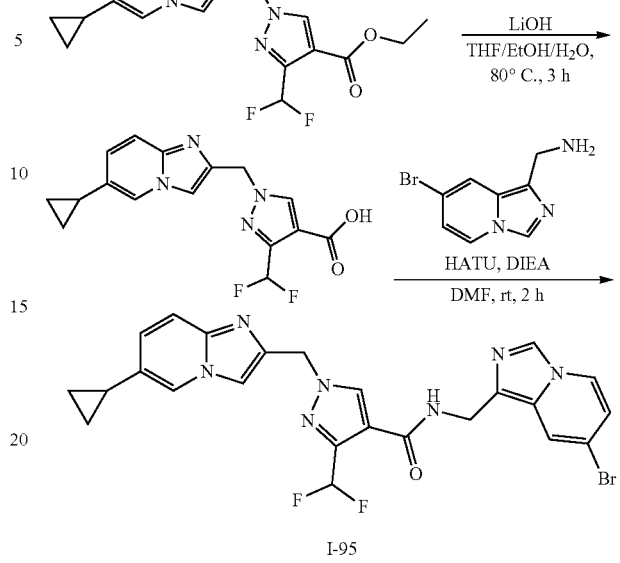

I-95

Synthesis of Ethyl 1-((6-cyclopropylimidazo[1,2-a]pyridin-2-yl)methyl)-3-(difluoromethyl)-1H-pyrazole-4-carboxylate A solution of 2-(chloromethyl)-6-cyclopropylimidazo[1,2-a]pyrimidine (40 mg, 0.19 mmol), N-((7-bromoimidazo[1,5-a]pyridin-1-yl)methyl)-1H-pyrazole-4-carboxamide (60 mg, 0.19 mmol), and Cs$_2$CO$_3$ (248 mg, 0.76 mmol) in DMF (3 mL) was stirred at RT for 2 h. Then the reaction mixture was diluted with H$_2$ (40 mL) and extracted with EtOAc (30 mL×3). The combined organic layers were dried over Na$_2$SO$_4$ and concentrated to give the desired compound ethyl 1-((6-cyclopropylimidazo[1,2-a]pyridin-2-yl)methyl)-3-(difluoromethyl)-1H-pyrazole-4-carboxylate (400 mg, yield: 67%) as brown oil, which was used in the next step without purification. ESI-MS [M+H]$^+$: 361.1.

Synthesis of 1-((6-cyclopropylimidazo[1,2-a]pyridin-1-yl)methyl)-3-(difluoromethyl)-1H-pyrazole-4-carboxylic A solution of ethyl 1-((6-cyclopropylimidazo[1,2-a]pyridin-2-yl)methyl)-3-(difluoromethyl)-1H-pyrazole-4-carboxylate (400 mg, 1.11 mmol) and LiOH (233 mg, 5.55 mmol) in THF/EtOH/H$_2$O (10 mL/10 mL/5 mL) was stirred at RT for 3 h. Most of the solvent was concentrated and the pH of the residue was adjusted to 4 by adding 1M HCl solution. Solid was precipitated and filtered to give 1-((6-cyclopropylimidazo[1,2-a]pyridin-2-yl)methyl)-3-(difluoromethyl)-1H-pyrazole-4-carboxylic acid (300 mg, yield: 81%) as a brown solid, which was used in the next step without purification. ESI-MS [M+H]$^+$: 333.1.

Synthesis of N-((7-bromoimidazo[1,5-a]pyridin-1-yl)methyl)-1-((6-cyclopropylimidazo[1,2-a]pyridin-2-yl)methyl)-3-(difluoromethyl)-1H-pyrazole-4-carboxamide (I-95)

A solution of 1-((6-cyclopropylimidazo[1,2-a]pyridin-2-yl)methyl)-3-(difluoromethyl)-1H-pyrazole-4-carboxylic acid (65 mg, 0.19 mmol), (7-bromoimidazo[1,5-a]pyridin-1-yl)methanamine hydrochloride (50 mg, 0.19 mmol), HATU (149 mg, 0.39 mmol) and DIPEA (76 mg, 0.58 mmol) in DMF (5 mL) was stirred at RT for 2 h. Then the reaction mixture was diluted with H$_2$O (25 mL) and extracted with EtOAc (25 mL×3). The combined organic layers were washed with brine, dried over Na$_2$SO$_4$ and concentrated in vacuo to give the crude, which was purified by column chromatography (PE/EA=10/1) to give the desired compound N-((7-bromoimidazo[1,5-a]pyridin-1-yl)methyl)-1-((6-cyclopropylimidazo[1,2-a]pyridin-2-yl)methyl)-3-(difluoromethyl)-1H-pyrazole-4-carboxamide (18 mg, yield: 18%) as a white solid. ESI-MS [M+H]$^+$: 540.1. Purity: 98.48%. $^1$H NMR (400 MHz, DMSO): δ 8.77 (s, 1H), 8.66 (s, 1H), 8.48 (s, 1H), 8.39 (s, 1H), 8.26 (d, J=7.4 Hz, 1H), 8.14 (s, 1H), 7.97 (s, 1H), 7.73 (d, J=9.3 Hz, 1H), 7.58 (d, J=8.7 Hz, 1H), 7.38 (t, J=53.8 Hz, 2H), 6.83-6.76 (m, 1H), 5.69 (s, 2H), 4.59 (s, 2H), 2.11-2.02 (m, 1H), 1.07-0.98 (m, 2H), 0.82-0.72 (m, 2H).

Example 96

Scheme 95

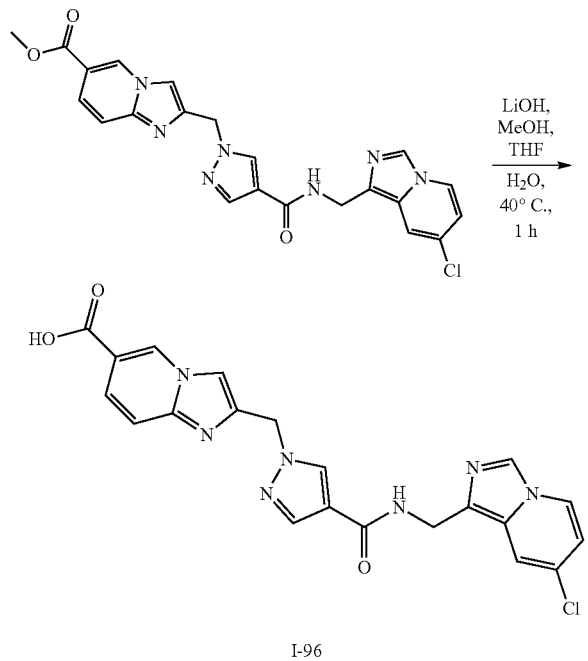

I-96

Synthesis of 2-((4-(((7-chloroimidazo[1,5-a]pyridin-1-yl)methyl)carbamoyl)-1H-pyrazol-1-yl)methyl)imidazo[1,2-a]pyridine-6-carboxylic acid (I-96)

To a solution of methyl 2-((4-(((7-chloroimidazo[1,5-a]pyridin-1-yl)methyl)carbamoyl)-1H-pyrazol-1-yl)methyl)imidazo[1,2-a]pyridine-6-carboxylate (35 mg, 0.075 mmol) in methanol (2 mL), THF (2 mL) and H$_2$O (1 mL) was added lithium hydroxide monohydrate (44 mg, 1.05 mmol). The mixture was stirred for 1 h at 40° C. The pH value of the residue was adjusted to 4 by adding 1 M HCl solution. The resulting mixture was concentrated and purified by prep-HPLC to give 2-((4-(((7-chloroimidazo[1,5-a]pyridin-1-yl)methyl)carbamoyl)-1H-pyrazol-1yl)methyl)imidazo[1,2-a]pyridine-6-carboxylic acid (25 mg, 74%) as a white solid. ESI-MS [M+H]$^+$: 225.1. Purity: 93.06%. $^1$H NMR (400 MHz, DMSO): δ 13.15 (s, 1H), 9.25 (s, 1H), 8.59 (t, J=5.8 Hz, 1H), 8.31 (m, 2H), 8.25 (s, 1H), 7.98 (s, 1H), 7.87 (s, 1H), 7.79 (s, 1H), 7.59 (m, 2H), 6.65 (dd, J=7.5, 2.0 Hz, 1H), 5.45 (s, 2H), 4.56 (d, J=5.7 Hz, 2H).

Example 97

Scheme 96

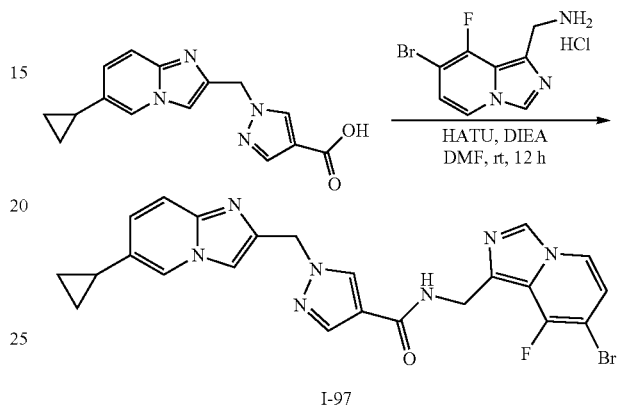

I-97

Synthesis of N-((7-bromo-8-fluoroimidazo[1,5-a]pyridin-1-yl)methyl)-1-((6-cyclopropylimidazo[1,2-a]pyridin-2-yl)methyl)-1H-pyrazole-4-carboxamide (I-97)

To a solution of 1-((6-cyclopropylimidazo[1,2-a]pyridin-2-yl)methyl)-1H-pyrazole-4-carboxylic acid (60 mg, 0.21 mmol), (7-bromo-8-fluoroimidazo[1,5-a]pyridin-1-yl)methanamine hydrochloride (84 mg, 0.32 mmol) and HATU (120 mg, 0.31 mmol) in DMF (5 mL) was added DIPEA (81 mg, 0.63 mmol). The resulting reaction was stirred at RT for 12 h. H$_2$O (25 mL) was added to the reaction, extracted with EtOAc (30 mL×3). The combined organic layers were washed with brine, dried over Na$_2$SO$_4$ and concentrated in vacuo to give the crude, which was purified with prep-TLC (DCM/MeOH=10/1) to the N-((7-bromo-8-fluoroimidazo[1,5-a]pyridin-1-yl)methyl)-1-((6-cyclopropylimidazo[1,2-a]pyridin-2-yl)methyl)-1H-pyrazole-4-carboxamide (20 mg, yield: 19%) as a white solid. ESI-MS [M+H]$^+$: 508.1. Purity: 98.9%. $^1$H NMR (400 MHz, DMSO): δ 8.46 (d, J=2.2 Hz, 1H), 8.42 (t, J=4.8 Hz, 1H), 8.33 (s, 1H), 8.20 (s, 1H), 8.14 (d, J=7.3 Hz, 1H), 7.84 (s, 1H), 7.72 (s, 1H), 7.39 (d, J=9.3 Hz, 1H), 6.99 (d, J=9.3 Hz, 1H), 6.82 (t, J=6.6 Hz, 1H), 5.39 (s, 2H), 4.62 (d, J=5.2 Hz, 2H), 1.94-1.88 (m, 1H), 0.95-0.87 (m, 2H), 0.71-0.61 (m, 2H).

Example 98

Scheme 97

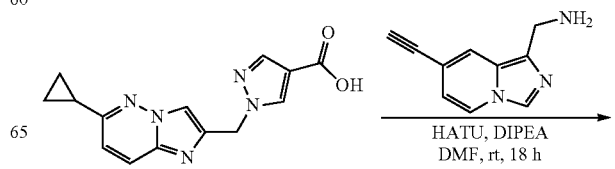

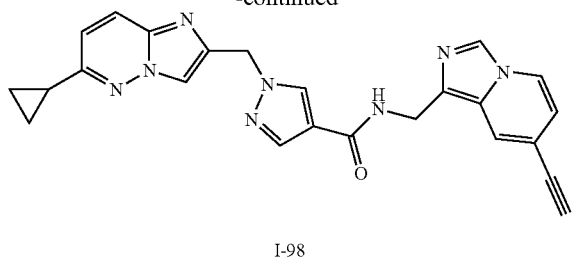

I-98

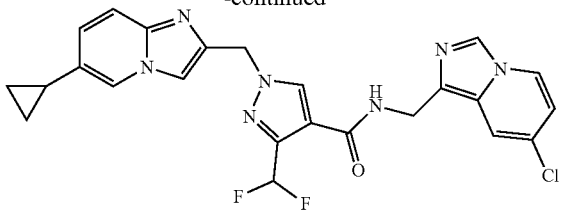

I-99

Synthesis of 1-((6-cyclopropylimidazo[1,2-b]pyridazin-2-yl)methyl)-N-((7-ethynylimidazo[1,5-a]pyridin-1-yl)methyl)-1H-pyrazole-4-carboxamide (I-98)

A solution of 1-((6-cyclopropylimidazo[1,2-b]pyridazin-2-yl)methyl)-1H-pyrazole-4-carboxylic acid (66 mg, 0.23 mmol), (7-ethynylimidazo[1,5-a]pyridin-1-yl)methanamine hydrochloride (47 mg, 0.23 mmol), HATU (175 mg, 0.46 mmol) and DIPEA (89 mg, 0.69 mmol) in DMF (5 mL) was stirred at RT for 2 h. Then the reaction mixture was diluted with H$_2$O (30 mL) and extracted with EtOAc (30 mL×3). The combined organic layers were washed with brine, dried over Na$_2$SO$_4$ and concentrated to give the crude, which was purified by prep-HPLC to give 1-((6-cyclopropylimidazo[1,2-b]pyridazin-2-yl)methyl)-N-((7-ethynylimidazo[1,5-a]pyridin-1-yl)methyl)-1H-pyrazole-4-carboxamide (10 mg, yield: 10%) as a white solid. ESI-MS [M+H]$^+$: 437.2. Purity: 97.51%. $^1$H NMR (400 MHz, DMSO): δ 8.61 (t, J=5.6 Hz, 1H), 8.48 (s, 1H), 8.27 (d, J=7.1 Hz, 1H), 8.22 (s, 1H), 8.10 (s, 1H), 7.96-7.91 (m, 2H), 7.85 (s, 1H), 7.11 (t, J=7.7 Hz, 1H), 6.63 (d, J=7.3 Hz, 1H), 5.42 (s, 2H), 4.60 (d, J=5.7 Hz, 2H), 4.30 (s, 1H), 2.22-2.13 (m, 1H), 1.10-1.03 (m, 2H), 1.00-0.94 (m, 2H).

Example 99

Scheme 98

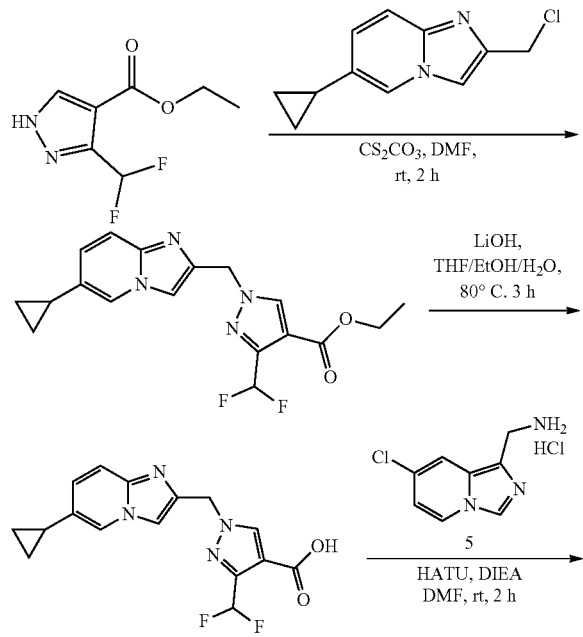

Synthesis of Ethyl 1-((6-cyclopropylimidazo[1,2-a]pyridin-2-yl)methyl)-3-(difluoromethyl)-1H-pyrazole-4-carboxylate A mixture of 2-(chloromethyl)-6-cyclopropylimidazo[1,2-a]pyrimidine (40 mg, 0.19 mmol), N-((7-bromoimidazo[1,5-a]pyridin-1-yl)methyl)-1H-pyrazole-4-carboxamide (60 mg, 0.19 mmol) and Cs$_2$CO$_3$ (248 mg, 0.76 mmol) in DMF (2 mL) was stirred at RT for 2 h. Then the reaction mixture was diluted with H$_2$O (40 mL) and extracted with EtOAc (30 mL×3). The combined organic layers were washed with brine, dried over Na$_2$SO$_4$ and concentrated to give the desired compound ethyl 1-((6-cyclopropylimidazo[1,2-a]pyridin-2-yl)methyl)-3-(difluoromethyl)-1H-pyrazole-4-carboxylate (400 mg, yield: 67%) as brown oil, which was used in the next step without purification. ESI-MS [M+H]$^+$: 361.1.

Synthesis of 1-((6-cyclopropylimidazo[1,2-a]pyridin-2-yl)methyl)-3-(difluoromethyl)-1H-pyrazole-4-carboxylic A solution of ethyl 1-((6-cyclopropylimidazo[1,2-a]pyridin-2-yl)methyl)-3-(difluoromethyl)-1H-pyrazole-4-carboxylate (400 mg, 1.11 mmol) and LiOH (233 mg, 5.55 mmol) in THF/EtOH/H$_2$O (10 mL/10 mL/5 mL) was stirred at RT for 3 h. Most of the solvent was concentrated and the pH of the residue was adjusted to 4 by adding 1 M HCl solution. Solid was precipitated and filtered to give the desired compound 1-((6-cyclopropylimidazo[1,2-a]pyridin-2-yl)methyl)-3-(difluoromethyl)-1H-pyrazole-4-carboxylic acid (300 mg, yield: 81%) as a brown solid, which was used in the next step without purification. ESI-MS [M+H]$^+$: 333.2.

Synthesis of N-((7-chloroimidazo[1,5-a]pyridin-1-yl)methyl)-1-((6-cyclopropylimidazo[1,2-a]pyridin-2-yl)methyl)-3-(difluoromethyl)-1H-pyrazole-4-carboxamide (I-99)

A solution of 1-((6-cyclopropylimidazo[1,2-a]pyridin-2-yl)methyl)-3-(difluoromethyl)-1H-pyrazole-4-carboxylic acid (65 mg, 0.19 mmol), (7-chloroimidazo[1,5-a]pyridin-1-yl)methanamine hydrochloride (41 mg, 0.19 mmol), HATU (149 mg, 0.39 mmol) and DIPEA (76 mg, 0.58 mmol) in DMF (5 mL) was stirred at RT for 2 h. Then the reaction mixture was diluted with H$_2$O (30 mL) and extracted with EtOAc (30 mL×3). The combined organic layers were washed with brine, dried over Na$_2$SO$_4$ and concentrated to give the crude, which was purified by column chromatography (DCM/MeOH=10/1) to give the desired compound N-((7-chloroimidazo[1,5-a]pyridin-1-yl)methyl)-1-((6-cyclopropylimidazo[1,2-a]pyridin-2-yl)methyl)-3-(difluoromethyl)-1H-pyrazole-4-carboxamide (18 mg, yield: 18%) as a white solid. ESI-MS [M+H]+: 496.2. Purity: 91.43%. ¹H NMR (400 MHz, DMSO): δ 8.61 (t, J=5.6 Hz, 1H), 8.48 (s, 1H), 8.27 (d, J=7.1 Hz, 1H), 8.22 (s, 1H), 8.10 (s, 1H), 7.96-7.91 (m, 2H), 7.85 (s, 1H), 7.11 (t, J=7.7 Hz, 1H), 6.63 (d, J=7.3 Hz, 1H), 5.42 (s, 2H), 4.60 (d, J=5.7 Hz, 2H), 4.30 (s, 1H), 2.22-2.13 (m, 1H), 1.10-1.03 (m, 2H), 1.00-0.94 (m, 2H).
Example 100
Scheme 99
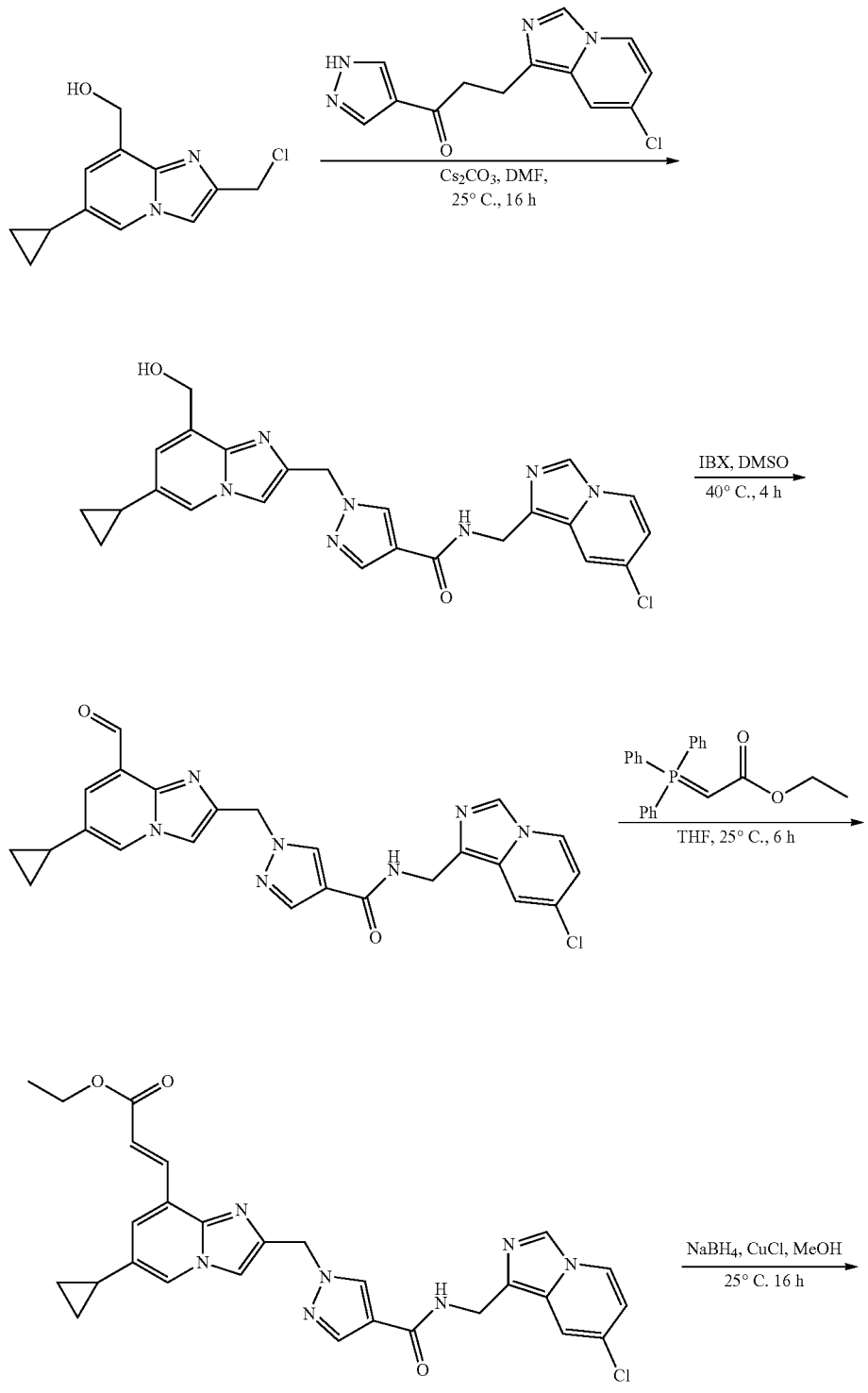

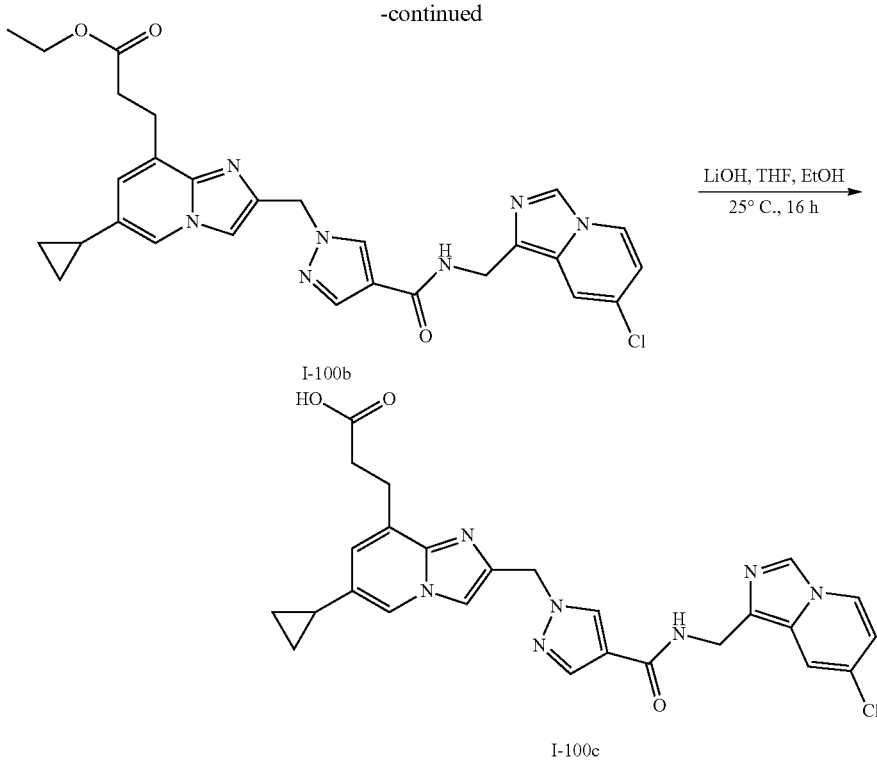

Synthesis of N-((7-chloroimidazo[1,5-a]pyridin-1-yl)methyl)-1-((6-cyclopropyl-8-(hydroxymethyl)imidazo [1,2-a]pyridin-2-yl)methyl)-1H-pyrazole-4-carboxamide To a mixture of (2-(chloromethyl)-6-cyclopropylimidazo[1,2-a]pyridin-8-yl)methanol (370 mg, 1.56 mmol) in dry DMF (10 mL) was added N-((7-chloroimidazo[1,5-a]pyridin-1-yl)methyl)-1H-pyrazole-4-carboxamide (430 mg, 1.56 mmol) and $Cs_2CO_3$ (1.53 g, 4.68 mmol). The mixture was stirred at 25° C. for 16 h. Then $H_2O$ (50 mL) was added and extracted with EtOAc (50 mL×3). The combined organic layers were washed with brine, dried over $Na_2SO_4$, filtered and concentrated to give the crude, which was purified by silica gel chromatography (DCM/MeOH=10/1) to give N-((7-chloroimidazo[1,5-a]pyridin-1-yl)methyl)-1-((6-cyclopropyl-8-(hydroxymethyl)imidazo[1,2-a]pyridin-2-yl)methyl)-1H-pyrazole-4-carboxamide (400 mg, yield: 53.8%) as a yellow solid. ESI-MS [M+H]$^+$: 476.2.

Synthesis of N-((7-chloroimidazo[1,5-a]pyridin-1-yl)methyl)-1-((6-cyclopropyl-8-formylimidazo[1,2-a]pyridin-2-yl)methyl)-1H-pyrazole-4-carboxamide To a mixture of N-((7-chloroimidazo[1,5-a]pyridin-1-yl)methyl)-1-((6-cyclopropyl-8-(hydroxymethyl)imidazo[1,2-a]pyridin-2-yl)methyl)-1H-pyrazole-4-carboxamide (400 mg, 0.84 mmol) in DMSO (10 mL) was added 2-iodoxybenzoic acid (472 mg, 1.68 mmol). The mixture was stirred at 40° C. for 4 h. Then $H_2O$ (80 mL) was added, and the precipitate was filtered and dried to give N-((7-chloroimidazo[1,5-a]pyridin-1-yl)methyl)-1-((6-cyclopropyl-8-formylimidazo[1,2-a]pyridin-2-yl)methyl)-1H-pyrazole-4-carboxamide (200 mg, yield: 50%) as a white solid, which was used in the next step without purification. ESI-MS [M+H]$^+$: 474.1.

Synthesis of Ethyl 3-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)acrylate (I-100a)

To a mixture of N-((7-chloroimidazo[1,5-a]pyridin-1-yl)methyl)-1-((6-cyclopropyl-8-formylimidazo[1,2-a]pyridin-2-yl)methyl)-1H-pyrazole-4-carboxamide (200 mg, 0.4 mmol) in dry THF (8 mL) was added Ethyl (triphenylphosphoranylidene)acetate (152 mg, 0.44 mmol) at 0° C. The mixture was stirred at 25° C. for 6 h, concentrated to give the crude, which was purified by Pre-TLC (DCM/MeOH=10/1) to give ethyl 3-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)acrylate (120 mg, yield: 52%) as a yellow solid. ESI-MS [M+H]$^+$: 544.2. purity: 93.12%.

$^1$H NMR (400 MHz, DMSO) δ 8.59 (t, J=5.7 Hz, 1H), 8.43-8.42 (m, 1H), 8.31-8.29 (m, 2H), 8.22 (s, 1H), 7.90 (s, 1H), 7.79-7.75 (m, 3H), 7.64-7.60 (m, 1H), 7.44-7.43 (m, 1H), 6.64 (dd, J=7.4, 2.1 Hz, 1H), 5.47 (s, 2H), 4.55 (d, J=5.7 Hz, 2H), 4.20 (q, J=7.1 Hz, 2H), 1.95-1.91 (m, 1H), 1.27 (t, J=7.1 Hz, 3H), 0.94-0.91 (m, 2H), 0.76-0.72 (m, 2H).

Synthesis of Ethyl 3-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)propanoate (I-100b)

To a mixture of ethyl 3-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)acrylate (120 mg, 0.22 mmol) in MeOH (5 mL) was CuCl (43 mg, 0.44 mmol) and $NaBH_4$ (25 mg, 0.66 mmol). The mixture was stirred at 25° C. for 16 h. Water (30 mL) was added and extracted with EtOAc (50 mL×3). The combined organic layers were washed with brine, dried over Na$_2$SO$_4$, filtered and concentrated to give the crude, which was purified by prep-TLC (DCM/MeOH=10/1) to give ethyl 3-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)propanoate (110 mg, yield: 91%) as a yellow solid. ESI-MS [M+H]$^+$: 546.2. Purity: 99.11%. H NMR (400 MHz, DMSO): δ 8.59 (t, J=5.5 Hz, 1H), 8.31-8.29 (m, 2H), 8.20-8.19 (m, 2H), 7.88 (s, 1H), 7.78 (s, 1H), 7.66 (s, 1H), 6.82 (s, 1H), 6.64 (dd, J=7.4, 2.0 Hz, 1H), 5.40 (s, 2H), 4.55 (d, J=5.6 Hz, 2H), 4.04 (q, J=7.1 Hz, 2H), 3.07 (t, J=7.6 Hz, 2H), 2.77 (t, J=7.6 Hz, 2H), 1.90-1.84 (m, 1H), 1.14 (t, J=7.1 Hz, 3H), 0.92-0.87 (m, 2H), 0.66-0.62 (m, 2H).

Synthesis of 3-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)propanoic acid (I-100c)

To a mixture of ethyl 3-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)propanoate (40 mg, 0.07 mmol) in THF/EtOH/H$_2$O (1 mL/1 mL/1 mL) was added LiOH (5.3 mg, 0.22 mmol). The mixture was stirred at 25° C. for 6 h. The pH of the residue was adjusted to 4 by adding 1 M HCl solution. The mixture was concentrated and purified by prep-HPLC to give 3-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)propanoic acid (14 mg, yield: 37%) as a yellow solid. ESI-MS [M+H]$^+$: 518.2. Purity: 99.18%. $^1$H NMR (400 MHz, DMSO) δ 12.18 (s, 1H), 8.59 (t, J=5.6 Hz, 1H), 8.31-8.29 (m, 2H), 8.20-8.18 (m, 2H), 7.88 (s, 1H), 7.78 (s, 1H), 7.65 (s, 1H), 6.82 (s, 1H), 6.66-6.63 (m, 1H), 5.40 (s, 2H), 4.55 (d, J=5.6 Hz, 2H), 3.04 (t, J=7.5 Hz, 2H), 2.69 (t, J=7.6 Hz, 2H), 1.89-1.85 (m, 1H), 0.90-0.88 (m, 2H), 0.66-0.64 (m, 2H).

Example 101

Scheme 100

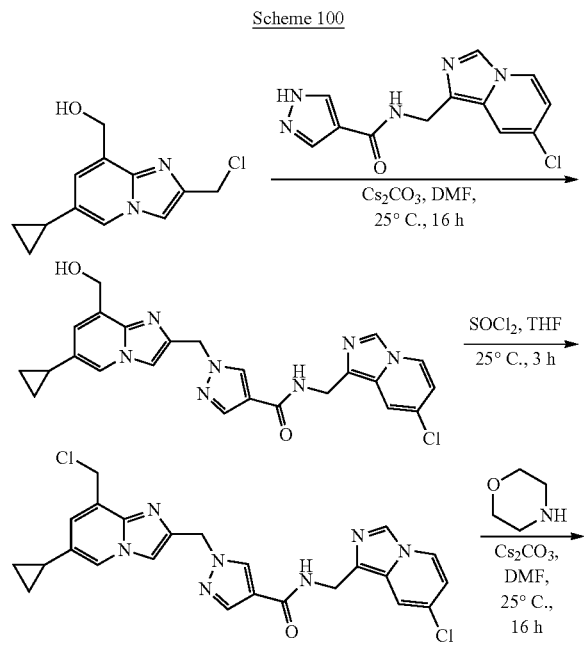

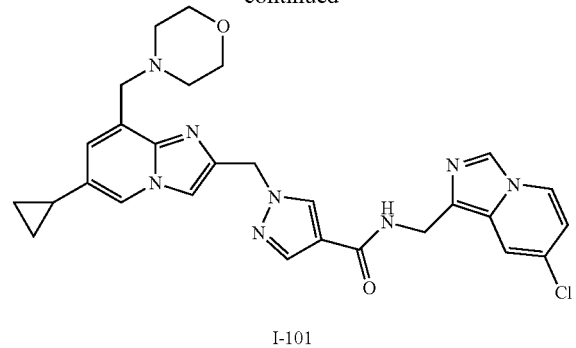

I-101

Synthesis of N-((7-chloroimidazo[1,5-a]pyridin-1-yl)methyl)-1-((6-cyclopropyl-8-(hydroxymethyl)imidazo[1,2-a]pyridin-2-yl)methyl)-1H-pyrazole-4-carboxamide To a mixture of (2-(chloromethyl)-6-cyclopropylimidazo[1,2-a]pyridin-8-yl)methanol (370 mg, 1.56 mmol) in dry DMF (10 mL) was added N-((7-chloroimidazo[1,5-a]pyridin-1-yl)methyl)-1H-pyrazole-4-carboxamide (430 mg, 1.56 mmol) and Cs$_2$CO$_3$ (1.53 g, 4.68 mmol). The mixture was stirred at 25° C. for 16 h. Then H$_2$O (100 mL) was added to the reaction and extracted with EtOAc (100 mL×3). The combined organic layers were washed with brine, dried over Na$_2$SO$_4$, filtered and concentrated to give the crude, which was purified by prep-TLC (DCM/MeOH=10/1) to give N-((7-chloroimidazo[1,5-a]pyridin-1-yl)methyl)-1-((6-cyclopropyl-8-(hydroxymethyl)imidazo[1,2-a]pyridin-2-yl)methyl)-1H-pyrazole-4-carboxamide (400 mg, yield: 53.9%) as a yellow solid. ESI-MS [M+H]$^+$: 476.1.

Synthesis of N-((7-chloroimidazo[1,5-a]pyridin-1-yl)methyl)-1-((8-(chloromethyl)-6-cyclopropylimidazo[1,2-a]pyridin-2-yl)methyl)-1H-pyrazole-4-carboxamide To a mixture of N-((7-chloroimidazo[1,5-a]pyridin-1-yl)methyl)-1-((6-cyclopropyl-8-(hydroxymethyl)imidazo[1,2-a]pyridin-2-yl)methyl)-1H-pyrazole-4-carboxamide (50 mg, 0.1 mmol) in THF (2 mL) was added SOCl$_2$ (0.5 mL). The mixture was stirred at 25° C. for 3 h. Then the reaction mixture was concentrated to give N-((7-chloroimidazo[1,5-a]pyridin-1-yl)methyl)-1-((8-(chloromethyl)-6-cyclopropylimidazo[1,2-a]pyridin-2-yl)methyl)-1H-pyrazole-4-carboxamide (50 mg, yield: 96%) as a yellow solid, which was used into the next step without purification. ESI-MS [M+H]$^+$: 494.1.

Synthesis of N-((7-chloroimidazo[1,5-a]pyridin-1-yl)methyl)-1-((6-cyclopropyl-8-(morpholinomethyl)imidazo[1,2-a]pyridin-2-yl)methyl)-1H-pyrazole-4-carboxamide (I-101)

To a mixture of N-((7-chloroimidazo[1,5-a]pyridin-1-yl)methyl)-1-((8-(chloromethyl)-6-cyclopropylimidazo[1,2-a]pyridin-2-yl)methyl)-1H-pyrazole-4-carboxamide (50 mg, 0.1 mmol) in dry DMF (3 mL) was added morpholine (17.6 mg, 0.2 mmol) and Cs$_2$CO$_3$ (163 mg, 0.5 mmol). The mixture was stirred at 25° C. for 16 h. Water (30 mL) was added and extracted with EtOAc (50 mL×3). The combined organic layers were washed with brine, dried over Na$_2$SO$_4$, filtered and concentrated to give the crude, which was purified by prep-TLC (DCM/MeOH=8/1) to give N-((7-chloroimidazo[1,5-a]pyridin-1-yl)methyl)-1-((6-cyclopropyl-8-(morpholinomethyl)imidazo[1,2-a]pyridin-2-yl)methyl)-1H-pyrazole-4-carboxamide (11.6 mg, yield: 21%) as a white solid. ESI-MS [M+H]+: 545.2. Purity: 99.15%. 1H NMR (400 MHz, DMSO): δ 8.58 (t, J=5.7 Hz, 1H), 8.31-8.29 (m, 2H), 8.22-8.19 (m, 2H), 7.87 (s, 1H), 7.77 (m, 1H), 7.68 (s, 1H), 6.99 (s, 1H), 6.64 (dd, J=7.5, 2.1 Hz, 1H), 5.39 (s, 2H), 4.55 (d, J=5.7 Hz, 2H), 3.75 (s, 2H), 3.60-3.58 (m, 4H), 2.44 (s, 4H), 1.96-1.89 (m, 1H), 0.94-0.89 (m, 2H), 0.66-0.62 (m, 2H).

Example 102

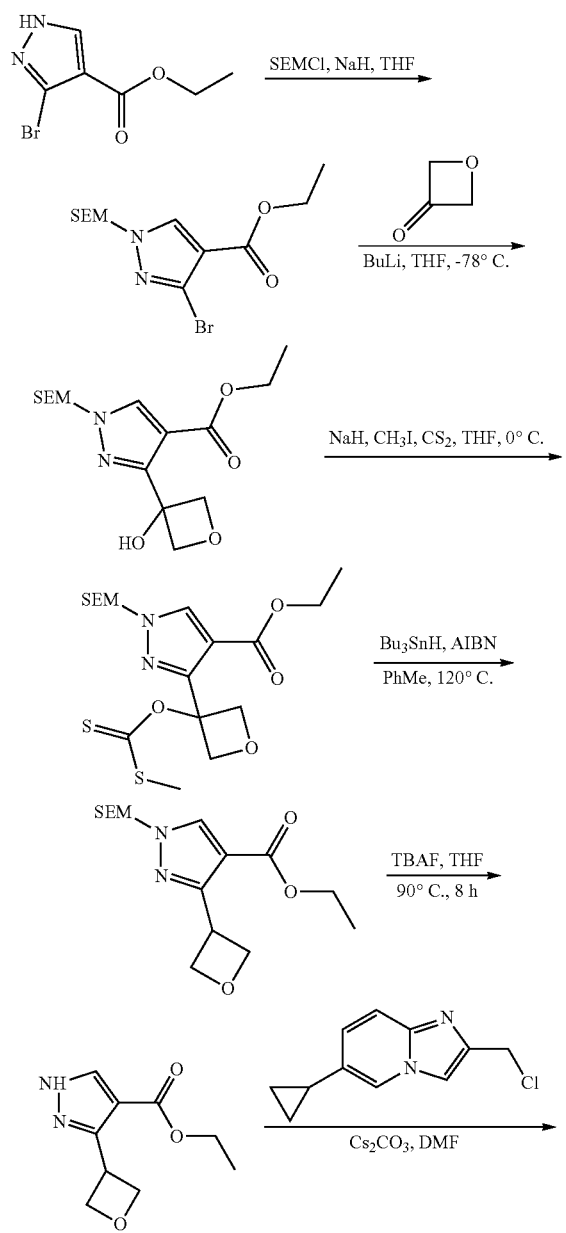

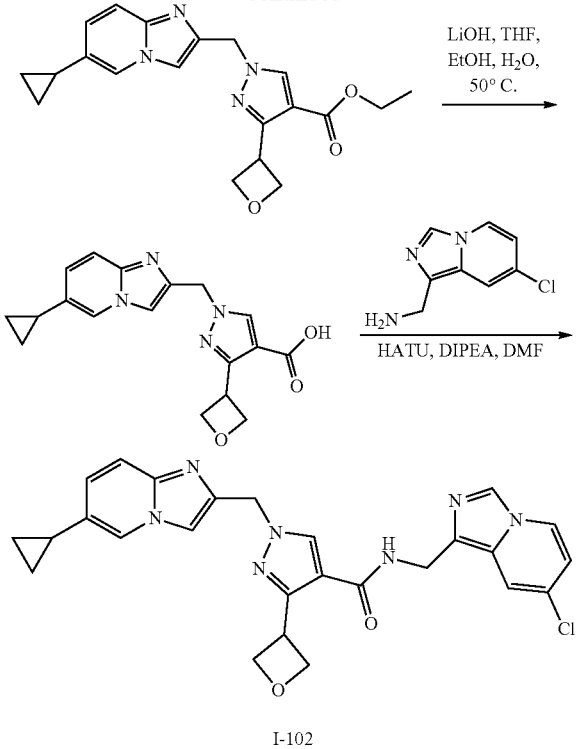

Synthesis of Ethyl 3-bromo-1-((2-(trimethylsilyl)ethoxy)methyl)-1H-pyrazole-4-carboxylate To a solution of ethyl 3-bromo-1H-pyrazole-4-carboxylate (547 mg, 2.5 mmol) and NaH (150 mg, 3.75 mmol, 60% oil) in THF (5 mL) and under N2 was added SEMCl (458 mg, 2.75 mmol) at 0° C. The reaction mixture was stirred at RT for 2 h. The reaction was quenched with H2O (30 mL) and extracted with EtOAc (30 mL×2). The combined organic layers were washed with brine, dried over Na2SO4 and concentrated in vacuo to afford ethyl 3-bromo-1-((2-(trimethylsilyl)ethoxy)methyl)-1H-pyrazole-4-carboxylate as a yellow oil (873 mg, yield: 99%) and a mixture of N1 and N2 regioisomers. ESI-MS [M+H]+: 350.1.

Synthesis of Ethyl 3-(3-hydroxyoxetan-3-yl)-1-((2-(trimethylsilyl)ethoxy)methyl)-1H-pyrazole-4-carboxylate To a solution of ethyl 3-bromo-1-((2-(trimethylsilyl)ethoxy)methyl)-1H-pyrazole-4-carboxylate (615 mg, 1.76 mmol) in THF (8 mL) under N2 was added BuLi (0.9 mL, 2.11 mmol, 2.4 M solution in hexane) at −78° C. Then oxetan-3-one (2.1 mL, 35.2 mmol) was added. The reaction was allowed to warm to RT and stirred for 2 h. The reaction mixture was quenched with saturated NH4Cl solution (20 mL) and extracted with EtOAc (50 mL×3). The combined organic layers were washed with brine, dried over Na2SO4 and concentrated in vacuo to give crude, which was purified by a column flash (PE:EA=2:1) to get ethyl 3-(3-hydroxyoxetan-3-yl)-1-((2-(trimethylsilyl)ethoxy)methyl)-1H-pyrazole-4-carboxylate (169 mg, yield: 28%) as a yellow oil. ESI-MS [M+H]+: 343.2.

Synthesis of Ethyl 3-(3-(((methylthio)carbonothioyl)oxy)oxetan-3-yl)-1-((2-(trimethylsilyl)ethoxy)methyl)-1H-pyrazole-4-carboxylate To a mixture of NaH (54 mg, 1.34 mmol, 60% oil) in THF (1 mL) was added a solution of ethyl 3-(3-hydroxyoxetan-3-yl)-1-((2-(trimethylsilyl)ethoxy)methyl)-1H-pyrazole-4-carboxylate (306 mg, 0.89 mmol) in THF (0.5 mL) at 0° C. dropwise. The resulting solution was stirred at 0° C. for 30 min. Then a solution of $CS_2$ (102 mg, 1.34 mmol) in THF (0.5 mL) was added to the reaction at 0° C. dropwise. The resulting solution was stirred at 0° C. for another 1 h. To the mixture above was added a solution of iodomethane (190 mg, 1.34 mmol) in THF (0.5 mL) dropwise at 0° C. The resulting solution was stirred at 0° C. for 1 h, then quenched with aqueous $NH_4Cl$ (10 mL), and extracted with EtOAc (50 mL×3). The combined organic layers were washed with brine, dried over $Na_2SO_4$ and concentrated in vacuo to afford ethyl 3-(3-(((methylthio)carbonothioyl)oxy)oxetan-3-yl)-1-((2-(trimethylsilyl)ethoxy)methyl)-1H-pyrazole-4-carboxylate (385 mg crude) as yellow oil, which was used into next step without further purification. ESI-MS $[M+H]^+$: 433.1.

Synthesis of Ethyl 3-(oxetan-3-yl)-1-((2-(trimethylsilyl)ethoxy)methyl)-1H-pyrazole-4-carboxylate To a solution of ethyl 3-(3-(((methylthio)carbonothioyl)oxy)oxetan-3-yl)-1-((2-(trimethylsilyl)ethoxy)methyl)-1H-pyrazole-4-carboxylate (385 crude from previous step) in toluene (10 mL) were added $Bu_3SnH$ (311 mg, 1.07 mmol) and AIBN (29 mg, 0.18 mmol). The resulting mixture was stirred at 120° C. for 3 h. The reaction was cooled to RT and concentrate in vacuo to give the crude, which was purified by silica gel column (PE/EA=5/1) to isolate ethyl 3-(oxetan-3-yl)-1-((2-(trimethylsilyl)ethoxy)methyl)-1H-pyrazole-4-carboxylate (204 mg, yield: 70%) as yellow oil. ESI-MS $[M+H]^+$: 327.2.

Synthesis of Ethyl 3-(oxetan-3-yl)-1H-pyrazole-4-carboxylate

To a solution of TBAF (3.2 mL, 3.13 mmol, 1 M solution in THF) was added ethyl 3-(oxetan-3-yl)-1-((2-(trimethylsilyl)ethoxy)methyl)-1H-pyrazole-4-carboxylate (204 mg, 0.63 mmol). The mixture was stirred at 90° C. for 8 h. $H_2O$ (25 mL) was added to the reaction and extracted with EtOAc (35 mL×3). The combined organic layer were washed with brine, dried over $Na_2SO_4$ and concentrated in vacuo. The residue was purified by silica gel column (PE/EA=1/2) to isolate ethyl 3-(oxetan-3-yl)-1H-pyrazole-4-carboxylate (81 mg, yield: 66%) as a white solid. ESI-MS $[M+H]^+$: 197.2.

Synthesis of Ethyl 1-((6-cyclopropylimidazo[1,2-a]pyridin-2-yl)methyl)-3-(oxetan-3-yl)-1H-pyrazole-4-carboxylate To a solution of ethyl 3-(oxetan-3-yl)-1H-pyrazole-4-carboxylate (50 mg, 0.25 mmol) in DMF (5 mL) was added 2-(chloromethyl)-6-cyclopropylimidazo[1,2-a]pyridine (63 mg, 0.31 mmol) and $Cs_2CO_3$ (245 mg, 0.75 mmol). The mixture was stirred at RT for 3 h. Water (20 mL) was added and extracted with EtOAc (30 mL×2). The combined organic layers were washed with brine, dried over $Na_2SO_4$ and concentrated in vacuo to give a residue, which was purified by silica gel column (DCM/MeOH=20/1) to give ethyl 1-((6-cyclopropylimidazo [1,2-a]pyridin-2-yl) methyl)-3-(oxetan-3-yl)-1H-pyrazole-4-carboxylate (90 mg, yield: 98%) as a white solid. ESI-MS $[M+H]^+$: 367.2.

Synthesis of 1-((6-cyclopropylimidazo[1,2-a]pyridin-2-yl)methyl)-3-(oxetan-3-yl)-1H-pyrazole-4-carboxylic Acid To a solution of ethyl 1-((6-cyclopropylimidazo[1,2-a]pyridin-2-yl)methyl)-3-(oxetan-3-yl)-1H-pyrazole-4-carboxylate (45 mg, 0.12 mmol) in THF/EtOH/$H_2O$ (2 mL/2 mL/1 mL) was added LiOH (10 mg, 0.24 mmol). The resulting mixture was stirred at 50° C. for 3 h. The mixture was freeze-dried to give 1-((6-cyclopropylimidazo[1,2-a]pyridin-2-yl)methyl)-3-(oxetan-3-yl)-1H-pyrazole-4-carboxylic acid as a lithium salt (50 mg crude), which was used in the next step without purification. ESI-MS $[M+H]^+$: 339.2.

Synthesis of N-((7-chloroimidazo[1,5-a]pyridin-1-yl)methyl)-1-((6-cyclopropylimidazo[1,2-a]pyridin-2-yl)methyl)-3-(oxetan-3-yl)-1H-pyrazole-4-carboxamide (I-102)

To a solution of ethyl 1-((6-cyclopropylimidazo[1,2-a]pyridin-2-yl)methyl)-3-(oxetan-3-yl)-1H-pyrazole-4-carboxylic acid (50 mg crude from previous step) in DMF (3 mL) was added (7-chloroimidazo[1,5-a]pyridin-1-yl)methanamine (22 mg, 0.12 mmol), HATU (91 mg, 0.24 mmol) and DIPEA (47 mg, 0.36 mmol). The mixture was stirred at RT for 14 h. $H_2O$ (20 mL) was added to the reaction and extracted with EtOAc (30 mL×3). The combined organic layers were washed with brine, dried over $Na_2SO_4$ and concentrated in vacuo to give a residue. The residue was purified by flash silica gel column (DCM/MeOH=8/1) to isolate N-((7-chloroimidazo[1,5-a]pyridin-1-yl)methyl)-1-((6-cyclopropylimidazo[1,2-a]pyridin-2-yl)methyl)-3-(oxetan-3-yl)-1H-pyrazole-4-carboxamide (34.8 mg, yield: 58%) as a white solid. ESI-MS $[M+H]^+$: 502.1. Purity: 97.10%. $^1$H NMR (400 MHz, DMSO): δ 8.43 (t, J=5.8 Hz, 1H), 8.34 (s, 1H), 8.30-8.29 (m, 2H), 8.21 (s, 1H), 7.77 (s, 1H), 7.74 (d, J=1.9 Hz, 1H), 7.39 (d, J=9.3 Hz, 1H), 7.00 (dd, J=9.4, 1.7 Hz, 1H), 6.64 (dd, J=7.5, 2.1 Hz, 1H), 5.36 (s, 2H), 4.83-4.82 (m, J=8.4, 2H), 4.71-4.68 (m, 2H), 4.60-4.54 (m, 1H), 4.50 (d, J=5.7 Hz, 2H), 1.95-1.88 (m, 1H), 0.94-0.89 (m, 2H), 0.68-0.64 (m, 2H).

Example 103

Scheme 102

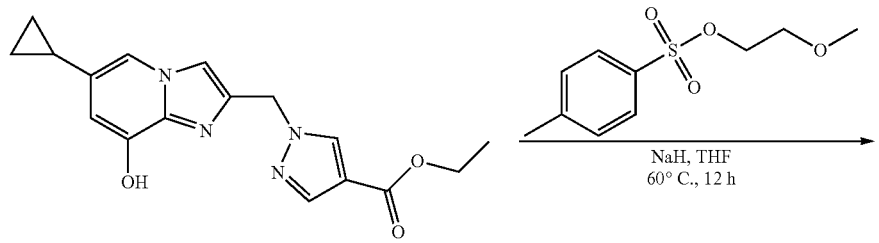

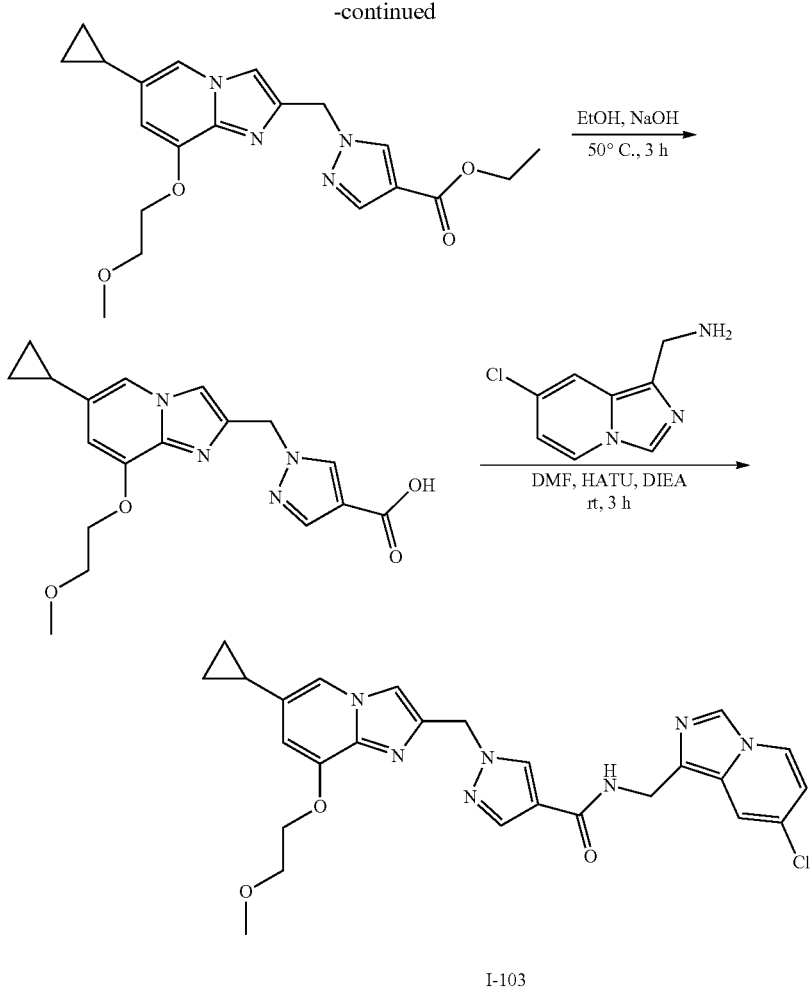

I-103

Synthesis of Ethyl 1-((8-((2-methoxyethoxy)methyl)imidazo[1,2-a]pyridin-2-yl)methyl)-1H-pyrazole-4-carboxylate To a mixture of ethyl 1-((8-(hydroxymethyl)imidazo[1,2-a]pyridin-2-yl)methyl)-1H-pyrazole-4-carboxylate (200 mg, 0.59 mmol) in THF (10 mL) was added 2-methoxyethyl 4-methylbenzenesulfonate (1.4 g, 5.9 mmol) and NaH (25 mg, 0.88 mmol). The resulting mixture was stirred at 60° C. for 12 h. Then reaction was quenched with $H_2O$ (10 mL) and extracted with EtOAc (30 mL×3). The combined organic layers were washed with brine, dried over $Na_2SO_4$ and concentrated in vacuo to give the crude. The crude was purified with prep-TLC (PE/EA=3/1) to give the ethyl 1-((8-((2-methoxyethoxy)methyl)imidazo[1,2-a]pyridin-2-yl)methyl)-1H-pyrazole-4-carboxylate (158 mg, yield: 70%) as a white solid. ESI-MS [M+H]$^+$: 385.1.

Synthesis of 1-((6-cyclopropyl-8-(2-methoxyethoxy)imidazo[1,2-a]pyridin-2-yl)methyl)-1H-pyrazole-4-carboxylic Acid To a mixture of ethyl 1-((6-cyclopropyl-8-(2-methoxyethoxy)imidazo[1,2-a]pyridin-2-yl)methyl)-1H-pyrazole-4-carboxylate (158 mg, 0.41 mmol) in EtOH (5 mL) was added NaOH (64 mg, 1.6 mmol) in $H_2O$ (2 mL). The mixture was stirred at 50° C. for 3 h. The pH value of the reaction was adjusted to 2-3. The resulting mixture was concentrated to give 1-((6-cyclopropyl-8-(2-methoxyethoxy)imidazo[1,2-a]pyridin-2-yl)methyl)-1H-pyrazole-4-carboxylic acid (210 mg, crude) as a white solid which was used in the next step without purification. ESI-MS [M+H]$^+$: 357.1.

Synthesis of N-((7-chloroimidazo[1,5-a]pyridin-1-yl)methyl)-1-((6-cyclopropyl-8-(2-methoxyethoxy)imidazo[1,2-a]pyridin-2-yl)methyl)-1H-pyrazole-4-carboxamide (I-103)

To a mixture of 1-((6-cyclopropyl-8-(2-methoxyethoxy)imidazo[1,2-a]pyridin-2-yl)methyl)-1H-pyrazole-4-carboxylic acid (210 mg, crude from last step) in DMF (5 mL) was added (7-chloroimidazo[1,5-a]pyridin-1-yl)methanamine hydrochloride (126 mg, 0.58 mmol), DIPEA (146 mg, 1.45 mmol) and HATU (1.67 g, 0.44 mmol). The mixture was stirred at RT for 3 h. The reaction was quenched with $H_2O$ (30 mL) and was extracted with EtOAc (30 mL×3). The combined organic layers were washed with brine, dried over $Na_2SO_4$ and concentrated in vacuo to give the crude, which was purified with prep-TLC (DCM/MeOH=10/1) to give the N-((7-chloroimidazo[1,5-a]pyridin-1-yl)methyl)-1-((6-cyclopropyl-8-(2-methoxyethoxy)imidazo[1,2-a]pyridin-2-yl)methyl)-1H-pyrazole-4-carboxamide (28.7 mg, yield: 13% in 2 steps) as a white solid. ESI-MS [M+H]$^+$: 534.2. Purity:

98.1%. ¹H NMR (400 MHz, DMSO): δ 8.69 (t, J=5.6 Hz, 1H), 8.62 (s, 1H), 8.57 (s, 1H), 8.36 (d, J=7.5 Hz, 1H), 8.32 (s, 1H), 8.11 (s, 1H), 7.97 (s, 1H), 7.87 (s, 1H), 7.64 (s, 1H), 6.77 (d, J=7.3 Hz, 1H), 5.63 (s, 2H), 4.78 (s, 2H), 4.61 (d, J=5.6 Hz, 2H), 3.63-3.56 (m, 2H), 3.53-3.37 (m, 2H), 3.20 (s, 3H), 2.10-2.04 (m, 1H), 1.06-1.02 (m, 2H), 0.79-0.75 (m, 2H).

Example 104

Scheme 103

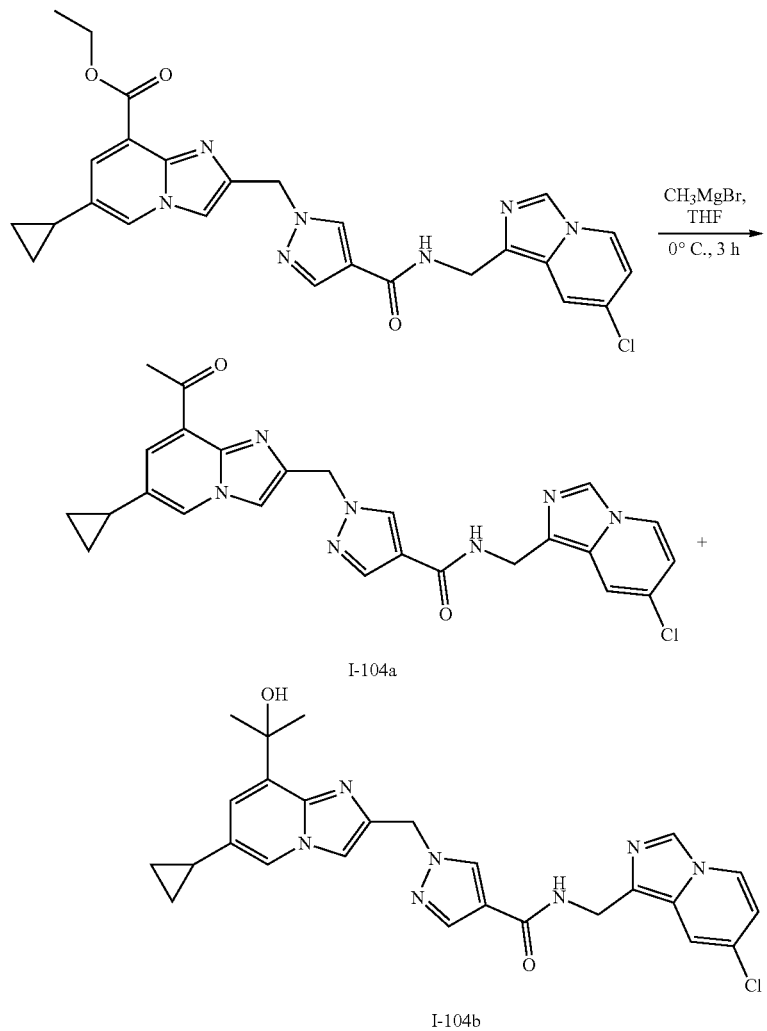

Synthesis of 1-((8-acetyl-6-cyclopropylimidazo[1,2-a]pyridin-2-yl)methyl)-N-((7-chloroimidazo[1,5-a]pyridin-1-yl)methyl)-1H-pyrazole-4-carboxamide (I-104a)

A mixture of ethyl 2-((4-(((7-chloroimidazo[1,5-a]pyridin-1-yl)methyl)carbamoyl)-1H-pyrazol-1-yl)methyl)-6-cyclopropylimidazo[1,2-a]pyridine-8-carboxylate (150 mg, 0.29 mmol) in THF (5 mL) was added CH₃MgBr (1 M in THF, 1.45 mL, 1.45 mmol) at 0° C. The mixture was stirred at 0° C. for 3 h under N₂. The reaction was quenched with saturated NH₄Cl (aq., 3 mL) and extracted with EtOAc (30 mL×3). The combined organic layers were washed with brine, dried over Na₂SO₄ and concentrated in vacuo to give the crude, which was purified with prep-HPLC to give 1-((8-acetyl-6-cyclopropylimidazo[1,2-a]pyridin-2-yl)methyl)-N-((7-chloroimidazo[1,5-a]pyridin-1-yl)methyl)-1H-pyrazole-4-carboxamide (1.5 mg, yield: 1.05%) as a white solid. ESI-MS [M+H]⁺: 488.2. Purity: 95.1%. ¹H NMR (400 MHz, MeOD): δ 8.85 (s, 1H), 8.72 (d, J=1.0 Hz, 1H), 8.45 (d, J=1.4 Hz, 1H), 8.34-8.30 (m, 2H), 8.06 (s, 1H), 7.98 (s, 1H), 7.92 (s, 1H), 6.89 (dd, J=7.5, 1.8 Hz, 1H), 5.71 (s, 2H), 4.77 (s, 2H), 2.78 (s, 3H), 2.22-2.17 (m, 1H), 1.20-1.12 (m, 2H), 1.01-0.87 (m, 2H).

From the above reaction, N-((7-chloroimidazo[1,5-a]pyridin-1-yl)methyl)-1-((6-cyclopropyl-8-(2-hydroxypropan-2-yl)imidazo[1,2-a]pyridin-2-yl)methyl)-1H-pyrazole-4-carboxamide (I-104b) was also isolated (3.8 mg, yield: 2.6%) as a white solid. ESI-MS [M+H]⁺: 504.2. Purity: 98.1%. ¹H NMR (400 MHz, MeOD): δ 8.15 (s, 1H), 8.06-8.05 (m, 2H), 7.98 (s, 1H), 7.82 (s, 1H), 7.63 (s, 1H), 7.55 (s, 1H), 7.06 (s, 1H), 6.55-6.49 (m, 1H), 5.38 (s, 2H), 4.58 (s, 2H), 1.87-1.79 (m, 1H), 1.58 (s, 6H), 0.91-0.83 (m, 2H), 0.65-0.58 (m, 2H).

Example 105

Scheme 104

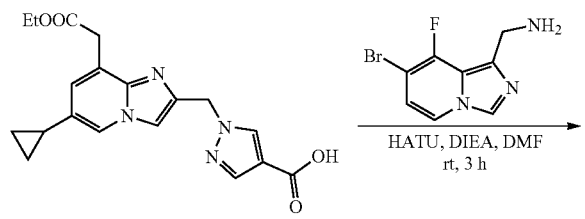

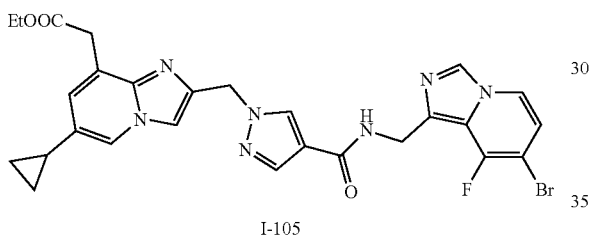

I-105

Synthesis of Ethyl 2-(2-((4-(((7-bromo-8-fluoroimidazo[1,5-a]pyridin-1-yl)methyl)carbamoyl)-1H-pyrazol-1-yl)methyl)-6-cyclopropylimidazo[1,2-a]pyridin-8-yl)acetate (I-105)

To a mixture of 1-((6-cyclopropyl-8-(2-ethoxy-2-oxoethyl)imidazo[1,2-a]pyridin-2-yl)methyl)-1H-pyrazole-4-carboxylic acid (150 mg, 0.42 mmol) in DMF (5 mL) was added (7-bromo-8-fluoroimidazo[1,5-a]pyridin-1-yl)methanamine hydrochloride (235 mg, 0.84 mmol), DIPEA (150 mg, 1.15 mmol) and HATU (240 mg, 0.63 mmol). The mixture was stirred at RT for 3 h. H$_2$O (30 mL) was added and the reaction was extracted with EtOAc (50 mL×3). The combined organic layers were washed with brine, dried over Na$_2$SO$_4$ and concentrated in vacuo to give the crude, which was purified with prep-HPLC to give the 2-(2-((4-(((7-bromo-8-fluoroimidazo[1,5-a]pyridin-1-yl)methyl)carbamoyl)-1H-pyrazol-1-yl)methyl)-6-cyclopropylimidazo[1,2-a]pyridin-8-yl)acetate (21.6 mg, yield: 10.2%) as a white solid. ESI-MS [M+H]$^+$: 494.1. Purity: 97.7%. $^1$H NMR (400 MHz, DMSO): δ 8.61 (s, 1H), 8.49-8.47 (m, 2H), 8.30 (s, 1H), 8.15 (d, J=7.4 Hz, 1H), 8.08 (s, 1H), 7.96 (s, 1H), 7.56 (s, 1H), 6.84 (dd, J=7.2, 6.2 Hz, 1H), 5.62 (s, 2H), 4.64 (d, J=5.2 Hz, 2H), 4.11-4.06 (m, 4H), 2.07-2.00 (m, 1H), 1.16 (t, J=7.1 Hz, 3H), 1.06-1.01 (m, 2H), 0.77-0.73 (m, 2H).

Example 106

Scheme 105

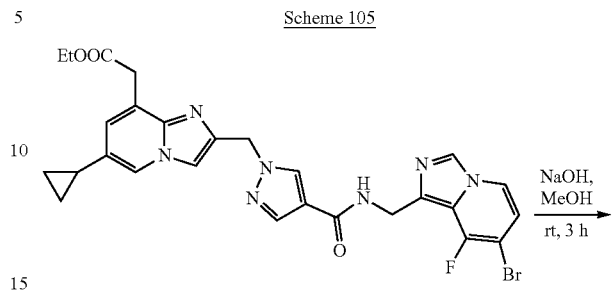

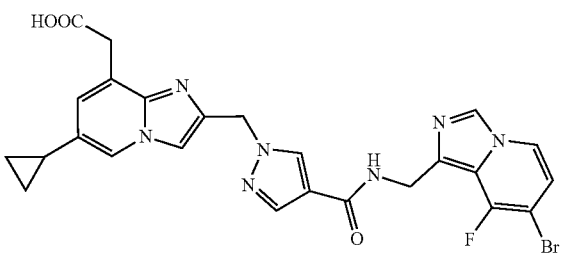

I-106

Synthesis of 2-(2-((4-(((7-bromo-8-fluoroimidazo[1,5-a]pyridin-1-yl)methyl)carbamoyl)-1H-pyrazol-1-yl)methyl)-6-cyclopropylimidazo[1,2-a]pyridin-8-yl)acetic acid (I-106)

To a solution of ethyl 2-(2-((4-(((7-bromo-8-fluoroimidazo[1,5-a]pyridin-1-yl)methyl)carbamoyl)-1H-pyrazol-1-yl)methyl)-6-cyclopropylimidazo[1,2-a]pyridin-8-yl)acetate (20 mg, 0.034 mmol) in EtOH (2 mL) was added NaOH (4 mg, 0.16 mmol) in H$_2$O (1 mL). The mixture was stirred at RT for 3 h. The pH of the mixture was adjusted to 2-3. The resulting mixture was concentrated to give the crude, which was purified by prep-HPLC to give 2-(2-((4-(((7-bromo-8-fluoroimidazo[1,5-a]pyridin-1-yl)methyl)carbamoyl)-1H-pyrazol-1-yl)methyl)-6-cyclopropylimidazo[1,2-a]pyridin-8-yl)acetic acid (7.1 mg, yield: 37%) as a white solid. ESI-MS [M+H]$^+$: 566.1. Purity: 92.9%. $^1$H NMR (400 MHz, DMSO): δ 8.48-8.38 (m, 2H), 8.36 (s, 1H), 8.20-8.18 (m, 2H), 8.14 (d, J=7.3 Hz, 1H), 7.86 (s, 1H), 7.65 (s, 1H), 6.91 (s, 1H), 6.82 (t, J=6.6 Hz, 1H), 5.38 (s, 2H), 4.62 (d, J=4.9 Hz, 2H), 3.72 (s, 2H), 1.90-1.86 (m, 1H), 0.93-0.85 (m, 2H), 0.66-0.61 (m, 2H).

Example 107

Scheme 106

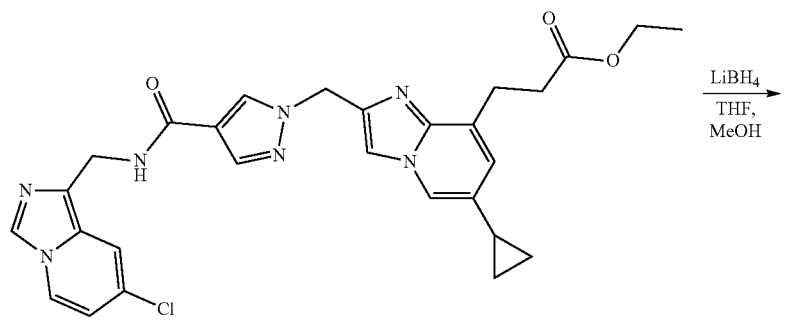

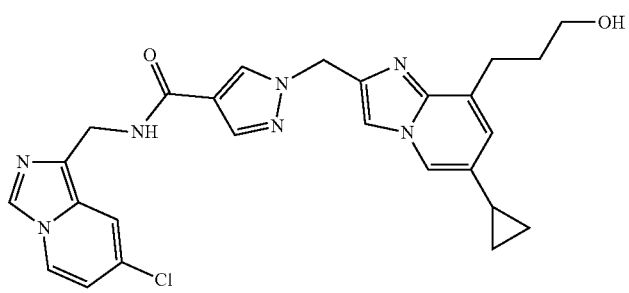
I-107

Synthesis of N-((7-chloroimidazo[1,5-a]pyridin-1-yl)methyl)-1-((6-cyclopropyl-8-(3-hydroxypropyl) imidazo[1,2-a]pyridin-2-yl)methyl)-1H-pyrazole-4-carboxamide (I-107)

To a solution of ethyl 3-(2-((4-((7-chloroimidazo[1,5-a]pyridin-1-yl) methylcarbamoyl)-1H-pyrazol-1-yl)methyl)-6-cyclopropylimidazo[1,2-a]pyridin-8-yl)propanoate (35 mg, 0.064 mmol) in THF/MeOH (5 mL/0.5 mL) was added LiBH$_4$ (7 mg, 0.321 mmol) at 0° C. The resulting reaction was stirred at RT for 4 h. H$_2$O (15 mL) was added to the reaction and extracted with EtOAc (30 mL×3). The combined organic layers were washed with brine, dried over Na$_2$SO$_4$ and concentrated in vacuo to give the crude, which was purified with prep-TLC (DCM/MeOH=10/1) to give N-((7-chloroimidazo[1,5-a]pyridin-1-yl)methyl)-1-((6-cyclopropyl-8-(3-hydroxypropyl)imidazo[1,2-a]pyridin-2-yl)methyl)-1H-pyrazole-4-carboxamide (10 mg, yield: 31%) as a white solid. ESI-MS [M+H]$^+$: 504.2. Purity: 97.9%. $^1$H NMR (400 MHz, DMSO): δ 8.58 (t, J=5.7 Hz, 1H), 8.32-8.28 (m, 2H), 8.22-8.15 (m, 2H), 7.88 (s, 1H), 7.78 (s, 1H), 7.64 (s, 1H), 6.80 (s, 1H), 6.66-6.62 (m, 1H), 5.39 (s, 2H), 4.57-4.52 (m, 3H), 3.44-3.92 (m, 2H), 2.88-2.78 (m, 2H), 1.94-1.77 (m, 3H), 0.92-0.87 (m, 2H), 0.69-0.59 (m, 2H).

Example 108

Scheme 107

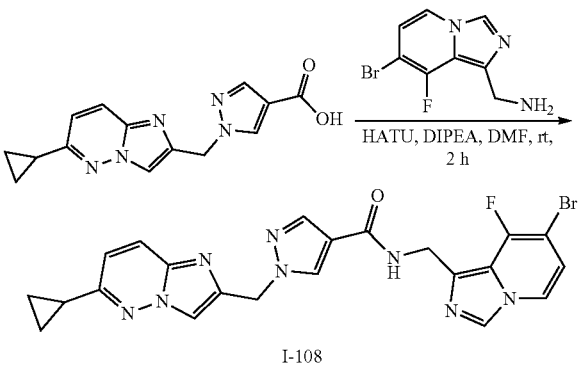
I-108

Synthesis of N-((7-bromo-8-fluoroimidazo[1,5-a]pyridin-1-yl)methyl)-1-((6-cyclopropylimidazo[1,2-b]pyridazin-2-yl)methyl)-1H-pyrazole-4-carboxamide (I-108)

A mixture of 1-((6-cyclopropylimidazo[1,2-b]pyridazin-2-yl)methyl)-1H-pyrazole-4-carboxylic acid (46 mg, 0.16 mmol), HATU (76 mg, 0.20 mmol) and DIPEA (103 mg, 0.80 mmol) in dry DMF (4 mL) was stirred at RT for 1 h. Then (7-bromo-8-fluoroimidazo[1,5-a]pyridin-1-yl)methanamine (40 mg, 0.16 mmol) was added. The resulting mixture was stirred at RT for another 1 h. Water (30 mL) was added and the mixture was extracted with ethyl acetate (30 mL×3). The combined organic layers were washed with brine, dried over anhydrous $Na_2SO_4$ and concentrated to give a residue, which was purified by prep-HPLC to give N-((7-bromo-8-fluoroimidazo[1,5-a]pyridin-1-yl)methyl)-1-((6-cyclopropylimidazo[1,2-b]pyridazin-2-yl)methyl)-1H-pyrazole-4-carboxamide (8 mg, yield: 9.7%) as a white solid. ESI-MS [M+H]$^+$: 509.1. Purity: 98.27%. $^1$H NMR (400 MHz, DMSO): δ 8.46 (d, J=2.4 Hz, 1H), 8.40 (t, J=5.2 Hz, 1H), 8.20 (s, 1H), 8.14 (d, J=7.4 Hz, 1H), 8.10 (s, 1H), 7.93 (d, J=9.5 Hz, 1H), 7.83 (s, 1H), 7.11 (d, J=9.5 Hz, 1H), 6.85-6.79 (m, 1H), 5.42 (s, 2H), 4.62 (d, J=5.2 Hz, 2H), 2.22-2.13 (m, 1H), 1.12-1.03 (m, 2H), 1.00-0.94 (m, 2H).

Example 109

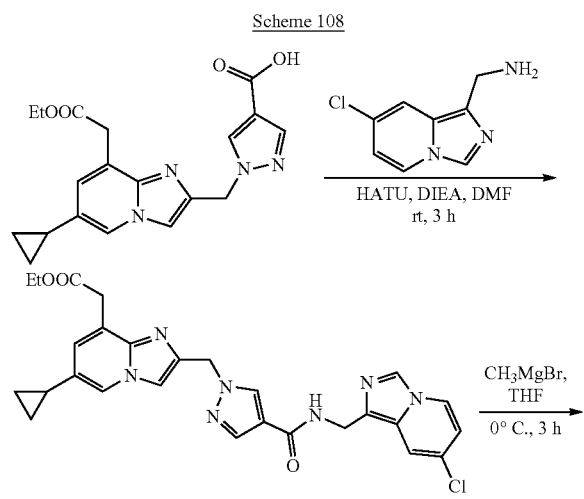

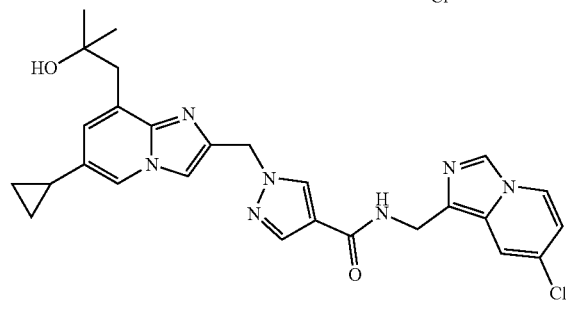

I-109

Synthesis of Ethyl 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)acetate To a mixture of 1-((6-cyclopropyl-8-(2-ethoxy-2-oxo-ethyl)imidazo[1,2-a]pyridin-2-yl)methyl)-1H-pyrazole-4-carboxylic acid (150 mg, 0.41 mmol) in DMF (3 mL) was added (7-chloroimidazo[1,5-a]pyridin-1-yl)methanamine hydrochloride (107 mg, 0.49 mmol), DIPEA (0.49 mL, 3 mmol) and HATU (234 mg, 0.62 mmol). The mixture was stirred at RT for 3 h. The reaction was diluted with $H_2O$ (30 mL) and extracted with EtOAc (30 mL×3). The combined organic layers were washed with brine, dried over $Na_2SO_4$, and concentrated in vacuo to give the crude which was purified by prep-TLC (DCM/MeOH=10/1) to give ethyl 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)acetate (70 mg, yield: 32%) as a white solid. ESI-MS [M+H]$^+$: 532.1.

Synthesis of N-((7-chloroimidazo[1,5-a]pyridin-1-yl)methyl)-1-((6-cyclopropyl-8-(2-hydroxy-2-methylpropyl)imidazo[1,2-a]pyridin-2-yl)methyl)-1H-pyrazole-4-carboxamide (I-109)

To a mixture of ethyl 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)acetate (70 mg, 0.13 mmol) in THF (5 mL) was added $CH_3MgBr$ (1 M in THF, 0.65 mL, 0.65 mmol) at 0° C. The mixture was stirred at 0° C. for 3 h under $N_2$. The reaction was quenched with $NH_4Cl$ (10 mL) and extracted with EtOAc (30 mL×3). The combined organic layers were washed with brine, dried over $Na_2SO_4$ and concentrated in vacuo to give the crude, which was purified by prep-HPLC to give N-((7-chloroimidazo[1,5-a]pyridin-1-yl)methyl)-1-((6-cyclopropyl-8-(2-hydroxy-2-methylpropyl)imidazo[1,2-a]pyridin-2-yl)methyl)-1H-pyrazole-4-carboxamide (5.4 mg, yield: 8%) as a white solid. ESI-MS [M+H]$^+$: 518.2. Purity: 99.1%. 1H NMR (400 MHz, DMSO): δ 8.58 (s, 1H), 8.32-8.30 (m, 2H), 8.18 (d, J=8.3 Hz, 2H), 7.88 (s, 1H), 7.78 (s, 1H), 7.65 (s, 1H), 6.90 (s, 1H), 6.65 (d, J=7.3 Hz, 1H), 5.39 (s, 2H), 5.24 (s, 1H), 4.56 (d, J=5.2 Hz, 2H), 2.98 (s, 2H), 1.92-1.85 (m, 1H), 1.06 (s, 6H), 0.94-0.88 (m, 2H), 0.67-0.62 (m, 2H).

Example 110

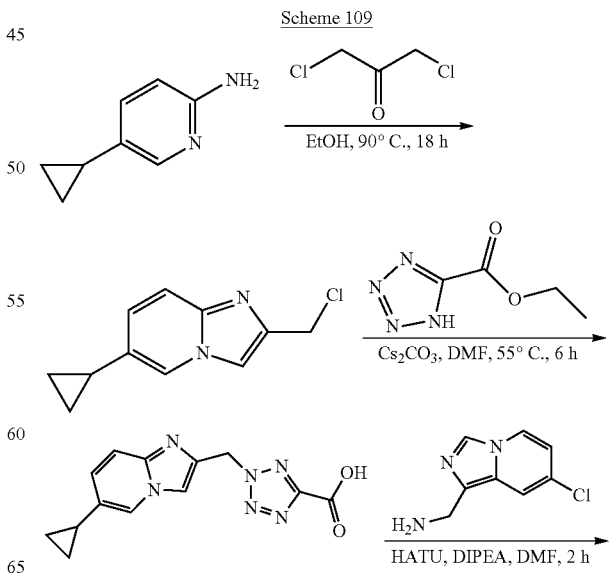

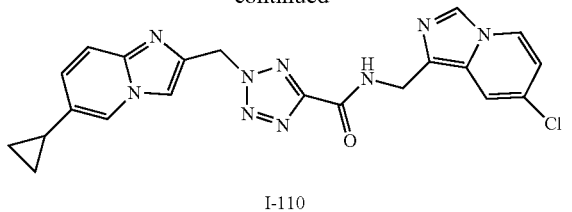

I-110

Synthesis of 2-(chloromethyl)-6-cyclopropylimidazo[1,2-a]pyridine

A mixture of 5-cyclopropylpyridin-2-amine (320 mg, 2.38 mmol), 1,3-dichloropropan-2-one (906 mg, 7.14 mmol) in EtOH (5 mL) was stirred at 90° C. for 18 h. Saturated aqueous NaHCO₃ (20 mL) was added and the mixture was extracted with EtOAc (50 mL×2). The combined organic layers were washed with brine, dried over Na₂SO₄ and concentrated to give the crude product which was purified by silica gel chromatography (EA/PE=2/1) to give 2-(chloromethyl)-6-cyclopropylimidazo[1,2-a]pyridine (200 mg, yield: 41%) as a brown solid. ESI-MS [M+H]⁺: 207.1.

Synthesis of 2-((6-cyclopropylimidazo[1,2-a]pyridin-2-yl)methyl)-2H-tetrazole-5-carboxylic Acid A mixture of 2-(chloromethyl)-6-cyclopropylimidazo[1,2-a]pyridine (104 mg, 0.5 mmol), ethyl 1H-tetrazole-5-carboxylate (71 mg, 0.5 mmol) and Cs₂CO₃ (978 mg, 3 mmol) in DMF (5 mL) was stirred at 55° C. for 6 h. After cooled to RT, H₂O (30 mL) was added and the mixture was extracted with EtOAc (30 mL×3). The pH value of the H₂O layer was adjusted to 5-6 by adding 1 M aqueous HCl solution, then freeze-dried to give 2-((6-cyclopropylimidazo[1,2-a]pyridin-2-yl)methyl)-2H-tetrazole-5-carboxylic acid (71 mg, yield: 50%) as a yellow solid. This was used into next step without purification. ESI-MS [M+H]⁺: 285.1.

Synthesis of N-((7-chloroimidazo[1,5-a]pyridin-1-yl)methyl)-2-((6-cyclopropylimidazo[1,2-a]pyridin-2-yl)methyl)-2H-tetrazole-5-carboxamide (I-109)

A mixture of 2-((6-cyclopropylimidazo[1,2-a]pyridin-2-yl)methyl)-2H-tetrazole-5-carboxylic acid (71 mg, 0.25 mmol), (7-chloroimidazo[1,5-a]pyridin-1-yl)methanamine (36 mg, 0.2 mmol), HATU (190 mg, 0.5 mmol) and DIPEA (97 mg, 0.75 mmol) in DMF (3 mL) was stirred at RT for 2 h. Water (20 mL) was added and extracted with EtOAc (30 mL×3). The combined organic layers were washed with brine, dried over Na₂SO₄ and concentrated to give the crude product, which was purified by silica gel column chromatography (CH₂Cl₂/CH₃OH=10/1) to provide N-((7-chloroimidazo[1,5-a]pyridin-1-yl)methyl)-2-((6-cyclopropylimidazo[1,2-a]pyridin-2-yl)methyl)-2H-tetrazole-5-carboxamide (20.2 mg, yield: 23%) as a white solid. ESI-MS [M+H]⁺: 448.1. Purity: 98.48%. ¹H NMR (400 MHz, DMSO): δ 9.44 (t, J=5.8 Hz, 1H), 8.36 (s, 1H), 8.31-8.30 (m, 2H), 7.94 (s, 1H), 7.83 (s, 1H), 7.38 (d, J=9.3 Hz, 1H), 7.01 (dd, J=9.4, 1.6 Hz, 1H), 6.65 (dd, J=7.4, 2.0 Hz, 1H), 6.06 (s, 2H), 4.64 (d, J=5.9 Hz, 2H), 1.96-1.89 (m, 1H), 1.02-0.84 (m, 2H), 0.83-0.57 (m, 2H).

Example 111

Scheme 110

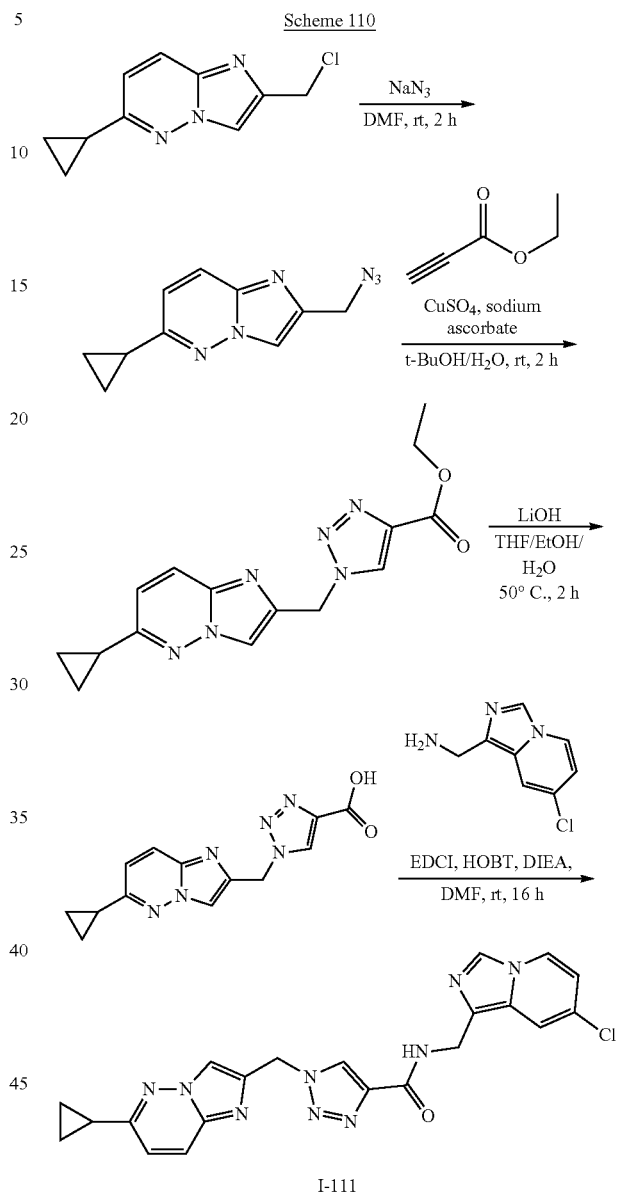

I-111

Synthesis of 2-(azidomethyl)-6-cyclopropylimidazo[1,2-b]pyridazine

To a solution of 2-(chloromethyl)-6-cyclopropylimidazo[1,2-b]pyridazine (900 mg, 4.33 mmol) in dry DMF (5 mL) was added NaN₃ (631 mg, 9.71 mmol). The reaction mixture was stirred at RT for 2 h. Water (30 mL) was added and the mixture was extracted with EtOAc (30 mL×3). The combined organic layers were washed with brine, dried over Na₂SO₄ and concentrated to give the crude product, which was purified by flash chromatography with silica gel (EtOAc/PE=40%) to give 2-(azidomethyl)-6-cyclopropylimidazo[1,2-b]pyridazine (735 mg, yield: 79%) as dark-red oil. ESI-MS [M+H]⁺: 215.2.

Synthesis of Ethyl 1-((6-cyclopropylimidazo[1,2-b]pyridazin-2-yl)methyl)-1H-1,2,3-triazole-4-carboxylate To a solution of 2-(azidomethyl)-6-cyclopropylimidazo[1,2-b]pyridazine (730 mg, 3.41 mmol) and ethyl propiolate (501.42 mg, 5.11 mmol) in a mixture of t-BuOH/H₂O (5 mL/5 mL) was added CuSO₄ (543.85 mg, 3.41 mmol) and sodium ascorbate (675.05 mg, 3.41 mmol). Then the mixture was stirred at RT for 2 h. The mixture was concentrated and purified by flash silica gel chromatography (EtOAc/PE=10%) to give ethyl 1-((6-cyclopropylimidazo[1,2-b]pyridazin-2-yl)methyl)-1H-1,2,3-triazole-4-carboxylate (600 mg, yield: 56.44%) as a red solid. ESI-MS [M+H]⁺: 313.2.

Synthesis of 1-((6-cyclopropylimidazo[1,2-b]pyridazin-2-yl)methyl)-1H-1,2,3-triazole-4-carboxylic Acid To a solution of ethyl 1-((6-cyclopropylimidazo[1,2-b]pyridazin-2-yl)methyl)-1H-1,2,3-triazole-4-carboxylate (100 mg, 0.32 mmol) in a mixture of THF/EtOH/H₂O (2 mL/2 mL/1 mL) was added LiOH (15.33 mg, 0.64 mmol). The mixture was heated to 50° C. for 2 h. Then the mixture was freeze-dried to give 1-((6-cyclopropylimidazo[1,2-b]pyridazin-2-yl)methyl)-1H-1,2,3-triazole-4-carboxylic acid (110 mg, crude) as a white solid which was used into next step without purification. ESI-MS [M+H]⁺: 285.1.

Synthesis of N-((7-chloroimidazo[1,5-a]pyridin-1-yl)methyl)-1-((6-cyclopropylimidazo[1,2-b]pyridazin-2-yl)methyl)-1H-1,2,3-triazole-4-carboxamide (I-111)

To a solution of 1-((6-cyclopropylimidazo[1,2-b]pyridazin-2-yl)methyl)-1H-1,2,3-triazole-4-carboxylic acid (30 mg, crude from last step) in DMF (2 mL) was added EDCI (30.35 mg, 0.158 mmol), HOBT (21.39 mg, 0.158 mmol), DIPEA (68.20 mg, 0.528 mmol) and (7-chloroimidazo[1,5-a]pyridin-1-yl)methanamine (19.17 mg, 0.106 mmol). Then the mixture was stirred at RT for 16 h. Water (15 mL) was added and the mixture was extracted with ethyl acetate (25 mL×4). The combined organic layers were concentrated to give the crude product, which was purified by prep-TLC to give N-((7-chloroimidazo[1,5-a]pyridin-1-yl)methyl)-1-((6-cyclopropylimidazo[1,2-b]pyridazin-2-yl)methyl)-1H-1,2,3-triazole-4-carboxamide (28 mg, yield: 59.09%) as a white solid. ESI-MS [M+H]⁺: 448.2. Purity: 96%. ¹H NMR (400 MHz, DMSO): δ 8.91 (t, J=5.8 Hz, 1H), 8.57 (s, 1H), 8.33-8.27 (m, 2H), 8.19 (s, 1H), 7.93 (d, J=9.4 Hz, 1H), 7.83 (s, 1H), 7.10 (d, J=9.4 Hz, 1H), 6.67-6.62 (m, 1H), 5.75 (s, 2H), 4.61 (d, J=5.9 Hz, 2H), 2.22-2.13 (m, 1H), 1.12-1.02 (m, 2H), 1.00-0.94 (m, 2H).

Example 112

Scheme 111

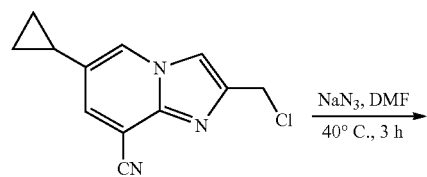

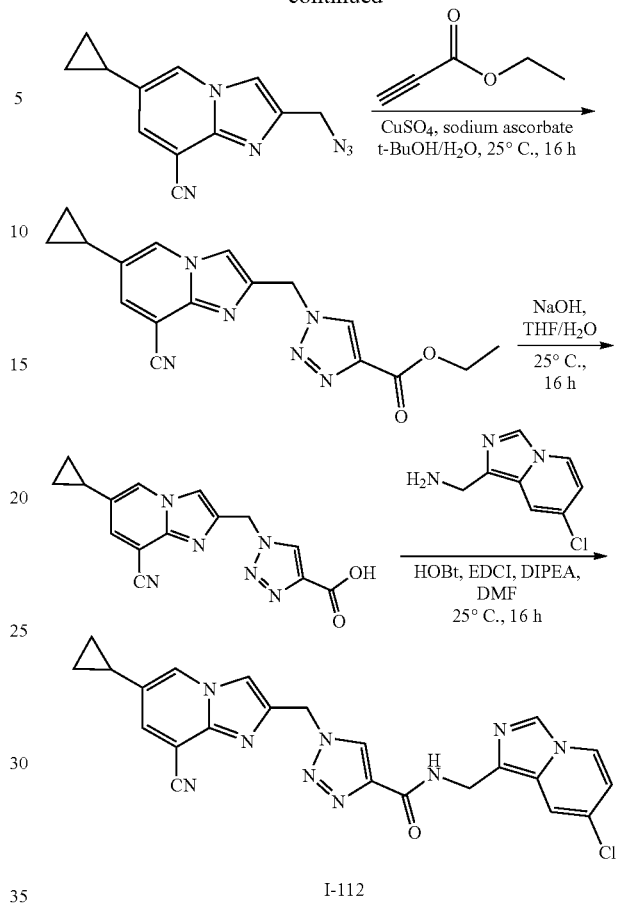

I-112

Synthesis of 2-(azidomethyl)-6-cyclopropylimidazo[1,2-a]pyridine-8-carbonitrile To a mixture of 2-(chloromethyl)-6-cyclopropylimidazo[1,2-a]pyridine-8-carbonitrile (100 mg, 0.43 mmol) in dry DMF (2 mL) was added NaN₃ (39 mg, 0.65 mmol). The mixture was stirred at 25° C. for 3 h. Then H₂O (20 mL) was added and extracted with EtOAc (20 mL×3). The combined organic layers were washed with brine, dried over Na₂SO₄ and concentrated to give the crude, which was purified by prep-TLC (EA/PE=3/2) to give 2-(azidomethyl)-6-cyclopropylimidazo[1,2-a]pyridine-8-carbonitrile (70 mg, yield: 68%) as a yellow solid. ESI-MS [M+H]⁺: 239.2.

Synthesis of Ethyl 1-((8-cyano-6-cyclopropylimidazo[1,2-a]pyridin-2-yl)methyl)-1H-1,2,3-triazole-4-carboxylate To a mixture of 2-(azidomethyl)-6-cyclopropylimidazo[1,2-a]pyridine-8-carbonitrile (70 mg, 0.29 mmol), CuSO₄ (24 mg, 0.15 mmol), sodium ascorbate (30 mg, 0.15 mmol) in t-BuOH/H₂O (3/3 mL) was added ethyl propiolate (43 mg, 0.44 mmol). The mixture was stirred at 25° C. for 16 h and then concentrated to give the crude product. PE/EA (10 mL/1 mL) was added, stirred at 25° C. for 5 min, and a solid was filtered and washed with PE to give ethyl 1-((8-cyano-6-cyclopropylimidazo[1,2-a]pyridin-2-yl)methyl)-1H-1,2,3-triazole-4-carboxylate (95 mg, yield: 96%) as a yellow solid, which was used into next step without purification. ESI-MS [M+H]⁺: 337.2.

Synthesis of 1-((8-cyano-6-cyclopropylimidazo[1,2-a]pyridin-2-yl)methyl)-1H-1,2,3-triazole-4-carboxylic Acid To a mixture of ethyl 1-((8-cyano-6-cyclopropylimidazo[1,2-a]pyridin-2-yl)methyl)-1H-1,2,3-triazole-4-carboxylate (95 mg, 0.28 mmol) in THF/H₂O (4 mL/2 mL) was added NaOH (34 mg, 0.85 mmol). The mixture was stirred at 25° C. for 16 h. The pH of the mixture was adjusted to 5 with 1 M HCl, then extracted with EtOAc (50 mL×3). The combined organic layers were washed with brine, dried over Na₂SO₄ and concentrated to give 1-((8-cyano-6-cyclopropylimidazo[1,2-a]pyridin-2-yl)methyl)-1H-1,2,3-triazole-4-carboxylic acid (70 mg, yield: 80%) as a grey solid. ESI-MS [M+H]⁺: 309.2.

Synthesis of N-((7-chloroimidazo[1,5-a]pyridin-1-yl)methyl)-1-((8-cyano-6-cyclopropylimidazo[1,2-a]pyridin-2-yl)methyl)-1H-1,2,3-triazole-4-carboxamide (I-112)

To a mixture of 1-((8-cyano-6-cyclopropylimidazo[1,2-a]pyridin-2-yl)methyl)-1H-1,2,3-triazole-4-carboxylic acid (60 mg, 0.19 mmol), (7-chloroimidazo[1,5-a]pyridin-1-yl)methanamine (42 mg, 0.23 mmol), HOBT (54 mg, 0.4 mmol), EDCI (75 mg, 0.4 mmol) in DMF (3 mL) was added DIPEA (126 mg, 0.98 mmol). The mixture was stirred at 25° C. for 16 h. Water (20 mL) was added, extracted with EtOAc (20 mL×3). The combined organic layers were washed with brine, dried over Na₂SO₄, filtered and concentrated to give the crude product, which was purified by prep-HPLC to give N-((7-chloroimidazo[1,5-a]pyridin-1-yl)methyl)-1-((8-cyano-6-cyclopropylimidazo[1,2-a]pyridin-2-yl)methyl)-1H-1,2,3-triazole-4-carboxamide (53.7 mg, yield: 58%) as a yellow solid. ESI-MS [M+H]+: 472.1. Purity: 99.54%. ¹H NMR (400 MHz, DMSO): δ 8.94 (s, 1H), 8.69-8.60 (m, 2H), 8.31-8.30 (m, 2H), 7.99 (s, 1H), 7.84-7.80 (m, 2H), 6.65 (s, 1H), 5.81 (s, 2H), 4.63 (s, 2H), 1.98-1.97 (m, 1H), 0.96-0.95 (m, 2H), 0.76-0.75 (m, 2H).

Example 113

Scheme 112

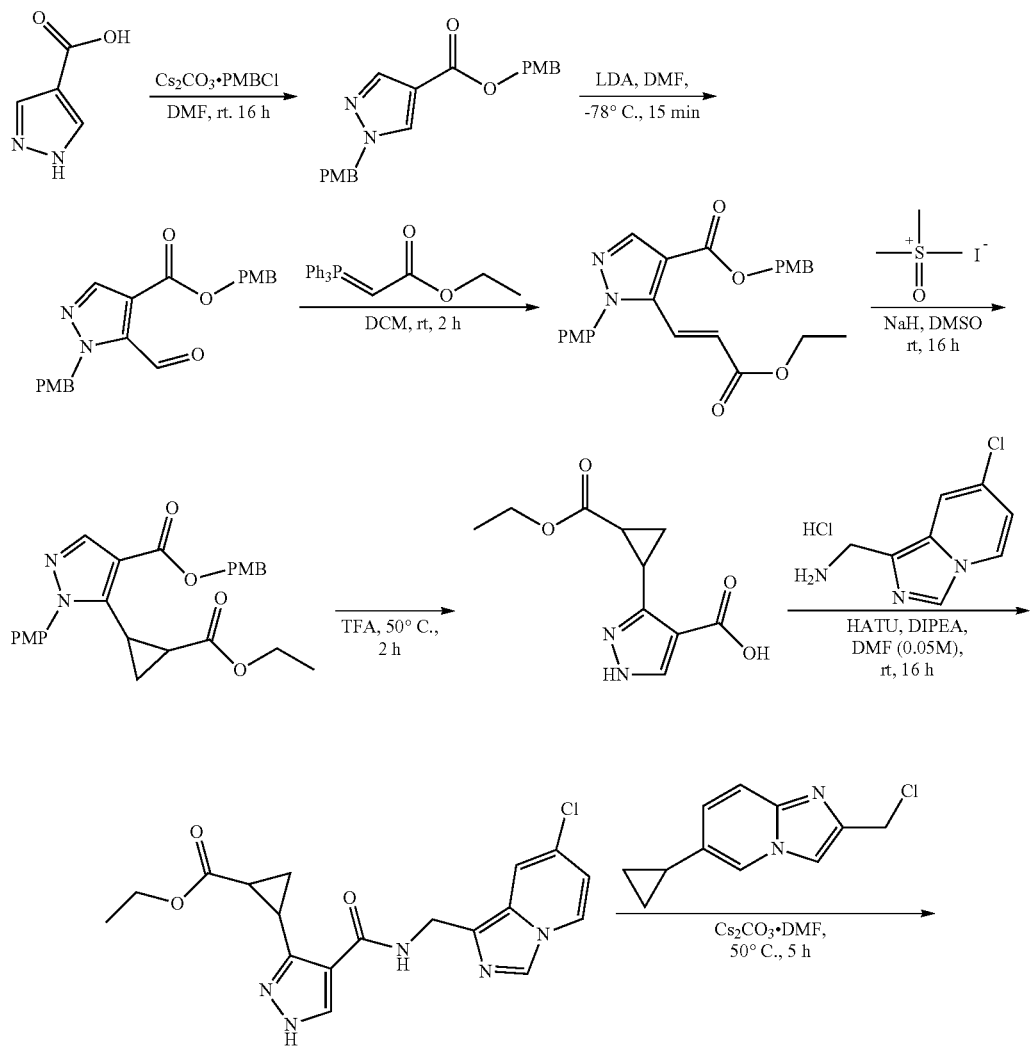

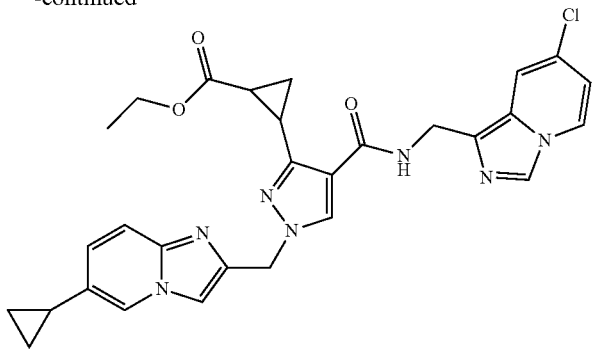

I-113

Synthesis of 4-methoxybenzyl 1-(4-methoxybenzyl)-1H-pyrazole-4-carboxylate

A solution of 1H-pyrazole-4-carboxylic acid (6 g, 53.53 mmol), PMBCl (18.4 g, 117.76 mmol) and Cs$_2$CO$_3$ (52.3 mg, 160.59 mmol) in DMF (100 mL) was stirred at RT for 16 h. The reaction mixture was poured into H$_2$O (600 mL) and extracted with EtOAc (500 mL×3). The combined organic layers were washed with brine (200 mL), dried over Na$_2$SO$_4$ and concentrated. The crude product was purified by silica gel chromatography (EA/PE=1/5) to give 4-methoxybenzyl 1-(4-methoxybenzyl)-1H-pyrazole-4-carboxylate (9.8 g, yield: 52%) as a white solid. ESI-MS [M+H]$^+$: 353.2.

Synthesis of 4-methoxybenzyl 5-formyl-1-(4-methoxybenzyl)-1H-pyrazole-4-carboxylate To a solution of 4-methoxybenzyl 1-(4-methoxybenzyl)-1H-pyrazole-4-carboxylate (9.8 g, 27.81 mmol) in THF (100 mL) was added dropwise of LDA (41.7 mL, 41.7 mmol) at −78° C. over 10 min. After stirring for 5 min DMF (12.2 g, 167.86 mmol) was added. The resulting mixture was stirred at −78° C. for another 10 min. The reaction was quenched with saturated NH$_4$Cl aqueous (100 mL) and extracted with EtOAc (200 mL×3). The combined organic layers were washed with brine, dried over Na$_2$SO$_4$, concentrated and purified by silica gel chromatography (EA/PE=1/3) to give 4-methoxybenzyl 5-formyl-1-(4-methoxybenzyl)-1H-pyrazole-4-carboxylate (4.9 g, yield: 44%) as a white solid. ESI-MS [M+H]$^+$: 403.1.

Synthesis of 4-methoxybenzyl (E)-5-(3-ethoxy-3-oxoprop-1-en-1-yl)-1-(4-methoxybenzyl)-1H-pyrazole-4-carboxylate To a solution of 4-methoxybenzyl 5-formyl-1-(4-methoxybenzyl)-1H-pyrazole-4-carboxylate (4.9 g, 12.88 mmol) in DCM (100 mL) was added ethyl 2-(triphenyl-15-phosphanylidene)acetate (5.83 g, 16.74 mmol) in portions at 0° C. The mixture was stirred at RT for 16 h. Water (200 mL) was added and the mixture was extracted with DCM (200 mL×3). The combined organic layers were concentrated to give the crude product, which was purified by silica gel chromatography (EA/PE=1/3) to give 4-methoxybenzyl (E)-5-(3-ethoxy-3-oxoprop-1-en-1-yl)-1-(4-methoxybenzyl)-1H-pyrazole-4-carboxylate (5.7 g, 98%) as a yellow solid. ESI-MS [M+H]$^+$: 451.2.

Synthesis of 4-methoxybenzyl 5-(2-(ethoxycarbonyl)cyclopropyl)-1-(4-methoxybenzyl)-1H-pyrazole-4-carboxylate To a suspension of NaH (102 mg, 2.68 mmol) in DMSO (10 mL) was added trimethylsulfoxonium iodide (967 mg, 4.39 mmol) at RT. The mixture was stirred at RT for 10 mins. Then a solution of 4-methoxybenzyl (E)-5-(3-ethoxy-3-oxoprop-1-en-1-yl)-1-(4-methoxybenzyl)-1H-pyrazole-4-carboxylate (1.1 g, 2.44 mmol) in DMSO/THF (6 mL, 1/1 (v/v)) was added. The resulting mixture was stirred at RT for 16 h. The reaction mixture was quenched with NH$_4$Cl aqueous (100 mL) and extracted with EtOAc (100 mL×3). The combined organic layers were washed with brine, dried over Na$_2$SO$_4$, concentrated and purified by silica gel chromatography (EA/PE=1/2) to give 4-methoxybenzyl 5-(2-(ethoxycarbonyl)cyclopropyl)-1-(4-methoxybenzyl)-1H-pyrazole-4-carboxylate (1.1 g, yield: 97%) as a yellow solid. ESI-MS [M+H]$^+$: 465.2.

Synthesis of 3-(2-(ethoxycarbonyl)cyclopropyl)-1H-pyrazole-4-carboxylic Acid A solution of 4-methoxybenzyl 5-(2-(ethoxycarbonyl)cyclopropyl)-1-(4-methoxybenzyl)-1H-pyrazole-4-carboxylate (1.1 g, 2.37 mmol) in TFA (10 mL) was stirred at 50° C. for 16 h. The reaction mixture was concentrated and diluted in H$_2$O (50 mL) and the pH was adjusted to 6-7 by adding saturated NaHCO$_3$ and then extracted with EtOAc (100 mL×3). The combined organic layers were washed with brine, dried over Na$_2$SO$_4$, concentrated and purified by silica gel chromatography (EA/PE=1/3) to give 3-(2-(ethoxycarbonyl)cyclopropyl)-1H-pyrazole-4-carboxylic acid (230 mg, yield: 43%) as a yellow solid. ESI-MS [M+H]$^+$: 225.1.

Synthesis of Ethyl 2-(4-(((7-chloroimidazo[1,5-a]pyridin-1-yl)methyl)carbamoyl)-1H-pyrazol-3-yl)cyclopropane-1-carboxylate A mixture of 3-(2-(ethoxycarbonyl)cyclopropyl)-1H-pyrazole-4-carboxylic acid (230 mg, 1.03 mmol), (7-chloroimidazo[1,5-a]pyridin-1-yl)methanamine hydrochloride (337 mg, 1.545 mmol), HATU (431 mg, 1.133 mmol) and DIPEA (399 mg, 3.09 mmol) in DMF (10 mL) was stirred at RT for 16 h. The reaction mixture was poured into H$_2$O (120 mL) and extracted with EtOAc/THF (80 mL×3, 5/1 (v/v)). The combined organic layers were washed with brine, dried over Na$_2$SO$_4$, concentrated and purified by silica gel chromatography (DCM/MeOH=20/1) to give ethyl 2-(4-

(((7-chloroimidazo[1,5-a]pyridin-1-yl)methyl)carbamoyl)-1H-pyrazol-3-yl)cyclopropane-1-carboxylate (150 mg, yield: 38%) as a yellow solid. ESI-MS [M+H]+: 388.1.

Synthesis of Ethyl 2-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)cyclopropane-1-carboxylate (I-113)

A mixture of ethyl 2-(4-(((7-chloroimidazo[1,5-a]pyridin-1-yl)methyl)carbamoyl)-1H-pyrazol-3-yl)cyclopropane-1-carboxylate (150 mg, 0.387 mmol), 2-(chloromethyl)-6-cyclopropylimidazo[1,2-a]pyridine (96 mg, 0.464 mmol) and $Cs_2CO_3$ (189 mg, 0.581 mmol) in DMF (6 mL) was stirred at 50° C. for 5 h. Water (50 mL) was added and extracted with EtOAc (50 mL×3). The combined organic layers were washed with brine, dried over $Na_2SO_4$, concentrated and purified by silica gel chromatography (DCM/MeOH=8/1) to give ethyl 2-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)cyclopropane-1-carboxylate (110 mg, yield: 51%) as a yellow solid. ESI-MS [M+H]+: 558.2. Purity: 95.76%. $^1$H NMR (400 MHz, DMSO): δ 8.45 (t, J=5.6 Hz, 1H), 8.35-8.28 (m, 3H), 8.14 (s, 1H), 7.75 (m, 2H), 7.39 (d, J=9.3 Hz, 1H), 6.99 (dd, J=9.4, 1.7 Hz, 1H), 6.64 (dd, J=7.4, 2.1 Hz, 1H), 5.27 (s, 2H), 4.53 (d, J=5.7 Hz, 2H), 4.08 (q, J=7.0 Hz, 2H), 3.22-3.16 (m, 1H), 2.01-1.95 (m, 1H), 1.91 (m, 1H), 1.41-1.32 (m, 2H), 1.18 (t, J=7.1 Hz, 3H), 0.94-0.88 (m, 2H), 0.69-0.63 (m, 2H).

Example 114

Synthesis of N-((7-chloroimidazo[1,5-a]pyridin-1-yl)methyl)-1-((6-cyclopropyl-8-(2-oxopyrrolidin-1-yl)imidazo[1,2-a]pyridin-2-yl)methyl)-1H-pyrazole-4-carboxamide (I-114)

A mixture of 1-(2-(chloromethyl)-6-cyclopropylimidazo[1,2-a]pyridin-8-yl)pyrrolidin-2-one (25 mg, 0.087 mmol), N-((7-chloroimidazo[1,5-a]pyridin-1-yl)methyl)-1H-pyrazole-4-carboxamide (26 mg, 0.095 mmol) and $Cs_2CO_3$ (70 mg, 0.216 mmol) in DMF (3 mL) was stirred at RT for 3 h. The reaction was quenched with $H_2O$ (30 mL) was added and extracted with EtOAc (30 mL×3). The combined organic layers were washed with brine, dried over $Na_2SO_4$ and concentrated in vacuo to give the crude, which was purified by prep-HPLC to give N-((7-chloroimidazo[1,5-a]pyridin-1-yl)methyl)-1-((6-cyclopropyl-8-(2-oxopyrrolidin-1-yl)imidazo[1,2-a]pyridin-2-yl)methyl)-1H-pyrazole-4-carboxamide (16.2 mg, yield: 35%) as a white solid. ESI-MS [M+H]+: 529.2. Purity: 99.4%. $^1$H NMR (400 MHz, DMSO): δ 8.58 (t, J=5.7 Hz, 1H), 8.31-8.30 (m, 2H), 8.26 (d, J=1.2 Hz, 1H), 8.19 (s, 1H), 7.89 (s, 1H), 7.78 (d, J=1.2 Hz, 1H), 7.71 (s, 1H), 7.16 (d, J=1.5 Hz, 1H), 6.65 (dd, J=7.5, 2.1 Hz, 1H), 5.41 (s, 2H), 4.55 (d, J=5.7 Hz, 2H), 4.10 (t, J=7.1 Hz, 2H), 2.45 (t, J=8.2 Hz, 2H), 2.14-2.03 (m, 2H), 1.95-1.88 (m, 1H), 0.98-0.89 (m, 2H), 0.68-0.59 (m, 2H).

Example 115

Scheme 113

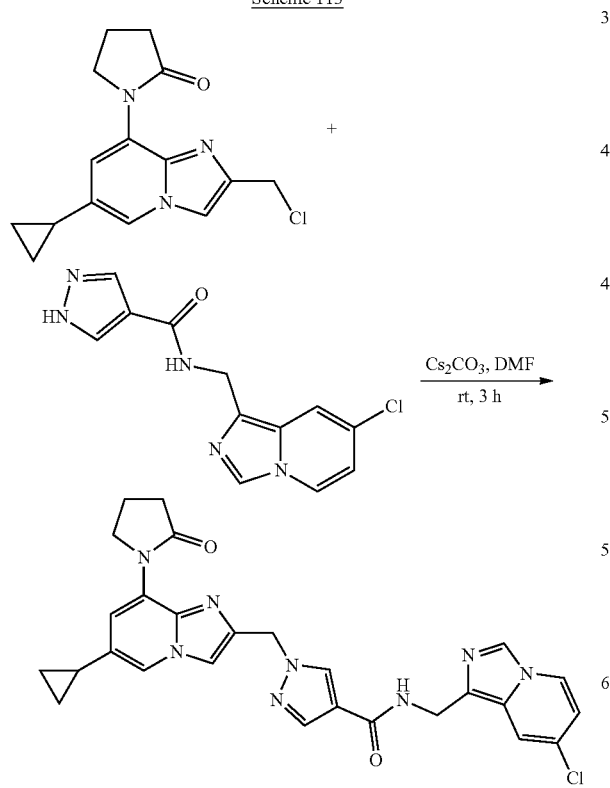

I-114

Scheme 114

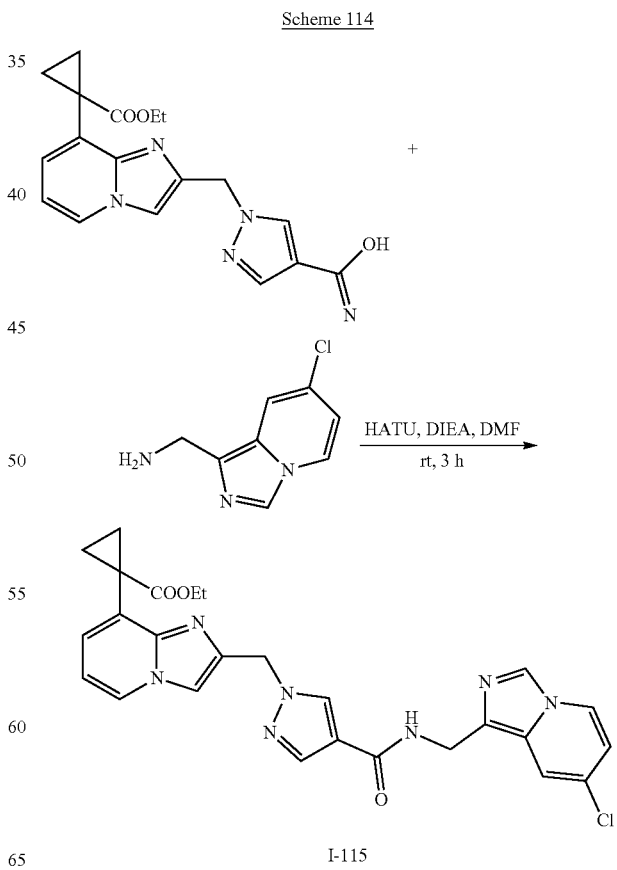

I-115

Synthesis of Ethyl 1-(2-((4-(((7-chloroimidazo[1,5-a]pyridin-1-yl)methyl)carbamoyl)-1H-pyrazol-1-yl)methyl)imidazo[1,2-a]pyridin-8-yl)cyclopropane-1-carboxylate (I-115)

A mixture of 1-((8-(1-(ethoxycarbonyl)cyclopropyl)imidazo[1,2-a]pyridin-2-yl)methyl)-1H-pyrazole-4-carboxylic acid (108 mg, 0.27 mmol), (7-chloroimidazo[1,5-a]pyridin-1-yl)methanamine hydrochloride (89 mg, 0.41 mmol), DIPEA (174 mg, 1.35 mmol) and HATU (205 mg, 0.54 mmol) in DMF (3 mL) was stirred at RT for 3 h. The reaction was diluted with H₂O (30 mL) and extracted with EtOAc (30 mL×3). The combined organic layers were washed with brine, dried over Na₂SO₄ and concentrated in vacuo to give the crude, which was purified by prep-HPLC to give ethyl 1-(2-((4-(((7-chloroimidazo[1,5-a]pyridin-1-yl)methyl)carbamoyl)-1H-pyrazol-1-yl)methyl)imidazo[1,2-a]pyridin-8-yl)cyclopropane-1-carboxylate (13.4 mg, yield: 8.9%) as a white solid. ESI-MS [M+H]⁺: 558.2. Purity: 98.1%. ¹H NMR (400 MHz, MeOD): δ 8.25 (s, 1H), 8.15 (d, J=7.5 Hz, 1H), 8.09 (d, J=2.1 Hz, 2H), 7.91 (s, 1H), 7.73 (s, 1H), 7.67 (s, 1H), 7.02 (d, J=1.3 Hz, 1H), 6.61 (dd, J=7.4, 1.6 Hz, 1H), 5.44 (s, 2H), 4.67 (s, 2H), 3.97 (q, J=7.1 Hz, 2H), 1.91 (ddd, J=13.5, 8.5, 5.2 Hz, 1H), 1.68 (dd, J=7.2, 4.2 Hz, 2H), 1.25 (dd, J=7.2, 4.2 Hz, 2H), 1.05-0.86 (m, 5H), 0.75-0.62 (m, 2H).

Example 116

Scheme 115

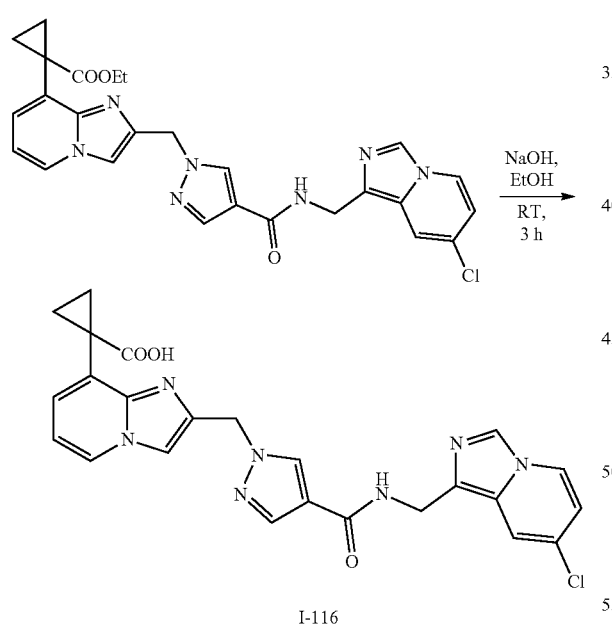

I-116

Synthesis of 1-(2-((4-(((7-chloroimidazo[1,5-a]pyridin-1-yl)methyl)carbamoyl)-1H-pyrazol-1-yl)methyl)imidazo[1,2-a]pyridin-8-yl)cyclopropane-1-carboxylic acid (I-116)

To a mixture of ethyl 1-(2-((4-(((7-chloroimidazo[1,5-a]pyridin-1-yl)methyl)carbamoyl)-1H-pyrazol-1-yl)methyl)imidazo[1,2-a]pyridin-8-yl)cyclopropane-1-carboxylate (50 mg, 0.09 mmol) in EtOH (2 mL) was added NaOH (6.4 mg, 0.16 mmol) in H₂O (1 mL). The mixture was stirred at RT for 3 h. The pH of the residue was adjusted to 4 by adding 1 M HCl solution. The mixture was then concentrated and purified by prep-HPLC to give the 1-(2-((4-(((7-chloroimidazo[1,5-a]pyridin-1-yl)methyl)carbamoyl)-1H-pyrazol-1-yl)methyl)imidazo[1,2-a]pyridin-8-yl)cyclopropane-1-carboxylic acid (21.6 mg, yield: 45%) as a white solid. ESI-MS [M+H]⁺: 530.2. Purity: 96.5%. ¹H NMR (400 MHz, MeOD): δ 8.25 (s, 1H), 8.16 (d, J=7.5 Hz, 1H), 8.11 (s, 2H), 7.91 (s, 1H), 7.73 (s, 1H), 7.67 (s, 1H), 7.09 (d, J=1.5 Hz, 1H), 6.62 (dd, J=7.5, 2.0 Hz, 1H), 5.46 (s, 2H), 4.67 (s, 2H), 1.93 (ddd, J=13.5, 8.4, 5.1 Hz, 1H), 1.72 (dd, J=7.1, 4.1 Hz, 2H), 1.25 (dd, J=7.2, 4.2 Hz, 2H), 1.01-0.91 (m, 2H), 0.78-0.66 (m, 2H).

Example 117

Scheme 116

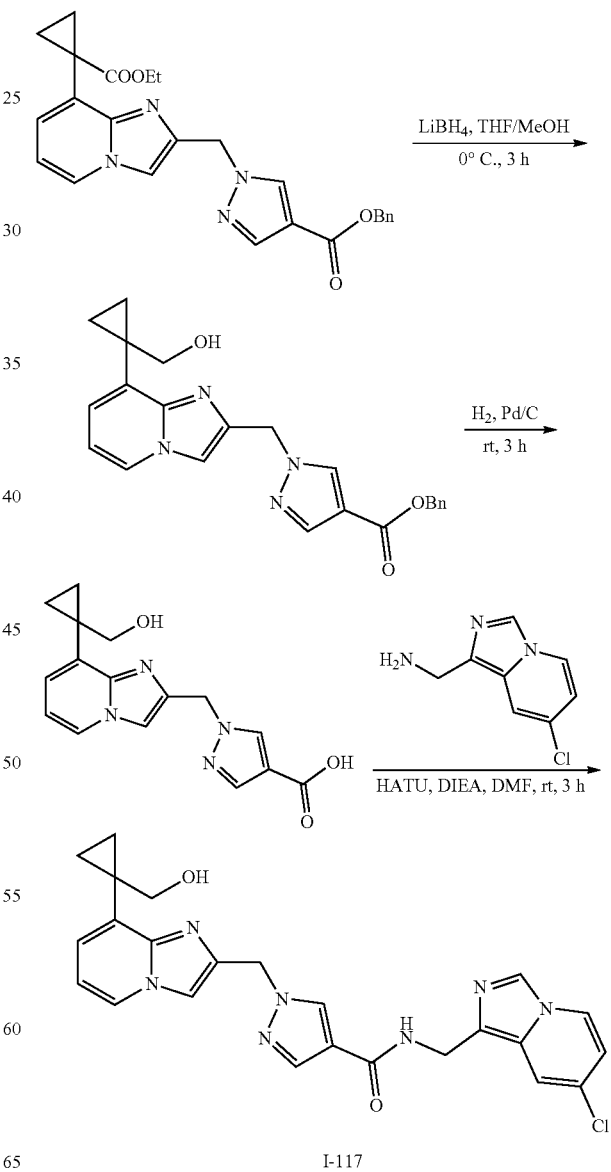

I-117

Synthesis of benzyl 1-((8-(1-(hydroxymethyl)cyclopropyl)imidazo[1,2-a]pyridin-2-yl)methyl)-1H-pyrazole-4-carboxylate To a mixture of benzyl 1-((8-(1-(ethoxycarbonyl)cyclopropyl)imidazo[1,2-a]pyridin-2-yl)methyl)-1H-pyrazole-4-carboxylate (266 mg, 0.6 mmol) in THF/MeOH (5 mL/0.5 mL) was added LiBH$_4$ (136 mg, 6 mmol) at 0° C. The mixture was stirred at 0° C. for 3 h. The reaction was quenched with H$_2$O (20 mL) and extracted with EtOAc (50 mL×3). The combined organic layers were washed with brine, dried over Na$_2$SO$_4$, and concentrated in vacuo to give the crude which was purified by prep-TLC (DCM/MeOH: 10/1) to give benzyl 1-((8-(1-(hydroxymethyl)cyclopropyl)imidazo[1,2-a]pyridin-2-yl)methyl)-1H-pyrazole-4-carboxylate (94 mg, yield: 38%) as a white solid. ESI-MS [M+H]$^+$: 403.1.

Synthesis of 1-((8-(1-(hydroxymethyl)cyclopropyl)imidazo[1,2-a]pyridin-2-yl)methyl)-1H-pyrazole-4-carboxylic Acid To a mixture of benzyl 1-((8-(1-(hydroxymethyl)cyclopropyl)imidazo[1,2-a]pyridin-2-yl)methyl)-1H-pyrazole-4-carboxylate (94 mg, 0.23 mmol) in MeOH (3 mL) was added Pd/C (30 mg, 0.3 mmol). The mixture was stirred at RT for 3 h under H$_2$. The reaction was filtered and concentrated in vacuo to give 1-((8-(1-(hydroxymethyl)cyclopropyl)imidazo[1,2-a]pyridin-2-yl)methyl)-1H-pyrazole-4-carboxylic acid (70 mg, yield: 97%) as a white solid, which was used into the next step without purification. ESI-MS [M+H]$^+$: 313.1.

Synthesis of N-((7-chloroimidazo[1,5-a]pyridin-1-yl)methyl)-1-((8-(1-(hydroxymethyl)cyclopropyl)imidazo[1,2-a]pyridin-2-yl)methyl)-1H-pyrazole-4-carboxamide (I-117)

A mixture of 1-((8-(1-(hydroxymethyl)cyclopropyl)imidazo[1,2-a]pyridin-2-yl)methyl)-1H-pyrazole-4-carboxylic acid (70 mg, 0.2 mmol), (7-chloroimidazo[1,5-a]pyridin-1-yl)methanamine hydrochloride (87.2 mg, 0.4 mmol), DIPEA (129 mg, 1 mmol) and HATU (152 mg, 0.4 mmol) in DMF (3 mL) was stirred at RT for 3 h. The reaction was diluted with H$_2$O (30 mL) and extracted with EtOAc (30 mL×3). The combined organic layers were washed with brine, dried over Na$_2$SO$_4$ and concentrated in vacuo to give the crude, which was purified with prep-HPLC to give N-((7-chloroimidazo[1,5-a]pyridin-1-yl)methyl)-1-((8-(1-(hydroxymethyl)cyclopropyl)imidazo[1,2-a]pyridin-2-yl)methyl)-1H-pyrazole-4-carboxamide (26 mg, yield: 23%) as a white solid. ESI-MS [M+H]$^+$: 516.2. Purity: 97.0%. $^1$H NMR (400 MHz, MeOD): δ 8.24 (s, 1H), 8.17-8.09 (m, 2H), 8.04 (s, 1H), 7.90 (d, J=9.6 Hz, 1H), 7.72 (s, 1H), 7.65 (s, 1H), 6.99 (d, J=1.3 Hz, 1H), 6.60 (dd, J=7.5, 1.9 Hz, 1H), 5.46 (s, 2H), 4.67 (s, 2H), 3.71 (s, 2H), 1.89 (ddd, J=13.4, 8.5, 5.1 Hz, 1H), 0.98-0.84 (m, 6H), 0.72-0.64 (m, 2H).

Example 118

Scheme 117

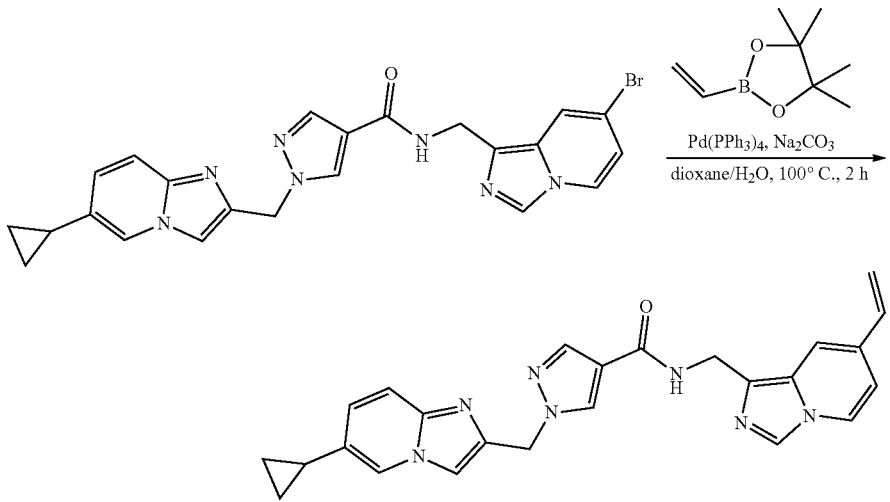

I-118

Synthesis of 1-((6-cyclopropylimidazo[1,2-a]pyridin-2-yl)methyl)-N-((7-vinylimidazo[1,5-a]pyridin-1-yl)methyl)-1H-pyrazole-4-carboxamide (I-118)

A mixture of N-((7-bromoimidazo[1,5-a]pyridin-1-yl)methyl)-1-((6-cyclopropylimidazo[1,2-a]pyridin-2-yl)methyl)-1H-pyrazole-4-carboxamide (50 mg, 0.16 mmol), 4,4,5,5-tetramethyl-2-vinyl-1,3,2-dioxaborolane (17 mg, 0.11 mmol), tetrakis(triphenylphosphine)palladium(0) (23 mg, 0.02 mmol) in dioxane/H$_2$O (2 mL/0.5 mL) was stirred at 100° C. for 2 h. Water (20 mL) was added and extracted with ethyl acetate (30 mL*3). The combined organic layers were washed with brine, dried over anhydrous sodium sulfate and concentrated. The residue was purified by Prep-HPLC to give 1-((6-cyclopropylimidazo[1,2-a]pyridin-2-yl)methyl)-N-((7-vinylimidazo[1,5-a]pyridin-1-yl)methyl)-1H-pyrazole-4-carboxamide (34 mg, yield: 75%) as a white solid. ESI-MS [M+H]⁺: 438.2. Purity: 93.19%. ¹H NMR (400 MHz, DMSO) δ 8.52 (t, J=5.5 Hz, 1H), 8.32 (s, 1H), 8.27 (s, 1H), 8.25-8.17 (m, 2H), 7.86 (s, 1H), 7.71 (s, 1H), 7.55 (s, 1H), 7.39 (d, J=9.3 Hz, 1H), 7.02-6.96 (m, 1H), 6.94-6.88 (m, 1H), 6.68-6.57 (m, 1H), 5.77 (d, J=17.5 Hz, 1H), 5.38 (s, 2H), 5.26 (d, J=11.0 Hz, 1H), 4.57 (d, J=5.6 Hz, 2H), 1.96-1.87 (m, 1H), 0.94-0.88 (m, 2H), 0.69-0.63 (m, 2H).

Example 119

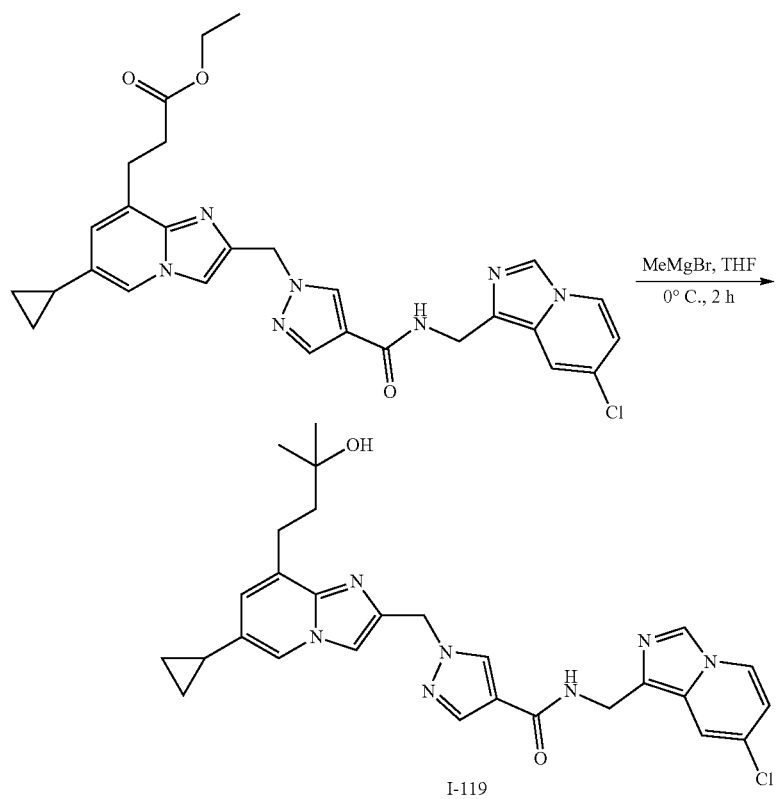

Synthesis of N-((7-chloroimidazo[1,5-a]pyridin-1-yl)methyl)-1-((6-cyclopropyl-8-(3-hydroxy-3-methylbutyl)imidazo[1,2-a]pyridin-2-yl)methyl)-1H-pyrazole-4-carboxamide (I-119)

To a solution of ethyl 3-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)propanoate (35 mg, 0.064 mmol) in THF (3 mL) was added MeMgBr (0.32 mL, 1.0 M solution in THF, 0.32 mmol) slowly 0° C. The reaction was stirred at 0° C. for 2 h., quenched with aqueous NH₄Cl (15 mL), and extracted with EtOAc (30 mL×3). The combined organic layers were washed with brine, dried over Na₂SO₄, and concentrated in vacuo to give the crude product, which was purified by prep-TLC (DCM/MeOH=10/1) to give N-((7-chloroimidazo[1,5-a]pyridin-1-yl)methyl)-1-((6-cyclopropyl-8-(3-hydroxy-3-methylbutyl)imidazo[1,2-a]pyridin-2-yl)methyl)-1H-pyrazole-4-carboxamide (20 mg, yield: 58.8%) as a white solid. ESI-MS [M+H]⁺: 532.2. Purity: 95.7%. ¹H NMR (400 MHz, DMSO): δ 8.60 (s, 1H), 8.32-8.30 (m, 2H), 8.18 (d, J=18.5 Hz, 2H), 7.89 (s, 1H), 7.79 (s, 1H), 7.63 (s, 1H), 6.80 (s, 1H), 6.65 (d, J=5.5 Hz, 1H), 5.41 (s, 2H), 4.56 (s, 2H), 4.31 (s, 1H), 2.87 (s, 2H), 2.00-1.85 (m, 1H), 1.75 (s, 2H), 1.16 (s, 6H), 1.00-0.85 (m, 2H), 0.72-0.63 (m, 2H).

Example 120

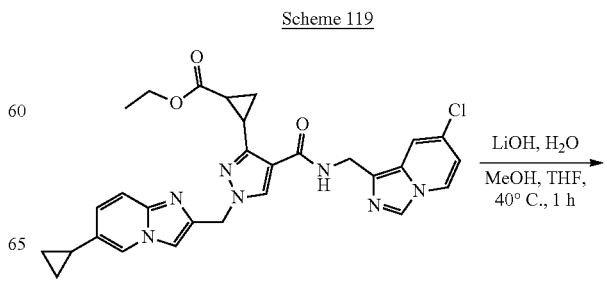

-continued

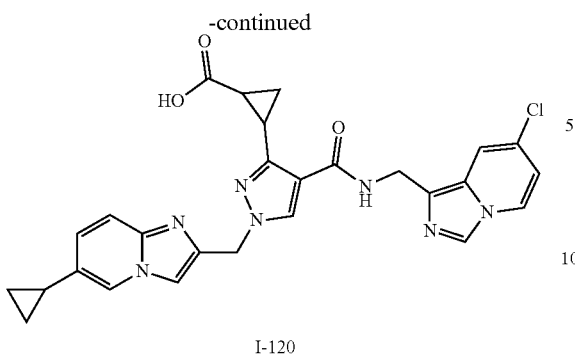

I-120

Synthesis of 2-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)cyclopropane-1-carboxylic Acid (I-120)

To a solution of ethyl 2-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)cyclopropane-1-carboxylate (80 mg, 0.143 mmol) in MeOH/THF/H$_2$O (3 mL/3 mL/2 mL) was added lithium hydroxide monohydrate (30 mg, 0.717 mmol). The mixture was stirred at 40° C. for 1 h. Most of the solvent was removed and the residue was diluted with H$_2$O (10 mL). The pH of the mixture was adjusted to 4-5 by adding HCl aqueous (1 M) and extracted with DCM/MeOH (30 mL×3, 10/1). The combined organic layers were washed with brine, dried over Na$_2$SO$_4$, concentrated and purified by prep-TLC (DCM/MeOH=10/1) to give 2-(4-(((7-chloroimidazo[1,5-a]pyridin-1-yl)methyl)carbamoyl)-1-((6-cyclopropylimidazo[1,2-a]pyridin-2-yl)methyl)-1H-pyrazol-3-yl)cyclopropane-1-carboxylic acid (6 mg, yield: 8%) as a yellow solid. ESI-MS [M+H]$^+$: 530.2. Purity: 95.64%. $^1$H NMR (400 MHz, DMSO): δ 12.16 (s, 1H), 8.43 (t, J=5.6 Hz, 1H), 8.39-8.26 (m, 3H), 8.13 (s, 1H), 7.75 (m, 2H), 7.39 (d, J=9.3 Hz, 1H), 7.00 (dd, J=9.4, 1.7 Hz, 1H), 6.64 (dd, J=7.5, 2.1 Hz, 1H), 5.27 (s, 2H), 4.60-4.48 (m, 2H), 3.21-3.13 (m, 1H), 1.96-1.85 (m, 2H), 1.36-1.29 (m, 2H), 0.91 (m, 2H), 0.72-0.63 (m, 2H).

Example 121

Scheme 120

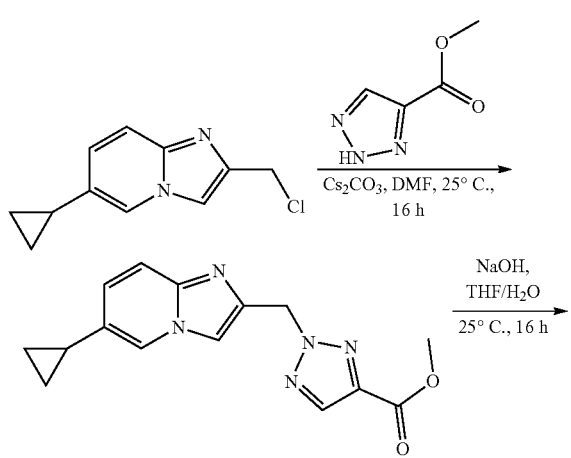

-continued

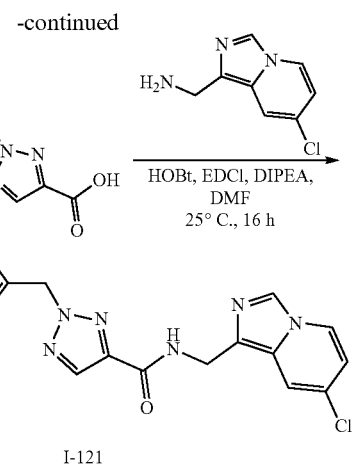

I-121

Synthesis of Methyl 2-((6-cyclopropylimidazo[1,2-a]pyridin-2-yl)methyl)-2H-1,2,3-triazole-4-carboxylate To the mixture of 2-(chloromethyl)-6-cyclopropylimidazo[1,2-a]pyridine (200 mg, 0.97 mmol) in dry DMF (5 mL) was added methyl 2H-1,2,3-triazole-4-carboxylate (135 mg, 1.06 mmol) and Cs$_2$CO$_3$ (949 mg, 2.91 mmol). The mixture was stirred at 25° C. for 16 h. Then H$_2$O (30 mL) was added and extracted with EtOAc (50 mL×3). The combined organic layers were washed with brine, dried over Na$_2$SO$_4$, filtered and concentrated to give the crude product, which was purified by prep-TLC (DCM/MeOH=10/1) to give methyl 2-((6-cyclopropylimidazo[1,2-a]pyridin-2-yl)methyl)-2H-1,2,3-triazole-4-carboxylate (90 mg, yield: 31%) as a yellow solid. ESI-MS [M+H]$^+$: 298.1.

Synthesis of 2-((6-cyclopropylimidazo[1,2-a]pyridin-2-yl)methyl)-2H-1,2,3-triazole-4-carboxylic Acid To a mixture of methyl 2-((6-cyclopropylimidazo[1,2-a]pyridin-2-yl)methyl)-2H-1,2,3-triazole-4-carboxylate (90 mg, 0.3 mmol) in THF/H$_2$O (3 mL/2 mL) was added NaOH (36 mg, 0.9 mmol). The mixture was stirred at 25° C. for 16 h and the pH of the mixture was adjusted to 5 by adding 1 M HCl. The mixture was then extracted with EtOAc (50 mL×3). The combined organic layers were washed with brine, dried over Na$_2$SO$_4$ and concentrated to give 2-((6-cyclopropylimidazo[1,2-a]pyridin-2-yl)methyl)-2H-1,2,3-triazole-4-carboxylic acid (80 mg, yield: 93%) as a yellow solid. ESI-MS [M+H]$^+$: 284.0.

Synthesis of N-((7-chloroimidazo[1,5-a]pyridin-1-yl)methyl)-2-((6-cyclopropylimidazo[1,2-a]pyridin-2-yl)methyl)-2H-1,2,3-triazole-4-carboxamide (I-121)

To a mixture of 2-((6-cyclopropylimidazo[1,2-a]pyridin-2-yl)methyl)-2H-1,2,3-triazole-4-carboxylic acid (60 mg, 0.21 mmol), (7-chloroimidazo[1,5-a]pyridin-1-yl)methanamine hydrochloride (54 mg, 0.25 mmol), HOBT (57 mg, 0.42 mmol), EDCI (81 mg, 0.42 mmol) in DMF (5 mL) was added DIPEA (135 mg, 1.04 mmol). The mixture was stirred at 25° C. for 16 h. Water (30 mL) was added and extracted with EtOAc (30 mL×3). The combined organic layers were washed with brine, dried over Na$_2$SO$_4$, filtered and concentrated to give the crude product, which was purified by prep-TLC (DCM/MeOH=10/1) to give N-((7-chloroimidazo[1,5-a]pyridin-1-yl)methyl)-2-((6-cyclopropylimidazo[1,2-a]pyridin-2-yl)methyl)-2H-1,2,3-triazole-4-carboxamide (39.1 mg, yield: 41%) as a white solid. ESI-MS [M+H]$^+$: 447.1. Purity: 99.57%. H NMR (400 MHz, DMSO): δ 8.90 (t, J=5.8 Hz, 1H), 8.31-8.30 (m, 3H), 8.15 (s, 1H), 7.83-7.82 (m, 1H), 7.77 (s, 1H), 7.39=7.36 (m, 1H), 7.00-6.98 (m, 1H), 6.66-6.64 (m, 1H), 5.74 (s, 2H), 4.60 (d, J=5.9 Hz, 2H), 1.95-1.88 (m, 1H), 0.94-0.89 (m, 2H), 0.68-0.64 (m, 2H).

Example 122

Scheme 121

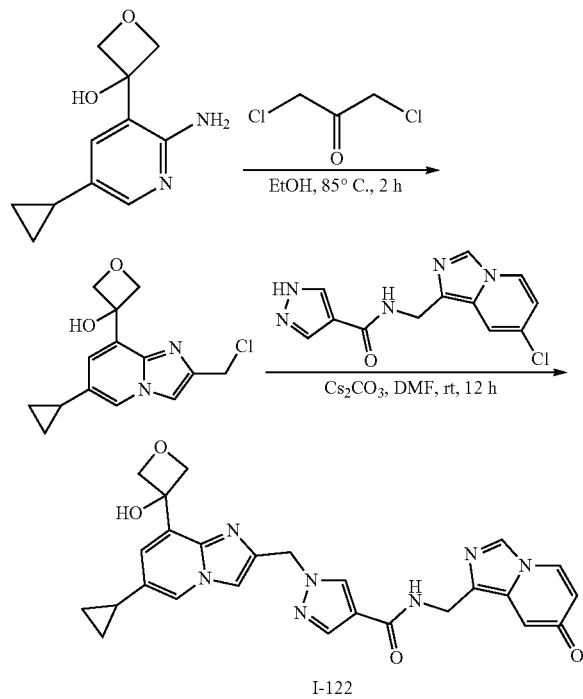

I-122

Synthesis of 3-(2-(chloromethyl)-6-cyclopropylimidazo[1,2-a]pyridin-8-yl)oxetan-3-ol To a solution of 3-(2-amino-5-cyclopropylpyridin-3-yl)oxetan-3-ol (800 mg, 3.88 mmol) in EtOH (10 mL) was added 1,3-dichloropropan-2-one (1.48 g, 11.6 mmol) at RT. The resulting reaction mixture was stirred at 85° C. for 2 h. Water (30 mL) was added and the pH was adjusted to 8 by adding saturated NaHCO$_3$ solution. The mixture was then extracted with EtOAc (30 mL×3). The combined organic layers were washed with brine, dried over Na$_2$SO$_4$ and concentrated in vacuo to give the crude product, which was purified by silica gel chromatography (PE/EtOAc=1/1) to give the 3-(2-(chloromethyl)-6-cyclopropylimidazo[1,2-a]pyridin-8-yl)oxetan-3-ol (900 mg, yield: 83%) as a light yellow oil. ESI-MS [M+H]$^+$: 279.2.

Synthesis of N-((7-chloroimidazo[1,5-a]pyridin-1-yl)methyl)-1-((6-cyclopropyl-8-(3-hydroxyoxetan-3-yl)imidazo[1,2-a]pyridin-2-yl)methyl)-1H-pyrazole-4-carboxamide (I-122)

To a solution 3-(2-(chloromethyl)-6-cyclopropylimidazo[1,2-a]pyridin-8-yl)oxetan-3-ol (90 mg, 0.33 mmol) in DMF (5 mL) was added N-((7-chloroimidazo[1,5-a]pyridin-1-yl)methyl)-1H-pyrazole-4-carboxamide (60 mg, 0.22 mmol) and Cs$_2$CO$_3$ (215 mg, 0.66 mmol) at RT. The resulting reaction mixture was stirred at RT for 12 h. Water (30 mL) was added and extracted with EtOAc (50 mL×3). The combined organic layers were washed with brine, dried over Na$_2$SO$_4$ and concentrated in vacuo to give the crude product, which was purified with prep-TLC (DCM/MeOH=10/1) to give the N-((7-chloroimidazo[1,5-a]pyridin-1-yl)methyl)-1-((6-cyclopropyl-8-(3-hydroxyoxetan-3-yl)imidazo[1,2-a]pyridin-2-yl)methyl)-1H-pyrazole-4-carboxamide (20 mg, yield: 12%) as a white solid. ESI-MS [M+H]$^+$: 518.1. Purity: 97.8%. $^1$H NMR (400 MHz, DMSO): δ 8.59 (s, 1H), 8.33-8.26 (m, 3H), 8.20 (s, 1H), 7.90 (s, 1H), 7.81-7.75 (m, 1H), 7.66 (s, 1H), 7.06 (d, J=1.6 Hz, 1H), 6.67-6.62 (m, 1H), 6.44 (s, 1H), 5.43 (s, 2H), 5.23 (d, J=6.5 Hz, 2H), 4.63 (d, J=6.5 Hz, 2H), 4.55 (d, J=5.7 Hz, 2H), 1.98-1.91 (m, 1H), 0.95-0.88 (m, 2H), 0.70-0.64 (m, 2H).

Example 123

Scheme 122

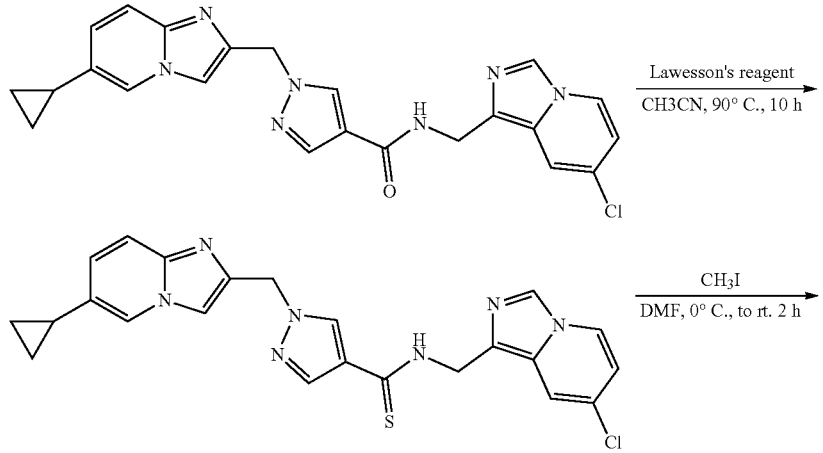

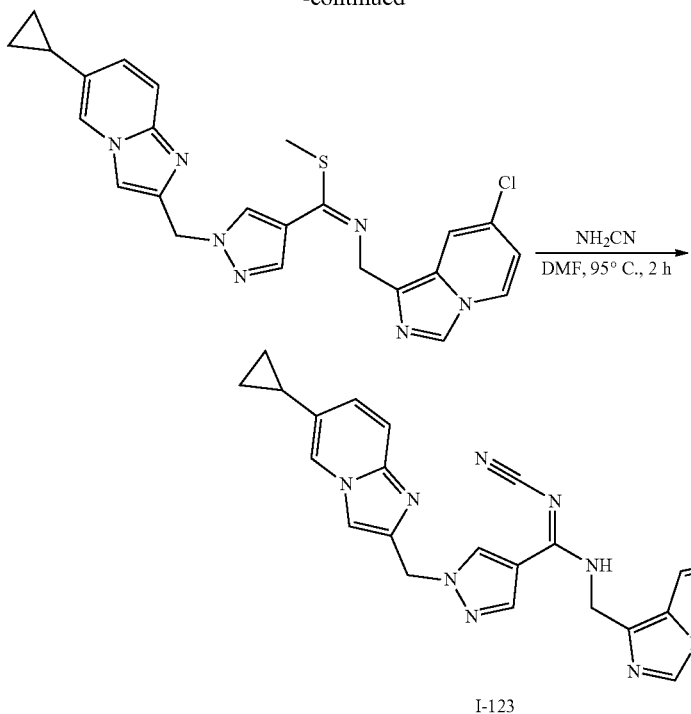

I-123

Synthesis of N-((7-chloroimidazo[1,5-a]pyridin-1-yl)methyl)-1-((6-cyclopropylimidazo[1,2-a]pyridin-2-yl)methyl)-1H-pyrazole-4-carbothioamide A mixture of N-((7-chloroimidazo[1,5-a]pyridin-1-yl)methyl)-1-((6-cyclopropylimidazo[1,2-a]pyridin-2-yl)methyl)-1H-pyrazole-4-carboxamide (400 mg, 0.9 mmol) and Lawesson's reagent (544 mg, 1.35 mmol) in CH$_3$CN (10 mL) was stirred at 90° C. for 16 h. The reaction mixture was cooled to RT and then filtered to provide the crude product (400 mg, yield: 96.6%) as a white solid which was used in the next step without purification. ESI-MS [M+H]$^+$: 462.1.

Synthesis of Methyl N-((7-chloroimidazo[1,5-a]pyridin-1-yl)methyl)-1-((6-cyclopropylimidazo[1,2-a]pyridin-2-yl)methyl)-1H-pyrazole-4-carbimidothioate To a solution of N-((7-chloroimidazo[1,5-a]pyridin-1-yl)methyl)-1-((6-cyclopropylimidazo[1,2-a]pyridin-2-yl)methyl)-1H-pyrazole-4-carbothioamide (440 mg, 0.95 mmol) in DMF (5 mL) was added NaH (76 mg, 1.9 mmol) and the reaction was stirred at 0° C. for 30 min. Then MeI (203 mg, 1.43 mmol) was added. The resulting reaction mixture was stirred at RT for 2 h. Water (30 mL) was added and extracted with EtOAc (30 mL×3). The combined organic layers were washed with brine, dried over Na$_2$SO$_4$, and concentrated to give methyl N-((7-chloroimidazo[1,5-a]pyridin-1-yl)methyl)-1-((6-cyclopropylimidazo[1,2-a]pyridin-2-yl)methyl)-1H-pyrazole-4-carbimidothioate (250 mg, crude), which was used in the next step without further purification. ESI-MS [M+H]$^+$: 476.2.

Synthesis of N'-((7-chloroimidazo[1,5-a]pyridin-1-yl)methyl)-N-cyano-1-((6-cyclopropylimidazo[1,2-a]pyridin-2-yl)methyl)-1H-pyrazole-4-carboximidamide (I-123)

A mixture of methyl N-((7-chloroimidazo[1,5-a]pyridin-1-yl)methyl)-1-((6-cyclopropylimidazo[1,2-a]pyridin-2-yl)methyl)-1H-pyrazole-4-carbimidothioate (250 mg, 0.53 mmol) and NH$_2$CN (88 mg, 2.1 mmol) in DMF (3 mL) was stirred at 90° C. for 2 h. The reaction mixture was diluted with H$_2$O (30 mL) and extracted with EtOAc (30 mL×3). The combined organic layers were washed with brine, dried over Na$_2$SO$_4$, and concentrated. The crude product was purified by prep-TLC (DCM/MeOH=10/1) to provide N'-((7-chloroimidazo[1,5-a]pyridin-1-yl)methyl)-N-cyano-1-((6-cyclopropylimidazo[1,2-a]pyridin-2-yl)methyl)-1H-pyrazole-4-carboximidamide (5 mg, yield: 2%). ESI-MS [M+H]$^+$: 470.2. Purity: 90.02%. $^1$H NMR (400 MHz, DMSO): δ 8.45 (s, 1H), 8.30 (s, 1H), 8.21-8.18 (m, 2H), 8.12 (s, 1H), 7.77-7.74 (m, 2H), 7.45 (d, J=8 Hz, 1H), 7.14 (t, J=12.0 Hz, 1H), 6.67 (m, 1H), 5.52 (s, 2H), 4.76 (s, 2H), 1.96-1.92 (m, 1H), 0.99-0.96 (m, 2H), 0.73-0.70 (s, 2H).

Example 124

Scheme 123

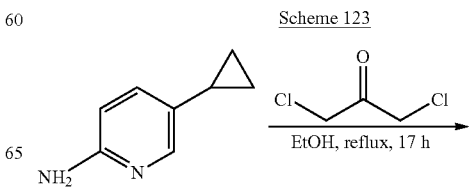

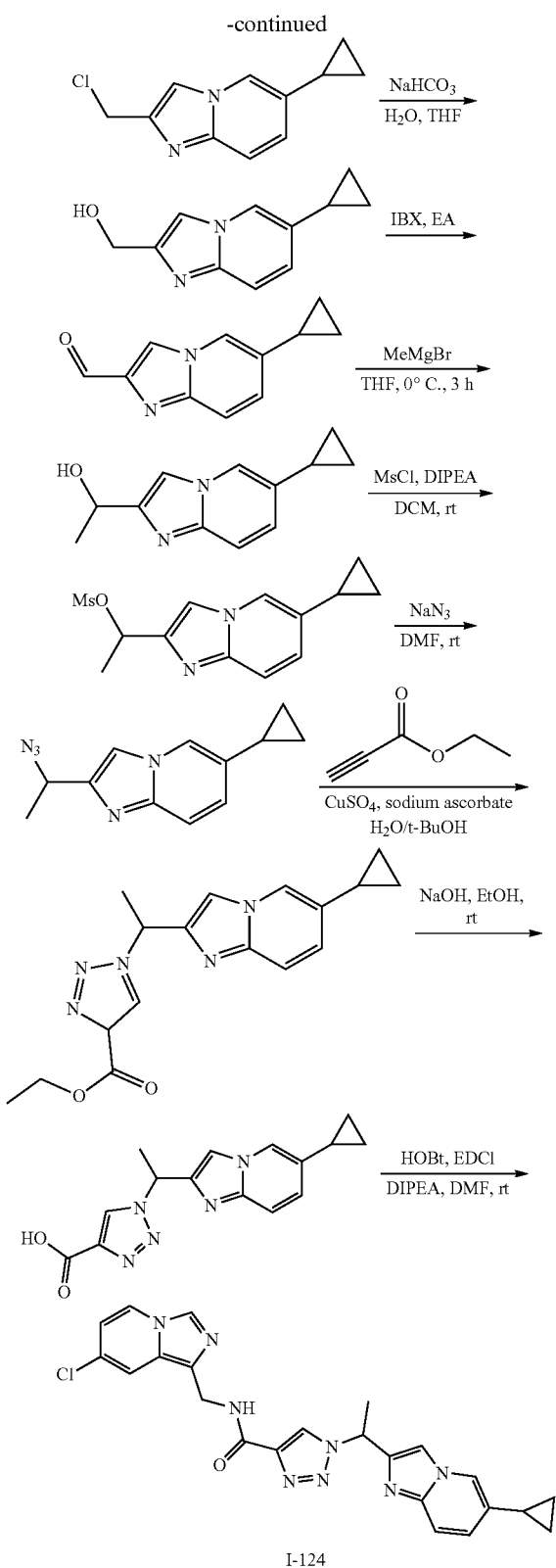

I-124

Synthesis of 2-(chloromethyl)-6-cyclopropylimidazo[1,2-a]pyridine

A mixture of 5-cyclopropylpyridin-2-amine (3.3 g, 25 mmol, 1.0 equiv) and 1,3-dichloropropan-2-one (12.4 g, 99 mmol, 4.0 equiv) in EtOH (60 mL) was stirred at 85° C. for 16 h. The solvent was removed in vacuo. Water (100 mL) was added and extracted with EtOAc (200 mL×3). The combined organic layers were concentrated and purified by silica gel chromatography (PE:EA=5:3) to provide 2-(chloromethyl)-6-cyclopropylimidazo[1,2-a]pyridine (1.8 g, yield: 34.9%). ESI-MS [M+H]$^+$: 207.1.

Synthesis of (6-cyclopropylimidazo[1,2-a]pyridin-2-yl)methanol

A solution of 2-(chloromethyl)-6-cyclopropylimidazo[1,2-a]pyridine (1.8 g, 8.7 mmol) and NaHCO$_3$ (5 mL, aq., sat.) in THF (10 mL) was stirred at 100° C. for 16 h. Then Water (50 mL) was added and the mixture was extracted with EtOAc (50 mL×3). The combined organic layers were concentrated to provide (6-cyclopropylimidazo[1,2-a]pyridin-2-yl)methanol (1.45 g, crude) which was used in the next step without further purification. ESI-MS [M+H]$^+$: 189.1.

Synthesis of 6-cyclopropylimidazo[1,2-a]pyridine-2-carbaldehyde

A mixture of (6-cyclopropylimidazo[1,2-a]pyridin-2-yl)methanol (1.45 g, crude from last step) and IBX (4.3 g, 15.4 mmol, 2.0 equiv.) in EtOAc (50 mL) was refluxed at 80° C. for 16 h. Then H$_2$O (50 mL) was added and extracted by EtOAc (50 mL×3). The combined organic layers were washed with brine, dried over Na$_2$SO$_4$, and concentrated to give the crude product, which was purified by silica gel chromatography (PE:EA=2:1) to provide 6-cyclopropylimidazo[1,2-a]pyridine-2-carbaldehyde (780 mg, yield: 48% in 2 steps). ESI-MS [M+H]$^+$: 187.1

Synthesis of 1-(6-cyclopropylimidazo[1,2-a]pyridin-2-yl)ethan-1-ol

To a solution of 6-cyclopropylimidazo[1,2-a]pyridine-2-carbaldehyde (750 mg, 4.0 mmol) in THF (10 mL) was added MeMgBr (2 mL, 6.0 mmol) dropwise at 0° C. The reaction mixture was stirred at 0° C. for 3 h. Then reaction mixture was quenched with saturated NH$_4$Cl solution (10 mL) and extracted by by EtOAc (50 mL×3). The combined organic layers were washed with brine, dried over Na$_2$SO$_4$, and concentrated to give the crude product, which was purified by silica gel chromatography (DCM:MeOH=10:1) to give 1-(6-cyclopropylimidazo[1,2-a]pyridin-2-yl)ethan-1-ol (725 mg, yield: 89.7%). ESI-MS [M+H]$^+$: 203.2.

Synthesis of 1-(6-cyclopropylimidazo[1,2-a]pyridin-2-yl)ethyl methanesulfonate A mixture of 1-(6-cyclopropylimidazo[1,2-a]pyridin-2-yl)ethan-1-ol (725 mg, 3.5 mmol), DIPEA (1.35 g, 10.5 mmol) and MsCl (519 mg, 4.55 mmol) in DCM (20 mL) was stirred at RT for 2 h. Water (20 mL) was added and extracted with EtOAc (50 mL×3). The combined organic layers were washed with brine, dried over Na$_2$SO$_4$, filtered and concentrated to give the crude compound (980 mg, crude), which was used into the next step directly.

Synthesis of 2-(1-azidoethyl)-6-cyclopropylimidazo[1,2-a]pyridine

A mixture of 1-(6-cyclopropylimidazo[1,2-a]pyridin-2-yl)ethyl methanesulfonate (980 mg, crude form last step)

and NaN₃ (680 mg, 10.5 mmol) in DMF (5 mL) was stirred at RT for 2 h. Water (30 mL) was added and extracted with EtOAc (50 mL×3). The combined organic layers were washed with brine, dried over Na₂SO₄, and concentrated to give the crude product which was purified by prep-TLC (PE:EA=2:1) to give 2-(1-azidoethyl)-6-cyclopropylimidazo[1,2-a]pyridine (225 mg, yield: 28% in 2 steps) as a yellow solid. ESI-MS [M+H]⁺: 228.2.

Synthesis of Ethyl 1-(1-(6-cyclopropylimidazo[1,2-a]pyridin-2-yl)ethyl)-1H-1,2,3-triazole-4-carboxylate A mixture of 2-(1-azidoethyl)-6-cyclopropylimidazo[1,2-a]pyridine (225 mg, 0.99 mmol), ethyl propiolate (107.0 mg, 1.09 mmol), CuSO₄ (173 mg, 1.09 mmol) and sodium ascorbate (200 mg, 0.99 mmol) in a mixture of t-BuOH (10 mL) and H₂O (10 mL) was stirred at RT for 16 h. Solid precipitated and filtered to give ethyl 1-(1-(6-cyclopropylimidazo[1,2-a]pyridin-2-yl)ethyl)-1H-1,2,3-triazole-4-carboxylate (250 mg, yield: 77%) as a yellow solid. ESI-MS [M+H]⁺: 326.2.

Synthesis of 1-(1-(6-cyclopropylimidazo[1,2-a]pyridin-2-yl)ethyl)-1H-1,2,3-triazole-4-carboxylic Acid A mixture of ethyl 1-(1-(6-cyclopropylimidazo[1,2-a]pyridin-2-yl)ethyl)-1H-1,2,3-triazole-4-carboxylate (250 mg, 0.77 mmol) and NaOH (111 mg, 2.77 mmol) in THF (10 mL) and H₂O (5 mL) was stirred at 50° C. for 3 h. Most of the solvent was removed and the residue was diluted with H₂O (5 mL). The pH of mixture was adjusted to 4-5 by adding HCl aqueous (1 M). The precipitate was collected and dried to give the 1-(1-(6-cyclopropylimidazo[1,2-a]pyridin-2-yl)ethyl)-1H-1,2,3-triazole-4-carboxylic acid (150 mg, 65%) as a yellow solid. ESI-MS [M+H]⁺: 298.1.

Synthesis of N-((7-chloroimidazo[1,5-a]pyridin-1-yl)methyl)-1-(1-(6-cyclopropylimidazo[1,2-a]pyridin-2-yl)ethyl)-1H-1,2,3-triazole-4-carboxamide (I-124)

A mixture of 1-(1-(6-cyclopropylimidazo[1,2-a]pyridin-2-yl)ethyl)-1H-1,2,3-triazole-4-carboxylic acid (150 mg, 0.51 mmol), (7-chloroimidazo[1,5-a]pyridin-1-yl)methanamine hydrochloride (132 mg, 0.61 mmol), HOBT (138 mg, 1.02 mmol), EDCI (196 mg, 1.02 mmol) and DIPEA (329 mg, 2.55 mmol) in DMF (5 mL) was stirred at RT for 16 h. Water (50 mL) was added and extracted with EtOAc (50 mL×3). The combined organic layers were washed with brine and dried over Na₂SO₄, and concentrated. The residue was purified by prep-TLC (DCM:MeOH=10:1) to give N-((7-chloroimidazo[1,5-a]pyridin-1-yl)methyl)-1-(1-(6-cyclopropylimidazo[1,2-a]pyridin-2-yl)ethyl)-1H-1,2,3-triazole-4-carboxamide (10 mg, yield: 4%). ESI-MS [M+H]⁺: 461.2. Purity: 100%. ¹H NMR (400 MHz, MeOD): δ 8.35 (s, 1H), 8.30 (s, 1H), 8.18-8.15 (m, 2H), 7.76 (s, 2H), 7.37 (d, J=8.0 Hz, 1H), 7.10 (d, J=8 Hz, 1H), 6.61 (d, J=8.0 Hz, 1H), 6.12-6.07 (m, 1H), 4.75 (s, 2H), 2.02 (d, J=8.0 Hz, 3H), 1.96-1.90 (m, 1H), 0.99-0.95 (m, 2H), 0.72-0.69 (s, 2H).

Example 125

Scheme 124

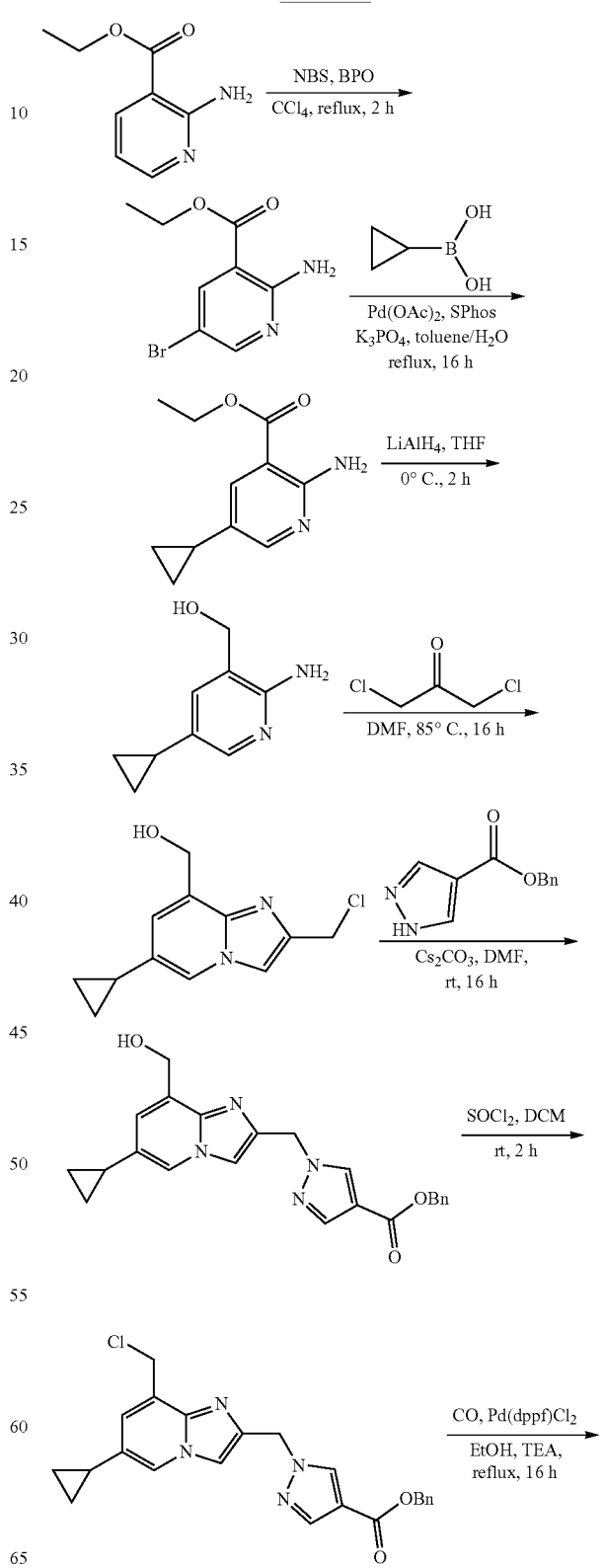

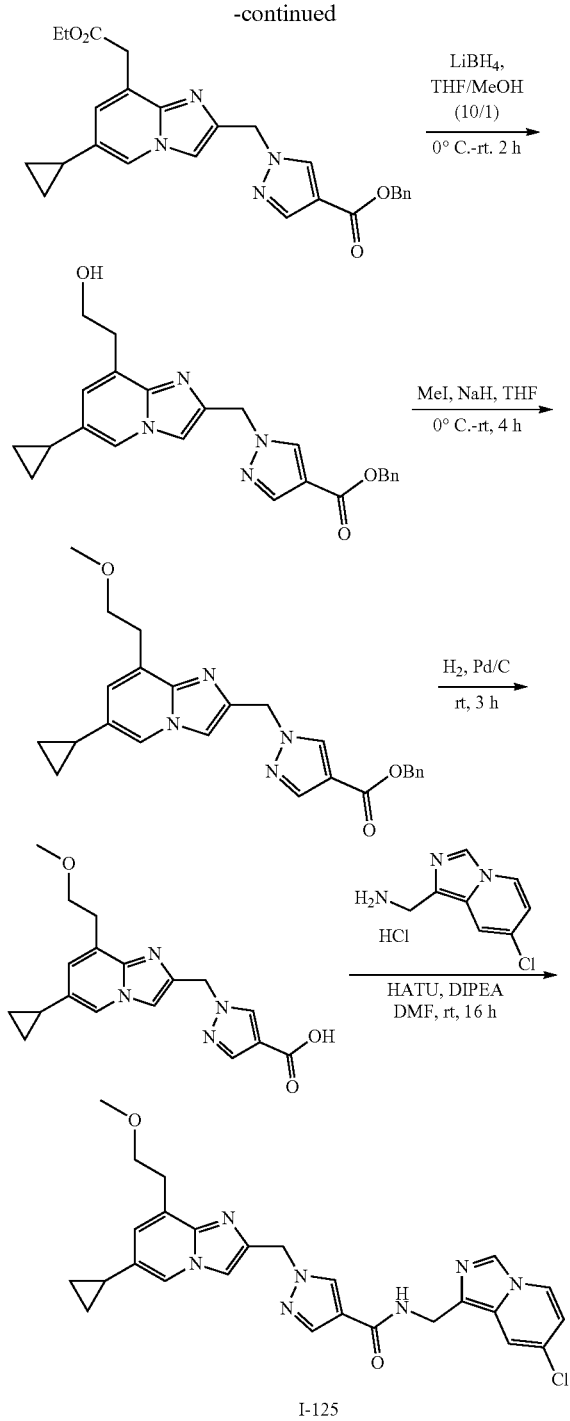

low solid, which was used in the next step without further purification. ESI-MS [M+H]⁺: 245.1.

Synthesis of Ethyl 2-amino-5-cyclopropylnicotinate

The mixture of ethyl 2-amino-5-bromonicotinate (14.7 g, 60.18 mmol), cyclopropylboronic acid (7.75 g, 90.27 mmol), Pd(OAc)$_2$ (1.35 g, 6.018 mmol), SPhos (4.94 g 12.04 mmol) and K$_3$P$_4$ (44.7 g, 210.58 mmol) in a mixture of toluene (200 mL) and H$_2$O (40 mL) was stirred at 100° C. for 16 h. The reaction mixture was filtered through celite and the filtrate was washed with EA (100 mL) and concentrated. The crude product was purified by silica gel chromatography (EA/PE=1/5) to give ethyl 2-amino-5-cyclopropylnicotinate (6.0 g, yield: 48%) as a yellow solid. ESI-MS [M+H]⁺: 207.1.

Synthesis of (2-amino-5-cyclopropylpyridin-3-yl)methanol

To a stirred suspension of LiAlH4 (2.21 g, 58.2 mmol) in THF (120 mL) was added dropwise a solution of ethyl 2-amino-5-cyclopropylnicotinate (6.0 g, 29.1 mmol) at 0° C. The mixture was stirred at 0° C. for 2 h. The reaction mixture was quenched with H$_2$O (2.2 mL), 15% (v/v) NaOH aqueous (2.2 mL) and H$_2$O (6.6 mL). The mixture was stirred for 30 min at 0° C. and for 2 h at RT. Filtered and washed with EtOAc (100 mL). The filtrate was dried, concentrated and purified by silica gel chromatography (EtOAc) to give (2-amino-5-cyclopropylpyridin-3-yl)methanol (4.4 g, yield: 92%) as a yellow solid. ESI-MS [M+H]⁺: 165.2.

Synthesis of (2-(chloromethyl)-6-cyclopropylimidazo[1,2-a]pyridin-8-yl)methanol

A mixture of (2-amino-5-cyclopropylpyridin-3-yl)methanol (2 g, 12.18 mmol) and 1,3-dichloropropan-2-one (4.6 g, 36.54 mmol) in DMF (20 mL) was stirred at 85° C. for 16 h. The reaction mixture was poured into H$_2$O (150 mL) and adjusted to pH 8 with a NaHCO$_3$ aqueous solution and then extracted with EtOAc (100 mL×3). The combined organic layers were washed with brine, dried over Na$_2$SO$_4$, concentrated and purified by silica gel chromatography (EA/PE=1/2) to give (2-(chloromethyl)-6-cyclopropylimidazo[1,2-a]pyridin-8-yl)methanol (913 mg, 32%) as a yellow solid. ESI-MS [M+H]⁺: 237.1.

Synthesis of benzyl 1-((6-cyclopropyl-8-(hydroxymethyl)imidazo[1,2-a]pyridin-2-yl)methyl)-1H-pyrazole-4-carboxylate A mixture of (2-(chloromethyl)-6-cyclopropylimidazo[1,2-a]pyridin-8-yl)methanol (730 mg, 3.08 mmol), benzyl 1H-pyrazole-4-carboxylate (624 mg, 3.08 mmol) and Cs$_2$CO$_3$ (1.5 g, 4.62 mmol) in DMF (10 mL) was stirred at RT for 16 h. The reaction mixture was poured into H$_2$O (100 mL) and extracted with EtOAc (100 mL×2). The combined organic layers were washed with brine, dried over Na$_2$SO$_4$, concentrated and purified by silica gel chromatography (EA/PE=1/1) to give benzyl 1-((6-cyclopropyl-8-(hydroxymethyl)imidazo[1,2-a]pyridin-2-yl)methyl)-1H-pyrazole-4-carboxylate (1.1 g, yield: 89%) as a yellow solid. ESI-MS [M+H]⁺: 403.2.

Synthesis of benzyl 1-((8-(chloromethyl)-6-cyclopropylimidazo[1,2-a]pyridin-2-yl)methyl)-1H-pyrazole-4-carboxylate To a solution of benzyl 1-((6-cyclopropyl-8-(hydroxymethyl)imidazo[1,2-a]pyridin-2-yl)methyl)-1H-pyrazole-4-

Synthesis of Ethyl 2-amino-5-bromonicotinate

To a solution of ethyl 2-aminonicotinate (25 g, 150.44 mmol) in CH$_3$CN (500 mL) was added NBS (32.1 g, 180.5 mmol) in portions over 30 min at 0° C. The mixture was warmed to RT and stirred for 2 h. The reaction mixture was concentrated. The residue was washed with NaHCO$_3$ aqueous (300 mL) and extracted with EtOAc (300 mL×3), the combined organic layers were concentrated to give ethyl 2-amino-5-bromonicotinate (36.9 g, yield: 100%) as a yelcarboxylate (1.1 g, 2.73 mmol) in DCM (10 mL) was added dropwise SOCl$_2$ (1.63 mg, 13.67 mmol) at 0° C. The mixture was stirred at for RT 1 h. The reaction mixture was concentrated. The residue was dissolved in EtOAc (100 mL) and washed with NaHCO$_3$ (100 mL) and brine (100 mL), dried over Na$_2$SO$_4$, concentrated and dried in vacuo to give benzyl 1-((8-(chloromethyl)-6-cyclopropylimidazo[1,2-a]pyridin-2-yl)methyl)-1H-pyrazole-4-carboxylate (1.15 g, yield: 100%) as a yellow solid. ESI-MS [M+H]$^+$: 421.1.

Synthesis of benzyl 1-((6-cyclopropyl-8-(2-ethoxy-2-oxoethyl)imidazo[1,2-a]pyridin-2-yl)methyl)-1H-pyrazole-4-carboxylate The mixture of benzyl 1-((8-(chloromethyl)-6-cyclopropylimidazo[1,2-a]pyridin-2-yl)methyl)-1H-pyrazole-4-carboxylate (1.15 g, 2.73 mmol), Pd(dppf)Cl$_2$ (200 mg, 0.273 mmol) and Et$_3$N (829 mg, 8.19 mmol) in EtOH (20 mL) was stirred at reflux for 16 h under CO. The reaction mixture was concentrated and dissolved in EtOAc (100 mL), filtered and the filtrate was washed with H$_2$O (50 mL) and brine (50 mL), dried over Na$_2$SO$_4$, concentrated and purified by silica gel chromatography (EA/PE=1/3) to give benzyl 1-((6-cyclopropyl-8-(2-ethoxy-2-oxoethyl)imidazo[1,2-a]pyridin-2-yl)methyl)-1H-pyrazole-4-carboxylate (800 mg, yield: 64%) as a yellow solid. ESI-MS [M+H]$^+$: 459.2.

Synthesis of benzyl 1-((6-cyclopropyl-8-(2-hydroxyethyl)imidazo[1,2-a]pyridin-2-yl)methyl)-1H-pyrazole-4-carboxylate To a solution of benzyl 1-((6-cyclopropyl-8-(2-ethoxy-2-oxoethyl)imidazo[1,2-a]pyridin-2-yl)methyl)-1H-pyrazole-4-carboxylate (500 mg, 1.09 mmol) in THF (10 mL) and MeOH (1 mL) was added LiBH$_4$ (119 mg, 5.45 mmol) in portions at 0° C. The mixture was stirred at RT for 2 h. The reaction mixture was quenched with saturated NH$_4$Cl aqueous solution (10 mL) and diluted with H$_2$O (50 mL). the mixture was extracted with EtOAc (50 mL×3). The combined organic layers were washed with brine, dried over Na$_2$SO$_4$, concentrated and purified by silica gel chromatography (EtOAc) to give benzyl 1-((6-cyclopropyl-8-(2-hydroxyethyl)imidazo[1,2-a]pyridin-2-yl)methyl)-1H-pyrazole-4-carboxylate (270 mg, yield: 59%) as a yellow solid. ESI-MS [M+H]$^+$: 417.2.

Synthesis of benzyl 1-((6-cyclopropyl-8-(2-methoxyethyl)imidazo[1,2-a]pyridin-2-yl)methyl)-1H-pyrazole-4-carboxylate To a solution of benzyl 1-((6-cyclopropyl-8-(2-hydroxyethyl)imidazo[1,2-a]pyridin-2-yl)methyl)-1H-pyrazole-4-carboxylate (250 mg, 0.60 mmol) in THF (6 mL) was added NaH (48 mg, 1.2 mmol) at 0° C. After stirring for 30 min, MeI (170 mg, 1.2 mmol) in THF (1 mL) was added. The mixture was stirred at RT for 3.5 h. The reaction mixture was quenched with H$_2$O (50 mL) and extracted with EtOAc (50 mL×2). The combined organic layers were washed with brine, dried over Na$_2$SO$_4$, concentrated and purified by silica gel chromatography (EA/PE=1/2) to give benzyl 1-((6-cyclopropyl-8-(2-methoxyethyl)imidazo[1,2-a]pyridin-2-yl)methyl)-1H-pyrazole-4-carboxylate (70 mg, yield: 27%) as a yellow solid. ESI-MS [M+H]$^+$: 417.2.

Synthesis of 1-((6-cyclopropyl-8-(2-methoxyethyl)imidazo[1,2-a]pyridin-2-yl)methyl)-1H-pyrazole-4-carboxylic Acid A mixture of benzyl 1-((6-cyclopropyl-8-(2-methoxyethyl)imidazo[1,2-a]pyridin-2-yl)methyl)-1H-pyrazole-4-carboxylate (70 mg, 0.163 mmol) and Pd/C (30 mg) in MeOH (5 mL) was stirred at RT for 2 h under H$_2$ (balloon). The reaction mixture was filtered and the filtrate was concentrated to give 1-((6-cyclopropyl-8-(2-methoxyethyl)imidazo[1,2-a]pyridin-2-yl)methyl)-1H-pyrazole-4-carboxylic acid (55 mg, yield: 100%) as a yellow solid, which was used into the next step without further purification. ESI-MS [M+H]$^+$: 341.2.

Synthesis of N-((7-chloroimidazo[1,5-a]pyridin-1-yl)methyl)-1-((6-cyclopropyl-8-(2-methoxyethyl)imidazo[1,2-a]pyridin-2-yl)methyl)-1H-pyrazole-4-carboxamide (I-125)

A mixture of 1-((6-cyclopropyl-8-(2-methoxyethyl)imidazo[1,2-a]pyridin-2-yl)methyl)-1H-pyrazole-4-carboxylic acid (90 mg, 0.264 mmol), HATU (110 mg, 0.29 mmol) and DIPEA (102 mg, 0.792 mmol) in DMF (4 mL) was stirred at RT for 10 min. (7-chloroimidazo[1,5-a]pyridin-1-yl)methanamine hydrochloride hydeochloride (58 mg, 0.264 mmol) was added and stirred at RT for 16 h. Water (30 mL) was added and extracted with EtOAc (50 mL×3). The combined organic layers were washed with brine, dried over Na$_2$SO$_4$, concentrated and purified by prep-HPLC to give N-((7-chloroimidazo[1,5-a]pyridin-1-yl)methyl)-1-((6-cyclopropyl-8-(2-methoxyethyl)imidazo[1,2-a]pyridin-2-yl)methyl)-1H-pyrazole-4-carboxamide (30 mg, yield: 23%) as a white solid. ESI-MS [M+H]$^+$: 504.2. Purity: 97.98%. $^1$H NMR (400 MHz, DMSO): δ 8.58 (t, J=5.7 Hz, 1H), 8.34-8.27 (m, 2H), 8.22-8.15 (m, 2H), 7.87 (s, 1H), 7.79-7.75 (m, 1H), 7.65 (s, 1H), 6.86 (s, 1H), 6.64 (dd, J=7.5, 2.1 Hz, 1H), 5.39 (s, 2H), 4.55 (d, J=5.7 Hz, 2H), 3.67 (t, J=6.8 Hz, 2H), 3.21 (s, 3H), 3.04 (t, J=6.8 Hz, 2H), 1.88 (m, 1H), 0.90 (m, 2H), 0.67-0.62 (m, 2H).

Example 126

Scheme 125

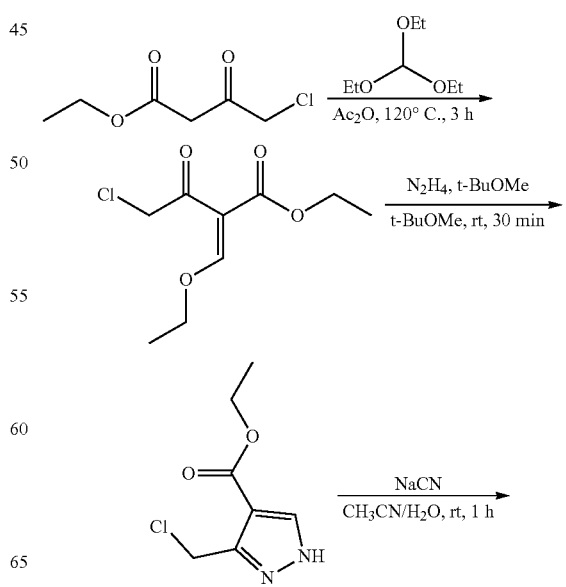

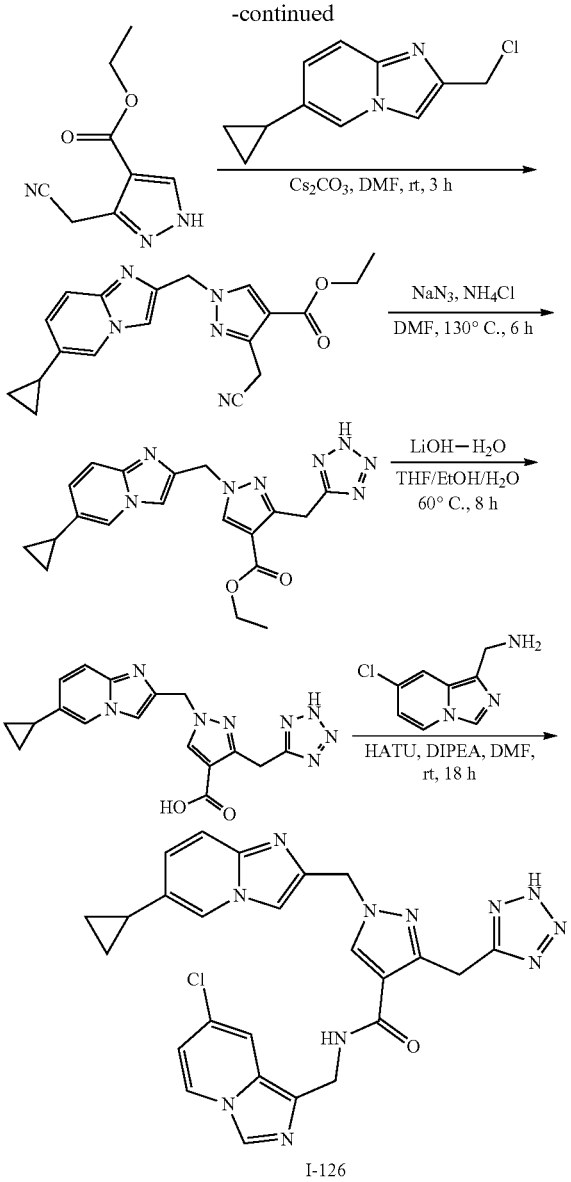

Synthesis of Ethyl-4-chloro-2-(ethoxymethylene)-3-oxobutanoate

A solution of ethyl 4-chloro-3-oxobutanoate (8 mL, 59 mmol), triethoxymethane (59 mL) and $Ac_2O$ (25 mL) was stirred at 120° C. for 3 h. The reaction mixture was concentrated and n-heptane was added to the residue. Solid precipitated and was filtered to give ethyl-4-chloro-2-(ethoxymethylene)-3-oxobutanoate (6 g, yield: 46%) as a yellow solid, which was used into next step without purification. ESI-MS [M+H]$^+$: 221.2.

Synthesis of Ethyl 3-(chloromethyl)-1H-pyrazole-4-carboxylate

To a solution of ethyl-4-chloro-2-(ethoxymethylene)-3-oxobutanoate (3 g, 13.6 mmol) in t-BuOMe (20 mL) was added $N_2H_4$ (3 mL). The reaction mixture was stirred at RT for 30 min. $H_2O$ (50 mL) was added and extracted with EtOAc (50 mL×3). The combined organic layers were washed with brine, dried over $Na_2SO_4$, and concentrated to give the crude product, which was purified by silica gel (PE/EA=10/1) to obtain ethyl 3-(chloromethyl)-1H-pyrazole-4-carboxylate (1.7 g, yield: 66.5%) as a yellow solid. ESI-MS [M+H]$^+$: 189.1.

Synthesis of Ethyl 3-(cyanomethyl)-1H-pyrazole-4-carboxylate

To a solution of NaCN (390 mg, 8.0 mmol) in a mixture of $CH_3CN$ (20 mL) and $H_2O$ (3 mL) was added ethyl 3-(chloromethyl)-1H-pyrazole-4-carboxylate (507 mg, 2.7 mmol). The reaction mixture was stirred at RT for 1 h. Water (50 mL) was added and extracted with EtOAc (50 mL×3). The combined organic layers were washed with brine, dried over $Na_2SO_4$, and concentrated to give the crude product, which was purified by C-18 reverse phase chromatography to afford ethyl 3-(cyanomethyl)-1H-pyrazole-4-carboxylate (200 mg, yield: 41%) as a white solid. ESI-MS [M+H]$^+$: 180.2.

Synthesis of Ethyl 3-(cyanomethyl)-1-((6-cyclopropylimidazo[1,2-a]pyridin-2-yl)methyl)-1H-pyrazole-4-carboxylate A mixture of 2-(chloromethyl)-6-cyclopropylimidazo[1,2-a]pyridine (103 mg, 0.5 mmol), ethyl 3-(cyanomethyl)-1H-pyrazole-4-carboxylate (90 mg, 0.5 mmol) and $Cs_2CO_3$ (489 mg, 3 mmol) in DMF (3 mL) was stirred at RT for 3 h. The reaction mixture was diluted with $H_2O$ (20 mL) and extracted with EtOAc (50 mL×2). The combined organic layers were washed with brine, dried over $Na_2SO_4$, and concentrated to give the crude product, which was purified by silica gel chromatography ($CH_2Cl_2$:$CH_3OH$=10:1) to give ethyl 3-(cyanomethyl)-1-((6-cyclopropylimidazo[1,2-a]pyridin-2-yl)methyl)-1H-pyrazole-4-carboxylate (55 mg, yield: 31%) as a brown solid. ESI-MS [M+H]$^+$: 350.2.

Synthesis of Ethyl 3-((2H-tetrazol-5-yl)methyl)-1-((6-cyclopropylimidazo[1,2-a]pyridin-2-yl)methyl)-1H-pyrazole-4-carboxylate A mixture of ethyl 3-(cyanomethyl)-1-((6-cyclopropylimidazo[1,2-a]pyridin-2-yl)methyl)-1H-pyrazole-4-carboxylate (460 mg, 1.32 mmol), $NaN_3$ (428 mg, 6.58 mmol), $NH_4Cl$ (352 mg, 6.58 mmol) in DMF (5 mL) was stirred in a sealed tube at 130° C. for 6 h. Water (50 mL) was added and extracted with EtOAc (50 mL×4). The combined organic layers were concentrated to give ethyl 3-((2H-tetrazol-5-yl)methyl)-1-((6-cyclopropylimidazo[1,2-a]pyridin-2-yl)methyl)-1H-pyrazole-4-carboxylate (121 mg, yield: 23%) as a brown solid which was used into next step without purification. ESI-MS [M+H]$^+$: 393.2.

Synthesis of 3-((2H-tetrazol-5-yl)methyl)-1-((6-cyclopropylimidazo[1,2-a]pyridin-2-yl)methyl)-1H-pyrazole-4-carboxylic Acid To a solution of ethyl 3-((2H-tetrazol-5-yl)methyl)-1-((6-cyclopropylimidazo[1,2-a]pyridin-2-yl)methyl)-1H-pyrazole-4-carboxylate (121 mg, 0.31 mmol) in a mixture of THF/EtOH/$H_2O$ (2 mL/2 mL/1 mL) was added LiOH $H_2O$ (26 mg, 0.62 mmol). The mixture was stirred at 60° C. for 8 h. The pH of the mixture was adjusted to 6 by adding 2 M aqueous HCl solution, and was filtered to give 3-((2H-tetrazol-5-yl)methyl)-1-((6-cyclopropylimidazo[1,2-a]pyridin-2-yl)methyl)-1H-pyrazole-4-carboxylic acid (96 mg, yield: 85%) as a brown solid. ESI-MS [M+H]⁺: 365.1.

Synthesis of 3-((2H-tetrazol-5-yl)methyl)-N-((7-chloroimidazo[1,5-a]pyridin-1-yl)methyl)-1-((6-cyclopropylimidazo[1,2-a]pyridin-2-yl)methyl)-1H-pyrazole-4-carboxamide (I-126)

A mixture of 3-((2H-tetrazol-5-yl)methyl)-1-((6-cyclopropylimidazo[1,2-a]pyridin-2-yl)methyl)-1H-pyrazole-4-carboxylic acid (40 mg, 0.11 mmol), (7-chloroimidazo[1,5-a]pyridin-1-yl)methanamine hydrochloride (24 mg, 0.11 mmol), HOBT (28 mg, 0.22 mmol), EDCI (40 mg, 0.22 mmol) and DIPEA (72 mg, 0.55 mmol) in DMF (2 mL) was stirred at RT for 18 h. Water (15 mL) was added and extracted with EtOAc (20 mL×3). The H₂O layer was concentrated to give the crude product, which was purified by prep-HPLC to give 3-((2H-tetrazol-5-yl)methyl)-N-((7-chloroimidazo[1,5-a]pyridin-1-yl)methyl)-1-((6-cyclopropylimidazo[1,2-a]pyridin-2-yl)methyl)-1H-pyrazole-4-carboxamide (9.9 mg, yield: 17%) as a white solid. ESI-MS [M+H]⁺: 528.1. Purity: 98.16%. ¹H NMR (400 MHz, DMSO): δ 9.08 (s, 1H), 8.32-8.28 (m, 3H), 8.17 (s, 1H), 7.76-7.75 (m, 2H), 7.39 (d, J=9.3 Hz, 1H), 6.99 (dd, J=9.4, 1.7 Hz, 1H), 6.63 (dd, J=7.4, 2.0 Hz, 1H), 5.30 (s, 2H), 4.54 (d, J=5.6 Hz, 2H), 4.36 (s, 2H), 1.95-1.88 (m, 1H), 0.93-0.88 (m, 2H), 0.68-0.64 (m, 2H).

Example 127

Scheme 126

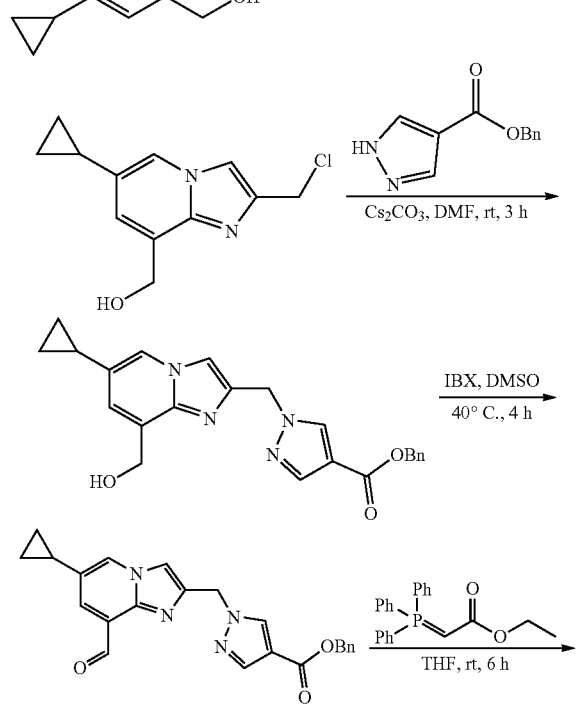

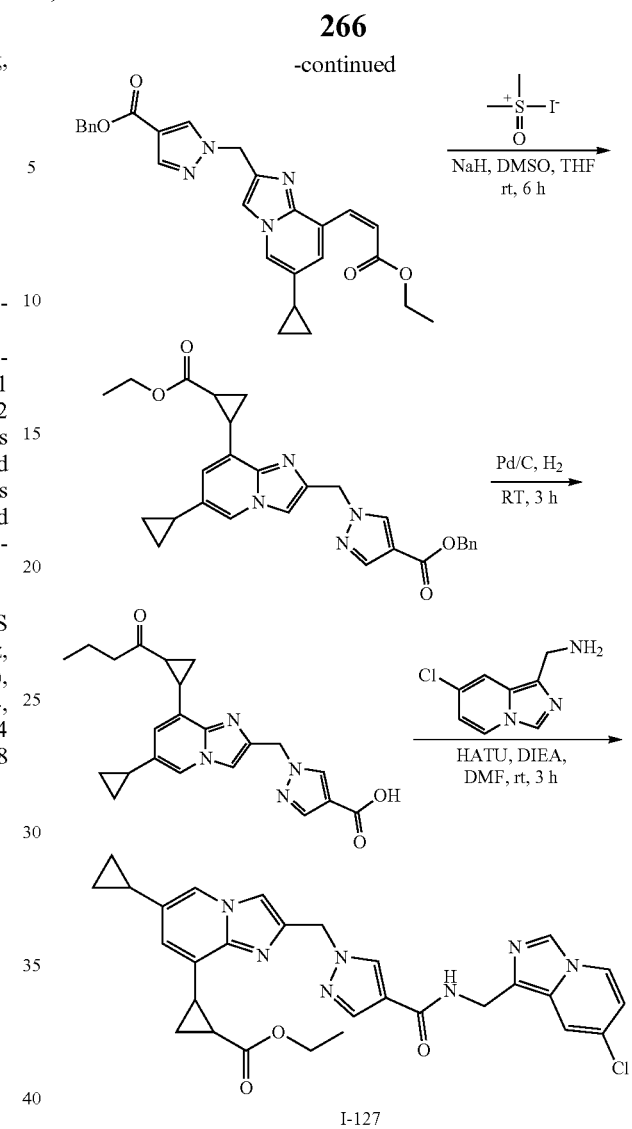

I-127

Synthesis of (2-(chloromethyl)-6-cyclopropylimidazo[1,2-a]pyridin-8-yl)methanol

To a solution of (2-amino-5-cyclopropylpyridin-3-yl)methanol (4.8 g, 29 mmol) in DMF (30 mL) was added 1,3-dichloropropan-2-one (14.8 g, 117 mmol). The mixture was stirred at 95° C. for 3 h. The reaction was quenched with NaHCO₃ aqueous (150 mL), and extracted with EtOAc (150 mL×3). The combined organic layers were washed with brine, dried over Na₂SO₄, concentrated in vacuo to give the crude, which was purified with silica gel chromatography (EtOAc/PE=1/2) to give the (2-(chloromethyl)-6-cyclopropylimidazo[1,2-a]pyridin-8-yl)methanol (3.5 g, yield: 51%) as a white solid. ESI-MS [M+H]⁺: 237.1.

Synthesis of benzyl 1-((6-cyclopropyl-8-(hydroxymethyl)imidazo[1,2-a]pyridin-2-yl)methyl)-1H-pyrazole-4-carboxylate The mixture of (2-(chloromethyl)-6-cyclopropylimidazo[1,2-a]pyridin-8-yl)methanol (3.5 g, 14.65 mmol), benzyl 1H-pyrazole-4-carboxylate (2.8 g, 14.7 mmol) and Cs₂CO₃ (11.9 g, 36.6 mmol) in DMF (15 mL) was stirred at RT for 3 h. The reaction was quenched with H$_2$O (100 mL) and extracted with EtOAc (100 mL×3). The combined organic layers were washed with brine, dried over Na$_2$SO$_4$ and concentrated in vacuo to give the crude, which was purified with silica gel chromatography (DCM/MeOH=10/1) to give benzyl 1-((6-cyclopropyl-8-(hydroxymethyl)imidazo[1,2-a]pyridin-2-yl)methyl)-1H-pyrazole-4-carboxylate (3.16 g, yield: 54%) as a white solid. ESI-MS [M+H]$^+$: 403.1.

Synthesis of benzyl 1-((6-cyclopropyl-8-formylimidazo[1,2-a]pyridin-2-yl)methyl)-1H-pyrazole-4-carboxylate The mixture of benzyl 1-((6-cyclopropyl-8-(hydroxymethyl)imidazo[1,2-a]pyridin-2-yl)methyl)-1H-pyrazole-4-carboxylate (3.16 g, 7.9 mmol) and IBX (4.4 g, 15.7 mmol) in DMSO (15 mL) was stirred at 40° C. for 4 h. The reaction was quenched with H$_2$O (60 mL) and extracted with EtOAc (100 mL×3). The combined organic layers were washed with brine, dried over Na$_2$SO$_4$ and concentrated in vacuo to give the crude, which was purified with silica gel chromatography (DCM/MeOH=10/1) to give 1-((6-cyclopropyl-8-formylimidazo[1,2-a]pyridin-2-yl)methyl)-1H-pyrazole-4-carboxylate (1.48 g, yield: 47%) as a yellow solid. ESI-MS [M+H]$^+$: 401.1.

Synthesis of benzyl (Z)-1-((6-cyclopropyl-8-(3-ethoxy-3-oxoprop-1-en-1-yl)imidazo[1,2-a]pyridin-2-yl)methyl)-1H-pyrazole-4-carboxylate To a solution of the benzyl 1-((6-cyclopropyl-8-formylimidazo[1,2-a]pyridin-2-yl)methyl)-1H-pyrazole-4-carboxylate (1.48 g, 3.7 mmol) in THF (30 mL) was added ethyl 2-(triphenyl-15-phosphanylidene)acetate (1.42 g, 41 mmol), the mixture was stirred at RT for 6 h. The reaction was concentrated in vacuo to give the crude, which was purified with silica gel chromatography (DCM/MeOH=15/1) to give benzyl 1-((6-cyclopropyl-8-(2-(ethoxycarbonyl)cyclopropyl)imidazo[1,2-a]pyridin-2-yl)methyl)-1H-pyrazole-4-carboxylate (890 mg, yield: 51%) as a white solid. ESI-MS [M+H]$^+$: 471.1.

Synthesis of benzyl 1-((6-cyclopropyl-8-(2-(ethoxycarbonyl)cyclopropyl)imidazo[1,2-a]pyridin-2-yl)methyl)-1H-pyrazole-4-carboxylate To a suspension of NaH (68.4 mg, 2.85 mmol) in DMSO (10 mL) was added trimethylsulfoxonium iodide (967 mg, 4.39 mmol) at RT. The mixture was stirred at RT for 10 min. Then a solution of 1-((6-cyclopropyl-8-(2-(ethoxycarbonyl)cyclopropyl)imidazo[1,2-a]pyridin-2-yl)methyl)-1H-pyrazole-4-carboxylate (890 mg, 1.9 mmol) in DMSO (3 mL) was added. The mixture was stirred at RT for 6 h. H$_2$O (50 mL) was added and extracted with EtOAc (50 mL×3). The combined organic layers were washed with brine, dried over Na$_2$SO$_4$ and concentrated in vacuo to give the crude, which was purified using a silica gel column (DCM/MeOH: 10/1) to give the benzyl 1-((6-cyclopropyl-8-(2-(ethoxycarbonyl)cyclopropyl)imidazo[1,2-a]pyridin-2-yl)methyl)-1H-pyrazole-4-carboxylate (545 mg, yield: 59%) as a yellow solid. ESI-MS [M+H]$^+$: 485.1.

Synthesis of 1-((6-cyclopropyl-8-(2-(ethoxycarbonyl)cyclopropyl)imidazo[1,2-a]pyridin-2-yl)methyl)-1H-pyrazole-4-carboxylic Acid To a mixture of 1-((6-cyclopropyl-8-(2-(ethoxycarbonyl)cyclopropyl)imidazo[1,2-a]pyridin-2-yl)methyl)-1H-pyrazole-4-carboxylate (545 mg, 1.13 mmol) in MeOH (10 mL) was added Pd/C (100 mg). The mixture was stirred at RT for 3 h. The reaction was filtered and concentrated in vacuo to give 1-((6-cyclopropyl-8-(2-(ethoxycarbonyl)cyclopropyl)imidazo[1,2-a]pyridin-2-yl)methyl)-1H-pyrazole-4-carboxylic acid (354 mg, yield: 80%) as a yellow solid, which was used into next step without purification. ESI-MS [M+H]$^+$: 495.1.

Synthesis Ethyl 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)cyclopropane-1-carboxylate (I-127)

A mixture of 1-((6-cyclopropyl-8-(2-(ethoxycarbonyl)cyclopropyl)imidazo[1,2-a]pyridin-2-yl)methyl)-1H-pyrazole-4-carboxylic acid (354 mg, 0.72 mmol), (7-chloroimidazo[1,5-a]pyridin-1-yl)methanamine hydrochloride (188 mg, 0.86 mmol), DIPEA (1 mL, 7.5 mmol) and HATU (410 mg, 1.08 mmol) in DMF (5 mL) was stirred at RT for 3 h. The reaction was diluted with H$_2$O (30 mL) and extracted with EtOAc (50 mL×3). The combined organic layers were washed with brine, dried over Na$_2$SO$_4$ and concentrated in vacuo to give the crude, which was purified with prep-TLC (DCM/MeOH=10/1) to give ethyl 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)cyclopropane-1-carboxylate (17.5 mg, yield: 4.4%) as a white solid. ESI-MS [M+H]$^+$: 558.2. $^1$H NMR (400 MHz, DMSO): δ 8.59 (t, J=5.7 Hz, 1H), 8.35-8.26 (m, 2H), 8.23-8.14 (m, 2H), 7.88 (s, 1H), 7.81-7.74 (m, 1H), 7.66 (s, 1H), 6.73 (d, J=1.4 Hz, 1H), 6.65 (dd, J=7.5, 2.1 Hz, 1H), 5.40 (s, 2H), 4.55 (d, J=5.7 Hz, 2H), 4.09 (q, J=7.1 Hz, 2H), 2.84-2.79 (m, 1H), 2.44-2.37 (m, 1H), 1.89-1.82 (m, 1H), 1.76-1.73 (m, 1H), 1.49-1.41 (m, 1H), 1.19 (t, J=7.1 Hz, 3H), 0.90-0.85 (m, 2H), 0.72-0.62 (m, 2H).

Example 128

Scheme 127

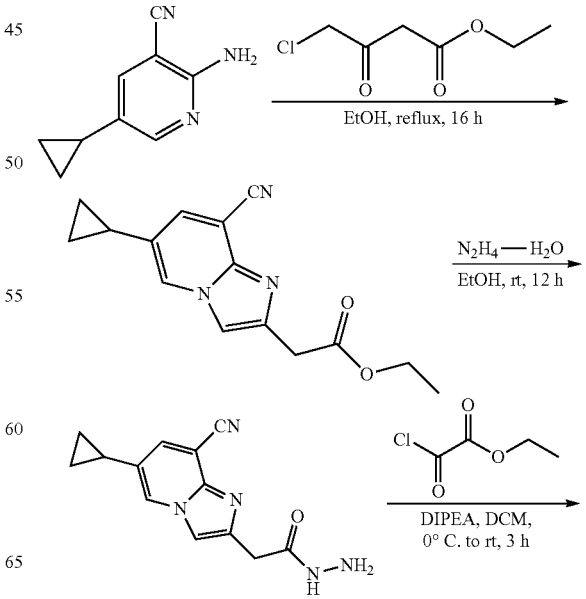

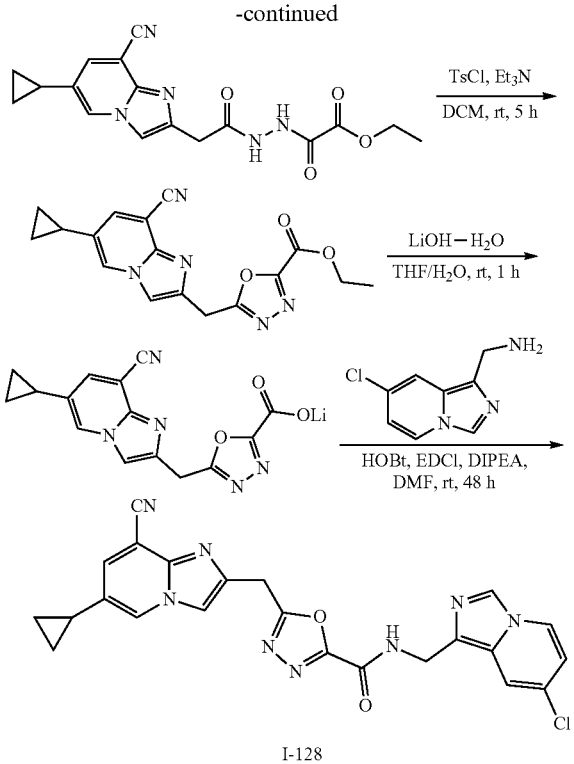

I-128

Synthesis of Ethyl 2-(8-cyano-6-cyclopropylimidazo[1,2-a]pyridin-2-yl)acetate To a solution of 2-amino-5-cyclopropylnicotinonitrile (1.5 g, 9.4 mmol) in EtOH (30 mL) was added ethyl 4-chloro-3-oxobutanoate (4.0 g, 28.2 mmol) at RT and the resulting mixture was stirred at reflux for 16 h. Water (100 mL) was added to the mixture adjusted to approximately pH 8 by adding a saturated NaHCO$_3$ solution. Then the mixture was extracted with EtOAc (100 mL×3). The combined organic layers were washed with brine, dried over Na$_2$SO$_4$ and concentrated to give the crude product, which was purified by silica gel chromatography (DCM/MeOH=10/1) to give ethyl 2-(8-cyano-6-cyclopropylimidazo[1,2-a]pyridin-2-yl)acetate (1.4 g, yield: 55%) as a yellow oil. ESI-MS [M+H]$^+$: 270.1.

Synthesis of 2-(8-cyano-6-cyclopropylimidazo[1,2-a]pyridin-2-yl)acetohydrazide A mixture of ethyl 2-(8-cyano-6-cyclopropylimidazo[1,2-a]pyridin-2-yl)acetate (1.4 g, 5.2 mmol) and N$_2$H$_4$.H$_2$O (2 mL) in EtOH (10 mL) was stirred at RT for 12 h. The mixture was then concentrated and purified by silica gel chromatography (DCM/MeOH=10/1) to give 2-(8-cyano-6-cyclopropylimidazo[1,2-a]pyridin-2-yl)acetohydrazide (1.3 g, yield: 98%) as a yellow solid, which was used in the next step without purification. ESI-MS [M+H]$^+$: 256.1.

Synthesis of Ethyl 2-(2-(2-(8-cyano-6-cyclopropylimidazo[1,2-a]pyridin-2-yl)acetyl)hydrazinyl)-2-oxoacetate To a solution of 2-(8-cyano-6-cyclopropylimidazo[1,2-a]pyridin-2-yl)acetohydrazide (700 mg, 2.7 mmol) and DIPEA (1.05 g, 8.1 mmol) in DCM (20 mL) was added ethyl 2-chloro-2-oxoacetate (561 mg, 4.1 mmol) slowly at 0° C. The reaction mixture was stirred at RT for 2 h. Water (30 mL) was added and the mixture was extracted with DCM (50 mL×3). The combined organic layers were concentrated to give the crude product, which was purified by silica gel chromatography (DCM/MeOH=10/1) to give ethyl 2-(2-(2-(8-cyano-6-cyclopropylimidazo[1,2-a]pyridin-2-yl)acetyl)hydrazinyl)-2-oxoacetate (500 mg, yield: 50%) as a yellow oil. ESI-MS [M+H]$^+$: 356.1.

Synthesis of Ethyl 5-((8-cyano-6-cyclopropylimidazo[1,2-a]pyridin-2-yl)methyl)-1,3,4-oxadiazole-2-carboxylate To a solution of ethyl 2-(2-(2-(8-cyano-6-cyclopropylimidazo[1,2-a]pyridin-2-yl)acetyl)hydrazinyl)-2-oxoacetate (500 mg, 1.4 mmol) and Et$_3$N (426 mg, 4.2 mmol) in DCM (10 mL) was added a solution of TsCl (400 mg, 2.1 mmol) in DCM (5 mL) at RT, the mixture was stirred at this temperature for 16 h. Water (30 mL) was added and the mixture was extracted with DCM (50 mL×3). The combined organic layers were washed with brine, dried over Na$_2$SO$_4$ and concentrated to give the crude product which was purified by silica gel chromatography (DCM/MeOH=10/1) to give ethyl 5-((8-cyano-6-cyclopropylimidazo[1,2-a]pyridin-2-yl)methyl)-1,3,4-oxadiazole-2-carboxylate (200 mg, yield: 42%) as a yellow oil. ESI-MS [M+H]$^+$: 338.1.

Synthesis of lithium 5-((8-cyano-6-cyclopropylimidazo[1,2-a]pyridin-2-yl)methyl)-1,3,4-oxadiazole-2-carboxylate A solution of ethyl 5-((8-cyano-6-cyclopropylimidazo[1,2-a]pyridin-2-yl)methyl)-1,3,4-oxadiazole-2-carboxylate (200 mg, 0.59 mmol) and LiOH (43 mg, 1.8 mmol) in a mixture of THF/H$_2$O (4 mL/2 mL) was stirred at RT for 1 h. THF were concentrated and the remaining H$_2$O phase was lyophilized to give lithium 5-((8-cyano-6-cyclopropylimidazo[1,2-a]pyridin-2-yl)methyl)-1,3,4-oxadiazole-2-carboxylate (220 mg, crude) as a red solid, which was used directly in the next step without further purification. ESI-MS [M+H]$^+$: 310.1.

Synthesis of N-((7-chloroimidazo[1,5-a]pyridin-1-yl)methyl)-5-((8-cyano-6-cyclopropylimidazo[1,2-a]pyridin-2-yl)methyl)-1,3,4-oxadiazole-2-carboxamide (I-128)

A mixture of lithium 5-((8-cyano-6-cyclopropylimidazo[1,2-a]pyridin-2-yl)methyl)-1,3,4-oxadiazole-2-carboxylate (100 mg, 0.31 mmol), (7-chloroimidazo[1,5-a]pyridin-1-yl)methanamine hydrochloride (82 mg, 0.38 mmol), EDCI (123 mg, 0.64 mmol), HOBT (86 mg, 0.64 mmol) and DIPEA (206 mg, 1.6 mmol) in DMF (5 mL) was stirred at RT for 48 h. The mixture was diluted with DCM/MeOH (30 mL, 10/1 (v/v)) and washed with H$_2$O (20 mL). The organic layer was separated, dried over Na$_2$SO$_4$ and concentrated in vacuo to give the crude product, which was purified by silica gel chromatography (DCM/MeOH=10/1) to give N-((7-chloroimidazo[1,5-a]pyridin-1-yl)methyl)-5-((8-cyano-6-cyclopropylimidazo[1,2-a]pyridin-2-yl)methyl)-1,3,4-oxadiazole-2-carboxamide (25 mg, yield: 17%) as a yellow solid. ESI-MS [M+H]$^+$: 473.1. Purity: 96.2%. $^1$H NMR (400 MHz, DMSO): δ 9.77 (t, J=5.7 Hz, 1H), 8.69 (d, J=1.4 Hz, 1H), 8.48 (s, 1H), 8.37-8.26 (m, 2H), 8.00 (s, 1H), 7.83 (d, J=1.9 Hz, 1H), 7.77 (d, J=1.6 Hz, 1H), 6.67 (dd, J=7.4, 2.1

Hz, 1H), 4.63 (d, J=5.8 Hz, 2H), 4.52 (s, 2H), 2.01-1.95 (m, 1H), 0.99-0.91 (m, 2H), 0.80-0.72 (m, 2H).

Example 129

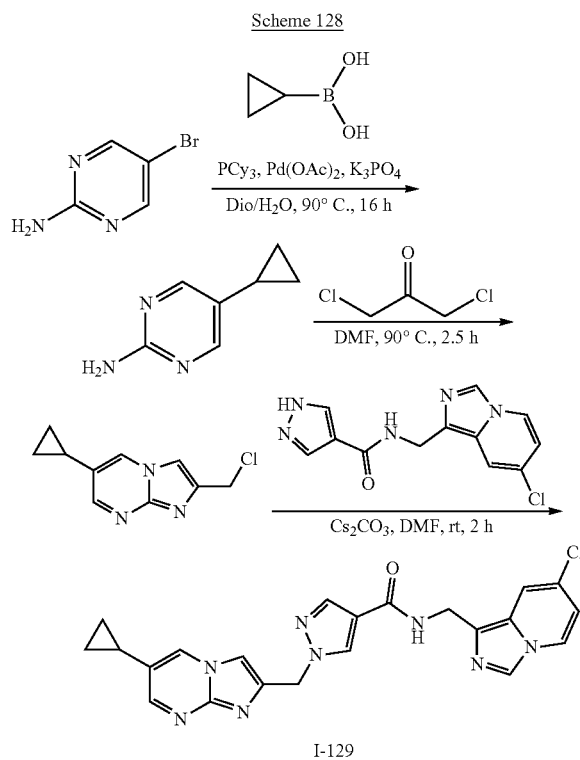

Synthesis of 5-cyclopropylpyrimidin-2-amine

To a solution of 5-bromopyrimidin-2-amine (1.0 g, 5.75 mmol) in dioxane/H₂O (20 mL/3 mL) was added cyclopropylboronic acid (1.98 g, 23 mmol), palladium diacetate (134 mg, 0.63 mmol), tricyclohexyl phosphine (322 mg, 1.15 mmol) and potassium phosphate (4.24 g, 20.12 mmol). The resulting mixture was stirred at 90° C. for 16 h. The reaction was diluted with H₂O (20 mL), extracted with ethyl acetate (3×50 mL), The combined organic layers were washed with brine, dried over anhydrous sodium sulfate and concentrated. The residue was purified by flash column chromatography to give 5-cyclopropylpyrimidin-2-amine (807 mg, yield: 95%). ESI-MS [M+H]⁺: 136.2.

Synthesis of 2-(chloromethyl)-6-cyclopropylimidazo [1,2-a]pyrimidine

To a solution of 5-cyclopropylpyrimidin-2-amine (600 mg, 4.44 mmol) in DMF (5 mL) was added 1,3-dichloropropan-2-one (2.73 g, 22.2 mmol). The resulting mixture was stirred at 80° C. for 2.5 h. The reaction mixture was diluted with H₂O (50 mL), extracted with ethyl acetate (3×30 mL), The organic layers were washed with brine, dried over anhydrous sodium sulfate and concentrated. The residue was purified by flash column chromatography to give 2-(chloromethyl)-6-cyclopropylimidazo[1,2-a]pyrimidine (80 mg, Yield: 9%). ESI-MS [M+H]⁺: 208.1.

Synthesis of N-((7-chloroimidazo[1,5-a]pyridin-1-yl)methyl)-1-((6-cyclopropylimidazo[1,2-a]pyrimidin-2-yl)methyl)-1H-pyrazole-4-carboxamide (I-129)

To a solution of 2-(chloromethyl)-6-cyclopropylimidazo [1,2-a]pyrimidine (75 mg, 0.36 mmol) in DMF (2 mL) was added cesium carbonate (234 mg, 0.72 mmol), N-((7-chloroimidazo[1,5-a]pyridin-1-yl)methyl)-1H-pyrazole-4-carboxamide (97 mg, 0.36 mmol). The resulting mixture was diluted with H₂O (50 mL), extracted with ethyl acetate (3×30 mL), The organic layer was washed with brine, dried over anhydrous sodium sulfate and concentrated. The residue was purified by prep-HPLC to give N-((7-chloroimidazo [1,5-a]pyridin-1-yl)methyl)-1-((6-cyclopropylimidazo[1,2-a]pyrimidin-2-yl)methyl)-1H-pyrazole-4-carboxamide (15 mg, Yield: 12%) as a white solid. ESI-MS [M+H]⁺: 447.1. Purity: 98.61%. ¹H NMR (400 MHz, DMSO): δ 8.69 (d, J=2.0 Hz, 1H), 8.60 (t, J=5.8 Hz, 1H), 8.41 (d, J=2.3 Hz, 1H), 8.30 (d, J=7.2 Hz, 2H), 8.24 (s, 1H), 7.88 (s, 1H), 7.78 (s, 1H), 7.63 (s, 1H), 6.64 (dd, J=7.4, 1.8 Hz, 1H), 5.43 (s, 2H), 4.55 (d, J=5.6 Hz, 2H), 1.97 (dd, J=8.9, 4.2 Hz, 1H), 0.97 (d, J=6.7 Hz, 2H), 0.74 (d, J=5.9 Hz, 2H).

Example 130

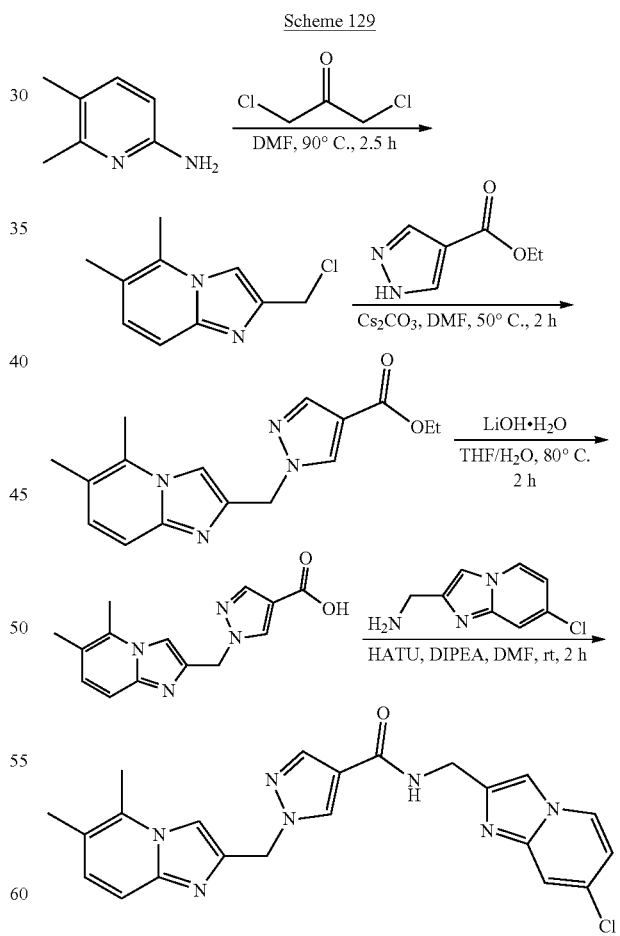

Synthesis of 5,6-dimethylpyridin-2-amine

To a solution of 5,6-dimethylpyridin-2-amine (1.0 g, 8.2 mmol) in DMF (10 mL) was added 1,3-dichloropropan-2- one (4.2 g, 32.8 mmol). The resulting mixture was stirred at 90° C. for 2 h. The reaction mixture was diluted with H₂O (150 mL) and extracted with ethyl acetate (3×30 mL). The combined organic layers were washed with brine, dried over anhydrous sodium sulfate and concentrated. The residue was purified by flash column chromatography to give 2-(chloromethyl)-5,6-dimethylimidazo[1,2-a]pyridine (1.0 g, yield: 63%). ESI-MS [M+H]⁺: 195.1.

Synthesis of Ethyl 1-((5,6-dimethylimidazo[1,2-a]pyridin-2-yl)methyl)-1H-pyrazole-4-carboxylate To a solution of 2-(chloromethyl)-5,6-dimethylimidazo[1,2-a]pyridine (150 mg, 0.77 mmol) in DMF (5 mL) was added cesium carbonate (500 mg, 1.54 mmol), ethyl 1H-pyrazole-4-carboxylate (119 mg, 0.85 mmol). The resulting mixture was stirred at 50° C. for 2 h, then diluted with H₂O (50 mL), and extracted with ethyl acetate (3×30 mL). The combined organic layers were washed with brine, dried over anhydrous sodium sulfate and concentrated. The residue was purified by flash column chromatography to give ethyl 1-((5,6-dimethylimidazo[1,2-a]pyridin-2-yl)methyl)-1H-pyrazole-4-carboxylate (200 mg, yield: 87%). ESI-MS [M+H]⁺: 299.2.

Synthesis of 1-((5,6-dimethylimidazo[1,2-a]pyridin-2-yl)methyl)-1H-pyrazole-4-carboxylic acid (I-131)

To a solution of ethyl 1-((5,6-dimethylimidazo[1,2-a]pyridin-2-yl)methyl)-1H-pyrazole-4-carboxylate (194 mg, 0.65 mmol) in a mixed solvent of THF/H₂O (3 mL/3 mL) was added Lithium hydroxide (78 mg, 3.3 mmol). The resulting mixture was stirred at 80° C. for 2 h. THF was evaporated and the pH of the H₂O phase was adjusted to 5 by adding 1 M HCl solution. The resulting solid precipitate was filtered to give 1-((5,6-dimethylimidazo[1,2-a]pyridin-2-yl)methyl)-1H-pyrazole-4-carboxylic acid (160 mg, yield: 90%) which was used in the next step without further purification. ESI-MS [M+H]⁺: 270.1.

Synthesis of N-((7-chloroimidazo[1,2-a]pyridin-2-yl)methyl)-1-((5,6-dimethylimidazo[1,2-a]pyridin-2-yl)methyl)-1H-pyrazole-4-carboxamide (I-130)

To the solution of 1-((5,6-dimethylimidazo[1,2-a]pyridin-2-yl)methyl)-1H-pyrazole-4-carboxylic acid (100 mg, 0.37 mmol) in dry DMF (5 mL) was added HATU (184 mg, 0.49 mmol), DIPEA (125 mg, 0.97 mmol) and (7-chloroimidazo[1,5-a]pyridin-1-yl)methanamine hydrochloride (58 mg, 0.37 mmol) at RT. The reaction was stirred at RT for 2 h. Water (30 mL) was added and the mixture was extracted with ethyl acetate (20 mL×3). The combined organic layers were washed with brine, dried over anhydrous sodium sulfate and concentrated. The residue was purified by prep-HPLC to give N-((7-chloroimidazo[1,2-a]pyridin-2-yl)methyl)-1-((5,6-dimethylimidazo[1,2-a]pyridin-2-yl)methyl)-1H-pyrazole-4-carboxamide (33.7 mg, yield: 21%). ESI-MS [M+H]⁺: 434.1. Purity: 99.2%. 1H NMR (400 MHz, DMSO): δ 8.80 (s, 1H), 8.72 (t, J=5.5 Hz, 1H), 8.40 (d, J=7.5 Hz, 1H), 8.38-8.32 (m, 2H), 7.98 (s, 1H), 7.95 (s, 1H), 7.84 (d, J=9.2 Hz, 1H), 7.71 (d, J=9.2 Hz, 1H), 6.87 (d, J=7.4 Hz, 1H), 5.67 (s, 2H), 4.64 (d, J=5.6 Hz, 2H), 2.67 (s, 3H), 2.42 (s, 3H).

Example 131

Scheme 130

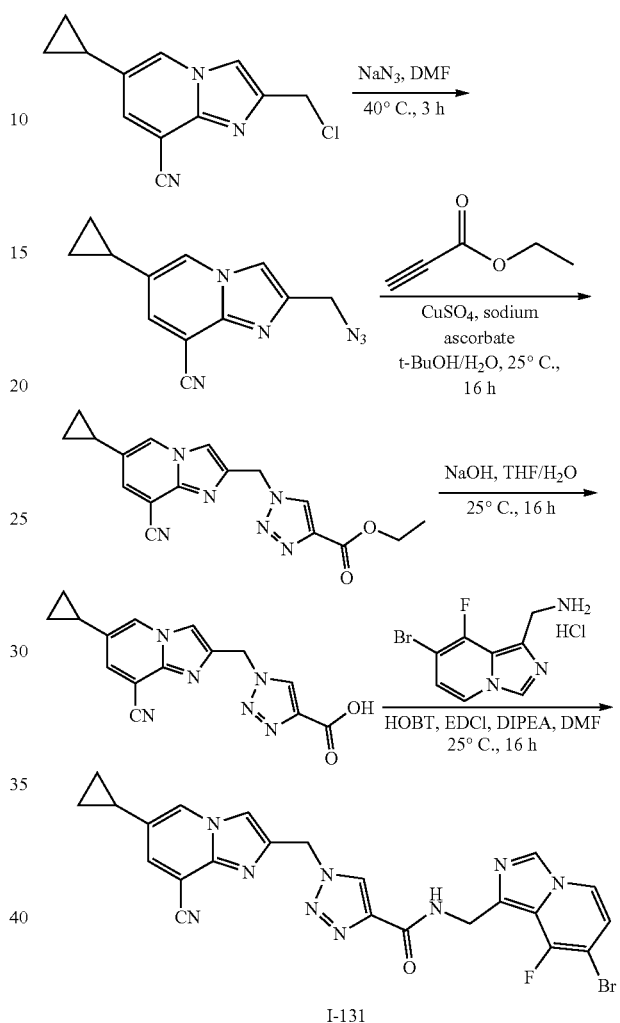

I-131

Synthesis of 2-(azidomethyl)-6-cyclopropylimidazo[1,2-a]pyridine-8-carbonitrile

To a mixture of 2-(chloromethyl)-6-cyclopropylimidazo[1,2-a]pyridine-8-carbonitrile (100 mg, 0.43 mmol) in dry DMF (2 mL) was added NaN₃ (39 mg, 0.65 mmol) and stirred at 25° C. for 3 h. Then H₂O (20 mL) was added and extracted with EtOAc (20 mL×3). The combined organic layers were washed with brine, dried over Na₂SO₄, filtered and concentrated to give the crude product, which was purified by Prep-TLC (EtOAc/PE=3/2) to give 2-(azidomethyl)-6-cyclopropylimidazo[1,2-a]pyridine-8-carbonitrile (70 mg, yield: 68%) as a yellow solid. ESI-MS [M+H]⁺: 239.2.

Synthesis of Ethyl 1-((8-cyano-6-cyclopropylimidazo[1,2-a]pyridin-2-yl)methyl)-1H-1,2,3-triazole-4-carboxylate To a mixture of 2-(azidomethyl)-6-cyclopropylimidazo[1,2-a]pyridine-8-carbonitrile (70 mg, 0.29 mmol), CuSO₄ (24 mg, 0.15 mmol), sodium ascorbate (30 mg, 0.15 mmol) in t-BuOH/H$_2$O (3/3 mL) was added ethyl propiolate (43 mg, 0.44 mmol). The mixture was stirred at 25° C. for 16 h. Then H$_2$O (20 mL) was added, extracted with EtOAc (30 mL×3). The combined organic layers were concentrated to give ethyl 1-((8-cyano-6-cyclopropylimidazo[1,2-a]pyridin-2-yl)methyl)-1H-1,2,3-triazole-4-carboxylate (95 mg, crude) as a yellow solid. ESI-MS [M+H]$^+$: 337.2.

Synthesis of 1-((8-cyano-6-cyclopropylimidazo[1,2-a]pyridin-2-yl)methyl)-1H-1,2,3-triazole-4-carboxylic Acid To a mixture of ethyl 1-((8-cyano-6-cyclopropylimidazo[1,2-a]pyridin-2-yl)methyl)-1H-1,2,3-triazole-4-carboxylate (95 mg, crude from last step) in THF/H$_2$O (2/2 mL) was added NaOH (34 mg, 0.85 mmol). The mixture was stirred at 25° C. for 16 h, 1 M HCl was added to adjust pH about 5, extracted with EtOAc/MeOH (10:1, 20 mL×3), the combined organic layers were concentrated to give 1-((8-cyano-6-cyclopropylimidazo[1,2-a]pyridin-2-yl)methyl)-1H-1,2,3-triazole-4-carboxylic acid (70 mg, crude) as a grey solid. ESI-MS [M+H]$^+$: 309.2.

Synthesis of N-((7-bromo-8-fluoroimidazo[1,5-a]pyridin-1-yl)methyl)-1-((8-cyano-6-cyclopropylimidazo[1,2-a]pyridin-2-yl)methyl)-1H-1,2,3-triazole-4-carboxamide (I-131)

To a mixture of 1-((8-cyano-6-cyclopropylimidazo[1,2-a]pyridin-2-yl)methyl)-1H-1,2,3-triazole-4-carboxylic acid (70 mg, crude from last step), (7-bromo-8-fluoroimidazo[1,5-a]pyridin-1-yl)methanamine hydrochloride (55 mg, 0.23 mmol), HOBT (54 mg, 0.4 mmol), EDCI (75 mg, 0.4 mmol) in DMF (3 mL) was added DIPEA (126 mg, 0.98 mmol). The mixture was stirred at 25° C. for 16 h. Then the reaction was poured into H$_2$O (20 mL), the precipitate was filtered and washed with DCM (10 mL) to give N-((7-bromo-8-fluoroimidazo[1,5-a]pyridin-1-yl)methyl)-1-((8-cyano-6-cyclopropylimidazo[1,2-a]pyridin-2-yl)methyl)-1H-1,2,3-triazole-4-carboxamide (60 mg, yield: 38%) as a white solid. ESI-MS [M+H]$^+$: 534.1. Purity: 96.81 (214 nm), 98.17 (254 nm). $^1$H NMR (400 MHz, DMSO-d$_6$) δ 8.73-8.69 (m, 2H), 8.59-8.50 (m, 2H), 8.14 (d, J=6.8 Hz, 1H), 7.99 (s, 1H), 7.80 (s, 1H), 6.82 (s, 1H), 5.81 (s, 2H), 4.70 (s, 2H), 1.99-1.98 (m, 1H), 0.97-0.96 (m, 2H), 0.76-075 (m, 2H).

Example 132

Scheme 131

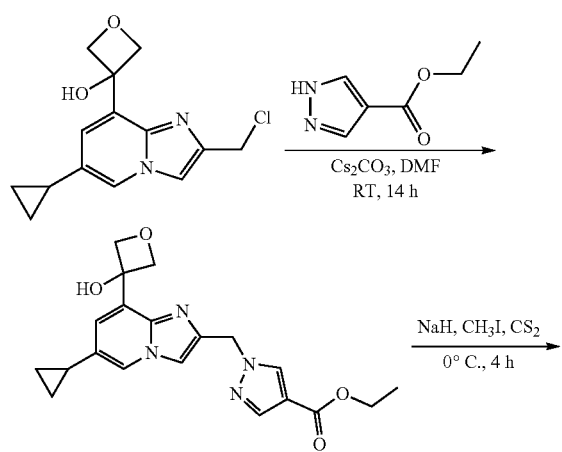

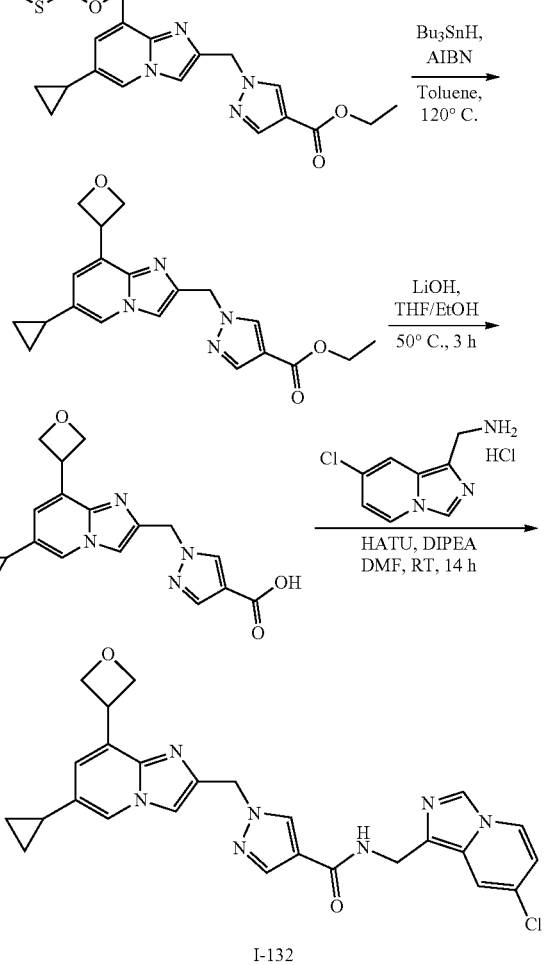

I-132

Synthesis of Ethyl 1-((6-cyclopropyl-8-(3-hydroxyoxetan-3-yl)imidazo[1,2-a]pyridin-2-yl)methyl)-1H-pyrazole-4-carboxylate A mixture of 3-(2-(chloromethyl)-6-cyclopropylimidazo[1,2-a]pyridin-8-yl)oxetan-3-ol (1.2 g, 4.3 mmol), ethyl 1H-pyrazole-4-carboxylate (725 mg, 5.2 mmol) and Cs$_2$CO$_3$ (2.1 g, 6.45 mmol) in DMF (30 mL) was stirred at RT for 14 h. Water (150 mL) was added to the reaction, extracted with EtOAc (100 mL×3). The combined organic layers were washed with brine, dried over Na$_2$SO$_4$, concentrated in vacuo to give the crude product which was purified with silica gel chromatography (DCM/MeOH=20/1) to give the ethyl 1-((6-cyclopropyl-8-(3-hydroxyoxetan-3-yl)imidazo[1,2-a]pyridin-2-yl)methyl)-1H-pyrazole-4-carboxylate (1.1 g, yield: 67%) as a yellow solid. ESI-MS [M+H]$^+$: 383.2.

Synthesis of Ethyl 1-((6-cyclopropyl-8-(3-(((methylthio)carbonothioyl)oxy)oxetan-3-yl)imidazo[1,2-a]pyridin-2-yl)methyl)-1H-pyrazole-4-carboxylate To a solution of ethyl 1-((6-cyclopropyl-8-(3-hydroxyoxetan-3-yl)imidazo[1,2-a]pyridin-2-yl)methyl)-1H-pyrazole-4-carboxylate (600 mg, 1.57 mmol) in THF (15 mL) was added NaH (127 mg, 3.14 mmol, 60% in oil) at 0° C. slowly. The resulting mixture was stirred at 0° C. for 30 min. Then CS$_2$ (239 mg, 3.14 mmol) was added thereto at 0° C. After stirring for 30 min, CH$_3$I (446 mg, 3.14 mmol) was added and stirred at RT for 1 h. The reaction was quenched with aqueous NH$_4$Cl, extracted with EtOAC (30 mL×3). The combined organic layers were washed with brine, dried over Na$_2$SO$_4$, concentrated in vacuo to give the ethyl 1-((6-cyclopropyl-8-(3-(((methylthio)carbonothioyl)oxy)oxetan-3-yl)imidazo[1,2-a]pyridin-2-yl)methyl)-1H-pyrazole-4-carboxylate (650 mg crude), which was used into next step without further purification. ESI-MS [M+H]$^+$: 473.1

Synthesis of Ethyl 1-((8-(oxetan-3-yl)imidazo[1,2-a]pyridin-2-yl)methyl)-1H-pyrazole-4-carboxylate A solution of ethyl 1-((6-cyclopropyl-8-(3-(((methylthio)carbonothioyl)oxy)oxetan-3-yl)imidazo[1,2-a]pyridin-2-yl)methyl)-1H-pyrazole-4-carboxylate (650 mg crude from previous step) and Bu$_3$SnH (917 mg, 3.14 mmol) and AIBN (515 mg, 3.14 mmol) in toluene (20 mL) was stirred at 120° C. for 12 h. The reaction was concentrated in vacuo to give the residue, which was diluted with H$_2$O (50 mL), extracted with EtOAc (50 mL×3). The combined organic layers were washed with brine, dried over Na$_2$SO$_4$, concentrated in vacuo to give the crude product, which was purified with silica gel chromatography (EA/PE=2/1) to give the ethyl 1-((8-(oxetan-3-yl)imidazo[1,2-a]pyridin-2-yl)methyl)-1H-pyrazole-4-carboxylate (100 mg, yield: 17% over 2 steps) as a white solid. ESI-MS [M+H]$^+$: 367.2.

Synthesis of 1-((8-(oxetan-3-yl)imidazo[1,2-a]pyridin-2-yl)methyl)-1H-pyrazole-4-carboxylic Acid A mixture of ethyl 1-((8-(oxetan-3-yl)imidazo[1,2-a]pyridin-2-yl)methyl)-1H-pyrazole-4-carboxylate (100 mg, 0.27 mmol) and LiOH (37 mg, 1.53 mmol) in THF/H$_2$O (10 mL/5 mL) was stirred at 50° C. for 3 h. The reaction was concentrate in vacuo to give the 1-((8-(oxetan-3-yl)imidazo[1,2-a]pyridin-2-yl)methyl)-1H-pyrazole-4-carboxylic acid sodium salt (150 mg crude), which was used into next step without further purification. ESI-MS [M+H]$^+$: 339.1.

Synthesis of N-((7-chloroimidazo[1,5-a]pyridin-1-yl)methyl)-1-((6-cyclopropyl-8-(oxetan-3-yl)imidazo[1,2-a]pyridin-2-yl)methyl)-1H-pyrazole-4-carboxamide (I-132)

To a solution of 1-((8-(oxetan-3-yl)imidazo[1,2-a]pyridin-2-yl)methyl)-1H-pyrazole-4-carboxylic acid (150 mg, crude from previous step), (7-chloroimidazo[1,5-a]pyridin-1-yl)methanamine hydrochloride (87 mg, 0.4 mmol), HATU (177 mg, 0.47 mmol) in DMF (10 mL) was added DIPEA (200 mg, 1.55 mmol). The resulting mixture was stirred at RT for 14 h. H$_2$O (30 mL) was added into the reaction, extracted with EtOAC (40 mL×3). The combined organic layers were washed with brine, dried over Na$_2$SO$_4$, concentrated in vacuo to give the crude product which was purified with Prep-TLC (DCM/MeOH=10/1) to give the N-((7-chloroimidazo[1,5-a]pyridin-1-yl)methyl)-1-((6-cyclopropyl-8-(oxetan-3-yl)imidazo[1,2-a]pyridin-2-yl)methyl)-1H-pyrazole-4-carboxamide (25 mg, yield: 18% over 2 steps) as a white solid. ESI-MS [M+H]$^+$: 502.2. Purity: 99.2 (214 nm), 99.0 (254 nm). $^1$H NMR (400 MHz, DMSO-d$_6$) δ 8.58 (t, J=5.7 Hz, 1H), 8.33-8.27 (m, 2H), 8.23 (s, 1H), 8.17 (m, 1H), 7.88 (s, 1H), 7.82-7.78 (m, 1H), 7.66 (s, 1H), 7.02 (s, 1H), 6.67-6.62 (m, 1H), 5.39 (s, 2H), 4.94-4.91 (m, 2H), 4.85-4.75 (m, 2H), 4.69-4.63 (m, 1H), 4.55 (d, J=5.7 Hz, 2H), 1.96-1.88 (m, 1H), 0.94-0.88 (m, 2H), 0.72-0.67 (m, 2H).

Example 133

Scheme 132

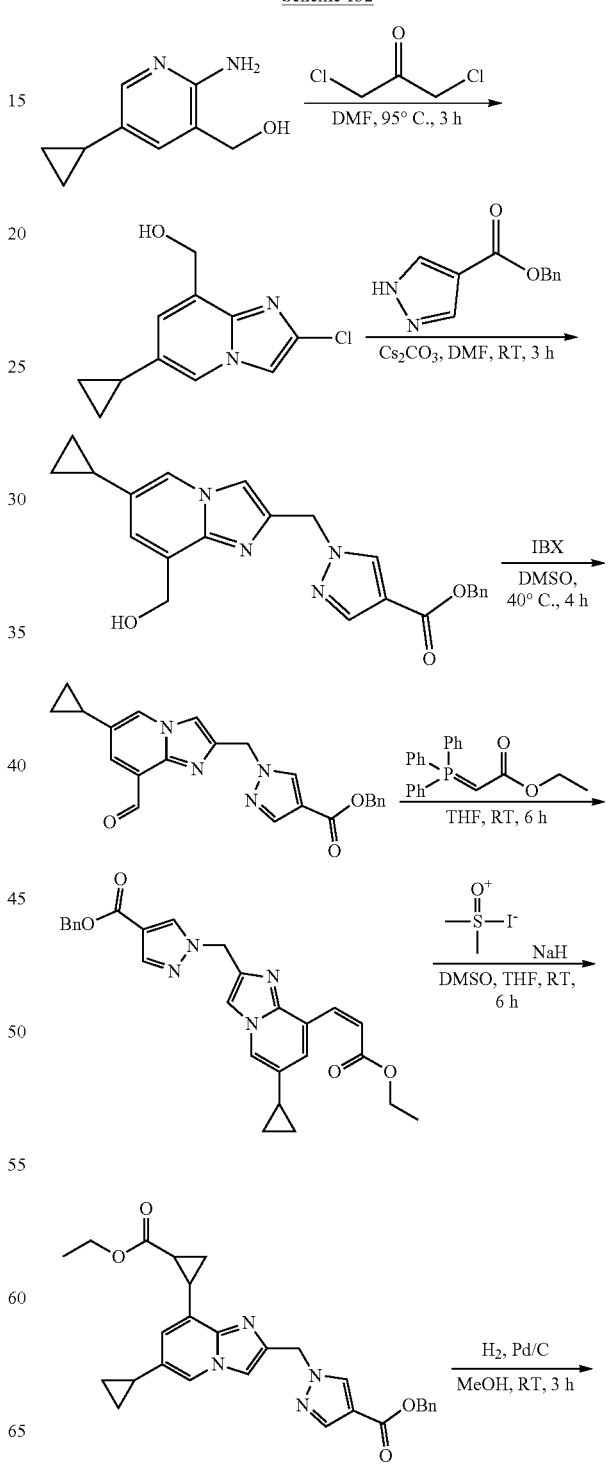

-continued

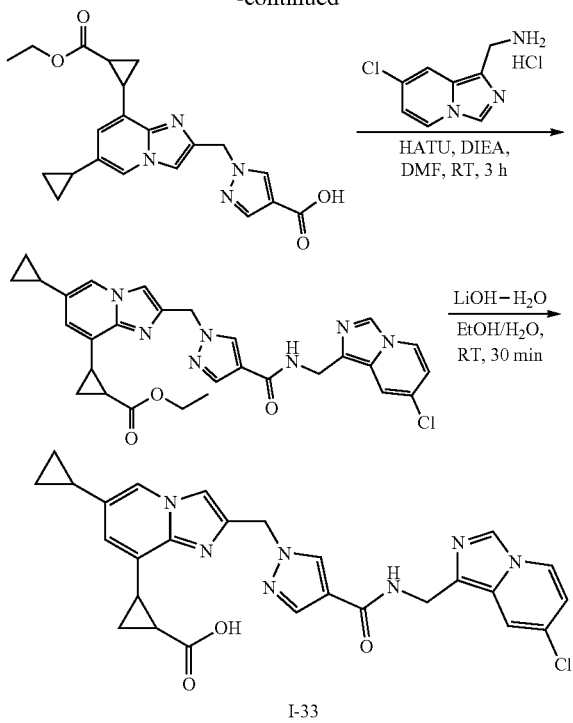

I-33

Synthesis of (2-(chloromethyl)-6-cyclopropylimidazo[1,2-a]pyridin-1-yl)methanol

To a solution of (2-amino-5-cyclopropylpyridin-3-yl)methanol (4.8 g, 29 mmol) in DMF (30 mL) was added 1,3-dichloropropan-2-one (14.8 g, 117 mmol) at RT and then heated at 95° C. The reaction was monitored by LCMS until the starting material consumed (~3 h). The reaction was cooled to RT, then quenched with NaHCO$_3$ until pH=8 and extracted with EtOAc (30 mL×3). The combined organic layers were washed with brine, dried over Na$_2$SO$_4$, concentrated in vacuo to give the crude product, which was purified with flash silica gel column (eluent: EtOAc/PE: 1/2) to give the (2-(chloromethyl)-6-cyclopropylimidazo[1,2-a]pyridin-8-yl)methanol (3.5 g, purity: 93%, yield: 51%) as a white solid. ESI-MS [M+H]$^+$: 236.1.

Synthesis of benzyl 1-((6-cyclopropyl-8-(hydroxymethyl)imidazo[1,2-a]pyridin-2-yl)methyl)-1H-pyrazole-4-carboxylate A mixture of (2-(chloromethyl)-6-cyclopropylimidazo[1,2-a]pyridin-8-yl)methanol (3.5 g, 14.65 mmol), benzyl 1H-pyrazole-4-carboxylate (2.8 g, 14.65 mmol) and Cs$_2$CO$_3$ (11.9 g, 36.6 mmol) in DMF (15 mL) was stirred at RT for 3 h. The reaction was quenched with H$_2$O (30 mL) and extracted with EtOAc (30 mL×3). The combined organic layers were washed with brine, dried over Na$_2$SO$_4$, concentrated in vacuo to give the crude product which was purified with prep-TLC (eluent: DCM/MeOH: 10/1) to give the benzyl 1-((6-cyclopropyl-8-(hydroxymethyl)imidazo[1,2-a]pyridin-2-yl)methyl)-1H-pyrazole-4-carboxylate (3.16 g, yield: 54%) as a white solid. ESI-MS [M+H]$^+$: 402.1.

Synthesis of benzyl 1-((6-cyclopropyl-8-formylimidazo[1,2-a]pyridin-2-yl)methyl)-1H-pyrazole-4-carboxylate A solution of benzyl 1-((6-cyclopropyl-8-(hydroxymethyl)imidazo[1,2-a]pyridin-2-yl)methyl)-1H-pyrazole-4-carboxylate (3.16 g, 7.9 mmol) in DMSO (15 mL) was added IBX (4.4 g, 15.7 mmol) at RT and then warmed to 40° C. and stirred for 4 h. The reaction was quenched with H$_2$O (30 mL) and extracted with EtOAc (30 mL×3). The combined organic layers were washed with brine, dried over Na$_2$SO$_4$, concentrated in vacuo to give the crude product, which was purified with silica gel column (eluent: DCM/MeOH: 10/1) to give the 1-((6-cyclopropyl-8-formylimidazo[1,2-a]pyridin-2-yl)methyl)-1H-pyrazole-4-carboxylate (1.48 g, yield: 54%) as a yellow solid. ESI-MS [M+H]$^+$: 401.1.

Synthesis of benzyl (Z)-1-((6-cyclopropyl-1-(3-ethoxy-3-oxoprop-1-en-1-yl)imidazo[1,2-a]pyridin-2-yl)methyl)-1H-pyrazole-4-carboxylate A solution of the benzyl 1-((6-cyclopropyl-8-formylimidazo[1,2-a]pyridin-2-yl)methyl)-1H-pyrazole-4-carboxylate (1.48 g, 3.7 mmol) in THF (30 mL) was added ethyl 2-(triphenyl-15-phosphanylidene)acetate (1.42 g, 41 mmol) at RT and stirred for 6 h. The reaction was concentrated in vacuo to give the crude mixture, which was purified with flash silica gel column (eluent: DCM/MeOH: 15/1) to give the benzyl 1-((6-cyclopropyl-8-(2-(ethoxycarbonyl)cyclopropyl)imidazo[1,2-a]pyridin-2-yl)methyl)-1H-pyrazole-4-carboxylate (890 mg, purity: 91.5%, yield: 51%) as a white solid. ESI-MS [M+H]$^+$: 470.1.

Synthesis of benzyl 1-((6-cyclopropyl-8-(2-(ethoxycarbonyl)cyclopropyl)imidazo[1,2-a]pyridin-2-yl)methyl)-1H-pyrazole-4-carboxylate A mixture of 1-((6-cyclopropyl-8-(2-(ethoxycarbonyl)cyclopropyl)imidazo[1,2-a]pyridin-2-yl)methyl)-1H-pyrazole-4-carboxylate (890 mg, 1.9 mmol) and trimethyl sulfoxonium iodide (627 mg, 2.85 mmol) in THF/DMSO (30/3 mL) was added NaH (190 mg, 2.85 mmol) was stirred at RT for 6 h. The reaction was quenched with H$_2$O (30 mL) and extracted with EtOAc (30 mL×3). The combined organic layers were washed with brine, dried over Na$_2$SO$_4$, concentrated in vacuo to give the crude product, which was purified with flash silica gel column (eluent: DCM/MeOH: 10/1) to give the benzyl 1-((6-cyclopropyl-8-(2-(ethoxycarbonyl)cyclopropyl)imidazo[1,2-a]pyridin-2-yl)methyl)-1H-pyrazole-4-carboxylate (545 mg, yield: 59%) as a yellow solid. ESI-MS [M+H]$^+$: 485.2.

Synthesis of 1-((6-cyclopropyl-8-(2-(ethoxycarbonyl)cyclopropyl)imidazo[1,2-a]pyridin-2-yl)methyl)-1H-pyrazole-4-carboxylic Acid A solution of 1-((6-cyclopropyl-8-(2-(ethoxycarbonyl)cyclopropyl)imidazo[1,2-a]pyridin-2-yl)methyl)-1H-pyrazole-4-carboxylate (545 mg, 1.13 mmol) in MeOH (10 mL) was added Pd/C (50 mg) and stirred at RT under hydrogen for 3 h. The reaction was filtered through a pad of Celite, washed with MeOH and concentrated in vacuo to give crude 1-((6-cyclopropyl-8-(2-(ethoxycarbonyl)cyclopropyl)imidazo[1,2-a]pyridin-2-yl)methyl)-1H-pyrazole-4-carboxylic acid (354 mg, yield: 80%) as a yellow solid. ESI-MS [M+H]$^+$: 394.1.

Synthesis Ethyl 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)cyclopropane-1-carboxylate A mixture of 1-((6-cyclopropyl-8-(2-(ethoxycarbonyl)cyclopropyl)imidazo[1,2-a]pyridin-2-yl) methyl)-1H-pyrazole-4-carboxylic acid (35.4 mg, 0.09 mmol) in DMF (3 mL) was added (7-chloroimidazo[1,5-a]pyridin-1-yl)methanamine hydrochloride (31 mg, 0.14 mmol), DIPEA (0.1 mL, 0.75 mmol), HATU (45 mg, 0.12 mmol) and stirred at RT for 3 h. The reaction was quenched with H$_2$O (30 mL) and extracted with EtOAc (30 mL×3). The combined organic layers were washed with brine, dried over Na$_2$SO$_4$, and concentrated in vacuo to give the crude product, which was purified by prep-TLC (eluent: DCM/MeOH: 10/1) to give ethyl 2-(2-((4-(((7-chloroimidazo[1,5-a]pyridin-1-yl)methyl)carbamoyl)-1H-pyrazol-1-yl)methyl)-6-cyclopropylimidazo[1,2-a] pyridin-8-yl)cyclopropane-1-carboxylate (17.5 mg, yield: 35%) as a white solid. ESI-MS [M+H]$^+$: 558.2. Purity: 96.0 (214 nm), 95.8 (254 nm). $^1$H NMR (400 MHz, DMSO-d$_6$) δ 8.59 (t, J=5.7 Hz, 1H), 8.35-8.26 (m, 2H), 8.23-8.14 (m, 2H), 7.88 (s, 1H), 7.81-7.74 (m, 1H), 7.66 (s, 1H), 6.73 (d, J=1.4 Hz, 1H), 6.65 (dd, J=7.5, 2.1 Hz, 1H), 5.40 (s, 2H), 4.55 (d, J=5.7 Hz, 2H), 4.09 (q, J=7.1 Hz, 2H), 2.84-2.79 (m, 1H), 2.44-2.37 (m, 1H), 1.89-1.82 (m, 1H), 1.76-1.73 (m, 1H), 1.49-1.41 (m, 1H), 1.19 (t, J=7.1 Hz, 3H), 0.90-0.85 (m, 2H), 0.72-0.62 (m, 2H).

Synthesis of 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)cyclopropane-1-carboxylic acid (I-133)

To a mixture of ethyl 2-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)cyclopropane-1-carboxylate (56 mg, 0.1 mmol) in EtOH/H$_2$O (3 mL/1 mL) was added LiOH.H$_2$O (24 mg, 0.56 mmol). The mixture was stirred at RT for 30 min. After adjusting to pH=6 with HCl(aq), the reaction mixture was extracted with EtOAc (30 mL×3), the combined organic layers were concentrated and the crude residue was purified by Prep-HPLC to give 2-(2-((4-(((7-chloroimidazo[1,5-a]pyridin-1-yl)methyl)carbamoyl)-1H-pyrazol-1-yl)methyl)-6-cyclopropylimidazo[1, 2-a]pyridin-8-yl)cyclopropane-1-carboxylic acid (30 mg, yield: 57%) as a white solid. ESI-MS [M−H]$^-$: 529.8. Purity: 97.1 (214 nm), 98.0 (254 nm). $^1$H NMR (400 MHz, DMSO-d$_6$) δ 11.95 (s, 1H), 8.59 (t, J=5.5 Hz, 1H), 8.31-8.29 (m, 2H), 8.20 (s, 1H), 8.17 (s, 1H), 7.88 (s, 1H), 7.78 (s, 1H), 7.65 (s, 1H), 6.70 (s, 1H), 6.65 (dd, J=7.4, 1.9 Hz, 1H), 5.41 (s, 2H), 4.56 (d, J=5.6 Hz, 2H), 2.84-2.75 (m, 1H), 2.26-2.16 (m, 1H), 1.90-1.82 (m, 1H), 1.76-1.68 (m, 1H), 1.49-1.35 (m, 1H), 0.92-1.84 (m, 2H), 0.75-0.58 (m, 2H).

Example 134

Scheme 133

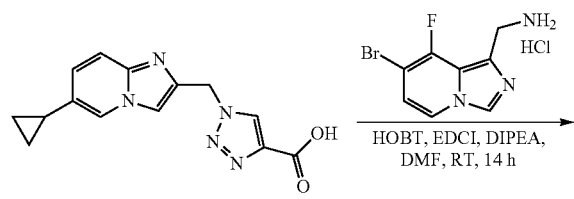

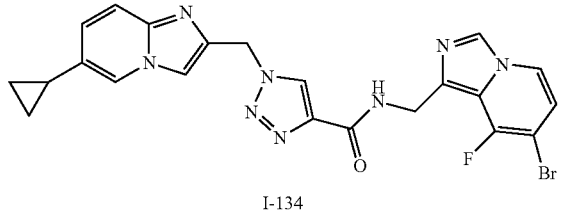

I-134

Synthesis of N-((7-bromo-8-fluoroimidazo[1,5-a]pyridin-1-yl)methyl)-1-((6-cyclopropylimidazo[1,2-a]pyridin-2-yl)methyl)-1H-1,2,3-triazole-4-carboxamide (I-134)

To a solution of 1-((6-cyclopropylimidazo[1,2-a]pyridin-2-yl)methyl)-1H-1,2,3-triazole-4-carboxylic acid (100 mg, 0.35 mmol), (7-bromo-8-fluoroimidazo[1,5-a]pyridin-1-yl)methanamine hydrochloride (114 mg, 0.41 mmol), HOBT (67 mg, 0.49 mmol) and EDCI (94 mg, 0.49 mmol) in DMF (5 mL) was added DIPEA (226 mg, 1.75 mmol). The resulting mixture was stirred at RT for 14 h. The reaction was poured into H$_2$O (40 mL), and yellow solid was precipitate out. The mixture was filtered and the cake was dried to give the crude product, which was triturated with DCM (25 mL) to give the N-((7-chloroimidazo[1,5-a]pyridin-1-yl)methyl)-1-((6-cyclopropylimidazo[1,2-a]pyridin-2-yl)methyl)-1H-1,2,3-triazole-4-carboxamide (65 mg, yield: 36%) as a white solid. ESI-MS [M+H]$^+$: 509.0, purity: 98.79 (214 nm), 98.38 (254 nm). $^1$H NMR (400 MHz, DMSO-d$_6$) δ 8.69 (t, J=5.2 Hz, 1H), 8.55 (s, 1H), 8.45 (s, 1H), 8.35 (s, 1H), 8.14 (d, J=7.3 Hz, 1H), 7.83 (s, 1H), 7.41 (d, J=9.3 Hz, 1H), 7.01 (dd, J=9.3, 1.5 Hz, 1H), 6.83-6.80 (m, 1H), 5.73 (s, 2H), 4.69 (d, J=5.4 Hz, 2H), 1.96-1.89 (m, 1H), 0.94-0.89 (m, 2H), 0.69-0.65 (m, 2H).

Example 135

Scheme 134

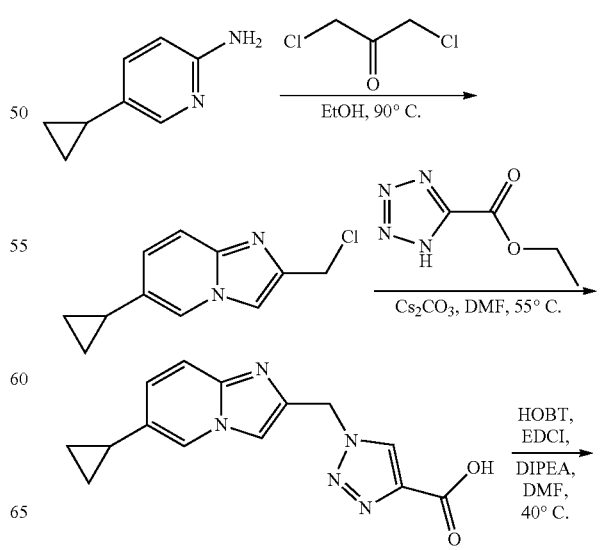

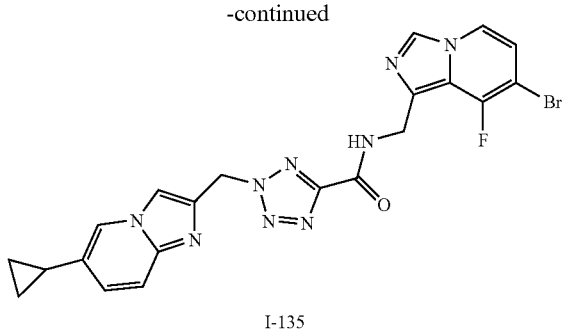

I-135

Synthesis of 2-(chloromethyl)-6-cyclopropylimidazo[1,2-a]pyridine

A mixture of 5-cyclopropylpyridin-2-amine (320 mg, 2.38 mmol), 1,3-dichloropropan-2-one (906 mg, 7.14 mmol) in EtOH (5 mL) was stirred at 90° C. overnight. The reaction mixture was concentrated and a saturated aqueous NaHCO₃ was added until pH to about 8, and then extracted with EtOAc (50 mL×2). The combined organic layers were concentrated and purified by silica gel chromatography (EA/PE=2/1) to give 2-(chloromethyl)-6-cyclopropylimidazo[1,2-a]pyridine (200 mg, yield: 41%) as a brown solid. ESI-MS [M+H]⁺: 207.1.

Synthesis of 2-((6-cyclopropylimidazo[1,2-a]pyridin-2-yl)methyl)-2H-tetrazole-5-carboxylic Acid A mixture of 2-(chloromethyl)-6-cyclopropylimidazo[1,2-a]pyridine (104 mg, 0.5 mmol), ethyl 1H-tetrazole-5-carboxylate (71 mg, 0.5 mmol) and Cs₂CO₃ (323 mg, 1 mmol) in DMF (3 mL) was stirred at 55° C. for 6 h. Then H₂O was added (10 mL), pH of the mixture was adjusted to 5 by adding HCl (2 N), then lyophilized to give 2-((6-cyclopropylimidazo[1,2-a]pyridin-2-yl)methyl)-2H-tetrazole-5-carboxylic acid (500 mg, crude) as a yellow solid, which was used into next step without purification. ESI-MS [M+H]⁺: 285.1.

Synthesis of N-((7-bromo-8-fluoroimidazo[1,5-a]pyridin-1-yl)methyl)-2-((6-cyclopropylimidazo[1,2-a]pyridin-2-yl)methyl)-2H-tetrazole-5-carboxamide (I-135)

A mixture of 2-((6-cyclopropylimidazo[1,2-a]pyridin-2-yl)methyl)-2H-tetrazole-5-carboxylic acid (250 mg, crude from last step), (7-bromo-8-fluoroimidazo[1,5-a]pyridin-1-yl)methanamine hydrochloride (45 mg, 0.16 mmol), HOBT (73 mg, 0.54 mmol), EDCI (103 mg, 0.54 mmol) and DIPEA (174 mg, 1.35 mmol) in DMF (2 mL) was stirred at 40° C. for 26 h. Water (20 mL) was added and extracted with EtOAc (30 mL×3), the combined organic layers were washed by H₂O (10 mL), then by brine, and then concentrated, the crude was purified by prep-HPLC to give N-((7-bromo-8-fluoroimidazo[1,5-a]pyridin-1-yl)methyl)-2-((6-cyclopropylimidazo[1,2-a]pyridin-2-yl)methyl)-2H-tetrazole-5-carboxamide (3.3 mg, yield: 4.03%) as a white solid. ESI-MS [M+H]⁺: 510.0. Purity: 97.65% (214 nm), 99.08% (254 nm). ¹H NMR (400 MHz, DMSO-d₆) δ 9.29 (t, J=5.4 Hz, 1H), 8.45 (d, J=2.4 Hz, 1H), 8.36 (s, 1H), 8.14 (d, J=7.3 Hz, 1H), 7.94 (s, 1H), 7.39 (d, J=9.3 Hz, 1H), 7.01 (dd, J=9.4, 1.7 Hz, 1H), 6.82 (t, J=8 Hz, 1H), 6.06 (s, 2H), 4.71 (d, J=5.5 Hz, 2H), 1.96-1.89 (m, 1H), 0.93-0.91 (m, 2H), 0.69-0.65 (m, 2H).

Example 136

Scheme 135

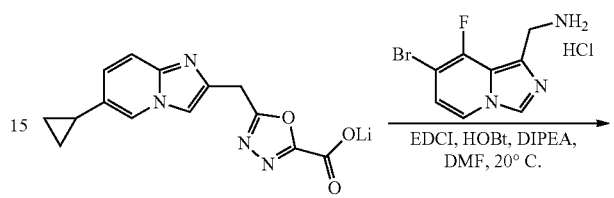

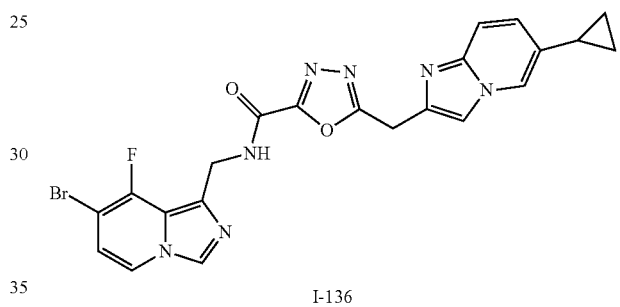

I-136

Synthesis of N-((7-bromo-8-fluoroimidazo[1,5-a]pyridin-1-yl)methyl)-5-((6-cyclopropylimidazo[1,2-a]pyridin-2-yl)methyl)-1,3,4-oxadiazole-2-carboxamide (I-136)

A mixture of lithium 5-((6-cyclopropylimidazo[1,2-a]pyridin-2-yl)methyl)-1,3,4-oxadiazole-2-carboxylate (100.0 mg, 0.35 mmol), (7-bromo-8-fluoroimidazo[1,5-a]pyridin-1-yl)-methanamine hydrochloride (98.6 mg, 0.35 mmol), EDCI (134.4 mg, 0.70 mmol), HOBT (94.5 mg, 0.70 mmol) and DIPEA (0.18 mL, 1.05 mmol) in DMF (5 mL) was stirred at 20° C. for 48 h. The mixture was concentrated to remove DMF, diluted with DCM/MeOH (300 mL, 10/1 (v/v)) and washed with H₂O (100 mL×2). The organic layer was separated, dried over Na₂SO₄, and concentrated in vacuo to give the crude product, which was purified by Prep-HPLC to give N-((7-bromo-8-fluoroimidazo[1,5-a]pyridin-1-yl)methyl)-5-((6-cyclopropylimidazo[1,2-a]pyridin-2-yl)methyl)-1,3,4-oxadiazole-2-carboxamide (25.5 mg, yield: 14.3%) as a light yellow solid. ESI-MS [M+H]⁺: 509.9. Purity: 95.1 (214 nm), 96.6 (254 nm). ¹H NMR (400 MHz, DMSO-d₆) δ 9.63 (t, J=5.5 Hz, 1H), 8.46 (d, J=2.4 Hz, 1H), 8.33 (s, 1H), 8.15 (d, J=7.3 Hz, 1H), 7.79 (s, 1H), 7.38 (d, J=9.3 Hz, 1H), 6.98 (dd, J=9.3, 1.8 Hz, 1H), 6.83 (dd, J=7.3, 6.1 Hz, 1H), 4.69 (d, J=5.5 Hz, 2H), 4.43 (s, 2H), 1.98-1.85 (m, 1H), 1.00-0.84 (m, 2H), 0.74-0.61 (m, 2H).

Example 137

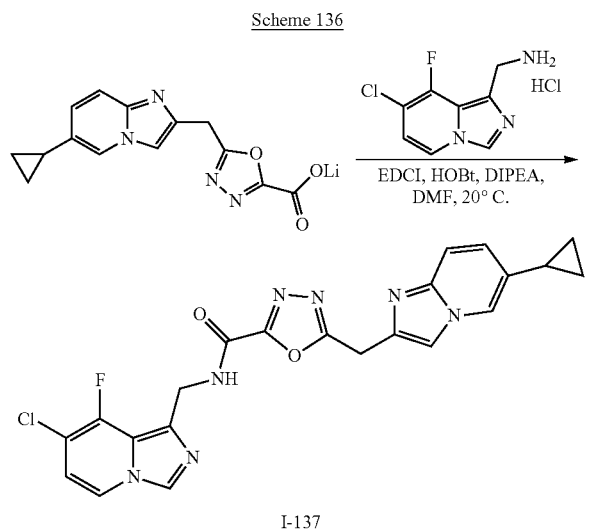

I-137

Synthesis of N-((7-bromo-8-fluoroimidazo[1,5-a]pyridin-1-yl)methyl)-5-((6-cyclopropylimidazo[1,2-a]pyridin-2-yl)methyl)-1,3,4-oxadiazole-2-carboxamide (I-137)

A mixture of lithium 5-((6-cyclopropylimidazo[1,2-a]pyridin-2-yl)methyl)-1,3,4-oxadiazole-2-carboxylate (100.0 mg, 0.35 mmol), (7-chloro-8-fluoroimidazo[1,5-a]pyridin-1-yl)methanamine hydrochloride (82.3 mg, 0.35 mmol), EDCI (134.4 mg, 0.70 mmol), HOBT (94.5 mg, 0.70 mmol) and DIPEA (0.18 mL, 1.05 mmol) in DMF (5 mL) was stirred at 20° C. for 48 h. The mixture was concentrated to remove DMF, diluted with DCM/MeOH (300 mL, 10/1 (v/v)) and washed with H$_2$O (100 mL). The organic layer was separated, dried over Na$_2$SO$_4$, and concentrated in vacuo to give the crude product, which was purified by Prep-HPLC to give N-((7-chloro-8-fluoroimidazo[1,5-a]pyridin-1-yl)methyl)-5-((6-cyclopropylimidazo[1,2-a]pyridin-2-yl)methyl)-1,3,4-oxadiazole-2-carboxamide (30.0 mg, yield: 18.4%) as a white solid. ESI-MS [M+H]$^+$: 466.2. Purity: 97.6 (214 nm), 99.1 (254 nm). $^1$H NMR (400 MHz, DMSO-d$_6$) δ 9.63 (t, J=5.4 Hz, 1H), 8.45 (d, J=2.4 Hz, 1H), 8.33 (s, 1H), 8.22 (d, J=7.4 Hz, 1H), 8.15 (s, 1H), 7.80 (s, 1H), 7.38 (d, J=9.3 Hz, 1H), 6.98 (dd, J=9.3, 1.7 Hz, 1H), 6.84-6.70 (m, 1H), 4.69 (d, J=5.5 Hz, 2H), 4.43 (s, 2H), 1.93-1.87 (m, 1H), 1.01-0.85 (m, 2H), 0.75-0.55 (m, 2H).

Example 138

Scheme 137

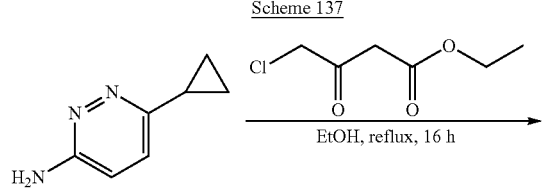

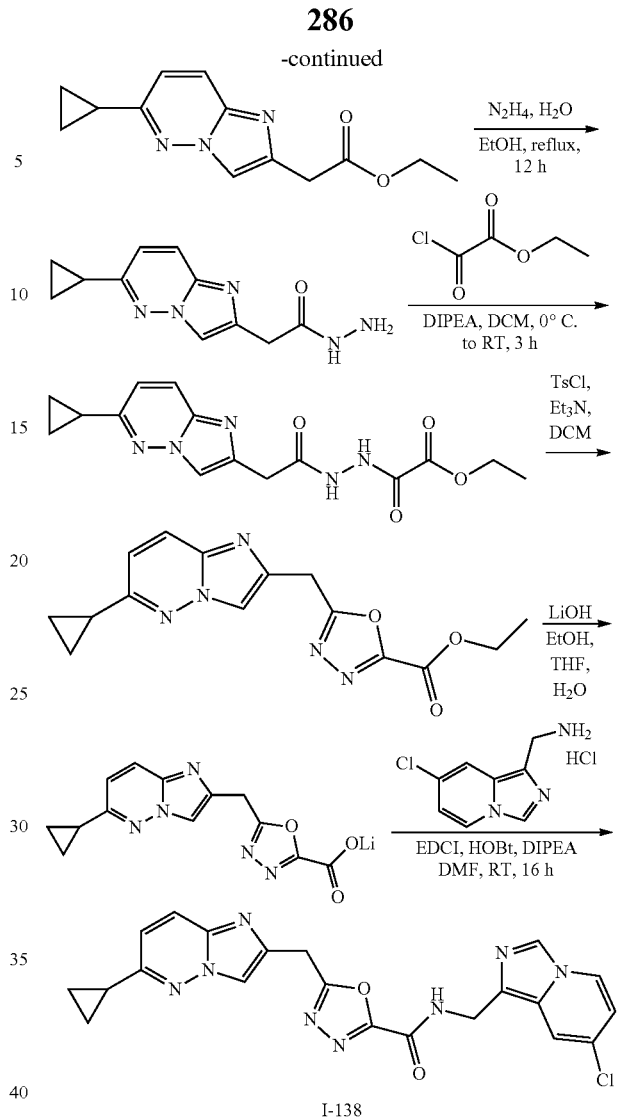

I-138

Synthesis of Ethyl 2-(6-cyclopropylimidazo[1,2-b]pyridazin-2-yl)acetate

A mixture of 6-cyclopropylpyridazin-3-amine (1.00 g, 7.40 mmol) in EtOH (10 mL) was added ethyl 4-chloro-3-oxobutanoate (3.65 g, 22.19 mmol) at RT. Then the mixture was heated to 80° C. and stirred for 16 h. The mixture was concentrated and purified by flash silica gel chromatography (0~10% MeOH in DCM) to give ethyl 2-(6-cyclopropylimidazo[1,2-b]pyridazin-2-yl)acetate (1.1 g, crude) as dark-red oil. ESI-MS [M+H]$^+$: 246.2.

Synthesis of 2-(6-cyclopropylimidazo[1,2-b]pyridazin-2-yl)acetohydrazide

To a solution of ethyl 2-(6-cyclopropylimidazo[1,2-b]pyridazin-2-yl)acetate (1.00 g, crude from last step) in EtOH (10 mL) was added hydrazine hydrate (1 mL) at RT. The mixture was heated to 80° C. and stirred for 12 h. The mixture were concentrated and purified by flash silica gel chromatography (0~100% EtOAc in PE) to give 2-(6-cyclopropylimidazo[1,2-b]pyridazin-2-yl)acetohydrazide (480 mg, 29% over 2 steps) as a red solid. ESI-MS [M+H]$^+$: 232.1.

Synthesis of Ethyl 2-(2-(2-(6-cyclopropylimidazo[1,2-b]pyridazin-2-yl)acetyl)hydrazinyl)-2-oxoacetate To a solution of 2-(6-cyclopropylimidazo[1,2-b]pyridazin-2-yl)acetohydrazide (477 mg, 2.06 mmol) in DCM (10 mL) was added DIPEA (533.18 mg, 4.13 mmol) and ethyl 2-chloro-2-oxoacetate (422.4 mg, 3.09 mmol) at 0° C. The mixture was stirred at 0° C. for 3 h. The mixture were concentrated and purified by flash silica gel chromatography (0~10% MeOH in DCM) to give ethyl 2-(2-(2-(6-cyclopropylimidazo[1,2-b]pyridazin-2-yl)acetyl)hydrazinyl)-2-oxoacetate (450 mg, yield: 65%) as a yellow solid. ESI-MS [M+H]$^+$: 332.2.

Synthesis of Ethyl 5-((6-cyclopropylimidazo[1,2-b]pyridazin-2-yl)methyl)-1,3,4-oxadiazole-2-carboxylate To a solution of ethyl 2-(2-(2-(6-cyclopropylimidazo[1,2-b]pyridazin-2-yl)acetyl)hydrazinyl)-2-oxoacetate (450 mg, 1.36 mmol) in DCM (10 mL) was added TsCl (258 mg, 1.36 mmol), Et$_3$N (274 mg, 2.72 mmol) at RT. The mixture was stirred for 2 h. Water (20 mL) was added and extracted with EtOAc (30 mL×3). The combined organic layers were concentrated and purified by flash silica gel chromatography (0~100% EtOAc in PE) to give ethyl 5-((6-cyclopropylimidazo[1,2-b]pyridazin-2-yl)methy)-1,3,4-oxadiazole-2-carboxylate (240 mg, yield: 56%) as a white solid. ESI-MS [M+H]$^+$: 314.2.

Synthesis of lithium 5-((6-cyclopropylimidazo[1,2-b]pyridazin-2-yl)methyl)-1,3,4-oxadiazole-2-carboxylate To a solution of ethyl 5-((6-cyclopropylimidazo[1,2-b]pyridazin-2-yl)methyl)-1,3,4-oxadiazole-2-carboxylate (40 mg, 0.128 mmol) in EtOH/THF/H$_2$O (1 mL/1 mL/1 mL) was added LiOH H$_2$O (10 mg, 0.255 mmol) at RT. The mixture was heated to 40° C. stirred for 0.5 h. The mixture was freeze-dried to give lithium 5-((6-cyclopropylimidazo[1,2-b]pyridazin-2-yl)methyl)-1,3,4-oxadiazole-2-carboxylate (50 mg, crude) as a pink solid. ESI-MS [M+H]$^+$: 286.1.

Synthesis of N-((7-chloroimidazo[1,5-a]pyridin-1-yl)methyl)-5-((6-cyclopropylimidazo[1,2-b]pyridazin-2-yl)methyl)-1,3,4-oxadiazole-2-carboxamide (I-138)

To a solution of lithium 5-((6-cyclopropylimidazo[1,2-b]pyridazin-2-yl)methyl)-1,3,4-oxadiazole-2-carboxylate (50 mg, crude from last step) in DMF (3 mL) was added EDCI (58 mg, 0.3 mmol), HOBT (40 mg, 0.2 mmol), DIPEA (65 mg, 0.5 mmol) and (7-chloroimidazo[1,5-a]pyridin-1-yl)methanamine hydrochloride (54 mg, 0.25 mmol) at RT. The mixture was stirred for 16 h. The mixture was concentrated and purified by Prep-HPLC to give N-((7-chloroimidazo[1,5-a]pyridin-1-yl)methyl)-5-((6-cyclopropylimidazo[1,2-b]pyridazin-2-yl)methyl)-1,3,4-oxadiazole-2-carboxamide (3 mg, yield: 5%) as a white solid. ESI-MS [M+H]$^+$: 449.0. Purity: 98.12 (214 nm), 97.17 (254 nm). $^1$H NMR (400 MHz, DMSO-d$_6$) δ 9.73 (t, J=5.8 Hz, 1H), 8.31-8.33 (m, 2H), 8.14 (s, 1H), 7.91 (d, J=9.6 Hz, 1H), 7.84-7.82 (m, 1H), 7.08 (d, J=9.4 Hz, 1H), 6.69-6.65 (m, 1H), 4.62 (d, J=5.9 Hz, 2H), 4.47 (s, 2H), 2.13-2.23 (m, 1H), 1.09-1.03 (m, 2H), 0.99-0.93 (m, 2H).

Example 139

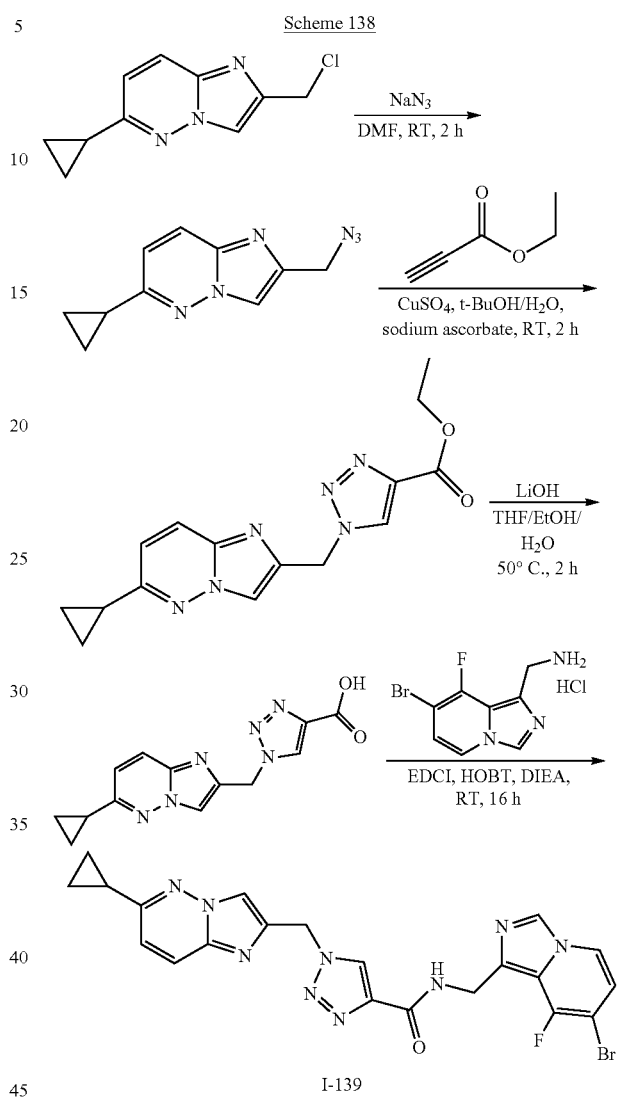

Scheme 138

I-139

Synthesis of 2-(azidomethyl)-6-cyclopropylimidazo[1,2-b]pyridazine

A mixture of 2-(chloromethyl)-6-cyclopropylimidazo[1,2-b]pyridazine (900 mg, 4.33 mmol) in dry DMF (5 mL) was added NaN$_3$ (631 mg, 9.71 mmol) at RT. After the mixture was stirred for 2 h, H$_2$O (50 mL) was added and the mixture was extracted with EtOAc (50 mL×3). The combined organic layers were concentrated and purified by flash silica gel chromatography (0-40% EtOAc in PE) to give 2-(azidomethyl)-6-cyclopropylimidazo[1,2-b]pyridazine (735 mg, yield: 79.16%) as dark-red oil. ESI-MS [M+H]$^+$: 215.2

Synthesis of Ethyl 1-((6-cyclopropylimidazo[1,2-b]pyridazin-2-yl)methyl)-1H-1,2,3-triazole-4-carboxylate To a solution of 2-(azidomethyl)-6-cyclopropylimidazo[1,2-b]pyridazine (730 mg, 3.4 mmol) and ethyl propiolate (501.42 mg, 5.11 mmol) in t-BuOH/H₂O (5 mL/5 mL) was added CuSO₄ (543 mg, 3.4 mmol) and sodium ascorbate (675 mg, 3.41 mmol) at RT. After the mixture was stirred for 2 h, it was concentrated and purified by flash silica gel chromatography (0~10% EtOAc in PE) to give ethyl 1-((6-cyclopropylimidazo[1,2-b]pyridazin-2-yl)methyl)-1H-1,2,3-triazole-4-carboxylate (600 mg, yield: 56%) as a red solid. ESI-MS [M+H]⁺: 313.2.

Synthesis of 1-((6-cyclopropylimidazo[1,2-b]pyridazin-2-yl)methyl)-1H-1,2,3-triazole-4-carboxylic Acid To a solution of ethyl 1-((6-cyclopropylimidazo[1,2-b]pyridazin-2-yl)methyl)-1H-1,2,3-triazole-4-carboxylate (100 mg, 0.32 mmol) in THF/EtOH/H₂O (0.2 mL/0.2 mL/0.2 mL) was added LiOH (15.33 mg, 0.64 mL). The mixture was heated to 50° C. for 2 h. pH of the mixture was adjust to 5 by adding HCl (2 M), and then the mixture was freeze-dried to give 1-((6-cyclopropylimidazo[1,2-b]pyridazin-2-yl)methyl)-1H-1,2,3-triazole-4-carboxylic acid (110 mg, crude) as a white solid. ESI-MS [M+H]⁺: 285.1.

Synthesis of N-((7-bromo-8-fluoroimidazo[1,5-a]pyridin-1-yl)methyl)-1-((6-cyclopropylimidazo[1,2-b]pyridazin-2-yl)methyl)-1H-1,2,3-triazole-4-carboxamide (I-139)

To a solution of 1-((6-cyclopropylimidazo[1,2-b]pyridazin-2-yl)methyl)-1H-1,2,3-triazole-4-carboxylic acid (110 mg, crude from last step) in DMF (5 mL) was added EDCI (101 mg, 0.53 mmol), HOBT (71 mg, 0.53 mmol), DIPEA (227 mg, 1.76 mmol) and (7-bromo-8-fluoroimidazo[1,5-a]pyridin-1-yl)methanamine hydrochloride (99 mg, 0.35 mmol) at RT. After the mixture was stirred for 16 h, the reaction was poured into H₂O, the precipitate was filtered and washed by MeOH to give N-((7-bromo-8-fluoroimidazo[1,5-a]pyridin-1-yl)methyl)-1-((6-cyclopropylimidazo[1,2-b]pyridazin-2-yl)methyl)-1H-1,2,3-triazole-4-carboxamide (25.8 mg, yield: 15%) as a white solid. ESI-MS [M+H]⁺: 510.0. Purity: 97.38 (214 nm), 93.35 (254 nm). ¹H NMR (400 MHz, DMSO-d₆) δ 8.69 (t, J=5.3 Hz, 1H), 8.56 (s, 1H), 8.45 (d, J=2.2 Hz, 1H), 8.20 (s, 1H), 8.14 (d, J=7.3 Hz, 1H), 7.94 (d, J=9.5 Hz, 1H), 7.11 (d, J=9.5 Hz, 1H), 6.85-6.77 (m, 1H), 5.75 (s, 2H), 4.69 (d, J=5.5 Hz, 2H), 2.23-2.13 (m, 1H), 1.10-1.02 (m, 2H), 1.00-0.93 (m, 2H).

Example 140

Synthesis of N-((7-bromo-8-fluoroimidazo[1,5-a]pyridin-1-yl)methyl)-5-((6-cyclopropylimidazo[1,2-b]pyridazin-2-yl)methyl)-1,3,4-oxadiazole-2-carboxamide (I-140)

To a solution of lithium 5-((6-cyclopropylimidazo[1,2-b]pyridazin-2-yl)methyl)-1,3,4-oxadiazole-2-carboxylate (50 mg, crude) in DMF (3 mL) was added EDCI (58 mg, 0.3 mmol), HOBT (40 mg, 0.3 mmol), DIPEA (65 mg, 0.5 mmol) and (7-bromo-8-fluoroimidazo[1,5-a]pyridin-1-yl)methanamine hydrochloride (70 mg, 0.25 mmol) at RT. The mixture was stirred for 16 h. The mixture was concentrated and purified by Prep-HPLC to give N-((7-bromo-8-fluoroimidazo[1,5-a]pyridin-1-yl)methyl)-5-((6-cyclopropylimidazo[1,2-b]pyridazin-2-yl)methyl)-1,3,4-oxadiazole-2-carboxamide (5 mg) as a yellow solid. ESI-MS [M+H]⁺: 511.0. Purity: 95.73 (214 nm), 96.89 (254 nm). ¹H NMR (400 MHz, DMSO-d₆) δ 9.63 (t, J=5.4 Hz, 1H), 8.46 (d, J=2.4 Hz, 1H), 8.15 (d, J=7.4 Hz, 2H), 7.91 (d, J=9.4 Hz, 1H), 7.09 (d, J=9.4 Hz, 1H), 6.83 (dd, J=7.3, 6.1 Hz, 1H), 4.69 (d, J=5.5 Hz, 2H), 4.47 (s, 2H), 2.21-2.14 (m, 1H), 1.12-1.02 (m, 2H), 1.01-0.92 (m, 2H).

Example 141

Scheme 139

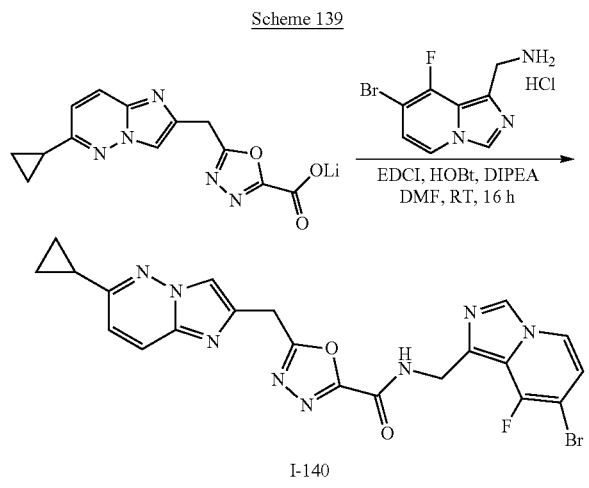

I-140

Scheme 140

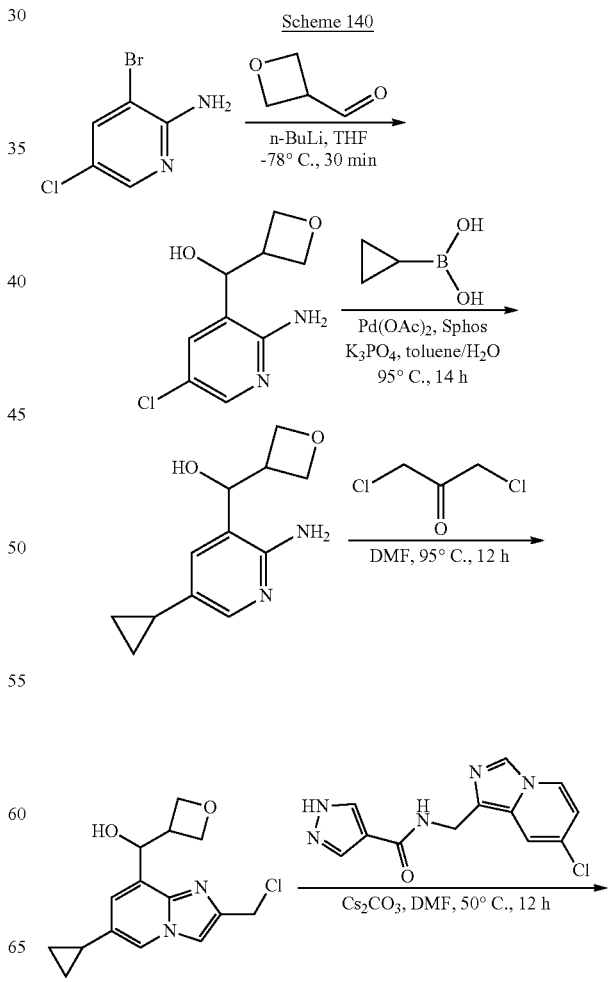

-continued

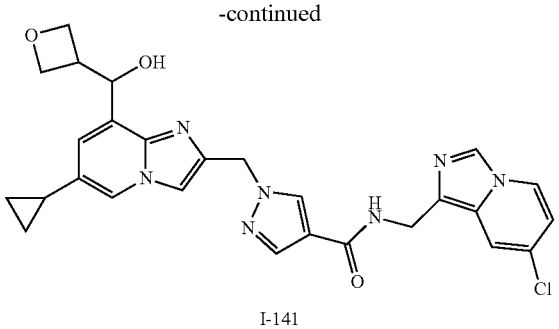

I-141

Synthesis of (2-amino-5-chloropyridin-3-yl)(oxetan-3-yl)methanol

To a solution of 3-bromo-5-chloropyridin-2-amine (800 mg, 3.86 mmol) in THF (20 mL) was added n-BuLi (6.4 mL, 15.5 mmol, 2.4 M solution in hexane) at −78° C. and stirred for 10 min. Then a solution of oxetane-3-carbaldehyde (1.3 g, 15.4 mmol) in 5 mL THF was added. The resulting reaction was stirred at −78° C. for 5 min. The reaction was quenched with aqueous NH$_4$Cl (20 mL), extracted with EtOAc (50 mL×3). The combined organic layers were washed with brine, dried over Na$_2$SO$_4$, concentrated in vacuo to give the crude product, which was purified with silica gel chromatography (DCM/MeOH=10/1) to give the (2-amino-5-chloropyridin-3-yl)(oxetan-3-yl)methanol (400 mg, yield: 48%) as a yellow solid. ESI-MS [M+H]$^+$: 215.2.

Synthesis of (2-amino-5-cyclopropylpyridin-3-yl)(oxetan-3-yl)methanol

A mixture of (2-amino-5-chloropyridin-3-yl)(oxetan-3-yl)methanol (400 mg, 1.87 mmol), cyclopropylboronic acid (209 mg, 2.43 mmol), Pd(OAc)$_2$ (42 mg, 0.187 mmol), SPhos (165 mg, 0.374 mmol) and K3PO4 (1.2 g, 5.61 mmol) in toluene/H$_2$O (25 mL/2.5 mL) was stirred at 95° C. for 14 h. The reaction mixture was filtered, and the filtrate was concentrated in vacuo to give the crude product, which was purified with silica gel chromatography (DCM/MeOH=10/1) to give the (2-amino-5-cyclopropylpyridin-3-yl)(oxetan-3-yl)methanol (250 mg, yield: 60.8%) as a yellow solid. ESI-MS [M+H]$^+$: 221.2.

Synthesis of (2-(chloromethyl)-6-cyclopropylimidazo[1,2-a]pyridin-8-yl)(oxetan-3-yl)methanol A mixture of (2-amino-5-cyclopropylpyridin-3-yl)(oxetan-3-yl)methanol (250 mg, 1.13 mmol) and 1,3-dichloropropan-2-one (572 mg, 4.5 mmol) in DMF (10 mL) was stirred at 95° C. for 12 h. H$_2$O (30 mL) was added to the reaction, extracted with EtOAc (30 mL×2). The aqueous layer was free-dried to give the (2-(chloromethyl)-6-cyclopropylimidazo[1,2-a]pyridin-8-yl)(oxetan-3-yl)methanol (200 mg crude), which was used into next step without further purification. ESI-MS [M+H]$^+$: 293.2

Synthesis of N-((7-chloroimidazo[1,5-a]pyridin-1-yl)methyl)-1-((6-cyclopropyl-8-(hydroxy(oxetan-3-yl)methyl)imidazo[1,2-a]pyridin-2-yl)methyl)-1H-pyrazole-4-carboxamide (I-141)

A mixture of (2-(chloromethyl)-6-cyclopropylimidazo[1,2-a]pyridin-8-yl)(oxetan-3-yl)methanol (100 mg, crude from last step), N-((7-chloroimidazo[1,5-a]pyridin-1-yl)methyl)-1H-pyrazole-4-carboxamide (94 mg, 0.34 mmol) and Cs$_2$CO$_3$ (332 mg, 1.02 mmol) in DMF (10 mL) was stirred at 50° C. for 12 h. H$_2$O (30 mL) was added to the reaction, extracted with EtOAc (40 mL×3). The combined organic layers were washed with brine, dried over Na$_2$SO$_4$, concentrated in vacuo to give the crude product, which was purified with Prep-HPLC to give the N-((7-chloroimidazo[1,5-a]pyridin-1-yl)methyl)-1-((6-cyclopropyl-8-(hydroxy(oxetan-3-yl)methyl)imidazo[1,2-a]pyridin-2-yl)methyl)-1H-pyrazole-4-carboxamide (22 mg, yield: 12%) as a white solid. ESI-MS [M+H]$^+$: 531.9. Purity: 97.2 (214 nm), 95.9 (254 nm). $^1$H NMR (400 MHz, DMSO-d$_6$) δ 8.75-8.68 (m, 1H), 8.64-8.59 (m, 1H), 8.53-8.30 (m, 3H), 8.22-8.18 (m, 1H), 7.99 (s, 1H), 7.79 (s, 1H), 7.63 (d, J=6.3 Hz, 1H), 6.67-6.63 (m, 1H), 5.83-5.76 (m, 2H), 5.02-4.98 (m, 0.5H), 4.88-4.86 (m, 0.5H), 4.61-4.46 (m, 3H), 4.13-4.07 (m, 1H), 3.91-3.82 (m, 1H), 3.76-3.69 (m, 1H), 3.64-3.58 (m, 1H), 3.54-3.44 (m, 1H), 2.14-2.08 (m, 1H), 1.08-1.04 (m, 2H), 0.78-0.75 (m, 2H).

Example 142

Scheme 141

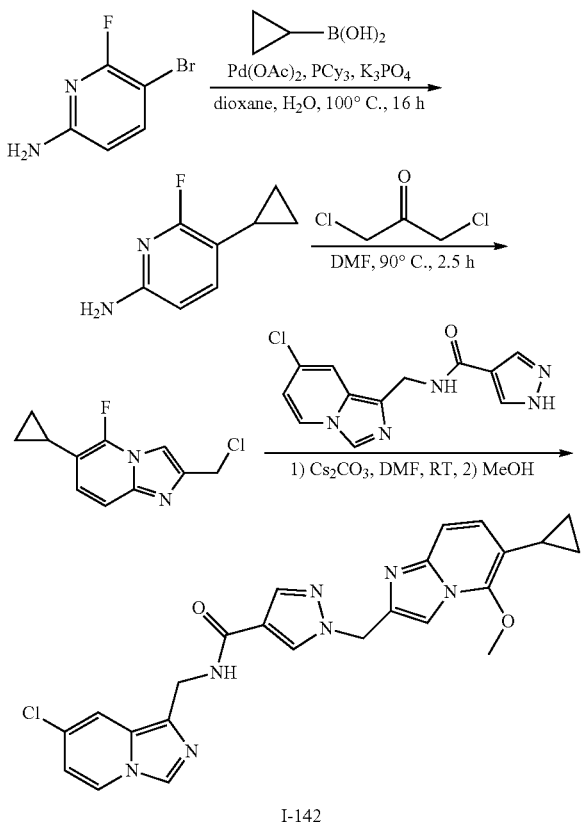

I-142

Synthesis of 5-cyclopropyl-6-fluoropyridin-2-amine

To a solution of 5-bromo-6-fluoropyridin-2-amine (40 g, 209 mmol) in dioxane/H$_2$O (400 mL/40 mL) was added cyclopropylboronic acid (36 g, 418 mmol), Pd(OAc)$_2$ (4.7 g, 21 mmol), PCy$_3$ (11.75 g, 42 mmol) and K$_3$PO$_4$ (133 g, 628 mmol), then the mixture was stirred at 100° C. for 16 h. The mixture was treated with H₂O (100 mL) and extracted with EtOAc (300 mL×3). The organic layers were concentrated to give the crude product, which was purified by flash silica gel chromatography (PE/EA=2/1) to give 5-cyclopropyl-6-fluoropyridin-2-amine (26 g, yield: 81%) as a white solid. ESI-MS [M+H]⁺: 153.1.

Synthesis of 2-(chloromethyl)-6-cyclopropyl-5-fluoroimidazo[1,2-a]pyridine

To a solution of 5-cyclopropyl-6-fluoropyridin-2-amine (30 g, 197 mmol) in EtOAc (50 mL) was added 1,3-dichloropropan-2-one (32.54 g, 256 mmol), then the mixture was stirred at 60° C. for 16 h. The mixture was treated with NaHCO₃ (aqueous) to adjust pH to 8 and then extracted with Ethyl Acetate. The organic layer was concentrated to give the crude product which was purified by flash silica gel chromatography (PE/EA=3:1) to give 2-(chloromethyl)-6-cyclopropyl-5-fluoroimidazo[1,2-a]pyridine (12.5 g, yield: 28%) as a white solid. ESI-MS [M+H]⁺: 224.9.

Synthesis of N-((7-chloroimidazo[1,5-a]pyridin-1-yl)methyl)-1-((6-cyclopropyl-5-methoxyimidazo[1,2-a]pyridin-2-yl)methyl)-1H-pyrazole-4-carboxamide To a solution of 2-(chloromethyl)-6-cyclopropyl-5-fluoroimidazo[1,2-a]pyridine (1.94 g, 8.64 mmol) in DMF (200 mL) at RT was added N-((7-chloroimidazo[1,5-a]pyridin-1-yl)methyl)-1H-pyrazole-4-carboxamide (2.38 g, 8.64 mmol) and Cs₂CO₃ (8.44 g, 25.9 mmol). The reaction mixture was stirred at RT for 16 h. The mixture was concentrated to remove DMF, diluted with MeOH (200 mL) and stirred at 60° C. for 4 h and then removed MeOH, diluted with EtOAc (200 mL), washed with H₂O (200 mL). The organic layer was separated, dried over Na₂SO₄, and concentrated in vacuo to give the crude product, which was purified by silica gel chromatography (DCM/MeOH=20:1 to 10:1) to give N-((7-chloroimidazo[1,5-a]pyridin-1-yl)methyl)-1-((6-cyclopropyl-5-methoxyimidazo[1,2-a]pyridin-2-yl)methyl)-1H-pyrazole-4-carboxamide (3.5 g, yield: 85%) as a gray solid. ESI-MS [M+H]⁺: 476.1. Purity: 97.35 (214 nm), 93.50 (254 nm). ¹H NMR (400 MHz, CDCl₃) S=8.0 (s, 2H), 7.82 (s, 1H), 7.78 (d, J=8.0 Hz, 1H), 7.66 (s, 1H), 7.52 (s, 1H), 7.26 (d, J=8.0 Hz, 1H), 6.84 (d, J=8.0 Hz 1H), 6.63 (t, J=4.0 Hz 1H), 6.50 (dd, J=7.2, 2.0 Hz, 1H), 5.45 (s, 2H), 4.74 (d, J=5.6, 2H), 4.08 (s, 3H), 2.10-2.02 (m, 1H), 1.04-0.98 (m, 2H), 0.74-0.69 (m, 2H).

Example 143

Scheme 142

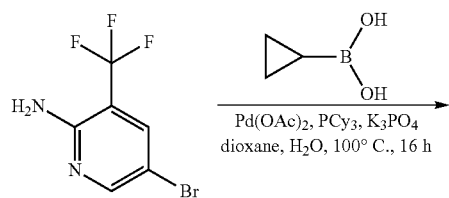

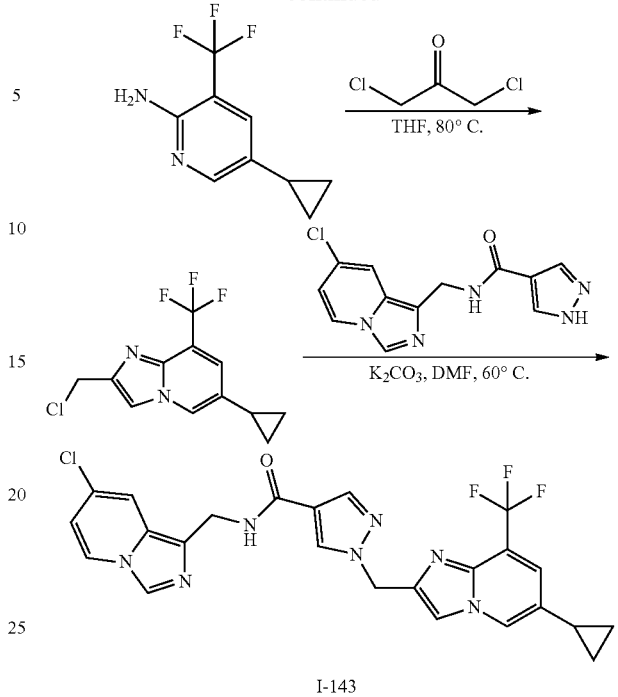

I-143

Synthesis of 5-cyclopropyl-3-(trifluoromethyl)pyridin-2-amine

To a solution of 5-bromo-3-(trifluoromethyl)pyridin-2-amine (2 g, 7.2 mmol) in dioxane/H₂O (100 mL/10 mL) was added cyclopropylboronic acid (1.425 g, 16.6 mmol), Pd(OAc)₂ (186 mg, 0.83 mmol), PCy₃ (465 mg, 1.66 mmol) and K₃PO₄ (3.523 g, 16.6 mmol). The reaction mixture was stirred at 100° C. for 14 h under nitrogen. Then the mixture was concentrated in vacuo. Water (100 mL) was added and the mixture was extracted with EtOAc (100 mL×3). The combined organic layers were concentrated to give the crude product, which was purified by silica gel chromatography (PE/EtOAc=10/1) to give the 5-cyclopropyl-3-(trifluoromethyl)pyridin-2-amine as a yellow solid (708 mg, yield: 48%). ESI-MS [M+H]⁺: 203.1.

Synthesis of 2-(chloromethyl)-6-cyclopropyl-8-(trifluoromethyl)imidazo[1,2-a]pyridine To a solution of 5-cyclopropyl-3-(trifluoromethyl)pyridin-2-amine (634 mg, 3.14 mmol) and 1,3-dichloropropan-2-one (1.194 g, 9.41 mmol) in THF (30 mL). The reaction mixture was stirred at 80° C. overnight. Then H₂O (50 mL) was added and extracted with EtOAc (50 mL×3). The combined organic layers were concentrated to give the crude product, which was purified by silica gel chromatography (PE/EtOAc=10/1) to give 2-(chloromethyl)-6-cyclopropyl-8-(trifluoromethyl)imidazo[1,2-a]pyridine (232 mg, yield: 27%) as a white solid. ESI-MS [M+H]⁺: 275.0.

Synthesis of N-((7-chloroimidazo[1,5-a]pyridin-1-yl)methyl)-1-((6-cyclopropyl-5-(trifluoromethyl)imidazo[1,2-a]pyridin-2-yl)methyl)-1H-pyrazole-4-carboxamide (I-143)

To a solution of 2-(chloromethyl)-6-cyclopropyl-8-(trifluoromethyl)imidazo[1,2-a]pyridine (126 mg, 0.45 mmol), N-((7-chloroimidazo[1,5-a]pyridin-1-yl)methyl)-1H-pyrazole-4-carboxamide (126 mg, 0.45 mmol) and K$_2$CO$_3$ (127 mg, 0.917 mmol) in DMF (10 mL). The resulting mixture was stirred overnight at 60° C. The mixture was concentrated to give the crude product, which was purified by silica gel chromatography (DCM/MeOH=20/1) to give N-((7-chloroimidazo[1,5-a]pyridin-1-yl)methyl)-1-((6-cyclopropyl-8-(trifluoromethyl)imidazo[1,2-a]pyridin-2-yl)methyl)-1H-pyrazole-4-carboxamide (58 mg, yield: 25%) as a white solid. ESI-MS [M+H]$^+$: 514.1. Purity: 95.44 (214 nm), 95.85 (254 nm). $^1$H NMR (400 MHz, MOD) δ 8.42 (s, 1H), 8.28 (s, 1H), 8.19 (s, 1H), 8.18 (d, J=0.9 Hz, 1H), 7.95 (s, 1H), 7.78 (s, 1H), 7.76 (s, 1H), 7.51 (s, 1H), 6.65 (dd, J=7.5, 2.0 Hz, 1H), 5.51 (s, 2H), 4.71 (s, 2H), 2.07-1.98 (m, 1H), 1.01-0.97 (m, 2H), 0.75-0.72 (m, 2H).

Example 144

Scheme 143

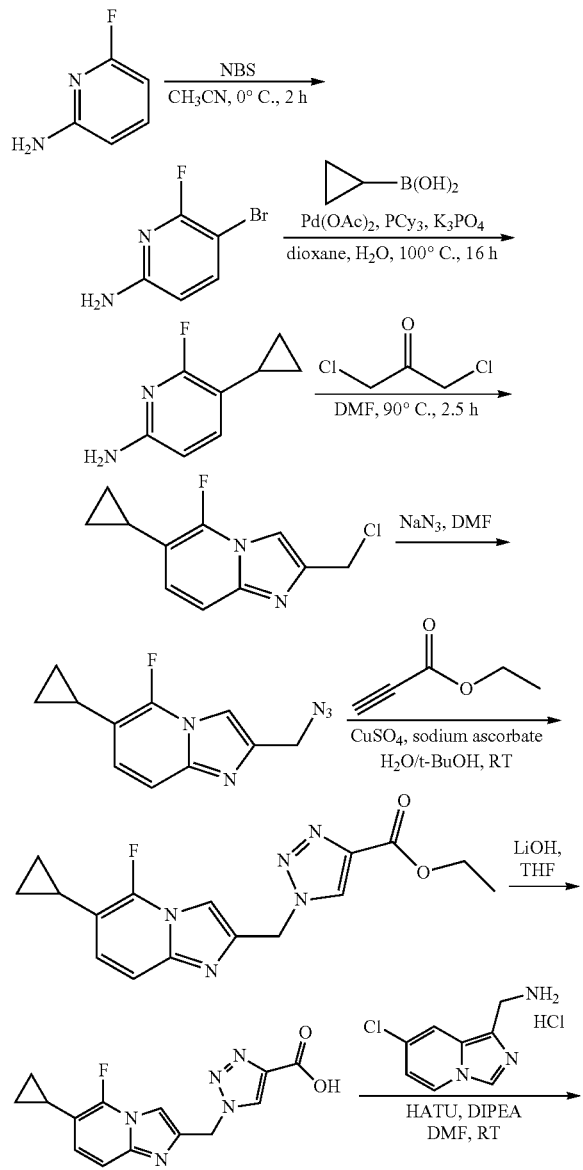

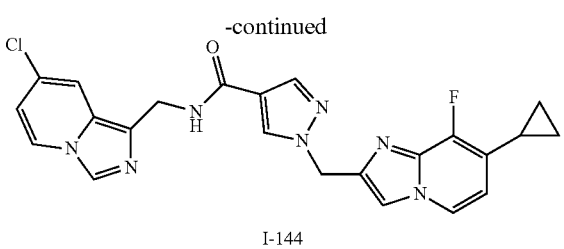

I-144

Synthesis of 5-cyclopropyl-6-fluoropyridin-2-amine

To a solution of 5-bromo-6-fluoropyridin-2-amine (40 g, 209 mmol) in dioxane/H$_2$O (400 mL/40 mL) was added cyclopropylboronic acid (36 g, 418 mmol), Pd(OAc)$_2$ (4.7 g, 21 mmol), PCy$_3$ (11.75 g, 42 mmol) and K$_3$PO$_4$ (133 g, 628 mmol), then the mixture was stirred at 100° C. for 16 h. The mixture was treated with H$_2$O (100 mL) and extracted with EtOAc (300 mL×3). The organic layers were concentrated to give the crude product, which was purified by flash silica gel chromatography (PE/EA=2/1) to give 5-cyclopropyl-6-fluoropyridin-2-amine (26 g, yield: 81%) as a white solid. ESI-MS [M+H]$^+$: 153.1.

Synthesis of 2-(chloromethyl)-6-cyclopropyl-5-fluoroimidazo[1,2-a]pyridine

To a solution of 5-cyclopropyl-6-fluoropyridin-2-amine (30 g, 197 mmol) in EtOAc (50 mL) was added 1,3-dichloropropan-2-one (32.54 g, 256 mmol), then the mixture was stirred at 60° C. for 16 h. The mixture was treated with NaHCO$_3$ (aqueous) to adjust pH to 8 and then extracted with Ethyl Acetate. The organic layer was concentrated to give the crude product which was purified by flash silica gel chromatography (PE/EA=3:1) to give 2-(chloromethyl)-6-cyclopropyl-5-fluoroimidazo[1,2-a]pyridine (12.5 g, yield: 28%) as a white solid. ESI-MS [M+H]$^+$: 224.9.

Synthesis of 2-(azidomethyl)-6-cyclopropyl-5-fluoroimidazo[1,2-a]pyridine

To a solution of 2-(chloromethyl)-6-cyclopropyl-5-fluoroimidazo[1,2-a]pyridine (200 mg, 0.89 mmol) in DMF (3 mL) was added NaN$_3$ (58 mg, 0.89 mmol), then the mixture was stirred at RT for 5 h. Water (30 mL) was added and extracted with EtOAc (50 mL×3). The combined organic layers were washed with brine, dried over Na$_2$SO$_4$, filtered and concentrated to give 2-(azidomethyl)-6-cyclopropyl-5-fluoroimidazo[1,2-a]pyridine (220 mg, crude) as a white solid that was used directly in the next step. ESI-MS [M+H]$^+$: 232.1.

Synthesis of Ethyl 1-((6-cyclopropyl-5-fluoroimidazo[1,2-a]pyridin-2-yl)methyl)-1H-1,2,3-triazole-4-carboxylate To a solution of 2-(azidomethyl)-6-cyclopropyl-5-fluoroimidazo[1,2-a]pyridine (220 mg, crude) in t-BuOH/H$_2$O (5 mL/5 mL) was added ethyl propiolate (186 mg, 1.9 mmol), CuSO$_4$ (30 mg, 0.19 mmol) and sodium ascorbate (56 mg, 0.28 mmol), then the mixture was stirred at RT for 0.5 h. The reaction mixture showed product precipitated which was filtered and washed with H$_2$O (10 mL) and methanol (10 mL) to give ethyl 1-((6-cyclopropyl-5-fluoroimidazo[1,2-a]

pyridin-2-yl)methyl)-1H-1,2,3-triazole-4-carboxylate (250 mg, yield: 85%) as a white solid. ESI-MS [M+H]$^+$: 330.1.

Synthesis of 1-((6-cyclopropyl-5-fluoroimidazo[1,2-a]pyridin-2-yl)methyl)-1H-1,2,3-triazole-4-carboxylic Acid To a solution of ethyl 1-((6-cyclopropyl-5-fluoroimidazo[1,2-a]pyridin-2-yl)methyl)-1H-1,2,3-triazole-4-carboxylate (250 mg, 0.75 mmol) in THF/H$_2$O (6 mL/3 mL) was added LiOH (42.03 mg, 1.76 mmol), then the mixture was stirred at RT overnight. The mixture was treated with HCl (aq) to adjust the pH to 4, the precipitate was filtered and washed with H$_2$O (10 mL) to give 1-((6-cyclopropyl-5-fluoroimidazo[1,2-a]pyridin-2-yl)methyl)-1H-1,2,3-triazole-4-carboxylic acid (120 mg, yield: 52%) as a white solid which was used into next step without further purification. ESI-MS [M+H]$^+$: 302.1.

Synthesis of N-((7-chloroimidazo[1,5-a]pyridin-1-yl)methyl)-1-((6-cyclopropyl-5-fluoroimidazo[1,2-a]pyridin-2-yl)methyl)-1H-1,2,3-triazole-4-carboxamide (I-144)

To a solution of 1-((6-cyclopropyl-5-fluoroimidazo[1,2-a]pyridin-2-yl)methyl)-1H-1,2,3-triazole-4-carboxylic acid (60 mg, 0.2 mmol) in DMF (2 mL) was added (7-chloroimidazo[1,5-a]pyridin-1-yl)methanamine hydrochloride (87 mg, 0.4 mmol), HATU (151 mg, 0.4 mmol) and DIPEA (154 mg, 1.19 mmol), then the mixture was stirred at RT for 0.5 h. The reaction mixture was poured into H$_2$O (15 mL), the solid formed, filtered and washed with H$_2$O and methanol to give N-((7-chloroimidazo[1,5-a]pyridin-1-yl)methyl)-1-((6-cyclopropyl-5-fluoroimidazo[1,2-a]pyridin-2-yl)methyl)-1H-1,2,3-triazole-4-carboxamide (53 mg, yield: 57%) as a white solid. ESI-MS [M+H]$^+$: 465.1. Purity: 98.44 (214 nm), 97.99 (254 nm). $^1$H NMR (400 MHz, DMSO-d$_6$) δ 8.93 (t, J=4.0 Hz, 1H), 8.58 (s, 1H), 8.30 (brs, 2H), 7.98 (s, 1H), 7.84 (s, 1H), 7.36 (t, J=4.0 Hz, 1H), 7.03 (t, J=4.0 Hz, 1H), 6.65 (q, J=4.0 Hz, 1H), 5.77 (s, 2H), 4.62 (d, J=8.0 Hz, 2H), 2.06-2.03 (m, 1H), 0.99-0.96 (m, 2H), 0.77-0.74 (m, 2H).

Example 145

Scheme 144

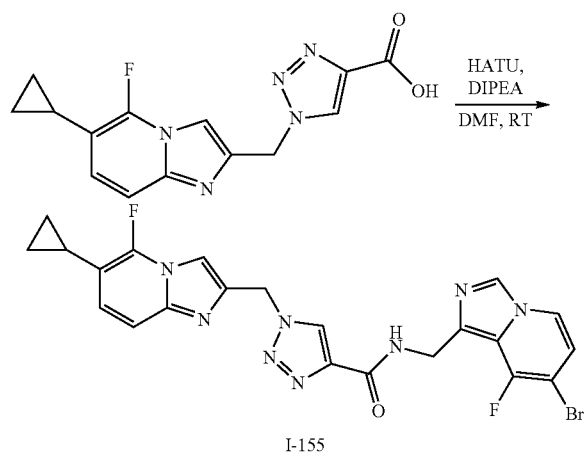

I-155

Synthesis of N-((7-bromo-8-fluoroimidazo[1,5-a]pyridin-1-yl)methyl)-1-((6-cyclopropyl-5-fluoroimidazo[1,2-a]pyridin-2-yl)methyl)-1H-1,2,3-triazole-4-carboxamide (I-145)

To a solution of 1-((6-cyclopropyl-5-fluoroimidazo[1,2-a]pyridin-2-yl)methyl)-1H-1,2,3-triazole-4-carboxylic acid (60 mg, 0.2 mmol) in DMF (2 mL) was added (7-bromo-8-fluoroimidazo[1,5-a]pyridin-1-yl)methanamine (97 mg, 0.4 mmol), HATU (151 mg, 0.4 mmol) and DIPEA (154 mg, 1.19 mmol), then the mixture was stirred at RT for 0.5 h. The mixture was filtrated to give N-((7-bromo-8-fluoroimidazo[1,5-a]pyridin-1-yl)methyl)-1-((6-cyclopropyl-5-fluoroimidazo[1,2-a]pyridin-2-yl)methyl)-1H-1,2,3-triazole-4-carboxamide (62 mg, yield: 59%) as a white solid. ESI-MS [M+H]$^+$: 527.0. Purity: 99.01 (214 nm), 98.76 (254 nm). $^1$H NMR (400 MHz, DMSO-d$_6$) δ 8.70 (t, J=4.0 Hz, 1H), 8.57 (s, 1H), 8.45 (d, J=4.0 Hz, 1H), 8.13 (d, J=4.0 Hz, 1H), 8.00 (s, 1H), 7.36 (d, J=4.0 Hz, 1H), 7.03 (t, J=4.0 Hz, 1H), 6.82 (t, J=8.0 Hz, 1H), 5.77 (s, 2H), 4.70 (d, J=4.0 Hz, 2H), 2.06-2.01 (m, 1H), 1.00-0.96 (m, 2H), 0.77-0.74 (m, 2H).

Example 146

Scheme 145

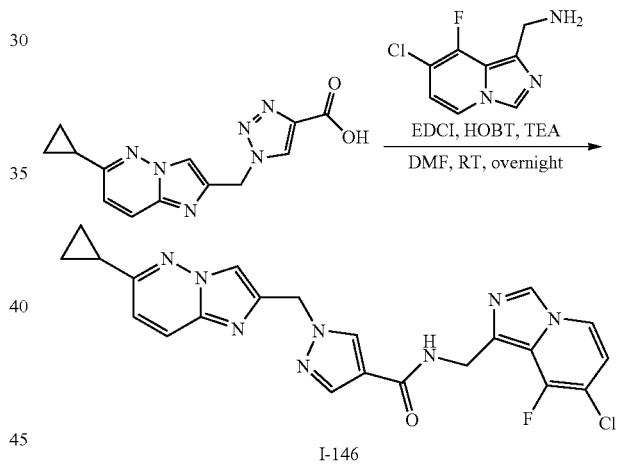

I-146

Synthesis of N-((7-chloro-8-fluoroimidazo[1,5-a]pyridin-1-yl)methyl)-1-((6-cyclopropylimidazo[1,2-b]pyridazin-2-yl)methyl)-1H-pyrazole-4-carboxamide (I-146)

A solution of 1-((6-cyclopropylimidazo[1,2-b]pyridazin-2-yl)methyl)-1H-pyrazole-4-carboxylic acid (105 mg, 0.37 mmol), (7-chloro-8-fluoroimidazo[1,5-a]pyridin-1-yl)methanamine hydrochloride (113 mg, 0.48 mmol), EDCI (86 mg, 0.45 mmol), HOBT (60 mg, 0.45 mmol) and TEA (112 mg, 1.1 mL, 0.15 mmol) in dry DMF (5 mL) was stirred at RT overnight. Then the reaction mixture was diluted with H$_2$O (30 mL) and extracted with EtOAC 50 mL×3). The combined organic layers were dried over Na$_2$SO$_4$, concentrated and purified by flash column chromatography (DCM: MeOH=10:1) to give the desired compound N-((7-chloro-8-fluoroimidazo[1,5-a]pyridin-1-yl)methyl)-1-((6-cyclopropylimidazo [1,2-b]pyridazin-2-yl)methyl)-1H-pyrazole-4-carboxamide (53.8 mg, yield: 31%) as a white solid. ESI-MS

[M+H]+: 465.1. Purity: 99.88 (214 nm), 100.00 (254 nm). 1H NMR (400 MHz, DMSO-d6) δ 8.44 (d, J=2.2 Hz, 1H), 8.41 (t, J=5.0 Hz, 1H), 8.21-8.20 (m, 2H), 8.09 (s, 1H), 7.92 (d, J=9.4 Hz, 1H), 7.83 (s, 1H), 7.09 (d, J=9.5 Hz, 1H), 6.76 (t, J=6.9 Hz, 1H), 5.41 (s, 2H), 4.62 (d, J=5.2 Hz, 2H), 2.19-2.15 (m, 1H), 1.08-1.04 (m, 2H), 0.98-0.94 (m, 2H).

Example 147

Scheme 146

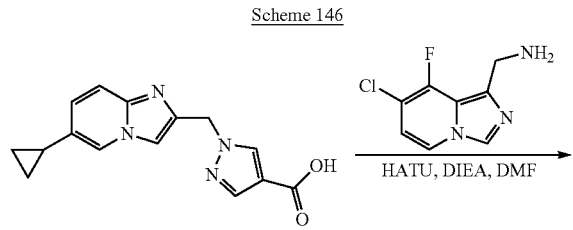

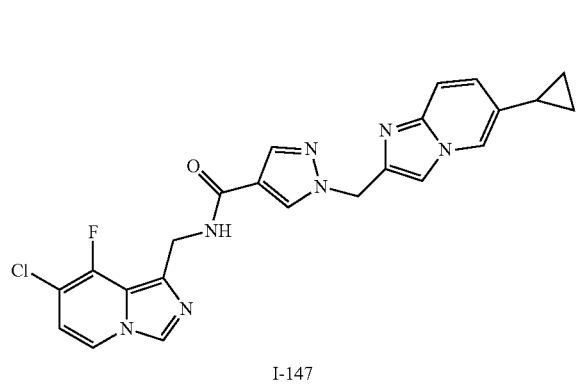

I-147

Synthesis of N-((7-chloro-8-fluoroimidazo[1,5-a]pyridin-1-yl)methyl)-1-((6-cyclopropylimidazo[1,2-a]pyridin-2-yl)methyl)-1H-pyrazole-4-carboxamide (I-147)

To a solution of 1-((6-cyclopropylimidazo[1,2-a]pyridin-2-yl)methyl)-1H-pyrazole-4-carboxylic acid (60 mg, 0.21 mmol), (7-chloro-8-fluoroimidazo[1,5-a]pyridin-1-yl)methanamine hydrochloride (75 mg, 0.32 mmol) and HATU (120 mg, 0.31 mmol) in DMF (3 mL) was added DIPEA (81 mg, 0.63 mmol). The resulting reaction was stirred at RT for 12 h. H2O (25 mL) was added to the reaction, extracted with EtOAc (30 mL×3). The combined organic layers were washed with brine, dried over Na2SO4, concentrated in vacuo to give the crude product, which was purified with Prep-TLC (DMC/MeOH=10/1) to give the N-((7-chloro-8-fluoroimidazo[1,5-a]pyridin-1-yl)methyl)-1-((6-cyclopropylimidazo[1,2-a]pyridin-2-yl)methyl)-1H-pyrazole-4-carboxamide (20 mg, yield: 21%) as a white solid. ESI-MS [M+H]+: 464.1. Purity: 99.3 (214 nm), 99.2 (254 nm). 1H NMR (400 MHz, DMSO-d6) δ 8.49-8.38 (m, 2H), 8.33 (s, 1H), 8.24-8.29 (m, 2H), 7.84 (s, 1H), 7.72 (s, 1H), 7.39 (d, J=9.3 Hz, 1H), 7.01-6.96 (m, 1H), 6.80-6.72 (m, 1H), 5.38 (s, 2H), 4.62 (d, J=5.2 Hz, 2H), 1.95-1.86 (m, 1H), 0.96-0.85 (m, 2H), 0.70-0.61 (m, 2H).

Example 148

Scheme 147

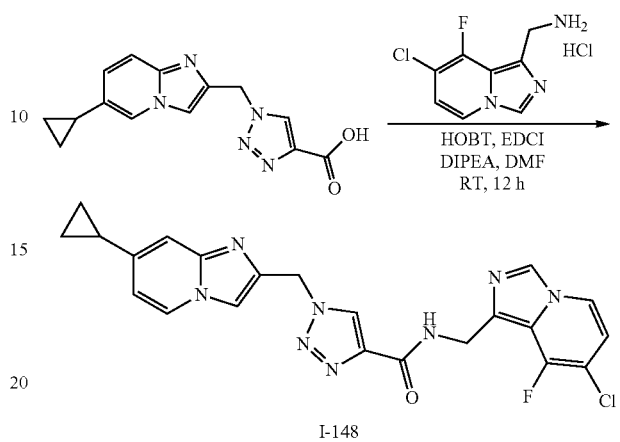

I-148

Synthesis of N-((7-chloro-8-fluoroimidazo[1,5-a]pyridin-1-yl)methyl)-1-((6-cyclopropylimidazo[1,2-a]pyridin-2-yl)methyl)-1H-1,2,3-triazole-4-carboxamide (I-148)

To a suspension of 1-((6-cyclopropylimidazo[1,2-a]pyridin-2-yl)methyl)-1H-1,2,3-triazole-4-carboxylic acid (37 mg, 0.13 mmol) and (7-chloro-8-fluoroimidazo[1,5-a]pyridin-1-yl)methanamine hydrochloride (35 mg, 0.15 mmol) in DMF (3 mL) was added HOBT (40 mg, 0.3 mmol) and EDCI (57 mg, 0.3 mmol), followed by DIPEA (65 mg, 0.5 mmol). The resulting mixture was stirred at RT for 12 h. The reaction mixture was poured into H2O (15 mL) slowly. The suspension mixture was stirred for 1 h, and filtered. The filtered cake was washed with H2O (20 mL) and MeOH (20 mL) then dried under vacuum pump to give the N-((7-chloro-8-fluoroimidazo[1,5-a]pyridin-1-yl)methyl)-1-((6-cyclopropylimidazo[1,2-a]pyridin-2-yl)methyl)-1H-1,2,3-triazole-4-carboxamide as pale solid (30 mg, yield: 50%). ESI-MS [M+H]+: 465.0. Purity: 98.4% (214 nm), 98.5% (254 nm). 1H NMR (400 MHz, DMSO-d6): 8.70 (t, J=5.4 Hz, 1H), 8.55 (s, 1H), 8.44 (d, J=2.4 Hz, 1H), 8.35 (s, 1H), 8.21 (d, J=7.4 Hz, 1H), 7.83 (s, 1H), 7.41 (d, J=9.3 Hz, 1H), 7.01 (dd, J=9.4, 1.8 Hz, 1H), 6.76 (dd, J=7.3, 6.6 Hz, 1H), 5.73 (s, 2H), 4.70 (d, J=5.5 Hz, 2H), 1.94-1.90 (m, 1H), 0.94-0.89 (m, 2H), 0.69-0.65 (m, 2H).

Example 149

Scheme 148

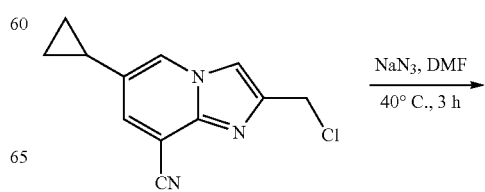

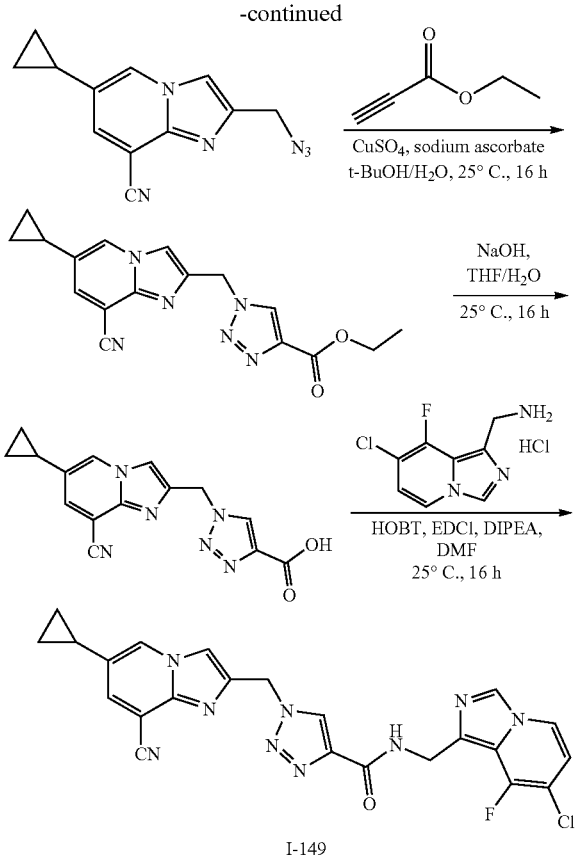

Synthesis of 2-(azidomethyl)-6-cyclopropylimidazo[1,2-a]pyridine-8-carbonitrile

To a mixture of 2-(chloromethyl)-6-cyclopropylimidazo[1,2-a]pyridine-8-carbonitrile (200 mg, 0.86 mmol) in DMF (5 mL) was added NaN$_3$ (91 mg, 1.4 mmol). The mixture was stirred at 25° C. for 3 h. Then H$_2$O (30 mL) was added, extracted with EtOAc (30 mL×3). The combined organic layers were washed with brine, dried over Na$_2$SO$_4$, filtered and concentrated to give the crude product, which was purified by Prep-TLC (EA/PE=3/2) to give 2-(azidomethyl)-6-cyclopropylimidazo[1,2-a]pyridine-8-carbonitrile (140 mg, yield: 68%) as a yellow solid. ESI-MS [M+H]$^+$: 239.2.

Synthesis of Ethyl 1-((8-cyano-6-cyclopropylimidazo[1,2-a]pyridin-2-yl)methyl)-1H-1,2,3-triazole-4-carboxylate To a mixture of 2-(azidomethyl)-6-cyclopropylimidazo[1,2-a]pyridine-8-carbonitrile (140 mg, 0.58 mmol), CuSO$_4$ (24 mg, 0.15 mmol), sodium ascorbate (30 mg, 0.15 mmol) in t-BuOH/H$_2$O (3/3 mL) was added ethyl propiolate (88 mg, 0.9 mmol). The mixture was stirred at 25° C. for 16 h. Water (30 mL) was added and extracted with EtOAc (50 mL×3). The combined organic layers were washed with brine, dried over Na$_2$SO$_4$, filtered and concentrated to give ethyl 1-((8-cyano-6-cyclopropylimidazo[1,2-a]pyridin-2-yl)methyl)-1H-1,2,3-triazole-4-carboxylate (95 mg, yield: 48%) as a yellow solid. ESI-MS [M+H]$^+$: 337.2.

Synthesis of 1-((8-cyano-6-cyclopropylimidazo[1,2-a]pyridin-2-yl)methyl)-1H-1,2,3-triazole-4-carboxylic Acid To a mixture of ethyl 1-((8-cyano-6-cyclopropylimidazo[1,2-a]pyridin-2-yl)methyl)-1H-1,2,3-triazole-4-carboxylate (95 mg, 0.28 mmol) in THF/H$_2$O (4/2 mL) was added NaOH (34 mg, 0.85 mmol). The mixture was stirred at 25° C. for 16 h. The pH of reaction was adjusted to 4 by 1 M HCl, then concentrated to give 1-((8-cyano-6-cyclopropylimidazo[1,2-a]pyridin-2-yl)methyl)-1H-1,2,3-triazole-4-carboxylic acid (130 mg, crude) as a grey solid. ESI-MS [M+H]$^+$: 309.2.

Synthesis of N-((7-chloro-8-fluoroimidazo[1,5-a]pyridin-1-yl)methyl)-1-((8-cyano-6-cyclopropylimidazo[1,2-a]pyridin-2-yl)methyl)-1H-1,2,3-triazole-4-carboxamide (I-149)

To a mixture of 1-((8-cyano-6-cyclopropylimidazo[1,2-a]pyridin-2-yl)methyl)-1H-1,2,3-triazole-4-carboxylic acid (130 mg, crude from last step), (7-chloro-8-fluoroimidazo[1,5-a]pyridin-1-yl)methanamine hydrochloride (58 mg, 0.25 mmol), HOBT (44 mg, 0.32 mmol), EDCI (62 mg, 0.32 mmol) in DMF (3 mL) was added DIPEA (103 mg, 0.8 mmol). The mixture was stirred at 25° C. for 16 h. The reaction was quenched by H$_2$O (20 mL), extracted with EtOAc (30 mL×3). The combined organic layers were washed with brine, dried over Na$_2$SO$_4$, filtered and concentrated to give the crude product, which was purified by Prep-HPLC to give N-((7-chloro-8-fluoroimidazo[1,5-a]pyridin-1-yl)methyl)-1-((8-cyano-6-cyclopropylimidazo[1,2-a]pyridin-2-yl)methyl)-1H-1,2,3-triazole-4-carboxamide (15.6 mg, yield: 13%) as a yellow solid. ESI-MS [M+H]$^+$: 489.9. Purity: 98.83 (214 nm), 99.11 (254 nm). $^1$H NMR (400 MHz, DMSO-d$_6$) δ 8.64-8.63 (m, 3H), 8.45 (s, 1H), 8.21 (s, 1H), 7.99-7.98 (m, 1H), 7.80 (s, 1H), 6.76 (s, 1H), 5.81 (s, 2H), 4.70 (s, 2H), 1.98-1.97 (m, 1H), 0.96-0.95 (m, 2H), 0.76-0.75 (m, 2H).

Example 150

Scheme 149

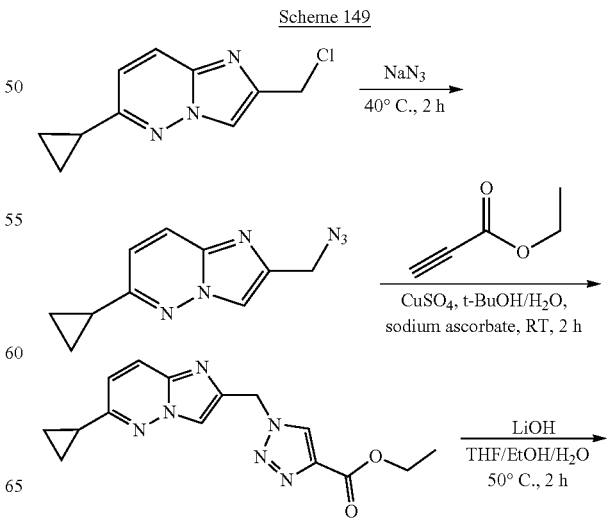

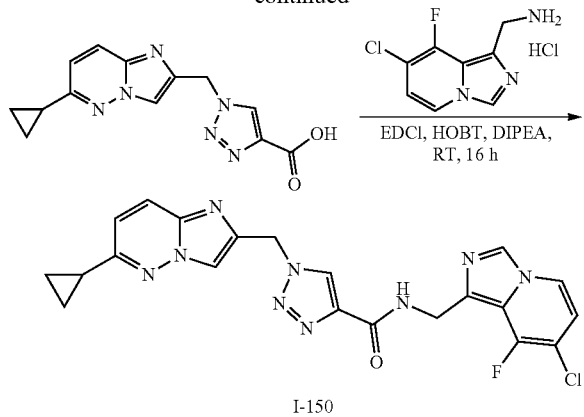

Synthesis of 2-(azidomethyl)-6-cyclopropylimidazo[1,2-b]pyridazine

A mixture of 2-(chloromethyl)-6-cyclopropylimidazo[1,2-b]pyridazine (900 mg, 4.33 mmol) in dry DMF (5 mL) was added NaN₃ (631 mg, 9.71 mmol) at RT. After the mixture was stirred for 2 h. Water (30 mL) was added and the mixture was extracted with EtOAc (50 mL×3). The combined organics were concentrated and purified by flash silica gel chromatography (0-40% EtOAc in PE) to give 2-(azidomethyl)-6-cyclopropylimidazo[1,2-b]pyridazine (735 mg, yield: 79%) as dark-red oil. ESI-MS [M+H]⁺: 215.2

Synthesis of Ethyl 1-((6-cyclopropylimidazo[1,2-b]pyridazin-2-yl)methyl)-1H-1,2,3-triazole-4-carboxylate To a solution of 2-(azidomethyl)-6-cyclopropylimidazo[1,2-b]pyridazine (730 mg, 3.41 mmol) and ethyl propiolate (501 mg, 5.11 mmol) in t-BuOH/H₂O (5 mL/5 mL) was added CuSO₄ (543 mg, 3.41 mmol) and sodium ascorbate (675 mg, 3.41 mmol) at RT. After the mixture was stirred for 2 h. The mixture were concentrated and purified by flash silica gel chromatography (0~10% EtOAc in PE) to give ethyl 1-((6-cyclopropylimidazo[1,2-b]pyridazin-2-yl)methyl)-1H-1,2,3-triazole-4-carboxylate (600 mg, yield: 56%) as a red solid. ESI-MS [M+H]⁺: 313.2.

Synthesis of 1-((6-cyclopropylimidazo[1,2-b]pyridazin-2-yl)methyl)-1H-1,2,3-triazole-4-carboxylic Acid To a solution of ethyl 1-((6-cyclopropylimidazo[1,2-b]pyridazin-2-yl)methyl)-1H-1,2,3-triazole-4-carboxylate (100 mg, 0.32 mmol) in THF/EtOH/H₂O (2 mL/2 mL/2 mL) was added LiOH (15.33 mg, 0.64 mL). The mixture was heated to 50° C. and refluxed for 2 h. HCl (2 M) was added to adjust the pH to 4 and the mixture was freeze-dried to give 1-((6-cyclopropylimidazo[1,2-b]pyridazin-2-yl)methyl)-1H-1,2,3-triazole-4-carboxylic acid (120 mg, crude) as a white solid. ESI-MS [M+H]⁺: 285.1.

Synthesis of N-((7-bromo-8-fluoroimidazo[1,5-a]pyridin-1-yl)methyl)-1-((6-cyclopropylimidazo[1,2-b]pyridazin-2-yl)methyl)-1H-1,2,3-triazole-4-carboxamide (I-150)

To a solution of 1-((6-cyclopropylimidazo[1,2-b]pyridazin-2-yl)methyl)-1H-1,2,3-triazole-4-carboxylic acid (120 mg, crude from last step) in DMF (3 mL) was added EDCI (111 mg, 0.58 mmol), HOBT (78 mg, 0.58 mmol), DIPEA (250.06 mg, 1.93 mmol) and (7-chloro-8-fluoroimidazo[1,5-a]pyridin-1-yl)methanamine hydrochloride (90 mg, 0.38 mmol) at RT. After the mixture was stirred for 16 h. The mixture was poured into H₂O, precipitate was filtered and washed with H₂O and methanol to give N-((7-chloro-8-fluoroimidazo[1,5-a]pyridin-1-yl)methyl)-1-((6-cyclopropylimidazo[1,2-b]pyridazin-2-yl)methyl)-1H-1,2,3-triazole-4-carboxamide (26.1 mg, yield: 17%) as a white solid. ESI-MS [M+H]⁺: 466.1. Purity: 98.56 (214 nm), 95.15 (254 nm). ¹H NMR (400 MHz, DMSO-d₆) δ 8.70 (t, J=5.4 Hz, 1H), 8.56 (s, 1H), 8.44 (d, J=2.3 Hz, 1H), 8.23-8.17 (m, 2H), 7.94 (d, J=9.5 Hz, 1H), 7.11 (d, J=9.5 Hz, 1H), 6.80-6.72 (m, 1H), 5.75 (s, 2H), 4.69 (d, J=5.5 Hz, 2H), 2.22-2.14 (m, 1H), 1.10-1.03 (m, 2H), 1.01-0.93 (m, 2H).

Example 151

Scheme 150

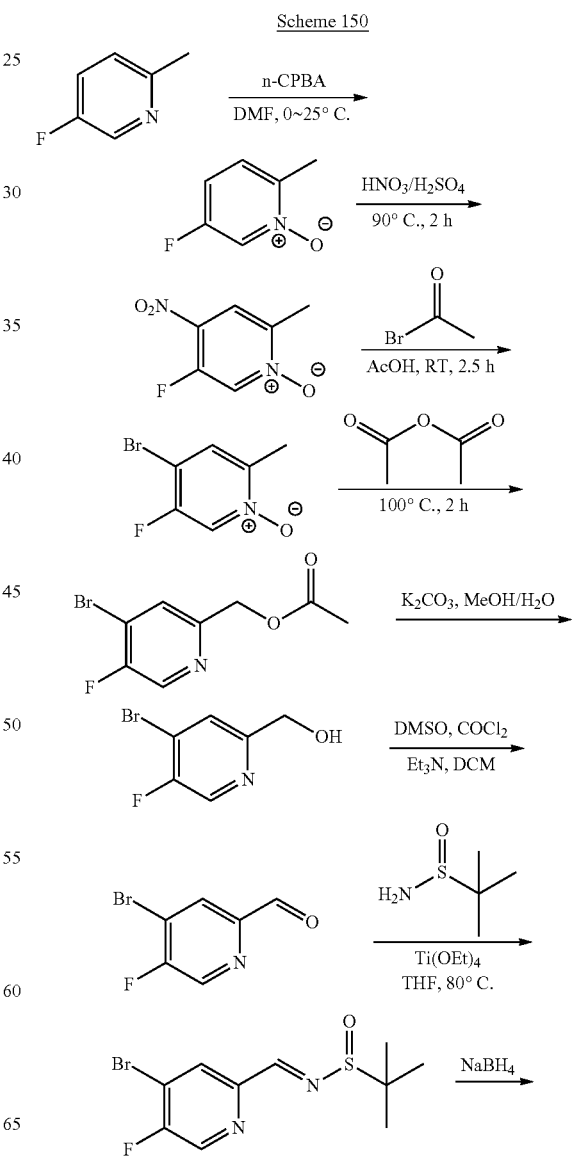

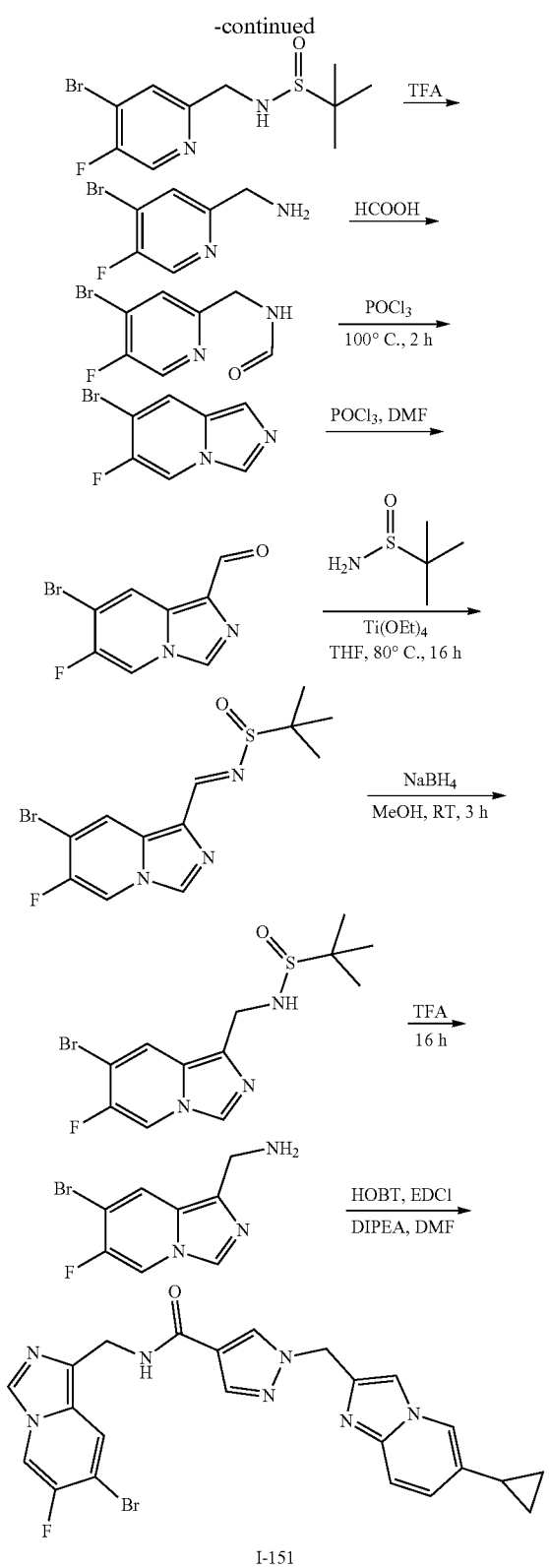

I-151

Synthesis of 5-fluoro-2-methylpyridine 1-oxide

To a stirred solution of 5-fluoro-2-methylpyridine (5 g, 45 mmol) in DCM (100 mL) was added m-CPBA (11.6 g, 67.5 mmol) at 0° C. and the mixture was stirred at 25° C. for 16 h. The mixture was quenched with saturated aqueous $Na_2S_2O_3$, stirred vigorously for 15 min, and then poured into saturated aqueous $NaHCO_3$. The layers were separated, and the aqueous layer was extracted twice more with DCM. The combined organic layers were dried over $MgSO_4$, filtered and concentrated to give 5-fluoro-2-methylpyridine 1-oxide (4.7 g, 82%) as a yellow solid which was used into next step without further purification. ESI-MS [M+H]$^+$: 128.2.

Synthesis of 5-fluoro-2-methyl-4-nitropyridine 1-oxide

Concentrated $H_2SO_4$ (15 mL) was slowly added to 5-fluoro-2-methylpyridine 1-oxide (4.7 g, 37 mmol) at 0° C. A mixture of fuming $HNO_3$ (10 mL) and concentrated $H_2SO_4$ (15 mL) was then added dropwise to the mixture at 0° C. Then the mixture was heated to 90° C. for 16 h. The mixture was slowly poured into 400 g of ice and then neutralized with solid $NH_4HCO_3$. The mixture was extracted three times with DCM, and the combined organic layers were dried over $MgSO_4$, filtered and concentrated to give 5-fluoro-2-methyl-4-nitropyridine 1-oxide (4.7 g, 74%) as a yellow solid which was used without further purification. ESI-MS [M+H]$^+$: 173.1.

Synthesis of 4-bromo-5-fluoro-2-methylpyridine 1-oxide

To a solution of 5-fluoro-2-methyl-4-nitropyridine 1-oxide (4.7 g, 27.3 mmol) in acetic acid (40 mL) was added acetyl bromide (15 mL) dropwise over 5 mins. After addition, the mixture was stirred at 80° C. for 16 h. The reaction mixture was poured into ice and the solution basified to pH 8 with cold 2 M sodium hydroxide. The aqueous layer was extracted with DCM (100 mL×3). The combined organic layers were washed with brine, dried over $Na_2SO_4$, filtered and concentrated to give 4-bromo-5-fluoro-2-methylpyridine 1-oxide (5.5 g, 98%) as a yellow solid. ESI-MS [M+H]$^+$: 206.0.

Synthesis of (4-bromo-5-fluoropyridin-2-yl)methyl acetate

A mixture of 4-bromo-5-fluoro-2-methylpyridine 1-oxide (5.5 g, 26.8 mmol) in acetic anhydride (30 mL) was stirred at 100° C. for 2 h, then cooled to 25° C., concentrated to give the crude product, $NaHCO_3$ (aq) was added to adjust pH about 9, extracted with DCM (100 mL×3). The combined organic layers were washed with brine, dried over $Na_2SO_4$, filtered and concentrated to give the crude product which was purified by column chromatography (PE:EA=20:1 to 10:1) to give (4-bromo-5-fluoropyridin-2-yl)methyl acetate (3.2 g, yield: 48%) as a yellow oil. ESI-MS [M+H]$^+$: 248.1.

Synthesis of (4-bromo-5-fluoropyridin-2-yl)methanol

To a mixture of (4-bromo-5-fluoropyridin-2-yl)methyl acetate (2.5 g, 10 mmol) in MeOH/$H_2O$ (20/2 mL) was added $K_2CO_3$ (7 g, 50 mmol). The mixture was stirred at 25° C. for 16 h. Then MeOH was remove. Water (20 mL) was added, extracted with EtOAc (50 mL×3). The combined organic layers were washed with brine, dried over $Na_2SO_4$, filtered and concentrated to give (4-bromo-5-fluoropyridin-2-yl)methanol (2 g, yield: 96%) as a yellow oil which was used into next step without further purification. ESI-MS [M+H]$^+$: 206.0.

Synthesis of 4-bromo-5-fluoropicolinaldehyde

To a solution of oxalyl chloride (1.86 g, 14.6 mmol) in DCM (50 mL) under nitrogen was added dropwise a solution of DMSO (1.52 g, 19.5 mmol) in DCM (20 mL) at −78° C. Stirring was continued for 10 minutes. A solution of (4-bromo-5-fluoropyridin-2-yl)methanol (2 g, 9.76 mmol) in DCM (20 mL) was then added dropwise over 20 minutes. The reaction was stirred for 1 h. Triethylamine (4.93 g, 48.8 mmol) was added dropwise and the reaction was allowed to warm to RT over 1.5 h. The reaction was then quenched by addition of $H_2O$ (50 mL). The organics were separated and $H_2O$ phase was extracted with DCM (50 mL×2). Concentrated in vacuo to give 4-bromo-5-fluoropicolinaldehyde (1.2 g, yield: 59%) as a brown oil which was used into next step without further purification. ESI-MS [M+H]$^+$: 204.2

Synthesis of (E)-N-((4-bromo-5-fluoropyridin-2-yl)methylene)-2-methylpropane-2-sulfinamide To a mixture of 4-bromo-5-fluoropicolinaldehyde (1.2 g, 5.9 mmol), 2-methylpropane-2-sulfinamide (857 mg, 7.08 mmol) in dry THF (20 mL) was added Ti(OEt)$_4$ (4.03 g, 17.7 mmol). The mixture was stirred at 75° C. for 16 h. Water (100 mL) was added and extracted with EtOAc (100 mL×3). The combined organic layers were washed with brine, dried over $Na_2SO_4$, filtered and concentrated to give (E)-N-((4-bromo-5-fluoropyridin-2-yl)methylene)-2-methylpropane-2-sulfinamide (1.8 g, crude). ESI-MS [M+H]$^+$: 307.1

Synthesis of N-((4-bromo-5-fluoropyridin-2-yl)methyl)-2-methylpropane-2-sulfinamide To a mixture of (E)-N-((4-bromo-5-fluoropyridin-2-yl)methylene)-2-methylpropane-2-sulfinamide (1.8 g, crude from last step) in dry THF (30 mL) was added NaBH$_4$ (897 mg, 23.6 mmol). The mixture was stirred at 25° C. for 3 h. Then $H_2O$ (20 mL) was added, extracted with EtOAc (50 mL×3). The combined organic layers were washed with brine, dried over $Na_2SO_4$, filtered and concentrated to give the crude product, which was purified by Prep-TLC (DCM/MeOH=10/1) to give N-((4-bromo-5-fluoropyridin-2-yl)methyl)-2-methylpropane-2-sulfinamide (900 mg, yield: 50% over 2 steps) as a yellow oil. ESI-MS [M+H]$^+$: 309.0.

Synthesis of (4-bromo-5-fluoropyridin-2-yl)methanamine

A mixture of N-((4-bromo-5-fluoropyridin-2-yl)methyl)-2-methylpropane-2-sulfinamide (900 mg, 2.92 mmol) in TFA (10 mL) was stirred at 40° C. for 16 h. Then concentrated to give (4-bromo-5-fluoropyridin-2-yl)methanamine (590 mg, yield: 99%) as a yellow oil which was used in the next step without further purification. ESI-MS [M+H]$^+$: 205.1.

Synthesis of N-((4-bromo-5-fluoropyridin-2-yl)methyl)formamide

A mixture of (4-bromo-5-fluoropyridin-2-yl)methanamine (590 mg, 2.89 mmol) in HCOOH (10 mL) was stirred at 90° C. for 3 h. Then concentrated to give the crude product, which was purified by Prep-TLC (DCM/MeOH=10/1) to give N-((4-bromo-5-fluoropyridin-2-yl)methyl)formamide (400 mg, yield: 60%) as a yellow solid. ESI-MS [M+H]$^+$: 233.1.

Synthesis of 7-bromo-6-fluoroimidazo[1,5-a]pyridine

A mixture of N-((4-bromo-5-fluoropyridin-2-yl)methyl)formamide (400 mg, 1.72 mmol) in POCl$_3$ (10 mL) was stirred at 100° C. for 1 h. Then POCl$_3$ was concentrated, $H_2O$ (20 mL) was added, followed by $Na_2CO_3$ (aq) to adjust pH about 8, extracted with EtOAc (50 mL×3). The combined organic layers were washed with brine, dried over $Na_2SO_4$, filtered and concentrated. The crude product was purified by Prep-TLC (EA/PE=2/1) to give 7-bromo-6-fluoroimidazo[1,5-a]pyridine (300 mg, yield: 81%) as a yellow solid. ESI-MS [M+H]$^+$: 215.0.

Synthesis of 7-bromo-6-fluoroimidazo[1,5-a]pyridine-1-carbaldehyde

To a mixture of 7-bromo-6-fluoroimidazo[1,5-a]pyridine (300 mg, 1.4 mmol) in dry DMF (1 mL) was added POCl$_3$ (321 mg, 2.1 mmol). The mixture was stirred at 100° C. for 1 h. Then cooled to 25° C. and poured into ice $H_2O$ (10 mL), the solution was basified with $NH_3.H_2O$ and extracted with DCM (50 mL×3). The combined organic layers were washed with brine, dried over $Na_2SO_4$, filtered and concentrated to give the crude product, which was purified by Prep-TLC (DCM/MeOH=25/1) to give 7-bromo-6-fluoroimidazo[1,5-a]pyridine-1-carbaldehyde (80 mg, yield: 23.6%) as a yellow solid. ESI-MS [M+H]$^+$: 243.0.

Synthesis of N-((7-bromo-6-fluoroimidazo[1,5-a]pyridin-1-yl)methylene)-2-methylpropane-2-sulfinamide To a mixture of 7-bromo-6-fluoroimidazo[1,5-a]pyridine-1-carbaldehyde (50 mg, 0.2 mmol), 2-methylpropane-2-sulfinamide (30 mg, 0.24 mmol) in dry THF (3 mL) was added Ti(OEt)$_4$ (137 mg, 0.6 mmol). The mixture was stirred at 80° C. for 16 h. Water (20 mL) was added and extracted with EtOAc (50 mL×3). The combined organic layers were washed with brine, dried over $Na_2SO_4$, filtered and concentrated to give N-((7-bromo-6-fluoroimidazo[1,5-a]pyridin-1-yl)methylene)-2-methylpropane-2-sulfinamide, which was used in the next step without further purification. (71.4 mg, crude). ESI-MS [M+H]$^+$: 346.2

Synthesis of N-((7-bromo-6-fluoroimidazo[1,5-a]pyridin-1-yl)methyl)-2-methylpropane-2-sulfinamide To a mixture of N-((7-bromo-6-fluoroimidazo[1,5-a]pyridin-1-yl)methylene)-2-methylpropane-2-sulfinamide (71.4 mg, crude from last step) in dry THF (3 mL) was added NaBH$_4$ (30 mg, 0.8 mmol). The mixture was stirred at 25° C. for 3 h. Then $H_2O$ (10 mL) was added, extracted with EtOAc (50 mL×3). The combined organic layers were washed with brine, dried over $Na_2SO_4$, filtered and concentrated to give the crude product which was purified by Prep-TLC (DCM/MeOH=10/1) to give N-((7-bromo-6-fluoroimidazo[1,5-a]pyridin-1-yl)methyl)-2-methylpropane-2-sulfinamide (60 mg, yield: 85% over 2 steps) as a yellow oil. ESI-MS [M+H]$^+$: 348.1

Synthesis of (7-bromo-6-fluoroimidazo[1,5-a]pyridin-1-yl)methanamine

A mixture of N-((7-bromo-6-fluoroimidazo[1,5-a]pyridin-1-yl)methyl)-2-methylpropane-2-sulfinamide (60 mg, 0.17 mmol) in TFA (2 mL) was stirred at RT for 16 h. Then concentrated to give (7-bromo-6-fluoroimidazo[1,5-a]pyridin-1-yl)methanamine (39 mg, crude) as a yellow solid which was used in the next step without further purification. ESI-MS [M+H]⁺: 227.0.

Synthesis of N-((7-bromo-6-fluoroimidazo[1,5-a]pyridin-1-yl)methyl)-1-((6-cyclopropylimidazo[1,2-a]pyridin-2-yl)methyl)-1H-pyrazole-4-carboxamide (I-151)

To a mixture of 1-((6-cyclopropylimidazo[1,2-a]pyridin-2-yl)methyl)-1H-pyrazole-4-carboxylic acid (20 mg, 0.071 mmol), (7-bromo-6-fluoroimidazo[1,5-a]pyridin-1-yl)methanamine (17.2 mg, 0.071 mmol), HOBT (19 mg, 0.14 mmol), EDCI (27 mg, 0.14 mmol) in DMF (3 mL) was added DIPEA (46 mg, 0.36 mmol). The mixture was stirred at 25° C. for 3 h. Water (20 mL) was added and the mixture was extracted with EtOAc (30 mL×3). The combined organic layers was concentrated and purified by Prep-TLC (DCM/MeOH=10/1) to give N-((7-bromo-6-fluoroimidazo[1,5-a]pyridin-1-yl)methyl)-1-((6-cyclopropylimidazo[1,2-a]pyridin-2-yl)methyl)-1H-pyrazole-4-carboxamide (18.9 mg, yield: 53%) as a yellow solid. ESI-MS [M+H]⁺: 507.9. Purity: 94.07 (214 nm), 96.76 (254 nm). ¹H NMR (400 MHz, DMSO-D₆) S 8.65-8.59 (m, 2H), 8.33-8.29 (m, 2H), 8.20-8.16 (m, 2H), 7.85 (s, 1H), 7.72 (s, 1H), 7.39 (d, J=9.3 Hz, 1H), 6.99 (dd, J=9.3, 1.4 Hz, 1H), 5.38 (s, 2H), 4.55 (d, J=5.7 Hz, 2H), 1.95-1.88 (m, 1H), 0.92-0.89 (m, 2H), 0.68-0.65 (m, 2H).

Example 152

Scheme 151

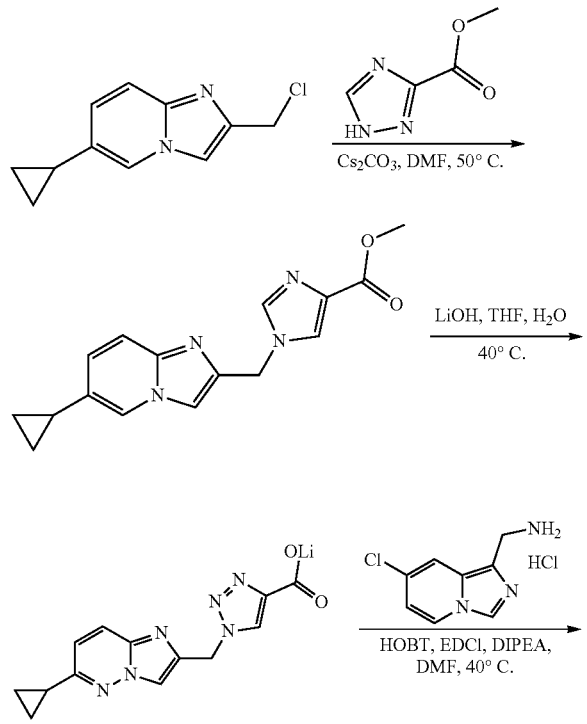

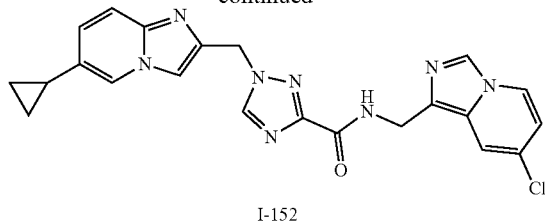

I-152

Synthesis of Methyl 1-((6-cyclopropylimidazo[1,2-a]pyridin-2-yl)methyl)-1H-1,2,4-triazole-3-carboxylate A mixture of 2-(chloromethyl)-6-cyclopropylimidazo[1,2-a]pyridine (207 mg, 1.0 mmol), methyl 1H-1,2,4-triazole-3-carboxylate (190 mg, 1.5 mmol) and Cs₂CO₃ (1.6 g, 5 mmol) in DMF (8 mL) was stirred at 50 for 2 h. H₂O (50 mL) was added to the reaction, then extracted with EtOAc (50 mL×2). The combined organic layers were concentrated, and purified by flash silica gel column (CH₂Cl₂/MeOH=15/1) to give methyl 1-((6-cyclopropylimidazo[1,2-a]pyridin-2-yl)methyl)-1H-1,2,4-triazole-3-carboxylate (130 mg, yield: 44%) as a white solid. ESI-MS [M+H]⁺: 298.1.

Synthesis of lithium 1-((6-cyclopropylimidazo[1,2-a]pyridin-2-yl)methyl)-1H-1,2,4-triazole-3-carboxylate To a solution of methyl 1-((6-cyclopropylimidazo[1,2-a]pyridin-2-yl)methyl)-1H-1,2,4-triazole-3-carboxylate (57 mg, 0.19 mmol) in THF/EtOH/H₂O (1 mL/1 mL/0.5 mL) was added LiOH (16 mg, 0.38 mmol). The mixture was stirred at 40° C. for 1 h. Then concentrated and lyophilized to give lithium 1-((6-cyclopropylimidazo[1,2-a]pyridin-2-yl)methyl)-1H-1,2,4-triazole-3-carboxylate (75 mg, crude) as a yellow solid. ESI-MS [M+H]⁺: 284.1.

Synthesis of N-((7-chloroimidazo[1,5-a]pyridin-1-yl)methyl)-1-((6-cyclopropylimidazo[1,2-a]pyridin-2-yl)methyl)-1H-1,2,4-triazole-3-carboxamide (I-152)

A mixture of lithium 1-((6-cyclopropylimidazo[1,2-a]pyridin-2-yl)methyl)-1H-1,2,4-triazole-3-carboxylate (75 mg, crude), (7-chloroimidazo[1,5-a]pyridin-1-yl)methanamine hydrochloride (41 mg, 0.19 mmol), HOBT (52 mg, 0.38 mmol), EDCI (73 mg, 0.38 mmol) and DIPEA (123 mg, 0.95 mmol) in DMF (2.5 mL) was stirred at 40° C. for 26 h. Water (10 mL) was added and extracted with EtOAc (30 mL×2), the combined organic layers were washed with brine, concentrated, the crude was purified by flash silica gel column (CH₂Cl₂/MeOH=5/1) to give N-((7-chloroimidazo[1,5-a]pyridin-1-yl)methyl)-1-((6-cyclopropylimidazo[1,2-a]pyridin-2-yl)methyl)-1H-1,2,4-triazole-3-carboxamide (27.9 mg, yield: 32%) as a yellow solid. ESI-MS [M+H]⁺: 447.1. Purity: 99.48% (214 nm), 100% (254 nm). ¹H NMR (400 MHz, DMSO-d₆) δ 8.83 (t, J=5.1 Hz, 1H), 8.72 (s, 1H), 8.34-8.29 (m, 3H), 7.83-7.79 (m, 2H), 7.38 (d, J=9.3 Hz, 1H), 7.00 (d, J=9.1 Hz, 1H), 6.64 (d, J=6.8 Hz, 1H), 5.54 (s, 2H), 4.60 (d, J=5.6 Hz, 2H), 1.95-1.88 (m, 1H), 0.96-0.85 (m, 2H), 0.70-0.61 (m, 2H).

Example 153

Scheme 152

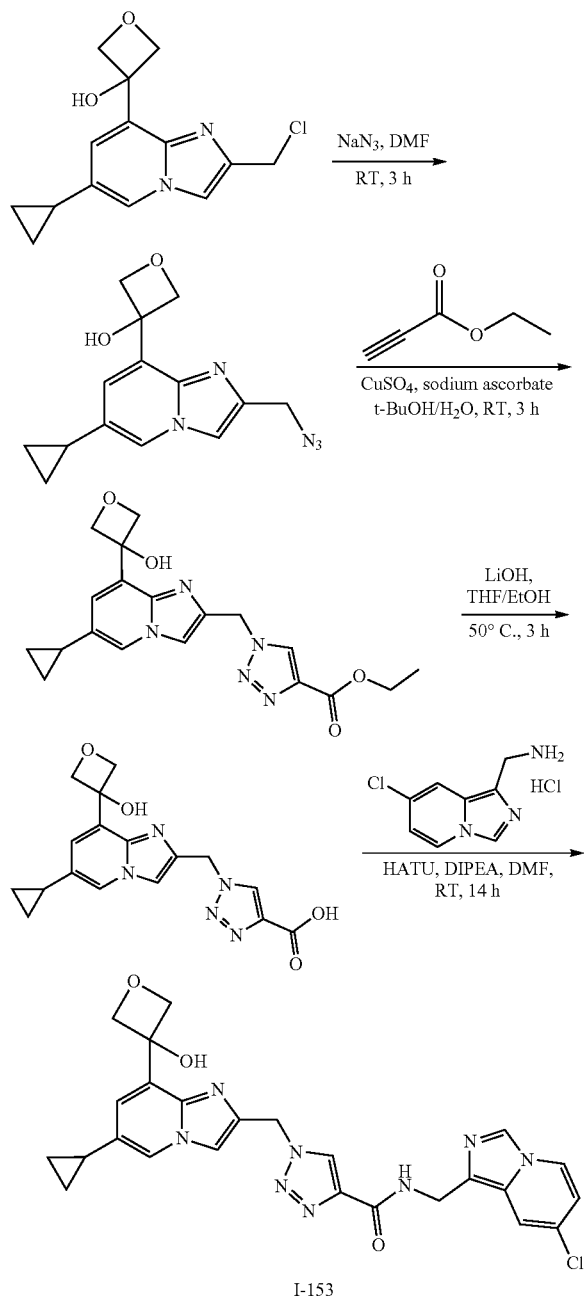

I-153

Synthesis of Ethyl 1-((6-cyclopropyl-8-(3-hydroxyoxetan-3-yl)imidazo[1,2-a]pyridin-2-yl)methyl)-1H-pyrazole-4-carboxylate A mixture of 3-(2-(chloromethyl)-6-cyclopropylimidazo[1,2-a]pyridin-8-yl)oxetan-3-ol (500 mg, 1.8 mmol) and NaN₃ (176 mg, 2.7 mmol) in DMF (15 mL) was stirred at RT for 3 h. H₂O (30 mL) was added to the reaction, extracted with EtOAc (50 mL×3). The combined organic layers were washed brine, dried over Na₂SO₄, concentrate in vacuo to give the crude product, which was purified with silica gel chromatography (EA/PE=1/1) to give the 3-(2-(azidomethyl)-6-cyclopropylimidazo[1,2-a]pyridin-8-yl)oxetan-3-ol (420 mg, yield: 82%) as a yellow solid. ESI-MS [M+H]⁺: 286.1

Synthesis of Ethyl 1-((8-(3-hydroxyoxetan-3-yl)imidazo[1,2-a]pyridin-2-yl)methyl)-1H-1,2,3-triazole-4-carboxylate To a solution of 3-(2-(azidomethyl)-6-cyclopropylimidazo[1,2-a]pyridin-8-yl)oxetan-3-ol (420 mg, 1.47 mmol) in t-BuOH/H₂O (10 mL/10 mL) was added ethyl propiolate (158 mg, 1.6 mmol), CuSO₄ (70 mg, 0.44 mmol) and sodium ascorbate (87 mg, 0.44 mmol). The resulting reaction was stirred at RT for 3 h. The reaction was concentrated in vacuo to give the residue, which was purified with silica gel chromatography (EA/PE=1/1) to give the ethyl 1-((8-(3-hydroxyoxetan-3-yl)imidazo[1,2-a]pyridin-2-yl)methyl)-1H-1,2,3-triazole-4-carboxylate (400 mg, yield: 71%) as a yellow solid. ESI-MS [M+H]⁺: 383.2

Synthesis of 1-((8-(3-hydroxyoxetan-3-yl)imidazo[1,2-a]pyridin-2-yl)methyl)-1H-1,2,3-triazole-4-carboxylic Acid A mixture of ethyl 1-((8-(3-hydroxyoxetan-3-yl)imidazo[1,2-a]pyridin-2-yl)methyl)-1H-1,2,3-triazole-4-carboxylate (400 mg, 1.05 mmol) and LiOH (140 mg, 5.8 mmol) in THF/H₂O (15 mL/5 mL) was stirred at 50° C. for 3 h. The reaction was concentrate in vacuo to give crude product, which was purified with Prep-HPLC to give 1-((8-(3-hydroxyoxetan-3-yl)imidazo[1,2-a]pyridin-2-yl)methyl)-1H-1,2,3-triazole-4-carboxylic acid (220 mg, yield: 58%) as a yellow solid. ESI-MS [M+H]⁺: 356.2

Synthesis of N-((7-chloroimidazo[1,5-a]pyridin-1-yl)methyl)-1-((6-cyclopropyl-8-(3-hydroxyoxetan-3-yl)imidazo[1,2-a]pyridin-2-yl)methyl)-1H-1,2,3-triazole-4-carboxamide (I-153)

To a solution of 1-((8-(3-hydroxyoxetan-3-yl)imidazo[1,2-a]pyridin-2-yl)methyl)-1H-1,2,3-triazole-4-carboxylic acid (100 mg, 0.28 mmol), (7-chloroimidazo[1,5-a]pyridin-1-yl)methanamine hydrochloride (87 mg, 0.4 mmol), HATU (177 mg, 0.47 mmol) in DMF (5 mL) was added DIPEA (200 mg, 1.55 mmol). The resulting mixture was stirred at RT for 14 h. H₂O (30 mL) was added into the reaction, extracted with EtOAC (50 mL×3). The combined organic layers were washed with brine, dried over Na₂SO₄, concentrated in vacuo to give the crude product, which was purified with Prep-TLC (DCM/MeOH=10/1) to give the N-((7-chloroimidazo[1,5-a]pyridin-1-yl)methyl)-1-((6-cyclopropyl-8-(3-hydroxyoxetan-3-yl)imidazo[1,2-a]pyridin-2-yl)methyl)-1H-1,2,3-triazole-4-carboxamide (30 mg, yield: 20%) as off white solid. ESI-MS [M+H]⁺: 518.9. Purity: 94.5 (214 nm), 93.5 (254 nm). ¹H NMR (400 MHz, DMSO-d₆) δ 8.92 (t, J=5.9 Hz, 1H), 8.56 (s, 1H), 8.34-8.28 (m, 3H), 7.85-7.82 (m, 1H), 7.79 (s, 1H), 7.07 (d, J=1.4 Hz, 1H), 6.66-6.62 (m, 1H), 6.42 (s, 1H), 5.76 (s, 2H), 5.22 (d, J=6.5 Hz, 2H), 4.62 (t, J=6.8 Hz, 4H), 1.98-1.91 (m, 1H), 0.95-0.90 (m, 2H), 0.70-0.66 (m, 2H).

Example 154

Scheme 153

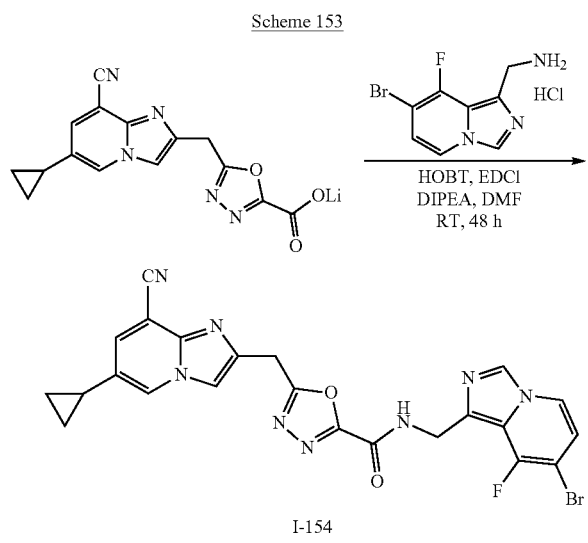

Synthesis of N-((7-bromo-8-fluoroimidazo[1,5-a]pyridin-1-yl)methyl)-5-((8-cyano-6-cyclopropylimidazo[1,2-a]pyridin-2-yl)methyl)-1,3,4-oxadiazole-2-carboxamide (I-154)

A mixture of lithium 5-((8-cyano-6-cyclopropylimidazo[1,2-a]pyridin-2-yl)methyl)-1,3,4-oxadiazole-2-carboxylate (100 mg, 0.32 mmol), (7-bromo-8-fluoroimidazo[1,5-a]pyridin-1-yl)methanamine hydrochloride (106 mg, 0.38 mmol), EDCI (123 mg, 0.64 mmol), HOBT (86 mg, 0.64 mmol) and DIPEA (206 mg, 1.6 mmol) in DMF (3 mL) was stirred at RT for 48 h. The mixture was concentrated to remove DMF, diluted with DCM/MeOH (30 mL, 10/1 (v/v)) and washed with $H_2O$ (10 mL×2). The organic layer was separated, dried over $Na_2SO_4$, and concentrated in vacuo to give the crude product, which was purified by silica gel chromatography (DCM/MeOH=10/1) to give N-((7-bromo-8-fluoroimidazo[1,5-a]pyridin-1-yl)methyl)-5-((8-cyano-6-cyclopropylimidazo[1,2-a]pyridin-2-yl)methyl)-1,3,4-oxadiazole-2-carboxamide (25.4 mg, yield: 15%) as a yellow solid. ESI-MS [M+H]$^+$: 535.0. Purity: 96.4 (214 nm), 96.4 (254 nm). $^1$H NMR (400 MHz, DMSO-d$_6$) δ 9.64 (t, J=5.4 Hz, 1H), 8.69 (s, 1H), 8.46 (d, J=2.2 Hz, 1H), 8.15 (d, J=7.3 Hz, 1H), 8.00 (s, 1H), 7.77 (s, 1H), 6.89-6.78 (m, 1H), 4.69 (d, J=5.4 Hz, 2H), 4.53 (s, 2H), 2.00-1.95 (m, 1H), 1.02-0.91 (m, 2H), 0.82-0.70 (m, 2H).

Example 155

Scheme 154

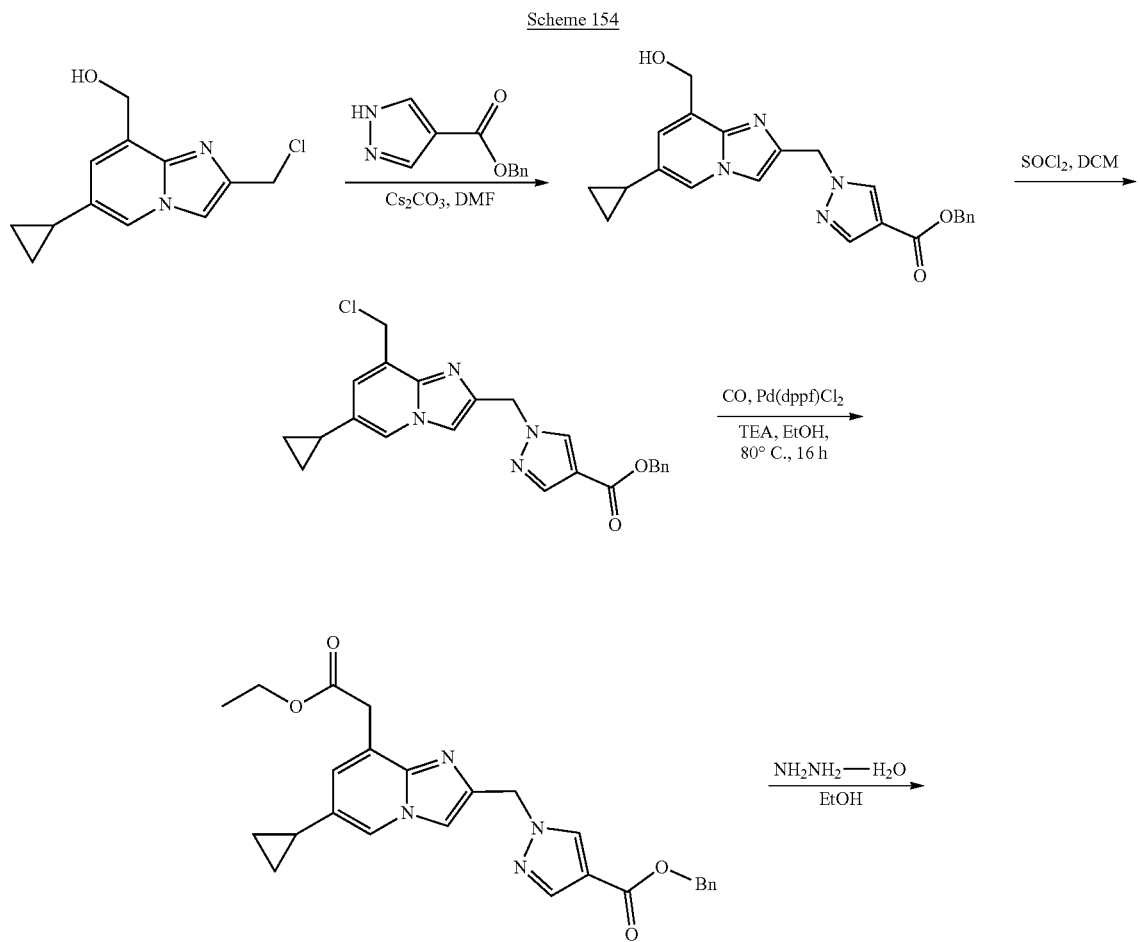

-continued

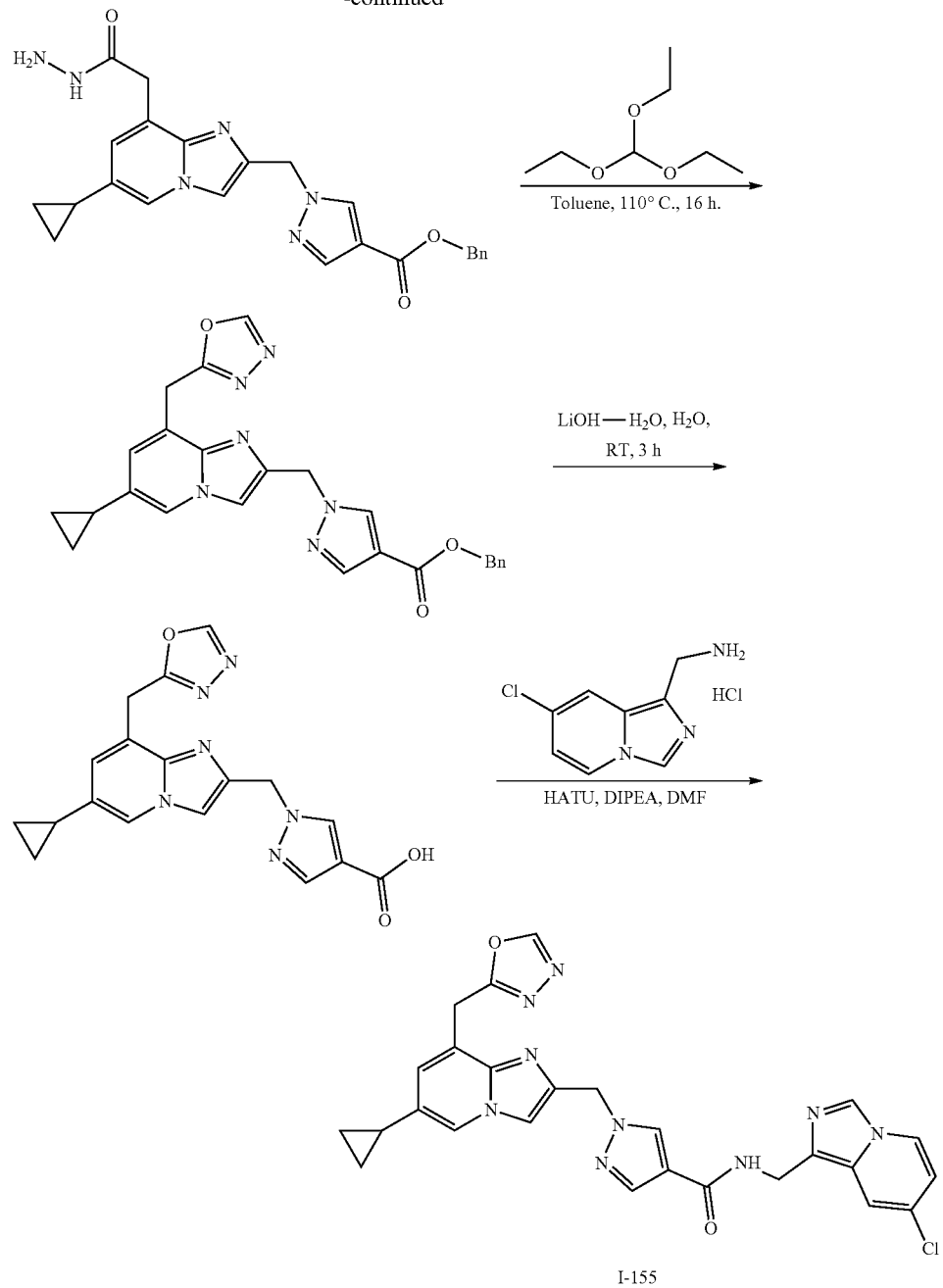

I-155

Synthesis of benzyl 1-((6-cyclopropyl-8-(hydroxymethyl)imidazo[1,2-a]pyridin-2-yl)methyl)-1H-pyrazole-4-carboxylate A mixture of (2-(chloromethyl)-6-cyclopropylimidazo[1,2-a]pyridin-8-yl)methanol (550 mg, 2.33 mmol), benzyl 1H-pyrazole-4-carboxylate (520 mg, 2.56 mmol) and $Cs_2CO_3$ (1.90 g, 5.83 mmol) in DMF (10 mL) was stirred at RT for 16 h. The mixture was concentrated and purified by flash silica gel chromatography (DCM/MeOH=15/1) to give benzyl 1-((6-cyclopropyl-8-(hydroxymethyl)imidazo[1,2-a]pyridin-2-yl)methyl)-1H-pyrazole-4-carboxylate (710 mg, yield: 75%) as a white solid. ESI-MS [M+H]$^+$: 403.1

Synthesis of benzyl 1-((8-(chloromethyl)-6-cyclopropylimidazo[1,2-a]pyridin-2-yl)methyl)-1H-pyrazole-4-carboxylate To a solution of benzyl 1-((6-cyclopropyl-8-(hydroxymethyl)imidazo[1,2-a]pyridin-2-yl)methyl)-1H-pyrazole-4-carboxylate (200 mg, 0.50 mmol) in DCM (5 mL) was added $SOCl_2$ (0.5 mL) at 0° C. and the mixture was stirred for 2 h. The mixture was concentrated to give benzyl 1-((8-(chloromethyl)-6-cyclopropylimidazo[1,2-a]pyridin-2-yl)methyl)-1H-pyrazole-4-carboxylate (200 mg, crude) as a yellow solid. ESI-MS [M+H]$^+$: 421.1.

Synthesis of benzyl 1-((6-cyclopropyl-8-(2-ethoxy-2-oxoethyl)imidazo[1,2-a]pyridin-2-yl)methyl)-1H-pyrazole-4-carboxylate A mixture of benzyl 1-((8-(chloromethyl)-6-cyclopropylimidazo[1,2-a]pyridin-2-yl)methyl)-1H-pyrazole-4-carboxylate (200 mg, 0.48 mmol), Pd(dppf)Cl$_2$ (40 mg, 0.048 mmol) and TEA (1.0 mL) in EtOH (6.0 mL) was stirred at 80° C. under CO for 16 h. The mixture was concentrated and purified by Prep-TLC (DCM/MeOH=20/1) to give benzyl 1-((6-cyclopropyl-8-(2-ethoxy-2-oxoethyl)imidazo[1,2-a]pyridin-2-yl)methyl)-1H-pyrazole-4-carboxylate (170 mg, yield: 77%) as a light yellow oil. ESI-MS [M+H]$^+$: 458.9.

Synthesis of benzyl 1-((6-cyclopropyl-8-(2-hydrazinyl-2-oxoethyl)imidazo[1,2-a]pyridin-2-yl)methyl)-1H-pyrazole-4-carboxylate A mixture of benzyl 1-((6-cyclopropyl-8-(2-ethoxy-2-oxoethyl)imidazo[1,2-a]pyridin-2-yl) methyl)-1H-pyrazole-4-carboxylate (100 mg, 0.22 mmol) and NH$_2$NH$_2$·H$_2$O (0.5 mL) in EtOH (6.0 mL) was stirred at RT for 16 h. The mixture was concentrated to give benzyl 1-((6-cyclopropyl-8-(2-hydrazinyl-2-oxoethyl)imidazo[1,2-a]pyridin-2-yl)methyl)-1H-pyrazole-4-carboxylate (100 mg, crude) as a white solid. ESI-MS [M+H]$^+$: 445.1.

Synthesis of benzyl 1-((8-((1,3,4-oxadiazol-2-yl)methyl)-6-cyclopropylimidazo[1,2-a]pyridin-2-yl)methyl)-1H-pyrazole-4-carboxylate A mixture of benzyl 1-((6-cyclopropyl-8-(2-hydrazinyl-2-oxoethyl)imidazo[1,2-a] pyridin-2-yl)methyl)-1H-pyrazole-4-carboxylate (50 mg, crude from last step), AcOH (0.15 mL) and triethoxymethane (0.15 mL) in toluene (3.0 mL) was stirred at 110° C. for 16 h. The mixture was concentrated and purified by Prep-TLC (DCM/MeOH=10/1) to give benzyl 1-((8-((1,3,4-oxadiazol-2-yl)methyl)-6-cyclopropylimidazo[1,2-a]pyridin-2-yl)methyl)-1H-pyrazole-4-carboxylate (40 mg, yield: 80%) as a yellow oil. ESI-MS [M+H]$^+$: 455.1.

Synthesis of 1-((8-((1,3,4-oxadiazol-2-yl)methyl)-6-cyclopropylimidazo[1,2-a]pyridin-2-yl)methyl)-1H-pyrazole-4-carboxylic Acid A solution of benzyl 1-((8-((1,3,4-oxadiazol-2-yl)methyl)-6-cyclopropylimidazo [1,2-a]pyridin-2-yl)methyl)-1H-pyrazole-4-carboxylate (20.0 mg, 0.044 mmol) and LiOH.H$_2$O (9.3 mg, 0.22 mmol) in a mixed solvent of THF/MeOH/H$_2$O (1 mL/1 mL/1 mL) was stirred at RT for 3 h. The pH value was adjusted to 3 by 1 M HCl solution and the mixture was extracted with i-PrOH/DCM=1/3 (30 mL×3). The combined organic layers were concentrated to give 1-((8-((1,3,4-oxadiazol-2-yl)methyl)-6-cyclopropylimidazo[1,2-a]pyridin-2-yl)methyl)-1H-pyrazole-4-carboxylic acid (10.0 mg, crude) as a yellow oil. This material was used directly in the next step without further purification. ESI-MS [M+H]$^+$: 365.1.

Synthesis of 1-((8-((1,3,4-oxadiazol-2-yl)methyl)-6-cyclopropylimidazo[1,2-a]pyridin-2-yl)methyl)-N-((7-chloroimidazo[1,5-a]pyridin-1-yl)methyl)-1H-pyrazole-4-carboxamide (I-157)

A mixture of 1-((8-((1,3,4-oxadiazol-2-yl)methyl)-6-cyclopropylimidazo[1,2-a] pyridin-2-yl)methyl)-1H-pyrazole-4-carboxylic acid (10.0 mg, crude from last step), (7-chloroimidazo[1,5-a]pyridin-1-yl)methanamine hydrochloride (7.5 mg, 0.034 mmol), HATU (15.4 mg, 0.041 mmol) and DIPEA (10.5 mg, 0.081 mmol) in DMF (2 mL) was stirred at 20° C. for 4 h. The mixture was concentrated and purified by Prep-HPLC to give 1-((8-((1,3,4-oxadiazol-2-yl)methyl)-6-cyclopropylimidazo[1,2-a]pyridin-2-yl)methyl)-N-((7-chloroimidazo[1,5-a]pyridin-1-yl)methyl)-1H-pyrazole-4-carboxamide (2.5 mg, yield: 11%) as a light yellow solid. ESI-MS [M+H]$^+$: 528.1. Purity: 98.5 (214 nm), 93.9 (254 nm). $^1$H NMR (400 MHz, DMSO-d$_6$) δ 9.10 (s, 1H), 8.58 (t, J=5.6 Hz, 1H), 8.30 (d, J=8.4 Hz, 3H), 8.17 (s, 1H), 7.87 (s, 1H), 7.78 (s, 1H), 7.69 (s, 1H), 7.00 (s, 1H), 6.65 (dd, J=7.4, 2.0 Hz, 1H), 5.38 (s, 2H), 4.55 (d, J=5.7 Hz, 2H), 4.50 (s, 2H), 1.98-1.84 (m, 1H), 0.93-0.89 (m, 2H), 0.66-0.63 (m, 2H).

Example 156

Scheme 155

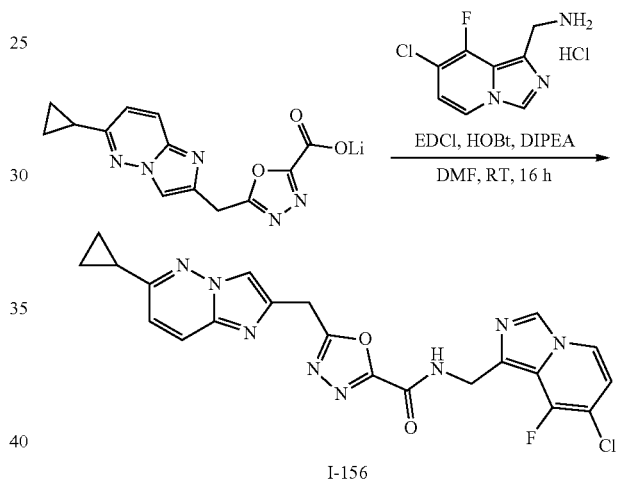

I-156

Synthesis of N-((7-chloro-8-fluoroimidazo[1,5-a]pyridin-1-yl)methyl)-5-((6-cyclopropylimidazo[1,2-b]pyridazin-2-yl)methyl)-1,3,4-oxadiazole-2-carboxamide (I-156)

To a solution of lithium 5-((6-cyclopropylimidazo[1,2-b]pyridazin-2-yl)methyl)-1,3,4-oxadiazole-2-carboxylate (50 mg, 0.13 mmol, crude) in DMF (5 mL) was added EDCI (58 mg, 0.3 mmol), HOBT (40 mg, 0.3 mmol), DIPEA (65 mg, 0.5 mmol) and (7-chloro-8-fluoroimidazo[1,5-a]pyridin-1-yl)methanamine hydrochloride (59 mg, 0.25 mmol). The reaction was stirred at RT for 16 h. The mixture was poured into H$_2$O, the solid formed, filtered and washed with H$_2$O and MeOH to give N-((7-chloro-8-fluoroimidazo[1,5-a]pyridin-1-yl)methyl)-5-((6-cyclopropylimidazo[1,2-b]pyridazin-2-yl)methyl)-1,3,4-oxadiazole-2-carboxamide (15 mg, yield: 25%) as a yellow solid. ESI-MS [M+H]$^+$: 467.1. Purity: 96.71% (214 nm), 96.91% (254 nm). H NMR (400 MHz, DMSO-d$_6$) δ 9.63 (t, J=5.4 Hz, 1H), 8.45 (d, J=2.2 Hz, 1H), 8.22 (d, J=7.4 Hz, 1H), 8.14 (s, 1H), 7.91 (d, J=9.4 Hz, 1H), 7.09 (d, J=9.4 Hz, 1H), 6.78 (t, J=6.9 Hz, 1H), 4.70 (d, J=5.5 Hz, 2H), 4.47 (s, 2H), 2.21-2.13 (m, 1H), 1.10-1.03 (m, 2H), 1.00-0.93 (m, 2H).

Example 157

Scheme 156

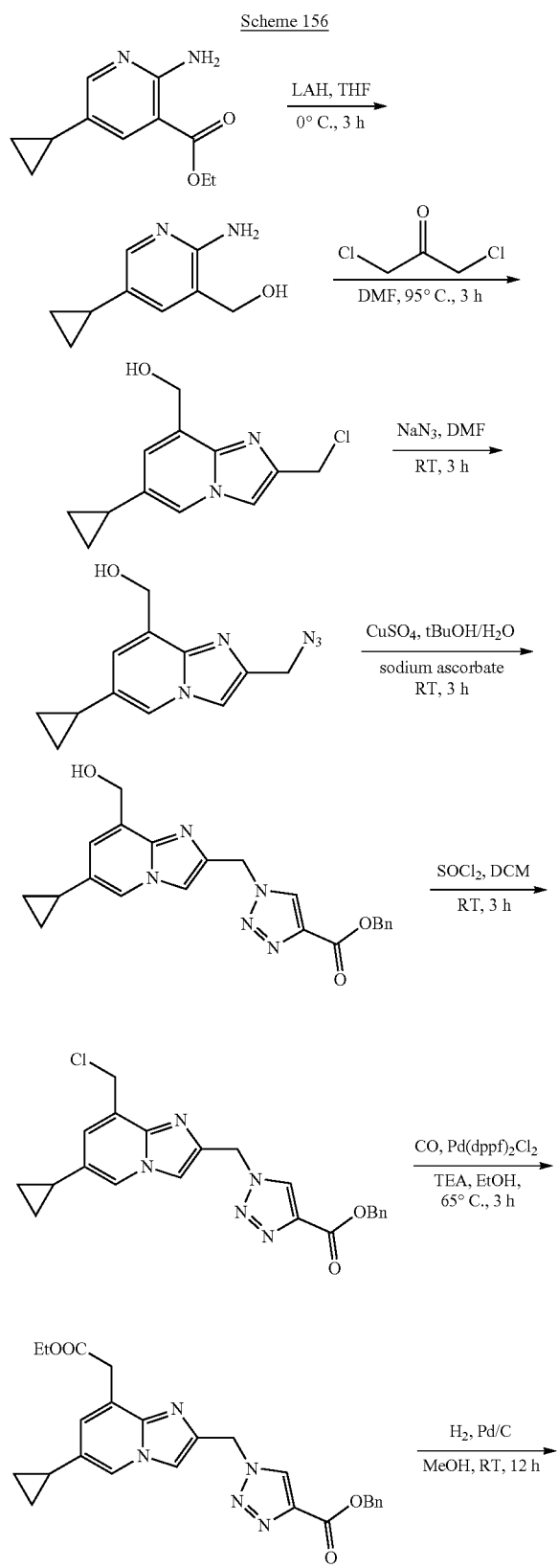

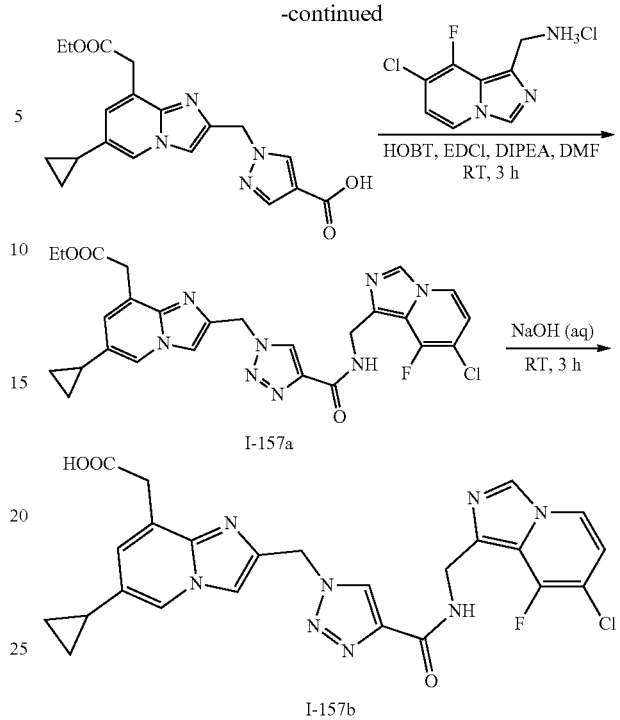

Synthesis of (2-amino-5-cyclopropylpyridin-3-yl)methanol

To a mixture of ethyl 2-amino-5-cyclopropylnicotinate (7.4 g, 36 mmol) in THF (70 mL) was added LAH (2.3 g, 61 mmol) was stirred at 0° C. The mixture was stirred at 0° C. for 3 h under $N_2$ atmosphere. The reaction was monitored by LCMS until the starting material consumed. The reaction was quenched with $H_2O$ (5 mL), NaOH (15% aq., 5 mL), $H_2O$ (15 mL), after the mixture was stirred for 10 min, the mixture was filtered through celite and concentrated to give a residue. Which was diluted with $H_2O$ (100 mL) and extracted with EtOAc (100 mL×5). The combined organic layers were washed with brine, dried over $Na_2SO_4$, concentrated in vacuo to give the crude product, which was purified with silica gel (eluent: EtOAc/PE: 1/2 to 1/0) to give the (2-amino-5-cyclopropylpyridin-3-yl)methanol (5 g, yield: 84%) as a white solid. ESI-MS [M+H]$^+$: 165.2.

Synthesis of (2-(chloromethyl)-6-cyclopropylimidazo[1,2-a]pyridin-8-yl)methanol To a solution of (2-amino-5-cyclopropylpyridin-3-yl)methanol (5 g, 30 mmol) in DMF (30 mL) was added 1,3-dichloropropan-2-one (14.8 g, 117 mmol). The mixture was stirred at 95° C. for 3 h. The reaction was monitored by LCMS until the starting material consumed. The reaction was quenched with saturated aqueous $NaHCO_3$ until pH=8 and extracted with EtOAc (100 mL×3). The combined organic layers were washed with brine, dried over $Na_2SO_4$, concentrated in vacuo to give the crude product, which was purified with silica gel (eluent: DCM/MeOH: 50/1 to 10/1) to give (2-(chloromethyl)-6-cyclopropylimidazo[1,2-a]pyridin-8-yl)methanol (4.7 g, yield: 66%) as a yellow solid. ESI-MS [M+H]$^+$: 237.1.

Synthesis of (2-(azidomethyl)-6-cyclopropylimidazo[1,2-a]pyridin-8-yl)methanol To a solution of (2-(chloromethyl)-6-cyclopropylimidazo[1,2-a]pyridin-8-yl)methanol (4.7 g, 20 mmol) in DMF (30 mL) was added sodium azide (1.82 g, 28 mmol). The mixture was stirred at RT for 3 h. The reaction was monitored by LCMS until the starting material consumed. The reaction was quenched with $H_2O$ (100 mL) and extracted with EtOAc (100 mL×3). The combined organic layers were washed with brine, dried over $Na_2SO_4$, concentrated in vacuo to give the crude product, which was purified with silica gel (eluent: DCM/MeOH: 50/1 to 10/1) to give (2-(azidomethyl)-6-cyclopropylimidazo[1,2-a]pyridin-8-yl)methanol (2.1 g, yield: 43%) as a white solid. ESI-MS [M+H]$^+$: 244.2.

Synthesis of benzyl 1-((6-cyclopropyl-8-(hydroxymethyl)imidazo[1,2-a]pyridin-2-yl)methyl)-1H-1,2,3-triazole-4-carboxylate A mixture of (2-(azidomethyl)-6-cyclopropylimidazo[1,2-a]pyridin-8-yl)methanol (2.1 g, 8.6 mmol) benzyl propiolate (2.1 g, 13 mmol), sodium ascorbate (1.7 g, 8.6 mmol), $CuSO_4$ (1.4 g, 8.6 mmol) in tBuOH/$H_2O$ (20 mL/20 mL) was stirred at RT for 3 h. The reaction was quenched with $H_2O$ (50 mL) and extracted with EtOAc (100 mL×3). The combined organic layers were washed with brine, dried over $Na_2SO_4$, concentrated in vacuo to give the crude product, which was purified with silica gel (eluent: DCM/MeOH: 50/1 to 10/1) to give benzyl 1-((6-cyclopropyl-8-(hydroxymethyl)imidazo[1,2-a]pyridin-2-yl)methyl)-1H-1,2,3-triazole-4-carboxylate (1.4 g, yield: 40%) as a white solid. ESI-MS [M+H]$^+$: 404.2.

Synthesis of benzyl 1-((8-(chloromethyl)-6-cyclopropylimidazo[1,2-a]pyridin-2-yl)methyl)-1H-1,2,3-triazole-4-carboxylate To a mixture of benzyl 1-((6-cyclopropyl-8-(hydroxymethyl)imidazo[1,2-a]pyridin-2-yl)methyl)-1H-1,2,3-triazole-4-carboxylate (1.4 g, 3.5 mmol) in DCM (15 mL) was added $SOCl_2$ (5 mL). The mixture was stirred at RT for 3 h. The reaction was concentrated in vacuo to give the crude of benzyl 1-((8-(chloromethyl)-6-cyclopropylimidazo[1,2-a]pyridin-2-yl)methyl)-1H-1,2,3-triazole-4-carboxylate (1.43 g, crude) as a yellow solid. ESI-MS [M+H]$^+$: 422.1.

Synthesis of benzyl 1-((6-cyclopropyl-8-(2-ethoxy-2-oxoethyl)imidazo[1,2-a]pyridin-2-yl)methyl)-1H-1,2,3-triazole-4-carboxylate To a mixture of benzyl 1-((8-(chloromethyl)-6-cyclopropylimidazo[1,2-a]pyridin-2-yl)methyl)-1H-1,2,3-triazole-4-carboxylate (1.4 g, 3.4 mmol) in EtOH (15 mL) was added Pd(dppf)$_2$Cl$_2$ (38 mg, 0.34 mmol) and TEA (1.7 g, 17 mmol), the mixture was stirred at 65° C. for 3 h under CO atmosphere. The reaction was concentrated in vacuo to give the crude product, which was purified with silica gel (eluent: DCM/MeOH: 50/1 to 10/1) to give benzyl 1-((6-cyclopropyl-8-(2-ethoxy-2-oxoethyl)imidazo[1,2-a]pyridin-2-yl)methyl)-1H-1,2,3-triazole-4-carboxylate (1.1 g, yield: 70%) as a white solid. ESI-MS [M+H]$^+$: 460.1.

Synthesis of 1-((6-cyclopropyl-8-(2-ethoxy-2-oxoethyl)imidazo[1,2-a]pyridin-2-yl)methyl)-1H-1,2,3-triazole-4-carboxylic Acid To a mixture of benzyl 1-((6-cyclopropyl-8-(2-ethoxy-2-oxoethyl)imidazo[1,2-a]pyridin-2-yl)methyl)-1H-1,2,3-triazole-4-carboxylate (1.1 g, 2.4 mmol) in MeOH (20 mL) was added Pd/C (10%, 200 mg). The mixture was stirred at RT under $H_2$ atmosphere for 12 h. The reaction was filtered and washed with methanol, the filtrate was concentrated in vacuo to give the 1-((6-cyclopropyl-8-(2-ethoxy-2-oxoethyl)imidazo[1,2-a]pyridin-2-yl)methyl)-1H-1,2,3-triazole-4-carboxylic acid (600 mg, yield: 67%) as a yellow solid. ESI-MS [M+H]$^+$: 370.2.

Synthesis of Ethyl 2-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)acetate (I-157a)

To a mixture of 1-((6-cyclopropyl-8-(2-ethoxy-2-oxoethyl)imidazo[1,2-a]pyridin-2-yl)methyl)-1H-1,2,3-triazole-4-carboxylic acid (300 mg, 0.81 mmol) in DMF (5 mL) was added (7-chloro-8-fluoroimidazo[1,5-a]pyridin-1-yl)methanamine HCl salt (228 mg, 0.97 mmol), HOBT (147 mg, 1.1 mmol), EDCI (211 mg, 1.1 mmol) and DIPEA (502 mg, 4 mmol). The mixture was stirred at RT for 3 h. The reaction was quenched with $H_2O$ (30 mL) and extracted with EtOAc (50 mL×3). The combined organic layers were washed with brine, dried over $Na_2SO_4$, concentrated in vacuo to give the crude product, which was purified with silica gel (eluent: DCM/MeOH: 50/1 to 10/1) to give the ethyl 2-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)acetate (200 mg, yield: 45%) as a white solid. ESI-MS [M+H]$^+$: 551.2. Purity: 96.2 (214 nm), 95.9 (254 nm). $^1$H NMR (400 MHz, DMSO-d$_6$) δ 8.69 (t, J=5.2 Hz, 1H), 8.51 (s, 1H), 8.45 (s, 1H), 8.28 (s, 1H), 8.21 (d, J=7.2 Hz, 1H), 7.81 (s, 1H), 6.96 (s, 1H), 6.76 (t, J=6.7 Hz, 1H), 5.72 (s, 2H), 4.70 (d, J=5.2 Hz, 2H), 4.04 (q, J=7.1 Hz, 2H), 3.87 (s, 2H), 1.97-1.87 (m, 1H), 1.12 (t, J=7.1 Hz, 3H), 0.98-0.88 (m, 2H), 0.70-0.62 (m, 2H).

Synthesis of 2-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)acetic acid (I-157b)

A mixture of ethyl 2-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)acetate (100 mg, 0.18 mmol) and NaOH (20 mg in 1 mL $H_2O$) in EtOH (20 mL) was stirred at RT for 3 h. The reaction was quenched with HCl (1N, 1 mL). The resulting mixture was concentrated to give the crude which was purified by Prep-HPLC to give 2-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)acetic acid (18 mg, 19% yield) as a white solid. ESI-MS [M+H]$^+$: 523.0. Purity: 91.0 (214 nm), 94.5 (254 nm). $^1$H NMR (400 MHz, DMSO-d$_6$) δ 8.72 (t, J=4.8 Hz, 1H), 8.53 (s, 1H), 8.45 (s, 1H), 8.31-8.17 (m, 2H), 7.78 (s, 1H), 6.94 (s, 1H), 6.76 (t, J=6.9 Hz, 1H), 5.72 (s, 2H), 4.70 (d, J=5.3 Hz, 2H), 3.75 (s, 2H), 1.95-1.86 (m, 1H), 0.95-0.85 (m, 2H), 0.67-0.62 (m, 2H).

Example 158

Scheme 157

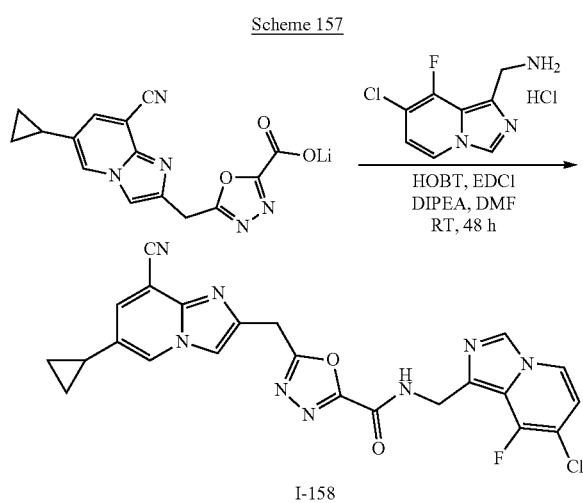

I-158

Synthesis of N-((7-chloro-8-fluoroimidazo[1,5-a]pyridin-1-yl)methyl)-5-((8-cyano-6-cyclopropylimidazo[1,2-a]pyridin-2-yl)methyl)-1,3,4-oxadiazole-2-carboxamide A mixture of lithium 5-((8-cyano-6-cyclopropylimidazo[1,2-a]pyridin-2-yl)methyl)-1,3,4-oxadiazole-2-carboxylate (100 mg, 0.32 mmol), (7-chloro-8-fluoroimidazo[1,5-a]pyridin-1-yl)methanamine (113 mg, 0.48 mmol), EDCI (123 mg, 0.64 mmol), HOBT (86 mg, 0.64 mmol) and DIPEA (206 mg, 1.6 mmol) in DMF (3 mL) was stirred at RT for 48 h. The mixture was concentrated to remove DMF, diluted with DCM/MeOH (30 mL, 10/1 (v/v)) and washed with H$_2$O (20 mL×2). The organic layers were separated, dried over Na$_2$SO$_4$, and concentrated in vacuo to give the crude product, which was purified by silica gel chromatography (DCM/MeOH=10/1) to give N-((7-chloro-8-fluoroimidazo[1,5-a]pyridin-1-yl)methyl)-5-((8-cyano-6-cyclopropylimidazo[1,2-a]pyridin-2-yl)methyl)-1,3,4-oxadiazole-2-carboxamide (20 mg, yield: 13%) as a yellow solid. ESI-MS [M+H]$^+$: 490.9. Purity: 99.0 (214 nm), 98.6 (254 nm). $^1$H NMR (400 MHz, DMSO-d$_6$) δ 9.65 (t, J=5.4 Hz, 1H), 8.69 (d, J=1.3 Hz, 1H), 8.45 (d, J=2.4 Hz, 1H), 8.22 (d, J=7.4 Hz, 1H), 8.00 (s, 1H), 7.78 (d, J=1.6 Hz, 1H), 6.83-6.73 (m, 1H), 4.70 (d, J=5.5 Hz, 2H), 4.53 (s, 2H), 2.02-1.95 (m, 1H), 1.02-0.89 (m, 2H), 0.78-0.74 (m, 2H).

Example 159

Scheme 158

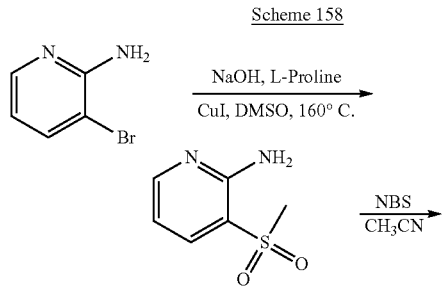

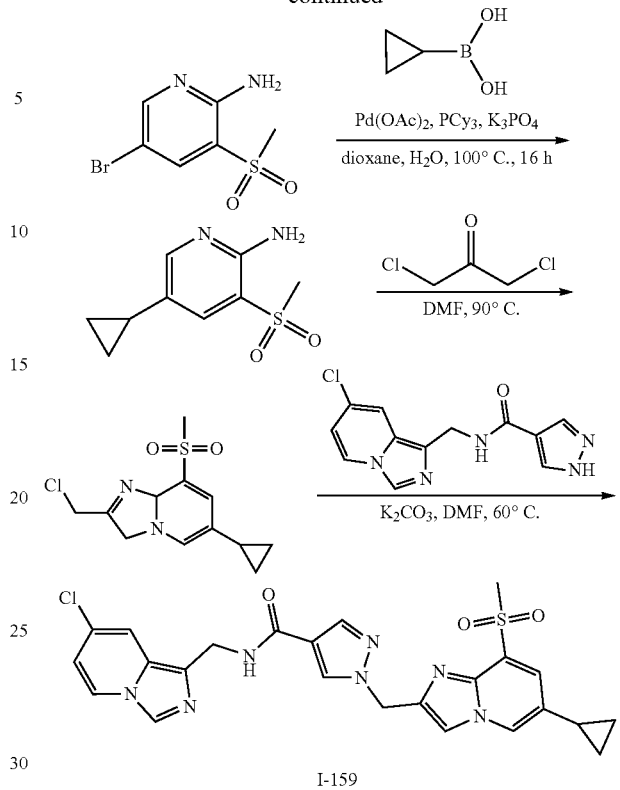

I-159

Synthesis of 3-(methylsulfonyl)pyridin-2-amine

To a solution of 3-bromopyridin-2-amine (2 g, 11.5 mmol) in DMSO (20 mL) was added sodium methanesulfonate (1.534 g, 15 mmol), L-Proline (266 mg, 2.31 mmol), CuI (220 mg, 1.16 mmol) and NaOH (92 mg, 2.31 mmol). The reaction mixture was degassed with nitrogen for 2 min and irradiated in microwave at 160° C. for 40 min, and subsequently quenched with H$_2$O (30 mL), extracted with EtOAc (50 mL×3). The combined organic layers were concentrated to give the crude product, which was purified by silica gel chromatography (PE/EtOAc=2/1) to give the 3-(methylsulfonyl)pyridin-2-amine as a yellow solid (843 mg, yield: 42%). ESI-MS [M+H]$^+$: 173.1.

Synthesis of Ethyl 5-bromo-3-(methylsulfonyl)pyridin-2-amine

To a solution 3-(methylsulfonyl)pyridin-2-amine (843 mg, 4.9 mmol) in CH$_3$CN (20 mL) was added NBS (915 mg, 5.14 mmol) at RT. The resulting mixture was stirred at RT for 0.5 h and subsequently concentrated to give the residue, which was diluted with H$_2$O (50 mL) and extracted with EtOAc (50 mL×3). The combined organic layers were washed with brine, dried over Na$_2$SO$_4$, and concentrated to give the crude product, which was purified by silica gel chromatography (PE/EtOAc=1/1) to give 5-bromo-3-(methylsulfonyl)pyridin-2-amine (1.161 g, yield: 94%) as a yellow solid. ESI-MS [M+H]$^+$: 250.9

Synthesis of 5-cyclopropyl-3-(methylsulfonyl)pyridin-2-amine

To a solution of 5-bromo-3-(methylsulfonyl)pyridin-2-amine (1.16 g, 4.62 mmol) in dioxane/H$_2$O (50 mL/50 mL)

was added cyclopropylboronic acid (794 mg, 9.25 mmol), Pd(OAc)₂ (104 mg, 0.46 mmol), PCy₃ (259 mg, 0.925 mmol) and K₃PO₄ (1.963 g, 9.25 mmol). The reaction mixture was stirred at 100° C. for 14 h under nitrogen. Then the mixture was concentrated in vacuo. Water (100 mL) was added and the mixture was extracted with EtOAc (100 mL×3). The combined organic layers were concentrated to give the crude product, which was purified by silica gel chromatography (PE/EtOAc=1/1) to give the 5-cyclopropyl-3-(methylsulfonyl)pyridin-2-amine as a yellow solid (619 mg, yield: 63%). ESI-MS [M+H]⁺: 213.1.

Synthesis of 2-(chloromethyl)-6-cyclopropyl-8-(methylsulfonyl)-3,8a-dihydroimidazo[1,2-a]pyridine To a solution of 5-cyclopropyl-3-(methylsulfonyl)pyridin-2-amine (102 mg, 0.45 mmol) and 1,3-dichloropropan-2-one (183 mg, 1.44 mmol) in EtOAc (10 mL). The reaction mixture was stirred at 90° C. for 20 h. Then H₂O (30 mL) was added and extracted with EtOAc (50 mL×3). The combined organic layers were concentrated to give the crude product, which was purified by silica gel chromatography (PE/EtOAc=2/1) to give 2-(chloromethyl)-6-cyclopropyl-8-(methylsulfonyl)-3,8a-dihydroimidazo[1,2-a]pyridine (97 mg, yield: 75%) as a yellow solid. ESI-MS [M+H]⁺: 285.0.

Synthesis of N-((7-chloroimidazo[1,5-a]pyridin-1-yl)methyl)-1-((6-cyclopropyl-8-(methylsulfonyl)imidazo[1,2-a]pyridin-2-yl)methyl)-1H-pyrazole-4-carboxamide (I-159)

To a solution of 2-(chloromethyl)-6-cyclopropyl-8-(methylsulfonyl)imidazo[1,2-a]pyridine (97 mg, 0.34 mmol), N-((7-chloroimidazo[1,5-a]pyridin-1-yl)methyl)-1H-pyrazole-4-carboxamide (94 mg, 0.68 mmol) and K₂CO₃ (94 mg, 0.68 mmol) in DMF (10 mL). The resulting mixture was stirred for overnight at 60° C. The mixture was concentrated to remove solvent to give the crude product, which was purified by prep-HPLC to give N-((7-chloroimidazo[1,5-a]pyridin-1-yl)methyl)-1-((6-cyclopropyl-8-(methylsulfonyl)imidazo[1,2-a]pyridin-2-yl)methyl)-1H-pyrazole-4-carboxamide (40 mg, yield: 23%) as a light yellow solid. ESI-MS [M+H]⁺: 523.9. Purity: 96.55% (214 nm), 95.34% (254 nm). ¹H NMR (400 MHz, MeOD) δ 9.07 (s, 1H), 8.54 (s, 1H), 8.36 (d, J=7.6 Hz, 1H), 8.24 (s, 1H), 7.98 (s, 1H), 7.92 (s, 2H), 7.81 (s, 1H), 7.00 (d, J=2.0 Hz, 1H), 5.56 (s, 2H), 4.80 (s, 2H), 3.40 (s, 3H), 2.11-2.03 (m, 1H), 1.11-1.03 (m, 2H), 0.81-0.76 (m, 2H).

Example 160

Scheme 159

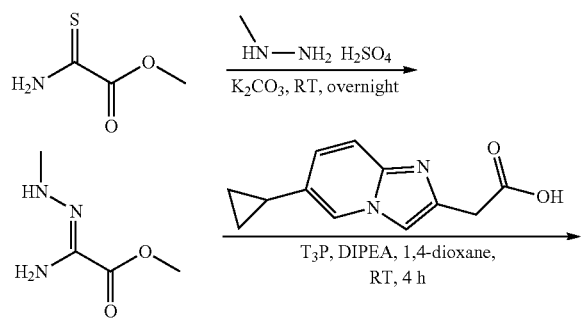

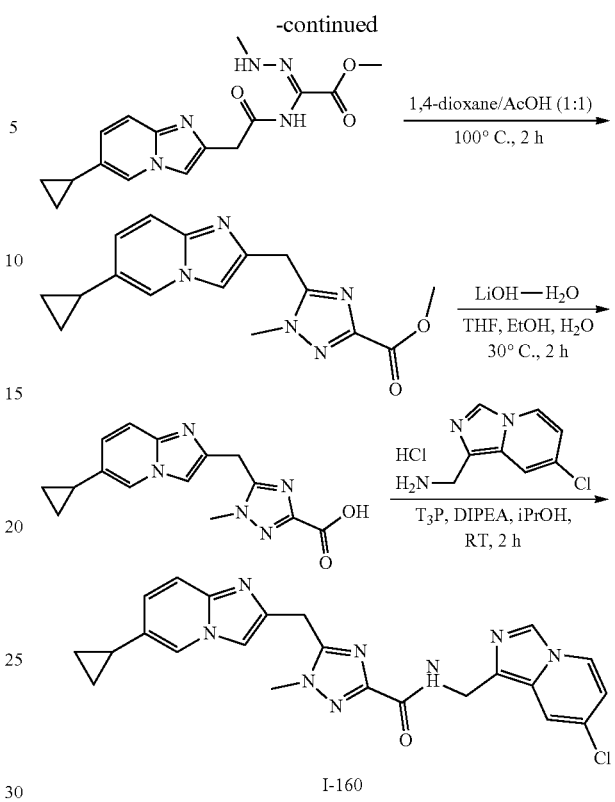

I-160

Synthesis of Methyl 2-amino-2-(2-methylhydrazono)acetate

A mixture of methylhydrazine sulfate (360 mg, 2.5 mmol) and K₂CO₃ (690 mg, 5.0 mmol) in ethanol (10 mL) was stirred at RT for 10 minutes, and then ethyl 2-amino-2-thioxoacetate (333 mg, 2.5 mmol) was added at 0° C. The mixture was stirred at RT overnight and filtered. The filtrate was concentrated and purified by Prep-TLC (DCM/MeOH=15:1) to give methyl 2-amino-2-(2-methylhydrazono)acetate (180 mg, yield: 55%) as a yellow solid. ESI-MS [M+H]⁺: 132.2

Synthesis of Methyl 2-(2-(6-cyclopropylimidazo[1,2-a]pyridin-2-yl)acetamido)-2-(2-methylhydrazono)acetate A solution of methyl 2-amino-2-(2-methylhydrazono)acetate (52 mg, 0.4 mmol), 2-(6-cyclopropylimidazo[1,2-a]pyridin-2-yl)acetic acid (86.4 mg, 0.4 mmol) in 1,4-dioxane (6 mL) was stirred at RT for 10 minutes, and then T₃P (50 wt. % in EA, 524 mg, 0.8 mmol) and DIPEA (100 mg, 0.8 mmol) were added. After the mixture was stirred at RT for 1.5 h, solvent was concentrated and the crude product was used into the next step without further purification. ESI-MS [M+H]⁺: 330.2.

Synthesis of Methyl 5-((6-cyclopropylimidazo[1,2-a]pyridin-2-yl)methyl)-1-methyl-1H-1,2,4-triazole-3-carboxylate A solution of methyl 2-(2-(6-cyclopropylimidazo[1,2-a]pyridin-2-yl)acetamido)-2-(2-methylhydrazono)acetate (crude from last step) in AcOH/1,4-dioxane (1:1, 5 mL) was stirred at 100° C. for 2 h. Water (20 mL) was added and the mixture was extracted with EtOAc (50 mL*3). The combined organic layers were concentrated and purified by Prep-TLC (DCM:MeOH=15:1) to give methyl 5-((6-cyclopropylimidazo[1,2-a]pyridin-2-yl)methyl)-1-methyl-1H-1,2,4-triazole-3-carboxylate (60 mg, yield: 48% over 2 steps) as a white solid. ESI-MS [M+H]$^+$: 312.2.

Synthesis of 5-((6-cyclopropylimidazo[1,2-a]pyridin-2-yl)methyl)-1-methyl-1H-1,2,4-triazole-3-carboxylic Acid To a solution of methyl 5-((6-cyclopropylimidazo[1,2-a]pyridin-2-yl)methyl)-1-methyl-1H-1,2,4-triazole-3-carboxylate (50 mg, 0.16 mmol) in ethanol (3 mL)/THF (3 mL)/H$_2$O (1.5 mL) was added LiOH.H$_2$O (16 mg, 0.39 mmol). The mixture was stirred at 30° C. for 2 h. The mixture was concentrated and the crude product (60 mg, crude) was used into the next step without further purification. ESI-MS [M+H]$^+$: 298.2.

Synthesis of N-((7-chloroimidazo[1,5-a]pyridin-1-yl)methyl)-5-((6-cyclopropylimidazo[1,2-a]pyridin-2-yl)methyl)-1-methyl-1H-1,2,4-triazole-3-carboxamide A mixture of 5-((6-cyclopropylimidazo[1,2-a]pyridin-2-yl)methyl)-1-methyl-1H-1,2,4-triazole-3-carboxylic acid (60 mg, crude from last step), (7-chloroimidazo[1,5-a]pyridin-1-yl)methanamine hydrochloride (41 mg, 0.19 mmol), and DIPEA (101 mg, 0.785 mmol) in isopropanol (6 mL) was stirred at RT for 10 minutes. T$_3$P (50 wt. % in EA, 250 mg, 0.39 mmol) was added. The mixture was stirred at RT overnight. Water (10 mL) was added and extracted with EtOAc (30 mL*3). The combined organic layers were concentrated and purified by Prep-HPLC to give N-((7-chloroimidazo[1,5-a]pyridin-1-yl)methyl)-5-((6-cyclopropylimidazo[1,2-a]pyridin-2-yl)methyl)-1-methyl-1H-1,2,4-triazole-3-carboxamide (7.3 mg, yield: 10% over 2 steps) as a yellow solid. ESI-MS [M+H]$^+$: 461.1. Purity: 98.14 (214 nm), 98.24 (254 nm). $^1$H NMR (400 MHz, DMSO-d$_6$) δ 8.70 (t, J=5.9 Hz, 1H), 8.28-8.25 (m, 3H), 7.81 (s, 1H), 7.64 (s, 1H), 7.32 (d, J=9.3 Hz, 1H), 6.92 (d, J=9.2 Hz, 1H), 6.61 (dd, J=7.4, 1.8 Hz, 1H), 4.56 (d, J=5.9 Hz, 2H), 4.25 (s, 2H), 3.86 (s, 3H), 1.91-1.85 (m, 1H), 0.90-0.85 (m, 2H), 0.64-0.61 (m, 2H).

Example 161

Scheme 160

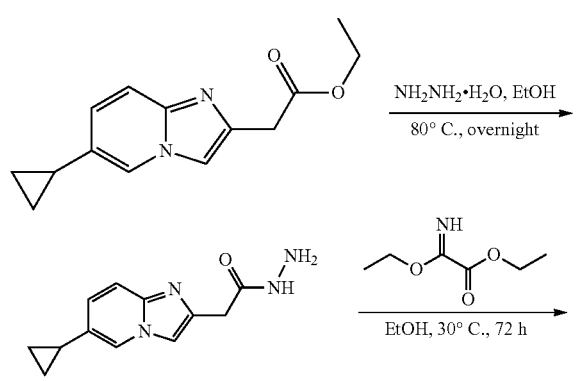

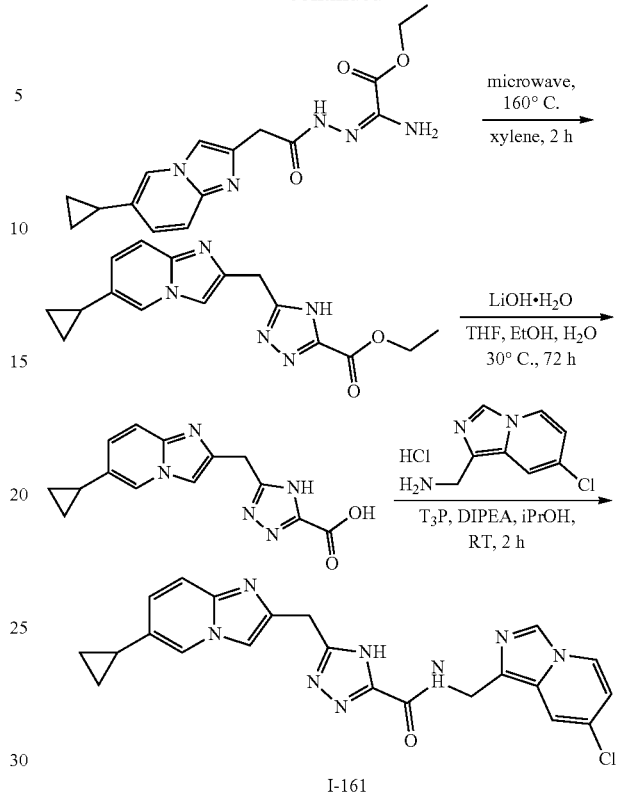

I-161

Synthesis of 2-(6-cyclopropylimidazo[1,2-a]pyridin-2-yl)acetohydrazide

A mixture of ethyl 2-(6-cyclopropylimidazo[1,2-a]pyridin-2-yl)acetate (650 mg, 2.66 mmol) and hydrazine hydrate (2.0 mL) in ethanol (8 mL) was stirred at 80° C. overnight. The mixture was concentrated and purified by silica gel chromatography (DCM/MeOH=5:1) to give 2-(6-cyclopropylimidazo[1,2-a]pyridin-2-yl)acetohydrazide (240 mg, yield: 39%) as a white solid. ESI-MS [M+H]$^+$: 231.1

Synthesis of Ethyl 2-amino-2-(2-(2-(6-cyclopropylimidazo[1,2-a]pyridin-2-yl)acetyl)hydrazono)acetate A solution of 2-(6-cyclopropylimidazo[1,2-a]pyridin-2-yl)acetohydrazide (115 mg, 0.5 mmol) and ethyl 2-ethoxy-2-iminoacetate (145 mg, 1.0 mmol) in ethanol (2.0 mL) was stirred at RT for 3 days. The mixture was concentrated to get a yellow solid (165 mg, crude) which was used into the next step without further purification. ESI-MS [M+H]$^+$: 330.1.

Synthesis of Ethyl 5-((6-cyclopropylimidazo[1,2-a]pyridin-2-yl)methyl)-4H-1,2,4-triazole-3-carboxylate A solution of ethyl 2-amino-2-(2-(2-(6-cyclopropylimidazo[1,2-a]pyridin-2-yl)acetyl)hydrazono)acetate (165 mg, crude from last step) in xylene (4.0 mL) was stirred at 160° C. under microwave irradiation for 3 h. The mixture was concentrated and purified by Prep-TLC (DCM/MeOH=5:1) to give ethyl 5-((6-cyclopropylimidazo[1,2-a]pyridin-2-yl)methyl)-4H-1,2,4-triazole-3-carboxylate (100 mg, yield: 64% over 2 steps) as a yellow solid. ESI-MS [M+H]$^+$: 312.1.

Synthesis of 5-((6-cyclopropylimidazo[1,2-a]pyridin-2-yl)methyl)-4H-1,2,4-triazole-3-carboxylic Acid To a solution of ethyl 5-((6-cyclopropylimidazo[1,2-a]pyridin-2-yl)methyl)-4H-1,2,4-triazole-3-carboxylate (50 mg, 0.16 mmol) in ethanol (3 mL)/THF (3 mL)/H$_2$O (0.5 mL) was added LiOH.H$_2$O (13.5 mg, 0.32 mmol). After the mixture was stirred at RT overnight, solvent was concentrated and the crude (60 mg) was used into the next step without further purification. ESI-MS [M+H]$^+$: 284.2.

Synthesis of N-((7-chloroimidazo[1,5-a]pyridin-1-yl)methyl)-5-((6-cyclopropylimidazo[1,2-a]pyridin-2-yl)methyl)-4H-1,2,4-triazole-3-carboxamide (I-161)

A solution of crude 5-((6-cyclopropylimidazo[1,2-a]pyridin-2-yl)methyl)-4H-1,2,4-triazole-3-carboxylic acid (60 mg, crude from last step), (7-chloroimidazo[1,5-a]pyridin-1-yl)methanamine hydrochloride (35 mg, 0.16 mmol), and DIPEA (83 mg, 0.64 mmol) in isopropanol (6 mL) was stirred at RT for 10 minutes. And then T$_3$P (50 wt. % in EA, 204 mg, 0.32 mmol) was added. The mixture was stirred at RT overnight, H$_2$O (15 mL) was added and extracted with DCM and MeOH (10:1, 50 mL*3). The combined organic layers were concentrated and purified by Prep-HPLC to give N-((7-chloroimidazo[1,5-a]pyridin-1-yl)methyl)-5-((6-cyclopropylimidazo[1,2-a]pyridin-2-yl)methyl)-4H-1,2,4-triazole-3-carboxamide (13.1 mg, yield: 18% over 2 steps) as a white solid. ESI-MS [M+H]$^+$: 447.2. Purity: 95.13 (214 nm), 96.02 (254 nm). $^1$H NMR (400 MHz, DMSO-d$_6$) δ 8.83 (s, 1H), 8.24-8.22 (m, 3H), 7.79 (s, 1H), 7.55 (s, 1H), 7.27 (d, J=9.3 Hz, 1H), 6.88 (d, J=9.3 Hz, 1H), 6.58 (dd, J=7.4, 1.8 Hz, 1H), 4.54 (d, J=5.9 Hz, 2H), 4.09 (s, 2H), 1.87-1.81 (m, 1H), 0.85-0.82 (m, 2H), 0.61-0.57 (m, 2H).

Example 162

Scheme 161

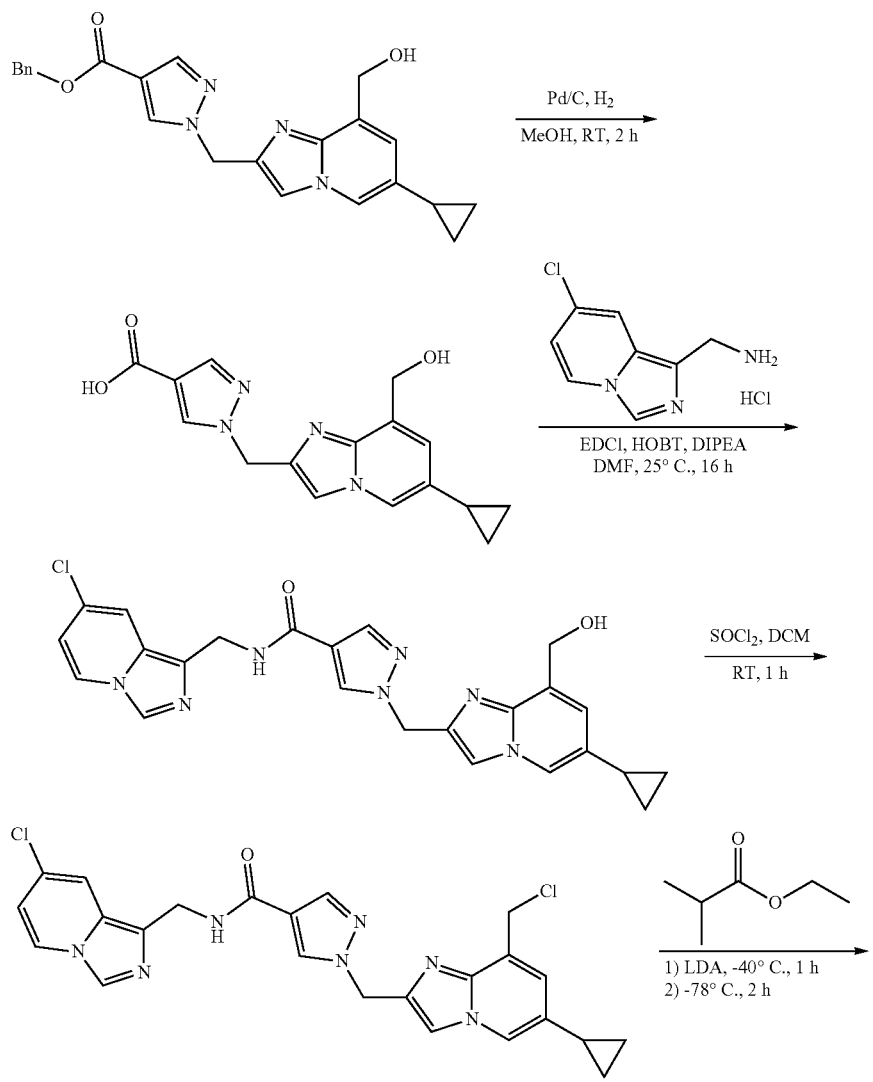

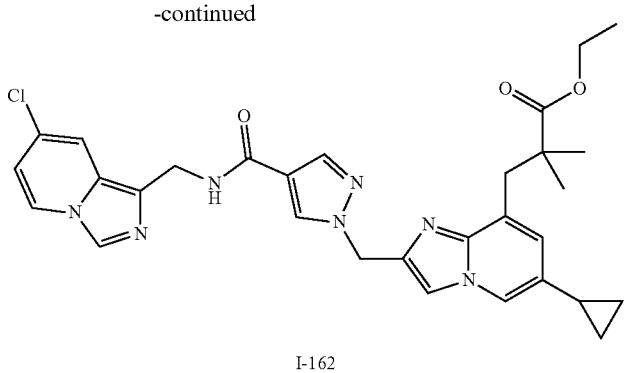

I-162

Synthesis of 1-((6-cyclopropyl-8-(hydroxymethyl)imidazo[1,2-a]pyridin-2-yl)methyl)-1H-pyrazole-4-carboxylic Acid The mixture of benzyl 1-((6-cyclopropyl-8-(hydroxymethyl)imidazo[1,2-a]pyridin-2-yl)methyl)-1H-pyrazole-4-carboxylate (260 mg, 0.646 mmol) and Pd/C (100 mg) in MeOH (6 mL) and THF (3 mL) was stirred at RT for 2 h under $H_2$ (balloon). The reaction mixture was filtered and the filtrate was concentrated and dried in vacuo to give 1-((6-cyclopropyl-8-(hydroxymethyl)imidazo[1,2-a]pyridin-2-yl)methyl)-1H-pyrazole-4-carboxylic acid (180 mg, yield: 89%) as a yellow solid. ESI-MS [M+H]$^+$: 313.0.

Synthesis of N-((7-chloroimidazo[1,5-a]pyridin-1-yl)methyl)-1-((6-cyclopropyl-8-(hydroxymethyl)imidazo[1,2-a]pyridin-2-yl)methyl)-1H-pyrazole-4-carboxamide The mixture of 1-((6-cyclopropyl-8-(hydroxymethyl)imidazo[1,2-a]pyridin-2-yl)methyl)-1H-pyrazole-4-carboxylic acid (180 mg, 0.576 mmol), (5-chloro-2-(1H-tetrazol-5-yl)phenyl)methanamine (188 mg, 0.864 mmol), EDCI (133 mg, 0.691 mmol), HOBT (93 mg, 0.691 mmol) and DIPEA (223 mg, 1.728 mmol) in DMF (6 mL) was stirred at 25° C. for 16 h. The reaction mixture was poured into $H_2O$ (60 mL) and the precipitate was collected, dried in vacuo to give N-((7-chloroimidazo[1,5-a]pyridin-1-yl)methyl)-1-((6-cyclopropyl-8-(hydroxymethyl)imidazo[1,2-a]pyridin-2-yl)methyl)-1H-pyrazole-4-carboxamide (200 mg, yield: 73%) as a pale white solid. ESI-MS [M+H]$^+$: 475.9.

Synthesis of N-((7-chloroimidazo[1,5-a]pyridin-1-yl)methyl)-1-((8-(chloromethyl)-6-cyclopropylimidazo[1,2-a]pyridin-2-yl)methyl)-1H-pyrazole-4-carboxamide To a stirred solution of N-((7-chloroimidazo[1,5-a]pyridin-1-yl)methyl)-1-((6-cyclopropyl-8-(hydroxymethyl)imidazo[1,2-a]pyridin-2-yl)methyl)-1H-pyrazole-4-carboxamide (180 mg, 0.378 mmol) in DCM (10 mL) and THF (4 mL) was added dropwise of $SOCl_2$ (450 mg, 3.78 mmol) at 0° C. The mixture was stirred at RT for 1 h. The reaction mixture was concentrated. The residue was dissolved in EtOAc (30 mL) and washed with $NaHCO_3$ (30 mL) and brine (30 mL), dried over $Na_2SO_4$, concentrated and dried in vacuo to give N-((7-chloroimidazo[1,5-a]pyridin-1-yl)methyl)-1-((8-(chloromethyl)-6-cyclopropylimidazo[1,2-a]pyridin-2-yl)methyl)-1H-pyrazole-4-carboxamide (150 mg, crude) as a yellow solid. ESI-MS [M+H]$^+$: 494.0.

Synthesis of Ethyl 3-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)-2,2-dimethylpropanoate (I-162)

To a stirred solution of ethyl isobutyrate (0.53 g, 4.5 mmol) in THF (6 mL) was added LDA (2.4 mL, 2 M in THF) at −40° C. under $N_2$. After 1 h, the solution above was added dropwise to the suspension of N-((7-chloroimidazo[1,5-a]pyridin-1-yl)methyl)-1-((8-(chloromethyl)-6-cyclopropylimidazo[1,2-a]pyridin-2-yl)methyl)-1H-pyrazole-4-carboxamide (150 mg, crude from last step) in THF (10 mL) at −78° C. The resulting mixture was stirred for 2 h at −78° C. The reaction mixture was quenched with saturated aqueous $NH_4C$ (30 mL), then adjusted the pH to 9-10 by $NaHCO_3$ aqueous, extracted with EtOAc/THF (50 mL×3). The combined organics were washed with brine, dried over $Na_2SO_4$, concentrated and purified by Prep-TLC (DCM/MeOH=8/1) to give ethyl 3-(2-((4-(((7-chloroimidazo[1,5-a]pyridin-1-yl)methyl)carbamoyl)-1H-pyrazol-1-yl)methyl)-6-cyclopropylimidazo[1,2-a]pyridin-8-yl)-2,2-dimethylpropanoate (10 mg, yield: 5%) as a white solid. ESI-MS [M+H]$^+$: 574.1. Purity: 96.55 (214 nm), 95.05 (254 nm). $^1$H NMR (400 MHz, DMSO-$d_6$) δ 8.55 (t, J=5.5 Hz, 1H), 8.33-8.28 (m, 2H), 8.20 (s, 1H), 8.15 (s, 1H), 7.87 (s, 1H), 7.77 (s, 1H), 7.65 (s, 1H), 6.70-6.62 (m, 2H), 5.37 (s, 2H), 4.55 (d, J=5.7 Hz, 2H), 3.95 (q, J=7.1 Hz, 2H), 3.09 (s, 2H), 1.91-1.83 (m, 1H), 1.24-1.07 (m, 9H), 0.93-0.86 (m, 2H), 0.62-0.57 (m, 2H).

Example 163

Scheme 162

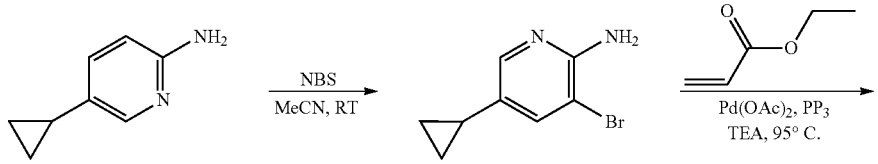

-continued
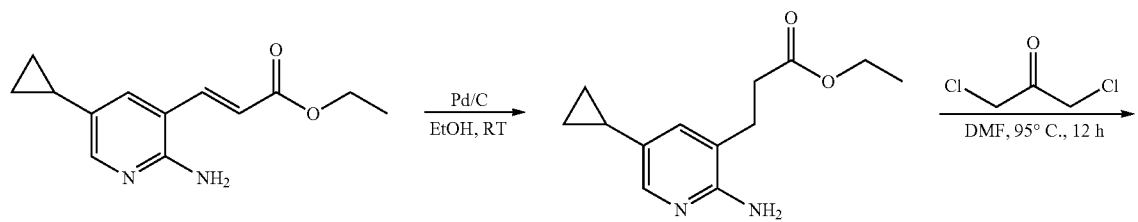
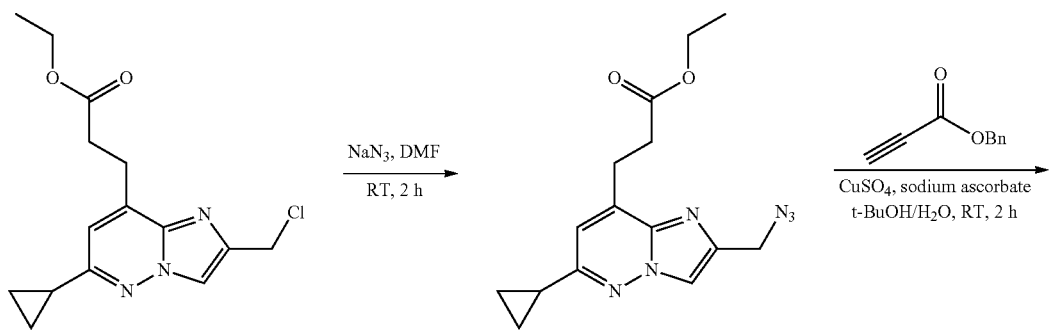
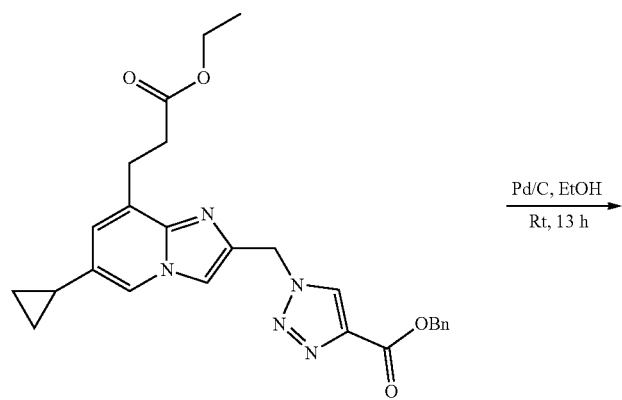
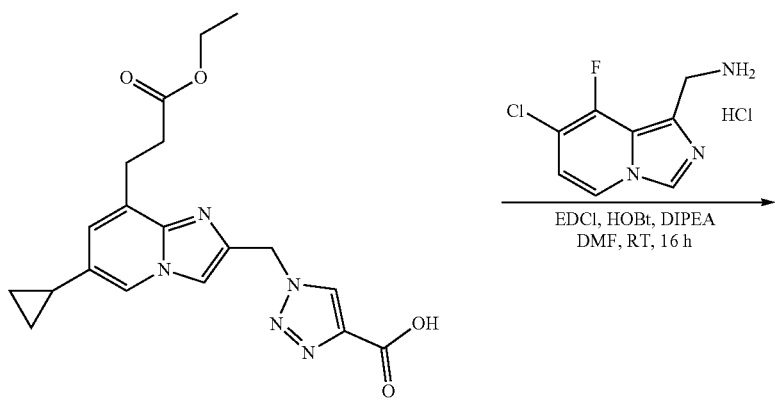

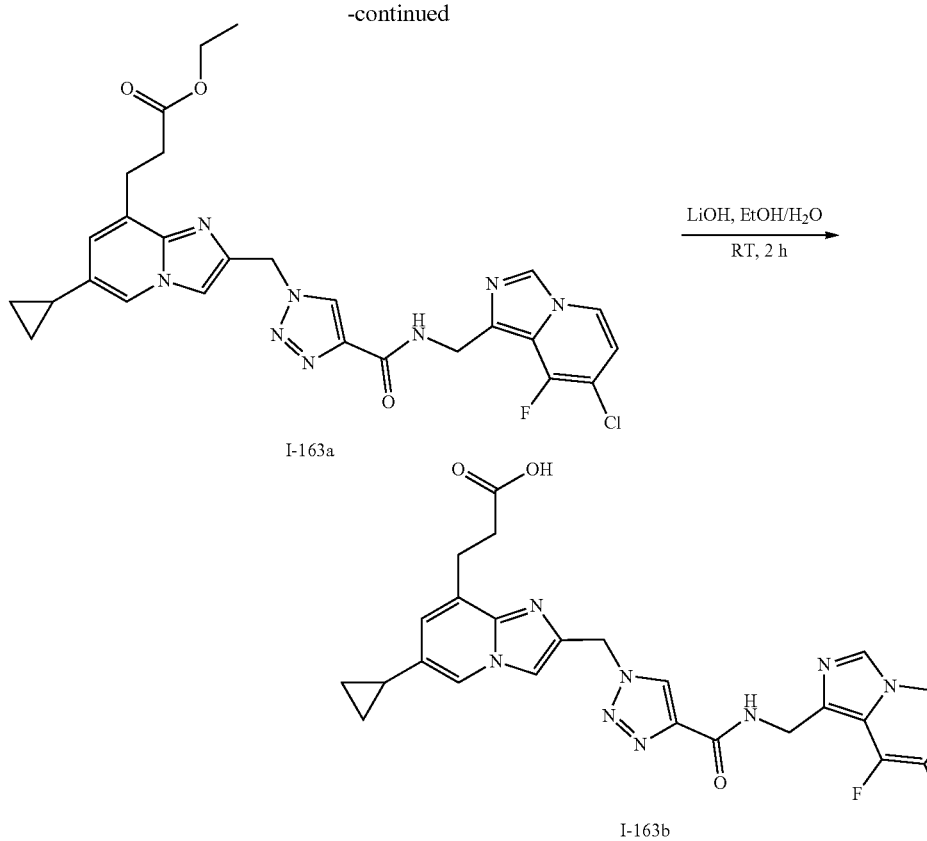

I-163a

I-163b

Synthesis of 3-bromo-5-cyclopropylpyridin-2-amine

A mixture of 5-cyclopropylpyridin-2-amine (10 g, 74.5 mmol) in MeCN (130 mL) was added 1-Bromo-2, 5-pyrrolidinedione (16 g, 89.4 mmol) at RT. The mixture was stirred for 3 h. The mixture was concentrated, diluted with $H_2O$ (200 mL) and exacted by EtOAc (200 mL×3) and $H_2O$ (250 mL). The combined organic phases were concentrated to give 3-bromo-5-cyclopropylpyridin-2-amine (15.0 g, crude) as a yellow solid. ESI-MS [M+H]$^+$: 213.0

Synthesis of Ethyl 3-(2-amino-5-cyclopropylpyridin-3-yl)acrylate

To a solution of 3-bromo-5-cyclopropylpyridin-2-amine (7.00 g, 33 mmol) in DMF (60 mL) was added TEA (15 mL), PPh$_3$ (1.74 g, 16.43 mmol), Pd(OAc)$_2$ (0.75 g 3.3 mmol) and ethyl acrylate (6 mL, 65.7 mmol) at RT. The mixture was heated to 95° C. and stirred for 16 h. Water (70 mL) was added and the mixture were exacted by EtOAc (100 mL×3). The organic phases were concentrated to give ethyl 3-(2-amino-5-cyclopropylpyridin-3-yl)acrylate (4 g, yield: crude) as a yellow solid. ESI-MS [M+H]$^+$: 233.1.

Synthesis of Ethyl 3-(2-amino-5-cyclopropylpyridin-3-yl)propanoate

To a solution of ethyl (E)-3-(2-amino-5-cyclopropylpyridin-3-yl)acrylate (4 g, crude from last step) in EtOH (50 mL)/EtOAc( ) (10 mL) was added Pd/C (400 mg) at RT. The mixture was stirred for 16 h. The mixture were filtered and concentrated to give ethyl 3-(2-amino-5-cyclopropylpyridin-3-yl)propanoate (4 g, crude) as a yellow oil. ESI-MS [M+H]$^+$: 235.1.

Synthesis of Ethyl 3-(2-(chloromethyl)-6-cyclopropylimidazo[1,2-a]pyridin-8-yl)propanoate To a solution of 3-(2-amino-5-cyclopropylpyridin-3-yl) propanoate (4 g, crude) in DMF (30 mL) was added 1,3-dichloropropan-2-one (11.7 g, 92 mmol) at RT. The mixture was heated to 95° C. and stirred for 16 h. $H_2O$ (100 mL) was added to reaction, exacted by EtOAc (100 mL×3). The organic phases were concentrated and purified by flash silica gel chromatography (0~60% EtOAc in PE) to give ethyl 3-(2-(chloromethyl)-6-cyclopropylimidazo[1,2-a]pyridin-8-yl)propanoate (2.2 g, yield: 22% over 3 steps) as a red oil. ESI-MS [M+H]$^+$: 307.1.

Synthesis of Ethyl 3-(2-(azidomethyl)-6-cyclopropylimidazo[1,2-a]pyridin-8-yl)propanoate To a solution of ethyl 3-(2-(chloromethyl)-6-cyclopropylimidazo[1,2-a]pyridin-8-yl)propanoate (2.2 g, 7.17 mmol) in DMF (30 mL) was added NaN$_3$ (416 mg, 6.40 mmol) at RT. The mixture was stirred for 2 h. $H_2O$ (100 mL) was added to reaction, exacted by EtOAc (100 mL×3). The combined organic phases were washed with brine, dried over Na$_2$SO$_4$, concentrated to give ethyl 3-(2-(azidomethyl)-6-cyclopropylimidazo[1,2-a]pyridin-8-yl)propanoate (1.6 g, crude) as a red oil. ESI-MS [M+H]$^+$: 314.1.

Synthesis of benzyl 1-((6-cyclopropyl-8-(3-ethoxy-3-oxopropyl)imidazo[1,2-a]pyridin-2-yl)methyl)-1H-1,2,3-triazole-4-carboxylate To a solution of ethyl 3-(2-(azidomethyl)-6-cyclopropylimidazo[1,2-a]pyridin-8-yl)propanoate (1.6 g, crude) in t-BuOH/H₂O (20 mL/20 mL) was added benzyl propiolate (0.98 g, 6.13 mmol), sodium ascorbate (0.202 g, 1.02 mmol) and CuSO₄ (0.163 g, 1.02 mmol) at RT. The mixture was stirred for 2 h. H₂O (50 mL) was added to reaction, exacted by DCM (50 mL×3). The combined organic phases were washed with brine, dried over Na₂SO₄, concentrated to give the benzyl 1-((6-cyclopropyl-8-(3-ethoxy-3-oxopropyl)imidazo[1,2-a]pyridin-2-yl)methyl)-1H-1,2,3-triazole-4-carboxylate (1.4 g, crude) as a red oil, which was used into next step without further purification. ESI-MS [M+H]⁺: 474.2.

Synthesis of 1-((6-cyclopropyl-8-(3-ethoxy-3-oxopropyl)imidazo[1,2-a]pyridin-2-yl)methyl)-1H-1,2,3-triazole-4-carboxylic Acid To a solution of benzyl 1-((6-cyclopropyl-8-(3-ethoxy-3-oxopropyl)imidazo[1,2-a]pyridin-2-yl)methyl)-1H-1,2,3-triazole-4-carboxylate (250 mg, crude) in EtOH/EtOAc (20 mL/20 mL) was added Pd/C (50 mg) at RT and stirred for 1 h. The mixture was filtered and washed with MeOH (100 mL), and the filtrate was concentrated to give 1-((6-cyclopropyl-8-(3-ethoxy-3-oxopropyl)imidazo[1,2-a]pyridin-2-yl)methyl)-1H-1,2,3-triazole-4-carboxylic acid (100 mg, crude) as a white solid. ESI-MS [M+H]⁺: 384.1.

Synthesis of Ethyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)propanoate (I-163a)

To a solution of 1-((6-cyclopropyl-8-(3-ethoxy-3-oxopropyl)imidazo[1,2-a]pyridin-2-yl)methyl)-1H-1,2,3-triazole-4-carboxylic acid (100 mg, 0.261 mmol) in DMF (3 mL) was added EDCI (75 mg, 0.391 mmol), HOBT (53 mg, 0.391 mmol), DIPEA (134 mg, 1.04 mmol) and (7-chloro-8-fluoroimidazo[1,5-a]pyridin-1-yl)methanamine hydrochloride (63 mg, 0.268 mmol) at RT. The mixture reaction was stirred for 16 h. H₂O (30 mL) was added to the reaction, extracted with EtOAc (50 mL×4). The combined organic layers were washed with brine, dried over Na₂SO₄, concentrated in vacuo to give the crude product, which was purified by prep-HPLC to give ethyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)propanoate (85 mg) as a white solid. ESI-MS [M+H]⁺: 565.1. Purity: 99.39 (214 nm), 99.06 (254 nm). ¹H NMR (400 MHz, DMSO-d₆) δ 8.70 (t, J=5.4 Hz, 1H), 8.54 (s, 1H), 8.44 (d, J=2.4 Hz, 1H), 8.26-8.18 (m, 2H), 7.77 (s, 1H), 6.84 (s, 1H), 6.80-6.72 (m, 1H), 5.73 (s, 2H), 4.69 (d, J=5.5 Hz, 2H), 4.03 (q, J=7.1 Hz, 2H), 3.06 (t, J=7.6 Hz, 2H), 2.76 (t, J=7.6 Hz, 2H), 1.92-1.84 (m, 1H), 1.14 (t, J=7.1 Hz, 3H), 0.94-0.85 (m, 2H), 0.68-0.62 (m, 2H).

Synthesis of 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)propanoic acid (I-163b)

To a solution of ethyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)propanoate (80 mg, 0.142 mmol) in EtOH/H₂O (2 mL/2 mL) was added LiOH H₂O (12 mg, 0.284 mmol) at RT. The mixture reaction was stirred for 2 h. The reaction was concentrated to give the crude product, which was purified by prep-HPLC to give 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)propanoic acid (15.4 mg, yield: 20%) as a white solid. ESI-MS [M+H]⁺: 537.1. Purity: 95.99 (214 nm), 96.01 (254 nm). ¹H NMR (400 MHz, DMSO-d₆) δ 12.00 (s, 1H), 8.71 (s, 1H), 8.55 (s, 1H), 8.45 (s, 1H), 8.26-8.14 (m, 2H), 7.78 (s, 1H), 6.84 (s, 1H), 6.76 (t, J=6.6 Hz, 1H), 5.74 (s, 2H), 4.70 (d, J=4.9 Hz, 2H), 3.03 (t, J=6.9 Hz, 2H), 2.69 (t, J=7.1 Hz, 2H), 1.95-1.85 (m, 1H), 0.95-0.83 (m, 2H), 0.70-0.60 (m, 2H).

Example 164

Scheme 163

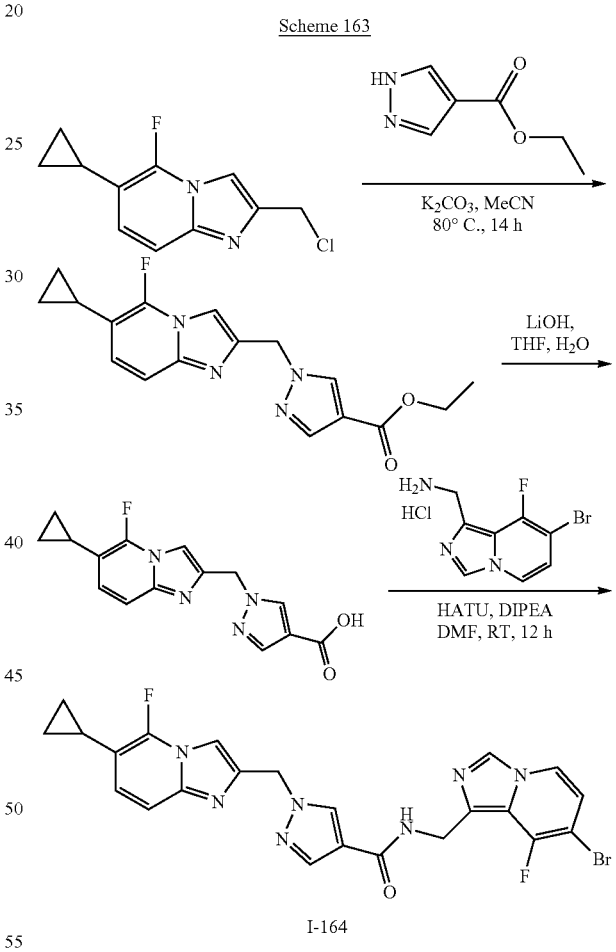

I-164

Synthesis of Ethyl 1-((6-cyclopropyl-5-fluoroimidazo[1,2-a]pyridin-2-yl)methyl)-1H-pyrazole-4-carboxylate To a solution of 2-(chloromethyl)-6-cyclopropyl-5-fluoroimidazo[1,2-a]pyridine (1 g, 4.5 mmol) in MeCN (20 mL) was added ethyl 1H-pyrazole-4-carboxylate (630 mg, 4.5 mmol) and K₂CO₃ (1.25 g, 9.0 mmol). The reaction mixture was stirred at 80° C. for 14 h under nitrogen. Then the mixture was concentrated in vacuo. Water (40 mL) was added and the mixture was extracted with EtOAc (50 mL×3). The combined organic layers were washed with brine, dried over Na$_2$SO$_4$, concentrated to give the crude product, which was purified by silica gel chromatography (EtOAc=100%) to give the ethyl 1-((6-cyclopropyl-5-fluoroimidazo[1,2-a]pyridin-2-yl)methyl)-1H-pyrazole-4-carboxylate as a yellow solid (800 mg, yield: 55%). ESI-MS [M+H]$^+$: 329.1.

Synthesis of 1-((6-cyclopropyl-5-fluoroimidazo[1,2-a]pyridin-2-yl)methyl)-1H-pyrazole-4-carboxylic Acid To a solution ethyl 1-((6-cyclopropyl-5-fluoroimidazo[1,2-a]pyridin-2-yl)methyl)-1H-pyrazole-4-carboxylate (800 mg, 2.44 mmol) in THF/H$_2$O (10 mL/2 mL) was added LiOH (585 mg, 24.4 mmol) at RT. The resulting mixture was stirred at RT for 16 h. The mixture was poured into H$_2$O (20 mL), pH was adjusted to 4 by HCl (1 M) and extracted with EtOAc (50 mL×3). The combined organic layers were washed with brine, dried over Na$_2$SO$_4$, and concentrated to give the crude product, which was purified by silica gel chromatography (DCM/MeOH=10/1) to give 1-((6-cyclopropyl-5-fluoroimidazo[1,2-a]pyridin-2-yl)methyl)-1H-pyrazole-4-carboxylic acid as a white solid (500 mg, yield: 68%). ESI-MS [M+H]$^+$: 301.1.

Synthesis of N-((7-bromo-8-fluoroimidazo[1,5-a]pyridin-1-yl)methyl)-1-((6-cyclopropyl-5-fluoroimidazo[1,2-a]pyridin-2-yl)methyl)-1H-pyrazole-4-carboxamide (I-164)

To a solution of 1-((6-cyclopropyl-5-fluoroimidazo[1,2-a]pyridin-2-yl)methyl)-1H-pyrazole-4-carboxylic acid (100 mg, 0.33 mmol) in DMF (5 mL) was added HATU (152 mg, 0.4 mmol) and DIPEA (0.2 mL, 1.16 mmol). After the reaction was stirred for 30 mins, (7-bromo-8-fluoroimidazo[1,5-a]pyridin-1-yl)methanamine hydrochloride (92 mg, 0.33 mmol) was added, the reaction mixture was stirred at RT for 12 h. The mixture was poured into 30 mL of H$_2$O, extracted with EtOAc (50 mL×3). The combined organic layers were washed with brine, dried over Na$_2$SO$_4$, and concentrated to give the crude product which was purified by prep-TLC (DCM/MeOH=10/1) to give N-((7-bromo-8-fluoroimidazo[1,5-a]pyridin-1-yl)methyl)-1-((6-cyclopropyl-5-fluoroimidazo[1,2-a]pyridin-2-yl)methyl)-1H-pyrazole-4-carboxamide as a yellow solid (30 mg, yield: 17.3%). ESI-MS [M+H]$^+$: 526.0, Purity: 96.93 (214 nm), 96.51 (254 nm). $^1$H NMR (400 MHz, DMSO-d$_6$) δ 8.11 (d, J=2.4 Hz, 1H), 8.01 (s, 1H), 7.81 (s, 1H), 7.60 (d, J=7.2 Hz, 1H), 7.53 (s, 1H), 7.34 (d, J=9.2 Hz, 1H), 6.91 (t, J=9.2 Hz, 1H), 6.65 (s, 1H), 6.61 (t, J=6.4 Hz, 1H), 5.47 (s, 2H), 4.87 (d, J=5.2 Hz, 2H), 2.05-1.98 (m, 1H), 1.02 (q, J=5.6 Hz, 2H), 0.73 (q, J=5.6 Hz, 2H).

Example 165

Scheme 164

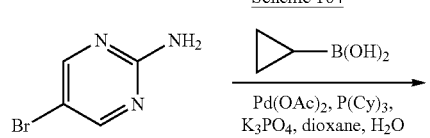

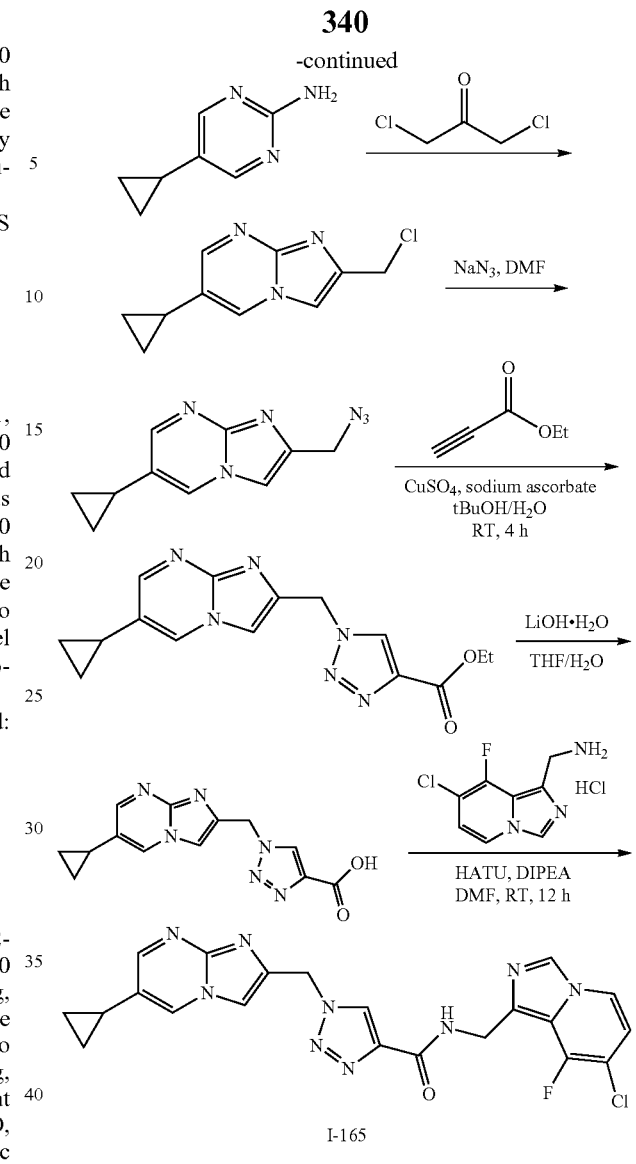

I-165

Synthesis of 5-cyclopropylpyrimidin-2-amine

To a solution of 5-bromopyrimidin-2-amine (3 g, 17.24 mmol) in dioxane/H$_2$O (30 mL/30 mL) was added cyclopropylboronic acid (2.96 g, 34.48 mmol), Pd(OAc)$_2$ (387 mg, 1.72 mmol), P(cy)$_3$ (967 mg, 3.45 mmol) and K$_3$PO$_4$ (7.32 g, 34.48 mmol). The reaction mixture was stirred at 100° C. for 14 h under nitrogen. Then the mixture was concentrated in vacuo. Water (40 mL) was added and the mixture was extracted with DCM (50 mL×3). The combined organic layers were concentrated to give the crude product, which was purified by silica gel chromatography (PE/EA=2/1) to give 5-cyclopropylpyrimidin-2-amine as a yellow solid (1.83 g, yield: 79%). ESI-MS [M+H]$^+$: 136.0.

Synthesis of 2-(chloromethyl)-6-cyclopropylimidazo[1,2-a]pyrimidine

To a solution 5-cyclopropylpyrimidin-2-amine (1 g, 7.4 mmol) in DME (20 mL) was added 1,3-dichloropropan-2-one (1.41 g, 11.1 mmol), then the mixture was stirred at 95° C. for 12 h. The reaction mixture was treated with saturated aqueous NaHCO$_3$ (30 mL) to adjust pH 8 and extracted with EtOAc (50 mL×3). The combined organic layers were concentrated to give the crude product which was purified with silica gel chromatography (PE/EA=5:1) to give 2-(chloromethyl)-6-cyclopropylimidazo[1,2-a]pyrimidine (230 mg, 15%) as a white solid. ESI-MS [M+H]⁺: 207.8.

Synthesis of 2-(azidomethyl)-6-cyclopropylimidazo [1,2-a]pyrimidine

To a solution of 2-(chloromethyl)-6-cyclopropylimidazo [1,2-a]pyrimidine (160 mg, 0.77 mmol) in DMF (3 mL) was added NaN₃ (60 mg, 0.92 mmol), then the mixture was stirred at RT for 3 h. H₂O (20 mL) was added to the reaction, extracted with EtOAc (30 mL×3). The combined organic layers were washed brine, dried over Na₂SO₄, concentrated to give the 2-(azidomethyl)-6-cyclopropylimidazo[1,2-a]pyrimidine (162 mg, yield: 98%) as a white solid which was used in next step without further purification. ESI-MS [M+H]⁺: 214.9.

Synthesis of Ethyl 1-((6-cyclopropylimidazo[1,2-a] pyrimidin-2-yl)methyl)-1H-1,2,3-triazole-4-carboxylate To a solution of 2-(azidomethyl)-6-cyclopropylimidazo [1,2-a]pyrimidine (162 mg, 0.75 mmol) in t-BuOH/H₂O (4 mL/4 mL) was added ethyl propiolate (148 mg, 1.51 mmol), CuSO₄ (24 mg, 0.15 mmol) and sodium ascorbate (45 mg, 0.23 mmol). The mixture reaction was stirred at RT for 0.5 h. H₂O (30 mL) was added to the reaction, extracted with EtOAc (30 mL×3). The combined organic layers were washed with brine, dried over Na₂SO₄, concentrated to give ethyl 1-((6-cyclopropylimidazo[1,2-a]pyrimidin-2-yl) methyl)-1H-1,2,3-triazole-4-carboxylate (109 mg, crude) as a white solid, which was used into next step without further purification. ESI-MS [M+H]⁺: 312.8.

Synthesis of 1-((6-cyclopropylimidazo[1,2-a]pyrimidin-2-yl)methyl)-1H-1,2,3-triazole-4-carboxylic Acid To a solution of ethyl 1-((6-cyclopropylimidazo[1,2-a] pyrimidin-2-yl)methyl)-1H-1,2,3-triazole-4-carboxylate (109 mg, crude) in THF/H₂O (5 mL/2 mL) was added LiOH (16.7 mg, 0.7 mmol), then the mixture was stirred at RT for overnight. The reaction was concentrated to remove THF to give the residue. The pH of the residue was adjusted with HCl (3 M) to 4. The aqueous layer was free-dried to give the 1-((6-cyclopropylimidazo[1,2-a]pyrimidin-2-yl)methyl)-1H-1,2,3-triazole-4-carboxylic acid (130 mg, crude) as a white solid which was used in next step without further purification. ESI-MS [M+H]⁺: 284.9.

Synthesis of N-((7-chloro-8-fluoroimidazo[1,5-a] pyridin-1-yl)methyl)-1-((6-cyclopropylimidazo[1,2-a]pyrimidin-2-yl)methyl)-1H-1,2,3-triazole-4-carboxamide (I-165)

To a solution of 1-((6-cyclopropylimidazo[1,2-a]pyrimidin-2-yl)methyl)-1H-1,2,3-triazole-4-carboxylic acid (130 mg, crude) in DMF (3 mL) was added (7-chloro-8-fluoroimidazo[1,5-a]pyridin-1-yl)methanamine hydrochloride (141 mg, 0.6 mmol), HATU (232 mg, 0.6 mmol) and DIPEA (237 mg, 1.84 mmol). The mixture reaction was stirred at RT for 12 h. The mixture reaction was poured into H₂O (30 mL) and yellow solid was precipitated and filtrated to give N-((7-chloro-8-fluoroimidazo[1,5-a]pyridin-1-yl) methyl)-1-((6-cyclopropylimidazo[1,2-a]pyrimidin-2-yl)methyl)-1H-1,2,3-triazole-4-carboxamide (77 mg, yield: 20% over 3 steps) as a yellow solid. ESI-MS [M+H]⁺: 465.8. Purity: 99.55 (214 nm), 99.25 (254 nm). ¹H NMR (400 MHz, DMSO-d₆) δ 8.71 (s, 2H), 8.58 (s, 1H), 8.44 (s, 2H), 8.21 (d, J=8.0 Hz, 1H), 7.77 (s, 1H), 6.76 (t, J=8.0 Hz, 1H), 5.78 (s, 2H), 4.71 (d, J=4.0 Hz, 2H), 1.99 (brs, 1H), 0.99-0.97 (m, 2H), 0.77-0.75 (m, 2H).

Example 166

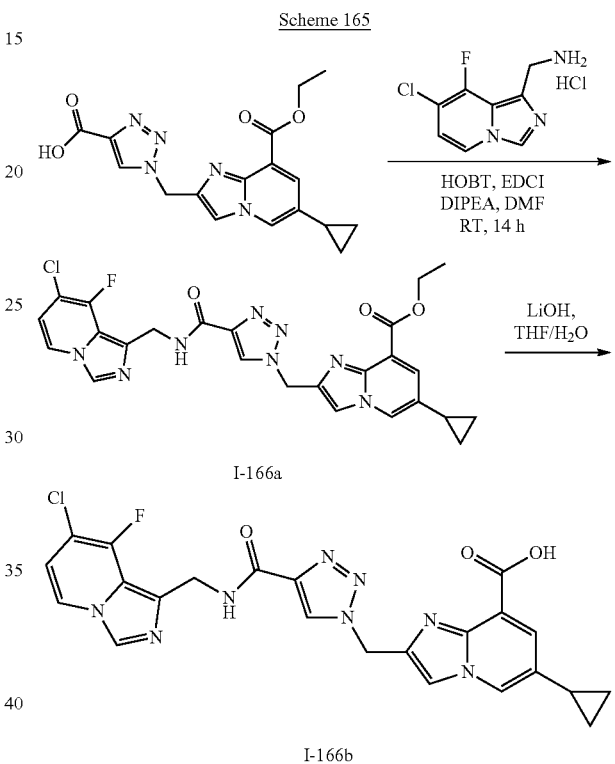

Scheme 165

Synthesis of Ethyl 2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridine-8-carboxylate (I-166a)

To a solution of 1-((6-cyclopropyl-8-(ethoxycarbonyl) imidazo[1,2-a]pyridin-2-yl)methyl)-1H-1,2,3-triazole-4-carboxylic acid (106 mg, 0.3 mmol), (7-chloro-8-fluoroimidazo[1,5-a]pyridin-1-yl)methanamine hydrochloride (84 mg, 0.36), HOBT (61 mg, 0.45 mmol) and EDCI (86 mg, 0.45 mmol) in DMF (5 mL) was added DIPEA (194 mg, 1.5 mmol). The resulting reaction was stirred at RT for 14 h. The reaction was poured into H₂O (100 mL), the white solid was formed. The solid was filtered and washed with DCM to give the ethyl 2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridine-8-carboxylate as a white solid. (135 mg, yield: 84%). ESI-MS [M+H]⁺: 537.2, purity: 95.93 (214 nm), 95.82 (254 nm). ¹H NMR (400 MHz, DMSO-d₆) δ 8.71 (t, J=5.4 Hz, 1H), 8.58-8.56 (m, 2H), 8.44 (d, J=2.3 Hz, 1H), 8.20 (d, J=7.4 Hz, 1H), 7.88 (s, 1H), 7.62 (d, J=1.6 Hz, 1H), 6.76 (t, J=6.9 Hz, 1H), 5.79 (s, 2H), 4.70

(d, J=5.5 Hz, 2H), 4.34 (q, J=7.1 Hz, 2H), 2.04-1.98 (m, 1H), 1.32 (t, J=7.1 Hz, 3H), 1.00-0.93 (m, 2H), 0.72-0.68 (m, 2H).

Synthesis of 2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridine-8-carboxylic acid (I-166b)

To a solution of ethyl 2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridine-8-carboxylate (100 mg, 0.19 mmol) in THF/H$_2$O (8 mL/8 mL) was added LiOH.H$_2$O (39 mg, 0.93 mmol). The reaction was stirred at RT for 3 h. The reaction was concentrated in vacuo to give the crude product, which was purified with Prep-HPLC to give the 2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridine-8-carboxylic acid as a white solid. (50 mg, yield: 51%). ESI-MS [M+H]$^+$: 509.1. Purity: 100 (214 nm), 100 (254 nm). $^1$H NMR (400 MHz, DMSO-d$_6$) δ 8.73 (t, J=4.0 Hz, 1H), 8.62 (s, 1H), 8.61 (s, 1H), 8.44 (d, J=2.4 Hz, 1H), 8.20 (d, J=4.0 Hz, 1H), 7.96 (s, 1H), 7.70 (d, J=4.0 Hz, 1H), 6.76 (t, J=8.0 Hz, 1H), 5.82 (s, 2H), 4.70 (d, J=8.0 Hz, 2H), 2.08-2.00 (m, 1H), 0.99-0.95 (m, 2H), 0.74-0.70 (m, 2H)

Example 167

Scheme 166

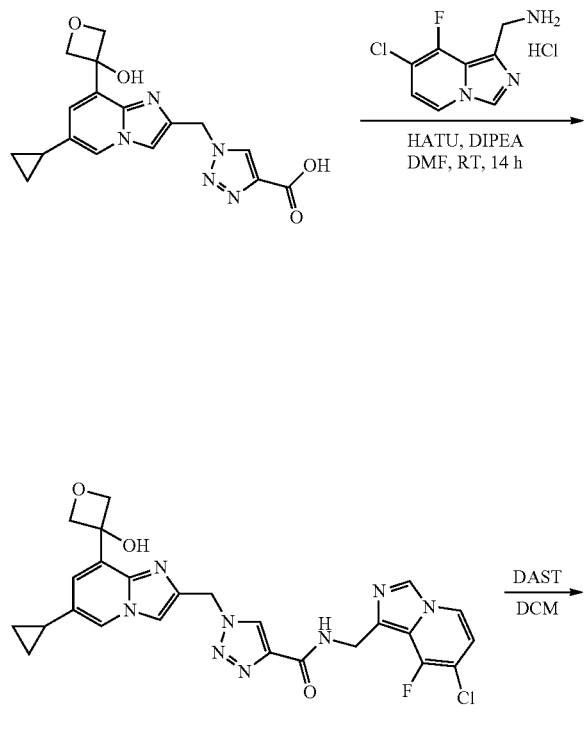

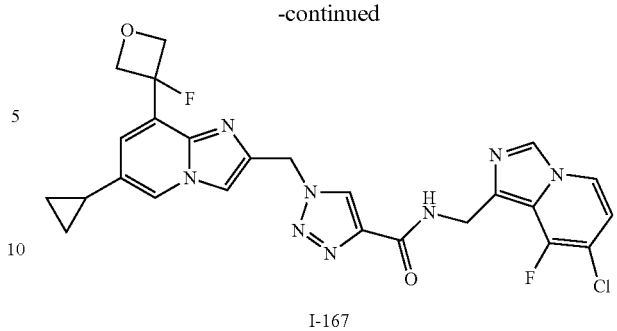

I-167

Synthesis of N-((7-chloro-8-fluoroimidazo[1,5-a]pyridin-1-yl)methyl)-1-((6-cyclopropyl-8-(3-hydroxyoxetan-3-yl)imidazo[1,2-a]pyridin-2-yl)methyl)-1H-1,2,3-triazole-4-carboxamide To a solution of 1-((8-(3-hydroxyoxetan-3-yl)imidazo[1,2-a]pyridin-2-yl)methyl)-1H-1,2,3-triazole-4-carboxylic acid (113 mg, 0.32 mmol), (7-chloro-8-fluoroimidazo[1,5-a]pyridin-1-yl)methanamine hydrochloride (94 mg, 0.4 mmol), HATU (177 mg, 0.47 mmol) in DMF (10 mL) was added DIPEA (200 mg, 1.55 mmol). The resulting mixture was stirred at RT for 14 h. H$_2$O (30 mL) was added into the reaction, extracted with EtOAC (40 mL×3). The combined organic layers were washed with brine, dried over Na$_2$SO$_4$, concentrated in vacuo to give the crude product, which was purified with Prep-TLC (DCM/MeOH=10/1) to give the N-((7-chloro-8-fluoroimidazo[1,5-a]pyridin-1-yl)methyl)-1-((6-cyclopropyl-8-(3-hydroxyoxetan-3-yl)imidazo[1,2-a]pyridin-2-yl)methyl)-1H-1,2,3-triazole-4-carboxamide (60 mg, yield: 35%) as a yellow solid. ESI-MS [M+H]$^+$: 537.1.

Synthesis of N-((7-chloro-8-fluoroimidazo[1,5-a]pyridin-1-yl)methyl)-1-((6-cyclopropyl-8-(3-fluorooxetan-3-yl)imidazo[1,2-a]pyridin-2-yl)methyl)-1H-1,2,3-triazole-4-carboxamide (I-167)

To a solution of N-((7-chloro-8-fluoroimidazo[1,5-a]pyridin-1-yl)methyl)-1-((6-cyclopropyl-8-(3-hydroxyoxetan-3-yl)imidazo[1,2-a]pyridin-2-yl)methyl)-1H-1,2,3-triazole-4-carboxamide (45 mg, 0.084 mmol) in DCM (8 mL) was added DAST (20 mg, 0.13 mmol) at −78° C. under nitrogen. The resulting mixture was stirred at −78° C. under nitrogen 1 h. The mixture was quenched with NaHCO$_3$ (aq., 20 mL) and extracted with DCM (30 mL×3). The combined organic layers were washed with brine, dried over Na$_2$SO$_4$, concentrated in vacuo to give the crude product, which was purified with Prep-TLC combiflash (DCM/MeOH=10/1) to give the compound as a light yellow solid (7 mg, yield: 15%). ESI-MS [M+H]$^+$: 539.1. Purity: 95.3 (214 nm), 95.2 (254 nm). $^1$H NMR (400 MHz, DMSO-d$_6$) δ 8.72 (t, J=5.4 Hz, 1H), 8.55 (s, 1H), 8.49-8.41 (m, 2H), 8.21 (d, J=7.4 Hz, 1H), 7.83 (s, 1H), 7.18 (s, 1H), 6.76 (t, J=5.4 Hz, 1H), 5.77 (s, 2H), 5.34-5.25 (m, 2H), 4.99-4.91 (m, 2H), 4.70 (d, J=5.4 Hz, 2H), 2.01-1.89 (m, 1H), 0.96-0.91 (m, 2H), 0.76-0.67 (m, 2H).

Example 168
Scheme 167
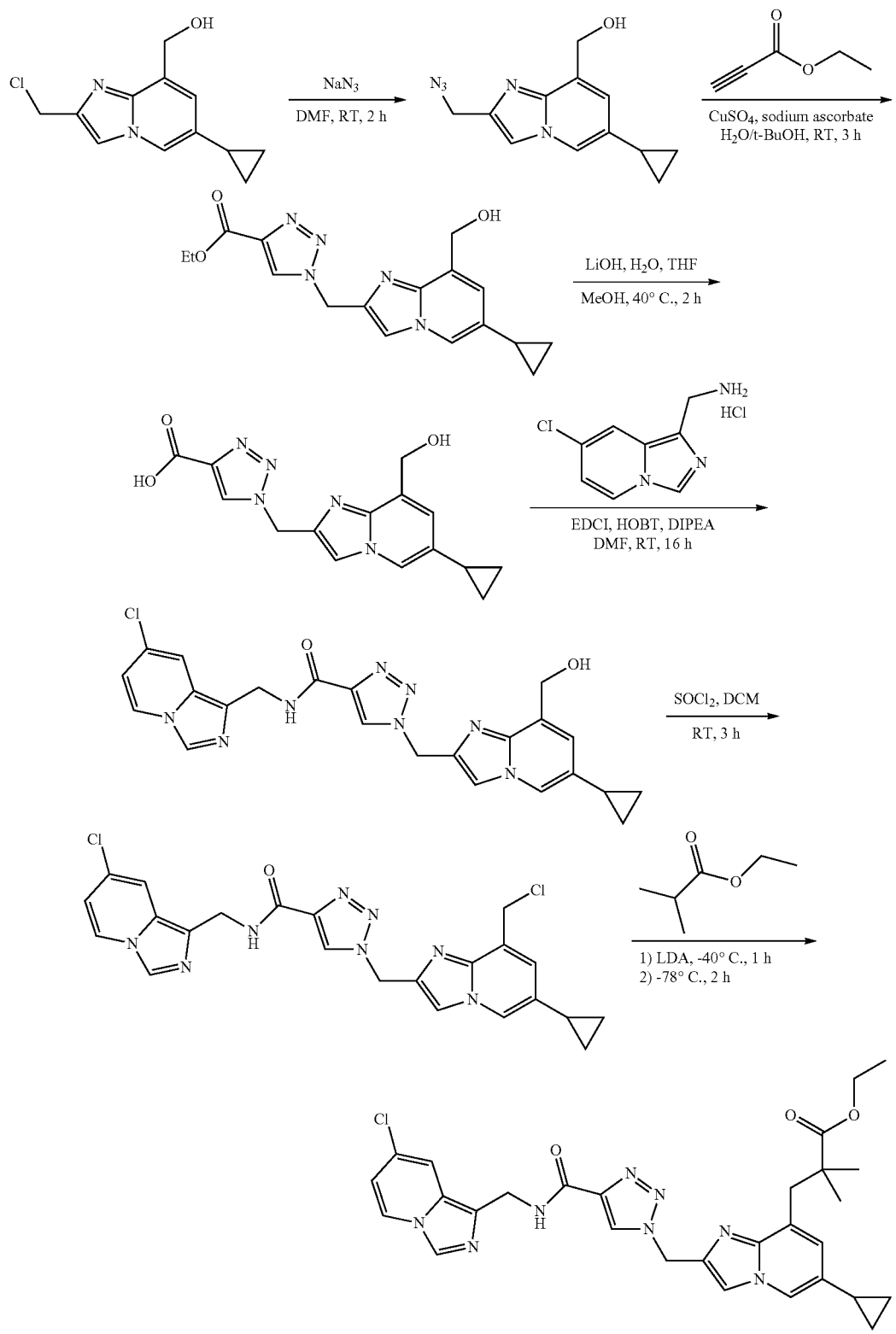
I-168

Synthesis of (2-(azidomethyl)-6-cyclopropylimidazo[1,2-a]pyridin-8-yl)methanol The mixture of (2-(chloromethyl)-6-cyclopropylimidazo[1,2-a]pyridin-8-yl)methanol (3.0 g, 12.6 mmol) and NaN$_3$ (988 mg, 15.2 mmol) in DMF (40 mL) was stirred at RT for 2 h. The reaction mixture was poured into H$_2$O (300 mL) and extracted with EtOAc (100 mL×2). The combined organics was washed with brine, dried over Na$_2$SO$_4$, concentrated and dried in vacuo to give (2-(azidomethyl)-6-cyclopropylimidazo[1,2-a]pyridin-8-yl)methanol (2.8 g, yield: 91%) as a pale solid. ESI-MS [M+H]$^+$: 244.2.

Synthesis of Ethyl 1-((6-cyclopropyl-8-(hydroxymethyl)imidazo[1,2-a]pyridin-2-yl)methyl)-1H-1,2,3-triazole-4-carboxylate The mixture of (2-(azidomethyl)-6-cyclopropylimidazo[1,2-a]pyridin-8-yl)methanol (2.8 g, 11.5 mmol), ethyl propiolate (1.35 g, 13.8 mmol), CuSO$_4$ (919 mg, 5.76 mmol) and sodium ascorbate (1.14 g, 5.76 mmol) in t-BuOH (20 mL) and H$_2$O (20 mL) was stirred at RT for 3 h. The reaction mixture was poured into H$_2$O (100 mL) and the precipitate was collected, and the crude solid was purified by silica gel chromatography (EA/PE=1/2) to give ethyl 1-((6-cyclopropyl-8-(hydroxymethyl)imidazo[1,2-a]pyridin-2-yl)methyl)-1H-1,2,3-triazole-4-carboxylate (3.1 g, yield: 78%) as a yellow solid. ESI-MS [M+H]$^+$: 342.2.

Synthesis of 1-((6-cyclopropyl-8-(hydroxymethyl)imidazo[1,2-a]pyridin-2-yl)methyl)-1H-1,2,3-triazole-4-carboxylic Acid To a solution of ethyl 1-((6-cyclopropyl-8-(hydroxymethyl)imidazo[1,2-a]pyridin-2-yl)methyl)-1H-1,2,3-triazole-4-carboxylate (3.1 g, 9.1 mmol) in a mixed solvent of methanol (20 mL), THF (20 mL) and H$_2$O (10 mL) was added lithium hydroxide monohydrate (756 mg, 18 mmol). The mixture was stirred at 40° C. for 1 h. The reaction was concentrated to remove THF and MeOH to give the residue. The pH of residue was adjusted with 1N HCl to 4 and the yellow solid was precipitated. The mixture was filtered and dried in vacuo to give 1-((6-cyclopropyl-8-(hydroxymethyl)imidazo[1,2-a]pyridin-2-yl)methyl)-1H-1,2,3-triazole-4-carboxylic acid (2.6 g, 91%) as a yellow solid. ESI-MS [M+H]$^+$: 314.1.

Synthesis of N-((7-chloroimidazo[1,5-a]pyridin-1-yl)methyl)-1-((6-cyclopropyl-8-(hydroxymethyl)imidazo[1,2-a]pyridin-2-yl)methyl)-1H-1,2,3-triazole-4-carboxamide A mixture of 1-((6-cyclopropyl-8-(hydroxymethyl)imidazo[1,2-a]pyridin-2-yl)methyl)-1H-1,2,3-triazole-4-carboxylic acid (1.0 g, 3.19 mmol), (5-chloro-2-(1H-tetrazol-5-yl)phenyl)methanamine hydrochloride (835 mg, 3.83 mmol), EDCI (734 mg, 3.83 mmol), HOBT (518 mg, 3.83 mmol) and DIPEA (1.24 g, 9.57 mmol) in DMF (15 mL) was stirred at 25° C. for 16 h. The reaction mixture was poured into H$_2$O (100 mL) and the precipitate was collected. The crude solid was filtered and purified by silica gel chromatography (DCM/MeOH=20/1) to give N-((7-chloroimidazo[1,5-a]pyridin-1-yl)methyl)-1-((6-cyclopropyl-8-(hydroxymethyl)imidazo[1,2-a]pyridin-2-yl)methyl)-1H-1,2,3-triazole-4-carboxamide (1.0 g, yield: 66%) as a pale white solid. ESI-MS [M+H]$^+$: 477.1.

Synthesis of N-((7-chloroimidazo[1,5-a]pyridin-1-yl)methyl)-1-((8-(chloromethyl)-6-cyclopropylimidazo[1,2-a]pyridin-2-yl)methyl)-1H-1,2,3-triazole-4-carboxamide To a stirred solution of N-((7-chloroimidazo[1,5-a]pyridin-1-yl)methyl)-1-((6-cyclopropyl-8-(hydroxymethyl)imidazo[1,2-a]pyridin-2-yl)methyl)-1H-1,2,3-triazole-4-carboxamide (600 mg, 1.26 mmol) in DCM (20 mL) and THF (10 mL) was added dropwise of SOCl$_2$ (1.5 g, 12.6 mmol) at 0° C. The mixture was stirred at RT for 3 h. The reaction mixture was concentrated. The residue was diluted in H$_2$O (50 mL) and the pH was adjusted to 9-10 with NaHCO$_3$ aqueous. The mixture was extracted with EtOAc (100 mL×3), the combined organic layers were concentrated purified by silica gel chromatography (DCM/MeOH=20/1) to give N-((7-chloroimidazo[1,5-a]pyridin-1-yl)methyl)-1-((8-(chloromethyl)-6-cyclopropylimidazo[1,2-a]pyridin-2-yl)methyl)-1H-1,2,3-triazole-4-carboxamide (520 mg, yield: 83%) as a yellow solid. ESI-MS [M+H]$^+$: 495.1.

Synthesis of Ethyl 3-(2-((4-(((7-chloroimidazo[1,5-a]pyridin-1-yl)methyl)carbamoyl)-1H-1,2,3-triazol-1-yl)methyl)-6-cyclopropylimidazo[1,2-a]pyridin-8-yl)-2,2-dimethylpropanote (I-168)

To a stirred solution of ethyl isobutyrate (0.93 g, 8 mmol) in THF (15 mL) was added dropwise LDA (4 mL, 2 M in THF) at −40° C. under N$_2$. After 1 h, the solution was added dropwise to the suspension of N-((7-chloroimidazo[1,5-a]pyridin-1-yl)methyl)-1-((8-(chloromethyl)-6-cyclopropylimidazo[1,2-a]pyridin-2-yl)methyl)-1H-1,2,3-triazole-4-carboxamide (520 mg, 1.05 mmol) in THF (15 mL) at −78° C. The resulting mixture was stirred for 2 h at −78° C. The reaction mixture was quenched with NH$_4$C aqueous, extracted with EtOAc (50 mL×3). The combined organics was washed with brine (100 mL), dried over Na$_2$SO$_4$, concentrated and purified by silica gel chromatography (DCM/MeOH=20/1) to give ethyl 3-(2-((4-(((7-chloroimidazo[1,5-a]pyridin-1-yl)methyl)carbamoyl)-1H-1,2,3-triazol-1-yl)methyl)-6-cyclopropylimidazo[1,2-a]pyridin-8-yl)-2,2-dimethylpropanoate (300 mg, yield: 50%) as a white solid. ESI-MS [M+H]$^+$: 575.2. Purity: 96.39 (214 nm), 97.14 (254 nm). $^1$H NMR (400 MHz, DMSO-d$_6$) δ 8.92 (t, J=5.9 Hz, 1H), 8.51 (s, 1H), 8.34-8.27 (m, 2H), 8.23 (s, 1H), 7.83-7.75 (m, 2H), 6.71-6.61 (m, 2H), 5.71 (s, 2H), 4.61 (d, J=5.9 Hz, 2H), 3.93 (q, J=7.1 Hz, 2H), 3.08 (s, 2H), 1.92-1.88 (m, 1H), 1.21-1.00 (m, 9H), 0.95-0.88 (m, 2H), 0.61 (m, 2H).

Example 169

Scheme 168

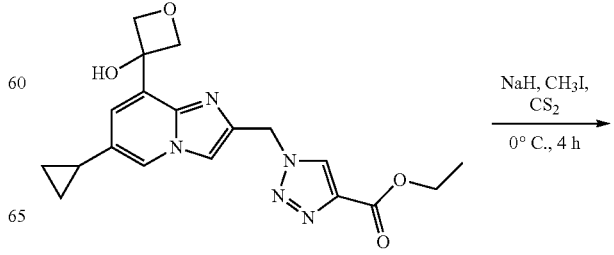

-continued

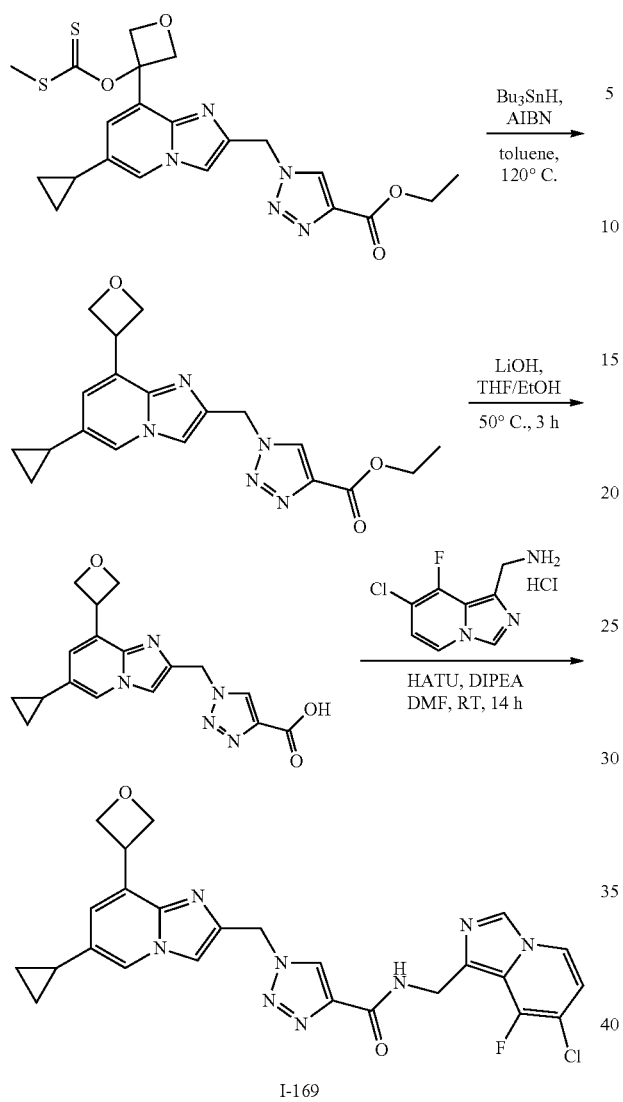

I-169

Synthesis of Ethyl 1-((6-cyclopropyl-8-(3-(((methylthio)carbonothioyl)oxy)oxetan-3-yl)imidazo[1,2-a]pyridin-2-yl)methyl)-1H-1,2,3-triazole-4-carboxylate To a solution of ethyl 1-((6-cyclopropyl-8-(3-hydroxyoxetan-3-yl)imidazo[1,2-a]pyridin-2-yl)methyl)-1H-1,2,3-triazole-4-carboxylate (400 mg, 1.04 mmol) in THF (20 mL) was added NaH (125 mg, 5.20 mmol, 60% in oil) at 0° C. slowly. The resulting mixture was stirred at 0° C. for 30 min. Then CS$_2$ (395 mg, 5.20 mmol) was added at 0° C. After stirring for 30 min, CH$_3$I (738 mg, 5.20 mmol) was added and stirred at at 0° C. for 4 h. The reaction was quenched with aqueous NH$_4$Cl, extracted with EtOAC (50 mL×3). The combined organic layers were washed with brine, dried over Na$_2$SO$_4$, concentrated in vacuo to give the ethyl 1-((6-cyclopropyl-8-(3-(((methylthio)carbonothioyl)oxy)oxetan-3-yl)imidazo[1,2-a]pyridin-2-yl)methyl)-1H-1,2,3-triazole-4-carboxylate (250 mg crude), which was used into next step without further purification. ESI-MS [M+H]$^+$: 474.1

Synthesis of Ethyl 1-((8-(oxetan-3-yl)imidazo[1,2-a]pyridin-2-yl)methyl)-1H-1,2,3-triazole-4-carboxylate A solution of ethyl 1-((6-cyclopropyl-8-(3-(((methylthio)carbonothioyl)oxy)oxetan-3-yl)imidazo[1,2-a]pyridin-2-yl)methyl)-1H-1,2,3-triazole-4-carboxylate (250 mg crude from previous step) and Bu$_3$SnH (772 mg, 2.64 mmol) and AIBN (87 mg, 0.53 mmol) in toluene (8 mL) was stirred at 125° C. for 0.5 h. The reaction was concentrated in vacuo to give the residue, which was diluted with H$_2$O (30 mL), extracted with EtOAc (30 mL×3). The combined organic layers were washed with brine, dried over Na$_2$SO$_4$, concentrated in vacuo to give the ethyl 1-((8-(oxetan-3-yl)imidazo[1,2-a]pyridin-2-yl)methyl)-1H-1,2,3-triazole-4-carboxylate (180 mg, crude). ESI-MS [M+H]$^+$: 368.2.

Synthesis of 1-((8-(oxetan-3-yl)imidazo[1,2-a]pyridin-2-yl)methyl)-1H-1,2,3-triazole-4-carboxylic Acid A mixture of ethyl ethyl 1-((8-(oxetan-3-yl)imidazo[1,2-a]pyridin-2-yl)methyl)-1H-1,2,3-triazole-4-carboxylate (180 mg, crude) and LiOH (59 mg, 2.45 mmol) in THF/H$_2$O (5 mL/5 mL) was stirred at 50° C. for 3 h. The reaction was concentrated in vacuo to give crude product, which was purified with Prep-HPLC to give the 1-((8-(oxetan-3-yl)imidazo[1,2-a]pyridin-2-yl)methyl)-1H-1,2,3-triazole-4-carboxylic acid (40 mg, yield: 12% over 3 steps) as a yellow solid. ESI-MS [M+H]$^+$: 340.1

Synthesis of N-((7-chloro-8-fluoroimidazo[1,5-a]pyridin-1-yl)methyl)-1-((6-cyclopropyl-8-(oxetan-3-yl)imidazo[1,2-a]pyridin-2-yl)methyl)-1H-1,2,3-triazole-4-carboxamide (I-169)

To a solution of 1-((8-(oxetan-3-yl)imidazo[1,2-a]pyridin-2-yl)methyl)-1H-1,2,3-triazole-4-carboxylic acid (20 mg 0.059 mmol), (7-chloro-8-fluoroimidazo[1,5-a]pyridin-1-yl)methanamine hydrochloride (21 mg, 0.088 mmol), HATU (33 mg, 0.088 mmol) in DMF (10 mL) was added DIPEA (23 mg, 0.177 mmol). The resulting mixture was stirred at RT for 14 h. H$_2$O (30 mL) was added into the reaction, extracted with EtOAC (30 mL×3). The combined organic layers were washed with brine, dried over Na$_2$SO$_4$, concentrated in vacuo to give the crude product, which was purified with Prep-TLC (DCM/MeOH=10/1) to give the N-((7-chloro-8-fluoroimidazo[1,5-a]pyridin-1-yl)methyl)-1-((6-cyclopropyl-8-(oxetan-3-yl)imidazo[1,2-a]pyridin-2-yl)methyl)-1H-1,2,3-triazole-4-carboxamide (15 mg, yield: 49%) as a white solid. ESI-MS [M+H]$^+$: 521.1. Purity: 97.8 (214 nm), 97.7 (254 nm). $^1$H NMR (400 MHz, DMSO-d$_6$) δ 8.78-8.71 (m, 1H), 8.55 (s, 1H), 8.45 (s, 1H), 8.34-8.32 (m, 1H), 8.21 (d, J=7.4 Hz, 1H), 7.91 (s, 1H), 7.28-7.20 (m, 1H), 6.81-6.71 (m, 1H), 5.78 (s, 2H), 4.98-4.89 (m, 2H), 4.84-4.76 (m, 2H), 4.72-4.59 (m, 3H), 2.05-1.98 (m, 1H), 0.98-0.94 (m, 2H), 0.79-0.72 (m, 2H).

Example 170

Scheme 169

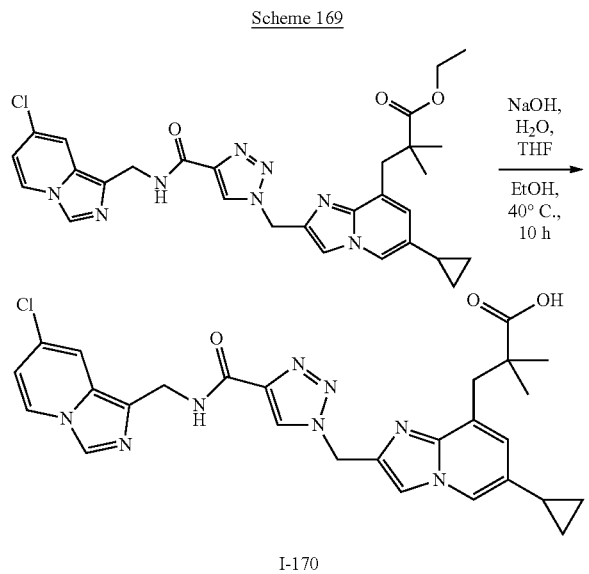

I-170

Synthesis of 3-(2-((4-(((7-chloroimidazo[1,5-a]pyridin-1-yl)methyl)carbamoyl)-1H-1,2,3-triazol-1-yl)methyl)-6-cyclopropylimidazo[1,2-a]pyridin-8-yl)-2,2-dimethylpropanoic Acid (I-170)

To a solution of ethyl 3-(2-((4-(((7-chloroimidazo[1,5-a]pyridin-1-yl)methyl)carbamoyl)-1H-1,2,3-triazol-1-yl)methyl)-6-cyclopropylimidazo[1,2-a]pyridin-8-yl)-2,2-dimethylpropanoate (120 mg, 0.21 mmol) in MeOH (6 mL), THF (6 mL) and H$_2$O (4 mL) was added NaOH (167 mg, 4.18 mmol). The mixture was stirred at 40° C. for 10 h. MeOH and THF was removed and the mixture was diluted in H$_2$O (40 mL), extracted with EtOAc (40 mL). The organic layer was discarded. The pH of aqueous layer was acidified to 5-6 and extracted with DCM/MeOH (10/1, 30 mL×2). The combined organics was washed with brine, dried over Na$_2$SO$_4$, concentrated and purified by silica gel chromatography (DCM/MeOH=10/1) to give 3-(2-((4-(((7-chloroimidazo[1,5-a]pyridin-1-yl)methyl)carbamoyl)-1H-1,2,3-triazol-1-yl)methyl)-6-cyclopropylimidazo[1,2-a]pyridin-8-yl)-2,2-dimethylpropanoic acid (35 mg, yield: 30%) as a white solid. ESI-MS [M+H]$^+$: 547.2. Purity: 99.05 (214 nm), 98.36 (254 nm). $^1$H NMR (400 MHz, DMSO-d$_6$) δ 12.33 (s, 1H), 8.91 (t, J=5.9 Hz, 1H), 8.52 (s, 1H), 8.36-8.27 (m, 2H), 8.21 (s, 1H), 7.86-7.80 (m, 1H), 7.76 (s, 1H), 6.74 (s, 1H), 6.64 (dd, J=7.5, 2.1 Hz, 1H), 5.72 (s, 2H), 4.61 (d, J=5.9 Hz, 2H), 3.09 (s, 2H), 1.90-1.83 (m, 1H), 1.05 (s, 6H), 0.94-0.87 (m, 2H), 0.66-0.58 (m, 2H).

Example 171

Scheme 170

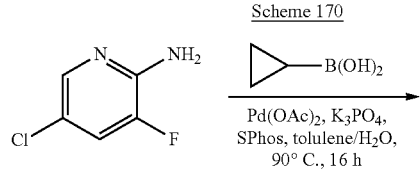

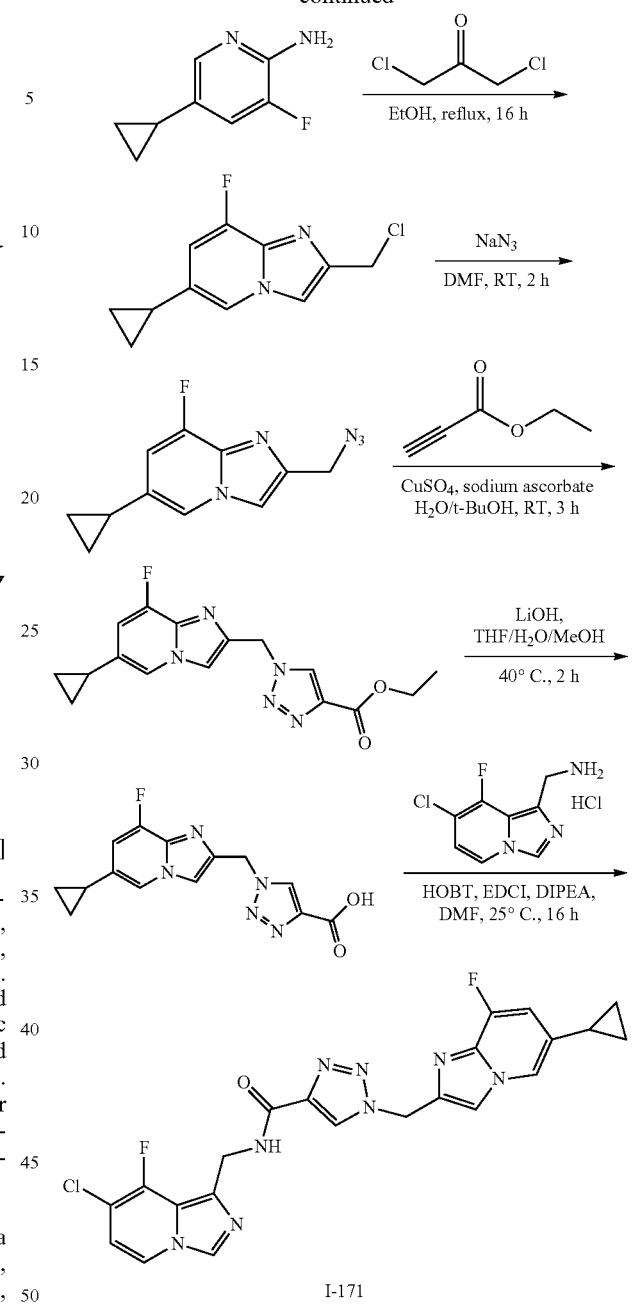

I-171

Synthesis of 5-cyclopropyl-3-fluoropyridin-2-amine

A mixture of 5-chloro-3-fluoropyridin-2-amine (2 g, 13.65 mmol), cyclopropylboronic acid (1.76 g, 20.47 mmol), Pd(OAc)$_2$ (306 mg, 1.365 mmol), SPhos (1.12 g, 2.73 mmol) and K$_3$PO$_4$ (10.14 g, 47.78 mmol) in toluene (40 mL) and H$_2$O (10 mL) was stirred at 90° C. for 16 h under N$_2$. The reaction mixture was filtered and washed with EtOAc. The combined filtrate was washed with H$_2$O (100 mL) and brine (100 mL), dried over Na$_2$SO$_4$, concentrated and purified by silica gel chromatography (EA/PE=1/2) to give 5-cyclopropyl-3-fluoropyridin-2-amine (2.2 g, yield: 100%) as a yellow syrup. ESI-MS [M+H]$^+$: 153.2.

Synthesis of 2-(chloromethyl)-6-cyclopropyl-8-fluoroimidazo[1,2-a]pyridine

A mixture of 5-cyclopropyl-3-fluoropyridin-2-amine (2.2 g, 13.65 mmol) and 1,3-dichloropropan-2-one (5.5 g, 43.38 mmol) in EtOH (40 mL) was stirred at 85° C. for 16 h. The reaction mixture was concentrated. The residue was washed with NaHCO$_3$ aqueous solution and extracted with EtOAc (100 mL×3). The organic layers were washed with brine (100 mL), dried over Na$_2$SO$_4$, concentrated and purified by silica gel chromatography (EA/PE=1/2) to give 2-(chloromethyl)-6-cyclopropyl-8-fluoroimidazo[1,2-a]pyridine (1.8 g, 58%) as a yellow solid. ESI-MS [M+H]$^+$: 225.1.

Synthesis of 2-(azidomethyl)-6-cyclopropyl-8-fluoroimidazo[1,2-a]pyridine

A mixture of 2-(chloromethyl)-6-cyclopropyl-8-fluoroimidazo[1,2-a]pyridine (1.8 g, 8.01 mmol) and NaN$_3$ (625 mg, 9.61 mmol) in DMF (20 mL) was stirred at RT for 3 h. The reaction mixture was poured into H$_2$O (100 mL) and extracted with EtOAc (80 mL×2). The combined organics was washed with brine (160 mL), concentrated and dried in vacuo to give 2-(azidomethyl)-6-cyclopropyl-8-fluoroimidazo[1,2-a]pyridine (1.75 g, yield: 95%) as a white solid. ESI-MS [M+H]$^+$: 232.1.

Synthesis of Ethyl 1-((6-cyclopropyl-8-fluoroimidazo[1,2-a]pyridin-2-yl)methyl)-1H-1,2,3-triazole-4-carboxylate A mixture of 2-(azidomethyl)-6-cyclopropyl-8-fluoroimidazo[1,2-a]pyridine (1.75 g, 7.57 mmol), ethyl propiolate (891 mg, 9.08 mmol), CuSO$_4$ (362 mg, 2.27 mmol) and sodium ascorbate (750 mg, 3.79 mmol) in t-BuOH (20 mL) and H$_2$O (20 mL) was stirred at RT for 3 h. H$_2$O (50 mL) was added to the reaction, extracted with EtOAc (100 mL×3). The combined organics were washed with brine (100 mL), dried over Na$_2$SO$_4$, concentrated to give the crude product, which was purified by silica gel chromatography (EA/PE=1/2) to give ethyl 1-((6-cyclopropyl-8-fluoroimidazo[1,2-a]pyridin-2-yl)methyl)-1H-1,2,3-triazole-4-carboxylate (1.0 g, yield: 40%) as a white solid. ESI-MS [M+H]$^+$: 330.1.

Synthesis of 1-((6-cyclopropyl-8-fluoroimidazo[1,2-a]pyridin-2-yl)methyl)-1H-1,2,3-triazole-4-carboxylic Acid To a solution of ethyl 1-((6-cyclopropyl-8-fluoroimidazo[1,2-a]pyridin-2-yl)methyl)-1H-1,2,3-triazole-4-carboxylate (270 mg, 0.82 mmol) in methanol (4 mL), THF (4 mL) and H$_2$O (2 mL) was added lithium hydroxide monohydrate (138 mg, 3.28 mmol). The mixture was stirred at 40° C. for 2 h. MeOH and THF was removed. The residue was diluted in H$_2$O (20 mL), the pH was acidified to 5-6 by HCl (1N) and yellow solid was precipitated. The mixture was filtered and dried in vacuo to give 1-((6-cyclopropyl-8-fluoroimidazo[1,2-a]pyridin-2-yl)methyl)-1H-1,2,3-triazole-4-carboxylic acid (220 mg, 89%) as a yellow solid. ESI-MS [M+H]$^+$: 302.1.

Synthesis of N-((7-chloro-8-fluoroimidazo[1,5-a]pyridin-1-yl)methyl)-1-((6-cyclopropyl-8-fluoroimidazo[1,2-a]pyridin-2-yl)methyl)-1H-1,2,3-triazole-4-carboxamide (I-171)

A mixture of 1-((6-cyclopropyl-8-fluoroimidazo[1,2-a]pyridin-2-yl)methyl)-1H-1,2,3-triazole-4-carboxylic acid (64 mg, 0.212 mmol), (7-chloro-8-fluoroimidazo[1,5-a]pyridin-1-yl)methanamine hydrochloride (50 mg, 0.212 mmol), EDCI (49 mg, 0.254 mmol), HOBT (34 mg, 0.254 mmol) and DIPEA (82 mg, 0.636 mmol) in DMF (3 mL) was stirred at 25° C. for 16 h. The reaction mixture was poured into H$_2$O (40 mL) and the yellow solid was precipitate. The mixture was filtered and washed with MeOH (30 mL), dried in vacuo to give N-((7-chloro-8-fluoroimidazo[1,5-a]pyridin-1-yl)methyl)-1-((6-cyclopropyl-8-fluoroimidazo[1,2-a]pyridin-2-yl)methyl)-1H-1,2,3-triazole-4-carboxamide (75 mg, yield: 74%) as a pale white solid. ESI-MS [M+H]$^+$: 483.1. Purity: 99.62 (214 nm), 100 (254 nm). $^1$H NMR (400 MHz, DMSO-d$_6$) δ 8.71 (t, J=5.2 Hz, 1H), 8.57 (s, 1H), 8.44 (d, J=2.2 Hz, 1H), 8.27 (s, 1H), 8.21 (d, J=7.4 Hz, 1H), 7.95 (d, J=2.7 Hz, 1H), 6.95 (d, J=12.4 Hz, 1H), 6.76 (t, J=6.9 Hz, 1H), 5.76 (s, 2H), 4.70 (d, J=5.4 Hz, 2H), 1.98-1.90 (m, 1H), 0.98-0.88 (m, 2H), 0.75-0.65 (m, 2H).

Example 172

Scheme 171

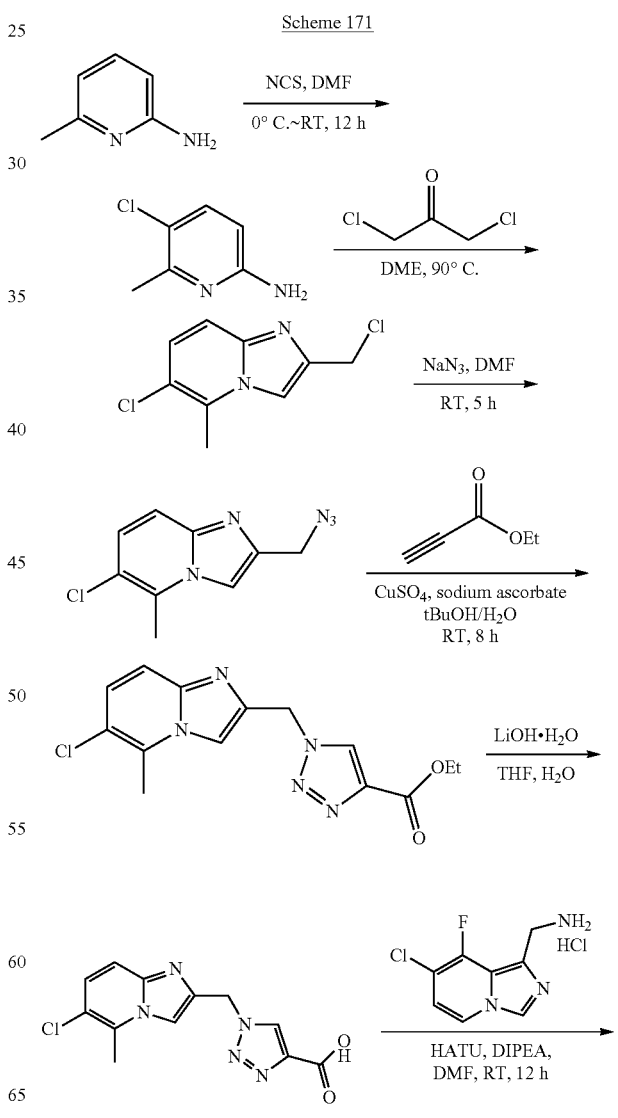

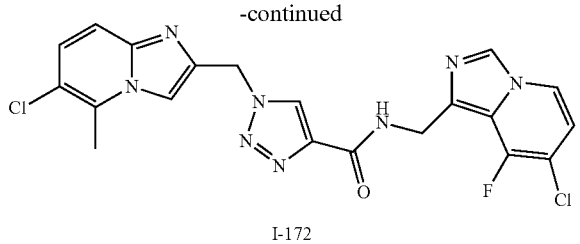

I-172

Synthesis of 5-chloro-6-methylpyridin-2-amine

To a solution of 6-methylpyridin-2-amine (1.08 g, 1 mmol) in DMF (10 mL) was added NCS (1.34 g, 1 mmol), then the mixture was stirred at RT for 12 h. The mixture was treated with ice $H_2O$ and extracted with EtOAc (100 mL). The organic layer was washed with brine, dried over $Na_2SO_4$, concentrated to give the crude product which was purified with silica gel chromatography (PE/EA=2:1) to give 5-chloro-6-methylpyridin-2-amine as a yellow solid (750 mg, yield: 53%). ESI-MS [M+H]$^+$: 142.9.

Synthesis of 6-chloro-2-(chloromethyl)-5-methyl-imidazo[1,2-a]pyridine

To a solution of 5-chloro-6-methylpyridin-2-amine (500 mg, 3.51 mmol) in DME (20 mL) was added 1,3-dichloro-propan-2-one (667 mg, 5.26 mmol), then the mixture was stirred at 90° C. for overnight. The mixture was treated with $NaHCO_3$ to adjust pH 8 and extracted with EtOAc (100 mL×3). The organic layers were washed with brine, dried over $Na_2SO_4$, concentrated to give the crude product which was purified with silica gel chromatography (EA/DCM=1:5) to give 6-chloro-2-(chloromethyl)-5-methylimidazo[1,2-a]pyridine (357 mg, yield: 47%) as white oil. ESI-MS [M+H]$^+$: 214.9.

Synthesis of 2-(azidomethyl)-6-chloro-5-methylimidazo[1,2-a]pyridine

To a solution of 6-chloro-2-(chloromethyl)-5-methylimidazo[1,2-a]pyridine (158 mg, 0.73 mmol) in DMF (3 mL) was added $NaN_3$ (48 mg, 0.73 mmol). And the mixture reaction was stirred at RT for 5 h. $H_2O$ (50 mL) was added to reaction, extracted with EtOAc (50 mL×3). The combined organic layers were washed with brine, dried over $Na_2SO_4$, concentrated to give the 2-(azidomethyl)-6-chloro-5-methylimidazo[1,2-a]pyridine (155 mg, yield: 95%) as a yellow solid. ESI-MS [M+H]$^+$: 221.8.

Synthesis of Ethyl 1-((6-chloro-5-methylimidazo[1,2-a]pyridin-2-yl)methyl)-1H-1,2,3-triazole-4-carboxylate To a solution of 2-(azidomethyl)-6-chloro-5-methylimidazo[1,2-a]pyridine (155 mg, 0.7 mmol) in t-BuOH/$H_2O$ (3 mL/3 mL) was added ethyl propiolate (137 mg, 1.4 mmol), $CuSO_4$ (22 mg, 0.14 mmol) and sodium ascorbate (42 mg, 0.21 mmol). And the resulting mixture was stirred at RT for 1 h. $H_2O$ (20 mL) was added to the reaction, extracted with EtOAc (50 mL×3). The combined organic layers were washed with brine, dried over $Na_2SO_4$, concentrated to give ethyl 1-((6-chloro-5-methylimidazo[1,2-a]pyridin-2-yl)methyl)-1H-1,2,3-triazole-4-carboxylate (220 mg, crude) as a yellow solid. ESI-MS [M+H]$^+$: 319.9.

Synthesis of 1-((6-chloro-5-methylimidazo[1,2-a]pyridin-2-yl)methyl)-1H-1,2,3-triazole-4-carboxylic Acid To a solution of ethyl 1-((6-chloro-5-methylimidazo[1,2-a]pyridin-2-yl)methyl)-1H-1,2,3-triazole-4-carboxylate (220 mg, crude) in THF/$H_2O$ (5 mL/2 mL) was added LiOH (33 mg, 1.38 mmol), then the mixture was stirred at RT overnight. The mixture was treated with HCl (aq) to adjust pH 4 and the yellow solid was precipitated. The mixture was filtered, washed with $H_2O$ (10 mL) and dried to give the 1-((6-chloro-5-methylimidazo[1,2-a]pyridin-2-yl) methyl)-1H-1,2,3-triazole-4-carboxylic acid (100 mg, yield: 50% over 2 steps) as a yellow solid. ESI-MS [M+H]$^+$: 291.9.

Synthesis of 1-((6-chloro-5-methylimidazo[1,2-a]pyridin-2-yl)methyl)-N-((7-chloro-8-fluoroimidazo[1,5-a]pyridin-1-yl)methyl)-1H-1,2,3-triazole-4-carboxamide (I-172)

To a solution of 1-((6-chloro-5-methylimidazo[1,2-a]pyridin-2-yl)methyl)-1H-1,2,3-triazole-4-carboxylic acid (100 mg, 0.34 mmol) in DMF (2 mL) was added (7-chloro-8-fluoroimidazo[1,5-a]pyridin-1-yl)methanamine hydrochloride (160 mg, 0.68 mmol), HATU (261 mg, 0.68 mmol) and DIPEA (265 mg, 2.06 mmol). The mixture reaction was stirred at RT for 12 h. $H_2O$ (20 mL) was added to the reaction, extracted with EtOAc (30 mL×3). The combined organic layers were washed with brine, dried over $Na_2SO_4$, concentrated to give the crude product, which was purified with Prep-HPLC to give 1-((6-chloro-5-methylimidazo[1,2-a]pyridin-2-yl)methyl)-N-((7-chloro-8-fluoroimidazo[1,5-a]pyridin-1-yl)methyl)-1H-1,2,3-triazole-4-carboxamide (137 mg, 84%) as a white solid. ESI-MS [M+H]$^+$: 472.5. Purity: 99.69 (214 nm), 99.83 (254 nm). $^1$H NMR (400 MHz, DMSO-d$_6$) δ 8.69 (t, J=8.0 Hz, 1H), 8.57 (s, 1H), 8.44 (s, 1H), 8.21 (d, J=8.0 Hz, 1H), 8.03 (s, 1H), 7.49 (d, J=8.0 Hz, 1H), 7.37 (d, J=12.0 Hz, 1H), 6.76 (t, J=8.0 Hz, 1H), 5.79 (s, 2H), 4.71 (d, J=4.0 Hz, 2H), 2.68 (s, 3H).

Example 173

Scheme 172

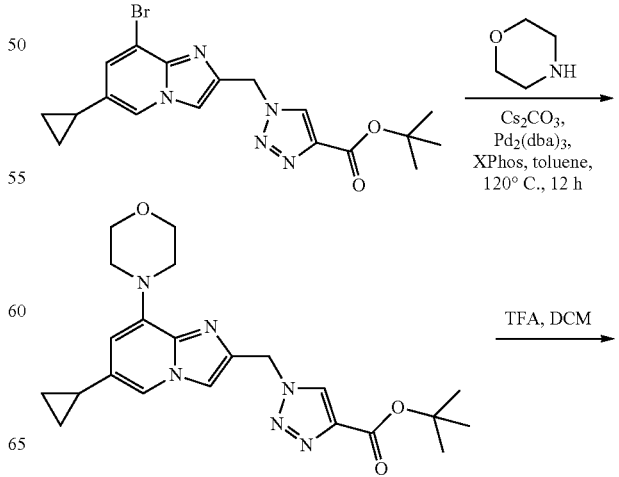

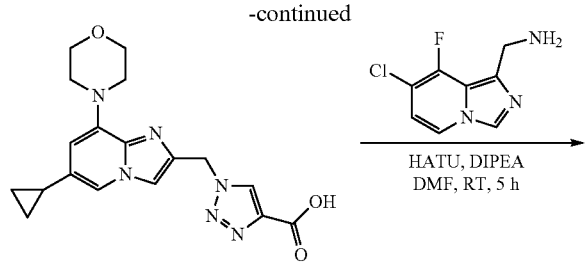

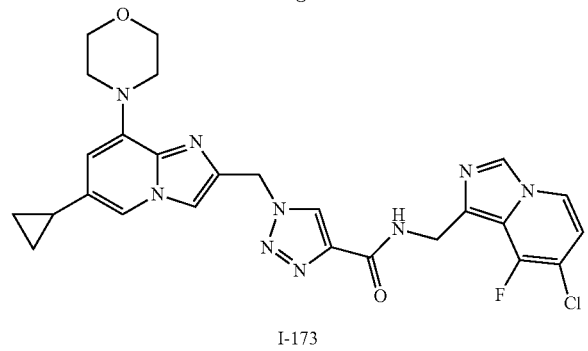

I-173

Synthesis of tert-butyl 1-((6-cyclopropyl-8-morpholinoimidazo[1,2-a]pyridin-2-yl)methyl)-1H-1,2,3-triazole-4-carboxylate To a solution of To a solution of tert-butyl 1-((8-bromo-6-cyclopropylimidazo[1,2-a]pyridin-2-yl)methyl)-1H-1,2,3-triazole-4-carboxylate (0.2 g, 0.48 mmol) and morpholine (0.05 g, 0.6 mmol) in toluene (20 mL) and H₂O (2 mL) was added CsCO₃ (0.4 g, 1.2 mmol), XPhos (0.04 g, 0.08 mmol) and Pd₂(dba)₃ (0.04 g, 0.04 mmol). After the mixture was stirred at 120° C. for 12 h under N₂, H₂O (100 mL) was added and extracted with EtOAc (20 mL*3). The combined organic layers were concentrated and purified by silica gel chromatography (DCM/MeOH=20/1) to give tert-butyl 1-((6-cyclopropyl-8-morpholinoimidazo[1,2-a]pyridin-2-yl)methyl)-1H-1,2,3-triazole-4-carboxylate (0.13 g, yield: 65%) as a yellow solid. ESI-MS [M+H]$^+$: 425.3.

Synthesis of 1-((6-cyclopropyl-8-morpholinoimidazo[1,2-a]pyridin-2-yl)methyl)-1H-1,2,3-triazole-4-carboxylic Acid To a solution of tert-butyl 1-((6-cyclopropyl-8-morpholinoimidazo[1,2-a]pyridin-2-yl)methyl)-1H-1,2,3-triazole-4-carboxylate (0.13 g, 0.3 mmol) in DCM (10 mL) was added TFA (2 mL). The mixture was stirred at 25° C. for 3 h. The solvent was removed by vacuo to give the crude 1-((6-cyclopropyl-8-morpholinoimidazo[1,2-a]pyridin-2-yl)methyl)-1H-1,2,3-triazole-4-carboxylic acid (0.1 g, yield: 90.9%) as a black solid which was used into next step without purification. ESI-MS [M+H]$^+$: 369.1.

Synthesis of N-((7-chloro-8-fluoroimidazo[1,5-a]pyridin-1-yl)methyl)-1-((6-cyclopropyl-8-morpholinoimidazo[1,2-a]pyridin-2-yl)methyl)-1H-1,2,3-triazole-4-carboxamide (I-173)

A solution of 1-((6-cyclopropyl-8-morpholinoimidazo[1,2-a]pyridin-2-yl)methyl)-1H-1,2,3-triazole-4-carboxylic acid (0.1 g, 0.27 mmol), (7-chloro-8-fluoroimidazo[1,5-a]pyridin-1-yl)methanamine hydrochloride (0.082 g, 0.35 mmol), HATU (0.17 g, 0.45 mmol) and DIPEA (0.12 g, 0.9 mmol) in DMF (5 mL) was stirred at 25° C. for 16 h. The solvent was removed by vacuo to give the crude and purified by Prep-HPLC to give N-((7-chloro-8-fluoroimidazo[1,5-a]pyridin-1-yl)methyl)-1-((6-cyclopropyl-8-morpholinoimidazo[1,2-a]pyridin-2-yl)methyl)-1H-1,2,3-triazole-4-carboxamide (70 mg, yield: 46.7%) as a white solid. ESI-MS [M+H]$^+$: 550.2. Purity: 100.00 (214 nm), 100.00 (254 nm). $^1$H NMR (400 MHz, DMSO-d₆) δ 8.70 (s, 1H), 8.52 (s, 1H), 8.44 (s, 1H), 8.20 (d, J=7.3 Hz, 1H), 7.94 (d, J=10.2 Hz, 1H), 7.72 (s, 1H), 6.76 (t, J=6.9 Hz, 1H), 6.20 (s, 1H), 5.71 (s, 2H), 4.69 (d, J=5.0 Hz, 2H), 3.76 (s, 3H), 3.43 (s, 3H), 2.89 (s, 1H), 2.73 (s, 1H), 1.79-1.99 (m, 1H), 0.88 (d, J=7.2 Hz, 2H), 0.67 (d, J=4.4 Hz, 2H).

Example 174

Scheme 173

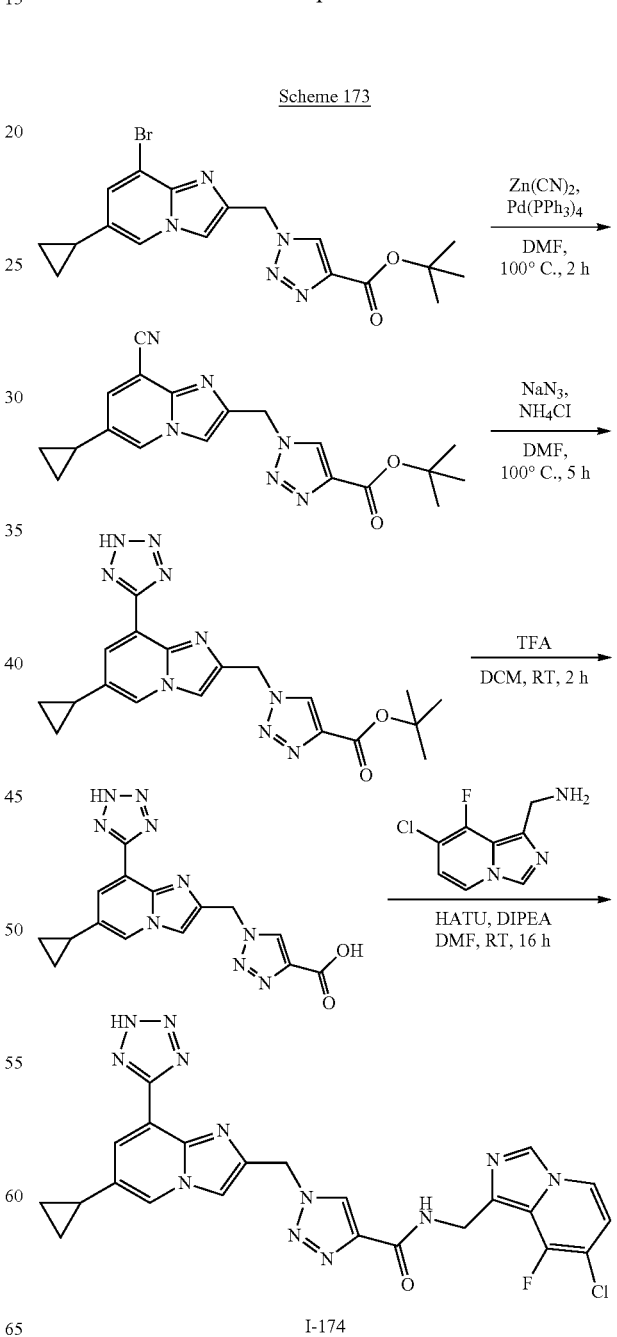

I-174

Synthesis of tert-butyl 1-((8-cyano-6-cyclopropylimidazo[1,2-a]pyridin-2-yl)methyl)-1H-1,2,3-triazole-4-carboxylate A mixture of tert-butyl 1-((8-bromo-6-cyclopropylimidazo[1,2-a]pyridin-2-yl)methyl)-1H-1,2,3-triazole-4-carboxylate (800 mg, 1.91 mmol), Zn(CN)2 (289 mg, 2.48 mmol) and Pd(PPh3)4 (553 mg, 0.47 mmol) in DMF (10 mL) was stirred at 100° C. for 2 h. Water (20 mL) was added and extracted with EtOAc (100 mL*3). The combined organics were concentrated and purified by silica gel chromatography (EA/PE=3/10) to give tert-butyl 1-((8-cyano-6-cyclopropylimidazo[1,2-a]pyridin-2-yl)methyl)-1H-1,2,3-triazole-4-carboxylate (650 mg, yield: 93%) as a white solid. ESI-MS [M+H]+: 365.1

Synthesis of tert-butyl 1-((6-cyclopropyl-8-(2H-tetrazol-5-yl)imidazo[1,2-a]pyridin-2-yl)methyl)-1H-1,2,3-triazole-4-carboxylate To a solution of tert-butyl 1-((8-cyano-6-cyclopropylimidazo[1,2-a]pyridin-2-yl)methyl)-1H-1,2,3-triazole-4-carboxylate (650 mg, 1.78 mmol) and NH4Cl (942 mg, 17.8 mmol) in DMF (10 mL) was added NaN3 (1.1 g, 17.8 mmol). After the mixture was stirred at 25° C. for 5 h, H2O (100 mL) was added and extracted with EtOAc (100 mL*3). The combined organic layers were concentrated and purified by silica gel chromatography (EA/PE=3/10) to tert-butyl 1-((6-cyclopropyl-8-(2H-tetrazol-5-yl)imidazo[1,2-a]pyridin-2-yl)methyl)-1H-1,2,3-triazole-4-carboxylate (300 mg, yield: 41.3%) as a yellow solid. ESI-MS [M+H]+: 408.1

Synthesis of 1-((6-cyclopropyl-8-(2H-tetrazol-5-yl)imidazo[1,2-a]pyridin-2-yl)methyl)-1H-1,2,3-triazole-4-carboxylic Acid A solution of tert-butyl 1-((6-cyclopropyl-8-(2H-tetrazol-5-yl)imidazo[1,2-a]pyridin-2-yl)methyl)-1H-1,2,3-triazole-4-carboxylate (300 mg, 0.73 mmol) in TFA/DCM (1.6 mL/4.8 mL) was stirred at 25° C. for 2 h. The mixture was concentrated to give the crude (250 mg, yield: 83%) as a yellow oil which was used into next step without purification. ESI-MS [M+H]+: 352.1

Synthesis of N-((7-chloro-8-fluoroimidazo[1,5-a]pyridin-1-yl)methyl)-1-((6-cyclopropyl-8-(2H-tetrazol-5-yl)imidazo[1,2-a]pyridin-2-yl)methyl)-1H-1,2,3-triazole-4-carboxamide (I-174)

To a solution of 1-((6-cyclopropyl-8-(2H-tetrazol-5-yl)imidazo[1,2-a]pyridin-2-yl)methyl)-1H-1,2,3-triazole-4-carboxylic acid (250 mg, 0.71 mmol), (7-chloro-8-fluoroimidazo[1,5-a]pyridin-1-yl)methanamine hydrochloride (190 mg, 0.81 mmol), HATU (404 mg, 1.0 mmol) in DMF (3 mL) was added DIPEA (458 mg, 3.5 mmol. After the mixture was stirred at 25° C. for 16 h, solvent was concentrated and purified by Prep-HPLC to give N-((7-chloro-8-fluoroimidazo[1,5-a]pyridin-1-yl)methyl)-1-((6-cyclopropyl-8-(2H-tetrazol-5-yl)imidazo[1,2-a]pyridin-2-yl)methyl)-1H-1,2,3-triazole-4-carboxamide (15.6 mg, yield: 4.1%) as a white solid. ESI-MS [M+H]+: 533.1. Purity: 97.16 (214 nm), 99.14 (254 nm). 1H NMR (400 MHz, DMSO-d6) 8.88 (s, 1H), 8.68 (t, J=5.4 Hz, 1H), 8.60 (s, 1H), 8.43 (d, J=2.4 Hz, 1H), 8.19 (d, J=7.4 Hz, 1H), 8.04 (s, 1H), 7.90 (s, 1H), 6.79-6.71 (m, 1H), 5.83 (s, 2H), 4.70 (d, J=5.5 Hz, 2H), 2.16-2.05 (m, 1H), 1.03-0.96 (m, 2H), 0.81-0.74 (m, 2H).

Example 175

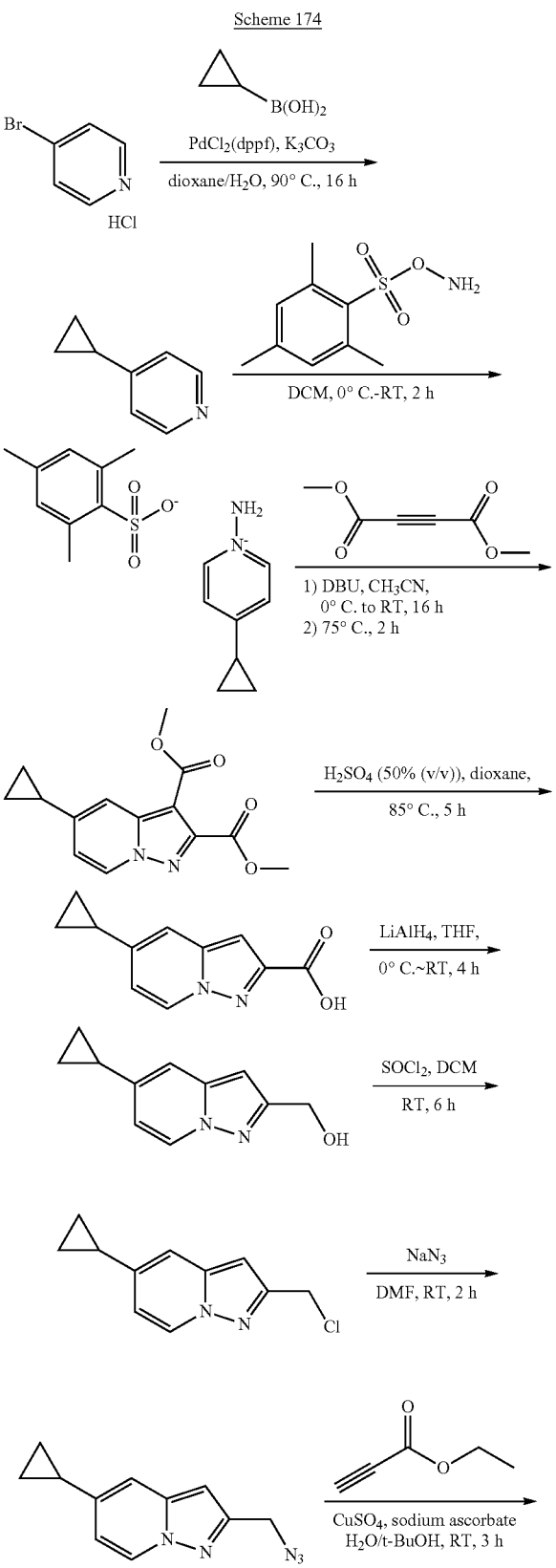

Scheme 174

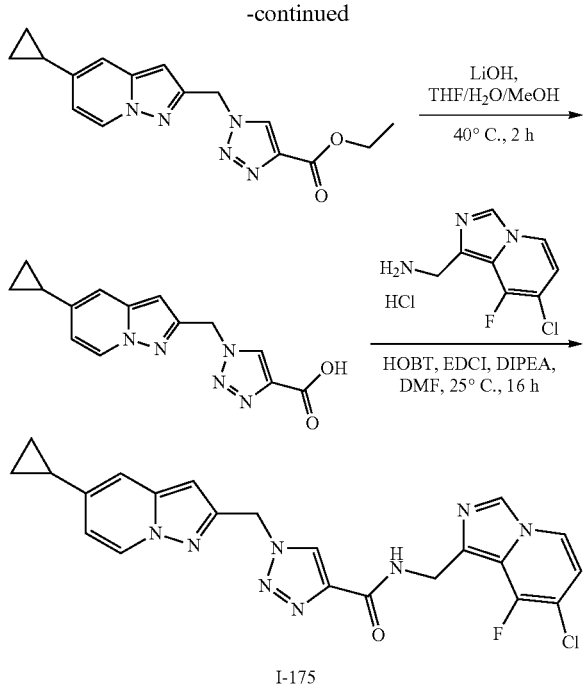

Synthesis of 4-cyclopropylpyridine

A mixture of 4-bromopyridine hydrochloride (21 g, 108 mmol), cyclopropylboronic acid (13.9 g, 162 mmol), $PdCl_2$ (dppf) (3.95 g, 5.4 mmol) and $K_2CO_3$ (4.78 g, 324 mmol) in 1,4-dioxane (200 mL) and $H_2O$ (50 mL) was stirred at 90° C. for 16 h under $N_2$. The reaction mixture was filtered through celite and 1,4-dioxane was removed. The residue was diluted with $H_2O$ (100 mL) and extracted with EtOAc (100 mL×3). The combined organics was washed with brine (200 mL×1), dried over $Na_2SO_4$, concentrated and purified by silica gel chromatography (EtOAc/PE=1/2) to give 4-cyclopropylpyridine (10 g, yield: 78%) as light brown oil. ESI-MS $[M+H]^+$: 120.2.

Synthesis of 1-amino-4-cyclopropylpyridin-1-ium 2,4,6-trimethylbenzenesulfonate To a stirred solution of 4-cyclopropylpyridine (8.7 g, 73 mmol) in DCM (100 mL) was added slowly a solution of O-(mesitylsulfonyl)hydroxylamine (15.7 g, 73 mmol) in DCM (50 mL) at 0° C. The mixture was stirred at 0° C. for 10 min and warmed to RT and stirred for 2 h. The reaction mixture was concentrated and dried in vacuo to give 1-amino-4-cyclopropylpyridin-1-ium 2,4,6-trimethylbenzenesulfonate (24.4 g, yield: 100%) as a yellow solid. ESI-MS $[M+H]^+$: 135.2.

Synthesis of dimethyl 5-cyclopropylpyrazolo[1,5-a]pyridine-2,3-dicarboxylate To a stirred solution of 1-amino-4-cyclopropylpyridin-1-ium 2,4,6-trimethylbenzenesulfonate (24.4 g, 73 mmol) and dimethyl but-2-ynedioate (20.75 g, 146 mmol) in acetonitrile (250 mL) was added dropwise of DBU (22.23 g, 146 mmol) at 0° C. The mixture was stirred at RT for 16 h and stirred at 75° C. for 2 h. The reaction mixture was concentrated and purified by silica gel chromatography (EA/PE=1/3) to give dimethyl 5-cyclopropylpyrazolo[1,5-a]pyridine-2,3-dicarboxylate (6.0 g, yield: 30%) as a yellow solid. ESI-MS $[M+H]^+$: 275.1.

Synthesis of 5-cyclopropylpyrazolo[1,5-a]pyridine-2-carboxylic Acid

A mixture of dimethyl 5-cyclopropylpyrazolo[1,5-a]pyridine-2,3-dicarboxylate (6 g, 21.88 mmol) in 50% $H_2SO_4$ (30 mL) and 1,4-dioxane (40 mL) was stirred at 85° C. for 5 h. The reaction mixture was poured into $H_2O$ (300 mL) and extracted with EtOAc/MeOH (10:1, 150 mL×3). The combined organics was washed with brine (400 mL×1), dried over $Na_2SO_4$, concentrated and dried in vacuo to give 5-cyclopropylpyrazolo[1,5-a]pyridine-2-carboxylic acid (3.6 g, yield: 81%) as a light brown solid. ESI-MS $[M+H]^+$: 203.1.

Synthesis of (5-cyclopropylpyrazolo[1,5-a]pyridin-2-yl)methanol

To a stirred suspension of $LiAlH_4$ (788 mg, 20.76 mmol) in THF (40 mL) was added dropwise the solution of 5-cyclopropylpyrazolo[1,5-a]pyridine-2-carboxylic acid (1.4 g, 6.92 mmol) in THF (30 mL) at 0° C. The mixture was stirred at RT for 4 h. The reaction mixture was quenched by adding $H_2O$ (1 mL), 15% NaOH aqueous (1 mL) and $H_2O$ (3 mL). The mixture was stirred for 30 min at 0° C. and then filtered and the filtrate was concentrated and purified by silica gel chromatography (EA/PE=1/1) to give (5-cyclopropylpyrazolo[1,5-a]pyridin-2-yl)methanol (350 mg, yield: 27%) as a yellow solid. ESI-MS $[M+H]^+$: 189.2.

Synthesis of 2-(chloromethyl)-5-cyclopropylpyrazolo[1,5-a]pyridine

To a stirred solution of (5-cyclopropylpyrazolo[1,5-a]pyridin-2-yl)methanol (350 mg, 1.86 mmol) in DCM (10 mL) was added $SOCl_2$ (2.21 g, 18.6 mmol) at 0° C. The mixture was stirred at RT for 6 h. The reaction mixture was concentrated to give 2-(chloromethyl)-5-cyclopropylpyrazolo[1,5-a]pyridine (350 mg, yield: 91%) as a yellow solid which was used into next step without purification. ESI-MS $[M+H]^+$: 207.1.

Synthesis of 2-(azidomethyl)-5-cyclopropylpyrazolo[1,5-a]pyridine

A mixture of 2-(chloromethyl)-5-cyclopropylpyrazolo[1,5-a]pyridine (350 mg, 1.69 mmol) and $NaN_3$ (132 mg, 2.03 mmol) in DMF (5 mL) was stirred at RT for 2 h. Water (50 mL) was added and extracted with EtOAc (50 mL×2). The combined organics was washed with brine (80 mL×3), concentrated and dried in vacuo to give 2-(azidomethyl)-5-cyclopropylpyrazolo[1,5-a]pyridine (360 mg, yield: 100%) as a yellow syrup. ESI-MS $[M+H]^+$: 214.2.

Synthesis of Ethyl 1-((5-cyclopropylpyrazolo[1,5-a]pyridin-2-yl)methyl)-1H-1,2,3-triazole-4-carboxylate The mixture of 2-(azidomethyl)-5-cyclopropylpyrazolo[1,5-a]pyridine (360 mg, 1.69 mmol), ethyl propiolate (199 mg, 2.03 mmol), $CuSO_4$ (135 mg, 0.845 mmol) and sodium ascorbate (167 mg, 0.845 mmol) in t-BuOH (5 mL) and $H_2O$ (5 mL) was stirred at RT for 3 h. The reaction mixture was concentrated. The residue was diluted in $H_2O$ (50 mL) and extracted with EtOAc (50 mL×3). The combined organics were washed with brine (80 mL×1), dried over Na₂SO₄, concentrated and purified by silica gel chromatography (EA/PE=1/1) to give ethyl 1-((5-cyclopropylpyrazolo[1,5-a]pyridin-2-yl)methyl)-1H-1,2,3-triazole-4-carboxylate (160 mg, yield: 30%) as a yellow solid. ESI-MS [M+H]⁺: 312.2.

Synthesis of 1-((5-cyclopropylpyrazolo[1,5-a]pyridin-2-yl)methyl)-1H-1,2,3-triazole-4-carboxylic Acid A solution of ethyl 1-((5-cyclopropylpyrazolo[1,5-a]pyridin-2-yl)methyl)-1H-1,2,3-triazole-4-carboxylate (160 mg, 0.51 mmol) in a mixed solvent of methanol (2 mL), THF (2 mL) and H₂O (1 mL) was added lithium hydroxide monohydrate (86 mg, 2.04 mmol). The mixture was stirred at 40° C. for 1 h. Most of the solvent was removed and the residue was diluted with H₂O (5 mL), the pH value of mixture was adjusted to 4-5 by adding HCl aqueous (1 M). The precipitate was collected and dried to give 1-((5-cyclopropylpyrazolo[1,5-a]pyridin-2-yl)methyl)-1H-1,2,3-triazole-4-carboxylic acid (120 mg, 83%) as a yellow solid. ESI-MS [M+H]⁺: 284.2.

Synthesis of N-((7-chloro-8-fluoroimidazo[1,5-a]pyridin-1-yl)methyl)-1-((5-cyclopropylpyrazolo[1,5-a]pyridin-2-yl)methyl)-1H-1,2,3-triazole-4-carboxamide (I-175)

A mixture of 1-((5-cyclopropylpyrazolo[1,5-a]pyridin-2-yl)methyl)-1H-1,2,3-triazole-4-carboxylic acid (54 mg, 0.191 mmol), (7-chloro-8-fluoroimidazo[1,5-a]pyridin-1-yl)methanamine hydrochloride (45 mg, 0.191 mmol), EDCI (55 mg, 0.287 mmol), HOBT (39 mg, 0.287 mmol) and DIPEA (123 mg, 0.955 mmol) in DMF (3 mL) was stirred at 25° C. for 16 h. The reaction mixture was poured into H₂O (30 mL) and the precipitate was collected, washed with H₂O (30 mL), dried in vacuo to give N-((7-chloro-8-fluoroimidazo[1,5-a]pyridin-1-yl)methyl)-1-((5-cyclopropylpyrazolo[1,5-a]pyridin-2-yl)methyl)-1H-1,2,3-triazole-4-carboxamide (65 mg, yield: 73%) as a pale white solid. ESI-MS [M+H]⁺: 465.1. Purity: 99.85 (214 nm), 100 (254 nm). ¹H NMR (400 MHz, DMSO-d₆) δ 8.72 (t, J=5.3 Hz, 1H), 8.60 (s, 1H), 8.49 (d, J=7.2 Hz, 1H), 8.44 (d, J=2.3 Hz, 1H), 8.21 (d, J=7.4 Hz, 1H), 7.35 (s, 1H), 6.76 (t, J=6.9 Hz, 1H), 6.59 (dd, J=7.3, 1.8 Hz, 1H), 6.38 (s, 1H), 5.80 (s, 2H), 4.70 (d, J=5.5 Hz, 2H), 2.01-1.93 (m, 1H), 1.03-0.94 (m, 2H), 0.79-0.71 (m, 2H).

Example 176

Scheme 175

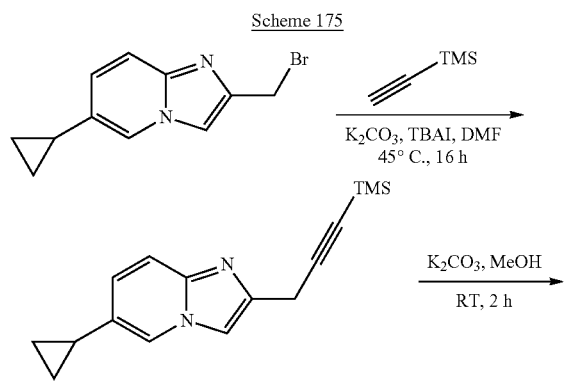

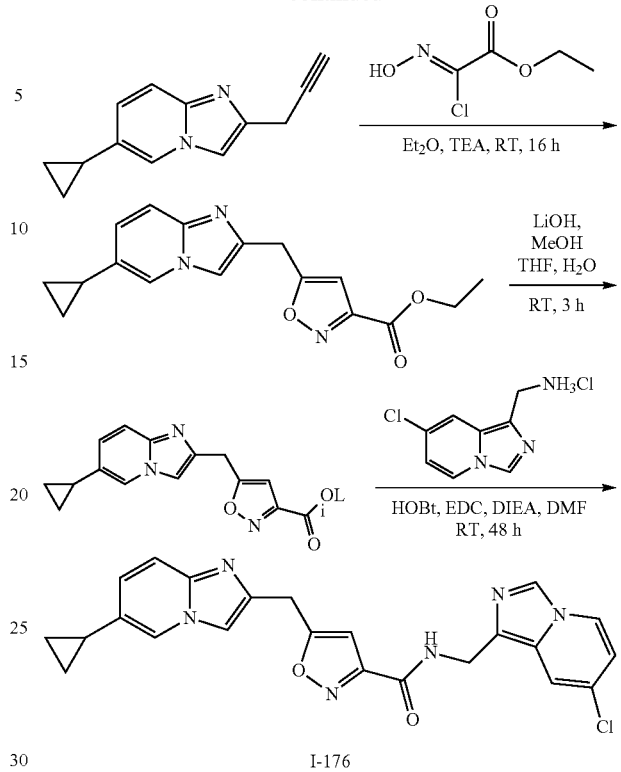

I-176

Synthesis of 6-cyclopropyl-2-(3-(trimethylsilyl)prop-2-yn-1-yl)imidazo[1,2-a]pyridine A mixture of 2-(bromomethyl)-6-cyclopropylimidazo[1,2-a]pyridine (1.0 g, 4 mmol), ethynyltrimethylsilane (1.2 g, 12 mmol), Cu (153 mg, 0.8 mmol), TBAI (295 mg, 0.8 mmol) and K₂CO₃ (2.75 g, 20 mmol) in DMEF (10 mL) was stirred at 45° C. for 16 h. The reaction was quenched with H₂O (100 mL) and extracted with EtOAc (100 mL×5). The combined organic layers were washed with brine, dried over Na₂SO₄, concentrated in vacuum to give the crude product which was purified by silica gel (eluent: EtOAc/PE: 1/5 to 1/1) to give 6-cyclopropyl-2-(3-(trimethylsilyl)prop-2-yn-1-yl)imidazo[1,2-a]pyridine (270 mg, yield: 25%) as a yellow oil. ESI-MS [M+H]⁺: 269.1.

Synthesis of 6-cyclopropyl-2-(prop-2-yn-1-yl)imidazo[1,2-a]pyridine

To a solution of 6-cyclopropyl-2-(3-(trimethylsilyl)prop-2-yn-1-yl)imidazo[1,2-a]pyridine (269 mg, 1.0 mmol) in MeOH (5 mL) was added K₂CO₃ (690 mg, 5 mmol). The mixture was stirred at RT for 2 h. The reaction was monitored by LCMS until the starting material consumed. Water (50 mL) was added and extracted with EtOAc (50 mL×3). The combined organic layers were washed with brine, dried over Na₂SO₄, concentrated in vacuo to give the crude product which was purified by silica gel (eluent: DCM/MeOH: 50/1 to 10/1) to give 6-cyclopropyl-2-(prop-2-yn-1-yl)imidazo[1,2-a]pyridine (158 mg, yield: 80%) as a yellow oil. ESI-MS [M+H]⁺: 197.1.

Synthesis of Ethyl 5-((6-cyclopropylimidazo[1,2-a]pyridin-2-yl)methyl)isoxazole-3-carboxylate To a solution of 6-cyclopropyl-2-(prop-2-yn-1-yl)imidazo[1,2-a]pyridine (158 mg, 0.8 mmol) and ethyl 2-chloro-2-

(hydroxyimino)acetate (606 mg, 4.0 mmol) in Et₂O (3 mL) was added TEA (485 mg, 4.8 mmol). The mixture was stirred at RT for 16 h. The reaction was quenched with H₂O (30 mL) and extracted with EtOAc (50 mL×3). The combined organic layers were washed with brine, dried over Na₂SO₄, concentrated in vacuo to give the crude product, which was purified by Prep-TLC (DCM/MeOH=20/1) to give ethyl 5-((6-cyclopropylimidazo[1,2-a]pyridin-2-yl)methyl)isoxazole-3-carboxylate (30 mg, yield: 12%) as a white solid. ESI-MS [M+H]⁺: 312.2.

Synthesis of lithium 5-((6-cyclopropylimidazo[1,2-a]pyridin-2-yl)methyl)isoxazole-3-carboxylate To a mixture of ethyl 5-((6-cyclopropylimidazo[1,2-a]pyridin-2-yl)methyl)isoxazole-3-carboxylate (30 mg, 0.1 mmol) in MeOH/THF/H₂O (1 mL/1 mL/1 mL) was added LiOH·H₂O (13 mg, 0.3 mmol). The mixture was stirred at RT for 3 h. The reaction was monitored by LCMS until the starting material consumed. The reaction was freeze-dried to give the crude lithium 5-((6-cyclopropylimidazo[1,2-a]pyridin-2-yl)methyl)isoxazole-3-carboxylate (50 mg) as a yellow solid. ESI-MS [M+H]⁺: 284.1.

Synthesis of N-((7-chloroimidazo[1,5-a]pyridin-1-yl)methyl)-5-((6-cyclopropylimidazo[1,2-a]pyridin-2-yl)methyl)isoxazole-3-carboxamide (I-176)

To a mixture of lithium 5-((6-cyclopropylimidazo[1,2-a]pyridin-2-yl)methyl)isoxazole-3-carboxylate (50 mg, crude from last step), (7-chloroimidazo[1,5-a]pyridin-1-yl)methanamine HCl salt (33 mg, 0.15 mmol) and DIPEA (65 mg, 0.65 mmol) in DMF (1 mL) was added HOBT (27 mg, 0.2 mmol) and EDCI (38 mg, 0.2 mmol). The mixture was stirred at RT for 48 h. The reaction was quenched with H₂O (10 mL) and extracted with EtOAc (30 mL×3). The combined organic layers were washed with brine, dried over Na₂SO₄, concentrated in vacuo to give the crude product which was purified by Pre-TLC (DCM/MeOH=10/1) to give N-((7-chloroimidazo[1,5-a]pyridin-1-yl)methyl)-5-((6-cyclopropylimidazo[1,2-a]pyridin-2-yl)methyl)isoxazole-3-carboxamide (2.5 mg, yield: 5.6% over 2 steps) as a white solid. ESI-MS [M+H]⁺: 447.0. Purity: 89.9 (214 nm), 88.6 (254 nm). ¹H NMR (400 MHz, DMSO-d₆) δ 9.18 (t, J=5.8 Hz, 1H), 8.37-8.28 (m, 3H), 7.82 (d, J=1.8 Hz, 1H), 7.70 (s, 1H), 7.38 (d, J=9.3 Hz, 1H), 6.97 (dd, J=9.3, 1.8 Hz, 1H), 6.66 (dd, J=7.5, 2.1 Hz, 1H), 6.59 (s, 1H), 4.60 (d, J=5.9 Hz, 2H), 4.27 (s, 2H), 1.96-1.89 (m, 1H), 0.94-0.87 (m, 2H), 0.71-0.64 (m, 2H).

Example 177

Scheme 176

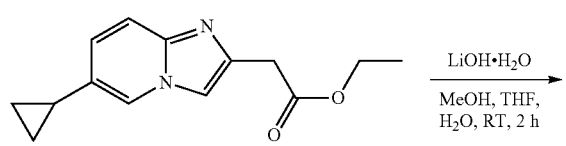

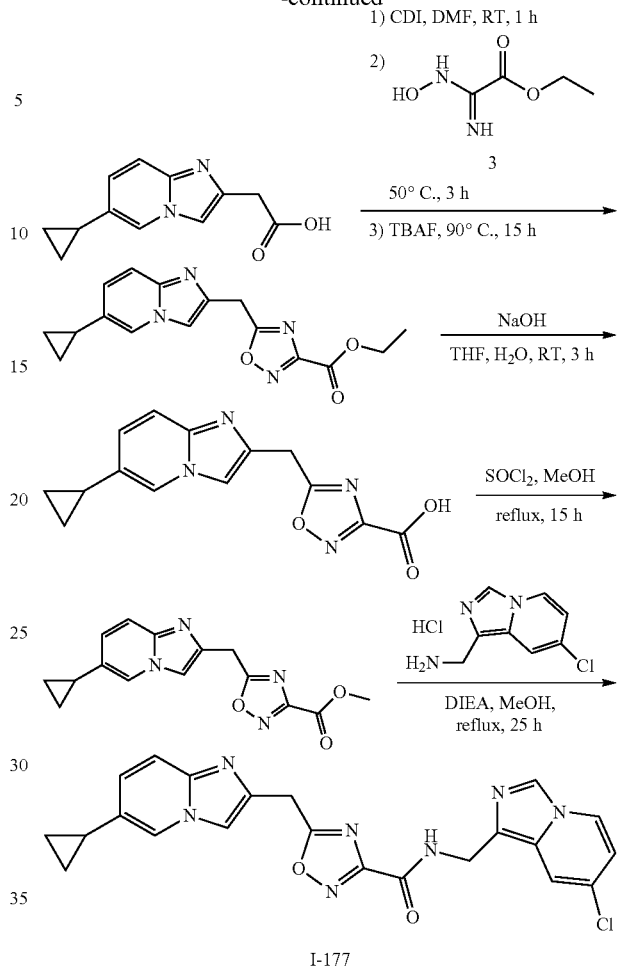

I-177

Synthesis of 2-(6-cyclopropylimidazo[1,2-a]pyridin-2-yl)acetic Acid

To a solution of ethyl 2-(6-cyclopropylimidazo[1,2-a]pyridin-2-yl)acetate (770 mg, 3.15 mmol) in MeOH (8 mL) and THF (8 mL) was added a solution of LiOH·H₂O (398 mg, 9.45 mmol) in H₂O (8 mL). The mixture was stirred at RT for 2 h. The volatile was removed in vacuo and the aqueous phase was acidified to pH 4-5 with 2N HCl, and concentrated to get the crude product which was purified by flash column chromatography (0-10% MeOH in DCM) to get 2-(6-cyclopropylimidazo[1,2-a]pyridin-2-yl)acetic acid (440 mg, yield: 65%) as a dark yellow solid. ESI-MS [M+H]⁺: 216.9.

Synthesis of Ethyl 5-((6-cyclopropylimidazo[1,2-a]pyridin-2-yl)methyl)-1,2,4-oxadiazole-3-carboxylate To a solution of 2-(6-cyclopropylimidazo[1,2-a]pyridin-2-yl)acetic acid (300 mg, 1.39 mmol) in DMF (8 mL) was added CDI (270 mg, 1.67 mmol). The resulting mixture was stirred at RT for 1 h. To the mixture was added ethyl 2-(hydroxyamino)-2-iminoacetate (238 mg, 1.81 mmol). The resulting mixture was stirred at 50° C. for 3 h. To the mixture was added TBAF (1.4 mL, 1 M). The resulting mixture was stirred at 90° C. overnight. The reaction mixture was concentrated. The residue was partitioned between DCM (20 mL) and H₂O (15 mL). The layers were separated and the aqueous phase was extracted with DCM (2×15 mL). The combined organic layers were washed with brine (15 mL), dried over Na₂SO₄, filtered and concentrated. The residue was purified by flash column chromatography (0-10% MeOH in DCM) to get ethyl 5-((6-cyclopropylimidazo[1,2-a]pyridin-2-yl)methyl)-1,2,4-oxadiazole-3-carboxylate (200 mg, yield: 46%) as a brown oil. ESI-MS [M+H]⁺: 313.0.

Synthesis of 5-((6-cyclopropylimidazo[1,2-a]pyridin-2-yl)methyl)-1,2,4-oxadiazole-3-carboxylic Acid To a solution of ethyl 5-((6-cyclopropylimidazo[1,2-a]pyridin-2-yl)methyl)-1,2,4-oxadiazole-3-carboxylate (200 mg, 0.64 mmol) in THF (10 mL) was added a solution of NaOH (38 mg, 0.96 mmol) in H₂O (10 mL). The mixture was stirred at RT for 3 h. The volatile was removed in vacuo and the aqueous phase was extracted with DCM (2×15 mL). The aqueous phase was acidified to pH 4-5 with 2N HCl, and lyophilized to get 5-((6-cyclopropylimidazo[1,2-a]pyridin-2-yl)methyl)-1,2,4-oxadiazole-3-carboxylic acid (200 mg, crude) as a dark yellow solid. ESI-MS [M+H]⁺: 285.2.

Synthesis of Methyl 5-((6-cyclopropylimidazo[1,2-a]pyridin-2-yl)methyl)-1,2,4-oxadiazole-3-carboxylate To a solution of 5-((6-cyclopropylimidazo[1,2-a]pyridin-2-yl)methyl)-1,2,4-oxadiazole-3-carboxylic acid (200 mg, crude) in MeOH (3 mL) was added SOCl2 (67 mg, 0.56 mmol). The resulting mixture was stirred at 55° C. overnight. The reaction mixture was concentrated. The residue was partitioned between DCM (20 mL) and aqueous saturated NaHCO₃ solution (20 mL). The layers were separated and the aqueous phase was extracted with DCM (2×20 mL). The combined organic layers were washed with brine (30 mL), dried over Na₂SO₄, filtered and concentrated to get methyl 5-((6-cyclopropylimidazo[1,2-a]pyridin-2-yl)methyl)-1,2,4-oxadiazole-3-carboxylate (60 mg, yield: 32%) as an orange solid. The crude product was used for next step directly without purification. ESI-MS [M+H]⁺: 299.0.

Synthesis of N-((7-chloroimidazo[1,5-a]pyridin-1-yl)methyl)-5-((6-cyclopropylimidazo[1,2-a]pyridin-2-yl)methyl)-1,2,4-oxadiazole-3-carboxamide (I-177)

To a mixture of methyl 5-((6-cyclopropylimidazo[1,2-a]pyridin-2-yl)methyl)-1,2,4-oxadiazole-3-carboxylate (60 mg, 0.20) and (7-chloroimidazo[1,5-a]pyridin-1-yl)methanamine hydrochloride (44 mg, 0.22 mmol) in MeOH (3 mL) was added DIPEA (52 mg, 0.4 mmol). The resulting mixture was stirred under reflux for 25 h. The reaction mixture was concentrated. The residue was partitioned between DCM (10 mL) and H₂O (10 mL). The layers were separated and the aqueous phase was extracted with DCM (2×20 mL). The combined organic phase was washed with brine (10 mL), dried over Na₂SO₄, filtered and concentrated to get the crude product. The crude product was purified by flash column chromatography (0-10% MeOH in DCM) and then prep-TLC (DCM/MeOH=17/1) to get N-((7-chloroimidazo[1,5-a]pyridin-1-yl)methyl)-5-((6-cyclopropylimidazo[1,2-a]pyridin-2-yl)methyl)-1,2,4-oxadiazole-3-carboxamide (10 mg, yield: 11.1%) as a yellow solid. ESI-MS [M+H]⁺: 448.0. Purity: 100.00 (214 nm), 100.00 (254 nm).

H NMR (400 MHz, DMSO-d₆) δ 8.03 (s, 1H), 7.86 (s, 1H), 7.81 (d, J=8 Hz, 1H), 7.68 (s, 2H), 7.51 (s, 1H), 7.47 (d, J=8 Hz, 1H), 6.95 (d, J=7.2 Hz, 1H), 6.52 (d, J=7.2 Hz, 1H), 4.82 (d, J=5.6 Hz, 2H), 4.46 (s, 2H), 1.90-1.87 (m, 1H), 0.98-0.91 (m, 2H), 0.69-0.65 (m, 2H)

Example 178

Scheme 177

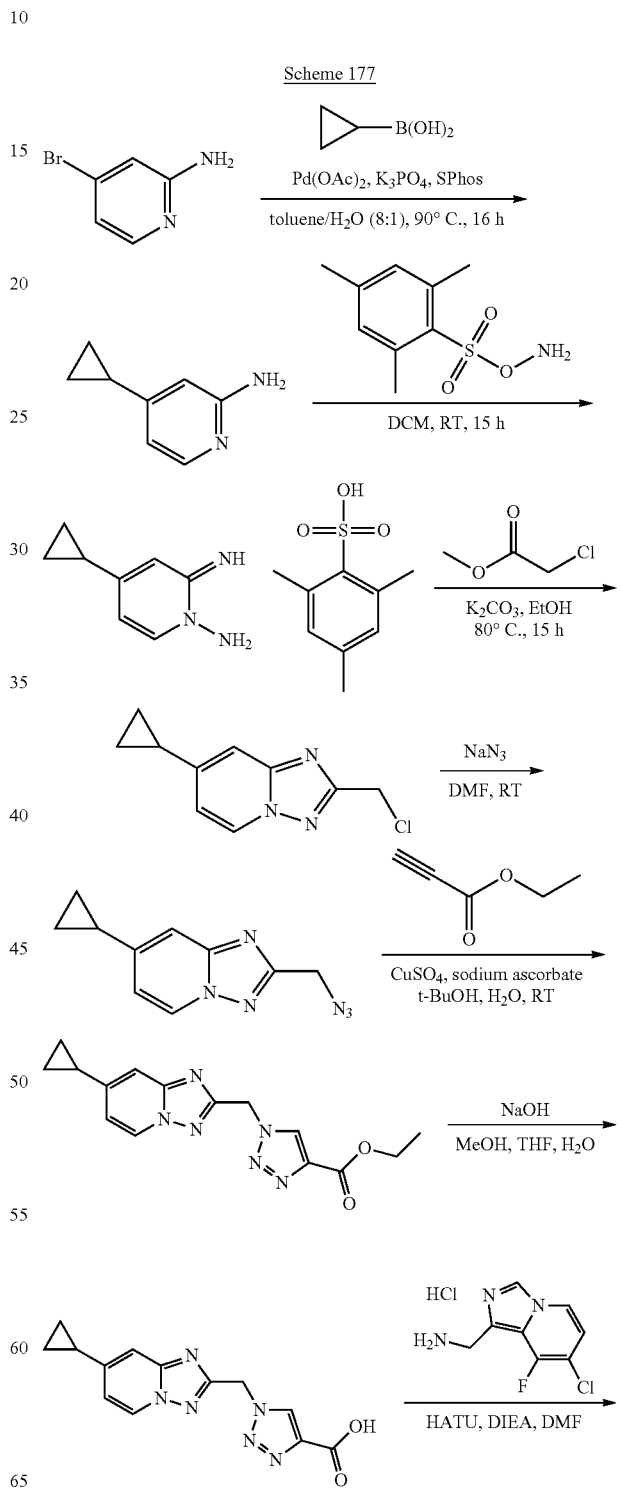

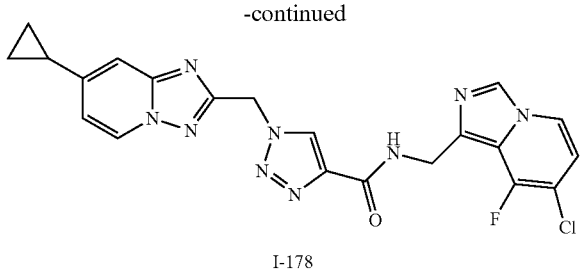

I-178

Synthesis of 4-cyclopropylpyridin-2-amine

A mixture of 4-bromopyridin-2-amine (5 g, 28.9 mmol), cyclopropylboronic acid (3.2 g, 37.6 mmol), Pd(OAc)$_2$ (325 mg, 1.45 mmol), SPhos (948 mg, 2.31 mmol) and K$_3$PO$_4$ (12.3 g, 57.8 mmol) in toluene (80 mL) and H$_2$O (10 mL) was stirred at 90° C. under nitrogen atmosphere overnight. The reaction mixture was cooled to RT, filtered and concentrated to get the crude product which was purified by flash column chromatography (0-60% EtOAc in Petroleum ether) to get 4-cyclopropylpyridin-2-amine (750 mg, 19%) as a yellow solid. ESI-MS [M+H]$^+$: 135.1.

Synthesis of 4-cyclopropyl-2-iminopyridin-1(2H)-amine 2,4,6-trimethylbenzenesulfonate To a solution of 4-cyclopropylpyridin-2-amine (536 mg, 4 mmol) in DCM (10 mL) was added a solution of O-(mesitylsulfonyl)hydroxylamine (2.58 g, 12 mmol) in DCM (10 mL). The resulting mixture was stirred at RT overnight and concentrated to get the crude product 4-cyclopropyl-2-iminopyridin-1(2H)-amine 2,4,6-trimethylbenzenesulfonate (3.12 g) which was used into next step directly without purification.

Synthesis of 2-(chloromethyl)-7-cyclopropyl-[1,2,4]triazolo[1,5-a]pyridine

A mixture of 4-cyclopropyl-2-iminopyridin-1(2H)-amine 2,4,6-trimethylbenzenesulfonate (3.12 g, crude), methyl 2-chloroacetate (1.3 g, 12 mmol) and K$_2$CO$_3$ (1.66 g, 12 mmol) in EtOH (15 mL) was stirred at 80° C. overnight. The reaction mixture was concentrated. The residue was partitioned between DCM (20 mL) and H$_2$O (20 mL). The layers were separated and the aqueous phase was extracted with DCM (2×30 mL). The combined organic layers were washed with brine (10 mL), dried over Na$_2$SO$_4$, filtered and concentrated to get the crude product which was purified by column chromatography (PE/EtOAc=10/1-3/1) to get 2-(chloromethyl)-7-cyclopropyl-[1,2,4]triazolo[1,5-a]pyridine (230 mg, 28% over 2 steps) as a light yellow solid. ESI-MS [M+H]$^+$: 208.0.

Synthesis of 2-(azidomethyl)-7-cyclopropyl-[1,2,4]triazolo[1,5-a]pyridine

To a solution of 2-(chloromethyl)-7-cyclopropyl-[1,2,4]triazolo[1,5-a]pyridine (230 mg, 1.1 mmol) in DMF (5 mL) was added sodium azide (145 mg, 2.2 mmol). The resulting mixture was stirred at RT overnight. The reaction mixture was concentrated. The residue was partitioned between DCM (30 mL) and H$_2$O (20 mL). The layers were separated and the aqueous phase was extracted with DCM (2×30 mL). The combined organic phase was washed with brine (10 mL), dried over Na$_2$SO$_4$, filtered and concentrated to get 2-(azidomethyl)-7-cyclopropyl-[1,2,4]triazolo[1,5-a]pyridine (185 mg, 77.8%) as a light yellow solid. The crude product was used into next step directly. ESI-MS [M+H]$^+$: 215.1.

Synthesis of Ethyl 1-((7-cyclopropyl-[1,2,4]triazolo[1,5-a]pyridin-2-yl)methyl)-1H-1,2,3-triazole-4-carboxylate To a solution of 2-(azidomethyl)-7-cyclopropyl-[1,2,4]triazolo[1,5-a]pyridine (180 mg, 0.84 mmol) in t-BuOH (2 mL) and H$_2$O (2 mL) was added sequentially of CuSO4.5H$_2$O (42 mg, 0.17 mmol), sodium ascorbate (51 mg, 0.25 mmol) and ethyl propiolate (165 mg, 1.68 mmol). The resulting mixture was stirred at RT for 3 h. The reaction mixture was concentrated to get the crude product which was purified by flash column chromatography (0-8% MeOH in DCM) to get ethyl 1-((7-cyclopropyl-[1,2,4]triazolo[1,5-a]pyridin-2-yl)methyl)-1H-1,2,3-triazole-4-carboxylate (155 mg, yield: 59%) as a dark yellow solid. ESI-MS [M+H]$^+$: 312.9. $^1$H NMR (400 MHz, MeOD) δ 7.80 (s, 1H), 7.69 (d, J=7.2 Hz, 1H), 6.52 (s, 1H), 6.03 (d, J=7.2 Hz, 1H), 5.05 (s, 2H), 3.99 (s, 3H), 3.51 (q, J=7.1 Hz, 2H), 1.28-1.16 (m, 1H), 0.50 (t, J=7.1 Hz, 3H), 0.32-0.22 (m, 2H), 0.06-0.01 (m, 2H).

Synthesis of 1-((7-cyclopropyl-[1,2,4]triazolo[1,5-a]pyridin-2-yl)methyl)-1H-1,2,3-triazole-4-carboxylic Acid To a solution of ethyl 1-((7-cyclopropyl-[1,2,4]triazolo[1,5-a]pyridin-2-yl)methyl)-1H-1,2,3-triazole-4-carboxylate (205 mg, 0.66 mmol) in THF (6 mL) and MeOH (6 mL) was added a solution of NaOH (78 mg, 1.97 mmol) in H$_2$O (6 mL). The mixture was stirred at RT for 3 h. The volatile was removed in vacuo and the aqueous phase was acidified to pH 4-5 with 2N HCl. The precipitate formed was collected by filtration and washed with H$_2$O, lyophilized to get 1-((7-cyclopropyl-[1,2,4]triazolo[1,5-a]pyridin-2-yl)methyl)-1H-1,2,3-triazole-4-carboxylic acid (145 mg, 78%) as a pale yellow solid. ESI-MS [M+H]$^+$: 285.0.

Synthesis of N-((7-chloro-8-fluoroimidazo[1,5-a]pyridin-1-yl)methyl)-1-((7-cyclopropyl-[1,2,4]triazolo[1,5-a]pyridin-2-yl)methyl)-1H-1,2,3-triazole-4-carboxamide (I-178)

To a mixture of 1-((7-cyclopropyl-[1,2,4]triazolo[1,5-a]pyridin-2-yl)methyl)-1H-1,2,3-triazole-4-carboxylic acid (70 mg, 0.25 mmol), HATU (105 mg, 0.27 mmol) and DIPEA (97 mg, 0.75 mmol) in DMF (5 mL) was added (7-chloro-8-fluoroimidazo[1,5-a]pyridin-1-yl)methanamine hydrochloride (61 mg, 0.26 mmol). The resulting mixture was stirred at RT for 1 h. The reaction mixture was concentrated. The residue was partitioned between DCM (10 mL) and H$_2$O (10 mL). The layers were separated and the aqueous phase was extracted with DCM (2×10 mL). The combined organic phase was washed with brine (10 mL), dried over Na$_2$SO$_4$, filtered and concentrated. The crude product was purified by flash column chromatography (0-10% MeOH in DCM) to get N-((7-chloro-8-fluoroimidazo[1,5-a]pyridin-1-yl)methyl)-1-((7-cyclopropyl-[1,2,4]triazolo[1,5-a]pyridin-2-yl)methyl)-1H-1,2,3-triazole-4-carboxamide (70 mg, 61%) as a white solid. ESI-MS [M+H]$^+$: 465.8. Purity: 100.00 (214 nm), 100.00 (254 nm). $^1$H NMR (400 MHz, CDCl₃) δ 8.36 (d, J=7.1 Hz, 1H), 8.32 (s, 1H), 8.21 (s, 1H), 7.77-7.66 (m, 2H), 7.34 (s, 1H), 6.74 (d, J=7.1 Hz, 1H), 6.54 (t, J=6.7 Hz, 1H), 5.81 (s, 2H), 4.97 (d, J=5.0 Hz, 2H), 2.07-1.96 (m, 1H), 1.20-1.09 (m, 2H), 0.89-0.77 (m, 2H).

Example 179

Scheme 178

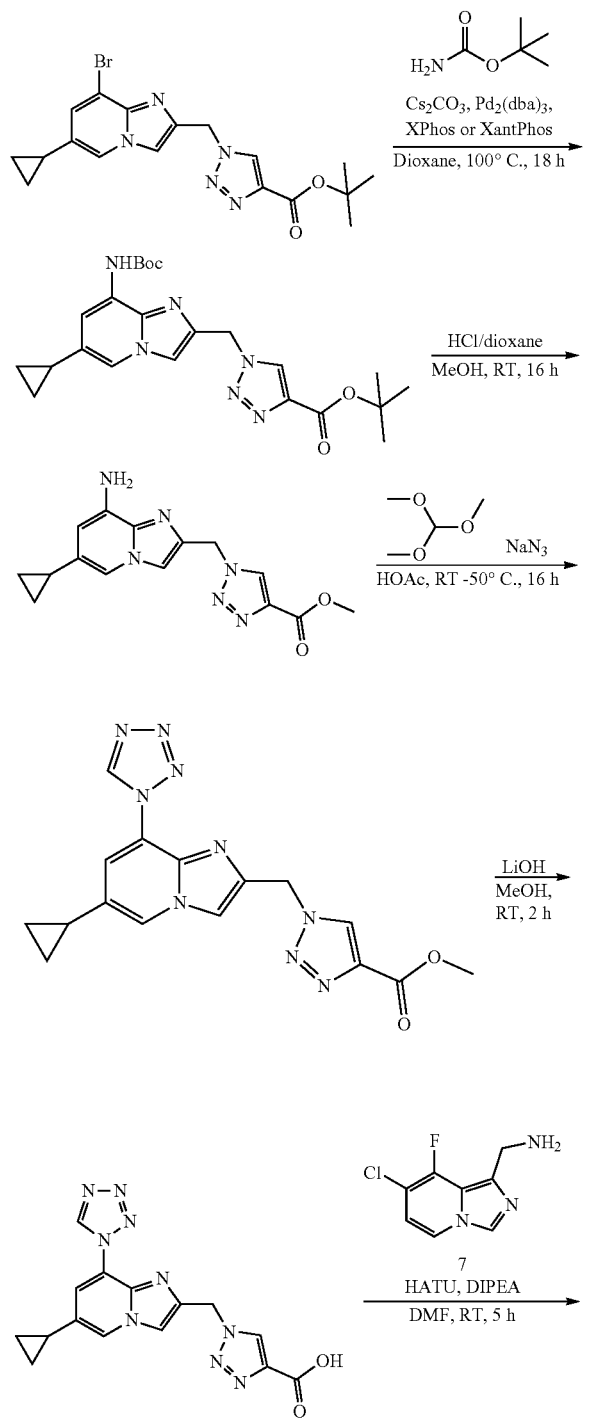

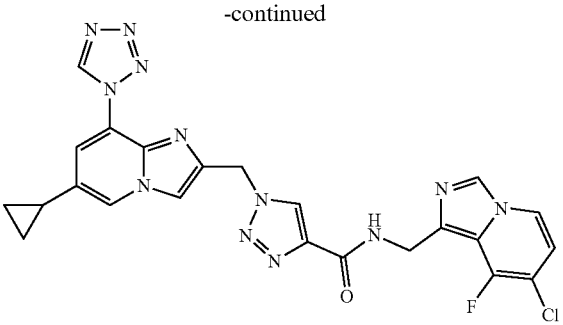

I-179

Synthesis of tert-butyl 1-((8-((tert-butoxycarbonyl)amino)-6-cyclopropylimidazo[1,2-a]pyridin-2-yl)methyl)-1H-1,2,3-triazole-4-carboxylate To a solution of tert-butyl 1-((8-bromo-6-cyclopropylimidazo[1,2-a]365yridine-2-yl)methyl)-1H-1,2,3-triazole-4-carboxylate (1 g, 2 mmol) and tert-butyl carbamate (0.56 g, 4 mmol) in dioxane (10 mL) was added Pd₂(dba)₃ (0.18 g, 0.2 mmol), XantPhos (0.23, 0.4 mmol), Cs₂CO₃ (1.95 g, 6 mmol). The reaction mixture was stirred at 100° C. for 16 h under N2. The reaction mixture was cooled to RT and H₂O (50 mL) was added. The aqueous phase was extracted with ethyl acetate (100 mL×3), the combined organic layers were dried over sodium sulfate, evaporated and the residue was purified by silica gel chromatography (DCM:MeOH=15:1) to give the tert-butyl 1-((8-((tert-butoxycarbonyl)amino)-6-cyclopropylimidazo[1,2-a]365yridine-2-yl)methyl)-1H-1,2,3-triazole-4-carboxylate (900 mg, 99%) as a yellow solids. ESI-MS [M+H]⁺: 455.2.

Synthesis of Methyl 1-((8-amino-6-cyclopropylimidazo[1,2-a]365yridine-2-yl)methyl)-1H-1,2,3-triazole-4-carboxylate A solution of tert-butyl 1-((8-((tert-butoxycarbonyl)amino)-6-cyclopropylimidazo[1,2-a]pyridin-2-yl)methyl)-1H-1,2,3-triazole-4-carboxylate (300 mg, 0.66 mmol) in MeOH (5 mL) and HCl in dioxane (4 M, 5 mL) was stirred at RT for 16 h. LCMS showed the reaction was complete. The solvent of the reaction mixture was evaporated to give the crude product which was used in next step without further purification. (230 mg, yield 100%) as a yellow solids. ESI-MS [M+H]⁺: 313.3.

Synthesis of Methyl 1-((6-cyclopropyl-8-(1H-tetrazol-1-yl)imidazo[1,2-a]pyridin-2-yl)methyl)-1H-1,2,3-triazole-4-carboxylate A solution of methyl 1-((8-amino-6-cyclopropylimidazo[1,2-a]pyridin-2-yl)methyl)-1H-1,2,3-triazole-4-carboxylate (230 mg, 0.74 mmol) in trimethoxymethane (4 mL) was added NaN₃ (192 mg, 2.96 mmol) at 0° C. The mixture was stirred at 0° C. for 0.5 h. Then HOAc (4 mL) was added, the mixture was stirred at 50° C. for 16 h, sat. NaHCO₃ (aq) was added to PH about 8, extracted with EtOAc (100 mL×3), The combined organic layers were washed with brine (50 mL×2), dried over anhydrous sodium sulfate and concentrated to give the crude product, which was purified by silica gel chromatography (DCM:MeOH=15:1) to give methyl 1-((6-cyclopropyl-8-(1H-tetrazol-1-yl)imidazo[1,2-a]pyridin-2-yl)methyl)-1H-1,2,3-triazole-4-carboxylate (130 mg, yield: 48%) as a yellow solid. ESI-MS [M+H]+: 366.3.

Synthesis of 1-((6-cyclopropyl-8-(1H-tetrazol-1-yl)imidazo[1,2-a]pyridin-2-yl)methyl)-1H-1,2,3-triazole-4-carboxylic Acid To a solution of methyl 1-((6-cyclopropyl-8-(1H-tetrazol-1-yl)imidazo[1,2-a]pyridin-2-yl)methyl)-1H-1,2,3-triazole-4-carboxylate (130 mg, 0.35 mmol) in MeOH (5 mL) and H₂O (5 mL) was added LiOH.H₂O (59.8 mg, 1.42 mmol) and the reaction mixture was stirred at 50° C. for 2 h. Most of the solvent was removed and the residue was diluted with H₂O (10 mL), the pH value of mixture was adjusted to 4-5 by adding HCl aqueous (1 M). The precipitate was collected and dried to give 1-((6-cyclopropyl-8-(1H-tetrazol-1-yl)imidazo[1,2-a]pyridin-2-yl)methyl)-1H-1,2,3-triazole-4-carboxylic acid (93 mg yield 75%) as a white solids. ESI-MS [M+H]+: 352.1.

Synthesis of N-((7-chloro-8-fluoroimidazo[1,5-a]pyridin-1-yl)methyl)-1-((6-cyclopropyl-8-(1H-tetrazol-1-yl)imidazo[1,2-a]pyridin-2-yl)methyl)-1H-1,2,3-triazole-4-carboxamide (I-179)

To a solution of 1-((6-cyclopropyl-8-(H-tetrazol-1-yl)imidazo[1,2-a]pyridin-2-yl)methyl)-1H-1,2,3-triazole-4-carboxylic acid (40 mg, 0.113 mmol) in dry DMF (3 mL), was added (7-chloro-8-fluoroimidazo[1,5-a]pyridin-1-yl)methanamine hydrochloride (40 mg, 0.17 mmol), HATU (51 mg, 0.136 mmol) and DIPEA (58 mg, 0.45 mmol), the reaction mixture was stirred at RT for 5 h. The reaction mixture diluted with H₂O (20 mL), extracted with ethyl acetate (30 mL×3). The combined organic layers were washed with brine (20 mL×2), dried over anhydrous sodium sulfate and concentrated in vacuo. The residue was purified by Prep-TLC (DCM/MeOH=10:1) to afford N-((7-chloro-8-fluoroimidazo[1,5-a]pyridin-1-yl)methyl)-1-((6-cyclopropyl-8-(1H-tetrazol-1-yl)imidazo[1,2-a]pyridin-2-yl)methyl)-1H-1,2,3-triazole-4-carboxamide (33 mg, yield: 55%) as a white solids. ESI-MS [M+H]+: 533.20. Purity: 96.16 (214 nm), 97.18 (254 nm). ¹H NMR (400 MHz, DMSO-d₆) δ 10.29 (s, 1H), 8.71 (m, 2H), 8.63 (s, 1H), 8.46 (d, J=1.7 Hz, 1H), 8.23 (d, J=7.3 Hz, 1H), 8.10 (s, 1H), 7.74 (s, 1H), 6.76 (t, J=6.9 Hz, 1H), 5.82 (s, 2H), 4.70 (d, J=5.3 Hz, 2H), 2.14-2.04 (m, 1H), 1.00 (m, 2H), 0.79 (m, 2H).

Example 180

Scheme 179

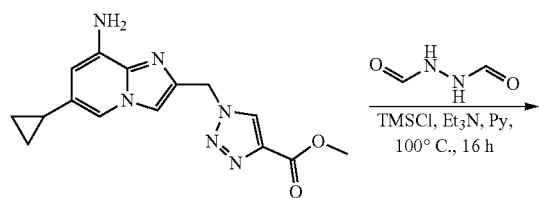

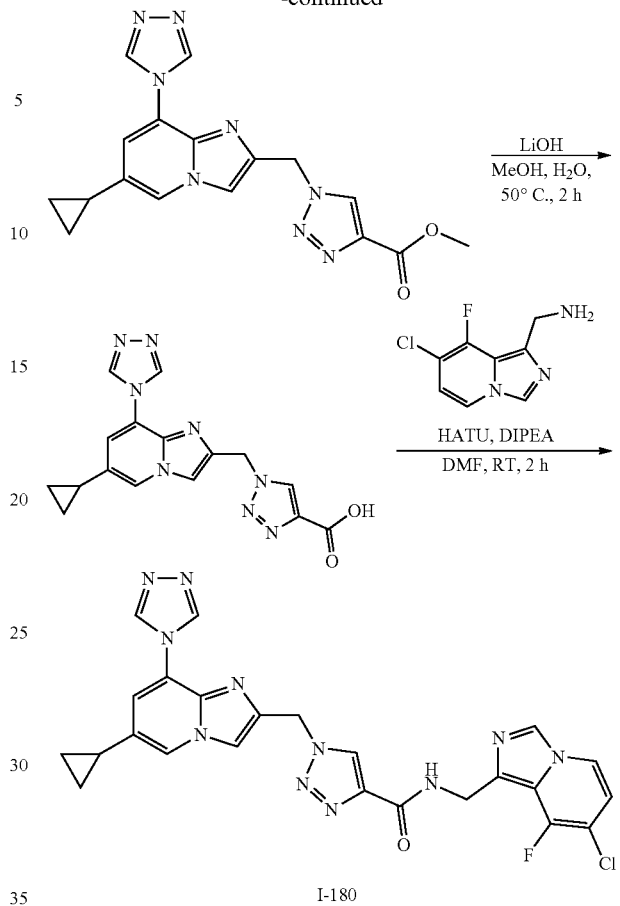

I-180

Synthesis of Methyl 1-((6-cyclopropyl-1-4H-1,2,4-triazol-4-yl)imidazo[1,2-a]pyridin-2-yl)methyl)-1H-1,2,3-triazole-4-carboxylate To a mixture of methyl 1-((8-amino-6-cyclopropylimidazo[1,2-a]pyridin-2-yl)methyl)-1H-1,2,3-triazole-4-carboxylate (240 mg, 0.77 mmol), N'-formylformohydrazide (203 mg, 2.3 mmol) and triethylamine (0.74 mL, 5.39 mmol) in pyridine (5 mL) was added chlorotrimethylsilane (1.25 g, 11.55 mmol) drop-wise and the resulting solution was stirred for 16 h at 100° C., then cooled to RT. The resulting mixture was concentrated and the residue was diluted with H₂O (20 mL), extracted with ethyl acetate (3×50 mL). the combined organic layers were washed with brine (50 mL), dried (MgSO₄), and concentrated under reduced pressure. The crude residue was purified by silica gel column chromatography (Dichloromethane:Methanol=10:1) to give the methyl 1-((6-cyclopropyl-8-(4H-1,2,4-triazol-4-yl)imidazo[1,2-a]pyridin-2-yl)methyl)-1H-1,2,3-triazole-4-carboxylate (150 mg, yield 54%) as a white solid. ESI-MS [M+H]+: 365.4.

Synthesis of 1-((6-cyclopropyl-8-(4H-1,2,4-triazol-4-yl)imidazo[1,2-a]pyridin-2-yl)methyl)-1H-1,2,3-triazole-4-carboxylic Acid To a solution of methyl 1-((6-cyclopropyl-8-(4H-1,2,4-triazol-4-yl)imidazo[1,2-a]pyridin-2-yl)methyl)-1H-1,2,3-triazole-4-carboxylate (145 mg, 0.398 mmol) in MeOH (5 mL) and H₂O (5 mL) was added LiOH.H₂O (66 mg, 1.589 mmol) and the reaction mixture was stirred at 50° C. for 3 h. Most of the solvent was removed and the residue was diluted with H₂O (10 mL), the pH value of mixture was adjusted to 4 by adding HCl aqueous (1 M). The precipitate was collected and dried to give the 1-((6-cyclopropyl-8-(4H-1,2,4-triazol-4-yl)imidazo[1,2-a]pyridin-2-yl)methyl)-1H-1,2,3-triazole-4-carboxylic acid (120 mg, yield 87%) as a white solids. ESI-MS [M+H]⁺: 351.1

Synthesis of N-((7-chloro-8-fluoroimidazo[1,5-a]pyridin-1-yl)methyl)-1-((6-cyclopropyl-8-(4H-1,2,4-triazol-4-yl)imidazo[1,2-a]pyridin-2-yl)methyl)-1H-1,2,3-triazole-4-carboxamide (I-180)

To a solution of 1-((6-cyclopropyl-8-(4H-1,2,4-triazol-4-yl)imidazo[1,2-a]pyridin-2-yl)methyl)-1H-1,2,3-triazole-4-carboxylic acid (120 mg, 0.34 mmol) in dry DMF (3 mL) was added (7-chloro-8-fluoroimidazo[1,5-a]pyridin-1-yl)methanamine hydrochloride (96 mg, 0.41 mmol), HATU (155.8 mg, 0.41 mmol) and DIPEA (175 mg, 1.36 mmol), the reaction mixture was stirred at RT for 2 h. The reaction mixture diluted with H₂O (20 mL), extracted with ethyl acetate (30 mL×3). The combined organic layers were washed with brine (20 mL×2), dried over anhydrous sodium sulfate and concentrated in vacuo. The residue was purified by Prep-TLC (DCM/MeOH=10:1) to afford N-((7-chloro-8-fluoroimidazo[1,5-a]pyridin-1-yl)methyl)-1-((6-cyclopropyl-8-(4H-1,2,4-triazol-4-yl)imidazo[1,2-a]pyridin-2-yl)methyl)-1H-1,2,3-triazole-4-carboxamide (50 mg, yield: 28%) as a white solid. ESI-MS [M+H]⁺: 532.20. Purity: 98.96 (214 nm), 99.41 (254 nm). ¹H NMR (400 MHz, DMSO-d₆) δ 9.40 (s, 2H), 8.71 (t, J=5.4 Hz, 1H), 8.64 (s, 1H), 8.47 (d, J=1.0 Hz, 1H), 8.44 (d, J=2.4 Hz, 1H), 8.20 (d, J=7.4 Hz, 1H), 8.01 (s, 1H), 7.46 (d, J=1.3 Hz, 1H), 6.79-6.71 (m, 1H), 5.81 (s, 2H), 4.70 (d, J=5.5 Hz, 2H), 2.04-1.95 (m, 1H), 1.02-0.94 (m, 2H), 0.86-0.79 (m, 2H).

Example 181

Scheme 180

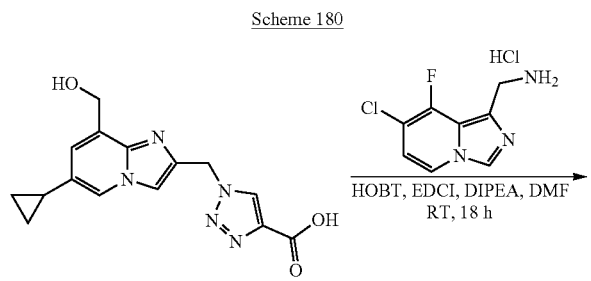

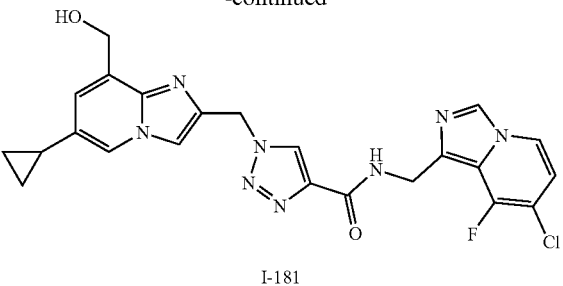

I-181

Synthesis of N-((7-chloro-8-fluoroimidazo[1,5-a]pyridin-1-yl)methyl)-1-((6-cyclopropyl-8-(hydroxymethyl)imidazo[1,2-a]pyridin-2-yl)methyl)-1H-1,2,3-triazole-4-carboxamide (I-181)

To the solution of 1-((6-cyclopropyl-8-(hydroxymethyl)imidazo[1,2-a]pyridin-2-yl)methyl)-1H-1,2,3-triazole-4-carboxylic acid (300 mg, 0.96 mmol) and (7-chloro-8-fluoroimidazo[1,5-a]pyridin-1-yl)methanamine hydrochloride (338 mg, 1.44 mmol) in dry DMF (5 mL) was added HOBT (156 mg, 1.15 mmol), EDCI (221 mg, 1.15 mmol) and DIPEA (371 mg, 2.88 mmol) at RT. The reaction mixture was stirred at RT for 18 h and then poured into H₂O (20 mL). The precipitate was filtered and washed with H₂O (10) and hexane (20). The solid was dried to afforded N-((7-chloro-8-fluoroimidazo[1,5-a]pyridin-1-yl)methyl)-1-((6-cyclopropyl-8-(hydroxymethyl)imidazo[1,2-a]pyridin-2-yl)methyl)-1H-1,2,3-triazole-4-carboxamide (410 mg, yield: 86%) as a white solid. ESI-MS [M+H]⁺: 495.1. Purity: 95.21 (214 nm), 97.34 (254 nm). ¹H NMR (400 MHz, DMSO-d₆) δ 8.71 (t, J=5.4 Hz, 1H), 8.54 (s, 1H), 8.44 (d, J=2.3 Hz, 1H), 8.26-8.17 (m, 2H), 7.81 (s, 1H), 7.01 (d, J=1.3 Hz, 1H), 6.80-6.72 (m, 1H), 5.72 (s, 2H), 5.33 (t, J=5.7 Hz, 1H), 4.74 (d, J=5.6 Hz, 2H), 4.70 (d, J=5.5 Hz, 2H), 1.98-1.90 (m, 1H), 0.96-0.89 (m, 2H), 0.69-0.62 (m, 2H).

Example 182

Scheme 181

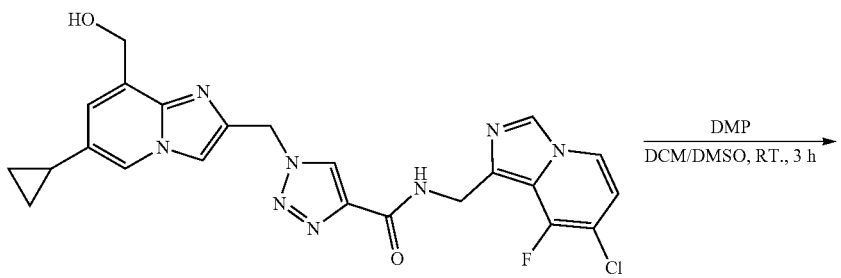

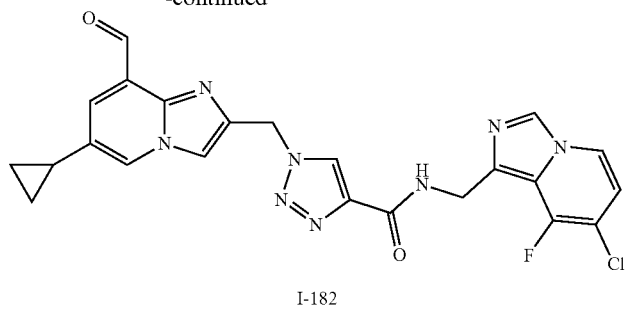

I-182

Synthesis of N-((7-chloro-8-fluoroimidazo[1,5-a]pyridin-1-yl)methyl)-1-((6-cyclopropyl-8-formylimidazo[1,2-a]pyridin-2-yl)methyl)-1H-1,2,3-triazole-4-carboxamide (I-182)

To the mixture of N-((7-chloro-8-fluoroimidazo[1,5-a]pyridin-1-yl)methyl)-1-((6-cyclopropyl-8-(hydroxymethyl)imidazo[1,2-a]pyridin-2-yl)methyl)-1H-1,2,3-triazole-4-carboxamide (300 mg, 0.61 mmol) in DCM/DMF (15 mL/15 mL) was added DMP (515 mg, 1.21 mmol) at RT. The reaction mixture was stirred at RT for 3 h and then quenched with sat. NaHCO₃ (30 mL). The mixture was extracted with DCM (30 mL*3). The combined organic layer was washed with saturated salt H₂O and concentrated. The residue was purified by flash column chromatography to afforded N-((7-chloro-8-fluoroimidazo[1,5-a]pyridin-1-yl)methyl)-1-((6-cyclopropyl-8-formylimidazo[1,2-a]pyridin-2-yl)methyl)-1H-1,2,3-triazole-4-carboxamide (130 mg, yield: 43%) as a brown solid and of which 50 mg target compound was further purified by prep-HPLC to give a light yellow solid (8.5 mg, yield: 17%). ESI-MS [M+H]$^+$: 493.1. Purity: 100% (214 nm), 100% (254 nm). $^1$H NMR (400 MHz, DMSO-d$_6$) δ 10.44 (s, 1H), 8.75-8.68 (m, 2H), 8.58 (s, 1H), 8.44 (d, J=2.4 Hz, 1H), 8.20 (d, J=7.4 Hz, 1H), 7.97 (s, 1H), 7.61 (d, J=1.7 Hz, 1H), 6.80-6.72 m, 1H), 5.82 (s, 2H), 4.70 (d, J=5.5 Hz, 2H), 2.10-2.00 (m, 1H), 1.01-0.95 (m, 2H), 0.77-0.71 (m, 2H).

Example 183

Scheme 182

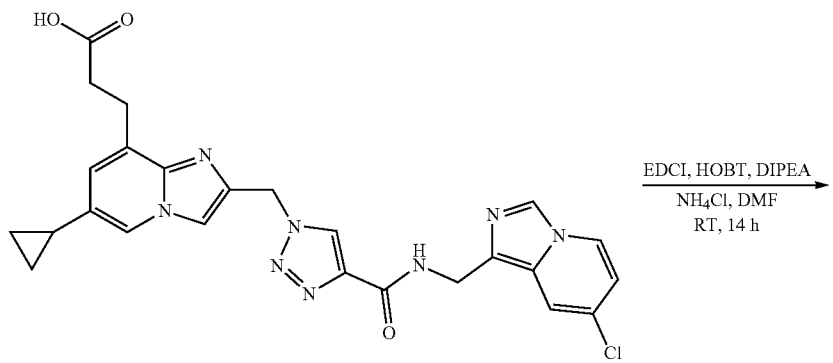

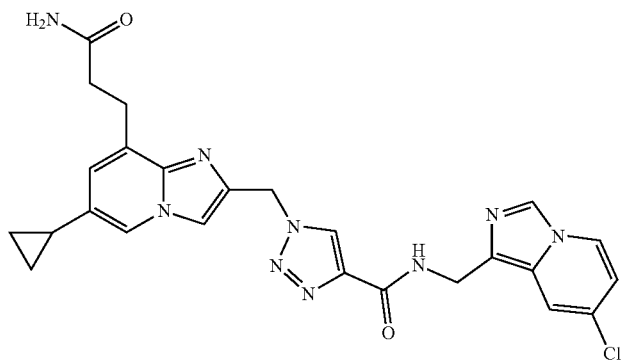

I-183

Synthesis of 1-((8-(3-amino-3-oxopropyl)-6-cyclopropylimidazo[1,2-a]pyridin-2-yl)methyl)-N-((7-chloroimidazo[1,5-a]pyridin-1-yl)methyl)-1H-1,2,3-triazole-4-carboxamide (I-183)

To a solution of 3-(2-((4-(((7-chloroimidazo[1,5-a]pyridin-1-yl)methyl)carbamoyl)-1H-1,2,3-triazol-1-yl)methyl)-6-cyclopropylimidazo[1,2-a]pyridin-8-yl)propanoic acid (145 mg, 0.28 mmol) in DMF (5 mL) was added EDCI (110 mg, 0.58 mmol), HOBT (78 mg, 0.58 mmol), DIPEA (195 mg, 1.5 mmol) and NH$_4$Cl (30 mg, 0.55 mmol) at RT. The mixture was stirred for 14 h. The mixture was concentrated and purified by Prep-HPLC to 1-((8-(3-amino-3-oxopropyl)-6-cyclopropylimidazo[1,2-a]pyridin-2-yl)methyl)-N-((7-chloroimidazo[1,5-a]pyridin-1-yl)methyl)-1H-1,2,3-triazole-4-carboxamide (5 mg, yield: 3.5%) as a white solid. ESI-MS [M+H]$^+$: 518.1. Purity: 97.17% (214 nm), 96.33% (254 nm). $^1$H NMR (400 MHz, DMSO-d$_6$) δ 8.92 (t, J=5.9 Hz, 1H), 8.57 (s, 1H), 8.34-8.28 (m, 2H), 8.19 (d, J=1.0 Hz, 1H), 7.89-7.82 (m, 1H), 7.77 (s, 1H), 7.30 (s, 1H), 6.85-6.75 (m, 2H), 6.65 (dd, J=7.5, 2.1 Hz, 1H), 5.73 (s, 2H), 4.62 (d, J=5.9 Hz, 2H), 3.02 (t, J=7.6 Hz, 2H), 2.49-2.46 (m, 2H) 1.92-1.82 (m, 1H), 0.95-0.84 (m, 2H), 0.70-0.59 (m, 2H).

Example 184

Synthesis of N-((7-chloroimidazo[1,5-a]pyridin-1-yl)methyl)-1-((8-(2-cyanoethyl)-6-cyclopropylimidazo[1,2-a]pyridin-2-yl)methyl)-1H-1,2,3-triazole-4-carboxamide (I-184)

A solution of 1-((8-(3-amino-3-oxopropyl)-6-cyclopropylimidazo[1,2-a]pyridin-2-yl)methyl)-N-((7-chloroimidazo[1,5-a]pyridin-1-yl)methyl)-1H-1,2,3-triazole-4-carboxamide (100 mg, 0.19 mmol) in POCl$_3$ (2 mL) was heated to 60° C. and stirred for 5 h. The mixture was concentrated and purified by prep-HPLC to give N-((7-chloroimidazo[1,5-a]pyridin-1-yl)methyl)-1-((8-(2-cyanoethyl)-6-cyclopropylimidazo[1,2-a]pyridin-2-yl)methyl)-1H-1,2,3-triazole-4-carboxamide (8.2 mg, yield: 8.6%) as a white solid. ESI-MS [M+H]$^+$: 500.2. Purity: 98.62% (214 nm), 98.42% (254 nm). $^1$H NMR (400 MHz, DMSO-d$_6$) δ 8.92 (t, J=5.9 Hz, 1H), 8.57 (s, 1H), 8.38-8.21 (m, 3H), 7.86-7.80 (m, 2H), 6.96 (s, 1H), 6.64 (dd, J=7.5, 2.1 Hz, 1H), 5.74 (s, 2H), 4.61 (d, J=5.9 Hz, 2H), 3.11 (t, J=7.1 Hz, 2H), 3.00 (t, J=6.8 Hz, 2H), 1.96-1.86 (m, 1H), 0.96-0.88 (m, 2H), 0.71-0.63 (m, 2H).

Scheme 183

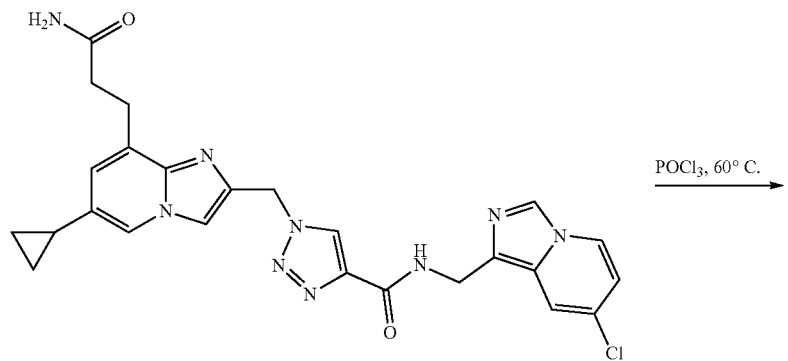

POCl$_3$, 60° C.

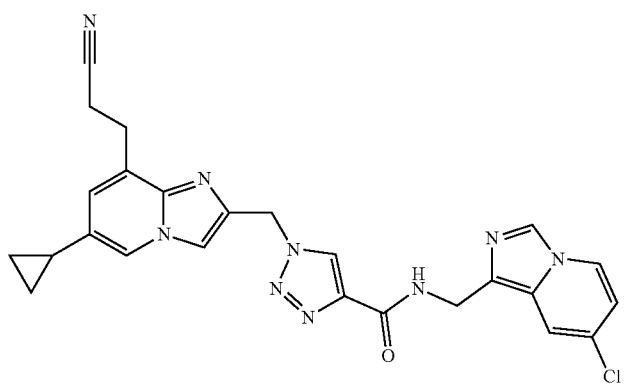

I-184

Example 185

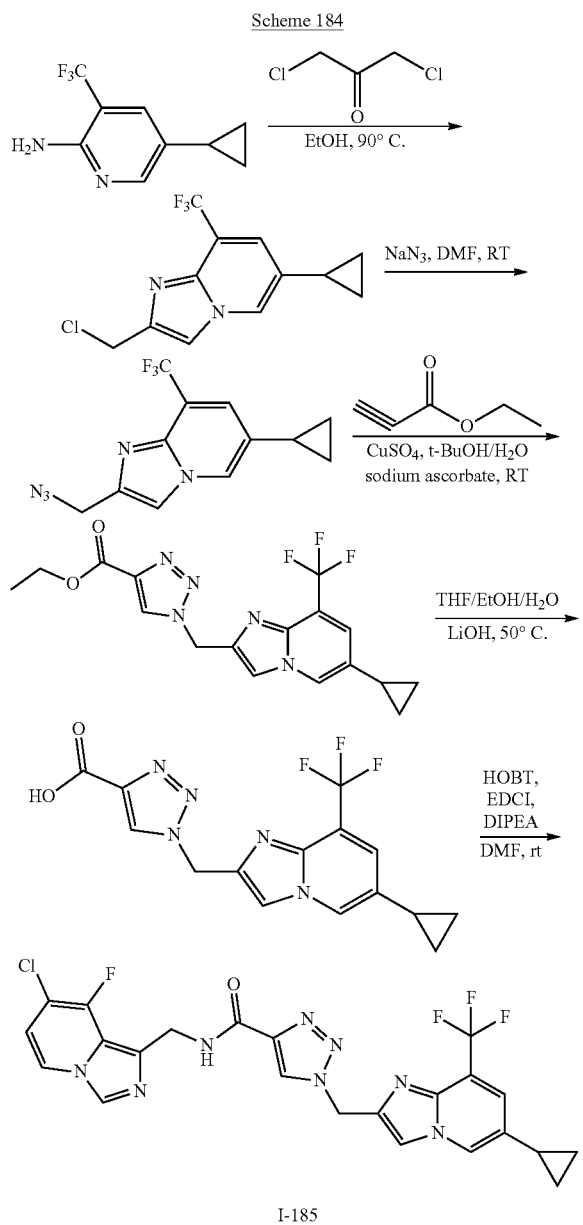

Scheme 184

I-185

Synthesis of 2-(chloromethyl)-6-cyclopropyl-8-(trifluoromethyl)imidazo[1,2-a]pyridine A mixture of 5-cyclopropyl-3-(trifluoromethyl)pyridin-2-amine (600 mg, 3 mmol) and 1,3-dichloropropan-2-one (1.14 g, 9 mmol) in EtOH (5 mL) was stirred at 85° C. overnight. The mixture was concentrated, saturated aqueous NaHCO$_3$ was added to adjust pH to about 8, then extracted with EtOAc (50 mL*2), the combined organic layers were dried over Na$_2$SO$_4$, concentrated and purified by silica gel chromatography (PE/EA=2/1) to give 2-(chloromethyl)-6-cyclopropyl-8-(trifluoromethyl)imidazo[1,2-a]pyridine (350 mg, yield: 43%) as a brown solid. ESI-MS [M+H]$^+$: 275.1.

Synthesis of 2-(azidomethyl)-6-cyclopropyl-8-(trifluoromethyl)imidazo[1,2-a]pyridine A mixture of 2-(chloromethyl)-6-cyclopropyl-8-(trifluoromethyl)imidazo[1,2-a]pyridine (43 mg, 0.16 mmol) and NaN$_3$ (13 mg, 0.19 mmol) in DMF (2 mL) was stirred at RT for 3 h. Water (20 mL) was added and extracted with EtOAc (30 mL*3). The combined organic layers were washed by brine (20 mL*2), dried over Na$_2$SO$_4$, concentrated to give 2-(azidomethyl)-6-cyclopropyl-8-(trifluoromethyl)imidazo[1,2-a]pyridine (40 mg, yield: 89%) as a yellow solid. ESI-MS [M+H]$^+$: 282.1

Synthesis of Ethyl 1-((6-cyclopropyl-8-(trifluoromethyl)imidazo[1,2-a]pyridin-2-yl)methyl)-1H-1,2,3-triazole-4-carboxylate A mixture of 2-(azidomethyl)-6-cyclopropyl-8-(trifluoromethyl)imidazo[1,2-a]pyridine (80 mg, 0.28 mmol), ethyl propiolate (84 mg, 0.85 mmol), CuSO$_4$ (23 mg, 0.14 mmol) and sodium ascorbate (25 mg, 0.14 mmol) in H$_2$O/i-PrOH (2 mL/2 mL) was stirred at RT for 3 h. Water (20 mL) was added and extracted with EtOAc (30 mL*3). The combined organic layers were washed by brine (20 mL), dried over Na$_2$SO$_4$, concentrated and purified by silica gel chromatography (CH$_2$Cl$_2$/MeOH=15/1) to give ethyl 1-((6-cyclopropyl-8-(trifluoromethyl)imidazo[1,2-a]pyridin-2-yl)methyl)-1H-1,2,3-triazole-4-carboxylate (40 mg, yield: 38%) as a yellow solid. ESI-MS [M+H]$^+$: 380.1.

Synthesis of 1-((6-cyclopropyl-8-(trifluoromethyl)imidazo[1,2-a]pyridin-2-yl)methyl)-1H-1,2,3-triazole-4-carboxylic Acid A mixture of ethyl 1-((6-cyclopropyl-8-(trifluoromethyl)imidazo[1,2-a]pyridin-2-yl)methyl)-1H-1,2,3-triazole-4-carboxylate (350 mg, 0.9 mmol) and LiOH.H$_2$O (76 mg, 1.8 mmol) in THF/EtOH/H$_2$O (4 mL/4 mL/2 mL) was stirred at 50 C for 3 h. Most of the solvent was removed and the residue was diluted with H$_2$O (5 mL), the pH value of mixture was adjusted to 4-5 by adding HCl aqueous (1 M). The precipitate was collected and dried to give 1-((6-cyclopropyl-8-(trifluoromethyl)imidazo[1,2-a]pyridin-2-yl)methyl)-1H-1,2,3-triazole-4-carboxylic acid (300 mg, yield: 95%) as a white solid. ESI-MS [M+H]$^+$: 352.1.

Synthesis of N-((7-chloro-8-fluoroimidazo[1,5-a]pyridin-1-yl)methyl)-1-((6-cyclopropyl-8-(trifluoromethyl)imidazo[1,2-a]pyridin-2-yl)methyl)-1H-1,2,3-triazole-4-carboxamide (I-185)

A mixture of 1-((6-cyclopropyl-8-(trifluoromethyl)imidazo[1,2-a]pyridin-2-yl)methyl)-1H-1,2,3-triazole-4-carboxylic acid (40 mg, 0.11 mmol), (7-chloro-8-fluoroimidazo[1,5-a]pyridin-1-yl)methanamine hydrochloride (26 mg, 0.11 mmol), HOBT (30 mg, 0.22 mmol), EDCI (43 mg, 0.22 mmol) and DIPEA (71 mg, 0.55 mmol) in DMF (3 mL) was stirred at RT for 16 h. The reaction mixture was poured into H$_2$O, the precipitated was filtrated and washed with CH$_3$OH to to give N-((7-chloro-8-fluoroimidazo[1,5-a]pyridin-1-yl)methyl)-1-((6-cyclopropyl-8-(trifluoromethyl)imidazo[1,2-a]pyridin-2-yl)methyl)-1H-1,2,3-triazole-4-carboxamide (38 mg, yield: 65%) as a white solid. ESI-MS [M+H]$^+$: 533.1. Purity: 99.13 (214 nm), 97.09 (254 nm). $^1$H NMR (400 MHz, DMSO-d$_6$) δ 8.72 (t, J=5.4 Hz, 1H), 8.61 (s, 1H), 8.57 (s, 1H), 8.44 (d, J=2.4 Hz, 1H), 8.20 (d, J=7.4 Hz, 1H), 7.93 (s, 1H), 7.51 (s, 1H), 6.77-6.74 (m, 1H), 5.81 (s, 2H), 4.70 (d, J=5.5 Hz, 2H), 2.06-1.99 (m, 1H), 0.98-093 (m, 2H), 0.77-0.73 (m, 2H).

Example 186

Scheme 185

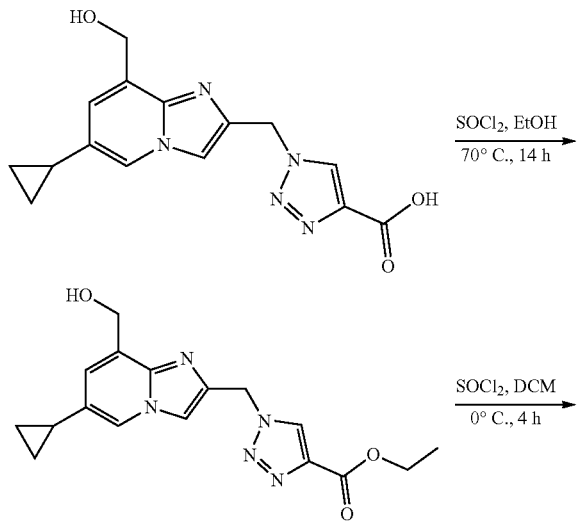

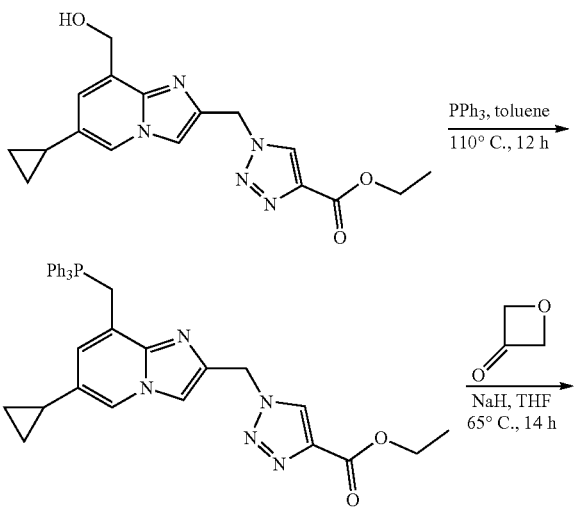

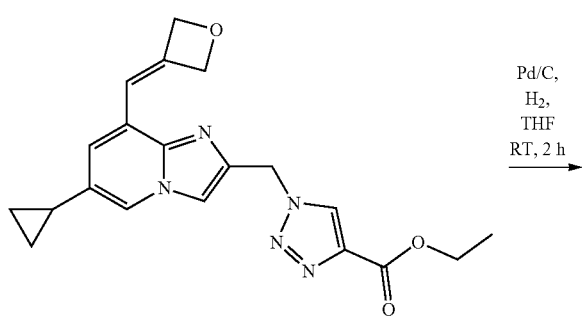

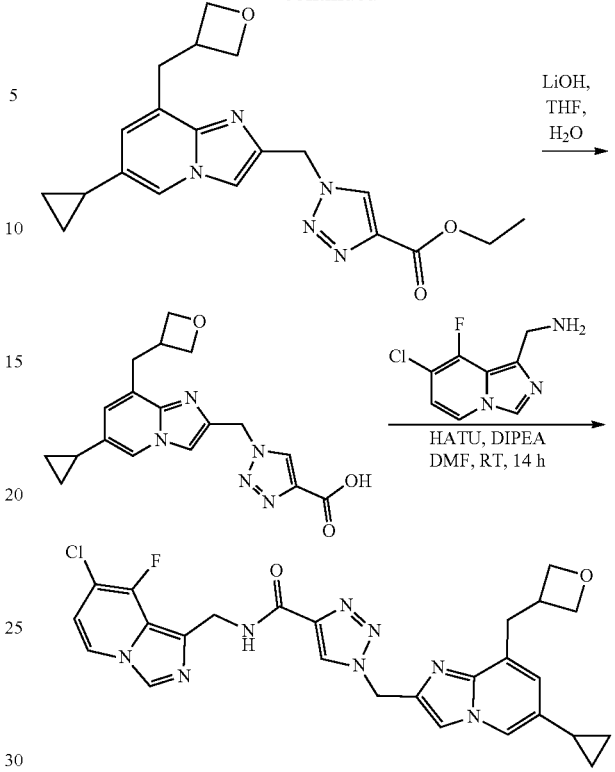

I-186

Synthesis of Ethyl 1-((6-cyclopropyl-8-(hydroxymethyl)imidazo[1,2-a]pyridin-2-yl)methyl)-1H-1,2,3-triazole-4-carboxylate To a solution of 1-((6-cyclopropyl-8-(hydroxymethyl)imidazo[1,2-a]pyridin-2-yl)methyl)-1H-1,2,3-triazole-4-carboxylic acid (800 mg, 2.56 mmol) in EtOH (50 mL) was added $SOCl_2$ (10 mL). The resulting reaction was stirred at 70° C. for 14 h. The reaction was concentrated in vacuo to give the ethyl 1-((6-cyclopropyl-8-(hydroxymethyl)imidazo[1,2-a]pyridin-2-yl)methyl)-1H-1,2,3-triazole-4-carboxylate as a yellow solid. (850 mg, 97.5%). ESI-MS[M+H]$^+$: 342.2

Synthesis of Ethyl 1-((8-(chloromethyl)-6-cyclopropylimidazo[1,2-a]pyridin-2-yl)methyl)-1H-1,2,3-triazole-4-carboxylate To a solution of ethyl 1-((6-cyclopropyl-8-(hydroxymethyl)imidazo[1,2-a]pyridin-2-yl)methyl)-1H-1,2,3-triazole-4-carboxylate (850 mg, 2.49 mmol) in DCM (25 mL) was added SOCl2 (3 mL) at 0° C. The resulting reaction was stirred at RT for 4 h. The reaction was concentrated in vacuo to give the ethyl 1-((8-(chloromethyl)-6-cyclopropylimidazo[1,2-a]pyridin-2-yl)methyl)-1H-1,2,3-triazole-4-carboxylate as a yellow solid (900 mg crude). ESI-MS [M+H]$^+$: 360.3

Synthesis of Ethyl 1-((6-cyclopropyl-8-((triphenyl-4-phosphanyl)methyl)imidazo[1,2-a]pyridin-2-yl)methyl)-1H-1,2,3-triazole-4-carboxylate A mixture of ethyl 1-((8-(chloromethyl)-6-cyclopropylimidazo[1,2-a]pyridin-2-yl)methyl)-1H-1,2,3-triazole-4- carboxylate (900 mg crude form previous step) and PPh3 (720 mg, 2.74 mmol) in toluene (40 mL) was stirred at 110° C. for 12 h. The reaction was concentrated in vacuo to give the ethyl 1-((6-cyclopropyl-8-((triphenyl-14-phosphanyl)methyl)imidazo[1,2-a]pyridin-2-yl)methyl)-1H-1,2,3-triazole-4-carboxylate as a yellow solid, which was used into next step without further purification (1.62 g crude). ESI-MS [M+H]+: 586.1.

Synthesis of Ethyl 1-((6-cyclopropyl-8-(oxetan-3-ylidenemethyl)imidazo[1,2-a]pyridin-2-yl)methyl)-1H-1,2,3-triazole-4-carboxylate A mixture of ethyl 1-((6-cyclopropyl-8-((triphenyl-14-phosphanyl)methyl)imidazo[1,2-a]pyridin-2-yl)methyl)-1H-1,2,3-triazole-4-carboxylate (1 g crude from previous step), oxetan-3-one (369 mg, 5.1 mmol) and NaH (340 mg, 8.5 mmol, 60 wt % in oil) in THF (30 mL) was stirred at 65° C. for 14 h under $N_2$. The reaction was quenched with aqueous $NH_4Cl$ (50 mL), extracted with EtOAc (50 mL×3). The combined organic layers were washed with brine, dried over $Na_2SO_4$, concentrated in vacuo to give the crude product, which was purified with silica gel (eluent: DCM/MeOH=30/1) to give the ethyl 1-((6-cyclopropyl-8-(oxetan-3-ylidenemethyl)imidazo[1,2-a]pyridin-2-yl)methyl)-1H-1,2,3-triazole-4-carboxylate as a yellow solid. (450 mg, 47.7% over 3 steps). ESI-MS [M+H]+: 380.2.

Synthesis of Ethyl 1-((6-cyclopropyl-8-(oxetan-3-ylmethyl)imidazo[1,2-a]pyridin-2-yl)methyl)-1H-1,2,3-triazole-4-carboxylate A mixture of ethyl 1-((6-cyclopropyl-8-(oxetan-3-ylidenemethyl)imidazo[1,2-a]pyridin-2-yl)methyl)-1H-1,2,3-triazole-4-carboxylate (450 mg, 1.19 mmol) and Pd/C (100 mg) in THF (25 mL) was stirred under $H_2$ atmosphere for 2 h. The reaction was filtered and concentrated in vacuo to give the ethyl 1-((6-cyclopropyl-8-(oxetan-3-ylmethyl)imidazo[1,2-a]pyridin-2-yl)methyl)-1H-1,2,3-triazole-4-carboxylate as a yellow solid (180 mg, 40%). ESI-MS [M+H]+: 382.2

Synthesis of 1-((6-cyclopropyl-8-(oxetan-3-ylmethyl)imidazo[1,2-a]pyridin-2-yl)methyl)-1H-1,2,3-triazole-4-carboxylic Acid To a solution of ethyl 1-((6-cyclopropyl-8-(oxetan-3-ylmethyl)imidazo[1,2-a]pyridin-2-yl)methyl)-1H-1,2,3-triazole-4-carboxylate (180 mg, 0.47 mmol) in THF/$H_2O$ (8 mL/8 mL) was added LiOH.$H_2O$ (79 mg, 1.88 mmol). The resulting mixture was stirred at RT for 4 h. The reaction was concentrated in vacuo to give the crude product, which was purified with Prep-HPLC to give 1-((6-cyclopropyl-8-(oxetan-3-ylmethyl)imidazo[1,2-a]pyridin-2-yl)methyl)-1H-1,2,3-triazole-4-carboxylic acid as a white solid (90 mg, 54%). ESI-MS [M+H]+: 354.2

Synthesis of N-((7-chloro-8-fluoroimidazo[1,5-a]pyridin-1-yl)methyl)-1-((6-cyclopropyl-8-(oxetan-3-ylmethyl)imidazo[1,2-a]pyridin-2-yl)methyl)-1H-1,2,3-triazole-4-carboxamide (I-186)

To a solution of 1-((6-cyclopropyl-8-(oxetan-3-ylmethyl)imidazo[1,2-a]pyridin-2-yl)methyl)-1H-1,2,3-triazole-4-carboxylic acid (40 mg, 0.11 mmol), (7-chloro-8-fluoroimidazo[1,5-a]pyridin-1-yl)methanamine hydrochloride (33 mg, 0.14 mmol), HATU (78 mg, 0.2 mmol) in DMF (6 mL) was added DIPEA (71 mg, 0.55 mmol). The resulting reaction was stirred at RT for 14 h. The reaction was poured into $H_2O$ (30 mL) and white solid was formed. The solid was filtered and washed with MeOH (30 mL) to give the N-((7-chloro-8-fluoroimidazo[1,5-a]pyridin-1-yl)methyl)-1-((6-cyclopropyl-8-(oxetan-3-ylmethyl)imidazo[1,2-a]pyridin-2-yl)methyl)-1H-1,2,3-triazole-4-carboxamide as a white solid. (20 mg, 34%). ESI-MS [M+H]+: 535.2. Purity: 89.80% (214 nm), 93.09 (254 nm). $^1$H NMR (400 MHz, DMSO-$d_6$) δ 8.72-8.65 (m, 1H), 8.54 (s, 1H), 8.44 (d, J=2.4 Hz, 1H), 8.21-8.20 (m, 2H), 7.78 (s, 1H), 6.80 (s, 1H), 6.78-6.74 (m, 1H), 5.73 (s, 2H), 4.70 (d, J=4.0 Hz, 2H), 4.62-4.59 (m, 2H), 4.36 (t, J=6.0 Hz, 2H), 3.42-3.39 (m, 1H), 3.16 (d, J=7.7 Hz, 2H), 1.91-1.85 (m, 1H), 0.92-0.88 (m, 2H), 0.68-0.64 (m, 2H).

Example 187

Scheme 186

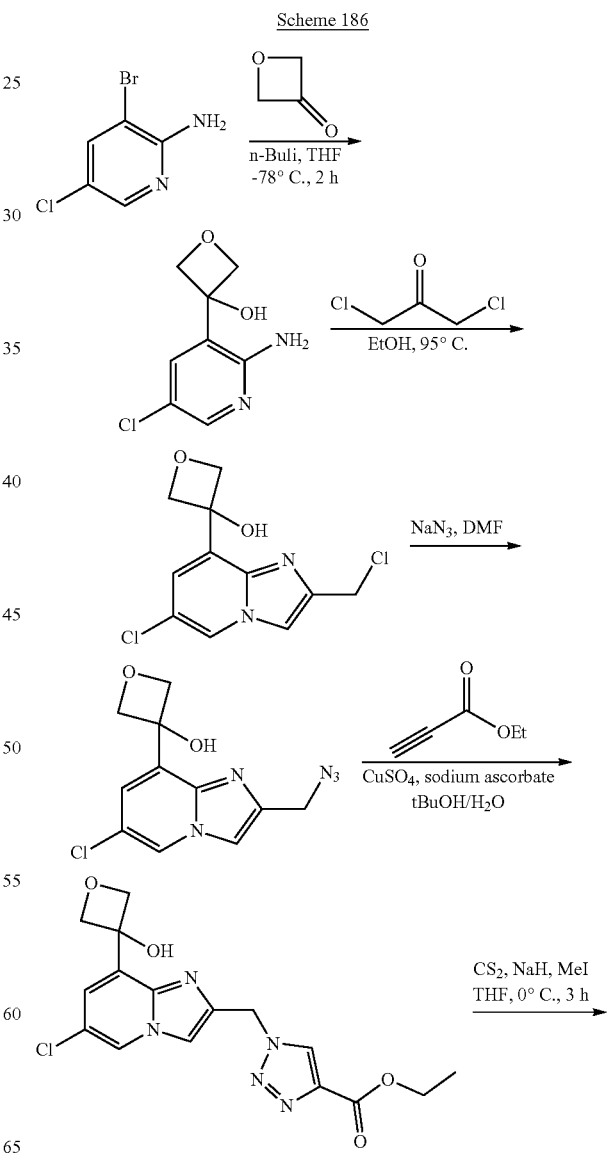

-continued

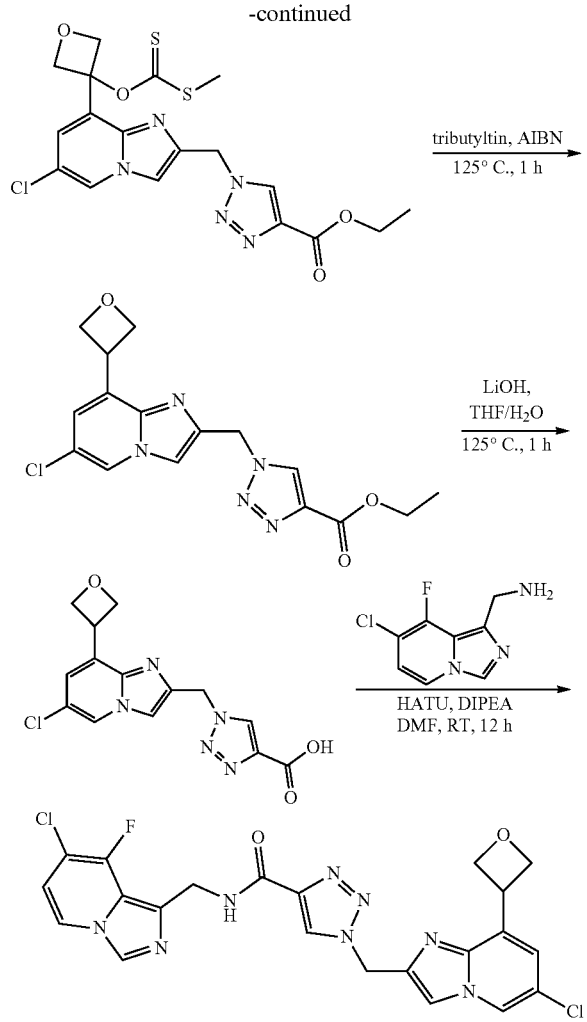

I-187

Synthesis of 3-(2-amino-5-chloropyridin-3-yl)oxetan-3-ol

To a solution of 3-bromo-5-chloropyridin-2-amine (2 g, 9.7 mmol) in THF (100 mL) was added n-BuLi (5.3 mL, 12.5 mmol, 2.4 M in hexane) slowly at −78° C. The reaction was stirred at −78° C. for another 20 min. Then oxetan-3-one (1.4 g, 19.4 mmol) in THF (20 mL) was added thereto. The reaction was stirred at −78° C. for 1 h. The reaction was quenched with aqueous NH$_4$Cl (100 mL), extracted with EtOAc (100 mL×3). The combined organic layers were washed with brine, dried over Na$_2$SO$_4$, concentrated in vacuo to give the crude product, which was purified with silica gel (DCM/MeOH=25/1) to give the 3-(2-amino-5-chloropyridin-3-yl)oxetan-3-ol as a yellow solid. (1.5 g, 77%). ESI-MS [M+H]$^+$: 201.3.

Synthesis of 3-(6-chloro-2-(chloromethyl)imidazo[1,2-a]pyridin-8-yl)oxetan-3-ol A mixture of 3-(2-amino-5-chloropyridin-3-yl)oxetan-3-ol (1.5 g, 7.5 mmol) and 1,3-dichloropropan-2-one (2.9 g, 22.5 mmol) in EtOH (50 mL) was stirred at 95° C. for 14 h. The reaction was concentrated in vacuo to remove the EtOH. The pH of residue was adjusted to 9 by saturated aqueous NaHCO$_3$, extracted with EtOAc (100 mL×3). The combined organic layers were washed with brine, dried over Na$_2$SO$_4$, concentrated in vacuo to give the 3-(6-chloro-2-(chloromethyl)imidazo[1,2-a]pyridin-8-yl)oxetan-3-ol as a brown solid. (1.1 g, 53.7%). ESI-MS [M+H]$^+$: 273.2.

Synthesis of 3-(2-(azidomethyl)-6-chloroimidazo[1,2-a]pyridin-8-yl)oxetan-3-ol A mixture of (1.1 g, 4.04 mmol) and NaN$_3$ (342 mg, 5.26 mmol) in DMF (30 mL) was stirred at RT for 2 h. H$_2$O (50 mL) was added to the reaction, extracted with EtOAc (100 mL×3). The combined organic layers were washed with brine, dried over Na$_2$SO$_4$, concentrated in vacuo to give the 3-(2-(azidomethyl)-6-chloroimidazo[1,2-a]pyridin-8-yl)oxetan-3-ol as yellow oil, which was used into next step without further purification (1.2 g crude). ESI-MS [M+H]$^+$: 280.2

Synthesis of Ethyl 1-((6-chloro-8-(3-hydroxyoxetan-3-yl)imidazo[1,2-a]pyridin-2-yl)methyl)-1H-1,2,3-triazole-4-carboxylate To a solution of 3-(2-(azidomethyl)-6-chloroimidazo[1,2-a]pyridin-8-yl)oxetan-3-ol (1.2 g crude from previous step) and ethyl propiolate (475 mg, 4.85 mmol) in t-BuOH/H$_2$O (20 mL/20 mL) was added CuSO$_4$ (64 mg, 0.41 mmol) and sodium ascorbate (81 mg, 0.41 mmol). The resulting mixture was stirred at RT for 2 h. H$_2$O (50 mL) was added to the reaction, extracted with EtOAc (100 mL×3). The combined organic layers were washed with brine, dried over Na$_2$SO$_4$, concentrated in vacuo to give the crude product, which was purified with silica gel (DCM/MeOH=40/1) to give the ethyl 1-((6-chloro-8-(3-hydroxyoxetan-3-yl)imidazo[1,2-a]pyridin-2-yl)methyl)-1H-1,2,3-triazole-4-carboxylate as a yellow solid (500 mg, 32.9% over 2 step). ESI-MS [M+H]$^+$: 378.2

Synthesis of Ethyl 1-((6-chloro-8-(3-(((methylthio)carbonothioyl)oxy)oxetan-3-yl)imidazo[1,2-a]pyridin-2-yl)methyl)-1H-1,2,3-triazole-4-carboxylate To a solution of ethyl 1-((6-chloro-8-(3-hydroxyoxetan-3-yl)imidazo[1,2-a]pyridin-2-yl)methyl)-1H-1,2,3-triazole-4-carboxylate (500 mg, 1.33 mmol) in THF (20 mL) was added NaH (266 mg, 6.65 mmol, 60 wt % in oil). After stirring at 0° C. for 30 min, a solution of CS$_2$ (505 mg, 6.65 mmol) in THF (5 mL) was added and stirred at 0° C. for another 30 min. A solution MeI (944 mg, 6.65 mmol) in THF (4 mL) was added, the resulting reaction was stirred at 0° C. for another 1 h. The reaction was quenched with aqueous NH$_4$Cl (50 mL), extracted with EtOAc (100 mL×3). The combined organic layers were washed with brine, dried over Na$_2$SO$_4$, concentrated in vacuo to give the ethyl 1-((6-chloro-8-(3-(((methylthio)carbonothioyl)oxy)oxetan-3-yl)imidazo[1,2-a]pyridin-2-yl)methyl)-1H-1,2,3-triazole-4-carboxylate as a yellow solid, which was used into next step without further purification (650 mg crude). ESI-MS [M+H]$^+$: 468.2.

Synthesis of Ethyl 1-((6-chloro-8-(oxetan-3-yl)imidazo[1,2-a]pyridin-2-yl)methyl)-1H-1,2,3-triazole-4-carboxylate A mixture of ethyl 1-((6-chloro-8-(3-(((methylthio)carbonothioyl)oxy)oxetan-3-yl)imidazo[1,2-a]pyridin-2-yl)

methyl)-1H-1,2,3-triazole-4-carboxylate (650 mg crude from previous step), Tributyltin (582 mg, 2 mmol) and AIBN (328 mg, 2 mmol) in toluene (20 mL) was stirred at 125° C. for 1 h. The reaction was concentrated in vacuo to give the crude product, which was purified with silica gel (DCM/MeOH=30/1) to give the ethyl 1-((6-chloro-8-(oxetan-3-yl)imidazo[1,2-a]pyridin-2-yl)methyl)-1H-1,2,3-triazole-4-carboxylate as a yellow solid (300 mg, 62.5%). ESI-MS [M+H]$^+$: 362.2.

Synthesis of 1-((6-chloro-8-(oxetan-3-yl)imidazo[1,2-a]pyridin-2-yl)methyl)-1H-1,2,3-triazole-4-carboxylic Acid To a solution of ethyl 1-((6-chloro-8-(oxetan-3-yl)imidazo[1,2-a]pyridin-2-yl)methyl)-1H-1,2,3-triazole-4-carboxylate (300 mg, 0.83 mmol) in THF/H$_2$O (15 mL/15 mL) was added LiOH.H$_2$O (105 mg, 2.5 mmol). The resulting reaction was stirred at RT for 3 h. The reaction was concentrated in vacuo to give the crude product, which was purified with Prep-HPLC to give the 1-((6-chloro-8-(oxetan-3-yl)imidazo[1,2-a]pyridin-2-yl)methyl)-1H-1,2,3-triazole-4-carboxylic acid as a white solid (180 mg, 65.2%). ESI-MS [M+H]$^+$: 334.2

Synthesis of 1-((6-chloro-8-(oxetan-3-yl)imidazo[1,2-a]pyridin-2-yl)methyl)-N-((7-chloro-8-fluoroimidazo[1,5-a]pyridin-1-yl)methyl)-1H-1,2,3-triazole-4-carboxamide (I-187)

To a solution 1-((6-chloro-8-(oxetan-3-yl)imidazo[1,2-a]pyridin-2-yl)methyl)-1H-1,2,3-triazole-4-carboxylic acid (80 mg, 0.24 mmol), (7-chloro-8-fluoroimidazo[1,5-a]pyridin-1-yl)methanamine hydrochloride (73 mg, 0.31 mmol) and HATU (148 mg, 0.39 mmol) in DMF (10 mL) was added DIPEA (155 mg, 1.2 mmol). The resulting reaction was stirred at RT for 12 h. The reaction was poured into H$_2$O (50 mL) and the white solid was formed. The solid was filtered and washed with MeOH (50 mL) to give the 1-((6-chloro-8-(oxetan-3-yl)imidazo[1,2-a]pyridin-2-yl)methyl)-N-((7-chloro-8-fluoroimidazo[1,5-a]pyridin-1-yl)methyl)-1H-1,2,3-triazole-4-carboxamide as a white solid. (50 mg, 40.6%). ESI-MS [M+H]$^+$: 515.2. Purity: 94.23 (214 nm), 96.17 (254 nm). $^1$H NMR (400 MHz, DMSO-d$_6$) δ 8.74-8.73 (m, 2H), 8.56 (s, 1H), 8.44 (s, 1H), 8.21 (d, J=7.0 Hz, 1H), 7.90 (s, 1H), 7.38 (s, 1H), 6.76 (t, J=6.1 Hz, 1H), 5.77 (s, 2H), 4.95-4.92 (m, 2H), 4.82-4.79 (m, 2H), 4.70-4.69 (m, 3H).

Example 188

Scheme 187

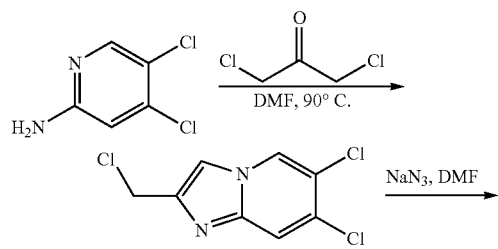

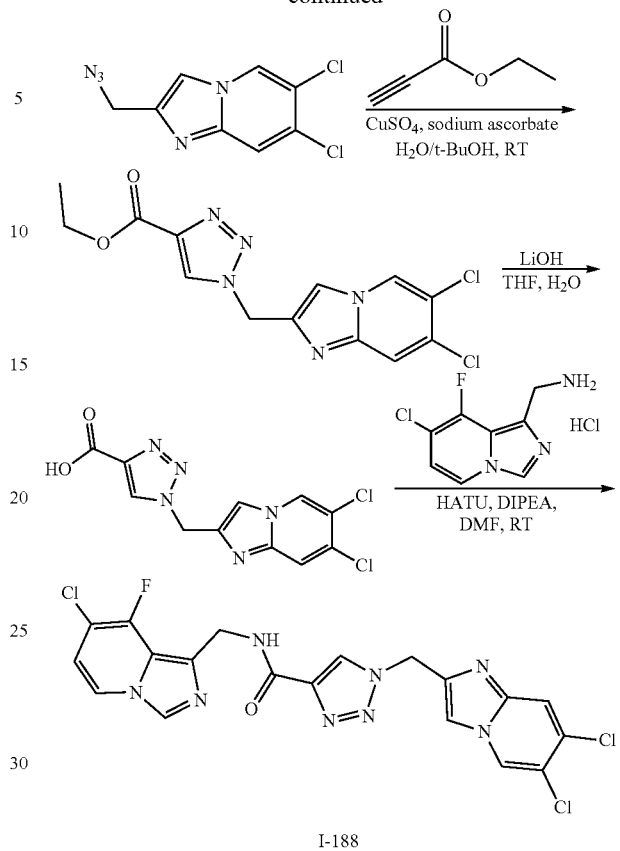

I-188

Synthesis of 6,7-dichloro-2-(chloromethyl)imidazo[1,2-a]pyridine

The mixture of 4,5-dichloropyridin-2-amine (1 g, 6.13 mmol) and 1,3-dichloropropan-2-one (10 g, 78.4 mmol) in DMF (20 mL) was stirred at 90° C. for 20 h. Then H$_2$O (100 mL) was added and extracted with EtOAc (100 mL×2). The combined organic layers were concentrated to give the crude product which was purified by silica gel chromatography (PE/EtOAc=3/1) to give 6,7-dichloro-2-(chloromethyl)imidazo[1,2-a]pyridine (471 mg, yield: 33%) as a yellow solid. ESI-MS [M+H]$^+$: 235.1

Synthesis of 2-(azidomethyl)-6,7-dichloroimidazo[1,2-a]pyridine

The reaction mixture of 6,7-dichloro-2-(chloromethyl)imidazo[1,2-a]pyridine (823 mg, 3.52 mmol) and NaN$_3$ (239 mg, 3.68 mmol) in DMF (10 mL) was stirred at RT overnight. Water (100 mL) was added and extracted with EtOAc (100 mL×2). The combined organic layers were concentrated to give 2-(azidomethyl)-6,7-dichloroimidazo[1,2-a]pyridine (433 mg, yield: 51%) as a yellow solid. This material was used directly in the next step without further purification. ESI-MS [M+H]$^+$: 243.1.

Synthesis of Ethyl 1-((6,7-dichloroimidazo[1,2-a]pyridin-2-yl)methyl)-1H-1,2,3-triazole-4-carboxylate A mixture 2-(azidomethyl)-6,7-dichloroimidazo[1,2-a]pyridine (433 mg, 1.79 mmol), ethyl propiolate (351 mg, 3.58 mmol), CuSO₄ (89 mg, 0.358 mmol) and sodium ascorbate (106 mg, 0.537 mmol) in t-BuOH (8 mL) and H₂O (8 mL) was stirred for 2 h at RT. The reaction was concentrated in vacuo. Water (20 mL) was added and extracted with EtOAc (50 mL×3). The combined organic layers were dried over Na₂SO₄, and concentrated to give the crude product which was purified by silica gel chromatography (PE/EtOAc=1/1) to give ethyl 1-((6,7-dichloroimidazo[1,2-a]pyridin-2-yl)methyl)-1H-1,2,3-triazole-4-carboxylate (509 mg, yield: 82%) as a yellow solid. ESI-MS [M+H]⁺: 340.2.

Synthesis of 1-((6,7-dichloroimidazo[1,2-a]pyridin-2-yl)methyl)-1H-1,2,3-triazole-4-carboxylic Acid A mixture of ethyl 1-((6,7-dichloroimidazo[1,2-a]pyridin-2-yl)methyl)-1H-1,2,3-triazole-4-carboxylate (100 mg, 0.294 mmol) and LiOH.H₂O (12 mg, 0.294 mmol) in THF/H₂O (4 mL/4 mL) was stirred at RT overnight. The reaction was adjusted the pH to 5 and concentrated in vacuo to give 1-((6,7-dichloroimidazo[1,2-a]pyridin-2-yl)methyl)-1H-1,2,3-triazole-4-carboxylic acid (120 mg, crude) as a yellow solid. This material was used directly in the next step without further purification. ESI-MS [M+Na]⁺: 313.2.

Synthesis of N-((7-chloro-8-fluoroimidazo[1,5-a]pyridin-1-yl)methyl)-1-((6,7-dichloroimidazo[1,2-a]pyridin-2-yl)methyl)-1H-1,2,3-triazole-4-carboxamide (I-188)

A mixture of 1-((6,7-dichloroimidazo[1,2-a]pyridin-2-yl)methyl)-1H-1,2,3-triazole-4-carboxylic acid (120 mg, crude), (7-chloro-8-fluoroimidazo[1,5-a]pyridin-1-yl)methanamine hydrochloride (80 mg, 0.342 mmol), HATU (217 mg, 0.57 mmol) and DIPEA (184 mg, 1.43 mmol) in DMF (5 mL) was stirred for 3 h at RT. Water (30 mL) was added and extracted with EtOAc (50 mL×3). The combined organic layers were dried over Na₂SO₄, and concentrated to give the crude product which was purified by prep-HPLC to give N-((7-chloro-8-fluoroimidazo[1,5-a]pyridin-1-yl)methyl)-1-((6,7-dichloroimidazo[1,2-a]pyridin-2-yl)methyl)-1H-1,2,3-triazole-4-carboxamide (50 mg, yield: 35% over 2 steps) as a light yellow solid. ESI-MS [M+H]⁺: 494.2. Purity: 97.67 (214 nm) 96.17 (254 nm). ¹H NMR (400 MHz, DMSO-d₆) δ 9.06 (s, 1H), 8.75-8.69 (m, 1H), 8.58 (s, 1H), 8.45 (s, 1H), 8.21 (d, J=7.2 Hz, 1H), 7.99 (d, J=12 Hz 2H), 7.96 (s, 1H), 6.77 (t, J=7.0 Hz, 1H), 5.79 (s, 2H), 4.71 (d, J=5.4 Hz, 2H).

Example 189

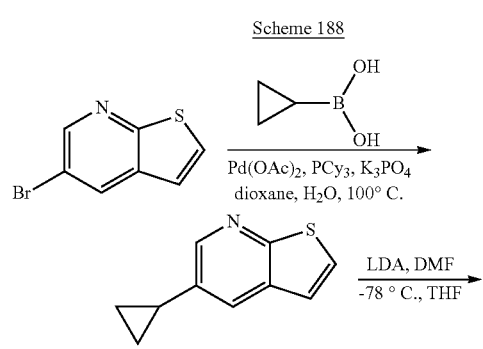

Scheme 188

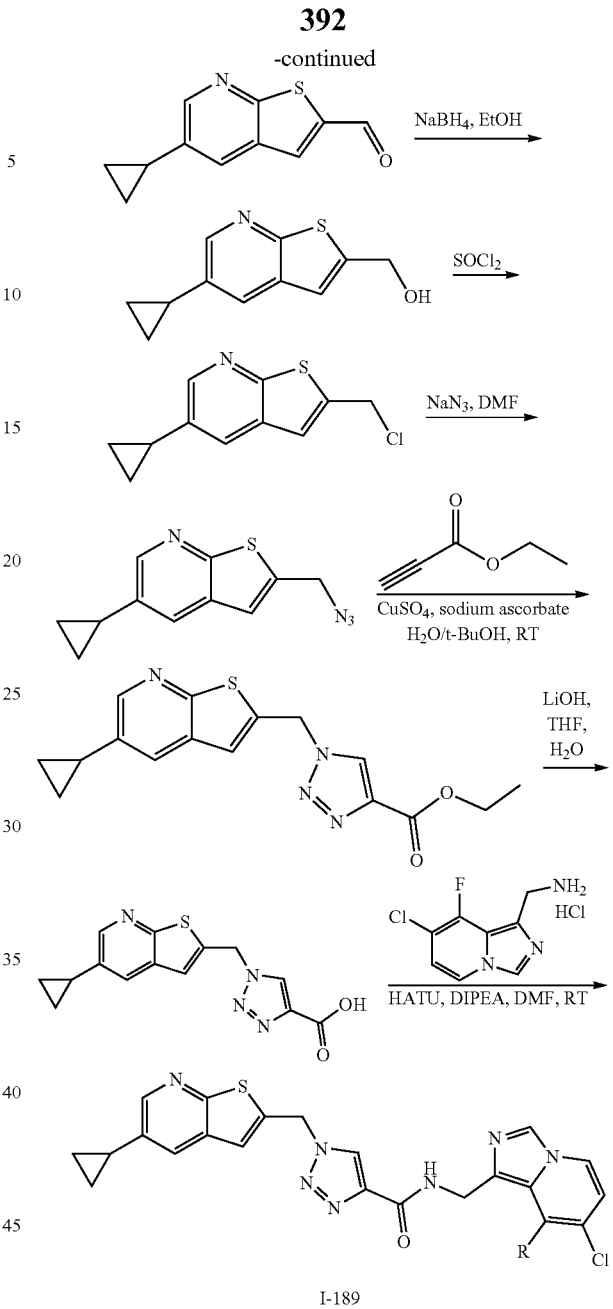

I-189

Synthesis of 5-cyclopropylthieno[2,3-b]pyridine

To a solution of 5-bromothieno[2,3-b]pyridine (2 g, 9.34 mmol) in dioxane/H₂O (100 mL/100 mL) was added cyclopropylboronic acid (1.605 g, 18.7 mmol), Pd(OAc)₂ (210 mg, 0.934 mmol), PCy₃ (524 mg, 1.87 mmol) and K₃PO₄ (5.949 g, 28 mmol). The reaction mixture was stirred at 100° C. for 14 h under nitrogen. The mixture was concentrated in vacuo. Water (100 mL) was added and the mixture was extracted with EtOAc (100 mL×3). The combined organic layers were washed with brine, dried over Na₂SO₄, concentrated to give the crude product, which was purified by silica gel chromatography (PE/EtOAc=30/1) to give the 5-cyclopropylthieno[2,3-b]pyridine as a yellow oil (1.067 g, yield: 65%). ESI-MS [M+H]⁺: 175.9.

Synthesis of 5-cyclopropylthieno[2,3-b]pyridine-2-carbaldehyde

To a solution 5-cyclopropylthieno[2,3-b]pyridine (1.067 g, 6.09 mmol) in dry THF (50 mL) at −78° C. was added LDA (17.2 mL, 1 M, 17.2 mmol) dropwise. The mixture was stirred for 30 min at −78° C. DMF (3 mL) was added to the reaction above dropwise. The resulting mixture was stirred overnight. The reaction was quenched with saturated aqueous NH$_4$Cl (50 mL), and extracted with EtOAc (80 mL×3). The combined organic layers were washed with brine, dried over Na$_2$SO$_4$, and concentrated to give the crude product, which was purified by silica gel chromatography (PE/EtOAc=5/1) to give 5-cyclopropylthieno[2,3-b]pyridine-2-carbaldehyde (871 mg, yield: 70%) as a yellow solid. ESI-MS [M+H]$^+$: 203.9.

Synthesis of (5-cyclopropylthieno[2,3-b]pyridin-2-yl)methanol

To a solution of 5-cyclopropylthieno[2,3-b]pyridine-2-carbaldehyde (871 mg, 4.29 mmol) in MeOH (30 mL) was added NaBH$_4$ (243 mg, 6.43 mmol). The reaction mixture was stirred at RT for 0.5 h. The reaction was quenched with H$_2$O, concentrated in vacuo and extracted with EtOAc (30 mL×3). The combined organic layers were washed with brine, dried over Na$_2$SO$_4$, and concentrated to give the crude product, which was purified by silica gel chromatography (PE/EtOAc=1/1) to give (5-cyclopropylthieno[2,3-b]pyridin-2-yl)methanol (778 mg, yield: 88%) as a yellow oil. ESI-MS [M+H]$^+$: 206.0.

Synthesis of 2-(chloromethyl)-5-cyclopropylthieno[2,3-b]pyridine

A solution of (5-cyclopropylthieno[2,3-b]pyridin-2-yl)methanol (778 mg, 3.79 mmol) in SOCl$_2$ (20 mL) was stirred at RT for 2 h. The reaction mixture was concentrated to give a residue. Water (40 mL) was added to the residue, and the pH was adjusted to 9 with NaHCO$_3$ solution, and then extracted with EtOAc (40 mL×2). The combined organic layers were washed with brine, dried over Na$_2$SO$_4$, concentrated to give the crude product, which was purified by silica gel chromatography (PE/EtOAc=10/1) to give 2-(chloromethyl)-5-cyclopropylthieno[2,3-b]pyridine (823 mg, yield: 97%) as a yellow oil. ESI-MS [M+H]$^+$: 224.0.

Synthesis of 2-(azidomethyl)-5-cyclopropylthieno[2,3-b]pyridine

A mixture of 2-(chloromethyl)-5-cyclopropylthieno[2,3-b]pyridine (823 mg, 3.68 mmol) and NaN$_3$ (239 mg, 3.68 mmol) in DMF (20 mL) was stirred at RT for overnight. H$_2$O (50 mL) was added to the reaction, extracted with EtOAc (50 mL×3). The combined organic layers were washed with brine, dried over Na$_2$SO$_4$, concentrated in vacuo to give 2-(azidomethyl)-5-cyclopropylthieno[2,3-b]pyridine (847 mg, yield: 99%) as a yellow solid. This material was used directly in the next step without further purification. ESI-MS [M+H]$^+$: 231.0.

Synthesis of Ethyl 1-((5-cyclopropylthieno[2,3-b]pyridin-2-yl)methyl)-1H-1,2,3-triazole-4-carboxylate A solution 2-(azidomethyl)-5-cyclopropylthieno[2,3-b]pyridine (847 mg, 3.68 mmol), ethyl propiolate (722 mg, 7.36 mmol), CuSO$_4$ (184 mg, 0.74 mmol) and sodium ascorbate (219 mg, 1.1 mmol) in t-BuOH (15 mL) and H$_2$O (15 mL) was stirred at RT for 2 h. The reaction was poured into H$_2$O (50 mL) and extracted with EtOAc (80 mL×3). The combined organic layers were washed with brine, dried over Na$_2$SO$_4$, and concentrated to give the crude product, which was purified by silica gel chromatography (PE/EtOAc=2/1) to give ethyl 1-((5-cyclopropylthieno[2,3-b]pyridin-2-yl)methyl)-1H-1,2,3-triazole-4-carboxylate (778 mg, yield: 64%) as a yellow solid. ESI-MS [M+H]$^+$: 329.1.

Synthesis of 1-((5-cyclopropylthieno[2,3-b]pyridin-2-yl)methyl)-1H-1,2,3-triazole-4-carboxylic Acid A solution of ethyl 1-((5-cyclopropylthieno[2,3-b]pyridin-2-yl)methyl)-1H-1,2,3-triazole-4-carboxylate (100 mg, 0.306 mmol) and LiOH.H$_2$O (13 mg, 0.306 mmol) in a mixed solvent of THF/H$_2$O (4 mL/4 mL) was stirred at RT for overnight. The reaction was concentrated in vacuo to remove the THF. The pH of residue was adjusted to 5, and concentrated in vacuo to give 1-((5-cyclopropylthieno[2,3-b]pyridin-2-yl)methyl)-1H-1,2,3-triazole-4-carboxylic acid (120 mg, crude) as a yellow solid. This material was used directly in the next step without further purification. ESI-MS [M+Na]$^+$: 301.1.

Synthesis of N-((7-chloro-8-fluoroimidazo[1,5-a]pyridin-1-yl)methyl)-1-((5-cyclopropylthieno[2,3-b]pyridin-2-yl)methyl)-1H-1,2,3-triazole-4-carboxamide (I-189)

A mixture of 1-((5-cyclopropylthieno[2,3-b]pyridin-2-yl)methyl)-1H-1,2,3-triazole-4-carboxylic acid (120 mg, crude from last step), (7-chloro-8-fluoroimidazo[1,5-a]pyridin-1-yl)methanamine hydrochloride (84 mg, 0.356 mmol), HATU (225 mg, 0.593 mmol) and DIPEA (192 mg, 1.48 mmol) in DMF (10 mL) was stirred at RT for 3 h. The reaction was poured into H$_2$O (50 mL), and a yellow solid precipitated. The mixture was filtered and washed with MeOH (50 mL) and dried in vacuo to give N-((7-chloro-8-fluoroimidazo[1,5-a]pyridin-1-yl)methyl)-1-((5-cyclopropylthieno[2,3-b]pyridin-2-yl)methyl)-1H-1,2,3-triazole-4-carboxamide (98 mg, yield: 68%) as a light yellow solid. ESI-MS [M+H]$^+$: 481.7. Purity: 98.12 (214 nm) 98.50 (254 nm). $^1$H NMR (400 MHz, DMSO-d$_6$) δ 8.80-8.72 (m, 1H), 8.68 (s, 1H), 8.44 (s, 1H), 8.39 (s, 1H), 8.20 (d, J=7.2 Hz, 1H), 7.87 (s, 1H), 7.35 (s, 1H), 6.80-6.70 (m, 1H), 5.99 (s, 2H), 4.70 (d, J=5.4 Hz, 2H), 2.08-2.02 (m, 1H), 1.02 (d, J=8.3 Hz, 2H), 0.77 (d, J=5.2 Hz, 2H).

Example 190

Scheme 189

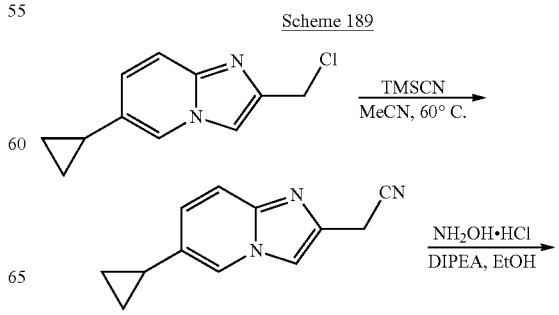

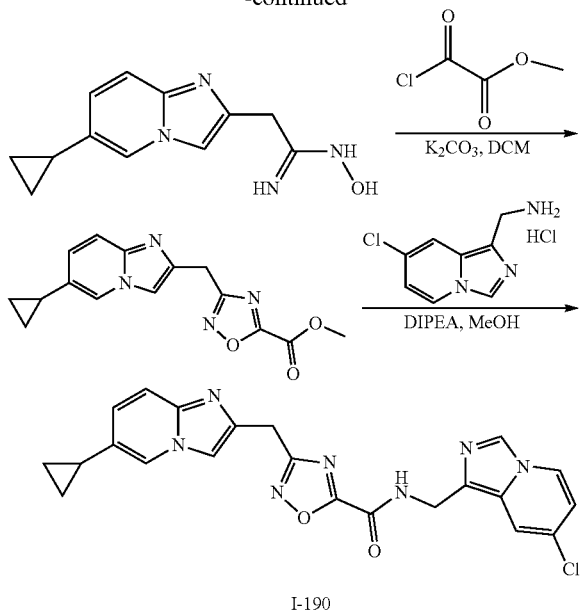

Synthesis of 2-(6-cyclopropylimidazo[1,2-a]pyridin-2-yl)acetonitrile

To a solution of 2-(chloromethyl)-6-cyclopropylimidazo[1,2-a]pyridine (2 g, 9.7 mmol) in MeCN (40 mL) was added TMSCN (1.4 g, 14 mmol). The reaction mixture was stirred at 60° C. overnight under nitrogen. Then the mixture was concentrated in vacuo. Water (20 mL) was added to the reaction, extracted with DCM (50 mL×2). The combined organic layers were washed with brine, dried over Na$_2$SO$_4$, concentrated to give the crude product, which was purified by silica gel chromatography (PE/EtOAc=1/1) to give the 2-(6-cyclopropylimidazo[1,2-a]pyridin-2-yl)acetonitrile as a yellow solid (650 mg, yield: 34%). ESI-MS [M+H]$^+$: 198.1.

Synthesis of Ethyl 2-(6-cyclopropylimidazo[1,2-a]pyridin-2-yl)-N-hydroxyacetimidamide To a solution 2-(6-cyclopropylimidazo[1,2-a]pyridin-2-yl)acetonitrile (400 mg, 2 mmol) and NH$_2$OH.HCl (352 mg, 5 mmol) in EtOH (20 mL) was added DIPEA (645 mg, 5 mmol). The resulting mixture was stirred at 80° C. overnight under nitrogen. The mixture was concentrated under vacuum. The residue was poured into H$_2$O (20 mL) and extracted with EtOAc (50 mL×2). The combined organic layers were washed with brine, dried over Na$_2$SO$_4$, and concentrated to give the crude product, which was purified by silica gel chromatography (PE/EA=2/1) to give 2-(6-cyclopropylimidazo[1,2-a]pyridin-2-yl)-N-hydroxyacetimidamide (340 mg, 73%) as a yellow solid. ESI-MS [M+H]$^+$: 231.1

Synthesis of Methyl 3-((6-cyclopropylimidazo[1,2-a]pyridin-2-yl)methyl)-1,2,4-oxadiazole-5-carboxylate A mixture of 2-(6-cyclopropylimidazo[1,2-a]pyridin-2-yl)-N-hydroxyacetimidamide (340 mg, 1.4 mmol), K$_2$CO$_3$ (408 mg, 3 mmol) and methyl 2-chloro-2-oxoacetate (180 mg) in DCM (15 mL) was stirred at 80° C. overnight. Water (5 mL) was added to the reaction, extracted with DCM (40 mL×2). The combined organic layers were washed with brine, dried over Na$_2$SO$_4$, concentrated to give the crude product, which was purified by silica gel chromatography (PE/EA=2/1) to give methyl 3-((6-cyclopropylimidazo[1,2-a]pyridin-2-yl)methyl)-1,2,4-oxadiazole-5-carboxylate (100 mg, yield: 22.7%) as a yellow solid. ESI-MS [M+H]$^+$: 299.2.

Synthesis of N-((7-chloroimidazo[1,5-a]pyridin-1-yl)methyl)-3-((6-cyclopropylimidazo[1,2-a]pyridin-2-yl)methyl)-1,2,4-oxadiazole-5-carboxamide (I-190)

To a solution of methyl 3-((6-cyclopropylimidazo[1,2-a]pyridin-2-yl)methyl)-1,2,4-oxadiazole-5-carboxylate (100 mg, 0.33 mmol) and DIPEA (106 mg, 0.825 mmol) in MeOH (10 mL) was added (7-chloroimidazo[1,5-a]pyridin-1-yl)methanamine hydrochloride (88 mg, 0.4 mmol). The reaction mixture was concentrated to give a residue, which was partitioned between DCM (30 mL) and H$_2$O (30 mL). The layers were separated and the aqueous phase was extracted with DCM (30×2 mL). The combined organic phase was washed with brine (20 mL), dried over Na$_2$SO$_4$, and concentrated to give the crude product, which was purified by silica gel chromatography (DCM/MeOH=10/1) to give N-((7-chloroimidazo[1,5-a]pyridin-1-yl)methyl)-3-((6-cyclopropylimidazo[1,2-a]pyridin-2-yl)methyl)-1,2,4-oxadiazole-5-carboxamide (11 mg, yield: 7.3%) as an off-white solid. ESI-MS [M+H]$^+$: 448.0. Purity: 99.78 (214 nm), 99.69 (254 nm). $^1$H NMR (400 MHz, DMSO-d$_6$) δ 9.81 (s, 1H), 8.35-8.26 (m, 3H), 7.82 (s, 1H), 7.72 (s, 1H), 7.35 (d, J=9.3 Hz, 1H), 6.96 (d, J=9.3 Hz, 1H), 6.67 (d, J=7.4 Hz, 1H), 4.62 (d, J=5.5 Hz, 2H), 4.25 (s, 2H), 1.96-1.87 (m, 1H), 0.94-0.88 (m, 2H), 0.69-0.63 (m, 2H).

Example 191

Scheme 190

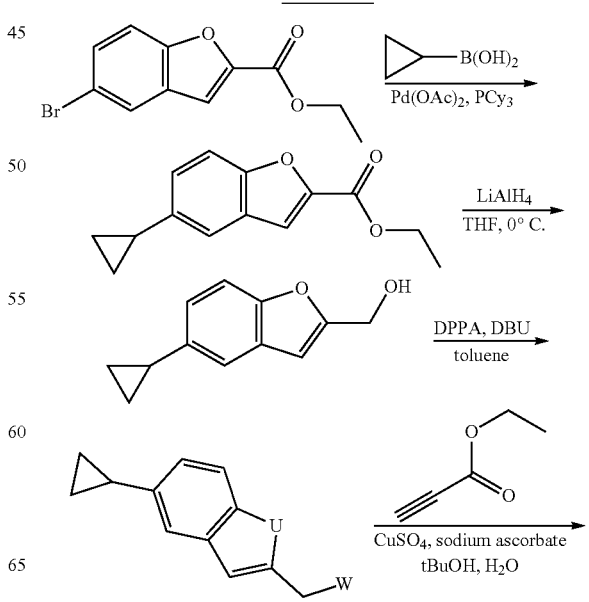

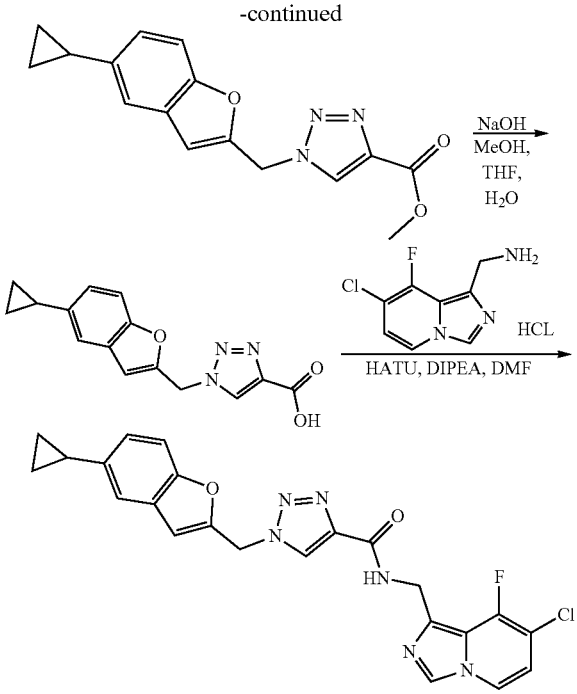

I-191

Synthesis of 2-(6-cyclopropylimidazo[1,2-a]pyridin-2-yl)acetonitrile

A mixture of ethyl 5-bromobenzofuran-2-carboxylate (538 mg, 2 mmol), cyclopropylboronic acid (223 mg, 2.6 mmol), Pd(OAc)$_2$ (23 mg, 0.01 mmol), PCy$_3$ (56 mg, 0.2 mmol) and K$_3$PO$_4$ (648 mg, 3 mmol) in toluene (17 mL) and H$_2$O (2 mL) was degassed with nitrogen and stirred under reflux under nitrogen atmosphere overnight. The reaction mixture was partitioned between EtOAc (30 mL) and H$_2$O (20 mL). The layers were separated and the aqueous phase was extracted with EtOAc (30 mL×3). The combined organic layer were washed with brine (25 mL), dried over Na$_2$SO$_4$, filtered and concentrated to give the crude product which was purified by column chromatography (MeOH/DCM=100/1) to get the product ethyl 5-cyclopropylbenzofuran-2-carboxylate (369 mg, 85.4%) as a yellow solid. ESI-MS [M+H]$^+$: 217.2

Synthesis of Ethyl (5-cyclopropylbenzofuran-2-yl)methanol

To a solution ethyl 5-cyclopropylbenzofuran-2-carboxylate (369 mg, 1.7 mmol) in THF (10 mL) was added LiAlH$_4$ (121 mg, 3.2 mmol). The resulting mixture was stirred at 0° C. for 2 h. The reaction was quenched sequentially with H$_2$O (0.5 mL), 15% NaOH (0.5 mL), and H$_2$O (1.5 mL). The resulting mixture was filtered and the filtrate was concentrated to give the crude product (5-cyclopropylbenzofuran-2-yl)methanol (305 mg, 95%) as a yellow oil which was used for next step directly. ESI-MS [M+H]$^+$: 189.1

Synthesis of 2-(azidomethyl)-5-cyclopropylbenzofuran

To a stirring solution of (5-cyclopropylbenzofuran-2-yl)methanol (305 mg, 1.6 mmol) and DPPA (528 mg, 1.92 mmol) in THF (20 mL) was added DBU (291 mg, 1.92 mmol) under 0 C. The resulting mixture was stirred at RT overnight. Water (30 mL) was added and extracted with EtOAc (30 mL×3). The combined organic layers were washed with brine, dried over Na$_2$SO$_4$, filtered and concentrated. The residue was purified by flash column chromatography (DCM/MeOH=20/1) to give the 2-(azidomethyl)-5-cyclopropylbenzofuran (250 mg, 72.3%) as a pale-yellow oil. ESI-MS [M+H]$^+$: 214.8

Synthesis of Methyl 1-((5-cyclopropylbenzofuran-2-yl)methyl)-1H-1,2,3-triazole-4-carboxylate A solution of 2-(azidomethyl)-5-cyclopropylbenzofuran (250 mg, 1.17 mmol) in t-BuOH (5 mL) and H$_2$O (5 mL) was added CuSO$_4$-5H$_2$O (58 mg, 0.234 mmol), sodium ascorbate (70 mg, 0.347 mmol) and ethyl propiolate (226 mg, 2.31 mmol). The resulting mixture was stirred at RT for 15 h. The reaction mixture was concentrated to get the crude product which was purified by flash column chromatography (0-3% MeOH in DCM) to give the product methyl 1-((5-cyclopropylbenzofuran-2-yl)methyl)-1H-1,2,3-triazole-4-carboxylate (287 mg, 82%) as an off-yellow oil. ESI-MS [M+H]$^+$: 298.1.

Synthesis of 1-((5-cyclopropylbenzofuran-2-yl)methyl)-1H-1,2,3-triazole-4-carboxylic Acid A solution of ethyl methyl 1-((5-cyclopropylbenzofuran-2-yl)methyl)-1H-1,2,3-triazole-4-carboxylate (287 mg, 0.96 mmol) in THF (5 mL) and MeOH (5 mL) was added with a solution of NaOH (83 mg, 2.08 mmol) in H$_2$O (5 mL) at RT and stirred for 2 h. The volatile was removed in vacuo and the aqueous phase was acidified to pH 4-5 with 2N HCl. The precipitate was filtered and the solid was washed with H$_2$O (3 mL*3). The solid was dried to give 1-((5-cyclopropylbenzofuran-2-yl)methyl)-1H-1,2,3-triazole-4-carboxylic acid (160 mg, 58%) as a light yellow solid. ESI-MS [M+H]$^+$: 284.1.

Synthesis of N-((7-chloro-8-fluoroimidazo[1,5-a]pyridin-1-yl)methyl)-1-((5-cyclopropylbenzofuran-2-yl)methyl)-1H-1,2,3-triazole-4-carboxamide (I-191)

To a mixture of 1-((5-cyclopropylbenzofuran-2-yl)methyl)-1H-1,2,3-triazole-4-carboxylic acid (160 mg, 0.56 mmol), HATU (159 mg, 0.42 mmol) and DIPEA (147 mg, 1.14 mmol) in DMF (3 mL) was added (7-chloro-8-fluoroimidazo[1,5-a]pyridin-1-yl)methanamine hydrochloride (90 mg, 0.38 mmol) was stirred at RT for 15 h. The reaction mixture was concentrated to get a residue. which was purified by flash column chromatography (0-8% MeOH in DCM) and then prep-TLC (DCM/MeOH=15/1) to give the product N-((7-chloro-8-fluoroimidazo[1,5-a]pyridin-1-yl)methyl)-1-((5-cyclopropylbenzofuran-2-yl)methyl)-1H-1,2,3-triazole-4-carboxamide (128 mg, 49%) as an off-white solid. ESI-MS [M+H]$^+$: 465.2. Purity: 98.89 (214 nm), 98.63 (254 nm). $^1$H NMR (400 MHz, DMSO-d$_6$) δ 8.74 (t, J=5.2 Hz, 1H), 8.63 (s, 1H), 8.44 (s, 1H), 8.20 (d, J=7.3 Hz, 1H), 7.40 (d, J=8.5 Hz, 1H), 7.33 (s, 1H), 7.04 (d, I=8.6 Hz, 1H), 6.93 (s, 1H), 6.76 (t, J=6.8 Hz, 1H), 5.87 (s, 2H), 4.70 (d, J=5.2 Hz, 2H), 2.05-1.91 (m, 1H), 0.97-0.90 (m, 2H), 0.68-0.62 (m, 2H).

Example 192

Scheme 191

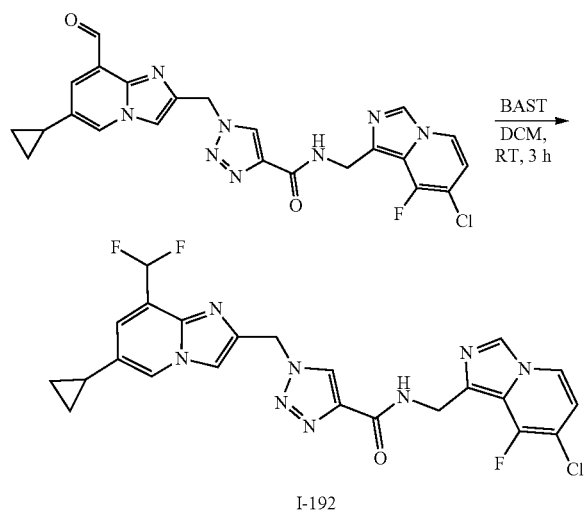

Synthesis of N-((7-chloro-8-fluoroimidazo[1,5-a]pyridin-1-yl)methyl)-1-((6-cyclopropyl-8-(difluoromethyl)imidazo[1,2-a]pyridin-2-yl)methyl)-1H-1,2,3-triazole-4-carboxamide (I-192)

To the suspension of N-((7-chloro-8-fluoroimidazo[1,5-a]pyridin-1-yl)methyl)-1-((6-cyclopropyl-8-formylimidazo[1,2-a]pyridin-2-yl)methyl)-1H-1,2,3-triazole-4-carboxamide (70 mg, 0.14 mmol) in DCM (3 mL) was added BAST (94 mg, 0.43 mmol) at 0° C. The reaction mixture was warmed to RT and stirred for 3 h. Then the reaction was quenched with sat. NaHCO$_3$ (30 mL), and extracted with DCM (30 mL×3). The combined organic layer was washed with brine, dried over Na$_2$SO$_4$ and concentrated to give the crude, which was purified by prep-HPLC (eluent: DCM/MeOH=10/1) to afforded N-((7-chloro-8-fluoroimidazo[1,5-a]pyridin-1-yl)methyl)-1-((6-cyclopropyl-8-(difluoromethyl)imidazo[1,2-a]pyridin-2-yl)methyl)-1H-1,2,3-triazole-4-carboxamide (10 mg, yield: 13.7%) as a white solid. ESI-MS [M+H]$^+$: 515.1. Purity: 99.23 (214 nm), 100 (254 nm). $^1$H NMR (400 MHz, DMSO-d$_6$) δ 8.72 (t, J=5.3 Hz, 1H), 8.56 (s, 1H), 8.51 (s, 1H), 8.44 (d, J=2.3 Hz, 1H), 8.20 (d, J=7.4 Hz, 1H), 7.92 (s, 1H), 7.44-7.15 (m, 2H), 6.76 (t, J=6.9 Hz, 1H), 5.78 (s, 2H), 4.70 (d, J=5.4 Hz, 2H), 2.05-1.97 (m, 1H), 0.98-0.92 (m, 2H), 0.74-0.68 (m, 2H).

Example 193

Scheme 192

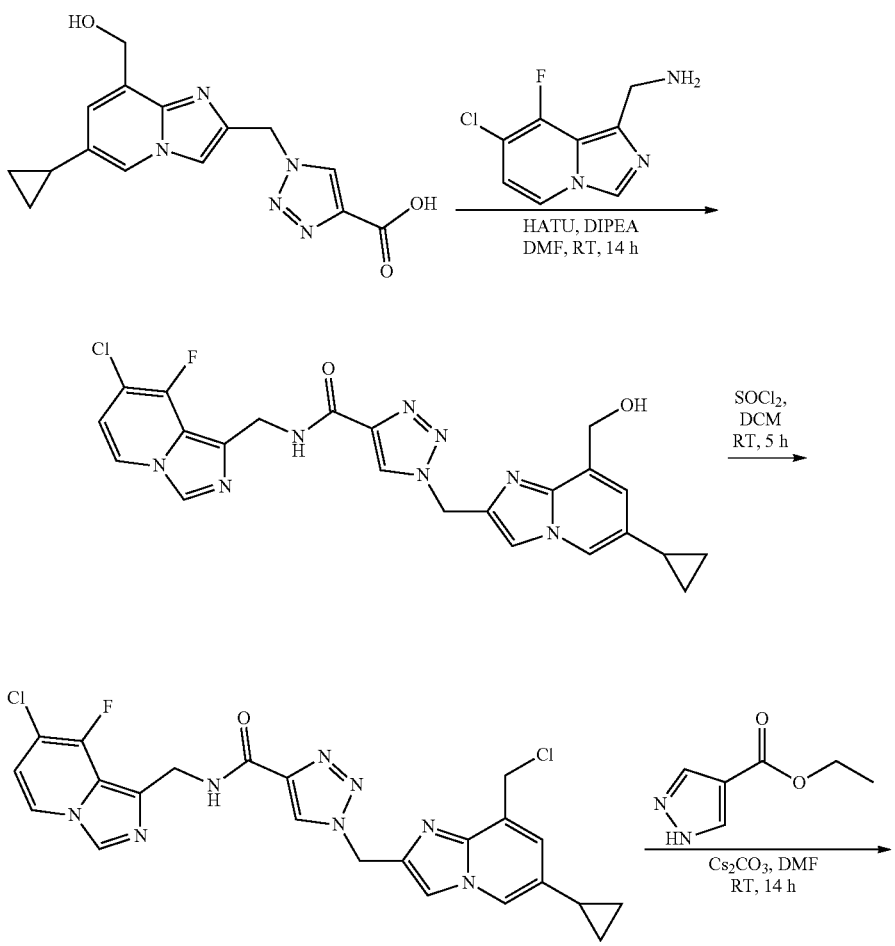

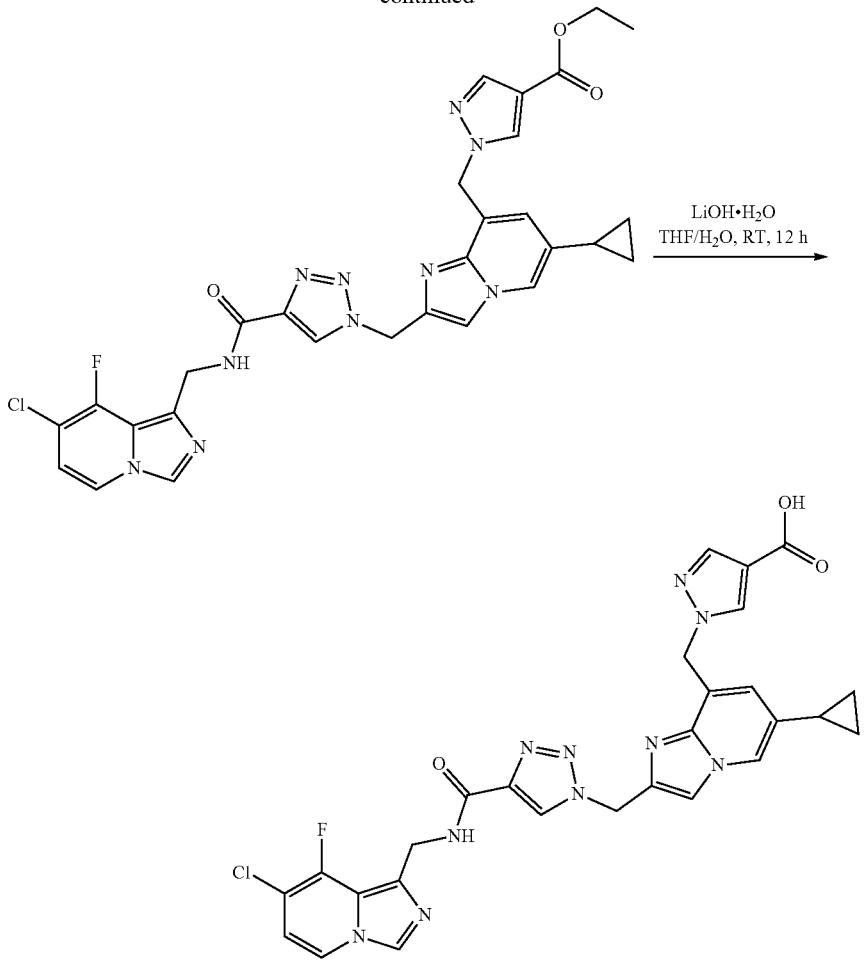

I-193

Synthesis of N-((7-chloro-8-fluoroimidazo[1,5-a]pyridin-1-yl)methyl)-1-((6-cyclopropyl-8-(hydroxymethyl)imidazo[1,2-a]pyridin-2-yl)methyl)-1H-1,2,3-triazole-4-carboxamide To a solution of 1-((6-cyclopropyl-8-(hydroxymethyl)imidazo[1,2-a]pyridin-2-yl)methyl)-1H-1,2,3-triazole-4-carboxylic acid (313 mg, 1 mmol), (7-chloro-8-fluoroimidazo[1,5-a]pyridin-1-yl)methanamine hydrochloride (307 mg, 1.3 mmol) and HATU (570 mg, 1.5 mmol) in DMF (10 mL) was added DIPEA (387 mg, 3 mmol). The resulting mixture was stirred at RT for 14 h. The reaction was poured into H₂O (75 mL) and white solid was formed. The mixture was filtered and dried to give the N-((7-chloro-8-fluoroimidazo[1,5-a]pyridin-1-yl)methyl)-1-((6-cyclopropyl-8-(hydroxymethyl)imidazo[1,2-a]pyridin-2-yl)methyl)-1H-1,2,3-triazole-4-carboxamide as a yellow solid (400 mg, 80.9%). ESI-MS [M+H]⁺: 495.2.

Synthesis of N-((7-chloro-8-fluoroimidazo[1,5-a]pyridin-1-yl)methyl)-1-((8-(chloromethyl)-6-cyclopropylimidazo[1,2-a]pyridin-2-yl)methyl)-1H-1,2,3-triazole-4-carboxamide To a solution of N-((7-chloro-8-fluoroimidazo[1,5-a]pyridin-1-yl)methyl)-1-((6-cyclopropyl-8-(hydroxymethyl)imidazo[1,2-a]pyridin-2-yl)methyl)-1H-1,2,3-triazole-4-carboxamide (400 mg, 0.81 mmol) in DCM (25 mL) was added SOCl₂ (3 mL). The resulting mixture was stirred at RT for 5 h. The reaction was concentrated in vacuo to give the N-((7-chloro-8-fluoroimidazo[1,5-a]pyridin-1-yl)methyl)-1-((8-(chloromethyl)-6-cyclopropylimidazo[1,2-a]pyridin-2-yl)methyl)-1H-1,2,3-triazole-4-carboxamide as a yellow solid, which was used into next step without further purification. (520 mg crude). ESI-MS [M+H]⁺: 513.2

Synthesis of Ethyl 1-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)-1H-pyrazole-4-carboxylate A mixture of N-((7-chloro-8-fluoroimidazo[1,5-a]pyridin-1-yl)methyl)-1-((8-(chloromethyl)-6-cyclopropylimidazo[1,2-a]pyridin-2-yl)methyl)-1H-1,2,3-triazole-4-carboxamide (100 mg, 0.19 mmol), ethyl 1H-pyrazole-4-carboxylate (26 mg, 0.19 mmol) and Cs₂CO₃ (123 mg, 0.38 mmol) in DMF (10 mL) was stirred at RT for 14 h. The resulting mixture was poured into H₂O (50 mL), extracted with EtOAc (75 mL×3). The combined organic layers were washed with brine, dried over Na₂SO₄, concentrated in vacuo to give the crude, which was purified with Prep-TLC (DCM/MeOH=10/1) to give the ethyl 1-((2-((4-(((7-chloro- 8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)-1H-pyrazole-4-carboxylate as a white solid. (65 mg, 54%). ESI-MS [M+H]⁺: 617.2.

Synthesis of 1-((2-((4-(((7-chloro-8-fluoroimidazo [1,5-a]pyridin-1-yl)methyl)carbamoyl)-1H-1,2,3-triazol-1-yl)methyl)-6-cyclopropylimidazo[1,2-a]pyridin-8-yl)methyl)-1H-pyrazole-4-carboxylic acid (I-193)

To a solution of ethyl 1-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)-1H-pyrazole-4-carboxylate (65 mg, 0.11 mmol) in THF/H₂O (7 mL/7 mL) was added LiOH.H₂O (11 mg, 0.25 mmol). The resulting mixture was stirred at RT for 12 h. The reaction was concentrated in vacuo to give the crude, which was purified with Prep-HPCL to give the 1-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)-1H-pyrazole-4-carboxylic acid (15 mg, 23%). ESI-MS [M+H]⁺: 589.2. Purity: 98.79% (214 nm), 98.89% (254 nm). ¹H NMR (400 MHz, DMSO-d₆) δ 8.73 (t, J=5.2 Hz, 1H), 8.57 (s, 1H), 8.46 (s, 1H), 8.34 (s, 1H), 8.31 (s, 1H), 8.21 (d, J=7.4 Hz, 1H), 7.85 (s, 1H), 7.82 (s, 1H), 6.77 (t, J=6.9 Hz, 1H), 6.67 (s, 1H), 5.76 (s, 2H), 5.59 (s, 2H), 4.71 (d, J=5.3 Hz, 2H), 1.92-1.85 (m, 1H), 0.92-0.87 (m, 2H), 0.60-0.57 (m, 2H).

Example 194 pyridin-2-yl)methyl)-1H-1,2,3-triazole-4-carboxamide (100 mg, 0.2 mmol) and NaN₃ (67 mg, 1 mol) in n-BuOH (2 mL) was added ZnCl₂ (1 M in THF, 0.4 mL). The mixture was stirred at 110° C. for 3 h. The reaction was concentrated in vacuo to give the crude which was purified by Prep-HPLC (eluent: DCM/MeOH=10/1) to give 1-((8-(2-(1H-tetrazol-5-yl)ethyl)-6-cyclopropylimidazo[1,2-a]pyridin-2-yl) methyl)-N-((7-chloroimidazo[1,5-a]pyridin-1-yl)methyl)-1H-1,2,3-triazole-4-carboxamide (4 mg, yield: 4%) as an off-white solid. ESI-MS [M+H]⁺: 543.2. Purity: 96.8 (214 nm), 95.0 (254 nm). ¹H NMR (400 MHz, DMSO-d₆) δ 8.93 (t, J=5.8 Hz, 1H), 8.57 (s, 1H), 8.31-8.29 (m, 2H), 8.20 (s, 1H), 7.84 (s, 1H), 7.77 (s, 1H), 6.75 (s, 1H), 6.64 (dd, J=7.4, 1.8 Hz, 1H), 5.74 (s, 2H), 4.61 (d, J=5.8 Hz, 2H), 3.23 (s, 4H), 1.90-1.82 (m, 1H), 0.92-0.84 (m, 2H), 0.63-0.56 (m, 2H).

Example 195

Scheme 194

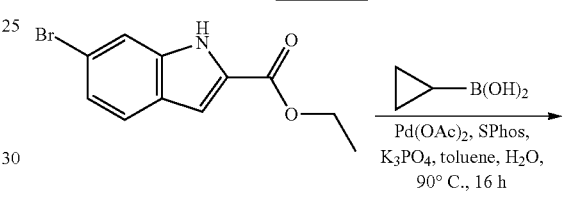

Scheme 193

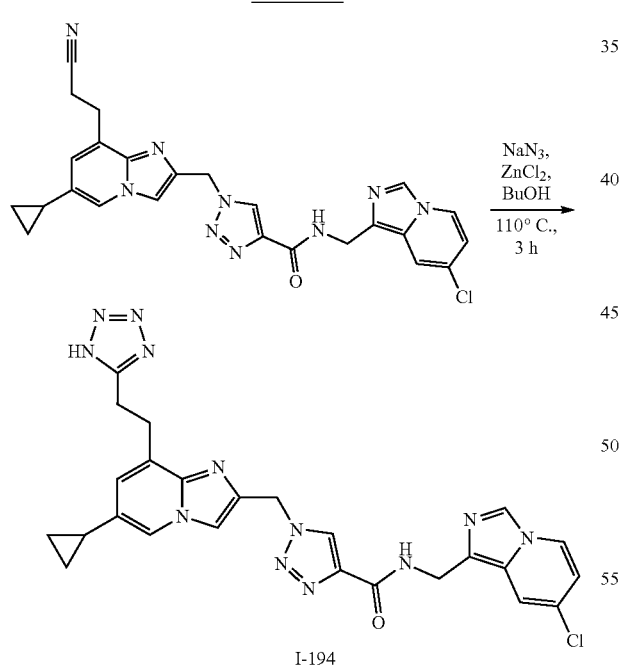

I-194

Synthesis of 1-((8-(2-(1H-tetrazol-5-yl)ethyl)-6-cyclopropylimidazo[1,2-a]pyridin-2-yl)methyl)-N-((7-chloroimidazo[1,5-a]pyridin-1-yl)methyl)-1H-1,2,3-triazole-4-carboxamide (I-194)

To a mixture of N-((7-chloroimidazo[1,5-a]pyridin-1-yl) methyl)-1-((8-(2-cyanoethyl)-6-cyclopropylimidazo[1,2-a]

-continued

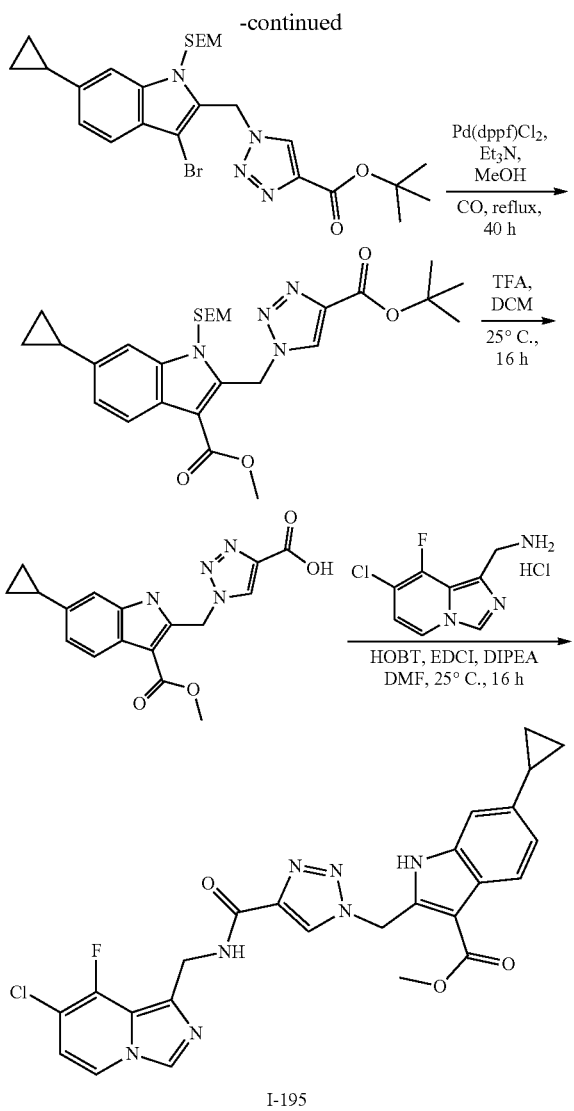

I-195

Synthesis of Ethyl 6-cyclopropyl-1H-indole-2-carboxylate

The mixture of ethyl 6-bromo-1H-indole-2-carboxylate (3.5 g, 13.05 mmol), cyclopropylboronic acid (2.24 g, 26.11 mmol), Pd(OAc)$_2$ (146 mg, 0.653 mmol), SPhos (536 mg, 1.31 mmol) and K$_3$PO$_4$ (8.31 g, 39.15 mmol) in toluene (60 mL) and H$_2$O (10 mL) was stirred at 100° C. for 16 h under N$_2$. The reaction mixture was filtered and washed with EtOAc (20 mL). The filtrate was concentrated and diluted with H$_2$O (100 mL), extracted with EtOAc (100 mL×3), the combined organic layers were concentrated and purified by silica gel chromatography (EA/PE=1/3) to give ethyl 6-cyclopropyl-1H-indole-2-carboxylate (2.8 g, yield: 93%) as a yellow solid. ESI-MS [M+H]$^+$: 230.1.

Synthesis of Ethyl 3-bromo-6-cyclopropyl-1H-indole-2-carboxylate

To a stirred solution of ethyl 6-cyclopropyl-1H-indole-2-carboxylate (2.8 g, 12.2 mmol) in THF (60 mL) was added NBS (2.79 g, 15.7 mmol) in portions at 0° C. The mixture was stirred at 25° C. for 2 h. The reaction mixture was diluted in EtOAc (100 mL), washed with NaHCO$_3$ aqueous (100 mL) and brine (100 mL), dried over Na$_2$SO$_4$, concentrated and dried in vacuo to give ethyl 3-bromo-6-cyclopropyl-1H-indole-2-carboxylate (3.5 g, 94%) as a yellow solid. ESI-MS [M+Na]$^+$: 330.0.

Synthesis of Ethyl 3-bromo-6-cyclopropyl-1-((2-(trimethylsilyl)ethoxy)methyl)-1H-indole-2-carboxylate To a stirred solution of NaH (564 mg, 14.1 mmol) in THF (20 mL) was added dropwise of the solution of ethyl 3-bromo-6-cyclopropyl-1H-indole-2-carboxylate (2.9 g, 9.41 mmol) in THF (28 mL) at 0° C. The mixture was stirred at 0° C. for 10 min and SEMCl (2.04 g, 12.24 mmol) was added dropwise at 0° C. The mixture was stirred at 25° C. for 2 h. The reaction mixture was quenched with H$_2$O (50 mL) and extracted with EtOAc (80 mL×2). The combined organic layers were washed with brine (150 mL), dried over Na$_2$SO$_4$, concentrated and dried in vacuo to give ethyl 3-bromo-6-cyclopropyl-1-((2-(trimethylsilyl)ethoxy) methyl)-1H-indole-2-carboxylate (3.8 g, yield: 93%) as a light brown syrup. ESI-MS [M+Na]$^+$: 460.1.

Synthesis of (3-bromo-6-cyclopropyl-1-((2-(trimethylsilyl)ethoxy)methyl)-1H-indol-2-yl)methanol To a stirred solution of ethyl 3-bromo-6-cyclopropyl-1-((2-(trimethylsilyl)ethoxy)methyl)-1H-indole-2-carboxylate (750 mg, 1.71 mmol) in DCM (30 mL) was added dropwise DIBAL-H (6.8 mL, 1 M in DCM, 6.8 mmol) at 0° C. The mixture was stirred at 0° C. for 1 h. The reaction mixture was quenched with NH$_4$Cl aqueous (30 mL) and extracted with DCM (30 mL×3). The combined organics was washed with brine (90 mL), dried over Na$_2$SO$_4$, and purified by silica gel chromatography (EA/PE=1/2) to give (3-bromo-6-cyclopropyl-1-((2-(trimethylsilyl)ethoxy)methyl)-1H-indol-2-yl) methanol (450 mg, yield: 66%) as a colorless syrup. ESI-MS [M+Na]$^+$: 418.0.

Synthesis of 2-(azidomethyl)-3-bromo-6-cyclopropyl-1-((2-(trimethylsilyl)ethoxy)methyl)-1H-indole To a stirred solution of (3-bromo-6-cyclopropyl-1-((2-(trimethylsilyl)ethoxy)methyl)-1H-indol-2-yl)methanol (400 mg, 1.01 mmol) and DPPA (834 mg, 3.03 mmol) in DCM (15 mL) was added dropwise the solution of DBU (500 mg, 3.03 mmol) in DCM (1 mL) at 0° C. The mixture was stirred at 25° C. for 16 h. The reaction mixture was concentrated and purified by silica gel chromatography (EA/PE=1/5) to give 2-(azidomethyl)-3-bromo-6-cyclopropyl-1-((2-(trimethylsilyl)ethoxy)methyl)-1H-indole (270 mg, yield: 64%) as a yellow syrup. ESI-MS [M+H]$^+$: 421.0.

Synthesis of tert-butyl 1-((3-bromo-6-cyclopropyl-1-((2-(trimethylsilyl)ethoxy)methyl)-1H-indol-2-yl)methyl)-1H-1,2,3-triazole-4-carboxylate The mixture of 2-(azidomethyl)-3-bromo-6-cyclopropyl-1-((2-(trimethylsilyl)ethoxy)methyl)-1H-indole (270 mg, 0.64 mmol), ethyl isobutyrate (105 mg, 0.832 mmol), CuSO$_4$ (51 mg, 0.32 mmol) and sodium ascorbate (63 mg, 0.32 mmol) in t-BuOH (5 mL) and H$_2$O (5 mL) was stirred at 25° C. for 16 h. t-BuOH was removed and diluted in H$_2$O (30 mL), extracted with DCM (30 mL×3). The combined organics was washed with brine (60 mL), dried over Na$_2$SO$_4$, concentrated and purified by silica gel chromatography (EA/PE=1/1) to afford tert-butyl 1-((3-bromo-6-cyclopropyl-1-((2-(trimethylsilyl)ethoxy)methyl)-1H-indol-2-yl)methyl)-1H-1,2,3-triazole-4-carboxylate (270 mg, yield: 77%) as a yellow solid. ESI-MS [M+Na]⁺: 569.1.

Synthesis of Methyl 2-((4-(tert-butoxycarbonyl)-1H-1,2,3-triazol-1-yl)methyl)-6-cyclopropyl-1-((2-(trimethylsilyl)ethoxy)methyl)-1H-indole-3-carboxylate A mixture of tert-butyl 1-((3-bromo-6-cyclopropyl-1-((2-(trimethylsilyl)ethoxy)methyl)-1H-indol-2-yl)methyl)-1H-1,2,3-triazole-4-carboxylate (270 mg, 0.493 mmol), Pd(dppf)Cl₂ (36 mg, 0.049 mmol) and Et₃N (748 mg, 7.40 mmol) in MeOH (25 mL) was stirred at 75° C. for 40 h under CO (balloon). The reaction mixture was concentrated and purified by silica gel chromatography (EA/PE=1/5) to afford methyl 2-((4-(tert-butoxycarbonyl)-1H-1,2,3-triazol-1-yl)methyl)-6-cyclopropyl-1-((2-(trimethylsilyl)ethoxy)methyl)-1H-indole-3-carboxylate (70 mg, yield: 27%) as a yellow solid. ESI-MS [M+Na]⁺: 549.2.

Synthesis of 1-((6-cyclopropyl-1-(hydroxymethyl)-3-(methoxycarbonyl)-1H-indol-2-yl)methyl)-1H-1,2,3-triazole-4-carboxylic Acid A mixture of methyl 2-((4-(tert-butoxycarbonyl)-1H-1,2,3-triazol-1-yl)methyl)-6-cyclopropyl-1-((2-(trimethylsilyl)ethoxy)methyl)-1H-indole-3-carboxylate (50 mg, 0.095 mmol) and TFA (0.3 mL) in DCM (2 mL) was stirred at 25° C. for 16 h. The reaction mixture was concentrated and dried in vacuo to give 1-((6-cyclopropyl-1-(hydroxymethyl)-3-(methoxycarbonyl)-1H-indol-2-yl)methyl)-1H-1,2,3-triazole-4-carboxylic acid (35 mg, crude) as a purple solid. ESI-MS [M+Na]⁺: 341.1.

Synthesis of Methyl 2-((4-(((7-chloro-8-fluoroimidazo[1,5-a]pyridin-1-yl)methyl)carbamoyl)-1H-1,2,3-triazol-1-yl)methyl)-6-cyclopropyl-1H-indole-3-carboxylate (I-272)

The mixture of 1-((6-cyclopropyl-1-(hydroxymethyl)-3-(methoxycarbonyl)-1H-indol-2-yl)methyl)-1H-1,2,3-triazole-4-carboxylic acid (35 mg, crude), (7-chloro-8-fluoroimidazo[1,5-a]pyridin-1-yl)methanamine hydrochloride (25 mg, 0.105 mmol), EDCI (36 mg, 0.19 mmol), HOBT (26 mg, 0.19 mmol) and DIPEA (123 mg, 0.95 mmol) in DMF (2 mL) was stirred at 25° C. for 16 h. The reaction mixture was poured into H₂O (20 mL) and the precipitate was collected, dried in vacuo and purified by silica gel chromatography (EA/MeOH=40/1) to give methyl 2-((4-(((7-chloro-8-fluoroimidazo[1,5-a]pyridin-1-yl)methyl)carbamoyl)-1H-1,2,3-triazol-1-yl)methyl)-6-cyclopropyl-1H-indole-3-carboxylate (14 mg, yield: 28%) as a white solid. ESI-MS [M+H]⁺: 522.1. Purity: 96.95% (214 nm), 96.72% (254 nm). ¹H NMR (400 MHz, DMSO-d₆) δ 12.06 (s, 1H), 8.73 (t, J=5.5 Hz, 1H), 8.53 (s, 1H), 8.43 (d, J=2.4 Hz, 1H), 8.20 (d, J=7.4 Hz, 1H), 7.83 (d, J=8.3 Hz, 1H), 7.12 (s, 1H), 6.94 (dd, J=8.4, 1.5 Hz, 1H), 6.78-6.73 (m, 1H), 6.06 (s, 2H), 4.69 (d, J=5.5 Hz, 2H), 3.84 (s, 3H), 2.05-1.96 (m, 1H), 0.98-0.91 (m, 2H), 0.69-0.62 (m, 2H).

Example 196

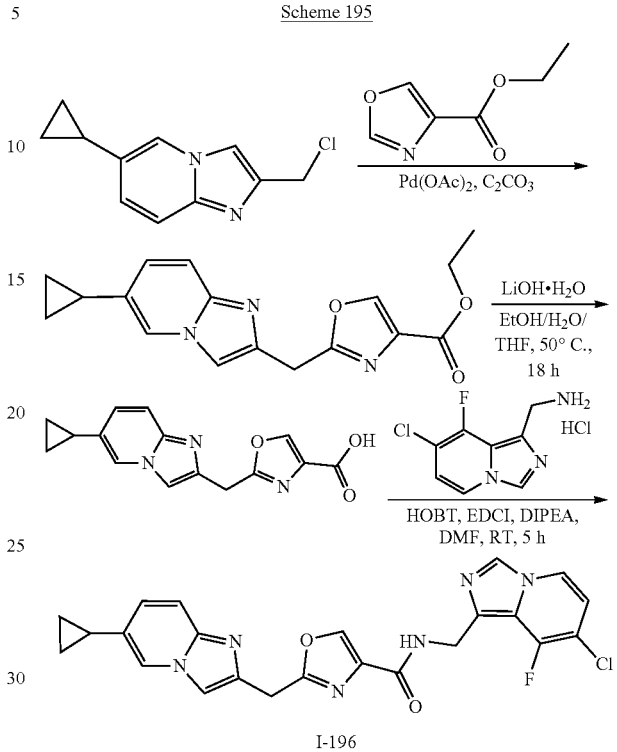

Scheme 195

I-196

Synthesis of Ethyl 2-((6-cyclopropylimidazo[1,2-a]pyridin-2-yl)methyl)oxazole-4-carboxylate The mixture of 2-(chloromethyl)-6-cyclopropylimidazo[1,2-a]pyridine (2.06 g, 10.0 mmol), ethyl oxazole-4-carboxylate (2.82 g, 20.0 mmol), (2-biphenyl)dicyclohexylphosphine (350 mg, 1.0 mmol), Pd(OAc)₂ (224 mg, 1.0 mmol) and Cs₂CO₃ (6.52 g, 20.0 mmol) in dioxane (30 mL) was degassed with N₂ and stirred at 100° C. for 18 h. The reaction mixture was cooled to RT and diluted with H₂O (100 mL). Then extracted with EtOAc (100 mL*3). The combined organic layer was washed with brine, dried over Na₂SO₄ and concentrated. The residue was purified by flash column chromatography to afforded ethyl 2-((6-cyclopropylimidazo[1,2-a]pyridin-2-yl)methyl)oxazole-4-carboxylate (420 mg, yield: 13.5%) as a brown oil. ESI-MS [M+H]⁺: 312.3.

Synthesis of 2-((6-cyclopropylimidazo[1,2-a]pyridin-2-yl)methyl)oxazole-4-carboxylic Acid A mixture of ethyl 2-((6-cyclopropylimidazo[1,2-a]pyridin-2-yl)methyl)oxazole-4-carboxylate (210 mg, 0.68 mmol) and LiOH.H₂O (142 mg, 3.38 mmol) in THF/H₂O/EtOH (5 mL/5 mL/5 mL) was degassed with N₂ and stirred at 50° C. for 18 h. The reaction mixture was cooled to RT and adjusted to pH-3. Then it was diluted with H₂O (50 mL) and extracted with DCM/MeOH (10:1, 30 mL*5). The combined organic layer was washed with brine, dried over Na₂SO₄ and concentrated to afforded 2-((6-cyclopropylimidazo[1,2-a]pyridin-2-yl)methyl)oxazole-4-carboxylic acid (220 mg, crude) which was used in next step directly. ESI-MS [M+H]⁺: 284.2

Synthesis of N-((7-chloro-8-fluoroimidazo[1,5-a]pyridin-1-yl)methyl)-2-((6-cyclopropylimidazo[1,2-a]pyridin-2-yl)methyl)oxazole-4-carboxamide (I-196)

The mixture of 2-((6-cyclopropylimidazo[1,2-a]pyridin-2-yl)methyl)oxazole-4-carboxylic acid (110 mg, 0.34 mmol), (7-chloro-8-fluoroimidazo[1,5-a]pyridin-1-yl)methanamine hydrochloride (127 mg, 0.51 mmol), HOBT (55 mg, 0.41 mmol), EDCI (78 mg, 0.41 mmol) and DIPEA (132 mg, 1.02 mmol) in DMF (3 mL) was stirred at to RT for 18 h. The reaction mixture was diluted with H$_2$O (30 mL) then it was extracted with EtOAc (30 mL*3). The combined organic layer was washed with brine, dried over Na$_2$SO$_4$ and concentrated. The residue was purified by prep-HPLC to afford N-((7-chloro-8-fluoroimidazo[1,5-a]pyridin-1-yl)methyl)-2-((6-cyclopropylimidazo[1,2-a]pyridin-2-yl)methyl)oxazole-4-carboxamide (8 mg) as a white solid. ESI-MS [M+H]$^+$: 465.1. Purity: 97.17 (214 nm), 96.01 (254 nm). $^1$H NMR (400 MHz, DMSO-d$_6$) δ 8.50 (s, 1H), 8.45 (d, J=1.7 Hz, 1H), 8.39 (t, J=5.2 Hz, 1H), 8.30 (s, 1H), 8.21 (d, J=7.4 Hz, 1H), 7.73 (s, 1H), 7.36 (d, J=9.3 Hz, 1H), 6.96 (d, J=9.0 Hz, 1H), 6.76 (t, J=6.9 Hz, 1H), 4.68 (d, J=5.3 Hz, 2H), 4.25 (s, 2H), 1.96-1.87 (m Hz, 1H), 0.95-0.88 (m, 2H), 0.69-0.63 (m, 2H).

Example 197

Scheme 196

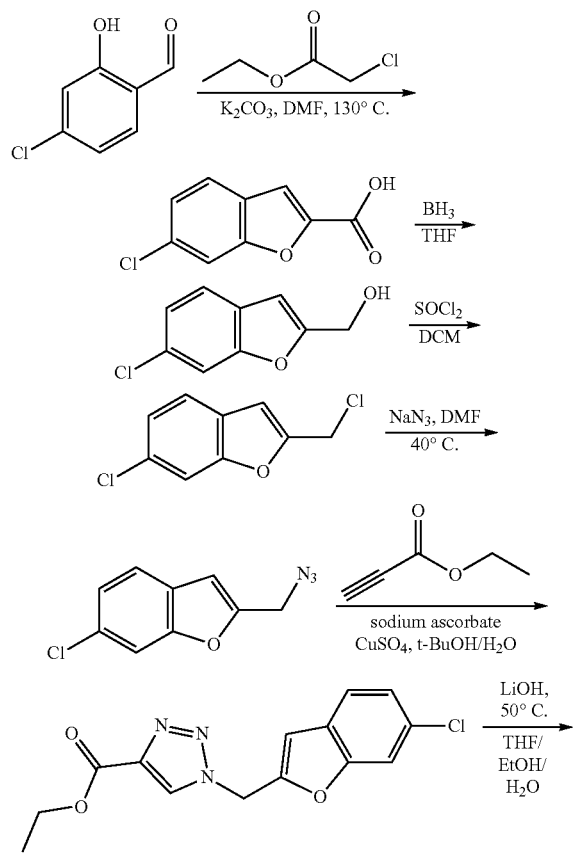

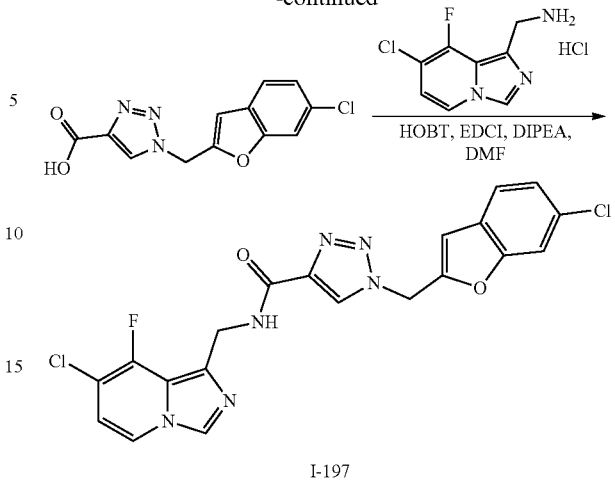

I-197

Synthesis of 6-chlorobenzofuran-2-carboxylic Acid

A mixture of 4-chloro-2-hydroxybenzaldehyde (156 mg, 1 mmol), ethyl 2-chloroacetate (123 mg, 1 mmol) and K$_2$CO$_3$ (553 mg, 4 mmol) in DMF (2 mL) was stirred at 130° C. for 4 h. Water (30 mL) was added and extracted with EtOAc (50 mL). The H$_2$O layer was acidified with HCl (6 M) to pH 3, then extracted with EtOAc (50 mL*3). The combined organic layer was washed by brine (50 mL*2), dried over Na$_2$SO$_4$, and concentrated to give 6-chlorobenzofuran-2-carboxylic acid (196 mg, yield: 100%) as a yellow solid. ESI-MS [M+H]$^+$: 197.1.

Synthesis of (6-chlorobenzofuran-2-yl)methanol

To a solution of 6-chlorobenzofuran-2-carboxylic acid (196 mg, 1 mmol) in THF was added BH$_3$ (2.5 mL, 1 M in THF, 2.5 mmol) dropwise at 0° C. The reaction mixture was stirred at RT for 16 h, CH$_3$OH (5 mL) was added at 0° C., then further stirred at RT for 2 h, and concentrated to give (6-chlorobenzofuran-2-yl)methanol (182 mg, crude) as a yellow oil which was used in next step directly. ESI-MS [M−17]$^+$: 165.1.

Synthesis of 6-chloro-2-(chloromethyl)benzofuran

A mixture of (6-chlorobenzofuran-2-yl)methanol (182 mg, crude from last step) and SOCl$_2$ (714 mg, 6 mmol) in DCM (2 mL) was stirred at RT for 3 h. Concentration and purification by silica gel chromatography (PE/EA=10/1) yielded 6-chloro-2-(chloromethyl)benzofuran (60 mg, yield: 30%) as a white solid, which was used into next step without purification.

Synthesis of 2-(azidomethyl)-6-chlorobenzofuran

A mixture of 6-chloro-2-(chloromethyl)benzofuran (60 mg, 0.29) and NaN$_3$ (25 mg, 0.36 mmol) in DMF (2 mL) was stirred at RT for 3 h. Water (20 mL) was added and extracted with EtOAc (30 mL*3). The combined organic layers were washed by brine (20 mL), dried over Na$_2$SO$_4$, concentrated to give 2-(azidomethyl)-6-chlorobenzofuran (60 mg, crude) as a yellow oil which was used in next step directly.

Synthesis of Ethyl 1-((6-chlorobenzofuran-2-yl)methyl)-1H-1,2,3-triazole-4-carboxylate A mixture of 2-(azidomethyl)-6-chlorobenzofuran (60 mg, crude), ethyl propiolate (84 mg, 0.85 mmol), CuSO₄ (27 mg, 0.17 mmol) and sodium ascorbate (30 mg, 0.17 mmol) in H₂O/t-BuOH (2 mL/2 mL) was stirred at RT for 3 h. Concentrated and H₂O (20 mL) was added, then extracted with EtOAc (20 mL*5), the combined organic layers were washed by brine (20 mL), dried over Na₂SO₄ and concentrated. The residue was purified by flash column chromatography to give ethyl 1-((6-chlorobenzofuran-2-yl)methyl)-1H-1,2,3-triazole-4-carboxylate (50 mg, yield: 55% over 2 steps) as a yellow solid. ESI-MS [M+H]⁺: 306.1.

Synthesis of 1-((6-chlorobenzofuran-2-yl)methyl)-1H-1,2,3-triazole-4-carboxylic Acid A mixture of ethyl 1-((6-chlorobenzofuran-2-yl)methyl)-1H-1,2,3-triazole-4-carboxylate (50 mg, 0.15 mmol) and LiOH·H₂O (13 mg, 0.32 mmol) in THF/EtOH/H₂O (2 mL/2 mL/1 mL) was stirred at 50° C. for 3 h. Then pH value was adjust to 4 by adding HCl (2 M), the concentrated to give 1-((6-chlorobenzofuran-2-yl)methyl)-1H-1,2,3-triazole-4-carboxylic acid (70 mg, crude) as a white solid. ESI-MS [M+H]⁺: 300.0

Synthesis of N-((7-chloro-8-fluoroimidazo[1,5-a]pyridin-1-yl)methyl)-1-((6-chlorobenzofuran-2-yl)methyl)-1H-1,2,3-triazole-4-carboxamide (I-197)

A mixture of 1-((6-chlorobenzofuran-2-yl)methyl)-1H-1,2,3-triazole-4-carboxylic acid (70 mg, crude from last step), (7-chloro-8-fluoroimidazo[1,5-a]pyridin-1-yl)methanamine hydrochloride (39 mg, 0.16 mmol), HOBT (43 mg, 0.32 mmol), EDCI (61 mg, 0.32 mmol) and DIPEA (103 mg, 0.8 mmol) in DMF (2.5 mL) was stirred at RT for 16 h. Water (10 mL) was added and solid forms. The solid was filtered and washed with H₂O (3 mL*3) and dried to give N-((7-chloro-8-fluoroimidazo[1,5-a]pyridin-1-yl)methyl)-1-((6-chlorobenzofuran-2-yl)methyl)-1H-1,2,3-triazole-4-carboxamide (50 mg, yield: 72% over 2 steps) as a white solid. ESI-MS [M+H]⁺: 459.0. Purity: 100 (214 nm), 100 (254 nm). ¹H NMR (400 MHz, DMSO-d₆) δ 8.76 (t, J=5.4 Hz, 1H), 8.65 (s, 1H), 8.44 (d, J=2.3 Hz, 1H), 8.20 (d, J=7.4 Hz, 1H), 7.75 (s, 1H), 7.67 (d, J=8.3 Hz, 1H), 7.31 (dd, J=8.3, J=1.8 Hz, 1H), 7.06 (s, 1H), 6.77-6.74 (m, 1H), 5.91 (s, 2H), 4.70 (d, J=5.5 Hz, 2H).

Example 198

Scheme 197

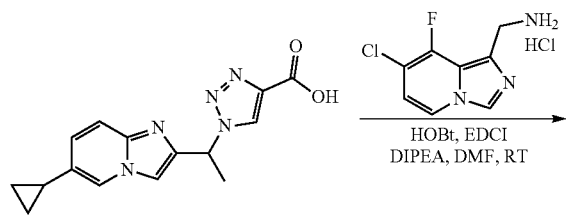

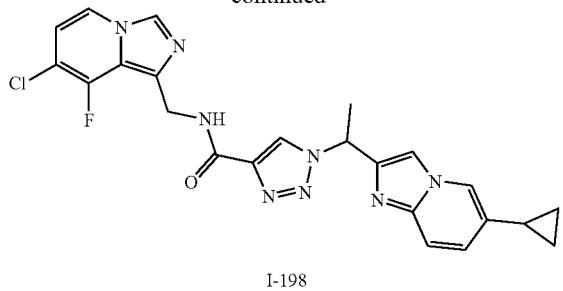

I-198

Synthesis of N-((7-chloro-8-fluoroimidazo[1,5-a]pyridin-1-yl)methyl)-1-(1-(6-cyclopropylimidazo[1,2-a]pyridin-2-yl)ethyl)-1H-1,2,3-triazole-4-carboxamide (I-198)

A mixture of 1-(1-(6-cyclopropylimidazo[1,2-a]pyridin-2-yl)ethyl)-1H-1,2,3-triazole-4-carboxylic acid (200 mg, 0.67 mmol), (7-chloro-8-fluoroimidazo[1,5-a]pyridin-1-yl)methanamine hydrochloride (190 mg, 0.81 mmol), HOBT (181 mg, 1.34 mmol), EDCI (257 mg, 1.34 mmol) and DIPEA (432 mg, 5.0 mmol) in DMF (6 mL) was stirred at RT for 16 h. Water (30 mL) was added to the reaction, extracted by EtOAc (30 mL×3). The organic layers were washed by brine, dried over Na₂SO₄, filtered, and concentrated to give the crude, which was purified by Prep-TLC (DCM/MeOH=10/1) to obtained N-((7-chloro-8-fluoroimidazo[1,5-a]pyridin-1-yl)methyl)-1-(1-(6-cyclopropylimidazo[1,2-a]pyridin-2-yl)ethyl)-1H-1,2,3-triazole-4-carboxamide as a white solid (60 mg, yield: 19%). ESI-MS [M+H]⁺: 479.1. Purity: 96.47 (214 nm), 97.74 (254 nm). ¹H NMR (400 MHz, DMSO-d₆) δ 8.68 (t, J=6.0 Hz, 1H), 8.59 (s, 1H), 8.44 (d, J=4 Hz, 1H), 8.32 (d, J=7.4 Hz, 1H), 8.20 (d, J=4.0 Hz, 1H), 7.77 (s, 1H), 7.42 (d, J=12 Hz, 1H), 7.01 (dd, J=4.0, 8.0 Hz, 1H), 6.76 (t, J=8.0 Hz, 1H), 6.12 (q, J=8.0 Hz, 1H), 4.70 (d, J=4.0 Hz, 2H), 1.93-1.91 (m, 4H), 0.94-0.89 (m, 2H), 0.68-0.64 (m, 2H).

Example 199

Scheme 198

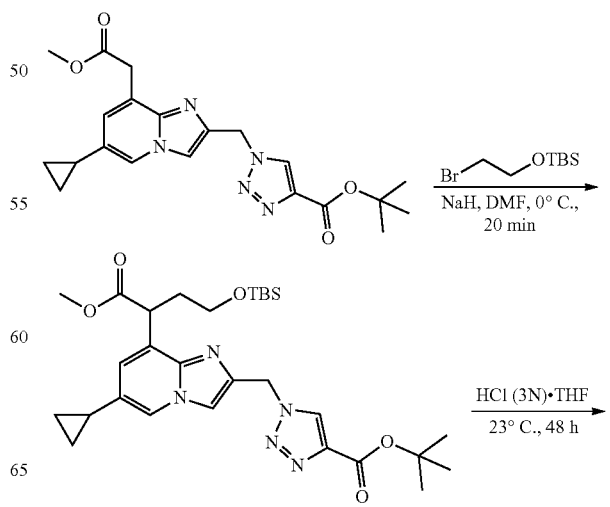

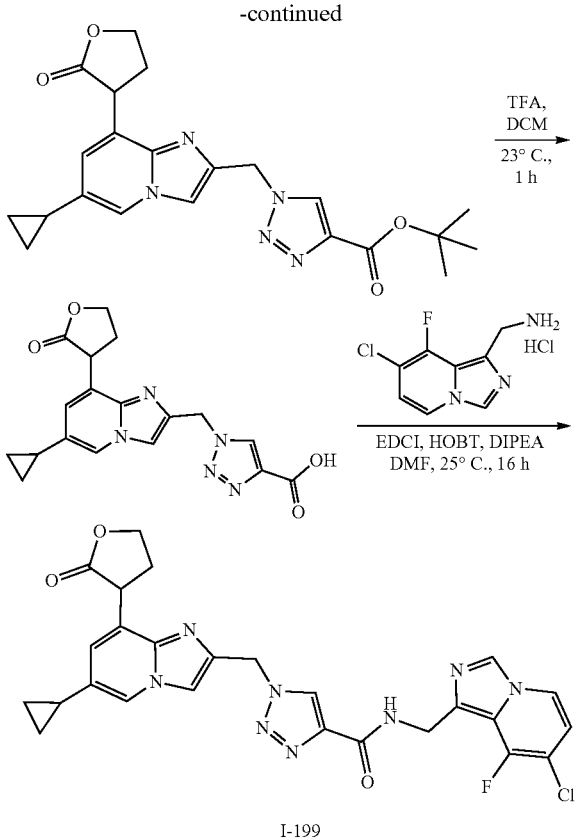

I-199

Synthesis of tert-butyl 1-((8-(4-((tert-butyldimethyl-silyl)oxy)-1-methoxy-1-oxobutan-2-yl)-6-cyclopropylimidazo[1,2-a]pyridin-2-yl)methyl)-1H-1,2,3-triazole-4-carboxylate To a stirred suspension of NaH (239 mg, 5.97 mmol, 60%) in DMF (12 mL) was added a solution of tert-butyl 1-((6-cyclopropyl-8-(2-methoxy-2-oxoethyl)imidazo[1,2-a]pyridin-2-yl)methyl)-1H-1,2,3-triazole-4-carboxylate (490 mg, 1.19 mmol) in DMF (2 mL) at 0° C. under N$_2$, and the mixture was stirred for 10 min. Then a solution of (2-bromoethoxy)(tert-butyl)dimethylsilane (1.14 g, 4.77 mmol) in DMF (2 mL) was added dropwise and the resulting mixture was stirred for 20 min at 0° C. The reaction was quenched with ice H$_2$O (60 mL) and extracted with EtOAc (50 mL×3). The combined organic layers was washed with brine (100 mL), dried over Na$_2$SO$_4$, concentrated to give the crude, which was purified by silica gel chromatography (EA/PE=1/2) to give tert-butyl 1-((8-(4-((tert-butyldimethylsilyl)oxy)-1-methoxy-1-oxobutan-2-yl)-6-cyclopropylimidazo[1,2-a]pyridin-2-yl)methyl)-1H-1,2,3-triazole-4-carboxylate (150 mg, yield: 22%) as a yellow syrup. ESI-MS [M+H]$^+$: 570.3.

Synthesis of tert-butyl 1-((6-cyclopropyl-8-(2-oxotetrahydrofuran-3-yl)imidazo[1,2-a]pyridin-2-yl)methyl)-1H-1,2,3-triazole-4-carboxylate To a stirred suspension of tert-butyl 1-((8-(4-((tert-butyldimethylsilyl)oxy)-1-methoxy-1-oxobutan-2-yl)-6-cyclopropylimidazo[1,2-a]pyridin-2-yl)methyl)-1H-1,2,3-triazole-4-carboxylate (150 mg, 0.26 mmol) in THF (5 mL) was added HCl (3 M, 0.1 mL) and the mixture was stirred at 23° C. for 48 h. The reaction mixture was diluted in EtOAc (50 mL), washed with NaHCO$_3$ aqueous solution and brine (50 mL), dried over Na$_2$SO$_4$, concentrated to give the crude, which was purified by silica gel chromatography (EA/PE=2/1) to give tert-butyl 1-((6-cyclopropyl-8-(2-oxotetrahydrofuran-3-yl)imidazo[1,2-a]pyridin-2-yl)methyl)-1H-1,2,3-triazole-4-carboxylate (95 mg, 86%) as a colorless syrup. ESI-MS [M+H]$^+$: 424.2.

Synthesis of 1-((6-cyclopropyl-8-(2-oxotetrahydrofuran-3-yl)imidazo[1,2-a]pyridin-2-yl)methyl)-1H-1,2,3-triazole-4-carboxylic Acid A mixture of tert-butyl 1-((6-cyclopropyl-8-(2-oxotetrahydrofuran-3-yl)imidazo[1,2-a]pyridin-2-yl)methyl)-1H-1,2,3-triazole-4-carboxylate (95 mg, 0.224 mmol) and TFA (0.5 mL) in DCM (1.5 mL) was stirred at RT for 1 h. The reaction mixture was concentrated and dried in vacuo to give 1-((6-cyclopropyl-8-(2-oxotetrahydrofuran-3-yl)imidazo[1,2-a]pyridin-2-yl)methyl)-1H-1,2,3-triazole-4-carboxylic acid (90 mg, crude) as a yellow solid, which was used into next step without further purification. ESI-MS [M+H]$^+$: 368.1.

Synthesis of N-((7-chloro-8-fluoroimidazo[1,5-a]pyridin-1-yl)methyl)-1-((6-cyclopropyl-8-(2-oxotetrahydrofuran-3-yl)imidazo[1,2-a]pyridin-2-yl)methyl)-1H-1,2,3-triazole-4-carboxamide (I-199)

A mixture of 1-((6-cyclopropyl-8-(2-oxotetrahydrofuran-3-yl)imidazo[1,2-a]pyridin-2-yl)methyl)-1H-1,2,3-triazole-4-carboxylic acid (90 mg, crude), (7-chloro-8-fluoroimidazo[1,5-a]pyridin-1-yl)methanamine hydrochloride (32 mg, 0.136 mmol), EDCI (39 mg, 0.204 mmol), HOBT (28 mg, 0.204 mmol) and DIPEA (176 mg, 1.36 mmol) in DMF (2 mL) was stirred at 25° C. for 16 h. The reaction mixture was poured into H$_2$O (30 mL) and the precipitate was collected, washed with H$_2$O (30 mL), dried to give the crude, which was purified by silica gel chromatography (DCM/MeOH=20/1) to give N-((7-chloro-8-fluoroimidazo[1,5-a]pyridin-1-yl)methyl)-1-((6-cyclopropyl-8-(2-oxotetrahydrofuran-3-yl)imidazo[1,2-a]pyridin-2-yl)methyl)-1H-1,2,3-triazole-4-carboxamide (33 mg, yield: 44%) as a white solid. ESI-MS [M+H]$^+$: 549.1. Purity: 99.48 (214 nm), 99.64 (254 nm). $^1$H NMR (400 MHz, DMSO-d$_6$) δ 8.71 (t, J=5.5 Hz, 1H), 8.53 (s, 1H), 8.44 (d, J=2.4 Hz, 1H), 8.30 (d, J=1.3 Hz, 1H), 8.21 (d, J=7.4 Hz, 1H), 7.79 (s, 1H), 7.02 (d, J=1.5 Hz, 1H), 6.80-6.73 (m, 1H), 5.74 (s, 2H), 4.70 (d, J=5.5 Hz, 2H), 4.55-4.48 (m, 1H), 4.47-4.20 (m, 2H), 2.72-2.60 (m, 1H), 2.59-2.53 (m, 1H), 1.96-1.89 (m, 1H), 0.97-0.88 (m, 2H), 0.70-0.65 (m, 2H).

Example 200

Scheme 199

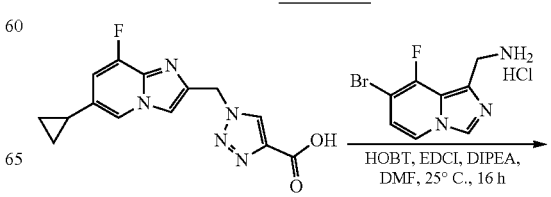

415

-continued

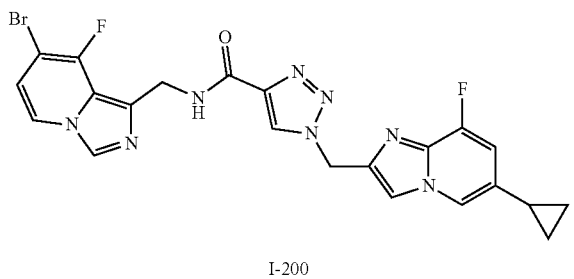

I-200

Synthesis of N-((7-bromo-8-fluoroimidazo[1,5-a]pyridin-1-yl)methyl)-1-((6-cyclopropyl-8-fluoroimidazo[1,2-a]pyridin-2-yl)methyl)-1H-1,2,3-triazole-4-carboxamide (I-200)

A mixture of 1-((6-cyclopropyl-8-fluoroimidazo[1,2-a]pyridin-2-yl)methyl)-1H-1,2,3-triazole-4-carboxylic acid (60 mg, 0.2 mmol), (7-bromo-8-fluoroimidazo[1,5-a]pyridin-1-yl)methanamine hydrochloride (56 mg, 0.2 mmol), EDCI (58 mg, 0.3 mmol), HOBT (41 mg, 0.3 mmol) and DIPEA (155 mg, 1.2 mmol) in DMF (3 mL) was stirred at 25° C. for 16 h. The reaction mixture was poured into $H_2O$ (40 mL) and the precipitate was collected, washed with $H_2O$ (30 mL), dried in vacuo to give the crude, which was purified by prep-TLC (DCM/MeOH=10/1) to give N-((7-bromo-8-fluoroimidazo[1,5-a]pyridin-1-yl)methyl)-1-((6-cyclopropyl-8-fluoroimidazo[1,2-a]pyridin-2-yl)methyl)-1H-1,2,3-triazole-4-carboxamide (66 mg, yield: 63%) as a white solid. ESI-MS [M+H]+: 527.0. Purity: 98.44 (214 nm), 99.43 (254 nm). $^1$H NMR (400 MHz, DMSO-$d_6$) δ 8.71 (t, J=5.4 Hz, 1H), 8.57 (s, 1H), 8.45 (d, J=2.3 Hz, 1H), 8.27 (s, 1H), 8.14 (d, J=7.4 Hz, 1H), 7.95 (d, J=2.8 Hz, 1H), 6.95 (d, J=12.4 Hz, 1H), 6.86-6.77 (m, 1H), 5.76 (s, 2H), 4.69 (d, J=5.5 Hz, 2H), 1.99-1.90 (m, 1H), 0.98-0.89 (m, 2H), 0.74-0.65 (m, 2H).

Example 201

Scheme 200

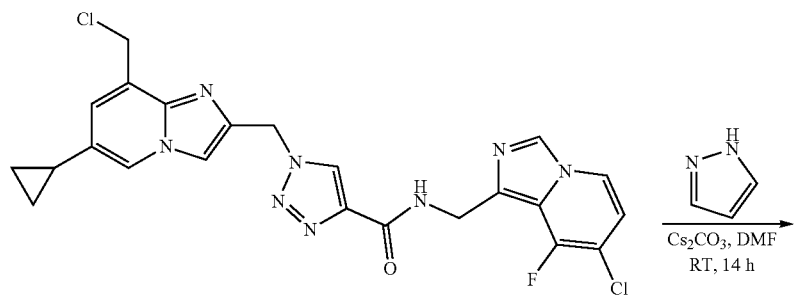

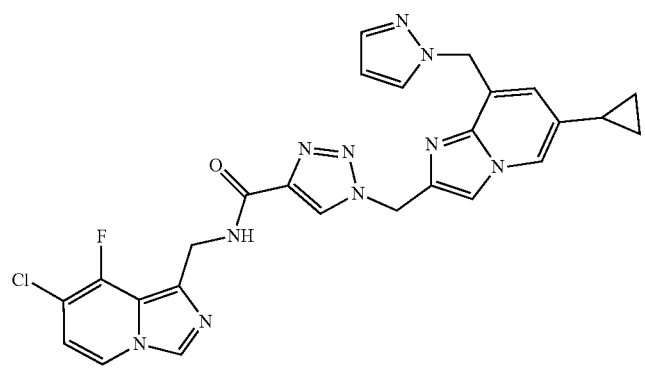

I-201

Synthesis of 1-((8-((1H-pyrazol-1-yl)methyl)-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide (I-201)

A mixture of N-((7-chloro-8-fluoroimidazo[1,5-a]pyridin-1-yl)methyl)-1-((8-(chloromethyl)-6-cyclopropylimidazo[1,2-a]pyridin-2-yl)methyl)-1H-1,2,3-triazole-4-carboxamide (100 mg, 0.19 mmol), 1H-pyrazole (13 mg, 0.19 mmol) and Cs$_2$CO$_3$ (124 mg, 0.38 mmol) in DMF (5 mL) was stirred at RT for 14 h. H$_2$O (30 mL) was added to the reaction, extracted with EtOAC (30 mL×3). The combined organic layers were washed with brine, dried over Na$_2$SO$_4$, concentrated in vacuo to give the crude, which was purified with Prep-HPLC to give the 1-((8-((1H-pyrazol-1-yl)methyl)-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide as a white solid. (22 mg, 21%). ESI-MS [M+H]$^+$: 545.2. Purity: 99.69% (214 nm), 99.66% (254 nm). $^1$H NMR (400 MHz, DMSO-d$_6$) δ 8.71 (t, J=5.4 Hz, 1H), 8.56 (s, 1H), 8.45 (d, J=2.4 Hz, 1H), 8.29 (s, 1H), 8.21 (d, J=7.4 Hz, 1H), 7.87-7.86 (m, 2H), 7.45 (d, J=1.4 Hz, 1H), 6.76 (t, J=7.0 Hz, 1H), 6.55 (s, 1H), 6.23 (t, J=2.0 Hz, 1H), 5.76 (s, 2H), 5.55 (s, 2H), 4.71 (d, J=5.5 Hz, 2H), 1.89-1.82 (m, 1H), 0.90-0.86 (m, 2H), 0.57-0.53 (m, 2H).

Example 202

Scheme 201

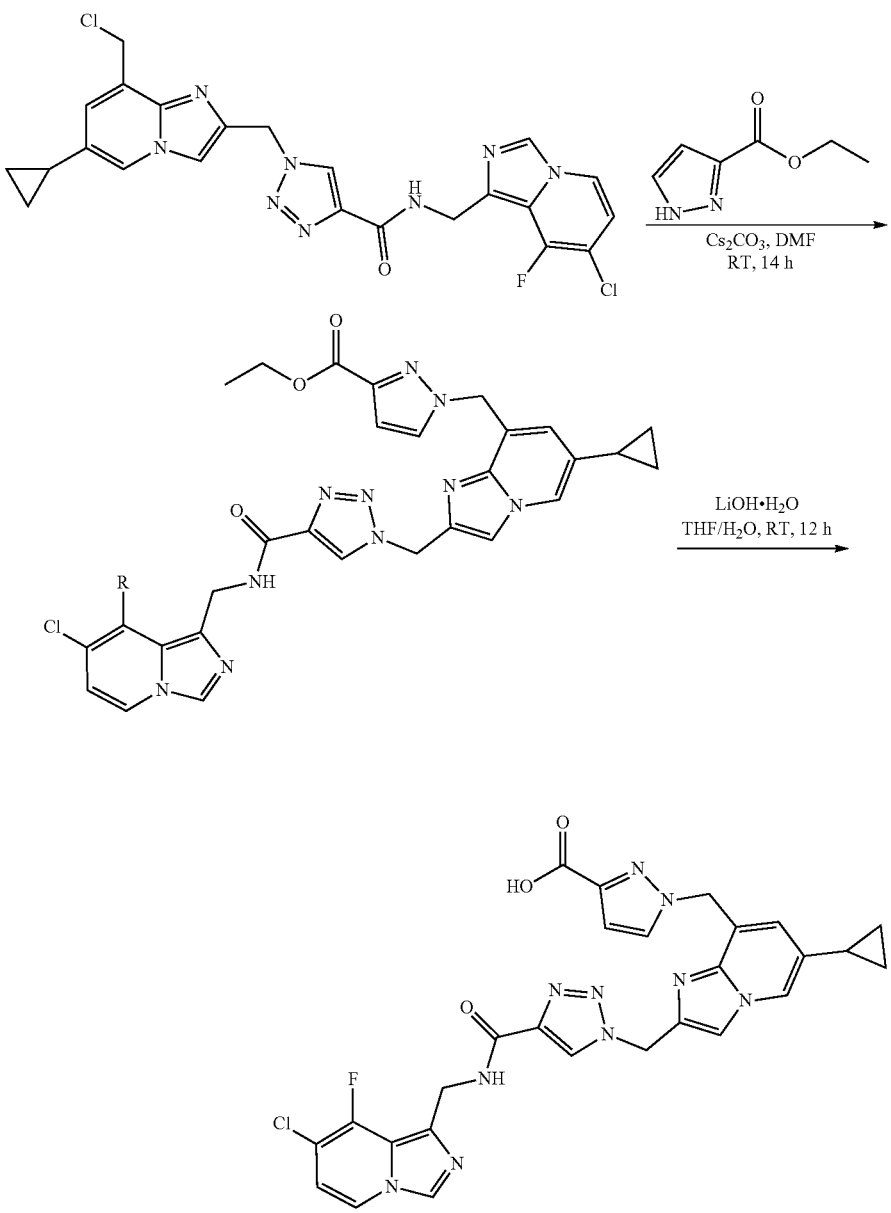

I-202

Synthesis ethyl 1-((2-((4-(((7-chloro-8-fluoroimi-dazo[1,5-a]pyridin-1-yl)methyl)carbamoyl)-1H-1,2,3-triazol-1-yl)methyl)-6-cyclopropylimidazo[1,2-a]pyridin-8-yl)methyl)-1H-pyrazole-3-carboxylate A mixture of N-((7-chloro-8-fluoroimidazo[1,5-a]pyridin-1-yl)methyl)-1-((8-(chloromethyl)-6-cyclopropylimidazo[1,2-a]pyridin-2-yl)methyl)-1H-1,2,3-triazole-4-carboxamide (100 mg, 0.19 mmol), ethyl 1H-pyrazole-3-carboxylate (27 mg, 0.19 mmol) and $Cs_2CO_3$ (124 mg, 0.38 mmol) in DMF (10 mL) was stirred at RT for 14 h. $H_2O$ (40 mL) was added to the reaction, extracted with EtOAc (40 mL×3). The combined organic layers were washed with brine, dried over $Na_2SO_4$, concentrated in vacuo to give the crude, which was purified with Prep-TLC (DCM/MeOH=10/1) to give the product as a yellow solid. (70 mg, 58%). ESI-MS [M+H]$^+$: 617.2.

Synthesis 1-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)-1H-pyrazole-3-carboxylic acid (I-202)

To a solution of ethyl 1-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)-1H-pyrazole-3-carboxylate (70 mg, 0.11 mmol) in $THF/H_2O$ (7 mL/7 mL) was added $LiOH.H_2O$ (13 mg, 0.33 mmol). The resulting mixture was stirred at RT for 12 h. The reaction was acidified to pH 4 by HCl (1 M) then concentrated in vacuo to give a crude residue, which was purified with Prep-HPLC to give the 1-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)-1H-pyrazole-3-carboxylic acid as a white solid. (10 mg, 15%). ESI-MS [M+H]$^+$: 589.2. Purity: 99.69 (214 nm), 99.66 (254 nm). $^1$H NMR (400 MHz, DMSO-$d_6$) 8.73 (t, J=5.3 Hz, 1H), 8.58 (s, 1H), 8.45 (d, J=2.1 Hz, 1H), 8.32 (s, 1H), 8.20 (d, J=7.4 Hz, 1H), 7.97 (s, 1H), 7.86 (s, 1H), 6.76 (t, J=7.0 Hz, 1H), 6.73 (s, 1H), 6.66 (s, 1H), 5.77 (s, 2H), 5.62 (s, 2H), 4.71 (d, J=5.4 Hz, 2H), 1.93-1.85 (m, 1H), 0.92-0.85 (m, 2H), 0.59-0.55 (m, 2H).

Example 203

Scheme 202

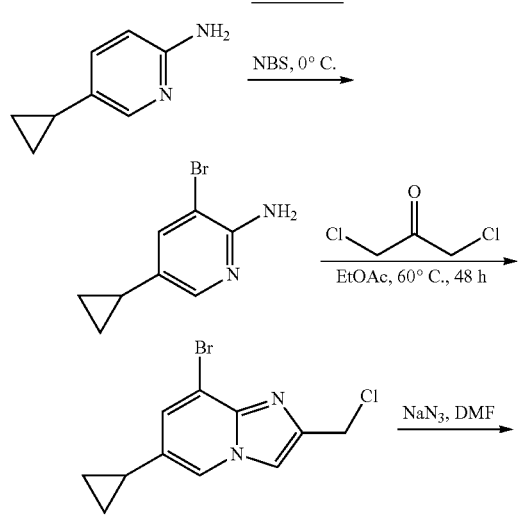

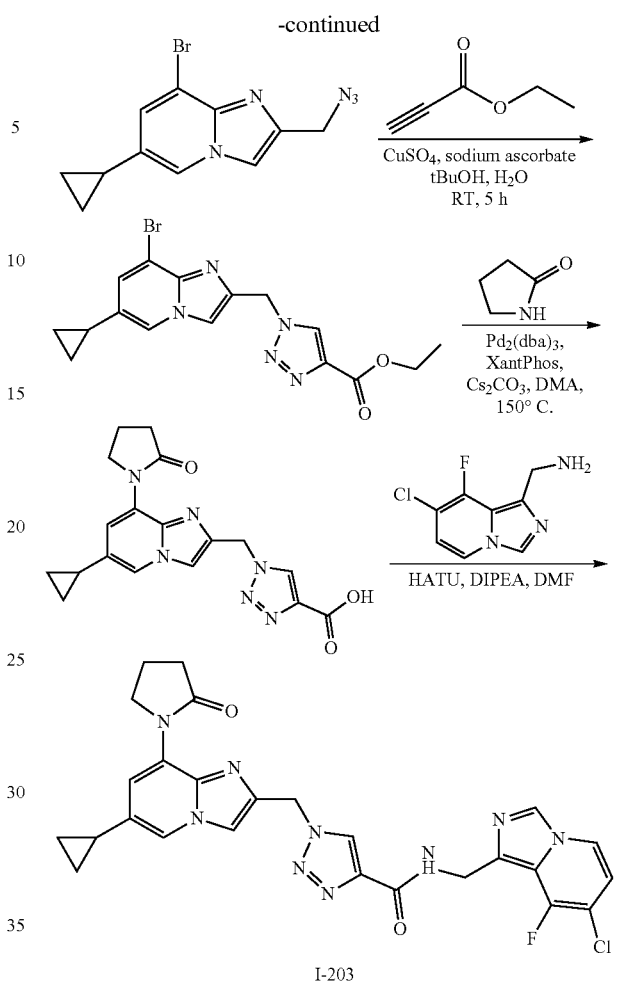

I-203

Synthesis of 3-bromo-5-cyclopropylpyridin-2-amine

To a solution of 5-cyclopropylpyridin-2-amine (8.08 g, 60 mmol) in MeCN (200 mL) was added NBS (11.72 g, 66 mmol) in portions at 0° C. during 30 min. The mixture was stirred at 0° C. for additional 30 min and then concentrated to give the crude, which was purified by silica gel chromatography (PE/EA=5/1 to 4/1) to afford 3-bromo-5-cyclopropylpyridin-2-amine as a white solid (8.23 g, yield: 64%). ESI-MS [M+H]$^+$: 212.8, Synthesis of 8-bromo-2-(chloromethyl)-6-cyclopropylimidazo[1,2-a]pyridine A solution of 3-bromo-5-cyclopropylpyridin-2-amine (8.23 g, 38.6 mmol) and 1,3-dichloropropan-2-one (7.46 g, 57.9 mmol) in EtOAc (80 mL) was stirred at 70° C. for 48° C. The reaction mixture was diluted with EtOAc (300 mL) and washed with saturate aqueous $NaHCO_3$ (100 mL). The organic layer was washed brine, dried over $Na_2SO_4$, concentrated in vacuo to give the crude, which was purified with silica gel (EtOAc/PE=1/2) to give (8 g, yield: 72.3%) as a yellow solid. ESI-MS [M+H]$^+$: 284.8

Synthesis of 2-(azidomethyl)-8-bromo-6-cyclopropylimidazo[1,2-a]pyridine

A solution of 8-bromo-2-(chloromethyl)-6-cyclopropylimidazo[1,2-a]pyridine (2.85 g, 10 mmol) in DMF (30 mL)

was added NaN₃ (1.3 g, 20 mmol) and the mixture was stirred at RT for 15 h. H₂O (100 mL) was added to the reaction, extracted with EtOAc (100 mL×3). The combined organic layers were washed with brine, dried over Na₂SO₄, filtered, and concentrated in vacuo to give 2-(azidomethyl)-8-bromo-6-cyclopropylimidazo[1,2-a]pyridine as a yellow powder which was used directly for next step without further purification (1.97 g, 67%). ESI-MS [M+H]⁺: 291.9.

Synthesis of Ethyl 1-((8-bromo-6-cyclopropylimidazo[1,2-a]pyridin-2-yl)methyl)-1H-1,2,3-triazole-4-carboxylate To a mixture of 2-(azidomethyl)-8-bromo-6-cyclopropylimidazo[1,2-a]pyridine (1.97 g, 6.7 mmol), ethyl propiolate (1 g, 10 mmol) in tBuOH/H₂O (10 mL/10 mL) was added CuSO₄ (320 mg, 2 mmol) and sodium ascorbate (397 mg, 2 mmol). The reaction mixture was stirred at RT for 5 h. The reaction was concentrated to remove tBuOH to give a yellow solid. The precipitate was collected. The filter cake was washed by H₂O (20 mL×3), followed by MeOH (20 mL), and then dried to give ethyl 1-((8-bromo-6-cyclopropylimidazo[1,2-a]pyridin-2-yl)methyl)-1H-1,2,3-triazole-4-carboxylate as a gray solid (1.8 g, 69%). ESI-MS [M+H]⁺: 389.8.

Synthesis of 1-((6-cyclopropyl-8-(2-oxopyrrolidin-1-yl)imidazo[1,2-a]pyridin-2-yl)methyl)-1H-1,2,3-triazole-4-carboxylic Acid A mixture of ethyl 1-((8-bromo-6-cyclopropylimidazo[1,2-a]pyridin-2-yl)methyl)-1H-1,2,3-triazole-4-carboxylate (78 mg, 0.2 mmol), pyrrolidin-2-one (25.4 mg, 0.3 mmol), Pd₂(dba)₃ (18 mg, 0.02 mmol), XantPhos (25 mg, 0.04 mmol) and Cs₂CO₃ (130 mg, 0.4 mmol) in DMA (2 mL) in a sealed tube was bubbled with argon for 10 min at RT and then the mixture was heated to 150° C. for 14 h. The mixture was cooled to RT and then filtered and washed with DCM (30 mL). Water (30 mL) was added to the filtrate, the aqueous phase was separated and extracted with DCM for 2 times and concentrated under reduced pressure to afford crude of 1-((6-cyclopropyl-8-(2-oxopyrrolidin-1-yl)imidazo[1,2-a]pyridin-2-yl)methyl)-1H-1,2,3-triazole-4-carboxylic acid (114 mg, crude) which was used directly for the next step. ESI-MS [M+H]⁺: 366.9.

Synthesis of N-((7-chloro-8-fluoroimidazo[1,5-a]pyridin-1-yl)methyl)-1-((6-cyclopropyl-8-(2-oxopyrrolidin-1-yl)imidazo[1,2-a]pyridin-2-yl)methyl)-1H-1,2,3-triazole-4-carboxamide (I-203)

To a solution of 1-((6-cyclopropyl-8-(2-oxopyrrolidin-1-yl)imidazo[1,2-a]pyridin-2-yl)methyl)-1H-1,2,3-triazole-4-carboxylic acid (114 mg, crude from previous step) in anhydrous DMF (5 mL) was added (7-chloro-8-fluoroimidazo[1,5-a]pyridin-1-yl)methanamine (20 mg, 0.1 mmol), DIPEA (26 mg, 0.2 mmol), HATU (58 mg, 0.15 mmol) in sequence. The mixture was stirred at RT for 2.5 h. The reaction was partitioned between DCM (50 mL) and H₂O (50 mL). The aqueous phase was extracted with DCM (50 mL×2). The combined organic layers were washed with brine, dried over Na₂SO₄, concentrated by evaporation to give the crude, which was purified by prep-HPLC to give N-((7-chloro-8-fluoroimidazo[1,5-a]pyridin-1-yl)methyl)-1-((6-cyclopropyl-8-(2-oxopyrrolidin-1-yl)imidazo[1,2-a]pyridin-2-yl)methyl)-1H-1,2,3-triazole-4-carboxamide (5.1 mg, 9% over 2 steps). ESI-MS [M+H]⁺: 547.8. Purity: 99.91 (214 nm) 99.63 (254 nm). ¹H NMR (400 MHz, CDCl₃) δ 8.24 (s, 1H), 8.10 (s, 1H), 7.78 (s, 1H), 7.66 (m, 2H), 7.51 (s, 1H), 7.29 (s, 1H), 6.52 (t, J=6.7 Hz, 1H), 5.70 (s, 2H), 4.95 (d, J=5.1 Hz, 2H), 4.23 (t, J=7.0 Hz, 2H), 2.63 (t, J=8.1 Hz, 2H), 2.26 (dt, J=15.1, 7.6 Hz, 2H), 1.94-1.85 (m, 1H), 1.02-0.93 (m, 2H), 0.70 (m, 2H).

Example 204

Scheme 203

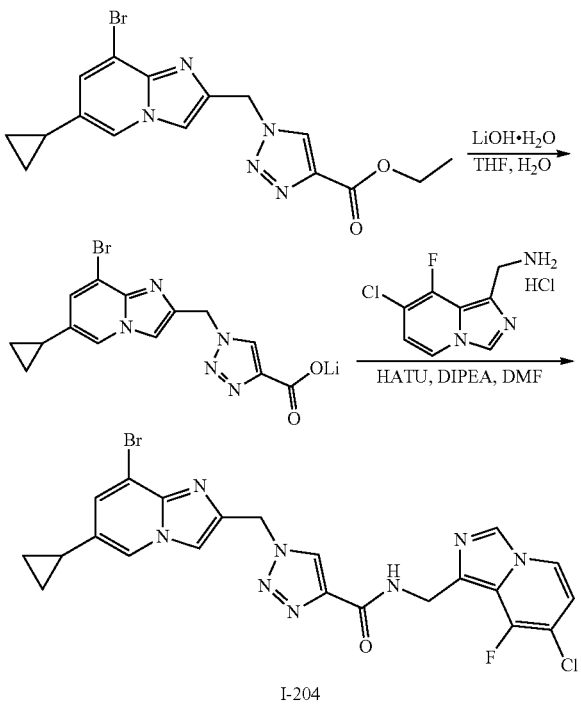

Synthesis of lithium 1-((8-bromo-6-cyclopropylimidazo[1,2-a]pyridin-2-yl)methyl)-1H-1,2,3-triazole-4-carboxylate To a solution of ethyl 1-((8-bromo-6-cyclopropylimidazo[1,2-a]pyridin-2-yl)methyl)-1H-1,2,3-triazole-4-carboxylate (39.8 mg, 0.1 mmol) in THF (3 mL) and H₂O (3 mL) was added LiOH.H₂O (42 mg, 1 mmol) and the mixture was stirred at RT for 16 h. The mixture was lyophilized to afford lithium 1-((8-bromo-6-cyclopropylimidazo[1,2-a]pyridin-2-yl)methyl)-1H-1,2,3-triazole-4-carboxylate as as a white solid which was used directly for the next step without further purification (82 mg crude). ESI-MS [M+H]⁺: 361.8

Synthesis of 1-((8-bromo-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide (I-204)

The crude of lithium 1-((8-bromo-6-cyclopropylimidazo[1,2-a]pyridin-2-yl)methyl)-1H-1,2,3-triazole-4-carboxylate (82 mg, crude from previous step) in anhydrous DMF (2 mL) was added (7-chloro-8-fluoroimidazo[1,5-a]pyridin-1-yl)methanamine hydrochloride (22 mg, 0.1 mmol), DIPEA (28.7 mg, 0.2 mmol) and HATU (58.6 mg, 0.15 mmol) in sequence. The mixture was stirred at RT for 2 h. The reaction was poured into H₂O (20 mL) and yellow solid was precipitated. The mixture was filtered and washed with MeOH (20 mL) to afford 1-((8-bromo-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide as pale yellow solid (18.8 mg, 35% over 2 steps). ESI-MS [M+H]⁺: 542.7. Purity: 97.09 (214 nm) 95.14 (254 nm). ¹H NMR (400 MHz, DMSO-d₆) δ 8.73 (brs, 1H), 8.57 (s, 1H), 8.43 (m, 2H), 8.21 (d, J=7.4 Hz, 1H), 7.94 (s, 1H), 7.40 (s, 1H), 6.77 (t, J=6.9 Hz, 1H), 5.77 (s, 2H), 4.70 (s, 2H), 1.94 (m, 1H), 0.92 (m, 2H), 0.71 (m, 2H).

Example 205

Scheme 204

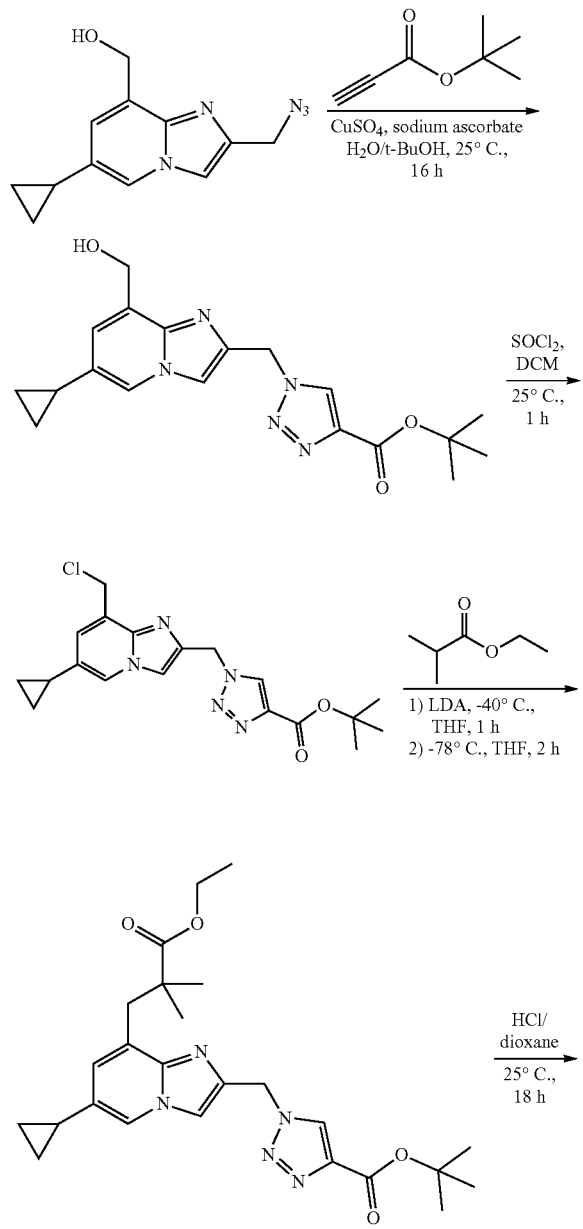

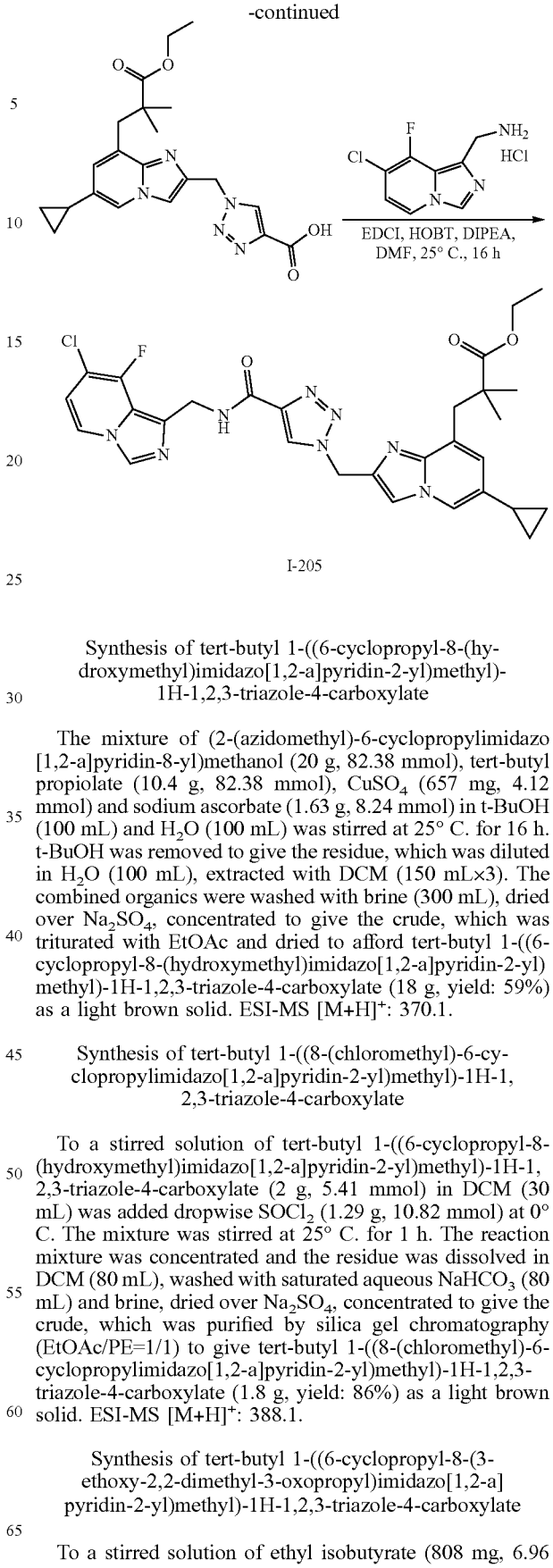

I-205

Synthesis of tert-butyl 1-((6-cyclopropyl-8-(hydroxymethyl)imidazo[1,2-a]pyridin-2-yl)methyl)-1H-1,2,3-triazole-4-carboxylate The mixture of (2-(azidomethyl)-6-cyclopropylimidazo[1,2-a]pyridin-8-yl)methanol (20 g, 82.38 mmol), tert-butyl propiolate (10.4 g, 82.38 mmol), CuSO₄ (657 mg, 4.12 mmol) and sodium ascorbate (1.63 g, 8.24 mmol) in t-BuOH (100 mL) and H₂O (100 mL) was stirred at 25° C. for 16 h. t-BuOH was removed to give the residue, which was diluted in H₂O (100 mL), extracted with DCM (150 mL×3). The combined organics were washed with brine (300 mL), dried over Na₂SO₄, concentrated to give the crude, which was triturated with EtOAc and dried to afford tert-butyl 1-((6-cyclopropyl-8-(hydroxymethyl)imidazo[1,2-a]pyridin-2-yl)methyl)-1H-1,2,3-triazole-4-carboxylate (18 g, yield: 59%) as a light brown solid. ESI-MS [M+H]⁺: 370.1.

Synthesis of tert-butyl 1-((8-(chloromethyl)-6-cyclopropylimidazo[1,2-a]pyridin-2-yl)methyl)-1H-1,2,3-triazole-4-carboxylate To a stirred solution of tert-butyl 1-((6-cyclopropyl-8-(hydroxymethyl)imidazo[1,2-a]pyridin-2-yl)methyl)-1H-1,2,3-triazole-4-carboxylate (2 g, 5.41 mmol) in DCM (30 mL) was added dropwise SOCl₂ (1.29 g, 10.82 mmol) at 0° C. The mixture was stirred at 25° C. for 1 h. The reaction mixture was concentrated and the residue was dissolved in DCM (80 mL), washed with saturated aqueous NaHCO₃ (80 mL) and brine, dried over Na₂SO₄, concentrated to give the crude, which was purified by silica gel chromatography (EtOAc/PE=1/1) to give tert-butyl 1-((8-(chloromethyl)-6-cyclopropylimidazo[1,2-a]pyridin-2-yl)methyl)-1H-1,2,3-triazole-4-carboxylate (1.8 g, yield: 86%) as a light brown solid. ESI-MS [M+H]⁺: 388.1.

Synthesis of tert-butyl 1-((6-cyclopropyl-8-(3-ethoxy-2,2-dimethyl-3-oxopropyl)imidazo[1,2-a]pyridin-2-yl)methyl)-1H-1,2,3-triazole-4-carboxylate To a stirred solution of ethyl isobutyrate (808 mg, 6.96 mmol) in THF (20 mL) was added LDA (3.7 mL, 2 M, 7.4 mmol) dropwise at −40° C. under N₂. After 1 h, the solution of tert-butyl 1-((8-(chloromethyl)-6-cyclopropylimidazo[1,2-a]pyridin-2-yl)methyl)-1H-1,2,3-triazole-4-carboxylate (1.8 g, 4.64 mmol) in THF (15 mL) was added to the reaction above at −78° C. over 30 min. The resulting mixture was stirred at −78° C. for another 1.5 h. The reaction mixture was quenched with NH₄Cl aqueous (100 mL), extracted with EtOAc (100 mL×3). The combined organics were washed with brine (140 mL), dried over Na₂SO₄, concentrated to give the crude, which was purified by silica gel chromatography (EtOAc/PE=1/2) to give tert-butyl 1-((6-cyclopropyl-8-(3-ethoxy-2,2-dimethyl-3-oxopropyl)imidazo[1,2-a]pyridin-2-yl)methyl)-1H-1,2,3-triazole-4-carboxylate (1.24 g, yield: 57%) as a colorless syrup. ESI-MS [M+H]⁺: 468.2.

Synthesis of 1-((6-cyclopropyl-8-(3-ethoxy-2,2-dimethyl-3-oxopropyl)imidazo[1,2-a]pyridin-2-yl)methyl)-1H-1,2,3-triazole-4-carboxylic Acid A mixture of tert-butyl 1-((6-cyclopropyl-8-(3-ethoxy-2,2-dimethyl-3-oxopropyl)imidazo[1,2-a]pyridin-2-yl)methyl)-1H-1,2,3-triazole-4-carboxylate (1.24 g, 2.65 mmol) and HCl in dioxane (10 mL, 4N) was stirred at 25° C. for 18 h. The reaction mixture was concentrated and dried in vacuo to afford give 1-((6-cyclopropyl-8-(3-ethoxy-2,2-dimethyl-3-oxopropyl)imidazo[1,2-a]pyridin-2-yl)methyl)-1H-1,2,3-triazole-4-carboxylic acid (1.3 g, yield: 100%) as a colorless syrup. ESI-MS [M+H]⁺: 412.2.

Synthesis of Ethyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2,2-dimethylpropanoate (I-205)

A mixture of 1-((6-cyclopropyl-8-(3-ethoxy-2,2-dimethyl-3-oxopropyl)imidazo[1,2-a]pyridin-2-yl)methyl)-1H-1,2,3-triazole-4-carboxylic acid (61.7 mg, 0.15 mmol), (7-chloro-8-fluoroimidazo[1,5-a]pyridin-1-yl)methanamine hydrochloride (35.4 mg, 0.15 mmol), EDCI (57.5 mg, 0.3 mmol), HOBT (40.5 mg, 0.3 mmol) and DIPEA (194 mg, 1.5 mmol) in DMF (6 mL) was stirred at 25° C. for 16 h. The reaction mixture was poured into H₂O (30 mL) and extracted with EtOAc/THF (40 mL×3, 5/1). The combined organics were washed with brine (70 mL), dried over Na₂SO₄, concentrated to give the crude, which was purified by silica gel chromatography (DCM/MeOH=20/1) to give ethyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2,2-dimethylpropanoate (50 mg, yield: 56%) as a pale white solid. ESI-MS [M+H]⁺: 593.2. Purity: 99.13 (214 nm), 100 (254 nm). ¹H NMR (400 MHz, DMSO-d₆) δ 8.69 (t, J=5.4 Hz, 1H), 8.50 (s, 1H), 8.44 (d, J=2.3 Hz, 1H), 8.26-8.18 (m, 2H), 7.78 (s, 1H), 6.78-6.74 (m, 1H), 6.67 (d, J=1.3 Hz, 1H), 5.71 (s, 2H), 4.69 (d, J=5.4 Hz, 2H), 3.94 (q, J=7.1 Hz, 2H), 3.09 (s, 2H), 1.93-1.84 (m, 1H), 1.16-1.03 (m, 9H), 0.95-0.88 (m, 2H), 0.64-0.57 (m, 2H).

Example 206

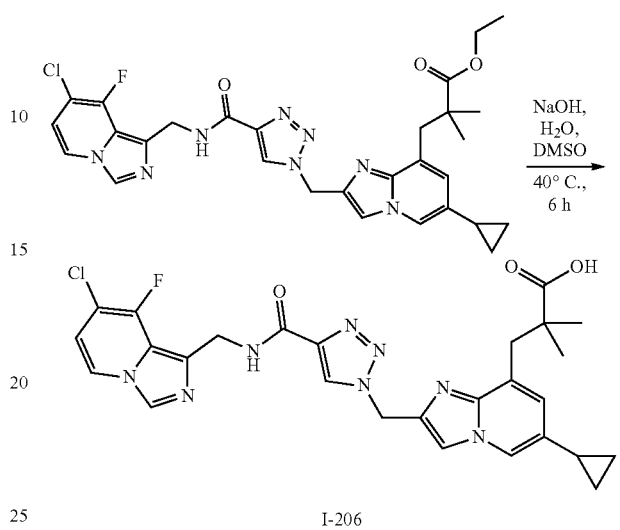

Scheme 205

I-206

Synthesis of 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2,2-dimethylpropanoic acid (I-206)

To a solution of ethyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2,2-dimethylpropanoate (78 mg, 0.13 mmol) and NaOH (52 mg, 1.3 mmol) in DMSO (2 mL) and H₂O (2 mL) was stirred at 40° C. for 6 h. The reaction mixture was poured into H₂O (20 mL). The mixture was acidified to pH 4-5 by HCl (1N) and extracted with EtOAc/THF (30 mL×3, 5/1). The combined organics were washed with brine (40 mL), dried over Na₂SO₄, concentrated to give the crude, which was purified by silica gel chromatography (DCM/MeOH=20/1) to give 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2,2-dimethylpropanoic acid (30 mg, yield: 40%) as a pale white solid. ESI-MS [M+H]⁺: 565.1. Purity: 100 (214 nm), 100 (254 nm). ¹H NMR (400 MHz, DMSO-d₆) δ 12.44 (s, 1H), 8.69 (t, J=5.5 Hz, 1H), 8.51 (s, 1H), 8.44 (d, J=2.4 Hz, 1H), 8.24-8.17 (m, 2H), 7.76 (s, 1H), 6.79-6.71 (m, 2H), 5.72 (s, 2H), 4.69 (d, J=5.5 Hz, 2H), 3.09 (s, 2H), 1.90-1.83 (m, 1H), 1.08 (s, 6H), 0.93-0.88 (m, 2H), 0.65-0.59 (m, 2H).

Example 207

Scheme 206

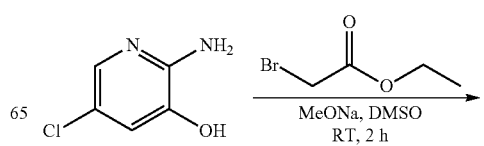

-continued

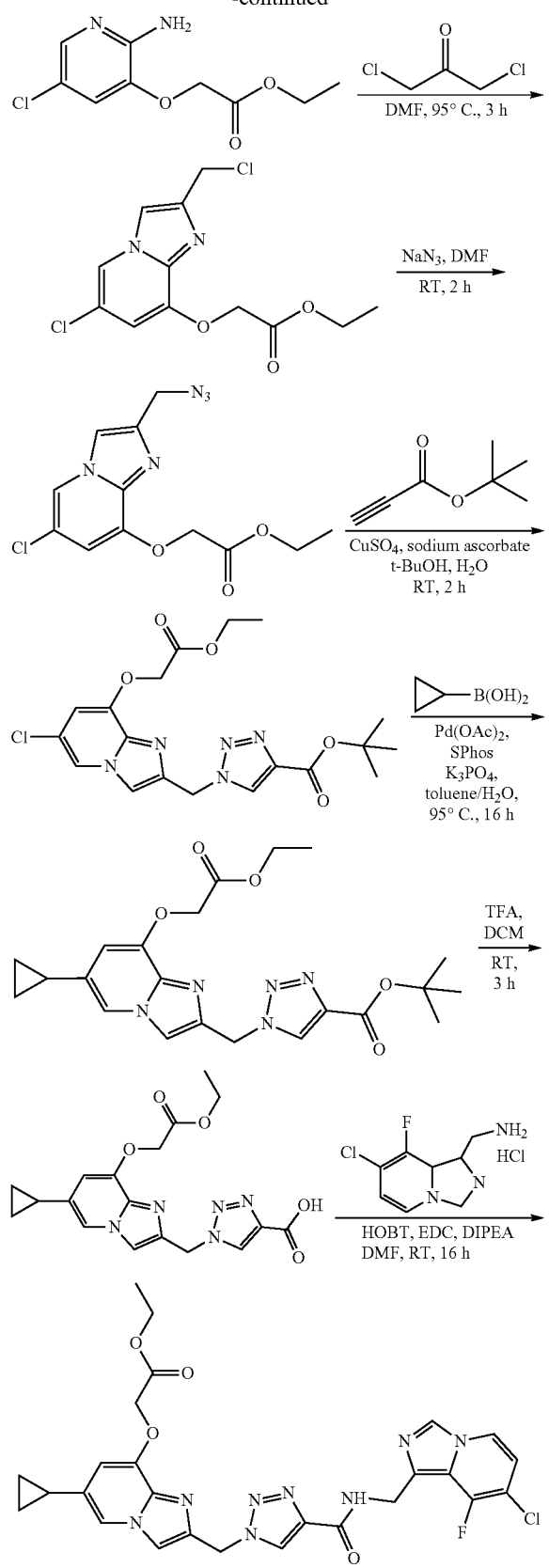

Synthesis of Ethyl 2-((2-amino-5-chloropyridin-3-yl)oxy)acetate

To a mixture of 2-amino-5-chloropyridin-3-ol (2.9 g, 20 mmol) in DMSO (50 mL) was added NaOMe (1.08 g, 20 mmol). The reaction mixture was stirred at RT for 30 min. Then ethyl 2-bromoacetate (3.34 g, 20 mmol) was added thereto. The mixture was stirred at RT for another 2 h. Water (300 mL) was added to the reaction, extracted with EtOAc (200 mL×3). The combined organic phase was washed with brine, dried over Na$_2$SO$_4$, filtrated and concentrated to give ethyl 2-((2-amino-5-chloropyridin-3-yl)oxy)acetate (4.0 g, yield: 87%) as a yellow oil, which was used into next step without further purification. ESI-MS [M+H]$^+$: 231.1.

Synthesis of Ethyl 2-((6-chloro-2-(chloromethyl) imidazo[1,2-a]pyridin-8-yl)oxy)acetate A mixture of ethyl 2-((2-amino-5-chloropyridin-3-yl)oxy) acetate (4.0 g, 17.3 mmol) and 1,3-dichloropropan-2-one (6.7 g, 52 mmol) in DMF (50 mL) was stirred at 95° C. for 3 h. After cooled, the reaction was quenched with saturated aqueous NaHCO$_3$ (100 mL) and extracted with EtOAc (200 mL×3). The combined organic phase was washed with brine, dried over Na$_2$SO$_4$, filtrated and concentrated to give the residue, which was purified by silica gel chromatography (PE/EA=5/1 to 2/1) to give ethyl 2-((6-chloro-2-(chloromethyl)imidazo[1,2-a]pyridin-8-yl)oxy)acetate (900 mg, yield: 17.3%) as a yellow solid. ESI-MS [M+H]$^+$: 303.1.

Synthesis of Ethyl 2-((2-(azidomethyl)-6-chloroimidazo[1,2-a]pyridin-8-yl)oxy)acetate To a mixture of ethyl 2-((6-chloro-2-(chloromethyl)imidazo[1,2-a]pyridin-8-yl)oxy)acetate (900 mg, 3 mmol) in DMF (5 mL) was added NaN$_3$ (234 mg, 3.6 mmol). The mixture was stirred at RT for 2 h. The reaction was quenched with H$_2$O (50 mL), extracted with EtOAc (50 mL×3). The combined organic phase was washed with brine, dried over Na$_2$SO$_4$, filtrated and concentrated. The residue was purified by silica gel chromatography (PE/EA=5/1 to 2/1) to give ethyl 2-((2-(azidomethyl)-6-chloroimidazo[1,2-a]pyridin-8-yl)oxy)acetate (650 mg, yield: 70%) as a yellow solid. ESI-MS [M+H]$^+$: 310.1.

Synthesis of tert-butyl 1-((6-chloro-8-(2-ethoxy-2-oxoethoxy)imidazo[1,2-a]pyridin-2-yl)methyl)-1H-1,2,3-triazole-4-carboxylate To a mixture of ethyl 2-((2-(azidomethyl)-6-chloroimidazo[1,2-a]pyridin-8-yl)oxy)acetate (650 mg, 2.1 mmol), CuSO$_4$ (67 mg, 0.42 mmol) and sodium ascorbate (83 mg, 0.42 mmol) in t-BuOH/H$_2$O (10 mL/10 mL) was added tert-butyl propiolate (319 mg, 2.5 mmol). The mixture was stirred at RT for 2 h. Water (50 mL) was added to the reaction and extracted with EtOAc (50 mL×3). The combined organic phase was washed with brine, dried over Na$_2$SO$_4$, filtrated and concentrated to give the crude, which was triturated with EA/PE (20 mL/20 mL) to give tert-butyl 1-((6-chloro-8-(2-ethoxy-2-oxoethoxy)imidazo[1,2-a]pyridin-2-yl)methyl)-1H-1,2,3-triazole-4-carboxylate (850 mg, yield: 93%) as a blue solid. ESI-MS [M+H]$^+$: 436.2.

Synthesis of tert-butyl 1-((6-cyclopropyl-8-(2-ethoxy-2-oxoethoxy)imidazo[1,2-a]pyridin-2-yl)methyl)-1H-1,2,3-triazole-4-carboxylate To a mixture of tert-butyl 1-((6-chloro-8-(2-ethoxy-2-oxoethoxy)imidazo[1,2-a]pyridin-2-yl)methyl)-1H-1,2,3- triazole-4-carboxylate (436 mg, 1 mmol), cyclopropylboronic acid (180 mg, 2 mmol) and K$_3$PO$_4$ (850 mg, 4 mmol) in toluene/H$_2$O (10 mL/1 mL) was added Pd(OAc)$_2$ (44 mg, 0.2 mmol) and SPhos (82 mg, 0.2 mmol). The mixture was stirred at 95° C. for 16 h under N$_2$ atmosphere. Water (50 mL) was added to the reaction and extracted with EtOAc (50 mL×3). The combined organic layers were washed with brine, dried over Na$_2$SO$_4$, filtrated and concentrated to give the crude, which was purified by silica gel chromatography (DCM/MeOH=50/1 to 20/1) to give tert-butyl 1-((6-cyclopropyl-8-(2-ethoxy-2-oxoethoxy)imidazo[1,2-a]pyridin-2-yl)methyl)-1H-1,2,3-triazole-4-carboxylate (200 mg, yield: 45%) as a yellow solid. ESI-MS [M+H]$^+$: 442.2.

Synthesis of 1-((6-cyclopropyl-8-(2-ethoxy-2-oxoethoxy)imidazo[1,2-a]pyridin-2-yl)methyl)-1H-1,2,3-triazole-4-carboxylic Acid To a suspension of tert-butyl 1-((6-cyclopropyl-8-(2-ethoxy-2-oxoethoxy)imidazo[1,2-a]pyridin-2-yl)methyl)-1H-1,2,3-triazole-4-carboxylate (200 mg, 0.46 mmol) in DCM (8 mL) was added TFA (1 mL). The mixture was stirred at RT for 3 h. The reaction was concentrated to give 1-((6-cyclopropyl-8-(2-ethoxy-2-oxoethoxy)imidazo[1,2-a]pyridin-2-yl)methyl)-1H-1,2,3-triazole-4-carboxylic acid (200 mg, crude) as a yellow oil, which was used into next step without further purification. ESI-MS [M+H]$^+$: 386.1.

Synthesis of Ethyl 2-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)oxy)acetate (I-207)

To a mixture of 1-((6-cyclopropyl-8-(2-ethoxy-2-oxoethoxy)imidazo[1,2-a]pyridin-2-yl)methyl)-1H-1,2,3-triazole-4-carboxylic acid (100 mg, crude form previous step), (7-chloro-8-fluoroimidazo[1,5-a]pyridin-1-yl)methanamine hydrochloride (118 mg, 0.5 mmol) and DIPEA (336 mg, 2.6 mmol) in DMF (10 mL) was added HOBT (140 mg, 1.04 mmol) and EDC (200 mg, 1.04 mmol). The mixture was stirred at RT for 16 h. Water (50 mL) was added to the reaction and extracted with EtOAc (50 mL×3). The combined organic phase was washed with brine, dried over Na$_2$SO$_4$, filtrated and concentrated. The residue was purified by Prep-TLC (DCM/MeOH=10/1) to give ethyl 2-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)oxy)acetate (50 mg, yield: 20%) as a white solid. ESI-MS [M+H]$^+$: 567.1. Purity: 95.4 (214 nm), 96.5 (254 nm). $^1$H NMR (400 MHz, DMSO-d$_6$) δ 8.70 (t, J=5.4 Hz, 1H), 8.54 (s, 1H), 8.44 (d, J=2.4 Hz, 1H), 8.20 (d, J=7.4 Hz, 1H), 8.01 (d, J=0.7 Hz, 1H), 7.83 (s, 1H), 6.76 (dd, J=7.3, 6.6 Hz, 1H), 6.35 (d, J=1.2 Hz, 1H), 5.71 (s, 2H), 5.00 (s, 2H), 4.70 (d, J=5.5 Hz, 2H), 4.16 (q, J=7.1 Hz, 2H), 1.91-1.84 (m, 1H), 1.19 (t, J=7.1 Hz, 3H), 0.95-0.84 (m, 2H), 0.72-0.60 (m, 2H).

Example 208

Scheme 207

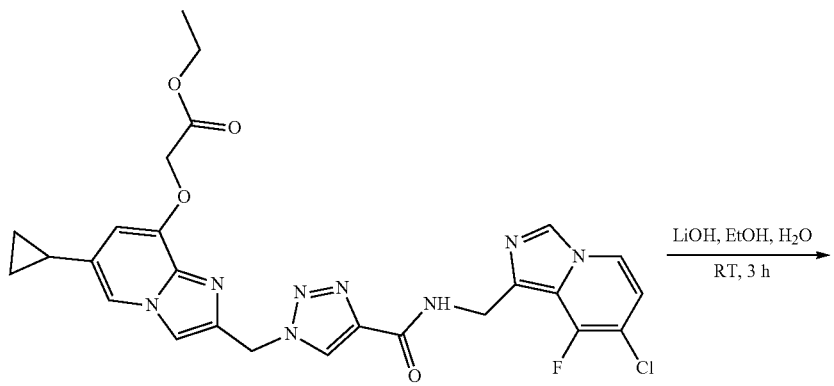

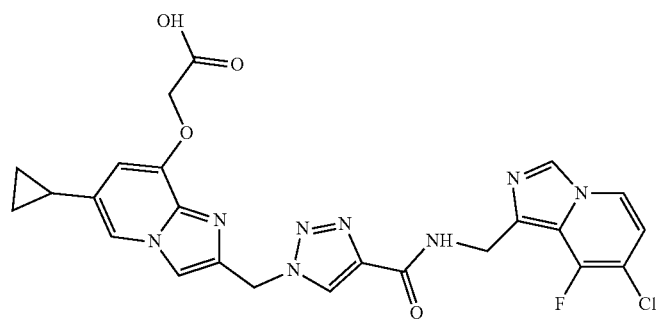

I-208

Synthesis of 2-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)oxy)acetic acid (I-208)

To a mixture of ethyl 2-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)oxy)acetate (60 mg, 0.11 mmol) in EtOH/H$_2$O (2 mL/0.2 mL) was added LiOH.H$_2$O (13 mg, 0.3 mmol). The mixture was stirred at RT for 3 h. The pH of the reaction was adjusted to 5 by HCl (1N), and white solid was precipitated. The mixture was filtrated and dried to give 2-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)oxy)acetic acid (35 mg, yield: 59%) as an off-white solid. ESI-MS [M+H]$^+$: 539.1. Purity: 98.0 (214 nm), 100.0 (254 nm). $^1$H NMR (400 MHz, DMSO-d$_6$) δ 13.27 (s, 1H), 8.76 (t, J=5.4 Hz, 1H), 8.63 (s, 1H), 8.47 (d, J=2.4 Hz, 1H), 8.26-8.19 (m, 2H), 8.14-8.12 (m, 1H), 6.91 (s, 1H), 6.77 (dd, J=7.3, 6.6 Hz, 1H), 5.87 (s, 2H), 5.03 (s, 2H), 4.71 (d, J=5.5 Hz, 2H), 2.02-1.96 (m, 1H), 1.10-0.91 (m, 2H), 0.84-0.67 (m, 2H).

Example 209

Scheme 208

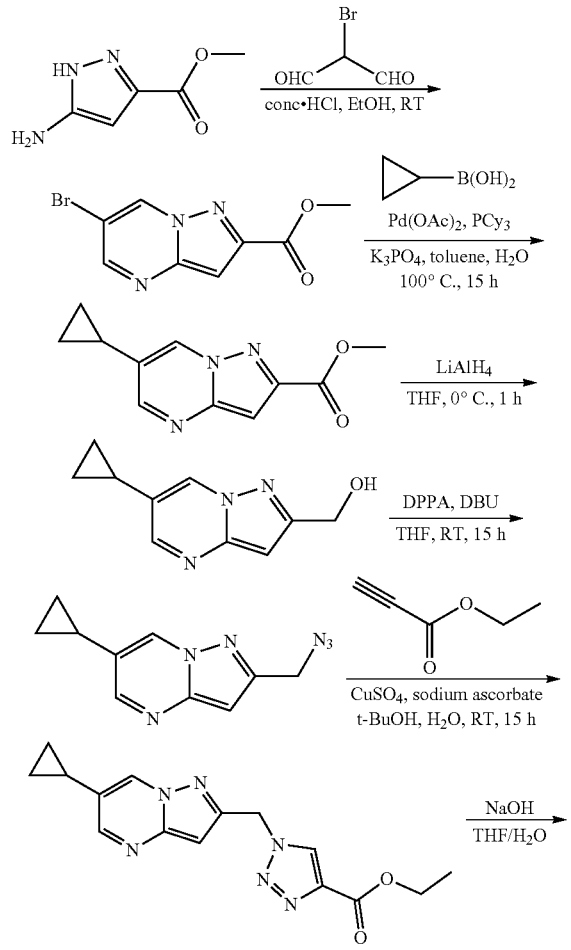

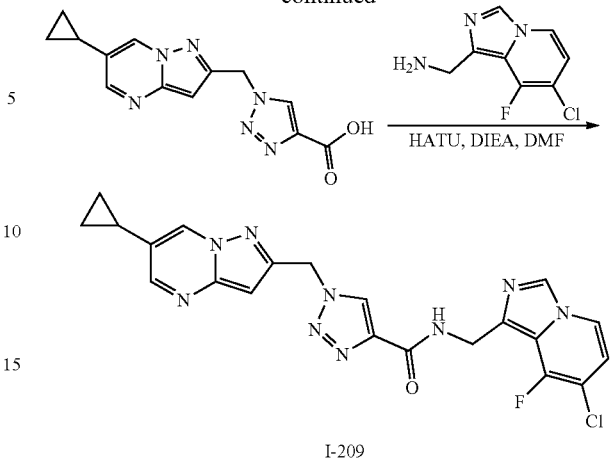

I-209

Synthesis of Methyl 6-bromopyrazolo[1,5-a]pyrimidine-2-carboxylate

To a solution of methyl 5-amino-1H-pyrazole-3-carboxylate (1 g, 7.09 mmol) and con. HCl (0.67 mL, 8.15 mmol) in EtOH (20 mL) was added 2-bromomalonaldehyde (1.1 g, 7.37 mmol). The resulting mixture was stirred at RT for 15 h. The precipitate formed and collected by filtration and washed with diethyl ether, dried in vacuo to get the product methyl 6-bromopyrazolo[1,5-a]pyrimidine-2-carboxylate (1.5 g, 82.6%) as a dark yellow solid which was used in next step directly. ESI-MS [M+H]$^+$: 255.7, 257.7. $^1$H NMR (400 MHz, DMSO-d$_6$) δ 9.71 (s, 1H), 8.76 (s, 1H), 7.27 (s, 1H), 3.91 (s, 3H).

Synthesis of Methyl 6-cyclopropylpyrazolo[1,5-a]pyrimidine-2-carboxylate

A mixture of methyl 6-bromopyrazolo[1,5-a]pyrimidine-2-carboxylate (1.9 g, 7.4 mmol), cyclopropylboronic acid (0.83 g, 9.6 mmol), Pd(OAc)$_2$ (85 mg, 0.37 mmol), PCy$_3$ (207 mg, 0.74 mmol) and K$_3$PO$_4$ (2.4 g, 11.1 mmol) in toluene (35 mL) and H$_2$O (4 mL) was stirred under reflux under nitrogen atmosphere overnight. The reaction mixture was partitioned between EtOAc (50 mL) and H$_2$O (50 mL). The organic layer were separated and the aqueous phase was extracted with EtOAc (3×100 mL). The combined organic layers were washed with brine (25 mL), dried over Na$_2$SO$_4$, filtered and concentrated to get the crude product. The crude product was purified by column chromatography (MeOH/DCM=0-1%) to get methyl 6-cyclopropylpyrazolo[1,5-a]pyrimidine-2-carboxylate (850 mg, 53%) as a yellow solid. ESI-MS [M+H]$^+$: 217.8. $^1$H NMR (400 MHz, CDCl$_3$) δ 8.44 (s, 1H), 8.42 (s, 1H), 7.20 (s, 1H), 4.01 (s, 3H), 2.02-1.93 (m, 1H), 1.15-1.07 (m, 2H), 0.82-0.74 (m, 2H).

Synthesis of (6-cyclopropylpyrazolo[1,5-a]pyrimidin-2-yl)methanol

To a solution of methyl 6-cyclopropylpyrazolo[1,5-a]pyrimidine-2-carboxylate (230 mg, 1.1 mmol) in dry THF (20 mL) at 0° C. was added LiAlH4 portion-wise (114 mg, 3 mmol). The resulting mixture was stirred at 0° C. for 1 h. The reaction was quenched sequentially with H$_2$O (0.5 mL), 15% NaOH (0.5 mL) and H$_2$O (1.5 mL). The resulting mixture was filtered and the filtrate was concentrated to get the crude product (6-cyclopropylpyrazolo[1,5-a]pyrimidin-2-yl)methanol (190 mg, 91%) as a light yellow oil which was used into next step directly without purification. ESI-MS [M+H]⁺: 189.9.

Synthesis of 2-(azidomethyl)-6-cyclopropylpyrazolo[1,5-a]pyrimidine

To a solution of (6-cyclopropylpyrazolo[1,5-a]pyrimidin-2-yl)methanol (190 mg, 1 mmol) and DPPA (330 mg, 1.2 mmol) in dry THF (20 mL) stirring at 0° C. was added DBU (182 mg, 1.2 mmol). The resulting mixture was stirred at RT overnight. The reaction mixture was concentrated to get a residue which was purified by flash column chromatography (0-5% MeOH in DCM) to get the product 2-(azidomethyl)-6-cyclopropylpyrazolo[1,5-a]pyrimidine (127 mg, 58%) as a light yellow oil. ESI-MS [M+H]⁺: 214.8.

Synthesis of Ethyl 1-((6-cyclopropylpyrazolo[1,5-a]pyrimidin-2-yl)methyl)-1H-1,2,3-triazole-4-carboxylate To a solution of 2-(azidomethyl)-6-cyclopropylpyrazolo[1,5-a]pyrimidine (145 mg, 0.68 mmol) in t-BuOH (3 mL) and H₂O (3 mL) was added sequentially of CuSO₄-5H₂O (34 mg, 0.136 mmol), sodium ascorbate (40 mg, 0.204 mmol) and ethyl propiolate (133 mg, 1.36 mmol). The resulting mixture was stirred at RT for 15 h. The reaction mixture was concentrated to get the crude product which was purified by flash column chromatography (0-3% MeOH in DCM) to get the product ethyl 1-((6-cyclopropylpyrazolo[1,5-a]pyrimidin-2-yl)methyl)-1H-1,2,3-triazole-4-carboxylate (120 mg, 56%) as a light yellow oil. ESI-MS [M+H]⁺: 313.2

Synthesis of 1-((6-cyclopropylpyrazolo[1,5-a]pyrimidin-2-yl)methyl)-1H-1,2,3-triazole-4-carboxylic Acid To a solution of ethyl 1-((6-cyclopropylpyrazolo[1,5-a]pyrimidin-2-yl)methyl)-1H-1,2,3-triazole-4-carboxylate (120 mg, 0.38 mmol) in THF (5 mL) was added a solution of NaOH (38 mg, 0.95 mmol) in H₂O (5 mL). The mixture was stirred at RT for 2 h. The volatile was removed in vacuo and the aqueous phase was acidified to pH 4-5 with 2N HCl, then concentrated in vacuo to give 1-((6-cyclopropylpyrazolo[1,5-a]pyrimidin-2-yl)methyl)-1H-1,2,3-triazole-4-carboxylic acid (160 mg, crude) as a light yellow solid which was used into next step directly. ESI-MS [M+H]⁺: 285.1

Synthesis of N-((7-chloro-8-fluoroimidazo[1,5-a]pyridin-1-yl)methyl)-1-((6-cyclopropylpyrazolo[1,5-a]pyrimidin-2-yl)methyl)-1H-1,2,3-triazole-4-carboxamide (I-209)

To a mixture of 1-((6-cyclopropylpyrazolo[1,5-a]pyrimidin-2-yl)methyl)-1H-1,2,3-triazole-4-carboxylic acid (160 mg, crude), HATU (159 mg, 0.42 mmol) and DIPEA (147 mg, 1.14 mmol) in DMF (3 mL) was added (7-chloro-8-fluoroimidazo[1,5-a]pyridin-1-yl)methanamine hydrochloride (89 mg, 0.38 mmol). The resulting mixture was stirred at RT for 15 h. The reaction mixture was concentrated to get a residue which was purified by flash column chromatography (0-8% MeOH in DCM) and then prep-TLC (DCM/MeOH=15/1) to get N-((7-chloro-8-fluoroimidazo[1,5-a]pyridin-1-yl)methyl)-1-((6-cyclopropylpyrazolo[1,5-a]pyrimidin-2-yl)methyl)-1H-1,2,3-triazole-4-carboxamide (70 mg, 39% over 2 steps) as an off-white solid. ESI-MS [M+H]⁺: 465.9. Purity: 96.42 (214 nm), 99.68 (254 nm). ¹H NMR (400 MHz, DMSO-d₆) δ 8.85 (s, 1H), 8.73 (t, J=5.4 Hz, 1H), 8.63 (s, 1H), 8.45 (s, 2H), 8.21 (d, J=7.4 Hz, 1H), 6.77 (t, J=6.9 Hz, 1H), 6.68 (s, 1H), 5.87 (s, 2H), 4.71 (d, J=5.4 Hz, 2H), 2.05-1.96 (m, 1H), 1.01-0.93 (m, 2H), 0.87-0.81 (m, 2H).

Example 210

Scheme 209

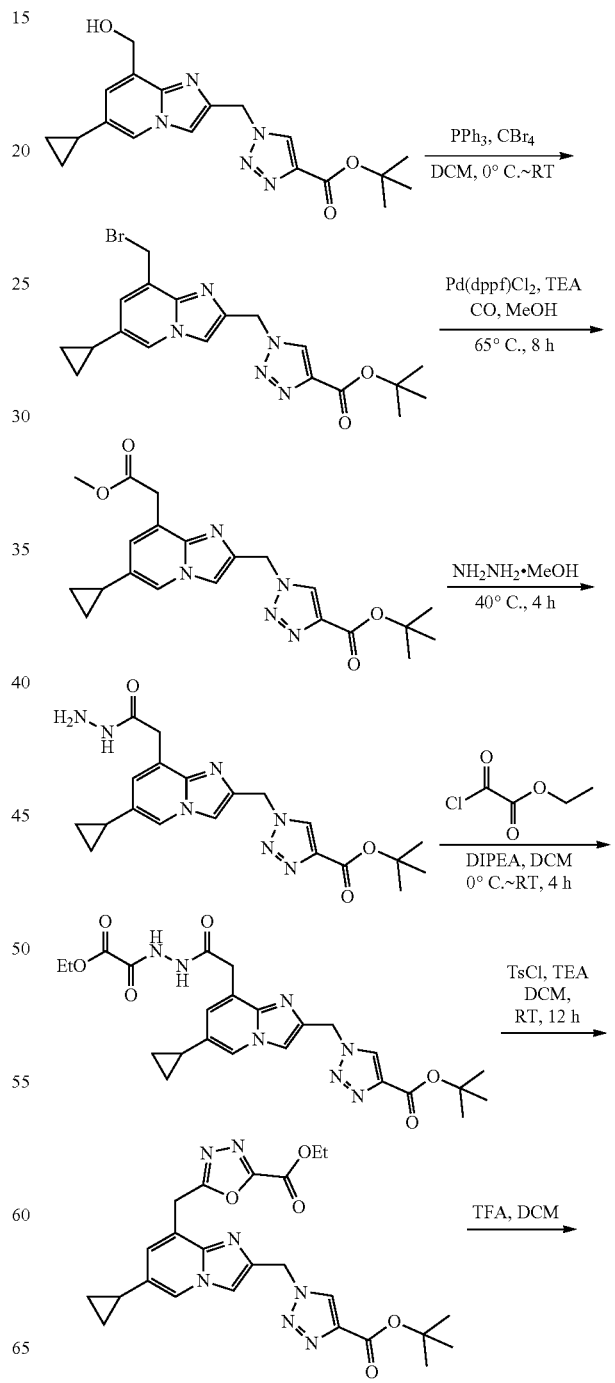

-continued

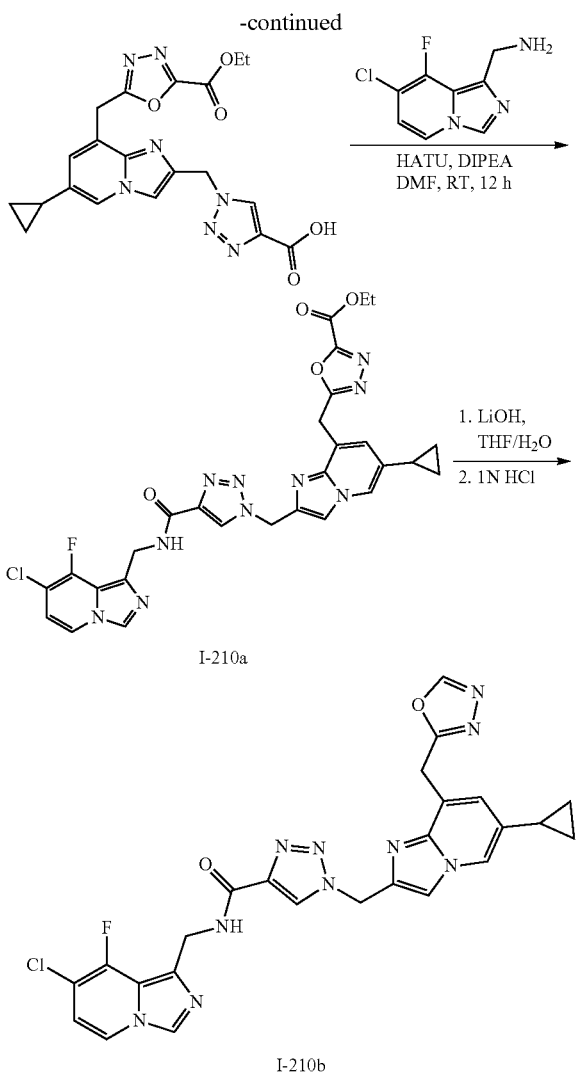

Synthesis of tert-butyl 1-((8-(bromomethyl)-6-cyclopropylimidazo[1,2-a]pyridin-2-yl)methyl)-1H-1,2,3-triazole-4-carboxylate To a solution of tert-butyl 1-((6-cyclopropyl-8-(hydroxymethyl)imidazo[1,2-a]pyridin-2-yl)methyl)-1H-1,2,3-triazole-4-carboxylate (1 g, 2.7 mmol) and PPh₃ (855 mg, 3.25 mmol) in DCM (50 mL) was added CBr₄ (1.06 g, 3.25 mmol) at 0° C. The reaction was stirred at RT for 12 h. H₂O (100 mL) was added to the reaction, extracted with DCM (100 mL×3). The combined organic layers were washed with brine, dried over Na₂SO₄, concentrated in vacuo to give crude, which was purified with silica gel (EA/PE=1/2) to give the tert-butyl 1-((8-(bromomethyl)-6-cyclopropylimidazo[1,2-a]pyridin-2-yl)methyl)-1H-1,2,3-triazole-4-carboxylate as a yellow solid. (1.0 g, 86%). ESI-MS [M+H]⁺: 432.3.

Synthesis of tert-butyl 1-((6-cyclopropyl-1-(2-methoxy-2-oxoethyl)imidazo[1,2-a]pyridin-2-yl)methyl)-1H-1,2,3-triazole-4-carboxylate A mixture of tert-butyl 1-((8-(bromomethyl)-6-cyclopropylimidazo[1,2-a]pyridin-2-yl)methyl)-1H-1,2,3-triazole-4-carboxylate (1 g, 2.32 mmol), Pd(dppf)C₂ (170 mg, 0.23 mmol) and TEA (703 mg, 6.96 mmol) in MeOH (75 mL) was stirred at 65° C. under CO atmosphere for 8 h. The reaction was concentrated in vacuo to give the crude, which was purified with silica gel (DCM/MeOH=25/1) to give the tert-butyl 1-((6-cyclopropyl-8-(2-methoxy-2-oxoethyl)imidazo[1,2-a]pyridin-2-yl)methyl)-1H-1,2,3-triazole-4-carboxylate as a yellow solid. (850 mg, 89%). ESI-MS [M+H]⁺: 412.2.

Synthesis of tert-butyl 1-((6-cyclopropyl-8-(2-methoxy-2-oxoethyl)imidazo[1,2-a]pyridin-2-yl)methyl)-1H-1,2,3-triazole-4-carboxylate A solution of tert-butyl 1-((6-cyclopropyl-8-(2-methoxy-2-oxoethyl)imidazo[1,2-a]pyridin-2-yl)methyl)-1H-1,2,3-triazole-4-carboxylate (850 mg, 2.06 mmol), NH₂NH₂—H₂O (20 mL) and MeOH (60 mL) in a sealed tube and stirred at 40° C. for 4 h. The reaction was concentrated in vacuo to give the crude, which was purified with silica gel (DCM/MeOH=15/1) to give the tert-butyl 1-((6-cyclopropyl-8-(2-hydrazinyl-2-oxoethyl)imidazo[1,2-a]pyridin-2-yl)methyl)-1H-1,2,3-triazole-4-carboxylate as a yellow solid, which was used into next step without further purification. (450 mg, 53%). ESI-MS [M+H]⁺: 412.2.

Synthesis of tert-butyl 1-((6-cyclopropyl-8-(2-(2-(2-ethoxy-2-oxoacetyl)hydrazinyl)-2-oxoethyl)imidazo[1,2-a]pyridin-2-yl)methyl)-1H-1,2,3-triazole-4-carboxylate To a solution of tert-butyl 1-((6-cyclopropyl-8-(2-hydrazinyl-2-oxoethyl)imidazo[1,2-a]pyridin-2-yl)methyl)-1H-1,2,3-triazole-4-carboxylate (450 mg, 1.1 mmol) and DIPEA (426 mg, 3.3 mmol) in DCM (40 mL) was added ethyl 2-chloro-2-oxoacetate (538 mg, 3.96 mmol) at 0° C. The reaction was allowed to warm to RT and stirred for 4 h. The reaction was quenched with H₂O (70 mL), extracted with DCM (70 mL×3). The combined organic layers were washed with brine, dried over Na₂SO₄, concentrated in vacuo to give the crude, which was purified with silica gel (DCM/MeOH=30/1) to give the tert-butyl 1-((6-cyclopropyl-8-(2-(2-(2-ethoxy-2-oxoacetyl)hydrazinyl)-2-oxoethyl)imidazo[1,2-a]pyridin-2-yl)methyl)-1H-1,2,3-triazole-4-carboxylate as a yellow solid. (380 mg, 68%). ESI-MS [M+H]⁺: 512.2.

Synthesis of Ethyl 5-((2-((4-(tert-butoxycarbonyl)-1H-1,2,3-triazol-1-yl)methyl)-6-cyclopropylimidazo[1,2-a]pyridin-8-yl)methyl)-1,3,4-oxadiazole-2-carboxylate solution of tert-butyl 1-((6-cyclopropyl-8-(2-(2-(2-ethoxy-2-oxoacetyl)hydrazinyl)-2-oxoethyl)imidazo[1,2-a]pyridin-2-yl)methyl)-1H-1,2,3-triazole-4-carboxylate (380 mg. 0.74 mmol), tosyl chloride (211 mg, 1.11 mmol) and TEA (187 mg, 1.85 mmol) in DCM (30 mL) was stirred at RT for 12 h. The reaction was concentrated in vacuo to give the crude, which was purified with Prep-TLC (DCM/MeOH=15/1) to give the ethyl 5-((2-((4-(tert-butoxycarbonyl)-1H-1,2,3-triazol-1-yl)methyl)-6-cyclopropylimidazo[1,2-a]pyridin-8-yl)methyl)-1,3,4-oxadiazole-2-carboxylate as a white solid. (300 mg, 82%). ESI-MS [M+H]⁺: 494.2

Synthesis of 1-((6-cyclopropyl-8-((5-(ethoxycarbonyl)-1,3,4-oxadiazol-2-yl)methyl)imidazo[1,2-a]pyridin-2-yl)methyl)-1H-1,2,3-triazole-4-carboxylic Acid A solution of ethyl 5-((2-((4-(tert-butoxycarbonyl)-1H-1,2,3-triazol-1-yl)methyl)-6-cyclopropylimidazo[1,2-a]pyridin-8-yl)methyl)-1,3,4-oxadiazole-2-carboxylate (300 mg, 0.61 mmol) in TFA/DCM (5 mL/15 mL) was stirred at RT for 14 h. The reaction was concentrated in vacuo to give the 1-((6-cyclopropyl-8-((5-(ethoxycarbonyl)-1,3,4-oxadiazol-2-yl)methyl)imidazo[1,2-a]pyridin-2-yl)methyl)-1H-1,2,3-triazole-4-carboxylic acid as a yellow solid, which was used into next step without further purification. (290 mg crude). ESI-MS [M+H]$^+$: 438.2

Synthesis of Ethyl 5-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)-1,3,4-oxadiazole-2-carboxylate (I-210a)

To a solution of 1-((6-cyclopropyl-8-((5-(ethoxycarbonyl)-1,3,4-oxadiazol-2-yl)methyl)imidazo[1,2-a]pyridin-2-yl)methyl)-1H-1,2,3-triazole-4-carboxylic acid (290 mg, crude from previous step) and in DMF (20 mL) was added HATU (342 mg, 0.9 mmol) and DIPEA (232 mg, 1.8 mmol). The resulting mixture was stirred at RT for 1 h. Then (7-chloro-8-fluoroimidazo[1,5-a]pyridin-1-yl)methanamine hydrochloride (173 mg, 0.73 mmol) was added thereto. The reaction mixture was stirred at RT for 12 h. H$_2$O (50 mL) was added, and the reaction was extracted with EtOAc (80 mL×3). The combined organic layers were washed with brine, dried over Na$_2$SO$_4$, concentrated in vacuo to give the crude, which was purified with Prep-TLC (DCM/MeOH=10/1) to give the ethyl 5-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)-1,3,4-oxadiazole-2-carboxylate as a white solid. (100 mg, 26% over 2 steps). ESI-MS [M+H]$^+$: 619.2. Purity: 98.86 (214 nm), 98.65 (254 nm). $^1$H NMR (400 MHz, DMSO-d$_6$) δ 8.68 (t, J=5.5 Hz, 1H), 8.49 (s, 1H), 8.44 (d, J=2.4 Hz, 1H), 8.33 (d, J=1.1 Hz, 1H), 8.21 (d, J=7.4 Hz, 1H), 7.83 (s, 1H), 7.06 (s, 1H), 6.83-6.70 (m, 1H), 5.71 (s, 2H), 4.70 (d, J=5.5 Hz, 2H), 4.58 (s, 2H), 4.38 (q, J=7.1 Hz, 2H), 1.96-1.90 (m, 1H), 1.31 (t, J=7.1 Hz, 3H), 0.95-0.90 (m, 2H), 0.69-0.65 (m, 2H).

Synthesis of 1-((8-((1,3,4-oxadiazol-2-yl)methyl)-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide (I-210a)

To a solution of ethyl 5-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)-1,3,4-oxadiazole-2-carboxylate (65 mg, 0.105 mmol) in THF/H$_2$O (5 mL/5 mL) was added LiOH.H$_2$O (18 mg, 0.42 mmol). The resulting mixture was stirred at RT for 3 h. The reaction was concentrated in vacuo to give the crude, which was re-dissolved in 1N HCl (5 mL) and stirred for another 1 h. The reaction was concentrated in vacuo to give the crude, which was purified with Prep-HPLC to give the 1-((8-((1,3,4-oxadiazol-2-yl)methyl)-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide as a white solid (21 mg, 37%). ESI-MS [M+H]$^+$: 547.2. Purity: 94.34 (214 nm), 96.58 (254 nm). $^1$H NMR (400 MHz, DMSO-d$_6$) δ 9.16 (d, J=2.4 Hz, 1H), 8.75 (t, J=5.3 Hz, 1H), 8.59 (d, J=6.9 Hz, 1H), 8.53-8.47 (m, 2H), 8.21 (d, J=7.4 Hz, 1H), 8.02 (s, 1H), 7.33-7.27 (m, 2H), 7.18 (d, J=12.9 Hz, 1H), 7.03 (s, 1H), 6.79-6.76 (m, 1H), 5.83 (s, 2H), 4.71 (d, J=5.5 Hz, 2H), 4.57 (s, 2H), 2.05-1.93 (m, 1H), 1.03-0.95 (m, 1H), 0.76-0.68 (m, 2H).

Example 211

Scheme 210

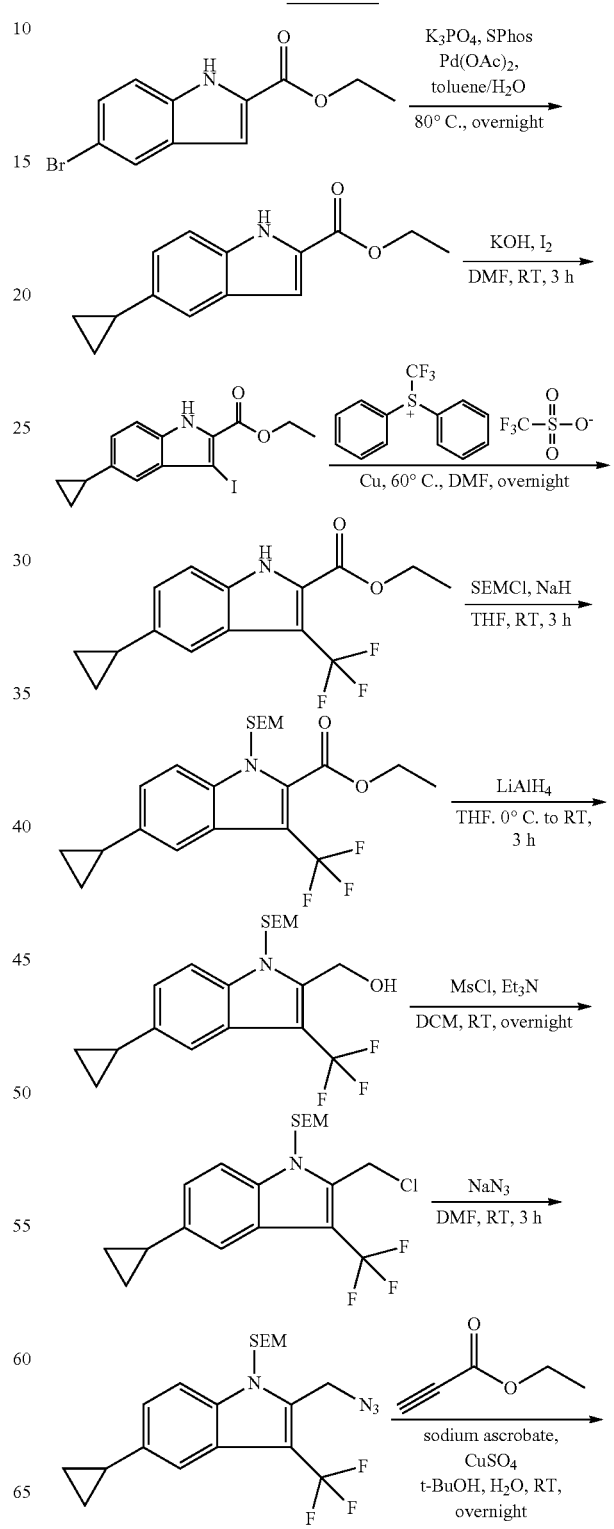

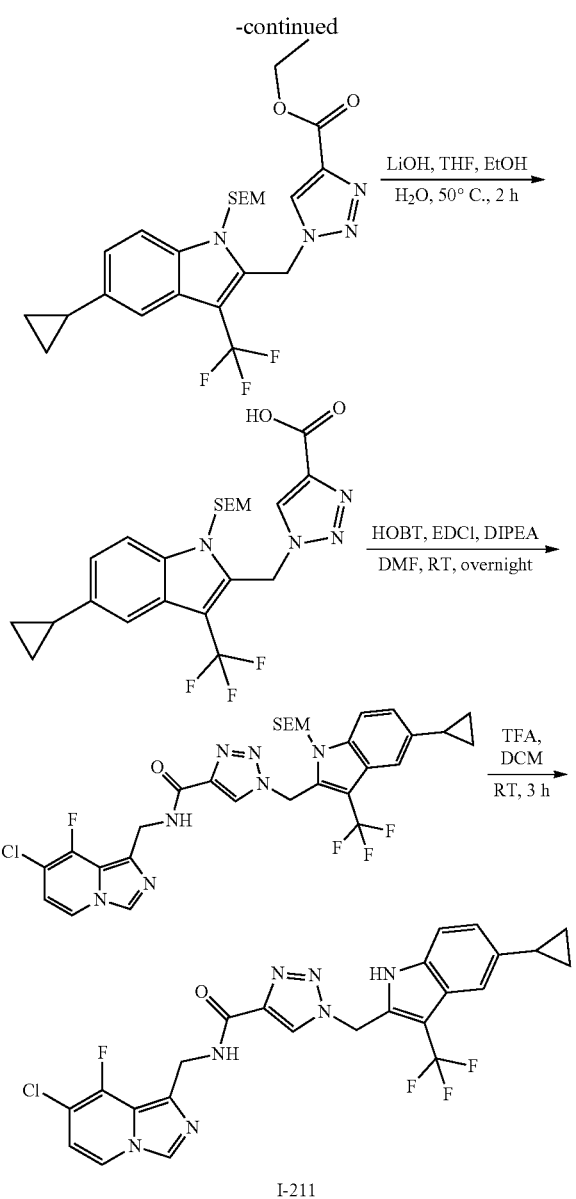

I-211

Synthesis of Ethyl 5-cyclopropyl-1H-indole-2-carboxylate

A solution of ethyl 5-bromo-1H-indole-2-carboxylate (2.68 g, 10 mmol), cyclopropylboronic acid (1.29 g, 15 mmol), Pd(OAc)$_2$ (113 mg, 0.5 mmol), K$_3$PO$_4$ (4.25 g, 20 mmol) and SPhos (205 mg, 0.5 mmol) in toluene (20 mL) and H$_2$O (4 mL) was stirred at 80° C. under N$_2$ overnight. Toluene was concentrated and H$_2$O was added (30 mL), extracted by EtOAc (100 mL*3). The combined organic layers were concentrated and purified by silica gel chromatography (EA/PE=1:8) to give ethyl 5-cyclopropyl-1H-indole-2-carboxylate (1.6 g, yield: 70%) as a yellow solid. ESI-MS [M+H]$^+$: 230.2.

Synthesis of Ethyl 5-cyclopropyl-3-iodo-1H-indole-2-carboxylate

A solution of ethyl 5-cyclopropyl-1H-indole-2-carboxylate (1.55 g, 6.76 mmol), I$_2$ (1.72 g, 6.76 mmol) and KOH (1.52 g, 27.04 mmol) in DMF (10 mL) was stirred at RT for 3 h. The mixture was quenched by adding a saturated thiosulfate solution. Water (50 mL) was added, extracted by EtOAc (100 mL*3). The combined organic layers were concentrated to give crude ethyl 5-cyclopropyl-3-iodo-1H-indole-2-carboxylate (2.33 g, yield: 97%) as a yellow solid. ESI-MS [M+H]$^+$: 356.0.

Synthesis of Ethyl 5-cyclopropyl-3-(trifluoromethyl)-1H-indole-2-carboxylate A mixture of ethyl 5-cyclopropyl-3-iodo-1H-indole-2-carboxylate (1.06 g, 3 mmol), diphenyl(trifluoromethyl)sulfonium trifluoromethanesulfonate (2.43 g, 6 mmol) and copper powder (572 mg, 9 mmol) in DMF (20 mL) was stirred at 60° C. overnight. The mixture was filtered, Water (50 mL) was added to the filtrate and extracted by EtOAc (100 mL×3). The combined organic layers were concentrated and purified by silica gel chromatography (EA/PE=1:5) to give ethyl 5-cyclopropyl-3-(trifluoromethyl)-1H-indole-2-carboxylate (350 mg, yield: 39%) as a yellow oil. ESI-MS [M+H]$^+$: 298.1.

Synthesis of Ethyl 5-cyclopropyl-3-(trifluoromethyl)-1-((2-(trimethylsilyl)ethoxy)methyl)-1H-indole-2-carboxylate To a solution of ethyl 5-cyclopropyl-3-(trifluoromethyl)-1H-indole-2-carboxylate (330 mg, 1.11 mmol) in THF (10 mL) added NaH (110 mg, 60 wt %, 1.67 mmol) at RT slowly. The mixture was stirred at RT for 10 minutes. Then (2-(chloromethoxy)ethyl)trimethylsilane (222 mg, 1.33 mmol) was added. After the mixture was stirred at RT for 3 h, H$_2$O (50 mL) was added and extracted by EtOAc (100 mL×3). The combined organic layers were concentrated to give crude ethyl 5-cyclopropyl-3-(trifluoromethyl)-1-((2-(trimethylsilyl)ethoxy)methyl)-1H-indole-2-carboxylate (460 mg, crude) as a yellow solid, which was used into the next step without further purification. ESI-MS [M+Na]$^+$: 450.3

Synthesis of (5-cyclopropyl-3-(trifluoromethyl)-1-((2-(trimethylsilyl)ethoxy)methyl)-1H-indol-2-yl)methanol To a solution of ethyl 5-cyclopropyl-3-(trifluoromethyl)-1-((2-(trimethylsilyl)ethoxy)methyl)-1H-indole-2-carboxylate (460 mg, 1.11 mmol) in THF (15 mL) added LiAlH$_4$ (63 mg, 1.67 mmol) slowly at 0° C. The mixture was stirred at RT for 3 h. After that, NaSO$_4$.10H$_2$O was added to quench the reaction and the mixture was stirred at RT for another 0.5 h. The mixture was filtered, and the filtrate was concentrated and purified by silica gel chromatography (PE:EA=8:1) to give (5-cyclopropyl-3-(trifluoromethyl)-1-((2-(trimethylsilyl)ethoxy)methyl)-1H-indol-2-yl)methanol (207 mg, 48%) as a yellow solid. ESI-MS [M+H]$^+$: 386.1.

Synthesis of 2-(chloromethyl)-5-cyclopropyl-3-(trifluoromethyl)-1-((2-(trimethylsilyl)ethoxy)methyl)-1H-indole A mixture of (5-cyclopropyl-3-(trifluoromethyl)-1-((2-(trimethylsilyl)ethoxy)methyl)-1H-indol-2-yl)methanol (207 mg, 0.54 mmol), MsCl (92 mg, 0.81 mmol) and Et$_3$N (163 mg, 1.6 mmol) in DCM (10 mL) was stirred at RT overnight. Water was added and extracted with EtOAc, combined organic layers were concentrated to give the crude product (230 mg, crude) which was used into next step without further purification.

Synthesis of 2-(azidomethyl)-5-cyclopropyl-3-(trifluoromethyl)-1-((2-(trimethylsilyl)ethoxy)methyl)-1H-indole A mixture of 2-(chloromethyl)-5-cyclopropyl-3-(trifluoromethyl)-1-((2-(trimethylsilyl)ethoxy)methyl)-1H-indole (230 mg, crude from last step) and NaN₃ (72 mg, 1.2 mmol) in DMF (5 mL) was stirred at RT for 3 h. Water (20 mL) was added and extracted by EtOAc (30 mL×3). The organic layers was concentrated to give 2-(azidomethyl)-5-cyclopropyl-3-(trifluoromethyl)-1-((2-(trimethylsilyl)ethoxy) methyl)-1H-indole (256 mg, crude) as a yellow oil.

Synthesis of Ethyl 1-((5-cyclopropyl-3-(trifluoromethyl)-1-((2-(trimethylsilyl)ethoxy)methyl)-1H-indol-2-yl)methyl)-1H-1,2,3-triazole-4-carboxylate A solution of 2-(azidomethyl)-5-cyclopropyl-3-(trifluoromethyl)-1-((2-(trimethylsilyl)ethoxy)methyl)-1H-indole (256 mg, crude), ethyl propiolate (123 mg, 1.25 mmol) sodium ascorbate (109 mg, 0.62 mmol) and CuSO₄ (49 mg, 0.31 mmol) in tert-BuOH (10 mL) and H₂O (10 mL) was stirred at RT overnight. Water (30 mL) was added and extracted with EtOAc (30 mL×3). The combined organic layers were concentrated to give ethyl 1-((5-cyclopropyl-3-(trifluoromethyl)-1-((2-(trimethylsilyl)ethoxy)methyl)-1H-indol-2-yl)methyl)-1H-1,2,3-triazole-4-carboxylate (250 mg, crude) as a yellow solid, which was used into next step without purification.

Synthesis of 1-((5-cyclopropyl-3-(trifluoromethyl)-1-((2-(trimethylsilyl)ethoxy)methyl)-1H-indol-2-yl)methyl)-1H-1,2,3-triazole-4-carboxylic Acid A solution of ethyl 1-((5-cyclopropyl-3-(trifluoromethyl)-1-((2-(trimethylsilyl)ethoxy)methyl)-1H-indol-2-yl) methyl)-1H-1,2,3-triazole-4-carboxylate (125 mg, crude from last step) and LiOH.H₂O (22 mg, 0.5 mmol) in THF (4 mL), EtOH (2 mL) and H₂O (1 mL) was stirred at 50° C. for 2 h. The mixture was concentrated and H₂O (3 mL) was added, pH value was adjusted to 3 by adding 1 M HCl. Concentrated to afford 1-((5-cyclopropyl-3-(trifluoromethyl)-1-((2-(trimethylsilyl)ethoxy)methyl)-1H-indol-2-yl) methyl)-1H-1,2,3-triazole-4-carboxylic acid as a yellow solid (150 mg, crude), which was used into the next step without purification. ESI-MS [M+Na]⁺: 503.2.

Synthesis of N-((7-chloro-8-fluoroimidazo[1,5-a]pyridin-1-yl)methyl)-1-((5-cyclopropyl-3-(trifluoromethyl)-1-((2-(trimethylsilyl)ethoxy)methyl)-1H-indol-2-yl)methyl)-1H-1,2,3-triazole-4-carboxamide A mixture of crude 1-((5-cyclopropyl-3-(trifluormethyl)-1-((2-(trimethylsilyl)ethoxy)methyl)-1H-indol-2-yl) methyl)-1H-1,2,3-triazole-4-carboxylic acid (150 mg, crude from last step), (7-chloro-8-fluoroimidazo[1,5-a]pyridin-1-yl)methanamine hydrochloride (59 mg, 0.25 mmol), HOBT (67 mg, 0.5 mmol), EDCI (96 mg, 0.5 mmol) and DIPEA (162 mg, 1.25 mmol) in DMF (5 mL) was stirred at RT overnight. Water (20 mL) was added and extracted by EtOAc (30 mL×3). The combined organic layers were concentrated to give the crude product, which was used into the next step without further purification. ESI-MS [M+H]⁺: 662.1.

Synthesis of N-((7-chloro-8-fluoroimidazo[1,5-a]pyridin-1-yl)methyl)-1-((5-cyclopropyl-3-(trifluoromethyl)-1H-indol-2-yl)methyl)-1H-1,2,3-triazole-4-carboxamide (I-211)

A solution of N-((7-chloro-8-fluoroimidazo[1,5-a]pyridin-1-yl)methyl)-1-((5-cyclopropyl-3-(trifluoromethyl)-1-((2-(trimethylsilyl)ethoxy)methyl)-1H-indol-2-yl)methyl)-1H-1,2,3-triazole-4-carboxamide (crude from above step) in TFA/DCM (v:v=1:1, 4 mL) was stirred at RT for 3 h. The solvent was removed by evaporation and the residue was diluted with H₂O. The aqueous layer was adjust to pH=9 with saturated Na₂CO₃ solution and extracted by EtOAc (50 mL*3). The combined organic layers were concentrated and purified by Prep-HPLC to give N-((7-chloro-8-fluoroimidazo[1,5-a]pyridin-1-yl)methyl)-1-((5-cyclopropyl-3-(trifluoromethyl)-1H-indol-2-yl)methyl)-1H-1,2,3-triazole-4-carboxamide (7.5 mg) as a white solid. ESI-MS [M+H]⁺: 532.1. Purity: 99.65 (214 nm), 100.00 (254 nm). ¹H NMR (400 MHz, DMSO-d₆) δ 12.10 (s, 1H), 8.75 (t, J=5.4 Hz, 1H), 8.55 (s, 1H), 8.43 (d, J=2.3 Hz, 1H), 8.20 (d, J=7.4 Hz, 1H), 7.37 (d, J=8.5 Hz, 1H), 7.30 (s, 1H), 6.97 (dd, J=8.6, 1.5 Hz, 1H), 6.77-6.74 (m, 1H), 5.89 (s, 2H), 4.69 (d, J=5.5 Hz, 2H), 2.05-1.99 (m, 1H), 0.93-0.90 (m, 2H), 0.65-0.61 (m, 2H).

Example 212

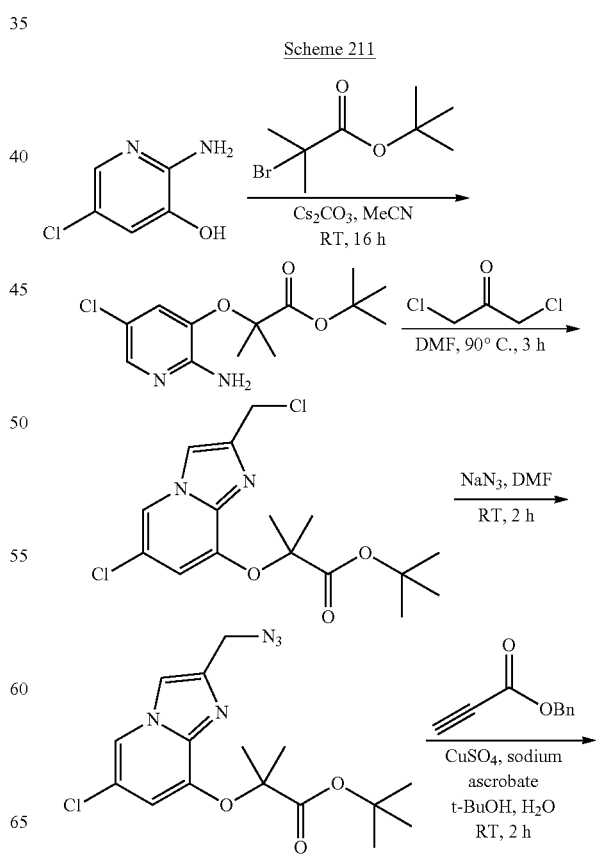

Scheme 211

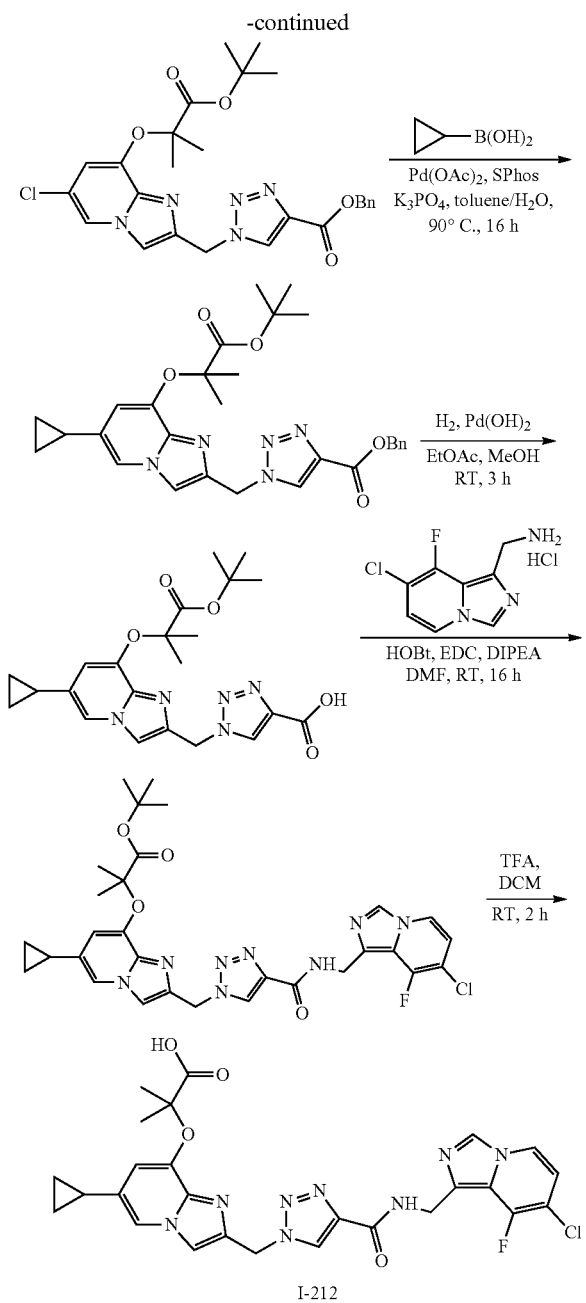

I-212

Synthesis of tert-butyl 2-((2-amino-5-chloropyridin-3-yl)oxy)-2-methylpropanoate To a mixture of 2-amino-5-chloropyridin-3-ol (2.9 g, 20 mmol) and Cs$_2$CO$_3$ (9.8 g, 60 mmol) in MeCN (50 mL) was added tert-butyl 2-bromo-2-methylpropanoate (5.4 g, 24 mmol). The mixture was stirred at RT for 16 h. Water (300 mL) was added to the reaction, extracted with EtOAc (200 mL×3). The combined organic phase was washed with brine, dried over Na$_2$SO$_4$, filtrated and concentrated to give tert-butyl 2-((2-amino-5-chloropyridin-3-yl)oxy)-2-methylpropanoate (2.3 g, yield: 40%) as a yellow oil, which was used into next step without further purification. ESI-MS[M+H]$^+$: 287.1.

Synthesis of tert-butyl 2-((6-chloro-2-(chloromethyl)imidazo[1,2-a]pyridin-8-yl)oxy)-2-methylpropanoate A mixture of tert-butyl 2-((2-amino-5-chloropyridin-3-yl)oxy)-2-methylpropanoate (2.3 g, 8 mmol) and 1,3-dichloropropan-2-one (4.1 g, 32 mmol) in DMF (25 mL) was stirred at 90° C. for 3 h. After cooled, the reaction was quenched with saturated aqueous NaHCO$_3$ (100 mL), extracted with EtOAc (200 mL×3). The combined organic phase was washed with brine, dried over Na$_2$SO$_4$, filtrated and concentrated. The residue was purified by silica gel chromatography (PE/EA=5/1 to 2/1) to give tert-butyl 2-((6-chloro-2-(chloromethyl)imidazo[1,2-a]pyridin-8-yl)oxy)-2-methylpropanoate (1.1 g, yield: 38%) as a yellow oil. ESI-MS [M+H]$^+$: 359.1.

Synthesis of tert-butyl 2-((2-(azidomethyl)-6-chloroimidazo[1,2-a]pyridin-8-yl)oxy)-2-methylpropanoate To a mixture of tert-butyl 2-((6-chloro-2-(chloromethyl)imidazo[1,2-a]pyridin-8-yl)oxy)-2-methylpropanoate (1.1 g, 3.1 mmol) in DMF (10 mL) was added NaN$_3$ (300 mg, 4.6 mmol). The mixture was stirred at RT for 2 h. Water (50 mL) was added to the reaction, and extracted with EtOAc (50 mL×3). The combined organic phase was washed with brine, dried over Na$_2$SO$_4$, filtrated and concentrated to give tert-butyl 2-((2-(azidomethyl)-6-chloroimidazo[1,2-a]pyridin-8-yl)oxy)-2-methylpropanoate (1.1 g, yield: 96%) as a yellow oil, which was used into next step without further purification. ESI-MS [M+H]$^+$: 366.1.

Synthesis of benzyl 1-((8-((1-(tert-butoxy)-2-methyl-1-oxopropan-2-yl)oxy)-6-chloroimidazo[1,2-a]pyridin-2-yl)methyl)-1H-1,2,3-triazole-4-carboxylate To a mixture of tert-butyl 2-((2-(azidomethyl)-6-chloroimidazo[1,2-a]pyridin-8-yl)oxy)-2-methylpropanoate (1.1 g, 3.0 mmol), CuSO$_4$ (67 mg, 0.42 mmol) and sodium ascorbate (83 mg, 0.42 mmol) in t-BuOH/H$_2$O (15 mL/15 mL) was added benzyl propiolate (577 mg, 3.6 mmol). The mixture was stirred at RT for 2 h. Water (50 mL) was added to the reaction and extracted with EtOAc (50 mL×3). The combined organic phase was washed with brine, dried over Na$_2$SO$_4$, filtrated and concentrated to give crude, which was triturated with PE/EA (20 mL/20 mL) to give benzyl 1-((8-((1-(tert-butoxy)-2-methyl-1-oxopropan-2-yl)oxy)-6-chloroimidazo[1,2-a]pyridin-2-yl)methyl)-1H-1,2,3-triazole-4-carboxylate (1.1 g, yield: 68%) as a blue solid. ESI-MS [M+H]$^+$: 526.2.

Synthesis of benzyl 1-((8-((1-(tert-butoxy)-2-methyl-1-oxopropan-2-yl)oxy)-6-cyclopropylimidazo[1,2-a]pyridin-2-yl)methyl)-1H-1,2,3-triazole-4-carboxylate To a mixture of benzyl 1-((8-((1-(tert-butoxy)-2-methyl-1-oxopropan-2-yl)oxy)-6-chloroimidazo[1,2-a]pyridin-2-yl)methyl)-1H-1,2,3-triazole-4-carboxylate (526 mg, 1 mmol), cyclopropylboronic acid (180 mg, 2 mmol) and K$_3$PO$_4$ (850 mg, 4 mmol) in toluene/H$_2$O (10 mL/1 mL) was added Pd(OAc)$_2$ (44 mg, 0.2 mmol) and SPhos (82 mg, 0.2 mmo). The mixture was stirred at 90° C. for 16 h. Water (50 mL) was added to the reaction, and extracted with EtOAc (50 mL×3). The combined organic phase was washed with brine, dried over Na$_2$SO$_4$, filtrated and concentrated to give the residue, which was purified by silica gel chromatography (DCM/MeOH=50/1 to 20/1) to give benzyl 1-((8-((1-(tert-butoxy)-2-methyl-1-oxopropan-2-yl)oxy)-6-cyclopropylimidazo[1,2-a]pyridin-2-yl)methyl)-1H-1,2,3-triazole-4-carboxylate (300 mg, yield: 56%) as a yellow solid. ESI-MS [M+H]$^+$: 532.2.

Synthesis of 1-((8-((1-(tert-butoxy)-2-methyl-1-oxopropan-2-yl)oxy)-6-cyclopropylimidazo[1,2-a]pyridin-2-yl)methyl)-1H-1,2,3-triazole-4-carboxylic Acid To a mixture of benzyl 1-((8-((1-(tert-butoxy)-2-methyl-1-oxopropan-2-yl)oxy)-6-cyclopropylimidazo[1,2-a]pyridin-2-yl)methyl)-1H-1,2,3-triazole-4-carboxylate (300 mg, 0.56 mmol) in EtOAc/MeOH (30 mL/10 mL) was added Pd(OH)$_2$ (60 mg). The mixture was stirred at RT for 3 h under H$_2$ atmosphere. The reaction was filtrated and washed with MeOH (100 mL). The filtrate was concentrated to give 1-((8-((1-(tert-butoxy)-2-methyl-1-oxopropan-2-yl)oxy)-6-cyclopropylimidazo[1,2-a]pyridin-2-yl)methyl)-1H-1,2,3-triazole-4-carboxylic acid (250 mg, yield: 100%) as a yellow oil, which was used into next step without further purification. ESI-MS [M+H]$^+$: 442.1.

Synthesis of tert-butyl 2-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)oxy)-2-methylpropanoate To a mixture of 1-((8-((1-(tert-butoxy)-2-methyl-1-oxopropan-2-yl)oxy)-6-cyclopropylimidazo[1,2-a]pyridin-2-yl)methyl)-1H-1,2,3-triazole-4-carboxylic acid (250 mg, 0.56 mmol), (7-chloro-8-fluoroimidazo[1,5-a]pyridin-1-yl)methanamine hydrochloride (200 mg, 0.85 mmol) and DIPEA (371 mg, 2.85 mmol) in DMF (5 mL) was added HOBT (154 mg, 1.14 mmol) and EDC (210 mg, 1.14 mmol). The mixture was stirred at RT for 16 h. Water (50 mL) was added to the reaction, and extracted with EtOAc (50 mL×3). The combined organic phase was washed with brine, dried over Na$_2$SO$_4$, filtrated and concentrated to give the residue, which was purified by Prep-TLC (DCM/MeOH=10/1) to give tert-butyl 2-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)oxy)-2-methylpropanoate (160 mg, yield: 45%) as a white solid. ESI-MS [M+H]$^+$: 623.1.

Synthesis of 2-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)oxy)-2-methylpropanoic acid (I-212)

To a mixture of tert-butyl 2-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)oxy)-2-methylpropanoate (80 mg, 0.13 mmol) in DCM (5 mL) was added TFA (2 mL). The mixture was stirred at RT for 2 h. The reaction was concentrated to give the residue. The pH of the residue was adjusted to 5 by saturated aqueous Na$_2$CO$_3$, and the white solid was precipitated. The mixture was filtered, the cake washed with DCM (20 mL) and dried to give 2-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)oxy)-2-methylpropanoic acid (50 mg, yield: 67%) as a white solid. ESI-MS [M+H]$^+$: 567.1. Purity: 99.4 (214 nm), 100.0 (254 nm). $^1$H NMR (400 MHz, DMSO-d$_6$) δ 13.34 (s, 1H), 8.70 (t, J=5.4 Hz, 1H), 8.54 (s, 1H), 8.44 (d, J=2.4 Hz, 1H), 8.20 (d, J=7.4 Hz, 1H), 8.01 (s, 1H), 7.80 (s, 1H), 6.80-6.71 (m, 1H), 6.12 (s, 1H), 5.71 (s, 2H), 4.70 (d, J=5.5 Hz, 2H), 1.93-1.83 (m, 1H), 1.59 (s, 6H), 1.01-0.86 (m, 2H), 0.65-0.49 (m, 2H).

Example 213

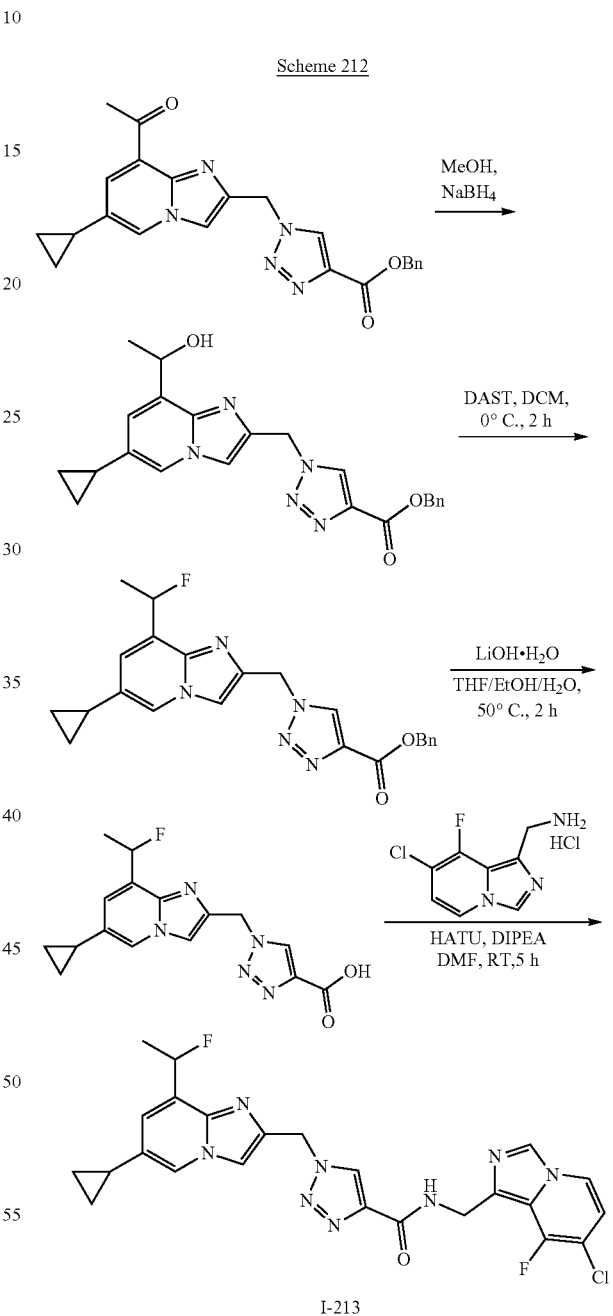

Scheme 212

I-213

Synthesis of Methyl 1-((6-cyclopropyl-8-(1-hydroxyethyl)imidazo[1,2-a]pyridin-2-yl)methyl)-1H-1,2,3-triazole-4-carboxylate To a solution of benzyl 1-((8-acetyl-6-cyclopropylimidazo[1,2-a]pyridin-2-yl)methyl)-1H-1,2,3-triazole-4-carboxylate (500 mg, 1.2 mmol) in MeOH (10 mL) was added NaBH$_4$ (137 mg, 3.6 mmol) at 0° C. The reaction mixture was stirred at RT for 2 h. The reaction was quenched with H$_2$O (30 mL) and extracted by EtOAc (30 mL×3). Then the combined organic layers were washed with brine, dried over Na$_2$SO$_4$, concentrated to give the crude, which was purified by flash silica gel chromatography (PE/EA=1/1) to give methyl 1-((6-cyclopropyl-8-(1-hydroxyethyl)imidazo[1,2-a]pyridin-2-yl)methyl)-1H-1,2,3-triazole-4-carboxylate (300 mg, yield: 73%) as a white solid. ESI-MS [M+H]$^+$: 342.1.

Synthesis of Methyl 1-((6-cyclopropyl-8-(1-fluoroethyl)imidazo[1,2-a]pyridin-2-yl)methyl)-1H-1,2,3-triazole-4-carboxylate To a solution of methyl 1-((6-cyclopropyl-8-(1-hydroxyethyl)imidazo[1,2-a]pyridin-2-yl)methyl)-1H-1,2,3-triazole-4-carboxylate (300 mg, 0.88 mmol) in DCM (10 mL) was added DAST (213 mg, 1.32 mmol) at 0° C. The mixture was stirred at 0° C. for another 2 h. The reaction was quenched by H$_2$O (30 mL), and extracted by EtOAc (30 mL×3). Then the combined organic layers were washed with brine, dried over Na$_2$SO$_4$, concentrated to give the crude, which was purified by flash silica gel chromatography (PE/EA=1/1) to give methyl 1-((6-cyclopropyl-8-(1-fluoroethyl)imidazo[1,2-a]pyridin-2-yl)methyl)-1H-1,2,3-triazole-4-carboxylate (80 mg, yield: 26.6%) as a red solid. ESI-MS [M+H]$^+$: 344.1

Synthesis of 1-((6-cyclopropyl-8-(1-fluoroethyl)imidazo[1,2-a]pyridin-2-yl)methyl)-1H-1,2,3-triazole-4-carboxylic Acid To a solution of methyl 1-((6-cyclopropyl-8-(1-fluoroethyl)imidazo[1,2-a]pyridin-2-yl)methyl)-1H-1,2,3-triazole-4-carboxylate (80 mg, 0.233 mmol) in EtOH/THF/H$_2$O (2 mL/2 mL/1 mL) was added LiOH.H$_2$O (19.1 mg, 0.466 mmol) at RT. The mixture was stirred for 2 h. The pH of the reaction was adjusted to 5 by HCl (1N), and then freeze-dried to give 1-((6-cyclopropyl-8-(1-fluoroethyl)imidazo[1,2-a]pyridin-2-yl)methyl)-1H-1,2,3-triazole-4-carboxylic acid (100 mg, crude) as a white solid, which was used into next step without further purification. ESI-MS [M+H]$^+$: 330.1.

Synthesis of N-((7-chloro-8-fluoroimidazo[1,5-a]pyridin-1-yl)methyl)-1-((6-cyclopropyl-8-(1-fluoroethyl)imidazo[1,2-a]pyridin-2-yl)methyl)-1H-1,2,3-triazole-4-carboxamide (I-213)

To a solution of 1-((6-cyclopropyl-8-(1-fluoroethyl)imidazo[1,2-a]pyridin-2-yl)methyl)-1H-1,2,3-triazole-4-carboxylic acid (100 mg, crude from previous step), (7-chloro-8-fluoroimidazo[1,5-a]pyridin-1-yl)methanamine hydrochloride (72 mg, 0.3 mmol), HATU (171 mg, 0.45 mmol) in DMF (5 mL) was added DIPEA (90 mg, 0.7 mmol). The resulting reaction was stirred at RT for 14 h. Water (50 mL) was added to the reaction, extracted with EtOAc (50 mL×3). The combined organic layers were washed with brine, dried over Na$_2$SO$_4$, concentrated to give the crude, which was purified by Prep-TLC (DCM/MeOH=10/1) to give N-((7-chloro-8-fluoroimidazo[1,5-a]pyridin-1-yl)methyl)-1-((6-cyclopropyl-8-(1-fluoroethyl)imidazo[1,2-a]pyridin-2-yl)methyl)-1H-1,2,3-triazole-4-carboxamide (14.6 mg, yield: 12% over 2 steps) as a yellow solid. ESI-MS [M+H]$^+$: 511.1. Purity: 98.8 (214 nm), 100.00 (254 nm). $^1$H NMR (400 MHz, DMSO-d$_6$) 8.72 (t, J=5.4 Hz, 1H), 8.56 (s, 1H), 8.44 (d, J=2.4 Hz, 1H), 8.33 (s, 1H), 8.20 (d, J=7.4 Hz, 1H), 7.85 (s, 1H), 7.07 (s, 1H), 6.78-6.74 (m, 1H), 6.17-5.99 (m, 1H), 5.76 (s, 2H), 4.70 (d, J=5.5 Hz, 2H), 2.00-1.93 (m, 1H), 1.71 (dd, J=24.4, 6.4 Hz, 3H), 0.96-0.91 (m, 2H), 0.73-0.65 (m, 2H).

Example 214

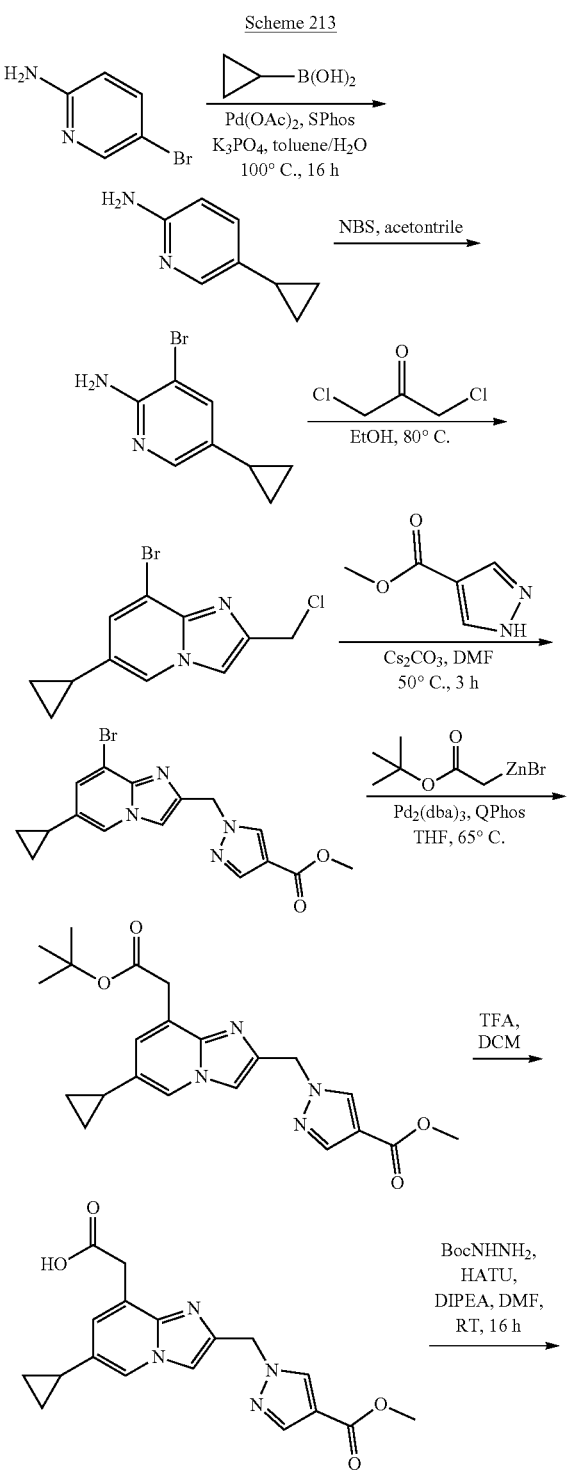

Scheme 213

-continued

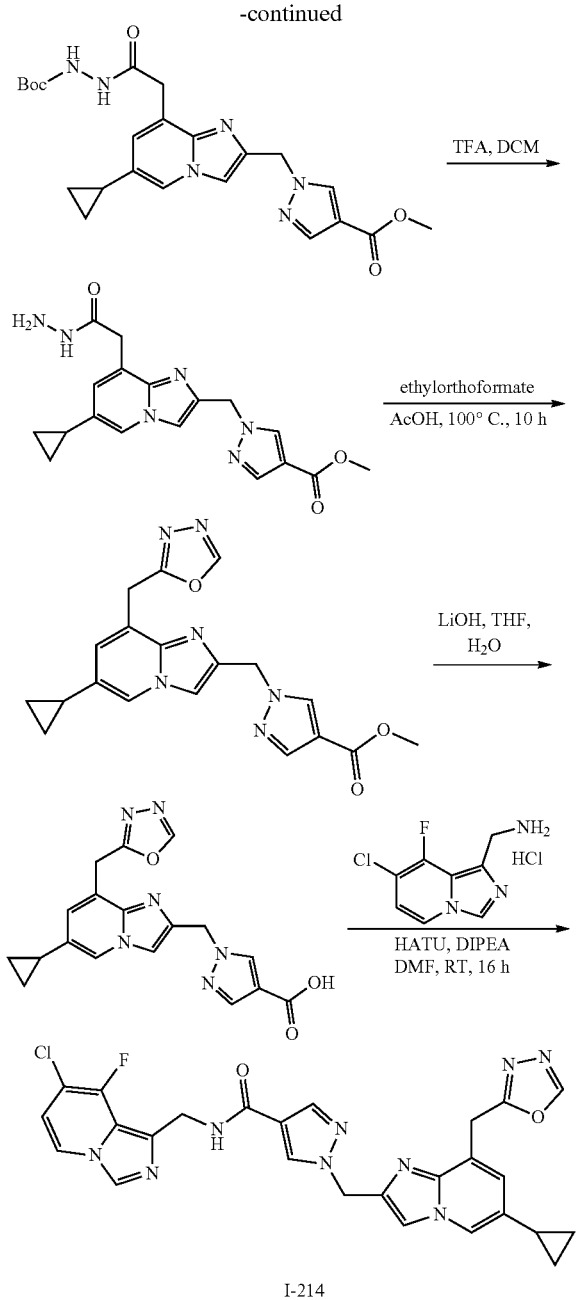

I-214

Synthesis of 5-cyclopropylpyridin-2-amine

A mixture of 5-bromopyridin-2-amine (5 g, 29 mmol), cyclopropylboronic acid (4.97 g, 58 mmol), Pd(OAc)$_2$ (0.65 g, 2.9 mol), SPhos (2.37 g, 5.8 mol) and K$_3$PO$_4$ (18.38 g, 87 mol) in toluene/H$_2$O (150 mL/15 mL) was stirred at 100° C. for 16 h. The reaction mixture was filtered through celite, washed with EtOAc (300 mL). The filtrate was concentrated to give the crude, which was purified by flash (ethyl acetate) to give 5-cyclopropylpyridin-2-amine (3.8 g, 97% yield) as a yellow oil. ESI-MS [M+H]$^+$: 135.2.

Synthesis of 3-bromo-5-cyclopropylpyridin-2-amine

To a solution of 5-cyclopropylpyridin-2-amine (3.7 g, 28 mol) in MeCN (100 mL) was added NBS (4.9 g, 0.028 mol) at 0° C. The resulting reaction was stirred at 0° C. for 2 h. The reaction was concentrated to give the crude, which was purified by silica gel column chromatography (PE/EA=1/1) to give 3-bromo-5-cyclopropylpyridin-2-amine (4.5 g, 75% yield) as a yellow solid. ESI-MS [M+H]$^+$: 213.0

Synthesis of 8-bromo-2-(chloromethyl)-6-cyclopropylimidazo[1,2-a]pyridine

The mixture of 3-bromo-5-cyclopropylpyridin-2-amine (4.4 g, 20 mol), 1,3-dichloropropan-2-one (10.5 g, 80 mol) in EtOH (200 mL) was stirred at 80° C. for 16 h. The reaction was concentrated to give the residue, which was diluted with ethyl acetate (100 mL), washed by saturated aqueous NaHCO$_3$ (50 mL), H$_2$O (50 mL) and brine (50 mL), dried over Na$_2$SO$_4$, concentrated to give the crude, which was purified by silica gel column chromatography (EA/PE=1/1) to give 8-bromo-2-(chloromethyl)-6-cyclopropylimidazo[1,2-a]pyridine (2.2 g, 37% yield). ESI-MS [M+H]$^+$: 285.0.

Synthesis of Methyl 1-((8-bromo-6-cyclopropylimidazo[1,2-a]pyridin-2-yl)methyl)-1H-pyrazole-4-carboxylate The mixture of 8-bromo-2-(chloromethyl)-6-cyclopropylimidazo[1,2-a]pyridine (2.2 g, 7.7 mmol), methyl 1H-pyrazole-4-carboxylate (0.97 g, 7.7 mmol), and Cs$_2$CO$_3$ (5 g, 15.4 mmol) in DMF (30 mL) was stirred at 50° C. for 3 h. H$_2$O (150 mL) was added to the reaction, extracted with ethyl acetate (200 mL×3). The combined organic layers were washed with brine, dried over Na$_2$SO$_4$, concentrated to give the crude, which was purified by silica gel column chromatography (PE/EA=1/2) to give methyl 1-((8-bromo-6-cyclopropylimidazo[1,2-a]pyridin-2-yl)methyl)-1H-pyrazole-4-carboxylate (2.4 g, 83%) as a yellow solid. ESI-MS [M+H]$^+$: 375.1. $^1$H NMR (400 MHz, DMSO-d$_6$) δ 8.43 (d, J=0.5 Hz, 1H), 8.38 (d, J=1.0 Hz, 1H), 7.89 (d, J=0.6 Hz, 1H), 7.85 (s, 1H), 7.39 (d, J=1.5 Hz, 1H), 5.49 (s, 2H), 3.74 (s, 3H), 1.97-1.86 (m, 1H), 0.94-0.90 (m, 2H), 0.78-0.66 (m, 2H).

Synthesis of Methyl 1-((8-(2-tert-butoxy-2-oxoethyl)-6-cyclopropylimidazo[1,2-a]pyridin-2-yl)methyl)-1H-pyrazole-4-carboxylate A mixture of methyl 1-((8-bromo-6-cyclopropylimidazo[1,2-a]pyridin-2-yl)methyl)-1H-pyrazole-4-carboxylate (1.2 g, 3.2 mmol), (2-tert-butoxy-2-oxoethyl)zinc(II) bromide (4.2 g, 16 mmol), Pd$_2$(dba)$_3$ (2.9 g, 3.2 mmol), QPhos (455 mg, 0.64 mmol) in THF (60 mL) was stirred at 65° C. for 16 h. The reaction was concentrated to give the crude, which was purified by silica gel column chromatography (DCM/EA=4/1) to give methyl 1-((8-(2-tert-butoxy-2-oxoethyl)-6-cyclopropylimidazo[1,2-a]pyridin-2-yl)methyl)-1H-pyrazole-4-carboxylate (540 mg, 42% yield) as a yellow solid. ESI-MS [M+H]$^+$: 411.2

Synthesis of 2-(6-cyclopropyl-2-((4-(methoxycarbonyl)-1H-pyrazol-1-yl)methyl)imidazo[1,2-a]pyridin-8-yl)acetic Acid A mixture of methyl 1-((8-(2-tert-butoxy-2-oxoethyl)-6-cyclopropylimidazo[1,2-a]pyridin-2-yl)methyl)-1H-pyrazole-4-carboxylate (540 mg, 1.3 mmol) in DCM (40 mL) was added TFA (10 mL) dropwise. The resulting mixture was stirred at RT for 1 h. The reaction was concentrated to give the crude, which was purified by silica gel column chromatography (DCM/MeOH=4/1) to give 2-(6-cyclopropyl-2-((4-(methoxycarbonyl)-1H-pyrazol-1-yl)methyl)imidazo[1,2-a]pyridin-8-yl)acetic acid (340 mg, 73% yield) as a yellow solid. ESI-MS [M+H]$^+$: 355.1.

Synthesis of Methyl 1-((8-(2-(2-(tert-butoxycarbonyl)hydrazinyl)-2-oxoethyl)-6-cyclopropylimidazo[1,2-a]pyridin-2-yl)methyl)-1H-pyrazole-4-carboxylate A mixture of 2-(6-cyclopropyl-2-((4-(methoxycarbonyl)-1H-pyrazol-1-yl)methyl)imidazo[1,2-a]pyridin-8-yl)acetic acid (310 mg, 0.88 mmol), BocNHNH$_2$ (232 mg, 1.76 mmol), HATU (401 mg, 1.056 mmol) and DIPEA (454 mg, 3.52 mmol) in DMF (6 mL) was stirred at RT for 16 h. Water (30 mL) was added to the reaction, extracted with ethyl acetate (50 mL×3). The combined organic layers were washed with brine (20 mL), dried over Na$_2$SO$_4$, concentrated to give the crude, which was purified by silica gel column chromatography (DCM/MeOH=15/1) to give methyl 1-((8-(2-(2-(tert-butoxycarbonyl)hydrazinyl)-2-oxoethyl)-6-cyclopropylimidazo[1,2-a]pyridin-2-yl)methyl)-1H-pyrazole-4-carboxylate (300 mg, 73% yield) as a yellow solid. ESI-MS [M+H]$^+$: 469.2

Synthesis of Methyl 1-((6-cyclopropyl-8-(2-hydrazinyl-2-oxoethyl)imidazo[1,2-a]pyridin-2-yl)methyl)-1H-pyrazole-4-carboxylate A mixture of methyl 1-((8-(2-(2-(tert-butoxycarbonyl)hydrazinyl)-2-oxoethyl)-6-cyclopropylimidazo[1,2-a]pyridin-2-yl)methyl)-1H-pyrazole-4-carboxylate (300 mg, 0.64 mmol) in DCM (30 mL) was added TFA (3 mL) dropwise. The resulting mixture was stirred at RT for 1 h. The reaction mixture was concentrated, diluted with DCM (50 mL), washed by saturated aqueous NaHCO$_3$ (30 mL), H$_2$O (30 mL), dried over Na$_2$SO$_4$, then concentrated to give methyl 1-((6-cyclopropyl-8-(2-hydrazinyl-2-oxoethyl)imidazo[1,2-a]pyridin-2-yl)methyl)-1H-pyrazole-4-carboxylate as a yellow oil, which was used into next step without further purification. ESI-MS [M+H]$^+$: 369.0

Synthesis of Methyl 1-((6-cyclopropyl-8-(2-hydrazinyl-2-oxoethyl)imidazo[1,2-a]pyridin-2-yl)methyl)-1H-pyrazole-4-carboxylate A mixture of methyl 1-((6-cyclopropyl-8-(2-hydrazinyl-2-oxoethyl)imidazo[1,2-a]pyridin-2-yl)methyl)-1H-pyrazole-4-carboxylate (150 mg, crude from last step), ethyl orthoformate (2.8 mL), and AcOH (1.4 mL) in toluene (7 mL) was stirred at 100° C. for 10 h. The reaction was concentrated to give the crude, which was purified by silica gel column chromatography (DCM/MeOH=90/10) to give methyl 1-((6-cyclopropyl-8-(2-hydrazinyl-2-oxoethyl)imidazo[1,2-a]pyridin-2-yl)methyl)-1H-pyrazole-4-carboxylate (40 mg, 16% yield over 2 steps) as yellow oil. ESI-MS [M+H]$^+$: 379.2

Synthesis of 1-((8-((1,3,4-oxadiazol-2-yl)methyl)-6-cyclopropylimidazo[1,2-a]pyridin-2-yl)methyl)-1H-pyrazole-4-carboxylic Acid A mixture of methyl 1-((8-((1,3,4-oxadiazol-2-yl)methyl)-6-cyclopropylimidazo[1,2-a]pyridin-2-yl)methyl)-1H-pyrazole-4-carboxylate (40 mg, 0.1 mmol), LiOH (18 mg, 0.4 mmol) in THF/H$_2$O (4 mL/2 mL) was stirred at 0° C. for 16 h. The reaction was concentrated and freeze-dried to give 1-((8-((1,3,4-oxadiazol-2-yl)methyl)-6-cyclopropylimidazo[1,2-a]pyridin-2-yl)methyl)-1H-pyrazole-4-carboxylic acid (60 mg, crude) as a yellow solid, which was used into next step without further purification. ESI-MS [M+H]$^+$: 365.1

Synthesis of 1-((8-((1,3,4-oxadiazol-2-yl)methyl)-6-cyclopropylimidazo[1,2-a]pyridin-2-yl)methyl)-N-((7-chloro-8-fluoroimidazo[1,5-a]pyridin-1-yl)methyl)-1H-pyrazole-4-carboxamide (I-214)

A mixture of 1-((8-((1,3,4-oxadiazol-2-yl)methyl)-6-cyclopropylimidazo[1,2-a]pyridin-2-yl)methyl)-1H-pyrazole-4-carboxylic acid (60 mg, crude from last step), (7-chloro-8-fluoroimidazo[1,5-a]pyridin-1-yl)methanamine hydrochloride (19 mg, 0.08 mmol), HATU (36 mg, 0.096 mmol), DIPEA (31 mg, 0.24 mmol) in DMF (3 mL) was stirred at RT for 16 h. Water (20 mL) was added to the reaction, extracted with ethyl acetate (20 mL×3). The combined organic layers were washed by brine (10 mL), dried over Na$_2$SO$_4$, concentrated to give the crude, which was purified by Prep-HPLC (DCM/MeOH=10/1) to give 1-((8-((1,3,4-oxadiazol-2-yl)methyl)-6-cyclopropylimidazo[1,2-a]pyridin-2-yl)methyl)-N-((7-chloro-8-fluoroimidazo[1,5-a]pyridin-1-yl)methyl)-1H-pyrazole-4-carboxamide (10 mg, 22% yield) as a white solid. ESI-MS [M+H]$^+$: 546.2. Purity: 100.00% (214 nm), 100.00% (254 nm). $^1$H NMR (400 MHz, DMSO-d$_6$) δ 9.14 (s, 1H), 8.46-8.39 (m, 3H), 8.22-8.13 (m, 2H), 7.88-7.81 (m, 2H), 7.19 (s, 1H), 6.79-6.75 (m, 1H), 5.45 (s, 2H), 4.63 (d, J=5.1 Hz, 2H), 4.53 (s, 2H), 1.96 (s, 1H), 0.95 (d, J=8.0 Hz, 2H), 0.68 (d, J=4.5 Hz, 2H).

Example 215

Scheme 214

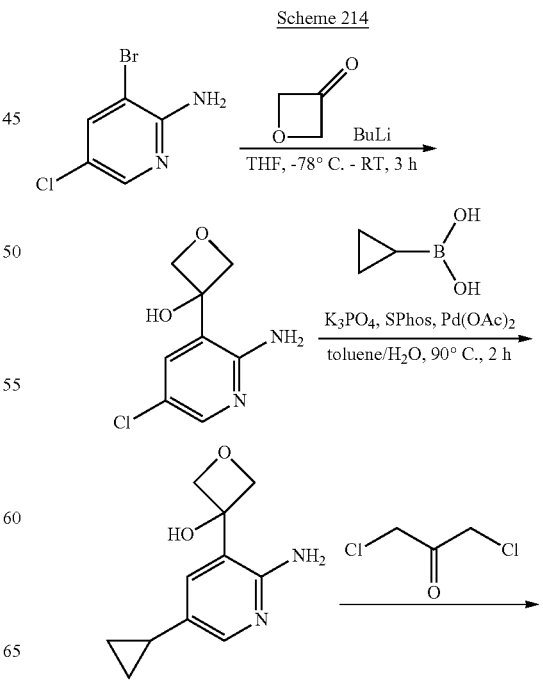

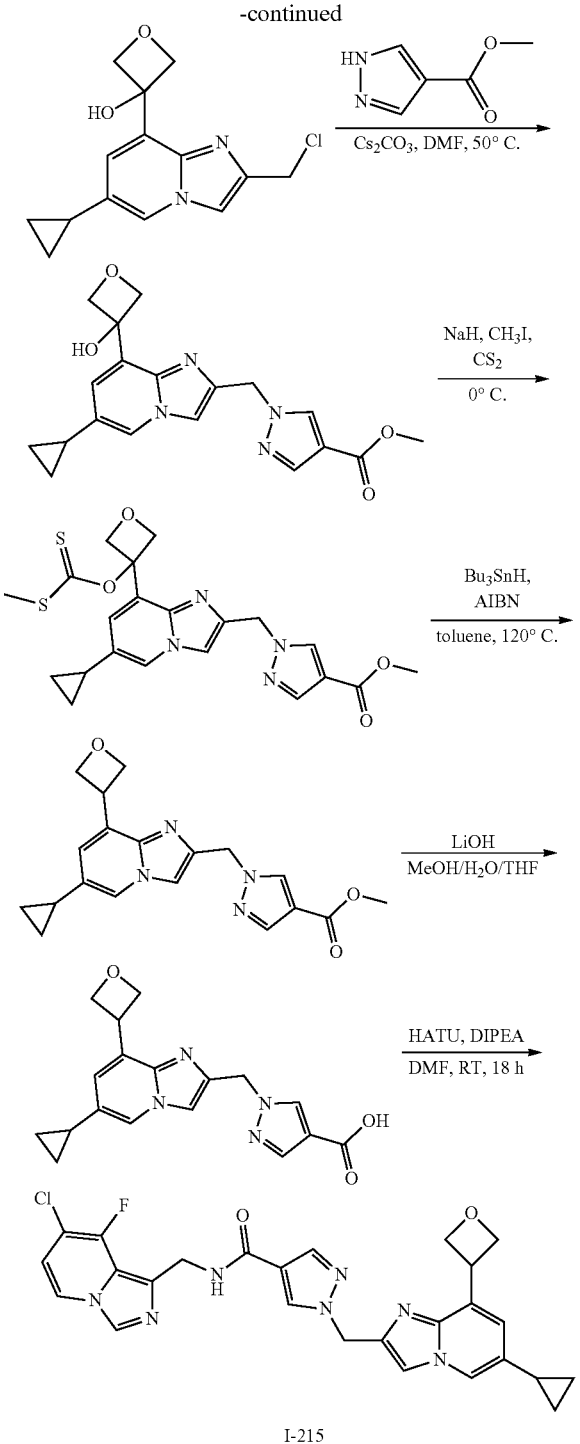

I-215

Synthesis of 3-(2-amino-5-chloropyridin-3-yl)oxetan-3-ol

To the solution of 3-bromo-5-chloropyridin-2-amine (5 g, 24 mmol) in THF (100 mL) was added n-BuLi (35 mL, 2.4 M solution in hexanes, 84 mmol) dropwise at −78° C. After 5 minutes, oxetan-3-one (17 g, 240 mmol) in THF (50 mL) was added thereto and stirred at −78° C. for 2 h. The reaction was quenched with saturated aqueous NH₄Cl (100 mL), extracted with ethyl acetate (100 mL×3). The combined organic layers were washed by brine (50 mL) and dried over Na₂SO₄, concentrated to give the crude, which was purified by silica gel column chromatography (DCM/MeOH=15/1) to give 3-(2-amino-5-chloropyridin-3-yl)oxetan-3-ol (2.8 g, 58% yield) as a yellow solid. ESI-MS [M+H]⁺: 201.1. ¹H NMR (400 MHz, DMSO-d₆) δ 7.93 (d, J=2.5 Hz, 1H), 7.61 (d, J=2.5 Hz, 1H), 6.49 (s, 1H), 5.81 (s, 2H), 4.84 (d, J=7.4 Hz, 2H), 4.72 (d, J=7.4 Hz, 2H).

Synthesis of 3-(2-amino-5-cyclopropylpyridin-3-yl)oxetan-3-ol

A mixture of 3-(2-amino-5-chloropyridin-3-yl)oxetan-3-ol (2.8 g, 14 mmol), cyclopropylboronic acid (2.4 g, 28 mmol), K₃PO₄ (8.9 g, 42 mmol), SPhos (1.1 g, 2.7 mmol) and Pd(OAc)₂ (0.3 g, 1.3 mmol) in toluene/H₂O (50 mL/5 mL) was stirred at 90° C. for 16 h. The reaction mixture was filtered through celite, washed with EtOAc (100 mL). The filtrate was concentrated to give the crude, which was purified by silica gel column chromatography (DCM/MeOH=8/1) to give 3-(2-amino-5-cyclopropylpyridin-3-yl)oxetan-3-ol (2.1 g, 73% yield) as a yellow solid. ESI-MS [M+H]⁺: 207.2. ¹H NMR (400 MHz, DMSO-d₆) δ 7.75 (d, J=1.8 Hz, 1H), 7.17 (d, J=2.1 Hz, 1H), 6.34 (s, 1H), 5.34 (s, 2H), 4.85 (d, J=7.1 Hz, 2H), 4.70 (d, J=7.2 Hz, 2H), 3.61 (s, 1H), 1.85-1.78 (m, 1H), 0.86-0.80 (m, 2H), 0.64-0.59 (m, 2H).

Synthesis of 3-(2-(chloromethyl)-6-cyclopropylimidazo[1,2-a]pyridin-8-yl)oxetan-3-ol A mixture of 3-(2-amino-5-cyclopropylpyridin-3-yl)oxetan-3-ol (2 g, 9.7 mmol), 1,3-dichloropropan-2-one (3.85 g, 31 mmol) in EtOH (50 mL) was stirred at 80° C. for 16 h. The reaction was concentrated and the residue was diluted with ethyl acetate (50 mL), washed by saturated aqueous NaHCO₃ (30 mL), H₂O (30 mL) and brine (30 mL), dried over Na₂SO₄, and concentrated to give the crude, which was purified by silica gel column chromatography (DCM/MeOH=8/1) to give 3-(2-(chloromethyl)-6-cyclopropylimidazo[1,2-a]pyridin-8-yl)oxetan-3-ol (1.2 g, 44% yield) as a yellow solid. ESI-MS [M+H]⁺: 279.1. ¹H NMR (400 MHz, DMSO-d₆) δ 8.54 (s, 1H), 8.15 (s, 1H), 7.54 (s, 1H), 5.10 (d, J=6.5 Hz, 2H), 4.96 (s, 2H), 4.80 (d, J=6.4 Hz, 2H), 2.07 (d, J=4.7 Hz, 1H), 1.06-0.98 (m, 2H), 0.80 (d, J=5.1 Hz, 2H).

Synthesis of Methyl 1-((6-cyclopropyl-8-(3-hydroxyoxetan-3-yl)imidazo[1,2-a]pyridin-2-yl)methyl)-1H-pyrazole-4-carboxylate A mixture of 3-(2-(chloromethyl)-6-cyclopropylimidazo[1,2-a]pyridin-8-yl)oxetan-3-ol (1.2 g, 4.3 mmol), methyl 1H-pyrazole-4-carboxylate (0.54 g, 4.3 mmol) and Cs₂CO₃ (2.8 g, 8.6 mmol) in DMF (10 mL) was stirred at 50° C. for 3 h. The reaction mixture was filtered through celite, and the filtrate was diluted with H₂O (100 mL) and extracted with ethyl acetate (100 mL). The combined organic layers were concentrated to give the crude, which was purified by silica gel column chromatography (DCM/MeOH=6/1) to give methyl 1-((6-cyclopropyl-8-(3-hydroxyoxetan-3-yl)imidazo[1,2-a]pyridin-2-yl)methyl)-1H-pyrazole-4-carboxylate (890 mg, 56% yield) as a yellow solid. ESI-MS [M+H]⁺: 369.2. ¹H NMR (400 MHz, DMSO-d₆) δ 8.41 (s, 1H), 8.30 (d, J=1.2 Hz, 1H), 7.90 (s, 1H), 7.70 (s, 1H), 6.45 (s, 1H), 5.50 (s, 2H), 5.24 (d, J=6.5 Hz, 2H), 4.66 (d, J=6.5 Hz, 2H), 3.74 (s, 3H), 1.94 (td, J=8.4, 4.2 Hz, 1H), 0.97-0.89 (m, 2H), 0.72-0.65 (m, 2H).

Synthesis of Methyl 1-((6-cyclopropyl-1-(3-(methylthiocarbonothioyloxy)oxetan-3-yl) imidazo[1,2-a]pyridin-2-yl)methyl)-1H-pyrazole-4-carboxylate To the mixture of methyl 1-((6-cyclopropyl-8-(3-hydroxyoxetan-3-yl)imidazo[1,2-a] pyridin-2-yl)methyl)-1H-pyrazole-4-carboxylate (830 mg, 2.3 mmol) in THF (85 mL) at 0° C. was added NaH (415 mg, 17.3 mmol) in portions. The mixture was stirred at 0° C. for 1 h, then $CS_2$ (1.6 g, 21 mmol) was added dropwise and stirred for another 1 h. $CH_3I$ (2.7 g, 19 mmol) was added dropwise at 0° C. and stirred for 1 h. The reaction was concentrated and then diluted with ethyl acetate (80 mL), washed with aqueous $NH_4Cl$ (100 mL), aqueous layer was extracted with ethyl acetate (80 mL×3). The combined organic layers were washed by brine (50 mL), dried over $Na_2SO_4$, concentrated at low temperature to give methyl 1-((6-cyclopropyl-8-(3-(methylthiocarbonothioyloxy) oxetan-3-yl)imidazo[1,2-a]pyridin-2-yl)methyl)-1H-pyrazole-4-carboxylate (1 g, crude) as a yellow oil, which was used into next step without further purification. ESI-MS $[M+H]^+$: 459.1

Synthesis of Methyl 1-((6-cyclopropyl-8-(oxetan-3-yl)imidazo[1,2-a]pyridin-2-yl)methyl)-1H-pyrazole-4-carboxylate A mixture of methyl 1-((6-cyclopropyl-8-(3-(methylthiocarbonothioyloxy) oxetan-3-yl)imidazo[1,2-a]pyridin-2-yl)methyl)-1H-pyrazole-4-carboxylate (1 g from previous step), $Bu_3SnH$ (3.28 g, 11 mmol), AIBN (609 mg, 3.7 mmol) in toluene (80 mL) was stirred at 120° C. for 0.5 h. The reaction was concentrated and purified by silica gel column chromatography (DCM/MeOH=10/1) to give methyl 1-((6-cyclopropyl-8-(oxetan-3-yl)imidazo[1,2-a]pyridin-2-yl)methyl)-1H-pyrazole-4-carboxylate (490 mg, 61% yield over 2 steps) as a yellow oil. ESI-MS $[M+H]^+$: 353.2. $^1H$ NMR (400 MHz, DMSO-$d_6$) δ 8.38 (d, J=0.5 Hz, 1H), 8.24 (d, J=1.5 Hz, 1H), 7.88 (d, J=0.6 Hz, 1H), 7.68 (s, 1H), 7.06-7.00 (m, 1H), 5.45 (s, 2H), 4.93 (dd, J=8.6, 5.8 Hz, 2H), 4.83 (dd, J=7.1, 5.8 Hz, 2H), 4.72-4.60 (m, 1H), 3.73 (s, 3H), 1.95 (qd, J=8.5, 4.3 Hz, 1H), 0.92 (ddd, J=8.3, 6.3, 4.2 Hz, 2H), 0.76-0.69 (m, 2H).

Synthesis of 1-((6-cyclopropyl-8-(oxetan-3-yl)imidazo[1,2-a]pyridin-2-yl)methyl)-1H-pyrazole-4-carboxylic Acid A mixture of methyl 1-((6-cyclopropyl-8-(oxetan-3-yl)imidazo[1,2-a]pyridin-2-yl)methyl)-1H-pyrazole-4-carboxylate (50 mg, 0.14 mmol) and LiOH (24 mg, 0.57 mmol) in MeOH/THF/$H_2O$ (1 mL/1 mL/1 mL) was stirred at RT for 16 h. The reaction was adjusted to pH-3 with HCl (1N), and concentrated to give 1-((6-cyclopropyl-8-(oxetan-3-yl)imidazo[1,2-a]pyridin-2-yl)methyl)-1H-pyrazole-4-carboxylic acid (80 mg, crude) as a yellow solid, which was used into next step without further purification. ESI-MS $[M+H]^+$: 339.2. $^1H$ NMR (400 MHz, DMSO-$d_6$) δ 11.72 (s, 1H), 8.29 (s, 1H), 8.25 (s, 1H), 7.81 (s, 1H), 7.69 (s, 1H), 7.03 (s, 1H), 5.44 (s, 2H), 4.93 (dd, J=8.6, 5.8 Hz, 2H), 4.83 (dd, J=7.1, 5.9 Hz, 2H), 4.65 (dd, J=16.1, 8.1 Hz, 1H), 1.97 (dd, J=7.0, 3.7 Hz, 1H), 0.95-0.89 (m, 2H), 0.72 (dt, J=6.4, 4.4 Hz, 2H).

Synthesis of N-((7-chloro-8-fluoroimidazo[1,5-a]pyridin-1-yl)methyl)-1-((6-cyclopropyl-8-(oxetan-3-yl)imidazo[1,2-a]pyridin-2-yl)methyl)-1H-pyrazole-4-carboxamide (I-215)

A mixture of 1-((6-cyclopropyl-8-(oxetan-3-yl)imidazo[1,2-a]pyridin-2-yl)methyl)-1H-pyrazole-4-carboxylic acid (80 mg, crude from last step), (7-chloro-8-fluoroimidazo[1,5-a]pyridin-1-yl)methanamine hydrochloride (33 mg, 0.14 mmol), HATU (114 mg, 0.3 mmol) and DIPEA (38.7 mg, 0.3 mmol) in DMF (3 mL) was stirred at RT for 16 h. The reaction mixture was poured into $H_2O$ (20 mL) and extracted with ethyl acetate (20 mL×3), the combined organic layers were concentrated to give the crude, which was purified by Prep-HPLC to give N-((7-chloro-8-fluoroimidazo[1,5-a]pyridin-1-yl)methyl)-1-((6-cyclopropyl-8-(oxetan-3-yl)imidazo[1,2-a]pyridin-2-yl)methyl)-1H-pyrazole-4-carboxamide (15 mg, 20% yield) as a white solid. ESI-MS $[M+H]^+$: 520.1. Purity: 100.00% (214 nm), 100.00% (254 nm). $^1H$ NMR (400 MHz, DMSO-$d_6$) δ 8.48-8.37 (m, 2H), 8.27-8.14 (m, 3H), 7.86 (s, 1H), 7.67 (s, 1H), 7.03 (s, 1H), 6.76 (dd, J=7.3, 6.5 Hz, 1H), 5.39 (s, 2H), 4.93 (dd, J=8.5, 5.8 Hz, 2H), 4.82 (dd, J=7.1, 5.9 Hz, 2H), 4.70-4.58 (m, 3H), 1.98-1.91 (m, 1H), 0.95-0.89 (m, 2H), 0.76-0.67 (m, 2H).

Example 216

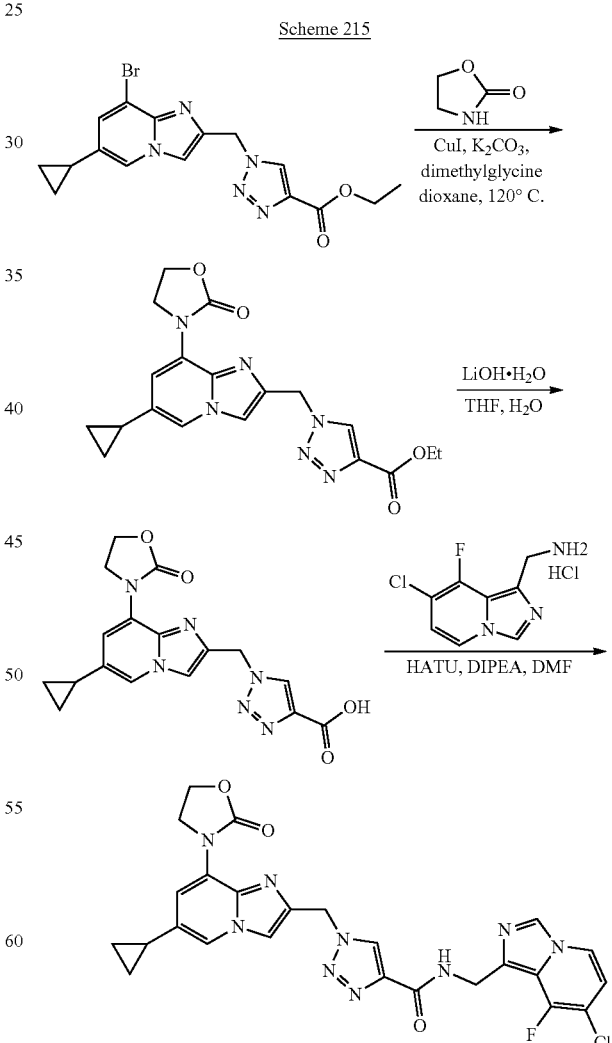

Scheme 215

I-216

Synthesis of Ethyl 1-((6-cyclopropyl-8-(2-oxooxazolidin-3-yl)imidazo[1,2-a]pyridin-2-yl)methyl)-1H-1,2,3-triazole-4-carboxylate A mixture of ethyl 1-((8-bromo-6-cyclopropylimidazo[1,2-a]pyridin-2-yl)methyl)-1H-1,2,3-triazole-4-carboxylate (196 mg, 0.5 mmol), CuI (48.5 mg, 0.25 mmol), dimethylglycine (25.7 mg, 0.25 mmol), $K_2CO_3$ (140.4 mg, 1 mmol) and oxazolidin-2-one (50.4 mg, 0.55 mmol) in dioxane (6 mL) was degassed by $N_2$ for 10 min in a sealed tube. The reaction mixture was heated to 120° C. for 15 h. The reaction mixture was cooled to RT and then partitioned between saturated aqueous $NH_4Cl$ (40 mL) and EtOAc (50 mL×3). The combined organic layers were washed with brine, dried over $Na_2SO_4$, concentrated under vacuum to give the crude, which was purified by silica gel chromatography (DCM/EA: 3/1-1/1) to afford ethyl 1-((6-cyclopropyl-8-(2-oxooxazolidin-3-yl)imidazo[1,2-a]pyridin-2-yl)methyl)-1H-1,2,3-triazole-4-carboxylate as a white solid (70 mg, yield: 35.4%). ESI-MS $[M+H]^+$: 396.7.

Synthesis of lithium 1-((6-cyclopropyl-8-(2-oxooxazolidin-3-yl)imidazo[1,2-a]pyridin-2-yl)methyl)-1H-1,2,3-triazole-4-carboxylate To a solution of ethyl 1-((6-cyclopropyl-8-(2-oxooxazolidin-3-yl)imidazo[1,2-a]pyridin-2-yl)methyl)-1H-1,2,3-triazole-4-carboxylate (70 mg, 0.18 mmol) in THF (3 mL) and $H_2O$ (3 mL) was added $LiOH·H_2O$ (24 mg, 0.54 mmol) and the reaction mixture was stirred at RT for 15 h. The pH of the reaction was adjusted by HCl (1N) to 4, and then lyophilized to afforded crude 1-((6-cyclopropyl-8-(2-oxooxazolidin-3-yl)imidazo[1,2-a]pyridin-2-yl)methyl)-1H-1,2,3-triazole-4-carboxylic acid as white solid which was used directly for the next step without further purification (100 mg crude). ESI-MS $[M+H]^+$: 368.7.

Synthesis of N-((7-chloro-8-fluoroimidazo[1,5-a]pyridin-1-yl)methyl)-1-((6-cyclopropyl-8-(2-oxooxazolidin-3-yl)imidazo[1,2-a]pyridin-2-yl)methyl)-1H-1,2,3-triazole-4-carboxamide (I-216)

To the crude of 1-((6-cyclopropyl-8-(2-oxooxazolidin-3-yl)imidazo[1,2-a]pyridin-2-yl)methyl)-1H-1,2,3-triazole-4-carboxylic acid (100 mg, crude from previous step) in DMF (4 mL) was added (7-chloro-8-fluoroimidazo[1,5-a]pyridin-1-yl)methanamine hydrochloride (43 mg, 0.18 mmol), DIPEA (47.1 mg, 0.36 mmol) and HATU (101.4 mg, 0.27 mmol) in sequence. The mixture was stirred at RT for 3.5 h. The reaction was diluted with $H_2O$ (30 mL), extracted with EtOAc (30 mL×3). The combined organic layers were washed with brine, dried over $Na_2SO_4$, concentrated to give the crude, which was purified by prep-HPLC to afford N-((7-chloro-8-fluoroimidazo[1,5-a]pyridin-1-yl)methyl)-1-((6-cyclopropyl-8-(2-oxooxazolidin-3-yl)imidazo[1,2-a]pyridin-2-yl)methyl)-1H-pyrazole-4-carboxamide as a white solid (24.1 mg, 24% over 2 steps). ESI-MS $[M+H]^+$: 549.5. Purity: 98.29 (214 nm) 97.72 (254 nm). $^1$H NMR (400 MHz, DMSO-$d_6$) δ 8.72 (s, 1H), 8.56 (s, 1H), 8.45 (s, 1H), 8.34 (s, 1H), 8.20 (d, J=7.4 Hz, 1H), 7.93 (s, 1H), 7.35 (s, 1H), 6.76 (t, J=6.8 Hz, 1H), 5.78 (s, 2H), 4.70 (d, J=5.4 Hz, 2H), 4.49 (t, J=7.7 Hz, 2H), 4.35 (t, J=7.8 Hz, 2H), 1.96 (s, 1H), 0.98-0.92 (m, 2H), 0.70-0.65 (m, 2H).

Example 217

Scheme 216

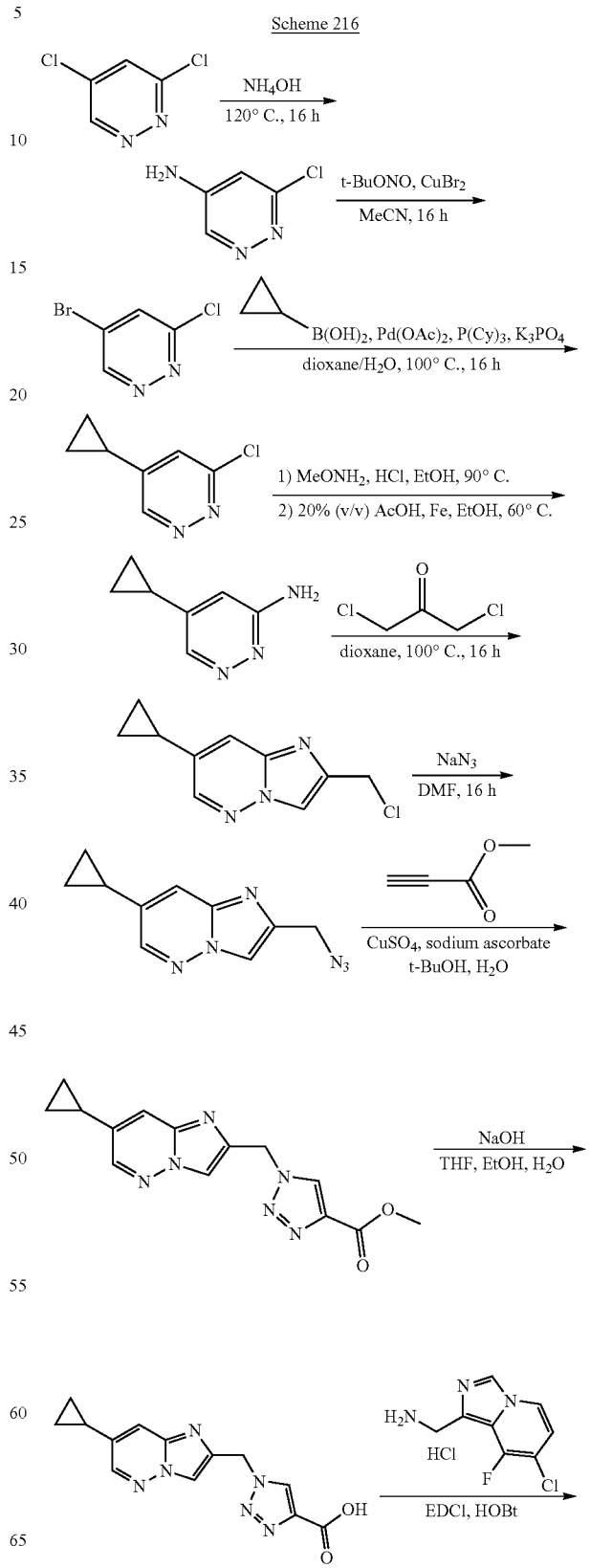

-continued

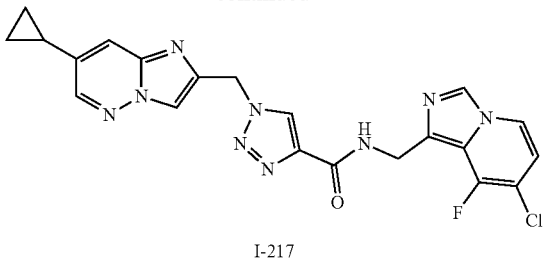

I-217

Synthesis of 6-chloropyridazin-4-amine

A solution of 3,5-dichloropyridazine (9 g, 60.8 mmol) in NH$_4$OH (25%, 100 mL) was stirred at 120° C. for 16 h in sealed tube. Then the mixture was concentrated in vacuo and triturated with ether to give the 6-chloropyridazin-4-amine as a brown solid (7.3 g, yield: 93%). ESI-MS [M+H]$^+$: 130.0.

Synthesis of 5-bromo-3-chloropyridazine

To a solution 6-chloropyridazin-4-amine (2 g, 15 mmol), t-BuONO (2.4 g, 23 mmol) in MeCN (40 mL) was added CuBr$_2$ (5 g, 23 mmol) at 0° C. The resulting mixture was stirred at RT for 16 h and then concentrated in vacuo. The mixture was diluted with EtOAc (50 mL) and added H$_2$O (50 mL). After filtered through celite, the filtrate was extracted with EtOAc (50 mL×3). The combined organic layers were washed with brine, dried over Na$_2$SO$_4$, and concentrated to give the crude product which was purified by silica gel chromatography (PE/EA=20/1) to give 5-bromo-3-chloropyridazine (1.32 g, yield: 43%) as a brown oil. ESI-MS [M+H]$^+$: 192.8, 194.8.

Synthesis of 3-chloro-5-cyclopropylpyridazine

To a mixture of 5-bromo-3-chloropyridazine (1.3 g, 6.7 mmol), Pd(OAc)$_2$ (156 mg, 0.67 mmol), P(Cy)$_3$ (196 mg, 0.67 mmol), K$_3$PO$_4$ (2.9 g, 13.4 mmol) in dioxane/H$_2$O (30 mL/8 mL) was added cyclopropylboronic acid (1.1 g, 13.4 mmol) at RT and stirred at 100° C. for 16 h. The mixture was concentrated and purified by silica gel chromatography (PE/EA=5/1) to give 3-chloro-5-cyclopropylpyridazine (280 mg, yield: 27%) as a brown oil. ESI-MS [M+H]$^+$: 155.1

Synthesis of 5-cyclopropylpyridazin-3-amine

A mixture of 3-chloro-5-cyclopropylpyridazine (500 mg, 3.2 mmol), CH$_3$ONH$_2$—HCl (531 mg, 6.4 mmol) in EtOH (20 mL) was stirred 90° C. for 16 h. After concentrated under reduced pressure, to the mixture was added Fe powder (900 mg, 16 mmol), 20% AcOH (10 mL) in EtOH (20 mL). The mixture was stirred 60° C. for 6 h and then neutralized by aqueous NaHCO$_3$. After filtered through celite, the mixture was extracted with EtOAc (60 mL*3). The combined organic layers were washed with brine, dried over Na$_2$SO$_4$, and concentrated to give the crude product which was purified by silica gel chromatography (PE/EA=3/1) to give 5-cyclopropylpyridazin-3-amine (180 mg, yield: 41%) as a brown solid. ESI-MS [M+H]$^+$: 136.0.

Synthesis of 2-(chloromethyl)-7-cyclopropylimidazo[1,2-b]pyridazine

To a solution of 5-cyclopropylpyridazin-3-amine (400 mg, 3 mmol) in dioxane (10 mL) was added 1,3-dichloropropan-2-one (780 mg, 6 mmol) at RT. The reaction mixture was stirred at 100° C. for 16 h and then neutralized by aqueous NaHCO$_3$. Water (20 mL) was added and the mixture was extracted with DCM (50 mL×2). The combined organic layers were concentrated and purified by silica gel chromatography (PE/EA=4/1) to give 2-(chloromethyl)-7-cyclopropylimidazo[1,2-b]pyridazine (160 mg, yield: 26%) as a brown solid. ESI-MS [M+H]$^+$: 207.9.

Synthesis of 2-(azidomethyl)-7-cyclopropylimidazo[1,2-b]pyridazine

A solution of ethyl 2-(chloromethyl)-7-cyclopropylimidazo[1,2-b]pyridazine (160 mg, 0.77 mmol) in DMF (5 mL) was added NaN$_3$ (97 mg, 1.5 mmol) at and stirred at RT for 10 h. The reaction was diluted with H$_2$O (30 mL) and extracted with DCM (50 mL×3). The combined organic layers were concentrated and purified by silica gel chromatography (PE/EA=4/1) to give 2-(azidomethyl)-7-cyclopropylimidazo[1,2-b]pyridazineine (140 mg, yield: 85%) as a white solid. ESI-MS [M+H]$^+$: 215.1.

Synthesis of Methyl 1-((7-cyclopropylimidazo[1,2-b]pyridazin-2-yl)methyl)-1H-1,2,3-triazole-4-carboxylate A mixture of 2-(azidomethyl)-7-cyclopropylimidazo[1,2-b]pyridazineine (140 mg, 0.65 mmol), methyl propiolate (84 mg, 1 mmol), CuSO$_4$.5H$_2$O (35 mg, 0.14 mmol), sodium ascorbate (40 mg, 0.2 mmol) in t-BuOH/H$_2$O (4 mL/4 mL) was stirred at RT for 16 h. The mixture was concentrated in vacuo to give the crude product which was purified by silica gel chromatography (PE/EA=1/4) to give methyl 1-((7-cyclopropylimidazo[1,2-b]pyridazin-2-yl)methyl)-1H-1,2,3-triazole-4-carboxylate (180 mg, yield: 88%) as a white solid. ESI-MS [M+H]$^+$: 312.9.

Synthesis of 1-((7-cyclopropylimidazo[1,2-b]pyridazin-2-yl)methyl)-1H-1,2,3-triazole-4-carboxylic Acid A mixture of 1-((7-cyclopropylimidazo[1,2-b]pyridazin-2-yl)methyl)-1H-1,2,3-triazole-4-carboxylate (180 mg, 0.58 mmol), NaOH (48 mg, 1.2 mmol) in THF/EtOH/H$_2$O (4 mL/4 mL/4 mL) was stirred at RT for 0.5 h. The mixture was acidified with 1N HCl solution, concentrated in vacuo to give the crude product of methyl 1-((7-cyclopropylimidazo[1,2-b]pyridazin-2-yl)methyl)-1H-1,2,3-triazole-4-carboxylic acid (250 mg, crude) as a white solid. ESI-MS [M+H]$^+$: 285.0.

Synthesis of N-((7-chloro-8-fluoroimidazo[1,5-a]pyridin-1-yl)methyl)-1-((7-cyclopropylimidazo[1,2-b]pyridazin-2-yl)methyl)-1H-1,2,3-triazole-4-carboxamide (I-217)

A mixture of 1-((7-cyclopropylimidazo[1,2-b]pyridazin-2-yl)methyl)-1H-1,2,3-triazole-4-carboxylic acid (125 mg, crude), (7-chloro-8-fluoroimidazo[1,5-a]pyridin-1-yl)methanamine hydrochloride (118 mg, 0.5 mmol), EDCI (105 mg, 0.55 mmol), HOBT (74 mg, 0.55 mmol), DIPEA (161 mg, 1.25 mmol) in DMF (5 mL) was stirred at RT for 16 h. The reaction was poured into H$_2$O (30 mL), solid was filtered and washed by H$_2$O (10 mL), EtOAc (10 mL), ether (10 mL) to give 2-(azidomethyl)-7-cyclopropylimidazo [1,2-b]pyridazineine (20 mg) as a white solid. ESI-MS [M+H]$^+$: 466.8. Purity: 96.85 (214 nm), 97.30 (254 nm). $^1$H NMR (400 MHz, CDCl$_3$) δ 8.24 (s, 1H), 8.16 (s, 1H), 8.08 (s, 1H), 7.86 (s, 1H), 7.66-7.64 (m, 2H), 7.45 (s, 1H), 6.51 (t, J=6.6 Hz, 1H), 5.72 (s, 2H), 4.95 (d, J=5.1 Hz, 2H), 2.00-1.91 (m, 1H), 1.17-1.12 (m, 2H), 0.85-0.81 (m, 2H).

Example 218

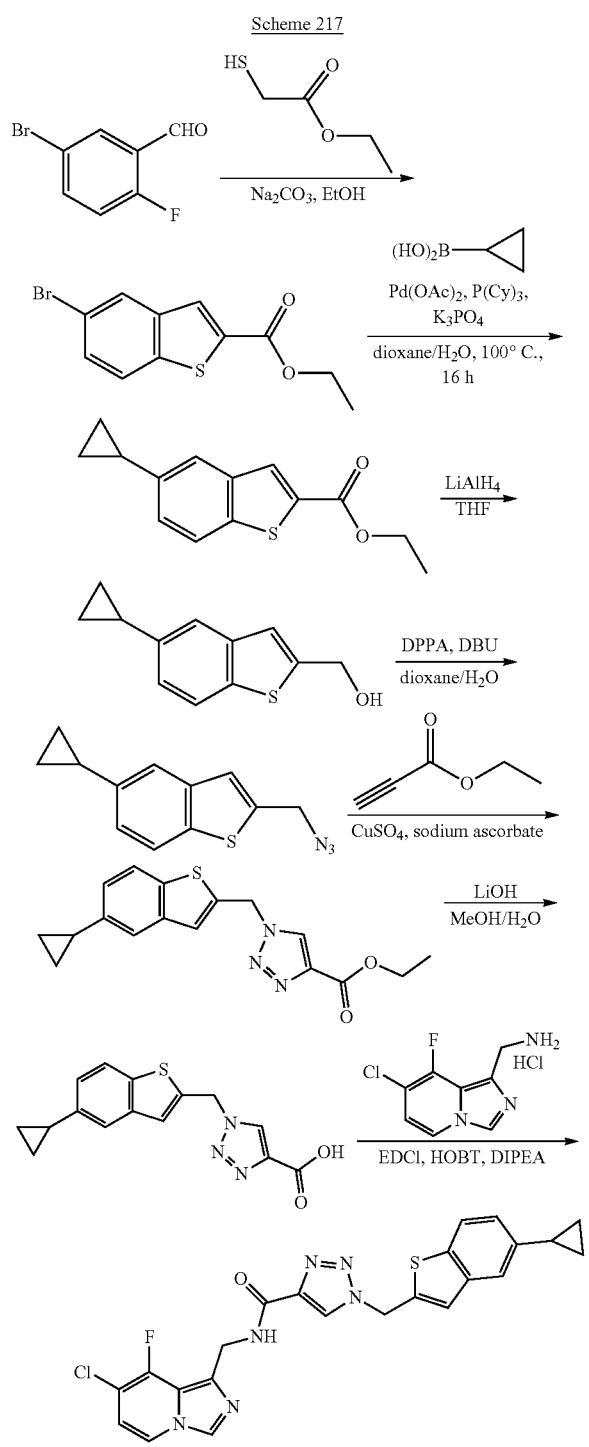

I-218

Synthesis of Ethyl 5-bromobenzo[b]thiophene-2-carboxylate

To a solution of 5-bromo-2-fluorobenzaldehyde (2.03 g, 10 mmol) and ethyl 2-mercaptoacetate (1.2 g, 10 mmol) in EtOH (40 mL) was added Na$_2$CO$_3$ (1.27 g, 12 mmol). The reaction mixture was stirred at reflux for 14 h. Then the mixture was concentrated in vacuo. Water (20 mL) was added and the mixture was extracted with DCM (50 mL×3). The combined organic layers were concentrated to give the crude product, which was purified by silica gel chromatography (PE/EtOAc=1/1) to give the ethyl 5-bromobenzo[b] thiophene-2-carboxylate as a yellow solid (2.3 g, yield: 80%). ESI-MS [M+H]$^+$: 284.7, 286.7.

Synthesis of Ethyl 5-cyclopropylbenzo[b]thiophene-2-carboxylate

A solution of 5-bromobenzo[b]thiophene-2-carboxylate (2.3 g, 8 mmol), cyclopropylboronic acid (1.7 g, 20 mmol), Pd(OAc)$_2$ (180 mg, 0.8 mmol), PCy$_3$ (448 mg, 1.6 mmol) and K$_3$PO$_4$ (4.24 g, 20 mmol) in toluene (40 mL)/MeOH (4 mL)/H$_2$O (4 mL) was stirred under reflux in nitrogen atmosphere overnight. The reaction mixture was concentrated to give a residue. The residue was diluted with H$_2$O (30 mL) and extracted with EtOAc (50 mL×3). The combined organic layers were washed with brine (20 mL), dried over Na$_2$SO$_4$, filtered and concentrated to give the crude product which was purified by flash column chromatography (PE/EA=10/1) to give the product ethyl 5-cyclopropylbenzo [b]thiophene-2-carboxylate (730 mg, 37%) as a light yellow solid. ESI-MS [M+H]$^+$: 246.9.

Synthesis of (5-cyclopropylbenzo[b]thiophen-2-yl) methanol

To a stirring solution of 5-cyclopropylbenzo[b]thiophene-2-carboxylate (180 mg, 0.73 mmol) in dry THF (15 mL) was added portion-wise LiAlH$_4$ (84 mg, 2.19 mmol) under ice H$_2$O bath. The resulting mixture was stirred at 0° C. for 1 h. The reaction was quenched sequentially with H$_2$O (0.5 mL), 15% NaOH (0.5 mL) and H$_2$O (1.5 mL). The resulting mixture was filtered and the filtrate was concentrated to give the crude product (5-cyclopropylbenzo[b]thiophen-2-yl) methanol (130 mg) as a light yellow oil which was used into next step directly. ESI-MS [M+H]$^+$: 205.0

Synthesis of 2-(azidomethyl)-5-cyclopropylbenzo[b] thiophene

To a stirring solution of (5-cyclopropylbenzo[b]thiophen-2-yl)methanol (130 mg, 0.64 mmol) and DPPA (211 mg, 0.77 mmol) in dry THF (20 mL) was added DBU (116 mg, 0.77 mmol) under ice H$_2$O bath. The resulting mixture was stirred at RT overnight. The reaction mixture was concentrated to give a residue which was purified by flash column chromatography (DCM/MeOH=20/1) to give the product 2-(azidomethyl)-5-cyclopropylbenzo[b]thiophene (120 mg, 82%) as a light yellow oil. ESI-MS [M+H]$^+$: 230.0.

Synthesis of Ethyl 1-((5-cyclopropylbenzo[b]thiophen-2-yl)methyl)-1H-1,2,3-triazole-4-carboxylate A solution of 2-(azidomethyl)-5-cyclopropylbenzo[b] thiophene (120 mg, 0.52 mmol) in t-BuOH (3 mL) and H$_2$O (3 mL) was added sequentially of CuSO$_4$-5H$_2$O (26 mg, 0.104 mmol), sodium ascorbate (25 mg, 0.123 mmol) and ethyl propiolate (101 mg, 1.04 mmol). The resulting mixture was stirred at RT for 15 h. The reaction mixture was concentrated to give the crude product. The crude product was purified by flash column chromatography (DCM/MeOH=20/1) to give the product ethyl 1-((5-cyclopropyl-benzo[b]thiophen-2-yl)methyl)-1H-1,2,3-triazole-4-carboxylate (80 mg, 47%) as a light yellow oil. ESI-MS [M+H]$^+$: 327.8

Synthesis of 1-((5-cyclopropylbenzo[b]thiophen-2-yl)methyl)-1H-1,2,3-triazole-4-carboxylic Acid A solution of ethyl 1-((5-cyclopropylbenzo[b]thiophen-2-yl)methyl)-1H-1,2,3-triazole-4-carboxylate (80 mg, 0.24 mmol) and LiOH.H$_2$O (29 mg, 0.72 mmol) in MeOH/H$_2$O (5 mL/5 mL) was stirred at RT for 2 h. The volatile was removed in vacuo and the aqueous phase was acidified to pH 4-5 with 2N HCl. Concentrated in vacuo to give the crude product 1-((5-cyclopropylbenzo[b]thiophen-2-yl)methyl)-1H-1,2,3-triazole-4-carboxylic acid (100 mg, crude) as a yellow solid, which used directly in the next step without further purification. ESI-MS [M+H]$^+$: 299.8.

Synthesis of N-((7-chloro-8-fluoroimidazo[1,5-a]pyridin-1-yl)methyl)-1-((5-cyclopropylbenzo[b]thiophen-2-yl)methyl)-1H-1,2,3-triazole-4-carboxamide (I-218)

To a solution of 1-((5-cyclopropylbenzo[b]thiophen-2-yl)methyl)-1H-1,2,3-triazole-4-carboxylic acid (100 mg, crude), (7-chloro-8-fluoroimidazo[1,5-a]pyridin-1-yl)methanamine (100 mg, 0.17), EDCI (38 mg, 0.2 mmol) and HOBT (27 mg, 0.2 mmol) in DMF (5 mL) was added DIPEA (64 mg, 0.5 mmol). The resulting mixture was stirred at RT for 15 h. The reaction mixture was diluted with H$_2$O (30 mL). Then it was extracted with EtOAc (30 mL*3). The combined organic layer was washed with brine, dried over Na$_2$SO$_4$ and concentrated. The residue was purified by flash column chromatography (DCM/MeOH=10/1) to give the product N-((7-chloro-8-fluoroimidazo[1,5-a]pyridin-1-yl)methyl)-1-((5-cyclopropylbenzo[b]thiophen-2-yl)methyl)-1H-1,2,3-triazole-4-carboxamide (17 mg, yield: 20%) as a white solid. ESI-MS [M+H]$^+$: 481.1 Purity: 96.52 (214 nm), 96.66 (254 nm). $^1$H NMR (400 MHz, DMSO-d$_6$) δ 8.76 (s, 1H), 8.67 (s, 1H), 8.45 (s, 1H), 8.21 (d, J=7.1 Hz, 1H), 7.78 (d, J=8.1 Hz, 1H), 7.55 (s, 1H), 7.39 (s, 1H), 7.09 (d, J=7.7 Hz, 1H), 6.76 (s, 1H), 5.97 (s, 2H), 4.71 (s, 2H), 2.06-1.96 (m, 1H), 1.03-0.92 (m, 2H), 0.75-0.66 (m, 2H).

Example 219

Scheme 218

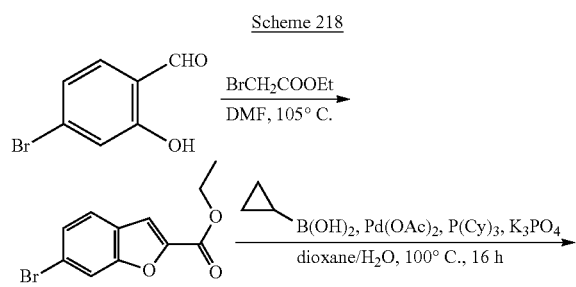

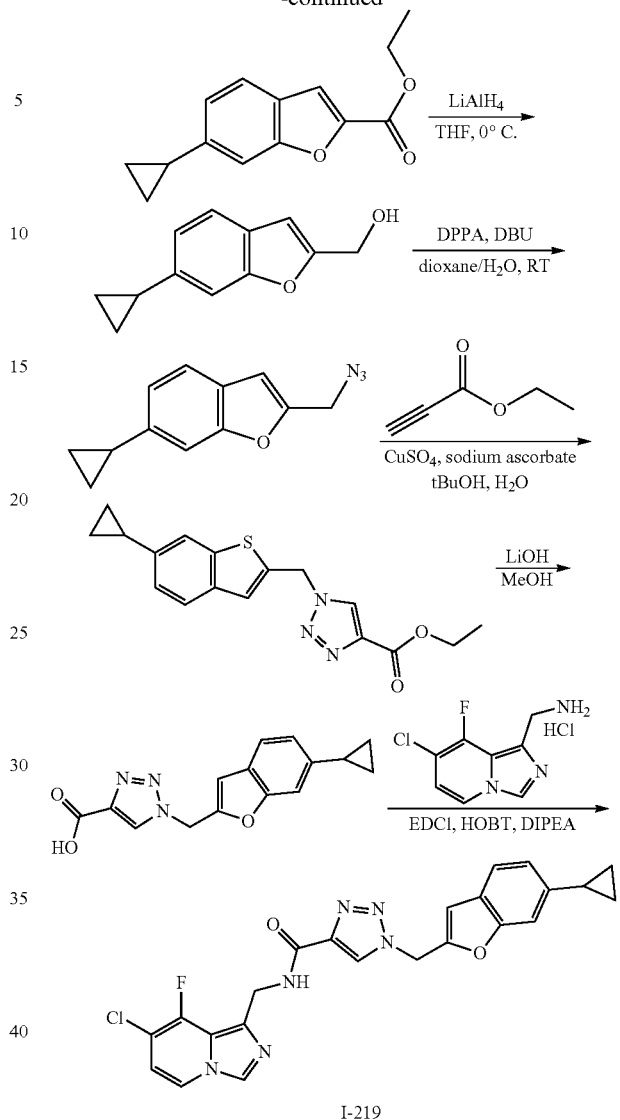

I-219

Synthesis of Ethyl 6-bromobenzofuran-2-carboxylate

A solution of 4-bromo-2-hydroxybenzaldehyde (2.01 g, 10 mmol) and ethyl 2-bromoacetate (1.9 g, 12 mmol) in DMF (20 mL). The reaction mixture was stirred at 75° C. overnight. Then the mixture was concentrated in vacuo. Water (50 mL) was added and the mixture was extracted with DCM (50 mL×3). The combined organic layer was washed with brine, dried over Na$_2$SO$_4$ and concentrated to give the crude product which was purified by silica gel chromatography (PE/EtOAc=1/1) to give ethyl 6-bromobenzofuran-2-carboxylate as a yellow solid (1.6 g, yield: 59%). ESI-MS [M+H]$^+$: 268.7, 270.7.

Synthesis of Ethyl Ethyl 6-cyclopropylbenzofuran-2-carboxylate

A mixture of ethyl 6-bromobenzofuran-2-carboxylate (800 mg, 3 mmol), cyclopropylboronic acid (638 g, 7.5 mmol), Pd(OAc)$_2$ (67.5 mg, 0.3 mmol), PCy$_3$ (138 mg, 0.6 mmol) and K₃PO₄ (1.59 g, 7.5 mmol) in dioxane (20 mL) and H₂O (2 mL) was stirred under reflux in nitrogen atmosphere overnight. The reaction mixture was diluted with H₂O (50 mL), then extracted with EtOAc (50 mL×3). The combined organic layers were washed with brine, dried over Na₂SO₄ and concentrated. The crude product was purified by flash column chromatography (PE/EA=10/1) to give ethyl ethyl 6-cyclopropylbenzofuran-2-carboxylate (360 mg, 52%) as a light yellow solid. ESI-MS [M+H]⁺: 230.9.

Synthesis of (5-cyclopropylbenzo[b]thiophen-2-yl) methanol

To a stirring solution of ethyl 6-cyclopropylbenzofuran-2-carboxylate (360 mg, 1.56 mmol) in dry THF (15 mL) was added portion-wise LiAlH₄ (177 mg, 4.68 mmol) under ice H₂O bath. The resulting mixture was stirred at 0° C. for 1 h. The reaction was quenched sequentially with H₂O (0.2 mL), 15% NaOH (0.2 mL) and H₂O (0.6 mL). The resulting mixture was filtered and the filtrate was concentrated to give (6-cyclopropylbenzofuran-2-yl)methanol (280 mg, crude) as a light yellow oil which was used for next step directly. ESI-MS [M+H]⁺: 171.0

Synthesis of 2-(azidomethyl)-6-cyclopropylbenzofuran

To a stirring solution of (6-cyclopropylbenzofuran-2-yl) methanol (280 mg, crude) and DPPA (493 mg, 1.8 mmol) in dry THF (20 mL) was added DBU (271 mg, 1.8 mmol) under ice H₂O bath. The resulting mixture was stirred at RT overnight. The reaction mixture was diluted with H₂O (30 mL) and extracted with EtOAc (30 mL×3). The combined organic layers were washed with brine, dried over Na₂SO₄ and concentrated. The residue was purified by flash column chromatography (DCM/MeOH=20/1) to give 2-(azidomethyl)-6-cyclopropylbenzofuran (228 mg, 68% over 2 steps) as a pale-yellow oil. ESI-MS [M+H]⁺: 214.0.

Synthesis of Ethyl 1-((6-cyclopropylbenzofuran-2-yl)methyl)-1H-1,2,3-triazole-4-carboxylate A solution of 2-(azidomethyl)-6-cyclopropylbenzofuran (228 mg, 1.07 mmol) in t-BuOH (3 mL) and H₂O (3 mL) was added sequentially of CuSO₄·5H₂O (53 mg, 0.214 mmol), sodium ascorbate (55 mg, 0.270 mmol) and ethyl propiolate (2.07 mg, 2.14 mmol). The resulting mixture was stirred at RT for 15 h. The reaction mixture was diluted with H₂O (50 mL). Then it was extracted with EtOAc (50 mL×3). The combined organic layers were washed with brine, dried over Na₂SO₄ and concentrated. The crude product which was purified by flash column chromatography (DCM/MeOH=20/1) to give ethyl 1-((6-cyclopropylbenzofuran-2-yl)methyl)-1H-1,2,3-triazole-4-carboxylate (140 mg, 42%) as a light yellow oil. ESI-MS [M+H]⁺: 311.8

Synthesis of 1-((6-cyclopropylbenzofuran-2-yl) methyl)-1H-1,2,3-triazole-4-carboxylic Acid A solution of ethyl 1-((6-cyclopropylbenzofuran-2-yl) methyl)-1H-1,2,3-triazole-4-carboxylate (140 mg, 0.45 mmol) and LiOH·H₂O (54 mg, 1.35 mmol) in MeOH/H₂O (10 mL/10 mL) was stirred at RT for 2 h. The volatiles were removed in vacuo and the aqueous phase was acidified to pH 4-5 with 2N HCl, then concentrated in vacuo to give 1-((6-cyclopropylbenzofuran-2-yl)methyl)-1H-1,2,3-triaz-ole-4-carboxylic acid (200 mg, crude) as a yellow solid, which was used directly in the next step without further purification. ESI-MS [M+H]⁺: 300.1

Synthesis of N-((7-chloro-8-fluoroimidazo[1,5-a] pyridin-1-yl)methyl)-1-((6-cyclopropylbenzofuran-2-yl)methyl)-1H-1,2,3-triazole-4-carboxamide (I-218)

To a solution of 1-((6-cyclopropylbenzofuran-2-yl) methyl)-1H-1,2,3-triazole-4-carboxylic acid (200 mg, crude), (7-chloro-8-fluoroimidazo[1,5-a]pyridin-1-yl)meth-anamine hydrochloride (100 mg, 0.42), EDCI (93 mg, 0.5 mmol) and HOBT (68 mg, 0.5 mmol) in DMF (5 mL) was added DIPEA (80 mg, 1.25 mmol). The resulting mixture was stirred at RT for 15 h. The reaction mixture was diluted with H₂O (30 mL), then extracted with EtOAc (50 mL×3). The combined organic layers were washed with brine, dried over Na₂SO₄ and concentrated. The residue was purified by flash column chromatography (DCM/MeOH=10/1) to give N-((7-chloro-8-fluoroimidazo[1,5-a]pyridin-1-yl)methyl)-1-((6-cyclopropylbenzofuran-2-yl)methyl)-1H-1,2,3-triaz-ole-4-carboxamide (17 mg, 8.7%) as a white solid. ESI-MS [M+H]⁺: 464.7. Purity: 98.95 (214 nm), 98.84 (254 nm). ¹H NMR (400 MHz, DMSO-d₆) δ 8.75 (s, 1H), 8.62 (s, 1H), 8.44 (s, 1H), 8.21 (d, J=7.4 Hz, 1H), 7.49 (d, J=8.1 Hz, 1H), 7.23 (s, 1H), 7.02 (d, J=8.1 Hz, 1H), 6.96 (s, 1H), 6.76 (t, J=6.7 Hz, 1H), 5.87 (s, 2H), 4.70 (d, J=5.1 Hz, 2H), 2.04-1.94 (m, 1H), 0.99-0.91 (m, 2H), 0.73-0.66 (m, 2H).

Example 220

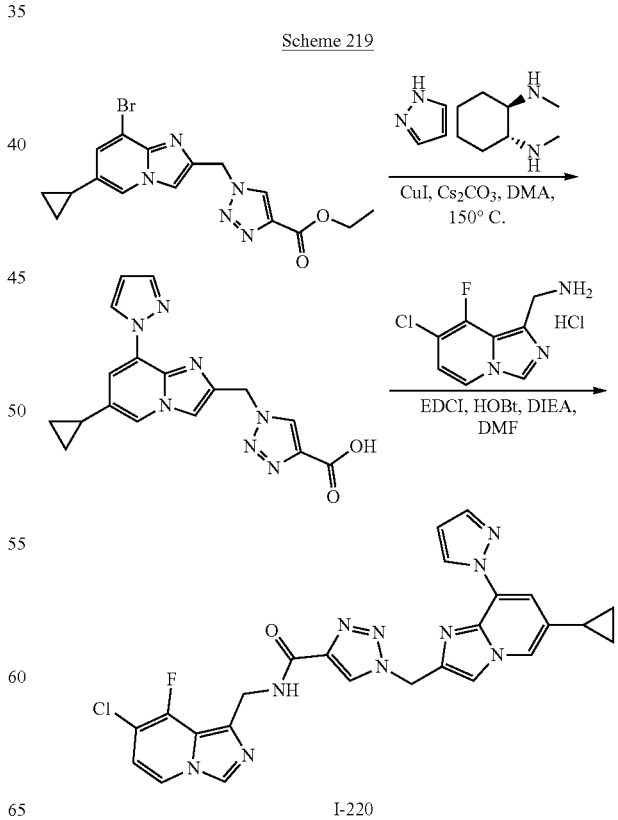

Synthesis of 1-((6-cyclopropyl-8-(1H-pyrazol-1-yl)imidazo[1,2-a]pyridin-2-yl)methyl)-1H-1,2,3-triazole-4-carboxylic Acid A mixture of ethyl 1-((8-bromo-6-cyclopropylimidazo[1,2-a]pyridin-2-yl)methyl)-1H-1,2,3-triazole-4-carboxylate (300 mg, 0.77 mmol), 1H-pyrazole (130 mg, 1.93 mmol), CuI (15 mg, 0.077 mmol), (1R,2R)—N1,N2-dimethylcyclohexane-1,2-diamine (22 mg, 0.154 mmol) and $Cs_2CO_3$ (550 mg, 1.70 mmol) in DMA (5 mL) was degassed by N2 for 10 min in a sealed tube. The reaction mixture was stirred at 150° C. for 12 h. Then the mixture was poured into 30 mL of $H_2O$, extracted with EtOAc (30 mL×3). The combined organic layers were washed with brine, dried over $Na_2SO_4$, concentrated in vacuo to give 1-((6-cyclopropyl-8-(H-pyrazol-1-yl)imidazo[1,2-a]pyridin-2-yl)methyl)-1H-1,2,3-triazole-4-carboxylic acid (300 mg, crude) which was used in next step without further purification. ESI-MS [M+H]$^+$: 349.8.

Synthesis of N-((7-chloro-8-fluoroimidazo[1,5-a]pyridin-1-yl)methyl)-1-((6-cyclopropyl-8-(1H-pyrazol-1-yl)imidazo[1,2-a]pyridin-2-yl)methyl)-1H-1,2,3-triazole-4-carboxamide (I-220)

To a solution of 1-((6-cyclopropyl-8-(H-pyrazol-1-yl)imidazo[1,2-a]pyridin-2-yl)methyl)-1H-1,2,3-triazole-4-carboxylic acid (300 mg, crude from previous step) in DMF (5 mL) was added EDCI (145 mg, 0.756 mmol), HOBT (103 mg, 0.756 mmol), DIPEA (0.32 mL, 1.72 mmol) and (7-chloro-8-fluoroimidazo[1,5-a]pyridin-1-yl)methanamine hydrochloride (179 mg, 0.756 mmol). The reaction mixture was stirred at RT for 12 h. The mixture was poured into 20 mL of $H_2O$, extracted with EtOAc (30 mL×3). The combined organic layers were washed with brine, dried over $Na_2SO_4$, and concentrated to give the crude product which was purified by prep-HPLC to give N-((7-chloro-8-fluoroimidazo[1,5-a]pyridin-1-yl)methyl)-1-((6-cyclopropyl-8-(1H-pyrazol-1-yl)imidazo[1,2-a]pyridin-2-yl)methyl)-1H-1,2,3-triazole-4-carboxamide (36 mg, 9% over 2 steps) as a white solid. ESI-MS [M+H]$^+$: 530.8. Purity: 97.94 (214 nm) 97.53 (254 nm). $^1$H NMR (400 MHz, DMSO-$d_6$) S=9.28 (s, 1H), 8.73 (t, J=4.0 Hz, 1H), 8.63 (s, 1H), 8.47 (s, 1H), 8.40 (s, 1H), 8.21 (d, J=4.0 Hz, 1H), 8.02 (s, 1H), 7.85 (s, 1H), 7.66 (s, 1H), 6.77 (t, J=4.0 Hz, 1H), 6.60 (s, 1H), 5.84 (s, 2H), 4.70 (d, J=4.0 Hz, 2H), 1.24-1.21 (m, 1H), 0.98 (dd, J=8.0, 4.0 Hz, 2H), 0.74 (dd, J=8.0, 4.0 Hz, 2H).

Example 221

Scheme 220

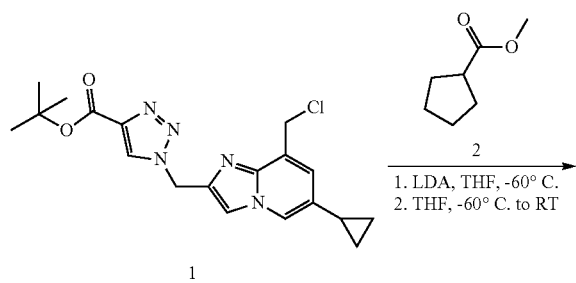

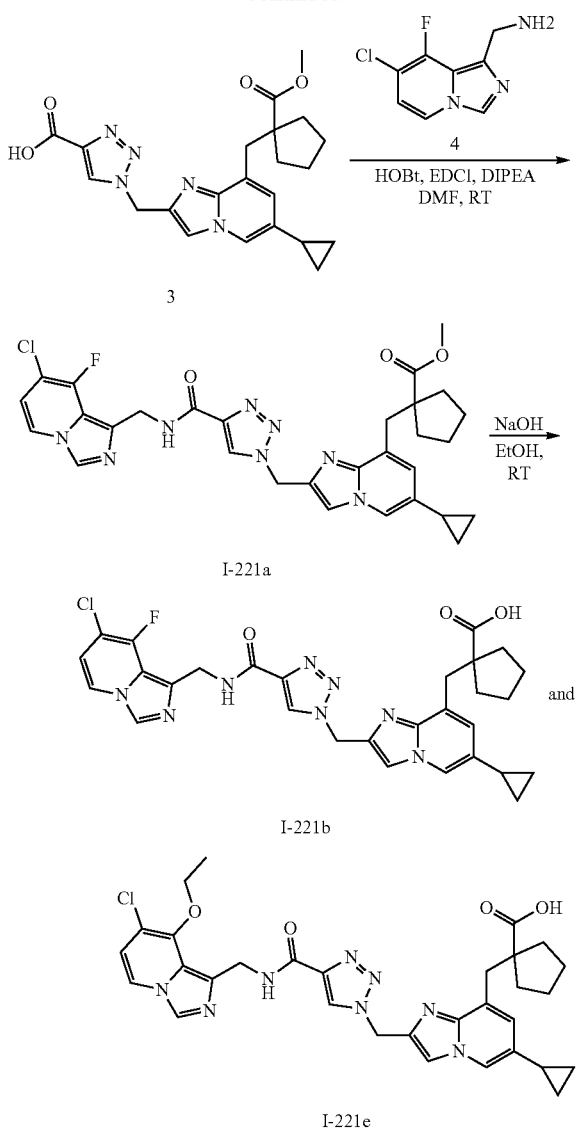

Synthesis of 1-((6-cyclopropyl-8-((1-methoxycarbonyl)cyclopentyl)methyl)imidazo[1,2-a]pyridin-2-yl)methyl)-1H-1,2,3-triazole-4-carboxylic Acid To a mixture of methyl cyclopentanecarboxylate (330 mg, 2.58 mmol) in THF (10 mL) was added LDA (2.0 M, 1.48 mL, 2.967 mmol) dropwise at −78° C. and the mixture was stirred at −78° C. for 4 h. tert-butyl 1-((8-(chloromethyl)-6-cyclopropylimidazo[1,2-a]pyridin-2-yl)methyl)-1H-1,2,3-triazole-4-carboxylate (500 mg, 1.29 mmol) in THF (5 mL) was added to the reaction mixture dropwise. The resulting reaction mixture was warmed to RT and stirred at RT for 2 h. $NH_4Cl$ aq. added to the reaction mixture and extracted with EtOAc (30 mL×3). The organic layers were washed by brine, dried over $Na_2SO_4$ and concentrated to afford 1-((6-cyclopropyl-8-((1-(methoxycarbonyl)cyclopentyl)methyl)imidazo[1,2-a]pyridin-2-yl)methyl)-1H-1,2,3-triazole-4-carboxylic acid (157 mg, yield: 29%) which was used in next step directly. ESI-MS [M+H]$^+$: 424.1

Synthesis of Methyl 1-((2-((4-(((7-chloro-8-fluoro-imidazo[1,5-a]pyridin-1-yl)methyl)carbamoyl)-1H-1,2,3-triazol-1-yl)methyl)-6-cyclopropylimidazo[1,2-a]pyridin-8-yl)methyl)cyclopentane-1-carboxylate (I-221a)

A solution of 1-((6-cyclopropyl-8-((1-(methoxycarbonyl)cyclopentyl)methyl)imidazo[1,2-a]pyridin-2-yl)methyl)-1H-1,2,3-triazole-4-carboxylic acid (157 mg, 0.37 mmol), (7-chloro-8-fluoroimidazo[1,5-a]pyridin-1-yl)methanamine hydrochloride (113 mg, 0.48 mmol), HOBT (100 mg, 0.74 mmol), EDCI (142 mg, 0.74 mmol) and DIPEA (239 mg, 1.85 mmol) in DMF (5 mL) was stirred at RT for 16 h. The reaction mixture was diluted with H$_2$O (50 mL). Then it was extracted with EtOAc (50 mL×3). The combined organic layers were washed with brine, dried over Na$_2$SO$_4$ and concentrated. The residue was purified by Prep-TLC (DCM:MeOH=10:1) to give methyl 1-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)cyclopentane-1-carboxylate (102 mg, 46%). ESI-MS [M+H]$^+$: 605.2. Purity: 98.88 (214 nm), 98.20 (254 nm). $^1$H NMR (400 MHz, DMSO-d$_6$) δ 8.67 (t, J=6.0 Hz, 1H), 8.50 (s, 1H), 8.44 (d, J=4 Hz, 1H), 8.22-8.19 (m, 1H), 7.79 (s, 1H), 6.78-6.74 (m, 1H), 6.61 (d, J=4.0 Hz, 1H), 5.71 (s, 2H), 4.70 (d, J=4.0 Hz, 1H), 3.50 (s, 3H), 3.17-3.16 (m, 4H), 1.91-1.86 (m, 3H), 1.63-1.62 (s, 4H), 0.93-0.89 (m, 2H), 0.62-0.58 (m, 2H).

Synthesis of 1-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)cyclopentane-1-carboxylic acid (I-221b) and 1-((2-((4-(((7-chloro-8-ethoxyimidazo[1,5-a]pyridin-1-yl)methyl)carbamoyl)-1H-1,2,3-triazol-1-yl)methyl)-6-cyclopropylimidazo[1,2-a]pyridin-8-yl)methyl)cyclopentane-1-carboxylic acid (I-221c)

A solution of methyl 1-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)cyclopentane-1-carboxylate (91 mg, 0.15 mmol) and NaOH (20 mg, 0.45 mmol) in EtOH (3 mL) and H$_2$O (1 mL) was stirred at RT for 16 h. The solvent was removed under reduced pressure and the residue was purified by reversed phase flash chromatography (acetonitrile:H$_2$O=5% to 95%) to give 1-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)methyl)cyclopentane-1-carboxylic acid (50 mg, yield: 57%) and 1-((2-((4-(((7-chloro-8-ethoxyimidazo[1,5-a]pyridin-1-yl)methyl)carbamoyl)-1H-1,2,3-triazol-1-yl)methyl)-6-cyclopropylimidazo[1,2-a]pyridin-8-yl)methyl)cyclopentane-1-carboxylic acid. (7 mg, 8%). I-221b: ESI-MS [M+H]$^+$: 591.1. Purity: 96.55 (214 nm), 98.91 (254 nm). $^1$H NMR (400 MHz, DMSO-d$_6$) δ 8.68 (t, J=8.0 Hz, 1H), 8.51 (s, 1H), 8.44 (d, J=4 Hz, 1H), 8.21-8.19 (m, 2H), 7.78 (s, 1H), 6.76 (t, J=4.0 Hz, 1H), 6.71 (s, 1H) 5.72 (s, 2H), 4.70 (d, J=4.0 Hz, 2H), 3.17 (s, 2H), 1.91-1.83 (m, 3H), 1.55 (s, 5H), 0.91-0.88 (m, 2H), 0.60-0.58 (m, 2H). I-221c: ESI-MS [M+H]$^+$: 617.2. Purity: 99.56 (214 nm), 100.0 (254 nm). $^1$H NMR (400 MHz, DMSO-d$_6$) δ 12.35 (s, 1H), 8.53 (s, 1H), 8.42 (t, J=6.0 Hz, 1H), 8.37 (s, 1H), 8.21 (s, 1H), 8.13 (d, J=8.0 Hz, 1H), 7.78 (s, 1H), 6.71 (s, 1H), 6.67 (t, J=8.0 Hz, 1H), 5.73 (s, 2H), 4.76 (d, J=8.0 Hz, 2H), 4.23 (q, J=6.7 Hz, 2H), 3.18 (s, 2H), 1.92-1.83 (m, 3H), 1.60-1.50 (m, 6H), 1.40 (t, J=6.0 Hz, 3H), 0.93-0.88 (m, 2H), 0.62-0.58 (m, 2H).

Example 222

Scheme 221

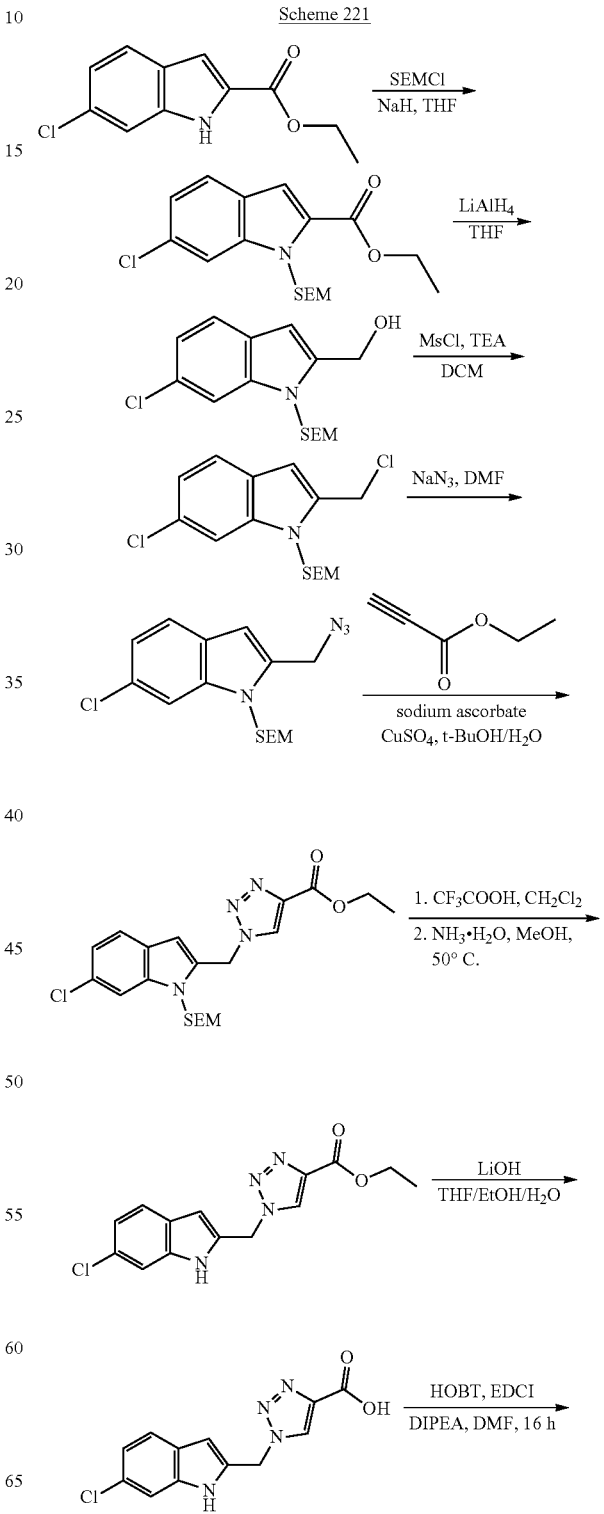

-continued

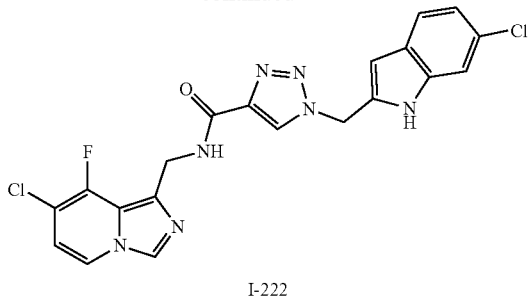 [SMILES: O=C(NCc1ncn2ccc(Cl)c(F)c12)c1cn(Cc2cc3ccc(Cl)cc3[nH]2)nn1]

I-222

Synthesis of Ethyl 6-chloro-1-((2-(trimethylsilyl)ethoxy)methyl)-1H-indole-2-carboxylate To a solution of ethyl 6-chloro-1H-indole-2-carboxylate (2 g, 8.9 mmol) in THF (15 mL) was added NaH (890 mg, 60 wt %, 13.35 mmol) portion-wise at 0° C. The mixture was stirred at RT for 1 h. SEMCl (1.6 g, 9.8 mmol) was added at 0° C. The reaction mixture was stirred at RT for 2 h. Quenched with $H_2O$ (50 mL) and extracted with EtOAc (50 mL×3), the combined organic layers were washed by brine, dried over $Na_2SO_4$, and concentrated to give ethyl 6-chloro-1-((2-(trimethylsilyl)ethoxy)methyl)-1H-indole-2-carboxylate (3 g, yield: 95%) as a yellow solid which was used in next step directly. ESI-MS [M+H]$^+$: 354.0.

Synthesis of (6-chloro-1-((2-(trimethylsilyl)ethoxy)methyl)-1H-indol-2-yl)methanol To a solution of LiAlH$_4$ (405 mg, 10 mmol) in THF (15 mL) was added ethyl 6-chloro-1-((2-(trimethylsilyl)ethoxy)methyl)-1H-indole-2-carboxylate (3 g, 8.5 mmol) in THF (15 mL) dropwise at 0° C. The reaction mixture was stirred at RT for 2 h, then quenched with $H_2O$ (2 mL) at 0° C. and filtered. The filtrate was concentrated to give (6-chloro-1-((2-(trimethylsilyl)ethoxy)methyl)-1H-indol-2-yl)methanol (2 g) as a brown oil, which was used into next step directly. ESI-MS [M+1]$^+$: 312.1

Synthesis of 6-chloro-2-(chloromethyl)-1-((2-(trimethylsilyl)ethoxy)methyl)-1H-indole A mixture of (6-chloro-1-((2-(trimethylsilyl)ethoxy)methyl)-1H-indol-2-yl)methanol (1.5 g, crude from last step), MsCl (826 mg, 7.2 mmol) and TEA (1.4 g, 14.4 mmol) in DCM (10 mL) was stirred at RT for 3 h. Water (50 mL) was added and extracted with DCM (50 mL×3), combined organic layers were concentrated to give 6-chloro-2-(chloromethyl)-1-((2-(trimethylsilyl)ethoxy)methyl)-1H-indole (1.5 g, crude) as a yellow solid.

Synthesis of 2-(azidomethyl)-6-chloro-1-((2-(trimethylsilyl)ethoxy)methyl)-1H-indole A mixture of 6-chloro-2-(chloromethyl)-1-((2-(trimethylsilyl)ethoxy)methyl)-1H-indole (1.5 g, crude from last step) and NaN$_3$ (374 mg, 5.76 mmol) in DMF (5 mL) was stirred at RT overnight. Water (50 mL) was added and extracted with EtOAc (50 mL×3). The combined organic layers were washed by brine (20 mL×2), dried over $Na_2SO_4$, concentrated. The residue was purified by silica gel (PE/EA=10/1) to give 2-(azidomethyl)-6-chloro-1-((2-(trimethylsilyl)ethoxy)methyl)-1H-indole (200 mg) as a yellow oil.

Synthesis of Ethyl 1-((6-chloro-1-((2-(trimethylsilyl)ethoxy)methyl)-1H-indol-2-yl)methyl)-1H-1,2,3-triazole-4-carboxylate A mixture of 2-(azidomethyl)-6-chloro-1-((2-(trimethylsilyl)ethoxy)methyl)-1H-indole (200 mg, 0.59 mmol), ethyl propiolate (175 mg, 1.78 mmol), CuSO$_4$ (47 mg, 0.3 mmol) and sodium ascorbate (53 mg, 0.3 mmol) in $H_2O$/t-BuOH (5 mL/5 mL) was stirred at RT for 3 h. The reaction mixture was diluted with $H_2O$ (30 mL). Then it was extracted with EtOAc (50 mL×3). The combined organic layers were washed with brine, dried over $Na_2SO_4$ and concentrated. The residue was purified by silica gel ($CH_2Cl_2$/MeOH=10/1) to give ethyl 1-((6-chloro-1-((2-(trimethylsilyl)ethoxy)methyl)-1H-indol-2-yl)methyl)-1H-1,2,3-triazole-4-carboxylate (200 mg, yield: 78%) as a yellow solid. ESI-MS [M+Na]+: 457.1.

Synthesis of Ethyl 1-((6-chloro-1H-indol-2-yl)methyl)-1H-1,2,3-triazole-4-carboxylate To a solution of ethyl 1-((6-chloro-1-((2-(trimethylsilyl)ethoxy)methyl)-1H-indol-2-yl)methyl)-1H-1,2,3-triazole-4-carboxylate (120 mg, 0.27 mmol) in DCM (10 mL) was added TFA (1 mL) at 0° C. The reaction mixture was stirred at RT for 6 h. $NH_3.H_2O$ was added until pH to 9 at 0° C. Concentrated, the residue was purified by silica gel ($CH_2Cl_2$/MeOH=10/1) to give ethyl 1-((6-chloro-1H-indol-2-yl)methyl)-1H-1,2,3-triazole-4-carboxylate (27 mg, yield: 33%) as a yellow oil. ESI-MS [M+Na]+: 327.0.

Synthesis of 1-((6-chloro-1H-indol-2-yl)methyl)-1H-1,2,3-triazole-4-carboxylic Acid A mixture of ethyl 1-((6-chloro-1H-indol-2-yl)methyl)-1H-1,2,3-triazole-4-carboxylate (27 mg, 0.09 mmol) and LiOH.H$_2$O (8 mg, 0.18 mmol) in THF/EtOH/H$_2$O (1 mL/1 mL/0.5 mL) was stirred at 50° C. for 1 h. Water (5 mL) was added, pH of the mixture was adjusted to 5 by HCl (2 M). Extracted with EtOAc (30 mL×5). The combined organic layers were was washed with brine, dried over $Na_2SO_4$ and concentrated to give 1-((6-chloro-1H-indol-2-yl)methyl)-1H-1,2,3-triazole-4-carboxylic acid (25 mg, crude) as a white solid which was used into next step directly. ESI-MS [M+Na]+: 299.1

Synthesis of 1-((6-chloro-1H-indol-2-yl)methyl)-N-((7-chloro-8-fluoroimidazo[1,5-a]pyridin-1-yl)methyl)-1H-1,2,3-triazole-4-carboxamide (I-222)

A mixture of 1-((6-chloro-1H-indol-2-yl)methyl)-1H-1,2,3-triazole-4-carboxylic acid (25 mg, crude from last step), (7-chloro-8-fluoroimidazo[1,5-a]pyridin-1-yl)methanamine hydrochloride (24 mg, 0.1 mmol), HOBT (27 mg, 0.2 mmol), EDCI (38 mg, 0.2 mmol) and DIPEA (65 mg, 0.5 mmol) in DMF (2.5 mL) was stirred at RT for 16 h. Water (20 mL) was added and extracted with EtOAc (30 mL×3). The combined organic layers were washed by brine, dried over $Na_2SO_4$ and concentrated. The residue was purified by prep-HPLC to give 1-((6-chloro-1H-indol-2-yl)methyl)-N-((7-chloro-8-fluoroimidazo[1,5-a]pyridin-1-yl)methyl)-1H-1,2,3-triazole-4-carboxamide (16.1 mg, yield: 38% over 2 steps) as a white solid. ESI-MS [M+H]$^+$: 458.0. Purity: 98.76 (214 nm), 99.73 (254 nm). $^1$H NMR (400 MHz, DMSO-d$_6$) δ 11.47 (s, 1H), 8.72 (t, J=5.4 Hz, 1H), 8.58 (s, 1H), 8.43 (d, J=2.4 Hz, 1H), 8.20 (d, J=7.4 Hz, 1H), 7.51 (d, J=8.4 Hz, 1H), 7.39 (s, 1H), 7.00 (dd, J=8.4 Hz, J=1.9 Hz, 1H), 6.77-6.74 (m, 1H), 6.49 (d, J=1.0 Hz, 1H), 5.79 (s, 2H), 4.69 (d, J=5.5 Hz, 2H).

Example 223

Scheme 222

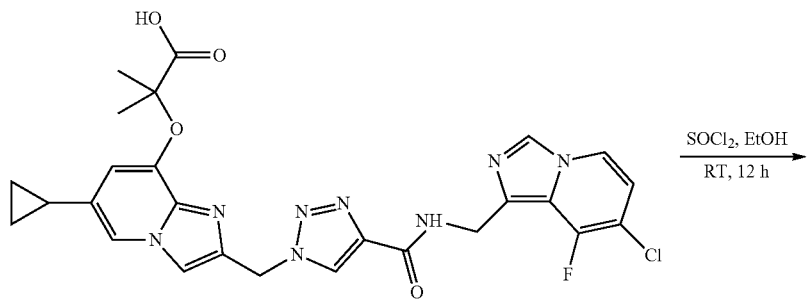

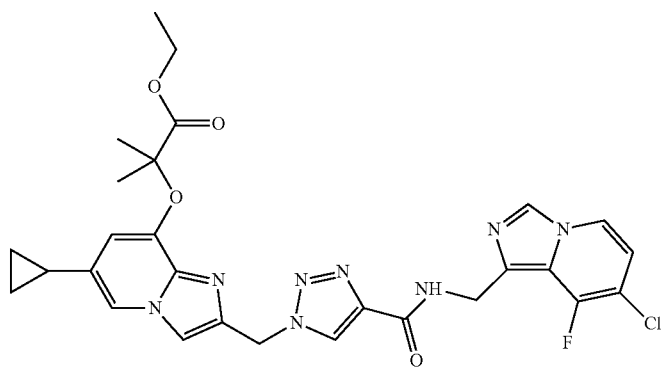

I-223

Synthesis of Ethyl 2-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)oxy)-2-methylpropanoate (I-223)

To a mixture of 2-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)oxy)-2-methylpropanoic acid (90 mg, 0.16 mmol) in EtOH (5 mL) was added SOCl₂ (0.5 mL). The mixture was stirred at RT for 12 h. After concentrated to give crude, which was purified with Prep-TLC (DCM/MeOH=10/1) to give ethyl 2-((2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)oxy)-2-methylpropanoate (70 mg, yield: 74%) as a yellow solid. ESI-MS [M+H]⁺: 595.1. Purity: 98.9 (214 nm), 100.0 (254 nm). ¹H NMR (400 MHz, DMSO-d₆) δ 8.79 (t, J=5.4 Hz, 1H), 8.68 (s, 1H), 8.52 (d, J=2.3 Hz, 1H), 8.33 (s, 1H), 8.23 (d, J=7.4 Hz, 1H), 8.19 (s, 1H), 6.84-6.77 (m, 1H), 6.72 (s, 1H), 5.94 (s, 2H), 4.71 (d, J=5.5 Hz, 2H), 4.18 (q, J=7.1 Hz, 2H), 2.10-2.03 (m, 1H), 1.69 (s, 6H), 1.14 (t, J=7.1 Hz, 3H), 1.05-0.97 (m, 2H), 0.72-0.62 (m, 2H).

Example 224

Scheme 223

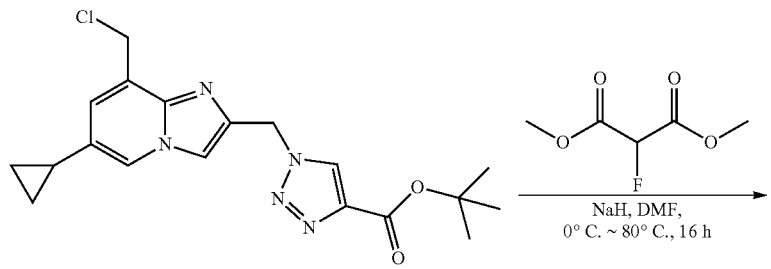

-continued
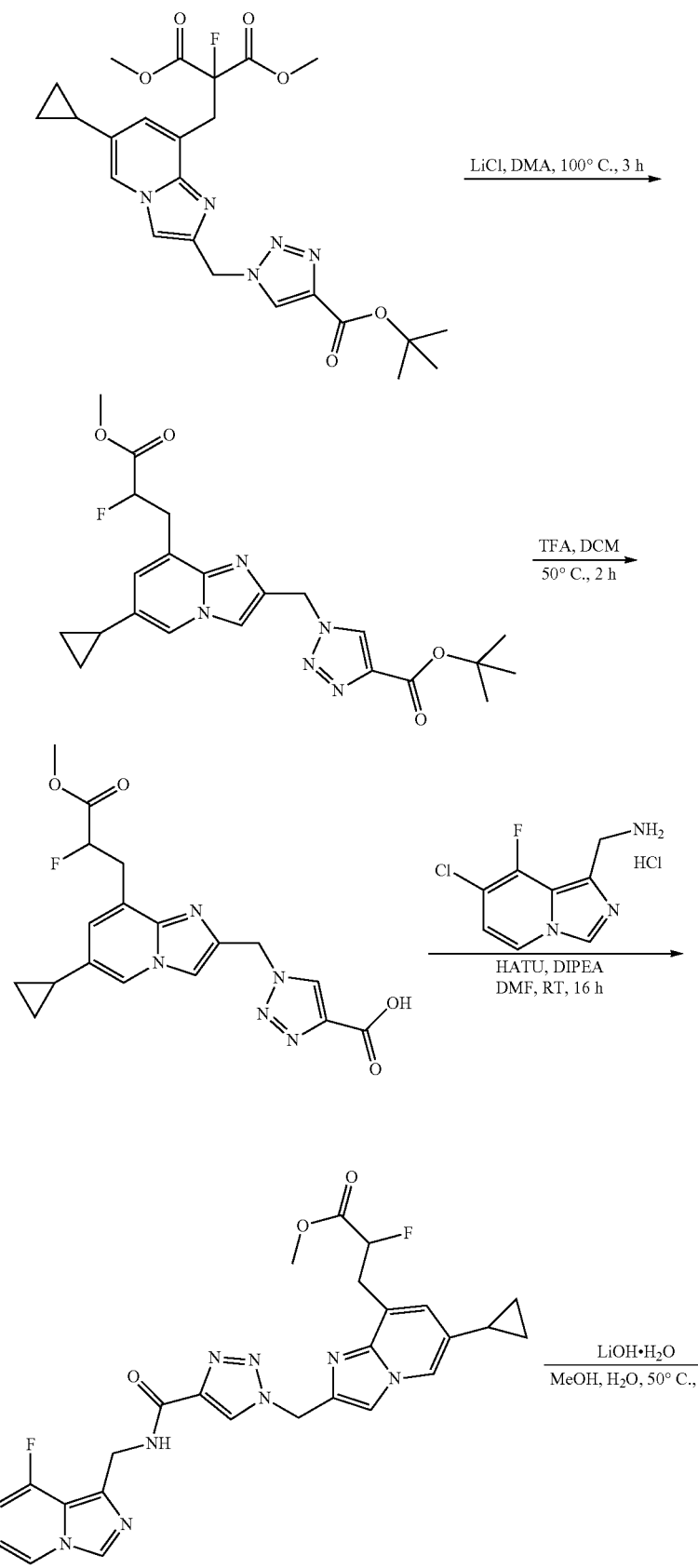
I-224a

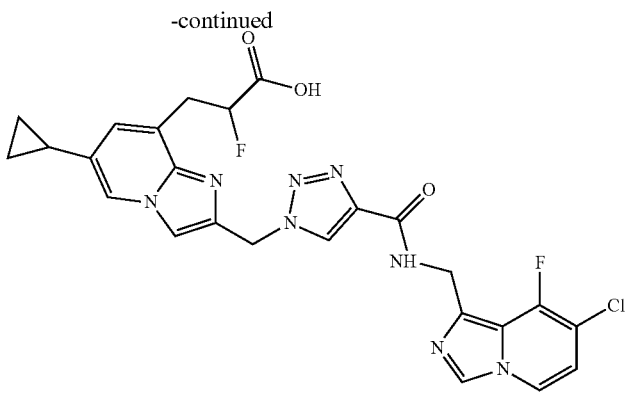

I-224b

Synthesis of dimethyl 2-((2-((4-(tert-butoxycarbonyl)-1H-1,2,3-triazol-1-yl)methyl)-6-cyclopropylimidazo[1,2-a]pyridin-8-yl)methyl)-2-fluoromalonate To a solution of compound dimethyl 2-fluoromalonate (0.54 g, 3.6 mmol) in anhydrous DMF (10 mL) was added NaH (140 mg, 3.6 mmol, 60% in mineral oil) and the reaction was stirred at 0° C. for 0.5 h under $N_2$ atmosphere. Then the solution of tert-butyl 1-((8-(chloromethyl)-6-cyclopropylimidazo[1,2-a]pyridin-2-yl)methyl)-1H-1,2,3-triazole-4-carboxylate (1 g, 2.5 mmol) in DMF (2 mL) was added, The resulting mixture was stirred at 80° C. for 16 h. The reaction was quenched with saturated aqueous $NH_4Cl$ solution (20 mL), and extracted with ethyl acetate (100 mL×2). The combined organic phases were dried over $Na_2SO_4$, evaporated to give the crude, which was purified with silica gel chromatography (DCM/MeOH=100/1) to give the dimethyl 2-((2-((4-(tert-butoxycarbonyl)-1H-1,2,3-triazol-1-yl)methyl)-6-cyclopropylimidazo[1,2-a]pyridin-8-yl)methyl)-2-fluoromalonate (1.1 g, 85%) as a yellow solids. ESI-MS [M+H]$^+$: 502.3.

Synthesis of tert-butyl 1-((6-cyclopropyl-8-(2-fluoro-3-methoxy-3-oxopropyl)imidazo[1,2-a]pyridin-2-yl)methyl)-1H-1,2,3-triazole-4-carboxylate To a solution of compound dimethyl 2-((2-((4-(tert-butoxycarbonyl)-1H-1,2,3-triazol-1-yl)methyl)-6-cyclopropylimidazo[1,2-a]pyridin-8-yl)methyl)-2-fluoromalonate (500 mg, 1 mmol) in DMA (5 mL) was added lithium chloride (126 mg, 2.99 mmol) and then the reaction mixture was stirred at 80° C. for 3 h. After cooling to RT, the reaction was quenched with $H_2O$ (50 mL), extracted with EtOAc (100 mL×3), washed with brine (50 mL), dried over sodium sulfate, concentrated to give the residue, which was purified by silica gel chromatography (DCM/MeOH=50/1) to give the tert-butyl 1-((6-cyclopropyl-8-(2-fluoro-3-methoxy-3-oxopropyl)imidazo[1,2-a]pyridin-2-yl)methyl)-1H-1,2,3-triazole-4-carboxylate (440 mg, 99%) as yellow oil. ESI-MS [M+H]$^+$: 444.2.

Synthesis of 1-((6-cyclopropyl-8-(2-fluoro-3-methoxy-3-oxopropyl)imidazo[1,2-a]pyridin-2-yl)methyl)-1H-1,2,3-triazole-4-carboxylic Acid To a solution of tert-butyl 1-((6-cyclopropyl-8-(2-fluoro-3-methoxy-3-oxopropyl)imidazo[1,2-a]pyridin-2-yl)methyl)-1H-1,2,3-triazole-4-carboxylate (330 mg, 0.75 mmol) in DCM (10 mL) was added TFA (2 mL). The resulting reaction mixture was stirred at 50° C. for 2 h. The reaction mixture was evaporated under reduced pressure to give 1-((6-cyclopropyl-8-(2-fluoro-3-methoxy-3-oxopropyl)imidazo[1,2-a]pyridin-2-yl)methyl)-1H-1,2,3-triazole-4-carboxylic acid, which was used in next step without further purification. (350 mg crude) as yellow oil. ESI-MS [M+H]$^+$: 388.3.

Synthesis of Methyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2-fluoropropanoate (I-224a)

To a solution of 1-((6-cyclopropyl-8-(2-fluoro-3-methoxy-3-oxopropyl)imidazo[1,2-a]pyridin-2-yl)methyl)-1H-1,2,3-triazole-4-carboxylic acid (350 mg crude from previous step) in dry DMF (5 mL) was added (7-chloro-8-fluoroimidazo[1,5-a]pyridin-1-yl)methanamine hydrochloride (227 mg, 0.96 mmol), HATU (422 mg, 1.11 mmol) and DIPEA (287 mg, 2.2 mmol). The reaction mixture was stirred at RT for 16 h. The reaction was quenched with $H_2O$ (50 mL) and extracted with ethyl acetate (50 mL×3). The combined organic layers were washed with brine (50 mL), dried over anhydrous sodium sulfate and concentrated in vacuo to give the residue, which was purified by Prep-TLC (DCM/MeOH=10/1) to afford methyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2-fluoropropanoate (130 mg, yield: 30% over 2 steps) as a white solids. ESI-MS [M+H]$^+$: 569.3. Purity: 98.42 (214 nm), 97.32 (254 nm). $^1$H NMR (400 MHz, DMSO-d6) δ 8.71 (t, J=5.5 Hz, 1H), 8.55 (s, 1H), 8.44 (d, J=2.4 Hz, 1H), 8.28 (d, J=1.3 Hz, 1H), 8.20 (d, J=7.4 Hz, 1H), 7.81 (s, 1H), 6.94 (s, 1H), 6.80-6.73 (m, 1H), 5.74 (s, 2H), 5.69-5.52 (m, 1H), 4.70 (d, J=5.5 Hz, 2H), 3.67 (s, 3H), 3.55-3.34 (m, 2H), 1.96-1.86 (m, 1H), 0.96-0.88 (m, 2H), 0.72-0.63 (m, 2H).

Synthesis of 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2-fluoropropanoic acid (I-224b)

To a solution of methyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8- yl)-2-fluoropropanoate (100 mg, 0.176 mmol) in MeOH/H$_2$O (5 mL/5 mL) was added LiOH.H$_2$O (37 mg, 0.88 mmol). The resulting reaction mixture was stirred at 50° C. for 5 h. The solvent of the reaction mixture was evaporated under reduced pressure. The pH of the residue was acidified by HCl (1N) to around 2, and the yellow solid was precipitated. The mixture was filtered to give the crude, which was purified by Prep-HPLC to give the 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2-fluoropropanoic acid (50 mg, yield 50%) as a white solid. ESI-MS [M+H]+: 555.1. Purity: 99.11 (214 nm), 100.00 (254 nm). $^1$H NMR (400 MHz, DMSO-d6) δ 13.50 (s, 1H), 8.71 (t, J=5.4 Hz, 1H), 8.56 (s, 1H), 8.44 (d, J=2.4 Hz, 1H), 8.27 (d, J=1.0 Hz, 1H), 8.20 (d, J=7.4 Hz, 1H), 7.80 (s, 1H), 6.95 (s, 1H), 6.81-6.71 (m, 1H), 5.75 (s, 2H), 5.47-5.40 (m, 1H), 4.70 (d, J=5.5 Hz, 2H), 3.52-3.28 (m, 2H), 1.92-1.85 (m, 1H), 1.01-0.82 (m, 2H), 0.68-0.64 (m, 2H).

Example 225

Scheme 224

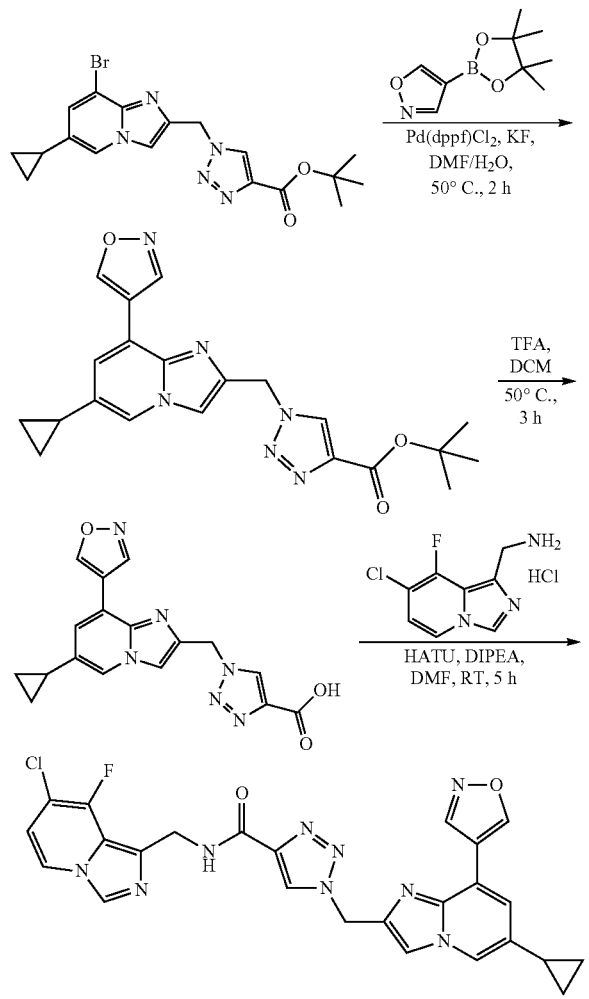

I-225

Synthesis of tert-butyl 1-((6-cyclopropyl-8-(isoxazol-4-yl)imidazo[1,2-a]pyridin-2-yl)methyl)-1H-1,2,3-triazole-4-carboxylate To a solution of tert-butyl 1-((8-bromo-6-cyclopropylimidazo[1,2-a]pyridin-2-yl)methyl)-1H-1,2,3-triazole-4-carboxylate (300 mg, 0.72 mmol) and 4-(4,4,5,5-tetramethyl-1,3,2-dioxaborolan-2-yl)isoxazole (210.6 mg, 1.08 mmol) in DMF/H$_2$O (6 mL/0.6 mL) was added Pd(dppf)Cl$_2$ (52.63 mg, 0.072 mmol), potassium fluoride (125.28 mg, 2.16 mmol). The resulting reaction mixture was stirred at 50° C. for 2 h under argon atmosphere. The reaction mixture was diluted with EtOAC (100 mL), washed with H$_2$O (50 mL). The organic layer was dried over sodium sulfate, evaporated to give the residue, which was purified by silica gel chromatography (DCM/MeOH=15/1) to give the tert-butyl 1-((6-cyclopropyl-8-(isoxazol-4-yl)imidazo[1,2-a]pyridin-2-yl)methyl)-1H-1,2,3-triazole-4-carboxylate (280 mg, 95%) as a yellow solid. ESI-MS [M+H]$^+$: 407.2.

Synthesis of 1-((6-cyclopropyl-8-(isoxazol-4-yl)imidazo[1,2-a]pyridin-2-yl)methyl)-1H-1,2,3-triazole-4-carboxylic Acid To a solution of tert-butyl 1-((6-cyclopropyl-8-(isoxazol-4-yl)imidazo[1,2-a]pyridin-2-yl)methyl)-1H-1,2,3-triazole-4-carboxylate (280 mg, 0.68 mmol) in DCM (5 mL) was added TFA (393 mg, 3.45 mmol). The reaction mixture was stirred at 50° C. for 3 h. The reaction mixture was evaporated under reduced pressure to give 1-((6-cyclopropyl-8-(isoxazol-4-yl)imidazo[1,2-a]pyridin-2-yl)methyl)-1H-1,2,3-triazole-4-carboxylic acid, which was used in next step without further purification (300 mg crude) as yellow oil. ESI-MS [M+H]$^+$: 351.3.

Synthesis of N-((7-chloro-8-fluoroimidazo[1,5-a]pyridin-1-yl)methyl)-1-((6-cyclopropyl-8-(isoxazol-4-yl)imidazo[1,2-a]pyridin-2-yl)methyl)-1H-1,2,3-triazole-4-carboxamide (I-225)

To a solution of 1-((6-cyclopropyl-8-(isoxazol-4-yl)imidazo[1,2-a]pyridin-2-yl)methyl)-1H-1,2,3-triazole-4-carboxylic acid (300 mg, crude from previous step) in dry DMF (5 mL), was added (7-chloro-8-fluoroimidazo[1,5-a]pyridin-1-yl)methanamine hydrochloride (194 mg, 0.82 mmol), HATU (393.3 mg, 1.03 mmol) and DIPEA (267 mg, 2.06 mmol). The reaction mixture was stirred at RT for 5 h. The reaction was quenched with H$_2$O (30 mL), extracted with ethyl acetate (50 mL×3). The combined organic layers were washed with brine (50 mL), dried over anhydrous sodium sulfate and concentrated in vacuo. The residue was purified by Prep-TLC (DCM/MeOH=10/1) to afford N-((7-chloro-8-fluoroimidazo[1,5-a]pyridin-1-yl)methyl)-1-((6-cyclopropyl-8-(isoxazol-4-yl)imidazo[1,2-a]pyridin-2-yl)methyl)-1H-1,2,3-triazole-4-carboxamide (40 mg, yield: 11% over 2 steps) as a white solid. ESI-MS [M+H]$^+$: 532.10. Purity: 98.73 (214 nm), 99.42 (254 nm). $^1$H NMR (400 MHz, DMSO-d6) δ 9.80 (s, 1H), 9.50 (s, 1H), 8.79-8.65 (m, 2H), 8.44 (d, J=2.1 Hz, 1H), 8.38 (s, 1H), 8.20 (d, J=7.4 Hz, 1H), 7.91 (s, 1H), 7.52 (s, 1H), 6.75 (t, J=6.9 Hz, 1H), 5.80 (s, 2H), 4.70 (d, J=5.4 Hz, 2H), 2.00-1.93 (m, 1H), 1.01-0.90 (m, 2H), 0.83-0.76 (m, 2H).

Example 226
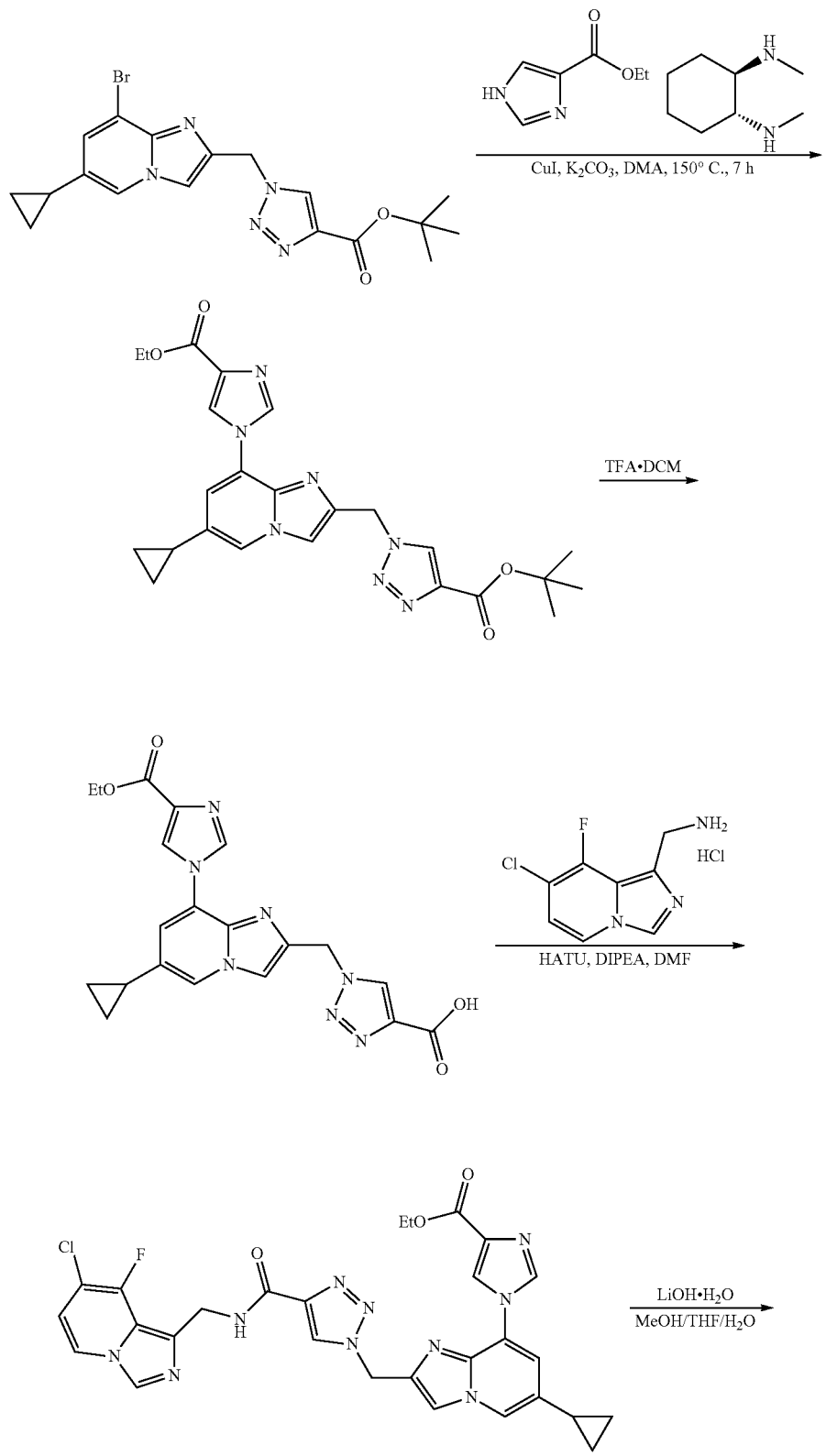
Scheme 225

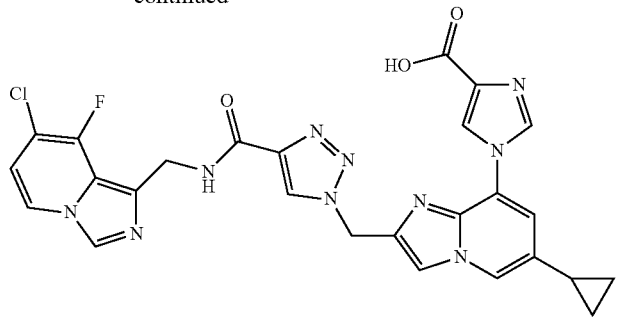

I-226

Synthesis of tert-butyl 1-((6-cyclopropyl-8-(4-(ethoxycarbonyl)-1H-imidazol-1-yl)imidazo[1,2-a]pyridin-2-yl)methyl)-1H-1,2,3-triazole-4-carboxylate A mixture of tert-butyl 1-((8-bromo-6-cyclopropylimidazo[1,2-a]pyridin-2-yl)methyl)-1H-1,2,3-triazole-4-carboxylate (300 mg, 0.72 mmol), ethyl 1H-imidazole-4-carboxylate (150 mg, 1.07 mmol), CuI (203 mg, 1.07 mmol), (1R,2R)—N1,N2-dimethylcyclohexane-1,2-diamine (152 mg, 1.07 mmol) and K$_2$CO$_3$ (199 mg, 1.44 mmol) in DMA (5 mL) was stirred at 140° C. under N$_2$ for 7 h. The mixture was concentrated to give the crude, which was purified by silica gel column chromatography (DCM/MeOH=15/1) to give tert-butyl 1-((6-cyclopropyl-8-(4-(ethoxycarbonyl)-1H-imidazol-1-yl)imidazo[1,2-a]pyridin-2-yl)methyl)-1H-1,2,3-triazole-4-carboxylate (48 mg, yield: 14%) as yellow oil. ESI-MS [M+H]$^+$: 478.1

Synthesis of 1-((6-cyclopropyl-8-(4-(ethoxycarbonyl)-1H-imidazol-1-yl)imidazo[1,2-a]pyridin-2-yl)methyl)-1H-1,2,3-triazole-4-carboxylic Acid To a solution of tert-butyl 1-((6-cyclopropyl-8-(4-(ethoxycarbonyl)-1H-imidazol-1-yl)imidazo[1,2-a]pyridin-2-yl)methyl)-1H-1,2,3-triazole-4-carboxylate (48 mg, 0.10 mmol) in DCM (5.0 mL) was added TFA (1.0 mL) at RT. The resulting reaction mixture was stirred for 6 h. The mixture was concentrated to give 1-((6-cyclopropyl-8-(4-(ethoxycarbonyl)-1H-imidazol-1-yl)imidazo [1,2-a]pyridin-2-yl)methyl)-1H-1,2,3-triazole-4-carboxylic acid (55 mg, crude) as a yellow oil, which was used for the step directly without purification. ESI-MS [M+H]$^+$: 422.1.

Synthesis of Ethyl 1-(2-((4-((7-chloro-8-fluoroimidazo[1,5-a]pyridin-1-yl)methylcarbamoyl)-1H-1,2,3-triazol-1-yl)methyl)-6-cyclopropylimidazo[1,2-a]pyridin-8-yl)-1H-imidazole-4-carboxylate A mixture of 1-((6-cyclopropyl-8-(4-(ethoxycarbonyl)-1H-imidazol-1-yl)imidazo[1,2-a] pyridin-2-yl)methyl)-1H-1,2,3-triazole-4-carboxylic acid (50 mg, crude from previous step), (7-chloro-8-fluoroimidazo[1,5-a]pyridin-1-yl)methanamine hydrochloride (28.2 mg, 0.12 mmol), HATU (76.0 mg, 0.20 mmol) and DIPEA (64.5 mg, 0.5 mmol) in DMF (2 mL) was stirred at RT for 16 h. Water (50 mL) was added to the reaction, extracted with EtOAc (30 mL×3). The combined organic layers were washed with brine, dried over Na$_2$SO$_4$, then concentrated. The crude was purified by Prep-TLC (DCM/MeOH=10/1) to give ethyl 1-(2-((4-((7-chloro-8-fluoroimidazo[1,5-a]pyridin-1-yl)methylcarbamoyl)-1H-1,2,3-triazol-1-yl)methyl)-6-cyclopropylimidazo [1,2-a]pyridin-8-yl)-1H-imidazole-4-carboxylate (40.0 mg, yield: 66% over 2 steps) as a white yellow solid. ESI-MS [M+H]$^+$: 603.1.

Synthesis of 1-(2-((4-((7-chloro-8-fluoroimidazo[1,5-a]pyridin-1-yl)methylcarbamoyl)-1H-1,2,3-triazol-1-yl)methyl)-6-cyclopropylimidazo[1,2-a]pyridin-8-yl)-1H-imidazole-4-carboxylic acid (I-226)

A solution of ethyl 1-(2-((4-((7-chloro-8-fluoroimidazo[1,5-a]pyridin-1-yl)methylcarbamoyl)-1H-1,2,3-triazol-1-yl)methyl)-6-cyclopropylimidazo[1,2-a]pyridin-8-yl)-1H-imidazole-4-carboxylate (40.0 mg, 0.066 mmol) and LiOH.H$_2$O (13.9 mg, 0.33 mmol) in THF/MeOH/H$_2$O (1 mL/1 mL/1 mL) was stirred at RT for 2 h. The pH value was adjusted to 3 by HCl (1 M), and then the mixture was concentrated to give the crude, which was purified by Prep-HPLC to give 1-(2-((4-((7-chloro-8-fluoroimidazo[1,5-a]pyridin-1-yl)methylcarbamoyl)-1H-1,2,3-triazol-1-yl)methyl)-6-cyclopropylimidazo[1,2-a]pyridin-8-yl)-1H-imidazole-4-carboxylic acid (7.4 mg, 19.5%) as a yellow solid. ESI-MS [M+H]$^+$: 575.1. Purity: 96.9 (214 nm), 95.9 (254 nm). $^1$H NMR (400 MHz, DMSO-d$_6$) δ 8.74 (s, 1H), 8.72-8.63 (m, 2H), 8.56 (s, 1H), 8.41 (s, 2H), 8.17 (d, J=7.3 Hz, 2H), 7.95 (s, 1H), 7.42 (s, 1H), 6.72 (t, J=6.9 Hz, 1H), 5.79 (s, 2H), 4.67 (d, J=5.4 Hz, 2H), 2.03-1.89 (m, 1H), 0.96-0.91 (m, 2H), 0.86-0.74 (m, 2H).

Example 227
Scheme 226
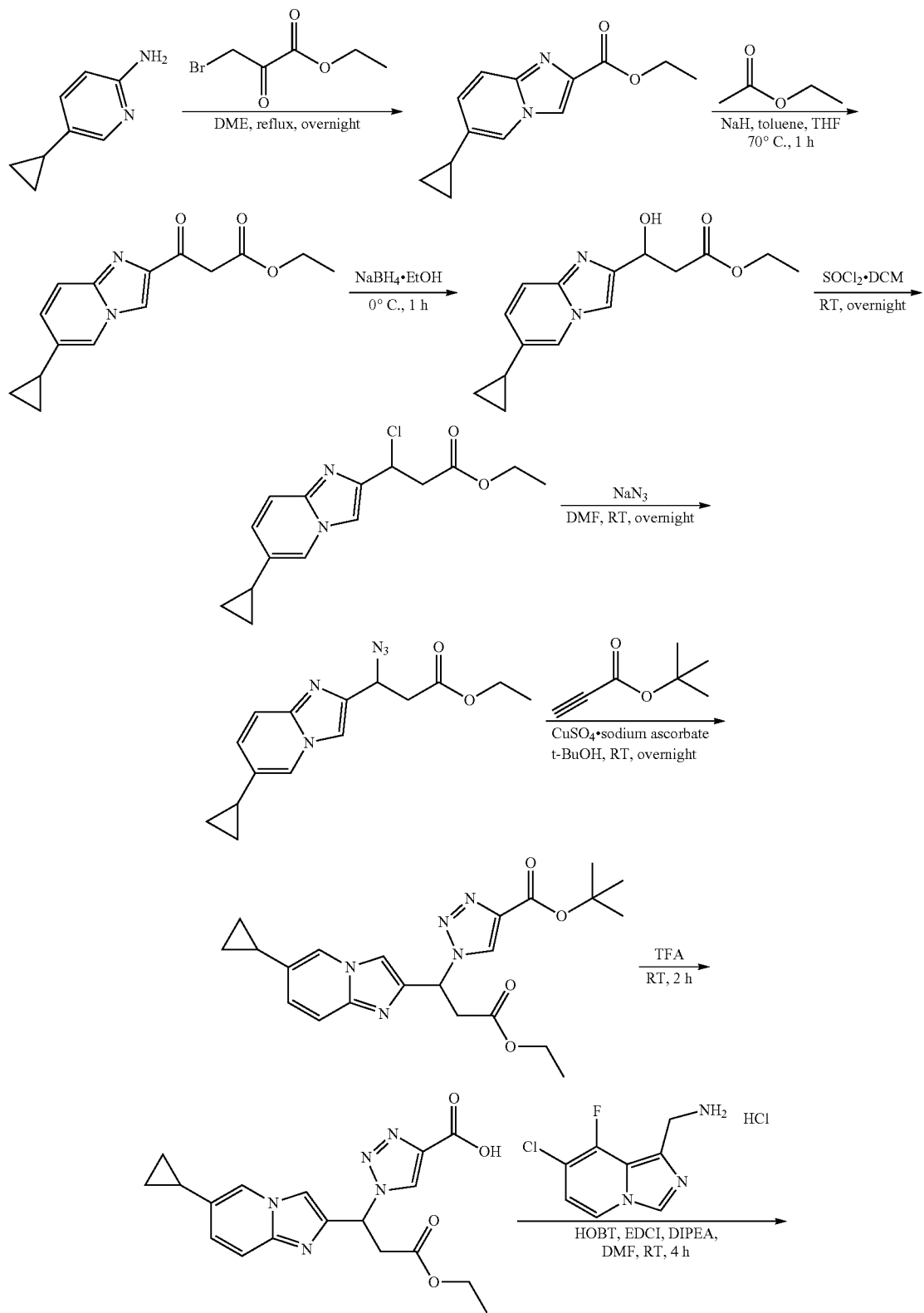

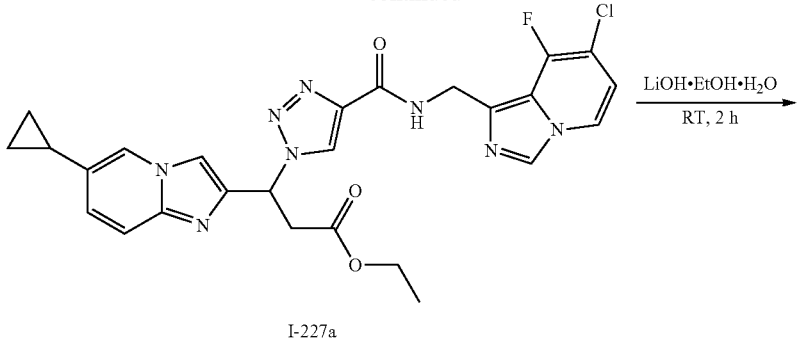

I-227a

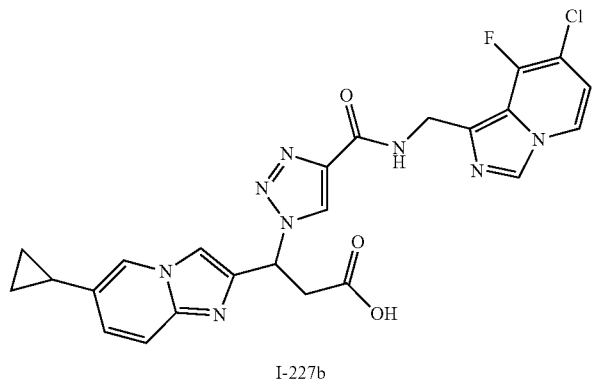

I-227b

Synthesis of Ethyl 6-cyclopropylimidazo[1,2-a]pyridine-2-carboxylate

A solution of 5-cyclopropylpyridin-2-amine (1.4 g, 10.4 mmol) and ethyl 3-bromo-2-oxopropanoate (3.05 g, 15.7 mmol) in DME (10 mL) was stirred at 80° C. overnight. The mixture was adjusted to pH=7 by adding $Na_2CO_3$ solution and extracted with EtOAc (100 mL×3). The combined organic layers were washed with brine, dried over $Na_2SO_4$ and concentrated. The residue was purified by silica gel chromatography (EA/PE=13:1) to give ethyl 6-cyclopropylimidazo[1,2-a]pyridine-2-carboxylate (614 mg, yield: 26%) as a yellow solid. ESI-MS [M+H]+: 231.2

Synthesis of Ethyl 3-(6-cyclopropylimidazo[1,2-a]pyridin-2-yl)-3-oxopropanoate A solution of ethyl 6-cyclopropylimidazo[1,2-a]pyridine-2-carboxylate (424 mg, 1.84 mmol), ethyl acetate (811 mg, 9.2 mmol) and NaH (147 mg, 3.68 mmol) in toluene/THF ((v/v)=1/2, 12 mL) was stirred at 70° C. for 1 h. The mixture was quenched by saturated $NH_4Cl$ solution (30 mL) and extracted by EtOAc (50 mL×3). The combined organic layers were washed with brine, dried over $Na_2SO_4$ and concentrated to give crude ethyl 3-(6-cyclopropylimidazo[1,2-a]pyridin-2-yl)-3-oxopropanoate (458 mg, crude) as a yellow solid which was used to the next step without further purification. ESI-MS [M+H]+: 273.1.

Synthesis of Ethyl 3-(6-cyclopropylimidazo[1,2-a]pyridin-2-yl)-3-hydroxypropanoate A solution of ethyl 3-(6-cyclopropylimidazo[1,2-a]pyridin-2-yl)-3-oxopropanoate (458 mg, crude) in EtOH (10 mL) was added $NaBH_4$ (70 mg, 1.85 mmol) slowly at 0° C. After the mixture was stirred at 0° C. for 45 min, the solution was quenched by $H_2O$ (30 mL) and extracted with EtOAc (50 mL×2). The combined organic layers were washed with brine, dried over $Na_2SO_4$ and concentrated. The residue was purified by Prep-TLC (DCM/MeOH=10:1) to give ethyl 3-(6-cyclopropylimidazo[1,2-a]pyridin-2-yl)-3-hydroxypropanoate (300 mg, yield: 59% over 2 steps) as a yellow solid. ESI-MS [M+H]+: 275.1.

Synthesis of Ethyl 3-chloro-3-(6-cyclopropylimidazo[1,2-a]pyridin-2-yl)propanoate To a solution of ethyl 3-(6-cyclopropylimidazo[1,2-a]pyridin-2-yl)-3-hydroxypropanoate (200 mg, 0.73 mmol) in DCM (6 mL) was added $SOCl_2$ (0.5 mL). The mixture was stirred at RT overnight. The mixture was concentrated (200 mg, crude) and used into next step without further purification. ESI-MS [M+H]+: 293.1.

Synthesis of Ethyl 3-azido-3-(6-cyclopropylimidazo[1,2-a]pyridin-2-yl)propanoate A mixture of ethyl 3-chloro-3-(6-cyclopropylimidazo[1,2-a]pyridin-2-yl)propanoate (200 mg, crude from above step), $NaN_3$ (72 mg, 1.1 mmol) in DMF (5 mL) was stirred at RT overnight. The reaction mixture was diluted with $H_2O$ (30 mL) and extracted with EtOAc (50 mL×3). The combined organic layers were washed with brine, dried over $Na_2SO_4$ and concentrated. The residue was purified by column (DCM:MeOH=20:1) to give crude ethyl 3-azido-3-(6-cyclopropylimidazo[1,2-a]pyridin-2-yl)propanoate (160 mg, yield: 73% over 2 steps) as a yellow solid. ESI-MS [M+H]+: 300.1.

Synthesis of tert-butyl 1-(1-(6-cyclopropylimidazo[1,2-a]pyridin-2-yl)-3-ethoxy-3-oxopropyl)-1H-1,2,3-triazole-4-carboxylate A mixture of crude ethyl 3-azido-3-(6-cyclopropylimidazo[1,2-a]pyridin-2-yl)propanoate (160 mg, 0.53 mmol), tert-butyl propiolate (101 mg, 0.8 mmol), CuSO$_4$ (26 mg, 0.16 mmol) and sodium ascorbate (28 mg, 0.16 mmol) in t-BuOH/H$_2$O ((v/v)=2/1, 9 mL) was stirred at RT overnight. The reaction mixture was diluted with H$_2$O (20 mL) then it was extracted with EtOAc (30 mL×3). The combined organic layers were washed with brine, dried over Na$_2$SO$_4$ and concentrated. The residue was purified by Prep-TLC (DCM:MeOH=15:1) to give tert-butyl 1-(1-(6-cyclopropylimidazo[1,2-a]pyridin-2-yl)-3-ethoxy-3-oxopropyl)-1H-1,2,3-triazole-4-carboxylate (100 mg, yield: 44%) as a yellow solid. ESI-MS [M+H]$^+$: 426.2.

Synthesis of 1-(1-(6-cyclopropylimidazo[1,2-a]pyridin-2-yl)-3-ethoxy-3-oxopropyl)-1H-1,2,3-triazole-4-carboxylic Acid A solution of tert-butyl 1-(1-(6-cyclopropylimidazo[1,2-a]pyridin-2-yl)-3-ethoxy-3-oxopropyl)-1H-1,2,3-triazole-4-carboxylate (100 mg, 0.24 mmol) in TFA (2 mL) and DCM (2 mL) was stirred at RT for 2 h. The mixture was concentrated to give crude 1-(1-(6-cyclopropylimidazo[1,2-a]pyridin-2-yl)-3-ethoxy-3-oxopropyl)-1H-1,2,3-triazole-4-carboxylic acid (100 mg, crude) which was used to the next step without further purification. ESI-MS [M+H]$^+$: 370.1.

Synthesis of Ethyl 3-(4-(((7-chloro-8-fluoroimidazo[1,5-a]pyridin-1-yl)methyl)carbamoyl)-1H-1,2,3-triazol-1-yl)-3-(6-cyclopropylimidazo[1,2-a]pyridin-2-yl)propanoate (I-227a)

A mixture of crude 1-(1-(6-cyclopropylimidazo[1,2-a]pyridin-2-yl)-3-ethoxy-3-oxopropyl)-1H-1,2,3-triazole-4-carboxylic acid (100 mg, crude from last step), (7-chloro-8-fluoroimidazo[1,5-a]pyridin-1-yl)methanamine hydrochloride (52 mg, 0.22 mmol), HOBT (59 mg, 0.44 mmol), EDCI (84 mg, 0.44 mmol) and DIPEA (142 mg, 5.0 mmol) in DMF (6 mL) was stirred at RT for 4 h. The reaction mixture was diluted with H$_2$O (50 mL) and extracted with EtOAc (50 mL×3). The combined organic layers were washed with brine, dried over Na$_2$SO$_4$ and concentrated. The residue was purified by Prep-TLC (DCM:MeOH=20:1) to give 1 ethyl 3-(4-(((7-chloro-8-fluoroimidazo[1,5-a]pyridin-1-yl)methyl)carbamoyl)-1H-1,2,3-triazol-1-yl)-3-(6-cyclopropylimidazo[1,2-a]pyridin-2-yl)propanoate (66 mg, yield: 53%) as a white solid. ESI-MS [M+H]$^+$: 551.2. Purity: 98.80% (214 nm), 100% (254 nm). $^1$H NMR (400 MHz, DMSO-d$_6$) δ 8.72-8.69 (m, 2H), 8.44 (d, J=2.1 Hz, 1H), 8.33 (s, 1H), 8.21 (d, J=7.4 Hz, 1H), 7.77 (s, 1H), 7.42 (d, J=9.3 Hz, 1H), 7.02 (d, J=9.4 Hz, 1H), 6.76 (t, J=6.8 Hz, 1H), 6.37-6.34 (m, 1H), 4.70 (d, J=5.4 Hz, 2H), 4.05-3.99 (m, 2H), 3.62-3.51 (m, 2H), 1.95-1.89 (m, 1H), 1.10 (t, J=7.1 Hz, 3H), 0.94-0.89 (m, 2H), 0.68-0.64 (m, 2H).

Synthesis of 3-(4-(((7-chloro-8-fluoroimidazo[1,5-a]pyridin-1-yl)methyl)carbamoyl)-1H-1,2,3-triazol-1-yl)-3-(6-cyclopropylimidazo[1,2-a]pyridin-2-yl)propanoic acid (I-227b)

A solution of ethyl 3-(4-(((7-chloro-8-fluoroimidazo[1,5-a]pyridin-1-yl)methyl)carbamoyl)-1H-1,2,3-triazol-1-yl)-3-(6-cyclopropylimidazo[1,2-a]pyridin-2-yl)propanoate (50 mg, 0.09 mmol) and LiOH.H$_2$O (97 mg, 2.32 mmol) in ethanol (1 mL), THF (4 mL) and H$_2$O (1 mL) was stirred at RT for 2 h. The mixture was adjusted to pH-2 by adding HCl (1 M). The mixture was then extracted with EtOAc (50 mL×3). The combined organic layers were concentrated and purified by Prep-HPLC to get 3-(4-(((7-chloro-8-fluoroimidazo[1,5-a]pyridin-1-yl)methyl)carbamoyl)-1H-1,2,3-triazol-1-yl)-3-(6-cyclopropylimidazo[1,2-a]pyridin-2-yl)propanoic acid (4.4 mg, yield: 9%) as a white solid. ESI-MS [M+H]$^+$: 523.1. Purity: 96.99% (214 nm), 97.64% (254 nm). $^1$H NMR (400 MHz, DMSO-d$_6$) δ 8.58-8.53 (m, 2H), 8.33 (d, J=2.0 Hz, 1H), 8.26 (s, 1H), 8.19 (s, 1H), 8.10 (d, J=7.4 Hz, 1H), 7.61 (s, 1H), 7.28 (d, J=9.3 Hz, 1H), 6.88 (d, J=9.4 Hz, 1H), 6.65 (t, J=6.8 Hz, 1H), 6.19 (t, J=7.4 Hz, 1H), 4.59 (d, J=5.4 Hz, 2H), 3.10-3.09 (m, 2H), 1.83-1.77 (m, 1H), 0.81-0.77 (m, 2H), 0.56-0.53 (m, 2H).

Example 228

Scheme 227

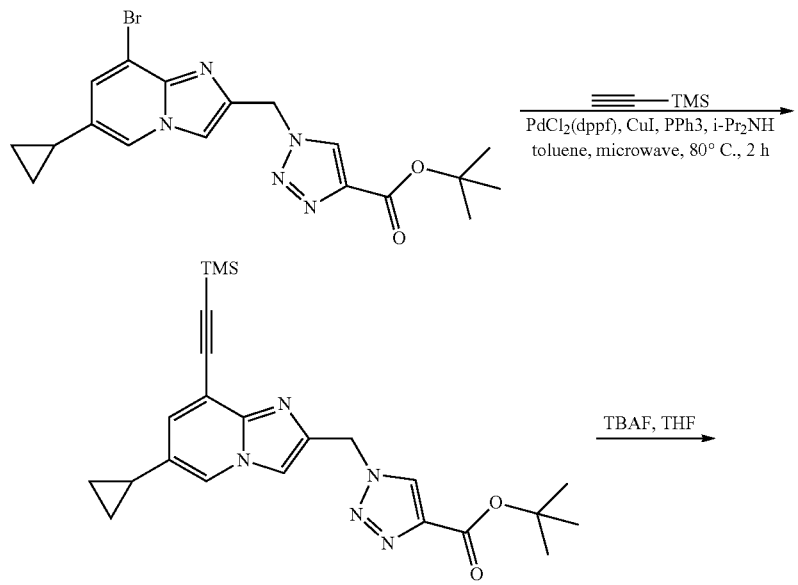

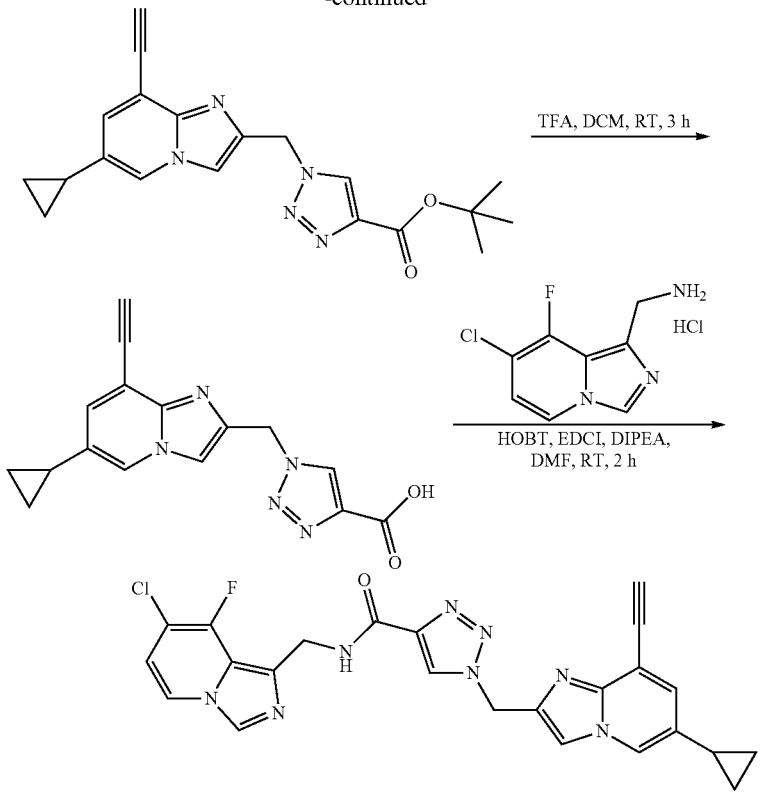

I-228

Synthesis of tert-butyl 1-((6-cyclopropyl-8-((trimethylsilyl)ethynyl)imidazo[1,2-a]pyridin-2-yl)methyl)-1H-1,2,3-triazole-4-carboxylate A solution of tert-butyl 1-((8-bromo-6-cyclopropylimidazo[1,2-a]pyridin-2-yl)methyl)-1H-1,2,3-triazole-4-carboxylate (210 mg, 0.5 mmol), ethynyltrimethylsilane (98 mg, 1.0 mmol), Pd(dppf)Cl$_2$ (37 mg, 0.05 mmol), CuI (10 mg, 0.05 mmol) and PPh$_3$ (875 mg, 3.12 mmol) in i-Pr$_2$NH (1 mL) and toluene (3 mL) was degassed by N$_2$ and stirred at 80° C. (microwave) for 2 h. Water (30 mL) was added to the reaction, extracted with EtOAc (30 mL×3). The combined organic layers were washed with brine, dried over Na$_2$SO$_4$, and concentrated to give the crude which was purified with Prep-TLC (DCM/MeOH=15/1) to give tert-butyl 1-((6-cyclopropyl-8-((trimethylsilyl)ethynyl)imidazo[1,2-a]pyridin-2-yl)methyl)-1H-1,2,3-triazole-4-carboxylate (170 mg, 78%) as a yellow solid. ESI-MS [M+H]$^+$: 436.2.

Synthesis of tert-butyl 1-((6-cyclopropyl-8-ethynylimidazo[1,2-a]pyridin-2-yl)methyl)-1H-1,2,3-triazole-4-carboxylate To a solution of tert-butyl 1-((6-cyclopropyl-8-((trimethylsilyl)ethynyl)imidazo[1,2-a]pyridin-2-yl)methyl)-1H-1,2,3-triazole-4-carboxylate (170 mg, 0.39 mmol) in THF was added TBAF (1.2 mL, 1 M solution in THF, 1.2 mmol). The mixture was stirred at RT for another 1 h. The reaction was quenched with saturated aqueous NH$_4$Cl (30 mL), extracted with EtOAc (30 mL×3). The combined organic layers were washed with brine, dried over Na$_2$SO$_4$, and concentrated to give the crude, which was purified by Prep-TLC (DCM/MeOH=20/1) to give tert-butyl 1-((6-cyclopropyl-8-((trimethylsilyl)ethynyl)imidazo[1,2-a]pyridin-2-yl)methyl)-1H-1,2,3-triazole-4-carboxylate (95 mg, yield: 66.9%) as a pale solid. ESI-MS [M+H]$^+$: 364.1

Synthesis of 1-((6-cyclopropyl-8-ethynylimidazo[1,2-a]pyridin-2-yl)methyl)-1H-1,2,3-triazole-4-carboxylic Acid A solution of tert-butyl 1-((6-cyclopropyl-8-ethynylimidazo[1,2-a]pyridin-2-yl)methyl)-1H-1,2,3-triazole-4-carboxylate (50 mg, 0.14 mmol) in TFA (1 mL) and DCM (1 mL) was stirred at RT for 3 h. The mixture was concentrated to give 1-((6-cyclopropyl-8-ethynylimidazo[1,2-a]pyridin-2-yl)methyl)-1H-1,2,3-triazole-4-carboxylic acid, which was used to the next reaction without further purification (55 mg crude). ESI-MS [M+H]$^+$: 308.1.

Synthesis of N-((7-chloro-8-fluoroimidazo[1,5-a]pyridin-1-yl)methyl)-1-((6-cyclopropyl-8-ethynylimidazo[1,2-a]pyridin-2-yl)methyl)-1H-1,2,3-triazole-4-carboxamide (I-228)

A solution of crude 1-((6-cyclopropyl-8-ethynylimidazo[1,2-a]pyridin-2-yl)methyl)-1H-1,2,3-triazole-4-carboxylic acid (55 mg, crude from previous step), (7-chloro-8-fluoroimidazo[1,5-a]pyridin-1-yl)methanamine hydrochloride (36 mg, 0.15 mmol), HOBT (38 mg, 0.28 mmol), EDCI (54 mg, 0.28 mmol) and DIPEA (91 mg, 0.7 mmol) in DMF (2 mL) was stirred at RT for 2 h. Water (20 mL) was added to the reaction, and the mixture was extracted by EtOAc (30 mL×3). The combined organic layers were washed with brine, dried over Na₂SO₄, and concentrated to give the crude, which was purified by Prep-TLC (DCM/MeOH=20/1) to give N-((7-chloro-8-fluoroimidazo[1,5-a]pyridin-1-yl)methyl)-1-((6-cyclopropyl-8-ethynylimidazo[1,2-a]pyridin-2-yl)methyl)-1H-1,2,3-triazole-4-carboxamide (21.8 mg, yield: 32% over 2 steps) as a white solid. ESI-MS [M+H]⁺: 489.1. Purity: 97.56 (214 nm), 97.42 (254 nm) ¹H NMR (400 MHz, DMSO-d₆) δ 8.70 (t, J=5.4 Hz, 1H), 8.57 (s, 1H), 8.44-8.41 (m, 2H), 8.21 (d, J=7.4 Hz, 1H), 7.87 (s, 1H), 7.25 (d, J=1.5 Hz, 1H), 6.76 (t, J=7.2 Hz, 1H), 5.76 (s, 2H), 4.71 (d, J=5.5 Hz, 2H), 4.50 (s, 1H), 1.93-1.90 (m, 1H), 0.95-0.90 (m, 2H), 0.72-0.69 (m, 2H).

Example 229

Scheme 228

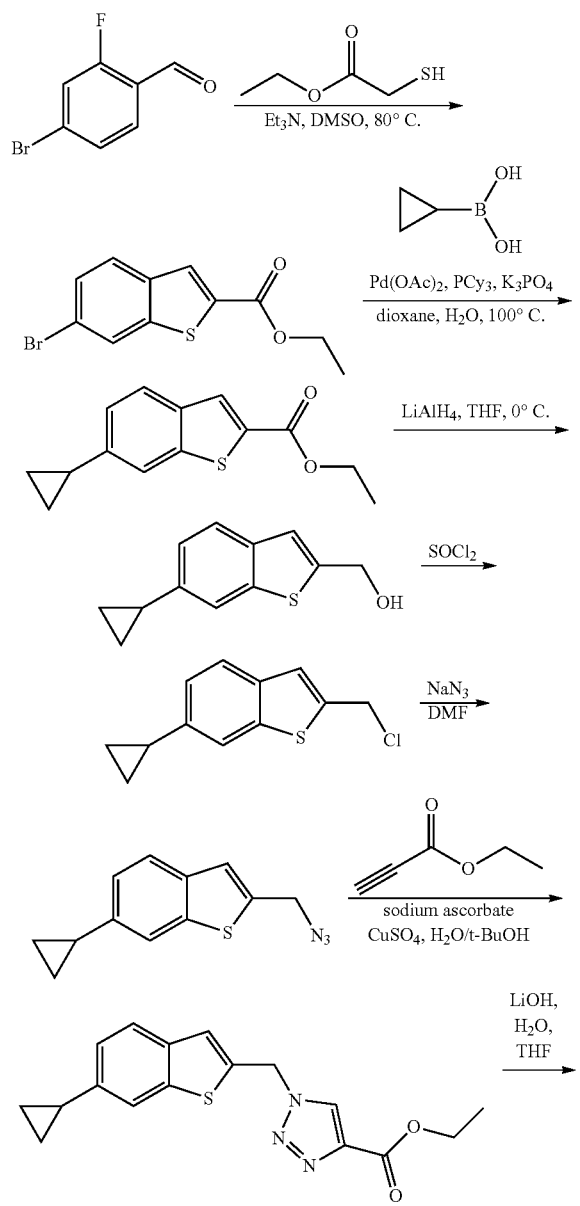

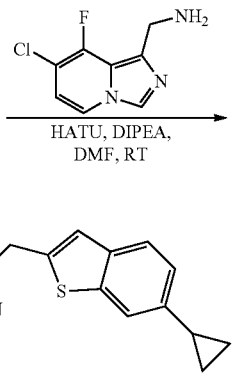

I-229

Synthesis of Ethyl 6-bromobenzo[b]thiophene-2-carboxylate

To a solution of 4-bromo-2-fluorobenzaldehyde (1 g, 4.93 mmol) in DMSO (25 mL) was added ethyl 2-mercaptoacetate (651 mg, 5.42 mmol), followed by Et₃N (997 mg, 9.85 mmol). The reaction mixture was stirred at 80° C. for 3 h. The resulting mixture was poured into H₂O (20 mL) and extracted with EtOAc (50 mL×3). The combined organic layers were concentrated to give the crude product, which was purified by silica gel chromatography (PE/EtOAc=40/1) to give the ethyl 6-bromobenzo[b]thiophene-2-carboxylate as a yellow solid (1.304 g, yield: 93%). ESI-MS [M+H]⁺: 284.7, 286.7.

Synthesis of Ethyl 6-cyclopropylbenzo[b]thiophene-2-carboxylate

To a solution of ethyl 6-bromobenzo[b]thiophene-2-carboxylate (1.304 g, 4.57 mmol) in dioxane/H₂O (50 mL/5 mL) was added cyclopropylboronic acid (786 mg, 9.15 mmol), Pd(OAc)₂ (103 mg, 0.457 mmol), PCy₃ (256 mg, 0.915 mmol) and K₃PO₄ (2.912 g, 13.7 mmol). The reaction mixture was stirred at 100° C. for 14 h under nitrogen. Then the mixture was concentrated in vacuo. Water (40 mL) was added and the mixture was extracted with EtOAc (50 mL×3). The combined organic layers were concentrated to give the crude product, which was purified by silica gel chromatography (PE/EtOAc=40/1) to give the ethyl 6-cyclopropylbenzo[b]thiophene-2-carboxylate as a yellow solid (938 mg, yield: 83%). ESI-MS [M+H]⁺: 246.9.

Synthesis of (6-cyclopropylbenzo[b]thiophen-2-yl)methanol

To a solution ethyl ethyl 6-cyclopropylbenzo[b]thiophene-2-carboxylate (938 mg, 3.81 mmol) in THF (15 mL) was added LiAlH₄ (145 mg, 3.81 mmol) slowly. The mixture was stirred for 2 h at 0° C. Then the reaction was quenched with H₂O (1 mL) and aqueous NaOH (10%, 1 mL) and the resulting mixture was filtered through celite. The filtrate was concentrated in vacuo to give the crude product, which was purified by silica gel chromatography (PE/EtOAc=5/1) to give (6-cyclopropylbenzo[b]thiophen-2-yl)methanol (542 mg, yield: 76%) as a yellow solid. ESI-MS [M−OH]⁺: 187.1.

Synthesis of 2-(chloromethyl)-6-cyclopropylbenzo[b]thiophene

A solution of (6-cyclopropylbenzo[b]thiophen-2-yl)methanol (276 mg, 1.35 mmol) in $SOCl_2$ (10 mL) was stirred at RT for 2 h. Then the mixture was concentrated in vacuo to give 2-(chloromethyl)-6-cyclopropylbenzo[b]thiophene (300 mg, crude) as a yellow oil, which was used directly into the next step without further purification.

Synthesis of 2-(azidomethyl)-6-cyclopropylbenzo[b]thiophene

A solution of 2-(chloromethyl)-6-cyclopropylbenzo[b]thiophene (300 mg, crude from above step) and $NaN_3$ (56 mg, 0.858 mmol) in DMF (5 mL) was stirred at RT for 5 h. Water (20 mL) was added and extracted with EtOAc (30 mL×3). The combined organic layers were concentrated to give 2-(azidomethyl)-6-cyclopropylbenzo[b]thiophene (195 mg, crude) as a yellow solid, which was used directly into the next step without further purification.

Synthesis of Ethyl 1-((6-cyclopropylbenzo[b]thiophen-2-yl)methyl)-1H-1,2,3-triazole-4-carboxylate A solution 2-(azidomethyl)-6-cyclopropylbenzo[b]thiophene (195 mg, from above step), ethyl propiolate (167 mg, 1.7 mmol), $CuSO_4$ (42 mg, 0.17 mmol) and sodium ascorbate (51 mg, 0.255 mmol) in t-BuOH (8 mL) and $H_2O$ (8 mL) was stirred for 2 h at RT. Water (20 mL) was added and the mixture was extracted with EtOAc (50 mL×3). The combined organic layers were dried over $Na_2SO_4$, and concentrated to give the crude product, which was purified by silica gel chromatography (PE/EtOAc=3/1) to give ethyl 1-((6-cyclopropylbenzo[b]thiophen-2-yl)methyl)-1H-1,2,3-triazole-4-carboxylate (253 mg, yield: 53% over 3 steps) as a yellow solid. ESI-MS $[M+Na]^+$: 350.0

Synthesis of 1-((6-cyclopropylbenzo[b]thiophen-2-yl)methyl)-1H-1,2,3-triazole-4-carboxylic Acid A solution of ethyl 1-((6-cyclopropylbenzo[b]thiophen-2-yl)methyl)-1H-1,2,3-triazole-4-carboxylate (100 mg, 0.305 mmol) and $LiOH \cdot H_2O$ (13 mg, 0.305 mmol) in a mixed solvent of $THF/H_2O$ (4 mL/4 mL) was stirred at RT overnight. The pH value of the mixture was adjusted to 5 and then concentrated to give 1-((6-cyclopropylbenzo[b]thiophen-2-yl)methyl)-1H-1,2,3-triazole-4-carboxylic acid (120 mg, crude) as a yellow solid, which was used directly in the next step without further purification. ESI-MS $[M+Na]^+$: 322.0.

Synthesis of N-((7-chloro-8-fluoroimidazo[1,5-a]pyridin-1-yl)methyl)-1-((6-cyclopropylbenzo[b]thiophen-2-yl)methyl)-1H-1,2,3-triazole-4-carboxamide (I-229)

A mixture of 1-((6-cyclopropylbenzo[b]thiophen-2-yl)methyl)-1H-1,2,3-triazole-4-carboxylic acid (120 mg, crude from last step), (7-chloro-8-fluoroimidazo[1,5-a]pyridin-1-yl)methanamine hydrochloride (82 mg, 0.35 mmol), HATU (221 mg, 0.58 mmol) and DIPEA (188 mg, 1.45 mmol) in DMF (10 mL). The resulting mixture was stirred for 3 h at RT. The mixture was concentrated to remove DMF to give the crude product, which was purified by Prep-HPLC to give N-((7-chloro-8-fluoroimidazo[1,5-a]pyridin-1-yl)methyl)-1-((6-cyclopropylbenzo[b]thiophen-2-yl)methyl)-1H-1,2,3-triazole-4-carboxamide (25 mg, yield: 17% over 2 steps) as a light yellow solid. ESI-MS $[M+H]^+$: 480.9. Purity: 99.65 (214 nm) 99.59 (254 nm). $^1H$ NMR (400 MHz, $CDCl_3$) δ 8.09 (s, 2H), 7.63-7.48 (m, 3H), 7.48 (s, 1H), 7.11 (d, J=8.2 Hz, 1H), 6.54 (t, J=4.6 Hz, 1H), 5.77 (s, 2H), 4.98 (d, J=4.6 Hz, 2H), 2.01-1.98 (m, 1H), 1.02-0.99 (m, 2H), 0.75-0.77 (m, 2H).

Example 230

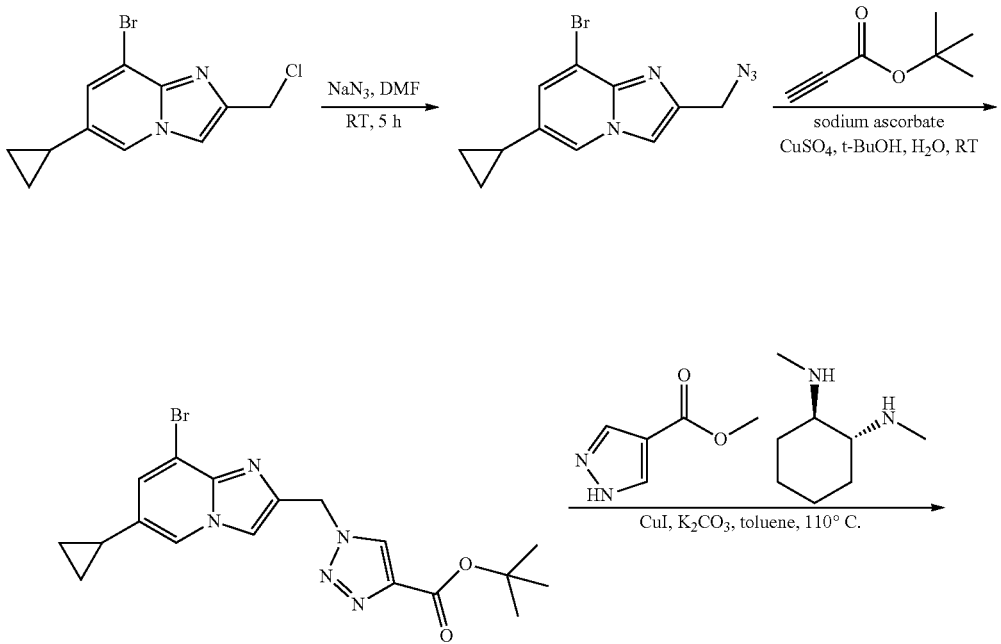

Scheme 229

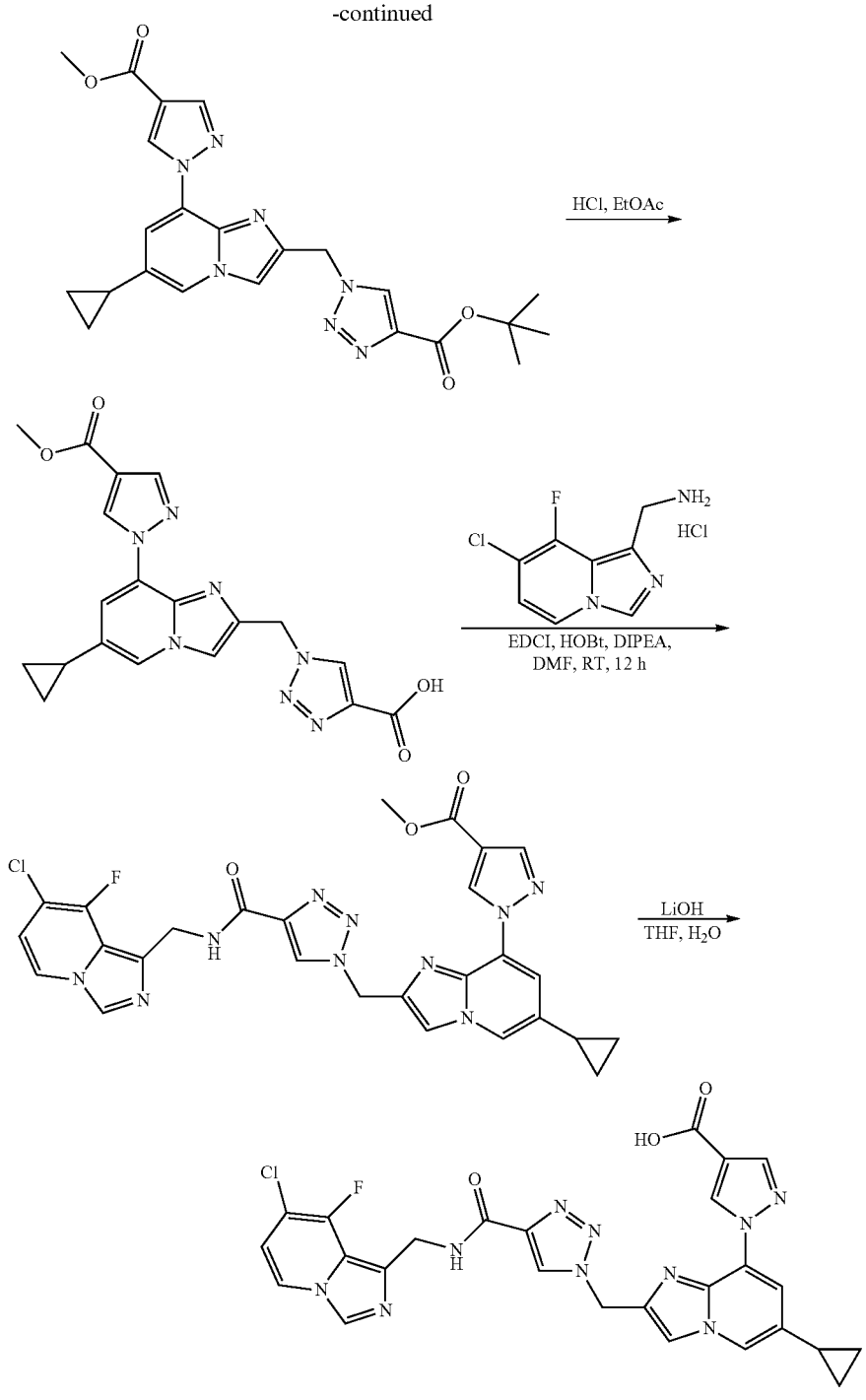

I-230

Synthesis of 2-(azidomethyl)-8-bromo-6-cyclopropylimidazo[1,2-a]pyridine

To a solution of 8-bromo-2-(chloromethyl)-6-cyclopropylimidazo[1,2-a]pyridine (1 g, 3.5 mmol) in DMF (15 mL) was added NaN$_3$ (230 mg, 3.5 mmol). The resulting mixture was stirred at 50° C. for 24 h under nitrogen. H$_2$O (50 mL) was added to the reaction, extracted with EtOAc (50 mL×3). The combined organic layers were washed brine, dried over Na$_2$SO$_4$, concentrated in vacuo to give 2-(azidomethyl)-8-bromo-6-cyclopropylimidazo[1,2-a]pyridine (1.1 g, crude), which was used into next step without further purification. ESI-MS [M+H]$^+$: 292.0.

Synthesis of tert-butyl 1-((8-bromo-6-cyclopropylimidazo[1,2-a]pyridin-2-yl)methyl)-1H-1,2,3-triazole-4-carboxylate To a solution 2-(azidomethyl)-8-bromo-6-cyclopropylimidazo[1,2-a]pyridine (1.1 g, crude from previous step)

and tert-butyl propiolate (860 mg, 6.8 mmol) in t-BuOH/H$_2$O (15 mL/15 mL) was added CuSO$_4$ (170 mg, 0.68 mmol), sodium ascorbate (180 mg, 1.02 mmol). The reaction mixture was stirred at RT for 12 h. The mixture was concentrated in vacuo to give the crude product, which was purified by silica gel chromatography (PE/EtOAc=1/2) to give tert-butyl 1-((8-bromo-6-cyclopropylimidazo[1,2-a]pyridin-2-yl)methyl)-1H-1,2,3-triazole-4-carboxylate (500 mg, 34% over 2 steps) as brown oil. ESI-MS [M+H]$^+$: 417.7.

Synthesis of tert-butyl 1-((6-cyclopropyl-8-(4-(methoxycarbonyl)-1H-pyrazol-1-yl)imidazo[1,2-a]pyridin-2-yl)methyl)-1H-1,2,3-triazole-4-carboxylate A solution of tert-butyl 1-((8-bromo-6-cyclopropylimidazo[1,2-a]pyridin-2-yl)methyl)-1H-1,2,3-triazole-4-carboxylate (440 mg, 1.05 mmol) methyl 1H-pyrazole-4-carboxylate (330 mg, 2.62 mmol), CuI (20 mg, 0.105 mmol), (1R,2R)—N1,N2-dimethylcyclohexane-1,2-diamine (30 mg, 0.21 mmol) and K$_2$CO$_3$ (290 mg, 2.1 mmol) in toluene (5 mL) was degassed by N$_2$ for 10 min in in a sealed tube. The reaction mixture was stirred at 110° C. for 12 h. The reaction was concentrated to remove the toluene. Water (30 mL) was added to the residue, and extracted with EtOAc (30 mL×3). The combined organic layers were washed with brine, dried over Na$_2$SO$_4$, concentrated in vacuo to give crude, which was purified with Prep-TLC (DCM/MeOH=15/1) to give the tert-butyl 1-((6-cyclopropyl-8-(4-(methoxycarbonyl)-1H-pyrazol-1-yl)imidazo [1,2-a]pyridin-2-yl)methyl)-1H-1,2,3-triazole-4-carboxylate (250 mg, 51.4%) as a yellow solid. ESI-MS [M+H]$^+$: 463.9

Synthesis of 1-((6-cyclopropyl-8-(4-(methoxycarbonyl)-1H-pyrazol-1-yl)imidazo[1,2-a]pyridin-2-yl)methyl)-1H-1,2,3-triazole-4-carboxylic Acid A Tert-butyl 1-((6-cyclopropyl-8-(4-(methoxycarbonyl)-1H-pyrazol-1-yl)imidazo[1,2-a]pyridin-2-yl)methyl)-1H-1,2,3-triazole-4-carboxylate (250 mg, 0.54 mmol) in HCl (5 mL, 4 M solution in EtOAc, 20 mmol) was stirred at RT for 12 h. The mixture was concentrated to give 1-((6-cyclopropyl-8-(4-(methoxycarbonyl)-1H-pyrazol-1-yl)imidazo[1,2-a]pyridin-2-yl) methyl)-1H-1,2,3-triazole-4-carboxylic acid (270 mg, crude), which was used into next step without further purification. ESI-MS [M+H]$^+$: 407.9

Synthesis of Methyl 1-(2-((4-(1-(((7-chloro-8-fluoroimidazo[1,5-a]pyridin-1-yl)methyl)amino)vinyl)-1H-1,2,3-triazol-1-yl)methyl)-6-cyclopropylimidazo[1,2-a]pyridin-8-yl)-1H-pyrazole-4-carboxylate To a solution of 1-((6-cyclopropyl-8-(4-(methoxycarbonyl)-1H-pyrazol-1-yl)imidazo[1,2-a] pyridin-2-yl)methyl)-1H-1,2,3-triazole-4-carboxylic acid (270 mg crude from previous step) in DMF (5 mL) was added EDCI (155 mg, 0.81 mmol), HOBT (109 mg, 0.81 mmol), DIPEA (0.2 mL, 1.1 mmol) and (7-chloro-8-fluoroimidazo[1,5-a]pyridin-1-yl)methanamine hydrochloride (153.4 mg, 0.65 mmol). The reaction mixture was stirred at RT for 12 h. The mixture was poured into 20 mL of H$_2$O, extracted with EtOAc (30 mL×3). The combined organic layers were washed with brine, dried over Na$_2$SO$_4$, and concentrated to give the crude, which was purified by Prep-TLC (DCM/MeOH=10/1) to give methyl 1-(2-((4-(1-(((7-chloro-8-fluoroimidazo[1,5-a]pyridin-1-yl)methyl)amino)vinyl)-1H-1,2,3-triazol-1-yl)methyl)-6-cyclopropylimidazo[1,2-a]pyridin-8-yl)-1H-pyrazole-4-carboxylate (46 mg, 14.5% over 2 steps) as a white solid. ESI-MS [M+H]$^+$: 587.7

Synthesis of 1-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-1H-pyrazole-4-carboxylic acid (I-230)

To a solution of methyl 1-(2-((4-(1-(((7-chloro-8-fluoroimidazo[1,5-a]pyridin-1-yl)methyl)amino) vinyl)-1H-1,2,3-triazol-1-yl)methyl)-6-cyclopropylimidazo[1,2-a]pyridin-8-yl)-1H-pyrazole-4-carboxylate (46 mg, 0.078 mmol) in THF/H$_2$O (2 mL/2 mL) was added LiOH (10 mg, 0.39 mmol). The reaction mixture was stirred at RT for 12 h. The mixture was concentrated to give the crude product, which was purified by Prep-HPLC to give 1-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-1H-pyrazole-4-carboxylic acid (5 mg, yield: 11%) as a white solid. ESI-MS [M+H]$^+$: 574.8. Purity: 100 (214 nm) 100 (254 nm). $^1$H NMR (400 MHz, DMSO-d$_6$) δ=9.74 (s, 1H), 8.71 (t, J=5.2 Hz, 1H), 8.59 (s, 1H), 8.45 (s, 1H), 8.43 (s, 1H), 8.21 (s, 1H), 8.18 (d, J=3.6 Hz, 1H), 7.99 (s, 1H), 7.69 (s, 1H), 6.76 (t, J=6.8 Hz, 1H), 5.86 (s, 2H), 4.70 (d, J=5.2 Hz, 2H), 1.27-1.21 (m, 1H), 0.97 (dd, J=14.8, 6.8 Hz, 2H), 0.74 (dd, J=10.4, 5.6 Hz, 2H).

Example 231

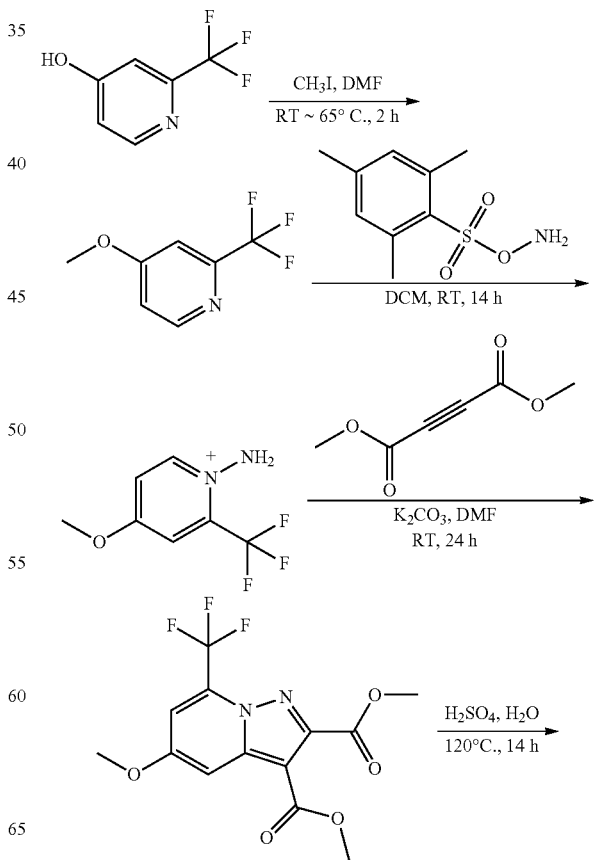

Scheme 230

-continued

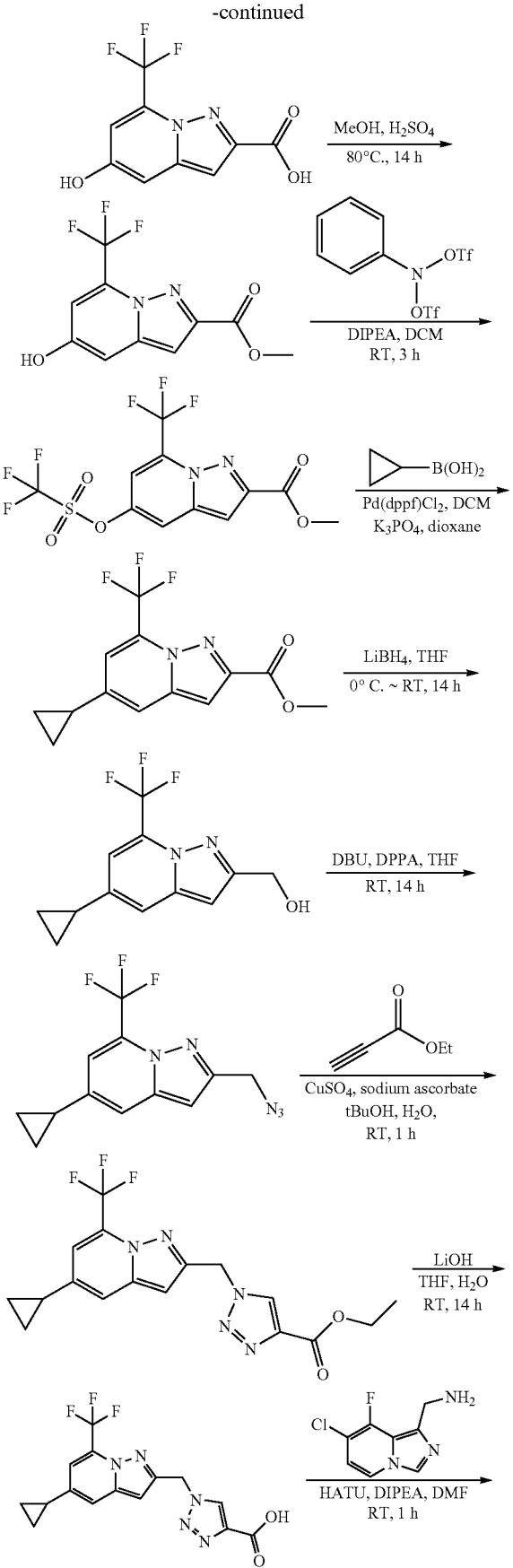

-continued

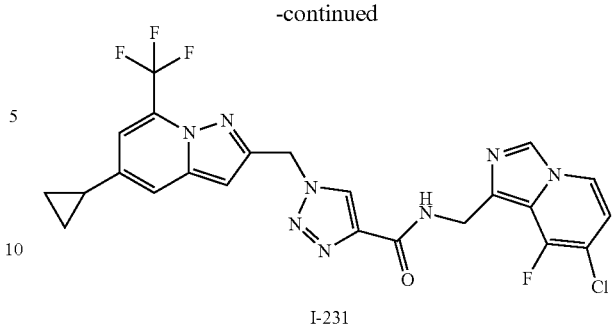

I-231

Synthesis of 4-methoxy-2-(trifluoromethyl)pyridine

To a solution of 2-(trifluoromethyl)pyridin-4-ol (5.8 g, 35.56 mmol) in DMF (40 mL) was added iodomethane (11.1 g, 78.23 mmol) and $K_2CO_3$ (6.05 g, 43.74 mmol). Then the reaction mixture was stirred at 65° C. for 2 h. The mixture was treated with $H_2O$ (100 mL) and extracted with EtOAc (70 mL×3). The combined organic layers were washed with brine, dried over $Na_2SO_4$, concentrated to give 4-methoxy-2-(trifluoromethyl)pyridine as a yellow oil (3.5 g, yield: 55%) which was used in next step without further purification. ESI-MS $[M+H]^+$: 178.1.

Synthesis of 1-amino-4-hydroxy-2-(trifluoromethyl)pyridin-1-ium

To a solution 4-methoxy-2-(trifluoromethyl)pyridine (3 g, 16.9 mmol) in DCM (50 mL) was added 0-(mesitylsulfonyl)hydroxylamine (3.6 g, 17 mmol) at RT. The mixture was stirred at RT for 14 h. The reaction mixture was concentrated to give the crude product, which was washed with tert-Butyl methyl ether (100 mL) and filtered to give 1-amino-4-hydroxy-2-(trifluoromethyl)pyridin-1-ium (6 g, crude) as a yellow solid. ESI-MS $[M+Na]^+$: 192.9.

Synthesis of dimethyl 5-methoxy-7-(trifluoromethyl)pyrazolo[1,5-a]pyridine-2,3-dicarboxylate To a solution of 1-amino-4-hydroxy-2-(trifluoromethyl)pyridin-1-ium (6 g, crude from previous step) in DMF (25 mL) was added dimethyl but-2-ynedioate (5.39 g, 37.96 mmol) slowly, followed by $K_2CO_3$ (5.25 g, 37.96 mmol). Then the resulting reaction mixture was stirred at RT for 24 h. The reaction was poured into $H_2O$ (100 mL), and the yellow solid was precipitated. The mixture was filtrated, washed with $H_2O$ (20 mL) and dried to give dimethyl 5-methoxy-7-(trifluoromethyl)pyrazolo[1,5-a]pyridine-2,3-dicarboxylate (2.3 g, yield: 41.1% over 2 steps) as a yellow solid. ESI-MS $[M+H]^+$: 332.8.

Synthesis of 5-hydroxy-7-(trifluoromethyl)pyrazolo[1,5-a]pyridine-2-carboxylic Acid A mixture of dimethyl 5-methoxy-7-(trifluoromethyl)pyrazolo[1,5-a]pyridine-2,3-dicarboxylate (2.3 g, 6.92 mmol) in $H_2O$ (150 mL) was dissolved in con. $H_2SO_4$ (5 mL). And the resulting mixture was stirred at 120° C. for 14 h. The mixture was poured into ice $H_2O$, and white solid was precipitated. The mixture was filtrated and dried to give 5-hydroxy-7-(trifluoromethyl)pyrazolo[1,5-a]pyridine-2- carboxylic acid (1.5 g crude) as a white solid, which was used into next step without further purification. ESI-MS [M+H]⁺: 246.7.

Synthesis of Methyl 5-hydroxy-7-(trifluoromethyl)pyrazolo[1,5-a]pyridine-2-carboxylate To a solution of 5-hydroxy-7-(trifluoromethyl)pyrazolo[1,5-a]pyridine-2-carboxylic acid (1.5 g, crude from last step) in MeOH (30 mL) was added con. $H_2SO_4$ (1 mL), then the mixture was stirred at 80° C. for 14 h. The reaction was concentrated to remove the solvent to give the residue, which was washed with $H_2O$ (50 mL) and extracted with EtOAc (50 mL×3). The combined organic layers were concentrated to give the crude product, which was purified by silica gel chromatography (MeOH/DCM=1/10) to give methyl 5-hydroxy-7-(trifluoromethyl)pyrazolo[1,5-a]pyridine-2-carboxylate (820 mg, yield: 45% over 2 steps) as a yellow solid. ESI-MS [M+H]⁺: 260.8.

Synthesis of Methyl 7-(trifluoromethyl)-5-(((trifluoromethyl)sulfonyl)oxy)pyrazolo[1,5-a]pyridine-2-carboxylate To a solution of methyl 5-hydroxy-7-(trifluoromethyl)pyrazolo[1,5-a]pyridine-2-carboxylate (820 mg, 3.15 mmol) in DCM (30 mL) was added 1,1,1-trifluoro-N-phenyl-N-((trifluoromethyl)sulfonyl)methanesulfonamide (1.41 g, 3.94 mmol) and DIPEA (815 mg, 6.3 mmol), then the mixture was stirred at 3 h. The solvent was removed to give the crude product which was purified silica gel chromatography (PE/EA=10/1) to give 7-(trifluoromethyl)-5-(((trifluoromethyl)sulfonyl)oxy)pyrazolo[1,5-a]pyridine-2-carboxylate (970 mg, 78%) as a yellow solid. ESI-MS [M+H]⁺: 392.7.

Synthesis of Methyl 5-cyclopropyl-7-(trifluoromethyl)pyrazolo[1,5-a]pyridine-2-carboxylate To a solution of 7-(trifluoromethyl)-5-(((trifluoromethyl)sulfonyl)oxy)pyrazolo[1,5-a]pyridine-2-carboxylate (970 mg, 2.5 mmol) in Dioxane (20 mL) was added cyclopropylboronic acid (403 mg, 4.69 mmol), $K_3PO_4$ (1.49 g, 7.04 mmol) and Pd(dppf)Cl₂-DCM (115 mg, 0.14 mmol). The resulting mixture was stirred at 90° C. for 14 h. Water (60 mL) was added to the reaction, and extracted with EtOAc (60 mL×3). The combined organic layers were washed with brine, dried over $Na_2SO_4$, concentrated to give the crude product, which was purified with silica gel chromatography (PE/EA=4/1) to give methyl 5-cyclopropyl-7-(trifluoromethyl)pyrazolo[1,5-a]pyridine-2-carboxylate (520 mg, yield: 73%) as a yellow oil. ESI-MS [M+H]⁺: 284.9.

Synthesis of (5-cyclopropyl-7-(trifluoromethyl)pyrazolo[1,5-a]pyridin-2-yl)methanol To a solution of methyl 5-cyclopropyl-7-(trifluoromethyl)pyrazolo[1,5-a]pyridine-2-carboxylate (555 mg, 1.95 mmol) in THF (20 mL) was added LiBH4 (85 mg, 3.91 mmol) at 0° C. Then the reaction mixture was stirred at RT for 14 h. The reaction was quenched with $H_2O$ (50 mL) and extracted with EtOAc (50 mL×3). The combined organic layers were concentrated to give (5-cyclopropyl-7-(trifluoromethyl)pyrazolo[1,5-a]pyridin-2-yl)methanol (500 mg crude) as yellow oil, which was used in next step without further purification. ESI-MS [M+H]⁺: 257.1.

Synthesis of 2-(azidomethyl)-5-cyclopropyl-7-(trifluoromethyl)pyrazolo[1,5-a]pyridine To a solution of (5-cyclopropyl-7-(trifluoromethyl)pyrazolo[1,5-a]pyridin-2-yl)methanol (250 mg crude from previous step) in THF (10 mL) was added DBU (164 mg, 1.08 mmol) and DPPA (296 mg, 1.08 mmol). Then the resulting reaction mixture was stirred at RT for 14 h. Water (40 mL) was added to the reaction, and extracted with EtOAc (40 mL×3). The combined organic layers were washed with brine, dried over $Na_2SO_4$, concentrated to give the crude product, which was purified with silica gel chromatography (PE/EA=2/1) to give 2-(azidomethyl)-5-cyclopropyl-7-(trifluoromethyl)pyrazolo[1,5-a]pyridine (110 mg, yield: 40% over 2 steps) as a white solid. ESI-MS [M+H]⁺: 281.8.

Synthesis of Ethyl 1-((5-cyclopropyl-7-(trifluoromethyl)pyrazolo[1,5-a]pyridin-2-yl)methyl)-1H-1,2,3-triazole-4-carboxylate To a solution of 2-(azidomethyl)-5-cyclopropyl-7-(trifluoromethyl)pyrazolo[1,5-a]pyridine (110 mg, 0.39 mmol) in t-BuOH/$H_2O$ (4 mL/4 mL) was added ethyl propiolate (77 mg, 0.78 mmol), $CuSO_4$ (12.5 mg, 0.078 mmol) and sodium ascorbate (24 mg, 0.12 mmol). Then the mixture was stirred at RT for 1 h. Then concentrated to give the crude product, which was purified with silica gel chromatography (PE/EA=2/1) to give ethyl 1-((5-cyclopropyl-7-(trifluoromethyl)pyrazolo[1,5-a]pyridin-2-yl)methyl)-1H-1,2,3-triazole-4-carboxylate (50 mg, yield: 34%) as a yellow solid. ESI-MS [M+H]⁺: 379.7.

Synthesis of 1-((5-cyclopropyl-7-(trifluoromethyl)pyrazolo[1,5-a]pyridin-2-yl)methyl)-1H-1,2,3-triazole-4-carboxylic Acid To a solution of ethyl 1-((5-cyclopropyl-7-(trifluoromethyl)pyrazolo [1,5-a]pyridin-2-yl)methyl)-1H-1,2,3-triazole-4-carboxylate (55 mg, 0.14 mmol) in THF/$H_2O$ (3 mL/3 mL) was added LiOH.$H_2O$ (12 mg, 0.29 mmol). Then the mixture was stirred at RT for 14 h. The pH of the reaction was adjusted by HCl (1N), and concentrated to give 1-((5-cyclopropyl-7-(trifluoromethyl)pyrazolo[1,5-a]pyridin-2-yl)methyl)-1H-1,2,3-triazole-4-carboxylic acid (70 mg, crude) as a yellow solid, which was used into next step without further purification. ESI-MS [M+H]⁺: 351.7.

Synthesis of N-((7-chloro-8-fluoroimidazo[1,5-a]pyridin-1-yl)methyl)-1-((5-cyclopropyl-7-(trifluoromethyl)pyrazolo[1,5-a]pyridin-2-yl)methyl)-1H-1,2,3-triazole-4-carboxamide (I-231)

To a solution of 1-((5-cyclopropyl-7-(trifluoromethyl)pyrazolo[1,5-a]pyridin-2-yl)methyl)-1H-1,2,3-triazole-4-carboxylic acid (70 mg, crude from previous step) in DMF (5 mL) was added (7-chloro-8-fluoroimidazo[1,5-a]pyridin-1-yl)methanamine hydrochloride (66 mg, 0.28 mmol), HATU (108 mg, 0.28 mmol) and DIPEA (110 mg, 0.85 mmol). Then the mixture was stirred at RT for 1 h. The mixture was poured into $H_2O$ (20 mL), and solid was precipitated. The mixture was filtrated, washed with MeOH (30 mL), and then dried to give N-((7-chloro-8-fluoroimidazo[1,5-a]pyridin-1-yl)methyl)-1-((5-cyclopropyl-7-(trifluoromethyl)pyrazolo[1,5-a]pyridin-2-yl)methyl)-1H-1,2,3-triazole-4-carboxamide (10.5 mg, yield: 14% over 2 steps) as a white solid. ESI-MS [M+H]⁺: 532.4. Purity: 100% (214 nm) 100% (254 nm). ¹H NMR (300 MHz, DMSO-d₆)

δ=8.71 (t, J=8.0 Hz, 1H), 8.61 (s, 1H), 8.42 (s, 1H), 8.19 (d, J=12.0 Hz, 1H), 7.65 (s, 1H), 7.25 (s, 1H), 6.74 (t, J=12.0 Hz, 1H), 6.55 (s, 1H), 5.87 (s, 2H), 4.69 (d, J=8.0 Hz, 2H), 2.10-2.04 (m, 1H), 1.04-1.00 (m, 2H), 0.87-0.81 (m, 2H).

Example 232

Scheme 231

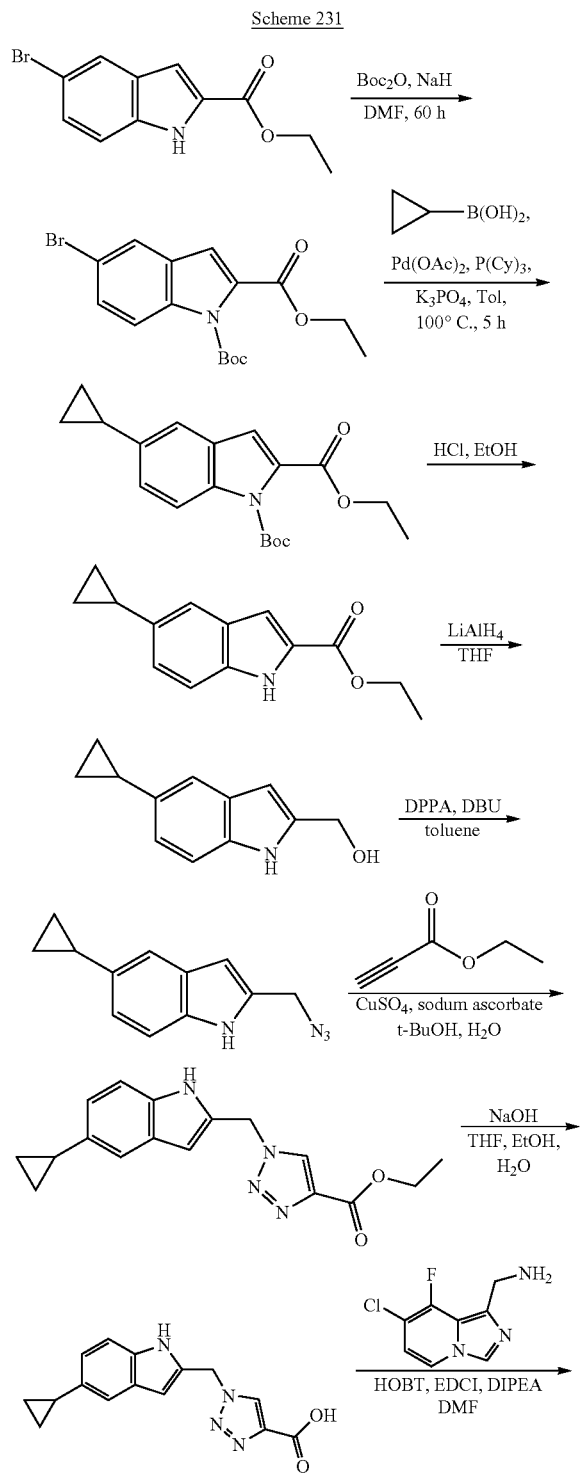

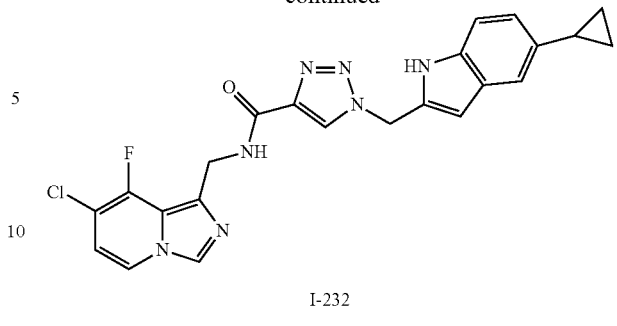

I-232

Synthesis of 1-(tert-butyl) 2-ethyl 5-bromo-1H-indole-1,2-dicarboxylate

To a solution of ethyl 5-bromo-1H-indole-2-carboxylate (3 g, 11.2 mmol) in DMF (40 mL) was added NaH (672 mg, 60%, 16.8 mmol) at 0° C. and stirred for 1 h at this temperature. Then Boc₂O (4.9 g, 22.4 mmol) was added. The reaction mixture was stirred at RT for 16 h. The reaction was quenched with H₂O (200 mL) and extracted with DCM (150 mL×3). The combined organic layers were concentrated to give the crude product, which was purified by silica gel chromatography (PE/EA=20/1) to give the 1-(tert-butyl) 2-ethyl 5-bromo-1H-indole-1,2-dicarboxylate as a yellow solid (4 g, yield: 97%). ESI-MS [M+Na]⁺: 390.0.

Synthesis of 1-(tert-butyl) 2-ethyl 5-cyclopropyl-1H-indole-1,2-dicarboxylate To a solution of 1-(tert-butyl) 2-ethyl 5-bromo-1H-indole-1,2-dicarboxylate (4 g, 10.9 mmol) in toluene (50 mL) was added cyclopropylboronic acid (1.9 g, 21.8 mmol), Pd(OAc)₂ (246 mg, 1.1 mmol), P(Cy)₃ (308 mg, 1.1 mmol) and K₃PO₄ (4.6 g, 21.8 mmol). The reaction mixture was stirred at 100° C. for 5 h under nitrogen. Then the mixture was concentrated in vacuo. Water (100 mL) was added to the residue and extracted with DCM (150 mL×3). The combined organic layers were concentrated to give the crude product, which was purified by silica gel chromatography (PE/EA=20/1) to give the 1-(tert-butyl) 2-ethyl 5-cyclopropyl-1H-indole-1,2-dicarboxylate as a yellow solid (3.1 g, yield: 87%). ESI-MS [M+Na]⁺: 351.8.

Synthesis of Ethyl 5-cyclopropyl-1H-indole-2-carboxylate

A solution of 1-(tert-butyl) 2-ethyl 5-cyclopropyl-1H-indole-1,2-dicarboxylate (3.1 g, 9.4 mmol) in HCl in EtOH (33%, 45 mL) was stirred at RT for 6 h. The mixture was then concentrated and purified by silica gel chromatography (PE/EA=10/1) to give ethyl 5-cyclopropyl-1H-indole-2-carboxylate (2.1 g, yield: 96%) as a yellow solid. ESI-MS [M+H]⁺: 230.0

Synthesis of (5-cyclopropyl-1H-indol-2-yl)methanol

To a solution of ethyl 5-cyclopropyl-1H-indole-2-carboxylate (1.1 g, 4.8 mmol) in THF (15 mL) was added LiAlH₄ (273 mg, 7.2 mmol) slowly at 0° C. The reaction mixture was stirred at RT for 6 h. The reaction was quenched by H₂O (0.5 mL), 10% NaOH (0.5 mL) and H₂O (1.5 mL), the mixture was then filtered through celite and filtrate was concentrated to give the crude product, which was purified by silica gel chromatography (PE/EA=1/1) to give (5-cy-clopropyl-1H-indol-2-yl)methanol (780 mg, yield: 86%) as a white solid. ESI-MS [M+H]$^+$: 187.9.

Synthesis of 2-(azidomethyl)-5-cyclopropyl-1H-indole

To a solution of (5-cyclopropyl-1H-indol-2-yl)methanol (780 mg, 4.1 mmol) and DPPA (1.2 g, 4.5 mmol) in toluene (15 mL) was added DBU (760 mg, 4.9 mmol) at 0° C. The reaction mixture was stirred at RT for 16 h. Water (40 mL) was added and the mixture was extracted with DCM (50 mL×2). The combined organic layers were concentrated and purified by silica gel chromatography (PE/EA=20/1) to give 2-(azidomethyl)-5-cyclopropyl-1H-indole (570 mg, yield: 65%) as a brown oil. ESI-MS [M+H]$^+$: 212.9

Synthesis of Ethyl 1-((5-cyclopropyl-1H-indol-2-yl)methyl)-1H-1,2,3-triazole-4-carboxylate A mixture of 2-(azidomethyl)-5-cyclopropyl-1H-indole (570 mg, 2.7 mmol), ethyl propiolate (392 mg, 4.0 mmol), $CuSO_4 \cdot 5H_2O$ (135 mg, 0.54 mmol), sodium ascorbate (158 mg, 0.8 mmol) in t-BuOH/$H_2O$ (8 mL/8 mL) was stirred at RT for 16 h. Water (30 mL) was added and extracted with EtOAc (50 mL×3). The combined organic layers concentrated in vacuo to give the crude product, which was purified by silica gel chromatography (PE/EA=1/4) to give ethyl 1-((5-cyclopropyl-1H-indol-2-yl)methyl)-1H-1,2,3-triazole-4-carboxylate (400 mg, yield: 48%) as a yellow solid. ESI-MS [M]$^+$: 311.1

Synthesis of 1-((5-cyclopropyl-1H-indol-2-yl)methyl)-1H-1,2,3-triazole-4-carboxylic Acid A mixture of ethyl 1-((5-cyclopropyl-1H-indol-2-yl)methyl)-1H-1,2,3-triazole-4-carboxylate (400 mg, 1.3 mmol), NaOH (103 mg, 2.6 mmol) in THF/EtOH/$H_2O$ (5 mL/5 mL/5 mL) was stirred at RT for 0.5 h. The mixture was acidified with 1N HCl solution to pH around 5, then concentrated to give 1-((5-cyclopropyl-1H-indol-2-yl)methyl)-1H-1,2,3-triazole-4-carboxylic acid (340 mg, crude) as a white solid. ESI-MS [M+Na]$^+$: 305.0.

Synthesis of N-((7-chloro-8-fluoroimidazo[1,5-a]pyridin-1-yl)methyl)-1-((5-cyclopropyl-1H-indol-2-yl)methyl)-1H-1,2,3-triazole-4-carboxamide (I-232)

A mixture of 1-((5-cyclopropyl-1H-indol-2-yl)methyl)-1H-1,2,3-triazole-4-carboxylic (34 mg, crude), (7-chloro-8-fluoroimidazo[1,5-a]pyridin-1-yl)methanamine hydrochloride (35 mg, 0.14 mmol), EDCI (29 mg, 0.15 mmol), HOBT (20 mg, 0.15 mmol), DIPEA (45 mg, 0.35 mmol) in DMF (3 mL) was stirred at RT for 16 h. Water (20 mL) was added and extracted with EtOAc (50 mL×3), the combined organic layers were concentrated to give the crude product, which was purified by Prep-TLC to give N-((7-chloro-8-fluoroimidazo[1,5-a]pyridin-1-yl)methyl)-1-((5-cyclopropyl-1H-indol-2-yl)methyl)-1H-1,2,3-triazole-4-carboxamide (17 mg) as a white solid. ESI-MS [M+H]$^+$: 463.8. Purity: 97.38% (214 nm), 98.22 (254 nm). $^1$H NMR (400 MHz, DMSO-$d_6$) δ 11.15 (s, 1H), 8.70 (s, 1H), 8.55 (s, 1H), 8.43 (s, 1H), 8.20 (d, J=7.4 Hz, 1H), 7.23-7.20 (m, 2H), 6.84 (d, J=8.3 Hz, 1H), 6.75 (t, J=6.8 Hz, 1H), 6.37 (s, 1H), 5.75 (s, 2H), 4.70 (d, J=5.2 Hz, 2H), 1.96-1.92 (m, 1H), 0.88-0.86 (m, 2H), 0.60-0.59 (m, 2H).

Example 233

Scheme 232

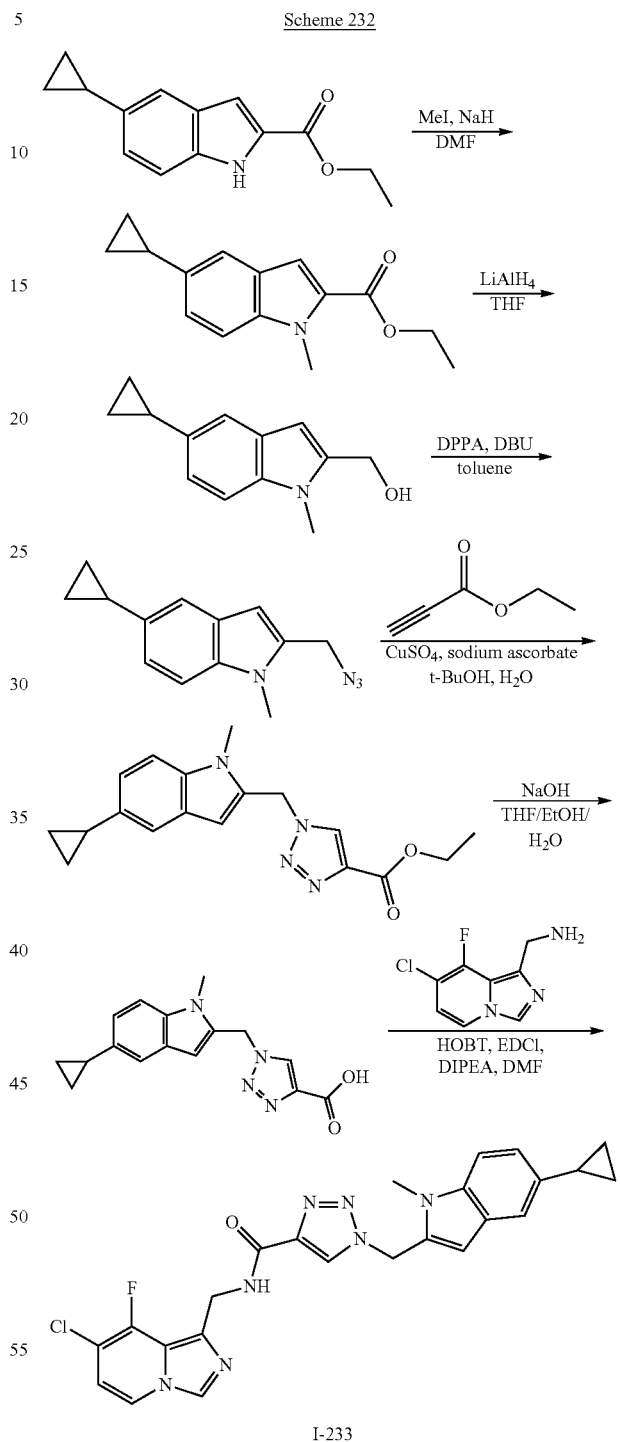

I-233

Synthesis of Ethyl 5-cyclopropyl-1-methyl-1H-indole-2-carboxylate

To a solution of ethyl 5-cyclopropyl-1H-indole-2-carboxylate (1 g, 4.3 mmol) in DMF (15 mL) was added NaH (256 mg, 60%, 6.4 mmol) at 0° C. and stirred for 1 h at this temperature. Then MeI (1.2 g, 8.6 mmol) was added. The reaction mixture was stirred at RT for 16 h. The reaction was quenched by H$_2$O (100 mL) and extracted with DCM (100 mL×3). The combined organic layers were concentrated to give the crude product, which was purified by silica gel chromatography (PE/EA=20/1) to give the ethyl 5-cyclopropyl-1-methyl-1H-indole-2-carboxylate as a yellow solid (900 mg, yield: 84%). ESI-MS [M+Na]$^+$: 244.0.

Synthesis of
(5-cyclopropyl-1-methyl-1H-indol-2-yl)methanol

To a solution of ethyl 5-cyclopropyl-1-methyl-1H-indole-2-carboxylate (900 mg, 3.7 mmol) in THF (15 mL) was added LiAlH$_4$ (211 mg, 5.5 mmol) slowly at 0° C. The reaction mixture was stirred at RT for 6 h. The reaction was quenched by H$_2$O (0.5 mL) and 10% NaOH (0.5 mL) and H$_2$O (1.5 mL). The mixture was filtered through celite and filtrate was concentrated to give the crude product, which was purified by silica gel chromatography (PE/EA=1/1) to give (5-cyclopropyl-1-methyl-1H-indol-2-yl)methanol (600 mg, yield: 80%) as a white solid. ESI-MS [M+H]$^+$: 202.2.

Synthesis of
2-(azidomethyl)-5-cyclopropyl-1-methyl-1H-indole

To a solution of (5-cyclopropyl-1-methyl-1H-indol-2-yl)methanol (600 mg, 3 mmol) and DPPA (907 mg, 3.3 mmol) in toluene (15 mL) was added DBU (547 mg, 3.6 mmol) at 0° C. The reaction mixture was stirred at RT for 16 h. Water (40 mL) was added and the mixture was extracted with DCM (50 mL×3). The combined organic layers were concentrated and purified by silica gel chromatography (PE/EA=20/1) to give 2-(azidomethyl)-5-cyclopropyl-1-methyl-1H-indole (450 mg, yield: 67%) as a white solid. ESI-MS [M+H]$^+$: 227.1

Synthesis of Ethyl 1-((5-cyclopropyl-1-methyl-1H-indol-2-yl)methyl)-1H-1,2,3-triazole-4-carboxylate A mixture of 2-(azidomethyl)-5-cyclopropyl-1-methyl-1H-indole (450 mg, 2.0 mmol), ethyl propiolate (252 mg, 3.0 mmol), CuSO$_4$.5H$_2$O (100 mg, 0.4 mmol), sodium ascorbate (60 mg, 0.6 mmol) in t-BuOH/H$_2$O (10 mL/10 mL) was stirred at RT for 16 h. Water (30 mL) was added and extracted with EtOAc (50 mL×3). The combined organic layers were concentrated to give the crude product, which was purified by silica gel chromatography (PE/EA=1/1) to give ethyl 1-((5-cyclopropyl-1-methyl-1H-indol-2-yl)methyl)-1H-1,2,3-triazole-4-carboxylate (380 mg, yield: 59%) as a white solid. ESI-MS [M+H]$^+$: 325.1

Synthesis of 1-((5-cyclopropyl-1-methyl-1H-indol-2-yl)methyl)-1H-1,2,3-triazole-4-carboxylic Acid A mixture of ethyl 1-((5-cyclopropyl-1-methyl-1H-indol-2-yl)methyl)-1H-1,2,3-triazole-4-carboxylate (380 mg, 1.2 mmol), NaOH (95 mg, 2.6 mmol) in THF/EtOH H$_2$O (3 mL/3 mL/3 mL) was stirred at RT for 0.5 h. The mixture was acidified with 1N HCl solution then concentrated to give the crude product 1-((5-cyclopropyl-1-methyl-1H-indol-2-yl) methyl)-1H-1,2,3-triazole-4-carboxylic acid (400 mg, crude) as a white solid. ESI-MS [M+H]$^+$: 297.1

Synthesis of N-((7-chloro-8-fluoroimidazo[1,5-a] pyridin-1-yl)methyl)-1-((5-cyclopropyl-1-methyl-1H-indol-2-yl)methyl)-1H-1,2,3-triazole-4-carboxamide (I-233)

A mixture of 1-((5-cyclopropyl-1-methyl-1H-indol-2-yl)methyl)-1H-1,2,3-triazole-4-carboxylic acid (30 mg, crude from last step), (7-chloro-8-fluoroimidazo[1,5-a]pyridin-1-yl)methanamine hydrochloride (23.5 mg, 0.1 mmol), EDCI (21 mg, 0.11 mmol), HOBT (15 mg, 0.11 mmol), DIPEA (32.2 mg, 0.25 mmol) in DMF (3 mL) was stirred at RT for 16 h. Water (20 mL) was added and extracted with EtOAc (50 mL×3), the combined organic layers were concentrated to give the crude product, which was purified by Prep-TLC to give N-((7-chloro-8-fluoroimidazo[1,5-a]pyridin-1-yl) methyl)-1-((5-cyclopropyl-1-methyl-1H-indol-2-yl) methyl)-1H-1,2,3-triazole-4-carboxamide (9 mg) as a white solid. ESI-MS [M+H]$^+$: 477.6. Purity: 98.79% (214 nm), 98.35% (254 nm). $^1$H NMR (400 MHz, DMSO-d$_6$) δ 8.71 (s, 1H), 8.52 (s, 1H), 8.44 (s, 1H), 8.20 (d, J=7.4 Hz, 1H), 7.30 (d, J=8.5 Hz, 1H), 7.23 (s, 1H), 6.91 (d, J=8.3 Hz, 1H), 6.75 (t, J=6.8 Hz, 1H), 6.42 (s, 1H), 5.89 (s, 2H), 4.69 (d, J=5.0 Hz, 2H), 3.67 (s, 3H), 1.99-1.92 (m, 1H), 0.90-0.87 (m, 2H), 0.62-0.60 (m, 2H).

Example 234

Scheme 233

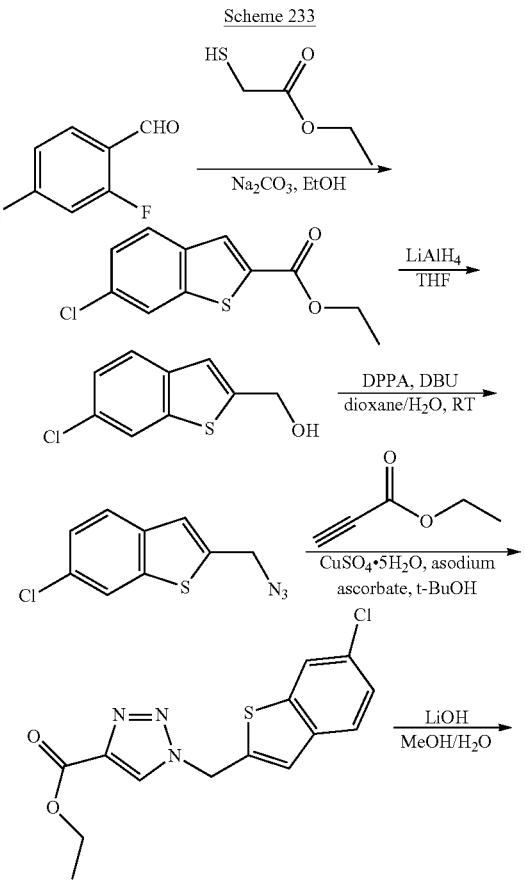

-continued

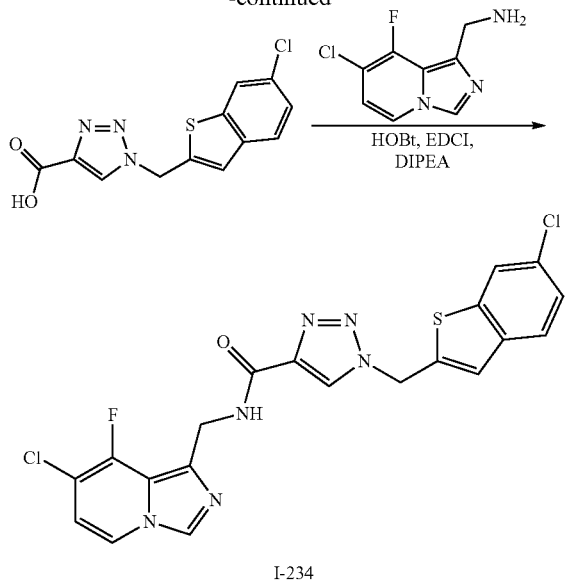

I-234

Synthesis of Ethyl 5-bromobenzo[b]thiophene-2-carboxylate

To a solution of 4-chloro-2-fluorobenzaldehyde (2 g, 12.6 mmol) and ethyl 2-mercaptoacetate (1.58 g, 12.6 mmol) in EtOH (40 mL) was added Na$_2$CO$_3$ (1.58 g, 15.1 mmol). The reaction mixture was stirred at reflux for 14 h. Then the mixture was concentrated in vacuo. Water (30 mL) was added and the mixture was extracted with DCM (50 mL×3). The combined organic layers were concentrated to give the crude product, which was purified by silica gel chromatography (PE/EtOAc=1/1) to give the ethyl 5-bromobenzo[b]thiophene-2-carboxylate as a yellow solid (2.36 g, yield: 78%). ESI-MS [M+H]$^+$: 240.9.

Synthesis of (6-cyclopropylbenzofuran-2-yl)methanol

To a stirring solution of ethyl 6-chlorobenzo[b]thiophene-2-carboxylate (1.2 g, 5 mmol) in dry THF (25 mL) was added portion-wise of LiAlH$_4$ (570 mg, 15 mmol) under 0° C. The resulting mixture was stirred at 0° C. for 1 h. The reaction was quenched sequentially with H$_2$O (1 mL), 15% NaOH (1 mL) and H$_2$O (3 mL). The resulting mixture was filtered through celite and the filtrate was concentrated to give the crude product (6-chlorobenzo[b]thiophen-2-yl)methanol (970 mg, crude) as a light yellow oil, which was used for the next step directly. ESI-MS [M+H]$^+$: 181.0

Synthesis of 2-(azidomethyl)-6-chlorobenzo[b]thiophene

To a solution of (6-cyclopropylbenzofuran-2-yl)methanol (970 mg, crude from last step) and DPPA (1.61 mg, 5.9 mmol) in dry THF (15 mL) at 0° C. was added DBU (888 mg, 5.9 mmol). The resulting mixture was stirred at RT overnight. Water (50 mL) was added and extracted with EtOAc (50 mL×3). The combined organic layers were concentrated and purified by flash silica gel column chromatography (DCM/MeOH=20/1) to give the product 2-(az-idomethyl)-6-chlorobenzo[b]thiophene (862 mg, 78% over 2 steps) as a light yellow oil. ESI-MS [M+H]$^+$: 224.1.

Synthesis of Ethyl 1-((6-chlorobenzo[b]thiophen-2-yl)methyl)-1H-1,2,3-triazole-4-carboxylate To a solution of 2-(azidomethyl)-6-chlorobenzo[b]thiophene (862 mg, 3.8 mmol) in t-BuOH (10 mL) and H$_2$O (10 mL) was added sequentially of CuSO$_4$·5H$_2$O (188 mg, 0.76 mmol), L(+)-Ascorbic acid sodium salt (193 mg, 0.95 mmol) and ethyl propiolate (724 mg, 7.49 mmol). The resulting mixture was stirred at RT for 15 h. The reaction mixture was concentrated to get the crude product, which was purified by flash column chromatography (DCM/MeOH=20/1) to give the product ethyl 1-((6-chlorobenzo[b]thiophen-2-yl)methyl)-1H-1,2,3-triazole-4-carboxylate (1 g, 82%) as an off-yellow oil. ESI-MS [M+H]$^+$: 328.2

Synthesis of 1-((6-chlorobenzo[b]thiophen-2-yl)methyl)-1H-1,2,3-triazole-4-carboxylic Acid A solution of ethyl 1-((6-chlorobenzo[b]thiophen-2-yl)methyl)-1H-1,2,3-triazole-4-carboxylic acid (1 g, 3 mmol) and LiOH·H$_2$O (467 mg, 11.4 mmol) in a mixed solvent of MeOH/H$_2$O (15 mL/15 mL) was stirred at RT for 2 h. The volatiles was removed in vacuo and the aqueous phase was acidified to pH 4-5 with 2N HCl. The precipitate was collected and dried to give the product 1-((6-chlorobenzo[b]thiophen-2-yl)methyl)-1H-1,2,3-triazole-4-carboxylic acid (720 mg, 80% yield) as a yellow solid. ESI-MS [M+H]$^+$: 300.1

Synthesis of N-((7-chloro-8-fluoroimidazo[1,5-a]pyridin-1-yl)methyl)-1-((6-chlorobenzo[b]thiophen-2-yl)methyl)-1H-1,2,3-triazole-4-carboxamide (I-234)

To a solution of 1-((6-cyclopropylbenzofuran-2-yl)methyl)-1H-1,2,3-triazole-4-carboxylic acid (90 mg, 0.3 mmol), (7-chloro-8-fluoroimidazo[1,5-a]pyridin-1-yl)methanamine hydrochloride (70 mg, 0.3 mmol), EDCI (86 mg, 0.45 mmol) and HOBT (60 mg, 0.45 mmol) in DMF (5 mL) was added DIPEA (77 mg, 0.6 mmol). The resulting mixture was stirred at RT for 15 h. Water (20 mL) was added and extracted with EtOAc (50 mL×3), the combined organic layers were concentrated and purified by Prep-TLC to give product N-((7-chloro-8-fluoroimidazo[1,5-a]pyridin-1-yl)methyl)-1-((6-chlorobenzo[b]thiophen-2-yl)methyl)-1H-1,2,3-triazole-4-carboxamide (9 mg, 6% yield) as an off-white solid. ESI-MS [M+H]$^+$: 474.5. Purity: 97.25% (214 nm), 97.53% (254 nm). $^1$H NMR (400 MHz, DMSO-d$_6$) δ 8.75 (s, 1H), 8.69 (s, 1H), 8.44 (s, 1H), 8.21 (d, J=7.3 Hz, 1H), 8.11 (s, 1H), 7.86 (d, J=8.5 Hz, 1H), 7.49 (s, 1H), 7.41 (d, J=8.4 Hz, 1H), 6.76 (t, J=6.9 Hz, 1H), 6.00 (s, 2H), 4.70 (d, J=5.2 Hz, 2H).

Example 235

Scheme 234

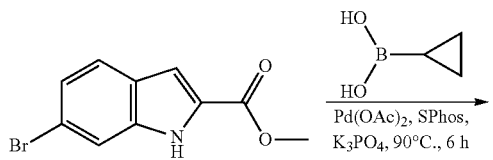

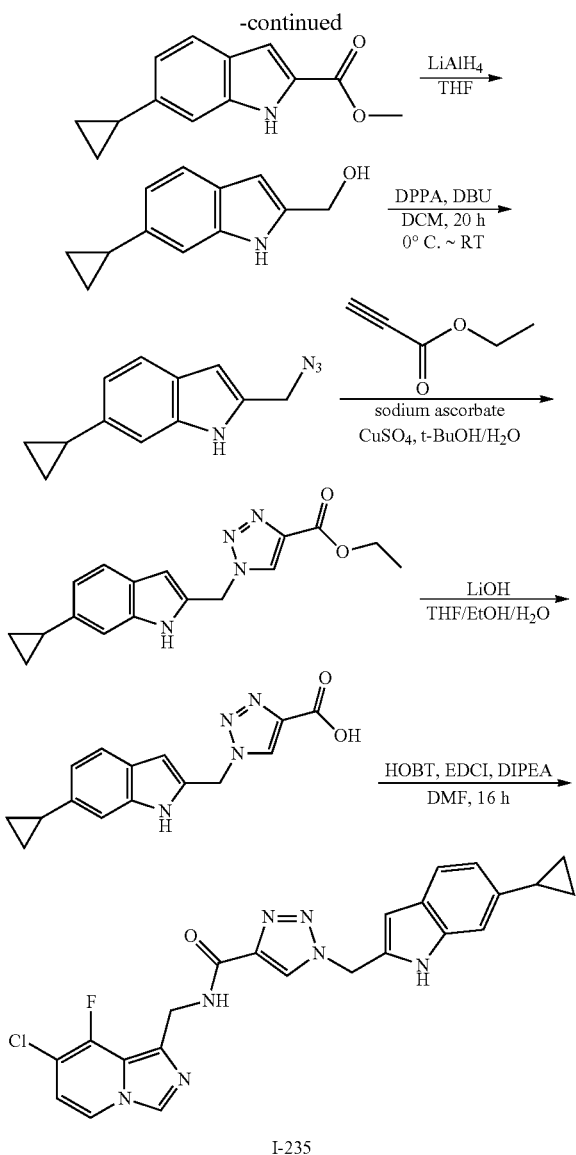

I-235

Synthesis of Methyl 6-cyclopropyl-1H-indole-2-carboxylate

A mixture of methyl 6-bromo-1H-indole-2-carboxylate (100 mg, 0.39 mmol), cyclopropylboronic acid (66 mg, 0.78 mmol), Pd(OAc)$_2$ (9 mg, 0.04 mmol), SPhos (16 mg, 0.04 mmol) and K$_3$PO$_4$ (76 mg, 1.36 mmol) in Tol/H$_2$O (2 mL/1 mL) was stirred at 90° C. for 4 h. Water (15 mL) was added and extracted with EtOAc (50 mL), the combined organic layer were concentrated and purified by silica gel chromatography (PE/EA=10/1) to give methyl 6-cyclopropyl-1H-indole-2-carboxylate (60 mg, yield: 72%) as a white solid. ESI-MS [M+H]$^+$: 216.1.

Synthesis of (6-cyclopropyl-1H-indol-2-yl)methanol

To a solution of methyl 6-cyclopropyl-1H-indole-2-carboxylate (60 mg, 0.28 mmol) in THF (1 mL) was added LiAlH$_4$ (13 mg, 0.34 mmol) in dry THF (2 mL) dropwise at 0° C. The reaction mixture was stirred at RT for 2 h, quenched with H$_2$O at 0° C., filtered, and the filtrate was extracted with EtOAc (30 mL×3). The combined organic layers were washed by brine (10 mL), dried over Na$_2$SO$_4$, concentrated and purified by silica gel chromatography (PE/EA=2/1) to give (6-cyclopropyl-1H-indol-2-yl)methanol (50 mg, yield: 96%) as a white solid. ESI-MS [M+H]$^+$: 188.1.

Synthesis of 2-(azidomethyl)-6-cyclopropyl-1H-indole

To a solution of (6-cyclopropyl-1H-indol-2-yl)methanol (300 mg, 1.6 mmol) and DPPA (1 g, 3.8 mmol) in dry CH$_2$Cl$_2$ (6 mL) was added DBU (580 mg, 3.8 mmol) dropwise at 0° C. The reaction mixture was stirred at 0° C. for 2 h and then at RT for 16 h. Water (30 mL) was added and extracted with CH$_2$Cl$_2$ (60 mL×3), the organic layers were concentrated and purified by silica gel chromatography (PE/EA=10/1) to give 2-(azidomethyl)-6-cyclopropyl-1H-indole (230 mg, yield: 68%) as yellow oil. ESI-MS [M+H]$^+$: 213.1

Synthesis of Ethyl 1-((6-cyclopropyl-1H-indol-2-yl)methyl)-1H-1,2,3-triazole-4-carboxylate A mixture of 2-(azidomethyl)-6-cyclopropyl-1H-indole (230 mg, 1.1 mmol), ethyl propiolate (324 mg, 3.3 mmol), CuSO$_4$ (18 mg, 0.11 mmol) and sodium ascorbate (20 mg, 0.11 mmol) in H$_2$O/t-BuOH (3 mL/3 mL) was stirred at RT for 4 h. Water (20 mL) was added then extracted with EtOAc (50 mL*3), the combined organic layers were concentrated and purified by silica gel chromatography (DCM/MeOH=8/1) to give ethyl 1-((6-cyclopropyl-1H-indol-2-yl)methyl)-1H-1,2,3-triazole-4-carboxylate (300 mg, yield: 89%) as a white solid. ESI-MS [M+Na]$^+$: 333.1.

Synthesis of 1-((6-cyclopropyl-1H-indol-2-yl)methyl)-1H-1,2,3-triazole-4-carboxylic Acid A mixture of ethyl 1-((6-cyclopropyl-1H-indol-2-yl)methyl)-1H-1,2,3-triazole-4-carboxylate (300 mg, 0.97 mmol) and LiOH.H$_2$O (80 mg, 1.9 mmol) in THF/EtOH/H$_2$O (2 mL/2 mL/1 mL) was stirred at 50° C. for 1 h. Most of the solvent was removed and the residue was diluted with H$_2$O (5 mL), the pH value of mixture was adjusted to 4-5 by adding HCl aqueous (1 M). The precipitate was collected and dried to give 1-((6-cyclopropyl-1H-indol-2-yl)methyl)-1H-1,2,3-triazole-4-carboxylic acid (200 mg, yield: 73%) as a white solid. ESI-MS [M+H]$^+$: 283.1.

Synthesis of N-((7-chloro-8-fluoroimidazo[1,5-a]pyridin-1-yl)methyl)-1-((6-cyclopropyl-1H-indol-2-yl)methyl)-1H-1,2,3-triazole-4-carboxamide (I-235)

A mixture of 1-((6-cyclopropyl-1H-indol-2-yl)methyl)-1H-1,2,3-triazole-4-carboxylic acid (56 mg, 0.2 mmol), (7-chloro-8-fluoroimidazo[1,5-a]pyridin-1-yl)methanamine hydrochloride (57 mg, 0.24 mmol), HOBT (54 mg, 0.4 mmol), EDCI (77 mg, 0.4 mmol) and DIPEA (129 mg, 1.0 mmol) in DMF (4 mL) was stirred at RT for 16 h. Water (20 mL) was added and extracted with EtOAc (30 mL×3), the combined organic layers were washed by brine (20 mL), dried over Na$_2$SO$_4$, concentrated and purified by prep-HPLC to give N-((7-chloro-8-fluoroimidazo[1,5-a]pyridin-1-yl)methyl)-1-((6-cyclopropyl-1H-indol-2-yl)methyl)-1H-1,2,3-triazole-4-carboxamide (40 mg, yield: 43%) as a white solid. ESI-MS [M+H]$^+$: 464.1. Purity: 90.87 (214 nm), 95.46 (254 nm). $^1$H NMR (400 MHz, DMSO-d$_6$) δ 11.11 (s, 1H), 8.71 (t, J=5.5 Hz, 1H), 8.54 (s, 1H), 8.43 (d, J=2.4 Hz, 1H), 8.20 (d, J=7.4 Hz, 1H), 7.36 (d, J=8.2 Hz, 1H), 7.03 (s, 1H), 6.77-6.71 (m, 2H), 6.40 (d, J=1.2 Hz, 1H), 5.75 (s, 2H), 4.69 (d, J=5.5 Hz, 2H), 1.98-1.94 (m, 1H), 0.93-0.88 (m, 2H), 0.64-0.60 (m, 2H).

Example 236

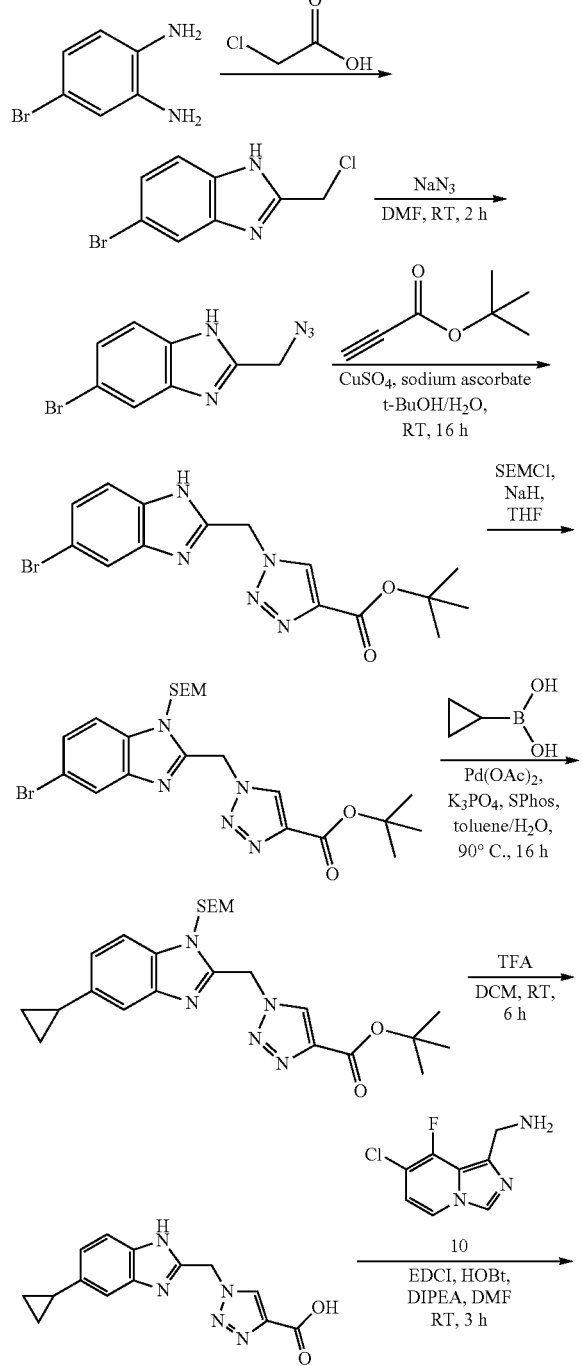

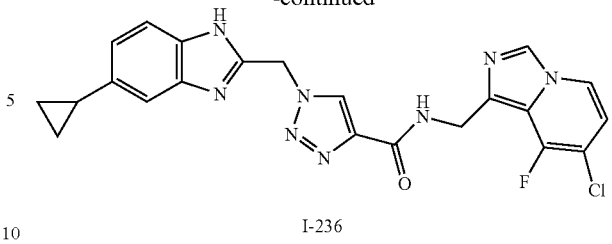

I-236

Synthesis of 5-bromo-2-(chloromethyl)-1H-benzo[d]imidazole

A mixture of 4-bromobenzene-1,2-diamine (2.0 g, 10.8 mmol) and 2-chloroacetic acid (1.5 g, 16.2 mmol) in HCl (2 M, 20 mL) was stirred at 100° C. for 16 h. The pH value of the reaction mixture was adjusted to 7-8 with aqueous NaOH and extracted with EtOAc (100 mL×3). The combined organic layers were concentrated to give 5-bromo-2-(chloromethyl)-1H-benzo[d]imidazole (2.2 g, crude) as a black solid which was used into next step without purification. ESI-MS [M+H]$^+$: 244.9.

Synthesis of 2-(azidomethyl)-5-bromo-1H-benzo[d]imidazole

A solution of 5-bromo-2-(chloromethyl)-1H-benzo[d]imidazole (1.0 g, crude from last step) and NaN$_3$ (0.4 g, 6.12 mmol) in DMF (10 mL) was stirred at 25° C. for 2 h, H$_2$O (50 mL) was added and extracted with EtOAc (50 mL×3). The combined organic layers were concentrated to give 2-(azidomethyl)-5-bromo-1H-benzo[d]imidazole (0.8 g, crude) as a yellow solid. ESI-MS [M+H]$^+$: 252.0.

Synthesis of tert-butyl 1-((5-bromo-1H-benzo[d]imidazol-2-yl)methyl)-1H-1,2,3-triazole-4-carboxylate A solution of 2-(azidomethyl)-5-bromo-1H-benzo[d]imidazole (0.8 g, crude from last step), tert-butyl propiolate (0.5 g, 3.8 mmol), CuSO$_4$ (0.1 g, 0.6 mmol), sodium ascorbate (0.12 g, 0.6 mmol) in t-BuOH (10 mL) and H$_2$O (10 mL) was stirred at 25° C. for 16 h. Water (30 mL) was added and extracted with EtOAc (50 mL×3), the combined organic layers were concentrated and purified by silica gel chromatography (DCM/MeOH=20/1) to give tert-butyl 1-((5-bromo-1H-benzo[d]imidazol-2-yl)methyl)-1H-1,2,3-triazole-4-carboxylate (0.5 g) as a yellow solid. ESI-MS [M+H]$^+$: 378.1.

Synthesis of tert-butyl 1-((5-bromo-1-((2-(trimethylsilyl)ethoxy)methyl)-1H-benzo[d]imidazol-2-yl)methyl)-1H-1,2,3-triazole-4-carboxylate To a solution of tert-butyl 1-((5-bromo-1H-benzo[d]imidazol-2-yl)methyl)-1H-1,2,3-triazole-4-carboxylate (0.5 g, 1.32 mmol) in dry THF (15 mL) was added NaH (63 mg, 1.58 mmol). The mixture was stirred at 0° C. for 20 min. Then SEMCl (0.24 g, 1.45 mmol) was added and stirred at RT for 1 h. The mixture was quenched with H$_2$O (50 mL), extracted with EtOAc (60 mL×3). The combined organic layers were washed with brine, dried over Na$_2$SO$_4$, filtered and concentrated to give the crude, which was purified by silica gel chromatography (DCM/MeOH=20/1) to give tert-butyl 1-((5-bromo-1-((2-(trimethylsilyl)ethoxy)methyl)-1H- benzo[d]imidazol-2-yl)methyl)-1H-1,2,3-triazole-4-carboxylate (0.25 g, yield: 37.3%) as a yellow solid. ESI-MS [M+H]+: 510.1.

Synthesis of tert-butyl 1-((5-cyclopropyl-1-((2-(trimethylsilyl)ethoxy)methyl)-1H-benzo[d]imidazol-2-yl)methyl)-1H-1,2,3-triazole-4-carboxylate A solution of tert-butyl 1-((5-bromo-1-((2-(trimethylsilyl)ethoxy)methyl)-1H-benzo[d]imidazol-2-yl)methyl)-1H-1,2,3-triazole-4-carboxylate (0.25 g, 0.5 mmol), cyclopropylboronic acid (0.09 g, 1.0 mmol), $K_3PO_4$ (0.37 g, 1.75 mmol), SPhos (0.06 g, 0.15 mmol) and Pd(OAc)$_2$ (0.03 g, 0.08 mmol). in a mixed solvent of toluene (30 mL) and $H_2O$ (3 mL) was stirred at 90° C. for 16 h under $N_2$, Water (100 mL) was added and extracted with EtOAc (50 mL×3). The combined organic layers were concentrated and purified by silica gel chromatography (DCM/MeOH=60/1) to give tert-butyl 1-((5-cyclopropyl-1-((2-(trimethylsilyl)ethoxy)methyl)-1H-benzo[d]imidazol-2-yl)methyl)-1H-1,2,3-triazole-4-carboxylate (0.2 g, yield: 86.0%) as a yellow solid. ESI-MS [M+H]+: 470.2.

Synthesis of 1-((5-cyclopropyl-1H-benzo[d]imidazol-2-yl)methyl)-1H-1,2,3-triazole-4-carboxylic Acid To a solution of tert-butyl 1-((5-cyclopropyl-1-((2-(trimethylsilyl)ethoxy)methyl)-1H-benzo[d]imidazol-2-yl)methyl)-1H-1,2,3-triazole-4-carboxylate (0.2 g, 0.4 mmol) in DCM (9 mL) was added TFA (3 mL). The mixture was stirred at 25° C. for 5 h. The solvent was removed to give the crude 1-((5-cyclopropyl-1H-benzo[d]imidazol-2-yl)methyl)-1H-1,2,3-triazole-4-carboxylic acid (0.13 g, crude) as a black solid which was used into next step without purification. ESI-MS [M+H]+: 284.1.

Synthesis of N-((7-chloro-8-fluoroimidazo[1,5-a]pyridin-1-yl)methyl)-1-((5-cyclopropyl-1H-benzo[d]imidazol-2-yl)methyl)-1H-1,2,3-triazole-4-carboxamide (I-236)

To a solution of 1-((5-cyclopropyl-1H-benzo[d]imidazol-2-yl)methyl)-1H-1,2,3-triazole-4-carboxylic acid (0.13 g, crude from last step) was added (7-chloro-8-fluoroimidazo[1,5-a]pyridin-1-yl)methanamine hydrochloride (0.1 g, 0.42 mmol), HATU (0.2 g, 0.53 mmol) and DIPEA (0.14 g, 1.05 mmol) in DMF (5 mL). The mixture was stirred at 25° C. for 3 h. The solvent was removed to give the crude and purified by Prep-HPLC to give N-((7-chloro-8-fluoroimidazo[1,5-a]pyridin-1-yl)methyl)-1-((5-cyclopropyl-1H-benzo[d]imidazol-2-yl)methyl)-1H-1,2,3-triazole-4-carboxamide (35 mg, yield: 19% over 2 steps) as a pale solid. ESI-MS [M+H]+: 465.1. Purity: 96.17% (214 nm), 100.00% (254 nm). $^1$H NMR (400 MHz, DMSO-d$_6$) δ 8.77 (t, J=5.4 Hz, 1H), 8.66 (s, 1H), 8.45 (d, J=2.4 Hz, 1H), 8.21 (d, J=7.4 Hz, 1H), 7.42 (d, J=8.4 Hz, 1H), 7.23 (s, 1H), 6.95 (dd, J=8.4, 1.5 Hz, 1H), 6.81-6.71 (m, 1H), 5.92 (s, 2H), 4.71 (d, J=5.5 Hz, 2H), 1.96-2.05 (m, 2H), 0.97-0.89 (m, 2H), 0.69-0.62 (m, 2H).

Example 237

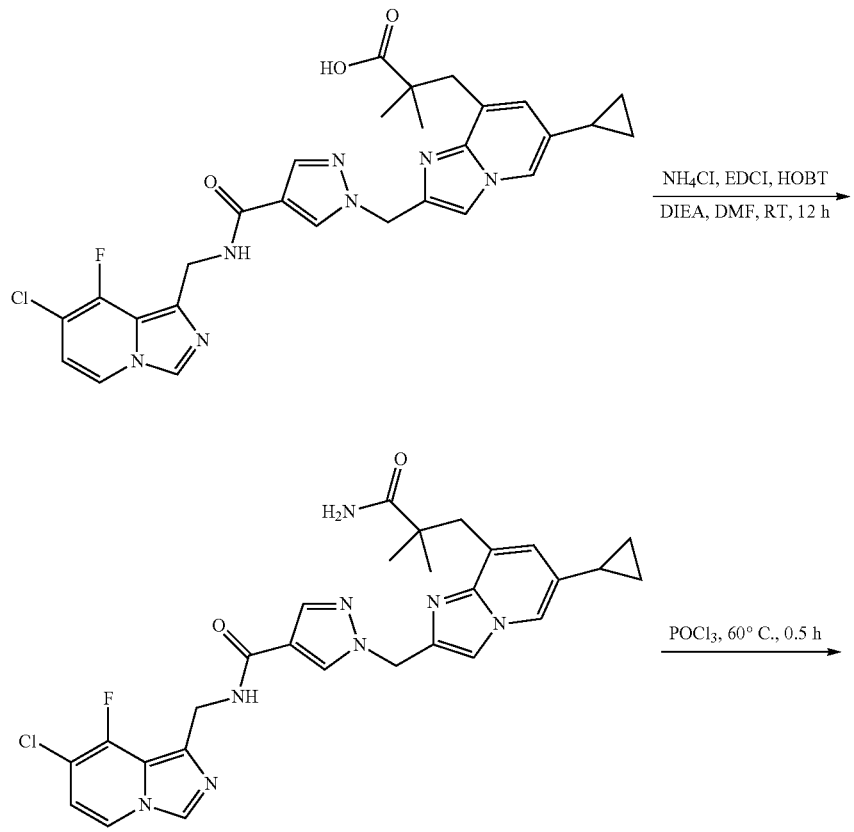

-continued

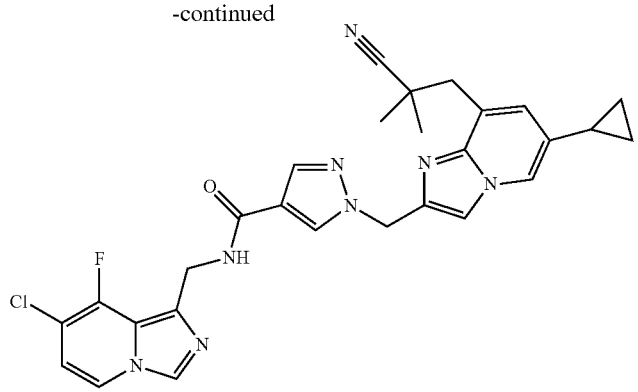

I-237

Synthesis of 1-((8-(3-amino-2,2-dimethyl-3-oxopropyl)-6-cyclopropylimidazo[1,2-a]pyridin-2-yl)methyl)-N-((7-chloro-8-fluoroimidazo[1,5-a]pyridin-1-yl)methyl)-1H-pyrazole-4-carboxamide To a solution of 3-(2-((4-(((7-chloro-8-fluoroimidazo[1,5-a]pyridin-1-yl)methyl)carbamoyl)-1H-pyrazol-1-yl)methyl)-6-cyclopropylimidazo[1,2-a]pyridin-8-yl)-2,2-dimethylpropanoic acid (120 mg, 0.21 mmol), NH$_4$Cl (113 mg, 2.1 mmol), EDCI (61 mg, 0.32 mmol) and HOBT (43 mg, 0.32 mmol) in DMF (10 mL) was added DIPEA (135 mg, 1.05 mmol). The resulting reaction was stirred at RT for 12 h. H$_2$O (25 mL) was added to the reaction, extracted with EtOAc (15 mL×3). The combined organic layers were washed with brine, dried over Na$_2$SO$_4$, concentrated in vacuo to give the crude, which was purified with Prep-TLC (DMC/MeOH=10/1) to give the 1-((8-(3-amino-2,2-dimethyl-3-oxopropyl)-6-cyclopropylimidazo [1,2-a]pyridin-2-yl)methyl)-N-((7-chloro-8-fluoroimidazo[1,5-a]pyridin-1-yl)methyl)-1H-pyrazole-4-carboxamide (80 mg, yield: 67.6%) as a light yellow solid. ESI-MS [M+H]$^+$: 563.2.

Synthesis of N-((7-chloro-8-fluoroimidazo[1,5-a]pyridin-1-yl)methyl)-1-((8-(2-cyano-2-methylpropyl)-6-cyclopropylimidazo[1,2-a]pyridin-2-yl)methyl)-1H-pyrazole-4-carboxamide (I-237)

To a solution of 1-((8-(3-amino-2,2-dimethyl-3-oxopropyl)-6-cyclopropylimidazo [1,2-a]pyridin-2-yl)methyl)-N-((7-chloro-8-fluoroimidazo[1,5-a]pyridin-1-yl)methyl)-1H-pyrazole-4-carboxamide (80 mg, 0.14 mmol) in POCl$_3$ (5 mL) was stirred at 60° C. for 0.5 h. The mixture was evaporated. The pH of the residue was adjust 8 by aqueous NaHCO$_3$, extracted with EtOAc (25 mL×3). The combined organic layers were washed with brine, dried over Na$_2$SO$_4$, concentrated in vacuo to give the crude, which was purified with Prep-TLC (DMC/MeOH=15/1) to give the N-((7-chloro-8-fluoroimidazo[1,5-a]pyridin-1-yl)methyl)-1-((8-(2-cyano-2-methylpropyl)-6-cyclopropylimidazo[1,2-a]pyridin-2-yl)methyl)-1H-pyrazole-4-carboxamide (40 mg, yield: 52%) as a white solid. ESI-MS [M+H]$^+$: 546.2. Purity: 99.8% (214 nm), 100.0% (254 nm). $^1$H NMR (400 MHz, DMSO-d$_6$) δ 8.67 (t, J=5.3 Hz, 1H), 8.50 (s, 1H), 8.44 (d, J=2.1 Hz, 1H), 8.32 (s, 1H), 8.21 (d, J=7.4 Hz, 1H), 7.82 (s, 1H), 6.95 (s, 1H), 6.76 (t, J=6.9 Hz, 1H), 5.73 (s, 2H), 4.69 (d, J=5.4 Hz, 2H), 3.13 (s, 2H), 1.97-1.87 (m, 1H), 1.29 (s, 6H), 0.97-0.88 (m, 2H), 0.72-0.63 (m, 2H).

Example 238

Scheme 237

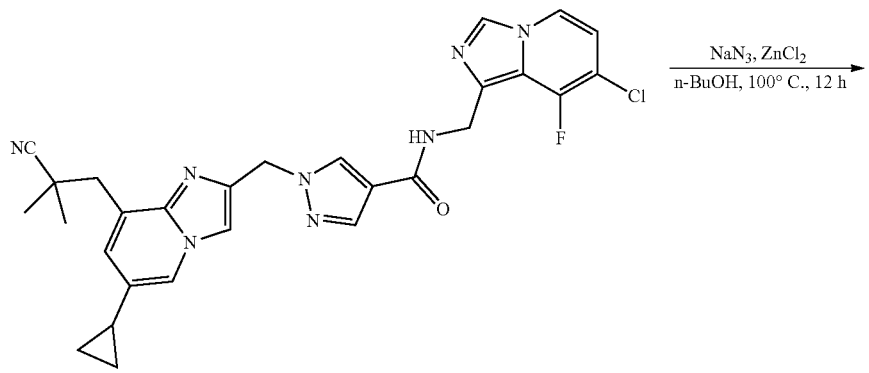

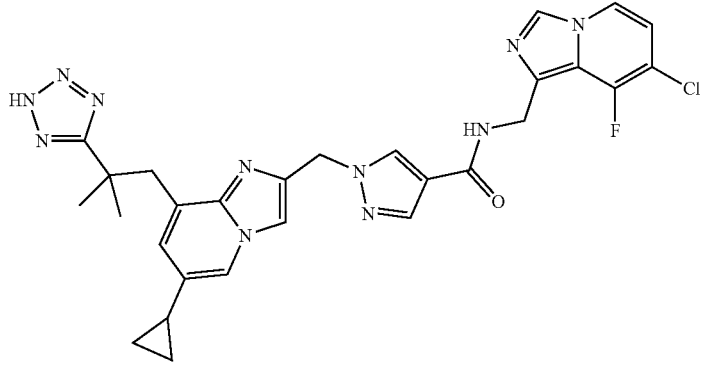

I-238

Synthesis of N-((7-chloro-8-fluoroimidazo[1,5-a]pyridin-1-yl)methyl)-1-((6-cyclopropyl-8-(2-methyl-2-(2H-tetrazol-5-yl)propyl)imidazo[1,2-a]pyridin-2-yl)methyl)-1H-pyrazole-4-carboxamide (I-238)

To a solution of N-((7-chloro-8-fluoroimidazo[1,5-a]pyridin-1-yl)methyl)-1-((8-(2-cyano-2-methylpropyl)-6-cyclopropylimidazo[1,2-a]pyridin-2-yl)methyl)-1H-pyrazole-4-carboxamide (20 mg, 0.037 mmol) in n-BuOH (3 mL) was added $NaN_3$ (12 mg, 0.18 mmol) and $ZnCl_2$ (0.074 mL, 1 M) at RT. The reaction was stirred at 110° C. for 12 h under nitrogen. The mixture was quenched with $H_2O$ (10 mL) and extracted with EtOAc (20 mL×3). The combined organic layers were washed with brine, dried over $Na_2SO_4$, concentrated in vacuo to give the crude, which was purified with Prep-TLC (DMC/MeOH=10/1) to give the N-((7-chloro-8-fluoroimidazo[1,5-a]pyridin-1-yl)methyl)-1-((6-cyclopropyl-8-(2-methyl-2-(2H-tetrazol-5-yl)propyl)imidazo[1,2-a]pyridin-2-yl)methyl)-1H-pyrazole-4-carboxamide (5 mg, yield: 23%) as a white solid. ESI-MS [M+H]$^+$: 589.2. Purity: 98.2 (214 nm), 96.4 (254 nm). $^1$H NMR (400 MHz, CDCl$_3$) δ 8.70 (t, J=5.5 Hz, 1H), 8.50 (s, 1H), 8.44 (d, J=2.4 Hz, 1H), 8.24-8.14 (m, 3H), 7.72 (s, 1H), 6.78-6.73 (m, 1H), 5.99 (s, 1H), 5.68 (s, 2H), 4.69 (d, J=5.5 Hz, 2H), 3.23 (s, 2H), 1.76-1.70 (m, 1H), 1.33 (s, 6H), 0.85-0.77 (m, 2H), 0.43-0.37 (m, 2H).

Example 239

Scheme 238

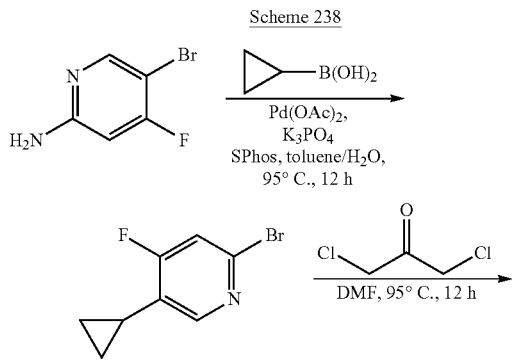

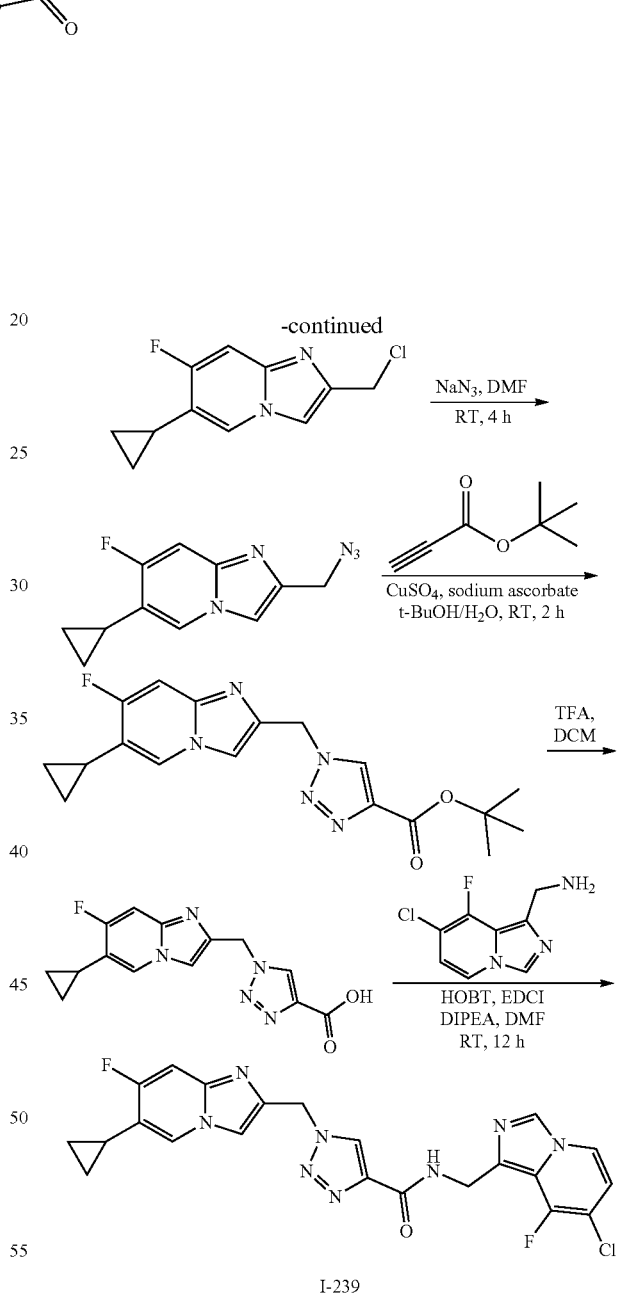

I-239

Synthesis of 5-cyclopropyl-4-fluoropyridin-2-amine

A solution of 5-bromo-4-fluoropyridin-2-amine (300 mg, 1.57 mmol) in toluene/$H_2O$ (3 mL/0.3 mL) was added cyclopropylboronic acid (203 mg, 2.36 mmol), Pd(OAc)$_2$ (35 mg, 0.157 mmol), K$_3$PO$_4$ (789 mg, 3.72 mmol) and SPhos (65 mg, 0.157 mmol) at RT. The mixture was stirred at 95° C. for 3 h under N$_2$ atmosphere. The mixture was concentrated and the residue was purified by flash silica gel chromatography (0~40% EtOAc in PE) to give 5-cyclopropyl-4-fluoropyridin-2-amine (180 mg, yield: 75%) as a yellow solid. ESI-MS [M+H]$^+$: 153.0

Synthesis of 2-(chloromethyl)-6-cyclopropyl-7-fluoroimidazo[1,2-a]pyridine

To a solution of 5-cyclopropyl-4-fluoropyridin-2-amine (180 mg, 1.18 mmol) in DMF (3 mL) was added 1,3-dichloropropan-2-one (601 mg, 4.72 mmol) at RT. The mixture was heated to 95° C. and stirred for 16 h. Water (20 mL) was added and exacted with EtOAc (50 mL×3). The combined organic layers were concentrated and purified by flash silica gel chromatography (0~50% EtOAc in PE) to give 2-(chloromethyl)-6-cyclopropyl-7-fluoroimidazo[1,2-a]pyridine (100 mg, yield: 37%) as a red oil. ESI-MS [M+H]$^+$: 225.0.

Synthesis of 2-(azidomethyl)-6-cyclopropyl-7-fluoroimidazo[1,2-a]pyridine

To a solution of 2-(chloromethyl)-6-cyclopropyl-7-fluoroimidazo[1,2-a]pyridine (100 mg, 0.45 mmol) in DMF (5 mL) was added NaN$_3$ (29 mg, 0.45 mmol) at RT. The mixture was stirred at RT for 2 h. Water (20 mL) was added and exacted by EtOAc (50 mL×3). The combined organic layers were concentrated to give 2-(azidomethyl)-6-cyclopropyl-7-fluoroimidazo[1,2-a]pyridine (80 mg, crude) as a red oil which was used into next step without purification. ESI-MS [M+H]$^+$: 232.0.

Synthesis of tert-butyl 1-((6-cyclopropyl-7-fluoroimidazo[1,2-a]pyridin-2-yl)methyl)-1H-1,2,3-triazole-4-carboxylate To a solution of 2-(azidomethyl)-6-cyclopropyl-7-fluoroimidazo[1,2-a]pyridine (80 mg, crude from last step) in t-BuOH/H$_2$O (2 mL/2 mL) was added t-butyl propiolate (51.7 mg, 0.41 mmol), sodium ascorbate (13.7 mg, 0.07 mmol) and CuSO$_4$ (11.0 mg, 0.07 mmol) at RT. The mixture was stirred for 2 h. Water (15 mL) was added and exacted by DCM (30 mL×3). The combined organic layers were concentrated to give tert-butyl 1-((6-cyclopropyl-7-fluoroimidazo[1,2-a]pyridin-2-yl)methyl)-1H-1,2,3-triazole-4-carboxylate (70 mg, crude) as a red oil. ESI-MS [M+H]$^+$: 358.2.

Synthesis of 1-((6-cyclopropyl-7-fluoroimidazo[1,2-a]pyridin-2-yl)methyl)-1H-1,2,3-triazole-4-carboxylic Acid To a solution of tert-butyl 1-((6-cyclopropyl-7-fluoroimidazo[1,2-a]pyridin-2-yl)methyl)-1H-1,2,3-triazole-4-carboxylate (70 mg, crude) in DCM (3 mL) was added TFA (1 mL) at RT. The mixture was stirred for 1 h. The mixture was filtered and concentrated to give 1-((6-cyclopropyl-7-fluoroimidazo[1,2-a]pyridin-2-yl)methyl)-1H-1,2,3-triazole-4-carboxylic acid (80 mg, crude) as a brown oil. ESI-MS [M+H]$^+$: 302.1.

Synthesis of N-((7-chloro-8-fluoroimidazo[1,5-a]pyridin-1-yl)methyl)-1-((6-cyclopropyl-7-fluoroimidazo[1,2-a]pyridin-2-yl)methyl)-1H-1,2,3-triazole-4-carboxamide (I-239)

To a solution of 1-((6-cyclopropyl-7-fluoroimidazo[1,2-a]pyridin-2-yl)methyl)-1H-1,2,3-triazole-4-carboxylic acid (80 mg, rrude) in DMF (2 mL) was added EDCI (76.4 mg, 0.40 mmol), HOBT (54 mg, 0.40 mmol), DIPEA (137 mg, 1.06 mmol) and (7-chloro-8-fluoroimidazo[1,5-a]pyridin-1-yl)methanamine hydrochloride (62 mg, 0.26 mmol) at RT. The mixture was stirred for 16 h. The mixture was concentrated and the residue was purified by prep-HPLC to give N-((7-chloro-8-fluoroimidazo[1,5-a]pyridin-1-yl)methyl)-1-((6-cyclopropyl-7-fluoroimidazo[1,2-a]pyridin-2-yl)methyl)-1H-1,2,3-triazole-4-carboxamide (5.7 mg, yield: 8% over 4 steps) as a white solid. ESI-MS [M+H]$^+$: 483.0. Purity: 98.37% (214 nm), 96.66% (254 nm). $^1$H NMR (400 MHz, DMSO-d$_6$) δ 8.70 (t, J=5.5 Hz, 1H), 8.54 (s, 1H), 8.44 (d, J=2.3 Hz, 1H), 8.39 (d, J=7.5 Hz, 1H), 8.21 (d, J=7.4 Hz, 1H), 7.80 (s, 1H), 7.35 (d, J=10.9 Hz, 1H), 6.80-6.74 (m, 1H), 5.71 (s, 2H), 4.69 (d, J=5.5 Hz, 2H), 1.96-1.87 (m, 1H), 0.98-0.89 (m, 2H), 0.74-0.64 (m, 2H).

Example 240

Scheme 239

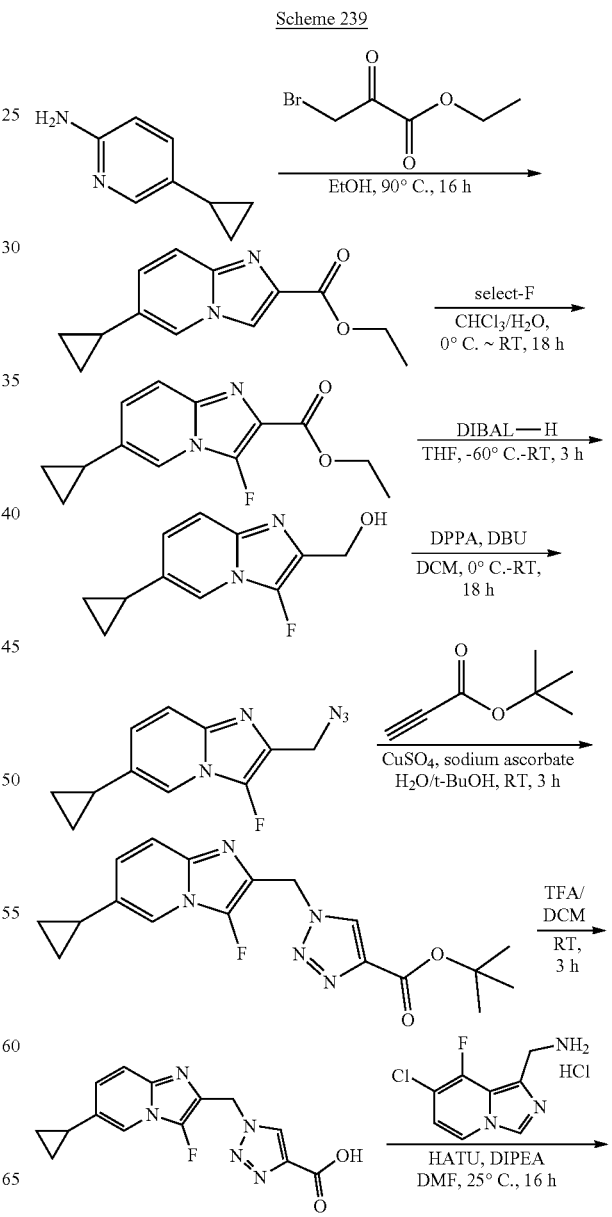

-continued

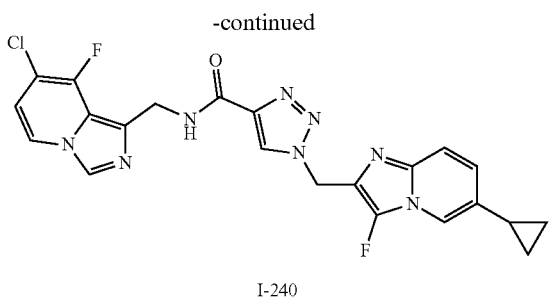

I-240

Synthesis of Ethyl 6-cyclopropylimidazo[1,2-a]pyridine-2-carboxylate

A mixture of ethyl 5-cyclopropylpyridin-2-amine (6 g, 44.8 mmol) and ethyl 3-bromo-2-oxopropanoate (13.0 g, 67.2 mmol) in EtOH (100 mL) was stirred at 90° C. for 16 h. The reaction mixture was cooled to RT and diluted with H$_2$O (200 mL), extracted with EtOAc (50 mL×4). The combined organic layers were washed with brine, dried over Na$_2$SO$_4$ and concentrated to give the crude product, which was purified by flash column chromatography (PE/EA=1/1) to give ethyl 6-cyclopropylimidazo[1,2-a]pyridine-2-carboxylate (3.5 g, yield: 34%) as a brown oil. ESI-MS [M+H]$^+$: 231.2.

Synthesis of Ethyl 6-cyclopropyl-3-fluoroimidazo[1,2-a]pyridine-2-carboxylate To a solution of ethyl 6-cyclopropylimidazo[1,2-a]pyridine-2-carboxylate (3.5 g, 15.2 mmol) in CHCl$_3$/H$_2$O (45 mL/15 mL) was added DMAP (1.96 g, 16.1 mmol) and select-F (11.4 g, 32.2 mmol) at 0° C. The mixture was stirred at RT for 18 h. The reaction was quenched with H$_2$O (100 mL) and extracted with EtOAc (100 mL×3). The combined organic layers were washed with brine and concentrated to give the residue, which was purified by flash column chromatography to afford ethyl 6-cyclopropyl-3-fluoroimidazo[1,2-a]pyridine-2-carboxylate (1.5 g, yield: 38%) as a yellow oil. ESI-MS [M+H]$^+$: 249.1

Synthesis of (6-cyclopropyl-3-fluoroimidazo[1,2-a]pyridin-2-yl)methanol

To the mixture of ethyl 6-cyclopropyl-3-fluoroimidazo[1,2-a]pyridine-2-carboxylate (1.3 g, 5.2 mmol) in THF (50 mL) was added DIBAL-H (15.7 mL, 15.7 mmol) at –60° C. The reaction mixture was warmed to RT and stirred for 3 h. The reaction mixture quenched with saturated aqueous NH$_4$Cl (50 mL), and extracted with EtOAc (50 mL×3). The combined organic layers were washed with brine, dried over Na$_2$SO$_4$, and concentrated to give the residue, which was purified by flash column chromatography (PE/EA=1/2) to afford (6-cyclopropyl-3-fluoroimidazo[1,2-a]pyridin-2-yl)methanol (0.95 g, yield: 88.7%). ESI-MS [M+H]$^+$: 207.1

Synthesis of 2-(azidomethyl)-6-cyclopropyl-3-fluoroimidazo[1,2-a]pyridine

To a mixture of (5-cyclopropyl-1H-indol-2-yl)methanol (0.95 g, 4.6 mmol) and DPPA (3.8 g, 13.8 mmol) in DCM (20 mL) was added DBU (2.1 g, 13.8 mmol) at 0° C. The reaction mixture was degassed with N$_2$ and stirred at RT for 18 h. The reaction mixture quenched with H$_2$O (30 mL) and extracted with DCM (50 mL×3). The combined organic layers were washed with brine, dried over Na$_2$SO$_4$, and concentrated to give the residue, which was purified by flash column chromatography (PE/EA=1/1) to afforded 2-(azidomethyl)-6-cyclopropyl-3-fluoroimidazo[1,2-a]pyridine (0.8 g, yield: 75%). ESI-MS [M+H]$^+$: 232.2

Synthesis of tert-butyl 1-((6-cyclopropyl-3-fluoroimidazo[1,2-a]pyridin-2-yl)methyl)-1H-1,2,3-triazole-4-carboxylate The mixture of 2-(azidomethyl)-5-cyclopropyl-1H-indole (1.12 g, 4.484 mmol), tert-butyl propiolate (734 mg, 5.81 mmol), sodium ascorbate (192 mg, 0.96 mmol) and CuSO$_4$ (155 mg, 1.96 mmol) in t-BuOH/H$_2$O (5 mL/5 mL) was stirred at RT for 3 h. The reaction was diluted with H$_2$O (50 mL), extracted with DCM/MeOH (10/1, 500 mL×3). The combined organic layers were washed with brine and concentrated to give the crude, which was purified by flash column chromatography (DCM/MeOH=20/1) to afford tert-butyl 1-((6-cyclopropyl-3-fluoroimidazo[1,2-a]pyridin-2-yl)methyl)-1H-1,2,3-triazole-4-carboxylate (500 mg, yield: 30%) as a yellow solid. ESI-MS [M+H]$^+$: 357.1

Synthesis of 1-((6-cyclopropyl-3-fluoroimidazo[1,2-a]pyridin-2-yl)methyl)-1H-1,2,3-triazole-4-carboxylic Acid A mixture of tert-butyl 1-((6-cyclopropyl-3-fluoroimidazo[1,2-a]pyridin-2-yl)methyl)-1H-1,2,3-triazole-4-carboxylate (400 mg, 1.12 mmol) in TFA/DCM (0.5 mL/1.5 mL) was stirred at RT for 3 h. The reaction was evaporated to remove the solvent to afford 1-((6-cyclopropyl-3-fluoroimidazo[1,2-a]pyridin-2-yl)methyl)-1H-1,2,3-triazole-4-carboxylic acid (400 mg, crude) as a black oil, which was used into next step directly. ESI-MS [M+H]$^+$: 301.9

Synthesis of N-((7-chloro-8-fluoroimidazo[1,5-a]pyridin-1-yl)methyl)-1-((6-cyclopropyl-3-fluoroimidazo[1,2-a]pyridin-2-yl)methyl)-1H-1,2,3-triazole-4-carboxamide (I-240)

The mixture of 1-((6-cyclopropyl-3-fluoroimidazo[1,2-a]pyridin-2-yl)methyl)-1H-1,2,3-triazole-4-carboxylic acid (400 mg, crude from last step), (7-chloro-8-fluoroimidazo[1,5-a]pyridin-1-yl)methanamine hydrochloride (249 mg, 1.06 mmol), HATU (509 mg, 1.33 mmol) and DIPEA (808 mg, 6.23 mmol) in DMF (5 mL) was stirred at to RT for 16 h. The reaction mixture was diluted with H$_2$O (80 mL) and extracted with EtOAc (100 mL×3). The combined organic layers were washed with brine and concentrated to give the crude, which was purified by prep-HPLC to afford N-((7-chloro-8-fluoroimidazo[1,5-a]pyridin-1-yl)methyl)-1-((6-cyclopropyl-3-fluoroimidazo[1,2-a]pyridin-2-yl)methyl)-1H-1,2,3-triazole-4-carboxamide (50 mg, yield: 10%) as white solid. ESI-MS [M+H]$^+$: 483.0. Purity: 99.06 (214 nm), 100 (254 nm). $^1$H NMR (400 MHz, DMSO-d$_6$) δ 8.71 (s, 1H), 8.56 (s, 1H), 8.47 (s, 1H), 8.20 (d, J=7.4 Hz, 1H), 8.09 (s, 1H), 7.39 (d, J=9.1 Hz, 1H), 7.03-6.96 (m, 1H), 6.76 (t, J=6.9 Hz, 1H), 5.77 (s, 2H), 4.69 (s, 2H), 2.05-1.95 (m Hz, 1H), 0.99-0.89 (m, 2H), 0.78-0.70 (m, 2H).

Example 241

Scheme 240

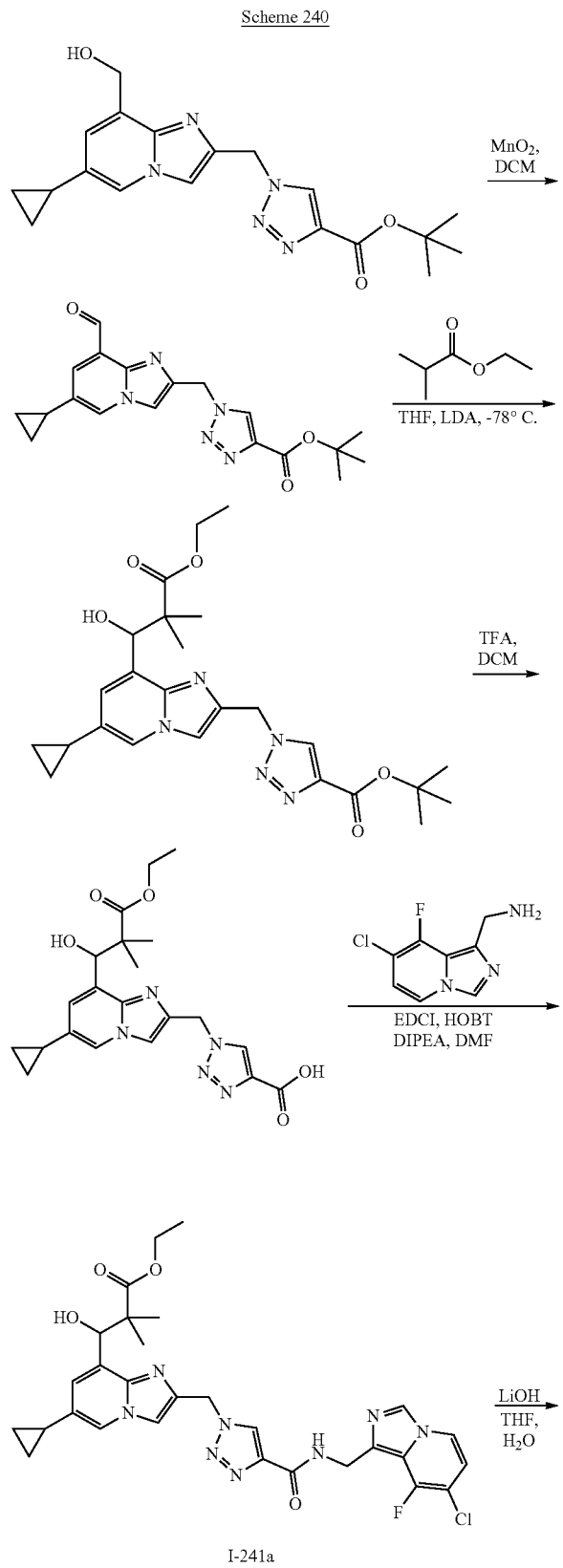

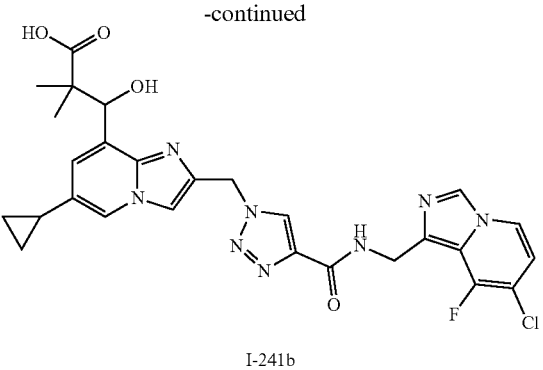

I-241b

Synthesis of tert-butyl 1-(((6-cyclopropyl-8-formylimidazo[1,2-a]pyridin-2-yl)methyl)-1H-1,2,3-triazole-4-carboxylate To a solution of tert-butyl 1-(((6-cyclopropyl-8-(hydroxymethyl)imidazo[1,2-a]pyridin-2-yl)methyl)-1H-1,2,3-triazole-4-carboxylate (2.0 g, 5.4 mmol) in DCM (50 mL) was added MnO₂ (939.6 mg, 10.8 mmol). The mixture was stirred at RT for 48 h. The mixture was filtered, and washed with DCM (100 mL). The filtrate was concentrated to give tert-butyl 1-((6-cyclopropyl-8-formylimidazo[1,2-a]pyridin-2-yl)methyl)-1H-1,2,3-triazole-4-carboxylate (1.4 g, yield: 70.7%) as a yellow solid. ESI-MS [M+H]⁺: 368.2

Synthesis of tert-butyl 1-((6-cyclopropyl-8-(3-ethoxy-1-hydroxy-2,2-dimethyl-3-oxopropyl)imidazo[1,2-a]pyridin-2-yl)methyl)-1H-1,2,3-triazole-4-carboxylate To a solution of ethyl isobutyrate (474 mg, 4.08 mmol) in dry THF (30 mL) was added LDA (4.28 mL, 1 M solution in THF, 4.28 mmol) at −78° C. The reaction mixture was stirred for 30 min at −78° C. Then a solution of tert-butyl 1-((6-cyclopropyl-8-formylimidazo[1,2-a]pyridin-2-yl)methyl)-1H-1,2,3-triazole-4-carboxylate (300 mg, 0.817 mmol) in THF (3 mL) was added thereto. The resulting reaction mixture was stirred for another 50 min at −78° C. The reaction was quenched with saturated aqueous NH₄Cl (50 mL), extracted with EtOAc (40 mL×3). The combined organic layers were washed with brine, dried over Na₂SO₄, concentrated to give the c rude, which was purified by Prep-TLC (DCM/MeOH=15/1) to tert-butyl 1-((6-cyclopropyl-8-(3-ethoxy-1-hydroxy-2,2-dimethyl-3-oxopropyl)imidazo[1,2-a]pyridin-2-yl)methyl)-1H-1,2,3-triazole-4-carboxylate (240 mg, yield: 60.7%) as a yellow solid. ESI-MS [M+H]⁺: 484.2.

Synthesis of 1-((6-cyclopropyl-8-(3-ethoxy-1-hydroxy-2,2-dimethyl-3-oxopropyl)imidazo[1,2-a]pyridin-2-yl)methyl)-1H-1,2,3-triazole-4-carboxylic Acid To a solution of tert-butyl 1-((6-cyclopropyl-8-(3-ethoxy-1-hydroxy-2,2-dimethyl-3-oxopropyl)imidazo[1,2-a]pyridin-2-yl)methyl)-1H-1,2,3-triazole-4-carboxylate (240 mg, 0.49 mmol) in DCM (5 mL) was added TFA (1 mL) at RT. The mixture was stirred at RT for 3 h. The reaction was concentrated in vacuo to give 1-((6-cyclopropyl-8-(3-ethoxy-1-hydroxy-2,2-dimethyl-3-oxopropyl)imidazo[1,2-a]pyridin-2-yl)methyl)-1H-1,2,3-triazole-4-carboxylic acid, which was used into next step without further purification (225 mg crude). ESI-MS [M+H]+: 428.2.

Synthesis of Ethyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-3-hydroxy-2,2-dimethylpropanoate (I-241a)

To a solution of 1-((6-cyclopropyl-8-(1-fluoroethyl)imidazo[1,2-a]pyridin-2-yl)methyl)-1H-1,2,3-triazole-4-carboxylic acid (225 mg, crude from previous step), (7-chloro-8-fluoroimidazo[1,5-a]pyridin-1-yl)methanamine hydrochloride (125 mg, 0.53 mmol), EDCI (151 mg, 0.79 mmol), HOBT (106.7 mg, 0.79 mmol) in DMF (5 mL) was added DIPEA (340 mg, 2.63 mmol). The resulting reaction was stirred at RT for 16 h. Water (50 mL) was added, extracted with EtOAc (20 mL×3). The combined organic layers were concentrated and purified by Prep-TLC (DCM/MeOH=10/1) to give ethyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-3-hydroxy-2,2-dimethylpropanoate. (170 mg, yield: 56%) as a white solid. ESI-MS [M+H]+: 609.2. Purity: 98.6% (214 nm), 100.0% (254 nm). $^1$H NMR (400 MHz, DMSO-d$_6$) δ 8.68 (t, J=5.5 Hz, 1H), 8.49 (s, 1H), 8.44 (d, J=2.4 Hz, 1H), 8.26 (d, J=1.4 Hz, 1H), 8.20 (d, J=7.4 Hz, 1H), 7.80 (s, 1H), 6.97 (d, J=1.5 Hz, 1H), 6.78-6.74 (m, 1H), 5.73 (s, 2H), 5.62 (s, 1H), 5.51 (s, 1H), 4.69 (d, J=5.5 Hz, 3H), 3.97 (q, J=7.1 Hz, 2H), 1.98-1.91 (m, 1H), 1.13-1.07 (m, 6H), 0.96-0.91 (m, 5H), 0.68-0.59 (m, 2H).

Synthesis of 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-3-hydroxy-2,2-dimethylpropanoic acid (I-241b)

To a solution of ethyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-3-hydroxy-2,2-dimethylpropanoate (160 mg, 0.26 mmol) in THF/H$_2$O (4 mL/2 mL) was added LiOH.H$_2$O (32 mg, 0.78 mmol). The resulting mixture was stirred at RT for 2 h. The reaction was concentrated in vacuo to give the crude, which was purified with Prep-HPLC to give the 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-3-hydroxy-2,2-dimethylpropanoic acid (91 mg, 59.6%). ESI-MS [M+H]+: 581.2. Purity: 99.52% (214 nm), 100% (254 nm). $^1$H NMR (400 MHz, DMSO-d$_6$) δ 12.14 (s, 1H), 8.69 (t, J=5.5 Hz, 1H), 8.50 (s, 1H), 8.44 (d, J=2.4 Hz, 1H), 8.26 (d, J=1.2 Hz, 1H), 8.20 (d, J=7.4 Hz, 1H), 7.79 (s, 1H), 6.97 (d, J=1.4 Hz, 1H), 6.77-6.74 (m, 1H), 5.74 (s, 2H), 5.58 (s, 1H), 4.69 (d, J=5.5 Hz, 2H), 1.97-1.91 (m, 1H), 1.01 (s, 2H), 0.96-0.92 (m, 2H), 0.87 (s, 2H), 0.71-0.59 (m, 2H).

Example 242

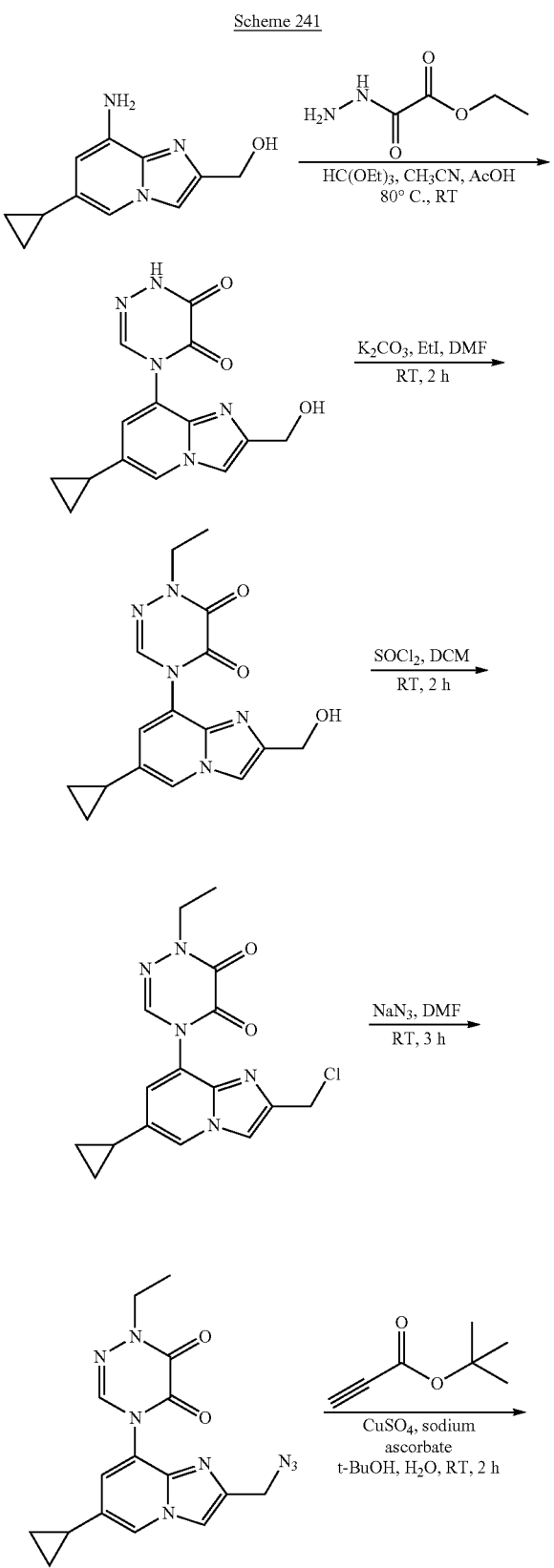

Scheme 241

-continued

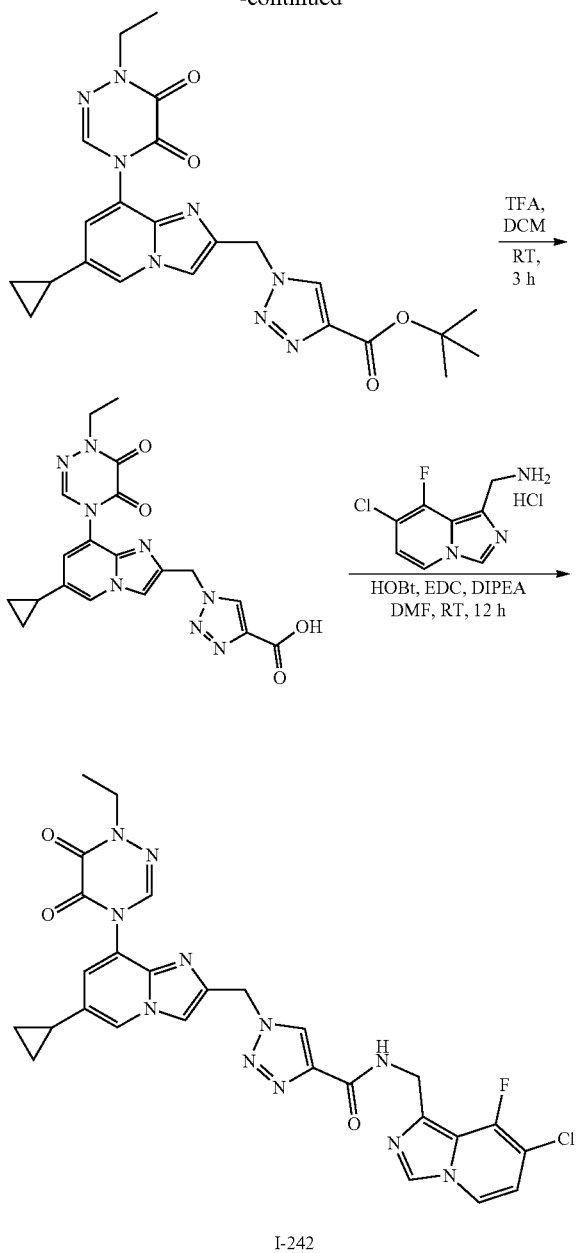

I-242

Synthesis of 4-(6-cyclopropyl-2-(hydroxymethyl) imidazo[1,2-a]pyridin-8-yl)-1,4-dihydro-1,2,4-triazine-5,6-dione To a mixture of (8-amino-6-cyclopropylimidazo[1,2-a]pyridin-2-yl)methanol (406 mg, 2 mmol) in MeCN (25 mL) was added HC(OEt)₃ (1.2 g, 8 mmol). The mixture was stirred at 80° C. for 1 h. Then AcOH (180 mg, 3 mmol) and ethyl 2-hydrazinyl-2-oxoacetate (670 mg, 5 mmol) was added. The resulting reaction was stirred at 80° C. for another 16 h. The reaction mixture was filtered and dried to give 4-(6-cyclopropyl-2-(hydroxymethyl)imidazo[1,2-a]pyridin-8-yl)-1,4-dihydro-1,2,4-triazine-5,6-dione (200 mg, yield: 33%) as a yellow solid, which was used for the next step without further purification. ESI-MS [M+H]⁺: 300.1.

Synthesis of 4-(6-cyclopropyl-2-(hydroxymethyl) imidazo[1,2-a]pyridin-8-yl)-1-ethyl-1,4-dihydro-1,2,4-triazine-5,6-dione To a mixture of 4-(6-cyclopropyl-2-(hydroxymethyl)imidazo[1,2-a]pyridin-8-yl)-1,4-dihydro-1,2,4-triazine-5,6-dione (175 mg, 0.6 mmol) and K₂CO₃ (400 mg, 2.9 mmol) in DMF (5 mL) was added EtI (273 mg, 1.8 mmol). The mixture was stirred at RT for 2 h. Water (30 mL) was added and extracted with EtOAc (50 mL×3). The filtrate was washed with brine, dried over Na₂SO₄, concentrated to give 4-(6-cyclopropyl-2-(hydroxymethyl)imidazo[1,2-a]pyridin-8-yl)-1-ethyl-1,4-dihydro-1,2,4-triazine-5,6-dione (200 mg, crude) as a yellow oil, which was used for the next step without further purification. ESI-MS [M+H]⁺: 328.1.

Synthesis of 4-(2-(chloromethyl)-6-cyclopropylimidazo[1,2-a]pyridin-8-yl)-1-ethyl-1,4-dihydro-1,2,4-triazine-5,6-dione To a mixture of 4-(6-cyclopropyl-2-(hydroxymethyl)imidazo[1,2-a]pyridin-8-yl)-1-ethyl-1,4-dihydro-1,2,4-triazine-5,6-dione (200 mg crude) in DCM (5 mL) was added SOCl₂ (1 mL). The reaction mixture was stirred at RT for 2 h. The reaction was concentrated to give 4-(2-(chloromethyl)-6-cyclopropylimidazo[1,2-a]pyridin-8-yl)-1-ethyl-1,4-dihydro-1,2,4-triazine-5,6-dione (220 mg, crude) as yellow oil, which was used into next step without further purification. ESI-MS [M+H]⁺: 346.1.

Synthesis of 4-(2-(azidomethyl)-6-cyclopropylimidazo[1,2-a]pyridin-8-yl)-1-ethyl-1,4-dihydro-1,2,4-triazine-5,6-dione To a mixture of 4-(2-(chloromethyl)-6-cyclopropylimidazo[1,2-a]pyridin-8-yl)-1-ethyl-1,4-dihydro-1,2,4-triazine-5,6-dione (220 mg, crude from previous step) in DMF (5 mL) was added NaN₃ (65 mg, 1 mmol). The resulting reaction mixture was stirred at RT for 3 h. Water (25 mL) was added to the reaction, and extracted with EtOAc (30 mL×3). The combined organic layers were washed with brine and dried over Na₂SO₄, concentrated to give the crude, which was purified with Prep-TLC (DCM/MeOH=15/1) to give 4-(2-(azidomethyl)-6-cyclopropylimidazo[1,2-a]pyridin-8-yl)-1-ethyl-1,4-dihydro-1,2,4-triazine-5,6-dione (170 mg, 80% over 3 steps) as yellow oil. ESI-MS [M+H]⁺: 353.1.

Synthesis of tert-butyl 1-((6-cyclopropyl-8-(1-ethyl-5,6-dioxo-5,6-dihydro-1,2,4-triazin-4(1H)-yl)imidazo[1,2-a]pyridin-2-yl)methyl)-1H-1,2,3-triazole-4-carboxylate To a mixture of 4-(2-(azidomethyl)-6-cyclopropylimidazo[1,2-a]pyridin-8-yl)-1-ethyl-1,4-dihydro-1,2,4-triazine-5,6-dione (170 mg, 0.48 mmol), CuSO₄ (32 mg, 0.2 mmol) and sodium ascorbate (40 mg, 0.2 mmol) in t-BuOH/H₂O (10 mL/10 mL) was added tert-butyl propiolate (95 mg, 0.75 mmol). The reaction mixture was stirred at RT for 2 h. Water (30 mL) was added and the mixture was extracted with EtOAc (30 mL×3). The combined organic layers were washed with brine and dried over Na₂SO₄, concentrated to give crude, which was purified with Prep-TLC (DCM/MeOH=15/1) to give tert-butyl 1-((6-cyclopropyl-8-(1-ethyl-5,6-dioxo-5,6-dihydro-1,2,4-triazin-4(1H)-yl)imidazo[1,2-a]pyridin-2-yl)methyl)-1H-1,2,3-triazole-4-carboxylate

[1,2-a]pyridin-2-yl)methyl)-1H-1,2,3-triazole-4-carboxylate (200 mg, yield: 87%) as yellow oil. ESI-MS [M+H]+: 479.2.

Synthesis of 1-((6-cyclopropyl-8-(1-ethyl-5,6-dioxo-5,6-dihydro-1,2,4-triazin-4(1H)-yl)imidazo[1,2-a]pyridin-2-yl)methyl)-1H-1,2,3-triazole-4-carboxylic Acid To a mixture of tert-butyl 1-((6-cyclopropyl-8-(1-ethyl-5,6-dioxo-5,6-dihydro-1,2,4-triazin-4(1H)-yl)imidazo[1,2-a]pyridin-2-yl)methyl)-1H-1,2,3-triazole-4-carboxylate (200 mg, 0.42 mmol) in DCM (10 mL) was added TFA (3 mL). The reaction solution was stirred at RT for 3 h. The reaction was concentrated to give 1-((6-cyclopropyl-8-(1-ethyl-5,6-dioxo-5,6-dihydro-1,2,4-triazin-4(1H)-yl)imidazo[1,2-a]pyridin-2-yl)methyl)-1H-1,2,3-triazole-4-carboxylic acid (230 mg crude) as yellow oil, which was used into next step without further purification. ESI-MS [M+H]+: 423.2.

Synthesis of N-((7-chloro-8-fluoroimidazo[1,5-a]pyridin-1-yl)methyl)-1-((6-cyclopropyl-8-(1-ethyl-5,6-dioxo-5,6-dihydro-1,2,4-triazin-4(1H)-yl)imidazo[1,2-a]pyridin-2-yl)methyl)-1H-1,2,3-triazole-4-carboxamide (I-242)

To a mixture of 1-((6-cyclopropyl-8-(1-ethyl-5,6-dioxo-5,6-dihydro-1,2,4-triazin-4(1H)-yl)imidazo[1,2-a]pyridin-2-yl)methyl)-1H-1,2,3-triazole-4-carboxylic acid (230 mg, crude), (7-chloro-8-fluoroimidazo[1,5-a]pyridin-1-yl)methanamine hydrochloride (142 mg, 0.6 mmol) and DIPEA (325 mg, 2.5 mmol) in DMF (8 mL) was added HOBT (135 mg, 1 mmol) and EDCI (193 mg, 1 mmol). The reaction mixture was stirred at RT for 12 h. Water (40 mL) was added and the mixture was extracted with EtOAc (40 mL×3). The combined organic layers were washed with brine and dried over Na2SO4, concentrated to give the crude, which was purified by Prep-HPLC (DCM/MeOH=10/1) to give N-((7-chloro-8-fluoroimidazo[1,5-a]pyridin-1-yl)methyl)-1-((6-cyclopropyl-8-(1-ethyl-5,6-dioxo-5,6-dihydro-1,2,4-triazin-4(1H)-yl)imidazo[1,2-a]pyridin-2-yl)methyl)-1H-1,2,3-triazole-4-carboxamide (150 mg, yield: 59%) as an off-white solid. ESI-MS [M+H]+: 604.1. Purity: 98.3% (214 nm), 98.2% (254 nm). $^1$H NMR (400 MHz, DMSO-d$_6$) δ 8.70 (t, J=5.3 Hz, 1H), 8.54-8.53 (m, 2H), 8.44 (s, 1H), 8.20 (d, J=7.4 Hz, 1H), 7.98 (s, 1H), 7.94 (s, 1H), 7.32 (d, J=1.5 Hz, 1H), 6.76 (t, J=7.4 Hz, 1H), 5.75 (s, 2H), 4.69 (d, J=5.4 Hz, 2H), 3.92 (q, J=7.2 Hz, 2H), 2.03-1.96 (m, 1H), 1.28 (t, J=7.2 Hz, 3H), 1.05-0.91 (m, 2H), 0.74-0.59 (m, 2H).

Example 243

Scheme 242

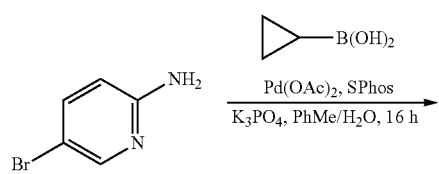

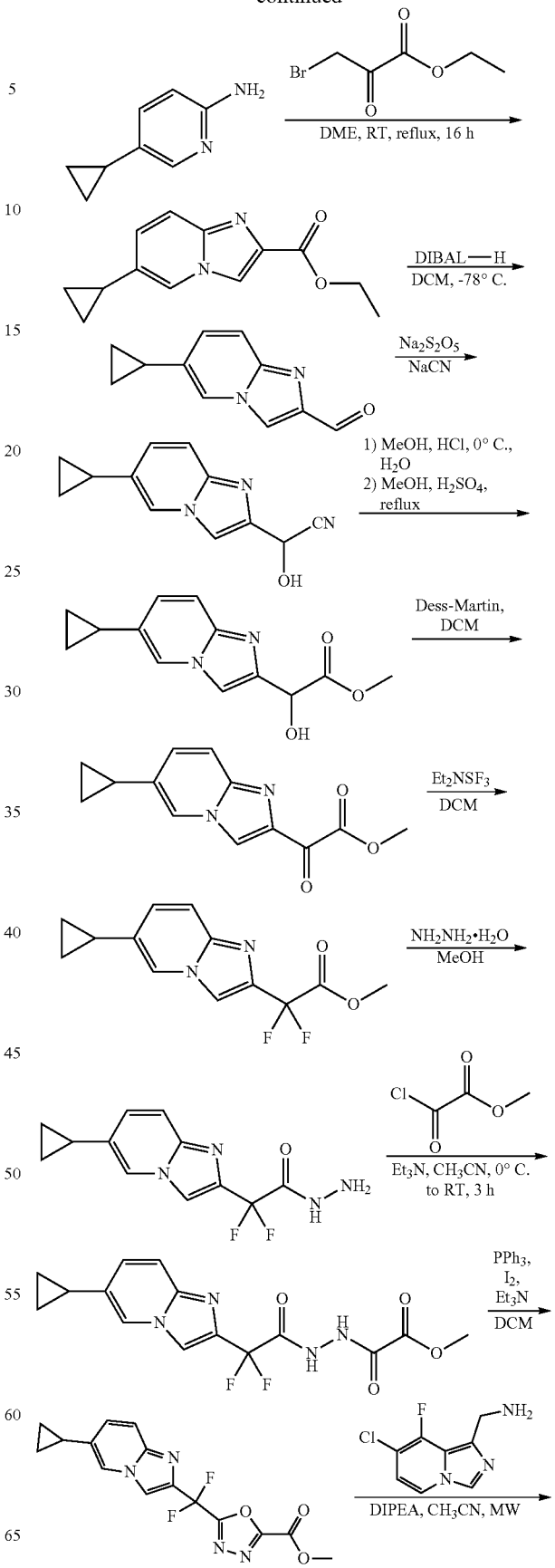

-continued

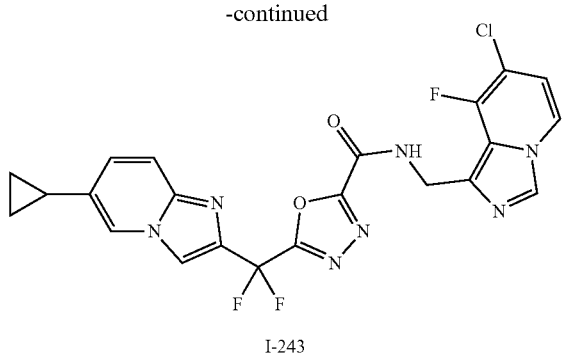

I-243

Synthesis of 5-cyclopropylpyridin-2-amine

To a solution of 5-bromopyridin-2-amine (40 g, 232 mmol) in toluene/H₂O (500 mL/50 mL) was added cyclopropylboronic acid (29.92 g, 348 mmol), Pd(OAc)₂ (65.19 g, 23.2 mmol), SPhos (10.24 g, 23.2 mmol) and K₃P₄ (147.5 g, 696 mmol). The reaction mixture was stirred at 95° C. for 16 h under nitrogen. Then the mixture was concentrated in vacuo. Water (400 mL) was added and the mixture was extracted with DCM (500 mL×2). The combined organic layers were concentrated to give the crude product, which was purified by silica gel chromatography (PE/EtOAc=1/1) to give the 5-cyclopropylpyridin-2-amine as a yellow solid (26 g, yield: 84%). ESI-MS [M+H]⁺: 135.1.

Synthesis of Ethyl 6-cyclopropylimidazo[1,2-a] pyridine-2-carboxylate

To a solution 5-cyclopropyl-4-methylpyridin-2-amine (5 g, 37.31 mmol) in DME (50 mL) was added ethyl 3-bromo-2-oxopropanoate (7.27 g, 37.26 mmol) at RT. The resulting mixture was stirred at 90° C. for 16 h and then concentrated in vacuo. H₂O (500 mL) was added, the pH value of the mixture was adjusted to 8 by adding saturated NaHCO₃ solution, and then the mixture was extracted with EtOAc (400 mL×3). The combined organic layers were washed with brine, dried over Na₂SO₄, and concentrated to give the crude product, which was purified by silica gel chromatography (DCM/EA=5/1) to give ethyl 6-cyclopropylimidazo [1,2-a]pyridine-2-carboxylate (3.8 g, yield: 44%) as a solid. ESI-MS [M+H]⁺: 230.9.

Synthesis of 6-cyclopropylimidazo[1,2-a]pyridine-2-carbaldehyde

A solution of ethyl 6-cyclopropylimidazo[1,2-a]pyridine-2-carboxylate (3.8 g, 16.5 mmol) in DCM (60 mL) was added DIBAL-H by dropwise (16.5 mL, 1 M in DCM, 16.5 mmol) was stirred at −78° C. for 5 h. The mixture was quenched with NaHCO₃ (20 mL) and extracted with DCM (100 mL×3). The combined organic layers were concentrated under and purified by silica gel chromatography (EA/PE=10/1) to give 6-cyclopropylimidazo[1,2-a]pyridine-2-carbaldehyde (1.65 g, yield: 54%) as a white solid. ESI-MS [M+H]⁺: 187.0

Synthesis of 2-(6-cyclopropylimidazo[1,2-a]pyridin-2-yl)-2-hydroxyacetonitrile To a solution of Na₂S₂O₅ (1.68 g, 8.86 mmol) in H₂O (150 mL) was added 6-cyclopropylimidazo[1,2-a]pyridine-2-carbaldehyde (1.65 g, 8.86 mmol). After the mixture was stirred for 2 h at RT, NaCN (869 mg, 17.72 mmol) was added and the mixture was stirred for another 15 h. The precipitate was collected and washed with H₂O (50 mL), and dried to give 2-(6-cyclopropylimidazo[1,2-a]pyridin-2-yl)-2-hydroxyacetonitrile (1.62 g, yield: 85%) as a white solid. ESI-MS [M+H]⁺: 214.0.

Synthesis of Methyl 2-(6-cyclopropylimidazo[1,2-a] pyridin-2-yl)-2-hydroxyacetate A solution of 2-(6-cyclopropylimidazo[1,2-a]pyridin-2-yl)-2-hydroxyacetonitrile (1.3 g, 6.1 mmol) in MeOH.HCl (100 mL) was stirred at 0° C. for 5 h. The mixture was treated with ice H₂O slowly at 0° C., stirred at RT for 2 h, adjusted pH>7 with sodium bicarbonate, then extracted with DCM (100 mL×3), washed with brine, dried over sodium sulfate, and concentrated to give crude mixture. The crude was dissolved in MeOH (50 mL) and H₂SO₄ (2 M, 5 mL) was added and the resulting mixture was refluxed for 5 h. The mixture was concentrated to give methyl 2-(6-cyclopropylimidazo[1,2-a]pyridin-2-yl)-2-hydroxyacetate (1.5 g, yield: 99%) as a white solid. ESI-MS [M+H]⁺: 246.9.

Synthesis of Methyl 2-(6-cyclopropylimidazo[1,2-a] pyridin-2-yl)-2-oxoacetate A solution of methyl 2-(6-cyclopropylimidazo[1,2-a]pyridin-2-yl)-2-hydroxyacetate (1.5 g, 6.09 mmol) in DCM (60 mL) was added Dess-Martin (3.10 g, 7.31 mmol), then the mixture was stirred at RT for 5 h. The mixture was treated with aqueous NaHCO₃ and extracted with DCM. The combined organic layers were concentrated to obtain the product, which was purification by silica gel chromatography (PE/EA=1:1) to give methyl 2-(6-cyclopropylimidazo[1,2-a]pyridin-2-yl)-2-oxoacetate (1.0 g, yield: 67%) as a white solid. ESI-MS [M+H]⁺: 244.9.

Synthesis of Methyl 2-(6-cyclopropylimidazo[1,2-a] pyridin-2-yl)-2,2-difluoroacetate To a solution of methyl 2-(6-cyclopropylimidazo[1,2-a]pyridin-2-yl)-2-oxoacetate (700 mg, 2.87 mmol) in DCM (30 mL) was added DAST (2.31 g, 14.33 mmol) at 0° C., then the mixture was stirred at RT overnight. Water (30 mL) was added then extracted with DCM (50 mL×3), the combined organic layers were concentrated to give methyl 2-(6-cyclopropylimidazo[1,2-a]pyridin-2-yl)-2,2-difluoroacetate (950 mg crude) which was used into next step without further purification. ESI-MS [M+H]⁺: 266.8.

Synthesis of 2-(6-cyclopropylimidazo[1,2-a]pyridin-2-yl)-2,2-difluoroacetohydrazide To a solution of methyl 2-(6-cyclopropylimidazo[1,2-a]pyridin-2-yl)-2,2-difluoroacetate (950 mg crude, from last step) in MeOH (20 mL) was added hydrazine hydrate (357 mg, 7.14 mmol), then the mixture was stirred at RT overnight. The solvent was removed to give 2-(6-cyclopropylimidazo[1,2-a]pyridin-2-yl)-2,2-difluoroacetohydrazide (1 g, crude) which was used in next step without further purification. ESI-MS [M+H]⁺: 267.0.

Synthesis of Methyl 2-(2-(2-(6-cyclopropylimidazo [1,2-a]pyridin-2-yl)-2,2-difluoroacetyl)hydrazinyl)-2-oxoacetate To a solution of 2-(6-cyclopropylimidazo[1,2-a]pyridin-2-yl)-2,2-difluoroacetohydrazide (275 mg, crude from last step) in CH₃CN (12 mL) was added methyl 2-chloro-2-oxoacetate (133 mg, 1.86 mmol), then the mixture was stirred at 0° C. for 0.5 h. The mixture was treated with H₂O (20 mL) and extracted with EtOAc (50 mL×3). The combined organic layers were concentrated to give the crude product which was purification by silica gel chromatography (PE/EA=1:1) to give methyl 2-(2-(2-(6-cyclopropylimidazo[1,2-a]pyridin-2-yl)-2,2-difluoroacetyl)hydrazinyl)-2-oxoacetate (297 mg) as a yellow solid. ESI-MS [M+H]⁺: 352.9.

Synthesis of Methyl 5-((6-cyclopropylimidazo[1,2-a]pyridin-2-yl)difluoromethyl)-1,3,4-oxadiazole-2-carboxylate A 50 mL 3-neck flask equipped with a stir-bar and a nitrogen inlet was charged with triphenylphosphine (313 mg, 1.19 mmol) and anhydrous DCM (17 mL) and the temperature was maintained with an ambient-temperature. Iodine (303 mg, 1.19 mmol) was added in portions over 10 minutes, allowing the iodine to dissolve before continuing the addition. The resulting dark red solution was stirred for further 15 min. A separate 50 mL 3-neck flask equipped with a stir bar, nitrogen inlet was placed in an ambient-temperature and charged with methyl 2-(2-(2-(6-cyclopropylimidazo[1,2-a]pyridin-2-yl)-2,2-difluoroacetyl)hydrazinyl)-2-oxoacetate (280 mg, 0.79 mmol) and anhydrous DCM (10 mL) to give a thick white suspension. Triethylamine (321 mg, 3.18 mmol) was added and the resulting solution was stirred for 15 minutes to give a light brown solution. The phosphorane solution was added. The dark red solution was stirred for another 60 min at RT. Water was added and extracted with ethyl acetate. The combined organic layers were dried (NaSO4), filtered and concentrated to give a dark brown solid which was purified by silica gel chromatography (PE/EA=1:1) to give methyl 5-((6-cyclopropylimidazo[1,2-a]pyridin-2-yl)difluoromethyl)-1,3,4-oxadiazole-2-carboxylate (130 mg, yield: 49%) as a yellow solid. ESI-MS [M+H]⁺: 334.7.

Synthesis of N-((7-chloro-8-fluoroimidazo[1,5-a]pyridin-1-yl)methyl)-5-((6-cyclopropylimidazo[1,2-a]pyridin-2-yl)difluoromethyl)-1,3,4-oxadiazole-2-carboxamide (I-243)

To a solution of methyl 5-((6-cyclopropylimidazo[1,2-a]pyridin-2-yl)difluoromethyl)-1,3,4-oxadiazole-2-carboxylate (45 mg, 0.134 mmol) in CH₃CN (3 mL) was added DIPEA (67 mg, 0.336 mmol), then the mixture was stirred at 80° C. under microwave for 1 h. The solvent was removed to give the crude which was purified by Prep-HPLC to give N-((7-chloro-8-fluoroimidazo[1,5-a]pyridin-1-yl)methyl)-5-((6-cyclopropylimidazo[1,2-a]pyridin-2-yl)difluoromethyl)-1,3,4-oxadiazole-2-carboxamide (14.8 mg, yield: 22%) as a white solid ESI-MS [M+H]⁺: 501.4. Purity: 97.42% (214 nm) 97.90% (254 nm). ¹H NMR (400 MHz, DMSO-d₆) δ 9.88 (t, J=4.0 Hz, 1H), 8.48 (d, J=4.0 Hz, 1H), 8.42 (d, J=8.0 Hz, 2H), 8.23 (d, J=8.0 Hz, 1H), 7.55 (d, J=8.0 Hz, 1H), 7.17 (d, J=8.0 Hz, 1H), 6.79 (t, J=8.0 Hz, 1H), 4.74 (d, J=4.0 Hz, 2H), 2.01-1.98 (m, 1H), 0.98-0.94 (m, 2H), 0.74-0.71 (m, 2H).

Example 244

Scheme 243

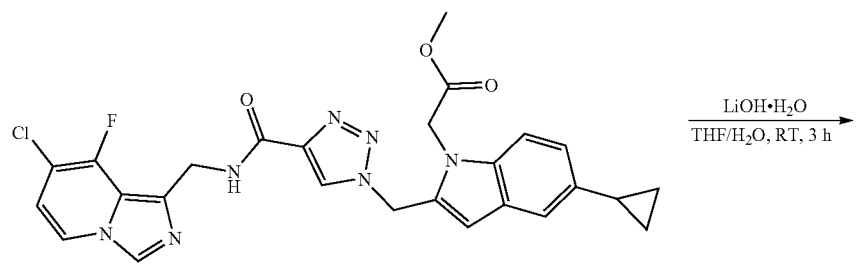

LiOH·H₂O
THF/H₂O, RT, 3 h

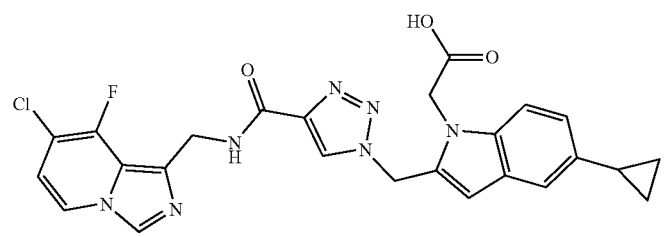

I-244

Synthesis of 2-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)acetic acid (I-244)

A mixture of methyl 2-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)acetate (40 mg, 0.075 mmol) and LiOH.H₂O (16 mg, 0.37 mmol) in THF/H₂O (5 mL/2 mL) was stirred at RT for 3 h. LCMS confirmed the starting material consumed completely and target material was detected. The reaction mixture was adjusted to pH-3. Then Water was added and extracted with DCM/MeOH (30 mL×5). The combined organic layers were washed with brine and concentrated. The crude product was purified by prep-HPLC to afforded 2-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)acetic acid (1.2 mg, yield: 3%) as a brown solid. ESI-MS [M+H]⁺: 522.1. Purity: 96.69% (214 nm), 82.74% (254 nm). ¹H NMR (400 MHz, DMSO-d₆) δ 12.89 (s, 1H), 8.67 (s, 1H), 8.50-8.41 (m, 2H), 8.20 (d, J=7.3 Hz, 1H), 7.28-7.19 (m, 2H), 6.89 (d, J=8.5 Hz, 1H), 6.76 (t, J=6.8 Hz, 1H), 6.48 (s, 1H), 5.84 (s, 2H), 5.04 (s, 2H), 4.68 (d, J=5.0 Hz, 2H), 1.96 (s, 1H), 0.89 (d, J=7.2 Hz, 2H), 0.62 (d, J=4.2 Hz, 2H).

Example 245

Scheme 244

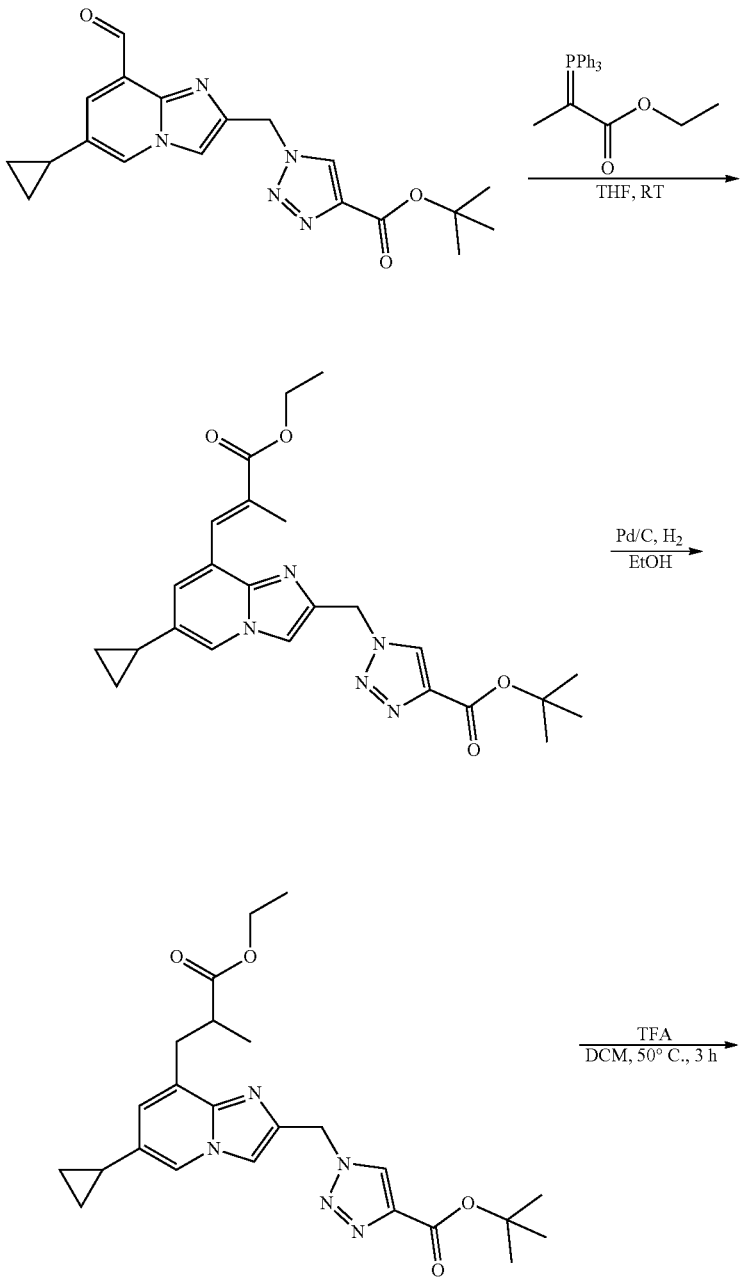

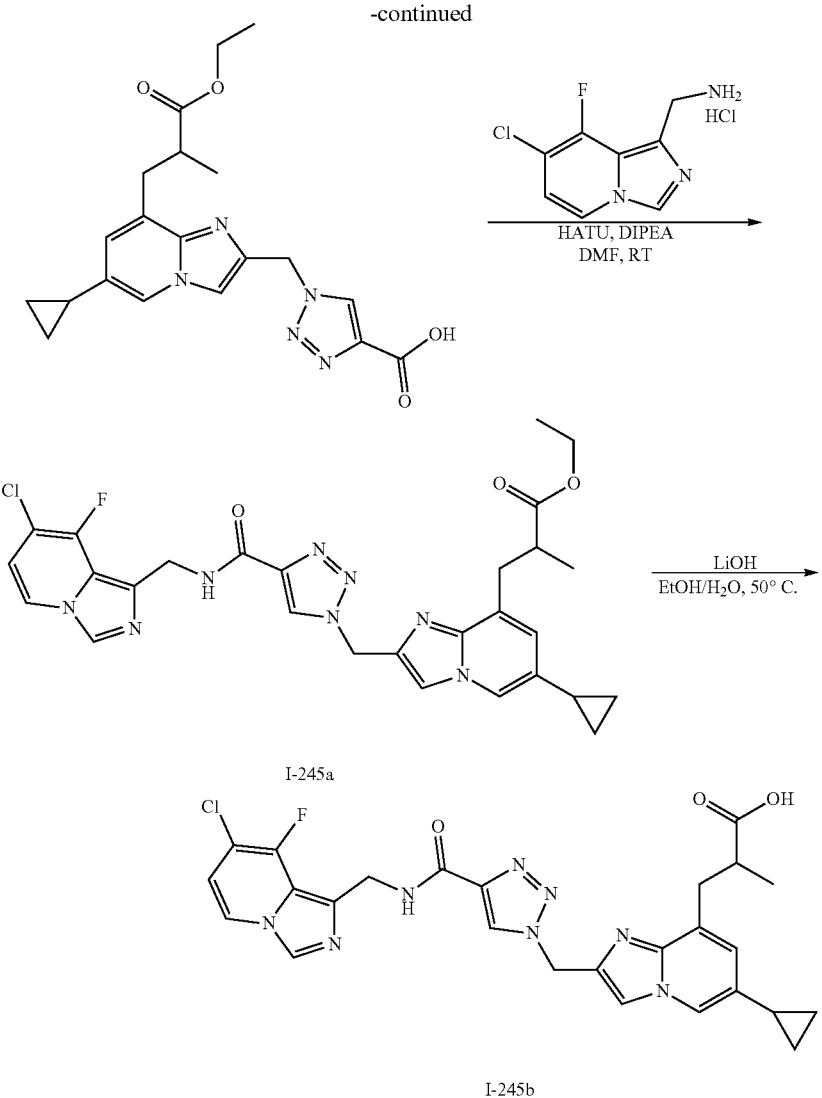

Synthesis of tert-butyl 1-((6-cyclopropyl-8-(3-ethoxy-2-methyl-3-oxoprop-1-en-1-yl)imidazo[1,2-a]pyridin-2-yl)methyl)-1H-1,2,3-triazole-4-carboxylate To a suspension of tert-butyl 1-((6-cyclopropyl-8-formylimidazo[1,2-a]pyridin-2-yl)methyl)-1H-1,2,3-triazole-4-carboxylate (450 mg, 1.23 mmol) in THF (20 mL) was added dropwise ethyl 2-(triphenyl-15-phosphanylidene)propanoate (445 mg, 1.23 mmol). The resulting reaction solution was stirred at 50° C. for 5 h. The reaction was quenched with saturated aqueous NH₄Cl solution (20 mL). The layers were separated and the aqueous phase was extracted with EtOAc (100 mL×3). The combined organic layers were washed with saturated aqueous brine (50 mL×2), dried over sodium sulfate and concentrated in vacuo to give the crude, which was purification by column chromatography (DCM:MeOH=50:1) to afforded the tert-butyl 1-((6-cyclopropyl-8-(3-ethoxy-2-methyl-3-oxoprop-1-en-1-yl)imidazo[1,2-a]pyridin-2-yl)methyl)-1H-1,2,3-triazole-4-carboxylate (450 mg, 81%) as a yellow solid. ESI-MS [M+H]⁺: 452.3.

Synthesis of tert-butyl 1-((6-cyclopropyl-8-(3-ethoxy-2-methyl-3-oxopropyl)imidazo[1,2-a]pyridin-2-yl)methyl)-1H-1,2,3-triazole-4-carboxylate To a solution of tert-butyl 1-((6-cyclopropyl-8-(3-ethoxy-2-methyl-3-oxoprop-1-en-1-yl)imidazo[1,2-a]pyridin-2-yl)methyl)-1H-1,2,3-triazole-4-carboxylate (450 mg, 1 mmol) in ethanol (20 mL) was added Pd/C (200 mg). A balloon of hydrogen gas was added and the reaction was evacuated and back-filled with hydrogen three times. The reaction was stirred under a hydrogen balloon at 0° C. for 3 h, filtered through a pad of celite and concentrated in vacuo to crude compound. The crude compound was purified by flash silica gel chromatography (EA/PE=1:2) to give the tert-butyl 1-((6-cyclopropyl-8-(3-ethoxy-2-methyl-3-oxopropyl)imidazo[1,2-a]pyridin-2-yl)methyl)-1H-1,2,3-triazole-4-carboxylate (300 mg, 66%) as a yellow solid. ESI-MS [M+H]⁺: 454.2.

Synthesis of 1-((6-cyclopropyl-8-(3-ethoxy-2-methyl-3-oxopropyl)imidazo[1,2-a]pyridin-2-yl)methyl)-1H-1,2,3-triazole-4-carboxylic Acid To a solution of tert-butyl 1-((6-cyclopropyl-8-(3-ethoxy-2-methyl-3-oxopropyl)imidazo[1,2-a]pyridin-2-yl)methyl)-1H-1,2,3-triazole-4-carboxylate (288 mg, 0.64 mmol) in DCM (10 mL) was added TFA (2 mL). The reaction mixture was stirred at 50° C. for 3 h. LCMS showed the reaction was complete. The solvent of the reaction mixture was evaporated under reduced pressure to give 1-((6-cyclopropyl-8-(3-ethoxy-2-methyl-3-oxopropyl)imidazo[1,2-a]pyridin-2-yl)methyl)-1H-1,2,3-triazole-4-carboxylic acid. The crude product was used in next step without further purification (300 mg, crude) as a yellow solid. ESI-MS [M+H]$^+$: 398.2.

Synthesis of Ethyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2-methylpropanoate (I-245a)

To a solution of 1-((6-cyclopropyl-8-(3-ethoxy-2-methyl-3-oxopropyl)imidazo[1,2-a]pyridin-2-yl)methyl)-1H-1,2,3-triazole-4-carboxylic acid (150 mg, crude) in dry DMF (5 mL), was added (7-chloro-8-fluoroimidazo[1,5-a]pyridin-1-yl)methanamine hydrochloride (141 mg, 0.60 mmol), HATU (274 mg, 0.72 mmol) and DIPEA (387 mg, 3 mmol), the reaction mixture was stirred at RT for 2 h. The reaction was quenched with H$_2$O (20 mL), extracted with ethyl acetate (50 mL×3). The combined organic layers were washed with brine (20 mL×2), dried over anhydrous sodium sulfate and concentrated in vacuo. The residue was purified by Prep-TLC (DCM/MeOH=10:1) to afford ethyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2-methylpropanoate (100 mg, yield: 54% over 2 steps) as a white solids. ESI-MS [M+H]$^+$: 579.2. Purity: 97.70% (214 nm), 98.50% (254 nm). $^1$H NMR (400 MHz, DMSO-d6) δ 8.71 (t, J=5.4 Hz, 1H), 8.54 (s, 1H), 8.44 (d, J=2.3 Hz, 1H), 8.21 (m, 2H), 7.76 (s, 1H), 6.77 (m, 2H), 5.74 (s, 2H), 4.70 (d, J=5.5 Hz, 2H), 3.96 (m, 2H), 3.08 (m, 2H), 2.90 (m, 1H), 1.93-1.83 (m, 1H), 1.05 (m, 6H), 0.96-0.85 (m, 2H), 0.68-0.58 (m, 2H).

Synthesis of 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2-methylpropanoic acid (I-245b)

To a solution of ethyl 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2-methylpropanoate (90 mg, 0.16 mmol) was dissolved in MeOH (5 mL) and H$_2$O (5 mL) was added LiOH.H$_2$O (54.6 mg, 1.3 mmol) at RT. The reaction mixture was stirred at 50° C. for 5 h. The solvent of the reaction mixture was evaporated under reduced pressure. Then pH of the mixture was acidified by HCl (1N) to around 2, and the precipitated solid was collected by filtration to obtain the crude product. The crude product was purified by prep-HPLC to give the 3-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-2-methylpropanoic acid (25 mg, yield 28%) as a white solid. ESI-MS [M+H]$^+$: 551.2. Purity: 99.76% (214 nm), 100% (254 nm). $^1$H NMR (400 MHz, DMSO-d6) δ 12.18 (s, 1H), 8.71 (t, J=5.4 Hz, 1H), 8.55 (s, 1H), 8.44 (d, J=2.3 Hz, 1H), 8.20 (m, 2H), 7.75 (s, 1H), 6.77 (m, 2H), 5.74 (s, 2H), 4.70 (d, J=5.4 Hz, 2H), 3.12 (m, 1H), 2.99 (m, 1H), 2.83 (m, 1H), 1.88 (m, 1H), 1.05 (d, J=6.9 Hz, 3H), 0.95-0.85 (m, 2H), 0.70-0.58 (m, 2H).

Example 246

Scheme 245

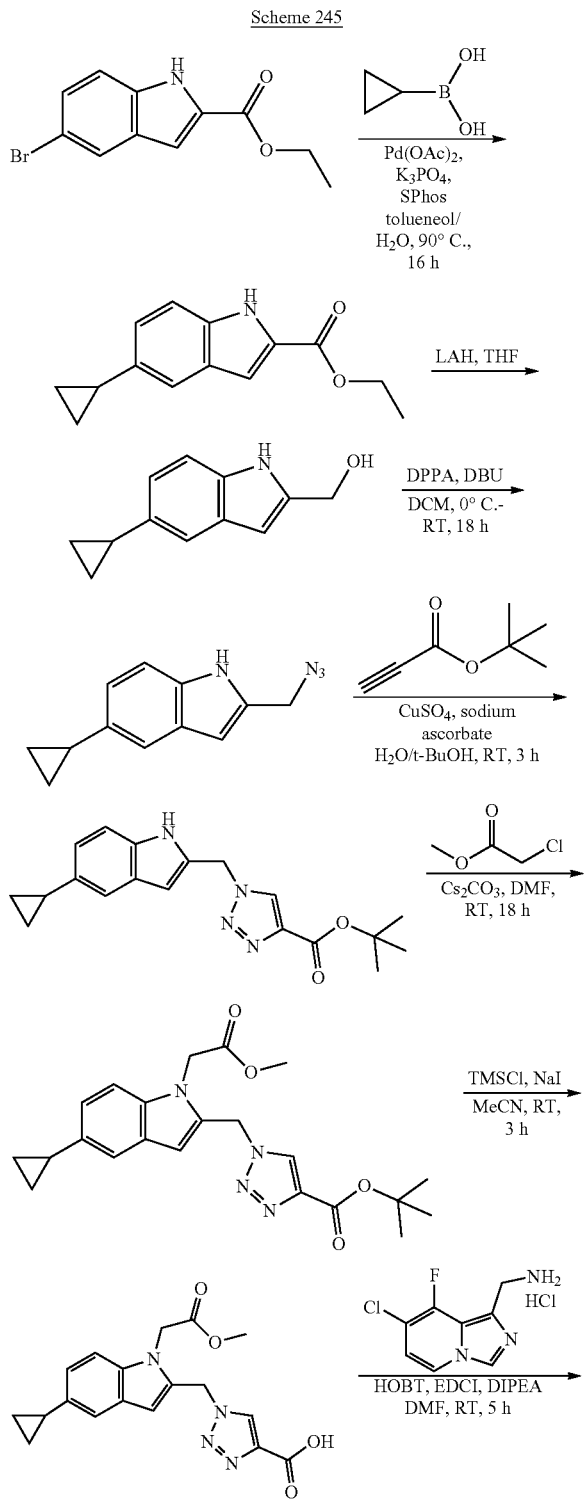

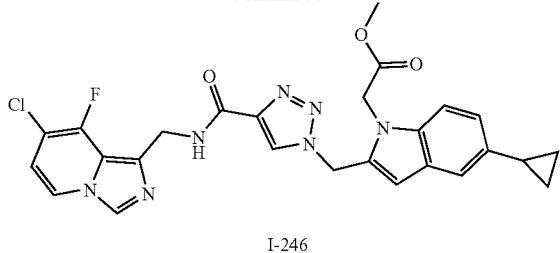

I-246

Synthesis of Ethyl 5-cyclopropyl-1H-indole-2-carboxylate

A mixture of ethyl 5-bromo-1H-indole-2-carboxylate (15 g, 55.9 mmol), cyclopropylboronic acid (14.4 g, 167.7 mmol), Pd(OAc)$_2$ (1.29 g, 5.59 mmol), SPhos (2.29 g, 5.59 mmol) and K$_3$PO$_4$ (35.6 g, 167.7 mmol) in toluene/H$_2$O (150 mL/15 mL) was stirred at 90° C. for 16 h. The reaction mixture was filtered, washed with EtOAc (300 mL). The filtrate was concentrated in vacuo to give the crude product, which was purified with silica gel chromatography (EA/PE=1/3) to give ethyl 5-cyclopropyl-1H-indole-2-carboxylate (7.2 g, yield: 56.7%) as a yellow solid. ESI-MS [M+H]$^+$: 230.1

Synthesis of (5-cyclopropyl-1H-indol-2-yl)methanol

To the solution of 2-(chloromethyl)-6-cyclopropylimidazo[1,2-a]pyridine (9.0 g, 39.3 mmol) in THF (100 mL) was added LAH (1.8 g, 47.2 mmol) at 0° C. portionwise. The mixture was stirred at 0° C. for 2 h. The reaction was quenched with H$_2$O (2 mL), 10% NaOH solution (2 mL) and then H$_2$O (6 mL) at 0° C. The mixture was filtered and the cake was washed with EtOAc (100 mL). The filtrate was concentrate to give the crude, which was purified by flash column chromatography (PE/EA=1/2) to afforded (5-cyclopropyl-1H-indol-2-yl)methanol (7.0 g, yield: 95%) as yellow oil. ESI-MS [M+H]$^+$: 188.0

Synthesis of 2-(azidomethyl)-5-cyclopropyl-1H-indole

To the mixture of (5-cyclopropyl-1H-indol-2-yl)methanol (5.61 g, 30.0 mmol) and DPPA (2.48 g, 90.0 mmol) in DCM (100 mL) was added DBU (13.7 g, 90 mmol) at 0° C. The reaction mixture was degassed with N$_2$ and stirred at RT for 18 h. The reaction mixture was quenched with H$_2$O (200 mL) and extracted with DCM (100 mL×3). The combined organic layers were washed with brine, dried over Na$_2$SO$_4$, concentrated to give the crude, which was purified by flash column chromatography (PE/EA=1/1) to afforded 2-(azidomethyl)-5-cyclopropyl-1H-indole (2.5 g, yield: 39%). ESI-MS [M+H]$^+$: 213.0

Synthesis of tert-butyl 1-((5-cyclopropyl-1H-indol-2-yl)methyl)-1H-1,2,3-triazole-4-carboxylate A mixture of 2-(azidomethyl)-5-cyclopropyl-1H-indole (4.9 g, 23.11 mmol), tert-butyl propiolate (3.49 g, 27.73 mmol), sodium ascorbate (915 mg, 4.62 mmol) and CuSO$_4$ (735 mg, 4.62 mmol) in t-BuOH/H$_2$O (25 mL/25 mL) was stirred at RT for 3 h. The reaction was diluted with H$_2$O (100 mL), extracted with DCM/MeOH (10/1, 100 mL×3). The combined organic layers were washed with brine and dried over Na$_2$SO$_4$, concentrated to give the crude, which was purified by flash column chromatography (DCM/MeOH=20/1) to afforded tert-butyl 1-((5-cyclopropyl-1H-indol-2-yl)methyl)-1H-1,2,3-triazole-4-carboxylate (3 g, yield: 38%) as a solid. ESI-MS [M+H]$^+$: 339.1

Synthesis of tert-butyl 1-((5-cyclopropyl-1-(2-methoxy-2-oxoethyl)-1H-indol-2-yl)methyl)-1H-1,2,3-triazole-4-carboxylate A mixture of tert-butyl 1-((5-cyclopropyl-1H-indol-2-yl)methyl)-1H-1,2,3-triazole-4-carboxylate (400 mg, 1.18 mmol), methyl 2-chloroacetate (256 mg, 2.37 mmol), and Cs$_2$CO$_3$ (770 mg, 2.37 mmol) in DMF (4 mL) was stirred at RT for 18 h. The reaction mixture was diluted with H$_2$O (50 mL), extracted with EtOAc (50 mL×3). The combined organic layers were washed with brine, dried over Na$_2$SO$_4$, and concentrated. The residue was purified by flash column chromatography (DCM/MeOH=25/1) to afforded ethyl 2-((6-cyclopropylimidazo[1,2-a]pyridin-2-yl)methyl)oxazole-4-carboxylate (450 mg, yield: 93%) as a yellow solid. ESI-MS [M+H]$^+$: 411.2

Synthesis of 1-((5-cyclopropyl-1-(2-methoxy-2-oxoethyl)-1H-indol-2-yl)methyl)-1H-1,2,3-triazole-4-carboxylic Acid To the mixture of ethyl 2-((6-cyclopropylimidazo[1,2-a]pyridin-2-yl)methyl)oxazole-4-carboxylate (450 mg, 1.1 mmol) and NaI (495 mg, 3.3 mmol) in MeCN (10 mL) was added TMSCl (356 mg, 3.3 mmol) at RT. And the reaction was stirred at RT for 3 h. Water (5 mL) was added to the reaction, and the mixture was freeze-dried to afforded 1-((5-cyclopropyl-1-(2-methoxy-2-oxoethyl)-1H-indol-2-yl)methyl)-1H-1,2,3-triazole-4-carboxylic acid (900 mg, crude) as a yellow-red solid which was used in next step directly. ESI-MS [M+H]$^+$: 354.9

Synthesis of Methyl 2-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)acetate (I-246)

A mixture of 1-((5-cyclopropyl-1-(2-methoxy-2-oxoethyl)-1H-indol-2-yl)methyl)-1H-1,2,3-triazole-4-carboxylic acid (900 mg, crude), (7-chloro-8-fluoroimidazo[1,5-a]pyridin-1-yl)methanamine hydrochloride (389 mg, 1.65 mmol), HOBT (223 mg, 1.65 mmol), EDCI (315 mg, 1.65 mmol) and DIPEA (426 mg, 3.3 mmol) in DMF (5 mL) was stirred at to RT for 3 h. The reaction mixture was diluted with H$_2$O (80 mL) and extracted with EtOAc (100 mL×3). The combined organic layers were washed with brine, dried over Na$_2$SO$_4$, and concentrated. The residue was purified by prep-HPLC to afforded methyl 2-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)acetate (40 mg, yield: 7%) as a white solid. ESI-MS [M+H]$^+$: 536.1. Purity: 99.72% (214 nm), 97.06% (254 nm). $^1$H NMR (400 MHz, DMSO-d$_6$) δ 8.70 (t, J=5.4 Hz, 1H), 8.46 (s, 1H), 8.43 (d, J=2.4 Hz, 1H), 8.20 (d, J=7.4 Hz, 1H), 7.28-7.22 (m, 2H), 6.93-6.86 (m, 1H), 6.80-6.72 (m, 1H), 6.54 (s, 1H), 5.86 (s, 2H), 5.18 (s, 2H), 4.68 (d, J=5.5 Hz, 2H), 3.49 (s, 3H), 2.01-1.90 (m, 1H), 0.93-0.86 (m, 2H), 0.66-0.59 (m, 2H).

Example 247
Scheme 246
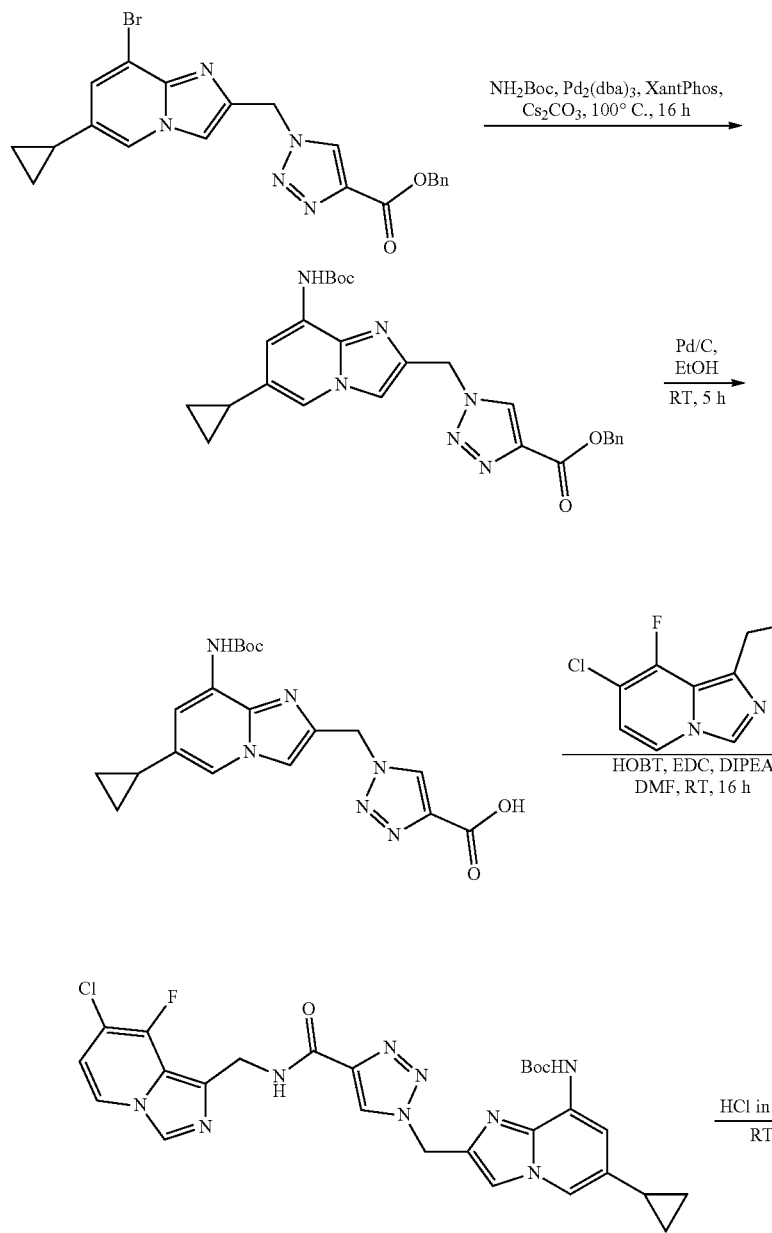
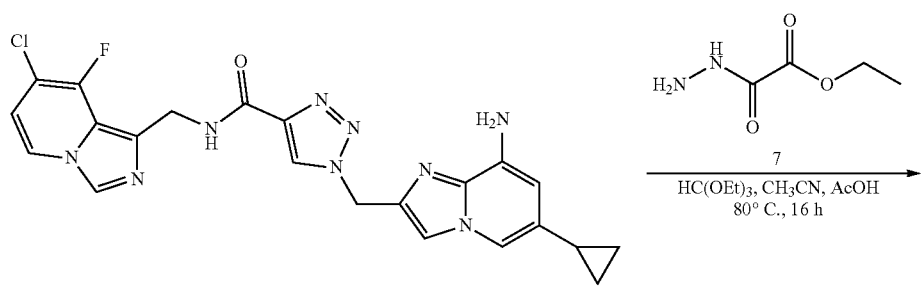

-continued

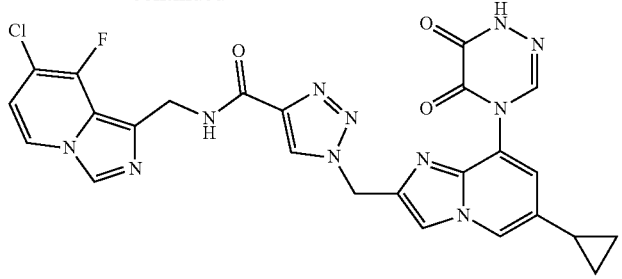

I-247

Synthesis of benzyl 1-((8-((tert-butoxycarbonyl)amino)-6-cyclopropylimidazo[1,2-a]pyridin-2-yl)methyl)-1H-1,2,3-triazole-4-carboxylate To a mixture of benzyl 1-((8-bromo-6-cyclopropylimidazo[1,2-a]pyridin-2-yl)methyl)-1H-1,2,3-triazole-4-carboxylate (1.2 g, 2.65 mmol), NH$_2$Boc (372 mg, 3.2 mol) and Cs$_2$CO$_3$ (2.16 g, 6.63 mmol) in dioxane (20 mL) was added Pd$_2$(dba)$_3$ (280 mg, 0.27 mmol) and XantPhos (156 mg, 0.27 mmol). The reaction mixture was stirred at 100° C. for 16 h. Water (50 mL) was added to the reaction, extracted with EtOAc (50 mL×3). The combined organic layers were washed with brine, dried over Na$_2$SO$_4$, filtrated and concentrated to get the residue, which was purified by silica gel chromatography (PE/EA=3/1 to 1/1) to give benzyl 1-((8-((tert-butoxycarbonyl)amino)-6-cyclopropylimidazo[1,2-a]pyridin-2-yl)methyl)-1H-1,2,3-triazole-4-carboxylate (800 mg, yield: 62%) as a yellow oil. ESI-MS [M+H]$^+$: 489.2

Synthesis of 1-((8-((tert-butoxycarbonyl)amino)-6-cyclopropylimidazo[1,2-a]pyridin-2-yl)methyl)-1H-1,2,3-triazole-4-carboxylic Acid A mixture of benzyl 1-((8-((tert-butoxycarbonyl)amino)-6-cyclopropylimidazo[1,2-a]pyridin-2-yl)methyl)-1H-1,2,3-triazole-4-carboxylate (800 mg, 1.64 mmol) and Pd/C (100 mg, 10%) in EtOH (30 mL) was stirred at RT for 5 h under H$_2$ atmosphere. The reaction mixture was filtered, the cake was washed with MeOH (50 mL). The filtrate was concentrated to give 1-((8-((tert-butoxycarbonyl)amino)-6-cyclopropylimidazo[1,2-a]pyridin-2-yl)methyl)-1H-1,2,3-triazole-4-carboxylic acid (650 mg, yield: 100%) as a yellow solid, which was used into next step without further purification. ESI-MS [M+H]$^+$: 399.1.

Synthesis of tert-butyl (2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)carbamate To the mixture of 1-((8-((tert-butoxycarbonyl)amino)-6-cyclopropylimidazo[1,2-a]pyridin-2-yl)methyl)-1H-1,2,3-triazole-4-carboxylic acid (650 mg, 1.63 mmol), (7-chloro-8-fluoroimidazo[1,5-a]pyridin-1-yl)methanamine hydrochloride (460 mg, 1.95 mmol) and DIPEA (1.1 g, 8.15 mmol) in DMF (10 mL) was added HOBT (440 mg, 3.26 mmol) and EDC (626 mg, 3.26 mmol). The mixture was stirred at RT for 16 h. Water (50 mL) was added to the reaction, extracted with EtOAc (50 mL×3). The combined organic layers were washed with brine, dried over Na$_2$SO$_4$, filtrated and concentrated. The residue was purified by silica gel chromatography (DCM/MeOH=10/1) to give tert-butyl (2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)carbamate (850 mg, yield: 90%) as a yellow solid. ESI-MS [M+H]$^+$: 581.1.

Synthesis of 1-((8-amino-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide A mixture of tert-butyl (2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)carbamate (850 mg, 1.46 mmol) in 10 mL of HCl (4N solution in dioxane) was stirred at RT for 3 h. The reaction was concentrated to give 1-((8-amino-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide (700 mg, crude) as a yellow solid. ESI-MS [M+H]$^+$: 480.1.

Synthesis of N-((7-chloro-8-fluoroimidazo[1,5-a]pyridin-1-yl)methyl)-1-((6-cyclopropyl-8-(5,6-dioxo-5,6-dihydro-1,2,4-triazin-4(1H)-yl)imidazo[1,2-a]pyridin-2-yl)methyl)-1H-1,2,3-triazole-4-carboxamide To a mixture of 1-((8-amino-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide (350 mg, 0.73 mmol) and TEA (147 mg, 1.46 mmol) in McCN (15 mL) was added HC(OEt)$_3$ (432 mg, 2.92 mmol). The reaction mixture was stirred at 80° C. for 1 h. Then AcOH (66 mg, 1.1 mmol) and ethyl 2-hydrazinyl-2-oxoacetate (241 mg, 1.82 mmol) was added thereto. After stirred at 80° C. for 16 h, the reaction was concentrated to give the crude, which was purified by Prep-TLC (DCM/MeOH=10/1) to give N-((7-chloro-8-fluoroimidazo[1,5-a]pyridin-1-yl)methyl)-1-((6-cyclopropyl-8-(5,6-dioxo-5,6-dihydro-1,2,4-triazin-4(1H)-yl)imidazo[1,2-a]pyridin-2-yl)methyl)-1H-1,2,3-triazole-4-carboxamide (20 mg, yield: 4.5%) as a white solid. ESI-MS [M+H]$^+$: 576.1. Purity: 98.2% (214 nm), 98.0% (254 nm). $^1$H NMR (400 MHz, DMSO-d$_6$) δ 12.53 (s, 1H), 8.71 (t, J=5.3 Hz, 1H), 8.54-8.53 (m, 2H), 8.44 (d, J=2.1 Hz, 1H), 8.20 (d, J=7.4 Hz, 1H), 7.92 (s, 1H), 7.87 (s, 1H), 7.32 (s, 1H), 6.80-6.72 (m, 1H), 5.74 (s, 2H), 4.69 (d, J=5.4 Hz, 2H), 2.03-1.95 (m, 1H), 1.00-0.96 (m, 2H), 0.71-0.67 (m, 2H).

Example 248

Scheme 247

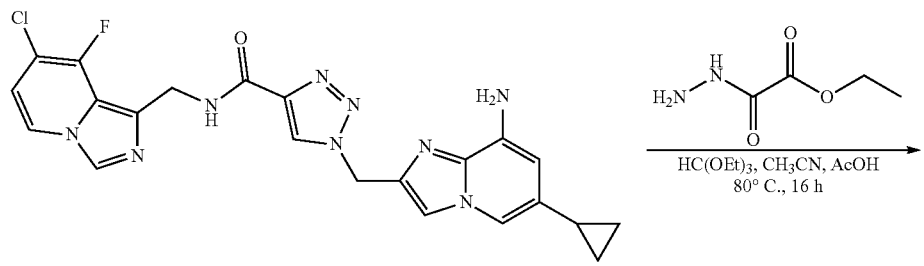

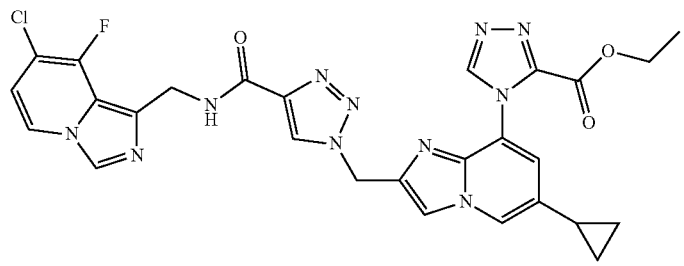

I-248

Synthesis of Ethyl 4-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-4H-1,2,4-triazole-3-carboxylate (I-248)

To a mixture of 1-((8-amino-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide (350 mg, 0.73 mmol) and TEA (147 mg, 1.46 mmol) in McCN (15 mL) was added HC(OEt)$_3$ (432 mg, 2.92 mmol). The mixture was stirred at 80° C. for 1 h. Then AcOH (66 mg, 1.1 mmol) and ethyl 2-hydrazinyl-2-oxoacetate (241 mg, 1.82 mmol) was added. After stirred at 80° C. for 16 h, cooled, concentrated and purified by Prep-TLC (DCM/MeOH=10/1) to ethyl 4-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)-4H-1,2,4-triazole-3-carboxylate (10 mg, yield: 2.3%) as a white solid. ESI-MS [M+H]$^+$: 604.1. Purity: 96.6% (214 nm), 94.4% (254 nm). $^1$H NMR (400 MHz, DMSO-d$_6$) δ 9.07 (s, 1H), 8.69 (t, J=5.5 Hz, 1H), 8.55 (d, J=1.3 Hz, 1H), 8.51-8.37 (m, 2H), 8.20 (d, J=7.4 Hz, 1H), 7.97 (s, 1H), 7.43 (d, J=1.5 Hz, 1H), 6.76 (dd, J=7.3, 6.6 Hz, 1H), 5.69 (s, 2H), 4.69 (d, J=5.5 Hz, 2H), 3.97 (q, J=7.1 Hz, 2H), 2.03-1.97 (m, 1H), 1.06-0.94 (m, 2H), 0.87 (t, J=7.1 Hz, 3H), 0.81-0.68 (m, 2H).

Example 249

Scheme 248

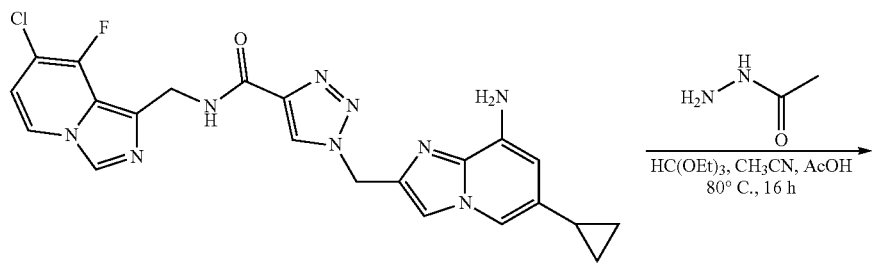

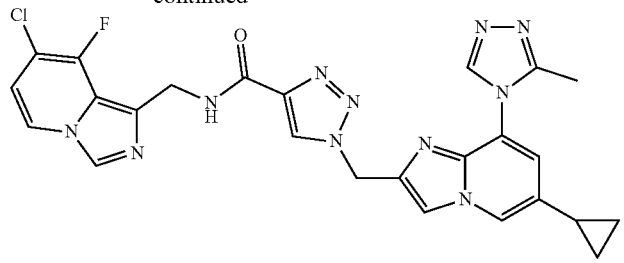

I-249

Synthesis of N-((7-chloro-8-fluoroimidazo[1,5-a]pyridin-1-yl)methyl)-1-((6-cyclopropyl-8-(3-methyl-4H-1,2,4-triazol-4-yl)imidazo[1,2-a]pyridin-2-yl)methyl)-1H-1,2,3-triazole-4-carboxamide (I-249)

To a mixture of 1-((8-amino-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide (48 mg, 0.1 mmol) and TEA (20 mg, 0.2 mmol) in MeCN (3 mL) was added HC(OEt)3 (60 mg, 0.4 mmol). The mixture was stirred at 80° C. for 1 h. Then AcOH (18 mg, 0.3 mmol) and acetohydrazide (19 mg, 0.25 mmol) was added to the reaction above. After stirred at 80° C. for 16 h, The reaction was concentrated to give the crude, which was purified by Prep-TLC (DCM/MeOH=10/1) to N-((7-chloro-8-fluoroimidazo[1,5-a]pyridin-1-yl)methyl)-1-((6-cyclopropyl-8-(3-methyl-4H-1,2,4-triazol-4-yl)imidazo[1,2-a]pyridin-2-yl)methyl)-1H-1,2,3-triazole-4-carboxamide (20 mg, yield: 37%) as a yellow solid. ESI-MS [M+H]$^+$: 546.1. Purity: 97.0% (214 nm), 98.3% (254 nm). $^1$H NMR (400 MHz, DMSO-d$_6$) δ 8.77-8.65 (m, 2H), 8.54 (s, 2H), 8.44 (d, J=2.4 Hz, 1H), 8.21 (d, J=7.4 Hz, 1H), 7.98 (s, 1H), 7.30 (d, J=1.4 Hz, 1H), 6.82-6.72 (m, 1H), 5.74 (s, 2H), 4.69 (d, J=5.5 Hz, 2H), 2.26 (s, 3H), 2.03-1.96 (m, 1H), 1.00-0.92 (m, 2H), 0.81-0.71 (m, 2H).

Example 250

Scheme 249

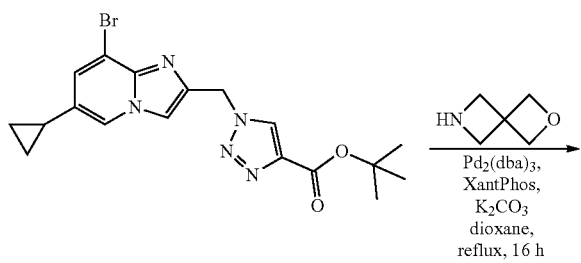

I-250

Synthesis of tert-butyl 1-((6-cyclopropyl-8-(2-oxa-6-azaspiro[3.3]heptan-6-yl)imidazo[1,2-a]pyridin-2-yl)methyl)-1H-1,2,3-triazole-4-carboxylate A mixture of tert-butyl 1-((8-bromo-6-cyclopropylimidazo[1,2-a]pyridin-2-yl)methyl)-1H-1,2,3-triazole-4-carboxylate (350 mg, 0.837 mmol), 2-oxa-6-azaspiro[3.3]heptane (124 mg, 1.255 mmol), Pd$_2$(dba)$_3$ (77 mg, 0.0837 mmol), XantPhos (97 mg, 0.167 mmol) and K$_2$CO$_3$ (347 mg, 2.51 mmol) in dioxane (8 mL) was stirred at 100° C. for 16 h under N$_2$. The reaction mixture was concentrated and diluted in DCM (80 mL), washed with H$_2$O (80 mL) and brine (80 mL), dried over Na$_2$SO$_4$, concentrated to give the crude, which was purified by silica gel chromatography (EA/PE=1/2) to give tert-butyl 1-((6-cyclopropyl-8-(2-oxa-6-azaspiro[3.3]heptan-6-yl)imidazo[1,2-a]pyridin-2-yl)methyl)-1H-1,2,3-triazole-4-carboxylate (290 mg, yield: 79%) as a light brown solid. ESI-MS [M+H]⁺: 437.2.

Synthesis of 1-((6-cyclopropyl-8-(2-oxa-6-azaspiro[3.3]heptan-6-yl)imidazo[1,2-a]pyridin-2-yl)methyl)-1H-1,2,3-triazole-4-carboxylic Acid To a solution of tert-butyl 1-((6-cyclopropyl-8-(2-oxa-6-azaspiro[3.3]heptan-6-yl)imidazo[1,2-a]pyridin-2-yl)methyl)-1H-1,2,3-triazole-4-carboxylate (120 mg, 0.275 mmol) in methanol (3 mL), THF (3 mL) and H₂O (1 mL) was added lithium hydroxide monohydrate (46 mg, 1.1 mmol). The mixture was stirred at 40° C. for 5 h. The reaction was concentrated to remove MeOH and THF. And the residue was diluted in H₂O (20 mL), then the pH was acidified to 5-6 by HCl (0.5 M) and extracted with DCM (30 mL×5). The combined organic layers were dried over Na₂SO₄, concentrated and dried in vacuo to give 1-((6-cyclopropyl-8-(2-oxa-6-azaspiro[3.3]heptan-6-yl)imidazo[1,2-a]pyridin-2-yl)methyl)-1H-1,2,3-triazole-4-carboxylic acid (80 mg, 76%) as a white solid. ESI-MS [M+H]⁺: 381.1.

Synthesis of N-((7-chloro-8-fluoroimidazo[1,5-a]pyridin-1-yl)methyl)-1-((6-cyclopropyl-8-(2-oxa-6-azaspiro[3.3]heptan-6-yl)imidazo[1,2-a]pyridin-2-yl)methyl)-1H-1,2,3-triazole-4-carboxamide (I-250)

A mixture of 1-((6-cyclopropyl-8-(2-oxa-6-azaspiro[3.3]heptan-6-yl)imidazo[1,2-a]pyridin-2-yl)methyl)-1H-1,2,3-triazole-4-carboxylic acid (80 mg, 0.21 mmol), (7-chloro-8-fluoroimidazo[1,5-a]pyridin-1-yl)methanamine hydrochloride (59 mg, 0.25 mmol), EDCI (81 mg, 0.42 mmol), HOBT (57 mg, 0.42 mmol) and DIPEA (163 mg, 1.26 mmol) in DMF (5 mL) was stirred at 25° C. for 16 h. The reaction mixture was poured into H₂O (50 mL) and extracted with EtOAc/THF (50 mL×2, 5/1). The combined organics were washed with brine (100 mL), dried over Na₂SO₄, concentrated and purified by prep-TLC (DCM/MeOH=15/1) to give N-((7-chloro-8-fluoroimidazo[1,5-a]pyridin-1-yl)methyl)-1-((6-cyclopropyl-8-(2-oxa-6-azaspiro[3.3]heptan-6-yl)imidazo[1,2-a]pyridin-2-yl)methyl)-1H-1,2,3-triazole-4-carboxamide (70 mg, yield: 59%) as a white solid. ESI-MS [M+H]⁺: 562.1. Purity: 98.96% (214 nm), 98.79% (254 nm). ¹H NMR (400 MHz, DMSO-d₆) δ 8.71 (t, J=5.3 Hz, 1H), 8.50 (s, 1H), 8.44 (d, J=2.2 Hz, 1H), 8.20 (d, J=7.4 Hz, 1H), 7.72-7.68 (m, 2H), 6.76 (t, J=6.9 Hz, 1H), 5.70-5.67 (m, 3H), 4.73-4.68 (m, 6H), 4.24 (s, 4H), 1.86-1.78 (m, 1H), 0.88-0.82 (m, 2H), 0.67-0.56 (m, 2H).

Example 251

Scheme 250

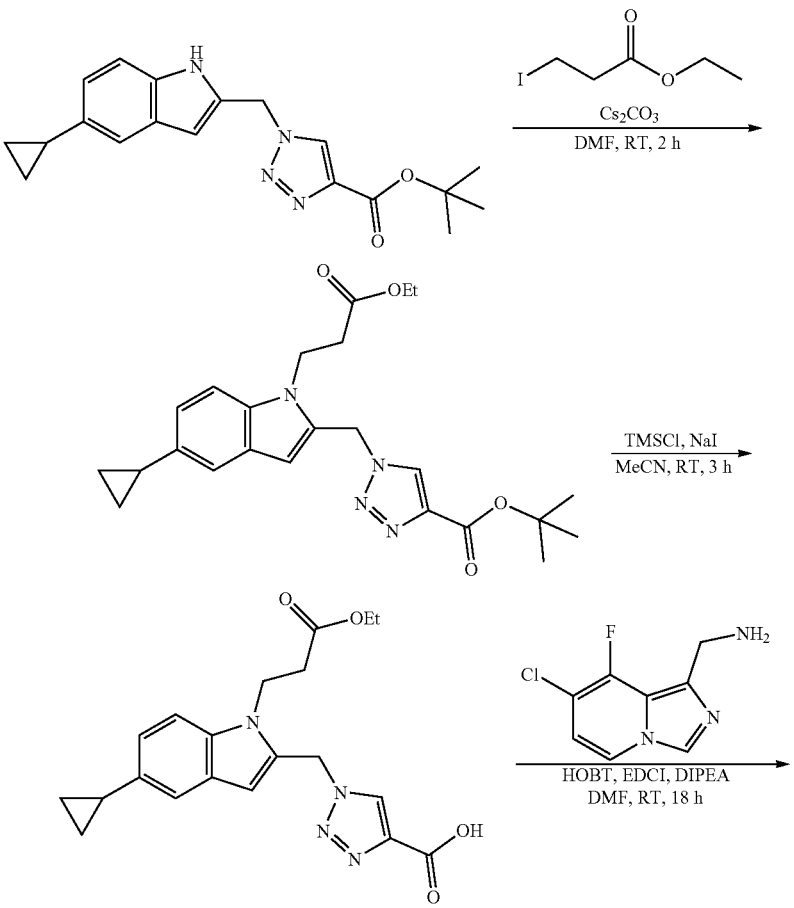

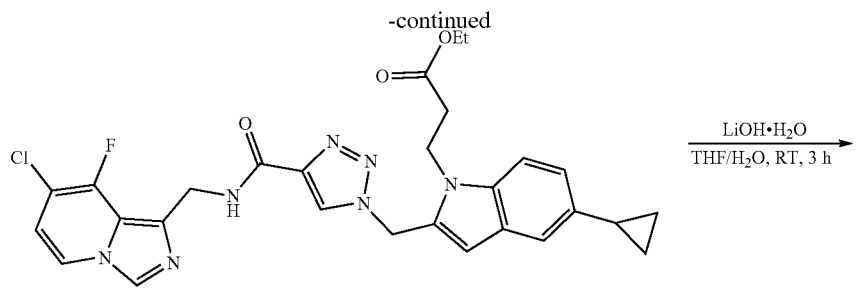

I-251a

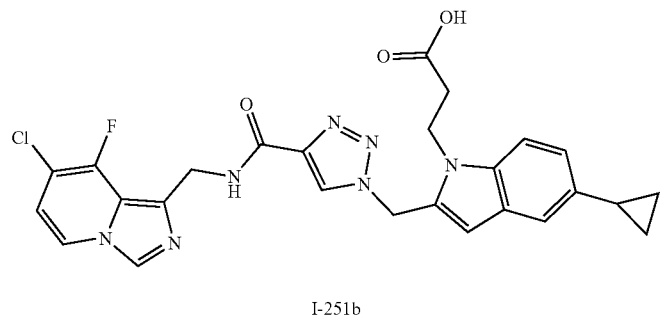

I-251b

Synthesis of tert-butyl 1-((5-cyclopropyl-1-(3-ethoxy-3-oxopropyl)-1H-indol-2-yl)methyl)-1H-1,2,3-triazole-4-carboxylate The mixture of tert-butyl 1-((5-cyclopropyl-1H-indol-2-yl)methyl)-1H-1,2,3-triazole-4-carboxylate (500 mg, 1.48 mmol), ethyl 3-iodopropanoate (508 mg, 2.23 mmol) and $Cs_2CO_3$ (1.45 mg, 4.44 mmol) in DMF (10 mL) was stirred at RT for 3 h. The reaction mixture was diluted with $H_2O$ (100 mL) and extracted with EtOAc (30 mL×3). The combined organic layers were washed with saturated brine and concentrated. The residue was purified by flash column chromatography to afforded tert-butyl 1-((5-cyclopropyl-1-(3-ethoxy-3-oxopropyl)-1H-indol-2-yl)methyl)-1H-1,2,3-triazole-4-carboxylate (550 mg, yield: 85%) as a yellow oil. ESI-MS $[M+H]^+$: 439.1

Synthesis of 1-((5-cyclopropyl-1-(3-ethoxy-3-oxopropyl)-1H-indol-2-yl)methyl)-1H-1,2,3-triazole-4-carboxylic Acid To the mixture of tert-butyl 1-((5-cyclopropyl-1-(3-ethoxy-3-oxopropyl)-1H-indol-2-yl)methyl)-1H-1,2,3-triazole-4-carboxylate (500 mg, 1.14 mmol) and NaI (342 mg, 2.28 mmol) in MeCN (50 mL) was added TMSCl (370 mg, 3.38 mmol) at RT and it was stirred at RT for 3 h. The reaction was evaporated to remove the solvent to afford 1-((5-cyclopropyl-1-(3-ethoxy-3-oxopropyl)-1H-indol-2-yl)methyl)-1H-1,2,3-triazole-4-carboxylic acid (800 mg, crude) as a light red oil which was used in next step directly. ESI-MS $[M+H]^+$: 383.2

Synthesis of Ethyl 3-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)propanoate The mixture of 1-((5-cyclopropyl-1-(2-methoxy-2-oxoethyl)-1H-indol-2-yl)methyl)-1H-1,2,3-triazole-4-carboxylic acid (800 mg, 1.14 mmol, crude), (7-chloro-8-fluoroimidazo[1,5-a]pyridin-1-yl)methanamine hydrochloride (404 mg, 1.71 mmol), HOBT (231 mg, 1.71 mmol), EDCI (327 mg, 1.71 mmol) and DIPEA (441 mg, 3.42 mmol) in DMF (5 mL) was stirred at to RT for 3 h. The reaction mixture was diluted with $H_2O$ (80 mL) and extracted with EtOAc (30 mL×3). The combined organic layers were washed with saturated salt $H_2O$ and concentrated. The residue was purified by prep-HPLC to afford ethyl 3-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)propanoate (110 mg, yield: 18%) as a white solid. ESI-MS $[M+H]^+$: 564.2. Purity: 99.21% (214 nm), 98.16% (254 nm). $^1H$ NMR (400 MHz, DMSO-$d_6$) δ 8.72 (t, J=5.4 Hz, 1H), 8.54 (s, 1H), 8.44 (d, J=2.4 Hz, 1H), 8.20 (d, J=7.4 Hz, 1H), 7.34 (d, J=8.5 Hz, 1H), 7.23 (d, J=1.3 Hz, 1H), 6.94-6.87 (m, 1H), 6.80-6.70 (m, 1H), 6.39 (s, 1H), 5.93 (s, 2H), 4.69 (d, J=5.5 Hz, 2H), 4.43 (t, J=7.1 Hz, 2H), 4.00 (q, J=7.1 Hz, 2H), 2.58 (t, J=7.1 Hz, 2H), 2.00-1.90 (m, 1H), 1.10 (t, J=7.1 Hz, 3H), 0.94-0.84 (m, 2H), 0.66-0.57 (m, 2H).

Synthesis of 3-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)propanoic acid (I-251)

The mixture of methyl 2-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)acetate (80 mg, 0.142 mmol) and $LiOH·H_2O$ (30 mg, 0.710 mmol) in THF/$H_2O$ (5 mL/2 mL) was stirred at RT for 3 h. The reaction mixture was adjusted to pH-3. The mixture was filtered and the solid was washed with $H_2O$ (5 mL×3). Then the solid was freeze-drying to give 3-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)propanoic acid (50 mg, yield: 65.8%) as a white solid. ESI-MS $[M+H]^+$: 536.2. Purity: 98.73% (214 nm), 96.40% (254 nm). $^1H$ NMR (400 MHz, DMSO-$d_6$) δ 12.41 (s, 1H), 8.72 (t, J=5.4 Hz, 1H), 8.53 (s, 1H), 8.45 (d, J=2.3 Hz, 1H), 8.20 (d, J=7.4 Hz, 1H), 7.34 (d, J=8.5 Hz, 1H), 7.23 (d, J=1.1 Hz, 1H), 6.94-6.87 (m, 1H), 6.80-6.72 (m, 1H), 6.36 (s, 1H), 5.94 (s, 2H), 4.69 (d, J=5.4 Hz, 2H), 4.40 (t, J=7.1 Hz, 2H), 2.54 (t, J=7.1 Hz, 2H), 1.99-1.91 (m, 1H), 0.94-0.83 (m, 2H), 0.67-0.56 (m, 2H).

Example 252

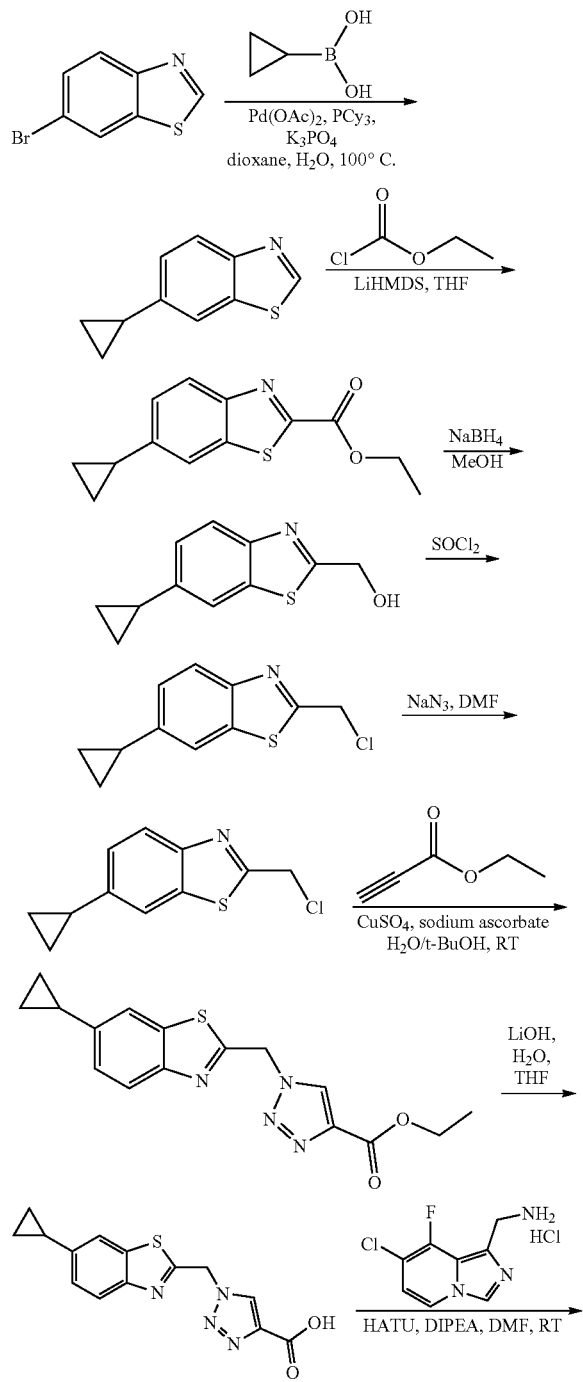

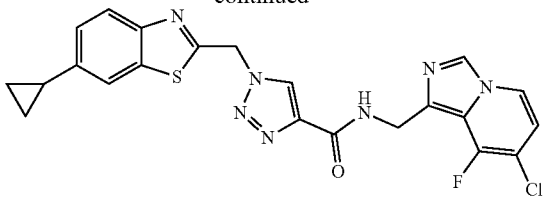

I-252

Synthesis of 6-cyclopropylbenzo[d]thiazole

To a solution of 6-bromobenzo[d]thiazole (1 g, 4.67 mmol) in dioxane/$H_2O$ (60 mL/6 mL) was added cyclopropylboronic acid (803 mg, 9.34 mmol), $Pd(OAc)_2$ (105 mg, 0.467 mmol), $PCy_3$ (262 mg, 0.934 mmol) and $K_3PO_4$ (2.974 g, 14 mmol). The reaction mixture was stirred at 100° C. for 14 h under nitrogen. Then the mixture was concentrated in vacuo. Water (40 mL) was added and the mixture was extracted with EtOAc (60 mL×3). The combined organic layers were concentrated to give the crude product, which was purified by silica gel chromatography (PE/EtOAc=20/1) to give the 6-cyclopropylbenzo[d]thiazole as a yellow solid (769 mg, yield: 94%). ESI-MS [M+H]$^+$: 176.1.

Synthesis of Ethyl 6-cyclopropylbenzo[d]thiazole-2-carboxylate

To a solution 6-cyclopropylbenzo[d]thiazole (689 mg, 3.93 mmol) in dry THF (30 mL) at −78° C. was added LiHMDS (921 mg, 5.5 mmol) dropwise and the mixture was stirred for 30 min at −78° C. And the ethyl carbonochloridate (640 mg, 5.9 mmol) was added dropwise over a period of 5 min. The resulting mixture was stirred at −78° C. for additional 30 min. Then the reaction was quenched with $H_2O$ (30 mL), THF was concentrated in vacuo and extracted with EtOAc (50 mL×3). The combined organic layers were dried over $Na_2SO_4$, and concentrated to give the crude product, which was purified by silica gel chromatography (PE/EtOAc=20/1) to give ethyl 6-cyclopropylbenzo[d]thiazole-2-carboxylate (236 mg, yield: 24%) as a yellow oil. ESI-MS [M+H]$^+$: 247.9.

Synthesis of (6-cyclopropylbenzo[d]thiazol-2-yl)methanol

To a solution ethyl 6-cyclopropylbenzo[d]thiazole-2-carboxylate (186 mg, 0.75 mmol) in MeOH (6 mL) was added $NaBH_4$ (57 mg, 1.5 mmol). The mixture was stirred for 2 h at RT. Then the reaction was quenched with $H_2O$ (20 mL), concentrated in vacuo and extracted with EtOAc (30 mL×3). The combined organic layers were dried over $Na_2SO_4$, and concentrated to give the crude product, which was purified by silica gel chromatography (PE/EtOAc=2/1) to give ethyl (6-cyclopropylbenzo[d]thiazol-2-yl)methanol (107 mg, yield: 69%) as a yellow oil. ESI-MS [M+H]$^+$: 206.0.

Synthesis of 2-(chloromethyl)-6-cyclopropylbenzo[d]thiazole

To a solution of ethyl (6-cyclopropylbenzo[d]thiazol-2-yl)methanol (107 mg, 0.52 mmol) in $SOCl_2$ (10 mL). The reaction mixture was stirred at RT for 2 h. Then the mixture was concentrated in vacuo to give 2-(azidomethyl)-6-cyclopropylbenzo[d]thiazole (116 mg, crude) as a yellow oil. ESI-MS [M+H]⁺: 223.9.

Synthesis of 2-(azidomethyl)-6-cyclopropylbenzo[d]thiazole

To a solution of ethyl 2-(chloromethyl)-6-cyclopropylbenzo[d]thiazole (116 mg, crude from last step) and NaN₃ (34 mg, 0.52 mmol) in DMF (5 mL). The reaction mixture was stirred at RT for 5 h. Water (50 mL) was added and extracted with EtOAc (50 mL×3). The combined organic layers were washed with brine, dried over Na₂SO₄, filtered and concentrated to give 2-(azidomethyl)-6-cyclopropylbenzo[d]thiazole (105 mg, crude) as a yellow solid. This material was used directly in the next step without further purification. ESI-MS [M+H]⁺: 231.0.

Synthesis of Ethyl 1-((6-cyclopropylbenzo[d]thiazol-2-yl)methyl)-1H-1,2,3-triazole-4-carboxylate To a solution 2-(azidomethyl)-6-cyclopropylbenzo[d]thiazole (105 mg, crude), ethyl propiolate (89 mg, 0.91 mmol), CuSO₄ (23 mg, 0.091 mmol) and sodium ascorbate (27 mg, 0.136 mmol) in t-BuOH (3 mL) and H₂O (3 mL). The mixture was stirred for 2 h at RT. Then the reaction was concentrated in vacuo. Water (20 mL) was added to the residue, and extracted with EtOAc (20 mL×3). The combined organic layers were dried over Na₂SO₄, and concentrated to give the crude product, which was purified by silica gel chromatography (DCM/MeOH=30/1) to give ethyl 1-((6-cyclopropylbenzo[d]thiazol-2-yl)methyl)-1H-1,2,3-triazole-4-carboxylate (130 mg, yield: 76% over 3 steps) as a yellow solid. ESI-MS [M+H]⁺: 329.0.

Synthesis of 1-((6-cyclopropylbenzo[d]thiazol-2-yl)methyl)-1H-1,2,3-triazole-4-carboxylic Acid A solution of ethyl 1-((6-cyclopropylbenzo[d]thiazol-2-yl)methyl)-1H-1,2,3-triazole-4-carboxylate (87 mg, 0.26 mmol) and LiOH.H₂O (22 mg, 0.52 mmol) in a mixed solvent of THF/H₂O (3 mL/3 mL) was stirred at RT overnight. Then the reaction was concentrated to give the residue. The pH of the residue was adjusted to 5 by HCl (2N) and then concentrated in vacuo to give 1-((6-cyclopropylbenzo[d]thiazol-2-yl)methyl)-1H-1,2,3-triazole-4-carboxylic acid (100 mg, crude) as a yellow solid. This material was used directly in the next step without further purification. ESI-MS [M+H]⁺: 300.8.

Synthesis of N-((7-chloro-8-fluoroimidazo[1,5-a]pyridin-1-yl)methyl)-1-((6-cyclopropylbenzo[d]thiazol-2-yl)methyl)-1H-1,2,3-triazole-4-carboxamide (I-252)

A mixture of 1-((6-cyclopropylbenzo[d]thiazol-2-yl)methyl)-1H-1,2,3-triazole-4-carboxylic acid (100 mg, crude), (7-chloro-8-fluoroimidazo[1,5-a]pyridin-1-yl)methanamine hydrochloride (71 mg, 0.30 mmol), HATU (98 mg, 0.51 mmol) and DIPEA (164 mg, 1.27 mmol) in DMF (5 mL). The resulting mixture was stirred for 3 h at RT. The mixture was concentrated to remove DMF to give the crude product, which was purified by prep-HPLC to give N-((7-chloro-8-fluoroimidazo[1,5-a]pyridin-1-yl)methyl)-1-((6-cyclopropylbenzo[d]thiazol-2-yl)methyl)-1H-1,2,3-triazole-4-carboxamide (17 mg, yield: 14%) as a light yellow solid. ESI-MS [M+H]⁺: 482.0. Purity: 100% (214 nm) 97.96% (254 nm). ¹H NMR (400 MHz, DMSO-d₆) δ 8.81 (t, J=4.0 Hz, 1H), 8.74 (s, 1H), 8.45 (s, 1H), 8.21 (d, J=7.4 Hz, 1H), 7.85 (d, J=8.5 Hz, 1H), 7.79 (s, 1H), 7.24 (d, J=8.4 Hz, 1H), 6.76 ((t, J=4.2 Hz, 1H), 6.18 (s, 2H), 4.71 (d, J=5.2 Hz, 2H), 2.01-1.98 (m, 1H), 1.01-0.97 (m, 2H), 0.75-0.72 (m, 2H).

Example 253

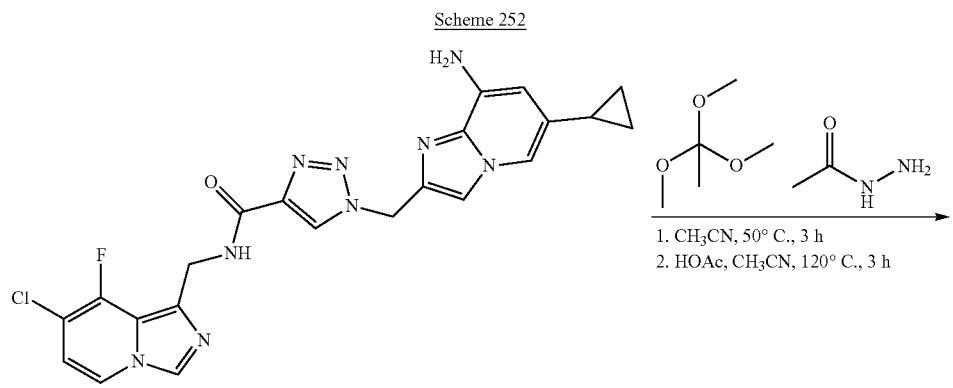

Scheme 252

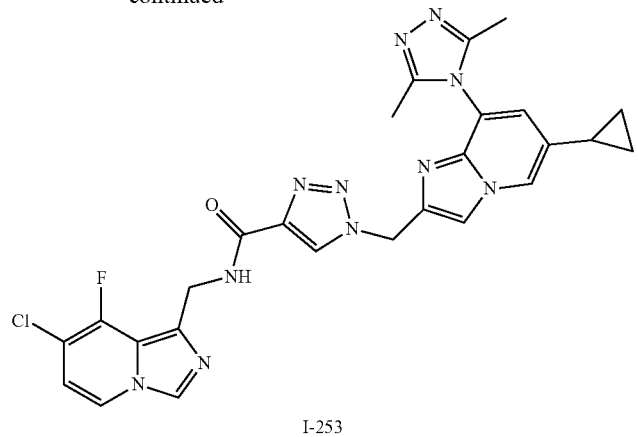

I-253

Synthesis of N-((7-chloro-8-fluoroimidazo[1,5-a]pyridin-1-yl)methyl)-1-((6-cyclopropyl-8-(3,5-dimethyl-4H-1,2,4-triazol-4-yl)imidazo[1,2-a]pyridin-2-yl)methyl)-1H-1,2,3-triazole-4-carboxamide (I-253)

To a mixture of 1-((8-amino-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide (100 mg, 0.2 mmol) in CH$_3$CN (2 mL) was added 1,1,1-trimethoxyethane (124 mg, 1.0 mmol), mixture was stirred at 80° C. for 1 h. And then acetohydrazide (81 mg, 1.1 mmol) and AcOH (72 mg, 1.2 mmol) was added to the reaction above. The resulting reaction mixture was stirred at 80° C. for another 16 h. The reaction mixture was added saturated aqueous NaHCO$_3$, extracted by EtOAc (50 mL×3). The combined organic layers were washed by brine, dried over Na$_2$SO$_4$, filtered, concentrated to give the crude, which was purified by Prep-HPLC to obtain N-((7-chloro-8-fluoroimidazo[1,5-a]pyridin-1-yl)methyl)-1-((6-cyclopropyl-8-(3,5-dimethyl-4H-1,2,4-triazol-4-yl)imidazo[1,2-a]pyridin-2-yl)methyl)-1H-1,2,3-triazole-4-carboxamide (24 mg, yield: 21%) as a white solid. ESI-MS [M+H]$^+$: 560.1. Purity: 99.08% (214 nm), 99.27% (254 nm). $^1$H NMR (400 MHz, DMSO-d$_6$) δ 8.70 (t, J=6.0 Hz, 1H), 8.55-8.54 (m, 2H), 8.45 (d, J=4 Hz, 1H), 8.21 (d, J=8.0 Hz, 1H), 7.95 (s, 1H), 7.33 (d, J=4.0 Hz, 1H), 6.76 (t, J=6.0 Hz, 1H) 5.73 (s, 2H), 4.70 (d, J=4.0 Hz, 2H), 2.11 (s, 6H), 2.03-1.96 (m, 1H), 0.99-0.95 (m, 2H), 0.78-0.74 (m, 2H).

Example 254

Scheme 253

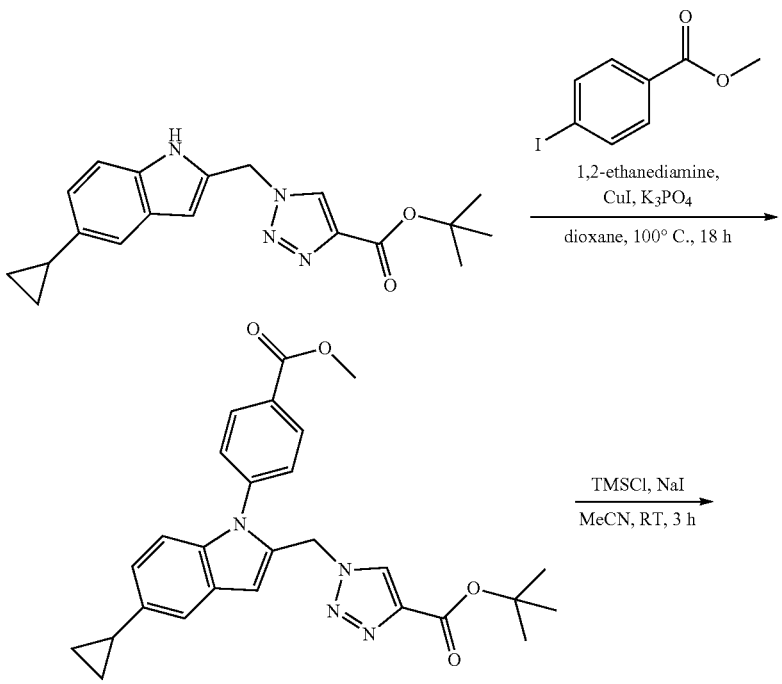

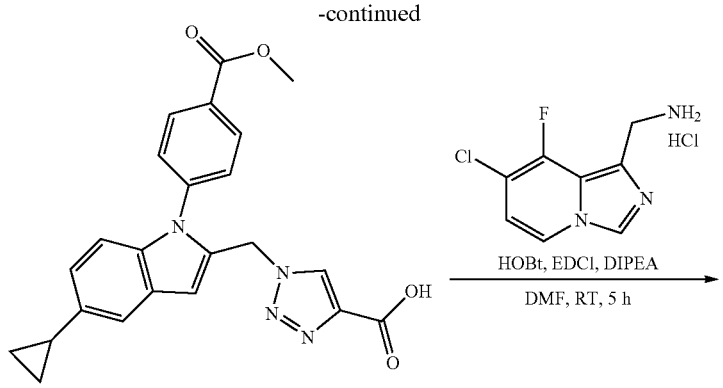

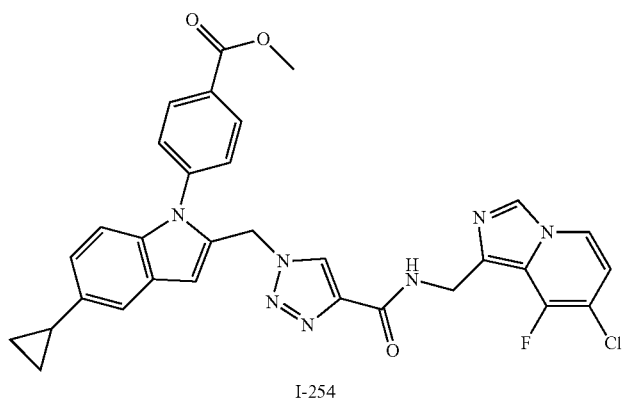

I-254

Synthesis of tert-butyl 1-((5-cyclopropyl-1-(4-(methoxycarbonyl)phenyl)-1H-indol-2-yl)methyl)-1H-1,2,3-triazole-4-carboxylate A mixture of tert-butyl 1-((5-cyclopropyl-1H-indol-2-yl)methyl)-1H-1,2,3-triazole-4-carboxylate (600 mg, 1.78 mmol), methyl 4-iodobenzoate (1.86 g, 7.10 mmol), 1,2-ethanediamine (32 mg, 0.36 mmol), CuI (69 g, 0.36 mmol) and $K_3PO_4$ (755 mg, 3.56 mmol) in dioxane (10 mL) was degassed with $N_2$ and stirred at 100° C. for 18 h. The reaction mixture was cooled to RT and diluted with $H_2O$ (50 mL) and extracted with EtOAc (50 mL×3). The combined organic layers were washed with saturated salt $H_2O$ and concentrated. The residue was purified by flash column chromatography to afforded tert-butyl 1-((5-cyclopropyl-1-(4-(methoxycarbonyl)phenyl)-1H-indol-2-yl)methyl)-1H-1,2,3-triazole-4-carboxylate (430 mg yield: 51%) as a yellow solid. ESI-MS $[M+H]^+$: 473.1

Synthesis of 1-((5-cyclopropyl-1-(4-(methoxycarbonyl)phenyl)-1H-indol-2-yl)methyl)-1H-1,2,3-triazole-4-carboxylic Acid To a mixture of tert-butyl 1-((5-cyclopropyl-1-(4-(methoxycarbonyl)phenyl)-1H-indol-2-yl)methyl)-1H-1,2,3-triazole-4-carboxylate (310 mg, 0.66 mmol) and NaI (197 mg, 1.31 mmol) in MeCN (10 mL) was added TMSCl (213 mg, 1.97 mmol) at RT and it was stirred at RT for 3 h. Evaporated to remove the solvent to afforded 1-((5-cyclopropyl-1-(4-(methoxycarbonyl)phenyl)-1H-indol-2-yl)methyl)-1H-1,2,3-triazole-4-carboxylic acid (600 mg, crude) as a yellow-red oil which was used into next step directly. ESI-MS $[M+H]^+$: 417.2

Synthesis of Methyl 4-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)benzoate (I-254)

The mixture of 1-((5-cyclopropyl-1-(2-methoxy-2-oxoethyl)-1H-indol-2-yl)methyl)-1H-1,2,3-triazole-4-carboxylic acid (60 mg, crude from last step), (7-chloro-8-fluoroimidazo[1,5-a]pyridin-1-yl)methanamine hydrochloride (23.3 mg, 0.1 mmol), HOBT (134 mg, 0.1 mmol), EDCI (190 mg, 0.1 mmol) and DIPEA (25.4 mg, 0.2 mmol) in DMF (4 mL) was stirred at to RT for 3 h. The reaction mixture was diluted with $H_2O$ (30 mL) and extracted with EtOAc (30 mL×3). The combined organic layer was washed with brine and concentrated. The residue was purified by prep-HPLC to afforded methyl 4-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)benzoate (11 mg, yield: 28%) as white solid. ESI-MS $[M+H]^+$: 598.2. Purity: 98.49% (214 nm), 96.69% (254 nm). $^1$H NMR (400 MHz, DMSO-$d_6$) δ 8.64 (t, J=5.4 Hz, 1H), 8.44 (d, J=2.4 Hz, 1H), 8.26 (s, 1H), 8.20 (d, J=7.4 Hz, 1H), 8.09 (d, J=8.5 Hz, 2H), 7.52 (d, J=8.5 Hz, 2H), 7.35 (s, 1H), 7.00 (d, J=8.5 Hz, 1H), 6.95-6.88 (m, 1H), 6.80-6.72 (m, 1H), 6.64 (s, 1H), 5.80 (s, 2H), 4.66 (d, J=5.4 Hz, 2H), 3.90 (s, 3H), 2.04-1.93 (m, 1H), 0.97-0.86 (m, 2H), 0.68-0.58 (m, 2H).

Example 255

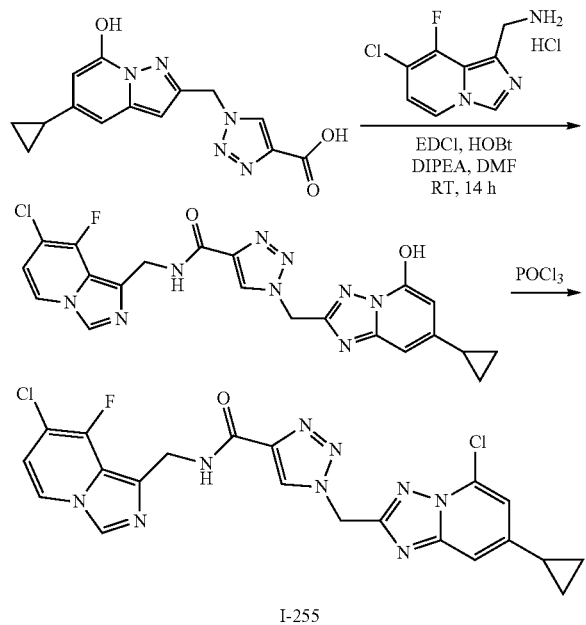

I-255

Synthesis of N-((7-chloro-8-fluoroimidazo[1,5-a]pyridin-1-yl)methyl)-1-((7-cyclopropyl-5-hydroxy-[1,2,4]triazolo[1,5-a]pyridin-2-yl)methyl)-1H-1,2,3-triazole-4-carboxamide To a solution of 1-((6-cyclopropylbenzofuran-2-yl)methyl)-1H-1,2,3-triazole-4-carboxylic acid (100 mg, 0.33 mmol), (7-chloro-8-fluoroimidazo[1,5-a]pyridin-1-yl)methanamine hydrochloride (85 mg, 0.36 mmol), EDCI (75 mg, 0.4 mmol) and HOBT (54 mg, 0.4 mmol) in DMF (5 mL) was added DIPEA (129 mg, 1 mmol). The resulting mixture was stirred at RT for 15 h. The reaction mixture was concentrated to give a residue. The residue was purified by flash column chromatography (DCM/MeOH=10/1) to give N-((7-chloro-8-fluoroimidazo[1,5-a]pyridin-1-yl)methyl)-1-((7-cyclopropyl-5-hydroxy-[1,2,4]triazolo[1,5-a]pyridin-2-yl)methyl)-1H-1,2,3-triazole-4-carboxamide (60 mg, 37.5%) as a pale-yellow solid. ESI-MS [M+H]$^+$: 482.0.

Synthesis of 1-((5-chloro-7-cyclopropyl-[1,2,4]triazolo[1,5-a]pyridin-2-yl)methyl)-N-((7-chloro-8-fluoroimidazo[1,5-a]pyridin-1-yl)methyl)-1H-1,2,3-triazole-4-carboxamide (I-255)

A solution of N-((7-chloro-8-fluoroimidazo[1,5-a]pyridin-1-yl)methyl)-1-((7-cyclopropyl-5-hydroxy-[1,2,4]triazolo[1,5-a]pyridin-2-yl)methyl)-1H-1,2,3-triazole-4-carboxamide (40 mg, 0.08 mmol) in POCl$_3$ (10 mL) was stirred at 80° C. overnight. The mixture was concentrated under vacuum. The residue was poured into NaHCO$_3$ (10 mL) and extracted with EtOAc (30 mL×2). The combined organic layers were washed with brine, dried over Na$_2$SO$_4$, and concentrated to give the crude product. The residue was purified by flash column chromatography (DCM/MeOH=10/1) to give 1-((5-chloro-7-cyclopropyl-[1,2,4]triazolo[1,5-a]pyridin-2-yl)methyl)-N-((7-chloro-8-fluoroimidazo[1,5-a]pyridin-1-yl)methyl)-1H-1,2,3-triazole-4-carboxamide (12 mg, 29%) as a pale-yellow solid. ESI-MS [M+H]$^+$: 499.6. Purity: 97.34% (214 nm), 97.80% (254 nm). $^1$H NMR (400 MHz, CDCl3) δ 8.23 (s, 1H), 8.17 (s, 1H), 7.77-7.68 (m, 2H), 6.89 (s, 1H), 6.55 (s, 1H), 6.46 (s, 1H), 5.80 (s, 2H), 4.97 (d, J=4.2 Hz, 2H), 2.07-1.98 (m, 1H), 1.19-1.09 (m, 4H).

Example 256

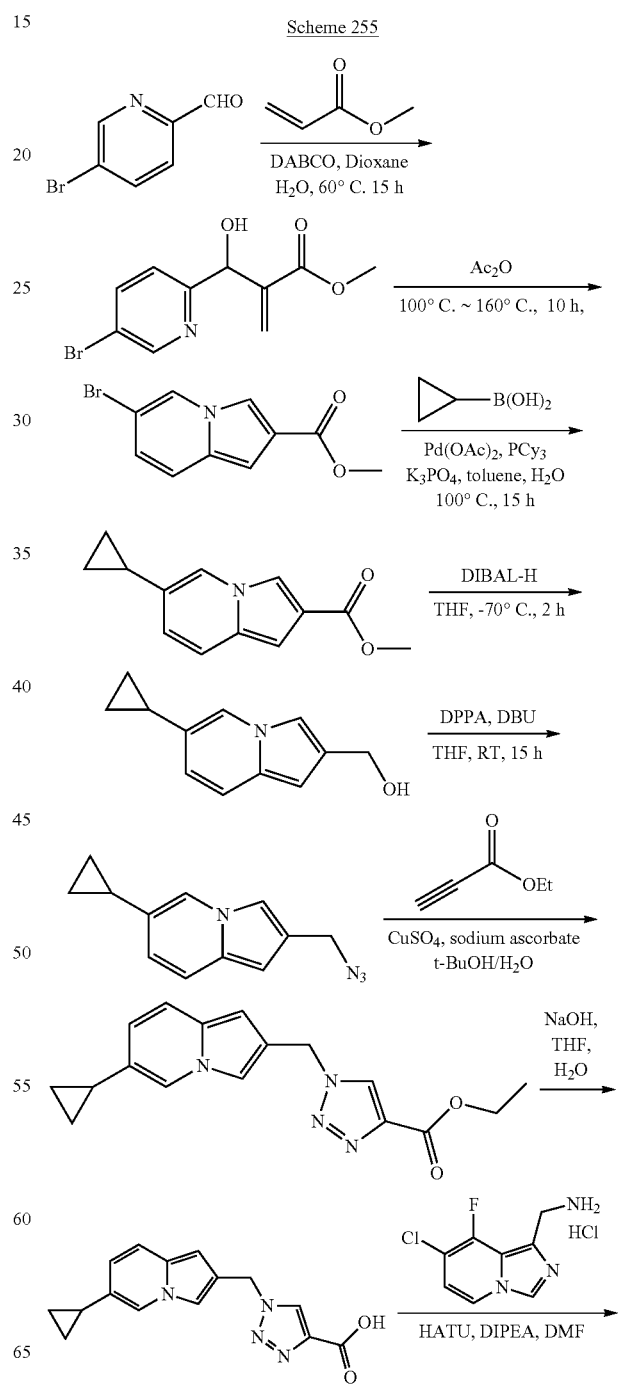

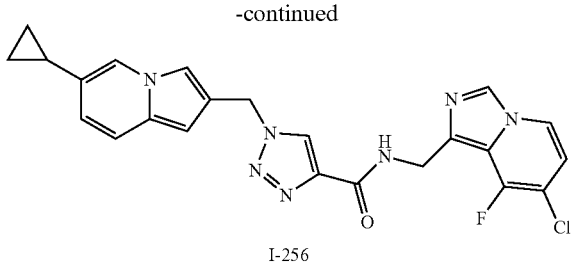

I-256

Synthesis of Methyl 2-((5-bromopyridin-2-yl)(hydroxy)methyl)acrylate

To a solution of 5-bromopicolinaldehyde (1.5 g, 8.06 mmol) and DABCO (91 mg, 0.81 mmol) in 1,4-dioxane (15 mL) and H$_2$O (5 mL) was added methyl acrylate (2.08 g, 24.2 mmol). The resulting mixture was stirred in a sealed tube at 60° C. overnight. The reaction mixture was concentrated to get a residue. The residue was purified by flash column chromatography (0-18% EtOAc in Petroleum ether) to get the product methyl 2-((5-bromopyridin-2-yl)(hydroxy)methyl)acrylate (1.8 g, 82%) as a yellow oil. ESI-MS [M+H]$^+$: 271.7, $^1$H NMR (400 MHz, CDCl$_3$) δ 8.61 (s, 1H), 7.84 (dd, J=8.4, 1.9 Hz, 1H), 7.40 (d, J=8.4 Hz, 1H), 6.38 (s, 1H), 6.00 (s, 1H), 5.59 (s, 1H), 3.74 (s, 3H).

Synthesis of Methyl 6-bromoindolizine-2-carboxylate

A solution of methyl 2-((5-bromopyridin-2-yl)(hydroxy)methyl)acrylate (1.8 g, 6.6 mmol) in Ac$_2$O (10 mL) was stirred at 100° C. for 5 h. LCMS showed raw material conversion to an intermediate product. The reaction mixture was then stirred at 160° C. for 5 h. The mixture was concentrated to get a residue. The residue was purified by flash column chromatography (0-5% EtOAc in Petroleum ether) to get the product methyl 6-bromoindolizine-2-carboxylate (1.15 g, 68%) as a light yellow solid. ESI-MS [M+H]$^+$: 253.7. $^1$H NMR (400 MHz, CDCl$_3$) δ 8.02 (s, 1H), 7.75 (s, 1H), 7.27 (d, J=7.5 Hz, 2H), 6.86 (s, 1H), 6.75 (d, J=9.5 Hz, 1H), 3.88 (s, 3H).

Synthesis of Methyl 6-cyclopropylindolizine-2-carboxylate

A mixture of methyl 6-bromoindolizine-2-carboxylate (0.88 g, 3.46 mmol), cyclopropylboronic acid (740 mg, 8.66 mmol), Pd(OAc)$_2$ (79 mg, 0.35 mmol), PCy$_3$ (196 mg, 0.7 mmol) and K$_3$PO$_4$ (1.84 g, 8.66 mmol) in toluene (30 mL)/H$_2$O (3 mL) was stirred under reflux under nitrogen atmosphere overnight. The reaction mixture was concentrated to get a residue. The residue was partitioned between EtOAc (30 mL) and H$_2$O (30 mL). The layers were separated and the aqueous phase was extracted with EtOAc (2×30 mL). The combined organic layers were washed with brine (20 mL), dried over Na$_2$SO$_4$, filtered and concentrated to get the crude product. The crude product was purified by flash column chromatography (0-5% EtOAc in Petroleum ether) to get the product methyl 6-cyclopropylindolizine-2-carboxylate (660 mg, 88%) as a light yellow solid. ESI-MS [M+H]$^+$: 216.0. $^1$H NMR (400 MHz, CDCl$_3$) δ 7.71 (s, 1H), 7.65 (s, 1H), 7.25 (d, J=6.0 Hz, 2H), 6.75 (s, 1H), 6.44 (d, J=9.4 Hz, 1H), 3.87 (s, 3H), 1.84-1.74 (m, 1H), 0.95-0.84 (m, 2H), 0.64 (t, J=5.1 Hz, 2H).

Synthesis of (6-cyclopropylindolizin-2-yl)methanol

To a solution of methyl 6-cyclopropylindolizine-2-carboxylate (660 mg, 3.1 mmol) in dry THF (25 mL) stirring at −70° C. under nitrogen atmosphere was added DIBAL-H (9.2 mL, 9.2 mmol) dropwise. The resulting mixture was stirred at −70° C. for 2 h. The reaction mixture was quenched with saturated aqueous NH$_4$Cl solution (30 mL), extracted with EtOAc (3×30 mL). The combined organic phase was washed with brine (20 mL), dried over Na$_2$SO$_4$, filtered and concentrated to get the crude product. The crude product was purified by flash column chromatography (0-18% EtOAc in Petroleum ether) to get the product methyl 6-cyclopropylindolizine-2-carboxylate (345 mg, 60%) as an off-white solid. ESI-MS [M+H]$^+$: 187.9. $^1$H NMR (400 MHz, CDCl$_3$) δ 7.66 (s, 1H), 7.24-7.17 (m, 2H), 6.43 (d, J=9.3 Hz, 1H), 6.34 (s, 1H), 4.75 (s, 2H), 1.88-1.71 (m, 1H), 0.95-0.78 (m, 2H), 0.69-0.56 (d, J=5.0 Hz, 2H).

Synthesis of 2-(azidomethyl)-6-cyclopropylindolizine

To a solution of methyl 6-cyclopropylindolizine-2-carboxylate (125 mg, 0.67 mmol) and DPPA (239 mg, 0.87 mmol) in dry THF (8 mL) stirring at ice H$_2$O bath was added DBU (132 mg, 0.87 mmol). The resulting mixture was stirred at RT overnight. The reaction mixture was partitioned between EtOAc (50 mL) and H$_2$O (30 mL). The layers were separated and the aqueous phase was extracted with EtOAc (2×30 mL). The combined organic phase was washed with brine (15 mL), dried over Na$_2$SO$_4$, filtered and concentrated to get the crude product. The crude product was purified by column chromatography (Petroleum ether/EtOAc=100/1) to get the product 2-(azidomethyl)-6-cyclopropylindolizine (120 mg, 84.5%) as a light yellow oil. ESI-MS [M+H]$^+$: 212.9.

Synthesis of Ethyl 1-((6-cyclopropylindolizin-2-yl)methyl)-1H-1,2,3-triazole-4-carboxylate To a solution of 2-(azidomethyl)-6-cyclopropylindolizine (90 mg, 0.42 mmol) in t-BuOH (3 mL) and H$_2$O (3 mL) was added sequentially of CuSO$_4$-5H$_2$O (21 mg, 0.084 mmol), sodium ascorbate (25 mg, 0.126 mmol) and ethyl propiolate (54 mg, 0.55 mmol). The resulting mixture was stirred at RT for 15 h. The reaction mixture was partitioned between DCM (20 mL) and H$_2$O (20 mL). The layers were separated and the aqueous phase was extracted with DCM (2×30 mL). The combined organic phase was washed with brine (15 mL), dried over Na$_2$SO$_4$, filtered and concentrated to get the crude product. The crude product was purified by flash column chromatography (0-50% EtOAc in Petroleum ether) to get the product ethyl 1-((6-cyclopropylindolizin-2-yl)methyl)-1H-1,2,3-triazole-4-carboxylate (13 mg, 10%) as a light yellow solid. ESI-MS [M+H]$^+$: 311.2.

Synthesis of 1-((2-cyclopropylimidazo[1,2-a]pyridin-7-yl)methyl)-1H-1,2,3-triazole-4-carboxylic Acid To a solution of ethyl 1-((6-cyclopropylindolizin-2-yl)methyl)-1H-1,2,3-triazole-4-carboxylate (13 mg, 0.042 mmol) in THF (3 mL) was added a solution of NaOH (8 mg, 0.2 mmol) in H$_2$O (3 mL). The mixture was stirred at RT for 1 h. THF was removed in vacuo and the pH of aqueous phase was acidified to 4-5 with 2N HCl, lyophilized to give the product 1-((6-cyclopropylindolizin-2-yl)methyl)-1H-1,2,3-triazole-4-carboxylic acid (25 mg, crude) as a yellow solid. ESI-MS [M+H]+: 283.0.

Synthesis of N-((7-chloro-8-fluoroimidazo[1,5-a]pyridin-1-yl)methyl)-1-((6-cyclopropylindolizin-2-yl)methyl)-1H-1,2,3-triazole-4-carboxamide (I-256)

To a mixture of 1-((6-cyclopropylindolizin-2-yl)methyl)-1H-1,2,3-triazole-4-carboxylic acid (25 mg, crude from last step), EDCI (10 mg, 0.05 mmol), HOBT (7 mg, 0.05 mmol) and DIPEA (16 mg, 0.126 mmol) in DMF (2 mL) was added (7-chloro-8-fluoroimidazo[1,5-a]pyridin-1-yl)methanamine (10 mg, 0.042 mmol). The resulting mixture was stirred at RT for 15 h. The reaction mixture was concentrated to get a residue. The residue was purified by prep-HPLC to get N-((7-chloro-8-fluoroimidazo[1,5-a]pyridin-1-yl)methyl)-1-((6-cyclopropylindolizin-2-yl)methyl)-1H-1,2,3-triazole-4-carboxamide (5 mg, 25%) as an off-white solid. ESI-MS [M+H]+: 464.0. Purity: 98.76 (214 nm), 98.85 (254 nm). $^1$H NMR (400 MHz, CDCl3) δ 8.22 (s, 1H), 7.98 (s, 1H), 7.79-7.67 (m, 2H), 7.65 (s, 1H), 7.24-7.15 (m, 2H), 6.54 (t, J=6.6 Hz, 1H), 6.47 (d, J=9.3 Hz, 1H), 6.27 (s, 1H), 5.60 (s, 2H), 4.96 (d, J=5.2 Hz, 2H), 1.84-1.74 (m, 1H), 0.92-0.82 (m, 2H), 0.67-0.58 (m, 2H).

Example 257

Scheme 256

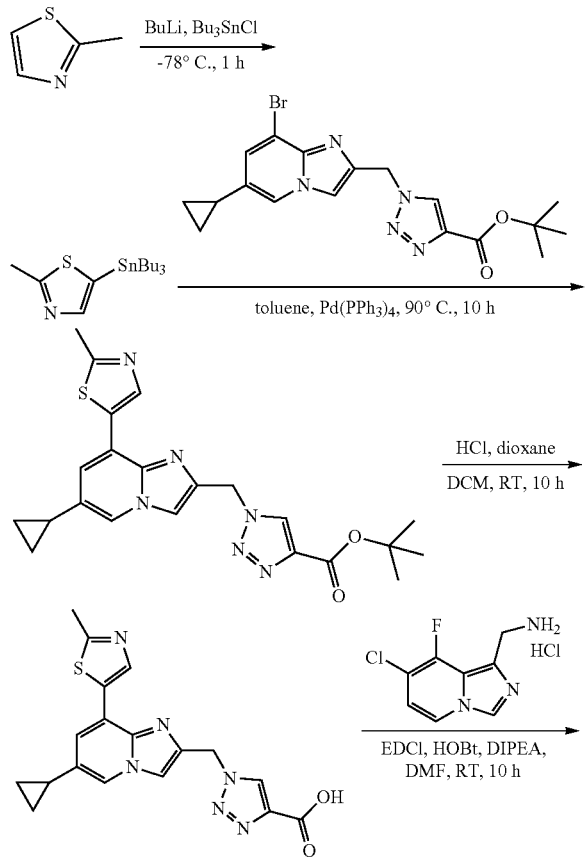

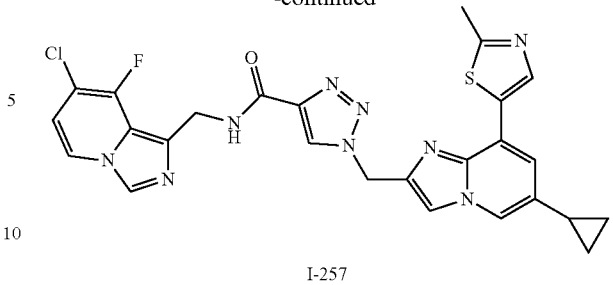

I-257

Synthesis of 2-methyl-5-(tributylstannyl)thiazole

To a solution of 2-methylthiazole (0.5 g, 5.1 mmol) in THF (15 mL) was added n-BuLi (2.4 M, 5 mL, 12 mmol) dropwise at −78° C. under N$_2$ atmosphere. The reaction mixture was stirred for 1 h at −78° C., then Chlorotributyltin (1.98 g, 6.1 mmol) was added thereto. Then the resulting reaction was stirred for additional 1 h. The reaction was quenched with H$_2$O (20 mL) and extracted with EtOAc (50 mL×2). The combined organic layers were washed with brine, dried over Na$_2$SO$_4$, concentrated to give the crude product, which was purified by silica gel chromatography (PE/EtOAc=10/1) to give the 2-methyl-5-(tributylstannyl)thiazole as a colorless oil (1.3 g, yield: 66%). $^1$H NMR (400 MHz, CDCl$_3$) δ 7.59 (d, J=6.4 Hz, 1H), 2.78 (s, 3H), 1.60-1.51 (m, 5H), 1.37-1.33 (m, 8H), 1.15-1.09 (m, 5H), 0.94-0.87 (m, 9H).

Synthesis of tert-butyl 1-((6-cyclopropyl-8-(2-methylthiazol-5-yl)imidazo[1,2-a]pyridin-2-yl)methyl)-1H-1,2,3-triazole-4-carboxylate To a solution of 2-methyl-5-(tributylstannyl)thiazole (360 mg, 0.93 mmol) in toluene (15 mL) was added tert-butyl 1-((8-bromo-6-cyclopropylimidazo[1,2-a]pyridin-2-yl)methyl)-1H-1,2,3-triazole-4-carboxylate (325 mg, 0.78 mmol) and Pd(PPh$_3$)$_4$ (30 mg, 0.025 mmol) at RT. The resulting mixture was stirred at 90° C. for 10 h under Ar atmosphere. The reaction was concentrated in vacuo to give the crude, which was purified by silica gel chromatography (DCM/MeOH=10/1) to give tert-butyl 1-((6-cyclopropyl-8-(2-methylthiazol-5-yl)imidazo[1,2-a]pyridin-2-yl)methyl)-1H-1,2,3-triazole-4-carboxylate (200 mg, yield: 50%) as a white solid. ESI-MS [M+H]+: 437.1.

Synthesis of 1-((6-cyclopropyl-8-(2-methylthiazol-5-yl)imidazo[1,2-a]pyridin-2-yl)methyl)-1H-1,2,3-triazole-4-carboxylic Acid To the solution of tert-butyl 1-((6-cyclopropyl-8-(2-methylthiazol-5-yl)imidazo[1,2-a]pyridin-2-yl) methyl)-1H-1,2,3-triazole-4-carboxylate (170 mg, 0.39 mmol) in DCM (10 mL) was added HCl (4 M solution in dioxane, 5 mL). The resulting reaction was stirred at RT for 10 h. The mixture was concentrated to get 1-((6-cyclopropyl-8-(2-methylthiazol-5-yl)imidazo [1,2-a]pyridin-2-yl)methyl)-1H-1,2,3-triazole-4-carboxylic acid (180 mg, crude) as a white solid, which was used into next step without further purification. ESI-MS [M+H]+: 381.0

Synthesis of N-((7-chloro-8-fluoroimidazo[1,5-a]pyridin-1-yl)methyl)-1-((6-cyclopropyl-8-(2-methylthiazol-5-yl)imidazo[1,2-a]pyridin-2-yl)methyl)-1H-1,2,3-triazole-4-carboxamide (I-257)

To a solution of 1-((6-cyclopropyl-8-(2-methylthiazol-5-yl)imidazo[1,2-a]pyridin-2-yl) methyl)-1H-1,2,3-triazole-4-carboxylic acid (180 mg crude) in 10 mL of DMF was added EDCI (61 mg, 0.32 mmol) HOBT (43 mg, 0.32 mmol), DIPEA (168 mg, 1.3 mmol) and (7-chloro-8-fluoroimidazo[1,5-a]pyridin-1-yl) methanamine hydrochloride (76 mg, 0.32 mmol). The reaction mixture was stirred at RT for 10 h. Water (30 mL) was added to the reaction and extracted with EtOAc (50 mL×3). The combined organic layers were washed with brine, dried over Na$_2$SO$_4$, concentrated to give the crude product, which was purified by silica gel chromatography (DCM/MeOH=10/1) to give N-((7-chloro-8-fluoroimidazo[1,5-a]pyridin-1-yl)methyl)-1-((6-cyclopropyl-8-(2-methylthiazol-5-yl)imidazo[1,2-a]pyridin-2-yl) methyl)-1H-1,2,3-triazole-4-carboxamide (102 mg, yield: 47%) as a white solid. ESI-MS [M+H]$^+$: 561.7. Purity: 95.50% (214 nm), 95.62% (254 nm). $^1$H NMR (400 MHz, DMSO-d$_6$) δ 8.72 (t, J=5.1 Hz, 1H), 8.63-8.59 (m, 2H), 8.44 (s, 1H), 8.35 (s, 1H), 8.20 (d, J=7.4 Hz, 1H), 7.89 (s, 1H), 7.46 (s, 1H), 6.76 (t, J=6.8 Hz, 1H), 5.81 (s, 2H), 4.70 (d, J=5.1 Hz, 2H), 2.69 (s, 3H), 2.02-1.95 (m, 1H), 0.99-0.92 (m, 2H), 0.79-0.75 (m, 2H).

Example 258

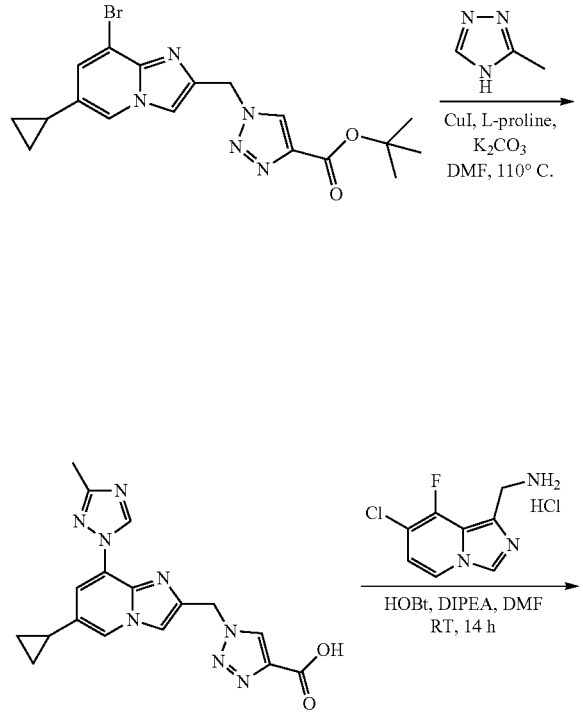

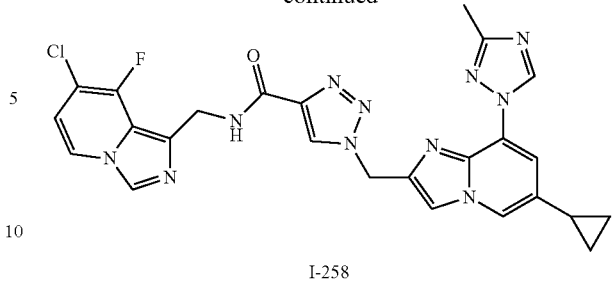

I-258

Synthesis of 1-((6-cyclopropyl-8-(3-methyl-1H-1,2,4-triazol-1-yl)imidazo[1,2-a]pyridin-2-yl)methyl)-1H-1,2,3-triazole-4-carboxylic Acid A mixture of tert-butyl 1-((8-bromo-6-cyclopropylimidazo[1,2-a]pyridin-2-yl)methyl)-1H-1,2,3-triazole-4-carboxylate (199 mg, 0.48 mmol), CuI (28.2 mg, 0.14 mmol), L-proline (34.6 mg, 0.29 mmol), K$_2$CO$_3$ (199 mg, 1.44 mmol) and 3-methyl-4H-1,2,4-triazole (121 mg, 1.44 mmol) in DMF (5 mL) was degassed by N$_2$ for 10 min and sealed tube. The resulting reaction mixture was heated to 110° C. for 60 h. The mixture was cooled to RT and concentrated to give the crude product, which was purified by prep-HPLC to obtain 1-((6-cyclopropyl-8-(3-methyl-1H-1,2,4-triazol-1-yl)imidazo[1,2-a]pyridin-2-yl)methyl)-1H-1,2,3-triazole-4-carboxylic acid as a white solid (16 mg, 9.2% yield). ESI-MS [M+H]$^+$: 364.8.

Synthesis of N-((7-chloro-8-fluoroimidazo[1,5-a]pyridin-1-yl)methyl)-1-((6-cyclopropyl-8-(3-methyl-1H-1,2,4-triazol-1-yl)imidazo[1,2-a]pyridin-2-yl)methyl)-1H-1,2,3-triazole-4-carboxamide (I-258)

A solution of 1-((6-cyclopropyl-8-(3-methyl-4H-1,2,4-triazol-4-yl)imidazo[1,2-a]pyridin-2-yl)methyl)-1H-1,2,3-triazole-4-carboxylic acid (12 mg, 0.033 mmol) in anhydrous DMF (3 mL) was added (7-chloro-8-fluoroimidazo[1,5-a]pyridin-1-yl)methanamine hydrochloride (7.7 mg, 0.033 mmol), DIPEA (8.5 mg, 0.066 mmol) and HATU (20 mg, 0.05 mmol) in sequence. The mixture was stirred at RT for 14 h. The reaction was diluted with H$_2$O (20 mL) and extracted with EtOAc (30 mL×3). The combined organic layers were washed with brine, dried over Na$_2$SO$_4$, concentrated to give the crude, which was purified by prep-HPLC to afford N-((7-chloro-8-fluoroimidazo[1,5-a]pyridin-1-yl)methyl)-1-((6-cyclopropyl-8-(3-methyl-1H-1,2,4-triazol-1-yl)imidazo[1,2-a]pyridin-2-yl)methyl)-1H-1,2,3-triazole-4-carboxamide as pale a yellow solid (6.2 mg, 34%). ESI-MS [M+H]$^+$: 546.1. Purity: 100.00 (214 nm) 97.96 (254 nm). $^1$H NMR (400 MHz, DMSO-d$_6$) δ 9.75 (s, 1H), 8.70 (t, J=5.1 Hz, 1H), 8.67 (s, 1H), 8.42 (d, J=10.7 Hz, 2H), 8.19 (d, J=7.3 Hz, 1H), 8.01 (s, 1H), 7.54 (s, 1H), 6.75 (t, J=6.9 Hz, 1H), 5.82 (s, 2H), 4.69 (d, J=5.4 Hz, 2H), 2.40 (s, 3H), 2.09-2.01 (m, 1H), 1.03-0.94 (m, 2H), 0.76-0.68 (m, 2H).

Example 259

Scheme 258

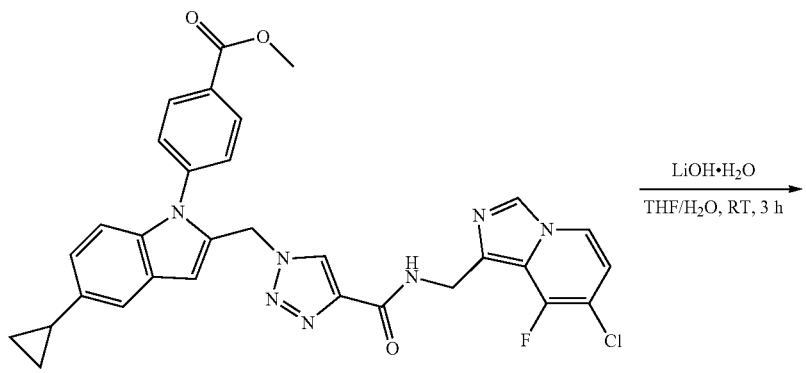

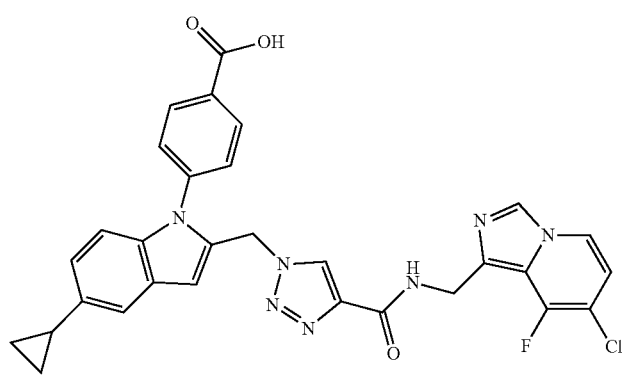

I-259

Synthesis of 4-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)benzoic Acid (I-259)

A mixture of methyl 2-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)acetate (80 mg, 0.13 mmol) and LiOH.H$_2$O (28 mg, 0.67 mmol) in THF/H$_2$O (5 mL/2 mL) was stirred at RT for 3 h. The pH of reaction mixture was adjusted to around 3 and white solid was precipitated. The mixture was filtered and the solid was washed with H$_2$O (5 mL×3). Then the solid was freeze-dried to give 2-(2-((4-(((7-chloro-8-fluoroimidazo[1,5-a]pyridin-1-yl)methyl)carbamoyl)-1H-1,2,3-triazol-1-yl)methyl)-5-cyclopropyl-1H-indol-1-yl)acetic acid (54 mg, yield: 70%) as a white solid. ESI-MS [M+H]$^+$: 584.1. Purity: 97.25% (214 nm), 96.00% (254 nm). $^1$H NMR (400 MHz, DMSO-d$_6$) δ 13.20 (s, 1H), 8.65 (t, J=5.4 Hz, 1H), 8.44 (d, J=2.2 Hz, 1H), 8.28 (s, 1H), 8.20 (d, J=7.4 Hz, 1H), 8.08 (d, J=8.4 Hz, 2H), 7.49 (d, J=8.4 Hz, 2H), 7.34 (s, 1H), 7.00 (d, J=8.5 Hz, 1H), 6.91 (d, J=8.6 Hz, 1H), 6.75 (t, J=6.9 Hz, 1H), 6.62 (s, 1H), 5.80 (s, 2H), 4.67 (d, J=5.4 Hz, 2H), 2.04-1.93 (m, 1H), 0.96-0.88 (m, 2H), 0.67-0.60 (m, 2H).

Example 260

Scheme 259

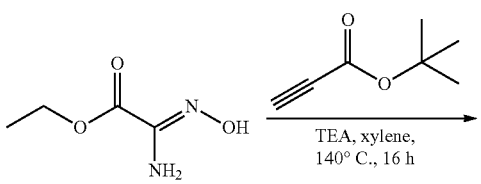

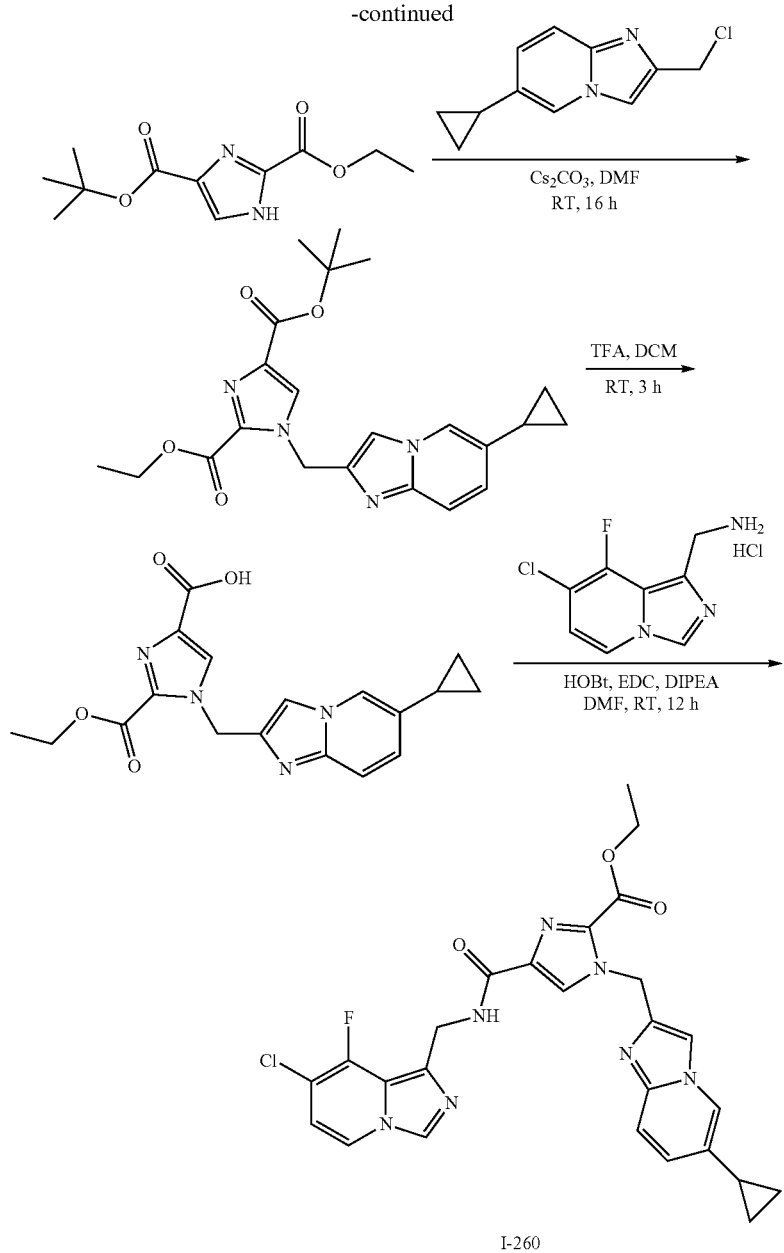

I-260

Synthesis of 4-(tert-butyl) 2-ethyl 1H-imidazole-2,4-dicarboxylate

To a mixture of ethyl (Z)-2-amino-2-(hydroxyimino)acetate (660 mg, 5 mmol) and tert-butyl propiolate (694 mg, 5.5 mmol) in Xylene (10 mL) was added TEA (606 mg, 6 mmol). The mixture was stirred at 140° C. for 16 h. After cooled to RT, H$_2$O (25 mL) was added and the mixture was extracted with EtOAc (35 mL×3). The combined organic layers were washed with brine and dried over Na$_2$SO$_4$, concentrated to give the crude, which was purified by silica gel chromatography (PE/EA=1/1) to give 4-(tert-butyl) 2-ethyl 1H-imidazole-2,4-dicarboxylate (400 mg, yield: 33%) as a yellow solid. ESI-MS [M+H]$^+$: 241.1.

Synthesis of 4-(tert-butyl) 2-ethyl 1-((6-cyclopropylimidazo[1,2-a]541yridine-2-yl)methyl)-1H-imidazole-2,4-dicarboxylate To a mixture of 4-(tert-butyl) 2-ethyl 1H-imidazole-2,4-dicarboxylate (240 mg, 1.0 mmol) and Cs$_2$CO$_3$ (1.0 g, 3.0 mmol) in DMF (10 mL) was added 2-(chloromethyl)-6-cyclopropylimidazo[1,2-a]pyridine (310 mg, 1.5 mmol). The reaction mixture was stirred at RT for 16 h. Water (40 mL) was added to the reaction, extracted with EtOAc (40 mL×3). The combined organic layers were washed with brine and dried over Na$_2$SO$_4$, concentrated to give the crude, which was purified by silica gel chromatography (DCM/MeOH=50/1 to 20/1) to give 4-(tert-butyl) 2-ethyl 1-((6-cyclopropylimidazo[1,2-a]pyridin-2-yl)methyl)-1H-imidazole-2,4-dicarboxylate (240 mg, yield: 59%) as a white solid. ESI-MS [M+H]$^+$: 411.2.

Synthesis of 1-((6-cyclopropylimidazo[1,2-a]pyridin-2-yl)methyl)-2-(ethoxycarbonyl)-1H-imidazole-4-carboxylic Acid To the solution of 4-(tert-butyl) 2-ethyl 1-((6-cyclopropylimidazo[1,2-a]pyridin-2-yl)methyl)-1H-imidazole-2,4-dicarboxylate (240 mg, 0.6 mmol) in DCM (10 mL) was added TFA (1 mL). The mixture was stirred at RT for 3 h. The reaction solution was concentrated to give 1-((6-cyclopropylimidazo[1,2-a]pyridin-2-yl)methyl)-2-(ethoxycarbonyl)-1H-imidazole-4-carboxylic acid (250 mg crude) as yellow oil, which was used into next step without further purification. ESI-MS [M+H]⁺: 355.1.

Synthesis of Ethyl 4-(((7-chloro-8-fluoroimidazo[1,5-a]pyridin-1-yl)methyl)carbamoyl)-1-((6-cyclopropylimidazo[1,2-a]pyridin-2-yl)methyl)-1H-imidazole-2-carboxylate (I-260)

To the mixture of 1-((6-cyclopropylimidazo[1,2-a]pyridin-2-yl)methyl)-2-(ethoxycarbonyl)-1H-imidazole-4-carboxylic acid (250 mg, crude from previous step), (7-chloro-8-fluoroimidazo[1,5-a]pyridin-1-yl)methanamine hydrochloride (170 mg, 0.72 mmol) and DIPEA (400 mg, 3.0 mmol) in DMF (5 mL) was added HOBT (165 mg, 1.22 mmol) and EDCI (235 mg, 1.22 mmol). The reaction mixture was stirred at RT for 12 h. Water (40 mL) was added and the mixture was extracted with EtOAc (45 mL×3). The combined organic layers were washed with brine and dried over Na₂SO₄, concentrated to give the crude, which was purified by Prep-TLC (DCM/MeOH=10/1) to give ethyl 4-(((7-chloro-8-fluoroimidazo[1,5-a]pyridin-1-yl)methyl)carbamoyl)-1-((6-cyclopropylimidazo[1,2-a]pyridin-2-yl)methyl)-1H-imidazole-2-carboxylate (200 mg, yield: 61%) as a white solid. ESI-MS [M+H]⁺: 536.1. Purity: 97.1% (214 nm), 96.4% (254 nm). ¹H NMR (400 MHz, DMSO-d₆) δ 8.64 (s, 1H), 8.48 (s, 1H), 8.33 (t, J=5.5 Hz, 1H), 8.22 (d, J=7.4 Hz, 1H), 8.13 (s, 1H), 8.05 (s, 1H), 7.78 (d, J=9.3 Hz, 1H), 7.63 (d, J=9.0 Hz, 1H), 6.81-6.74 (m, 1H), 5.88 (s, 2H), 4.70 (d, J=5.6 Hz, 2H), 4.33 (q, J=7.1 Hz, 2H), 2.10-2.04 (m, 1H), 1.29 (t, J=7.1 Hz, 3H), 1.10-0.95 (m, 2H), 0.84-0.70 (m, 2H).

Example 261

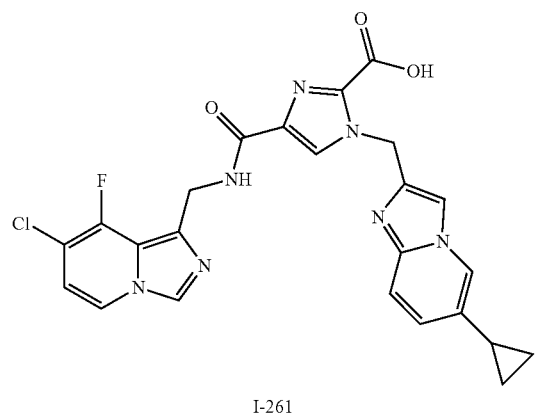

I-261

Synthesis of 4-(((7-chloro-8-fluoroimidazo[1,5-a]pyridin-1-yl)methyl)carbamoyl)-1-((6-cyclopropylimidazo[1,2-a]pyridin-2-yl)methyl)-1H-imidazole-2-carboxylic acid (I-261)

To the mixture of ethyl 4-(((7-chloro-8-fluoroimidazo[1,5-a]pyridin-1-yl)methyl)carbamoyl)-1-((6-cyclopropylimidazo[1,2-a]pyridin-2-yl)methyl)-1H-imidazole-2-carboxylate (100 mg, 0.19 mmol) in EtOH/H₂O (8 mL/2 mL) was added LiOH.H₂O (24 mg, 0.56 mmol). The resulting mixture was stirred at RT for 30 min. The pH of reaction was adjusted around 6 by HCl (1N), and then concentrated to give the crude, which was purified by Prep-HPLC to give 4-(((7-chloro-8-fluoroimidazo[1,5-a]pyridin-1-yl)methyl)carbamoyl)-1-((6-cyclopropylimidazo[1,2-a]pyridin-2-yl)methyl)-1H-imidazole-2-carboxylic acid (30 mg, yield: 31%) as a white solid. ESI-MS [M–H]–: 506.0. Purity: 83.9% (214 nm), 91.2% (254 nm). ¹H NMR (400 MHz, DMSO-d₆) δ 8.45 (d, J=2.4 Hz, 1H), 8.32 (s, 1H), 8.26-8.09 (m, 2H), 7.95 (s, 1H), 7.65 (s, 1H), 7.39 (d, J=9.3 Hz, 1H), 7.00 (d, J=9.3 Hz, 1H), 6.80-6.71 (m, 1H), 5.72 (s, 2H), 4.69 (d, J=5.5 Hz, 2H), 1.94-1.87 (m, 1H), 0.93-0.88 (m, 2H), 0.69-0.56 (m, 2H).

Example 262

Scheme 260

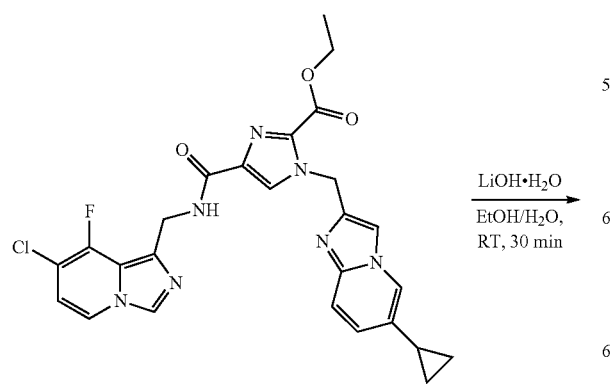

LiOH·H₂O
EtOH/H₂O,
RT, 30 min

Scheme 261

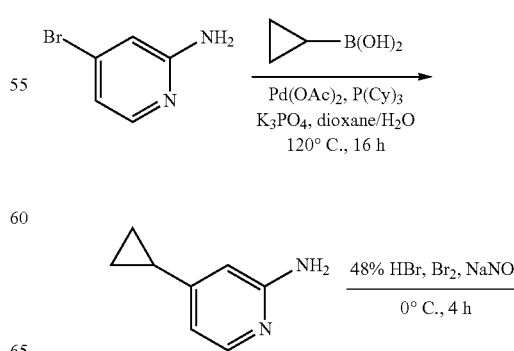

581

-continued

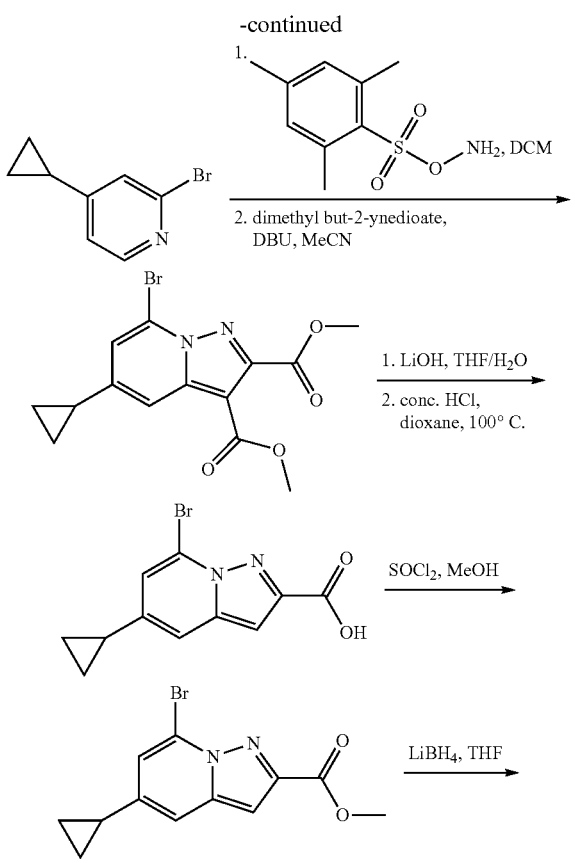

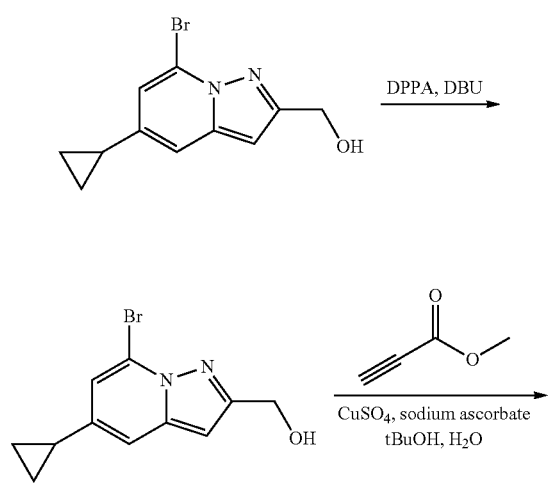

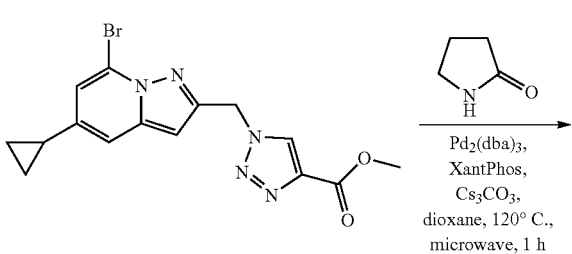

582

-continued

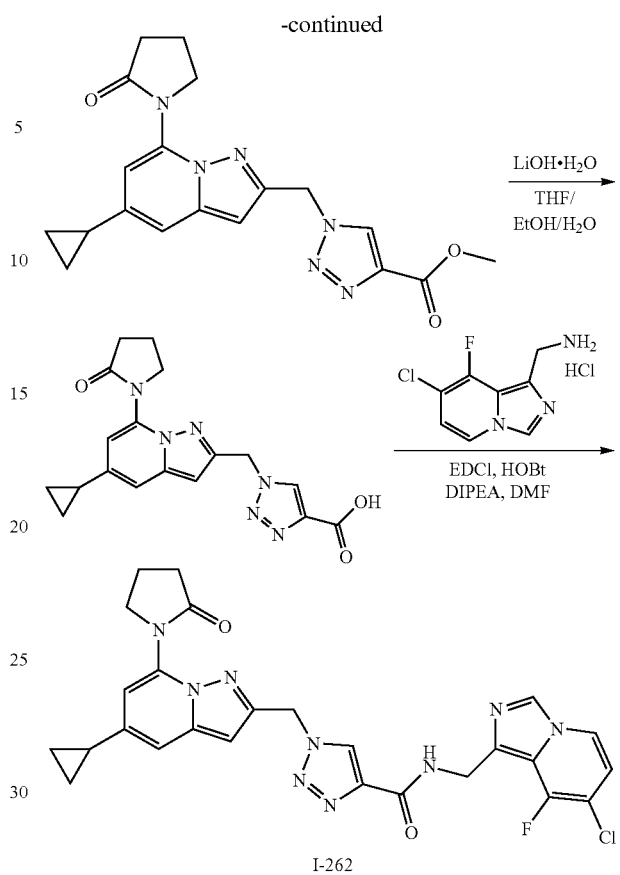

I-262

Synthesis of 5-cyclopropylpyridin-2-amine

To the solution of 4-bromopyridin-2-amine (5 g, 29.0 mmol) in dioxane/H$_2$O (50 mL/5 mL) were added cyclopropylboronic acid (5 g, 58.0 mmol), Pd(OAc)$_2$ (320 mg, 1.45 mmol), P(Cy)$_3$ (400 mg, 1.45 mmol) and K$_3$PO$_4$ (12 g, 58.0 mmol). The resulting reaction mixture was stirred at 120° C. for 16 h under nitrogen. Then the mixture was concentrated in vacuo. Water (400 mL) was added and the mixture was extracted with DCM (100 mL×3). The combined organic layers were washed with brine, dried over Na$_2$SO$_4$, concentrated to give the crude product, which was purified by silica gel chromatography (PE/EA=1/1) to give the 5-cyclopropylpyridin-2-amine as a white solid (2.3 g, yield: 60%). ESI-MS [M+H]$^+$: 135.1.

Synthesis of 2-bromo-4-cyclopropylpyridine

To a mixture of 5-cyclopropylpyridin-2-amine (800 mg, 6.0 mmol) in 48% HBr (20 mL) was add a solution of NaNO$_2$ (1.2 g, 18.0 mmol) in H$_2$O (10 mL) at 0° C. The reaction was stirred at 0° C. for 30 min. Then Br$_2$ (2.9 g, 18 mmol) was added thereto slowly at 0° C. The resulting mixture was stirred at 0° C. for 4 h. The reaction solution was concentrated in vacuo. H$_2$O (50 mL) was added to the residue, pH of the mixture was adjusted to 7 by adding saturated NaHCO$_3$ solution, and then the mixture was extracted with EtOAc (40 mL×3). The combined organic layers were washed with brine, dried over Na$_2$SO$_4$, and concentrated to give the crude product, which was purified by silica gel chromatography (PE/EA=10/1) to give 2-bromo-4-cyclopropylpyridine (770 mg, 65%) as a brown oil. ESI-MS [M+H]$^+$: 197.9.

Synthesis of dimethyl 7-bromo-5-cyclopropylpyrazolo[1,5-a]pyridine-2,3-dicarboxylate To a solution of 2-bromo-4-cyclopropylpyridine (2 g, 10.1 mmol) in DCM (30 mL) was added O-(mesitylsulfonyl)hydroxylamine (4.6 g, 20.5 mmol) at RT and stirred at this temperature for 6 h. After evaporated to give the crude intermediate, which was re-dissolved in MeCN (30 mL), DBU (3.1 g, 20.5 mmol), dimethyl but-2-ynedioate (2.9 g, 20.5 mmol) was added at RT. The resulting mixture was stirred at RT for 7 h. The reaction was concentrated and purified by silica gel chromatography (PE/EA=5/1) to give dimethyl 7-bromo-5-cyclopropylpyrazolo[1,5-a]pyridine-2,3-dicarboxylate (520 mg, 14.5%) as a white solid. ESI-MS [M+H]$^+$: 352.8

Synthesis of 7-bromo-5-cyclopropylpyrazolo[1,5-a]pyridine-2-carboxylic Acid

A mixture of dimethyl 7-bromo-5-cyclopropylpyrazolo[1,5-a]pyridine-2,3-dicarboxylate (200 mg, 0.57 mmol) and LiOH (47 mL, 1.14 mmol) in THF/H$_2$O (10 mL/2 mL) was stirred at RT for 5 h. After evaporated, the mixture was re-dissolved in 12 N HCl (2 mL) and dioxane (2 mL) at RT. The reaction mixture was stirred at 100° C. for another 5 h. The pH value of reaction was adjusted to 5 by adding saturated NaHCO$_3$ solution, and then extracted with EtOAc (50 mL×3). The combined organic layers were washed with brine, dried over Na$_2$SO$_4$, and concentrated to give the crude product, which was purified by silica gel chromatography (DCM/MeOH=5/1) to give 7-bromo-5-cyclopropylpyrazolo[1,5-a]pyridine-2-carboxylic acid (100 mg, 63%) as a white solid. ESI-MS [M+H]$^+$: 280.9.

Synthesis of Methyl 7-bromo-5-cyclopropylpyrazolo[1,5-a]pyridine-2-carboxylate A mixture of 7-bromo-5-cyclopropylpyrazolo[1,5-a]pyridine-2-carboxylic acid (610 mg, 2.2 mmol), SOCl$_2$ (0.5 mL) in CH$_3$OH (10 mL) was stirred at RT for 16 h. The mixture was concentrated in vacuo to give the crude, which was purified by silica gel chromatography (PE/EA=5/1) to give methyl 7-bromo-5-cyclopropylpyrazolo[1,5-a] pyridine-2-carboxylate (400 mg, 62%) as a white solid. ESI-MS [M+H]$^+$: 296.9.

Synthesis of (7-bromo-5-cyclopropylpyrazolo[1,5-a]pyridin-2-yl)methanol

To the solution of 7-bromo-5-cyclopropylpyrazolo[1,5-a]pyridine-2-carboxylate (200 mg, 0.68 mmol) in THF (15 mL) was added LiBH$_4$ (28 mg, 1.36 mmol) at 0° C. and the mixture was stirred at RT for 6 h. The reaction was quenched by the saturated aqueous NH$_4$Cl (320 mL), and extracted with EtOAc (35 mL×3). The combined organic layers were washed with brine, dried over Na$_2$SO$_4$, and concentrated to give the crude product, which was purified by silica gel chromatography (PE/EA=2/1) to give (7-bromo-5-cyclopropylpyrazolo[1,5-a]pyridin-2-yl)methanol (160 mg, 89%) as a white oil. ESI-MS [M+H]$^+$: 266.9.

Synthesis of 2-(azidomethyl)-7-bromo-5-cyclopropylpyrazolo[1,5-a]pyridine

To the solution of (7-bromo-5-cyclopropylpyrazolo[1,5-a]pyridin-2-yl)methanol (150 mg, 0.56 mmol) and DPPA (170 mg, 0.62 mmol) in toluene (7 mL) was added DBU (102 mg, 0.67 mmol) at 0° C. The reaction mixture was stirred at RT for 16 h. Water (15 mL) was added and the mixture was extracted with DCM (30 mL×3). The combined organic layers were concentrated and purified by silica gel chromatography (PE/EA=10/1) to give 2-(azidomethyl)-7-bromo-5-cyclopropylpyrazolo[1,5-a]pyridine (120 mg, 73%) as a colorless oil. ESI-MS [M+H]$^+$: 291.9.

Synthesis of Methyl 1-((7-bromo-5-cyclopropylpyrazolo[1,5-a]pyridin-2-yl)methyl)-1H-1,2,3-triazole-4-carboxylate A mixture of 2-(azidomethyl)-7-bromo-5-cyclopropylpyrazolo[1,5-a]pyridine (120 mg, 0.41 mmol), methyl propiolate (52 mg, 0.62 mmol), CuSO$_4$.5H$_2$O (20 mg, 0.08 mmol), NaVc (24 mg, 0.12 mmol) in t-BuOH/H$_2$O (4 mL/3 mL) was stirred at RT for 16 h. The mixture was concentrated in vacuo to give the crude product, which was purified by Prep-TLC to give methyl 1-((7-bromo-5-cyclopropylpyrazolo[1,5-a]pyridin-2-yl)methyl)-1H-1,2,3-triazole-4-carboxylate (130 mg, 84%) as a white oil. ESI-MS [M]$^+$: 375.8.

Synthesis of Methyl 1-((5-cyclopropyl-7-(2-oxopyrrolidin-1-yl)pyrazolo[1,5-a]pyridin-2-yl)methyl)-1H-1,2,3-triazole-4-carboxylate To the solution of methyl 1-((7-bromo-5-cyclopropylpyrazolo[1,5-a]pyridin-2-yl)methyl)-1H-1,2,3-triazole-4-carboxylate (90 mg, 0.24 mmol) in dioxane (10 mL) were added pyrrolidin-2-one (30 mg, 0.36 mmol), Pd$_2$(dba)$_3$ (27 mg, 0.03 mmol), XantPhos (29 mg, 0.05 mmol) and Cs$_2$CO$_3$ (162 mg, 0.5 mmol). The reaction mixture was stirred at 120° C. for 1 h under nitrogen under microwave conditions. Then the mixture was concentrated in vacuo. Water (40 mL) was added to the residue and extracted with DCM (70 mL×3). The combined organic layers were concentrated to give the crude product, which was purified by silica gel chromatography (PE/EA=1/4) to give the methyl 1-((5-cyclopropyl-7-(2-oxopyrrolidin-1-yl)pyrazolo[1,5-a]pyridin-2-yl)methyl)-1H-1,2,3-triazole-4-carboxylate as a white solid (40 mg, 44%). ESI-MS [M+H]$^+$: 381.1.

Synthesis of 1-((5-cyclopropyl-7-(2-oxopyrrolidin-1-yl)pyrazolo[1,5-a]pyridin-2-yl)methyl)-1H-1,2,3-triazole-4-carboxylic Acid A mixture of ethyl 1-((5-cyclopropyl-1H-indol-2-yl)methyl)-1H-1,2,3-triazole-4-carboxylate (40 mg, 0.1 mmol), LiOH.H$_2$O (9 mg, 0.2 mmol) in THF/EtOH/H$_2$O (2 mL/2 mL/2 mL) was stirred at RT for 0.5 h. The pH of reaction mixture was acidified by HCl (1N), concentrated in vacuo to give the crude product, which was washed by ether to give 1-((5-cyclopropyl-7-(2-oxopyrrolidin-1-yl)pyrazolo[1,5-a]pyridin-2-yl)methyl)-1H-1,2,3-triazole-4-carboxylic acid (50 mg, crude) as a white solid. ESI-MS [M+H]$^+$: 367.2.

Synthesis of N-((7-chloro-8-fluoroimidazo[1,5-a]pyridin-1-yl)methyl)-1-((5-cyclopropyl-7-(2-oxopyrrolidin-1-yl)pyrazolo[1,5-a]pyridin-2-yl)methyl)-1H-1,2,3-triazole-4-carboxamide (I-262)

A mixture of 1-((5-cyclopropyl-7-(2-oxopyrrolidin-1-yl)pyrazolo[1,5-a]pyridin-2-yl)methyl)-1H-1,2,3-triazole-4-carboxylic acid (50 mg, crude), (7-chloro-8-fluoroimidazo[1,5-a]pyridin-1-yl)methanamine hydrochloride (19 mg, 0.08 mmol), EDCI (17 mg, 0.09 mmol), HOBT (12 mg, 0.09 mmol), DIPEA (26 mg, 0.2 mmol) in DMF (3 mL) was stirred at RT for 16 h. H₂O (20 mL) was added to the reaction, extracted with EtOAc (30 mL×5). The combined organic layers were washed with brine, dried over Na₂SO₄, concentrated to give the crude, which was purified by Prep-TLC to give N-((7-chloro-8-fluoroimidazo[1,5-a]pyridin-1-yl)methyl)-1-((5-cyclopropyl-7-(2-oxopyrrolidin-1-yl)pyrazolo[1,5-a]pyridin-2-yl)methyl)-1H-1,2,3-triazole-4-carboxamide (3 mg, yield: 5%) as a white solid. ESI-MS [M+H]⁺: 547.8. Purity: 99.82% (214 nm), 99.61% (254 nm). ¹H NMR (400 MHz, CDCl₃) δ 8.39 (s, 1H), 8.13 (s, 1H), 7.84 (s, 1H), 7.77 (s, 1H), 7.11 (s, 1H), 6.60-6.56 (m, 2H), 6.34 (s, 1H), 5.72 (s, 2H), 4.98 (s, 2H), 4.04 (t, J=6.8 Hz, 2H), 2.65 (t, J=8.0 Hz, 2H), 2.35-2.25 (m, 2H), 1.94-1.88 (m, 1H), 1.04-1.02 (m, 2H), 0.77-0.76 (m, 2H).

Example 263

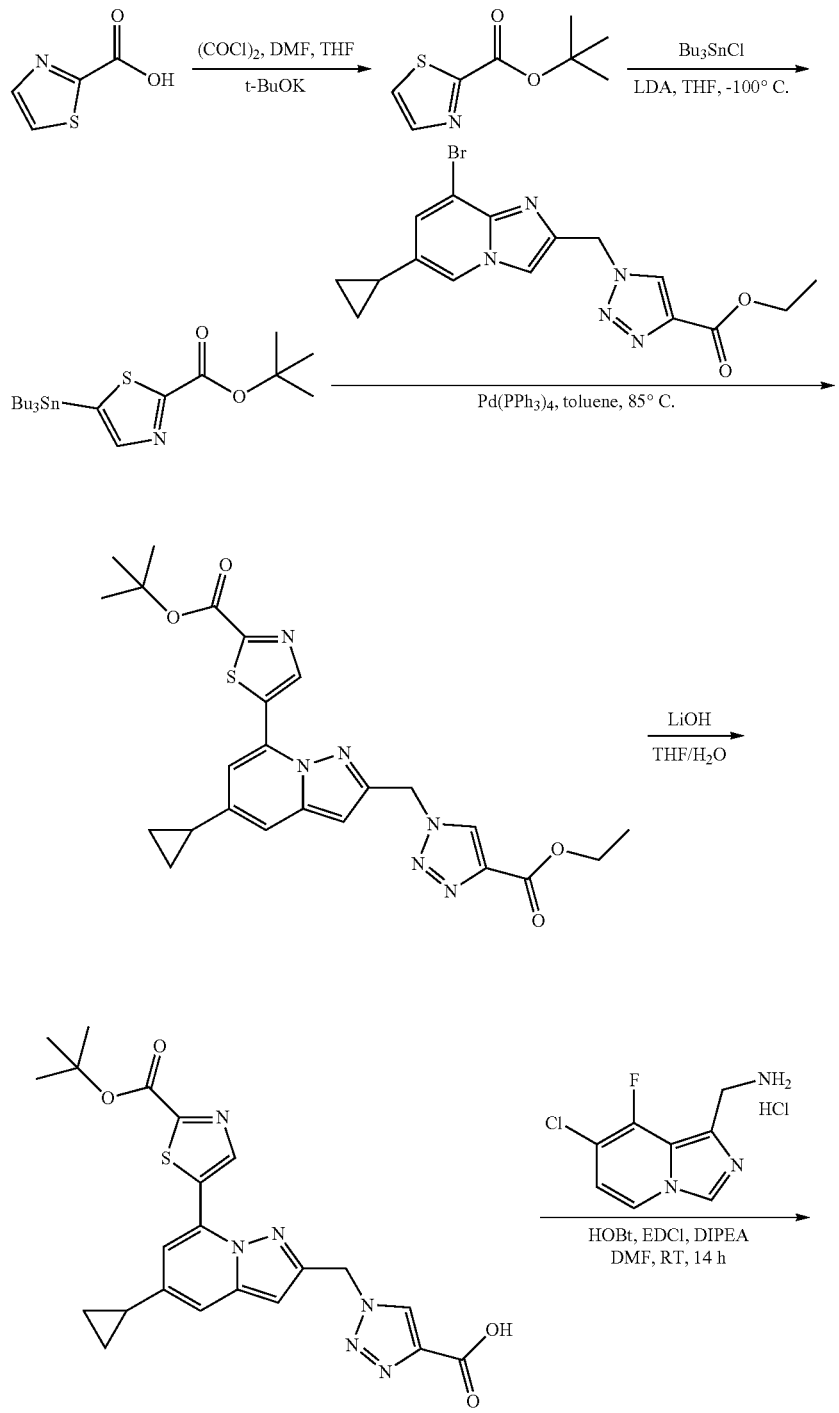

Scheme 262

-continued

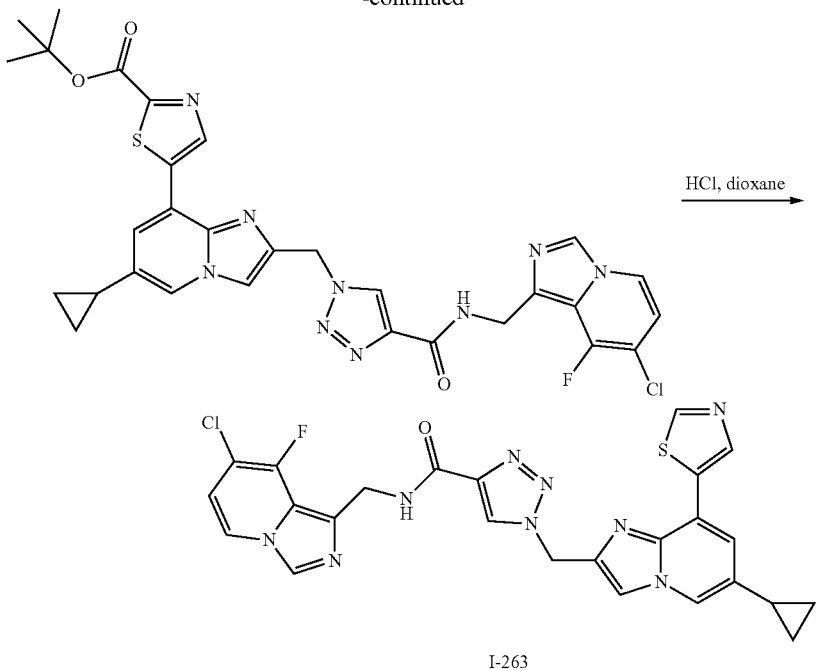

I-263

Synthesis of tert-butyl thiazole-2-carboxylate

To the solution of thiazole-2-carboxylic acid (300 mg, 2.3 mmol) in THF (6 mL) was added (COCl)$_2$ (590 mg, 4.6 mmol) and DMF (0.1 mL). The reaction mixture was stirred at RT for 5 h and then t-BuOK (386 mg, 3.5 mmol) was added thereto. The reaction mixture was stirred at RT for 1 h. The reaction was quenched with saturated aqueous NH$_4$Cl (20 mL), extracted with EtOAc (40 mL×3). The combined organic layers were washed with brine, dried over Na$_2$SO$_4$, concentrated to give the crude product, which was purified by silica gel chromatography (PE/EA=1/2) to give the tert-butyl thiazole-2-carboxylate as a yellow solid (250 mg, yield: 58%). ESI-MS [M+H]$^+$: 186.0.

Synthesis of tert-butyl 5-(tributylstannyl)thiazole-2-carboxylate

To the solution of tert-butyl thiazole-2-carboxylate (510 mg, 2.7 mmol) in THF (40 mL) was added LDA (1.5 mL, 2 M, 3.0 mmol) at −100° C. The reaction mixture was stirred at this temperature for 15 min and then Bu$_3$SnCl (980 mg, 3.0 mmol) was added. The reaction mixture was stirred for 10 min at −100° C. for another 1 h. The reaction was quenched by saturated aqueous NH$_4$Cl (15 mL), extracted with EtOAc (30 mL×3). The combined organic layers were washed with brine, dried over Na$_2$SO$_4$, concentrated to give the crude product, which was purified by silica gel chromatography (PE/EA=1/1) to give the tert-butyl 5-(tributylstannyl)thiazole-2-carboxylate as a clear oil (900 mg, yield: 69%).

Synthesis of tert-butyl 5-(6-cyclopropyl-2-((4-(ethoxycarbonyl)-1H-1,2,3-triazol-1-yl)methyl)imidazo[1,2-a]pyridin-8-yl)thiazole-2-carboxylate A mixture of tert-butyl 5-(tributylstannyl)thiazole-2-carboxylate (520 mg, 1.1 mmol), ethyl 1-((8-bromo-6-cyclopropylimidazo[1,2-a]pyridin-2-yl)methyl)-1H-1,2,3-triazole-4-carboxylate (386 mg, 0.99 mmol), Pd(PPh$_3$)$_4$ (127 mg, 0.11 mmol) in toluene (10 mL) was stirred at 85° C. for 16 h under N$_2$. The mixture was concentrated to give the crude product, which was purified by silica gel chromatography ((PE/EA=3/1)) to give tert-butyl 5-(6-cyclopropyl-2-((4-(ethoxycarbonyl)-1H-1,2,3-triazol-1-yl)methyl)imidazo[1,2-a]pyridin-8-yl)thiazole-2-carboxylate (290 mg, yield: 59%) as a red oil. ESI-MS [M+H]$^+$: 494.9.

Synthesis of 1-((8-(2-(tert-butoxycarbonyl)thiazol-5-yl)-6-cyclopropylimidazo[1,2-a]pyridin-2-yl)methyl)-1H-1,2,3-triazole-4-carboxylic Acid A mixture of tert-butyl 5-(6-cyclopropyl-2-((4-(ethoxycarbonyl)-1H-1,2,3-triazol-1-yl) methyl) imidazo[1,2-a]pyridin-8-yl)thiazole-2-carboxylate (190 mg, 0.38 mmol), LiOH (24 mg, 0.57 mmol) in THF/H$_2$O (5 mL/5 mL) was stirred at RT for 0.5 h. The reaction solution was concentrated in vacuo to give 1-((8-(2-(tert-butoxycarbonyl)thiazol-5-yl)-6-cyclopropylimidazo[1,2-a]pyridin-2-yl)methyl)-1H-1,2,3-triazole-4-carboxylic acid as a white solid, which was used into next step without further purification (210 mg crude). ESI-MS [M+H]$^+$: 466.9

Synthesis of tert-butyl 5-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)thiazole-2-carboxylate A mixture of 1-((8-(2-(tert-butoxycarbonyl)thiazol-5-yl)-6-cyclopropylimidazo[1,2-a]pyridin-2-yl)methyl)-1H-1,2,3-triazole-4-carboxylic acid (105 mg, crude from previous step), (7-chloroimidazo[1,5-a]pyridin-1-yl)methanamine hydrochloride (50 mg, 0.21 mmol), EDCI (42 mg, 0.24 mmol), HOBT (32 mg, 0.24 mmol) and DIPEA (69 mg, 0.54 mmol) in DMF (7 mL) was stirred at RT for 16 h. H$_2$O (30 mL) was added to the reaction, extracted with EtOAc (50 mL×3). The combined organic layers were washed with brine, dried over Na$_2$SO$_4$, concentrated in vacuo to give the crude, which was purified by Prep-TLC to give tert-butyl 5-(2-((4-(((7-chloro-8-fluoroimidazo [1,5-a]pyridin-1-yl)methyl)carbamoyl)-1H-1,2,3-triazol-1-yl)methyl)-6-cyclopropylimidazo[1,2-a]pyridin-8-yl)thiazole-2-carboxylate (80 mg, yield: 65% over 2 steps) as a white solid. ESI-MS [M+H]$^+$: 647.5.

Synthesis of N-((7-chloro-8-fluoroimidazo[1,5-a]pyridin-1-yl)methyl)-1-((6-cyclopropyl-8-(thiazol-5-yl)imidazo[1,2-a]pyridin-2-yl)methyl)-1H-1,2,3-triazole-4-carboxamide (I-263)

To the mixture of tert-butyl 5-(2-((4-(((7-chloro-8-fluoroimidazo [1,5-a]pyridin-1-yl)methyl)carbamoyl)-1H-1,2,3-triazol-1-yl)methyl)-6-cyclopropylimidazo[1,2-a]pyridin-8-yl)thiazole-2-carboxylate (50 mg, 0.077 mmol) in dioxane (5 mL) was added HCl (4 M solution in dioxane, 3 mL). The resulting reaction was stirred at RT for 16 h. The mixture was concentrated and the residue was diluted with DCM/MeOH (30 mL, 10/1 (v/v)), washed with H$_2$O (10 mL). The organic layer was separated, dried over Na$_2$SO$_4$, and concentrated in vacuo to give the crude product, which was purified by Prep-TLC to give N-((7-chloro-8-fluoroimidazo [1,5-a]pyridin-1-yl)methyl)-1-((6-cyclopropyl-8-(thiazol-5-yl)imidazo[1,2-a]pyridin-2-yl)methyl)-1H-1,2,3-triazole-4-carboxamide (10 mg, yield: 23.7%) as a white solid. ESI-MS [M+H]$^+$: 547.8. Purity: 100.00 (214 nm), 100.00 (254 nm). $^1$H NMR (400 MHz, DMSO-d$_6$) δ 9.15 (s, 1H), 8.88 (s, 1H), 8.70 (t, J=5.3 Hz, 1H), 8.62 (s, 1H), 8.44 (d, J=2.1 Hz, 1H), 8.38 (s, 1H), 8.20 (d, J=7.4 Hz, 1H), 7.91 (s, 1H), 7.56 (s, 1H), 6.75 (t, J=6.9 Hz, 1H), 5.82 (s, 2H), 4.70 (d, J=5.4 Hz, 2H), 2.05-1.95 (m, 1H), 1.01-0.92 (m, 2H), 0.82-0.75 (m, 2H).

Example 264

Scheme 263

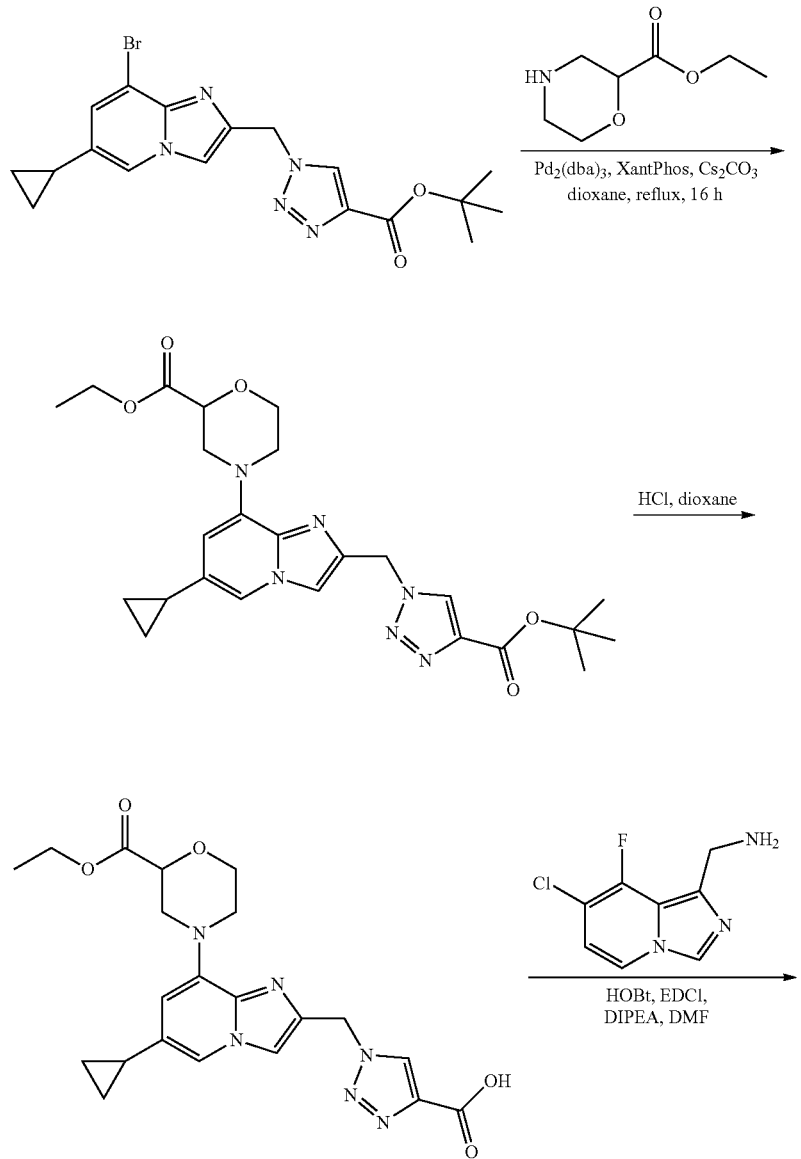

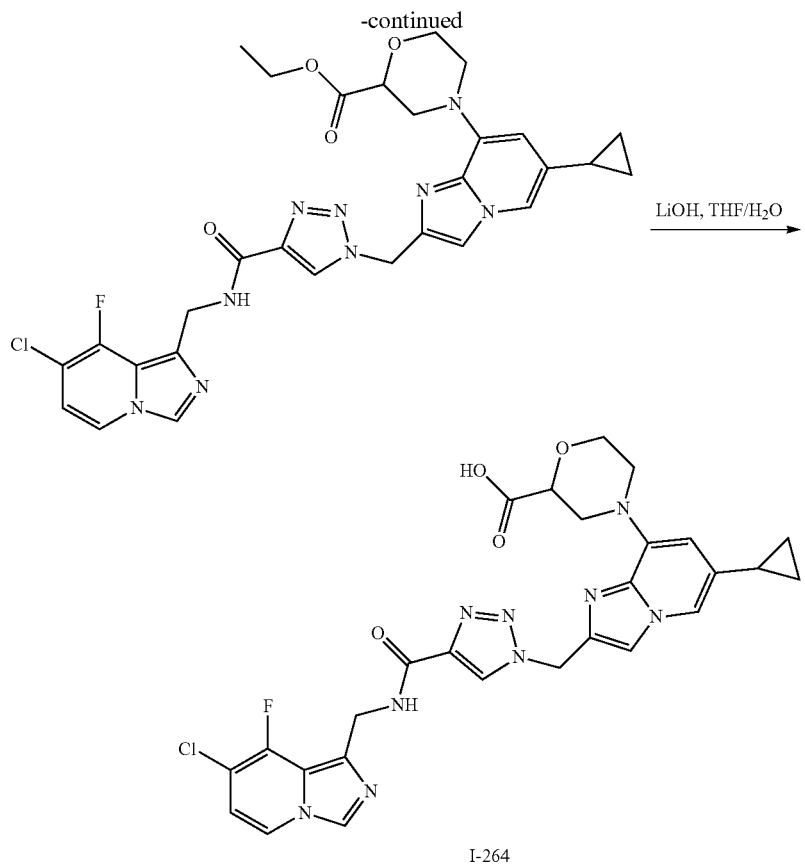

I-264

Synthesis of Ethyl 4-(2-((4-(tert-butoxycarbonyl)-1H-1,2,3-triazol-1-yl)methyl)-6-cyclopropylimidazo[1,2-a]pyridin-8-yl)morpholine-2-carboxylate To the mixture of tert-butyl 1-((8-bromo-6-cyclopropylimidazo[1,2-a]pyridin-2-yl)methyl)-1H-1,2,3-triazole-4-carboxylate (100 mg, 0.24 mmol), ethyl morpholine-2-carboxylate (114 mg, 0.72 mmol) and $Cs_2CO_3$ (235 mg, 0.72 mmol) in Dioxane (5 mL) was added $Pd_2(dba)_3$ (22 mg, 0.024 mmol) and XantPhos (28 mg, 0.048 mmol). The mixture was stirred at 100° C. for 16 h. Water (30 mL) was added to the reaction, extracted with EtOAc (30 mL×3), concentrated to give the crude, which was purified by Prep-TLC (EA/PE=2/1) to give ethyl 4-(2-((4-(tert-butoxycarbonyl)-1H-1,2,3-triazol-1-yl)methyl)-6-cyclopropylimidazo[1,2-a]pyridin-8-yl)morpholine-2-carboxylate (60 mg, yield: 50%) as a yellow solid. ESI-MS [M+H]$^+$: 497.2

Synthesis of 1-((6-cyclopropyl-8-(2-(ethoxycarbonyl)morpholino)imidazo[1,2-a]pyridin-2-yl)methyl)-1H-1,2,3-triazole-4-carboxylic Acid A mixture of ethyl 4-(2-((4-(tert-butoxycarbonyl)-1H-1,2,3-triazol-1-yl)methyl)-6-cyclopropylimidazo[1,2-a]pyridin-8-yl)morpholine-2-carboxylate (60 mg, 0.12 mmol) in dioxane (2 mL) was added HCl (4 M solution in doxane, 1 mL). The resulting reaction was stirred at 25° C. for 2 h. The reaction was concentrated to give 1-((6-cyclopropyl-8-(2-(ethoxycarbonyl)morpholino)imidazo[1,2-a]pyridin-2-yl)methyl)-1H-1,2,3-triazole-4-carboxylic acid (65 mg, yield: 100%) as a yellow solid, which was used into next step without further purification. ESI-MS [M+H]$^+$: 441.2.

Synthesis of Ethyl 4-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)morpholine-2-carboxylate To the mixture of 1-((6-cyclopropyl-8-(2-(ethoxycarbonyl)morpholino)imidazo[1,2-a]pyridin-2-yl)methyl)-1H-1,2,3-triazole-4-carboxylic acid (65 mg, from previous step), (7-chloro-8-fluoroimidazo[1,5-a]pyridin-1-yl)methanamine hydrochloride (43 mg, 0.18 mmol), HOBT (33 mg, 0.24 mmol), EDCI (46 mg, 0.24 mmol) in DMF (5 mL) was added DIPEA (93 mg, 0.72 mmol). The reaction mixture was stirred at 25° C. for 16 h. Water (30 mL) was added to the reaction, extracted with EtOAc (30 mL×3). The combined organic layers were washed with brine, dried over $Na_2SO_4$, concentrated to give the crude product, which was purified with Prep-TLC (DCM/MeOH=10/1) to offer ethyl 4-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)morpholine-2-carboxylate (70 mg, yield: 93%) as a yellow solid. ESI-MS [M+H]$^+$: 622.2.

Synthesis of 4-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)morpholine-2-carboxylic acid (I-264)

To the mixture of ethyl 4-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)morpholine-2-carboxylate (70 mg, 0.11 mmol) in THF/

H₂O (2/2 mL) was added LiOH (8.1 mg, 0.33 mmol). The mixture was stirred at 25° C. for 2 h. The pH of reaction was adjusted by HCl (1N), concentrated to give the crude, purified by Prep-HPLC to give 4-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)morpholine-2-carboxylic acid (20.4 mg, yield: 30%) as a white solid. ESI-MS [M+H]⁺: 594.2. Purity: 98.05% (214 nm), 97.76% (254 nm). ¹H NMR (400 MHz, DMSO-d₆) δ 8.74 (t, J=5.5 Hz, 1H), 8.54 (s, 1H), 8.45 (d, J=2.4 Hz, 1H), 8.21 (d, J=7.4 Hz, 1H), 7.94 (s, 1H), 7.71 (s, 1H), 6.78-6.76 (m, 1H), 6.26 (s, 1H), 5.72 (s, 2H), 4.70 (d, J=5.5 Hz, 2H), 4.26-4.24 (m, 1H), 4.14-4.11 (m, 1H), 4.05-4.03 (m, 1H), 3.87-3.84 (m, 1H), 3.75-3.70 (m, 1H), 3.77-3.06 (m, 1H), 2.99-2.94 (m, 1H), 1.91-1.85 (m, 1H), 0.90-0.85 (m, 2H), 0.69-0.65 (m, 2H).

Example 265

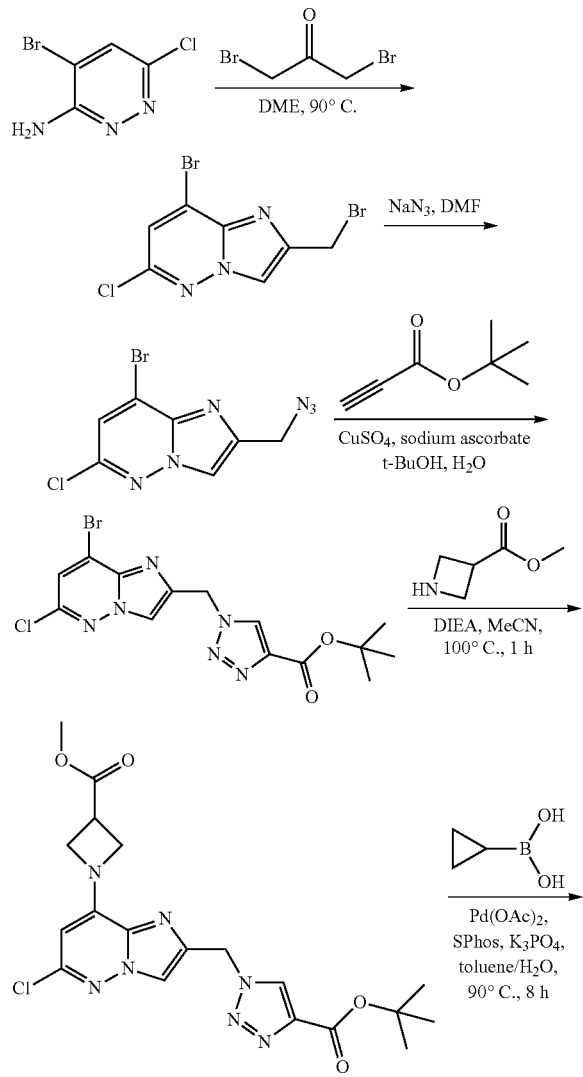

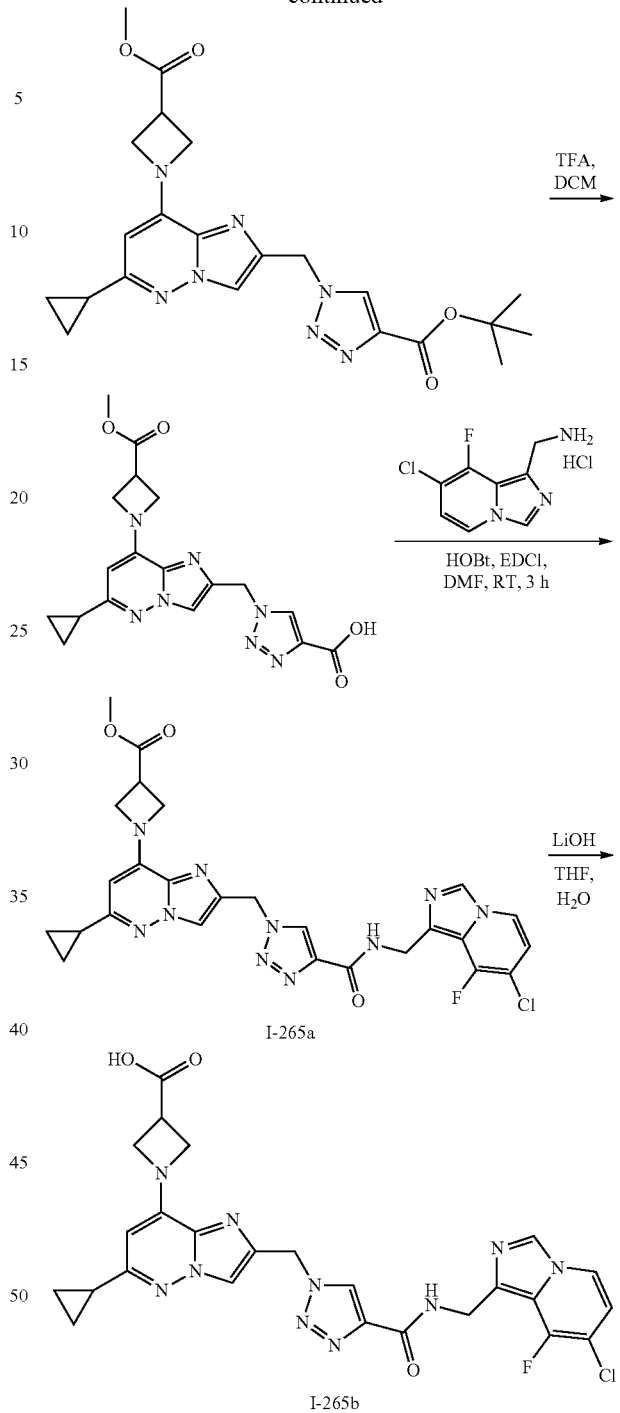

I-265a

I-265b

Synthesis of 8-bromo-2-(bromomethyl)-6-chloroimidazo[1,2-b]pyridazine

A mixture of 4-bromo-6-chloropyridazin-3-amine (13.0 g, 62.5 mmol) and 1,3-dibromopropan-2-one (40.5 g, 187.5 mmol) in DME (100 mL) was stirred at 90° C. for 16 h. The reaction was quenched with saturated aqueous NaHCO₃ (100 mL), extracted with EtOAc (100 mL×3). The combined organic layers were washed with brine, dried over Na₂SO₄, concentrated to give the crude, which was purified by silica gel chromatography (PE/EA=15/1) to give 8-bromo-2-(bromomethyl)-6-chloroimidazo[1,2-b]pyridazine (13.5 g, yield: 66.5%) as a yellow solid. ESI-MS [M+H]$^+$: 325.9.

Synthesis of 2-(azidomethyl)-8-bromo-6-chloroimidazo[1,2-b]pyridazine

To the solution of 8-bromo-2-(bromomethyl)-6-chloroimidazo[1,2-b]pyridazine (7.5 g, 23.1 mmol) in DMF (30 mL) was added NaN$_3$ (2.0 g, 30.0 mmol). The resulting reaction was stirred at 25° C. for 3 h. H$_2$O (80 mL) was added to the reaction, extracted with EtOAc (60 mL×3). The combined organic layers were washed with brine, dried over Na$_2$SO$_4$, concentrated to give 2-(azidomethyl)-8-bromo-6-chloroimidazo[1,2-b]pyridazine (5.1 g, yield: 77%) as a yellow solid, which was used into next step without further purification. ESI-MS [M+H]$^+$: 286.0.

Synthesis of tert-butyl 1-((8-bromo-6-chloroimidazo[1,2-b]pyridazin-2-yl)methyl)-1H-1,2,3-triazole-4-carboxylate To the solution of 2-(azidomethyl)-8-bromo-6-chloroimidazo[1,2-b]pyridazine (5.1 g, 17.8 mmol) was added tert-butyl propiolate (6.7 g, 53.4 mmol), CuSO$_4$ (0.6 g, 3.6 mmol), sodium ascorbate (0.7 g, 3.6 mmol) in t-BuOH (15 mL) and H$_2$O (15 mL). The resulting mixture was stirred at 25° C. for 16 h. The solvent was concentrated to give the crude, which was purified by silica gel chromatography (DCM/MeOH=20/1) to give tert-butyl 1-((8-bromo-6-chloroimidazo[1,2-b]pyridazin-2-yl)methyl)-1H-1,2,3-triazole-4-carboxylate (3.5 g, yield: 47%) as a yellow solid. ESI-MS [M+H]$^+$: 413.1

Synthesis of tert-butyl 1-((6-chloro-8-(3-(methoxycarbonyl)azetidin-1-yl)imidazo[1,2-b]pyridazin-2-yl)methyl)-1H-1,2,3-triazole-4-carboxylate To the solution of tert-butyl 1-((8-bromo-6-chloroimidazo[1,2-b]pyridazin-2-yl)methyl)-1H-1,2,3-triazole-4-carboxylate (600 mg, 1.5 mmol) in acetonitrile (20 mL) was added methyl azetidine-3-carboxylate (300 mg, 2.3 mmol) and DIPEA (600 mg, 4.5 mmol). The mixture was stirred at 100° C. for 2 h. Water (50 mL) was added to the reaction, extracted with EtOAc (50 mL×3). The combined organic layers were washed with brine, dried over Na$_2$SO$_4$, filtered and concentrated to give the crude, which was purified by silica gel chromatography (PE/EA=1/1) to give tert-butyl 1-((6-chloro-8-(3-(methoxycarbonyl)azetidin-1-yl)imidazo[1,2-b]pyridazin-2-yl)methyl)-1H-1,2,3-triazole-4-carboxylate (550 mg, yield: 82%) as a yellow solid. ESI-MS [M+H]$^+$: 448.2.

Synthesis of tert-butyl 1-((6-cyclopropyl-8-(3-(methoxycarbonyl)azetidin-1-yl)imidazo[1,2-b]pyridazin-2-yl)methyl)-1H-1,2,3-triazole-4-carboxylate To the solution of tert-butyl 1-((6-chloro-8-(3-(methoxycarbonyl)azetidin-1-yl)imidazo[1,2-b]pyridazin-2-yl)methyl)-1H-1,2,3-triazole-4-carboxylate (550 mg, 1.2 mmol) and cyclopropylboronic acid (320 mg, 3.69 mmol) in toluene (20 mL) and H$_2$O (2 mL) was added K$_3$PO$_4$ (900 mg, 4.3 mmol), SPhos (50 mg, 0.12 mmol) and Pd(OAc)$_2$ (30 mg, 0.12 mmol). After the mixture was stirred at 90° C. for 8 h under N$_2$. Water (40 mL) was added and extracted with EtOAc (40 mL×3). The combined organic layers were washed with brine, dried over Na$_2$SO$_4$, concentrated to give the crude, which was purified by silica gel chromatography (DCM/MeOH=20/1) to give tert-butyl 1-((6-cyclopropyl-8-(3-(methoxycarbonyl)azetidin-1-yl)imidazo[1,2-b]pyridazin-2-yl)methyl)-1H-1,2,3-triazole-4-carboxylate (550 mg, yield: 98.7%) as a yellow solid. ESI-MS [M+H]$^+$: 454.2.

Synthesis of 1-((6-cyclopropyl-8-(3-(methoxycarbonyl)azetidin-1-yl)imidazo[1,2-b]pyridazin-2-yl)methyl)-1H-1,2,3-triazole-4-carboxylic Acid To a solution of tert-butyl 1-((6-cyclopropyl-8-(3-(methoxycarbonyl)azetidin-1-yl)imidazo[1,2-b]pyridazin-2-yl)methyl)-1H-1,2,3-triazole-4-carboxylate (550 mg, 1.2 mmol) in DCM (10 mL) was added TFA (3 mL). The resulting reaction mixture was stirred at 25° C. for 3 h. The reaction was concentrated to give the crude 1-((6-cyclopropyl-8-(3-(methoxycarbonyl)azetidin-1-yl)imidazo[1,2-b]pyridazin-2-yl)methyl)-1H-1,2,3-triazole-4-carboxylic acid (600 mg crude) as a black solid, which was used into next step without further purification. ESI-MS [M+H]$^+$: 398.1.

Synthesis of Methyl 1-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-b]pyridazin-8-yl)azetidine-3-carboxylate (I-265a)

To the solution of 1-((6-cyclopropyl-8-(3-(methoxycarbonyl)azetidin-1-yl)imidazo[1,2-b]pyridazin-2-yl)methyl)-1H-1,2,3-triazole-4-carboxylic acid (600 mg, crude from previous step) was added (7-chloro-8-fluoroimidazo[1,5-a]pyridin-1-yl)methanamine hydrochloride (470 mg, 2.0 mmol), HOBT (270 mg, 2.0 mmol), EDCI (380 mg, 2.0 mmol) and DIPEA (500 mg, 3.9 mmol) in DMF (20 mL). The mixture was stirred at 25° C. for 3 h. H$_2$O (50 mL) was added to the reaction, extracted with EtOAc (100 mL×3), combined organic layers were concentrated to give the crude, which was purified by silica gel chromatography (DCM/MeOH=10/1) to give methyl 1-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-b]pyridazin-8-yl)azetidine-3-carboxylate (350 mg, yield: 50%) as a pale solid. ESI-MS [M+H]$^+$: 579.1. Purity: 95.43% (214 nm), 95.27 (254 nm). $^1$H NMR (400 MHz, DMSO-d$_6$) δ 8.68 (t, J=5.4 Hz, 1H), 8.51 (s, 1H), 8.44 (d, J=2.4 Hz, 1H), 8.20 (d, J=7.4 Hz, 1H), 7.94 (s, 1H), 6.80-6.71 (m, 1H), 5.72 (s, 1H), 5.66 (s, 2H), 4.69 (d, J=5.5 Hz, 2H), 4.49 (s, 2H), 4.36 (s, 2H), 3.74-3.62 (m, 4H), 2.00-1.90 (m, 1H), 0.98-0.83 (m, 4H).

Synthesis of 1-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-b]pyridazin-8-yl)azetidine-3-carboxylic acid (I-265b)

To the solution of methyl 1-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-b]pyridazin-8-yl)azetidine-3-carboxylate (150 mg, 0.26 mmol) in THF/H$_2$O (4 mL/4 mL) was added LiOH (32 mg, 0.77 mmol). The mixture was stirred for 3 h at 25° C. The pH of the reaction was adjusted by HCl (1N), and white solid was precipitated. The mixture was filtered, and the cake was dried to give 1-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-b]pyridazin-8-yl)azetidine-3-carboxylic acid (46 mg, yield: 31.4%) as a white solid. ESI-MS [M+H]+: 565.2. Purity: 95.74% (214 nm), 95.45% (254 nm). ¹H NMR (400 MHz, DMSO-$d_6$) δ 8.68 (t, J=5.5 Hz, 1H), 8.51 (s, 1H), 8.44 (d, J=2.4 Hz, 1H), 8.20 (d, J=7.4 Hz, 1H), 7.93 (s, 1H), 6.79-6.73 (m, 1H), 5.70 (s, 1H), 5.67 (s, 2H), 4.70 (d, J=5.5 Hz, 2H), 4.46 (s, 2H), 4.34 (s, 2H), 3.61-3.53 (m, 1H), 1.98-1.90 (m, 1H), 0.95-0.85 (m, 4H).

Example 266

Scheme 265

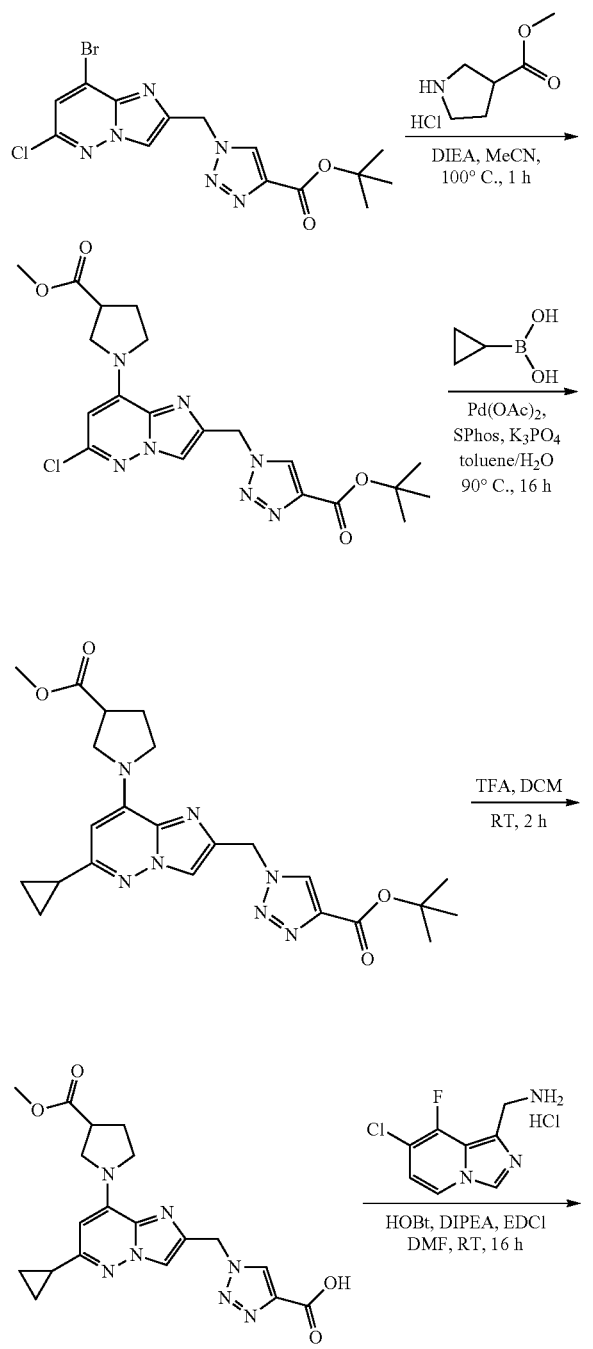

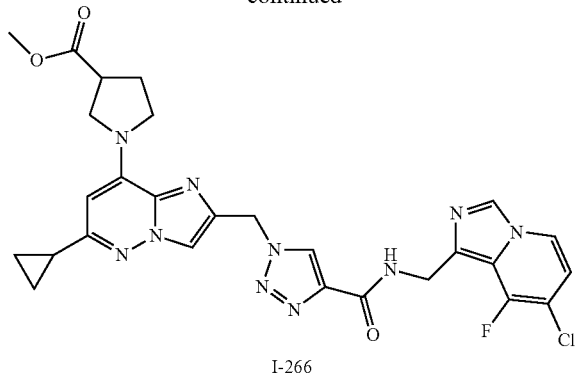

I-266

Synthesis of tert-butyl 1-((6-chloro-8-(3-(methoxycarbonyl)pyrrolidin-1-yl)imidazo[1,2-b]pyridazin-2-yl)methyl)-1H-1,2,3-triazole-4-carboxylate To a solution of tert-butyl 1-((8-bromo-6-chloroimidazo[1,2-b]pyridazin-2-yl)methyl)-1H-1,2,3-triazole-4-carboxylate (300 mg, 0.73 mmol), methyl pyrrolidine-3-carboxylate hydrochloride (725 mg, 4.38 mmol) and DIPEA, (723 mg, 5.11 mmol) in acetonitrile (10 mL). The mixture was stirred at 100° C. for 1 h. The reaction was quenched with saturated aqueous NH₄Cl, extracted with DCM (50 mL×3). The combined organic layers were washed with brine, dried over Na₂SO₄, concentrated to give the crude, which was purified by silica gel chromatography (MeOH/DCM=1/30) to give tert-butyl 1-((6-chloro-8-(3-(methoxycarbonyl)pyrrolidin-1-yl)imidazo[1,2-b]pyridazin-2-yl)methyl)-1H-1,2,3-triazole-4-carboxylate (250 mg, yield: 74.6%) as a white solid. ESI-MS [M+H]+: 462.1

Synthesis of tert-butyl 1-((6-cyclopropyl-8-(3-(methoxycarbonyl)pyrrolidin-1-yl)imidazo[1,2-b]pyridazin-2-yl)methyl)-1H-1,2,3-triazole-4-carboxylate To the solution of tert-butyl 1-((6-chloro-8-(3-(methoxycarbonyl)pyrrolidin-1-yl)imidazo[1,2-b]pyridazin-2-yl)methyl)-1H-1,2,3-triazole-4-carboxylate (250 mg, 0.54 mmol), cyclopropylboronic acid (140 mg, 1.62 mmol), SPhos (22 mg, 0.05 mmol), Pd(OAc)₂ (12 mg, 0.05 mmol) and K₃PO₄ (345 mg, 1.62 mmol) in toluene/H₂O (10 mL/1 mL). The mixture was stirred at 90° C. for 16 h. The reaction was concentrated to give the crude, which was purified by silica gel chromatography (MeOH/DCM=1/20) to give tert-butyl 1-((6-cyclopropyl-8-(3-(methoxycarbonyl)pyrrolidin-1-yl)imidazo[1,2-b]pyridazin-2yl)methyl)-1H-1,2,3-triazole-4-carboxylate (200 mg, yield: 79.0%) as a white solid. ESI-MS [M+H]+: 468.2

Synthesis of 1-((6-cyclopropyl-8-(3-(methoxycarbonyl)pyrrolidin-1-yl)imidazo[1,2-b]pyridazin-2-yl)methyl)-1H-1,2,3-triazole-4-carboxylic Acid To the solution tert-butyl 1-((6-cyclopropyl-8-(3-(methoxycarbonyl)pyrrolidin-1-yl)imidazo[1,2-b]pyridazin-2-yl)methyl)-1H-1,2,3-triazole-4-carboxylate (200 mg, 0.43 mmol) in DCM (5 mL) was added TFA (1 mL). The resulting mixture was stirred at 25° C. for 2 h. The reaction was concentrated to give 1-((6-cyclopropyl-8-(3-(methoxycarbonyl)pyrrolidin-1-yl)imidazo[1,2-b]

pyridazin-2-yl)methyl)-1H-1,2,3-triazole-4-carboxylic acid (210 mg, crude) as yellow oil, which was used into next step without further purification. ESI-MS [M+H]+: 412.1

Synthesis of Methyl 1-(2-((4-(((7-chloro-8-fluoro-imidazo[1,5-a]pyridin-1-yl)methyl)carbamoyl)-1H-1,2,3-triazol-1-yl)methyl)-6-cyclopropylimidazo[1,2-b]pyridazin-8-yl)pyrrolidine-3-carboxylate (I-266)

To the solution of 1-((6-cyclopropyl-8-(3-(methoxycarbonyl)pyrrolidin-1-yl)imidazo[1,2-b]pyridazin-2-yl)methyl)-1H-1,2,3-triazole-4-carboxylic acid (210 mg, crude from previous step), (7-chloro-8-fluoroimidazo[1,5-a]pyridin-1-yl)methanamine hydrochloride (132 mg, 0.56 mmol) in DMF (10 mL) was added HOBT (104 mg, 0.77 mmol), EDCI (148 mg, 0.77 mmol) and DIPEA (300 mg, 2.28 mmol). The resulting reaction mixture was stirred at 25° C. for 16 h. H$_2$O (40 mL) was added to the reaction, extracted with EtOAc (50 mL×3). The combined organic layers were washed with brine, dried over Na$_2$SO$_4$, concentrated to give the crude, which was purified by Prep-HPLC to give methyl 1-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-b]pyridazin-8-yl)pyrrolidine-3-carboxylate (70 mg, yield: 26% over 2 steps) as a white solid. ESI-MS [M+H]+: 593.2. Purity: 99.08% (214 nm), 99.10% (254 nm). $^1$H NMR (400 MHz, DMSO-d$_6$) δ 8.68 (t, J=5.4 Hz, 1H), 8.50 (s, 1H), 8.44 (d, J=2.3 Hz, 1H), 8.20 (d, J=7.4 Hz, 1H), 7.93 (s, 1H), 6.76 (t, J=6.9 Hz, 1H), 5.77 (s, 1H), 5.67 (s, 2H), 4.69 (d, J=5.5 Hz, 2H), 4.01 (s, 2H), 3.81 (s, 2H), 3.65 (s, 3H), 3.29 (s, 1H), 2.27-2.19 (m, 1H), 2.19-2.10 (m, 1H), 2.00-1.91 (m, 1H), 0.94-0.86 (m, 4H).

Example 267

Scheme 266

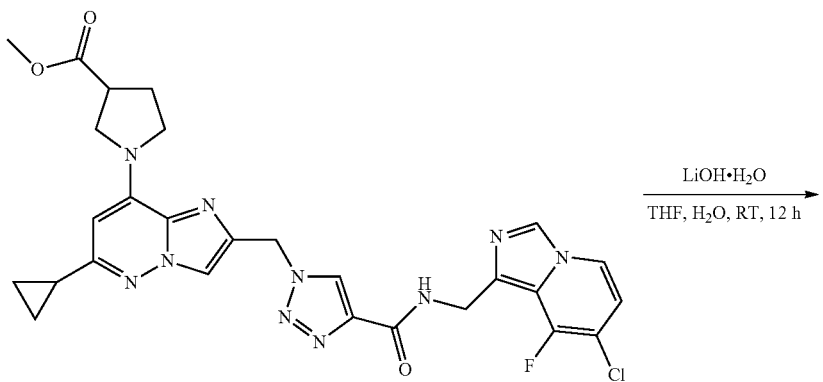

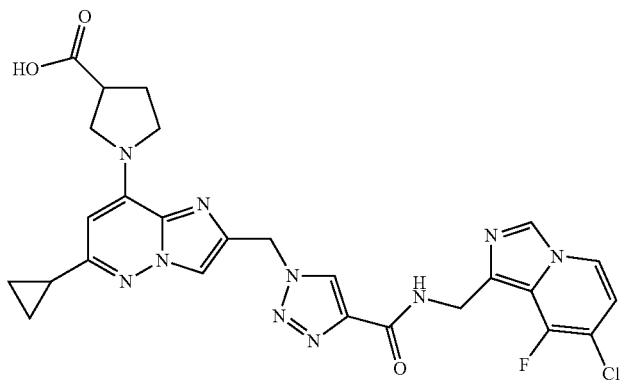

I-267

601

Synthesis of 1-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-b]pyridazin-8-yl)pyrrolidine-3-carboxylic acid (I-267)

To the solution of methyl 1-(2-((4-(((7-chloro-8-fluoroimidazo[1,5-a]pyridin-1-yl)methyl) carbamoyl)-1H-1,2,3-triazol-1-yl)methyl)-6-cyclopropylimidazo[1,2-b]pyridazin-8-yl)pyrrolidine-3-carboxylate (56 mg, 0.09 mmol) in THF/H$_2$O (4 mL/2 mL) was added LiOH.H$_2$O (12 mg, 0.28 mmol). The reaction mixture was stirred at 25° C. for 2 h, The pH of reaction was adjusted to 4 by HCl (1N) and the mixture were concentrated to give the crude, which was purified by Prep-HPLC to give 1-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-b]pyridazin-8-yl)pyrrolidine-3-carboxylic acid (15 mg, yield: 28%) as a white solid. ESI-MS [M+H]$^+$: 579.1. Purity: 92.22% (214 nm), 95.13% (254 nm). $^1$H NMR (400 MHz, DMSO-d$_6$) S=8.68 (s, 1H), 8.50 (s, 1H), 8.44 (s, 1H), 8.20 (d, J=7.3, 1H), 7.92 (s, 1H), 6.76 (t, J=7.2 Hz, 1H), 5.75-5.67 (m, 2H), 4.69 (d, J=5.4, 2H), 4.00 (s, 2H), 3.77 (s, 2H), 3.12 (s, 1H), 2.17-1.95 (m, 3H), 0.98-0.89 (m, 4H).

Example 268

Scheme 267

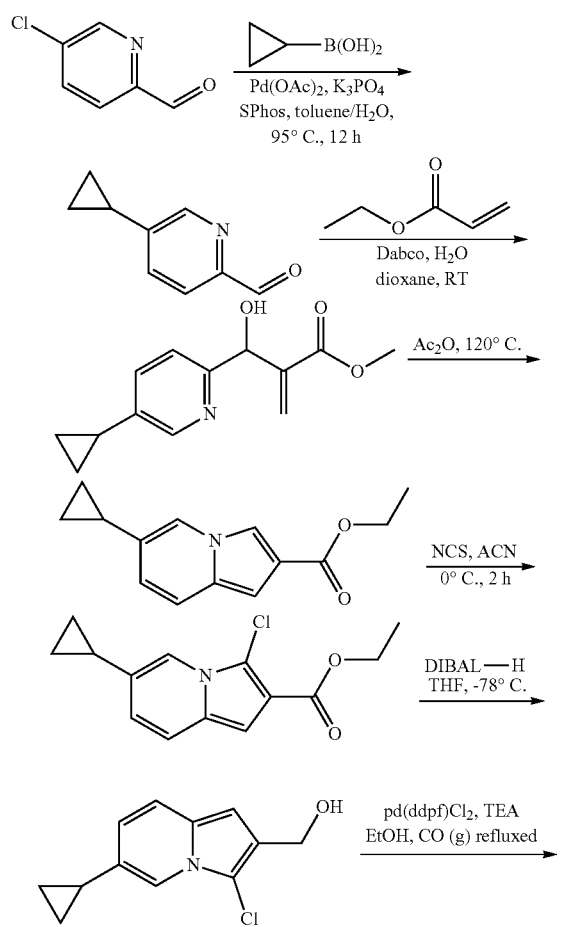

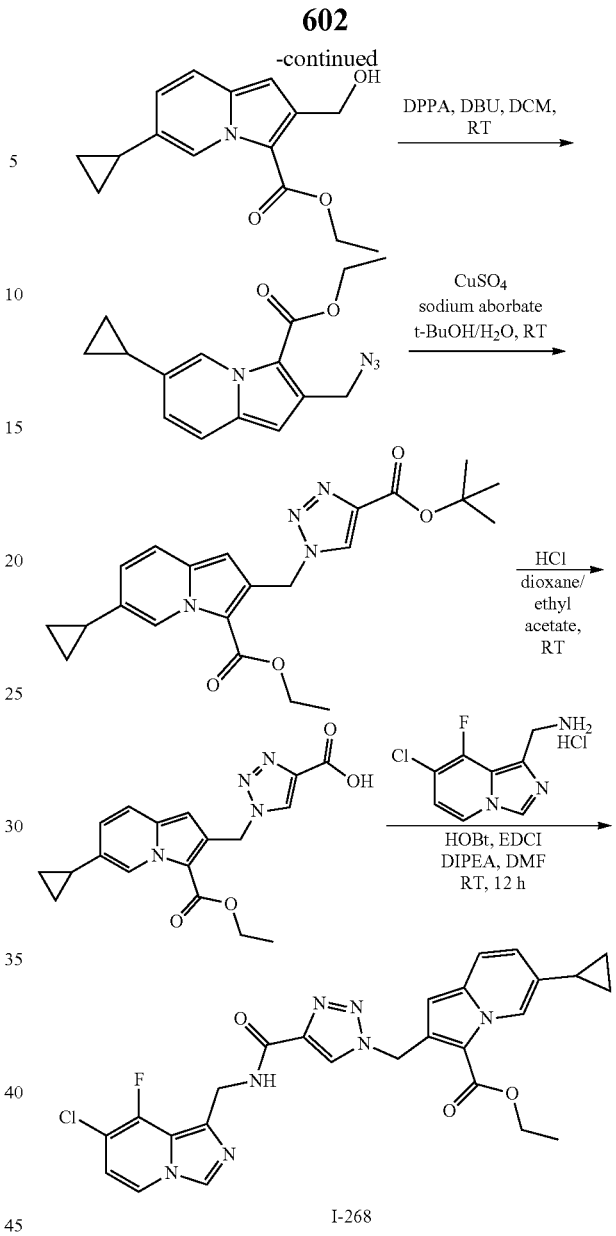

I-268

Synthesis of 5-cyclopropylpicolinaldehyde

A mixture of 5-chloropicolinaldehyde (10.0 g, 71 mmol), cyclopropylboronic acid (8.5 g, 99 mmol), Pd(OAc)$_2$ (1.6 g, 7.1 mmol), SPhos (5.8 g, 14.2 mmol) and K$_3$PO$_4$ (45 g, 213 mmol) in toluene (200 mL) and H$_2$O (30 mL) was stirred at 100° C. for 16 h. Toluene was evaporated, H$_2$O (100 mL) was added and extracted by EtOAc (100 mL×3). The combined organic layers were washed by H$_2$O and brine, dried over Na$_2$SO$_4$, filtered and concentrated to crude, which was purified by column chromatography on silica gel (PE:EA=5:1) to give the 5-cyclopropylpicolinaldehyde (7.4 g, yield: 71%), as a white solid. ESI-MS [M+H]$^+$: 148.1

Synthesis of Methyl 2-((5-cyclopropylpyridin-2-yl)(hydroxy)methyl)acrylate

A solution of 5-cyclopropylpicolinaldehyde (7.4 g, 50 mmol), ethyl acrylate (20 g, 200 mmol) and Dabco (5.6 g, 50 mmol) in 1,4-dioxane (100 mL) and H$_2$O (100 mL) was stirred at RT for 4 h. Water (50 mL) was added to the reaction and extracted by EtOAc (100 mL×3). The combined organic layers were washed by brine, dried over Na$_2$SO$_4$ and concentrated to give crude, which was purified by column chromatography on silica gel (PE:EA=3:1) to give methyl 2-((5-cyclopropylpyridin-2-yl)(hydroxy) methyl)acrylate (10.4 g, 84%), ESI-MS [M+H]$^+$: 248.1

Synthesis of Ethyl 6-cyclopropylindolizine-2-carboxylate

A mixture of 2-((5-cyclopropylpyridin-2-yl)(hydroxy) methyl)acrylate (9.4 g, 38.0 mmol) in Ac$_2$O (100 mL) was stirred at 130° C. for 1 h. Then Ac$_2$O was removed under reduce press to give the crude, which was purified by column chromatography on silica gel (PE:EA=10:1) to obtain ethyl 6-cyclopropylindolizine-2-carboxylate (5.49 g, yield: 63.0%). ESI-MS [M+H]$^+$: 230.1

Synthesis of Ethyl 3-chloro-6-cyclopropylindolizine-2-carboxylate

A mixture of ethyl 6-cyclopropylindolizine-2-carboxylate (1.5 g, 6.6 mmol) and NCS (1.05 g, 7.9 mmol) in CH$_3$CN (30 mL) was stirred at RT for 2 h. Then saturated aqueous NaHCO$_3$ was added to the reaction, extracted with EtOAc (70 mL×3). The combined organic layers were washed with brine, dried over Na$_2$SO$_4$, filtered, and concentrated to give the crude, which was purified by column chromatography on silica gel (PE:EA=20:1) to give ethyl 3-chloro-6-cyclopropylindolizine-2-carboxylate (900 mg, yield: 52%). ESI-MS [M+H]$^+$: 264.1

Synthesis of (3-chloro-6-cyclopropylindolizin-2-yl)methanol

A mixture of ethyl 3-chloro-6-cyclopropylindolizine-2-carboxylate (1.5 g, 5.7 mmol) in THF (25 mL) was added DIBAL-H (14 mL, 1 M, 14.25 mmol) dropwise at 0° C. The reaction was stirred at 0° C. for 2 h. The reaction was quenched with NH$_4$Cl solution (30 mL) and extracted with EtOAc (50 mL×3). The combined organic layers were concentrated to give (3-chloro-6-cyclopropylindolizin-2-yl) methanol (1 g, crude), which was used into next step without further purification. ESI-MS [M+H]$^+$: 222.1

Synthesis of Ethyl 6-cyclopropyl-2-(hydroxymethyl) indolizine-3-carboxylate

A mixture of (3-chloro-6-cyclopropylindolizin-2-yl) methanol (1 g, crude), Pd(dppf)Cl$_2$ (329 mg, 0.45 mmol) and TEA (1.36 g, 13.5 mmol) in EtOH (40 mL) was refluxed under CO for 24 h. The reaction was concentrated to give the crude, which was purified by column chromatography on silica gel (PE:EA=10:1) to obtain ethyl 6-cyclopropyl-2-(hydroxymethyl) indolizine-3-carboxylate (248 mg, yield: 17% over 2 steps). ESI-MS [M+H]$^+$: 260.1

Synthesis of Ethyl 2-(azidomethyl)-6-cyclopropylindolizine-3-carboxylate

To a mixture of ethyl 6-cyclopropyl-2-(hydroxymethyl) indolizine-3-carboxylate (248 mg, 0.95 mmol) and DPPA (790 mg, 2.87 mmol) in DCM (8.0 mL) was added DBU (436 mg, 2.87 mmol) dropwise at 0° C. The resulting mixture was stirred at RT for 16 h. The reaction was concentrated in vacuo to give the crude, which was purified by column chromatography on silica gel (PE:EA=10:1), obtained ethyl 2-(azidomethyl)-6-cyclopropylindolizine-3-carboxylate (203 mg, yield: 75%). ESI-MS [M+H]$^+$: 285.1

Synthesis of Ethyl 2-((4-(tert-butoxycarbonyl)-1H-1,2,3-triazol-1-yl)methyl)-6-cyclopropylindolizine-3-carboxylate A reaction mixture of ethyl 2-(azidomethyl)-6-cyclopropylindolizine-3-carboxylate (203 mg, 0.71 mmol), tert-butyl propiolate (120 mg, 0.94 mmol), CuSO$_4$ (150 mg, 0.94 mmol) and sodium ascorbate (681 mg, 3.44 mmol) in t-BuOH (8 mL) and H$_2$O (4 mL) was stirred at RT for 16 h. H$_2$O (30 mL) was added to the reaction, extracted with EtOAc (30 mL×3). The combined organic layers were dried by Na$_2$SO$_4$, filtered, and concentrated to give the crude, which was purified by column chromatography on silica gel (PE:EA=10:1) to obtain ethyl 2-((4-(tert-butoxycarbonyl)-1H-1,2,3-triazol-1-yl)methyl)-6-cyclopropylindolizine-3-carboxylate (204 mg, yield: 70%). ESI-MS [M+H]$^+$: 411.1

Synthesis of 1-((6-cyclopropyl-3-(ethoxycarbonyl) indolizin-2-yl)methyl)-1H-1,2,3-triazole-4-carboxylic Acid A reaction mixture of ethyl 2-((4-(tert-butoxycarbonyl)-1H-1,2,3-triazol-1-yl)methyl)-6-cyclopropylindolizine-3-carboxylate (203 mg, 0.5 mmol) in HCl (2 M in 1,4-dioxane, 6 mL) and EtOAc (2 mL) was stirred at RT for 3 h. The reaction was concentrated to give the crude, which was purified by Prep-HPLC to obtain 1-((6-cyclopropyl-3-(ethoxycarbonyl) indolizin-2-yl)methyl)-1H-1,2,3-triazole-4-carboxylic acid (41 mg, yield: 23%). ESI-MS [M+H]$^+$: 355.1

Synthesis of Ethyl 2-((4-(((7-chloro-8-fluoroimidazo[1,5-a]pyridin-1-yl)methyl)carbamoyl)-1H-1,2,3-triazol-1-yl)methyl)-6-cyclopropylindolizine-3-carboxylate (I-268)

A mixture of 1-((6-cyclopropyl-3-(ethoxycarbonyl) indolizin-2-yl)methyl)-1H-1,2,3-triazole-4-carboxylic acid (41 mg, 0.12 mmol), (7-chloro-8-fluoroimidazo[1,5-a]pyridin-1-yl)methanamine hydrochloride (49 mg, 0.21 mmol), HOBT (41 mg, 0.3 mmol), EDCI (58 mg, 0.3 mmol), and DIPEA (77 mg, 0.6 mmol) in DMF (2 mL) was stirred at RT for 16 h. Water (30 mL) was added to the reaction, extracted by EtOAc (30 mL×3). The combined organic layers were washed by brine, dried over Na$_2$SO$_4$, filtered, and concentrated to give the crude, which was purified by Prep-TLC (DCM:MeOH=10:1) to obtain ethyl 2-((4-(((7-chloro-8-fluoroimidazo[1,5-a]pyridin-1-yl)methyl)carbamoyl)-1H-1,2,3-triazol-1-yl)methyl)-6-cyclopropylindolizine-3-carboxylate (28 mg, yield: 44%). ESI-MS [M+H]$^+$: 536.1. Purity: 93.82% (214 nm), 99.00% (254 nm). $^1$H NMR (400 MHz, DMSO-d$_6$) δ 9.23 (s, 1H), 8.72 (t, J=6.0 Hz, 1H), 8.52 (s, 1H), 8.45 (d, J=4 Hz, 1H), 8.21 (d, J=8.0 Hz, 1H), 7.56 (d, J=12 Hz, 1H), 6.92-6.89 (m, 1H), 6.76 (t, J=6.0 Hz, 1H), 6.14 (s, 1H) 5.95 (s, 2H), 4.70 (d, J=4.0 Hz, 2H), 4.33 (q, J=6.6 Hz, 2H), 2.02-1.97 (m, 1H), 1.31 (t, J=8 Hz, 3H), 0.97-0.94 (m, 2H), 0.71-0.67 (m, 2H).

Example 269

Scheme 268

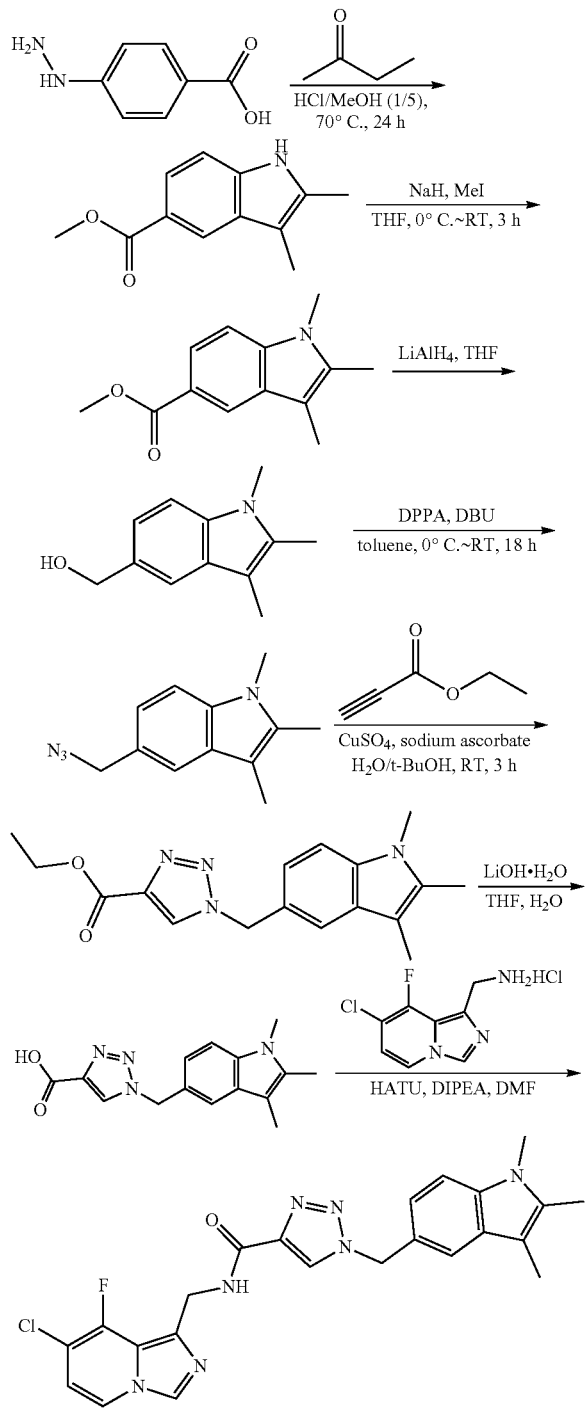

I-269

Synthesis of Methyl 2,3-dimethyl-1H-indole-5-carboxylate

A mixture of 4-hydrazinylbenzoic acid (3.04 g, 20.0 mmol) and butan-2-one (2.88 g, 40.0 mmol) in HCl/MeOH (5 mL/30 mL) was stirred at 70° C. for 24 h. The mixture was concentrated and purified by silica gel column chromatography (DCM/MeOH=40/1) to give methyl 2,3-dimethyl-1H-indole-5-carboxylate (2.50 g, yield: 61.6%) as a yellow solid. ESI-MS [M+H]$^+$: 204.1

Synthesis of Methyl 1,2,3-trimethyl-1H-indole-5-carboxylate

To a mixture of methyl 2,3-dimethyl-1H-indole-5-carboxylate (2.3 g, 11.33 mmol) in dry THF (25 mL) was added NaH (1.05 g, 60 wt %, 15.86 mmol) at 0° C. After 0.5 h, MeI (0.85 mL, 13.60 mmol) in THF (5 mL) was added and stirred at RT for 3 h. The reaction was quenched with 2 M H$_2$O (50 mL) and the pH value was adjusted to 6. The mixture was extracted EtOAc (50 mL×3). The combined organic layers were concentrated and purified by silica gel column chromatography (PE/EA=9/1) to give methyl 1,2,3-trimethyl-1H-indole-5-carboxylate (1.80 g, 73%) as a yellow solid. ESI-MS [M+H]$^+$: 218.1.

Synthesis of (1,2,3-trimethyl-1H-indol-5-yl)methanol

To a mixture of methyl 1,2,3-trimethyl-1H-indole-5-carboxylate (1.6 g, 7.37 mmol) in dry THF (30 mL) was stirred LiAlH$_4$ (336.0 mg, 8.8 mmol) at 0° C. under N$_2$. The mixture was stirred at 0° C. for 2 h. It was quenched with H$_2$O (5 mL) and filtered. The filtrate was concentrated and dried to give (1,2,3-trimethyl-1H-indol-5-yl)methanol (1.4 g, crude) as a light yellow solid. ESI-MS [M+H]$^+$: 190.1. It was used for the next step directly without purification.

Synthesis of 5-(azidomethyl)-1,2,3-trimethyl-1H-indole

To a mixture of (1,2,3-trimethyl-1H-indol-5-yl)methanol (800 mg, crude) and DPPA (2.7 mL, 12.70 mmol) in dry DCM (20.0 mL) was added DBU (1.9 mL, 12.70 mmol) at 0° C. slowly. The mixture was stirred at RT for 18 h. Then diluted with DCM (50 mL) and washed with H$_2$O (50 mL). The organic layer was concentrated and purified by silica gel column chromatography (PE/EA=10/1) to give 5-(azidomethyl)-1,2,3-trimethyl-1H-indole as a yellow solid. (350 mg). ESI-MS [M+H]$^+$: 215.1.

Synthesis of Ethyl 1-((1,2,3-trimethyl-1H-indol-5-yl)methyl)-1H-1,2,3-triazole-4-carboxylate A mixture of 5-(azidomethyl)-1,2,3-trimethyl-1H-indole (350 mg, 1.63 mmol), ethyl propiolate (208 mg, 2.13 mmol), CuSO$_4$ (130 mg, 0.82 mmol) and sodium ascorbate (162 mg, 0.82 mmol) in H$_2$O/t-BuOH (5.0 mL/5.0 mL) was stirred at RT for 3 h. The mixture was concentrated and purified by flash silica gel chromatography (DCM/MeOH=25/1) to give ethyl 1-((1,2,3-trimethyl-1H-indol-5-yl)methyl)-1H-1,2,3-triazole-4-carboxylate (250 mg, yield: 49%) as a yellow solid. ESI-MS [M+H]$^+$: 313.1.

Synthesis of 1-((1,2,3-trimethyl-1H-indol-5-yl)methyl)-1H-1,2,3-triazole-4-carboxylic Acid A solution of ethyl 1-((1,2,3-trimethyl-1H-indol-5-yl)methyl)-1H-1,2,3-triazole-4-carboxylate (100.0 mg, 0.32 mmol) and LiOH.H$_2$O (40.3 mg, 0.96 mmol) in a mixed solvent of THF/H$_2$O (2 mL/2 mL) was stirred at RT for 3 h. The pH value was adjusted to 3 by 1 M HCl solution and the white solid was participated. The solid was filtered and dried to give 1-((1,2,3-trimethyl-1H-indol-5-yl)methyl)-1H-1,2,3-triazole-4-carboxylic acid (60.0 mg, yield: 66%) as a white solid. ESI-MS [M+H]+: 285.1.

Synthesis of N-((7-chloro-8-fluoroimidazo[1,5-a]pyridin-1-yl)methyl)-1-((1,2,3-trimethyl-1H-indol-5-yl)methyl)-1H-1,2,3-triazole-4-carboxamide (I-269)

A mixture of 1-((1,2,3-trimethyl-1H-indol-5-yl)methyl)-1H-1,2,3-triazole-4-carboxylic acid (60.0 mg, 0.21 mmol), (7-chloro-8-fluoroimidazo[1,5-a]pyridin-1-yl)methanamine hydrochloride (58.8 mg, 0.25 mmol), HATU (119.7 mg, 0.315 mmol) and DIPEA (135.5 mg, 1.05 mmol) in DMF (5 mL) was stirred at RT for 16 h. The mixture was concentrated and purified by Prep-HPLC to give N-((7-chloro-8-fluoroimidazo[1,5-a]pyridin-1-yl)methyl)-1-((1,2,3-trimethyl-1H-indol-5-yl)methyl)-1H-1,2,3-triazole-4-carboxamide (30.0 mg, yield: 31%) as a white solid. ESI-MS [M+H]+: 466.1. Purity: 99.4% (214 nm), 98.6% (254 nm). 1H NMR (400 MHz, DMSO-$d_6$) δ 8.66 (t, J=5.4 Hz, 1H), 8.54 (s, 1H), 8.43 (s, 1H), 8.20 (d, J=7.4 Hz, 1H), 7.47 (s, 1H), 7.32 (d, J=8.4 Hz, 1H), 7.07 (dd, J=8.4, 1.5 Hz, 1H), 6.80-6.68 (m, 1H), 5.65 (s, 2H), 4.68 (d, J=5.5 Hz, 2H), 3.61 (s, 3H), 2.31 (s, 3H), 2.17 (s, 3H).

Example 270

Scheme 269

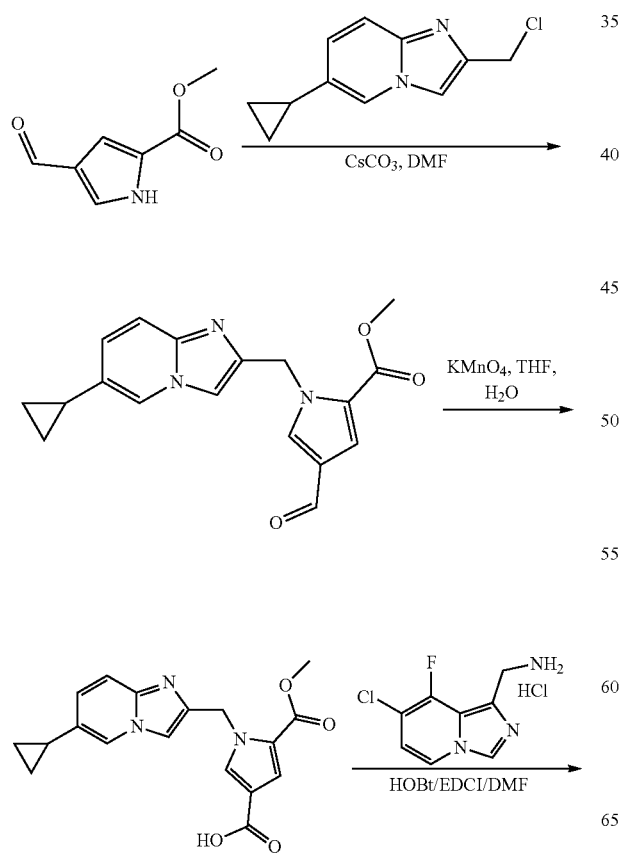

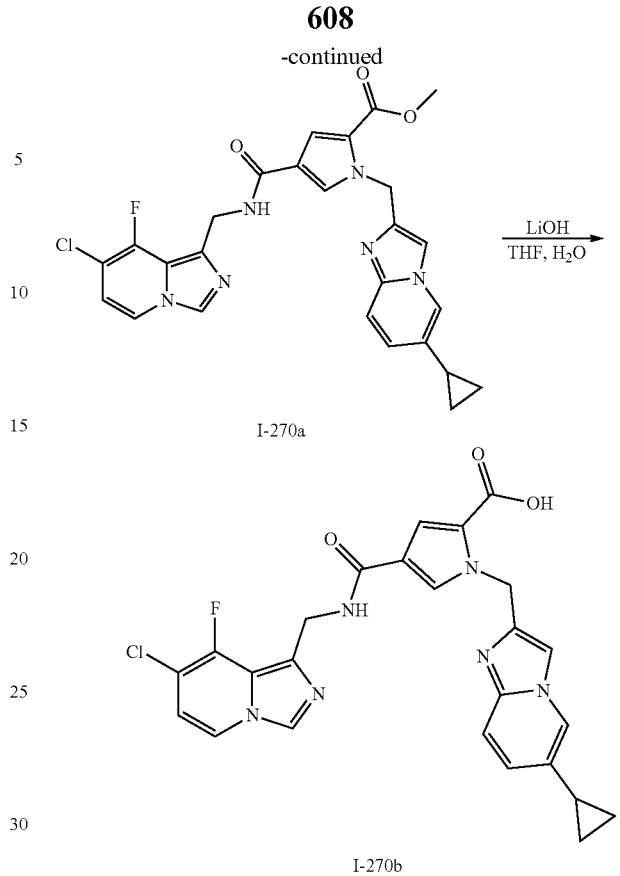

Synthesis of Methyl 1-((6-cyclopropylimidazo[1,2-a]pyridin-2-yl)methyl)-4-formyl-1H-pyrrole-2-carboxylate A mixture of methyl 4-formyl-1H-pyrrole-2-carboxylate (0.2 g, 1.3 mmol) and 2-(chloromethyl)-6-cyclopropylimidazo[1,2-a]pyridine (0.14 g, 1.7 mmol) in DMF (5 mL) was stirred at 25° C. for 3 h. Water (30 mL) was added to the reaction, and extracted with EtOAc (20 mL×3). The combined organic layers was washed with brine, dried over Na2SO4, concentrated to give the crude, which was purified by silica gel chromatography (PE/EA=1/1) to give methyl 1-((6-cyclopropylimidazo[1,2-a]pyridin-2-yl)methyl)-4-formyl-1H-pyrrole-2-carboxylate (251 mg, yield: 59%) as a pale solid. ESI-MS [M+H]+: 324.0.

Synthesis of 1-((6-cyclopropylimidazo[1,2-a]pyridin-2-yl)methyl)-5-(methoxycarbonyl)-1H-pyrrole-3-carboxylic Acid A solution of methyl 1-((6-cyclopropylimidazo[1,2-a]pyridin-2-yl)methyl)-4-formyl-1H-pyrrole-2-carboxylate (0.2 g, 0.62 mmol) and KMnO4 (0.15 g, 0.93 mmol) in THF (10 mL) and H2O (10 mL). was stirred at 25° C. for 5 h. The reaction mixture was filtered and the filtrate was concentrated to give the crude, which was purified by silica gel chromatography (DCM/MeOH=15/1) to give 1-((6-cyclopropylimidazo[1,2-a]pyridin-2-yl)methyl)-5-(methoxycarbonyl)-1H-pyrrole-3-carboxylic acid (0.2 g, yield: 95.6%) as a white solid. ESI-MS [M+H]+: 340.1.

Synthesis of Methyl 4-(((7-chloro-8-fluoroimidazo[1,5-a]pyridin-1-yl)methyl)carbamoyl)-1-((6-cyclopropylimidazo[1,2-a]pyridin-2-yl)methyl)-1H-pyrrole-2-carboxylate (I-270a)

To a solution of 1-((6-cyclopropylimidazo[1,2-a]pyridin-2-yl)methyl)-5-(methoxycarbonyl)-1H-pyrrole-3-carboxylic acid (0.2 g, 0.6 mmol) was added (7-chloro-8-fluoroimidazo[1,5-a]pyridin-1-yl)methanamine hydrochloride (0.2 g, 0.9 mmol), HOBT (0.86 g, 0.72 mmol), EDCI (0.14 g, 0.72 mmol) and DIPEA (0.22 g, 1.8 mmol) in DMF (10 mL). The mixture was stirred at 25° C. for 16 h. The solvent was removed by vacuo to give the crude, which was purified by Prep-HPLC to give methyl 4-(((7-chloro-8-fluoroimidazo[1,5-a]pyridin-1-yl)methyl)carbamoyl)-1-((6-cyclopropylimidazo[1,2-a]pyridin-2-yl)methyl)-1H-pyrrole-2-carboxylate (100 mg, yield: 33.3%) as a white solid. ESI-MS [M+H]$^+$: 521.1. Purity: 96.18% (214 nm), 96.94 (254 nm). $^1$H NMR (400 MHz, DMSO-d$_6$) δ 8.44 (d, J=2.4 Hz, 1H), 8.40 (t, J=5.2 Hz, 1H), 8.30 (s, 1H), 8.20 (t, J=6.0 Hz, 1H), 7.72 (d, J=1.9 Hz, 1H), 7.56 (s, 1H), 7.37 (t, J=5.7 Hz, 2H), 6.98 (dd, J=9.4, 1.8 Hz, 1H), 6.76 (dd, J=7.2, 6.6 Hz, 1H), 5.59 (s, 2H), 4.62 (t, J=3.5 Hz, 2H), 3.73 (s, 3H), 1.95-1.84 (m, 1H), 0.94-0.85 (m, 2H), 0.69-0.61 (m, 2H).

Synthesis of 4-(((7-chloro-8-fluoroimidazo[1,5-a]pyridin-1-yl)methyl)carbamoyl)-1-((6-cyclopropylimidazo[1,2-a]pyridin-2-yl)methyl)-1H-pyrrole-2-carboxylic acid (I-270b)

To a solution of methyl 4-(((7-chloro-8-fluoroimidazo[1,5-a]pyridin-1-yl)methyl)carbamoyl)-1-((6-cyclopropylimidazo[1,2-a]pyridin-2-yl)methyl)-1H-pyrrole-2-carboxylate (60 mg, 0.12 mmol was added LiOH (0.02 g, 0.6 mmol) in THF (5 mL) and H$_2$O (5 mL). The mixture was stirred for 4 h at 25° C. The reaction was concentrated to remove the THF. The pH of the residue was acidified with HCl (1N) and white solid was precipitated. The mixture was filtered and dried to give 4-(((7-chloro-8-fluoroimidazo[1,5-a]pyridin-1-yl)methyl)carbamoyl)-1-((6-cyclopropylimidazo[1,2-a]pyridin-2-yl)methyl)-1H-pyrrole-2-carboxylic acid (46 mg, yield: 75%) as a white solid. ESI-MS [M+H]$^+$: 507.1. Purity: 97.86% (214 nm), 98.12% (254 nm). $^1$H NMR (400 MHz, DMSO-d$_6$) δ 8.49 (s, 1H), 8.45 (d, J=2.4 Hz, 1H), 8.40 (t, J=5.2 Hz, 1H), 8.21 (d, J=7.4 Hz, 1H), 7.79-7.68 (m, 2H), 7.59 (d, J=9.4 Hz, 1H), 7.35-7.33 (m, 2H), 6.82-6.72 (m, 1H), 5.70 (s, 2H), 4.63 (d, J=5.2 Hz, 2H), 2.05-1.90 (m, 1H), 1.03-0.90 (m, 2H), 0.76-0.64 (m, 2H).

Example 271

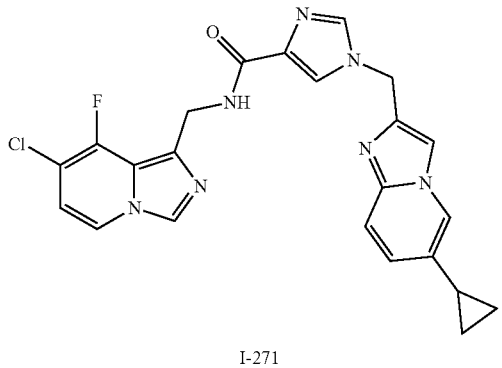

I-271

Synthesis of N-((7-chloro-8-fluoroimidazo[1,5-a]pyridin-1-yl)methyl)-1-((6-cyclopropylimidazo[1,2-a]pyridin-2-yl)methyl)-1H-imidazole-4-carboxamide (I-271)

A mixture of 4-(((7-chloro-8-fluoroimidazo[1,5-a]pyridin-1-yl)methyl)carbamoyl)-1-((6-cyclopropylimidazo[1,2-a]pyridin-2-yl)methyl)-1H-imidazole-2-carboxylic acid (10 mg, 0.02 mmol) in DMSO (1 mL) was stirred at RT for 48 h. Water (10 mL) was added and the mixture was extracted with EtOAc (10 mL×3). The combined organic layers were washed with brine and dried over Na$_2$SO$_4$. After concentrated, the residue was purified by Prep-TLC (MeOH/DCM=10/1) to give N-((7-chloro-8-fluoroimidazo[1,5-a]pyridin-1-yl)methyl)-1-((6-cyclopropylimidazo[1,2-a]pyridin-2-yl)methyl)-1H-imidazole-4-carboxamide (6.0 mg, yield: 66%) as a white solid. ESI-MS [M−H]$^−$: 464.1. Purity: 100% (214 nm), 99.7% (254 nm). $^1$H NMR (400 MHz, DMSO-d$_6$) δ 8.45 (d, J=2.4 Hz, 1H), 8.33 (s, 1H), 8.20 (d, J=7.4 Hz, 1H), 8.01 (t, J=5.5 Hz, 1H), 7.79 (d, J=1.2 Hz, 1H), 7.73 (s, 1H), 7.70 (d, J=1.2 Hz, 1H), 7.40 (d, J=9.3 Hz, 1H), 7.00 (dd, J=9.4, 1.7 Hz, 1H), 6.79-6.72 (m, 1H), 5.31 (s, 2H), 4.67 (d, J=5.5 Hz, 2H), 1.99-1.88 (m, 1H), 0.94-0.89 (m, 2H), 0.71-0.58 (m, 2H).

Example 272

Scheme 270

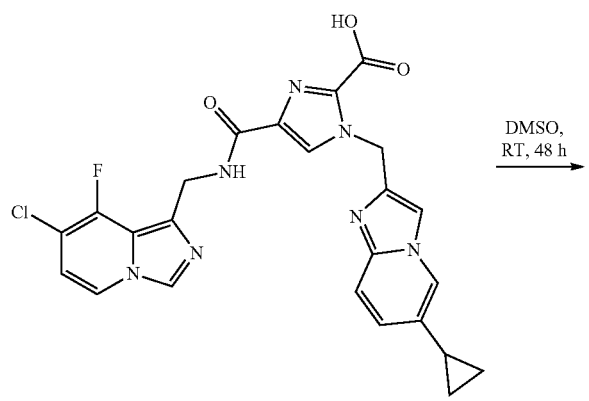

Scheme 271

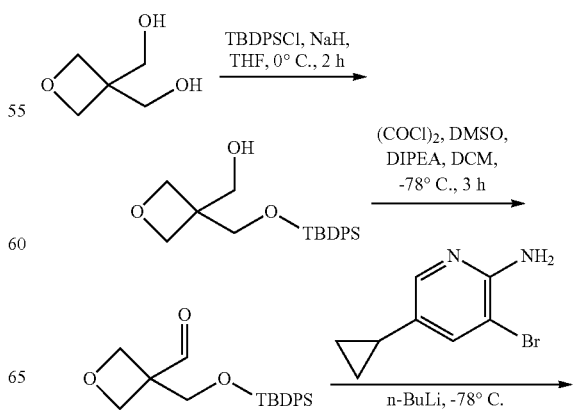

-continued

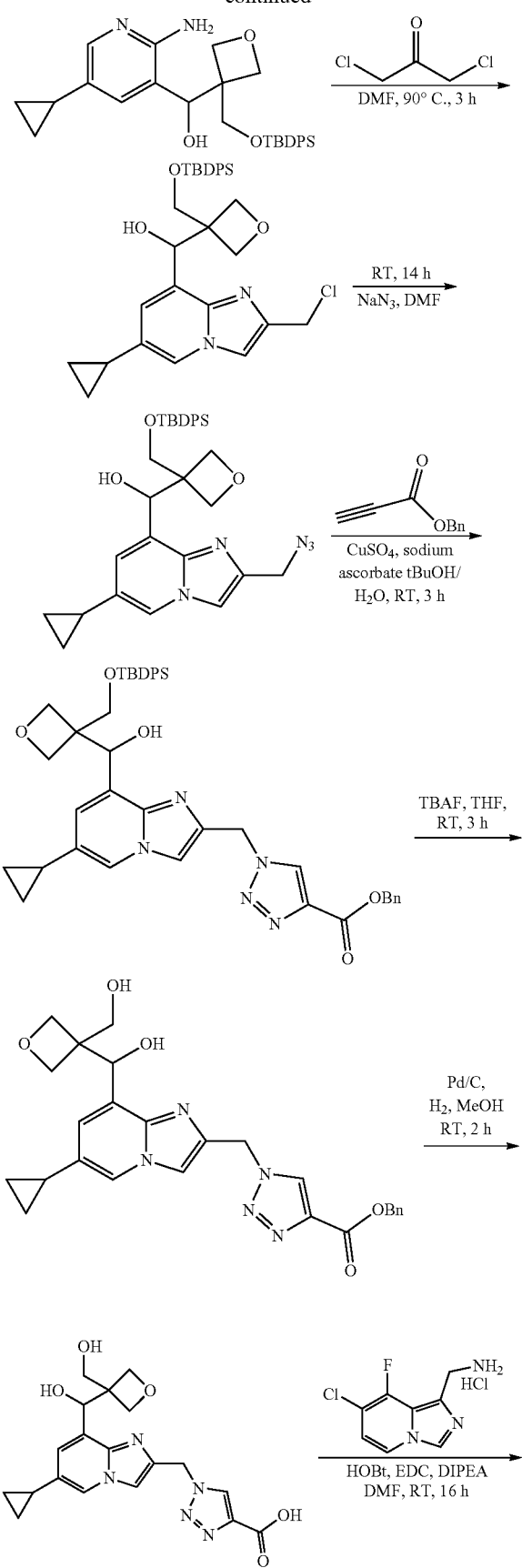

-continued

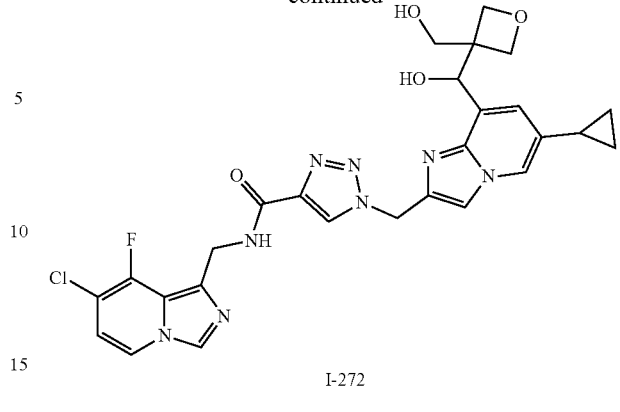

I-272

Synthesis of (3-(((tert-butyldiphenylsilyl)oxy) methyl)oxetan-3-yl)methanol

To a solution of oxetane-3,3-diyldimethanol (2.36 g, 20 mmol) in THF (120 mL) was added NaH (800 mg, 60% suspension in paraffin oil, 20 mmol) slowly at 0° C. The mixture was stirred at 0° C. for 30 min. Then a solution of TBDPSCl (5.48 g, 20 mmol) in THF (20 mL) was added to the reaction. The reaction was stirred at RT for 1 h. H$_2$O (150 mL) was added and the mixture was extracted with EtOAc (150 mL×3). The combined organic layers were washed with brine, dried over Na$_2$SO$_4$, and concentrated in vacuo to give (3-(((tert-butyldiphenylsilyl)oxy)methyl)oxetan-3-yl) methanol as a yellow oil, which was used in next step without further purification (6.5 g crude). ESI-MS [M+H]$^+$: 357.1.

Synthesis of 3-(((tert-butyldiphenylsilyl)oxy) methyl)oxetane-3-carbaldehyde

To a solution of oxalyl chloride (3.45 g, 28 mmol) in DCM (100 mL) was added DMSO (2.2 g, 28 mmol, solution in 10 mL DCM) slowly at −78° C. The reaction was stirred for 30 min. Then a solution of (3-(((tert-butyldiphenylsilyl) oxy)methyl)oxetan-3-yl)methanol (6.5 g crude from previous step) was added. The resulting reaction was stirred at −78° C. for 2 h. DIPEA (9.6 mL, 54 mmol) was added thereto. After stirring at −78° C. for 30 min, the reaction was quenched with aqueous saturated NH$_4$Cl (100 mL) and extracted with DCM (100 mL×3). The combined organic layers were washed with brine, dried over Na$_2$SO$_4$, and concentrated in vacuo to give the crude product as a yellow oil which was used into next step without further purification (5.2 g crude). ESI-MS [M+H]$^+$: 355.2.

Synthesis of (2-amino-5-cyclopropylpyridin-3-yl)(3-(((tert butyldiphenylsilyl)oxy)methyl)oxetan-3-yl) methanol To a solution of 3-bromo-5-cyclopropylpyridin-2-amine (1 g, 4.7 mmol) in dry THF (75 mL) was added n-BuLi (5.9 mL, 2.4 M in hexanes, 14 mmol) at −78° C. slowly. After stirring at −78° C. for 30 min, a solution of 3-(((tert-butyldiphenylsilyl)oxy)methyl)oxetane-3-carbaldehyde (5.2 g crude from previous step) in 20 mL THF was added thereto. The reaction was stirred at −78° C. for 1 h. The reaction was quenched with aqueous saturated NH$_4$Cl (100 mL) and extracted with EtOAc (100 mL×3). The combined organic layers were washed with brine, dried over Na$_2$SO$_4$, and concentrated in vacuo to give the crude product, which was purified silica gel chromatography (PE/EtOAc=1/1) to give (2-amino-5-cyclopropylpyridin-3-yl)(3-(((tert-butyldiphenylsilyl)oxy)methyl)oxetan-3-yl)methanol (600 mg, 26% over 2 steps). ESI-MS [M+H]+: 489.1.

Synthesis of (3-(((tert-butyldiphenylsilyl)oxy)methyl)oxetan-3-yl)(2-(chloromethyl)-6-cyclopropylimidazo[1,2-a]pyridin-8-yl)methanol A solution of (2-amino-5-cyclopropylpyridin-3-yl)(3-(((tert-butyldiphenylsilyl)oxy)methyl)oxetan-3-yl)methanol (600 mg, 1.23 mmol) and 1,3-dichloropropan-2-one (465 mg, 3.69 mmol) in DMF (15 mL) was stirred at 90° C. for 3 h. The reaction was quenched with saturated aqueous NaHCO₃ (50 mL) and extracted with EtOAc (75 mL×4). The combined organic layers were washed with brine, dried over Na₂SO₄, and concentrated in vacuo to give the crude product, which was purified with silica gel chromatography (DCM/MeOH=10/1) to give (3-(((tert-butyldiphenylsilyl)oxy)methyl)oxetan-3-yl)(2-(chloromethyl)-6-cyclopropylimidazo[1,2-a]pyridin-8-yl)methanol as yellow oil (350 mg, 50.8%). ESI-MS [M+H]+: 561.2.

Synthesis of (2-(azidomethyl)-6-cyclopropylimidazo[1,2-a]pyridin-8-yl)(3-(((tert-butyldiphenylsilyl)oxy)methyl)oxetan-3-yl)methanol A mixture of (3-(((tert-butyldiphenylsilyl)oxy)methyl)oxetan-3-yl)(2-(chloromethyl)-6-cyclopropylimidazo[1,2-a]pyridin-8-yl)methanol (350 mg, 0.625 mmol) and NaN₃ (81 mg, 1.25 mmol) in DMF (5 mL) was stirred at RT for 14 h. H₂O (50 mL) was added to the reaction, and the mixture was extracted with EtOAc (50 mL×3). The combined organic layers were washed with brine, dried over Na₂SO₄, and concentrated in vacuo to give the crude as a yellow oil which was used in the next step without further purification (360 mg crude). ESI-MS [M+H]+: 568.2.

Synthesis of benzyl 1-((8-((3-(((tert-butyldiphenylsilyl)oxy)methyl)oxetan-3-yl)(hydroxy)methyl)-6-cyclopropylimidazo[1,2-a]pyridin-2-yl)methyl)-1H-1,2,3-triazole-4-carboxylate To a solution of (2-(azidomethyl)-6-cyclopropylimidazo[1,2-a]pyridin-8-yl)(3-(((tert-butyldiphenylsilyl)oxy)methyl)oxetan-3-yl)methanol (360 mg crude) and benzyl propiolate (120 mg, 0.75 mmol) in t-BuOH/H₂O (5 mL/5 mL) was added CuSO₄ (20 mg, 0.125 mmol) and sodium ascorbate (25 mg, 0.125 mmol). The resulting mixture was stirred at RT for 3 h. H₂O (30 mL) was added to the reaction, and the mixture was extracted with EtOAc (50 mL×3). The combined organic layers were washed with brine, dried over Na₂SO₄, and concentrated in vacuo to give the crude product which was purified with Prep-TLC (DCM/MeOH=15/1) to give benzyl 1-((8-((3-(((tert-butyldiphenylsilyl)oxy)methyl)oxetan-3-yl)(hydroxy)methyl)-6-cyclopropylimidazo[1,2-a]pyridin-2-yl)methyl)-1H-1,2,3-triazole-4-carboxylate (400 mg, 88% over 2 steps). ESI-MS [M+H]+: 728.2.

Synthesis of benzyl 1-((6-cyclopropyl-8-(hydroxy(3-(hydroxymethyl)oxetan-3-yl)methyl)imidazo[1,2-a]pyridin-2-yl)methyl)-1H-1,2,3-triazole-4-carboxylate To a solution benzyl 1-((8-((3-(((tert-butyldiphenylsilyl)oxy)methyl)oxetan-3-yl)(hydroxy)methyl)-6-cyclopropylimidazo[1,2-a]pyridin-2-yl)methyl)-1H-1,2,3-triazole-4-carboxylate (200 mg, 0.275 mmol) in THF was added TBAF (0.275 mL, 1 M solution in THF, 0.275 mmol). The resulting reaction was stirred at RT for 3 h. H₂O (30 mL) was added to the reaction, and the mixture was extracted with EtOAc (30 mL×3). The combined organic layers were washed with brine, dried over Na₂SO₄, and concentrated in vacuo to give the crude product which was purified by Prep-TLC (DCM/MeOH=10/1) to give benzyl 1-((6-cyclopropyl-8-(hydroxy(3-(hydroxymethyl)oxetan-3-yl)methyl)imidazo[1,2-a]pyridin-2-yl)methyl)-1H-1,2,3-triazole-4-carboxylate as a yellow solid (81 mg, 60%). ESI-MS [M+H]+: 490.2.

Synthesis of 1-((6-cyclopropyl-8-(hydroxy(3-(hydroxymethyl)oxetan-3-yl)methyl)imidazo[1,2-a]pyridin-2-yl)methyl)-1H-1,2,3-triazole-4-carboxylic Acid A mixture of benzyl 1-((6-cyclopropyl-8-(hydroxy(3-(hydroxymethyl)oxetan-3-yl)methyl)imidazo[1,2-a]pyridin-2-yl)methyl)-1H-1,2,3-triazole-4-carboxylate (81 mg, 0.165 mmol) and Pd/C (10 mg) in MeOH (5 mL) was stirred at RT under H₂ atmosphere for 2 h. The reaction mixture was filtered and the filter cake was washed with MeOH (50 mL). The filtrate was concentrated in vacuo to give 1-((6-cyclopropyl-8-(hydroxy(3-(hydroxymethyl)oxetan-3-yl)methyl)imidazo[1,2-a]pyridin-2-yl)methyl)-1H-1,2,3-triazole-4-carboxylic acid (65 mg, 98%) which was used in the next step directly. ESI-MS [M+H]+: 400.2.

Synthesis of N-((7-chloro-8-fluoroimidazo[1,5-a]pyridin-1-yl)methyl)-1-((6-cyclopropyl-8-(hydroxy(3-(hydroxymethyl)oxetan-3-yl)methyl)imidazo[1,2-a]pyridin-2-yl)methyl)-1H-1,2,3-triazole-4-carboxamide To a solution of 1-((6-cyclopropyl-8-(hydroxy(3-(hydroxymethyl)oxetan-3-yl)methyl)imidazo[1,2-a]pyridin-2-yl)methyl)-1H-1,2,3-triazole-4-carboxylic acid (65 mg, 0.163 mmol), (7-chloro-8-fluoroimidazo[1,5-a]pyridin-1-yl)methanamine hydrochloride (50 mg, 0.211 mmol), HOBt (44 mg, 0.326 mmol) and EDCI (63 mg, 0.326 mmol) in DMF (5 mL) was added DIPEA (65 mg, 0.5 mmol). The resulting reaction was stirred at RT for 16 h. H₂O (25 mL) was added to the reaction, and the mixture was extracted with EtOAc (40 mL×4). The combined organic layers were washed with brine, dried over Na₂SO₄, and concentrated in vacuo to give the crude product which was purified by Prep-TLC (DCM/MeOH=10/1) to give N-((7-chloro-8-fluoroimidazo[1,5-a]pyridin-1-yl)methyl)-1-((6-cyclopropyl-8-(hydroxy(3-(hydroxymethyl)oxetan-3-yl)methyl)imidazo[1,2-a]pyridin-2-yl)methyl)-1H-1,2,3-triazole-4-carboxamide as a white solid (20 mg, 21%). ESI-MS [M+H]+: 581.2. Purity: 97.0% (214 nm), 98.0% (254 nm). ¹H NMR (400 MHz, DMSO): δ 8.81 (t, J=5.4 Hz, 1H), 8.70 (s, 1H), 8.58 (s, 1H), 8.49-8.40 (m, 2H), 8.29 (s, 1H), 8.21 (d, J=7.4 Hz, 1H), 7.60 (s, 1H), 7.14 (s, 1H), 6.76 (t, J=6.9 Hz, 1H), 6.14 (s, 2H), 5.73 (s, 1H), 5.04 (s, 1H), 4.70 (d, J=5.5 Hz, 2H), 4.29 (d, J=13.0 Hz, 1H), 4.17 (d, J=13.0 Hz, 1H), 3.54 (d, J=11.4 Hz, 1H), 3.45-3.25 (m, 3H), 2.15-2.08 (m, 1H), 1.13-1.00 (m, 2H), 0.83-0.70 (m, 2H).

Example 273

Scheme 272

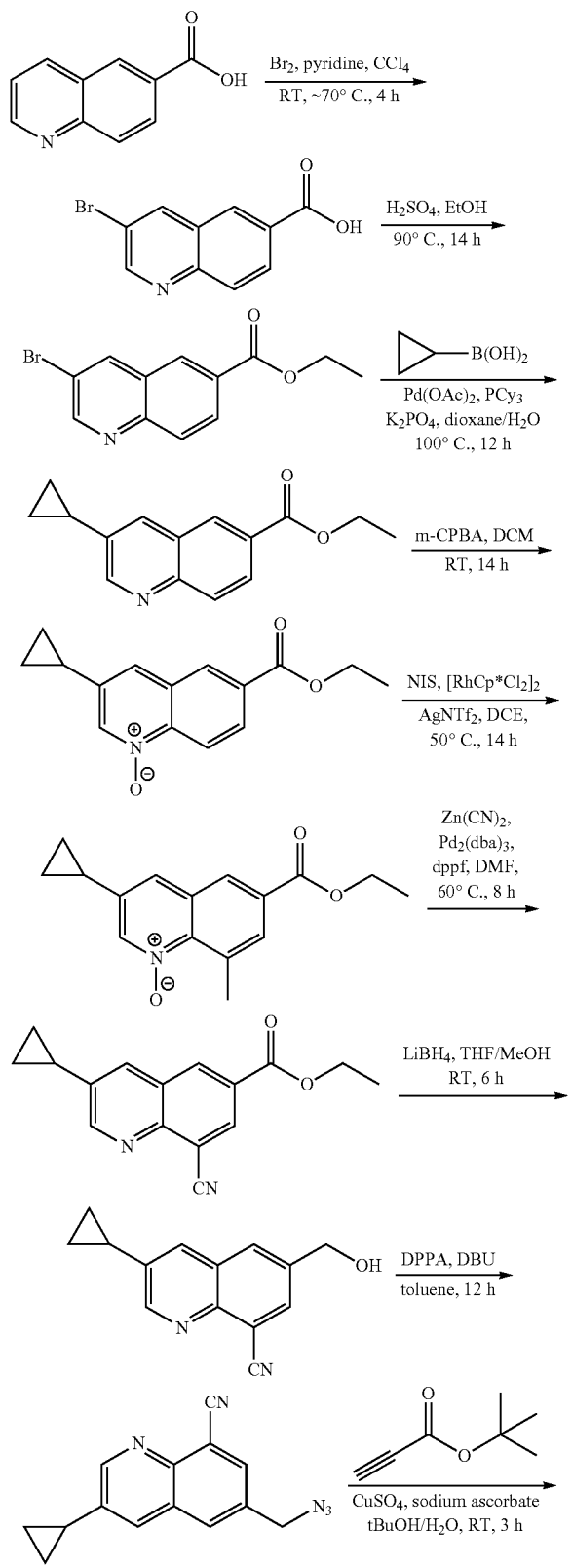

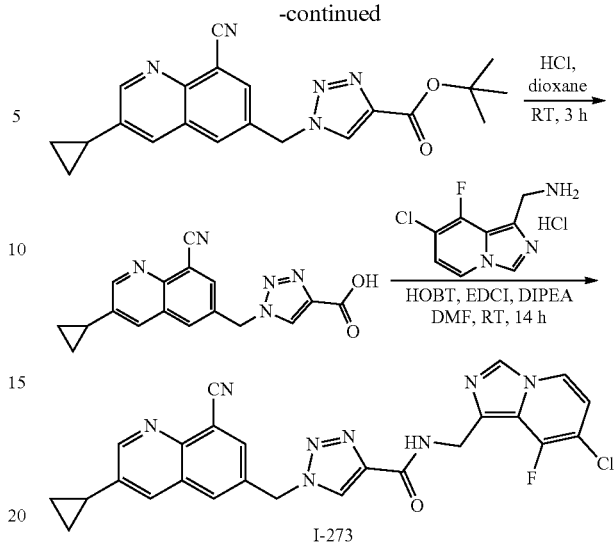

Synthesis of 3-bromoquinoline-6-carboxylic Acid

A mixture of quinoline-6-carboxylic acid (5 g, 28.9 mmol), pyridine (4.57 g, 57.8 mmol) and $Br_2$ (5.5 g, 34.7 mmol) in $CCl_4$ (100 mL) was stirred at 70° C. for 4 h. The reaction was cooled to RT, quenched with saturated $NaHCO_3$ (150 mL), and extracted with MeOH/DCM (10/1, 100 mL×5). The combined organic layers were washed with brine, dried over $Na_2SO_4$ and concentrated to give the crude product which was purified by flash column chromatography (DCM/MeOH=15/1) to give 3-bromoquinoline-6-carboxylic acid (6.2 g, yield: 85%) as a yellow solid. ESI-MS $[M+H]^+$: 253.1.

Synthesis of Ethyl 3-bromoquinoline-6-carboxylate

A mixture of 3-bromoquinoline-6-carboxylic acid (6.2 g, 24.7 mmol) in EtOH (100 mL) and $H_2SO_4$ (5 mL) was stirred at 90° C. for 14 h. The reaction was then cooled to RT and concentrated. The residue was quenched with saturated $NaHCO_3$ (150 mL) and extracted with EtOAc (100 mL×3). The combined organic layers were washed with brine, dried over $Na_2SO_4$, and concentrated to give the crude product which was purified by flash column chromatography (PE/EtOAc=2/1) to afford ethyl 3-bromoquinoline-6-carboxylate (3.6 g, yield: 53%) as an off-white solid. ESI-MS $[M+H]^+$: 281.1.

Synthesis of Ethyl 3-cyclopropylquinoline-6-carboxylate

A mixture of 3-bromoquinoline-6-carboxylate (3.6 g, 12.9 mmol), cyclopropylboronic acid (1.66 g, 19.4 mmol), $Pd(OAc)_2$ (291 mg, 1.3 mmol), $PCy_3$ (364 mg, 1.3 mmol) and $K_3PO_4$ (5.47 g, 25.8 mmol) in dioxane/$H_2O$ (50 mL/5 mL) was stirred at 100° C. for 12 h. The reaction mixture was diluted with water (150 mL) and extracted with EtOAc (100 mL×3). The combined organic layers were washed with brine, dried over $Na_2SO_4$, and concentrated. The crude product was purified by flash column chromatography (PE/EA=2/1) to afford ethyl 3-cyclopropylquinoline-6-carboxylate (2.2 g, yield: 71%) as a brown solid. ESI-MS $[M+H]^+$: 242.1.

Synthesis of 3-cyclopropyl-6-(ethoxycarbonyl)quinoline 1-oxide

A mixture of ethyl 3-cyclopropylquinoline-6-carboxylate (2.0 g, 8.3 mmol) and mCPBA (1.72 g, 10.0 mmol) in DCM (50 mL) was stirred at RT for 14 h. The reaction mixture was quenched with saturated aqueous $Na_2SO_3$ solution (50 mL) and extracted with DCM (70 mL×3). The combined organic layers were washed with brine, dried over $Na_2SO_4$, and concentrated. The residue was purified by flash column chromatography (PE/EtOAc=2/1) to afford 3-cyclopropyl-6-(ethoxycarbonyl)quinoline 1-oxide (1.1 g, yield: 43%) as an off-white solid. ESI-MS $[M+H]^+$: 258.1.

Synthesis of 3-cyclopropyl-6-(ethoxycarbonyl)-8-iodoquinoline 1-oxide

A mixture of 3-cyclopropyl-6-(ethoxycarbonyl)quinoline 1-oxide (1.0 g, 3.9 mmol), [RhCp*Cl$_2$]2 (247 mg, 0.4 mmol), NIS (963 mg, 4.28 mmol), and AgNTf$_2$ (155 mg, 0.4 mmol) in DCE (35 mL) was stirred at 50° C. for 14 h. The reaction mixture was filtered, and the filter cake washed with DCM (50 mL). The filtrate was concentrated to give the crude product which was purified by flash column chromatography (PE/EtOAc=1/2) to afford 3-cyclopropyl-6-(ethoxycarbonyl)-8-iodoquinoline 1-oxide (1.2 g, yield: 80%) as a yellow solid. ESI-MS $[M+H]^+$: 384.1.

Synthesis of Ethyl 8-cyano-3-cyclopropylquinoline-6-carboxylate

A mixture of 3-cyclopropyl-6-(ethoxycarbonyl)-8-iodoquinoline 1-oxide (800 mg, 2.1 mmol), $Zn(CN)_2$ (366 mg, 3.1 mmol), $Pd_2(dba)_3$ (183 mg, 0.2 mmol) and dppf (116 mg, 0.2 mmol) in DMF (20 mL) was stirred at 60° C. for 8 h. The reaction was diluted with water (100 mL) and extracted with EtOAc (80 mL×3). The combined organic layers were washed with brine, dried over $Na_2SO_4$, and concentrated to give the crude product which was purified by flash column chromatography (PE/EtOAc=1/1) to afford ethyl 8-cyano-3-cyclopropylquinoline-6-carboxylate (400 mg, yield: 72%) as a yellow solid. ESI-MS $[M+H]^+$: 267.1.

Synthesis of 3-cyclopropyl-6-(hydroxymethyl)quinoline-8-carbonitrile

To a mixture of ethyl 8-cyano-3-cyclopropylquinoline-6-carboxylate (400 mg, 1.5 mmol) in THF/MeOH (10 mL/5 mL) was added $LiBH_4$ (66 mg, 3.0 mmol). The mixture was stirred at RT for 6 h. The reaction was diluted with water (50 mL) and extracted with DCM/MeOH (10/1, 50 mL×3). The combined organic layers were washed with brine, dried over $Na_2SO_4$ and concentrated. The residue was purified by flash column chromatography (PE/EtOAc=1/3) to afford 3-cyclopropyl-6-(hydroxymethyl)quinoline-8-carbonitrile (240 mg, yield: 71%) as a yellow oil. ESI-MS $[M+H]^+$: 225.1.

Synthesis of 6-(azidomethyl)-3-cyclopropylquinoline-8-carbonitrile

To a mixture of 3-cyclopropyl-6-(hydroxymethyl)quinoline-8-carbonitrile (240 mg, 1.07 mmol) and DPPA (880 mg, 3.2 mmol) in toluene (10 mL) was added DBU (486 mg, 3.2 mmol) at 0° C. The reaction mixture was stirred at RT for 12 h. The reaction was diluted with water (30 mL) and extracted with EtOAc (50 mL×3). The combined organic layers were washed with brine, dried over $Na_2SO_4$ and concentrated to give the crude product which was purified by flash column chromatography (PE/EtOAc=2/1) to afford 6-(azidomethyl)-3-cyclopropylquinoline-8-carbonitrile (100 mg, yield: 37%) as brown oil. ESI-MS $[M+H]^+$: 250.1.

Synthesis of tert-butyl 1-((8-cyano-3-cyclopropylquinolin-6-yl)methyl)-1H-1,2,3-triazole-4-carboxylate A mixture of 6-(azidomethyl)-3-cyclopropylquinoline-8-carbonitrile (100 mg, 0.40 mmol), tert-butyl propiolate (76 mg, 0.60 mmol), $CuSO_4 \cdot 5H_2O$ (20 mg, 0.08 mmol) and sodium ascorbate (16 mg, 0.08 mmol) in t-BuOH/$H_2O$ (5 mL/1 mL) was stirred at RT for 3 h. The reaction was diluted with water (30 mL) and extracted with DCM/MeOH (10/1, 30 mL×3). The combined organic layers were washed with brine, dried over $Na_2SO_4$, and concentrated. The residue was purified by flash column chromatography (DCM/MeOH=15/1) to afford tert-butyl 1-((8-cyano-3-cyclopropylquinolin-6-yl)methyl)-1H-1,2,3-triazole-4-carboxylate (110 mg, yield: 73%) as a brown oil. ESI-MS $[M+H]^+$: 376.1.

Synthesis of 1-((S-cyano-3-cyclopropylquinolin-6-yl)methyl)-1H-1,2,3-triazole-4-carboxylic Acid A mixture of tert-butyl 1-((8-cyano-3-cyclopropylquinolin-6-yl)methyl)-1H-1,2,3-triazole-4-carboxylate (100 mg, 0.27 mmol) in HCl (5 mL, 4 M solution in dioxane, 20 mmol) was stirred at RT for 3 h. The mixture was concentrated to afford 1-((8-cyano-3-cyclopropylquinolin-6-yl)methyl)-1H-1,2,3-triazole-4-carboxylic acid (110 mg, crude) as a brown oil which was used in the next step without further purification. ESI-MS $[M+H]^+$: 320.1.

Synthesis of N-((7-chloro-8-fluoroimidazo[1,5-a]pyridin-1-yl)methyl)-1-((8-cyano-3-cyclopropylquinolin-6-yl)methyl)-1H-1,2,3-triazole-4-carboxamide A mixture of 1-((8-cyano-3-cyclopropylquinolin-6-yl)methyl)-1H-1,2,3-triazole-4-carboxylic acid (110 mg, 0.27 mmol crude), (7-chloro-8-fluoroimidazo[1,5-a]pyridin-1-yl)methanamine hydrochloride (97 mg, 0.41 mmol), HOBT (55 mg, 0.41 mmol), EDCI (78 mg, 0.41 mmol) and DIEA (105 mg, 0.81 mmol) in DMF (3 mL) was stirred at RT for 14 h. The reaction mixture was diluted with water (50 mL) and extracted with EtOAc (30 mL×3). The combined organic layers were washed with brine, dried over $Na_2SO_4$, and concentrated. The residue was purified by Prep-TLC (DCM/MeOH=10/1) to afford N-((7-chloro-8-fluoroimidazo[1,5-a]pyridin-1-yl)methyl)-1-((8-cyano-3-cyclopropylquinolin-6-yl)methyl)-1H-1,2,3-triazole-4-carboxamide (67 mg, yield: 50%) as white solid. ESI-MS $[M+H]^+$: 501.1. Purity: 97.79% (214 nm), 95.14% (254 nm). $^1$H NMR (400 MHz, DMSO): δ 8.96 (s, 1H), 8.74-8.72 (m, 2H), 8.32 (s, 1H), 8.21 (d, J=8.0 Hz, 1H), 8.13 (s, 1H), 8.05 (s, 1H), 6.79 (s, 1H), 5.89 (s, 2H), 4.71 (s, 2H), 2.20-2.18 (m, 1H), 1.14-1.12 (m, 2H), 0.94-0.91 (m, 2H).

Example 274

Scheme 273

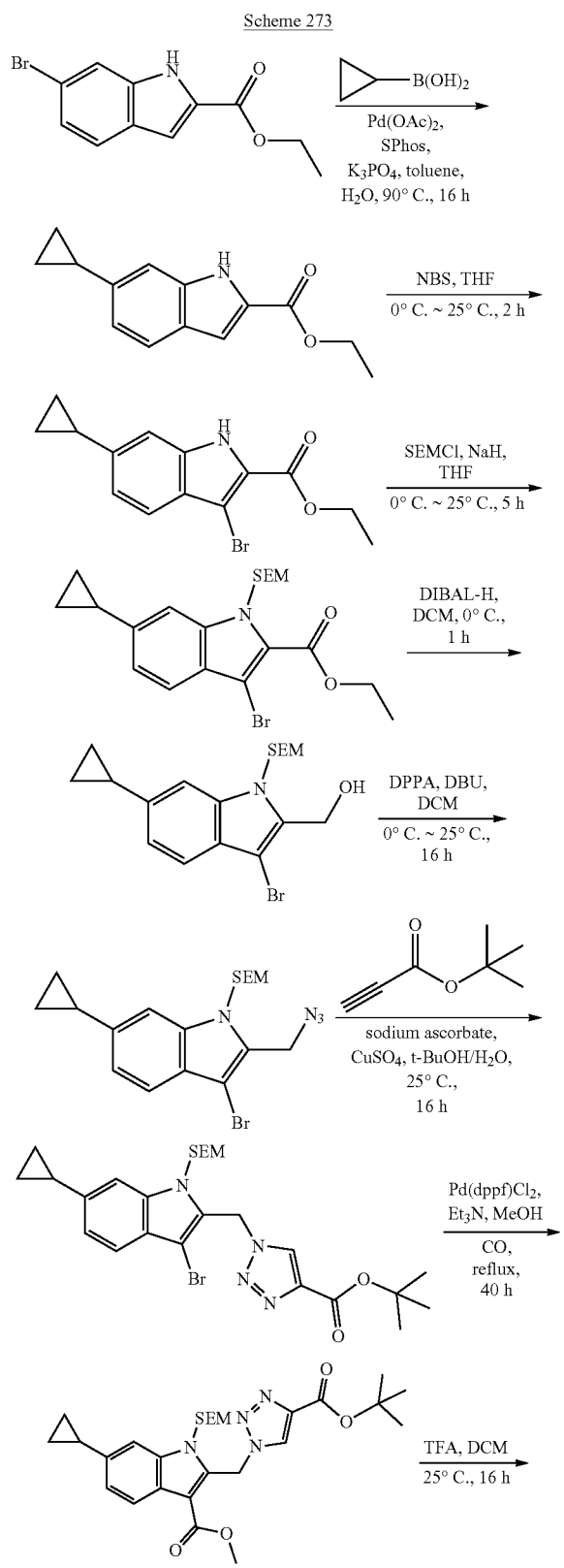

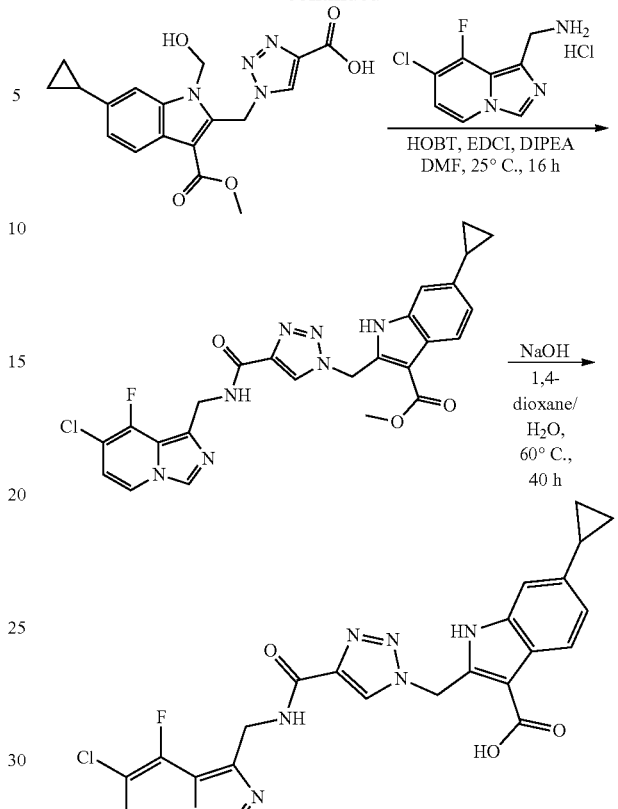

I-274

Synthesis of Ethyl 6-cyclopropyl-1H-indole-2-carboxylate

A mixture of ethyl 6-bromo-1H-indole-2-carboxylate (3.5 g, 13.05 mmol), cyclopropylboronic acid (2.24 g, 26.11 mmol), Pd(OAc)$_2$ (146 mg, 0.653 mmol), SPhos (537 mg, 1.31 mmol) and K$_3$PO$_4$ (8.30 g, 39.15 mmol) in toluene (60 mL) and water (10 mL) was stirred at 90° C. for 16 h under N$_2$. The reaction mixture was filtered and the filter cake rinsed with EtOAc (200 mL). The combined filtrate was washed with water (100 mL×1) and brine (100 mL×1), dried over Na$_2$SO$_4$, concentrated and purified by silica gel chromatography (EA/PE=1/3) to give ethyl 6-cyclopropyl-1H-indole-2-carboxylate (2.9 g, yield: 97%) as a yellow solid. ESI-MS [M+H]$^+$: 230.1.

Synthesis of Ethyl 3-bromo-6-cyclopropyl-1H-indole-2-carboxylate

To a stirred solution of ethyl 6-cyclopropyl-1H-indole-2-carboxylate (2.9 g, 12.66 mmol) in THF (60 mL) was added NBS (2.79 g, 15.7 mmol) in portions at 0° C. The mixture was stirred at 25° C. for 2 h. The reaction mixture was diluted in EtOAc (100 mL), washed with saturated aqueous NaHCO$_3$ (100 mL) and brine (100 mL), dried over Na$_2$SO$_4$, and concentrated in vacuo to give ethyl 3-bromo-6-cyclopropyl-1H-indole-2-carboxylate (4.0 g, crude) as a yellow solid. ESI-MS [M+Na]$^+$: 330.0.

Synthesis of Ethyl 3-bromo-6-cyclopropyl-1-((2-(trimethylsilyl)ethoxy)methyl)-1H-indole-2-carboxylate To a stirred solution of NaH (564 mg, 60% suspension in paraffin oil, 14.1 mmol) in THF (20 mL) was added dropwise the solution of ethyl 3-bromo-6-cyclopropyl-1H-indole-2-carboxylate (2.9 g, 9.45 mmol) in THF (30 mL) at 0° C. The mixture was stirred at 0° C. for 10 min and SEMCl (2.04 g, 12.24 mmol) was added dropwise at 0° C. The mixture was stirred at 25° C. for 2 h. The reaction mixture was quenched with water (80 mL) and extracted with EtOAc (80 mL×2). The combined organics were washed with brine (150 mL), dried over $Na_2SO_4$, concentrated in vacuo to give ethyl 3-bromo-6-cyclopropyl-1-((2-(trimethylsilyl)ethoxy)methyl)-1H-indole-2-carboxylate (4.1 g, crude) as a light brown syrup. ESI-MS $[M+Na]^+$: 460.1.

Synthesis of (3-bromo-6-cyclopropyl-1-((2-(trimethylsilyl)ethoxy)methyl)-1H-indol-2-yl)methanol To a stirred solution of ethyl 3-bromo-6-cyclopropyl-1-((2-(trimethylsilyl)ethoxy)methyl)-1H-indole-2-carboxylate (750 mg, 1.71 mmol) in DCM (30 mL) was added dropwise DIBAL-H (6.8 mL, 6.8 mmol) at 0° C. The mixture was stirred at 0° C. for 1 h. The reaction mixture was quenched with saturated aqueous $NH_4Cl$ and extracted with DCM (30 mL×3). The combined organics were washed with brine (90 mL), dried over $Na_2SO_4$, and purified by silica gel chromatography (EA/PE=1/2) to give (3-bromo-6-cyclopropyl-1-((2-(trimethylsilyl)ethoxy)methyl)-1H-indol-2-yl)methanol (450 mg, yield: 66%) as a colorless liquid. ESI-MS $[M+Na]^+$: 418.0.

Synthesis of 2-(azidomethyl)-3-bromo-6-cyclopropyl-1-((2-(trimethylsilyl)ethoxy)methyl)-1H-indole To a stirred solution of (3-bromo-6-cyclopropyl-1-((2-(trimethylsilyl)ethoxy)methyl)-1H-indol-2-yl)methanol (400 mg, 1.01 mmol) and DPPA (834 mg, 3.03 mmol) in DCM (15 mL) was added dropwise the solution of DBU (153 mg, 1.01 mmol) in DCM (1 mL) at 0° C. The mixture was stirred at 25° C. for 16 h. The reaction mixture was concentrated and purified by silica gel chromatography (EA/PE=1/5) to give 2-(azidomethyl)-3-bromo-6-cyclopropyl-1-((2-(trimethylsilyl)ethoxy)methyl)-1H-indole (270 mg, yield: 64%) as a yellow liquid. ESI-MS $[M+H]^+$: 421.0.

Synthesis of tert-butyl 1-((3-bromo-6-cyclopropyl-1-((2-(trimethylsilyl)ethoxy)methyl)-1H-indol-2-yl)methyl)-1H-1,2,3-triazole-4-carboxylate A mixture of 2-(azidomethyl)-3-bromo-6-cyclopropyl-1-((2-(trimethylsilyl)ethoxy)methyl)-1H-indole (270 mg, 0.64 mmol), ethyl isobutyrate (105 mg, 0.832 mmol), $CuSO_4$ (51 mg, 0.32 mmol), and sodium ascorbate (63 mg, 0.32 mmol) in t-BuOH (5 mL) and water (5 mL) was stirred at 25° C. for 16 h. The reaction was concentrated to remove t-BuOH, then diluted with water (30 mL) and extracted with DCM (30 mL×2). The combined organics were washed with brine (60 mL×1), dried over $Na_2SO_4$, concentrated and purified by silica gel chromatography (EA/PE=1/1) to afford tert-butyl 1-((3-bromo-6-cyclopropyl-1-((2-(trimethylsilyl)ethoxy)methyl)-1H-indol-2-yl)methyl)-1H-1,2,3-triazole-4-carboxylate (270 mg, yield: 77%) as a yellow solid. ESI-MS $[M+Na]^+$: 569.1.

Synthesis of Methyl 2-((4-(tert-butoxycarbonyl)-1H-1,2,3-triazol-1-yl)methyl)-6-cyclopropyl-1-((2-(trimethylsilyl)ethoxy)methyl)-1H-indole-3-carboxylate A mixture of tert-butyl 1-((3-bromo-6-cyclopropyl-1-((2-(trimethylsilyl)ethoxy)methyl)-1H-indol-2-yl)methyl)-1H-1,2,3-triazole-4-carboxylate (270 mg, 0.493 mmol), $Pd(dppf)Cl_2$ (36 mg, 0.049 mmol) and $Et_3N$ (748 mg, 7.40 mmol) in MeOH (25 mL) was stirred at 75° C. for 40 h under CO (balloon). The reaction mixture was concentrated and purified by silica gel chromatography (EA/PE=1/5) to afford methyl 2-((4-(tert-butoxycarbonyl)-1H-1,2,3-triazol-1-yl)methyl)-6-cyclopropyl-1-((2-(trimethylsilyl)ethoxy)methyl)-1H-indole-3-carboxylate (70 mg, yield: 27%) as a yellow solid. ESI-MS $[M+Na]^+$: 549.2.

Synthesis of 1-((6-cyclopropyl-1-(hydroxymethyl)-3-(methoxycarbonyl)-1H-indol-2-yl)methyl)-1H-1,2,3-triazole-4-carboxylic Acid A mixture of methyl 2-((4-(tert-butoxycarbonyl)-1H-1,2,3-triazol-1-yl)methyl)-6-cyclopropyl-1-((2-(trimethylsilyl)ethoxy)methyl)-1H-indole-3-carboxylate (50 mg, 0.095 mmol) and TFA (0.3 mL) in DCM (2 mL) was stirred at 25° C. for 16 h. The reaction mixture was concentrated in vacuo to give 1-((6-cyclopropyl-1-(hydroxymethyl)-3-(methoxycarbonyl)-1H-indol-2-yl)methyl)-1H-1,2,3-triazole-4-carboxylic acid (35 mg, 100%) as a purple solid. ESI-MS $[M+Na]^+$: 393.1.

Synthesis of Methyl 2-((4-(((7-chloro-8-fluoroimidazo[1,5-a]pyridin-1-yl)methyl)carbamoyl)-1H-1,2,3-triazol-1-yl)methyl)-6-cyclopropyl-1H-indole-3-carboxylate The mixture of 1-((6-cyclopropyl-1-(hydroxymethyl)-3-(methoxycarbonyl)-1H-indol-2-yl)methyl)-1H-1,2,3-triazole-4-carboxylic acid (35 mg, 0.095 mmol), (7-chloro-8-fluoroimidazo[1,5-a]pyridin-1-yl)methanamine hydrochloride (25 mg, 0.105 mmol), EDCI (36 mg, 0.19 mmol), HOBT (26 mg, 0.19 mmol), and DIPEA (123 mg, 0.95 mmol) in DMF (2 mL) was stirred at 25° C. for 16 h. The reaction mixture was poured into water (20 mL) and the precipitate was collected, dried in vacuo and purified by silica gel chromatography (EA/MeOH=40/1) to give methyl 2-((4-(((7-chloro-8-fluoroimidazo[1,5-a]pyridin-1-yl)methyl)carbamoyl)-1H-1,2,3-triazol-1-yl)methyl)-6-cyclopropyl-1H-indole-3-carboxylate (14 mg, yield: 28%) as a white solid. ESI-MS $[M+H]^+$: 522.1. Purity: 96.95% (214 nm), 96.72% (254 nm). $^1H$ NMR (400 MHz, DMSO): δ 12.06 (s, 1H), 8.73 (t, J=5.5 Hz, 1H), 8.53 (s, 1H), 8.43 (d, J=2.4 Hz, 1H), 8.20 (d, J=7.4 Hz, 1H), 7.83 (d, J=8.3 Hz, 1H), 7.12 (s, 1H), 6.94 (dd, J=8.4, 1.5 Hz, 1H), 6.78-6.73 (m, 1H), 6.06 (s, 2H), 4.69 (d, J=5.5 Hz, 2H), 3.84 (s, 3H), 2.05-1.96 (m, 1H), 0.98-0.91 (m, 2H), 0.69-0.62 (m, 2H).

Synthesis of 2-((4-(((7-chloro-8-fluoroimidazo[1,5-a]pyridin-1-yl)methyl)carbamoyl)-1H-1,2,3-triazol-1-yl)methyl)-6-cyclopropyl-1H-indole-3-carboxylic Acid To the solution of methyl 2-((4-(((7-chloro-8-fluoroimidazo[1,5-a]pyridin-1-yl)methyl)carbamoyl)-1H-1,2,3-triazol-1-yl)methyl)-6-cyclopropyl-1H-indole-3-carboxylate (50 mg, 0.096 mmol) in 1,4-dioxane (6 mL) and $H_2O$ (3 mL) was added NaOH (300 mg, 7.5 mmol) and the mixture was stirred at 60° C. for 40 h. The reaction mixture was diluted in water (20 mL), 1,4-dioxane was removed in vacuo, and the mixture was acidified to pH 4-5 by addition of HCl (2 M). The precipitate was collected and purified by Prep-HPLC to give 2-((4-(((7-chloro-8-fluoroimidazo[1,5-a]pyridin-1-yl)methyl)carbamoyl)-1H-1,2,3-triazol-1-yl)methyl)-6-cyclopropyl-1H-indole-3-carboxylic acid (3 mg, yield: 6%) as a white solid. ESI-MS [M+H]⁺: 508.1. Purity: 94.86% (214 nm), 92.71% (254 nm). ¹H NMR (400 MHz, DMSO): δ 11.92 (s, 1H), 8.73 (t, J=5.5 Hz, 1H), 8.54-8.40 (m, 2H), 8.20 (d, J=7.4 Hz, 1H), 7.87 (d, J=8.3 Hz, 1H), 7.10 (s, 1H), 6.93-6.86 (m, 1H), 6.81-6.71 (m, 1H), 6.07 (s, 2H), 4.69 (d, J=5.5 Hz, 2H), 2.05-1.96 (m, 1H), 0.95-0.91 (m, 2H), 0.67-0.63 (m, 2H).

Example 275

J=2.4 Hz, 1H), 8.75 (t, J=6.0 Hz, 1H), 8.73 (s, 1H), 8.44 (s, 1H), 8.41 (d, J=2.0 Hz, 1H), 8.20 (d, J=7.6, 1H), 7.99 (s, 1H), 7.97 (s, 1H), 7.33 (s, 1H), 5.91 (s, 2H), 4.71 (d, J=5.6 Hz, 2H), 2.35-2.31 (m, 1H), 0.81-0.88 (m, 4H).

Scheme 275

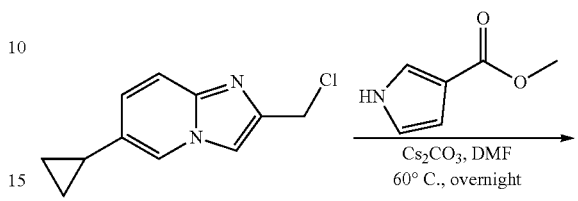

Scheme 274

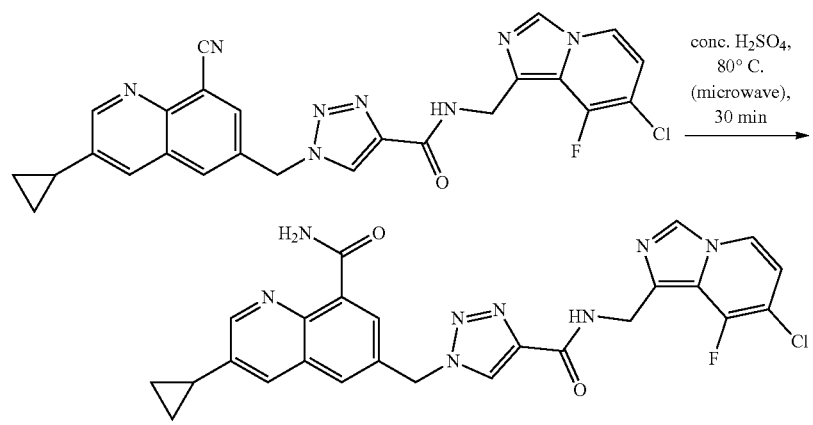

I-275

Synthesis of 6-((4-(((7-chloro-8-fluoroimidazo[1,5-a]pyridin-1-yl)methyl)carbamoyl)-1H-1,2,3-triazol-1-yl)methyl)-3-cyclopropylquinoline-s-carboxamide A mixture of N-((7-chloro-8-fluoroimidazo[1,5-a]pyridin-1-yl)methyl)-1-((8-cyano-3-cyclopropylquinolin-6-yl)methyl)-1H-1,2,3-triazole-4-carboxamide (50 mg, 0.1 mmol) in concentrated H₂SO₄ (2 mL) was heated to 80° C. by microwave for 30 min. The reaction mixture was adjusted to pH 7-8 with saturated aqueous NaHCO₃. The aqueous phase was extracted with EtOAc (30 mL×3). The combined organic layers were washed with brine, dried over Na₂SO₄, and concentrated in vacuo to give the crude product which was purified by Prep-TLC (DCM/MeOH=8/1) to give 6-((4-(((7-chloro-8-fluoroimidazo[1,5-a]pyridin-1-yl)methyl)carbamoyl)-1H-1,2,3-triazol-1-yl)methyl)-3-cyclopropylquinoline-8-carboxamide. (8 mg, 15.4%). ESI-MS [M+H]⁺: 518.7. Purity: 93.90% (214 nm) 96.01 (254 nm). ¹H NMR (400 MHz, DMSO): δ 10.06 (d, J=4.4 Hz, 1H), 9.14 (d, -continued

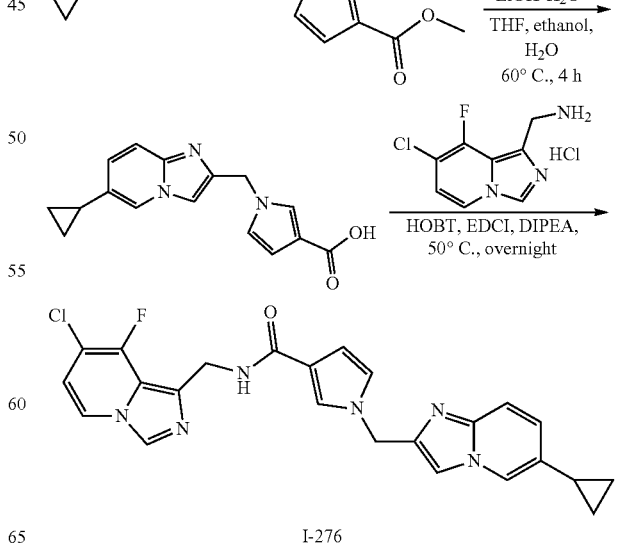

I-276

Synthesis of Methyl 1-((6-cyclopropylimidazo[1,2-a]pyridin-2-yl)methyl)-1H-pyrrole-3-carboxylate A solution of 2-(chloromethyl)-6-cyclopropylimidazo[1,2-a]pyridine (207 mg, 1.0 mmol), methyl 1H-pyrrole-3-carboxylate (250 mg, 2.0 mmol) and $Cs_2CO_3$ (652 mg, 2.0 mmol) in DMF (6 mL) was stirred at 60° C. overnight. The mixture was diluted with water (60 mL) and extracted by EtOAc (50 mL×3). The combined organic layers were washed with brine, dried over $Na_2SO_4$ and concentrated. The crude product was purified by Prep-TLC (DCM/MeOH=20/1) to afford methyl 1-((6-cyclopropylimidazo[1,2-a]pyridin-2-yl)methyl)-1H-pyrrole-3-carboxylate as a white solid (72 mg, 24%). ESI-MS [M+H]$^+$: 296.1.

Synthesis of 1-((6-cyclopropylimidazo[1,2-a]pyridin-2-yl)methyl)-1H-pyrrole-3-carboxylic Acid A solution of methyl 1-((6-cyclopropylimidazo[1,2-a]pyridin-2-yl)methyl)-1H-pyrrole-3-carboxylate (72 mg, 0.24 mmol) and LiOH*$H_2O$ (20 mg, 0.48 mmol) in THF (3 mL)/MeOH (3 mL)/$H_2O$ (1.5 mL) was stirred at 60° C. for 4 h. The mixture was concentrated to give the product (88 mg, crude), which was used into the next reaction without further purification. ESI-MS [M+H]$^+$: 282.1.

Synthesis of N-((7-chloro-8-fluoroimidazo[1,5-a]pyridin-1-yl)methyl)-1-((6-cyclopropylimidazo[1,2-a]pyridin-2-yl)methyl)-1H-pyrrole-3-carboxamide A solution of crude 1-((6-cyclopropylimidazo[1,2-a]pyridin-2-yl)methyl)-1H-pyrrole-3-carboxylic acid (45 mg, 0.160 mmol, crude), (7-chloro-8-fluoroimidazo[1,5-a]pyridin-1-yl)methanamine hydrochloride (42 mg, 0.176 mmol), HOBT (43 mg, 0.320 mmol), EDCI (62 mg, 0.320 mmol) and DIPEA (104 mg, 0.8 mmol) in DMF (1 mL) was stirred at 50° C. overnight. The mixture was diluted with water (10 mL) and extracted by EtOAc (50 mL×3). The combined organic layers were concentrated and purified by Prep-TLC (DCM/MeOH=7/1) to afford N-((7-chloro-8-fluoroimidazo[1,5-a]pyridin-1-yl)methyl)-1-((6-cyclopropylimidazo[1,2-a]pyridin-2-yl)methyl)-1H-pyrrole-3-carboxamide as a white solid (3.3 mg, 4.5%). MS [M+H]$^+$: 463.1. Purity: 94.04% (214 nm), 94.01% (254 nm). $^1$H NMR (400 MHz, DMSO): δ 8.43 (d, J=1.8 Hz, 1H), 8.32 (s, 1H), 8.19 (d, J=7.4 Hz, 1H), 8.06 (t, J=5.1 Hz, 1H), 7.64 (s, 1H), 7.39-7.37 (m, 2H), 6.98 (d, J=9.3 Hz, 1H), 6.80-6.73 (m, 2H), 6.44 (s, 1H), 5.14 (s, 2H), 4.60 (d, J=5.2 Hz, 2H), 1.94-1.87 (m, 1H), 0.93-0.88 (m, 2H), 0.67-0.64 (m, 2H).

Example 277

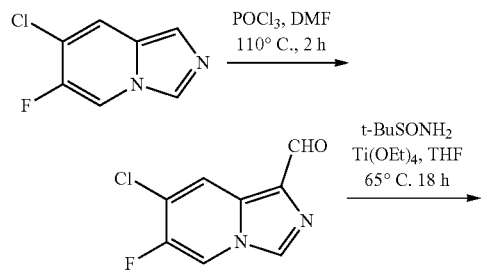

Scheme 276

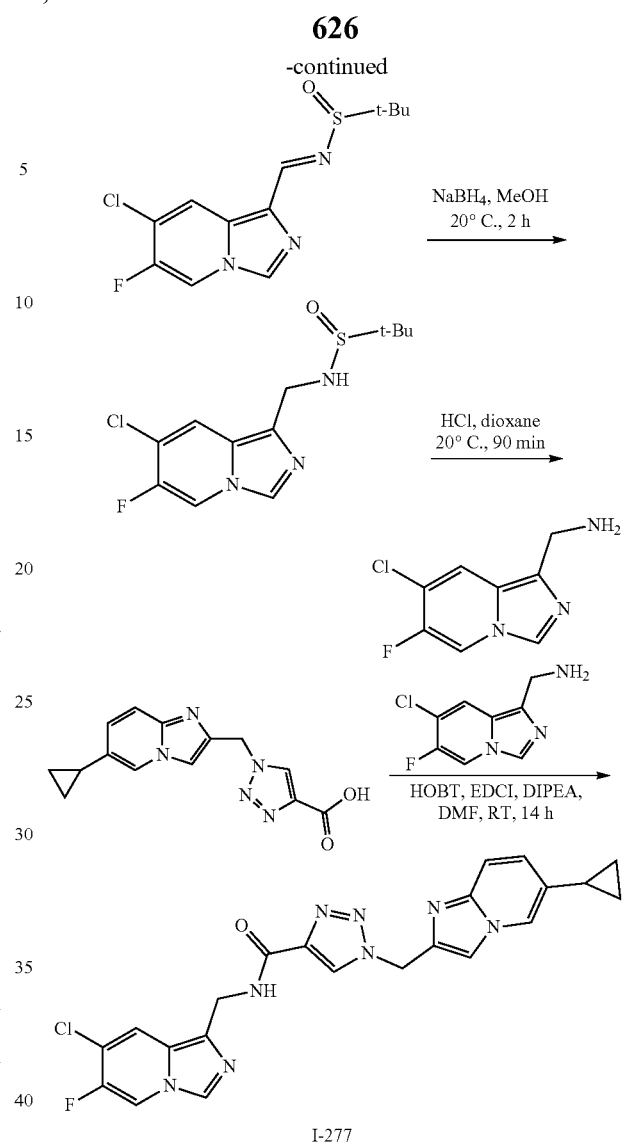

I-277

Synthesis of 7-chloro-6-fluoroimidazo[1,5-a]pyridine-1-carbaldehyde 7-chloro-6-fluoroimidazo[1,5-a]pyridine (358 mg, 2.09 mmol) was dissolved in dry N,N-dimethylformamide (1.8 mL) and the resulting solution was cooled in an ice-bath. Phosphorous oxychloride (196 μL, 2.09 mmol) was added and the resulting suspension heated to 110° C. for 2 h. The mixture was cooled to RT and mixed with ethyl acetate (10 mL) and saturated aqueous sodium bicarbonate (10 mL). Both layers were combined and evaporated to dryness. The resulting solid was mixed with acetone and the insoluble salts filtered off. The filtrate was purified by silica gel chromatography (heptane/EA=80/20 to 30/70) to obtain 7-chloro-6-fluoroimidazo[1,5-a]pyridine-1-carbaldehyde (182 mg, 44%) as a yellow solid. UPLC [M+H]$^+$: 199/201.

Synthesis of N-((7-chloro-6-fluoroimidazo[1,5-a]pyridin-1-yl)methylene)-2-methylpropane-2-sulfinamide To a solution of 7-chloro-6-fluoroimidazo[1,5-a]pyridine-1-carbaldehyde (206 mg, 1.04 mmol) and 2-methyl-2-propanesulfinamide (132 mg, 1.09 mmol) in anhydrous tetrahydrofuran (8 mL) was added titanium (IV) ethoxide (544 μL, 2.59 mmol). The resulting solution was heated under reflux overnight (65° C., 18 h). The solvent had evaporated overnight to leave an orange gum, which was dissolved in acetone, absorbed onto silica gel and purified by silica gel chromatography (EA/MeOH=9/1) to afford N-((7-chloro-6-fluoroimidazo[1,5-a]pyridin-1-yl)methylene)-2-methylpropane-2-sulfinamide (292 mg, 93%) as a bright yellow solid. UPLC [M+H]⁺: 302/303.

Synthesis of N-((7-chloro-6-fluoroimidazo[1,5-a]pyridin-1-yl)methyl)-2-methylpropane-2-sulfinamide To a solution of N-((7-chloro-6-fluoroimidazo[1,5-a]pyridin-1-yl)methylene)-2-methylpropane-2-sulfinamide (292 mg, 0.968 mmol) in methanol (8 mL) was added sodium borohydride (92 mg, 2.42 mmol) in small portions over 5 min. The resulting yellow solution was stirred for 90 min at RT. More sodium borohydride (ca. 20 mg, 0.53 mmol) was added and the mixture stirred for another 30 min. Water (2 mL) was added and the cloudy mixture poured into saturated aqueous sodium bicarbonate (15 mL). The product was extracted into ethyl acetate (3×15 mL). The combined organic solutions were washed with brine, dried (MgSO₄), filtered and concentrated to dryness to obtain N-((7-chloro-6-fluoroimidazo[1,5-a]pyridin-1-yl)methyl)-2-methylpropane-2-sulfinamide (272 mg, 92%) as a light yellow solid. LCMS [M+H]⁺: 304/306, [M−ᵗBuSONH]⁺: 183/185.

Synthesis of (7-chloro-6-fluoroimidazo[1,5-a]pyridin-1-yl)methanamine

To a suspension of N-((7-chloro-6-fluoroimidazo[1,5-a]pyridin-1-yl)methyl)-2-methylpropane-2-sulfinamide (272 mg, 0.897 mmol) in 1,4-dioxane (6.8 mL) was added a solution of hydrogen chloride in 1,4-dioxane (4 M, 2.2 mL, 8.8 mmol). The resulting suspension was stirred for 90 min at RT. The reaction mixture was concentrated to dryness and repeatedly evaporated from methanol to obtain an off-white solid (272 mg). The solid was dissolved in dimethylsulfoxide/15% aqueous ammonia=2:1 (ca. 3 mL) and applied to a Biotage SNAP ULTRA C₁₈ 30 g cartridge and eluted with a gradient of water/acetonitrile from 90/10 to 0:100 (each containing 0.1% (v/v) ammonia) to obtain (7-chloro-6-fluoroimidazo[1,5-a]pyridin-1-yl)methanamine (154 mg, 86%) as a yellow solid. LCMS [M+H−NH₃]⁺: 183/185.

Synthesis of N-((7-chloro-6-fluoroimidazo[1,5-a]pyridin-1-yl)methyl)-1-((6-cyclopropylimidazo[1,2-a]pyridin-2-yl)methyl)-1H-1,2,3-triazole-4-carboxamide To a solution of 1-((6-cyclopropylimidazo[1,2-a]pyridin-2-yl)methyl)-1H-1,2,3-triazole-4-carboxylic acid (42 mg, 0.15 mmol), (7-chloro-6-fluoroimidazo[1,5-a]pyridin-1-yl)methanamine (35 mg, 0.15 mmol), HOBT (30 mg, 0.226 mmol), and EDCI (43.4 mg, 0.226 mmol) in DMF (2 mL) was added DIPEA (78 mg, 0.6 mmol). The resulting mixture was stirred at RT for 14 h. Water (20 mL) was added, and the mixture was extracted with EtOAc (10 mL×3). The combined organic layers were washed with brine, dried over Na₂SO₄, filtered and concentrated to give the crude product which was purified by Prep-TLC (DCM/MeOH=10/1) to give N-((7-chloro-6-fluoroimidazo[1,5-a]pyridin-1-yl)methyl)-1-((6-cyclopropylimidazo[1,2-a]pyridin-2-yl)methyl)-1H-1,2,3-triazole-4-carboxamide (42 mg, yield: 60%) as a white solid. ESI-MS [M+H]⁺: 465.1. Purity: 99.01% (214 nm), 96.62% (254 nm). ¹H NMR (400 MHz, DMSO): δ 8.96 (t, J=5.9 Hz, 1H), 8.69 (dd, J=5.0, 0.5 Hz, 1H), 8.56 (s, 1H), 8.34 (s, 1H), 8.29 (s, 1H), 8.08 (d, J=7.3 Hz, 1H), 7.82 (s, 1H), 7.40 (d, J=9.3 Hz, 1H), 7.01 (dd, J=9.4, 1.8 Hz, 1H), 5.72 (s, 2H), 4.62 (d, J=5.9 Hz, 2H), 1.96-1.89 (m, 1H), 0.94-0.89 (m, 2H), 0.74-0.57 (m, 2H).

Example 278

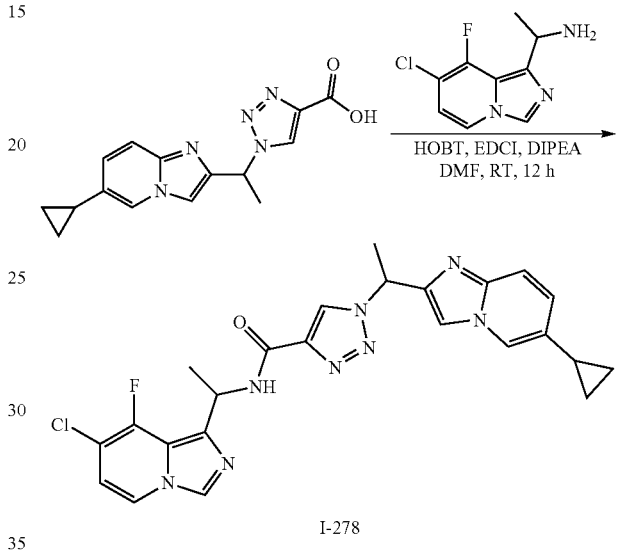

I-278

Synthesis of N-(1-(7-chloro-8-fluoroimidazo[1,5-a]pyridin-1-yl)ethyl)-1-(1-(6-cyclopropylimidazo[1,2-a]pyridin-2-yl)ethyl)-1H-1,2,3-triazole-4-carboxamide To a mixture of 1-(1-(6-cyclopropylimidazo[1,2-a]pyridin-2-yl)ethyl)-1H-1,2,3-triazole-4-carboxylic acid (60 mg, 0.2 mmol), 1-(7-chloro-8-fluoroimidazo[1,5-a]pyridin-1-yl)ethan-1-amine (52 mg, 0.24 mmol), HOBT (54 mg, 0.4 mmol), EDCI (76 mg, 0.4 mmol) in DMF (5 mL) was added DIPEA (130 mg, 1 mmol). The mixture was stirred at 25° C. for 16 h. Water (50 mL) was added, and the mixture was extracted with EtOAc (20 mL×3). The combined organic layers were washed with brine and concentrated. The crude product was purified by Prep-TLC (DCM/MeOH=10/1) to give N-(1-(7-chloro-8-fluoroimidazo[1,5-a]pyridin-1-yl)ethyl)-1-(1-(6-cyclopropylimidazo[1,2-a]pyridin-2-yl)ethyl)-1H-1,2,3-triazole-4-carboxamide (23.5 mg, yield: 23.9%) as a yellow solid. ESI-MS [M+H]⁺: 493.1. Purity: 100% (214 nm), 100 (254 nm). ¹H NMR (400 MHz, DMSO): δ 8.63 (d, J=3.2 Hz, 1H), 8.48 (d, J=2.4 Hz, 1H), 8.39 (d, J=7.7 Hz, 1H), 8.32 (s, 1H), 8.21 (d, J=7.4 Hz, 1H), 7.77 (d, J=1.8 Hz, 1H), 7.41 (d, J=9.4 Hz, 1H), 7.01 (d, J=9.6 Hz, 1H), 6.79-6.74 (m, 1H), 6.15-6.10 (m, 1H), 5.57-5.50 (m, 1H), 1.93-1.91 (m, 4H), 1.54 (d, J=6.8 Hz, 3H), 0.93-0.90 (m, 2H), 0.67-0.66 (m, 2H).

Example 279

Scheme 278

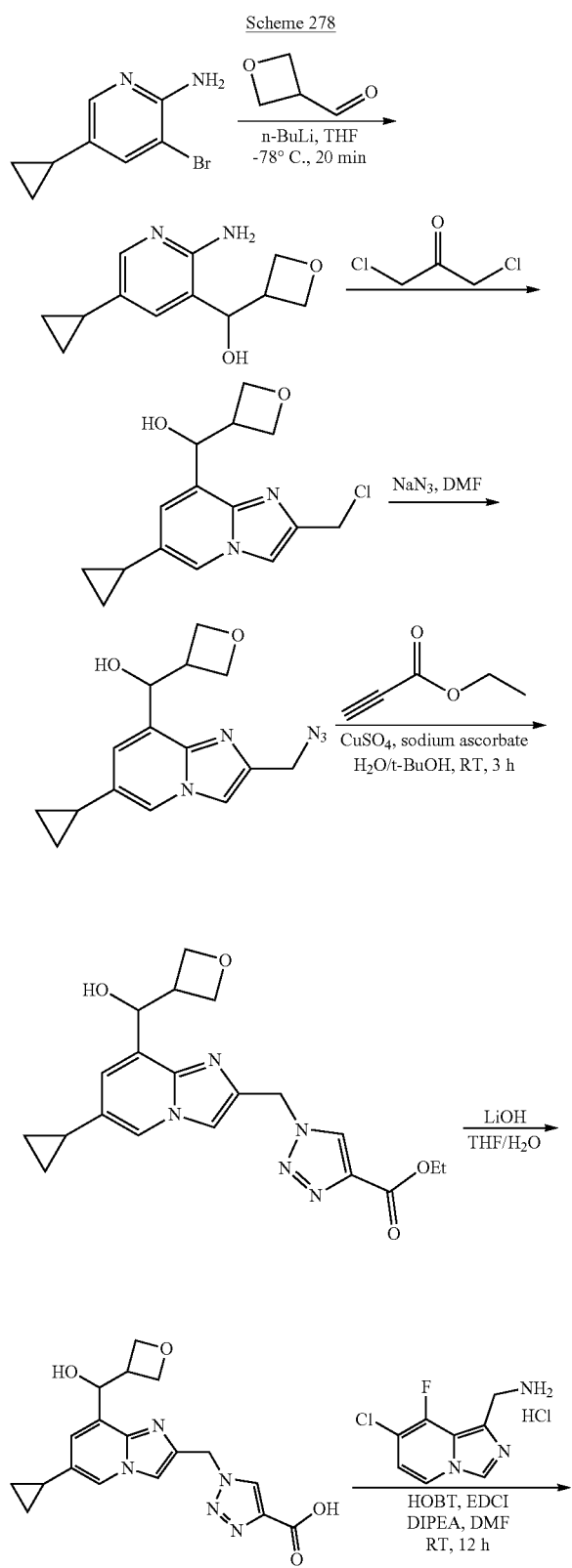

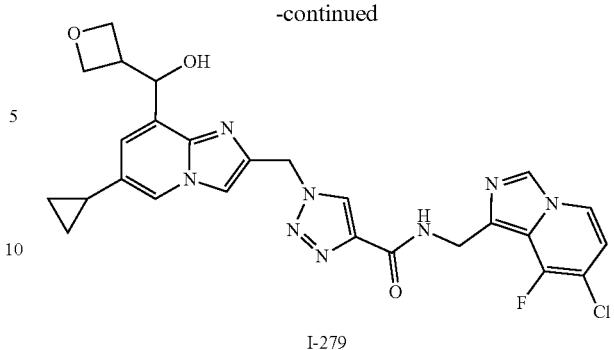

I-279

Synthesis of (2-amino-5-cyclopropylpyridin-3-yl)(oxetan-3-yl)methanol

To a solution of 3-bromo-5-cyclopropylpyridin-2-amine (500 mg, 2.35 mmol) in dry THF (25 mL) was added n-BuLi (3.5 mL, 2.4 M solution in hexanes, 8.4 mmol) at −60° C. The resulting mixture was stirred at −60° C. for 30 min. Then a solution of oxetane-3-carbaldehyde (714 mg, 8.3 mmol) in 3 mL THF was added slowly at −60° C. and stirred for another 30 min. The reaction was quenched with water (10 mL) and concentrated in vacuo to give the crude residue, which was purified by Prep-TLC (DCM/MeOH=6/1) to give (2-amino-5-cyclopropylpyridin-3-yl)(oxetan-3-yl)methanol as a yellow oil (310 mg, 60%). ESI-MS [M+H]$^+$: 221.2.

Synthesis of (2-(chloromethyl)-6-cyclopropylimidazo[1,2-a]pyridin-8-yl)(oxetan-3-yl)methanol A mixture of (2-amino-5-cyclopropylpyridin-3-yl)(oxetan-3-yl)methanol (310 mg, 1.41 mmol) and 1,3-dichloropropan-2-one (533 mg, 4.23 mmol) in EtOH (25 mL) was stirred at 80° C. for 14 h. The reaction mixture was adjusted to pH 8 using saturated aqueous NaHCO$_3$ and concentrated in vacuo to give the crude residue, which was purified by Prep-TLC (DCM/MeOH=10/1) to give (2-(chloromethyl)-6-cyclopropylimidazo[1,2-a]pyridin-8-yl)(oxetan-3-yl)methanol as a yellow oil (210 mg, 51%). ESI-MS [M+H]$^+$: 293.2.

Synthesis of (2-(chloromethyl)-6-cyclopropylimidazo[1,2-a]pyridin-8-yl)(oxetan-3-yl)methanol To a solution of (2-(chloromethyl)-6-cyclopropylimidazo[1,2-a]pyridin-8-yl)(oxetan-3-yl)methanol (210 mg, 0.72 mmol) in DMF (5 mL) was added NaN$_3$ (70 mg, 1.08 mmol). The resulting mixture was stirred at RT for 3 h. The reaction was concentrated in vacuo to give the crude residue (280 mg, crude), which was used in next step without further purification. ESI-MS [M+H]$^+$: 300.2.

Synthesis of Ethyl 1-((6-cyclopropyl-8-(hydroxy(oxetan-3-yl)methyl)imidazo[1,2-a]pyridin-2-yl)methyl)-1H-1,2,3-triazole-4-carboxylate To a solution of (2-(azidomethyl)-6-cyclopropylimidazo[1,2-a]pyridin-8-yl)(oxetan-3-yl)methanol (210 mg, 0.7 mmol) in t-BuOH/H$_2$O (15 mL/15 mL) was added ethyl propiolate (89 mg, 0.91 mmol), CuSO$_4$ (45 mg, 0.28 mmol) and sodium ascorbate (54 mg, 0.28 mmol). The reaction was stirred at RT for 3 h. Water (15 mL) was added to the reaction, and the mixture was extracted with DCM/MeOH (15/1, 30 mL×3). The combined organic layers were dried over Na₂SO₄ and concentrated in vacuo to give the crude residue, which was purified by Prep-TLC (DCM/MeOH=10/1) to give ethyl 1-((6-cyclopropyl-8-(hydroxy(oxetan-3-yl)methyl)imidazo[1,2-a]pyridin-2-yl)methyl)-1H-1,2,3-triazole-4-carboxylate as yellow solid. (210 mg, 75%). ESI-MS [M+H]⁺: 398.2.

Synthesis of 1-((6-cyclopropyl-8-(hydroxy(oxetan-3-yl)methyl)imidazo[1,2-a]pyridin-2-yl)methyl)-1H-1,2,3-triazole-4-carboxylic Acid To a solution of ethyl 1-((6-cyclopropyl-8-(hydroxy(oxetan-3-yl)methyl)imidazo[1,2-a]pyridin-2-yl)methyl)-1H-1,2,3-triazole-4-carboxylate (210 mg, 0.53 mmol) in THF/H₂O (8 mL/8 mL) was added LiOH.H₂O (65 mg, 1.58 mmol). The reaction was stirred at RT for 2 h. The reaction mixture was then adjusted to pH 5 using 1N HCl, and freeze-dried to give 1-((6-cyclopropyl-8-(hydroxy(oxetan-3-yl)methyl)imidazo[1,2-a]pyridin-2-yl)methyl)-1H-1,2,3-triazole-4-carboxylic acid (300 mg crude) which was used into next step without further purification. ESI-MS [M+H]⁺: 370.1.

Synthesis of N-((7-chloro-8-fluoroimidazo[1,5-a]pyridin-1-yl)methyl)-1-((6-cyclopropyl-8-(hydroxy(oxetan-3-yl)methyl)imidazo[1,2-a]pyridin-2-yl)methyl)-1H-1,2,3-triazole-4-carboxamide To a solution of 1-((6-cyclopropyl-8-(hydroxy(oxetan-3-yl)methyl)imidazo[1,2-a]pyridin-2-yl)methyl)-1H-1,2,3-triazole-4-carboxylic acid (100 mg crude from previous step) in DMF (3 mL) was added (7-chloro-8-fluoroimidazo[1,5-a]pyridin-1-yl)methanamine hydrochloride (54 mg, 0.23 mmol), HOBT (36.5 mg, 0.27 mmol), EDCI (52 mg, 0.27 mmol) and DIPEA (110 mg, 0.85 mmol). The resulting reaction was stirred at RT for 12 h. The reaction was concentrated in vacuo to give the crude product which was purified by Prep-HPLC to give N-((7-chloro-8-fluoroimidazo[1,5-a]pyridin-1-yl)methyl)-1-((6-cyclopropyl-8-(hydroxy(oxetan-3-yl)methyl)imidazo[1,2-a]pyridin-2-yl)methyl)-1H-1,2,3-triazole-4-carboxamide as a white solid (7 mg, 7.2% over 2 steps). ESI-MS [M+H]⁺: 551.1. Purity: 98.95% (214 nm), 100% (254 nm). ¹H NMR (400 MHz, DMSO): δ 8.88-8.77 (m, 1H), 8.71-8.61 (m, 2H), 8.48-8.44 (m, 2H), 8.32 (d, J=5.1 Hz, 1H), 8.21 (d, J=7.4 Hz, 1H), 7.65 (d, J=8.4 Hz, 1H), 6.76 (t, J=6.9 Hz, 1H), 6.14 (d, J=7.7 Hz, 2H), 5.02 (s, 0.5H), 4.88 (d, J=8.9 Hz, 0.5H), 4.70 (d, J=5.4 Hz, 2H), 4.56-4.52 (m, 1H), 4.11-4.06 (m, 0.5H), 3.92-3.87 (m, 0.5H), 3.77-3.60 (m, 2H), 3.51-3.47 (m, 1H), 2.17-2.08 (m, 1H), 1.11-1.06 (m, 2H), 0.85-0.75 (m, 2H).

Example 280

Scheme 279

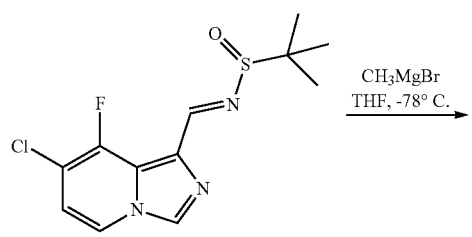

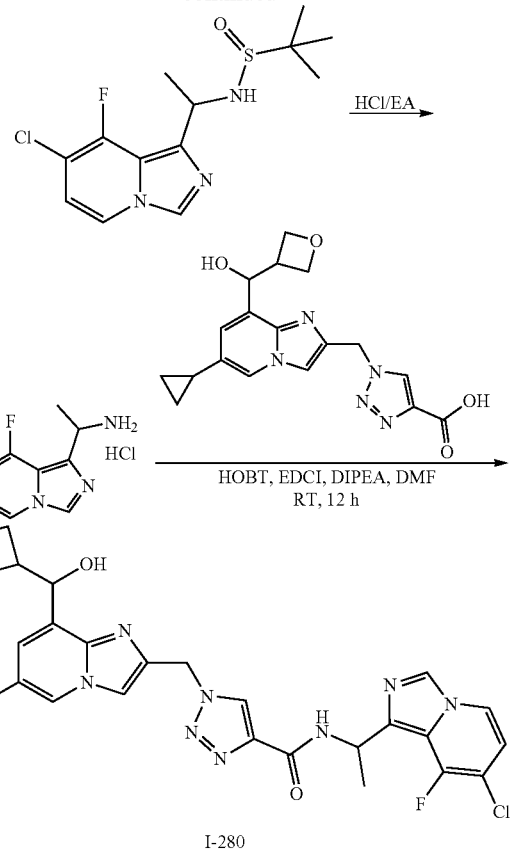

I-280

Synthesis of N-(1-(7-chloro-8-fluoroimidazo[1,5-a]pyridin-1-yl)ethyl)-2-methylpropane-2-sulfinamide Methyl magnesium bromide (3.0 M in ethyl ether, 34 mL, 102.0 mmol) was added slowly to a solution of N-((7-chloro-8-fluoroimidazo[1,5-a]pyridin-1-yl)methylene)-2-methylpropane-2-sulfinamide (12.0 g, 39.7 mmol) in tetrahydrofuran (100 mL) at −78° C. The resulting mixture was stirred for 0.5 h at −78° C. The reaction was quenched with saturated aqueous NH₄Cl (100 mL), and extracted with dichloromethane (200 mL×3). The combined organic layers were washed with brine, dried over with Na₂SO₄, filtered, and concentrated. The residue was purified by silica gel column chromatography (petroleum ether/ethyl acetate=3/1) to afford N-(1-(7-chloro-8-fluoroimidazo[1,5-a]pyridin-1-yl)ethyl)-2-methylpropane-2-sulfinamide (6.8 g, yield: 54%) as a yellow solid. ESI-MS [M+H]⁺: 318.1.

Synthesis of 1-(7-chloro-8-fluoroimidazo[1,5-a]pyridin-1-yl)ethan-1-amine hydrochloride A mixture of N-(1-(7-chloro-8-fluoroimidazo[1,5-a]pyridin-1-yl)ethyl)-2-methylpropane-2-sulfinamide (6.8 g, 21.4 mmol) and hydrochloric acid in ethyl acetate (3 M, 30 mL) was stirred at RT for 1 h. The reaction mixture was filtered to give the crude product, which was washed with dichloromethane and dried in vacuo to give 1-(7-chloro-8-fluoroimidazo[1,5-a]pyridin-1-yl)ethanamine hydrochloride (5.3 g, 100%) as a white solid. ESI-MS [M-NH₂]⁺: 197.0.

Synthesis of N-(1-(7-chloro-8-fluoroimidazo[1,5-a]pyridin-1-yl)ethyl)-1-((6-cyclopropyl-8-(hydroxy(oxetan-3-yl)methyl)imidazo[1,2-a]pyridin-2-yl)methyl)-1H-1,2,3-triazole-4-carboxamide To a solution of 1-((6-cyclopropyl-8-(hydroxy(oxetan-3-yl)methyl)imidazo[1,2-a]pyridin-2-yl)methyl)-1H-1,2,3-triazole-4-carboxylic acid (100 mg crude from previous step) in DMF (10 mL) was added 1-(7-chloro-8-fluoroimidazo[1,5-a]pyridin-1-yl)ethan-1-amine (49 mg, 0.23 mmol), HOBT (36.5 mg, 0.27 mmol), EDCI (52 mg, 0.27 mmol) and DIPEA (110 mg, 0.85 mmol). The reaction mixture was stirred at RT for 12 h. The reaction was concentrated in vacuo to give the crude product which was purified by prep-HPLC to give N-(1-(7-chloro-8-fluoroimidazo[1,5-a]pyridin-1-yl)ethyl)-1-((6-cyclopropyl-8-(hydroxy(oxetan-3-yl)methyl)imidazo[1,2-a]pyridin-2-yl)methyl)-1H-1,2,3-triazole-4-carboxamide as a white solid (17 mg, 17% for two steps). ESI-MS [M+H]$^+$: 565.1. Purity: 98.75% (214 nm), 96.56% (254 nm). $^1$H NMR (400 MHz, DMSO): δ 8.71 (d, J=11.2 Hz, 1H), 8.63 (d, J=20.3 Hz, 1H), 8.55-8.43 (m, 3H), 8.32 (d, J=5.4 Hz, 1H), 8.21 (d, J=7.4 Hz, 1H), 7.65 (d, J=9.4 Hz, 1H), 6.77 (t, J=7.0 Hz, 1H), 6.16 (t, J=12.5 Hz, 2H), 5.57-5.50 (m, 1H), 5.03 (s, 0.5H), 4.88 (d, J=8.8 Hz, 0.5H), 4.58-4.51 (m, 1H), 4.11-4.06 (m, 0.5H), 3.92-3.87 (m, 0.5H), 3.77-3.60 (m, 2H), 3.51-3.47 (m, 1H), 2.16-2.08 (m, 1H), 1.55 (d, J=6.8 Hz, 3H), 1.10-0.98 (m, 2H), 0.89-0.66 (m, 2H).

Example 281

Scheme 280

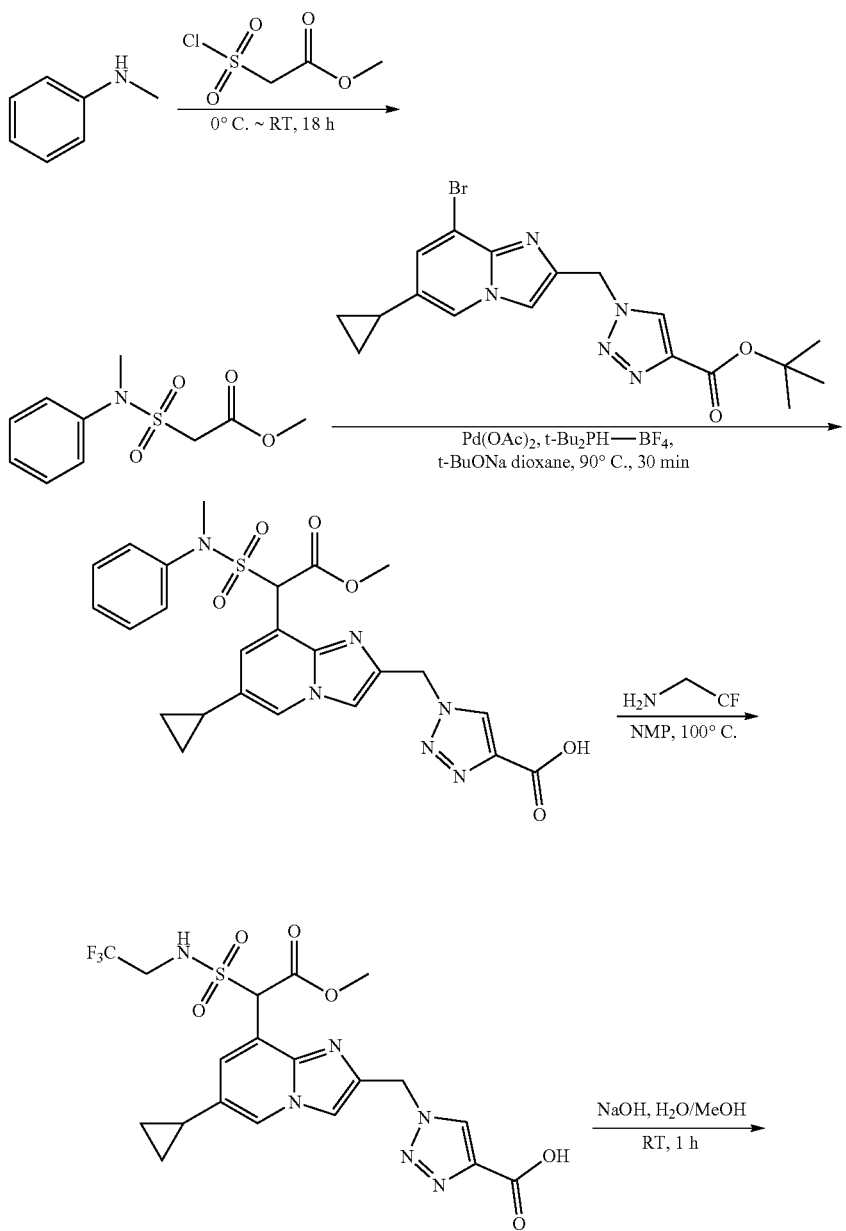

-continued

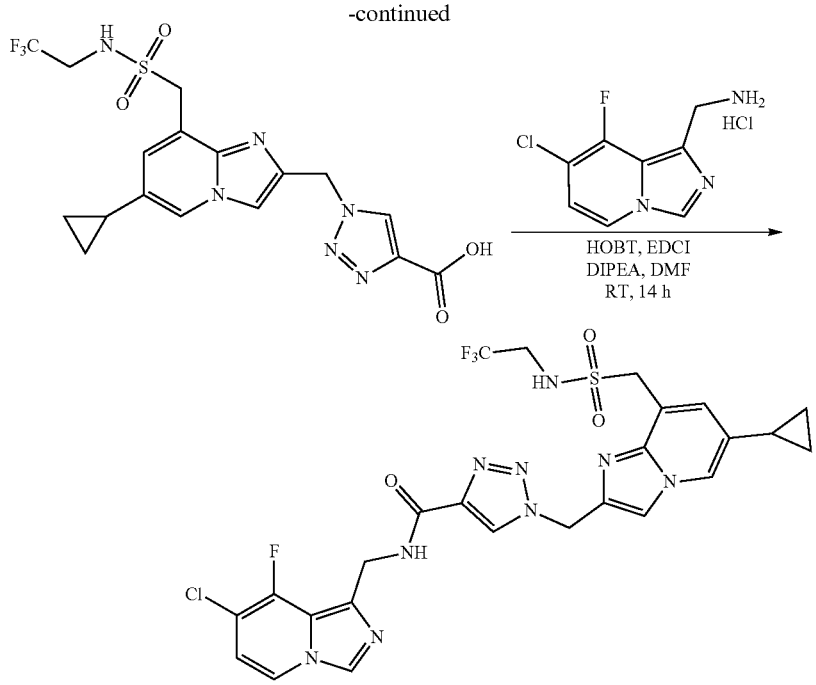

I-281

Synthesis of Methyl 2-(N-methyl-N-phenylsulfamoyl)acetate

To a solution of N-methylaniline (1.07 g, 10 mmol) in DCM (30 mL) was added methyl 2-(chlorosulfonyl)acetate (860 mg, 5 mmol) at 0° C. dropwise. The resulting mixture was stirred at RT for 18 h, then quenched with saturated aqueous NH$_4$Cl solution (50 mL) and extracted with EtOAc (100 mL×3). The combined organic layers were washed with brine, dried over Na$_2$SO$_4$, and concentrated in vacuo to give the crude product which was purified by silica gel column (PE/EtOAc=2/1) to give the methyl 2-(chlorosulfonyl)acetate as a white solid (850 mg, 70%). ESI-MS [M+H]$^+$: 244.1.

Synthesis of 1-((6-cyclopropyl-8-(2-methoxy-1-(N-methyl-N-phenylsulfamoyl)-2-oxoethyl)imidazo[1,2-a]pyridin-2-yl)methyl)-1H-1,2,3-triazole-4-carboxylic Acid To a solution of methyl 2-(N-methyl-N-phenylsulfamoyl) acetate (450 mg, 1.85 mmol) in dry dioxane (25 mL) was added t-BuONa (442 mg, 4.6 mmol) at 0° C. The resulting mixture was stirred at RT for 5 min. Then tert-butyl 1-((8-bromo-6-cyclopropylimidazo[1,2-a]pyridin-2-yl)methyl)-1H-1,2,3-triazole-4-carboxylate (385 mg, 0.92 mmol), Pd(OAc)$_2$ (43 mg, 0.184 mmol), and t-Bu$_3$PH—BF$_4$ (107 mg, 0.368 mmol) were added. The resulting mixture was stirred at 90° C. for 30 min. The reaction was poured into HCl (0.5M, 15 mL) and extracted with DCM/MeOH (15/1, 50 mL×3). The combined organic layers were washed with brine, dried over Na$_2$SO$_4$, and concentrated in vacuo to give the crude product, which was purified with silica gel column (10/1) to give 1-((6-cyclopropyl-8-(2-methoxy-1-(N-methyl-N-phenylsulfamoyl)-2-oxoethyl)imidazo[1,2-a]pyridin-2-yl)methyl)-1H-1,2,3-triazole-4-carboxylic acid as a yellow solid (200 mg, 41%). ESI-MS [M+H]$^+$: 525.2.

Synthesis of 1-((6-cyclopropyl-8-(2-methoxy-2-oxo-1-(N-(2,2,2-trifluoroethyl)sulfamoyl)ethyl)imidazo[1,2-a]pyridin-2-yl)methyl)-1H-1,2,3-triazole-4-carboxylic Acid A solution of 1-((6-cyclopropyl-8-(2-methoxy-1-(N-methyl-N-phenylsulfamoyl)-2-oxoethyl)imidazo[1,2-a] pyridin-2-yl)methyl)-1H-1,2,3-triazole-4-carboxylic acid (200 mg, 0.38 mmol) and 2,2,2-trifluoroethan-1-amine (376 mg, 3.8 mmol) in NMP (5 mL) was stirred at 100° C. for 12 h. The reaction was concentrated in vacuo to give the crude product which was used in the next step without further purification. (210 mg crude). ESI-MS [M+H]$^+$: 517.2.

Synthesis of 1-((6-cyclopropyl-8-((N-(2,2,2-trifluoroethyl)sulfamoyl)methyl)imidazo[1,2-a]pyridin-2-yl)methyl)-1H-1,2,3-triazole-4-carboxylic Acid To a solution of 1-((6-cyclopropyl-8-(2-methoxy-2-oxo-1-(N-(2,2,2-trifluoroethyl)sulfamoyl) ethyl)imidazo[1,2-a] pyridin-2-yl)methyl)-1H-1,2,3-triazole-4-carboxylic acid (210 mg crude from previous step) in MeOH (10 mL) was added NaOH (76 mg, 1.9 mmol) in water (2 mL). The resulting mixture was stirred at RT for 1 h. The reaction was concentrated and the residue was adjusted to about pH 5 using 1N hydrochloric acid. The solution was concentrated in vacuo to give the crude product which was used in the next step without further purification (190 mg crude). ESI-MS [M+H]$^+$: 459.1.

Synthesis of N-((7-chloro-8-fluoroimidazo[1,5-a]pyridin-1-yl)methyl)-1-((6-cyclopropyl-8-((N-(2,2,2-trifluoroethyl)sulfamoyl)methyl)imidazo[1,2-a]pyridin-2-yl)methyl)-1H-1,2,3-triazole-4-carboxamide To a solution of 1-((6-cyclopropyl-8-((N-(2,2,2-trifluoroethyl)sulfamoyl)methyl)imidazo[1,2-a]pyridin-2-yl)

methyl)-1H-1,2,3-triazole-4-carboxylic acid (190 mg crude from previous step) and (7-chloro-8-fluoroimidazo[1,5-a]pyridin-1-yl)methanamine hydrochloride (109 mg, 0.46 mmol) in DMF (10 mL) was added HOBT (66 mg, 0.49 mmol), EDCI (94 mg, 0.49 mmol), and DIPEA (147 mg, 1.14 mmol). The resulting mixture was stirred at RT for 14 h. Water (30 mL) was added and the mixture was extracted with EtOAc (40 mL×3). The combined organic layers were washed with brine, dried over Na$_2$SO$_4$, and concentrated in vacuo to give the crude product which was purified with prep-TLC (DCM/MeOH=10/1) to give N-((7-chloro-8-fluoroimidazo[1,5-a]pyridin-1-yl)methyl)-1-((6-cyclopropyl-8-((N-(2,2,2-trifluoroethyl)sulfamoyl)methyl)imidazo[1,2-a]pyridin-2-yl)methyl)-1H-1,2,3-triazole-4-carboxamide (18 mg, 7.4% over 3 steps). ESI-MS [M+H]$^+$: 640.1. Purity: 91.16% (214 nm), 93.03% (254 nm). $^1$H NMR (400 MHz, DMSO): δ 8.62 (t, J=5.5 Hz, 1H), 8.51 (s, 1H), 8.44 (s, 1H), 8.36 (s, 1H), 8.20 (d, J=7.2 Hz, 1H), 8.13 (s, 1H), 7.87 (s, 1H), 7.09 (s, 1H), 6.76 (t, J=6.5 Hz, 1H), 5.74 (s, 2H), 4.74-4.63 (m, 4H), 3.71-3.63 (m, 2H), 1.99-1.90 (m, 1H), 1.06-0.85 (m, 2H), 0.71-0.66 (m, 2H).

Example 282

Scheme 281

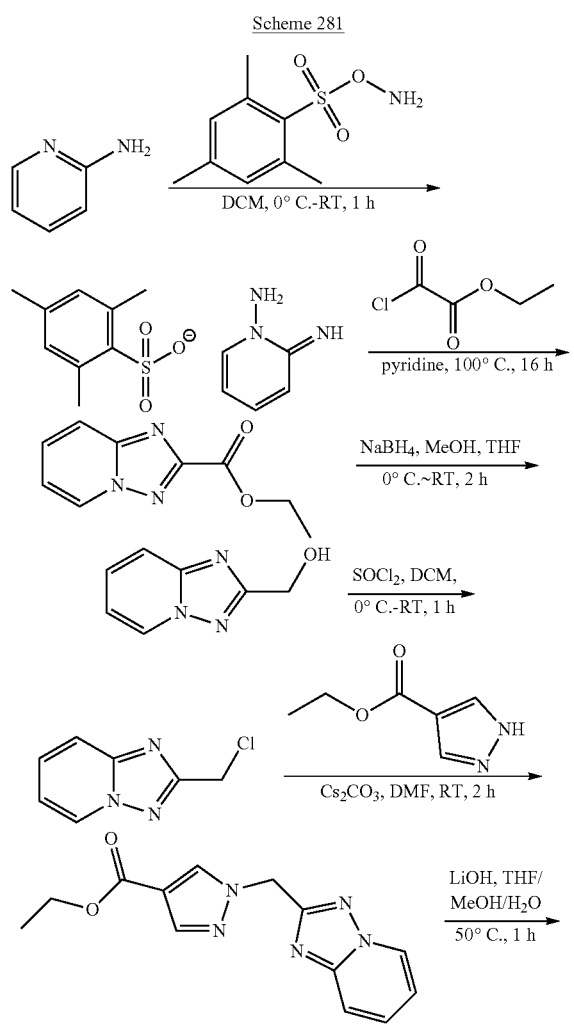

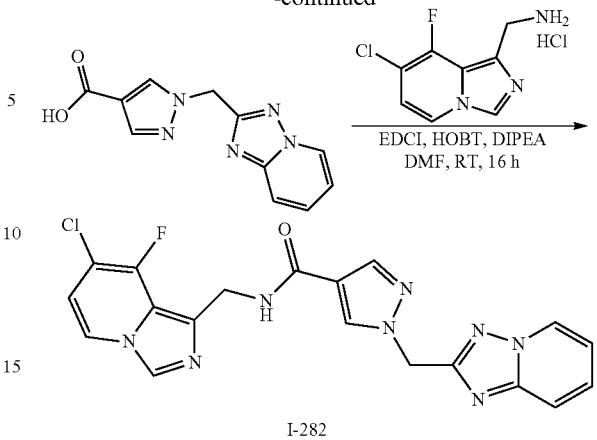

I-282

Synthesis of 2-iminopyridin-1(2H)-amine 2,4,6-trimethylbenzenesulfonate

To a stirred solution of O-(mesitylsulfonyl)hydroxylamine (12.57 g, 58.4 mmol) in DCM (200 mL) was added pyridin-2-amine (5.5 g, 58.4 mmol) in four portions at 0° C. The mixture was stirred at 0° C. for 10 min and then warmed to RT and stirred for 1 h. The reaction mixture was concentrated in vacuo to give 2-iminopyridin-1(2H)-amine 2,4,6-trimethylbenzenesulfonate (18.07 g, yield: 100%) as a light brown solid. ESI-MS [M+H]$^+$: 110.2.

Synthesis of Ethyl [1,2,4]triazolo[1,5-a]pyridine-2-carboxylate

To a stirred solution of 2-iminopyridin-1(2H)-amine 2,4,6-trimethylbenzenesulfonate (18.07 g, 58.4 mmol) in pyridine (70 mL) at RT was added ethyl 2-chloro-2-oxoacetate (15.9 g, 116.8 mmol) dropwise. The mixture was warmed to 100° C. and stirred for 16 h. The reaction mixture was concentrated and diluted with water (200 mL), adjusted to pH 9-10 with saturated aqueous NaHCO$_3$, and extracted with EtOAc (150 mL×5). The combined organics were washed with brine (200 mL×1), dried over Na$_2$SO$_4$, and concentrated to give the crude residue, which was triturated with EtOAc to give ethyl [1,2,4]triazolo[1,5-a]pyridine-2-carboxylate (7.0 g, yield: 63%) as a yellow solid. ESI-MS [M+H]$^+$: 192.1.

Synthesis of [1,2,4]triazolo[1,5-a]pyridin-2-ylmethanol

To a stirred solution of ethyl [1,2,4]triazolo[1,5-a]pyridine-2-carboxylate (2.4 g, 12.55 mmol) in MeOH (20 mL) and THF (10 mL) was added NaBH$_4$ (950 mg, 25.1 mmol) portionwise at 0° C. The mixture was stirred at RT for 2 h. The reaction mixture was quenched with saturated aqueous NH$_4$Cl and concentrated in vacuo. The residue was dissolved in DCM/MeOH (100 mL), filtered, and the filter cake was rinsed with DCM/MeOH (50 mL). The combined filtrate was concentrated and purified by silica gel chromatography (EA/PE=1/1) to give [1,2,4]triazolo[1,5-a]pyridin-2-ylmethanol (1.6 g, yield: 85%) as a yellow solid. ESI-MS [M+H]$^+$: 150.1.

Synthesis of 2-(chloromethyl)-[1,2,4]triazolo[1,5-a]pyridine

To a stirred solution of [1,2,4]triazolo[1,5-a]pyridin-2-ylmethanol (1.6 g, 10.73 mmol) in DCM (30 mL) was added dropwise SOCl₂ (12.8 g, 107.3 mmol) at 0° C. The mixture was stirred at RT for 1 h. The reaction mixture was concentrated and dried in vacuo to give 2-(chloromethyl)-[1,2,4]triazolo[1,5-a]pyridine (1.8 g, yield: 100%) as a yellow solid. ESI-MS [M+H]⁺: 168.0.

Synthesis of Ethyl 1-([1,2,4]triazolo[1,5-a]pyridin-2-ylmethyl)-1H-pyrazole-4-carboxylate A mixture of 2-(chloromethyl)-[1,2,4]triazolo[1,5-a]pyridine (0.78 g, 4.67 mmol), ethyl 1H-pyrazole-4-carboxylate (782 mg, 5.58 mmol) and Cs₂CO₃ (2.27 g, 6.98 mmol) in DMF (10 mL) was stirred at RT for 2 h. The reaction mixture was poured into water (50 mL) and extracted with EtOAc (50 mL×4). The combined organics were washed with water (150 mL×3) and brine (150 mL×1), dried over Na₂SO₄, and concentrated to give the crude product which was purified by silica gel chromatography (EA/PE=1/2) to give ethyl 1-([1,2,4]triazolo[1,5-a]pyridin-2-ylmethyl)-1H-pyrazole-4-carboxylate (1.26 g, yield: 100%) as a white solid. ESI-MS [M+H]⁺: 272.1.

Synthesis of 1-([1,2,4]triazolo[1,5-a]pyridin-2-ylmethyl)-1H-pyrazole-4-carboxylic Acid To a solution of ethyl 1-([1,2,4]triazolo[1,5-a]pyridin-2-ylmethyl)-1H-pyrazole-4-carboxylate (1.26 g, 4.64 mmol) in methanol (10 mL)/THF (10 mL)/H₂O (5 mL) was added lithium hydroxide monohydrate (761 mg, 18.58 mmol). The mixture was stirred at 50° C. for 1 h. The reaction was concentrated in vacuo to remove MeOH and THF. Then the mixture was diluted with water (40 mL), the pH was acidified to 5-6 using hydrochloric acid (2 M) and the precipitate was collected and dried in vacuo to give 1-([1,2,4]triazolo[1,5-a]pyridin-2-ylmethyl)-1H-pyrazole-4-carboxylic acid (720 mg, yield: 64%) as a white solid. ESI-MS [M+H]⁺: 244.1.

Synthesis of 1-([1,2,4]triazolo[1,5-a]pyridin-2-ylmethyl)-N-((7-chloro-s-fluoroimidazo[1,5-a]pyridin-1-yl)methyl)-1H-pyrazole-4-carboxamide A mixture of 1-([1,2,4]triazolo[1,5-a]pyridin-2-ylmethyl)-1H-pyrazole-4-carboxylic acid (150 mg, 0.617 mmol), (7-chloro-8-fluoroimidazo[1,5-a]pyridin-1-yl)methanamine hydrochloride (175 mg, 0.74 mmol), EDCI (235 mg, 1.23 mmol), HOBT (166 mg, 1.23 mmol) and DIPEA (477 mg, 3.70 mmol) in DMF (7 mL) was stirred at RT for 16 h. The reaction mixture was poured into water (70 mL) and the precipitate was collected and purified by silica gel chromatography (DCM/MeOH=10/1) to give 1-([1,2,4]triazolo[1,5-a]pyridin-2-ylmethyl)-N-((7-chloro-8-fluoroimidazo[1,5-a]pyridin-1-yl)methyl)-1H-pyrazole-4-carboxamide (160 mg, yield: 61%) as a pale white solid. ESI-MS [M+H]⁺: 425.1. Purity: 99%. ¹H NMR (400 MHz, DMSO): δ 8.93 (d, J=6.8 Hz, 1H), 8.50-8.45 (m, 1H), 8.32 (s, 1H), 8.22 (d, J=7.4 Hz, 1H), 7.86 (s, 1H), 7.79 (d, J=8.9 Hz, 1H), 7.72-7.63 (m, 1H), 7.20 (t, J=6.8 Hz, 1H), 6.77 (t, J=6.9 Hz, 1H), 5.61 (s, 2H), 4.65 (d, J=5.2 Hz, 2H).

Example 283

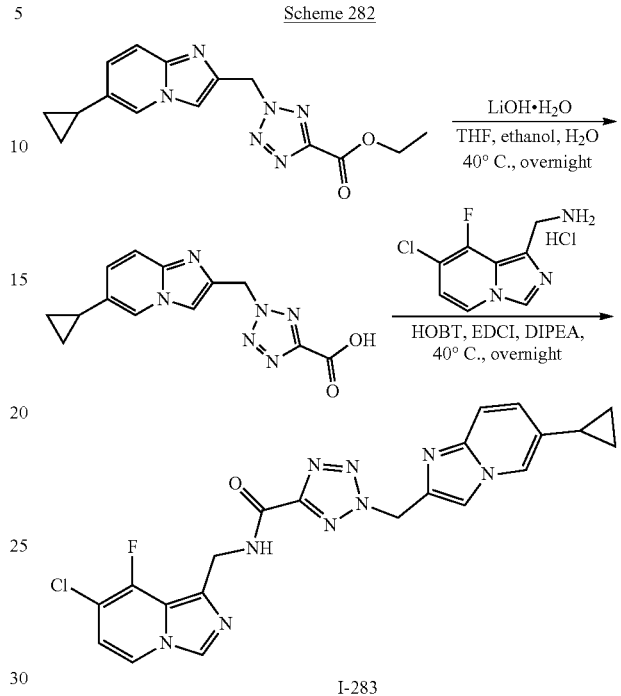

I-283

Synthesis of 2-((6-cyclopropylimidazo[1,2-a]pyridin-2-yl)methyl)-2H-tetrazole-5-carboxylic Acid A solution of ethyl 2-((6-cyclopropylimidazo[1,2-a]pyridin-2-yl)methyl)-2H-tetrazole-5-carboxylate (25 mg, 0.08 mmol) and LiOH.H₂O (7 mg, 0.160 mmol) in THF (2 mL), ethanol (2 mL), and H₂O (0.5 mL) was stirred at 40° C. overnight. The mixture was adjust to pH 1 using HCl (3 M). The mixture was then concentrated and used in the next reaction without further purification. ESI-MS [M+H]⁺: 285.1.

Synthesis of N-((7-chloro-8-fluoroimidazo[1,5-a]pyridin-1-yl)methyl)-2-((6-cyclopropylimidazo[1,2-a]pyridin-2-yl)methyl)-2H-tetrazole-5-carboxamide A solution of 2-((6-cyclopropylimidazo[1,2-a]pyridin-2-yl)methyl)-2H-tetrazole-5-carboxylic acid (23 mg, crude from previous step), (7-chloro-8-fluoroimidazo[1,5-a]pyridin-1-yl)methanamine hydrochloride (23 mg, 0.096 mmol), HOBT (22 mg, 0.16 mmol), EDCI (31 mg, 0.16 mmol) and DIPEA (31 mg, 0.24 mmol) in DMF (2 mL) was stirred at 40° C. overnight. The mixture was diluted with water (30 mL) and extracted with EtOAc (20 mL×3). The combined organic layers were washed with brine, dried over Na₂SO₄ and concentrated. The residue was purified by prep-HPLC to afford N-((7-chloro-8-fluoroimidazo[1,5-a]pyridin-1-yl)methyl)-2-((6-cyclopropylimidazo[1,2-a]pyridin-2-yl)methyl)-2H-tetrazole-5-carboxamide as a white solid (21.8 mg, 47%, 2 steps). ESI-MS [M+H]⁺: 466.1. Purity: 96.09% (214 nm), 97.06% (254 nm). ¹H NMR (400 MHz, DMSO): δ 9.29 (t, J=5.1 Hz, 1H), 8.44 (s, 1H), 8.36 (s, 1H), 8.21 (d, J=7.4 Hz, 1H), 7.94 (s, 1H), 7.39 (d, J=9.3 Hz, 1H), 7.02 (d, J=9.3 Hz, 1H), 6.76 (t, J=6.8 Hz, 1H), 6.07 (s, 2H), 4.72 (d, J=5.3 Hz, 2H), 1.96-1.90 (m, 1H), 0.93-0.91 (m, 2H), 0.68-0.67 (m, 2H).

Example 284

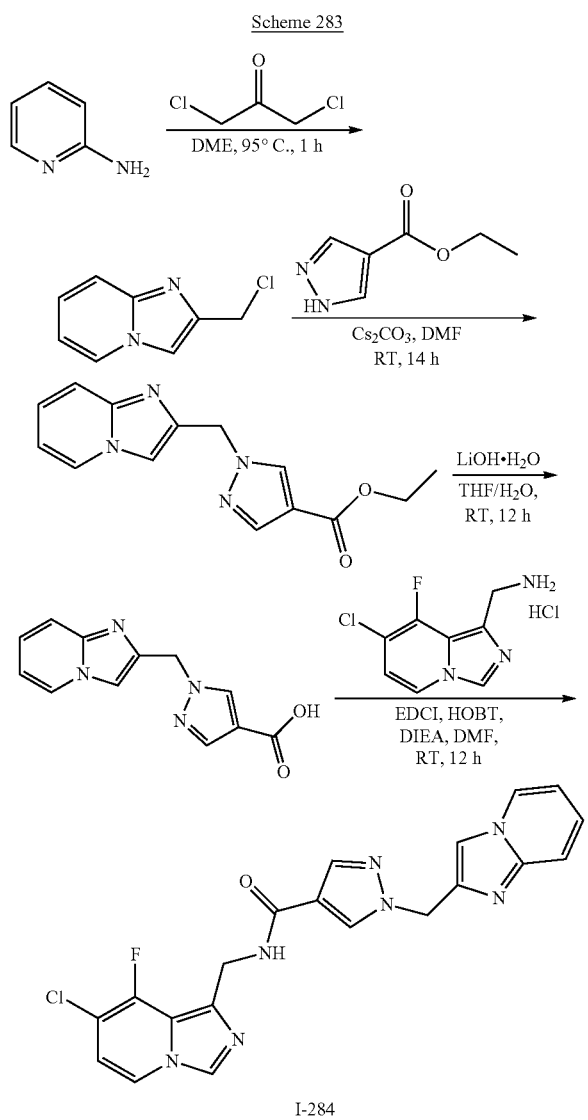

I-284

Synthesis of 2-(chloromethyl)imidazo[1,2-a]pyridine

To a solution of pyridin-2-amine (5 g, 53.19 mmol) in DME (200 mL) was added 1,3-dichloropropan-2-one (20.2 g, 159.42 mmol) at RT. The resulting reaction was stirred at 85° C. for 6 h. The solution was quenched with saturated aqueous NaHCO₃ (200 mL) and extracted with EtOAc (150 mL×3). The combined organic layers were washed with brine, dried over Na₂SO₄, and concentrated in vacuo to give the crude, which was purified by flash column chromatography to afford 2-(chloromethyl)imidazo[1,2-a]pyridine (6 g, yield: 68%) as a light yellow oil. ESI-MS [M+H]⁺: 167.2.

Synthesis of Ethyl 1-(imidazo[1,2-a]pyridin-2-ylmethyl)-1H-pyrazole-4-carboxylate To a solution of 2-(chloromethyl)imidazo[1,2-a]pyridine (3 g, 18.07 mmol) in DMF (30 mL) was added ethyl 1H-pyrazole-4-carboxylate (3.04 g, 21.68 mmol) and Cs₂CO₃ (17.67 g, 54.21 mmol) at RT. The resulting reaction was stirred at RT for 12 h. Water (300 mL) was added to the reaction, and the mixture was extracted with EtOAc (50 mL×3). The combined organic layers were washed with brine, dried over Na₂SO₄, and concentrated in vacuo to give the crude, which was purified was purified by flash column chromatography to give ethyl 1-(imidazo[1,2-a]pyridin-2-ylmethyl)-1H-pyrazole-4-carboxylate (3 g, yield: 61%) as a white solid. ESI-MS [M+H]⁺: 271.2.

Synthesis of 1-(imidazo[1,2-a]pyridin-2-ylmethyl)-1H-pyrazole-4-carboxylic Acid

To a solution of ethyl 1-(imidazo[1,2-a]pyridin-2-ylmethyl)-1H-pyrazole-4-carboxylate (3 g, 11.11 mmol) in THF (20 mL) and water (20 mL) was added LiOH.H₂O (1.3 g, 55.5 mmol). The mixture was stirred at RT for 6 h. The organic layer was evaporated, and the water phase was acidified with 1N hydrochloric acid to pH, 3 and then extracted with DCM/MeOH (10/1, 10 mL×3). The combined organic layers were washed with brine, dried over Na₂SO₄, and concentrated to give 1-(imidazo[1,2-a]pyridin-2-ylmethyl)-1H-pyrazole-4-carboxylic acid (2 g, 75% yield). ESI-MS [M+H]⁺: 243.2.

Synthesis of N-((7-chloro-8-fluoroimidazo[1,5-a]pyridin-1-yl)methyl)-1-(imidazo[1,2-a]pyridin-2-ylmethyl)-1H-pyrazole-4-carboxamide To a solution of 1-(imidazo[1,2-a]pyridin-2-ylmethyl)-1H-pyrazole-4-carboxylic acid (150 mg, 0.62 mmol), (7-chloro-8-fluoroimidazo[1,5-a]pyridin-1-yl)methanamine hydrochloride (190 mg, 0.81 mmol), EDCI (178 mg, 0.93 mmol) and HOBT (126 mg, 0.93 mmol) in DMF (5 mL) was added DIPEA (240 mg, 1.86 mmol). The resulting reaction was stirred at RT for 12 h. H₂O (20 mL) was added to the reaction, and the mixture was extracted with EtOAc (10 mL×3). The combined organic layers were washed with brine, dried over Na₂SO₄, and concentrated in vacuo to give the crude product which was purified by Prep-TLC (DMC/MeOH=10/1) to give N-((7-chloro-8-fluoroimidazo[1,5-a]pyridin-1-yl)methyl)-1-(imidazo[1,2-a]pyridin-2-ylmethyl)-1H-pyrazole-4-carboxamide (60 mg, yield: 23%) as a white solid. ESI-MS [M+H]⁺: 424.2. Purity: 97.15% (214 nm), 97.42% (254 nm). ¹H NMR (400 MHz, DMSO): δ 8.51 (d, J=6.7 Hz, 1H), 8.48-8.39 (m, 2H), 8.28-8.13 (m, 2H), 7.85 (d, J=5.3 Hz, 2H), 7.50 (d, J=9.1 Hz, 1H), 7.28-7.17 (m, 1H), 6.87 (t, J=6.7 Hz, 1H), 6.76 (t, J=6.9 Hz, 1H), 5.42 (s, 2H), 4.63 (d, J=5.1 Hz, 2H).

Example 285

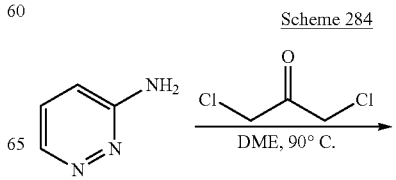

-continued

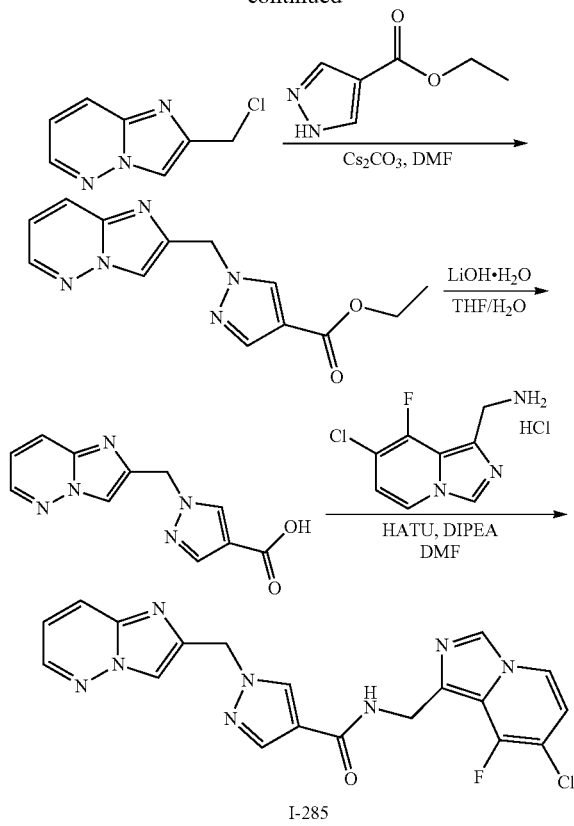

I-285

Synthesis of 2-(chloromethyl)imidazo[1,2-b]pyridazine

A solution of pyridazin-3-amine (5 g, 52.6 mmol) and 1,3-dichloropropan-2-one (8 g, 63.1 mmol) in DME (50 ml) was stirred at 90° C. for 18 h. The reaction was quenched with saturated aqueous NaHCO$_3$ and extracted by DCM/MeOH (5/1.4 L×3). The combined organic layer was washed with brine, dried over Na$_2$SO$_4$, and concentrated to give the crude product, which was purified by flash chromatography (DCM/MeOH=20/1) to afford 2-(chloromethyl)imidazo[1,2-b]pyridazine (1 g, yield: 11.5%) as a yellow solid. ESI-MS: [M+H]*, 168.1.

Synthesis of Ethyl 1-(imidazo[1,2-b]pyridazin-2-ylmethyl)-1H-pyrazole-4-carboxylate A mixture of 2-(chloromethyl)imidazo[1,2-b]pyridazine (300 mg, 1.8 mmol), ethyl 1H-pyrazole-4-carboxylate (302 mg, 2.16 mmol) and Cs$_2$CO$_3$ (1.76 g, 5.4 mmol) in DMF (5 mL) was stirred at RT for 18 h. Water (50 mL) was added to the reaction, and the mixture was extracted by EtOAc (100 mL×3). The combined organic layers were washed by brine, dried over Na$_2$SO$_4$, and concentrated to give the crude product, which was purified by flash chromatography (DCM/MeOH=100/1) to afford ethyl 1-(imidazo[1,2-b]pyridazin-2-ylmethyl)-1H-pyrazole-4-carboxylate (210 mg, yield: 43%) as a white solid. ESI-MS: [M+H]*, 272.2.

Synthesis of 1-(imidazo[1,2-b]pyridazin-2-ylmethyl)-1H-pyrazole-4-carboxylic Acid A mixture of ethyl 1-(imidazo[1,2-b]pyridazin-2-ylmethyl)-1H-pyrazole-4-carboxylate (180 mg, 0.664 mmol) and LiOH·H$_2$O (82 mg, 2.0 mmol) in THF (6 mL) and H$_2$O (6 mL) was stirred at RT for 3 h. The reaction mixture was concentrated to give the crude and the residue was adjusted to pH 3 with hydrochloric acid (3 M). The white solid precipitate was collected by filtration to afford 1-(imidazo[1,2-b]pyridazin-2-ylmethyl)-1H-pyrazole-4-carboxylic acid (130 mg, yield: 81%) as a white solid. ESI-MS: [M+H]*, 244.2.

Synthesis of N-((7-chloro-8-fluoroimidazo[1,5-a]pyridin-1-yl)methyl)-1-(imidazo[1,2-b]pyridazin-2-ylmethyl)-1H-pyrazole-4-carboxamide A mixture of 1-(imidazo[1,2-b]pyridazin-2-ylmethyl)-1H-pyrazole-4-carboxylic acid (50 mg, 0.2 mmol), (7-chloro-8-fluoroimidazo[1,5-a]pyridin-1-yl)methanamine hydrochloride (48 mg, 0.2 mmol), DIEA (103 mg, 0.8 mmol), and HATU (114 mg, 0.3 mmol) in DMF (1.5 mL) was stirred at RT for 18 h. Water (30 mL) was added to the reaction, and the mixture was extracted with EtOAc (30 mL×3). The combined organic layers were washed by brine, dried over Na$_2$SO$_4$, and concentrated to give the crude product which was purified by Prep-TLC (DCM/MeOH=10/1) to give N-((7-chloro-8-fluoroimidazo[1,5-a]pyridin-1-yl)methyl)-1-(imidazo[1,2-b]pyridazin-2-ylmethyl)-1H-pyrazole-4-carboxamide (46 mg, 54%) as a white solid. ESI-MS: [M+H]*, 425.1. Purity: 92.66% (214 nm), 93.26% (254 nm). $^1$H NMR (400 MHz, DMSO): δ 8.50 (d, J=3.6 Hz, 1H), 8.45-8.39 (m, 2H), 8.25 (d, J=4.5 Hz, 2H), 8.21 (d, J=7.4 Hz, 1H), 8.07 (d, J=9.2 Hz, 1H), 7.84 (s, 1H), 7.26-7.20 (m, 1H), 6.79-6.74 (m, 1H), 5.47 (s, 2H), 4.63 (d, J=5.2 Hz, 2H).

Example 286

Scheme 285

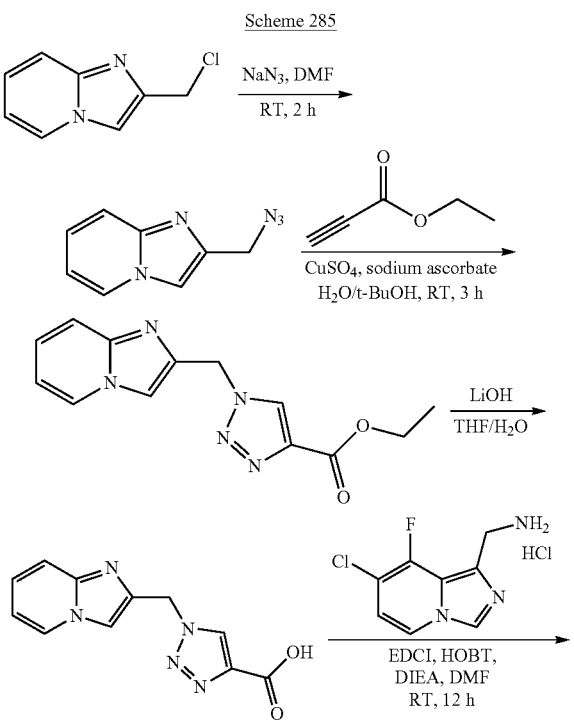

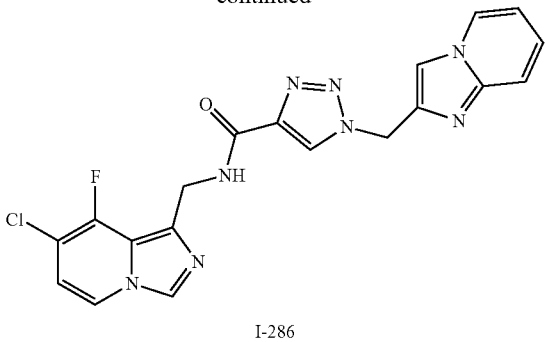

I-286

Synthesis of 2-(azidomethyl)imidazo[1,2-a]pyridine

A mixture of 2-(chloromethyl)imidazo[1,2-a]pyridine (4 g, 24.1 mmol) and NaN$_3$ (2.34 g, 36.15 mmol) in DMF (30 mL) was stirred at RT for 3 h. Water (300 mL) was added to the reaction, and the mixture was extracted with EtOAc (50 mL×3). The combined organic layers were washed with brine, dried over Na$_2$SO$_4$, and concentrated in vacuo to give the crude product which was purified with silica gel chromatography (EA/PE=1/1) to give 2-(azidomethyl)imidazo[1,2-a]pyridine (3.6 g, yield: 86%) as a yellow solid. ESI-MS [M+H]$^+$: 174.1.

Synthesis of Ethyl 1-(imidazo[1,2-a]pyridin-2-ylmethyl)-1H-1,2,3-triazole-4-carboxylate To a solution of 2-(azidomethyl)imidazo[1,2-a]pyridine (3.6 g, 20.8 mmol) in t-BuOH/H$_2$O (10 mL/1 mL) was added ethyl propiolate (2.71 g, 27.7 mmol), CuSO$_4$ (660 mg, 4.16 mmol) and sodium ascorbate (823 mg, 4.16 mmol). The resulting reaction was stirred at RT for 3 h. The reaction mixture was then concentrated in vacuo. The residue was triturated with H$_2$O (30 mL) and filtered to give ethyl 1-(imidazo[1,2-a]pyridin-2-ylmethyl)-1H-1,2,3-triazole-4-carboxylate (2.4 g, yield: 43%) as a yellow solid. ESI-MS [M+H]$^+$: 272.2.

Synthesis of 1-(imidazo[1,2-a]pyridin-2-ylmethyl)-1H-1,2,3-triazole-4-carboxylic Acid A mixture of ethyl 1-(imidazo[1,2-a]pyridin-2-ylmethyl)-1H-1,2,3-triazole-4-carboxylate (2.0 g, 7.38 mmol) and LiOH.H$_2$O (1.5 g, 36.9 mmol) in THF/H$_2$O (20 mL/20 mL) was stirred at RT for 3 h. The reaction was evaporated, and the aqueous phase was acidified with 1N hydrochloric acid to pH 3 and extracted with EtOAc/MeOH (10/1, 50 mL×3). The combined organic layers were washed with brine, dried over Na$_2$SO$_4$, and concentrated to give 1-(imidazo[1,2-a]pyridin-2-ylmethyl)-1H-1,2,3-triazole-4-carboxylic acid (1.5 g, yield: 84%) as a yellow solid. ESI-MS [M+H]$^+$: 244.2.

Synthesis of N-((7-chloro-8-fluoroimidazo[1,5-a]pyridin-1-yl)methyl)-1-(imidazo[1,2-a]pyridin-2-ylmethyl)-1H-1,2,3-triazole-4-carboxamide To a solution of 1-(imidazo[1,2-a]pyridin-2-ylmethyl)-1H-1,2,3-triazole-4-carboxylic acid (150 mg, 0.62 mmol), (7-chloro-8-fluoroimidazo[1,5-a]pyridin-1-yl)methanamine hydrochloride (190 mg, 0.81 mmol), EDCI (178 mg, 0.93 mmol) and HOBT (126 mg, 0.93 mmol) in DMF (3 mL) was added DIPEA (240 mg, 1.86 mmol). The resulting reaction was stirred at RT for 12 h. Water (30 mL) was added to the reaction, and the mixture was extracted with EtOAc (30 mL×3). The combined organic layers were washed with brine, dried over Na$_2$SO$_4$, and concentrated in vacuo. The crude product was purified by Prep-TLC (DCM/MeOH=10/1) to give N-((7-chloro-8-fluoroimidazo[1,5-a]pyridin-1-yl)methyl)-1-(imidazo[1,2-a]pyridin-2-ylmethyl)-1H-1,2,3-triazole-4-carboxamide as a white solid. (50 mg, yield: 19%). ESI-MS [M+H]$^+$: 425.1. Purity: 94.17% (214 nm), 95.28% (254 nm). $^1$H NMR (400 MHz, DMSO): δ 8.71 (t, J=5.4 Hz, 1H), 8.57 (s, 1H), 8.53 (d, J=6.8 Hz, 1H), 8.44 (d, J=2.4 Hz, 1H), 8.21 (d, J=7.4 Hz, 1H), 7.94 (s, 1H), 7.51 (d, J=9.1 Hz, 1H), 7.29-7.20 (m, 1H), 6.89 (t, J=6.4 Hz, 1H), 6.80-6.72 (m, 1H), 5.76 (s, 2H), 4.70 (d, J=5.5 Hz, 2H).

Example 287

Scheme 286

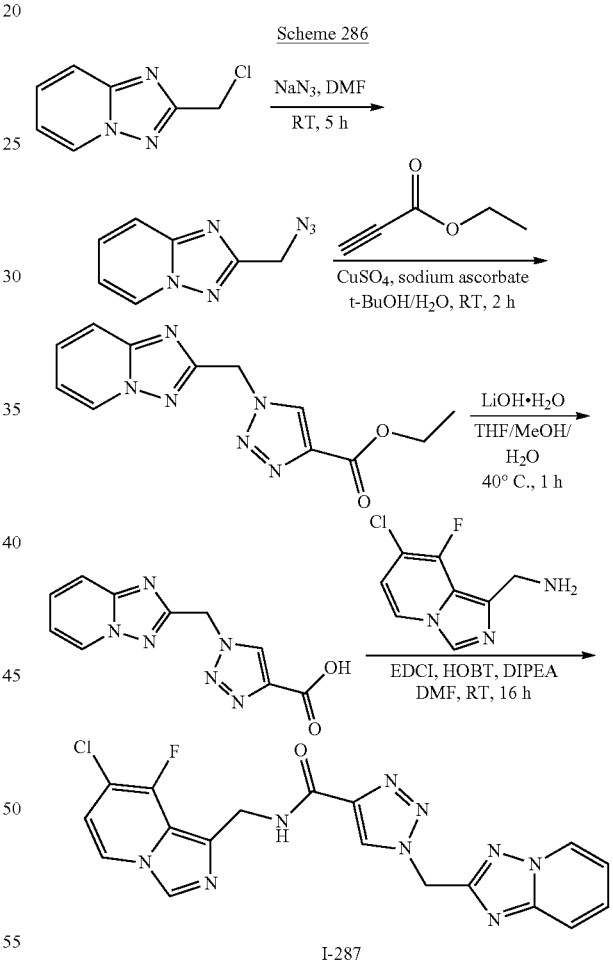

I-287

Synthesis of 2-(azidomethyl)-[1,2,4]triazolo[1,5-a]pyridine

A mixture of 2-(chloromethyl)-[1,2,4]triazolo[1,5-a]pyridine (1.0 g, 5.98 mmol) and NaN$_3$ (427 mg, 6.57 mmol) in DMF (10 mL) was stirred at RT for 5 h. The reaction mixture was poured into water (100 mL) and extracted with EtOAc (70 mL×3). The combined organics were washed with water (30 mL×3) and brine (150 mL×1), dried over Na$_2$SO$_4$, concentrated and dried in vacuo to give 2-(azidomethyl)-[1,2,4]triazolo[1,5-a]pyridine (1.04 g, yield: 100%) as a yellow solid which was used in next step directly. ESI-MS [M+H]⁺: 175.2.

Synthesis of Ethyl 1-([1,2,4]triazolo[1,5-a]pyridin-2-ylmethyl)-1H-1,2,3-triazole-4-carboxylate To a stirred solution of 2-(azidomethyl)-[1,2,4] triazolo[1,5-a]pyridine (1.0 g, 5.74 mmol) in t-BuOH/H₂O (20 mL/2 mL) was added sodium ascorbate (594 mg, 3.0 mmol), CuSO₄ (479 mg, 3.0 mmol) and ethyl propiolate (646 mg, 6.6 mmol) at 0° C. The reaction was stirred at RT for 2 h and then concentrated in vacuo. Water (40 mL) was added, and the mixture was extracted with EtOAc (30 mL×3). The combined organics were washed with brine (40 mL), dried over Na₂SO₄, concentrated, and purified by silica gel chromatography (EtOAc) to give ethyl 1-([1,2,4] triazolo[1,5-a] pyridin-2-ylmethyl)-1H-1,2,3-triazole-4-carboxylate (1.16 g, yield: 74%). ESI-MS [M+H]⁺: 273.1.

Synthesis of 1-([1,2,4]triazolo[1,5-a]pyridin-2-ylmethyl)-1H-1,2,3-triazole-4-carboxylic Acid To a solution of ethyl 1-([1,2,4] triazolo[1,5-a] pyridin-2-ylmethyl)-1H-1,2,3-triazole-4-carboxylate (1.16 g, 4.26 mmol) in THF/MeOH/H₂O (8 mL/8 mL/4 mL) was added LiOH.H₂O (700 mg, 17.06 mmol). The reaction mixture was stirred at 40° C. for 1 h. The reaction mixture was then concentrated and the water layer was adjusted to pH 4-5 with hydrochloric acid (2 M). The white solid precipitate was collected by filtration to get 1-([1,2,4]triazolo[1,5-a]pyridin-2-ylmethyl)-1H-1,2,3-triazole-4-carboxylic acid (929 mg, yield: 89%) as a white solid. ESI-MS [M+H]⁺: 245.1.

Synthesis of 1-([1,2,4]triazolo[1,5-a]pyridin-2-ylmethyl)-N-((7-chloro-s-fluoroimidazo[1,5-a]pyridin-1-yl)methyl)-1H-1,2,3-triazole-4-carboxamide To a solution of 1-([1,2,4]triazolo[1,5-a]pyridin-2-ylmethyl)-1H-1,2,3-triazole-4-carboxylic acid (100 mg, 0.41 mmol) in DMF (5 mL) was added EDCI (157 mg, 0.820 mmol), HOBT (111 mg, 0.820 mmol), DIPEA (265 mg, 2.05 mmol) and (7-chloro-8-fluoroimidazo[1,5-a]pyridin-1-yl) methanamine hydrochloride (116 mg, 0.492 mmol). The reaction was stirred at RT for 16 h. The reaction mixture was then poured into water (50 mL) and extracted with EtOAc (25 mL×3). The combined organics were washed with water (60 mL×3) and brine (60 mL×1), dried over Na₂SO₄, concentrated, and purified by silica gel chromatography (DCM/MeOH=10/1) to give 1-([1,2,4]triazolo[1,5-a]pyridin-2-ylmethyl)-N-((7-chloro-8-fluoroimidazo[1,5-a]pyridin-1-yl)methyl)-1H-1,2,3-triazole-4-carboxamide (117 mg, yield: 67%) as a white solid. ESI-MS [M+H]⁺: 426.0. Purity: 97.32% (214 nm), 96.53% (254 nm). ¹H NMR (400 MHz, DMSO): δ 8.95 (d, J=6.8 Hz, 1H), 8.77 (t, J=5.4 Hz, 1H), 8.67 (s, 1H), 8.45 (d, J=2.4 Hz, 1H), 8.21 (d, J=7.4 Hz, 1H), 7.81 (d, J=8.9 Hz, 1H), 7.73-7.65 (m, 1H), 7.21 (t, J=6.9, 1.2 Hz, 1H), 6.80-6.73 (m, 1H), 5.98 (s, 2H), 4.72 (d, J=5.5 Hz, 2H).

Example 288

Scheme 287

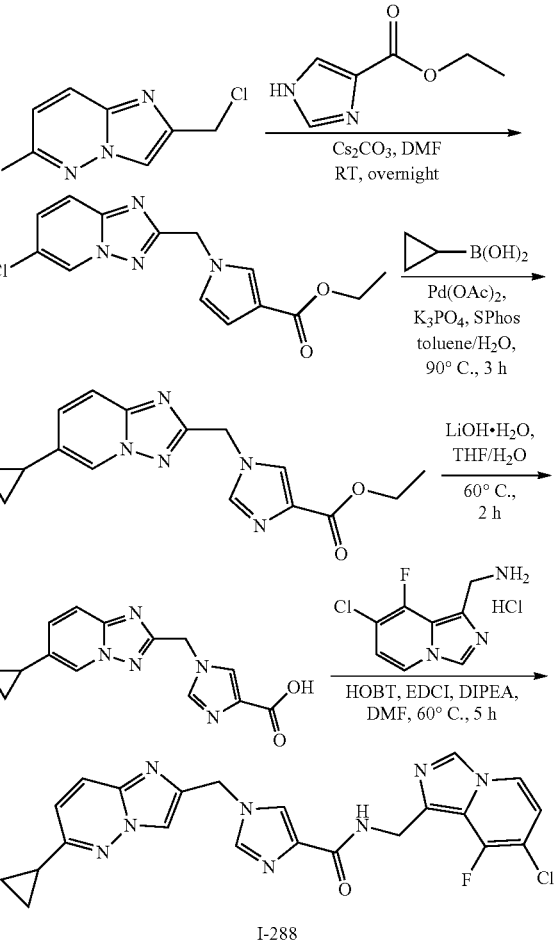

I-288

Synthesis of Ethyl 1-((6-chloroimidazo[1,2-b]pyridazin-2-yl)methyl)-1H-imidazole-4-carboxylate A solution of 6-chloro-2-(chloromethyl)imidazo[1,2-b]pyridazine (500 mg, 2.49 mmol), ethyl 1H-imidazole-4-carboxylate (522 mg, 3.73 mmol), and Cs₂CO₃ (1.6 g, 4.97 mmol) in DMF (10 mL) was stirred at RT overnight. The mixture was diluted with water (100 mL) and extracted with EtOAc (50 mL×3). The combined organic layers were washed with brine, dried over Na₂SO₄, and concentrated. The crude product was purified by Prep-TLC (DCM/MeOH=12/1) to afford ethyl 1-((6-chloroimidazo[1,2-b]pyridazin-2-yl)methyl)-1H-imidazole-4-carboxylate as a white solid (130 mg, 17%). ESI-MS [M+H]⁺: 306.1.

Synthesis of Ethyl 1-((6-cyclopropylimidazo[1,2-b]pyridazin-2-yl)methyl)-1H-imidazole-4-carboxylate A solution of ethyl 1-((6-chloroimidazo[1,2-b]pyridazin-2-yl)methyl)-1H-imidazole-4-carboxylate (130 mg, 0.426 mmol), cyclopropylboronic acid (73 mg, 0.852 mmol), Pd(OAc)₂ (29 mg, 0.128 mmol), K₃PO₄ (181 mg, 0.852 mmol) and SPhos (52 mg, 0.128 mmol) in toluene (5 mL)

and H₂O (0.5 mL) was stirred at 90° C. under N₂ for 3 h. The mixture was cooled to RT, filtered, and the filter cake was washed with DCM/MeOH (3/1, 50 mL). The filtrate was concentrated and purified by Prep-TLC (DCM/MeOH=10/1) to afford ethyl 1-((6-cyclopropylimidazo[1,2-b]pyridazin-2-yl)methyl)-1H-imidazole-4-carboxylate as a yellow solid (80 mg, 61%). ESI-MS [M+H]⁺: 312.2.

Synthesis of 1-((6-cyclopropylimidazo[1,2-b]pyridazin-2-yl)methyl)-1H-imidazole-4-carboxylic Acid A solution of ethyl 1-((6-cyclopropylimidazo[1,2-b]pyridazin-2-yl)methyl)-1H-imidazole-4-carboxylate (40 mg, 0.128 mmol) and LiOH.H₂O (11 mg, 0.256 mmol) in THF (2 mL) and H₂O (2 mL) was stirred at 60° C. for 2 h. The reaction mixture was adjusted to pH 5 with aqueous hydrochloric acid (3 M). The mixture was concentrated in vacuo to give the crude product which was used into the next reaction without further purification (55 mg crude). ESI-MS [M+H]⁺: 284.1.

Synthesis of N-((7-chloro-8-fluoroimidazo[1,5-a]pyridin-1-yl)methyl)-1-((6-cyclopropylimidazo[1,2-b]pyridazin-2-yl)methyl)-1H-imidazole-4-carboxamide A solution of 1-((6-cyclopropylimidazo[1,2-b]pyridazin-2-yl)methyl)-1H-imidazole-4-carboxylic acid (55 mg crude from previous step), (7-chloro-8-fluoroimidazo[1,5-a]pyridin-1-yl)methanamine hydrochloride (36 mg, 0.154 mmol), HOBT (70 mg, 0.518 mmol), EDCI (99 mg, 0.516 mmol) and DIPEA (100 mg, 0.771 mmol) in DMF (3 mL) was stirred at 60° C. for 5 h. The reaction was poured into H₂O (25 mL) and a white solid precipitated out. The mixture was filtered, and the filter cake was washed by MeOH (5 mL) to afford N-((7-chloro-8-fluoroimidazo[1,5-a]pyridin-1-yl)methyl)-1-((6-cyclopropylimidazo[1,2-b]pyridazin-2-yl)methyl)-1H-imidazole-4-carboxamide as a white solid (18.6 mg, 31%, 2 steps). ESI-MS [M+H]⁺: 465.1. Purity: 97.37% (214 nm), 97.90% (254 nm). ¹H NMR (400 MHz, DMSO): δ 8.44 (d, J=2.2 Hz, 1H), 8.20 (d, J=7.4 Hz, 1H), 8.12 (s, 1H), 8.00 (t, J=5.4 Hz, 1H), 7.93 (d, J=9.4 Hz, 1H), 7.79 (s, 1H), 7.70 (s, 1H), 7.09 (d, J=9.5 Hz, 1H), 6.75 (t, J=6.9 Hz, 1H), 5.33 (s, 2H), 4.66 (d, J=5.5 Hz, 2H), 2.22-2.13 (m, 1H), 1.08-1.03 (m, 2H), 0.98-0.94 (m, 2H).

Example 289

Scheme 288

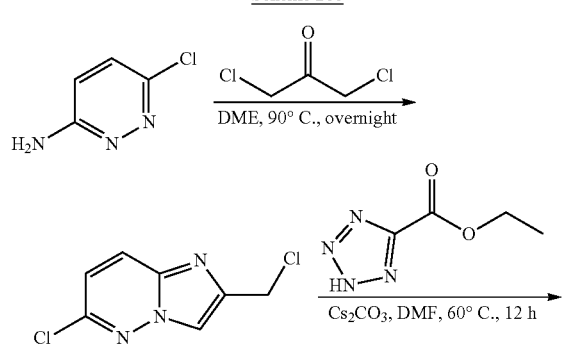

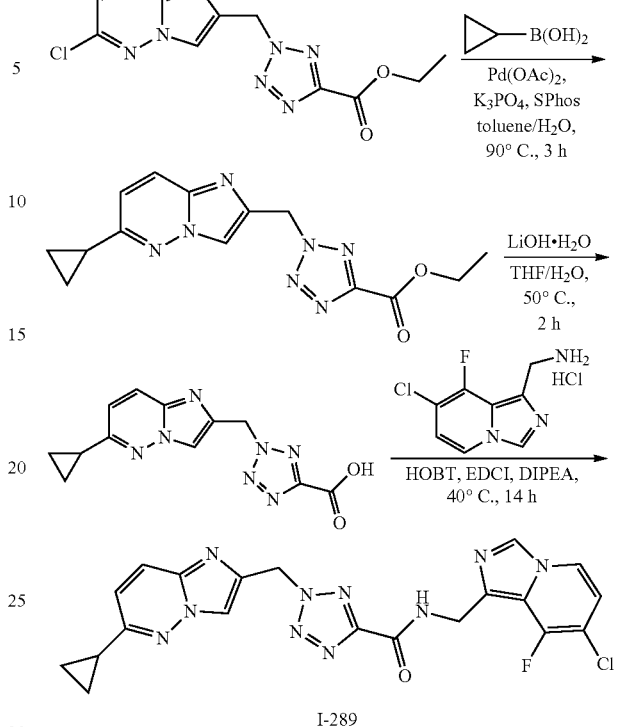

I-289

Synthesis of 6-chloro-2-(chloromethyl)imidazo[1,2-b]pyridazine

A solution of 6-chloropyridazin-3-amine (2.58 g, 20 mmol) and 1,3-dichloropropan-2-one (3.04 g, 24 mmol) in DME (30 mL) was stirred at 90° C. overnight. The mixture was concentrated and purified by flash column chromatography (PE/EtOAc=1/4) to afford 6-chloro-2-(chloromethyl)imidazo[1,2-b]pyridazine as a yellow solid (1.37 g, 34%). ESI-MS [M+H]⁺: 202.0.

Synthesis of Ethyl 2-((6-chloroimidazo[1,2-b]pyridazin-2-yl)methyl)-2H-tetrazole-5-carboxylate A solution of 6-chloro-2-(chloromethyl)imidazo[1,2-b]pyridazine (201 mg, 1.0 mmol), ethyl 2H-tetrazole-5-carboxylate (213 mg, 1.5 mmol) and Cs₂CO₃ (489 mg, 1.5 mmol) in DMF (5 mL) was stirred at 60° C. overnight. The mixture was diluted with water (50 mL) and extracted with EtOAc (30 mL×5). The combined organic layers were washed with brine, dried over Na₂SO₄ and concentrated. The residue was purified by flash column chromatography (DCM/MeOH=30/1) to afford ethyl 2-((6-chloroimidazo[1,2-b]pyridazin-2-yl)methyl)-2H-tetrazole-5-carboxylate as a white solid (140 mg, 45%). ESI-MS [M+H]⁺: 308.0.

Synthesis of Ethyl 2-((6-cyclopropylimidazo[1,2-b]pyridazin-2-yl)methyl)-2H-tetrazole-5-carboxylate A solution of ethyl 2-((6-chloroimidazo[1,2-b]pyridazin-2-yl)methyl)-2H-tetrazole-5-carboxylate (140 mg, 0.456 mmol), cyclopropylboronic acid (78 mg, 0.912 mmol), Pd(OAc)₂ (31 mg, 0.137 mmol), K₃PO₄ (193 mg, 0.912 mmol) and SPhos (56 mg, 0.137 mmol) in toluene (5 mL) and H₂O (0.5 mL) was stirred at 90° C. under N₂ for 3 h. The mixture was cooled to RT, filtered, and the filter cake was washed with DCM/MeOH (3/1, 50 mL). The filtrate was concentrated and purified by Prep-TLC (DCM/MeOH=40/1) to afford ethyl 2-((6-cyclopropylimidazo[1,2-b]pyridazin-2-yl)methyl)-2H-tetrazole-5-carboxylate as a white solid (44 mg, 31%). ESI-MS [M+H]$^+$: 314.2.

Synthesis of 2-((6-cyclopropylimidazo[1,2-b]pyridazin-2-yl)methyl)-2H-tetrazole-5-carboxylic Acid A solution of ethyl 2-((6-cyclopropylimidazo[1,2-b]pyridazin-2-yl)methyl)-2H-tetrazole-5-carboxylate (40 mg, 0.128 mmol) and LiOH*H$_2$O (11 mg, 0.256 mmol) in THF (2 mL)/H$_2$O (2 mL) was stirred at 50° C. for 2 h. The reaction mixture was concentrated to remove THF. The residue was adjusted to pH 5 using 3 M hydrochloric acid. Then the mixture was concentrated to give 2-((6-cyclopropylimidazo[1,2-b]pyridazin-2-yl)methyl)-2H-tetrazole-5-carboxylic acid, which was used into the next step without further purification (60 mg crude). ESI-MS [M+H]$^+$: 286.2.

Synthesis of N-((7-chloro-8-fluoroimidazo[1,5-a]pyridin-1-yl)methyl)-2-((6-cyclopropylimidazo[1,2-b]pyridazin-2-yl)methyl)-2H-tetrazole-5-carboxamide A solution of 2-((6-cyclopropylimidazo[1,2-b]pyridazin-2-yl)methyl)-2H-tetrazole-5-carboxylic acid (60 mg crude from previous step), (7-chloro-8-fluoroimidazo[1,5-a]pyridin-1-yl)methanamine hydrochloride (37 mg, 0.154 mmol), HOBT (70 mg, 0.518 mmol), EDCI (99 mg, 0.516 mmol) and DIPEA (100 mg, 0.771 mmol) in DMF (3 mL) was stirred at 40° C. overnight. The reaction mixture was poured into H$_2$O (30 mL) and white solid was precipitated out. The mixture was filtered, and the filter cake was washed with MeOH (5 mL) to afford N-((7-chloro-8-fluoroimidazo[1,5-a]pyridin-1-yl)methyl)-2-((6-cyclopropylimidazo[1,2-b]pyridazin-2-yl)methyl)-2H-tetrazole-5-carboxamide as a white solid (10.1 mg, 17%, over 2 steps). MS [M+H]$^+$: 467.1. Purity: 94.54% (214 nm), 95.52% (254 nm). $^1$H NMR (400 MHz, DMSO): δ 9.30 (t, J=5.3 Hz, 1H), 8.44 (d, J=1.7 Hz, 1H), 8.30 (s, 1H), 8.21 (d, J=7.4 Hz, 1H), 7.92 (d, J=9.4 Hz, 1H), 7.12 (d, J=9.5 Hz, 1H), 6.77 (t, J=6.9 Hz, 1H), 6.10 (s, 2H), 4.72 (d, J=5.4 Hz, 2H), 2.21-2.15 (m, 1H), 1.09-1.05 (m, 2H), 1.00-0.96 (m, 2H)

Example 290

Scheme 289

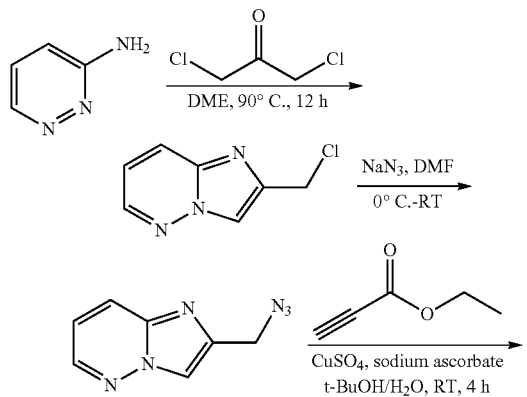

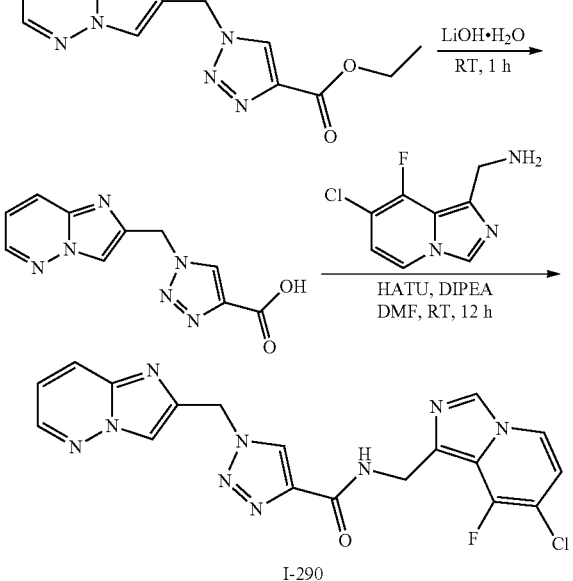

I-290

Synthesis of 2-(chloromethyl)imidazo[1,2-b]pyridazine

To a solution of pyridazin-3-amine (5 g, 52.6 mmol) in DME (50 mL) was added 1,3-dichloropropan-2-one (8 g, 63.2 mmol). After stirring at 90° C. for 12 h, the mixture was cooled to RT and concentrated to give the crude product, which was purified by silica gel chromatography (PE/EtOAc=10/3) to give the product as white solid (6 g, yield: 68%). ESI-MS [M+H]$^+$: 168.6.

Synthesis of 2-(azidomethyl)imidazo[1,2-b]pyridazine

To a mixture of 2-(chloromethyl)imidazo[1,2-b]pyridazine (300 mg, 1.8 mmol) in DMF (5 mL) at 0° C. was added NaN$_3$ (175 mg, 2.7 mmol). The mixture was stirred at RT for 18 h. Water (50 mL) was added and the mixture was extracted with EtOAc (30 mL×3). The combined organic layers were washed with water (50 mL) and brine (50 mL), dried over Na$_2$SO$_4$, and concentrated to give the crude product which was purified by silica gel chromatography (PE/EtOAc=10/3) to give the product as yellow oil (240 mg, yield: 77%). ESI-MS [M+H]$^+$: 175.2.

Synthesis of Ethyl 1-(imidazo[1,2-b]pyridazin-2-ylmethyl)-1H-1,2,3-triazole-4-carboxylate To a solution 2-(azidomethyl)imidazo[1,2-b]pyridazine (240 mg, 1.38 mmol) in t-BuOH/H$_2$O (10 mL/1 mL) was added sodium ascorbate (55 mg, 0.28 mmol), CuSO$_4$ (45 mg, 0.28 mmol) and ethyl propiolate (162 mg, 1.66 mmol). After stirring at RT for 3 h, H$_2$O (10 mL) was added and the mixture was extracted with EtOAc (10 mL×3). The combined organic layers were washed with brine (10 mL), dried over Na$_2$SO$_4$, and concentrated to give the crude product which was purified by silica gel chromatography (MeOH/DCM=1/10) to give the product as white solid (353 mg, yield: 94%). ESI-MS [M+H]$^+$: 273.1.

Synthesis of 1-(imidazo[1,2-b]pyridazin-2-ylmethyl)-1H-1,2,3-triazole-4-carboxylic Acid To a solution of ethyl 1-(imidazo[1,2-b]pyridazin-2-ylmethyl)-1H-1,2,3-triazole-4-carboxylate (353 mg, 1.3 mmol) in THF/EtOH/H2O (6 mL/6 mL/2 mL) was added LiOH H$_2$O (266 mg, 6.5 mmol). The mixture was stirred at RT for 1 h. Water (5 mL) was added and the mixture was extracted with CHCl$_3$/i-PrOH (3/1, 10 mL×5). The combined organic layers were washed with brine (10 mL), dried with Na$_2$SO$_4$, and concentrated to give the crude product as a white solid (190 mg, yield: 60%). This material was used in next step directly. ESI-MS [M+H]$^+$: 245.1.

Synthesis of N-((7-chloro-8-fluoroimidazo[1,5-a]pyridin-1-yl)methyl)-1-(imidazo[1,2-b]pyridazin-2-ylmethyl)-1H-1,2,3-triazole-4-carboxamide A mixture of 1-(imidazo[1,2-b]pyridazin-2-ylmethyl)-1H-1,2,3-triazole-4-carboxylic acid (70 mg 0.29 mmol), HATU (163 mg, 0.43 mmol), DIPEA (111 mg, 0.86 mmol), and (7-chloro-8-fluoroimidazo[1,5-a]pyridin-1-yl)methanamine hydrochloride (80 mg, 0.34 mmol) in DMF (3 mL) was stirred at RT for 12 h. Water (30 mL) was added and the mixture was extracted with EtOAc (30 mL×6). The combined organic layers were washed with water (20 mL×3) and brine (20 mL), dried over Na$_2$SO$_4$, and concentrated to give the crude product which was purified by prep-TLC (MeOH/DCM=1/10) to give the product as white solid (50 mg, yield: 41%). ESI-MS [M+H]$^+$: 426.1. Purity: 100% (214 nm), 100% (254 nm). $^1$H NMR (400 MHz, DMSO): δ 8.71 (t, J=5.4 Hz, 1H), 8.60 (s, 1H), 8.52 (d, J=4.4 Hz, 1H), 8.44 (d, J=2.2 Hz, 1H), 8.36 (s, 1H), 8.21 (d, J=7.4 Hz, 1H), 8.09 (d, J=8.7 Hz, 1H), 7.28-7.21 (m, 1H), 6.76 (t, J=6.9 Hz, 1H), 5.81 (s, 2H), 4.70 (d, J=5.5 Hz, 2H).

Example 291

Scheme 290

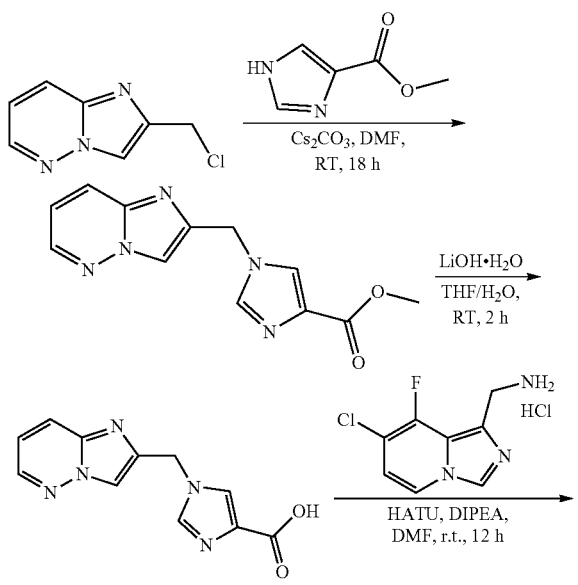

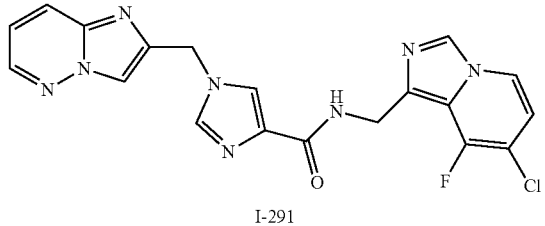

I-291

Synthesis of Methyl 1-(imidazo[1,2-b]pyridazin-2-ylmethyl)-1H-imidazole-4-carboxylate To a solution of 2-(chloromethyl)imidazo[1,2-b]pyridazine (1.0 g, 5.98 mmol) in DMF (10 mL) was added Cs$_2$CO$_3$ (2.92 g, 8.98 mmol) and methyl 1H-imidazole-4-carboxylate (904 mg, 7.18 mmol) under N$_2$ atmosphere. After stirring at RT for 18 h, H$_2$O (100 mL) was added. The mixture was extracted with EtOAc (100 mL×3). The combined organic layers were washed with brine, dried over Na$_2$SO$_4$, and concentrated to give the crude, which was purified by prep-TLC (MeOH/DCM=1/10) to give methyl 1-(imidazo[1,2-b]pyridazin-2-ylmethyl)-1H-imidazole-4-carboxylate as a white solid (600 mg, yield: 39%). ESI-MS [M+H]$^+$: 258.3.

Synthesis of 1-(imidazo[1,2-b]pyridazin-2-ylmethyl)-1H-imidazole-4-carboxylic Acid To a solution of methyl 1-(imidazo[1,2-b]pyridazin-2-ylmethyl)-1H-imidazole-4-carboxylate (257 mg, 1.0 mmol) in THF/H$_2$O (10 mL/10 mL) was added LiOH H$_2$O (253 mg, 6.0 mmol). The reaction mixture was stirred at RT for 1 h. The reaction was concentrated to remove THF, and the residue was adjusted to pH 3 using hydrochloric acid (1 M). The resulting precipitate was collected by filtration to give the product as a white solid (130 mg, yield: 53.4%). ESI-MS [M+H]$^+$: 244.1.

Synthesis of N-((7-chloro-8-fluoroimidazo[1,5-a]pyridin-1-yl)methyl)-1-(imidazo[1,2-b]pyridazin-2-ylmethyl)-1H-imidazole-4-carboxamide A mixture of 1-(imidazo[1,2-b]pyridazin-2-ylmethyl)-1H-imidazole-4-carboxylic acid (70 mg 0.29 mmol), HATU (164 mg, 0.43 mmol), and DIPEA (111 mg, 0.86 mmol) in DMF (3 mL) was stirred at RT for 20 min, then a solution of (7-chloro-8-fluoroimidazo[1,5-a]pyridin-1-yl)methanamine hydrochloride (82 mg, 0.35 mmol) in 2 mL was added. The resulting reaction was stirred at RT for 12 h. H$_2$O (50 mL) was added and the mixture was extracted with EtOAc (30 mL×3). The combined organic layers were washed with brine, dried over Na$_2$SO$_4$, and concentrated in vacuo. The crude product was purified by Prep-TLC (MeOH/DCM=1/10) to give N-((7-chloro-8-fluoroimidazo[1,5-a]pyridin-1-yl)methyl)-1-(imidazo[1,2-b]pyridazin-2-ylmethyl)-1H-imidazole-4-carboxamide as a white solid. (50 mg, yield: 41%). ESI-MS [M+H]$^+$: 425.1. Purity: 95.85% (214 nm), 96.36% (254 nm). $^1$H NMR (400 MHz, DMSO): δ 8.53-8.48 (m, 1H), 8.44 (d, J=2.4 Hz, 1H), 8.28 (s, 1H), 8.20 (d, J=7.4 Hz, 1H), 8.08 (d, J=9.2 Hz, 1H), 8.01 (t, J=5.5 Hz, 1H), 7.82 (d, J=1.0 Hz, 1H), 7.73 (d, J=1.0 Hz, 1H), 7.27-7.20 (m, 1H), 6.80-6.71 (m, 1H), 5.39 (s, 2H), 4.67 (d, J=5.5 Hz, 2H).

Example 292

Scheme 291

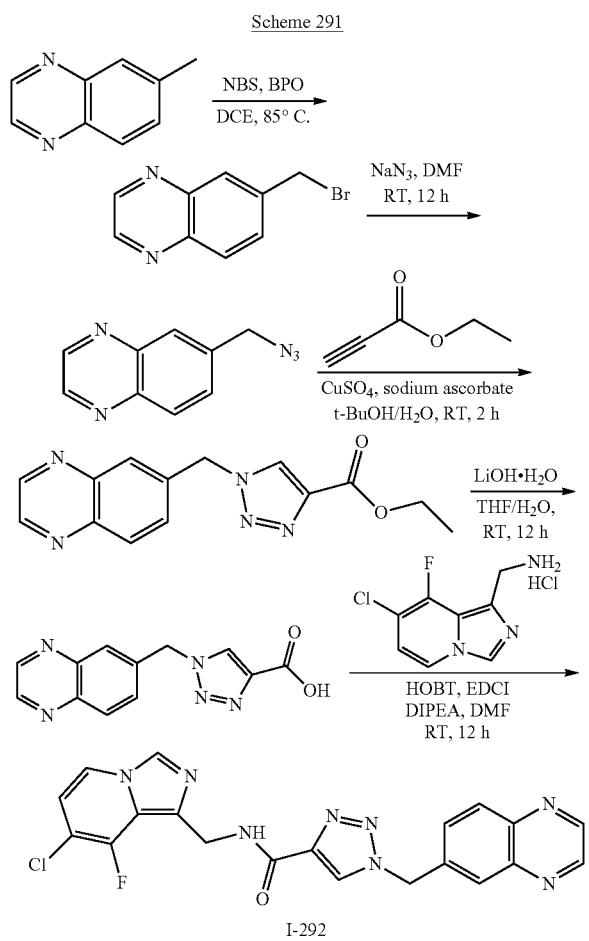

I-292

Synthesis of 6-(bromomethyl)quinoxaline

To a solution of 6-methylquinoxaline (5 g, 34.7 mmol) in DCE (100 mL) was added NBS (7.12 g, 40 mmol) and benzoyl peroxide (840 mg, 3.47 mmol). The reaction mixture was stirred at 85° C. for 16 h under nitrogen. H$_2$O (100 mL) was added, and the mixture was extracted with DCM (150 mL×3). The combine organic layers were washed with brine, dried over Na$_2$SO$_4$, and concentrated in vacuo to give the crude product which was purified by silica gel chromatography (PE/EtOAc=1/1) to give 6-(bromomethyl)quinoxaline as a yellow solid. (5.5 g, 71%). ESI-MS [M+H]$^+$: 224.1.

Synthesis of 6-(bromomethyl)quinoxaline

A mixture of 6-(bromomethyl)quinoxaline (3 g, 13.5 mmol) and NaN3 (1.2 g, 18.5 mmol) in DMF (50 mL) was stirred at RT for 12 h. The reaction was diluted with H$_2$O (500 mL) and extracted with EtOAc (70 mL×3). The combined organic layers were washed with brine, dried over Na$_2$SO$_4$, and concentrated in vacuo to give 6-(azidomethyl)quinoxaline as a yellow solid which was used in the next step without further purification. (2.5 g crude). ESI-MS [M+H]$^+$: 186.2.

Synthesis of Ethyl 1-(quinoxalin-6-ylmethyl)-1H-1,2,3-triazole-4-carboxylate To a solution of 6-(azidomethyl)quinoxaline (2.5 g crude from previous step) and ethyl propiolate (1.58 g, 16.2 mmol) in t-BuOH/H$_2$O (15 mL/15 mL) was added CuSO$_4$ (427 mg, 2.7 mmol) and sodium ascorbate (537 mg, 2.7 mmol) at RT. The resulting mixture was stirred at RT for 2 h. The reaction was diluted with H$_2$O (70 mL) and extracted with DCM/MeOH (10/1, 70 mL×3). The combined organic layers were washed with brine, dried over Na$_2$SO$_4$, and concentrated in vacuo to give the crude product which was purified by silica gel chromatography (DCM/MeOH=15/1) to give ethyl 1-(quinoxalin-6-ylmethyl)-1H-1,2,3-triazole-4-carboxylate as a yellow solid (1.5 g, 39% over 2 steps). ESI-MS [M+H]$^+$: 284.2.

Synthesis of 1-(quinoxalin-6-ylmethyl)-1H-1,2,3-triazole-4-carboxylic Acid

A mixture of ethyl 1-(quinoxalin-6-ylmethyl)-1H-1,2,3-triazole-4-carboxylate (1 g, 3.53 mmol) and LiOH.H$_2$O (444 mg, 10.56 mmol) in THF/H$_2$O (10 mL/5 mL) was stirred at RT for 12 h. The reaction was concentrated to remove THF. The pH of residue was adjusted to around 3 using hydrochloric acid, and white solid precipitated out. The suspension was filtered to give 1-(quinoxalin-6-ylmethyl)-1H-1,2,3-triazole-4-carboxylic acid as a white solid which was used in next step directly (650 mg, 72%). ESI-MS [M+H]$^+$: 256.2.

Synthesis of N-((7-chloro-8-fluoroimidazo[1,5-a]pyridin-1-yl)methyl)-1-(quinoxalin-6-ylmethyl)-1H-1,2,3-triazole-4-carboxamide To a solution of 1-(quinoxalin-6-ylmethyl)-1H-1,2,3-triazole-4-carboxylic acid (100 mg, 0.39 mmol) and (7-chloro-8-fluoroimidazo[1,5-a]pyridin-1-yl)methanamine hydrochloride (110.5 mg, 0.47 mmol) in DMF (5 mL) was added HOBT (81 mg, 0.6 mmol), EDCI (115 mg, 0.6 mmol) and DIPEA (151 mg, 1.17 mmol). The resulting mixture was stirred at RT for 12 h. The reaction was diluted with H$_2$O (25 mL) and extracted with EtAOc (40 mL×5). The combined organic layers were washed with brine, dried over Na$_2$SO$_4$, and concentrated in vacuo to give the crude product which was purified by Prep-TLC (DCM/MeOH=8/1) to give N-((7-chloro-8-fluoroimidazo[1,5-a]pyridin-1-yl)methyl)-1-(quinoxalin-6-ylmethyl)-1H-1,2,3-triazole-4-carboxamide as a white solid (35 mg, 20.6%). ESI-MS [M+H]$^+$: 436.8. Purity: 100% (214 nm) 99.16% (254 nm). $^1$H NMR (400 MHz, DMSO): δ 8.97 (s, 2H), 8.76 (s, 2H), 8.47 (d, J=2.3, 1H), 8.21 (d, J=7.4, 1H), 8.12 (d, J=8.6, 1H), 8.03 (s, 1H), 7.79 (dd, J=8.7, 1.8, 1H), 6.77 (t, J=6.9, 1H), 5.95 (s, 2H), 4.71 (d, J=5.4, 2H).

Example 293

Scheme 292

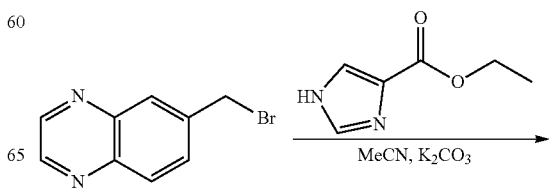

657

-continued

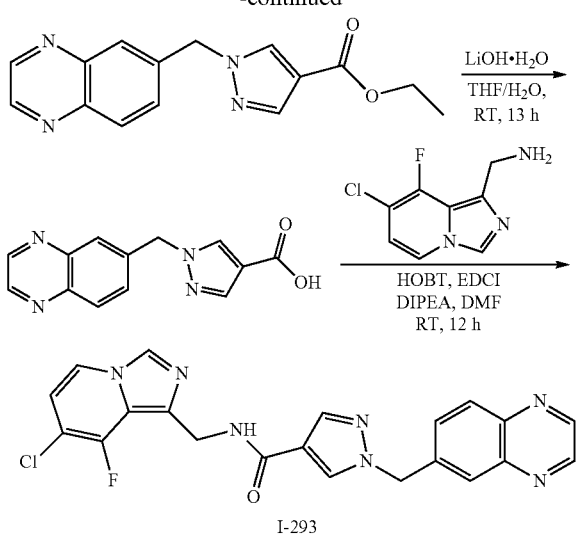

Synthesis of Ethyl 1-(quinoxalin-6-ylmethyl)-1H-pyrazole-4-carboxylate

To a solution of 6-(bromomethyl)quinoxaline (3 g, 13.5 mmol) in MeCN (50 ml) was added ethyl 1H-pyrazole-4-carboxylate (2.84 g, 20.3 mmol) and K₂CO₃ (5.6 g, 40.5 mmol) at RT. The reaction was stirred at RT for 12 h. H₂O (100 mL) was added, and the mixture was extracted with EtOAc (50 mL×3). The combined organic layers were washed with brine, dried over Na₂SO₄, and concentrated in vacuo to give the crude product which was purified by silica gel chromatography (DMC/MeOH=20/1) to give ethyl 1-(quinoxalin-6-ylmethyl)-1H-pyrazole-4-carboxylate (1 g, yield: 26%) as a yellow solid. ESI-MS [M+H]⁺: 283.2.

658

Synthesis of 1-(quinoxalin-6-ylmethyl)-1H-pyrazole-4-carboxylic Acid

To a solution of ethyl 1-(quinoxalin-6-ylmethyl)-1H-pyrazole-4-carboxylate (1 g, 3.5 mmol) in THF (30 mL) and water (30 mL) was added LiOH.H₂O (441 mg, 10.5 mmol). The mixture was stirred at RT for 13 h. The organic layer was evaporated, and the aqueous phase was acidified with 1N HCl to around pH 4. The resulting precipitate was collected by filtration to give 1-(quinoxalin-6-ylmethyl)-1H-pyrazole-4-carboxylic acid as a white solid which was used in next step directly (400 mg, yield: 45%). ESI-MS [M+H]⁺: 255.2.

Synthesis of N-((7-chloro-8-fluoroimidazo[1,5-a]pyridin-1-yl)methyl)-1-(quinoxalin-6-ylmethyl)-1H-pyrazole-4-carboxamide To a solution of 1-(quinoxalin-6-ylmethyl)-1H-pyrazole-4-carboxylic acid (100 mg, 0.39 mmol), (7-chloro-8-fluoroimidazo[1,5-a]pyridin-1-yl)methanamine hydrochloride (139 mg, 0.59 mmol), EDCI (114 mg, 0.59 mmol) and HOBT (80 mg, 0.59 mmol) in DMF (5 mL) was added DIPEA (151 mg, 1.17 mmol). The resulting reaction was stirred at RT for 12 h. H₂O (50 mL) was added, and the mixture was extracted with EtOAc (30 mL×3). The combined organic layers were washed with brine, dried over Na₂SO₄, and concentrated in vacuo to give the crude product which was purified by Prep-TLC (DMC/MeOH=10/1) to give N-((7-chloro-8-fluoroimidazo[1,5-a]pyridin-1-yl)methyl)-1-(quinoxalin-6-ylmethyl)-1H-pyrazole-4-carboxamide (50 mg, yield: 29%) as a white solid. ESI-MS [M+H]⁺: 435.8. Purity: 97.58 (214 nm), 97.29 (254 nm). ¹H NMR (400 MHz, DMSO): δ 8.95 (s, 2H), 8.51-8.44 (m, 2H), 8.36 (s, 1H), 8.22 (d, J=7.4 Hz, 1H), 8.09 (d, J=8.7 Hz, 1H), 7.92 (d, J=13.1 Hz, 2H), 7.72 (dd, J=8.6, 1.9 Hz, 1H), 6.80-6.74 (m, 1H), 5.64 (s, 2H), 4.64 (d, J=5.2 Hz, 2H).

Example 294

Scheme 293

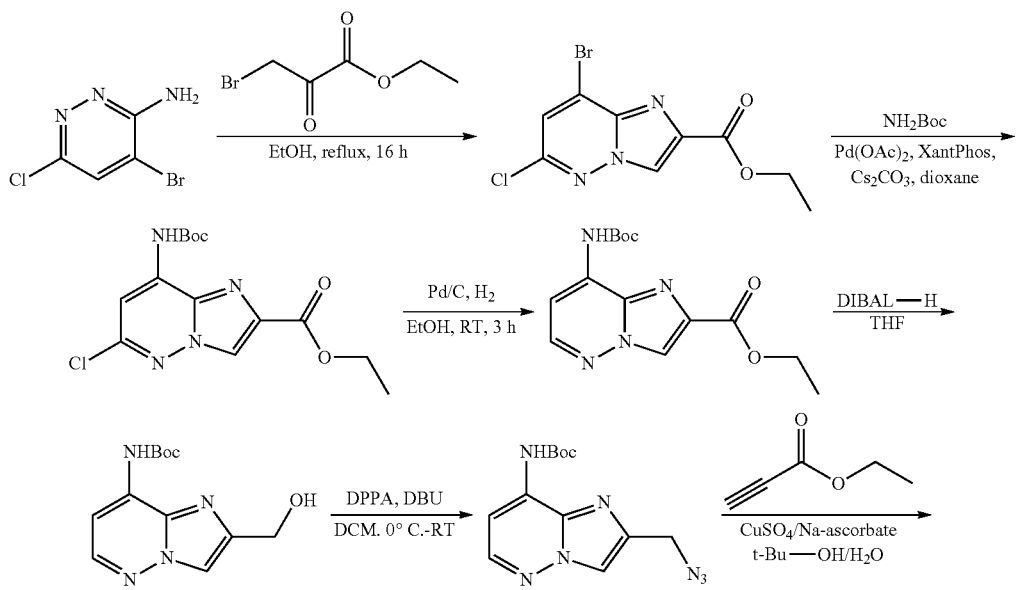

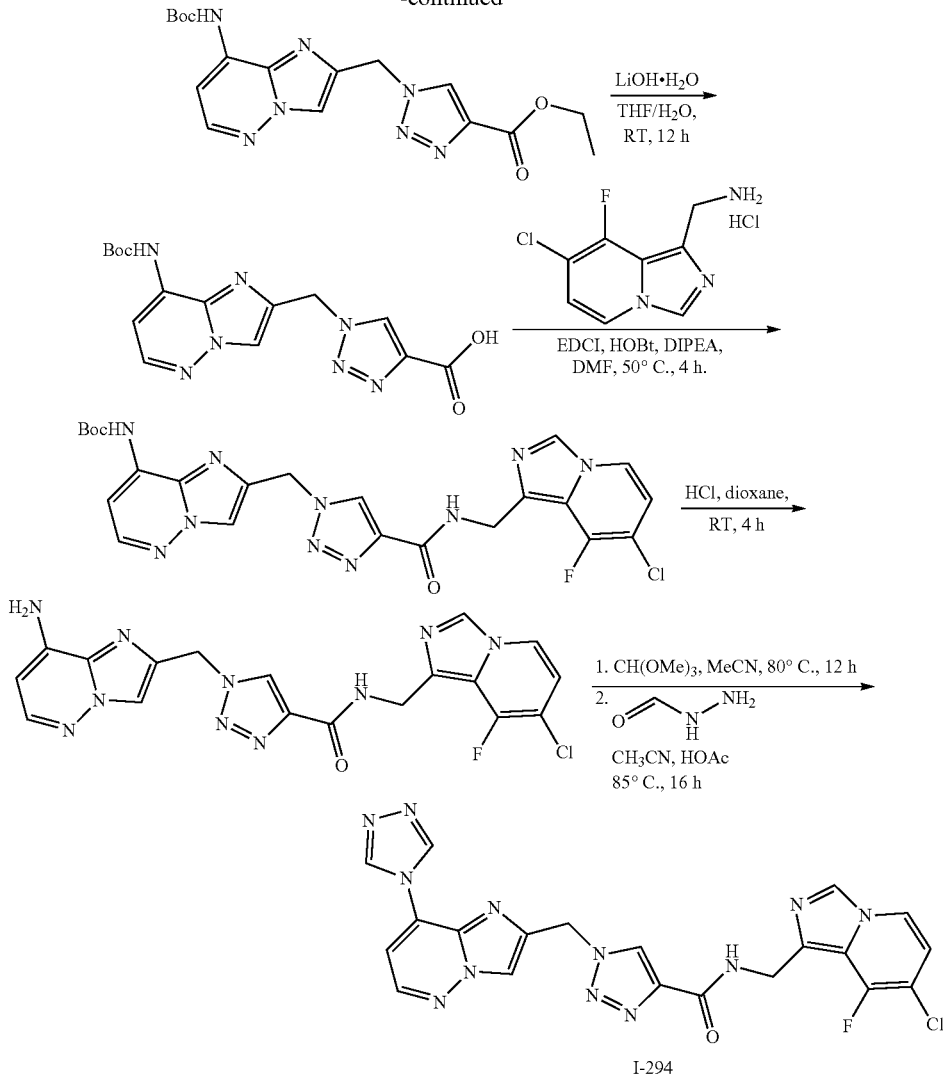

I-294

Synthesis of Ethyl 8-bromo-6-chloroimidazo[1,2-b]pyridazine-2-carboxylate

A mixture of 4-bromo-6-chloropyridazin-3-amine (25 g, 121 mmol) and ethyl 3-bromo-2-oxopropanoate (47 g, 242.0 mmol) in EtOH (300 mL) was stirred at 80° C. for 16 h under $N_2$. The mixture was then concentrated in vacuo, diluted with saturated aqueous $NaHCO_3$ solution (500 mL), and extracted with EtOAc (200 mL×3). The combined organic layer was washed with brine, dried over $Na_2SO_4$, and concentrated in vacuo. The residue was purified by flash column chromatography (DCM/MeOH=20/1) to give ethyl 8-bromo-6-chloroimidazo[1,2-b]pyridazine-2-carboxylate as a yellow solid (6.5 g, yield: 18%). ESI-MS $[M+H]^+$: 304.1.

Synthesis of Ethyl 8-((tert-butoxycarbonyl)amino)-6-chloroimidazo[1,2-b]pyridazine-2-carboxylate A mixture of ethyl 8-bromo-6-chloroimidazo[1,2-b]pyridazine-2-carboxylate (6.0 g, 19.8 mmol), $NH_2Boc$ (2.9 g, 24.8 mmol), $Pd(OAc)_2$ (224 mg, 1.0 mmol), XantPhos (579 mg, 1.0 mmol), and $Cs_2CO_3$ (19.4 g, 59.4 mmol) in dioxane (150 mL) was stirred at 95° C. for 16 h under $N_2$. The mixture was cooled, water (200 mL) was added, and the mixture was extracted with EtOAc (100 mL×3). The combined organic layer was washed with brine, dried over $Na_2SO_4$ and concentrated in vacuo. The residue was purified by flash column chromatography (DCM/MeOH=20/1) to give ethyl 8-((tert-butoxycarbonyl)amino)-6-chloroimidazo[1,2-b]pyridazine-2-carboxylate (3.0 g, yield: 44%) as a light yellow solid. ESI-MS $[M+H]^+$: 341.1.

Synthesis of Ethyl 8-((tert-butoxycarbonyl)amino)imidazo[1,2-b]pyridazine-2-carboxylate To a solution of ethyl 8-((tert-butoxycarbonyl)amino)-6-chloroimidazo[1,2-b]pyridazine-2-carboxylate (2.8 g, 8.24 mmol) in EtOH/DCM (30 mL/30 mL) was added Pd/C (280 mg). The mixture was stirred under hydrogen atmosphere at RT for 16 h. The mixture was filtered and the solid was washed with DCM/MeOH (10/1, 60 mL). Then the filtrate was concentrated and purified by flash column chromatography (DCM/MeOH=0-10%) to give ethyl 8-((tert-butoxycarbonyl)amino)imidazo[1,2-b]pyridazine-2-carboxylate (2.2 g, yield: 87%) as a yellow solid. ESI-MS [M+H]+: 307.1.

Synthesis of tert-butyl (2-(hydroxymethyl)imidazo [1,2-b]pyridazin-8-yl)carbamate To a mixture of ethyl 8-((tert-butoxycarbonyl)amino) imidazo[1,2-b]pyridazine-2-carboxylate (2.0 g, 6.54 mmol) in dry THF (30 mL) was added DIBAL-H (16.3 mL, 16.3 mmol) at 0° C. The mixture was stirred at 0° C. for 2 h under $N_2$ and then quenched with water (100 mL). The mixture was filtered and extracted with EtOAc (50 mL×3). The combined organic layer was washed with brine, dried over $Na_2SO_4$, and concentrated in vacuo. The residue was purified by flash column chromatography (DCM/MeOH=30:1) to give tert-butyl (2-(hydroxymethyl)imidazo[1,2-b] pyridazin-8-yl)carbamate (1.25 g, yield: 72%) as a yellow solid. ESI-MS [M+H]+: 265.2.

Synthesis of tert-butyl (2-(azidomethyl)imidazo[1,2-b]pyridazin-8-yl)carbamate To a mixture of tert-butyl (2-(hydroxymethyl)imidazo[1, 2-b]pyridazin-8-yl)carbamate (1.0 g, 3.78 mmol) and DPPA (2.7 g, 9.85 mmol) in DCM (15 mL) was added DBU (1.50 g, 9.85 mmol) at 0° C. under $N_2$. The mixture was stirred at RT for 16 h, then diluted with water (50 mL) and extracted with DCM (30 mL×5). The combined organic layer was washed with brine, dried over $Na_2SO_4$, and concentrated in vacuo. The residue was purified by flash column chromatography (DCM/MeOH=20:1) to give tert-butyl (2-(azidomethyl)imidazo[1,2-b]pyridazin-8-yl)carbamate (500 mg, yield: 46%) as a colorless oil. ESI-MS [M+H]+: 290.2.

Synthesis of Ethyl 1-((8-((tert-butoxycarbonyl) amino)imidazo[1,2-b]pyridazin-2-yl)methyl)-1H-1, 2,3-triazole-4-carboxylate A mixture of tert-butyl (2-(azidomethyl)imidazo[1,2-b] pyridazin-8-yl)carbamate (500 mg, 1.73 mmol), ethyl propiolate (254 mg, 2.60 mmol), $CuSO_4$ (138 mg, 0.87 mmol) and sodium ascorbate (172 mg, 0.87 mmol) in t-BuOH/$H_2O$ (10 mL/5 mL) was stirred at RT for 16 h. The reaction mixture was diluted with water (50 mL) and extracted with DCM (30 mL×3). The combined organic layer was washed with brine, dried over $Na_2SO_4$ and concentrated in vacuo. The residue was purified by flash column chromatography (DCM/MeOH=20/1) to give ethyl 1-((8-((tert-butoxycarbonyl)amino)imidazo[1,2-b]pyridazin-2-yl)methyl)-1H-1,2,3-triazole-4-carboxylate (350 mg, yield: 52%) as a white solid. ESI-MS [M+H]+: 388.2.

Synthesis of 1-((8-((tert-butoxycarbonyl)amino) imidazo[1,2-b]pyridazin-2-yl)methyl)-1H-1,2,3-triazole-4-carboxylic Acid A solution of ethyl 1-((8-((tert-butoxycarbonyl)amino) imidazo[1,2-b]pyridazin-2-yl)methyl)-1H-1,2,3-triazole-4-carboxylate (251 mg, 0.65 mmol) and $LiOH \cdot H_2O$ (40 mg, 0.97 mmol) in THF/water (5 mL/5 mL) was stirred at RT for 3 h. The reaction mixture was adjusted to pH 5 using hydrochloric acid (1 M) and concentrated in vacuo at 20° C. to give lithium 5-((6-cyclopropylimidazo[1,2-a]pyridin-2-yl)methyl)-1,3,4-oxadiazole-2-carboxylate as a yellow solid, which was used in next step without further purification (290 mg, yield: 100%). ESI-MS [M+H]+: 360.1.

Synthesis of tert-butyl (2-((4-(((7-chloro-8-fluoro-imidazo[1,5-a]pyridin-1-yl)methyl)carbamoyl)-1H-1,2,3-triazol-1-yl)methyl)imidazo[1,2-b]pyridazin-s-yl)carbamate A mixture of 1-((8-((tert-butoxycarbonyl)amino)imidazo [1,2-b]pyridazin-2-yl)methyl)-1H-1,2,3-triazole-4-carboxylic acid (80 mg crude from previous step), (7-chloroimidazo[1,5-a]pyridin-1-yl)methanamine hydrochloride (63 mg, 0.27 mmol), EDCI (63 mg, 0.33 mmol), HOBt (44 mg, 0.33 mmol) and DIPEA (85 mg, 0.66 mmol) in DMF (10 mL) was stirred at 50° C. for 16 h. The mixture was concentrated to remove DMF, diluted with DCM/MeOH (300 mL, 10/1), and washed with water (100 mL×2). The organic layer was separated, dried over $Na_2SO_4$, and concentrated in vacuo to give the crude product which was purified by silica gel chromatography (DCM/MeOH=10/1) to give tert-butyl (2-((4-(((7-chloro-8-fluoroimidazo[1,5-a] pyridin-1-yl)methyl)carbamoyl)-1H-1,2,3-triazol-1-yl) methyl)imidazo[1,2-b]pyridazin-8-yl)carbamate (80 mg, yield: 67%) as a light yellow solid. ESI-MS [M+H]+: 541.2.

Synthesis of 1-((8-aminoimidazo[1,2-b]pyridazin-2-yl)methyl)-N-((7-chloro-8-fluoroimidazo[1,5-a]pyridin-1-yl)methyl)-1H-1,2,3-triazole-4-carboxamide A mixture of tert-butyl (2-((4-(((7-chloro-8-fluoroimidazo[1,5-a]pyridin-1-yl)methyl)carbamoyl)-1H-1,2,3-triazol-1-yl)methyl)imidazo[1,2-b]pyridazin-8-yl)carbamate (80 mg, 0.15 mmol) in HCl/dioxane (4.0 M, 5 mL) was stirred at RT for 16 h. The mixture was concentrated to give 1-((8-aminoimidazo[1,2-b]pyridazin-2-yl)methyl)-N-((7-chloro-8-fluoroimidazo[1,5-a]pyridin-1-yl)methyl)-1H-1,2, 3-triazole-4-carboxamide (100 mg, crude) as a light yellow solid. ESI-MS [M+H]+: 441.2.

Synthesis of 1-((8-(4H-1,2,4-triazol-4-yl)imidazo[1, 2-b]pyridazin-2-yl)methyl)-N-((7-chloro-8-fluoro-imidazo[1,5-a]pyridin-1-yl)methyl)-1H-1,2,3-triazole-4-carboxamide A mixture of 1-((8-aminoimidazo[1,2-b]pyridazin-2-yl) methyl)-N-((7-chloro-8-fluoroimidazo[1,5-a] pyridin-1-yl) methyl)-1H-1,2,3-triazole-4-carboxamide (88 mg, 0.20 mmol, crude from previous step) and trimethoxymethane (2.0 mL) in $CH_3CN$ (8.0 mL) was stirred at reflux under $N_2$ for 6 h. The reaction was cooled to RT and formohydrazide (120 mg, 2.0 mmol) and HOAc (0.5 mL) were added. The resulting reaction was stirred at 85° C. for another 16 h under $N_2$. The mixture was concentrated. The crude product was purified by Prep-HPLC to give 1-((8-(4H-1,2,4-triazol-4-yl) imidazo[1,2-b]pyridazin-2-yl)methyl)-N-((7-chloro-8-fluoroimidazo[1,5-a]pyridin-1-yl)methyl)-1H-1,2,3-triazole-4-carboxamide (13.5 mg, yield: 14%) as a white solid. ESI-MS [M+H]+: 493.1. Purity: 100.0% (214 nm), 98.2% (254 nm). 1H NMR (400 MHz, DMSO): δ 9.66 (s, 2H), 8.73 (s, 3H), 8.57 (s, 1H), 8.43 (s, 1H), 8.20 (s, 1H), 7.78 (s, 1H), 6.75 (s, 1H), 5.88 (s, 2H), 4.70 (s, 2H).

Example 295

Scheme 294

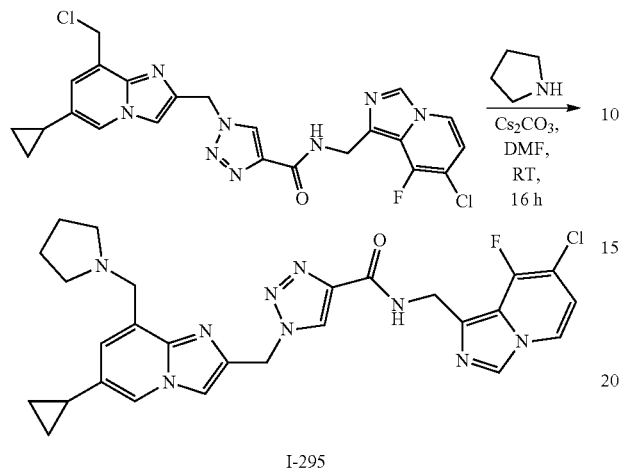

I-295

Synthesis of N-((7-chloro-8-fluoroimidazo[1,5-a]pyridin-1-yl)methyl)-1-((6-cyclopropyl-8-(pyrrolidin-1-ylmethyl)imidazo[1,2-a]pyridin-2-yl)methyl)-1H-1,2,3-triazole-4-carboxamide A mixture of N-((7-chloro-8-fluoroimidazo[1,5-a]pyridin-1-yl)methyl)-1-((8-(chloromethyl)-6-cyclopropylimidazo[1,2-a]pyridin-2-yl)methyl)-1H-1,2,3-triazole-4-carboxamide (50 mg, 0.097 mmol), pyrrolidine (8.5 mg, 0.117 mmol), and Cs₂CO₃ (126 mg, 0.388 mmol) in DMF (5 mL) was stirred at 25° C. for 16 h. Water (50 mL) was added and the mixture was extracted with EtOAc (50 mL×3). The combined organic layers were concentrated and purified by prep-HPLC to give N-((7-chloro-8-fluoroimidazo[1,5-a]pyridin-1-yl)methyl)-1-((6-cyclopropyl-8-(pyrrolidin-1-ylmethyl)imidazo[1,2-a]pyridin-2-yl)methyl)-1H-1,2,3-triazole-4-carboxamide (12 mg, yield: 22.6%) as a white solid. ESI-MS [M+H]⁺: 548.2. Purity: 5.14% 214 m), 95.15% (254 nm). ¹H NMR (400 MHz, DMSO): δ 8.69 (t, J=5.5, 1H), 8.53 (s, 1H), 8.44 (d, J=2.4, 1H), 8.23-8.18 (m, 2H), 7.79 (s, 1H), 6.99 (s, 1H), 6.81-6.70 (m, 1H), 5.72 (s, 2H), 4.68 (t, J=9.1, 2H), 3.84 (s, 2H), 2.49 (d, J=1.6, 4H), 2.00-1.88 (m, 1H), 1.70 (d, J=3.2, 4H), 0.95-0.87 (m, 2H), 0.68-0.57 (m, 2H).

Example 296

Scheme 295

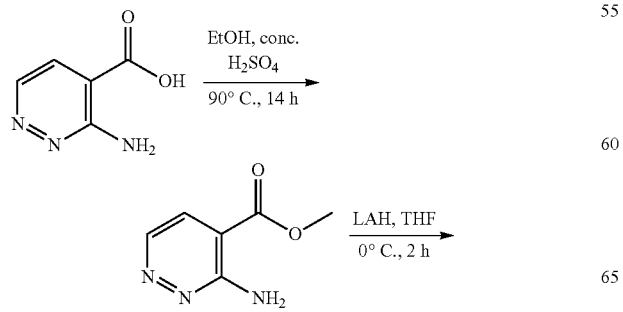

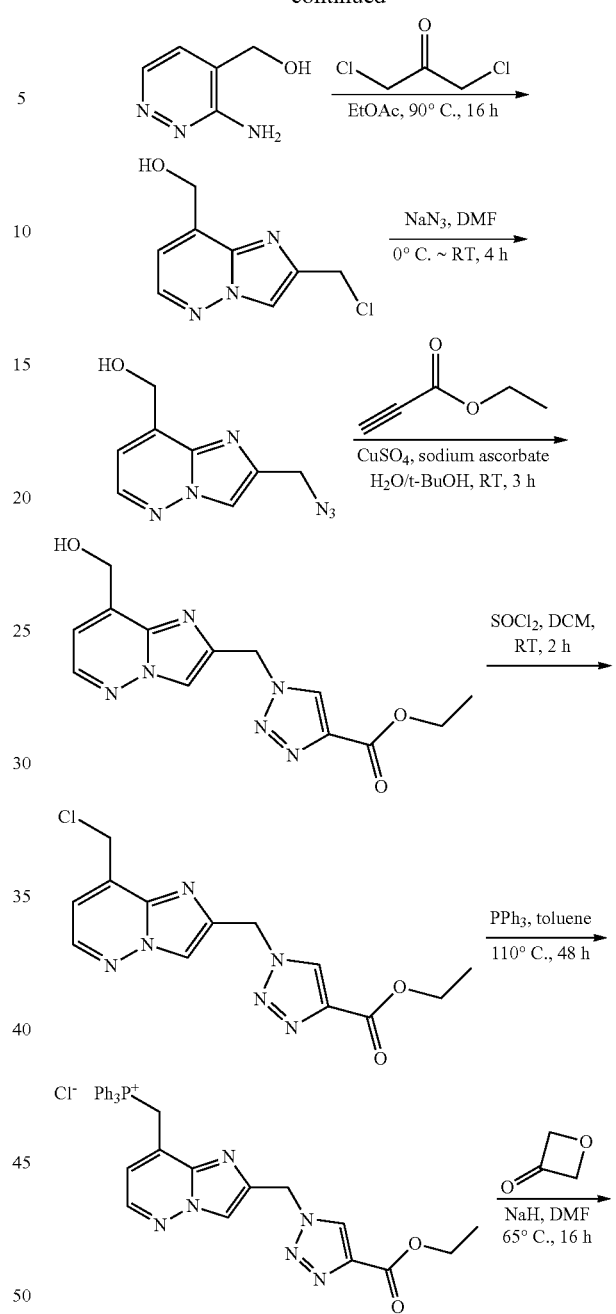

-continued

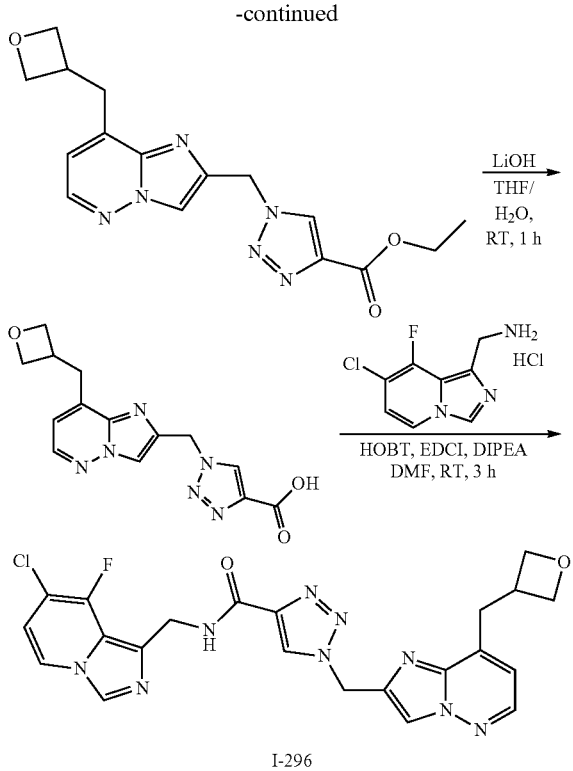

I-296

Synthesis of Methyl 3-aminopyridazine-4-carboxylate

To a mixture of 3-aminopyridazine-4-carboxylic acid (5.0 g, 36.0 mmol) in methanol (50 mL) was added $H_2SO_4$ (5 mL) slowly. The reaction was heated to reflux and stirred at 90° C. for 14 h. The mixture was concentrated. The residue was partitioned between EtOAc (200 mL) and saturated aqueous $Na_2CO_3$ (200 mL). The aqueous layer was extracted with EtOAc (200 mL×3). The combined organic layers were washed with brine, dried over $Na_2SO_4$, and concentrated in vacuo to give methyl 3-aminopyridazine-4-carboxylate as a yellow solid (4.0 g, yield: 73%). ESI-MS $[M+H]^+$: 154.2.

Synthesis of (3-aminopyridazin-4-yl)methanol

To a solution of methyl 3-aminopyridazine-4-carboxylate (4 g, 26.0 mmol) in dry THF (50 mL) was added LiAlH4 (60 mL, 1 M solution in THF, 60 mmol) at 0° C. dropwise. The reaction was stirred at 0° C. for 2 h. The reaction was quenched with $Na_2SO_4$ $10H_2O$, filtered, and washed with EtOAc (100 mL×3). The filtrate was concentrated to give (3-aminopyridazin-4-yl)methanol (1.2 g, yield: 37%) as a yellow solid. ESI-MS $[M+H]^+$: 126.2.

Synthesis of (2-(chloromethyl)imidazo[1,2-b]pyridazin-8-yl)methanol

To a solution of (3-aminopyridazin-4-yl)methanol (1.2 g, 9.6 mmol) in EtOAc (50 mL) was added 1,3-dichloropropan-2-one (1.45 g, 11.5 mmol). The reaction was stirred at 90° C. for 16 h. The mixture reaction was quenched with saturated aqueous $NaHCO_3$ (70 mL) and extracted with EtOAc (70 mL×3). The combined organic layers were washed with brine, dried over $Na_2SO_4$, and concentrated to give the crude product which was purified by silica gel chromatography (PE/EtOAc=1/2) to give (3-aminopyridazin-4-yl)methanol (1.0 g, yield: 53%) as a yellow solid. ESI-MS $[M+H]^+$: 198.1.

Synthesis of (2-(azidomethyl)imidazo[1,2-b]pyridazin-8-yl)methanol

To a solution of (3-aminopyridazin-4-yl)methanol (1.0 g, 5.04 mmol) in DMF (10 mL) was added $NaN_3$ (689 mg, 10.6 mmol) at 0° C. The reaction mixture was stirred at RT for 4 h. Water (100 mL) was added, and the mixture was extracted with EtOAc (100 mL×3). The combined organic layers were washed with brine, dried over $Na_2SO_4$, and concentrated in vacuo to give crude product which was purified by silica gel chromatography (PE/EtOAc=1/1) to give (2-(azidomethyl)imidazo[1,2-b]pyridazin-8-yl)methanol (400 mg, yield: 38.6%) as a yellow solid. ESI-MS $[M+H]^+$: 205.2.

Synthesis of Ethyl 1-((8-(hydroxymethyl)imidazo[1,2-b]pyridazin-2-yl)methyl)-1H-1,2,3-triazole-4-carboxylate To a solution of (2-(azidomethyl)imidazo[1,2-b]pyridazin-8-yl)methanol (400 mg, 1.96 mmol) in t-BuOH (15 mL) and water (5 mL) was added ethyl propiolate (254 mg, 2.6 mmol), $CuSO_4$ (63 mg, 0.4 mmoL), and sodium ascorbate (79 mg, 0.4 mmoL). The reaction mixture was stirred at RT for 3 h. The reaction mixture was poured into $H_2O$ (50 mL) and extracted with EtOAc (100 mL×3). The combined organic layers were washed with brine, dried over $Na_2SO_4$ and concentrated to give ethyl 1-((8-(hydroxymethyl)imidazo[1,2-b]pyridazin-2-yl)methyl)-1H-1,2,3-triazole-4-carboxylate (590 mg, yield: 100%) as a yellow solid which was used in next step directly. ESI-MS $[M+H]^+$: 303.1.

Synthesis Ethyl 1-((8-(chloromethyl)imidazo[1,2-b]pyridazin-2-yl)methyl)-1H-1,2,3-triazole-4-carboxylate To a solution of ethyl 1-((8-(hydroxymethyl)imidazo[1,2-b]pyridazin-2-yl)methyl)-1H-1,2,3-triazole-4-carboxylate (604 mg, 2 mmol) in dry DCM (30 mL) was added $SOCl_2$ (8 mL). After stirring at RT for 2 h, the mixture was quenched with saturated aqueous $NaHCO_3$ (100 mL) and extracted with DCM (100 mL×3). The combined organic layers were washed with brine, dried over $Na_2SO_4$, and concentrated to give ethyl 1-((8-(chloromethyl)imidazo[1,2-b]pyridazin-2-yl)methyl)-1H-1,2,3-triazole-4-carboxylate (450 mg, yield: 70%) as a yellow solid which was used in next step directly. ESI-MS $[M+H]^+$: 321.1.

Synthesis of ((2-((4-(ethoxycarbonyl)-1H-1,2,3-triazol-1-yl)methyl)imidazo[1,2-b]pyridazin-8-yl)methyl)triphenylphosphonium A solution of ethyl 1-((8-(chloromethyl)imidazo[1,2-b]pyridazin-2-yl)methyl)-1H-1,2,3-triazole-4-carboxylate (450 mg, 1.4 mmol) and triphenylphosphine (1.1 g, 4.2 mmol) in dry toluene (25 mL) was stirred at 110° C. for 48 h. The mixture was concentrated to give the crude product which was triturated with PE (100 mL), then filtered to give ((2-((4-(ethoxycarbonyl)-1H-1,2,3-triazol-1-yl)methyl)imidazo[1,2-b]pyridazin-8-yl)methyl)triphenylphosphonium (540 mg, yield: 66%) as a black solid which was used directly in the next step. ESI-MS [M+H]⁺: 547.2.

Synthesis of Ethyl 1-((8-(oxetan-3-ylidenemethyl)imidazo[1,2-b]pyridazin-2-yl)methyl)-1H-1,2,3-triazole-4-carboxylate To a solution of ((2-((4-(ethoxycarbonyl)-1H-1,2,3-triazol-1-yl)methyl)imidazo[1,2-b]pyridazin-8-yl)methyl)triphenylphosphonium (582 mg, 1 mmol) in dry DMF (15 mL) was added NaH (60 mg, 60% in oil, 1.5 mmol). The reaction was stirred at 0° C. for 30 min, then oxetan-3-one (720 mg, 10 mmol) was added. The reaction was stirred at 60° C. for another 16 h. The reaction was quenched with NH₄Cl solution (50 mL) and extracted with EtOAc (100 mL×3). The combined organic layers were washed with brine, dried over Na₂SO₄, and concentrated in vacuo to give the crude product which was purified by silica gel chromatography (DCM/MeOH=10/1) to give ethyl 1-((8-(oxetan-3-ylidenemethyl)imidazo[1,2-b]pyridazin-2-yl)methyl)-1H-1,2,3-triazole-4-carboxylate (300 mg, yield: 88%) as a yellow solid. ESI-MS [M+H]⁺: 341.2.

Synthesis of Ethyl 1-((8-(oxetan-3-ylmethyl)imidazo[1,2-b]pyridazin-2-yl)methyl)-1H-1,2,3-triazole-4-carboxylate To a solution of ethyl 1-((8-(oxetan-3-ylidenemethyl)imidazo[1,2-b]pyridazin-2-yl)methyl)-1H-1,2,3-triazole-4-carboxylate (150 mg, 0.44 mmol) in dry MeOH (8 mL) was added CuCl (65 mg, 0.66 mmol) and NaBH₄ (94 mg, 2.46 mmol) at 0° C. After stirring at RT for 3 h, the reaction was quenched with saturated aqueous NH₄Cl solution (30 mL) and extracted with EtOAc (100 mL×3). The combined organic layers were washed with brine, dried over Na₂SO₄, and concentrated in vacuo to give the crude product which was purified by silica gel chromatography (DCM/MeOH=20/1) to give ethyl 1-((8-(oxetan-3-ylmethyl)imidazo[1,2-b]pyridazin-2-yl)methyl)-1H-1,2,3-triazole-4-carboxylate (25 mg, yield: 16.6%) as a white solid. ESI-MS [M+H]⁺: 343.1.

Synthesis of 1-((8-(oxetan-3-ylmethyl)imidazo[1,2-b]pyridazin-2-yl)methyl)-1H-1,2,3-triazole-4-carboxylic Acid A solution of 1-(2-(chloromethyl)-3-fluoro-4-methoxyphenyl)-1H-tetrazole (25 mg, 0.07 mmol) and LiOH.H2O (5.7 mg, 0.14 mmol) in THF/H₂O (5 mL/5 mL) was stirred at RT for 1 h. The reaction mixture was adjusted to pH 6 with hydrochloric acid (0.5 M) and concentrated in vacuo to give 1-((8-(oxetan-3-ylmethyl)imidazo[1,2-b]pyridazin-2-yl)methyl)-1H-1,2,3-triazole-4-carboxylic acid (30 mg, crude, yield: 100%) as a white solid which was used in next step without further purification. ESI-MS [M+H]⁺: 315.1.

Synthesis of N-((7-chloro-8-fluoroimidazo[1,5-a]pyridin-1-yl)methyl)-1-((8-(oxetan-3-ylmethyl)imidazo[1,2-b]pyridazin-2-yl)methyl)-1H-1,2,3-triazole-4-carboxamide To a solution 1-((8-(oxetan-3-ylmethyl)imidazo[1,2-b]pyridazin-2-yl)methyl)-1H-1,2,3-triazole-4-carboxylic acid (30 mg, crude from previous step) in dry DMF (2 mL) was added (2-fluoro-3-methoxy-6-(1H-tetrazol-1-yl)phenyl)methanamine hydrochloride (9.4 mg, 0.04 mmol), HOBT (5.4 mg, 0.04 mmol), EDCI (7.6 mg, 0.04 mmol), and DIPEA (11.61 mg, 0.09 mmol). The reaction mixture was stirred at RT for 16 h. Water (30 mL) was added, and the mixture was extracted with EtOAc (50 mL×3). The combined organic layers were washed with brine, dried over Na₂SO₄, and concentrated in vacuo to give the crude product which was purified by Prep-TLC (DCM/MeOH=20/1) to give N-((7-chloro-8-fluoroimidazo[1,5-a]pyridin-1-yl)methyl)-1-((8-(oxetan-3-ylmethyl)imidazo[1,2-b]pyridazin-2-yl)methyl)-1H-1,2,3-triazole-4-carboxamide (6 mg, yield: 30.3%). ESI-MS [M+H]⁺: 496.1. Purity: 88.73% (214 nm), 89.50% (254 nm). ¹H NMR (400 MHz, DMSO): δ 8.71 (t, J=5.4 Hz, 1H), 8.59 (s, 1H), 8.45 (d, J=2.4 Hz, 1H), 8.41 (d, J=4.6 Hz, 1H), 8.32 (s, 1H), 8.21 (d, J=7.4 Hz, 1H), 7.03 (d, J=4.7 Hz, 1H), 6.78-6.75 (m, 1H), 5.80 (s, 2H), 4.71 (d, J=5.5 Hz, 2H), 4.67-4.64 (m, 2H), 4.39 (t, J=6.1 Hz, 2H), 3.48-3.41 (m, 1H), 3.29 (d, J=7.7 Hz, 2H).

Example 297

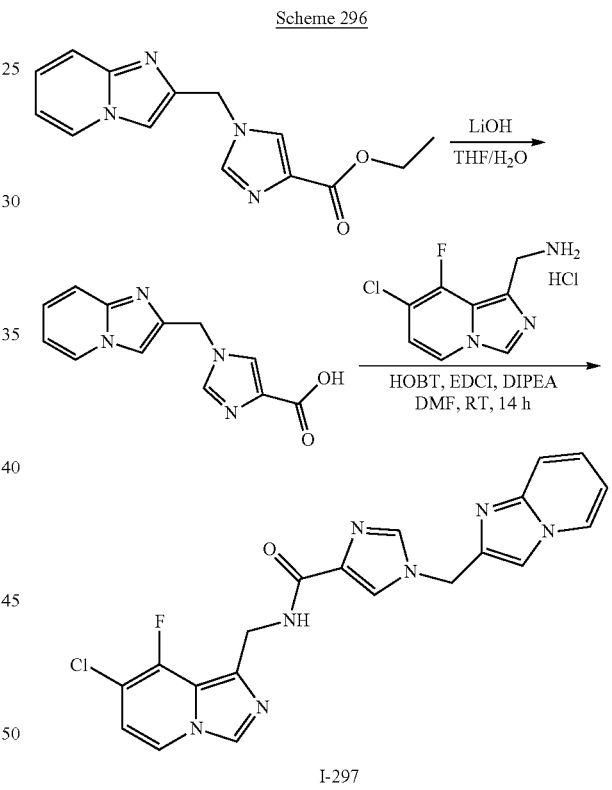

Scheme 296

I-297

Synthesis of 1-(imidazo[1,2-a]pyridin-2-ylmethyl)-1H-imidazole-4-carboxylic Acid To a solution of ethyl 1-(imidazo[1,2-a]pyridin-2-ylmethyl)-1H-imidazole-4-carboxylate (120 mg, 0.44 mmol) in THF (10 mL) was added LiOH.H₂O (54 mg, 1.33 mmol). The mixture was stirred at RT for 10 h. The reaction mixture was adjusted to pH 3-4 with hydrochloric acid (1 M) and then concentrated in vacuo to give 1-(imidazo[1,2-a]pyridin-2-ylmethyl)-1H-imidazole-4-carboxylic acid (177 mg crude) which was used directly in the next step. ESI-MS [M+H]⁺: 243.2.

Synthesis of N-((7-chloro-8-fluoroimidazo[1,5-a]pyridin-1-yl)methyl)-1-(imidazo[1,2-a]pyridin-2-ylmethyl)-1H-imidazole-4-carboxamide To a solution of 1-(imidazo[1,2-a]pyridin-2-ylmethyl)-1H-imidazole-4-carboxylic acid (85 mg, crude from last step, 0.21 mmol), (7-chloro-8-fluoroimidazo[1,5-a]pyridin-1-yl)methanamine hydrochloride (73 mg, 0.31 mmol), HOBT (57 mg, 0.42 mmol), EDCI (81 mg, 0.42 mmol) in DMF (5 mL) was added DIPEA (136 mg, 1.05 mmol). The resulting mixture was stirred at RT for 12 h under $N_2$. The reaction was quenched with water (50 mL) and extracted with EtOAc (30 mL×3). The combined organic layers were washed with brine, dried over $Na_2SO_4$, and concentrated in vacuo to give the crude product which was triturated with DCM (25 mL) to give N-((7-chloro-8-fluoroimidazo[1,5-a]pyridin-1-yl)methyl)-1-(imidazo[1,2-a]pyridin-2-ylmethyl)-1H-imidazole-4-carboxamide as a white solid (20 mg, 23%). ESI-MS [M+H]$^+$: 424.1. Purity: 96.72% (214 nm), 98.28% (254 nm). $^1$H NMR (400 MHz, DMSO): δ 8.56-8.47 (m, 1H), 8.45 (d, J=2.5 Hz, 1H), 8.20 (d, J=7.4 Hz, 1H), 8.01 (t, J=5.5 Hz, 1H), 7.85 (s, 1H), 7.81 (d, J=1.2 Hz, 1H), 7.72 (d, J=1.2 Hz, 1H), 7.55-7.45 (m, 1H), 7.30-7.17 (m, 1H), 6.95-6.81 (m, 1H), 6.81-6.68 (m, 1H), 5.34 (s, 2H), 4.67 (d, J=5.5 Hz, 2H).

Example 298

Scheme 297

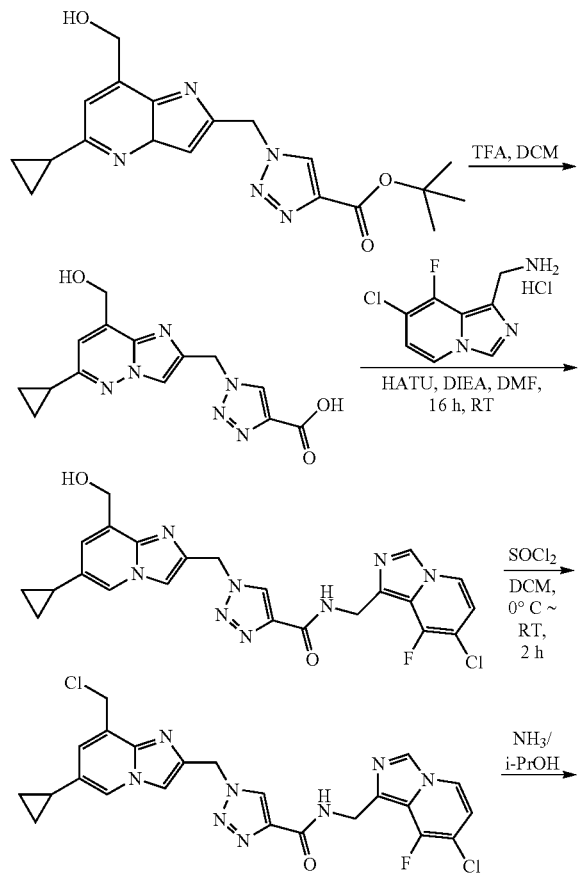

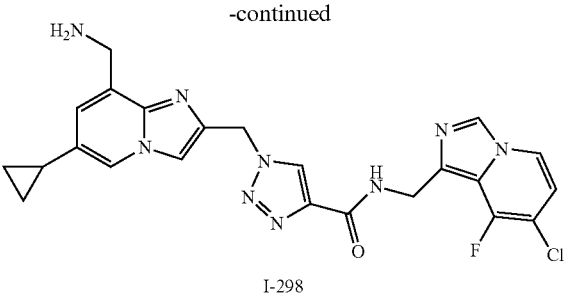

I-298

Synthesis of 1-((6-cyclopropyl-8-(hydroxymethyl)imidazo[1,2-a]pyridin-2-yl)methyl)-1H-1,2,3-triazole-4-carboxylic Acid A solution of tert-butyl 1-((6-cyclopropyl-8-(hydroxymethyl)imidazo[1,2-a]pyridin-2-yl)methyl)-1H-1,2,3-triazole-4-carboxylate (1 g, 2.71 mmol) in DCM/TFA (20 mL/4 mL) was stirred at 25° C. for 3 h. The reaction was concentrated in vacuo to give 1-((6-cyclopropyl-8-(hydroxymethyl)imidazo[1,2-a]pyridin-2-yl)methyl)-1H-1,2,3-triazole-4-carboxylic acid (800 mg) as a brown solid which was used in next step directly. ESI-MS [M+H]$^+$: 314.1.

Synthesis of N-((7-chloro-8-fluoroimidazo[1,5-a]pyridin-1-yl)methyl)-1-((6-cyclopropyl-8-(hydroxymethyl)imidazo[1,2-a]pyridin-2-yl)methyl)-1H-1,2,3-triazole-4-carboxamide To a solution of 1-((6-cyclopropyl-8-(hydroxymethyl)imidazo[1,2-a]pyridin-2-yl)methyl)-1H-1,2,3-triazole-4-carboxylic acid (800 mg, crude from previous step), (7-chloro-8-fluoroimidazo[1,5-a]pyridin-1-yl)methanamine hydrochloride (897 mg, 3.82 mmol), and HATU (1.45 g, 3.82 mmol) in DMF (10 mL) was added DIPEA (2.3 g, 17.85 mmol). The resulting mixture was stirred at 25° C. for 16 h. Water (100 mL) was added, and the mixture was extracted with EtOAc (50 mL×3). The combined organic layers were concentrated to give the crude product which was purified by silica gel chromatography (MeOH/DCM=1/50) to give N-((7-chloro-8-fluoroimidazo[1,5-a]pyridin-1-yl)methyl)-1-((6-cyclopropyl-8-(hydroxymethyl)imidazo[1,2-a]pyridin-2-yl)methyl)-1H-1,2,3-triazole-4-carboxamide (700 mg, yield: 52%) as a white solid. ESI-MS [M+H]$^+$: 495.1.

Synthesis of N-((7-chloro-8-fluoroimidazo[1,5-a]pyridin-1-yl)methyl)-1-((8-(chloromethyl)-6-cyclopropylimidazo[1,2-a]pyridin-2-yl)methyl)-1H-1,2,3-triazole-4-carboxamide To a solution of N-((7-chloro-8-fluoroimidazo[1,5-a]pyridin-1-yl)methyl)-1-((6-cyclopropyl-8-(hydroxymethyl)imidazo[1,2-a]pyridin-2-yl)methyl)-1H-1,2,3-triazole-4-carboxamide (700 mg, 1.42 mmol) in dry DCM (10 mL) was added $SOCl_2$ (3 mL) at 0° C. The reaction mixture was stirred at 0° C. for 3 h. The mixture was concentrated to give the crude product which was purified by silica gel chromatography (MeOH/DCM=1/50) to give N-((7-chloro-8-fluoroimidazo[1,5-a]pyridin-1-yl)methyl)-1-((8-(chloromethyl)-6-cyclopropylimidazo[1,2-a]pyridin-2-yl)methyl)-1H-1,2,3-triazole-4-carboxamide (500 mg, yield: 68.7%) as a yellow solid. ESI-MS [M+H]$^+$: 514.1.

Synthesis of 1-((8-(aminomethyl)-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide A solution of N-((7-chloro-8-fluoroimidazo[1,5-a]pyridin-1-yl)methyl)-1-((8-(chloromethyl)-6-cyclopropylimidazo[1,2-a]pyridin-2-yl)methyl)-1H-1,2,3-triazole-4-carboxamide (50 mg, 0.097 mmol) in NH$_3$ (5 mL, 2 M solution in i-PrOH) in a sealed tube was stirred at 70° C. for 16 h. The reaction mixture was concentrated to give the crude product which purified by Prep-HPLC to give 1-(3-(aminomethyl)phenyl)-N-(5-(3-cyclopropyl-1-hydroxypropyl)-2-fluorophenyl)-3-(trifluoromethyl)-1H-1,2,4-triazole-5-carboxamide (20 mg, yield: 41.7%) as a white solid. ESI-MS [M+H]$^+$: 494.1. Purity: 98.52% (214 nm), 99.24% (254 nm). $^1$H NMR (400 MHz, DMSO): δ 8.70 (t, J=5.3 Hz, 1H), 8.55 (s, 1H), 8.44 (d, J=2.4 Hz, 1H), 8.33 (s, 1H), 8.26 (s, 1H), 8.20 (d, J=7.4 Hz, 1H), 7.83 (s, 1H), 7.03 (s, 1H), 6.79-6.73 (m, 1H), 5.73 (s, 2H), 4.70 (d, J=5.5 Hz, 2H), 4.01 (s, 2H), 1.94-1.89 (m, 1H), 0.95-0.90 (m, 2H), 0.71-0.65 (m, 2H).

Example 299

Scheme 298

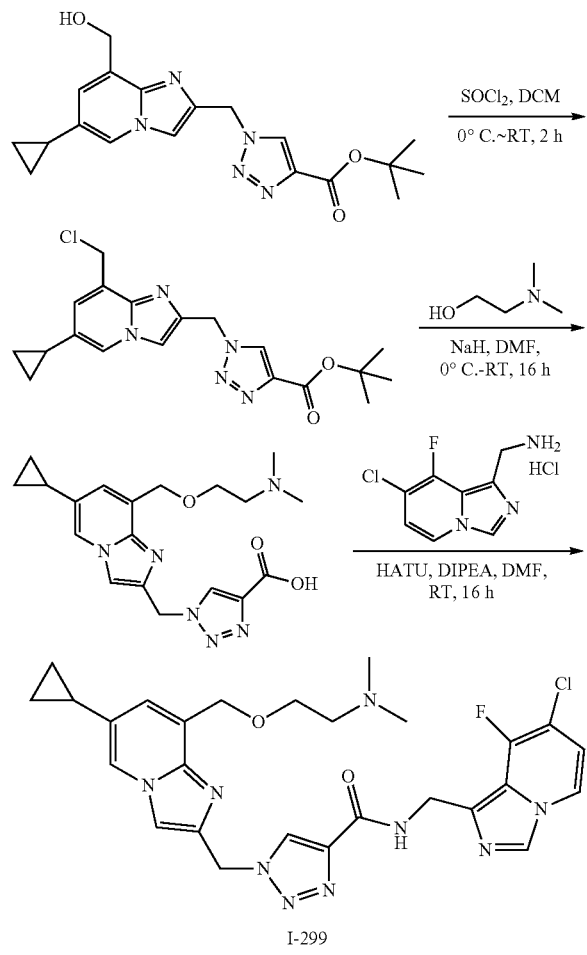

I-299

Synthesis of tert-butyl 1-((8-(chloromethyl)-6-cyclopropylimidazo[1,2-a]pyridin-2-yl)methyl)-1H-1,2,3-triazole-4-carboxylate To a solution of tert-butyl 1-((6-cyclopropyl-8-(hydroxymethyl)imidazo[1,2-a]pyridin-2-yl)methyl)-1H-1,2,3-triazole-4-carboxylate (500 mg, 1.355 mmol) in dry DCM (10 mL) was added SOCl$_2$ (320 mg, 2.7 mmol) at 0° C. The mixture was stirred at 25° C. for 3 h. The mixture was concentrated to give the crude product which was purified by silica gel chromatography (MeOH/DCM=1/50) to give tert-butyl 1-((8-(chloromethyl)-6-cyclopropylimidazo[1,2-a]pyridin-2-yl)methyl)-1H-1,2,3-triazole-4-carboxylate (420 mg, yield: 81%) as a yellow solid. ESI-MS [M+H]$^+$: 388.1.

Synthesis of 1-((6-cyclopropyl-8-((2-(dimethylamino)ethoxy)methyl)imidazo[1,2-a]pyridin-2-yl)methyl)-1H-1,2,3-triazole-4-carboxylic Acid To a suspension of NaH (320 mg, 60% suspension in paraffin oil, 8.0 mmol) in DMF (5 mL) was added 2-(dimethylamino)ethan-1-ol (144 mg, 1.61 mmol) at 0° C. The resulting reaction was stirred at 0° C. for 30 min, then a solution of tert-butyl 1-((8-(chloromethyl)-6-cyclopropylimidazo[1,2-a]pyridin-2-yl)methyl)-1H-1,2,3-triazole-4-carboxylate (418 mg, 1.08 mmol) was added. The reaction mixture was stirred at 25° C. for another 16 h. The reaction was quenched with water (20 mL) and concentrated in vacuo to give the crude product, which was purified by silica gel chromatography (MeOH/DCM=1/4) to give 1-((6-cyclopropyl-8-((2-(dimethylamino)ethoxy)methyl)imidazo[1,2-a]pyridin-2-yl)methyl)-1H-1,2,3-triazole-4-carboxylic acid (300 mg, yield: 72%) as a yellow solid. ESI-MS [M+H]$^+$: 385.1.

Synthesis of N-((7-chloro-8-fluoroimidazo[1,5-a]pyridin-1-yl)methyl)-1-((6-cyclopropyl-8-((2-(dimethylamino)ethoxy)methyl)imidazo[1,2-a]pyridin-2-yl)methyl)-1H-1,2,3-triazole-4-carboxamide A mixture of 1-((6-cyclopropyl-8-((2-(dimethylamino)ethoxy)methyl)imidazo[1,2-a]pyridin-2-yl)methyl)-1H-1,2,3-triazole-4-carboxylic acid (30 mg, 0.078 mmol), (7-chloro-8-fluoroimidazo[1,5-a]pyridin-1-yl)methanamine hydrochloride (22 mg, 0.094 mmol), HATU (44.4 mg, 0.117 mmol), DIPEA (70 mg, 0.54 mmol) in DMF (5 mL) was stirred at 25° C. for 16 h. The reaction was diluted with water (20 mL) and extracted with EtOAc (30 mL×3). The combined organic layers were washed with brine, dried over Na$_2$SO$_4$, and concentrated in vacuo to give the crude product which was purified by Prep-HPLC to give N-((7-chloro-8-fluoroimidazo[1,5-a]pyridin-1-yl)methyl)-1-((6-cyclopropyl-8-((2-(dimethylamino)ethoxy)methyl)imidazo[1,2-a]pyridin-2-yl)methyl)-1H-1,2,3-triazole-4-carboxamide (2.5 mg, yield: 56%) as a white solid. ESI-MS [M+H]$^+$: 567.1. Purity: 97.44% (214 nm), 97.03% (254 nm). $^1$H NMR (400 MHz, DMSO) δ 8.69 (t, J=5.4 Hz, 1H), 8.53 (s, 1H), 8.44 (d, J=2.4 Hz, 1H), 8.39 (d, J=2.4 Hz, 1H), 8.28 (s, 1H), 8.19 (dd, J=9.7, 7.4 Hz, 2H), 7.83 (s, 1H), 7.01 (s, 1H), 6.81-6.65 (m, 2H), 5.73 (s, 2H), 4.79-4.61 (m, 4H), 4.47 (s, 2H), 3.60 (t, J=5.9 Hz, 2H), 2.44 (t, J=5.8 Hz, 2H), 2.14 (s, 6H), 1.99-1.89 (m, 1H), 0.97-0.87 (m, 2H), 0.70-0.59 (m, 2H).

Example 300

Scheme 299

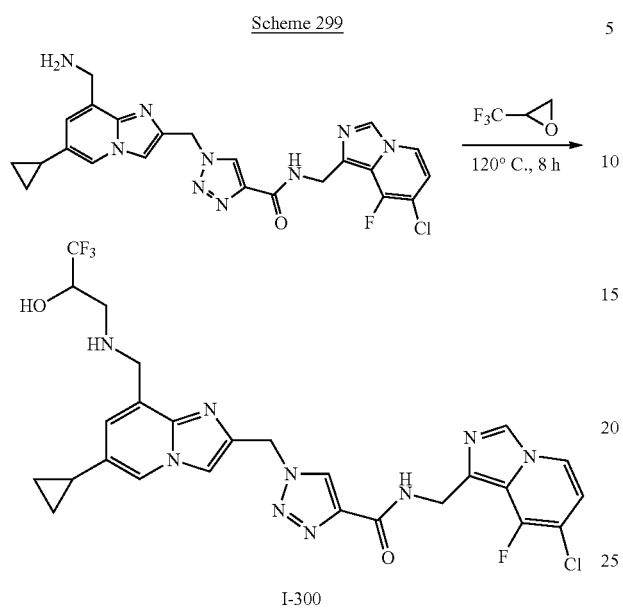

I-300

Synthesis of N-((7-chloro-8-fluoroimidazo[1,5-a]pyridin-1-yl)methyl)-1-(((6-cyclopropyl-8-(((3,3,3-trifluoro-2-hydroxypropyl)amino)methyl)imidazo[1,2-a]pyridin-2-yl)methyl)-1H-1,2,3-triazole-4-carboxamide A mixture of 1-((8-(aminomethyl)-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide (200 mg, 0.405 mmol) and 2-(trifluoromethyl)oxirane (20 ml) in a sealed tube was stirred at 120° C. for 8 h. The mixture was concentrated and purified by Prep-HPLC to give N-((7-chloro-8-fluoroimidazo[1,5-a]pyridin-1-yl)methyl)-1-((6-cyclopropyl-8-(((3,3,3-trifluoro-2-hydroxypropyl)amino)methyl)imidazo[1,2-a]pyridin-2-yl)methyl)-1H-1,2,3-triazole-4-carboxamide (20 mg, yield: 8.1%) as a white solid. ESI-MS [M+H]+: 606.1. Purity: 97.60% (214 nm), 96.73% (254 nm). 1H NMR (400 MHz, DMSO): δ 8.69-8.74 (m, 1H), 8.54 (s, 1H), 8.44 (d, J=2.2, 1H), 8.25 (s, 1H), 8.20 (d, J=7.4, 1H), 7.80 (s, 1H), 7.00 (s, 1H), 6.76 (t, J=6.9, 1H), 5.73 (s, 2H), 4.70 (d, J=5.4, 2H), 4.02-4.06 (m, 2H), 3.90-4.00 (m, 2H), 2.72-2.78 (m, 1H), 2.62-2.67 (m, 1H), 1.86-1.97 (m, 1H), 0.88-0.95 (m, 2H), 0.64-0.70 (m, 2H).

Example 301

Scheme 300

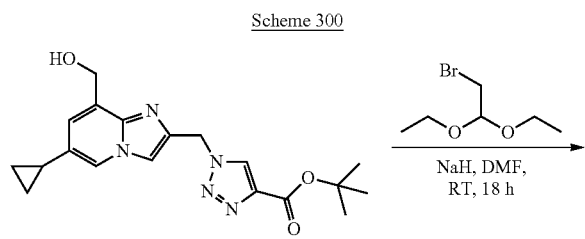

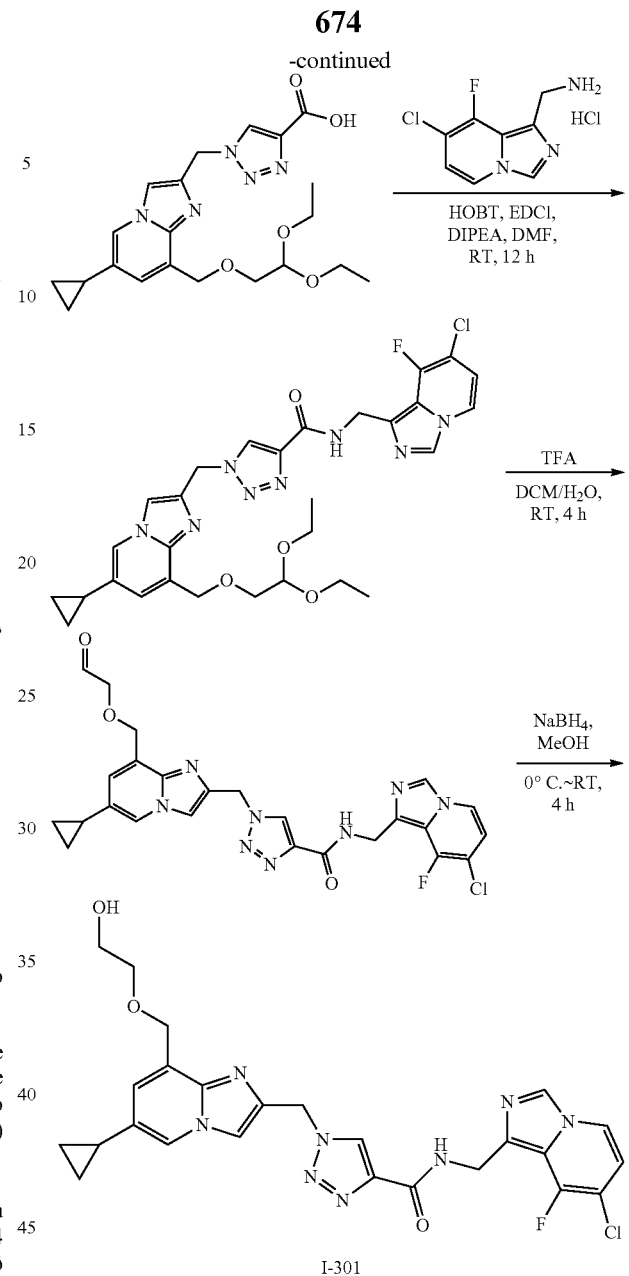

I-301

Synthesis of 1-((6-cyclopropyl-8-((2,2-diethoxyethoxy)methyl)imidazo[1,2-a]pyridin-2-yl)methyl)-1H-1,2,3-triazole-4-carboxylic Acid To a mixture of tert-butyl 1-((6-cyclopropyl-8-(hydroxymethyl)imidazo[1,2-a]pyridin-2-yl)methyl)-1H-1,2,3-triazole-4-carboxylate (740 mg, 2.0 mmol) in DMF (10 mL) was added NaH (400 mg, 60%, 10.0 mmol) at 0° C. The mixture was stirred at RT for 1 h and then 2-bromo-1,1-diethoxyethane (1.57 g, 8.0 mmol) was added. The reaction mixture was stirred at RT for 18 h. The reaction was quenched with saturated aqueous NH4Cl (100 mL), extracted with DCM/MeOH (10/1, 50 mL×5), and the combined organic layers were washed with brine, dried over Na2SO4 and concentrated in vacuo. The crude product was purified by flash column chromatography (DCM/MeOH=5/1) to give 1-((6-cyclopropyl-8-((2,2-diethoxyethoxy)

methyl)imidazo[1,2-a]pyridin-2-yl)methyl)-1H-1,2,3-triazole-4-carboxylic acid (300 mg, yield: 35%) as yellow oil. ESI-MS [M+H]$^+$: 430.1.

Synthesis of N-((7-chloro-8-fluoroimidazo[1,5-a]pyridin-1-yl)methyl)-1-((6-cyclopropyl-8-((2,2-diethoxyethoxy)methyl)imidazo[1,2-a]pyridin-2-yl)methyl)-1H-1,2,3-triazole-4-carboxamide A mixture of 1-((6-cyclopropyl-8-((2,2-diethoxyethoxy)methyl)imidazo[1,2-a]pyridin-2-yl)methyl)-1H-1,2,3-triazole-4-carboxylic acid (120 mg, 0.28 mmol), (7-chloro-8-fluoroimidazo[1,5-a]pyridin-1-yl)methanamine hydrochloride (99 mg, 0.42 mmol), HOBT (57 mg, 0.42 mmol), EDCI (80 mg, 0.42 mmol) and DIPEA (108 mg, 0.84 mmol) in DMF (5 mL) was stirred at 30° C. for 18 h. The reaction mixture was diluted with water (50 mL) and extracted with EtOAc (45 mL×3). The combined organic layers were washed with brine and concentrated. The residue was purified by silica gel chromatography (DCM/MeOH=15/1) to afford N-((7-chloro-8-fluoroimidazo[1,5-a]pyridin-1-yl)methyl)-1-((6-cyclopropyl-8-((2,2-diethoxyethoxy)methyl)imidazo[1,2-a]pyridin-2-yl)methyl)-1H-1,2,3-triazole-4-carboxamide (150 mg, yield: 88%) as a yellow solid. ESI-MS [M+H]$^+$: 612.1.

Synthesis of N-((7-chloro-8-fluoroimidazo[1,5-a]pyridin-1-yl)methyl)-1-((6-cyclopropyl-8-((2-oxoethoxy)methyl)imidazo[1,2-a]pyridin-2-yl)methyl)-1H-1,2,3-triazole-4-carboxamide A mixture of N-((7-chloro-8-fluoroimidazo[1,5-a]pyridin-1-yl)methyl)-1-((6-cyclopropyl-8-((2,2-diethoxyethoxy)methyl)imidazo[1,2-a]pyridin-2-yl)methyl)-1H-1,2,3-triazole-4-carboxamide (150 mg, 0.245 mmol) in TFA/H$_2$O/DCM (0.5 mL/0.5 mL/4 mL) was stirred at RT for 5 h. The reaction was quenched with saturated aqueous NaHCO$_3$ (10 mL) and extracted with DCM (20 mL×3). The combine organic layers were washed with brine, dried over Na$_2$SO$_4$, and concentrated. The residue was purified by silica gel chromatography (DCM/MeOH=10/1) to afford N-((7-chloro-8-fluoroimidazo[1,5-a]pyridin-1-yl)methyl)-1-((6-cyclopropyl-8-((2-oxoethoxy)methyl)imidazo[1,2-a]pyridin-2-yl)methyl)-1H-1,2,3-triazole-4-carboxamide (120 mg, yield: 91.6%). ESI-MS [M+H]$^+$: 537.1.

Synthesis of N-((7-chloro-8-fluoroimidazo[1,5-a]pyridin-1-yl)methyl)-1-((6-cyclopropyl-8-((2-hydroxyethoxy)methyl)imidazo[1,2-a]pyridin-2-yl)methyl)-1H-1,2,3-triazole-4-carboxamide To a mixture of N-((7-chloro-8-fluoroimidazo[1,5-a]pyridin-1-yl)methyl)-1-((6-cyclopropyl-8-((2-oxoethoxy)methyl)imidazo[1,2-a]pyridin-2-yl)methyl)-1H-1,2,3-triazole-4-carboxamide (120 mg, 0.22 mmol) in MeOH (10 mL) was added NaBH$_4$ (42 mg, 1.10 mmol) slowly at 0° C. The resulting reaction was stirred at RT for 1 h. The reaction was quenched with water (20 mL) and extracted with DCM/MeOH (10/1, 50 mL×3). The combined organic layer was washed with brine, dried over Na$_2$SO$_4$, and concentrated. The residue was purified by prep-HPLC to afford N-((7-chloro-8-fluoroimidazo[1,5-a]pyridin-1-yl)methyl)-1-((6-cyclopropyl-8-((2-hydroxyethoxy)methyl)imidazo[1,2-a]pyridin-2-yl)methyl)-1H-1,2,3-triazole-4-carboxamide (12 mg, yield: 10%) as a white solid. ESI-MS [M+H]$^+$: 539.2. Purity: 98.97% (214 nm), 99.65% (254 nm). $^1$H NMR (400 MHz, DMSO): δ 8.76 (t, J=5.3 Hz, 1H), 8.66 (d, J=7.2 Hz, 1H), 8.57 (s, 1H), 8.47 (d, J=2.3 Hz, 1H), 8.21 (d, J=7.4 Hz, 1H), 8.15 (s, 1H), 7.54 (s, 1H), 6.77 (t, J=6.9 Hz, 1H), 5.93 (d, J=5.9 Hz, 2H), 4.79 (s, 2H), 4.71 (d, J=5.4 Hz, 2H), 3.56 (s, 4H), 2.05 (s, 1H), 1.06-0.98 (m, 2H), 0.80-0.73 (m, 2H).

Example 302

Scheme 301

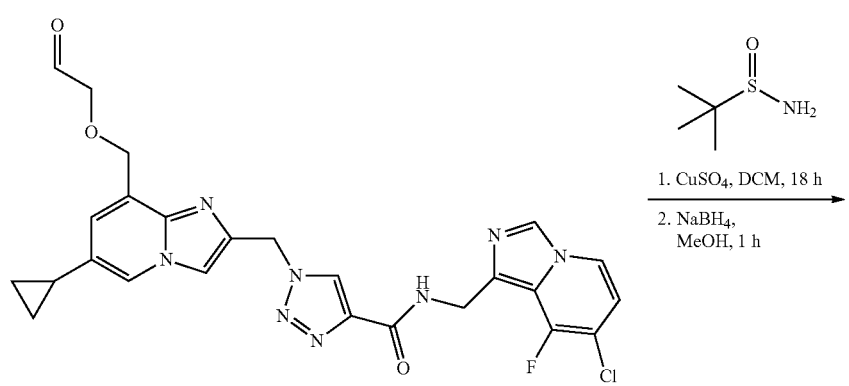

-continued

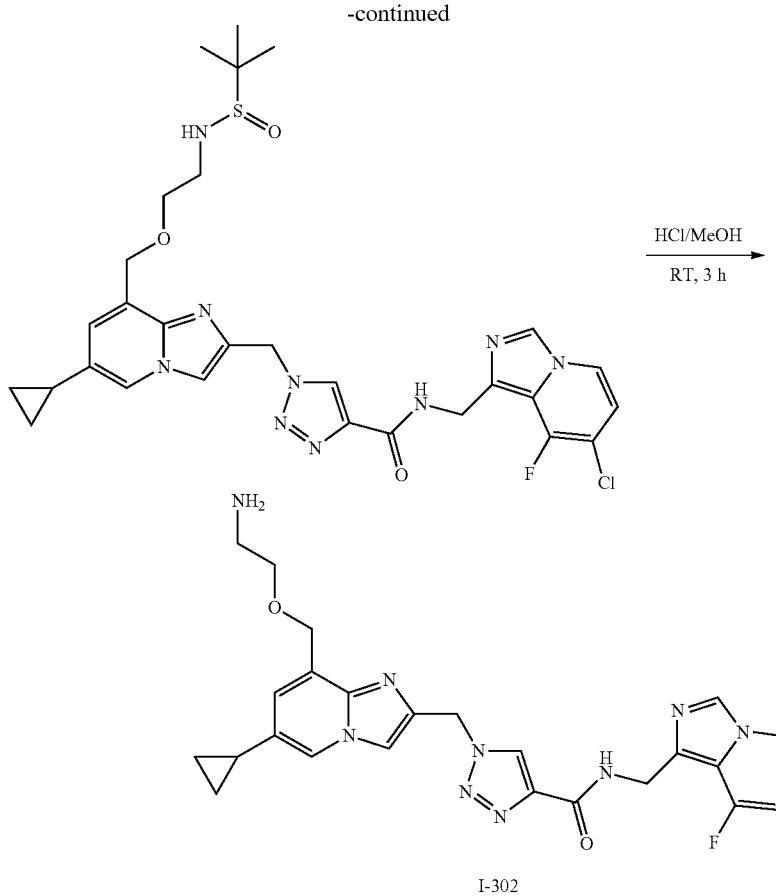

I-302

Synthesis of 1-((8-((2-((tert-butylsulfinyl)amino)ethoxy)methyl)-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide A mixture of N-((7-chloro-8-fluoroimidazo[1,5-a]pyridin-1-yl)methyl)-1-((6-cyclopropyl-8-((2-oxoethoxy)methyl)imidazo[1,2-a]pyridin-2-yl)methyl)-1H-1,2,3-triazole-4-carboxamide (110 mg, 0.21 mmol), 2-methylpropane-2-sulfinamide (38 mg, 0.31 mmol), and CuSO$_4$ (66 mg, 0.41 mmol) in MeOH (3 mL) was stirred at RT for 18 h. NaBH$_4$ (23 mg, 0.61 mmol) was added and the reaction mixture was stirred at RT for another 1 h. The reaction was quenched with saturated NH$_4$Cl solution (50 mL) and extracted with DCM/MeOH (10/1, 50 mL×5). The combined organic layers were washed with brine, dried over Na$_2$SO$_4$ and concentrated in vacuo. The crude product was purified by silica gel chromatography (DCM/MeOH=10/1) to give 1-((8-((2-((tert-butylsulfinyl)amino)ethoxy)methyl)-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide (100 mg, yield: 74%) as a yellow solid. ESI-MS [M+H]$^+$: 643.1.

Synthesis of 1-((8-((2-aminoethoxy)methyl)-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide A mixture of 1-((8-((2-((tert-butylsulfinyl)amino)ethoxy)methyl)-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide (100 mg, 0.16 mmol) in HCl/MeOH (4 mL, 4 M solution in MeOH, 16 mmol) was stirred at RT for 4 h. The reaction mixture was concentrated and the residue was purified by prep-HPLC to afford 1-((8-((2-aminoethoxy)methyl)-6-cyclopropylimidazo[1,2-a]pyridin-2-yl)methyl)-N-((7-chloro-8-fluoroimidazo[1,5-a]pyridin-1-yl)methyl)-1H-1,2,3-triazole-4-carboxamide (16 mg, yield: 19%) as a white solid. ESI-MS [M+H]$^+$: 538.2. Purity: 99.02% (214 nm), 100.00% (254 nm). $^1$H NMR (400 MHz, DMSO): δ 8.72 (t, J=5.2 Hz, 1H), 8.56 (s, 1H), 8.44 (d, J=1.9 Hz, 1H), 8.31 (s, 1H), 8.21 (d, J=7.4 Hz, 1H), 7.86 (s, 1H), 7.08 (s, 1H), 6.76 (t, J=6.9 Hz, 1H), 5.74 (s, 2H), 4.83-4.62 (m, 4H), 3.65 (s, 2H), 2.95 (s, 2H), 2.00-1.87 (m, 1H), 0.98-0.88 (m, 2H), 0.73-0.64 (m, 2H).

Example 303

Scheme 302

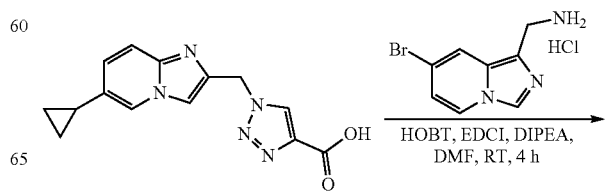

-continued

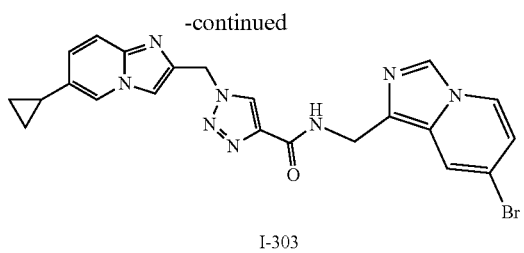

I-303

Synthesis of N-((7-bromoimidazo[1,5-a]pyridin-1-yl)methyl)-1-((6-cyclopropylimidazo[1,2-a]pyridin-2-yl)methyl)-1H-1,2,3-triazole-4-carboxamide To a solution of 1-((6-cyclopropylimidazo[1,2-a]pyridin-2-yl)methyl)-1H-1,2,3-triazole-4-carboxylic acid (100 mg, 0.35 mmol), (7-bromoimidazo[1,5-a]pyridin-1-yl)methanamine hydrochloride (110 mg, 0.41 mmol), HOBT (67 mg, 0.49 mmol) and EDCI (94 mg, 0.49 mmol) in DMF (5 mL) was added DIPEA (226 mg, 1.75 mmol). The resulting mixture was stirred at RT for 4 h. The reaction was poured into H$_2$O (50 mL) and a white solid precipitated out. The mixture was filtered, and the filter cake was washed with H$_2$O (100 mL) and dried to give N-((7-bromoimidazo[1,5-a]pyridin-1-yl)methyl)-1-((6-cyclopropylimidazo[1,2-a]pyridin-2-yl)methyl)-1H-1,2,3-triazole-4-carboxamide (30 mg, yield: 17.5%) as a white solid. ESI-MS [M+H]$^+$: 491.0. Purity: 97.57% (214 nm), 98.57 (254 nm). $^1$H NMR (400 MHz, DMSO): δ 8.91 (t, J=5.8 Hz, 1H), 8.56 (s, 1H), 8.34 (s, 1H), 8.31 (s, 1H), 8.24 (d, J=7.4 Hz, 1H), 8.01 (s, 1H), 7.82 (s, 1H), 7.40 (d, J=9.3 Hz, 1H), 7.00 (dd, J=9.4, 1.5 Hz, 1H), 6.72 (dd, J=7.4, 1.8 Hz, 1H), 5.72 (s, 2H), 4.61 (d, J=5.9 Hz, 2H), 1.95-1.89 (m, J=13.4, 8.4, 5.1 Hz, 1H), 0.94-0.89 (m, 2H), 0.69-0.65 (m, 2H).

Example 304

Inhibitory Activity of Exemplary Compounds Against Plasma Kallikrein.

Example compounds were evaluated for inhibition of the human activated kallikrein enzyme in two formats of an assay employing a fluorogenic peptide substrate. In one assay format, the concentrations of reagents were as follows: 20 mM Tris pH 7.5, 1 mM EDTA, 150 mM sodium chloride, 0.1% PEG-400, 0.1% Triton X-100, 500 pM activated kallikrein enzyme, 300 uM Pro-Phe-Arg-7-amido-4-methylcoumarin substrate. Prior to reaction initiation with substrate, enzyme and inhibitors were preincubated for 30 min at RT. After initiation with substrate, reactions were incubated for 10 min at RT and fluorescence emission at 460 nm from 380 nm excitation measured with a microplate reader. In another assay format, the concentrations of reagents were as follows: 20 mM Tris pH 7.5, 1 mM EDTA, 150 mM sodium chloride, 0.1% PEG-400, 0.1% Triton X-100, 5 pM activated kallikrein enzyme, 300 uM Pro-Phe-Arg-7-amido-4-methylcoumarin substrate. Prior to reaction initiation with substrate, enzyme and inhibitors were preincubated for 30 min at RT. After initiation with substrate, reactions were incubated for 18 h at RT and fluorescence emission at 460 nm from 380 nm excitation measured with a microplate reader.

Table 1 provides the results of the assay in the format with 500 pM activated kallikrein assay. For the compounds listed in Table 1, the EC$_{50}$ values are reported according to the following ranges: A≤1.0 nM; 1.0 nM<B≤10 nM; 10 nM<C≤100 nM; 100 nM<D≤2000 nM; 2000 nM<E.

TABLE 1

| Compound | Primary Dose Response Assay: Average EC50 |
|---|---|
| I-1 | C |
| I-2 | A |
| I-3 | C |
| I-4 | B |
| I-5 | A |
| I-6 | B |
| I-7 | B |
| I-8 | A |
| I-9 | C |
| I-10 | A |
| I-11 | B |
| I-12 | C |
| I-13 | A |
| I-14 | A |
| I-15 | A |
| I-16 | B |
| I-17 | B |
| I-18 | B |
| I-19 | B |
| I-20 | B |
| I-21 | B |
| I-22 | D |
| I-23 | A |
| I-24 | B |
| I-25 | B |
| I-26 | B |
| I-27 | B |
| I-28 | B |
| I-29 | C |
| I-30 | B |
| I-31 | A |
| I-32 | C |
| I-33 | C |
| I-34 | C |
| I-35 | D |
| I-36 | C |
| I-37 | C |
| I-38 | B |
| I-39 | B |
| I-40 | A |
| I-41 | C |
| I-42 | C |
| I-43 | A |
| I-44 | A |
| I-45 | B |
| I-46 | C |
| I-47 | B |
| I-48 | D |
| I-49 | C |
| I-50 | A |
| I-51 | A |
| I-52 | A |
| I-53 | D |
| I-54 | C |
| I-55 | C |
| I-56 | B |
| I-57 | A |
| I-58 | B |
| I-59 | A |
| I-60 | A |
| I-61 | B |
| I-62 | D |
| I-63 | C |
| I-64 | B |
| I-65 | A |

TABLE 1-continued

| Compound | Primary Dose Response Assay: Average EC50 |
|---|---|
| I-66 | A |
| I-67 | C |
| I-68 | A |
| I-69 | D |
| I-70 | C |
| I-71 | A |
| I-72 | B |
| I-73 | A |
| I-74 | B |
| I-75 | A |
| I-76 | A |
| I-77 | C |
| I-78 | A |
| I-79 | B |
| I-80 | A |
| I-81 | A |
| I-82 | C |
| I-83 | C |
| I-84 | C |
| I-85 | A |
| I-86 | A |
| I-87 | A |
| I-88 | B |
| I-89 | D |
| I-90 | A |
| I-91 | C |
| I-92 | A |
| I-93 | A |
| I-94 | C |
| I-95 | B |
| I-96 | E |
| I-97 | A |
| I-98 | A |
| I-99 | A |
| I-100a | A |
| I-100b | A |
| I-100c | A |
| I-101 | A |
| I-102 | A |
| I-103 | A |
| I-104a | A |
| I-104b | A |
| I-105 | A |
| I-106 | A |
| I-107 | A |
| I-108 | A |
| I-109 | A |
| I-110 | A |
| I-111 | A |
| I-112 | A |
| I-113 | B |
| I-114 | A |
| I-115 | A |
| I-116 | B |
| I-117 | A |
| I-118 | B |
| I-119 | A |
| I-120 | A |
| I-121 | A |
| I-122 | A |
| I-123 | B |
| I-124 | B |
| I-125 | A |
| I-126 | A |
| I-127 | A |
| I-128 | A |
| I-129 | A |
| I-130 | C |
| I-131 | A |

TABLE 1-continued

| Compound | Primary Dose Response Assay: Average EC50 |
|---|---|
| I-132 | A |
| I-133 | A |
| I-134 | A |
| I-135 | A |
| I-136 | A |
| I-137 | A |
| I-138 | A |
| I-139 | A |
| I-140 | A |
| I-141 | A |
| I-142 | B |
| I-143 | A |
| I-144 | A |
| I-145 | A |
| I-146 | A |
| I-147 | A |
| I-148 | A |
| I-149 | A |
| I-150 | A |
| I-151 | C |
| I-152 | A |
| I-153 | A |
| I-154 | A |
| I-155 | A |
| I-156 | A |
| I-157a | A |
| I-157b | A |
| I-158 | A |
| I-159 | A |
| I-160 | B |
| I-161 | B |
| I-162 | A |
| I-163a | A |
| I-163b | A |
| I-164 | A |
| I-165 | A |
| I-166a | A |
| I-166b | A |
| I-167 | A |
| I-168 | A |
| I-169 | A |
| I-170 | A |
| I-171 | A |
| I-172 | A |
| I-173 | A |
| I-174 | A |
| I-175 | A |
| I-176 | B |
| I-177 | B |
| I-178 | C |
| I-179 | A |
| I-180 | A |
| I-181 | A |
| I-182 | A |
| I-183 | A |
| I-184 | A |
| I-185 | A |
| I-186 | A |
| I-187 | A |
| I-188 | B |
| I-189 | A |
| I-190 | A |
| I-191 | B |
| I-192 | A |
| I-193 | A |
| I-194 | A |
| I-195 | D |
| I-196 | B |
| I-197 | D |
| I-198 | A |
| I-199 | A |
| I-200 | A |
| I-201 | A |
| I-202 | A |
| I-203 | A |
| I-204 | A |
| I-205 | A |

TABLE 1-continued

| Compound | Primary Dose Response Assay: Average EC50 |
|---|---|
| I-206 | A |
| I-207 | A |
| I-208 | A |
| I-209 | B |
| I-210a | A |
| I-210b | A |
| I-211 | C |
| I-212 | A |
| I-213 | A |
| I-214 | A |
| I-215 | A |
| I-216 | A |
| I-217 | B |
| I-218 | B |
| I-219 | C |
| I-220 | A |
| I-221a | A |
| I-221b | A |
| I-221c | C |
| I-222 | D |
| I-223 | A |
| I-224a | A |
| I-224b | A |
| I-225 | A |
| I-226 | A |
| I-227a | C |
| I-227b | D |
| I-228 | A |
| I-229 | C |
| I-230 | A |
| I-231 | A |
| I-232 | C |
| I-233 | B |
| I-234 | C |
| I-235 | D |
| I-236 | C |
| I-237 | A |
| I-238 | A |
| I-239 | B |
| I-240 | A |
| I-241a | A |
| I-241b | A |
| I-242 | A |
| I-243 | B |
| I-244 | C |
| I-245a | A |
| I-245b | A |
| I-246 | A |
| I-247 | A |
| I-248 | A |
| I-249 | A |
| I-250 | A |
| I-251a | B |
| I-251b | A |
| I-252 | C |
| I-253 | A |
| I-254 | B |
| I-255 | A |
| I-256 | B |
| I-257 | A |
| I-258 | A |
| I-259 | B |
| I-260 | A |
| I-261 | A |
| I-262 | A |
| I-263 | A |
| I-264 | A |
| I-265a | A |
| I-265b | A |

TABLE 1-continued

| Compound | Primary Dose Response Assay: Average EC50 |
|---|---|
| I-266 | A |
| I-267 | A |
| I-268 | B |
| I-269 | B |
| I-270a | B |
| I-270b | A |
| I-271 | A |
| I-272 | A |
| I-273 | B |
| I-274 | D |
| I-275 | C |
| I-276 | A |
| I-277 | C |
| I-278 | D |
| I-279 | A |
| I-280 | C |
| I-281 | A |
| I-282 | D |
| I-283 | A |
| I-284 | C |
| I-285 | C |
| I-286 | C |
| I-287 | D |
| I-288 | A |
| I-289 | A |
| I-290 | C |
| I-291 | C |
| I-292 | C |
| I-293 | C |
| I-294 | C |
| I-295 | A |
| I-296 | C |
| I-297 | C |
| I-298 | A |
| I-299 | A |
| I-300 | A |
| I-301 | A |
| I-302 | A |
| I-303 | A |

Example 305

Comparative Inhibitory Activity of Various Compounds Against Plasma Kallikrein

Table 2 provides comparative plasma kallikrein inhibition potency in the assay format with 500 pM activated kallikrein assay (described in detail in the preceding example). For the compounds listed in Table 1, the $EC_{50}$ values are reported according to the following ranges: A≤1.0 nM; 1.0 nM<B≤10 nM; 10 nM<C≤100 nM; 100 nM<D≤2000 nM; 2000 nM<E.

TABLE II

| Compound | Primary Dose Response Assay: Average EC50 |
|---|---|
| (structure) | C |
| (structure) | B |
| (structure) | C |
| (structure) | B |

TABLE II-continued
| Compound | Primary Dose Response Assay: Average EC50 |
|---|---|
| 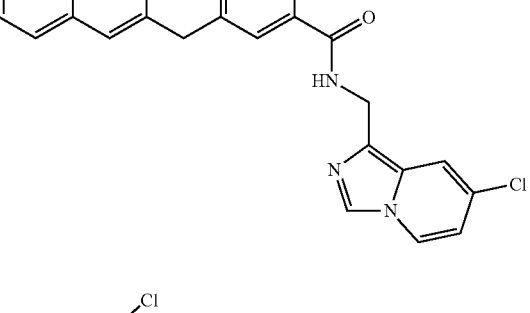 | C |
| 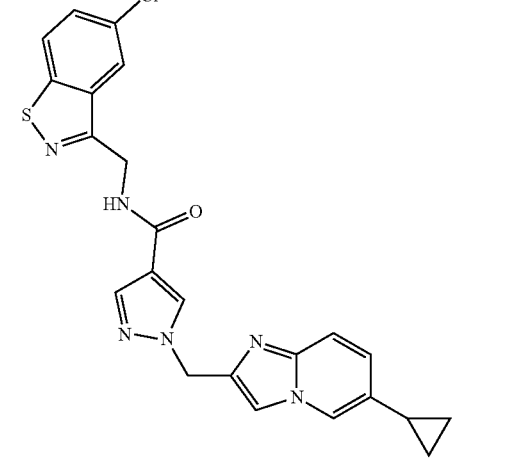 | C |
| 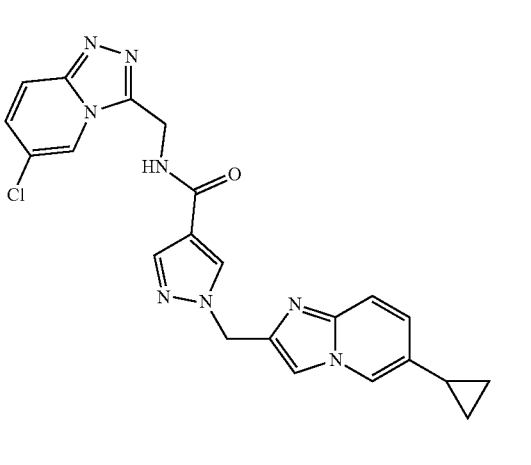 [SMILES: O=C(NCc1nnc2ccc(Cl)cn12)c1cnn(Cc2cn3cc(C4CC4)ccc3n2)c1] | D |
| 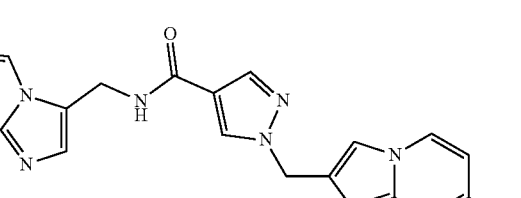 | D |

TABLE II-continued
| Compound | Primary Dose Response Assay: Average EC50 |
|---|---|
| 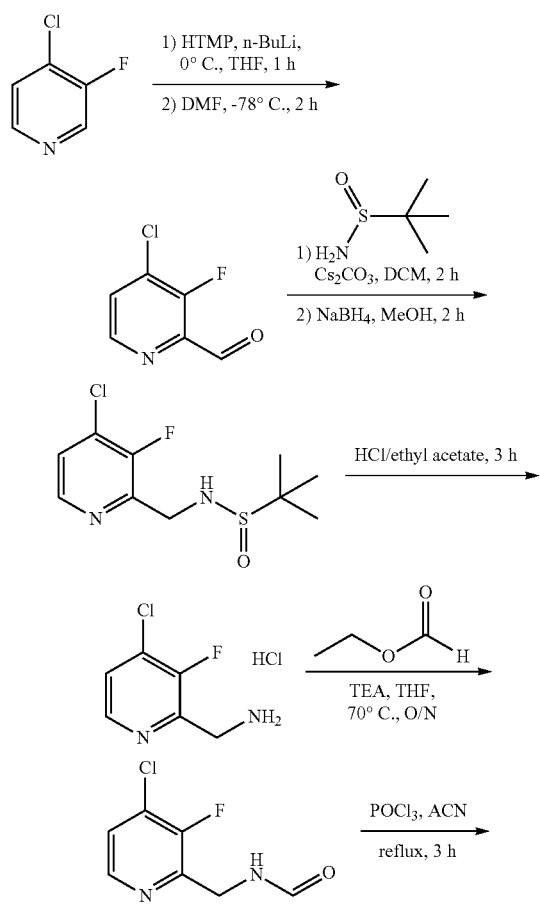 | D |
Example 306
Scheme 303
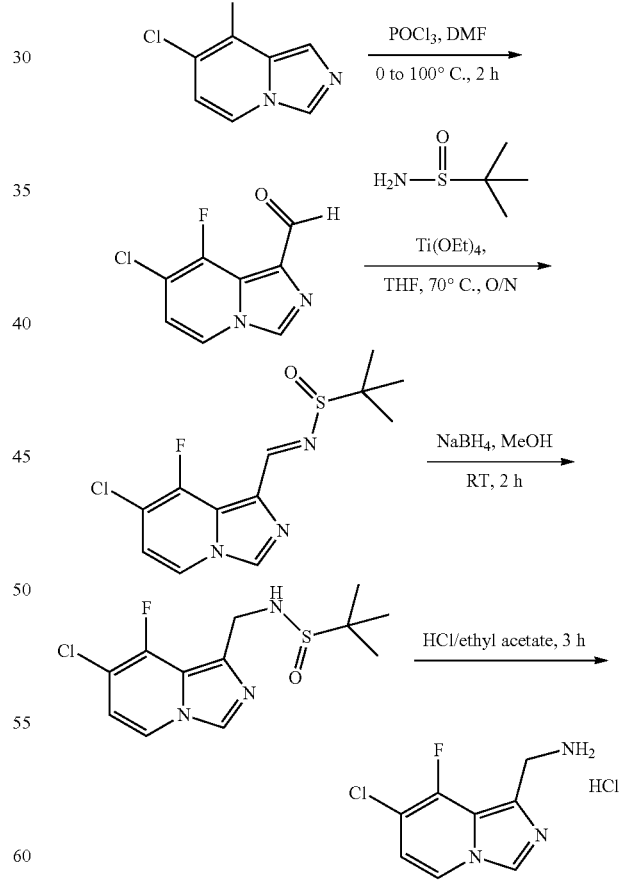
Synthesis of 4-chloro-3-fluoropicolinaldehyde
To a solution of 2, 2, 6, 6-tetramethylpiperidine (35.4 g, 250.88 mmol) in 200 mL THF was added n-Butyllithium (2.4 M in hexane, 100 mL, 240 mmol) dropwise at 0° C. The reaction mixture was cooled to −78° C. after stirring at 0° C. for 1 h and a solution of 4-chloro-3-fluoropyridine (30.0 g, 228.08 mmol) in THF (100 mL) was added dropwise. The resulting reaction mixture was stirred at −78° C. for 2 h, a solution of DMF (17.5 g, 239.48 mmol) in THF (50 mL) was added dropwise, and the resulting reaction mixture was stirred at −78° C. for another 1 h. The reaction was quenched with $H_2O$ (50 mL), and extracted with ethyl acetate (200 mL×3). The combined organic layers were washed with brine, dried over with anhydrous magnesium sulphate, filtered, and concentrated. The residue was purified by silica gel column chromatography (petroleum ether/ethyl acetate=3/1) to afford 4-chloro-3-fluoropicolinaldehyde (26.0 g, yield: 71%). ESI-MS $[M+H]^+$: 160.1.

Synthesis of N-((4-chloro-3-fluoropyridin-2-yl) methyl)-2-methylpropane-2-sulfinamide To a solution of 4-chloro-3-fluoropicolinaldehyde (26.0 g, mixture, 163.0 mmol) in DCM (100 mL) was added cesium carbonate (96.0 g, 293.3 mmol) and 2-methylpropane-2-sulfinamide (19.8 g, 163.0 mmol) at RT. The reaction mixture was stirred for 3 h at RT. After the reaction was complete, the reaction mixture was filtrated and washed with DCM three times. To the combined mixture was added MeOH (40 mL), and then the resulting mixture was cooled to 0° C. by ice-water bath. Sodium borohydride (15.5 g, 409.0 mmol) was added slowly in portions. The reaction mixture was warmed up to RT and stirred at this temperature for 2 h. The reaction was quenched with $H_2O$ carefully. The resulting mixture was extracted with DCM (100 mL×3), the combined organic solvent was dried by sodium sulfate, filtered, and concentrated to get crude N-((4-chloro-3-fluoropyridin-2-yl)methyl)-2-methylpropane-2-sulfinamide (43.3 g, crude) as yellow solid. ESI-MS $[M+H]^+$: 265.1.

Synthesis of (4-chloro-3-fluoropyridin-2-yl)methanamine hydrochloride

To a solution of N-((4-chloro-3-fluoropyridin-2-yl) methyl)-2-methylpropane-2-sulfinamide (about 162.4 mmol) in ethyl acetate (100 mL) was added a solution of hydrochloride acid in ethyl acetate (3 M, 200 mL). The resulting reaction mixture was stirred at RT for 3 h. After the reaction was completed, the reaction mixture was filtered to give the crude product, which was washed with ethyl acetate and dried in vacuum to afford (4-chloro-3-fluoropyridin-2-yl)methanamine hydrochloride (25.0 g, 78%, mixture) as a pink solid. $^1H$ NMR (400 MHz, DMSO) δ 8.75 (br, 3H), 8.47 (d, J=5.2 Hz, 1H), 7.80 (t, J=5.6 Hz, 1H), 4.28-4.26 (m, 2H).

Synthesis of N-((4-chloro-3-fluoropyridin-2-yl)methyl)formamide

To a solution of (4-chloro-3-fluoropyridin-2-yl)methanamine hydrochloride (25.0 g, mixture, 127.0 mmol) in THF (200 mL) was added triethylamine (38.5 g, 380.6 mmol) and ethyl formate (100 mL) at RT. The resulting reaction mixture was stirred at 70° C. overnight. After the reaction was complete, the reaction mixture was filtered, the solid was washed with DCM three times. The combined organic solvent was washed with brine, dried by sodium sulfate, filtrated, and concentrated to afford N-((4-chloro-3-fluoropyridin-2-yl)methyl)formamide (crude), which was used in the next step directly without purification. ESI-MS $[M+H]^+$: 189.1.

Synthesis of 7-chloro-8-fluoroimidazo[1,5-a]pyridine

To a solution of N-((4-chloro-3-fluoropyridin-2-yl) methyl)formamide (crude, about 126.89 mmol) in dry acetonitrile (200 mL) was added phosphoryl trichloride (18 mL, 1.5 eq), and the resulting reaction mixture was stirred at reflux for 3 h. After the reaction was completed, the reaction mixture was cooled down to RT, and then poured into $H_2O$ (200 mL) carefully. The pH was adjusted to 8 with saturated sodium bicarbonate, and then the resulting mixture was extracted with ethyl acetate (200 mL×3). The combined organic phase was washed with brine, dried over sodium sulphate, filtrated, and concentrated in vacuo. The residue was purified by silica gel chromatography (ethyl acetate) to afford 7-chloroimidazo[1,5-a]pyridine (12.0 g, yield: 56%) as a white solid. ESI-MS $[M+H]^+$: 171.1.

Synthesis of 7-chloro-8-fluoroimidazo[1,5-a]pyridine-1-carbaldehyde

A solution of 7-chloro-8-fluoroimidazo[1,5-a]pyridine (9.0 g, 52.6 mmol) in dry DMF (12 mL) was cooled with an ice-water bath to 0-5° C. Phosphorus oxychloride (7.4 g, 78.9 mmol, 1.5 eq) was added dropwise, and then the reaction mixture was stirred at 100° C. for 2 h. After the reaction was completed, the reaction mixture was cooled down to RT and poured into saturated sodium bicarbonate aqueous (200 mL) carefully. The resulting mixture was stirred at RT for 2 h and extracted with ethyl acetate (3×200 mL). The combined organic phase was washed with brine, dried over sodium sulphate, filtered, and concentrated in vacuo. The residue was purified by recrystallization (petroleum ether/ethyl acetate=1/1) to afford 7-chloroimidazo[1,5-a]pyridine-1-carbaldehyde (5.2 g, yield: 47%) as a brown solid. ESI-MS $[M+H]^+$: 181.1.

Synthesis of (Z)—N-((7-chloro-8-fluoroimidazo[1,5-a]pyridin-1-yl)methylene)-2-methylpropane-2-sulfinamide To a solution of 7-chloro-8-fluoroimidazo[1,5-a]pyridine-1-carbaldehyde (5.2 g, 26.19 mmol) and 2-methylpropane-2-sulfinamide (3.2 g, 26.71 mmol) in THF (200 mL) was added tetraethoxytitanium (15.0 g, 65.50 mol). The mixture was stirred at reflux overnight. After the reaction was completed, the reaction mixture was concentrated and the residue was purified by column chromatography (ethyl acetate) to give (E)-N-((7-chloro-8-fluoroimidazo[1,5-a]pyridin-1-yl)methylene)-2-methylpropane-2-sulfinamide (7.77 g, 98%) as a white solid. ESI-MS $[M+H]^+$: 302.1.

Synthesis of N-((7-chloro-8-fluoroimidazo[1,5-a]pyridin-1-yl)methyl)-2-methylpropane-2-sulfinamide To a solution of (E)-N-((7-chloro-8-fluoroimidazo[1,5-a]pyridin-1-yl)methylene)-2-methylpropane-2-sulfinamide (7.77 g, 25.75 mmol) in MeOH (200 mL) was added sodium borohydride (2.44 g, 64.37 mmol) slowly. The resulting reaction mixture was stirred at RT for 3 h. After the reaction was completed, the reaction was quenched with $H_2O$ (50 mL). The resulting mixture was extracted with ethyl acetate (200 mL×3), the combined organic phase was washed with brine, dried over anhydrous sodium sulphate, filtered, and concentrated in vacuum to afford N-((7-chloro-8-fluoroimidazo[1,5-a]pyridin-1-yl)methyl)-2-methylpropane-2-sulfinamide (7.77 g, 99%) as a white solid. ESI-MS [M+H]⁺: 304.1.

Synthesis of (7-chloro-8-fluoroimidazo[1,5-a]pyridin-1-yl)methanamine hydrochloride A mixture of N-((7-chloro-8-fluoroimidazo[1,5-a]pyridin-1-yl)methyl)-2-methylpropane-2-sulfinamide (7.77 g, 25.5 mmol) and hydrochloride acid in ethyl acetate (3 M, 100 mL) was stirred at RT for 2 h, and then the reaction mixture was filtered to give the crude product, which was washed with ethyl acetate and dried in vacuum to afford (7-chloro-8-fluoroimidazo[1,5-a]pyridin-1-yl)methanamine hydrochloride salt (6.03 g, quant.) as a white solid. ESI-MS [M-NH₂]⁺: 182.9. ¹H NMR (400 MHz, DMSO): δ 8.64 (d, J=2.0 Hz, 1H), 8.44 (br, 3H), 8.33 (d, J=7.2 Hz, 1H), 6.92 (t, J=6.8 Hz, 1H), 4.26-4.22 (m, 2H).

Example 307

Scheme 304

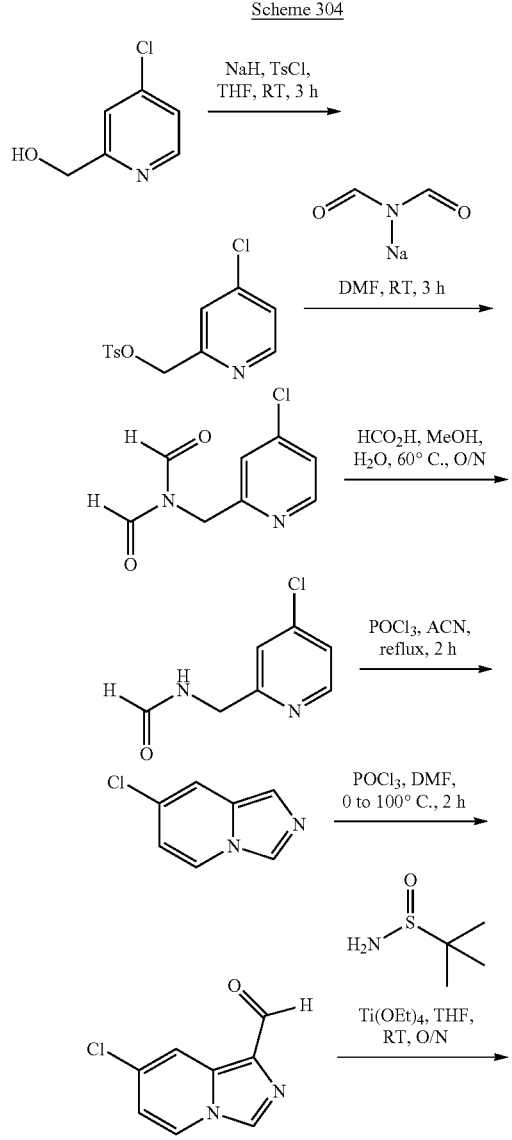

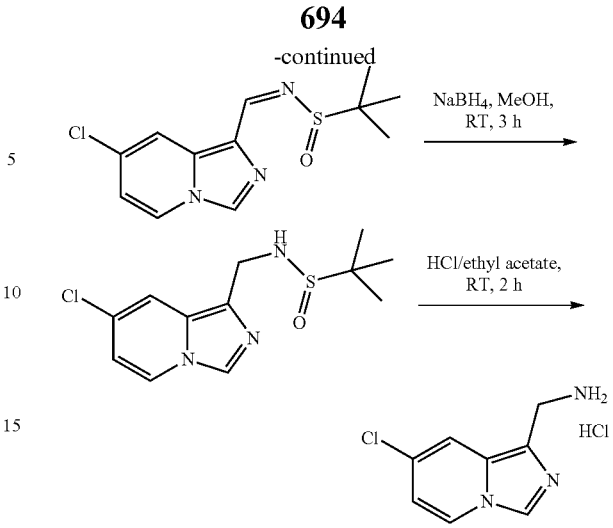

Synthesis of (4-chloropyridin-2-yl)methyl 4-methylbenzenesulfonate

Sodium hydride (44 g, 60%, 1.096 mol) was added to a cooled (0° C.) solution of (4-chloropyridin-2-yl)methanol (80 g, 548 mmol) in THF (1500 mL) at 0° C. The mixture was stirred at 0° C. for 1 h, and tosyl chloride (104 g, 548 mmol) was added. After stirring at 0° C. for another 3 h, the mixture was quenched with H₂O (50 mL), and extracted with ethyl acetate (120 mL×3), the combined organic layers were washed with brine, dried over with anhydrous magnesium sulphate, filtered, and concentrated to afford (4-chloropyridin-2-yl)methyl 4-methylbenzenesulfonate (162 g, crude) as a brown oil which was used in the next step without purification. ESI-MS [M+H]⁺: 296.1.

Synthesis of N-((4-chloropyridin-2-yl)methyl)-N-formylformamide

To a solution of (4-bromopyridin-2-yl)methyl 4-methylbenzenesulfonate (crude, 162 g, 548 mmol) in DMF (500 mL) was added sodium diformamide (52 g, 548 mmol) at RT. The mixture was stirred for 3 h and concentrated in vacuum. The residue was washed with ethyl acetate three times. The combined filtrate was concentrated and the crude product was purified by silica gel column chromatography (petroleum ether/ethyl acetate=1/1) to afford N-((4-chloropyridin-2-yl)methyl)-N-formylformamide (100 g, yield: 83%). ESI-MS [M+H]⁺: 198.1.

Synthesis of N-((4-chloropyridin-2-yl)methyl)formamide

To a solution of N-((4-chloropyridin-2-yl)methyl)-N-formylformamide (100 g, 465 mmol) in MeOH (100 mL) was added H₂O (8.4 g, 465 mol) and formic acid (55.7 g, 929 mmol) at RT. The mixture was stirred at 60° C. overnight and then concentrated to afford N-((4-chloropyridin-2-yl)methyl)formamide (crude) which was used in the next step without purification. ESI-MS [M+H]⁺: 171.1.

Synthesis of 7-chloroimidazo[1,5-a]pyridine

To a solution of N-((4-chloropyridin-2-yl)methyl)formamide (crude, about 465 mmol) in dry acetonitrile (300 mL) was added phosphorus oxybromide (100 mL, 1.5 eq) and the reaction mixture was stirred at reflux for 2 h. After cooling down, the mixture was poured onto H$_2$O (200 mL). The pH of the mixture was adjusted to 8 with saturated sodium bicarbonate and then extracted with ethyl acetate (200 mL×3). The combined organic phases were washed with brine and dried over sodium sulphate, filtered and concentrated in vacuo. The residue was purified by silica gel chromatography (ethyl acetate) to afford 7-chloroimidazo[1,5-a]pyridine (59 g, yield: 71%) as a yellow solid. ESI-MS [M+H]$^+$: 153.1.

Synthesis of 7-chloroimidazo[1,5-a]pyridine-1-carbaldehyde

A solution of 7-chloroimoimidazo[1,5-a]pyridine (47 g, 307 mmol) in dry DMF (26.9 g, 368 mmol) was cooled in an ice bath to 0-5° C. Phosphorus oxychloride (56.4 g, 368 mmol, 1.2 eq) was added dropwise at 0-5° C. and the reaction mixture was subsequently stirred at 100° C. for 2 h. The reaction mixture is cooled and poured onto saturated aqueous sodium bicarbonate (200 mL) and kept stirring for another 2 h and extracted with ethyl acetate (3×200 mL). The combined organic phases were washed with brine and dried over sodium sulphate, filtered, and concentrated in vacuo. The residue was purified by silica gel chromatography (petroleum ether/ethyl acetate=1/1) to afford 7-chloroimidazo[1,5-a]pyridine-1-carbaldehyde (32 g, yield: 58%) as a yellow solid. ESI-MS [M+H]$^+$: 181.1.

Synthesis of (Z)—N-((7-chloroimidazo[1,5-a]pyridin-1-yl)methylene)-2-methylpropane-2-sulfinamide To a solution of 7-chloroimidazo[1,5-a]pyridine-1-carbaldehyde (22 g, 121 mmol) and 2-methylpropane-2-sulfinamide (14.7 g, 121 mmol) in THF (500 mL) was added tetraethoxytitanium (Ti(OEt)$_4$) (55 g, 243 mol). The mixture was stirred at reflux overnight. The mixture was concentrated and the residues purified by column chromatography (ethyl acetate) to give (Z)—N-((7-chloroimidazo[1,5-a]pyridin-1-yl)methylene)-2-methylpropane-2-sulfinamide (32 g, quant.) as a yellow solid. ESI-MS [M+H]$^+$: 284.1.

Synthesis of N-((7-chloroimidazo[1,5-a]pyridin-1-yl)methyl)-2-methylpropane-2-sulfinamide To a solution of (Z)—N-((7-chloroimidazo[1,5-a]pyridin-1-yl)methylene)-2-methylpropane-2-sulfinamide (32 g, 121.67 mmol) in MeOH (200 mL), was added sodium borohydride (13.5 g, 365 mmol) slowly. The mixture was stirred at RT for 3 h and concentrated. The residue was diluted with 50 mL H$_2$O and extracted with ethyl acetate (200 mL×3). After washing with brine, the combined organic layers were dried over anhydrous sodium sulphate, filtered, and concentrated in vacuum to afford N-((7-chloroimidazo[1,5-a]pyridin-1-yl)methyl)-2-methylpropane-2-sulfinamide (32.3 g, quant.) as a white solid. ESI-MS [M+H]$^+$: 286.1.

Synthesis of (7-chloroimidazo[1,5-a]pyridin-1-yl) methanamine hydrochloride

A mixture of N-((7-chloroimidazo[1,5-a]pyridin-1-yl) methyl)-2-methylpropane-2-sulfinamide (33.73 g, 117.6 mmol) and hydrochloride in ethyl acetate (3 M, 100 mL) was stirred at RT for 2 h and then filter to give the crude product which was washed with ethyl acetate and dried in vacuum to afford (27.33 g, quant.) as a white solid. ESI-MS [M-NH$_2$]$^+$: 164.9. Purity: 98.7%. $^1$H NMR (400 MHz, DMSO) δ 8.91 (s, 1H), 8.58 (br, 3H), 8.52 (d, J=7.6 Hz, 1H), 8.18 (dd, J=0.8 Hz, 1H), 6.93 (dd, J=2.0, 7.6 Hz, 1H), 4.34 (q, J=5.6 Hz, 2H).

Example 308

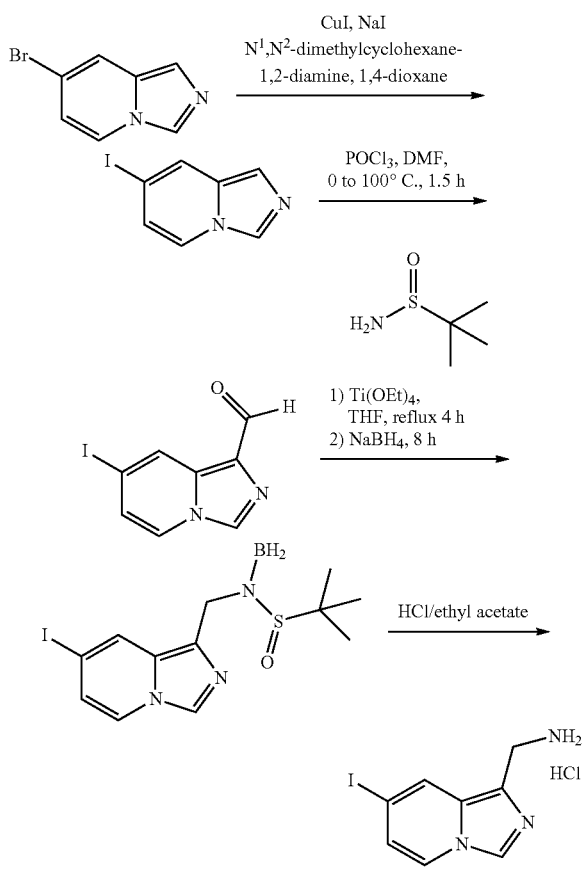

Synthesis of 7-iodoimidazo[1,5-a]pyridine

To a solution of 7-bromoimidazo[1,5-a]pyridine (2.8 g, 14.2 mmol) in a tube were added copper(I) iodide (270 mg, 1.42 mmol), sodium iodide (10.7 g, 71.1 mmol), N$^1$,N$^2$-dimethylcyclohexane-1,2-diamine (404 mg, 2.84 mmol) and 1,4-dioxane (15 mL). The mixture was stirred at 100° C. for 16 h. The mixture was diluted with H$_2$O (100 mL), extracted with ethyl acetate (30 mL×3). The combined organic layers were washed with brine, dried, evaporated and purified by silica gel chromatography (petroleum ether/ethyl acetate=1/1) to afford 7-iodoimidazo[1,5-a]pyridine (2.7 g, yield: 77%) as a yellow solid. ESI-MS [M+H]$^+$: 245.0.

Synthesis of 7-iodoimidazo[1,5-a]pyridine-1-carbaldehyde

A solution of 7-iodoimidazo[1,5-a]pyridine (2.45 g, 10 mmol) in dry DMF (3 mL) was cooled in an ice bath to 0° C. Phosphorus oxychloride (2.3 g, 15 mmol, 1.5 eq) was added dropwise at 0° C. and the reaction mixture is subsequently stirred at 100° C. over 1.5 h. After cooling down, the solvent was removed and the pH of the mixture was adjusted to 8 with aqueous saturated sodium bicarbonate and then extracted with ethyl acetate (50 mL×3). The combined organic phases were dried over sodium sulphate, filtered, and concentrated in vacuo. The residue was purified by silica gel chromatography (petroleum ether/ethyl acetate=1/1) to afford 7-iodoimidazo[1,5-a]pyridine-1-carbaldehyde (1.1 g, yield: 40%) as a yellow solid. ESI-MS [M+H]$^+$: 273.0.

Synthesis of N-boryl-N-((7-iodoimidazo[1,5-a]pyridin-1-yl)methyl)-2-methylpropane-2-sulfinamide A mixture of 7-iodoimidazo[1,5-a]pyridine-1-carbaldehyde (1.1 g, 4.04 mmol) in THF (50 mL) was added 2-methylpropane-2-sulfinamide (592 mg, 4.85 mmol) and tetraethoxytitanium (Ti(OEt)$_4$, 1.84 g, 8.09 mmol). The mixture was stirred at reflux for 4 h. After cooling down, sodium borohydride (615 mg, 16.18 mmol) was added slowly and the mixture was stirred at RT for 8 h. 30 mL of H$_2$O was added to the mixture, extracted with ethyl acetate (30 mL×3). The combined organic layers were dried over anhydrous sodium sulphate, filtered and concentrated in vacuum. The residue was purified by silica gel chromatography (petroleum ether:ethyl acetate=1:1) to afford N-boryl-N-((7-iodoimidazo[1,5-a]pyridin-1-yl)methyl)-2-methylpropane-2-sulfinamide (950 mg, yield: 60%) as a white solid. ESI-MS [M+H]$^+$: 390.0.

Synthesis of (7-iodoimidazo[1,5-a]pyridin-1-yl)methanamine hydrochloride

A mixture of N-boryl-N-((7-iodoimidazo[1,5-a]pyridin-1-yl)methyl)-2-methylpropane-2-sulfinamide (950 mg, 2.44 mmol) and hydrochloride in Ethyl acetate (3M, 20 mL) was stirred at RT for 4 h and then filtered to give the crude product which was washed with ethyl acetate and dried in vacuum to afford (7-iodoimidazo[1,5-a]pyridin-1-yl)methanamine hydrochloride (757 mg, quant.) as a white solid. ESI-MS [M-NH$_2$]$^+$: 256.9. Purity: 97.9%. $^1$H NMR (400 MHz, DMSO) δ 8.79 (s, 1H), 8.45 (br, 3H), 8.43 (s, 1H), 8.26 (d, J=7.2 Hz, 1H), 7.03 (d, J=7.6 Hz, 1H), 4.31 (q, J=5.6 Hz, 2H).

Example 309

Scheme 306

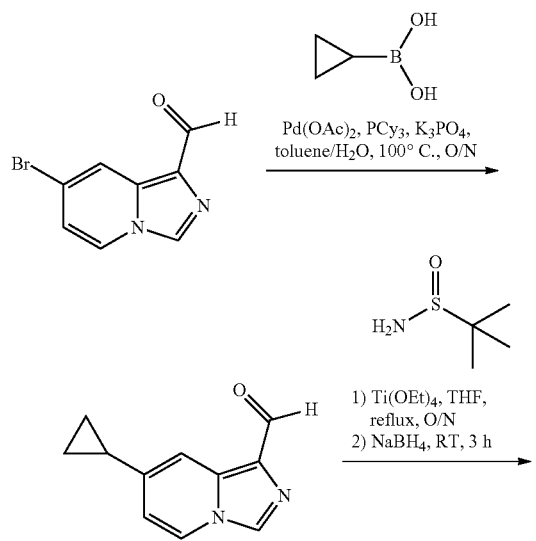

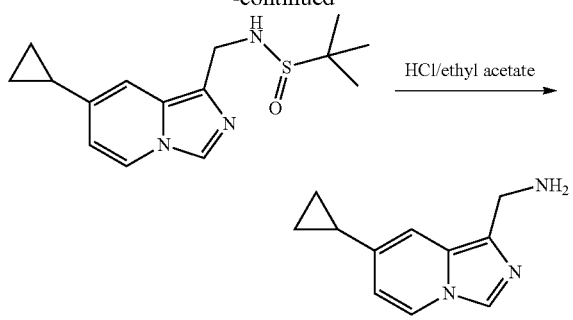

Synthesis of 7-cyclopropylimidazo[1,5-a]pyridine-1-carbaldehyde

A mixture of 7-bromoimidazo[1,5-a]pyridine-1-carbaldehyde (1.4 g, 6.22 mmol), cyclopropylboronic acid (5.4 g, 62.2 mmol), palladium diacetate (100 mg, 0.6 mmol), tricyclohexyl phosphine (200 mg, 06 mmol) and potassium phosphate (2.7 g, 12.4 mmol) in toluene/H$_2$O (30 mL, 10/1) was stirred at reflux overnight. The mixture was concentrated to yield the crude product, which was purified by flash chromatography (petroleum ether/ethyl acetate=1/1) to give 7-cyclopropylimidazo[1,5-a]pyridine-1-carbaldehyde (750 mg, yield: 64%) as a brown solid. ESI-MS [M+H]$^+$: 187.1.

Synthesis of N-((7-cyclopropylimidazo[1,5-a]pyridin-1-yl)methyl)-2-methylpropane-2-sulfinamide To a solution of 7-cyclopropylimidazo[1,5-a]pyridine-1-carbaldehyde (720 mg, 3.87 mmol) and 2-methylpropane-2-sulfinamide (710 mg, 5.86 mmol) in THF (10 mL) was added titanium ethoxide (2.7 g, 11.61 mmol). The mixture was stirred at reflux overnight. After the reaction was completed, sodium borohydride (580 mg 11.5 mmol) was added, stirred for another 3 h. Then the mixture was diluted with H$_2$O (100 mL), and extracted with ethyl acetate (100 mL×3). The combined organic layers were dried and concentrated. The residue was purified by silica column chromatography (petroleum ether/ethyl acetate=1/1) to give N-((7-cyclopropylimidazo[1,5-a]pyridin-1-yl)methyl)-2-methylpropane-2-sulfinamide (700 mg, yield: 62%) as a yellow solid.

Synthesis of (7-cyclopropylimidazo[1,5-a]pyridin-1-yl)methanamine

To a solution of N-((7-cyclopropylimidazo[1,5-a]pyridin-1-yl)methyl)-2-methylpropane-2-sulfinamide (650 mg, 2.14 mmol) in ethyl acetate (20 mL) was added hydrochloride in ethyl acetate (3 M, 10 mL). The mixture was stirred at RT for 3 h and then filtered to give the crude product which was washed with ethyl acetate and dried in vacuum to afford (7-cyclopropylimidazo[1,5-a]pyridin-1-yl)methanamine (500 mg, quant.) as a white solid. ESI-MS [M-NH$_2$]$^+$: 171.1. Purity: 92.4%. $^1$H NMR (400 MHz, DMSO) δ 9.36 (s, 1H), 8.81 (br, 3H), 8.48 (d, J=7.2 Hz, 1H), 7.81 (s, 1H), 6.87 (dd, J=7.2, 1.6 Hz, 1H), 4.42 (q, J=5.6 Hz, 2H), 2.00-1.94 (m, 1H), 1.05-1.00 (m, 2H), 0.87-0.85 (m, 2H).

Example 310

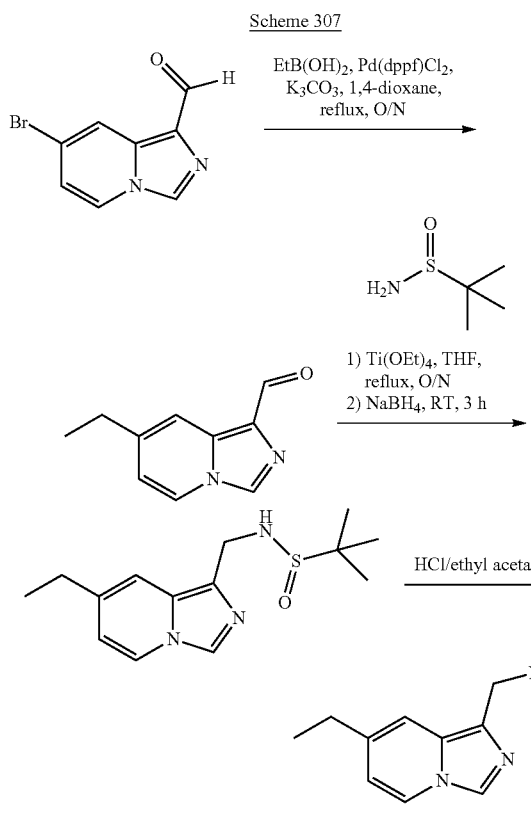

Scheme 307

Synthesis of 7-ethylimidazo[1,5-a]pyridine-1-carbaldehyde

A mixture of 7-bromoimidazo[1,5-a]pyridine-1-carbaldehyde (2.5 g, 11.11 mmol), ethylboronic acid (8.2 g, 111.1 mmol), potassium carbonate (3.2 g, 22.2 mmol), and [1,1'-Bis(diphenylphosphino)ferrocene]dichloropalladium(II) (880 mg, 1.2 mmol) in 1,4-dioxane (20 mL) was heated to reflux overnight. The mixture was diluted with H$_2$O (50 mL) and extracted with ethyl acetate (100 mL×3). The combined organic layers were dried and concentrated. The crude product was purified with flash chromatography (petroleum ether/ethyl acetate=1/1) to give 7-ethylimidazo[1,5-a]pyridine-1-carbaldehyde (1.2 g, yield: 62%) as a yellow solid. ESI-MS [M+H]$^+$: 175.2.

Synthesis of N-((7-ethylimidazo[1,5-a]pyridin-1-yl)methyl)-2-methylpropane-2-sulfinamide To a solution of 7-ethylimidazo[1,5-a]pyridine-1-carbaldehyde (1.2 g, 6.89 mmol) and 2-methylpropane-2-sulfinamide (880 mg, 7.23 mmol) in THF (10 mL) was added tetraethoxytitanium (Ti(OEt)$_4$) (7.9 g, 34.4 mmol). The mixture was stirred at reflux overnight. After cooling down, sodium borohydride (1.05 g, 27.5 mmol) was added, and the mixture was stirred at RT for another 3 h. Then the mixture was diluted with H$_2$O (50 mL), and extracted with ethyl acetate (50 mL×3). The combined organic layers were washed with brine, dried, and concentrated to give N-((7-ethylimidazo[1,5-a]pyridin-1-yl)methyl)-2-methylpropane-2-sulfinamide (1.4 g, yield: 73%) as a white solid. ESI-MS [M+H]$^+$: 280.1.

Synthesis of (7-ethylimidazo[1,5-a]pyridin-1-yl)methanamine

To a solution of N-((7-ethylimidazo[1,5-a]pyridin-1-yl)methyl)-2-methylpropane-2-sulfinamide (1.4 g, 5.0 mmol) in ethyl acetate (10 mL) was added hydrochloride in ethyl acetate (3 M, 10 mL). The mixture was stirred at RT for 3 h and then filtered to give the crude product which was washed with ethyl acetate and dried in vacuum to afford (7-ethylimidazo[1,5-a]pyridin-1-yl)methanamine (1.0 g, quant.) as a white solid. ESI-MS [M-NH$_2$]$^+$: 159.0. Purity: 97.4%. $^1$H NMR (400 MHz, DMSO) δ 9.36 (s, 1H), 8.78 (br, 3H), 8.51 (d, J=4.0 Hz, 1H), 7.87 (s, 1H), 6.99 (d, J=4.0 Hz, 1H), 4.45-4.43 (m, 2H), 2.59 (q, J=7.6 Hz, 2H), 1.24 (t, J=7.6 Hz, 3H).

Example 311

Scheme 308

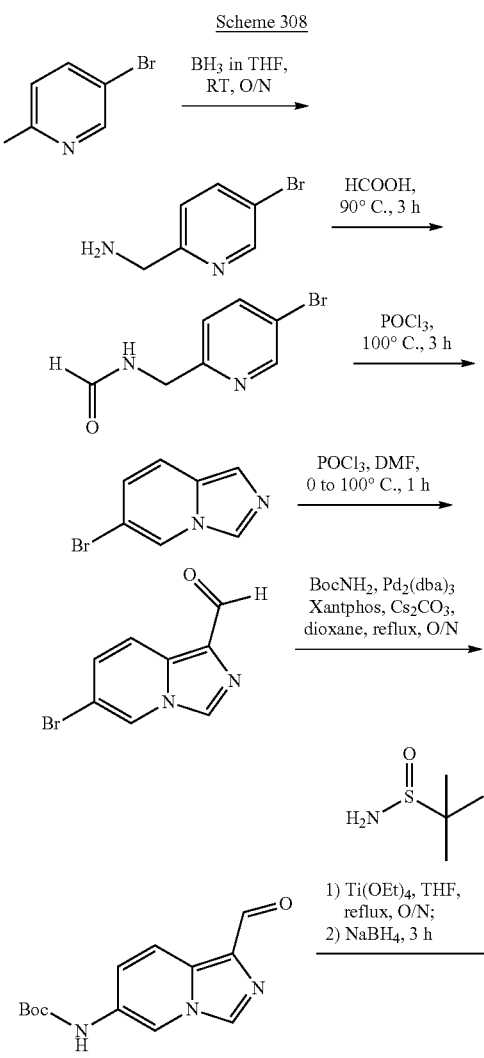

701

-continued

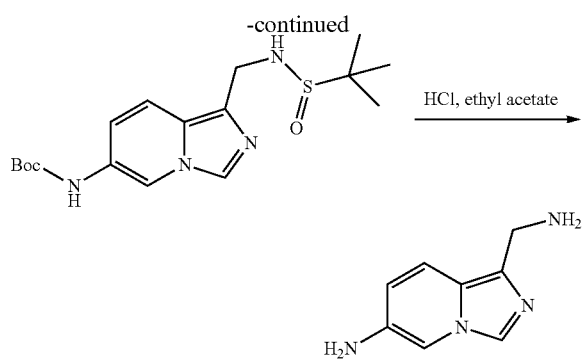

HCl, ethyl acetate
→

Synthesis of (5-bromopyridin-2-yl)methanamine

To a solution of 5-bromopicolinonitrile (15 g, 81.96 mol) was added a borane THF complex solution (107 mL, 1 M). The mixture was stirred at ambient temperature overnight. The reaction was quenched with MeOH (50 mL), stirred at RT for 1 h, and then concentrated to give (5-bromopyridin-2-yl)methanamine (crude) as a brown oil which was used in the next step without purification. ESI-MS [M+H]$^+$: 188.1.

Synthesis of N-((5-bromopyridin-2-yl)methyl)formamide

A solution of (5-bromopyridin-2-yl)methanamine (crude) in formic acid (150 mL) was stirred at 100° C. for 3 h, and then concentrated to give N-((5-bromopyridin-2-yl)methyl)formamide (crude) as a brown oil which was used in the next step without purification. ESI-MS [M+H]$^+$: 216.1.

Synthesis of 6-bromoimidazo[1,5-a]pyridine

A solution of N-((5-bromopyridin-2-yl)methyl)formamide (crude) in phosphorus oxychloride (50 mL) was heated to 100° C. for 3 h. Phosphorus oxychloride was removed in vacuum. The residue was poured into ice-water. The pH of the mixture was adjusted to 8 with aqueous saturated sodium bicarbonate and then extracted with ethyl acetate (200 mL×3). The combined organic phases were washed with brine and dried over sodium sulphate, filtered, and concentrated in vacuum. The residue was purified by silica gel chromatography (petroleum ether/ethyl acetate=1/1) to afford 6-bromoimidazo[1,5-a]pyridine (1.2 g, yield: 7.4%) as a yellow solid. ESI-MS [M+H]$^+$: 198.1.

Synthesis of 6-bromoimidazo[1,5-a]pyridine-1-carbaldehyde

A solution of 6-bromoimidazo[1,5-a]pyridine (1.7 g, 8.63 mmol) in dry DMF (944 mg, 12.9 mmol) was cooled in an ice bath to 0-5° C. Phosphorus oxychloride (1.98 g, 12.9 mmol, 1.5 eq) was added dropwise at 0-5° C. and the reaction mixture was subsequently stirred at 100° C. over 2 h. The reaction mixture was cooled and poured onto aqueous saturated sodium bicarbonate (200 mL), kept stirring for another 2 h, and extracted with ethyl acetate (50 mL×3). The combined organic phases were washed with brine and dried over sodium sulphate, filtered, and concentrated in vacuo. The residue was purified by silica gel chromatography (petroleum ether/ethyl acetate=1/1) to afford 6-bromoimidazo[1,5-a]pyridine-1-carbaldehyde (500 mg, yield: 26%) as a yellow solid. ESI-MS [M+H]$^+$: 226.0.

702

Synthesis of tert-butyl (1-formylimidazo[1,5-a]pyridin-6-yl)carbamate

To a solution of 6-bromoimidazo[1,5-a]pyridine-1-carbaldehyde (860 mg, 3.82 mmol) in dioxane (50 mL), was added tris(dibenzylideneacetone)dipalladium (Pd$_2$(dba)$_3$, 696 mg, 0.76 mmol), Xantphos (440 mg, 0.76 mmol), cesium carbonate (3 g, 9.51 mmol), tert-butyl carbamate (2.22 g, 9.0 mmol). The mixture was stirred at reflux overnight and concentrated. The residue was purified by column chromatography (ethyl acetate) to give N-((7-bromoimidazo[1,5-a]pyridin-1-yl)methylene)-2-methylpropane-2-sulfinamide (800 mg, yield: 80%) as a yellow solid. ESI-MS [M+H]$^+$: 262.0.

Synthesis of tert-butyl (1-((1,1-dimethylethylsulfinamido)methyl)imidazo[1,5-a]pyridin-6-yl)carbamate To a solution of tert-butyl (1-formylimidazo[1,5-a]pyridin-6-yl)carbamate (800 mg, 3 mmol) in THF (50 mL), was added 2-methylpropane-2-sulfinamide (370 mg, 3 mmol), tetraethoxytitanium (2.1 g, 9.2 mmol). The mixture was stirred at reflux overnight. After cooling down, sodium borohydride (348 mg, 9.2 mmol) was added slowly. The mixture was stirred at RT for 3 h. The mixture was concentrated and the residue was purified by column chromatography (petroleum ether/ethyl acetate=100/0 to 90/10) to afford tert-butyl (1-((1,1-dimethylethylsulfinamido)methyl)imidazo[1,5-a]pyridin-6-yl)carbamate (600 mg, yield: 54%) as a white solid. ESI-MS [M+BH$_2$]$^+$: 379.1.

Synthesis of 1-(aminomethyl)imidazo[1,5-a]pyridin-6-amine

To a solution of tert-butyl(1-((1,1-dimethylethylsulfinamido)methyl)imidazo[1,5-a]pyridin-6-yl)carbamate (600 mg, 1.63 mmol) in ethyl acetate (3 mL) was added hydrochloride in ethyl acetate (3 M, 2 mL). The mixture was stirred at RT for 3 h and then filtered to give the crude product which was washed with ethyl acetate and dried in vacuum to afford 1-(aminomethyl)imidazo[1,5-a]pyridin-6-amine hydrochloride (343 g, yield: 89%) as a white solid. ESI-MS [M-NH$_2$]$^+$: 146. Purity: 99.0%. $^1$H NMR (400 MHz, DMSO) δ 9.29 (s, 1H), 8.78 (br, 3H), 8.00 (s, 1H), 7.79 (dd, J=10 Hz, 1H), 7.70 (br, 3H), 7.79 (dd, J=10 Hz, 2 Hz, 1H), 4.41 (d, J=5.6 Hz, 2H).

Example 312

Scheme 309

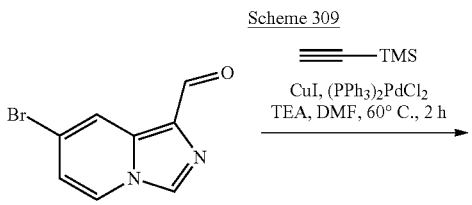

CuI, (PPh$_3$)$_2$PdCl$_2$
TEA, DMF, 60° C., 2 h
→

Synthesis of 7-((trimethylsilyl)ethynyl)imidazo[1,5-a]pyridine-1-carbaldehyde

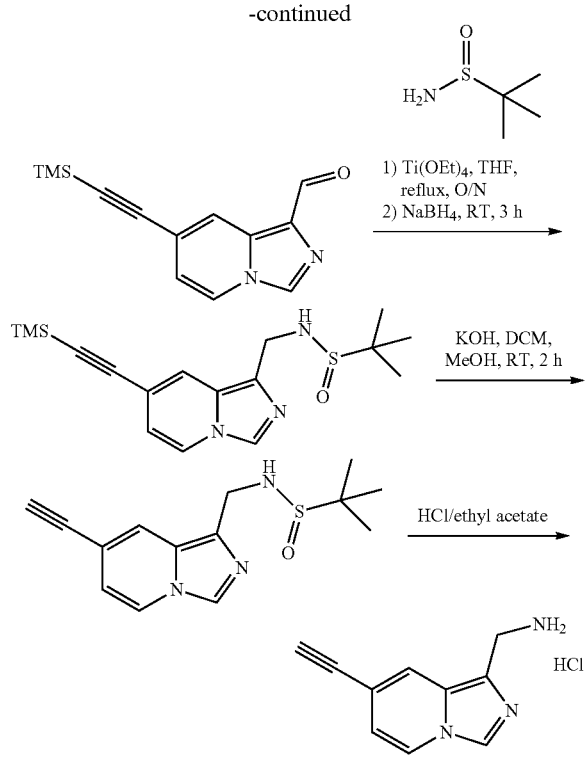

To a solution of 7-bromoimidazo[1,5-a]pyridine-1-carbaldehyde (660 mg, 2.93 mmol), trimethylsilylacetylene (350 mg, 3.52 mmol) in DMF (10 mL) was added cuprous iodide (60 mg, 0.3 mmol), bis(triphenylphosphine)palladium(II) chloride (210 mg, 0.3 mmol) and triethylamine (600 mg, 5.86 mmol). The mixture was stirred at 100° C. for 2 h. After the reaction was completed, the mixture was diluted with H₂O (20 mL), and extracted with ethyl acetate (50 mL×3). The combined organic layers were wash with brine, dried, and concentrated. The residue was purified with flash chromatography (petroleum ether/ethyl acetate=1/1) to give 7-((trimethylsilyl)ethynyl)imidazo[1,5-a]pyridine-1-carbaldehyde (430 mg, yield: 45%) as a yellow solid. ESI-MS [M+H]$^+$: 243.2.

Synthesis of 2-methyl-N-((7-((trimethylsilyl)ethynyl)imidazo[1,5-a]pyridin-1-yl)methyl)propane-2-sulfinamide To a solution of 7-((trimethylsilyl)ethynyl)imidazo[1,5-a]pyridine-1-carbaldehyde (430 mg, 1.77 mmol) and 2-methylpropane-2-sulfinamide (230 mg, 1.90 mmol) in THF (10 mL) was added titanium ethoxide (800 mg, 3.54 mmol). The mixture was stirred at reflux overnight. After cooling down, sodium borohydride (270 mg, 7.08 mmol) was added, and the mixture was stirred for another 3 h. After the reaction was completed, the mixture was diluted with H₂O (50 mL), and extracted with ethyl acetate (50 mL×3). The combined organic layers were dried and concentrated to give 2-methyl-N-((7-((trimethylsilyl)ethynyl)imidazo[1,5-a]pyridin-1-yl)methyl)propane-2-sulfinamide (500 mg, yield: 81%) as a yellow solid. ESI-MS [M+H]$^+$: 348.2.

Synthesis of N-((7-ethynylimidazo[1,5-a]pyridin-1-yl)methyl)-2-methylpropane-2-sulfinamide To a solution of 2-methyl-N-((7-((trimethylsilyl)ethynyl)imidazo[1,5-a]pyridin-1-yl)methyl)propane-2-sulfinamide (500 mg, 1.44 mmol) in DCM/MeOH (5/1, 6 mL) was added potassium hydroxide (162 mg, 2.88 mmol). The mixture was stirred at RT for 2 h, then diluted with H₂O (10 mL), and extracted with DCM (20 mL×3). The combined organic layers were washed with brine, dried, and concentrated to give N-((7-ethynylimidazo[1,5-a]pyridin-1-yl)methyl)-2-methylpropane-2-sulfinamide (380 mg crude, yield: 95%) which was used in the next step without further purification. ESI-MS [M+H]$^+$: 276.1.

Synthesis of (7-ethynylimidazo[1,5-a]pyridin-1-yl)methanamine

To a solution of N-((7-ethynylimidazo[1,5-a]pyridin-1-yl)methyl)-2-methylpropane-2-sulfinamide (380 mg, 1.32 mmol) in ethyl acetate (5 mL) was added hydrochloride in ethyl acetate (3 M, 10 mL). The mixture was stirred at RT for 3 h and then filtered to give the crude product which was washed with ethyl acetate and dried in vacuum to afford (7-ethynylimidazo[1,5-a]pyridin-1-yl)methanamine (270 mg, quant.) as a yellow solid. ESI-MS [M-NH₂]$^+$: 154.9. Purity: 99.1%. H NMR (400 MHz, DMSO) δ 8.99 (s, 1H), 8.63 (br, 3H), 8.47 (d, J=7.2 Hz, 1H), 8.22 (s, 1H), 8.86-8.84 (dd, J=3.6 Hz, 6.0 Hz, 1H), 4.48 (s, 1H), 4.37 (q, J=5.6 Hz, 2H).

Example 313

Scheme 310

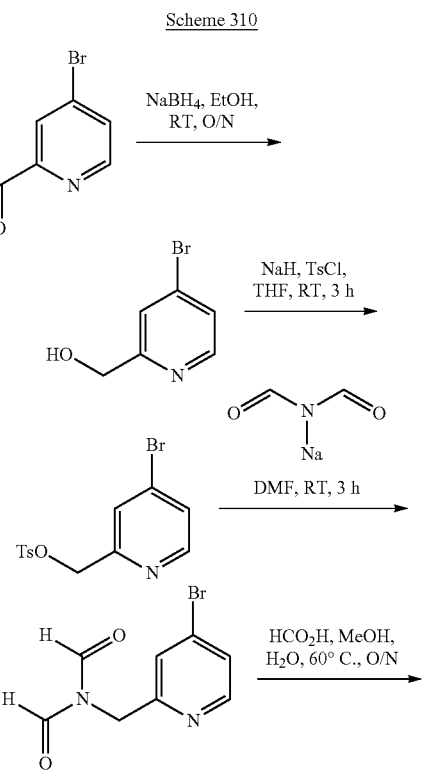

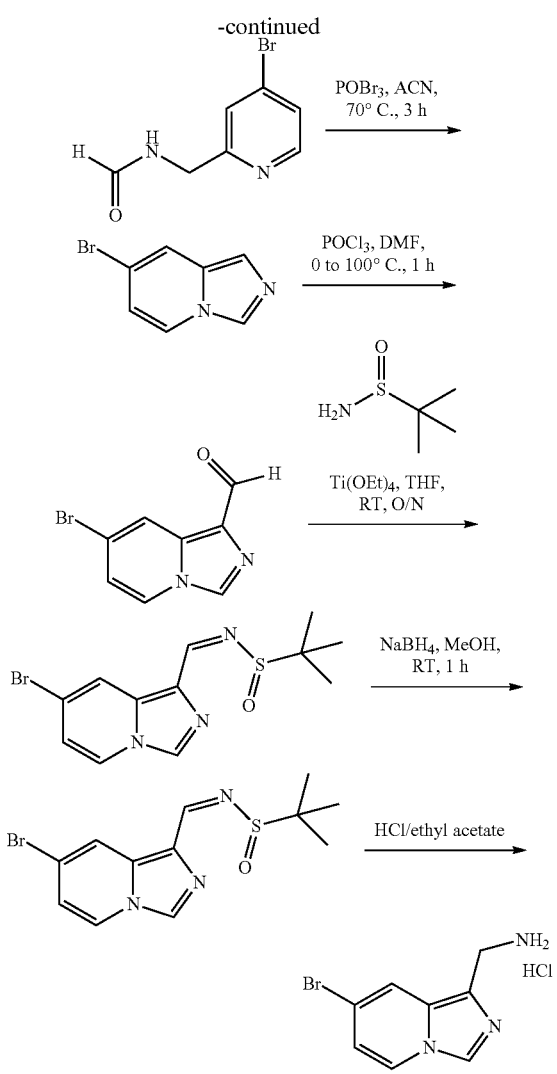

Synthesis of (4-bromopyridin-2-yl)methanol

A solution of methyl 4-bromopicolinate (30 g, 0.139 mol) in EtOH (150 mL) was cooled to 0° C. using ice-water bath. Sodium borohydride (11.61 g, 0.306 mol) was added slowly into the solution at 0° C. The resulting mixture was stirred at RT for 18 h and then quenched with acetone (50 mL). The resulting mixture was stirred for another 1 h. After removing the solvent, the residue was diluted with H$_2$O (100 mL) and extracted with ethyl acetate (200 mL×3). The combined organic layers were dried over anhydrous sodium sulfate, filtered, and concentrated to afford (4-bromopyridin-2-yl) methanol (24.4 g, crude) as a colorless oil. ESI-MS [M+H]$^+$: 188.0.

Synthesis of (4-bromopyridin-2-yl)methyl 4-methylbenzenesulfonate

A solution of (4-bromopyridin-2-yl)methanol (24.46 g, 0.13 mol) in THF (300 mL) was added sodium hydride (7.29 g, 0.183 mol, 60%) at 0° C. The resulting mixture was stirred at 0° C. for 1 h, and tosyl chloride (25.97 g, 0.137 mol) was added. After stirring for another 3 h, the reaction mixture was quenched with H$_2$O (50 mL), and extracted with ethyl acetate (120 mL×3), the combined organic layers were washed with brine, dried over anhydrous magnesium sulfate, filtered, and concentrated to afford (4-bromopyridin-2-yl) methyl 4-methylbenzenesulfonate (44.5 g, crude) as a brown oil, which was used directly in the next step without purification. ESI-MS [M+H]$^+$: 344.0.

Synthesis of N-((4-bromopyridin-2-yl)methyl)-N-formylformamide

To a solution of (4-bromopyridin-2-yl)methyl 4-methylbenzenesulfonate (44.5 g, crude, 0.13 mol) in DMF (100 mL) was added sodium diformamide (14.41 g, 0.136 mmol, 1.05 eq) at RT. The resulting reaction mixture was stirred for 3 h and concentrated in vacuum. The residue was washed with ethyl acetate three times. The combined organic layers were concentrated and the crude product was purified by silica gel column chromatography (petroleum ether/ethyl acetate=1/1) to afford N-((4-bromopyridin-2-yl)methyl)formamide (23.7 g, 70%). ESI-MS [M+H]$^+$: 244.1.

Synthesis of N-((4-bromopyridin-2-yl)methyl)formamide

To a solution of N-((4-bromopyridin-2-yl)methyl)formamide (17.6 g, 72.43 mmol) in MeOH (100 mL) was added H$_2$O (1.30 g, 72.43 mol) and formic acid (6.66 g, 144.86 mmol). The resulting mixture was stirred at 60° C. overnight, and then concentrated to afford N-((4-bromopyridin-2-yl)methyl)formamide (14.7 g, crude). ESI-MS [M+H]$^+$: 217.0.

Synthesis of 7-bromoimidazo[1,5-a]pyridine

To a solution of N-((4-bromopyridin-2-yl)methyl)formamide (10.0 g, 46.5 mmol) in dry acetonitrile (200 mL) was added phosphorus oxybromide (20 g, 69.75 mmol, 1.5 eq) and the resulting mixture was stirred at reflux for 2 h. After the reaction was complete, the reaction mixture was cooled down to RT and poured into H$_2$O (200 mL). The pH of the solution was adjusted to 8 with saturated aqueous sodium bicarbonate. The solution was extracted with ethyl acetate (200 mL×3). The combined organic phases were washed with brine and dried over sodium sulfate, filtered, and concentrated in vacuo to afford a residue. This residue was purified by silica gel chromatography (ethyl acetate) to afford 7-bromoimidazo[1,5-a]pyridine (7.5 g, 82%) as a yellow solid. ESI-MS [M+H]$^+$: 197.0.

Synthesis of 7-bromoimidazo[1,5-a]pyridine-1-carbaldehyde

A solution of 7-bromoimidazo[1,5-a]pyridine (7.5 g, 38.1 mmol) in dry DMF (10 mL) was cooled with ice bath to 0-5° C. Phosphorus oxychloride (8.76 g, 57.1 mmol, 1.5 eq) was added dropwise at this temperature, and then the reaction mixture was subsequently stirred at 100° C. for 2 h. After the reaction was completed, the reaction mixture was cooled to RT and poured into saturated aqueous sodium bicarbonate (200 mL) and kept stirring for another 2 h. The solution was extracted with ethyl acetate (200 mL×3). The combined organic phases were washed with brine, dried over sodium sulfate, filtered, and concentrated in vacuum to afford a residue which was purified by silica gel chromatography (petroleum ether/ethyl acetate=1/1) to afford 7-bromoimidazo[1,5-a]pyridine-1-carbaldehyde (5.5 g, 64%) as a yellow solid. ESI-MS [M+H]+: 224.9.

Synthesis of (E)-N-((7-bromoimidazo[1,5-a]pyridin-1-yl)methylene)-2-methylpropane-2-sulfinamide To a solution of 7-bromoimidazo[1,5-a]pyridine-1-carbaldehyde (4.3 g, 19.1 mmol) and 2-methylpropane-2-sulfinamide (2.36 g, 19.49 mmol) in THF (50 mL) was added titanium ethoxide (8.7 g, 38.21 mmol). The resulting mixture was stirred at reflux overnight. After the reaction was completion, the mixture was concentrated and the residue was purified by column chromatography (ethyl acetate) to give (E)-N-((7-bromoimidazo[1,5-a]pyridin-1-yl)methylene)-2-methylpropane-2-sulfinamide (5.7 g, 91%) as a yellow solid. ESI-MS [M+H]+: 327.9.

Synthesis of N-((7-bromoimidazo[1,5-a]pyridin-1-yl)methylene)-2-methylpropane-2-sulfinamide To a solution of N-((7-bromoimidazo[1,5-a]pyridin-1-yl)methylene)-2-methylpropane-2-sulfinamide (5.7 g, 17.26 mmol) in MeOH (50 mL) was added sodium borohydride (1.97 g, 51.78 mmol) slowly. The resulting mixture was stirred at RT for 3 h. The mixture was concentrated to afford a residue, which was diluted with 50 mL H₂O and extracted with ethyl acetate (200 mL×2). After washing with brine, the combined organic layers were dried over anhydrous sodium sulfate, filtered, and concentrated in vacuum to afford N-((7-bromoimidazo[1,5-a]pyridin-1-yl)methylene)-2-methylpropane-2-sulfinamide (5.6 g, 98%) as a white solid. ESI-MS [M+H]+: 330.0.

Synthesis of (7-bromoimidazo[1,5-a]pyridin-1-yl)methanamine hydrochloride acid salt To a solution of N-((7-bromoimidazo[1,5-a]pyridin-1-yl)methylene)-2-methylpropane-2-sulfinamide (5.6 g, 16.96 mmol) in ethyl acetate (30 mL) was added the solution of hydrochloride in ethyl acetate (3 M, 20 mL). The resulting mixture was stirred at RT for 3 h and then filtered to give the crude product, which was washed with ethyl acetate and dried in vacuum to afford (7-bromoimidazo[1,5-a]pyridin-1-yl)methanaminehydrochloride acid salt (3.9 g, quant.) as a white solid. ESI-MS [M-NH₂]+: 208.8. Purity: 98.5%. ¹H NMR (400 MHz, DMSO) δ 8.99 (s, 1H), 8.62 (br, 3H), 8.46 (d, J=7.2 Hz, 1H), 8.37 (s, 1H), 7.02 (dd, J=1.6, 7.2 Hz, 1H), 4.34 (q, J=5.6 Hz, 2H).

Example 314

Scheme 311

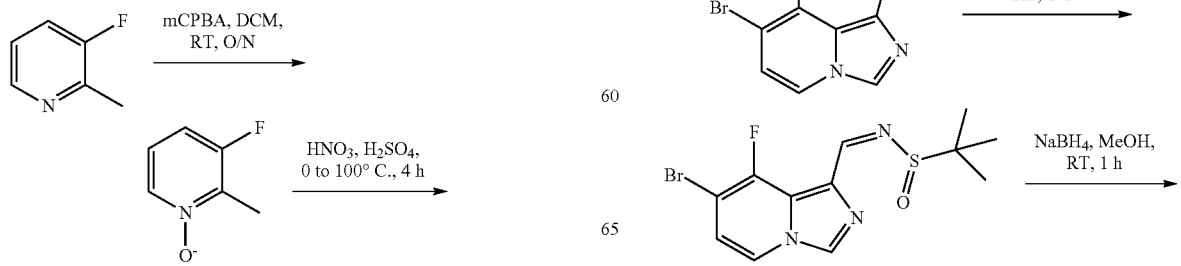

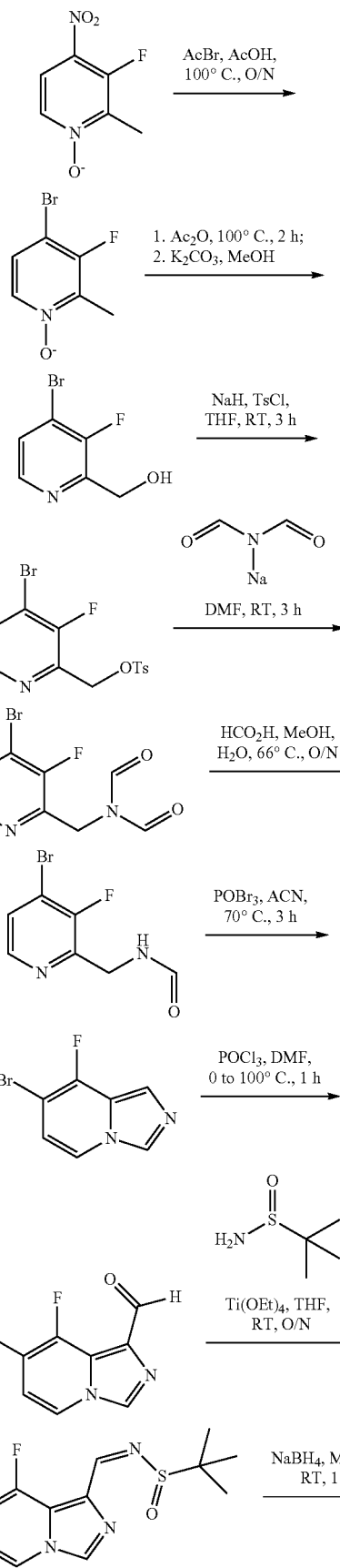

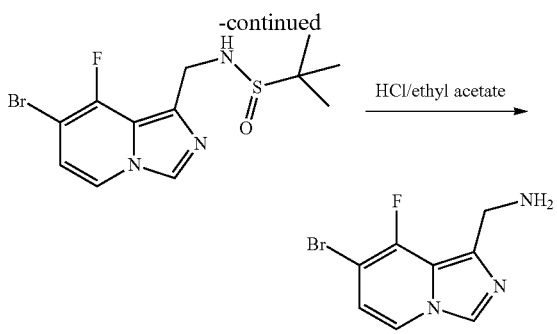

Synthesis of 3-fluoro-2-methylpyridine 1-oxide

To a solution of 3-fluoro-2-methylpyridine (5 g, 45.05 mmol) in dry DCM (150 mL) was added m-chloroperbenzoic acid (9.3 g, 54.05 mmol). The mixture was stirred at RT for 16 h and the precipitate was filtered off. The filtrate was evaporated to dryness and the residue was purified by silica gel chromatography (DCM/MeOH=20/1) to give 3-fluoro-2-methylpyridine 1-oxide (4.2 g, 73%) as a yellow solid. ESI-MS [M+H]$^+$: 128.1.

Synthesis of 3-fluoro-2-methyl-4-nitropyridine 1-oxide

Fuming nitric acid (10 mL) was added dropwise to a solution of 2-methyl-3-fluoropyridine-N-oxide (4.2 g, 33.07 mmol) in concentrated sulphuric acid (30 mL) at 0° C. The solution was stirred at RT for 1.5 h and then for 2 h at 100° C. After cooling, the mixture was poured onto ice and extracted with ethyl acetate (50 mL×3). The combined organic layers were washed with saturated sodium bicarbonate solution. After drying, the extracts were evaporated and purified by silica gel chromatography (DCM/MeOH=20/1) to give 2-methyl-3-fluoro-4-nitropyridine-N-oxide (4.6 g, yield: 81%) as a yellow solid. ESI-MS [M+H]$^+$: 173.1.

Synthesis of 4-bromo-3-fluoro-2-methylpyridine 1-oxide

To a solution of 2-methyl-3-fluoro-4-nitropyridine-N-oxide (4.4 g, 25.58 mmol) in acetic acid (50 mL) was added acetyl bromide (15.7 g, 128 mmol). The mixture was stirred at 100° C. overnight and then concentrated. The residue was diluted with H$_2$O (100 mL) and extracted with ethyl acetate (50 mL×3). The combined organic layers were washed with saturated sodium bicarbonate solution, brine, dried, evaporated, and then purified by silica gel chromatography (DCM/MeOH=20/1) to afford 4-bromo-3-fluoro-2-methylpyridine 1-oxide (4, 3.6 g, yield: 65%) as a white solid. ESI-MS [M+H]$^+$: 206.0, 208.0.

Synthesis of (4-bromo-3-fluoropyridin-2-yl)methanol

A solution of 4-bromo-3-fluoro-2-methylpyridine 1-oxide (3.4 g, 16.5 mmol) in acetic anhydride (50 mL) was stirred at 100° C. for 2 h. After removal of the solvent, the residue was dissolved in MeOH (100 mL) and potassium carbonate (4.6 g, 33 mmol) was added. The mixture was stirred at RT for 2 h. The mixture was diluted with H$_2$O and extracted with ethyl acetate (30 mL×3). The combined organic layers were washed with brine, dried, evaporated, and then purified by silica gel chromatography (petroleum ether/ethyl acetate=1/1) to afford (4-bromo-3-fluoropyridin-2-yl)methanol (1.6 g, yield: 44%) as a yellow solid. ESI-MS [M+H]$^+$: 206.0, 208.0.

Synthesis of (4-bromo-3-fluoropyridin-2-yl)methyl 4-methylbenzenesulfonate

To a solution of (4-bromo-3-fluoropyridin-2-yl)methanol (1.4 g, 6.8 mmol) in THF (50 mL) was added sodium hydride (326 mg, 8.16 mmol, 60%) in portions at 0° C. The mixture was stirred for 1 h, and tosyl chloride (1.3 g, 6.8 mmol) was added. After stirring at RT for another 3 h, the reaction was quenched with H$_2$O (50 mL), and the mixture was extracted with ethyl acetate (20 mL×3). The combined organic layers were washed with brine, dried over anhydrous magnesium sulphate, filtered, and concentrated to afford (4-bromo-3-fluoropyridin-2-yl)methyl 4-methylbenzenesulfonate (2.4 g, crude) as a yellow oil which was used in the next step without purification. ESI-MS [M+H]$^+$: 360.0.

Synthesis of N-((4-bromo-3-fluoropyridin-2-yl)methyl)-N-formylformamide

To a solution of (4-bromo-3-fluoropyridin-2-yl)methyl 4-methylbenzenesulfonate (2.4 g, crude, 6.67 mmol) in DMF (30 mL) was added sodium diformamide (950 mg, 10 mmol) at RT. The mixture was stirred for 3 h and concentrated in vacuum. The residue was washed with ethyl acetate three times. The combined filterate was concentrated to afford crude N-((4-bromo-3-fluoropyridin-2-yl)methyl)-N-formylformamide (1.6 g crude, yield: 92%) as yellow oil, which was used in the next step without further purification. ESI-MS [M+H]$^+$: 261.0.

Synthesis of N-((4-bromo-3-fluoropyridin-2-yl)methyl)formamide

To a solution of N-((4-bromo-3-fluoropyridin-2-yl)methyl)-N-formylformamide (1.6 g, 6.15 mmol) in MeOH (50 mL) was added H$_2$O (110 mg, 6.15 mmol) and formic acid (566 mg, 12.3 mmol) added at RT. The mixture was stirred at 60° C. overnight and then concentrated. The residue was purified by silica gel chromatography (ethyl acetate in petroleum ether, 0 to 100%) to afford to afford N-((4-bromo-3-fluoropyridin-2-yl)methyl)formamide (1.1 g, yield: 77%) as an off-white solid. ESI-MS [M+H]$^+$: 233.0.

Synthesis of 7-bromo-8-fluoroimidazo[1,5-a]pyridine

To a solution of N-((4-bromo-3-fluoropyridin-2-yl)methyl)formamide (1.1 g, 4.72 mmol) in dry acetonitrile (50 mL) was added phosphorus oxybromide (2.03 g, 7.08 mmol). The resulting he reaction mixture was stirred at reflux for 2 h. After cooling down, the mixture was poured onto H$_2$O (200 mL). The pH of the mixture was adjusted to 8 with aqueous saturated sodium bicarbonate and then extracted with ethyl acetate (30 mL×3). The combined organic phases were washed with brine and dried over sodium sulphate, filtered and concentrated in vacuum. The residue was purified by silica gel chromatography (ethyl acetate) to afford 7-bromo-8-fluoroimidazo[1,5-a]pyridine (950 mg, yield: 94%) as a yellow solid. ESI-MS [M+H]$^+$: 215.0.

Synthesis of 7-bromo-8-fluoroimidazo[1,5-a]pyridine-1-carbaldehyde

A solution of 7-bromo-8-fluoroimidazo[1,5-a]pyridine (944 mg, 4.39 mmol) in dry DMF (3 mL) was cooled in an ice bath to 0-5° C. Phosphorus oxychloride (950 mg, 6.62 mmol) was added dropwise at 0-5° C. and the reaction mixture is subsequently stirred at 100° C. over 2 h. The reaction mixture was cooled and poured onto saturated sodium bicarbonate aqueous (50 mL) and kept stirring for another 2 h and extracted with ethyl acetate (30 mL×3). The combined organic phases were washed with brine and dried over sodium sulphate, filtered, and concentrated in vacuum. The residue was purified by silica gel chromatography (petroleum ether/ethyl acetate=0 to 100%) to afford 7-bromo-8-fluoroimidazo[1,5-a]pyridine-1-carbaldehyde (550 mg, yield: 51%) as a yellow solid. ESI-MS [M+H]$^+$: 245.0.

Synthesis of N-((7-bromo-8-fluoroimidazo[1,5-a]pyridin-1-yl)methylene)-2-methylpropane-2-sulfinamide To a solution of 7-bromo-8-fluoroimidazo[1,5-a]pyridine-1-carbaldehyde (300 mg, 1.24 mmol) and 2-methylpropane-2-sulfinamide (182 mg, 1.49 mmol) in THF (30 mL) was added titanium(IV) ethoxide (565 mg, 2.48 mmol). The mixture was stirred at reflux overnight. The mixture was concentrated and the residue was purified by column chromatography (ethyl acetate) to give N-((7-bromo-8-fluoroimidazo[1,5-a]pyridin-1-yl)methylene)-2-methylpropane-2-sulfinamide (380 mg, yield: 89%) as a yellow solid. ESI-MS [M+H]$^+$: 346.0.

Synthesis of N-((7-bromo-8-fluoroimidazo[1,5-a]pyridin-1-yl)methyl)-2-methylpropane-2-sulfinamide To a solution of N-((7-bromo-8-fluoroimidazo[1,5-a]pyridin-1-yl)methylene)-2-methylpropane-2-sulfinamide (380 mg, 1.1 mmol) in MeOH (30 mL) was added sodium borohydride (126 mg, 3.3 mmol) slowly. The mixture was stirred at RT for 3 h. The mixture was concentrated and the residues were diluted with 50 mL of H$_2$O and extracted with ethyl acetate (30 mL×3). The combined organic layers were washed with brine, dried over anhydrous sodium sulphate, filtered, and concentrated in vacuum to afford N-((7-bromo-8-fluoroimidazo[1,5-a]pyridin-1-yl)methyl)-2-methylpropane-2-sulfinamide (345 mg, yield: 89%) as a white solid. ESI-MS [M+H]$^+$: 348.0.

Synthesis of (7-bromo-8-fluoroimidazo[1,5-a]pyridin-1-yl)methanamine

To a solution of N-((7-bromo-8-fluoroimidazo[1,5-a]pyridin-1-yl)methyl)-2-methylpropane-2-sulfinamide (340 mg, 0.98 mmol) in ethyl acetate (20 mL) was added hydrochloride in ethyl acetate (3 M, 20 mL). The mixture was stirred at RT for 3 h and then filtered to give the crude product which was washed with ethyl acetate and dried in vacuum to afford (7-bromo-8-fluoroimidazo[1,5-a]pyridin-1-yl)methanamine hydrochloride salt (270 mg, quant.) as a white solid. ESI-MS [M-NH$_2$]$^+$: 227.8. Purity: 95.8%. $^1$H NMR (400 MHz, DMSO) δ 8.65 (s, 1H), 8.44 (br, 3H), 8.25 (d, J=7.2 Hz, 1H), 6.95 (t, J=6.8 Hz, 1H), 4.24 (q, J=5.6 Hz, 2H).

Example 315

Scheme 312

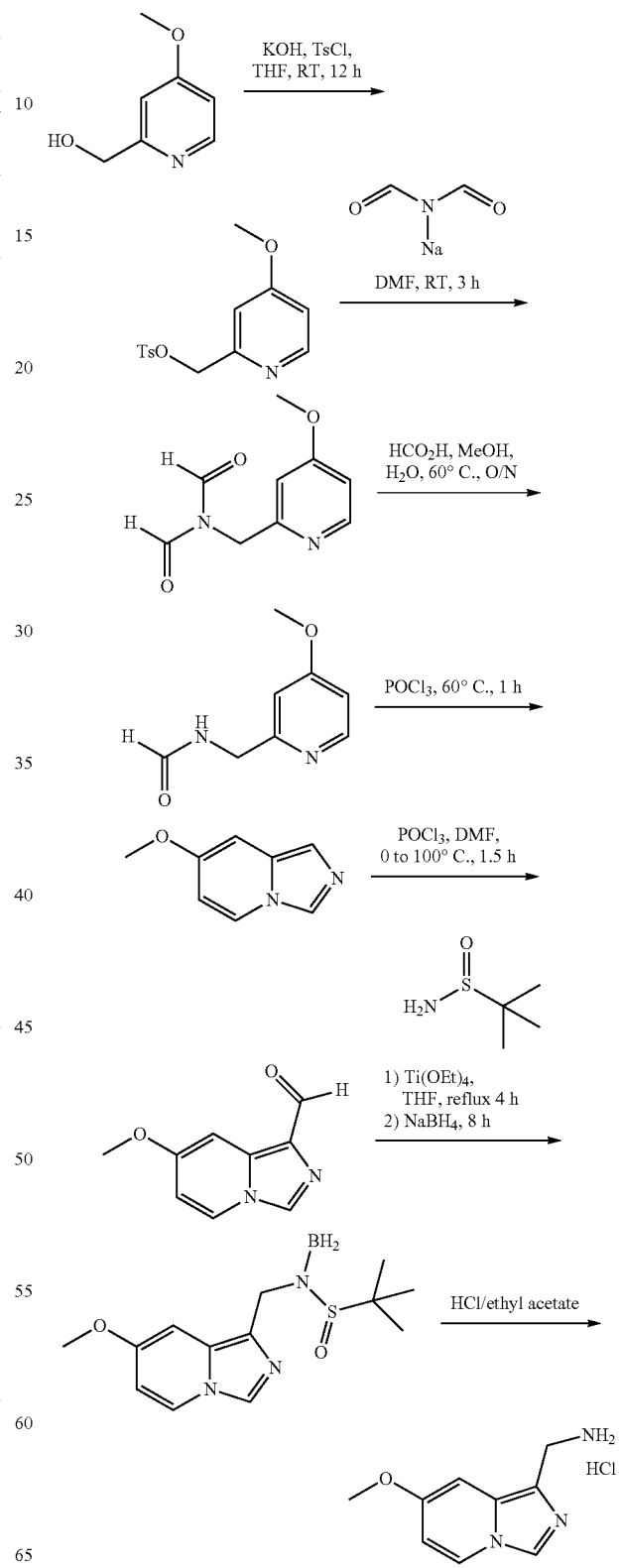

Synthesis of (4-methoxypyridin-2-yl)methyl 4-methylbenzenesulfonate

To a solution of (4-methoxypyridin-2-yl)methanol (10 g, 71.86 mmol) in THF (300 mL) was added potassium hydroxide (6.05 g, 107.8 mmol) followed by tosyl chloride (16.45 g, 86.24 mmol) at 0° C. the reaction mixture was warmed to RT with stirring for 12 h, and filtered with Celite. The filtrate was concentrated to afford (4-methoxypyridin-2-yl)methyl 4-methylbenzenesulfonate (21.0 g, crude) as a yellow oil which was used in the next step without purification. ESI-MS [M+H]$^+$: 294.0.

Synthesis of N-formyl-N-((4-methoxypyridin-2-yl)methyl)formamide

To a solution of (4-methoxypyridin-2-yl)methyl 4-methylbenzenesulfonate (21.0 g, crude, 71.86 mmol) in DMF (300 mL) was added sodium diformamide (8.2 g, 86.23 mmol, 1.2 eq) at RT. The mixture was stirred for 3 h and the solvent was removed, 50 mL of H$_2$O was added, and then extracted with ethyl acetate (50 mL×6). The combined organic layers were dried over anhydrous magnesium sulphate, filtered, and concentrated to afford N-formyl-N-((4-methoxypyridin-2-yl)methyl)formamide (12.0 g, crude) as brown oil which was used in the next step without purification. ESI-MS [M+H]$^+$: 194.1.

Synthesis of N-((4-methoxypyridin-2-yl)methyl)formamide

To a solution of N-formyl-N-((4-methoxypyridin-2-yl)methyl)formamide (12 g, crude, 61.85 mmol) in MeOH (150 mL) was added H$_2$O (1 mL) and formic acid (3 mL) added at RT. The mixture was stirred at 60° C. overnight and then concentrated to afford N-((4-methoxypyridin-2-yl)methyl)formamide (10.0 g, crude). ESI-MS [M+H]$^+$: 167.0.

Synthesis of 7-methoxyimidazo[1,5-a]pyridine

A mixture of N-((4-methoxypyridin-2-yl)methyl)formamide (10.0 g, 60.2 mmol) and phosphoryl trichloride (50 mL) was stirred at 60° C. for 1 h. After cooling down, the solvent was removed and the pH of the mixture was adjusted to 8 with saturated aqueous sodium bicarbonate and then extracted with ethyl acetate (100 mL×3). The combined organic phases were dried over sodium sulphate, filtered, and concentrated in vacuo. The residue was purified by silica gel chromatography (petroleum ether/ethyl acetate=1/1) to afford 7-methoxyimidazo[1,5-a]pyridine (2.37 g, yield: 27%) as a yellow oil. ESI-MS [M+H]$^+$: 149.0.

Synthesis of 7-methoxyimidazo[1,5-a]pyridine-1-carbaldehyde

A solution of 7-methoxyimidazo[1,5-a]pyridine (2.37 g, 16.02 mmol) in dry DMF (10 mL) was cooled in an ice bath to 0° C. Phosphorus oxychloride (3.68 g, 24.02 mmol, 1.5 eq) was added dropwise at 0° C. and the reaction mixture is subsequently stirred at 100° C. over 1.5 h. After cooling down, the solvent was removed and the pH of the mixture was adjusted to 8 with saturated sodium bicarbonate aqueous and then extracted with ethyl acetate (50 mL×3). The combined organic phases were dried over sodium sulphate, filtered and concentrated in vacuo. The residue was purified by silica gel chromatography (petroleum ether/ethyl acetate=1/1) to afford 7-methoxyimidazo[1,5-a]pyridine-1-carbaldehyde (727 mg, yield: 26%) as a yellow solid. ESI-MS [M+H]$^+$: 177.1.

Synthesis of N-boryl-N-((7-methoxyimidazo[1,5-a]pyridin-1-yl)methyl)-2-methylpropane-2-sulfinamide To a solution of 7-methoxyimidazo[1,5-a]pyridine-1-carbaldehyde (727 mg, 4.13 mmol) in THF (10 mL) was added 2-methylpropane-2-sulfinamide (525 mg, 4.34 mmol) and tetraethoxytitanium (Ti(OEt)$_4$, 2.83 g, 12.391 mmol). The mixture was stirred at reflux for 4 h. After cooling down, sodium borohydride (471 mg, 12.39 mmol) was added slowly and the mixture was stirred at RT for 8 h. 30 mL of H$_2$O was added to the mixture, and the mixture was extracted with ethyl acetate (30 mL×3). The combined organic layers were dried over anhydrous sodium sulphate, filtered and concentrated in vacuum. The residue was purified by silica gel chromatography (petroleum ether/ethyl acetate=1/1) to afford N-boryl-N-((7-methoxyimidazo[1,5-a]pyridin-1-yl)methyl)-2-methylpropane-2-sulfinamide (1.12 g, yield: 93%) as a yellow solid. ESI-MS [M+H]$^+$: 294.1.

Synthesis of (7-methoxyimidazo[1,5-a]pyridin-1-yl)methanamine

A mixture of N-boryl-N-((7-methoxyimidazo[1,5-a]pyridin-1-yl)methyl)-2-methylpropane-2-sulfinamide (720 mg, 2.45 mmol) and hydrochloride in ethyl acetate (3 M, 10 mL) was stirred at RT for 4 h and then filtered to give the crude product which was washed with ethyl acetate and dried in vacuum to afford (7-methoxyimidazo[1,5-a]pyridin-1-yl)methanamine (500.5 mg, yield: 95%) as a white solid. ESI-MS [M-NH$_2$]$^+$: 161.1. Purity: 97.4%. $^1$H NMR (400 MHz, DMSO) δ 9.30 (s, 1H), 8.81 (br, 3H), 8.49 (d, J=7.6 Hz, 1H), 7.56 (d, J=2.4 Hz, 1H), 6.84 (dd, J=7.6, 2.4 Hz, 1H), 4.41 (q, J=5.6 Hz, 2H), 3.88 (s, 3H).

Example 316

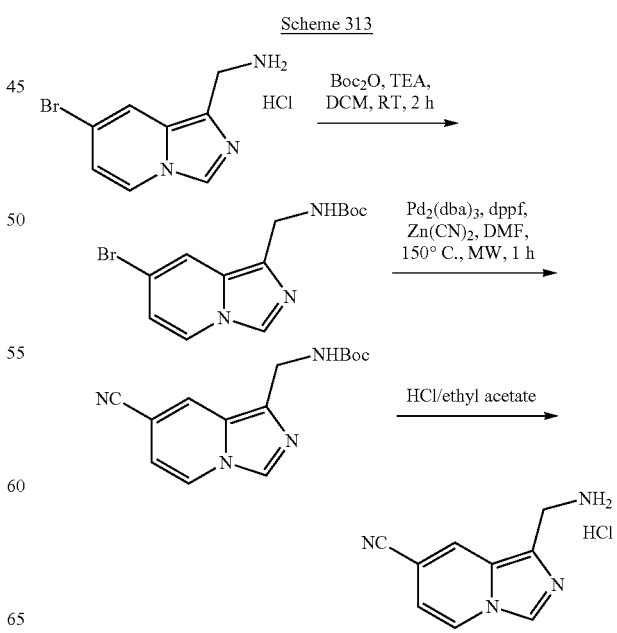

Scheme 313

Synthesis of tert-butyl ((7-bromoimidazo[1,5-a]pyridin-1-yl)methyl)carbamate To a solution of (7-bromoimidazo[1,5-a]pyridin-1-yl)methanamine hydrochloride salt (2 g, 7.66 mmol) in DCM (30 mL) was added triethylamine (4.3 mL, 30.6 mmol) and di-tert-butyl dicarbonate (3.5 mL, 15.3 mmol). The mixture was stirred at RT for 2 h. TLC showed that the reaction was completed. The mixture was concentrated, dissolved in ethyl acetate, washed with saturated ammonium chloride. The organic layer was concentrated, purified by column chromatography (DCM/MeOH=10/1) to give tert-butyl ((7-bromoimidazo[1,5-a]pyridin-1-yl)methyl)carbamate (2 g, yield: 80%) as a yellow oil. ESI-MS [M+H]$^+$: 326.1.

Synthesis of tert-butyl ((7-cyanoimidazo[1,5-a]pyridin-1-yl)methyl)carbamate To a solution of tert-butyl ((7-bromoimidazo[1,5-a]pyridin-1-yl)methyl)carbamate (200 mg, 0.615 mmol) in DMF (3 mL) was added 1,1'-bis(diphenylphosphino)ferrocene (64 mg, 0.12 mmol), tris(dibenzylideneacetone)dipalladium (Pd$_2$(dba)$_3$, 55 mg, 0.06 mmol) and zinc cyanide (144 mg, 1.23 mmol). The mixture was stirred at 150° C. in microwave reactor for 1 h and concentrated. The residue was purified by column chromatography (DCM/MeOH=10/1) to give tert-butyl ((7-cyanoimidazo[1,5-a]pyridin-1-yl)methyl)carbamate (117 mg, yield: 70%) as a yellow oil. ESI-MS [M+H]$^+$: 273.1.

Synthesis of 1-(aminomethyl)imidazo[1,5-a]pyridine-7-carbonitrile

A mixture of tert-butyl ((7-cyanoimidazo[1,5-a]pyridin-1-yl)methyl)carbamate (270 mg, 0.99 mmol) and hydrochloride in ethyl acetate (3 M, 20 mL) was stirred at RT for 2 h and then filtered to give the crude product which was washed with ethyl acetate and dried in vacuum to afford 1-(aminomethyl)imidazo[1,5-a]pyridine-7-carbonitrile (201.3 mg, quant.) as a yellow solid. ESI-MS [M–NH$_2$]$^+$: 156.0. Purity: 96.3%.

What is claimed is:

1. A method of treating diabetic macular edema comprising administering to a patient in need thereof a compound of Formula (I):

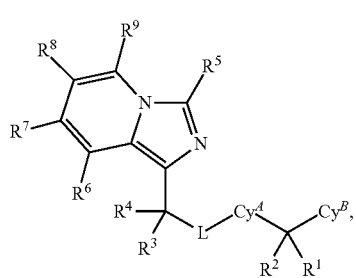

(I)

or a pharmaceutically acceptable salt thereof, wherein:

Cy$^A$ is selected from 3- to 7-membered saturated or partially unsaturated monocyclic heterocyclene having 1-2 heteroatoms selected from oxygen, nitrogen, and sulfur, 5- to 6-membered heteroarylene having 1-4 heteroatoms selected from oxygen, nitrogen, and sulfur, 7- to 10-membered saturated or partially unsaturated bicyclic heterocyclylene having 1-4 heteroatoms selected from oxygen, nitrogen, and sulfur, and 7- to 10-membered bicyclic heteroarylene having 1-4 heteroatoms selected from oxygen, nitrogen, and sulfur, wherein Cy$^A$ is substituted with 0-4 R$^A$ groups;

each R$^A$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

Cy$^B$ is selected from 3- to 7-membered saturated or partially unsaturated monocyclic heterocyclyl having 1-2 heteroatoms selected from oxygen, nitrogen, and sulfur, 5- to 6-membered heteroaryl having 1-4 heteroatoms selected from oxygen, nitrogen, and sulfur, 7- to 10-membered saturated or partially unsaturated bicyclic heterocyclyl having 1-5 heteroatoms selected from oxygen, nitrogen, and sulfur, and 7- to 10-membered bicyclic heteroaryl having 1-5 heteroatoms selected from oxygen, nitrogen, and sulfur, wherein Cy$^B$ is substituted with 0-5 R$^B$ groups;

each R$^B$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, and sulfur, 3- to -to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

L is selected from -QC(R)$_2$—, —C(R)$_2$Q-, -QC(Q)-, —C(Q)Q-, —C(R)$_2$QC(O)-, and —C(O)QC(R)$_2$—, wherein each Q is independently a monovalent or divalent group as valency allows, selected from the group consisting of O, N(R), and (S);

R$^1$, R$^2$, R$^3$, and R$^4$ are independently selected from hydrogen and C$_{1-6}$ aliphatic;

R$^5$, R$^6$, R$^7$, R$^8$, and R$^9$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur; and each R is independently hydrogen, —CN, or an optionally substituted group selected from C$_{1-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, and sulfur, and 5- to 6-membered heteroaryl having 1-4 heteroatoms selected from oxygen, nitrogen, and sulfur;

with the proviso that the compound is other than N-((7-chloroimidazo[1,5-a]pyridin-1-yl)methyl)-2-(3-chloroquinolin-6-yl)methyl)isonicotinamide.

2. The method of claim 1, wherein the compound is of Formula (IV):

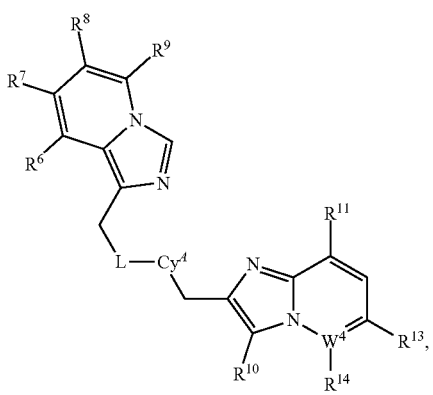

IV or a pharmaceutically acceptable salt thereof, wherein:

$Cy^4$ is a 5-membered heteroarylene having 1-4 heteroatoms selected from oxygen and nitrogen, wherein $Cy^4$ is substituted with 0-3 $R^4$ groups;

L is selected from —NC(O)— and —C(O)N—;

$R^6$, $R^8$, and $R^9$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

$R^7$ is —F, —Cl, or —Br;

$W^4$ is carbon or nitrogen;

$R^{10}$ and $R^{11}$ are each optionally present, and if present are independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

$R^{13}$ is selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{2-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

$R^{14}$ is optionally present, and if present and is selected from halogen, —CN, —C(R)=N(R), —C(O)R, —C(O)$_2$R, —C(O)N(R)$_2$, —NO$_2$, —N(R)—N(R)$_2$, —N(R)C(O)R, —N(R)C(O)$_2$R, —N(R)C(O)N(R)$_2$, —N(R)S(O)$_2$R, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{3-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur; and each R is independently hydrogen, —CN, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, and sulfur, and 5- to 6-membered heteroaryl having 1-4 heteroatoms selected from oxygen, nitrogen, and sulfur.

3. The method of claim 1, wherein the compound is of Formula (V):

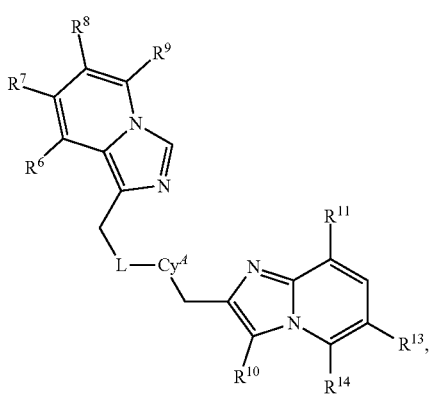

V or a pharmaceutically acceptable salt thereof,
wherein:
Cy$^A$ is a 5-membered heteroarylene having 1-4 nitrogens, wherein when Cy$^A$ comprises 3 nitrogens, Cy$^A$ is not

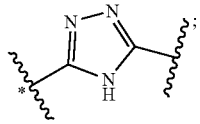 [SMILES: *c1nnc(*)[nH]1]

L is selected from —NC(O)— and —C(O)N—;

R$^6$, R$^8$, and R$^9$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

R$^7$ is —F, —Cl, or —Br;

R$^{10}$ is optionally present, and if present is selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

R$^{11}$ is optionally present, and if present is selected from halogen, —CN, —C(R)=N(R), —C(O)R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, and sulfur, 3- to to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

R$^{13}$ is selected from —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from phenyl, 5- to 6-membered heteroaryl having 1-4 heteroatoms selected from oxygen, nitrogen, and sulfur, 3- or 5-7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

R$^{14}$ is optionally present, and if present and is selected from halogen, —CN, —C(R)=N(R), —C(O)R, —C(O)$_2$R, —C(O)N(R)$_2$, —NO$_2$, —N(R)—N(R)$_2$, —N(R)C(O)R, —N(R)C(O)$_2$R, —N(R)C(O)N(R)$_2$, —N(R)S(O)$_2$R, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{3-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur; and each R is independently hydrogen, —CN, or an optionally substituted group selected from C$_{1-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, and sulfur, and 5- to 6-membered heteroaryl having 1-4 heteroatoms selected from oxygen, nitrogen, and sulfur.

4. The method of claim 1, wherein L is selected from the group consisting of:

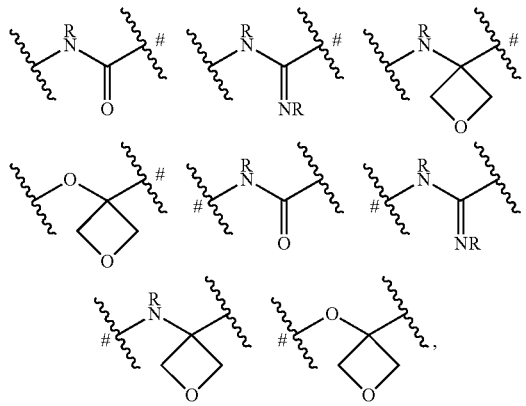

wherein # represents to point of attachment to Cy$^A$.

5. The method of claim 1, wherein the compound is of Formula (II):

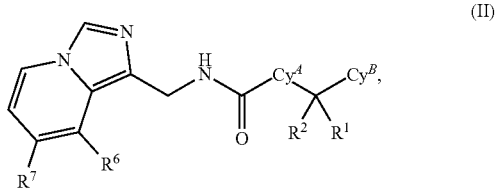

(II)

or a pharmaceutically acceptable salt thereof,
wherein:

Cy$^A$ is selected from 3- to 7-membered saturated or partially unsaturated monocyclic heterocyclylene having 1-2 heteroatoms selected from oxygen, nitrogen, and sulfur, 5- to 6-membered heteroarylene having 1-4 heteroatoms selected from oxygen, nitrogen, and sulfur, 7- to 10-membered saturated or partially unsaturated bicyclic heterocyclylene having 1-4 heteroatoms selected from oxygen, nitrogen, and sulfur, and 7- to 10-membered bicyclic heteroarylene having 1-4 heteroatoms selected from oxygen, nitrogen, and sulfur, wherein Cy$^A$ is substituted with 0-4 R$^A$ groups;

each R$^A$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, and sulfur, 3- to to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

Cy$^B$ is selected from 3- to 7-membered saturated or partially unsaturated monocyclic heterocyclyl having 1-2 heteroatoms selected from oxygen, nitrogen, and sulfur, 5- to 6-membered heteroaryl having 1-4 heteroatoms selected from oxygen, nitrogen, and sulfur, 7- to to 10-membered saturated or partially unsaturated bicyclic heterocyclyl having 1-5 heteroatoms selected from oxygen, nitrogen, and sulfur, and 7- to 10-membered bicyclic heteroaryl having 1-5 heteroatoms selected from oxygen, nitrogen, and sulfur, wherein Cy$^B$ is substituted with 0-5 R$^B$ groups;

each R$^B$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, and sulfur, 3- to to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

R$^1$ and R$^2$ are independently selected from hydrogen and C$_{1-6}$ aliphatic;

R$^6$ and R$^7$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur; and each R is independently hydrogen, —CN, or an optionally substituted group selected from C$_{1-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, and sulfur, and 5- to 6-membered heteroaryl having 1-4 heteroatoms selected from oxygen, nitrogen, and sulfur;

with the proviso that the compound is other than N-((7-chloroimidazo[1,5-a]pyridin-1-yl)methyl)-2-(3-chloroquinolin-6-yl)methyl)isonicotinamide.

6. The method of claim 1, wherein Cy$^A$ is selected from 5- to 6-membered heteroaryl having 1-4 heteroatoms selected from oxygen, nitrogen, and sulfur, and 7- to to 10-membered bicyclic heteroaryl having 1-4 heteroatoms selected from oxygen, nitrogen, and sulfur wherein Cy$^A$ is substituted with 0-4 R$^A$ groups.

7. The method of claim 1, wherein Cy$^A$ is a 5-membered heteroarylene having 1-4 heteroatoms selected from oxygen, nitrogen, and sulfur, wherein Cy$^A$ is substituted with 0-2 R$^A$ groups.

8. The method of claim 1, wherein Cy$^A$ is selected from the group consisting of:

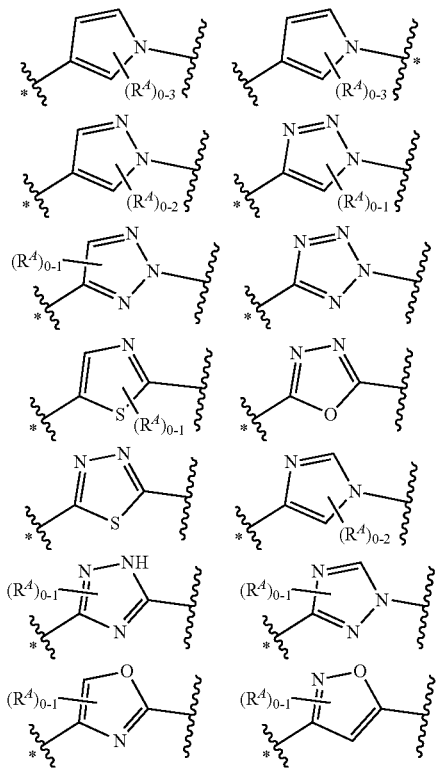

-continued

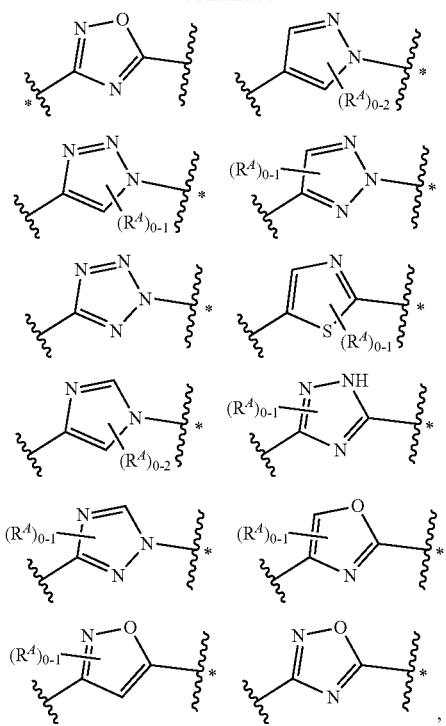

wherein * represents to point of attachment to L.

9. The method of claim 1, wherein the compound is of Formula (III-a) through (III-d):

(III-a)

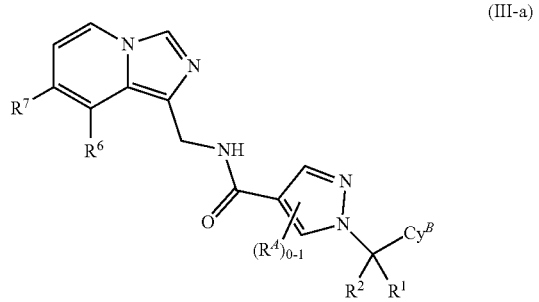

(III-b)

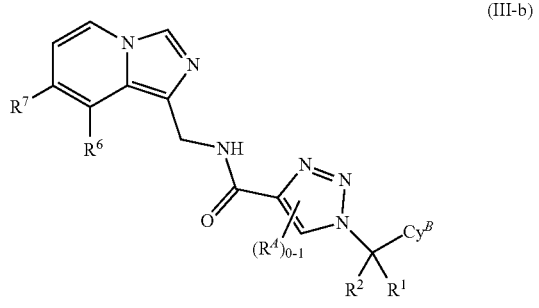

-continued (III-c)

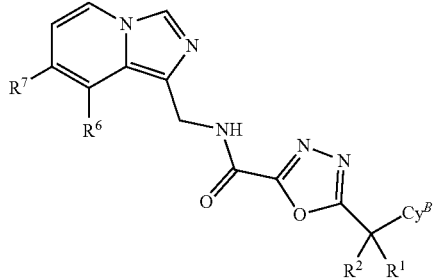

(III-d)

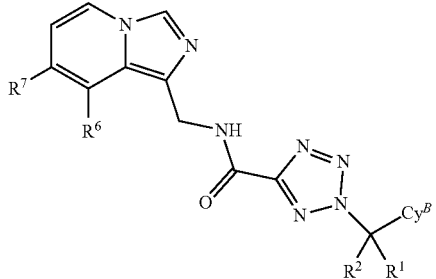

or a pharmaceutically acceptable salt thereof,
wherein:
each $R^A$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, and sulfur, 3- to to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

$Cy^B$ is selected from 3- to 7-membered saturated or partially unsaturated monocyclic heterocyclyl having 1-2 heteroatoms selected from oxygen, nitrogen, and sulfur, 5- to 6-membered heteroaryl having 1-4 heteroatoms selected from oxygen, nitrogen, and sulfur, 7- to to 10-membered saturated or partially unsaturated bicyclic heterocyclyl having 1-5 heteroatoms selected from oxygen, nitrogen, and sulfur, and 7- to 10-membered bicyclic heteroaryl having 1-5 heteroatoms selected from oxygen, nitrogen, and sulfur, wherein $Cy^B$ is substituted with 0-5 $R^B$ groups;

each $R^B$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, and sulfur, 3- to to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

$R^1$ and $R^2$ are independently selected from hydrogen and $C_{1-6}$ aliphatic;

$R^6$ and $R^7$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur; and each R is independently hydrogen, —CN, or an optionally substituted group selected from $C_{1-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, and sulfur, and 5- to 6-membered heteroaryl having 1-4 heteroatoms selected from oxygen, nitrogen, and sulfur.

10. The method of claim 1, wherein $Cy^B$ is a 7- to 10-membered bicyclic heteroaryl having 1-5 heteroatoms selected from oxygen, nitrogen, and sulfur, wherein $Cy^B$ is substituted with 0-5 $R^B$ groups.

11. The method of claim 1, wherein $Cy^B$ is

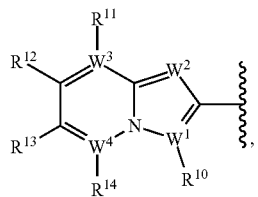

wherein:

$W^1$, $W^2$, $W^3$, and $W^4$ are independently selected from carbon and nitrogen;

$R^{10}$, $R^{11}$, $R^{12}$, $R^{13}$, and $R^{14}$ are each optionally present when attached to a carbon atom, and if present correspond to an occurrence of $R^B$ independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur; and each R is independently hydrogen, —CN, or an optionally substituted group selected from $C_{1-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, and sulfur, and 5- to 6-membered heteroaryl having 1-4 heteroatoms selected from oxygen, nitrogen, and sulfur.

12. The method of claim 1, wherein $Cy^B$ is selected from the group consisting of:

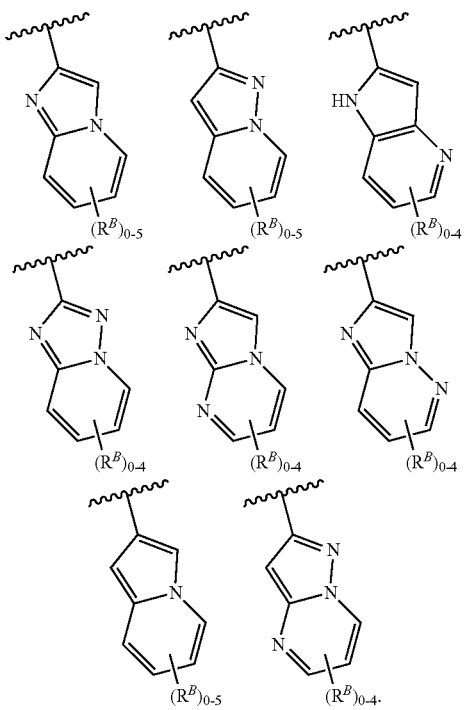

13. The method of claim 1, wherein $Cy^B$ is

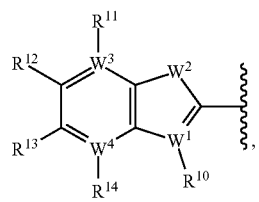

wherein:

$W^2$ is selected from carbon, nitrogen, oxygen, and sulfur;

$W^1$, $W^3$, and $W^4$ are independently selected from carbon and nitrogen;

$R^{10}$, $R^{11}$, $R^{12}$, $R^{13}$, and $R^{14}$ are each optionally present when attached to a carbon atom, and if present correspond to an occurrence of $R^B$ independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur; and each R is independently hydrogen, —CN, or an optionally substituted group selected from $C_{1-6}$ aliphatic, phenyl, 5- to 6-membered heteroaryl having 1-4 heteroatoms selected from oxygen, nitrogen, and sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, and sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, and sulfur, and 5- to 6-membered heteroaryl having 1-4 heteroatoms selected from oxygen, nitrogen, and sulfur.

14. The method of claim 1, wherein $Cy^B$ is selected from the group consisting of:

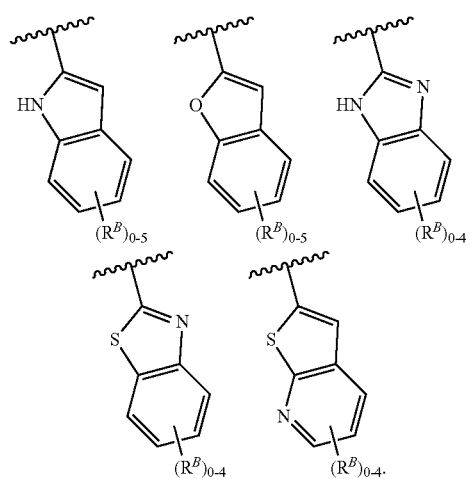

15. The method of claim 1, wherein $R^5$, $R^6$, $R^7$, $R^8$, and $R^9$ are independently selected from hydrogen, halogen, —CN, —N(R)$_2$, —OR, or an optionally substituted group selected from $C_{1-6}$ aliphatic, 3- to 7-membered saturated or partially unsaturated monocyclic carbocyclyl, wherein each R is independently hydrogen or $C_{1-6}$ aliphatic.

16. The method of claim 1, wherein $R^6$ is selected from hydrogen and halogen.

17. The method of claim 1, wherein the compound is any one of compounds I-1 through I-303 as shown in Table 1, or a pharmaceutically acceptable salt thereof.

18. The method of claim 1, wherein the compound is N-((7-chloroimidazo[1,5-a]pyridin-1-yl)methyl)-1-((3-chloroquinolin-6-yl)methyl)-1H-pyrazole-4-carboxamide, or a pharmaceutically acceptable salt thereof.

19. The method of claim 1, wherein the compound is N-((7-chloroimidazo[1,5-a]pyridin-1-yl)methyl)-1-((5-methylimidazo[1,2-a]pyridin-2-yl)methyl)-1H-pyrazole-4-carboxamide, or a pharmaceutically acceptable salt thereof.

20. The method of claim 1, wherein the compound is N-((7-chloroimidazo[1,5-a]pyridin-1-yl)methyl)-1-((6-cyclopropylimidazo[1,2-b]pyridazin-2-yl)methyl)-1H-pyrazole-4-carboxamide, or a pharmaceutically acceptable salt thereof.

21. The method of claim 1, wherein the compound is N-((7-bromoimidazo[1,5-a]pyridin-1-yl)methyl)-1-((7-chloro-6-cyclopropylimidazo[1,2-a]pyridin-2-yl)methyl)-1H-pyrazole-4-carboxamide, or a pharmaceutically acceptable salt thereof.

22. The method of claim 1, wherein the compound is N-((7-chloroimidazo[1,5-a]pyridin-1-yl)methyl)-1-((6-cyclopropylimidazo[1,2-a]pyridin-2-yl)methyl)-3-(methoxymethyl)-1H-pyrazole-4-carboxamide, or a pharmaceutically acceptable salt thereof.

23. The method of claim 1, wherein the compound is N-((7-chloroimidazo[1,5-a]pyridin-1-yl)methyl)-1-((6-cyclopropylimidazo[1,2-a]pyridin-2-yl)methyl)-1H-1,2,3-triazole-4-carboxamide, or a pharmaceutically acceptable salt thereof.

24. The method of claim 1, wherein the compound is N-((7-bromo-8-fluoroimidazo[1,5-a]pyridin-1-yl)methyl)-1-((6-cyclopropylimidazo[1,2-a]pyridin-2-yl)methyl)-1H-pyrazole-4-carboxamide, or a pharmaceutically acceptable salt thereof.

25. The method of claim 1, wherein the compound is N-((7-bromo-8-fluoroimidazo[1,5-a]pyridin-1-yl)methyl)-1-((6-cyclopropylimidazo[1,2-b]pyridazin-2-yl)methyl)-1H-1,2,3-triazole-4-carboxamide, or a pharmaceutically acceptable salt thereof.

26. The method of claim 1, wherein the compound is N-((7-chloro-8-fluoroimidazo[1,5-a]pyridin-1-yl)methyl)-1-((6-cyclopropylimidazo[1,2-a]pyridin-2-yl)methyl)-1H-1,2,3-triazole-4-carboxamide, or a pharmaceutically acceptable salt thereof or a pharmaceutically acceptable salt thereof.

27. The method of claim 1, wherein the compound is N-((7-chloro-8-fluoroimidazo[1,5-a]pyridin-1-yl)methyl)-1-((6,7-dichloroimidazo[1,2-a]pyridin-2-yl)methyl)-1H-1,2,3-triazole-4-carboxamide, or a pharmaceutically acceptable salt thereof.

28. The method of claim 1, wherein the compound is N-((7-chloro-8-fluoroimidazo[1,5-a]pyridin-1-yl)methyl)-1-((6-cyclopropylbenzofuran-2-yl)methyl)-1H-1,2,3-triazole-4-carboxamide, or a pharmaceutically acceptable salt thereof.

29. The method of claim 1, wherein the compound is 4-(((7-chloro-8-fluoroimidazo[1,5-a]pyridin-1-yl)methyl)carbamoyl)-1-((6-cyclopropylimidazo[1,2-a]pyridin-2-yl)methyl)-1H-imidazole-2-carboxylic acid, or a pharmaceutically acceptable salt thereof.

* * * * *